United States Patent
Ohmi et al.

(10) Patent No.: US 11,802,120 B2
(45) Date of Patent: Oct. 31, 2023

(54) FUSED CYCLIC UREA DERIVATIVES AS CRHR2 ANTAGONIST

(71) Applicants: RaQualia Pharma Inc., Aichi (JP); National University Corporation Tokai National Higher Education and Research System, Aichi (JP)

(72) Inventors: Masashi Ohmi, Aichi (JP); Takeshi Matsushita, Aichi (JP); Kazuo Ando, Aichi (JP); Ryuichi Yamaguchi, Aichi (JP); Yutaka Fukumoto, Aichi (JP); Ryohei Magara, Aichi (JP); Tatsuya Yamagishi, Aichi (JP); Mikito Takefuji, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 354 days.

(21) Appl. No.: 17/046,196

(22) PCT Filed: Apr. 9, 2019

(86) PCT No.: PCT/JP2019/015392
§ 371 (c)(1),
(2) Date: Oct. 8, 2020

(87) PCT Pub. No.: WO2019/198692
PCT Pub. Date: Oct. 17, 2019

(65) Prior Publication Data
US 2021/0078975 A1    Mar. 18, 2021

Related U.S. Application Data
(60) Provisional application No. 62/654,628, filed on Apr. 9, 2018.

(51) Int. Cl.
| | | |
|---|---|---|
| *C07D 401/14* | (2006.01) | |
| *A61P 9/00* | (2006.01) | |
| *C07D 405/14* | (2006.01) | |
| *C07D 413/14* | (2006.01) | |
| *C07D 417/14* | (2006.01) | |
| *C07D 471/04* | (2006.01) | |
| *A61K 45/06* | (2006.01) | |

(52) U.S. Cl.
CPC .............. *C07D 401/14* (2013.01); *A61P 9/00* (2018.01); *C07D 405/14* (2013.01); *C07D 413/14* (2013.01); *C07D 417/14* (2013.01); *C07D 471/04* (2013.01); *A61K 45/06* (2013.01)

(58) Field of Classification Search
CPC .. C07D 401/14; C07D 405/14; C07D 413/14; C07D 417/14; C07D 471/04; C07D 401/04; C07D 401/12; A61P 9/00; A61P 9/06; A61K 45/06; A61K 31/4439
See application file for complete search history.

(56) References Cited

U.S. PATENT DOCUMENTS

| | | |
|---|---|---|
| 2004/0176400 A1 | 9/2004 | Capelli et al. |
| 2005/0054661 A1 | 3/2005 | Di Fabio et al. |
| 2008/0064719 A1 | 3/2008 | Lanier et al. |
| 2008/0280928 A1 | 11/2008 | Nakazato et al. |
| 2011/0124862 A1 | 5/2011 | Nakazato et al. |
| 2011/0201629 A1* | 8/2011 | Atkinson et al. .... A61K 31/522 514/263.22 |

FOREIGN PATENT DOCUMENTS

| | | |
|---|---|---|
| JP | 2004-533465 | 11/2004 |
| JP | 2007-161585 | 6/2007 |
| JP | 2008-517060 | 5/2008 |
| WO | 99/57103 | 11/1999 |
| WO | 2010/015655 | 2/2010 |
| WO | 2011/092293 | 8/2011 |
| WO | 2011/095450 | 8/2011 |
| WO | 2013/160317 | 10/2013 |

OTHER PUBLICATIONS

International Preliminary Report on Patentability and Written Opinion of the International Searching Authority dated Oct. 22, 2020 in International (PCT) Application No. PCT/JP2019/015392.
International Search Report and Written Opinion of the International Searching Authority, dated Jun. 25, 2019 in corresponding International Patent Application No. PCT/JP2019/015392.
Beck et al., "Purin-8-Ones as Corticotropin-Releasing Hormone (CRH-R1) Receptor Antagonists", Bioorganic & Medicinal Chemistry Letters, 9(7), pp. 967-972 (1999).

(Continued)

*Primary Examiner* — Kortney L. Klinkel
*Assistant Examiner* — Padmaja S Rao
(74) *Attorney, Agent, or Firm* — Wenderoth, Lind & Ponack, L.L.P.

(57) ABSTRACT

The present invention relates to fused cyclic urea derivatives which have antagonistic activities against CRHR1 and/or CRHR2, and which are useful in the treatment or prevention of disorders and diseases in which CRHR1 and/or CRHR2 is involved. The invention also relates to pharmaceutical compositions comprising these compounds and the use of these compounds and compositions in the prevention or treatment of such diseases in which CRHR1 and/or CRHR2 is involved.

(I)

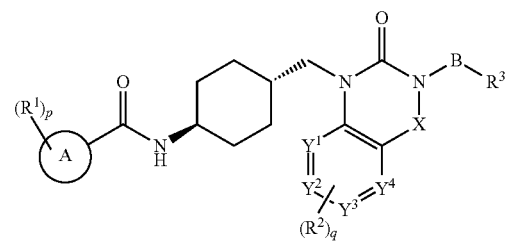

15 Claims, No Drawings

(56) References Cited

OTHER PUBLICATIONS

Hauger et al., "International Union of Pharmacology. XXXVI. Current Status of the Nomenclature for Receptors for Corticotropin-Releasing Factor and Their Ligands", Pharmacological Reviews, 55(1), pp. 21-26 (2003).
Grammatopoulos et al., "Functional characteristics of CRH receptors and potential clinical applications of CRH-receptor antagonists", Trends in Endocrinology & Metabolism, 13(10), pp. 436-444 (2002).
Aguilera et al., "Receptor-Mediated Actions of Corticotropin-Releasing Factor in Pituitary Gland and Nervous System", Progress in Neuroendocrinology, 43(1), pp. 79-88 (1986).
Tsuda et al., "Corticotropin releasing hormone receptor 2 exacerbates chronic cardiac dysfunction", The Journal of Experimental Medicine, 214(7), pp. 1877-1888 (2017).
Extended European Search Report dated Jul. 22, 2021 in corresponding European Patent Application No. 19785626.3.
Office Action and Search Report dated Dec. 29, 2021 in corresponding Russian Patent Application No. 2020134947, with English-language translation.
Berge, Stephen M. et al. "Pharmaceutical Salts", Journal of Pharmaceutical Sciences, Jan. 1977, vol. 66, No. 1, pp. 1-19.
Solvates, English version of internet source, https://xumuk.ru/encyklopedia/2/4130.html, published in Wayback Internet Archive Machine, Oct. 13, 2007, pp. 1-2.
Prodrug, English version of internet source, https://dic.academic.ru/dic.nsf/ruwiki/1108027, published in Wayback Internet Archive Machine, Dec. 16, 2013, pp. 1-2.
Belikov, V.G., "Chapter 2.6. Relationship between the chemical structure, properties of substances and their effect on the body", Farmatsevticheskaya Khimiya [Pharmaceutical Chemistry], Moscow, MEDpress-Inform, 2007, pp. 27-29, with English translation.
Ishitobi, Yoshinobu et al., "Association of CRHR1 and CRHR2 with Major Depressive Disorder and Panic Disorder in Japanese Population", American Journal of Medical Genetics Part B, vol. 159, pp. 429-436 (2012).
Pharmaceutical Composition, English version of internet source, https://official.academic.ru/28407%D0%A4%D0%B0%D1%80%D0%B%D0%B0%D1%86%D0%, published in Wayback Internet Archive Machine, Dec. 4, 2013.

\* cited by examiner

FUSED CYCLIC UREA DERIVATIVES AS CRHR2 ANTAGONIST

TECHNICAL FIELD

The present invention relates to fused cyclic urea derivatives which have antagonistic activities against both corticotropin releasing hormone receptor 1 (CRHR1) and corticotropin releasing hormone receptor 2 (CRHR2), and which are useful in the treatment or prevention of disorders and diseases in which CRHR1 and/or CRHR2 are involved. The invention also relates to pharmaceutical compositions comprising these compounds and the use of these compounds and compositions in the prevention or treatment of such diseases in which CRHR1 and/or CRHR2 is involved.

BACKGROUND ART

Corticotropin-releasing hormone receptors (CRHRs), also known as corticotropin-releasing factor receptors (CRFRs) are a G protein-coupled receptor family that binds corticotropin-releasing hormone (CRH) (NPL 1: Hauger R L, et al., Pharmacol. Rev. 55 (1): 21-6, 2003). There are two receptors in the family, designated as type 1 and 2, each encoded by a separate gene (CRHR1 and CRHR2 respectively). CRHRs are important mediators in the stress response. (NPL 2: Grammatopoulos D K, et al., Trends Endocrinol. Metab. 13 (10): 436-44, 2002). Cells in the anterior lobe of the pituitary gland known as corticotropes express the receptors and will secrete adrenocorticotropic hormone (ACTH) when stimulated. This binding of corticotropin releasing-hormone (CRH) activates the hypothalamic-pituitary-adrenal (HPA) axis, one of the two parts of the fight-or-flight response to stress. (NPL 3: Aguilera G, et al., Neuroendocrinology. 43 (1): 79-88, 1986). CRHRs are also present in other brain areas such as the amygdala, locus coeruleus and hippocampus. Chronic activation of CRHRs by CRH induced by early life stress has been shown to underlie memory deficits and learning impairments and anxiety in adulthood.

Recently, Takefuji et al., reported that the GPCR corticotropin releasing hormone receptor 2 (CRHR2) is highly expressed in the heart and facilitates heart failure (NPL 4: Takefuji et al., J. Experimental Medicine, 214, 1877-1888, 2017). The results indicate that CRHR2 may be a promising therapeutic target for chronic heart failure.

The fused cyclic urea derivatives of the present invention are CRHR1 and CRHR2 dual antagonists and have a number of therapeutic applications. More particularly, the fused cyclic urea derivatives of the invention show an excellent CRHR2 antagonistic activities.

CITATION LIST

Non Patent Literature

{NPL 1} Hauger R L, et al., Pharmacol. Rev. 55 (1): 21-6, 2003.
{NPL 2} Grammatopoulos D K, et al., Trends Endocrinol. Metab. 13 (10): 436-44, 2002.
{NPL 3} Aguilera G, et al., Neuroendocrinology. 43 (1): 79-88, 1986.
{NPL 4} Takefuji et al., J. Experimental Medicine, 214, 1877-1888, 2017.

Patent Literature

{PL 1} WO2011/092293
{PL 2} WO2011/095450

SUMMARY OF INVENTION

Technical Problem

It is an objective of the invention to provide new CRHR1 and CRHR2 dual antagonists that are good drug candidates. Preferred compounds should bind potently to CRHR1 and CRHR2 whilst showing little affinity for other CRHRs. They possess favorable pharmacokinetic properties such as absorption, distribution, metabolism, and excretion. They are non-toxic and demonstrate few side-effects. Furthermore, the ideal drug candidate will exist in a physical form that is stable, non-hygroscopic and easily formulated.

Solution to Problem

With respect to other compounds disclosed in the art, the compounds of the present invention may show less toxicity, favorable absorption and distribution, favorable solubility, favorable plasma protein binding, less drug-drug interaction, favorable metabolic stability, reduced inhibitory activity at HERG channel, and/or reduced QT prolongation.

This invention provides:

[1] A compound of the following formula (I):

[Chem.1]

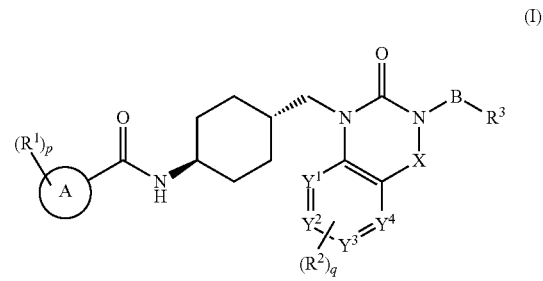

(I)

wherein:

A is aryl or heteroaryl; preferably A is phenyl or pyridyl;

$R^1$ is independently selected from the group consisting of: (1) hydrogen, (2) halogen, (3) $C_{1-6}$ alkyl, (4) $C_{3-7}$ cycloalkyl, (5) —O—$C_{1-6}$ alkyl, (6) $C_{1-6}$ alkoxy$C_{1-6}$ alkyl, (7) —NH$C_{1-6}$ alkyl, (8) —N($C_{1-6}$ alkyl)$_2$, and (9) —NH$C_{3-7}$ cycloalkyl, wherein the $C_{1-6}$ alkyl, the $C_{3-7}$ cycloalkyl, the —O—$C_{1-6}$ alkyl, the $C_{1-6}$ alkoxy$C_{1-6}$ alkyl, the —NH$C_{1-6}$ alkyl, the —N($C_{1-6}$ alkyl)$_2$, or the —NH$C_{3-7}$ cycloalkyl is unsubstituted or substituted with one or more substituents independently selected from the group consisting of: halogen and hydroxyl; or two $R^1$ may form a 5 to 7 membered cycloalkyl ring; preferably $R^1$ is independently selected from the group consisting of: (1) hydrogen, (2) halogen, and (3) $C_{1-6}$ alkyl; wherein the $C_{1-6}$ alkyl is unsubstituted or substituted with one or more halogens;

p is 1, 2, or 3; preferably p is 2 or 3; more preferably p is 2;

$R^2$ is independently selected from the group consisting of: (1) hydrogen, (2) halogen, (3) hydroxyl, (4) $C_{1-6}$ alkyl, (5) —O—$C_{1-6}$ alkyl, and (6) —CN; preferably $R^2$ is independently selected from the group consisting of: (1) hydrogen, (2) halogen, (4) $C_{1-6}$ alkyl, and (6) —CN; more preferably $R^2$ is independently selected from the group consisting of: (1) hydrogen, (2) halogen, and (4) $C_{1-6}$ alkyl;

q is 1, 2, or 3; preferably q is 1;

$Y^1$, $Y^2$, $Y^3$, and $Y^4$ are independently selected from the group consisting of CH, $CR^2$, and N, number of nitrogen atom is two at most at the same time; wherein the number of nitrogen atom is preferably one or zero;

X is a chemical bond or $CH_2$; preferably X is a chemical bond;

B is a chemical bond, —$C_{1-3}$ alkylene-, —$C_{1-3}$ alkylene-O—, or —$CH_2$—(C=O)—; preferably B is a chemical bond;

$R^3$ is selected from the group consisting of:
(1) aryl, preferably phenyl, (2) 5 to 6-membered heteroaryl with 1-3 heteroatoms independently selected from O, N, and S, preferably 5 to 6-membered heteroaryl with 1-2 heteroatoms independently selected from O, N, and S, (3) 8 to 10-membered unsaturated or partially saturated bi-cyclic heteroaryl with 1-4 heteroatoms independently selected from O, N, and S, (4) 5 to 6-membered heterocyclyl with 1-2 heteroatoms independently selected from O, N, and S; and (5) 8 to 10-membered unsaturated or partially saturated bi-cyclic aryl; wherein the aryl, preferably phenyl, the 5 to 6-membered heteroaryl, the 8 to 10-membered unsaturated or partially saturated bi-cyclic heteroaryl, the 5 to 6-membered heterocyclyl, or the 8 to 10-membered unsaturated or partially saturated bi-cyclic aryl is unsubstituted or substituted with one or more substituents independently selected from $R^4$; preferably $R^3$ is selected from the group consisting of: (1) phenyl, (2) 5 to 6-membered heteroaryl selected from pyrazole, pyridine, pyrazine, pyridazine, and pyrimidine, and (3) 8 to 10-membered unsaturated or partially saturated bi-cyclic heteroaryl with 1-4 heteroatoms which is selected from the group consisting of indole, pyrrolo[2,3-b]pyridine, pyrrolo[2,3-c]pyridine, indazole, pyrazolo[3,4-b]pyridine, pyrazolo[4,3-b]pyridine, benzoxazole, and 2,3-dihydro-pyrrolo[2,3-b]pyridine, wherein the phenyl the 5 to 6-membered heteroaryl or the 8 to 10-membered unsaturated or partially saturated bi-cyclic heteroaryl is unsubstituted or substituted with one or more substituents independently selected from $R^4$; more preferably $R^3$ is phenyl, pyrazole, pyridine, pyrazine, pyridazine, or pyrimidine;

$R^4$ is independently selected from the group consisting of:
(1) hydrogen, (2) halogen, (3) hydroxyl, (4) $C_{1-6}$ alkyl, (5) —O—$C_{1-6}$alkyl, (6) $C_{2-6}$ alkenyl, (7) $C_{3-7}$ cycloalkyl, (8) —O—$C_{3-7}$ cycloalkyl, (9) $C_{3-7}$ cycloalkyl$C_{1-6}$ alkoxyl, (10) —(C=O)—$R^5$, (11) —(C=O)—$NR^5R^6$, (12) —$NR^5$(C=O)$R^6$, (13) —$NR^5R^6$, (14) aryl, preferably phenyl, (15) heterocyclyl which is 4 to 7 membered partially unsaturated or saturated heterocyclic ring with 1-2 heteroatoms independently selected from O, N, and S, (16) —O-heterocyclyl, (17) heterocyclyl$C_{1-6}$ alkyl, (18) heterocyclyl$C_{1-6}$ alkoxyl, (19) —$NR^5$—$S(O)_2R^6$, (20) —$S(O)_2$—R, (21) —CN, (22) nitro, (23) heteroaryl, (24) —O-heteroaryl, (25) —S—$C_{1-6}$ alkyl, (26) —O—$C_{1-6}$ alkyl-(C=O)—$NR^5R^6$, and (26) —(C=O)—$NR^5OC_{1-6}$ alkyl, wherein the $C_{1-6}$ alkyl, the —O—$C_{1-6}$ alkyl, the $C_{3-7}$ cycloalkyl, the —O—$C_{3-7}$ cycloalkyl, or the —S—$C_{1-6}$ alkyl is unsubstituted or substituted with one or more substituents independently selected from halogen, hydroxyl, —$NR^5R^6$, —O—$C_{1-6}$ alkyl, and $C_{3-7}$ cycloalkyl, wherein the aryl, preferably phenyl, the heterocyclyl, the —O-heterocyclyl, the heterocyclyl$C_{1-6}$ alkyl, the heterocyclyl$C_{1-6}$ alkoxyl, the heteroaryl, or the —O-heteroaryl, is unsubstituted or substituted with one or more substituents independently selected from the group consisting of halogen, hydroxyl, $C_{1-6}$ alkyl, hydroxyl$C_{1-6}$ alkyl, $C_{1-6}$ alkoxyl, and —(C=O)—$R^5$; preferably $R^4$ is independently selected from the group consisting of: (1) hydrogen, (2) halogen, (3) hydroxyl, (4) $C_{1-6}$ alkyl, (5) —O—$C_{1-6}$alkyl, (7) $C_{3-7}$ cycloalkyl, (8) —O—$C_{3-7}$ cycloalkyl, (10) —(C=O)—$R^5$, (11) —(C=O)—$NR^5R^6$, (13) —$NR^5R^6$, (14) aryl, and (23) heteroaryl, wherein the $C_{1-6}$ alkyl, the —O—$C_{1-6}$ alkyl, the $C_{3-7}$ cycloalkyl, or the —O—$C_{3-7}$ cycloalkyl is unsubstituted or substituted with one or more substituents independently selected from halogen and hydroxyl; wherein the aryl or the heteroaryl is unsubstituted or substituted with one or more substituents independently selected from the group consisting of halogen, hydroxyl, $C_{1-6}$ alkyl, hydroxyl$C_{1-6}$ alkyl, and —(C=O)—$R^5$; more preferably $R^4$ is independently selected from the group consisting of: (1) hydrogen, (2) halogen, (3) hydroxyl, (4) $C_{1-6}$ alkyl, (5) —O—$C_{1-6}$ alkyl, and (11) —(C=O)—$NR^5R^6$; wherein the $C_{1-6}$ alkyl or the —O—$C_{1-6}$ alkyl is unsubstituted or substituted with one or more substituents independently selected from halogen and hydroxyl;

$R^5$ is independently selected from the group consisting of: (1) hydrogen and (2) $C_{1-6}$ alkyl;

$R^6$ is independently selected from the group consisting of: (1) hydrogen, (2) $C_{1-6}$ alkyl, (3) $C_{3-7}$ cycloalkyl, (4) heterocyclyl, (5) $C_{3-7}$ cycloalkyl$C_{1-6}$ alkyl, (6) heterocyclyl$C_{1-6}$ alkyl, (7) aryl, (8) aryl$C_{1-6}$ alkyl, (9) heteroaryl, and (10) heteroaryl$C_{1-6}$ alkyl, wherein the $C_{1-6}$ alkyl, the $C_{3-7}$ cycloalkyl, the heterocyclyl, the $C_{3-7}$ cycloalkyl$C_{1-6}$ alkyl, the heterocyclyl$C_{1-6}$ alkyl, the aryl, the aryl$C_{1-6}$ alkyl, the heteroaryl, or the heteroaryl$C_{1-6}$ alkyl is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, hydroxy$C_{1-6}$ alkoxyl, $C_{1-6}$ haloalkyl, and $C_{1-6}$ haloalkoxyl, —$NR^7R^8$, and —(C=O)—$NR^7R^8$; or $R^5$ may form a 4 to 7 membered ring with $R^6$ which may contain a nitrogen atom, an oxygen atom, or a carbonyl; or $R^5$ may form a 7 to 11 membered spiro-ring with $R^6$ which may contain a nitrogen atom, an oxygen atom, or a carbonyl; wherein the 4 to 7 membered ring or the 7 to 11 membered spiro-ring is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, $C_{1-6}$ haloalkyl, and $C_{1-6}$ haloalkoxyl; more preferably $R^6$ is independently selected from the group consisting of: (1) hydrogen, (2) $C_{1-6}$ alkyl, and (3) $C_{3-7}$ cycloalkyl, wherein the $C_{1-6}$ alkyl or $C_{3-7}$ cycloalkyl is unsubstituted or substituted with one or more substituents independently selected from the group consisting of: halogen and hydroxyl;

$R^7$ and $R^8$ are independently selected from the group consisting of: (1) hydrogen and (2) $C_{1-6}$ alkyl; or $R^7$ may form a 4 to 7 membered ring with $R^8$ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, and $C_{1-6}$ haloalkyl; or a pharmaceutically acceptable salt thereof or a prodrug thereof.

[2] The compound of the following formula (II) according to [1]:

[Chem.2]

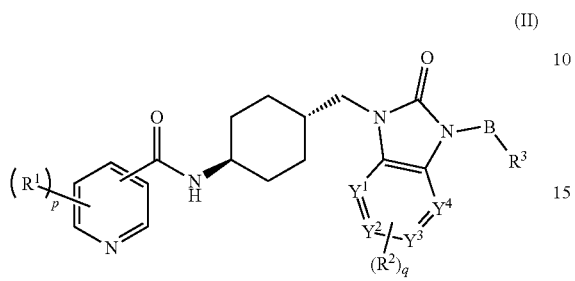

(II)

wherein:
$R^1$ is independently selected from the group consisting of:
(1) hydrogen, (2) halogen, (3) $C_{1-6}$ alkyl, (4) $C_{3-7}$ cycloalkyl, (5) —O—$C_{1-6}$ alkyl, (6) $C_{1-6}$ alkoxyl$C_{1-6}$ alkyl, (7) —NH$C_{1-6}$ alkyl, (8) —N($C_{1-6}$ alkyl)$_2$, and (9) —NH$C_{3-7}$ cycloalkyl wherein the $C_{1-6}$ alkyl, the $C_{3-7}$ cycloalkyl, the —O—$C_{1-6}$ alkyl, the $C_{1-6}$ alkoxyl$C_{1-6}$ alkyl, the —NH$C_{1-6}$ alkyl, the —N($C_{1-6}$ alkyl)$_2$, or the —NH$C_{3-7}$ cycloalkyl is unsubstituted or substituted with one or more substituents independently selected from the group consisting of: halogen and hydroxyl; or two $R^1$ may form a 5 to 7 membered cycloalkyl ring;
p is 1, 2, or 3;
$R^2$ is independently selected from the group consisting of:
(1) hydrogen, (2) halogen, (4) $C_{1-6}$ alkyl, and (6) —CN;
q is 1, 2, or 3;
$Y^1$, $Y^2$, $Y^3$, and $Y^4$ are independently selected from the group consisting of: CH, $CR^2$, and N,
number of nitrogen atom is two at most at the same time;
B is a chemical bond, —CH$_2$—, —CH$_2$CH$_2$—, or —CH$_2$—(C=O)—;
$R^3$ is selected from the group consisting of:
(1) aryl, preferably phenyl, (2) 5 to 6-membered heteroaryl with 1-3 heteroatoms independently selected from O, N, and S, (3) 8 to 10-membered unsaturated or partially saturated bi-cyclic heteroaryl with 1-4 heteroatoms independently selected from O, N, and S, (4) 5 to 6-membered heterocyclyl with 1-2 heteroatoms independently selected from O, N, and S, and (5) 8 to 10-membered unsaturated or partially saturated bi-cyclic aryl; wherein the aryl, preferably phenyl, the 5 to 6-membered heteroaryl, the 8 to 10-membered unsaturated or partially saturated bi-cyclic heteroaryl, the 5 to 6-membered heterocyclyl, or the 8 to 10-membered unsaturated or partially saturated bi-cyclic aryl is unsubstituted or substituted with one or more substituents independently selected from $R^4$;
$R^4$ is independently selected from the group consisting of:
(1) hydrogen, (2) halogen, (3) hydroxyl, (4) $C_{1-6}$ alkyl, (5) —O—$C_{1-6}$ alkyl, (6) $C_{2-6}$ alkenyl, (7) $C_{3-7}$ cycloalkyl, (8) —O—$C_{3-7}$ cycloalkyl, (9) $C_{3-7}$ cycloalkyl$C_{1-6}$ alkoxyl, (10) —(C=O)—$R^5$, (11) —(C=O)—NR$^5$R$^6$, (12) —NR$^5$(C=O)R$^6$, (13) —NR$^5$R$^6$, (14) aryl, preferably phenyl, (15) heterocyclyl which is 4 to 7 membered partially unsaturated or saturated heterocyclic ring with 1-2 heteroatoms independently selected from O, N, and S, (16) —O-heterocyclyl, (17) heterocyclyl$C_{1-6}$ alkyl, (18) heterocyclyl$C_{1-6}$ alkoxyl, (19) —NR$^5$—S(O)$_2$R$^6$, (20) —S(O)$_2$—R$^5$, (21) —CN, (22) nitro, (23) heteroaryl, (24) —O-heteroaryl, (25) —S—$C_{1-6}$ alkyl, (26) —O—$C_{1-6}$ alkyl-(C=O)—NR$^5$R$^6$, and (26) —(C=O)—NR$^5$O$C_{1-6}$ alkyl, wherein the $C_{1-6}$ alkyl, the —O—$C_{1-6}$ alkyl, the $C_{3-7}$ cycloalkyl, the —O—$C_{3-7}$ cycloalkyl, or the —S—$C_{1-6}$ alkyl is unsubstituted or substituted with one or more substituents independently selected from halogen, hydroxyl, —NR$^5$R$^6$, —O—$C_{1-6}$ alkyl, and $C_{3-7}$ cycloalkyl, wherein the aryl, preferably phenyl, the heterocyclyl, the —O-heterocyclyl, the heterocyclyl$C_{1-6}$ alkyl, the heterocyclyl$C_{1-6}$ alkoxyl, the heteroaryl, or the —O-heteroaryl is unsubstituted or substituted with one or more substituents independently selected from halogen, hydroxyl, $C_{1-6}$ alkyl, hydroxyl$C_{1-6}$ alkyl, and —(C=O)—$R^5$;

$R^5$ is independently selected from the group consisting of:
(1) hydrogen and (2) $C_{1-6}$ alkyl;

$R^6$ is independently selected from the group consisting of:
(1) hydrogen, (2) $C_{1-6}$ alkyl, (3) $C_{3-7}$ cycloalkyl, (4) heterocyclyl, (5) $C_{3-7}$ cycloalkyl$C_6$ alkyl, (6) heterocyclyl$C_{1-6}$ alkyl, (7) aryl, (8) aryl$C_{1-6}$ alkyl, (9) heteroaryl, and (10) heteroaryl$C_{1-6}$ alkyl, wherein the $C_{1-6}$ alkyl, the $C_{3-7}$ cycloalkyl, the heterocyclyl, the $C_{3-7}$ cycloalkyl$C_{1-6}$ alkyl, the heterocyclyl$C_{1-6}$ alkyl, the aryl, the aryl$C_{1-6}$ alkyl, the heteroaryl, or the heteroaryl$C_{1-6}$ alkyl is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, hydroxy$C_{1-6}$ alkoxyl, $C_{1-6}$ haloalkyl, and $C_6$ haloalkoxyl, —NR$^7$R$^8$, and —(C=O)—NR$^7$R$^8$; or $R^5$ may form a 4 to 7 membered ring with $R^6$ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, $C_{1-6}$ haloalkyl, and $C_{1-6}$ haloalkoxyl;

$R^7$ and $R^8$ are independently selected from the group consisting of: (1) hydrogen and (2) $C_{1-6}$ alkyl; or $R^7$ may form a 4 to 7 membered ring with $R^8$ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, and $C_{1-6}$ haloalkyl; or a pharmaceutically acceptable salt thereof or a prodrug thereof;

[3] The compound according to [1] or [2]:
wherein:
$R^1$ is independently selected from the group consisting of:
(1) hydrogen, (2) halogen, and (3) $C_{1-6}$ alkyl; wherein the $C_{1-6}$ alkyl is unsubstituted or substituted with one or more substituents independently selected from the group consisting of: halogen and hydroxyl; or a pharmaceutically acceptable salt thereof or a prodrug thereof;

4. The compound according to any one of [1] to [3]: wherein:

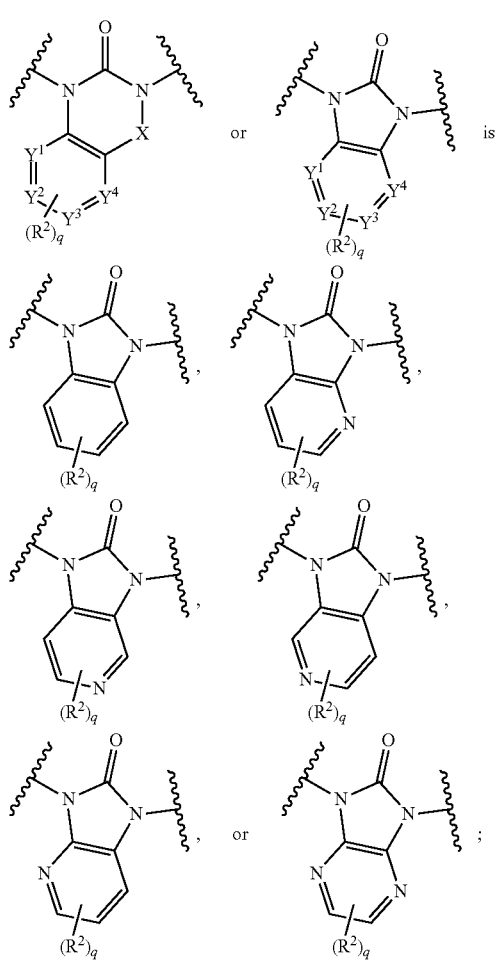

or a pharmaceutically acceptable salt thereof or a prodrug thereof;

[5] The compound according to any one of [1] to [4]: wherein:

B is a chemical bond or —$CH_2$—;

$R^3$ is selected from the group consisting of: (1) phenyl, (2) 5 to 6-membered heteroaryl selected from pyrazole, pyridine, pyrazine, pyridazine, and pyrimidine, and (3) 8 to 10-membered unsaturated or partially saturated bi-cyclic heteroaryl with 1-4 heteroatoms which is selected from the group consisting of indole, pyrrolo[2,3-b]pyridine, pyrrolo[2,3-c]pyridine, indazole, pyrazolo[3,4-b]pyridine, pyrazolo[4,3-b]pyridine, benzoxazole, and 2,3-dihydro-pyrrolo[2,3-b]pyridine, wherein the phenyl, the 5 to 6-membered heteroaryl or the 8 to 10-membered unsaturated or partially saturated bi-cyclic heteroaryl is unsubstituted or substituted with one or more substituents independently selected from $R^4$;

$R^4$ is independently selected from the group consisting of: (1) hydrogen, (2) halogen, (3) hydroxyl, (4) $C_{1-6}$ alkyl, (5) —O—$C_{1-6}$ alkyl, (7) $C_{3-7}$ cycloalkyl, (8) —O—$C_{3-7}$ cycloalkyl, (10) —(C=O)—$R^5$, (11) —(C=O)—$NR^5R^6$, (13) —$NR^5R^6$, (14) aryl, and (23) heteroaryl, wherein the $C_{1-6}$alkyl, the —O—$C_{1-6}$ alkyl, the $C_{3-7}$ cycloalkyl, or the —O—$C_{3-7}$ cycloalkyl is unsubstituted or substituted with one or more substituents independently selected from halogen and hydroxyl; wherein the aryl or the heteroaryl is unsubstituted or substituted with one or more substituents independently selected from halogen, hydroxyl, $C_{1-6}$ alkyl, hydroxyl$C_{1-6}$ alkyl, and —(C=O)—$R^5$;

$R^6$ is independently selected from the group consisting of: (1) hydrogen, (2) $C_{1-6}$ alkyl, (3) $C_{3-7}$ cycloalkyl, (4) heterocyclyl, (5) $C_{3-7}$ cycloalkyl$C_{1-6}$ alkyl, (6) heterocyclyl$C_{1-6}$ alkyl, (7) aryl, (8) aryl$C_{1-6}$ alkyl, (9) heteroaryl, and (10) heteroaryl$C_{1-6}$ alkyl, wherein the $C_{1-6}$ alkyl, the $C_{3-7}$cycloalkyl, the heterocyclyl, the $C_{3-7}$ cycloalkyl$C_{1-6}$ alkyl, the heterocyclyl$C_{1-6}$ alkyl, the aryl, the aryl$C_{1-6}$ alkyl, the heteroaryl, or the heteroaryl$C_{1-6}$ alkyl is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, hydroxy$C_{1-6}$ alkoxyl, $C_{1-6}$ haloalkyl, and $C_{1-6}$ haloalkoxyl, —$NR^7R^8$, and —(C=O)—$NR^7R^8$; or $R^5$ may form a 4 to 7 membered ring with $R^6$ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, $C_{1-6}$ haloalkyl, and $C_{1-6}$ haloalkoxyl;

$R^7$ and $R^8$ are independently selected from the group consisting of: (1) hydrogen and (2) $C_{1-6}$ alkyl; or $R^7$ may form a 4 to 7 membered ring with $R^8$ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, and $C_{1-6}$ haloalkyl; or a pharmaceutically acceptable salt thereof or a prodrug thereof;

[6] A compound which is selected from the group consisting of:

5-chloro-2-methyl-N-((1r,4r)-4-((2-oxo-3-phenyl-2,3-dihydro-1H-benzo[d]imidazol-1-yl)methyl)cyclohexyl)nicotinamide;

N-((1r,4r)-4-((3-benzyl-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-((tetrahydro-2H-pyran-4-yl)methyl)-2,3-dihydro-1H-benzo[d]imidazol-1-yl)methyl)cyclohexyl)nicotinamide;

5-chloro-2-methyl-N-((1r,4r)-4-((3-(3-(methylcarbamoyl)benzyl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(2-oxo-2-phenylethyl)-2,3-dihydro-1H-benzo[d]imidazol-1-yl)methyl)cyclohexyl)nicotinamide;

5-chloro-2-methyl-N-((1r,4r)-4-((2-oxo-3-(pyridin-2-ylmethyl)-2,3-dihydro-1H-benzo[d]imidazol-1-yl)methyl)cyclohexyl)nicotinamide;

5-chloro-2-methyl-N-((1r,4r)-4-((2-oxo-3-(pyridin-3-ylmethyl)-2,3-dihydro-1H-benzo[d]imidazol-1-yl)methyl)cyclohexyl)nicotinamide;

5-chloro-2-methyl-N-((1r,4r)-4-((2-oxo-3-(pyridin-4-ylmethyl)-2,3-dihydro-1H-benzo[d]imidazol-1-yl)methyl)cyclohexyl)nicotinamide;

5-chloro-N-((1r,4r)-4-((3-(2-(4-methoxyphenyl)-2-oxoethyl)-2-oxo-2,3-dihydro-1H-benzo[d]imidazol-1-yl)methyl)cyclohexyl)-2-methylnicotinamide;

5-chloro-N-((1r,4r)-4-((3-(2-(2-methoxyphenyl)-2-oxoethyl)-2-oxo-2,3-dihydro-1H-benzo[d]imidazol-1-yl)methyl)cyclohexyl)-2-methylnicotinamide;

5-chloro-N-((1r,4r)-4-((3-(2-(hydroxymethyl)benzyl)-2-oxo-2,3-dihydro-1H-benzo[d]imidazol-1-yl)methyl)cyclohexyl)-2-methylnicotinamide;

5-chloro-N-((1r,4r)-4-((3-(2-(2,4-difluorophenyl)-2-oxoethyl)-2-oxo-2,3-dihydro-1H-benzo[d]imidazol-1-yl)methyl)cyclohexyl)-2-methylnicotinamide;

5-chloro-N-((1r,4r)-4-((3-(2-(4-cyanophenyl)-2-oxoethyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(pyridin-4-yl)-2,3-dihydro-1H-benzo[d]imidazol-1-yl)methyl)cyclohexyl)nicotinamide;

5-chloro-N-((1r,4r)-4-((3-(4-fluorophenyl)-2-oxo-2,3-dihydro-1H-benzo[d]imidazol-1-yl)methyl)cyclohexyl)-2-methylnicotinamide;

5-chloro-N-((1r,4r)-4-((3-(3-fluorophenyl)-2-oxo-2,3-dihydro-1H-benzo[d]imidazol-1-yl)methyl)cyclohexyl)-2-methylnicotinamide;

N-((1r,4r)-4-((3-(3-acetylphenyl)-2-oxo-2,3-dihydro-1H-benzo[d]imidazol-1-yl)methyl)cyclohexyl)-5-chloro-2-methylnicotinamide;

N-((1r,4r)-4-((3-(4-acetylphenyl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(4-(1-hydroxyethyl)phenyl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)phenyl)-2-oxo-2,3-dihydro-1H-benzo[d]imidazol-1-yl)methyl)cyclohexyl)-2-methylnicotinamide;

5-chloro-N-((1r,4r)-4-((3-(4-(hydroxymethyl)phenyl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)benzyl)-2-oxo-2,3-dihydro-1H-benzo[d]imidazol-1-yl)methyl)cyclohexyl)-2-methylnicotinamide;

5-chloro-N-((1r,4r)-4-((3-(4-(hydroxymethyl)benzyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-phenethyl-2,3-dihydro-1H-benzo[d]imidazol-1-yl)methyl)cyclohexyl)nicotinamide;

5-chloro-2-methyl-N-((1r,4r)-4-((2-oxo-3-(p-tolyl)-2,3-dihydro-1H-benzo[d]imidazol-1-yl)methyl)cyclohexyl)nicotinamide;

5-chloro-N-((1r,4r)-4-((3-(4-chlorophenyl)-2-oxo-2,3-dihydro-1H-benzo[d]imidazol-1-yl)methyl)cyclohexyl)-2-methylnicotinamide;

5-chloro-N-((1r,4r)-4-((3-(4-methoxyphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(4-(trifluoromethyl)phenyl)-2,3-dihydro-1H-benzo[d]imidazol-1-yl)methyl)cyclohexyl)nicotinamide;

5-chloro-2-methyl-N-((1r,4r)-4-((2-oxo-3-(6-(trifluoromethyl)pyridin-3-yl)-2,3-dihydro-1H-benzo[d]imidazol-1-yl)methyl)cyclohexyl)nicotinamide;

5-chloro-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2-fluorophenyl)-2-oxo-2,3-dihydro-1H-benzo[d]imidazol-1-yl)methyl)cyclohexyl)-2-methylnicotinamide;

5-chloro-N-((1r,4r)-4-((3-(2-methoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(6-(2,2-difluoroethoxy)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-ethoxypyridin-3-yl)-2-oxo-2,3-dihydro-1H-benzo[d]imidazol-1-yl)methyl)cyclohexyl)-2-methylnicotinamide;

2-ethyl-N-((1r,4r)-4-((3-(4-methoxyphenyl)-2-oxo-2,3-dihydro-1H-benzo[d]imidazol-1-yl)methyl)cyclohexyl)-2H-indazole-3-carboxamide;

2-ethyl-N-((1r,4r)-4-((3-(6-methylpyridin-3-yl)-2-oxo-2,3-dihydro-1H-benzo[d]imidazol-1-yl)methyl)cyclohexyl)-2H-indazole-3-carboxamide;

2-ethyl-N-((1r,4r)-4-((3-(6-methoxypyridin-3-yl)-2-oxo-2,3-dihydro-1H-benzo[d]imidazol-1-yl)methyl)cyclohexyl)-2H-indazole-3-carboxamide;

2-(2-hydroxyethyl)-N-((1r,4r)-4-((2-oxo-3-(p-tolyl)-2,3-dihydro-1H-benzo[d]imidazol-1-yl)methyl)cyclohexyl)-2H-indazole-3-carboxamide;

N-((1r,4r)-4-((3-(4-acetylphenyl)-2-oxo-2,3-dihydro-1H-benzo[d]imidazol-1-yl)methyl)cyclohexyl)-2-ethyl-2H-indazole-3-carboxamide;

2-ethyl-N-((1r,4r)-4-((3-(4-(1-hydroxyethyl)phenyl)-2-oxo-2,3-dihydro-1H-benzo[d]imidazol-1-yl)methyl)cyclohexyl)-2H-indazole-3-carboxamide;

5-chloro-N-((1r,4r)-4-((3-(2-methoxypyrimidin-5-yl)-2-oxo-2,3-dihydro-1H-benzo[d]imidazol-1-yl)methyl)cyclohexyl)-2-methylnicotinamide;

5-chloro-N-((1r,4r)-4-((3-(3,4-dimethoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(2-methoxypyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(2,4-difluorophenyl)-2-oxo-2,3-dihydro-1H-benzo[d]imidazol-1-yl)methyl)cyclohexyl)-2-methylnicotinamide;

5-chloro-N-((1r,4r)-4-((3-(4-fluoro-2-methylphenyl)-2-oxo-2,3-dihydro-1H-benzo[d]imidazol-1-yl)methyl)cyclohexyl)-2-methylnicotinamide;

5-chloro-N-((1r,4r)-4-((3-(4-fluoro-3-methoxyphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(2-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(3-methylpyridin-4-yl)-2-oxo-2,3-dihydro-1H-benzo[d]imidazol-1-yl)methyl)cyclohexyl)nicotinamide;

5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((2-methoxyethyl)(methyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-morpholinopyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(4-methylpiperazin-1-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-methylpyridin-4-yl)-2-oxo-2,3-dihydro-1H-benzo[d]imidazol-1-yl)methyl)cyclohexyl)nicotinamide;

5-chloro-2-methyl-N-((1r,4r)-4-((4-methyl-3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(6-methoxypyridin-3-yl)-4-methyl-2-oxo-2,3-dihydro-1H-benzo[d]imidazol-1-yl)methyl)cyclohexyl)-2-methylnicotinamide;

5-chloro-N-((1r,4r)-4-((3-(6-(2-(dimethylamino)ethoxy)pyridin-3-yl)-4-methyl-2-oxo-2,3-dihydro-1H-benzo[d]imidazol-1-yl)methyl)cyclohexyl)-2-methylnicotinamide;

5-chloro-N-((1r,4r)-4-((3-(6-methoxypyridin-3-yl)-7-methyl-2-oxo-2,3-dihydro-1H-benzo[d]imidazol-1-yl)methyl)cyclohexyl)-2-methylnicotinamide;

5-chloro-N-((1S,4r)-4-((3-(6-((S)-3-(dimethylamino)pyrrolidin-1-yl)pyridin-3-yl)-2-oxo-2,3-dihydro-1H-benzo[d]imidazol-1-yl)methyl)cyclohexyl)-2-methylnicotinamide;

5-(3-((((1r,4r)-4-(5-chloro-2-methylnicotinamido)cyclohexyl)methyl)-2-oxo-2,3-dihydro-1H-benzo[d]imidazol-1-yl)picolinamide;

5-(3-((((1r,4r)-4-(5-chloro-2-methylnicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-(2-hydroxyethyl)piperazin-1-yl)pyridin-3-yl)-2-oxo-2,3-dihydro-1H-benzo[d]imidazol-1-yl)methyl)cyclohexyl)-2-methylnicotinamide;

N-((1r,4r)-4-((3-(6-bromopyridin-3-yl)-2-oxo-2,3-dihydro-1H-benzo[d]imidazol-1-yl) methyl)cyclohexyl)-5-chloro-2-methylnicotinamide;

5-chloro-N-((1r,4r)-4-((3-(6-(dimethylamino)pyridazin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(4-methylpiperazin-1-yl)pyridazin-3-yl)-2-oxo-2,3-dihydro-1H-benzo[d]imidazol-1-yl)methyl)cyclohexyl)nicotinamide;

5-chloro-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide;

N-((1r,4r)-4-((3-(2-bromopyridin-4-yl)-2-oxo-2,3-dihydro-1H-benzo[d]imidazol-1-yl) methyl)cyclohexyl)-5-chloro-2-methylnicotinamide;

5-chloro-N-((1r,4r)-4-((3-(6-ethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(4-(2-(dimethylamino)ethoxy)phenyl)-2-oxo-2,3-dihydro-1H-benzo[d]imidazol-1-yl)methyl)cyclohexyl)-2-methylnicotinamide;

5-chloro-2-methyl-N-((1R,4r)-4-((3-(6-((R)-morpholin-2-ylmethoxy)pyridin-3-yl)-2-oxo-2,3-dihydro-1H-benzo[d]imidazol-1-yl)methyl)cyclohexyl)nicotinamide;

5-chloro-2-methyl-N-((1S,4r)-4-((3-(6-(((S)-4-methylmorpholin-2-yl)methoxy)pyridin-3-yl)-2-oxo-2,3-dihydro-1H-benzo[d]imidazol-1-yl)methyl)cyclohexyl)nicotinamide;

5-chloro-2-methyl-N-((1R,4r)-4-((3-(6-(((R)-4-methylmorpholin-2-yl)methoxy)pyridin-3-yl)-2-oxo-2,3-dihydro-1H-benzo[d]imidazol-1-yl)methyl)cyclohexyl)nicotinamide;

N-((1R,4r)-4-((3-(6-(((R)-4-acetylmorpholin-2-yl)methoxy)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-((1-acetylazetidin-3-yl)oxy)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-((1-acetylazetidin-3-yl)methoxy)pyridin-3-yl)-2-oxo-2,3-dihydro-1H-benzo[d]imidazol-1-yl)methyl)cyclohexyl)-5-chloro-2-methylnicotinamide;

5-chloro-N-((1S,4r)-4-((3-(6-((S)-3-hydroxypyrrolidin-1-yl)pyridin-3-yl)-2-oxo-2,3-dihydro-1H-benzo[d]imidazol-1-yl)methyl)cyclohexyl)-2-methylnicotinamide;

5-chloro-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(2-vinylpyridin-4-yl)-2,3-dihydro-1H-benzo[d]imidazol-1-yl)methyl)cyclohexyl)nicotinamide;

5-chloro-N-((1r,4r)-4-((3-(2-ethylpyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3,6-dihydro-2H-pyran-4-yl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(1',2',3',6'-tetrahydro-[2,4'-bipyridin]-5-yl)-2,3-dihydro-1H-benzo[d]imidazol-1-yl)methyl)cyclohexyl)nicotinamide;

5-chloro-N-((1r,4r)-4-((3-(6-cyclopropylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-(tetrahydro-2H-pyran-4-yl)pyridin-3-yl)-2,3-dihydro-1H-benzo[d]imidazol-1-yl)methyl)cyclohexyl)nicotinamide;

5-chloro-2-methyl-N-((1r,4r)-4-((3-(1-methyl-1H-pyrazol-4-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-phenylpyridin-3-yl)-2,3-dihydro-1H-benzo[d]imidazol-1-yl)methyl)cyclohexyl)nicotinamide;

5-chloro-N-((1r,4r)-4-((3-(6-(2-(hydroxymethyl)phenyl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(ethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((3-hydroxypropyl)(methyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide;

N-((1r,4r)-4-((3-(6-acetamidopyridin-3-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-(2-(hydroxymethyl)morpholino)pyridin-3-yl)-2-oxo-2,3-dihydro-1H-benzo[d]imidazol-1-yl)methyl)cyclohexyl)-2-methylnicotinamide;

5-chloro-N-(4-((3-(6-(difluoromethyl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-methylnicotinamide;

5-chloro-2-methyl-N-((1R,4r)-4-((3-(6-(((R)-4-methylmorpholin-3-yl)methoxy)pyridin-3-yl)-2-oxo-2,3-dihydro-1H-benzo[d]imidazol-1-yl)methyl)cyclohexyl)nicotinamide;

5-chloro-2-methyl-N-((1S,4r)-4-((3-(6-(((S)-4-methylmorpholin-3-yl)methoxy)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(methylamino)pyridazin-3-yl)-2-oxo-2,3-dihydro-1H-benzo[d]imidazol-1-yl)methyl)cyclohexyl)nicotinamide;

5-chloro-N-((1r,4r)-4-((3-(6-((cyclopropylmethyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)nicotinamide;

5-chloro-2-methyl-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide;

5-chloro-N-((1r,4r)-4-((3-(6-((3,3-difluorocyclobutyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1S,4r)-4-((2-oxo-3-(6-((((S)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1R,4r)-4-((2-oxo-3-(6-((((R)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide;

5-chloro-N-(4-((3-(6-(cyclopropylmethoxy)pyridin-3-yl)-2-oxo-2,3-dihydro-1H-benzo[d]imidazol-1-yl)methyl)cyclohexyl)-2-methylnicotinamide;

5-chloro-N-(4-((3-(6-cyclopropoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2,3-dihydro-[1,4]dioxino[2,3-b]pyridin-7-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(methylamino)pyrazin-2-yl)-2-oxo-2,3-dihydro-1H-benzo[d]imidazol-1-yl)methyl)cyclohexyl)nicotinamide;

5-chloro-N-((1r,4r)-4-((3-(5-(dimethylamino)pyrazin-2-yl)-2-oxo-2,3-dihydro-1H-benzo[d]imidazol-1-yl)methyl)cyclohexyl)-2-methylnicotinamide;

5-chloro-N-((1S,4r)-4-((3-(5-((S)-3-hydroxypyrrolidin-1-yl)pyrazin-2-yl)-2-oxo-2,3-dihydro-1H-benzol-1-yl)methyl)cyclohexyl)-2-methylnicotinamide;

5-chloro-N-((1r,4r)-4-((3-(5,6-dimethoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxy-5-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((4-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((5-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((6-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((7-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclobutylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-methoxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)-4-methylphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide;

5-chloro-N-((1r,4r)-4-((3-(2-(hydroxymethyl)-4-methylphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-(oxetan-3-ylcarbamoyl)phenyl)-2-oxo-2,3-dihydro-1H-benzo[d]imidazol-1-yl)methyl)cyclohexyl)nicotinamide;

5-chloro-N-((1r,4r)-4-((5-cyano-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxy-4-methylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(3-hydroxypropoxy)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-phenyl-3,4-dihydroquinazolin-1(2H)-yl)methyl)cyclohexyl)nicotinamide;

5-chloro-2-methyl-N-((1r,4r)-4-((2-oxo-3-(p-tolyl)-2,3-dihydro-1H-imidazo[4,5-b]pyrazin-1-yl)methyl)cyclohexyl)nicotinamide;

5-chloro-N-((1r,4r)-4-((3-(6-(dimethylamino)pyridin-3-yl)-2-oxo-2,3-dihydro-1H-imidazo[4,5-b]pyridin-1-yl)methyl)cyclohexyl)-2-methylnicotinamide;

5-chloro-N-((1r,4r)-4-((1-(6-(dimethylamino)pyridin-3-yl)-
2-oxo-1H-imidazo[4,5-c]pyridin-3(2H)-yl)methyl)cyclo-
hexyl)-2-methylnicotinamide;
5-chloro-2-methyl-N-((1r,4r)-4-((3-(6-(oxetan-3-yloxy)
pyridin-3-yl)-2-oxo-2,3-dihydro-1H-benzo[d]imidazol-1-
yl)methyl)cyclohexyl)nicotinamide;
5-chloro-2-methyl-N-((1r,4r)-4-((3-(1-methyl-1H-indazol-
5-yl)-2-oxo-2,3-dihydro-1H-benzo[d]imidazol-1-yl)
methyl)cyclohexyl)nicotinamide;
N-((1r,4r)-4-((3-(1H-indol-6-yl)-2-oxo-2,3-dihydro-1H-
benzo[d]imidazol-1-yl)methyl) cyclohexyl)-5-chloro-2-
methylnicotinamide;
N-((1r,4r)-4-((3-(6-aminopyridin-3-yl)-2-oxo-2,3-dihydro-
1H-benzol[d]imidazol-1-yl) methyl)cyclohexyl)-5-
chloro-2-methylnicotinamide;
5-chloro-N-((1r,4r)-4-((3-(6-(3-methoxyazetidin-1-yl)pyri-
din-3-yl)-2-oxo-2,3-dihydro-1H-benzo[d]imidazol-1-yl)
methyl)cyclohexyl)-2-methylnicotinamide;
5-chloro-N-((1r,4r)-4-((3-(6-(3-fluoroazetidin-1-yl)pyridin-
3-yl)-2-oxo-2,3-dihydro-1H-benzo[d]imidazol-1-yl)
methyl)cyclohexyl)-2-methylnicotinamide;
5-chloro-N-((1r,4r)-4-((3-(6-(3,3-difluoroazetidin-1-yl)pyri-
din-3-yl)-2-oxo-2,3-dihydro-1H-benzo[d]imidazol-1-yl)
methyl)cyclohexyl)-2-methylnicotinamide;
5-chloro-2-methyl-N-((1r,4r)-4-((3-(6-(oxetan-3-ylamino)
pyridin-3-yl)-2-oxo-2,3-dihydro-1H-benzo[d]imidazol-1-
yl)methyl)cyclohexyl)nicotinamide;
5-chloro-2-methyl-N-((1r,4r)-4-((3-(1-methyl-1H-pyrrolo
[2,3-b]pyridin-5-yl)-2-oxo-2,3-dihydro-1H-benzol[d]imi-
dazol-1-yl)methyl)cyclohexyl)nicotinamide;
5-chloro-N-((1r,4r)-4-((3-(6-methoxy-2-methylpyridin-3-
yl)-2-oxo-2,3-dihydro-1H-benzo[d]imidazol-1-yl)
methyl)cyclohexyl)-2-methylnicotinamide;
5-chloro-2-methyl-N-((1r,4r)-4-((3-(2-methyl-6-(methyl-
amino)pyridin-3-yl)-2-oxo-2,3-dihydro-1H-benzo[d]imi-
dazol-1-yl)methyl)cyclohexyl)nicotinamide;
5-(3-(((1r,4r)-4-(5-chloro-2-methylnicotinamido)cyclo-
hexyl)methyl)-2-oxo-2,3-dihydro-1H-benzo[d]imidazol-
1-yl)-N-cyclopropylpicolinamide;
5-chloro-N-((1r,4r)-4-((3-(2,3-dihydro-1H-pyrrolo[2,3-b]
pyridin-5-yl)-2-oxo-2,3-dihydro-1H-benzo[d]imidazol-1-
yl)methyl)cyclohexyl)-2-methylnicotinamide;
N-((1r,4r)-4-((3-(benzo[d]oxazol-6-yl)-2-oxo-2,3-dihydro-
1H-benzo[d]imidazol-1-yl) methyl)cyclohexyl)-5-chloro-
2-methylnicotinamide;
5-chloro-2-methyl-N-((1r,4r)-4-((3-(1-methyl-2,3-dihydro-
1H-pyrrolo[2,3-b]pyridin-5-yl)-2-oxo-2,3-dihydro-1H-
benzo[d]imidazol-1-yl)methyl)cyclohexyl)nicotinamide;
N-((1r,4r)-4-((3-(1-acetyl-2,3-dihydro-1H-pyrrolo[2,3-b]
pyridin-5-yl)-2-oxo-2,3-dihydro-1H-benzo[d]imidazol-1-
yl)methyl)cyclohexyl)-5-chloro-2-methylnicotinamide;
and
5-chloro-2-methyl-N-((1r,4r)-4-((2-oxo-3-(pyridin-3-yl)-2,
3-dihydro-1H-benzo[d]imidazol-1-yl)methyl)cyclohexyl)
nicotinamide;
or a pharmaceutically acceptable salt thereof or a prodrug
thereof;
[7] The compound according to [6], which is selected
from the group consisting of:
N-((1r,4r)-4-((3-benzyl-2-oxo-2,3-dihydro-1H-benzo[d]
imidazol-1-yl)methyl)cyclohexyl)-5-chloro-2-methylni-
cotinamide;
5-chloro-2-methyl-N-((1r,4r)-4-((2-oxo-3-(2-oxo-2-phenyl-
ethyl)-2,3-dihydro-1H-benzo[d]imidazol-1-yl)methyl)cy-
clohexyl)nicotinamide;
5-chloro-N-((1r,4r)-4-((3-(2-(4-methoxyphenyl)-2-oxo-
ethyl)-2-oxo-2,3-dihydro-1H-benzo[d]imidazol-1-yl)
methyl)cyclohexyl)-2-methylnicotinamide;
5-chloro-N-((1r,4r)-4-((3-(2-(2-methoxyphenyl)-2-oxo-
ethyl)-2-oxo-2,3-dihydro-1H-benzo[d]imidazol-1-yl)
methyl)cyclohexyl)-2-methylnicotinamide;
5-chloro-N-((1r,4r)-4-((3-(2-(2,4-difluorophenyl)-2-oxo-
ethyl)-2-oxo-2,3-dihydro-1H-benzo[d]imidazol-1-yl)
methyl)cyclohexyl)-2-methylnicotinamide;
5-chloro-N-((1r,4r)-4-((3-(2-(4-cyanophenyl)-2-oxoethyl)-
2-oxo-2,3-dihydro-1H-benzo[d]imidazol-1-yl)methyl)cy-
clohexyl)-2-methylnicotinamide;
5-chloro-N-((1r,4r)-4-((3-(4-fluorophenyl)-2-oxo-2,3-di-
hydro-1H-benzo[d]imidazol-1-yl)methyl)cyclohexyl)-2-
methylnicotinamide;
N-((1r,4r)-4-((3-(4-acetylphenyl)-2-oxo-2,3-dihydro-1H-
benzo[d]imidazol-1-yl)methyl)cyclohexyl)-5-chloro-2-
methylnicotinamide;
5-chloro-2-methyl-N-((1r,4r)-4-((2-oxo-3-(p-tolyl)-2,3-di-
hydro-1H-benzo[d]imidazol-1-yl)methyl)cyclohexyl)
nicotinamide;
5-chloro-N-((1r,4r)-4-((3-(4-methoxyphenyl)-2-oxo-2,3-di-
hydro-1H-benzo[d]imidazol-1-yl)methyl)cyclohexyl)-2-
methylnicotinamide;
5-chloro-N-((1r,4r)-4-((3-(6-methoxypyridin-3-yl)-2-oxo-2,
3-dihydro-1H-benzo[d]imidazol-1-yl)methyl)cyclo-
hexyl)-2-methylnicotinamide;
5-chloro-N-((1r,4r)-4-((3-(2,6-dimethylpyridin-3-yl)-2-oxo-
2,3-dihydro-1H-benzo[d]imidazol-1-yl)methyl)cyclo-
hexyl)-2-methylnicotinamide;
5-chloro-N-((1r,4r)-4-((3-(2-fluorophenyl)-2-oxo-2,3-di-
hydro-1H-benzo[d]imidazol-1-yl)methyl)cyclohexyl)-2-
methylnicotinamide;
5-chloro-N-((1r,4r)-4-((3-(2-methoxyphenyl)-2-oxo-2,3-di-
hydro-1H-benzo[d]imidazol-1-yl)methyl)cyclohexyl)-2-
methylnicotinamide;
5-chloro-N-((1r,4r)-4-((3-(6-(2,2-difluoroethoxy)pyridin-3-
yl)-2-oxo-2,3-dihydro-1H-benzo[d]imidazol-1-yl)
methyl)cyclohexyl)-2-methylnicotinamide;
5-chloro-N-((1r,4r)-4-((3-(6-ethoxypyridin-3-yl)-2-oxo-2,3-
dihydro-1H-benzo[d]imidazol-1-yl)methyl)cyclohexyl)-
2-methylnicotinamide;
5-chloro-N-((1r,4r)-4-((3-(3,4-dimethoxyphenyl)-2-oxo-2,
3-dihydro-1H-benzo[d]imidazol-1-yl)methyl)cyclo-
hexyl)-2-methylnicotinamide;
5-chloro-N-((1r,4r)-4-((3-(2-methoxypyridin-4-yl)-2-oxo-2,
3-dihydro-1H-benzo[d]imidazol-1-yl)methyl)cyclo-
hexyl)-2-methylnicotinamide;
5-chloro-N-((1r,4r)-4-((3-(2,4-difluorophenyl)-2-oxo-2,3-
dihydro-1H-benzo[d]imidazol-1-yl)methyl)cyclohexyl)-
2-methylnicotinamide;
5-chloro-N-((1r,4r)-4-((3-(6-(2-hydroxyethoxy)pyridin-3-
yl)-2-oxo-2,3-dihydro-1H-benzo[d]imidazol-1-yl)
methyl)cyclohexyl)-2-methylnicotinamide;
5-chloro-N-((1r,4r)-4-((3-(6-(dimethylamino)pyridin-3-yl)-
2-oxo-2,3-dihydro-1H-benzo[d]imidazol-1-yl)methyl)cy-
clohexyl)-2-methylnicotinamide;
5-chloro-N-((1r,4r)-4-((3-(6-((2-methoxyethyl)(methyl)
amino)pyridin-3-yl)-2-oxo-2,3-dihydro-1H-benzol[d]
imidazol-1-yl)methyl)cyclohexyl)-2-methylnicotina-
mide;
5-chloro-2-methyl-N-((1r,4r)-4-((3-(6-morpholinopyridin-
3-yl)-2-oxo-2,3-dihydro-1H-benzo[d]imidazol-1-yl)
methyl)cyclohexyl)nicotinamide;
5-chloro-2-methyl-N-((1r,4r)-4-((3-(6-(4-methylpiperazin-
1-yl)pyridin-3-yl)-2-oxo-2,3-dihydro-1H-benzo[d]imida-
zol-1-yl)methyl)cyclohexyl)nicotinamide;

5-chloro-2-methyl-N-((1r,4r)-4-((4-methyl-3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(6-methoxypyridin-3-yl)-4-methyl-2-oxo-2,3-dihydro-1H-benzo[d]imidazol-1-yl)methyl)cyclohexyl)-2-methylnicotinamide;

5-(3-(((1r,4r)-4-(5-chloro-2-methylnicotinamido)cyclohexyl)methyl)-2-oxo-2,3-dihydro-1H-benzo[d]imidazol-1-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)-2-methylnicotinamide;

N-((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-(dimethylamino)pyridazin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide;

5-chloro-N-((1r,4r)-4-((3-(6-ethylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(2-vinylpyridin-4-yl)-2,3-dihydro-1H-benzo[d]imidazol-1-yl)methyl)cyclohexyl)nicotinamide;

5-chloro-N-((1r,4r)-4-((3-(6-(3,6-dihydro-2H-pyran-4-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-cyclopropylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-phenylpyridin-3-yl)-2,3-dihydro-1H-benzo[d]imidazol-1-yl)methyl)cyclohexyl)nicotinamide;

5-chloro-N-((1r,4r)-4-((3-(6-(2-(hydroxymethyl)phenyl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(ethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((3-hydroxypropyl)(methyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((cyclopropylmethyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide;

5-chloro-N-((1r,4r)-4-((3-(6-((3,3-difluorocyclobutyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1S,4r)-4-((2-oxo-3-(6-((((S)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1R,4r)-4-((2-oxo-3-(6-((((R)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide;

5-chloro-N-(4-((3-(6-(cyclopropylmethoxy)pyridin-3-yl)-2-oxo-2,3-dihydro-1H-benzo[d]imidazol-1-yl)methyl)cyclohexyl)-2-methylnicotinamide;

5-chloro-N-(4-((3-(6-cyclopropoxypyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(methylamino)pyrazin-2-yl)-2-oxo-2,3-dihydro-1H-benzo[d]imidazol-1-yl)methyl)cyclohexyl)nicotinamide;

5-chloro-N-((1r,4r)-4-((3-(5-(dimethylamino)pyrazin-2-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxy-5-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((4-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((5-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((6-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((7-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclobutylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-methoxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)-4-methylphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide;

5-chloro-2-methyl-N-((1r,4r)-4-((3-(4-(oxetan-3-ylcarbamoyl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(3-hydroxypropoxy)pyridin-3-yl)-2-oxo-2,3-dihydro-1H-benzo[d]imidazol-1-yl)methyl)cyclohexyl)-2-methylnicotinamide;

trans-5-chloro-2-methyl-N-(4-((3-(6-(oxetan-3-yloxy)pyridin-3-yl)-2-oxo-2,3-dihydro-1H-benzo[d]imidazol-1-yl)methyl)cyclohexyl)nicotinamide;

trans-5-chloro-2-methyl-N-(4-((3-(1-methyl-1H-indazol-5-yl)-2-oxo-2,3-dihydro-1H-benzo[d]imidazol-1-yl)methyl)cyclohexyl)nicotinamide;

trans-5-chloro-N-(4-((3-(6-(3-methoxyazetidin-1-yl)pyridin-3-yl)-2-oxo-2,3-dihydro-1H-benzo[d]imidazol-1-yl)methyl)cyclohexyl)-2-methylnicotinamide;

trans-5-chloro-N-(4-((3-(6-(3-fluoroazetidin-1-yl)pyridin-3-yl)-2-oxo-2,3-dihydro-1H-benzo[d]imidazol-1-yl)methyl)cyclohexyl)-2-methylnicotinamide;

trans-5-chloro-N-(4-((3-(6-(3,3-difluoroazetidin-1-yl)pyridin-3-yl)-2-oxo-2,3-dihydro-1H-benzo[d]imidazol-1-yl)methyl)cyclohexyl)-2-methylnicotinamide;

trans-5-chloro-2-methyl-N-(4-((3-(6-(oxetan-3-ylamino)pyridin-3-yl)-2-oxo-2,3-dihydro-1H-benzo[d]imidazol-1-yl)methyl)cyclohexyl)nicotinamide;

trans-5-chloro-2-methyl-N-(4-((3-(1-methyl-1H-pyrrolo[2,3-b]pyridin-5-yl)-2-oxo-2,3-dihydro-1H-benzo[d]imidazol-1-yl)methyl)cyclohexyl)nicotinamide;

trans-5-chloro-N-(4-((3-(6-methoxy-2-methylpyridin-3-yl)-2-oxo-2,3-dihydro-1H-benzo[d]imidazol-1-yl)methyl)cyclohexyl)-2-methylnicotinamide;

trans-5-chloro-2-methyl-N-(4-((3-(2-methyl-6-(methylamino)pyridin-3-yl)-2-oxo-2,3-dihydro-1H-benzo[d]imidazol-1-yl)methyl)cyclohexyl)nicotinamide;

trans-5-(3-((4-(5-chloro-2-methylnicotinamido)cyclohexyl)methyl)-2-oxo-2,3-dihydro-1H-benzo[d]imidazol-1-yl)-N-cyclopropylpicolinamide;

trans-5-chloro-N-(4-((3-(2,3-dihydro-1H-pyrrolo[2,3-b]pyridin-5-yl)-2-oxo-2,3-dihydro-1H-benzo[d]imidazol-1-yl)methyl)cyclohexyl)-2-methylnicotinamide;

trans-N-(4-((3-(benzo[d]oxazol-6-yl)-2-oxo-2,3-dihydro-1H-benzo[d]imidazol-1-yl)methyl)cyclohexyl)-5-chloro-2-methylnicotinamide;

trans-5-chloro-2-methyl-N-(4-((3-(1-methyl-2,3-dihydro-1H-pyrrolo[2,3-b]pyridin-5-yl)-2-oxo-2,3-dihydro-1H-benzo[d]imidazol-1-yl)methyl)cyclohexyl)nicotinamide;

trans-N-(4-((3-(1-acetyl-2,3-dihydro-1H-pyrrolo[2,3-b]pyridin-5-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(pyridin-3-yl)-2,3-dihydro-1H-benzo[d]imidazol-1-yl)methyl)cyclohexyl)nicotinamide;

5-chloro-2-methyl-N-((1r,4r)-4-((3-(1-methyl-1H-pyrrolo[3,2-b]pyridin-6-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(1H-pyrrolo[3,2-b]pyridin-6-yl)-2,3-dihydro-1H-benzo[d]imidazol-1-yl)methyl)cyclohexyl)nicotinamide;

5-chloro-N-((1r,4r)-4-((3-(3,4-dihydro-2H-pyrido[3,2-b][1,4]oxazin-7-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-methyl-3,4-dihydro-2H-pyrido[3,2-b][1,4]oxazin-7-yl)-2-oxo-2,3-dihydro-1H-benzo[d]imidazol-1-yl)methyl)cyclohexyl)nicotinamide 5-chloro-N-((1r,4r)-4-((3-(6-(3-(dimethylamino)azetidin-1-yl)pyridin-3-yl)-2-oxo-2,3-dihydro-1H-benzo[d]imidazol-1-yl)methyl)cyclohexyl)-2-methylnicotinamide;

N-((1r,4r)-4-((3-(6-(azetidin-1-yl)pyridin-3-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(1-methyl-1H-pyrazolo[3,4-b]pyridin-5-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methyl-2-oxo-2,3-dihydrobenzo[d]oxazol-6-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(quinoxalin-6-yl)-2,3-dihydro-1H-benzo[d]imidazol-1-yl)methyl)cyclohexyl)nicotinamide;

2-ethyl-N-((1r,4r)-4-((3-(6-(methylcarbamoyl)pyridin-3-yl)-2-oxo-2,3-dihydro-1H-benzo[d]imidazol-1-yl)methyl)cyclohexyl)-2H-indazole-3-carboxamide;

5-chloro-N-((1r,4r)-4-((3-(chroman-3-yl)-2-oxo-2,3-dihydro-1H-benzo[d]imidazol-1-yl)methyl)cyclohexyl)-2-methylnicotinamide;

5-chloro-N-((1r,4r)-4-((1',2'-dimethyl-2-oxo-1'H-[1,5'-bibenzo[d]imidazol]-3(2H)-yl)methyl)cyclohexyl)-2-methylnicotinamide;

5-chloro-N-((1r,4r)-4-((1',3'-dimethyl-2,2'-dioxo-2',3'-dihydro-1'H-[1,5'-bibenzo[d]imidazol]-3(2H)-yl)methyl)cyclohexyl)-2-methylnicotinamide;

5-chloro-2-methyl-N-((1r,4r)-4-((3-(3-methyl-1H-indazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methylbenzo[d]isoxazol-6-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methyl-1H-pyrazolo[4,3-b]pyridin-6-yl)-2-oxo-2,3-dihydro-1H-benzo[d]imidazol-1-yl)methyl)cyclohexyl)nicotinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(1-methyl-1H-pyrazol-3-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-2-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(pyridazin-3-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(isoxazol-3-ylmethyl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-3-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(pyrimidin-5-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(oxazol-4-ylmethyl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-((4-methylthiazol-2-yl)methyl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-4-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-ethylpicolinamide;

5-(3-(((1r,4r)-4-(5-chloro-2-methylnicotinamido)cyclohexyl)methyl)-2-oxo-2,3-dihydro-1H-benzol[d]imidazol-1-yl)-N-(1H-pyrazol-3-yl)picolinamide;

5-chloro-N-((1r,4r)-4-((3-(2,3-dihydro-1H-inden-2-yl)-2-oxo-2,3-dihydro-1H-benzo[d]imidazol-1-yl)methyl)cyclohexyl)-2-methylnicotinamide;

5-chloro-N-((1r,4r)-4-((3-(2,3-dimethyl-2H-indazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(imidazo[1,2-a]pyridin-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(quinazolin-5-yl)-2,3-dihydro-1H-benzo[d]imidazol-1-yl)methyl)cyclohexyl)nicotinamide;

N-((1r,4r)-4-((3-(2-acetylisoindolin-5-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2,3-dihydro-1H-inden-5-yl)-2-oxo-2,3-dihydro-1H-imidazo[4,5-b]pyridin-1-yl)methyl)cyclohexyl)-2-methylnicotinamide;

5-chloro-N-((1r,4r)-4-((3-(4-methoxyphenyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(1,3-dimethyl-1H-indazol-6-yl)-2-oxo-2,3-dihydro-1H-benzo[d]imidazol-1-yl)methyl)cyclohexyl)-2-methylnicotinamide;

5-(3-(((1r,4r)-4-(5-chloro-2-methylnicotinamido)cyclohexyl)methyl)-7-methyl-2-oxo-2,3-dihydro-1H-benzo[d]imidazol-1-yl)-N-methylpicolinamide;

5-(3-(((1r,4r)-4-(5-chloro-2-methylnicotinamido)cyclohexyl)methyl)-6-fluoro-2-oxo-2,3-dihydro-1H-benzo[d]imidazol-1-yl)-N-methylpicolinamide;

5-(3-(((1r,4r)-4-(5-chloro-2-methylnicotinamido)cyclohexyl)methyl)-5-methoxy-2-oxo-2,3-dihydro-1H-benzo[d]imidazol-1-yl)-N-methylpicolinamide;

5-chloro-N-((1r,4r)-4-((3-(3-(cyclopropylmethyl)-2-oxo-2,3-dihydrobenzo[d]oxazol-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-methyl-3-oxo-3,4-dihydro-2H-pyrido[3,2-b][1,4]oxazin-7-yl)-2-oxo-2,3-dihydro-1H-benzo[d]imidazol-1-yl)methyl)cyclohexyl)nicotinamide;

N-((1r,4r)-4-((3-(3-amino-1H-indazol-6-yl)-2-oxo-2,3-dihydro-1H-benzo[d]imidazol-1-yl)methyl)cyclohexyl)-5-chloro-2-methylnicotinamide;

N-((1r,4r)-4-((3-(3-aminobenzo[d]isoxazol-6-yl)-2-oxo-2,3-dihydro-1H-benzo[d]imidazol-1-yl)methyl)cyclohexyl)-5-chloro-2-methylnicotinamide;

5-(3-(((1r,4r)-4-(5-chloro-2-methylnicotinamido)cyclohexyl)methyl)-2-oxo-2,3-dihydro-1H-benzo[d]imidazol-1-yl)-N,4-dimethylpicolinamide;

N-((1r,4r)-4-((3-(benzo[d]thiazol-6-yl)-2-oxo-2,3-dihydro-1H-imidazo[4,5-b]pyridin-1-yl)methyl)cyclohexyl)-5-chloro-2-methylnicotinamide;

N-((1r,4r)-4-((3-([2,3'-bipyridin]-5-yl)-2-oxo-2,3-dihydro-1H-benzo[d]imidazol-1-yl) methyl)cyclohexyl)-5-chloro-2-methylnicotinamide;

5-chloro-2-methyl-N-((1r,4r)-4-((3-(6-(oxazol-5-yl)pyridin-3-yl)-2-oxo-2,3-dihydro-1H-benzo[d]imidazol-1-yl)methyl)cyclohexyl)nicotinamide;

N-((1r,4r)-4-((3-(6-(1H-pyrazol-4-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(4-bromo-2-cyanophenyl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(3-methyl-1H-indazol-6-yl)-2-oxo-2,3-dihydro-1H-benzo[d]imidazol-1-yl)methyl)cyclohexyl)nicotinamide;

5-chloro-2-methyl-N-((r,4r)-4-((1'-methyl-2-oxo-1'H-[1,5'-bibenzo[d]imidazol]-3(2H)-yl)methyl)cyclohexyl)nicotinamide;

5-chloro-2-methyl-N-((r,4r)-4-((3'-methyl-2-oxo-3'H-[1,5'-bibenzo[d]imidazol]-3(2H)-yl)methyl)cyclohexyl)nicotinamide;

5-chloro-N-((1r,4r)-4-((3-(3-chloro-1-methyl-1H-indazol-6-yl)-2-oxo-2,3-dihydro-1H-benzo[d]imidazol-1-yl)methyl)cyclohexyl)-2-methylnicotinamide;

5-chloro-N-((1r,4r)-4-((2',3'-dimethyl-2-oxo-3'H-[1,5'-bibenzo[d]imidazol]-3(2H)-yl)methyl)cyclohexyl)-2-methylnicotinamide;

5-chloro-N-((1r,4r)-4-((3-(3-chloro-1H-indazol-6-yl)-2-oxo-2,3-dihydro-1H-benzo[d]imidazol-1-yl)methyl)cyclohexyl)-2-methylnicotinamide;

N-((1r,4r)-4-((1-(5-bromo-2,3-dihydro-1H-inden-2-yl)-2-oxo-1H-imidazo[4,5-c]pyridin-3(2H)-yl)methyl)cyclohexyl)-5-chloro-2-methylnicotinamide;

5-chloro-2-methyl-N-((1r,4r)-4-((3-(3-methyl-1H-indazol-5-yl)-2-oxo-2,3-dihydro-1H-imidazo[4,5-b]pyridin-1-yl)methyl)cyclohexyl)nicotinamide;

5-chloro-N-((1r,4r)-4-((3-(1,3-dimethyl-1H-indazol-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(1-methyl-1H-pyrazol-4-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methyl-2-oxo-2,3-dihydrooxazolo[4,5-b]pyridin-6-yl)-2-oxo-2,3-dihydro-1H-benzo[d]imidazol-1-yl)methyl)cyclohexyl)nicotinamide;

N-((1r,4r)-4-((3-(6'-amino-[2,3'-bipyridin]-5-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(4-(pyridin-4-yloxy)phenyl)-2,3-dihydro-1H-benzo[d]imidazol-1-yl)methyl)cyclohexyl)nicotinamide;

N-((1r,4r)-4-((3-(2-acetyl-1,2,3,4-tetrahydroisoquinolin-6-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2-cyanophenyl)-2-oxo-2,3-dihydro-1H-benzo[d]imidazol-1-yl)methyl)cyclohexyl)-2-methylnicotinamide;

N-((1r,4r)-4-((3-(6-methoxypyridin-3-yl)-2-oxo-2,3-dihydro-1H-benzo[d]imidazol-1-yl)methyl)cyclohexyl)-2-methyl-2H-indazole-3-carboxamide;

N-((1r,4r)-4-((3-(6-methoxypyridin-3-yl)-2-oxo-2,3-dihydro-1H-benzo[d]imidazol-1-yl)methyl)cyclohexyl)-2-methyl-4,5,6,7-tetrahydro-2H-indazole-3-carboxamide;

5-chloro-N-((1r,4r)-4-((3-(3-chloro-1H-indazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxypyridin-3-yl)-2-oxo-2,3-dihydro-1H-benzo[d]imidazol-1-yl)methyl)cyclohexyl)-2-methylbenzamide;

5-chloro-2-methyl-N-((1r,4r)-4-((2-oxo-3-(3-oxo-3,4-dihydro-2H-pyrido[3,2-b][1,4]oxazin-7-yl)-2,3-dihydro-1H-benzo[d]imidazol-1-yl)methyl)cyclohexyl)nicotinamide;

5-(3-(((1r,4r)-4-(5-chloro-2-methylnicotinamido)cyclohexyl)methyl)-5-methyl-2-oxo-2,3-dihydro-1H-benzol[d]imidazol-1-yl)-N-methylpicolinamide;

5-(3-(((1r,4r)-4-(5-chloro-2-methylnicotinamido)cyclohexyl)methyl)-5-fluoro-2-oxo-2,3-dihydro-1H-benzo[d]imidazol-1-yl)-N-methylpicolinamide;

5-bromo-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxypyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(1-(2-(methoxymethoxy)ethyl)-3-methyl-1H-indazol-5-yl)-2-oxo-2,3-dihydro-1H-benzo[d]imidazol-1-yl)methyl)cyclohexyl)-2-methylnicotinamide 5-chloro-N-((1r,4r)-4-((3-(1-(2-hydroxyethyl)-3-methyl-1H-indazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-4-methoxyphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(1-methyl-1H-benzo[d][1,2,3]triazol-6-yl)-2-oxo-2,3-dihydro-1H-benzo[d]imidazol-1-yl)methyl)cyclohexyl)nicotinamide;

5-chloro-2-methyl-N-((1r,4r)-4-((3-(2-nitrophenyl)-2-oxo-2,3-dihydro-1H-benzo[d]imidazol-1-yl)methyl)cyclohexyl)nicotinamide;

5-chloro-N-((1r,4r)-4-((3-(2-chlorophenyl)-2-oxo-2,3-dihydro-1H-imidazo[4,5-b]pyridin-1-yl)methyl)cyclohexyl)-2-methylnicotinamide;

5-(3-(((1r,4r)-4-(5-chloro-2-methylnicotinamido)cyclohexyl)methyl)-7-fluoro-2-oxo-2,3-dihydro-1H-benzo[d]imidazol-1-yl)-N-methylpicolinamide;

5-chloro-2-methyl-N-((1r,4r)-4-((3-(2-(1-methyl-1H-pyrazol-4-yl)ethyl)-2-oxo-2,3-dihydro-1H-benzo[d]imidazol-1-yl)methyl)cyclohexyl)nicotinamide;

2,5-dichloro-N-((1r,4r)-4-((3-(6-methoxypyridin-3-yl)-2-oxo-2,3-dihydro-1H-benzo[d]imidazol-1-yl)methyl)cyclohexyl)nicotinamide;

5-chloro-N-((1r,4r)-4-((1-(2,3-dihydro-1H-inden-4-yl)-2-oxo-1H-imidazo[4,5-c]pyridin-3(2H)-yl)methyl)cyclohexyl)-2-methylnicotinamide;

5-chloro-N-((1r,4r)-4-((3-(2-cyanopyridin-3-yl)-2-oxo-2,3-dihydro-1H-benzo[d]imidazol-1-yl)methyl)cyclohexyl)-2-methylnicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(2-cyanobenzyl)-2-oxo-2,3-dihydro-1H-benzo[d]imidazol-1-yl)methyl)cyclohexyl)-2-methylnicotinamide;

5-chloro-N-((1r,4r)-4-((3-(3-cyanobenzyl)-2-oxo-2,3-dihydro-1H-benzo[d]imidazol-1-yl)methyl)cyclohexyl)-2-methylnicotinamide;

6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxamide;

6-(3-(((1r,4r)-4-(5-chloro-2-methylnicotinamido)cyclohexyl)methyl)-2-oxo-2,3-dihydro-1H-benzo[d]imidazol-1-yl)-N-methylbenzo[d]isoxazole-3-carboxamide;

6-(3-(((1r,4r)-4-(5-chloro-2-methylnicotinamido)cyclohexyl)methyl)-2-oxo-2,3-dihydro-1H-benzo[d]imidazol-1-yl)-N,N-dimethylbenzo[d]isoxazole-3-carboxamide;

5-chloro-N-((1r,4r)-4-((3-(2-cyano-3-methoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-4-methylphenyl)-2-oxo-2,3-dihydro-1H-benzo[d]imidazol-1-yl)methyl)cyclohexyl)-2-methylnicotinamide;

5-chloro-N-((1r,4r)-4-((3-(4-cyanopyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(3-cyanopyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(1-ethyl-1H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(2,4-dimethoxybenzyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(1-(cyclopropylmethyl)-1H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(1-(2-hydroxyethyl)-1H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(2-ethyl-2H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(1-methyl-1H-benzo[d][1,2,3]triazol-5-yl)-2-oxo-2,3-dihydro-1H-benzo[d]imidazol-1-yl)methyl)cyclohexyl)nicotinamide;

5-chloro-N-((1r,4r)-4-((1-(2-chlorophenyl)-2-oxo-1H-imidazo[4,5-b]pyridin-3(2H)-yl) methyl)cyclohexyl)-2-methylnicotinamide;

5-chloro-2-methyl-N-((1r,4r)-4-((2-oxo-1-(2-(trifluoromethyl)phenyl)-1H-imidazo[4,5-b]pyridin-3(2H)-yl)methyl)cyclohexyl)nicotinamide;

5-(3-(((1r,4r)-4-(5-chloro-2-methylnicotinamido)cyclohexyl)methyl)-6-methoxy-2-oxo-2,3-dihydro-1H-benzo[d]imidazol-1-yl)-N-methylpicolinamide;

5-chloro-N-((1r,4r)-4-((3-(2-cyano-5-methoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(3-methyl-1H-indazol-5-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(3-(hydroxymethyl)benzo[d]isoxazol-6-yl)-2-oxo-2,3-dihydro-1H-benzo[d]imidazol-1-yl)methyl)cyclohexyl)-2-methylnicotinamide;

5-chloro-N-((1r,4r)-4-((3-(3-chloropyridin-4-yl)-2-oxo-2,3-dihydro-1H-benzo[d]imidazol-1-yl)methyl)cyclohexyl)-2-methylnicotinamide;

N-((1r,4r)-4-((3-(2-aminobenzo[d]oxazol-5-yl)-2-oxo-2,3-dihydro-1H-benzo[d]imidazol-1-yl)methyl)cyclohexyl)-5-chloro-2-methylnicotinamide;

N-((1r,4r)-4-((3-(benzo[d]oxazol-5-yl)-2-oxo-2,3-dihydro-1H-benzo[d]imidazol-1-yl) methyl)cyclohexyl)-5-chloro-2-methylnicotinamide;

5-chloro-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)nicotinamide;

5-chloro-2-cyclopropyl-N-((1r,4r)-4-((3-(6-methylpyridin-3-yl)-2-oxo-2,3-dihydro-1H-benzo[d]imidazol-1-yl)methyl)cyclohexyl)benzamide;

5-chloro-2-methyl-N-((1r,4r)-4-((3-(6-methylpyridin-3-yl)-2-oxo-2,3-dihydro-1H-benzo[d]imidazol-1-yl)methyl)cyclohexyl)benzamide;

5-methyl-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)benzamide;

2,5-dichloro-N-((1r,4r)-4-((3-(6-methylpyridin-3-yl)-2-oxo-2,3-dihydro-1H-benzo[d]imidazol-1-yl)methyl)cyclohexyl)benzamide;

5-chloro-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)benzamide;

5-chloro-2-methyl-N-((1r,4r)-4-((3-(3-methyl-1H-pyrazolo[3,4-b]pyridin-5-yl)-2-oxo-2,3-dihydro-1H-benzo[d]imidazol-1-yl)methyl)cyclohexyl)nicotinamide;

5-chloro-N-((1r,4r)-4-((3-(imidazo[1,2-a]pyridin-7-yl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-5-(dimethylamino)phenyl)-2-oxo-2,3-dihydro-1H-benzo[d]imidazol-1-yl)methyl)cyclohexyl)-2-methylnicotinamide;

5-chloro-N-((1r,4r)-4-((3-(imidazo[1,5-a]pyridin-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(3-methyl-3H-[1,2,3]triazolo[4,5-b]pyridin-6-yl)-2-oxo-2,3-dihydro-1H-benzo[d]imidazol-1-yl)methyl)cyclohexyl)nicotinamide;

5-chloro-N-((1r,4r)-4-((3-(1-(2-hydroxyethyl)-1H-benzo[d][1,2,3]triazol-5-yl)-2-oxo-2,3-dihydro-1H-benzol[d]imidazol-1-yl)methyl)cyclohexyl)-2-methylnicotinamide;

5-chloro-N-((1r,4r)-4-((3-(3-ethyl-2-oxo-2,3-dihydrooxazolo[4,5-b]pyridin-6-yl)-2-oxo-2,3-dihydro-1H-benzo[d]imidazol-1-yl)methyl)cyclohexyl)-2-methylnicotinamide;

N-((1r,4r)-4-((3-([1,2,4]triazolo[1,5-a]pyridin-6-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-cyclobutylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((2-oxo-3-(pyridin-4-ylmethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(pyridin-4-ylmethyl)-2,3-dihydro-1H-benzo[d]imidazol-1-yl)methyl)cyclohexyl)-2-(trifluoromethyl)benzamide;

5-chloro-N-((1r,4r)-4-((2-oxo-3-(pyridin-2-ylmethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(pyridin-2-ylmethyl)-2,3-dihydro-1H-benzo[d]imidazol-1-yl)methyl)cyclohexyl)-2-(trifluoromethyl)benzamide;

5-chloro-N-((1r,4r)-4-((2-oxo-3-(pyridin-3-ylmethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(2-oxo-2-phenylethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(2-oxo-2-phenylethyl)-2,3-dihydro-1H-benzo[d]imidazol-1-yl)methyl)cyclohexyl)-2-(trifluoromethyl)benzamide;

2,5-dichloro-N-((1r,4r)-4-((2-oxo-3-(2-oxo-2-phenylethyl)-2,3-dihydro-1H-benzo[d]imidazol-1-yl)methyl)cyclohexyl)benzamide;

5-chloro-N-((1r,4r)-4-((3-(2-chlorophenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(3-methylpyridin-4-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(trifluoromethyl)nicotinamido)cyclohexyl)methyl)-5-fluoro-2-oxo-2,3-dihydro-1H-benzo[d]imidazol-1-yl)-N-methylpicolinamide;

5-chloro-N-((1r,4r)-4-((3-(2-cyanophenyl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-cyano-5-methoxyphenyl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-cyanopyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(1-(2-methoxyethyl)-1H-benzo[d][1,2,3]triazol-5-yl)-2-oxo-2,3-dihydro-1H-benzol[d]imidazol-1-yl)methyl)cyclohexyl)-2-methylnicotinamide;

5-chloro-N-((1r,4r)-4-((3-(2-ethyl-3-methyl-2H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(imidazo[1,5-a]pyridin-7-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(pyrido[2,3-b]pyrazin-7-yl)-2,3-dihydro-1H-benzo[d]imidazol-1-yl)methyl)cyclohexyl)nicotinamide;

5-chloro-N-((1r,4r)-4-((3-(5-(methylamino)pyrazin-2-yl)-2-oxo-2,3-dihydro-1H-benzo[d]imidazol-1-yl)methyl)cyclohexyl)-2-(trifluoromethyl)nicotinamide;

5-chloro-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)-2-(trifluoromethyl)nicotinamide;

5-chloro-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)-2-(trifluoromethyl)nicotinamide;

5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((4-methyl-3-(6-methylpyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-(1-methyl-1H-pyrazol-4-yl)ethyl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(1-ethyl-1H-benzo[d][1,2,3]triazol-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(4-oxo-3,4-dihydroquinazolin-7-yl)-2,3-dihydro-1H-benzo[d]imidazol-1-yl)methyl)cyclohexyl)nicotinamide;

5-chloro-N-((1r,4r)-4-((3-(2-cyano-4-formylphenyl)-2-oxo-2,3-dihydro-1H-benzo[d]imidazol-1-yl)methyl)cyclohexyl)-2-methylnicotinamide;

N-((1r,4r)-4-((3-(5-bromo-2-cyanophenyl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(4-cyano-6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-3-(dimethylamino)phenyl)-2-oxo-2,3-dihydro-1H-benzo[d]imidazol-1-yl)methyl)cyclohexyl)-2-methylnicotinamide;

5-chloro-N-((1r,4r)-4-((3-(4-cyano-6-((2-methoxyethyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(4-cyanopyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(3-cyanopyridin-2-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N,4-dimethylpicolinamide;

5-chloro-N-((1r,4r)-4-((2-oxo-3-(thiazol-4-ylmethyl)-2,3-dihydro-1H-benzo[d]imidazol-1-yl)methyl)cyclohexyl)-2-(trifluoromethyl)nicotinamide;

5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-methylpyridin-4-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-cyclopropylnicotinamido)cyclohexyl)methyl)-2-oxo-2,3-dihydro-1H-benzo[d]imidazol-1-yl)-N-methylpicolinamide;

5-chloro-2-methyl-N-((1r,4r)-4-((2-oxo-3-(2-(trifluoromethyl)pyridin-3-yl)-2,3-dihydro-1H-benzo[d]imidazol-1-yl)methyl)cyclohexyl)nicotinamide;

N-((1r,4r)-4-((3-(4-aminopyrido[3,2-d]pyrimidin-7-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(3-(trifluoromethyl)pyridin-4-yl)-2,3-dihydro-1H-benzo[d]imidazol-1-yl)methyl)cyclohexyl)nicotinamide;

5-(3-(((1r,4r)-4-(5-chloro-2-(2-methoxyethyl)nicotinamido)cyclohexyl)methyl)-2-oxo-2,3-dihydro-1H-benzo[d]imidazol-1-yl)-N-methylpicolinamide;

5-(3-(((1r,4r)-4-(5-chloro-2-cyclobutylnicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(6-methoxypyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-methylpyridin-3-yl)-2-oxo-2,3-dihydro-1H-benzo[d]imidazol-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((1'-methyl-2-oxo-1'H-[1,5'-bibenzo[d]imidazol]-3(2H)-yl)methyl)cyclohexyl)-2-(trifluoromethyl)nicotinamide;

5-chloro-N-((1r,4r)-4-((3-(imidazo[1,5-a]pyridin-6-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(dimethylamino)nicotinamido)cyclohexyl)methyl)-2-oxo-2,3-dihydro-1H-benzo[d]imidazol-1-yl)-N-methylpicolinamide;

5-chloro-2-(methoxymethyl)-N-((1r,4r)-4-((3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(4,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2,3-dimethylpyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(3-chloropyridin-4-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(methoxymethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(2,5-dimethylpyridin-4-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(quinolin-8-yl)-2,3-dihydro-1H-benzo[d]imidazol-1-yl)methyl)cyclohexyl)nicotinamide;

5-chloro-N-((1r,4r)-4-((3-(isoquinolin-4-yl)-2-oxo-2,3-dihydro-1H-benzo[d]imidazol-1-yl)methyl)cyclohexyl)-2-methylnicotinamide;

5-(3-(((1r,4r)-4-(5-chloro-2-methylnicotinamido)cyclohexyl)methyl)-7-methyl-2-oxo-2,3-dihydro-1H-benzo[d]imidazol-1-yl)-N,4-dimethylpicolinamide;

5-chloro-2-methyl-N-((1r,4r)-4-((3-(2-(oxetan-3-yl)-2H-benzo[d][1,2,3]triazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(1-(oxetan-3-yl)-1H-benzo[d][1,2,3]triazol-5-yl)-2-oxo-2,3-dihydro-1H-benzo[d]imidazol-1-yl)methyl)cyclohexyl)nicotinamide;

5-chloro-N-((1r,4r)-4-((3-(imidazo[1,5-a]pyridin-7-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(isoquinolin-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(quinolin-6-yl)-2,3-dihydro-1H-benzo[d]imidazol-1-yl)methyl)cyclohexyl)nicotinamide;

5-chloro-2-methyl-N-((1r,4r)-4-((2-oxo-3-(quinolin-5-yl)-2,3-dihydro-1H-benzo[d]imidazol-1-yl)methyl)cyclohexyl)nicotinamide;

5-chloro-2-methyl-N-((1r,4r)-4-((2-oxo-3-(quinolin-3-yl)-2,3-dihydro-1H-benzo[d]imidazol-1-yl)methyl)cyclohexyl)nicotinamide;

5-chloro-2-methyl-N-((1r,4r)-4-((3-(1-methyl-1H-indazol-4-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(3-phenyl-1H-indazol-5-yl)-2,3-dihydro-1H-benzo[d]imidazol-1-yl)methyl)cyclohexyl)nicotinamide;

5-(3-(((1r,4r)-4-(5-chloro-2-(2,2-difluoroethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(imidazo[1,2-a]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((2-oxo-3-(quinolin-6-yl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(quinolin-3-yl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(quinolin-8-yl)-2,3-dihydro-1H-benzo[d]imidazol-1-yl)methyl)cyclohexyl)-2-(trifluoromethyl)nicotinamide;

5-chloro-N-((1r,4r)-4-((3-(isoquinolin-4-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-ethyloxazolo[4,5-b]pyridin-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(2-methyloxazolo[4,5-b]pyridin-6-yl)-2-oxo-2,3-dihydro-1H-benzo[d]imidazol-1-yl)methyl)cyclohexyl)nicotinamide;

5-chloro-N-((1r,4r)-4-((3-(6-(2-hydroxyethoxy)-4-methylpyridin-3-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((2-oxo-1-(quinolin-6-yl)-1H-imidazo[4,5-b]pyridin-3(2H)-yl)methyl)cyclohexyl)nicotinamide;

5-chloro-2-methyl-N-((1r,4r)-4-((2-oxo-1-(quinolin-3-yl)-1H-imidazo[4,5-b]pyridin-3(2H)-yl)methyl)cyclohexyl)nicotinamide;

5-chloro-N-((1r,4r)-4-((2-oxo-1-(quinolin-6-yl)-1H-imidazo[4,5-b]pyridin-3(2H)-yl)methyl)cyclohexyl)-2-(trifluoromethyl)nicotinamide;

5-chloro-2-(difluoromethyl)-N-((1r,4r)-4-((2-oxo-1-(quinolin-6-yl)-1H-imidazo[4,5-b]pyridin-3(2H)-yl)methyl)cyclohexyl)nicotinamide;

5-chloro-2-(difluoromethyl)-N-((1r,4r)-4-((2-oxo-3-(quinolin-6-yl)-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N,4-dimethylpicolinamide;

5-chloro-2-(difluoromethyl)-N-((1r,4r)-4-((3-(2,3-dimethylpyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-hydroxyethoxy)pyridin-3-yl)-2-oxo-2,3-dihydro-1H-benzo[d]imidazol-1-yl)methyl)cyclohexyl)nicotinamide;

5-chloro-N-((1r,4r)-4-((3-(2-chlorophenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((1-(2-chlorophenyl)-2-oxo-1H-imidazo[4,5-c]pyridin-3(2H)-yl) methyl)cyclohexyl)-2-(difluoromethyl)nicotinamide;

5-chloro-N-((1r,4r)-4-((3-(2-cyanopyridin-3-yl)-2-oxo-2,3-dihydro-1H-benzo[d]imidazol-1-yl)methyl)cyclohexyl)-2-(difluoromethyl)nicotinamide;

5-chloro-N-((1r,4r)-4-((3-(3-cyanopyrazin-2-yl)-2-oxo-2,3-dihydro-1H-benzo[d]imidazol-1-yl)methyl)cyclohexyl)-2-(difluoromethyl)nicotinamide;

5-chloro-2-methyl-N-((1r,4r)-4-((2-oxo-3-(quinolin-4-yl)-2,3-dihydro-1H-benzo[d]imidazol-1-yl)methyl)cyclohexyl)nicotinamide;

5-chloro-N-((1r,4r)-4-((3-(isoquinolin-6-yl)-2-oxo-2,3-dihydro-1H-benzo[d]imidazol-1-yl)methyl)cyclohexyl)-2-methylnicotinamide;

5-chloro-2-(difluoromethyl)-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)nicotinamide;

5-chloro-N-((1r,4r)-4-((3-(4-cyanopyridin-3-yl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(1-methyl-1H-indazol-4-yl)-2-oxo-2,3-dihydro-1H-benzo[d]imidazol-1-yl)methyl)cyclohexyl)nicotinamide;

5-chloro-N-((1r,4r)-4-((3-(3-cyanopyridin-2-yl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(2,6-dimethylpyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methylpyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((1-(2,3-dihydro-1H-inden-4-yl)-2-oxo-1H-imidazo[4,5-c]pyridin-3(2H)-yl)methyl)cyclohexyl)nicotinamide;

5-chloro-2-(difluoromethyl)-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(methylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(dimethylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-morpholinopyridin-3-yl)-2-oxo-2,3-dihydro-1H-benzol[d]imidazol-1-yl)methyl)cyclohexyl)nicotinamide;

5-chloro-2-(difluoromethyl)-N-((1r,4r)-4-((3-(4-(hydroxymethyl)phenyl)-2-oxo-2,3-dihydro-1H-benzol[d]imidazol-1-yl)methyl)cyclohexyl)nicotinamide;

5-chloro-2-(difluoromethyl)-N-((1r,4r)-4-((3-(1-(2-hydroxyethyl)-1H-benzo[d][1,2,3]triazol-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((1'-methyl-2-oxo-1'H-[1,5'-bibenzo[d]imidazol]-3(2H)-yl)methyl)cyclohexyl)nicotinamide;

N-((1r,4r)-4-((3-(benzo[d]thiazol-6-yl)-2-oxo-2,3-dihydro-1H-imidazo[4,5-b]pyridin-1-yl)methyl)cyclohexyl)-5-chloro-2-(difluoromethyl)nicotinamide;

5-chloro-2-(difluoromethyl)-N-((1r,4r)-4-((3-(4-methoxyphenyl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((2-oxo-3-(p-tolyl)-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-6-meth oxy-2-oxo-2,3-dihydro-1H-benzo[d]imidazol-1-yl)-N-methylpicolinamide;

5-chloro-2-(difluoromethyl)-N-((1r,4r)-4-((3-(5-(methylamino)pyrazin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinolin-6-yl)-2,3-dihydro-1H-benzo[d]imidazol-1-yl)methyl)cyclohexyl)nicotinamide;

N-((1r,4r)-4-((3-(1,8-naphthyridin-3-yl)-2-oxo-2,3-dihydro-1H-benzo[d]imidazol-1-yl) methyl)cyclohexyl)-5-chloro-2-(difluoromethyl)nicotinamide;

5-chloro-2-(difluoromethyl)-N-((1r,4r)-4-((2-oxo-3-(quinazolin-6-yl)-2,3-dihydro-1H-benzo[d]imidazol-1-yl)methyl)cyclohexyl)nicotinamide;

5-chloro-2-methyl-N-((1r,4r)-4-((2-oxo-3-(quinolin-7-yl)-2,3-dihydro-1H-benzo[d]imidazol-1-yl)methyl)cyclohexyl)nicotinamide;

5-chloro-N-((1r,4r)-4-((3-(isoquinolin-7-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(isoquinolin-6-yl)-2-oxo-2,3-dihydro-1H-benzo[d]imidazol-1-yl)methyl)cyclohexyl)nicotinamide;

5-chloro-N-((1r,4r)-4-((3-(isoquinolin-6-yl)-2-oxo-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((3-(4-fluoro-3-methoxyphenyl)-2-oxo-2,3-dihydro-1H-benzo[d]imidazol-1-yl)methyl)cyclohexyl)nicotinamide;

N-((1r,4r)-4-((3-(4-acetylphenyl)-2-oxo-2,3-dihydro-1H-imidazo[4,5-b]pyridin-1-yl)methyl)cyclohexyl)-5-chloro-2-(difluoromethyl)nicotinamide;

5-chloro-N-((1r,4r)-4-((3-(3-(cyclopentyloxy)-4-methoxyphenyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(4-ethoxyphenyl)-2-oxo-2,3-dihydro-1H-imidazo[4,5-b]pyridin-1-yl)methyl)cyclohexyl)-2-methylnicotinamide;

5-(3-(((1r,4r)-4-(5-chloro-2-methylnicotinamido)cyclohexyl)methyl)-2-oxo-2,3-dihydro-1H-benzo[d]imidazol-1-yl)-1-methyl-1H-indole-2-carboxamide;

5-(3-(((1r,4r)-4-(5-chloro-2-methylnicotinamido)cyclohexyl)methyl)-2-oxo-2,3-dihydro-1H-benzo[d]imidazol-1-yl)-N,1-dimethyl-1H-indole-2-carboxamide;

5-(3-(((1r,4r)-4-(5-chloro-2-methylnicotinamido)cyclohexyl)methyl)-2-oxo-2,3-dihydro-1H-benzo[d]imidazol-1-yl)-N,N,1-trimethyl-1H-indole-2-carboxamide;

5-chloro-2-(difluoromethyl)-N-((1r,4r)-4-((3'-methyl-2-oxo-3'H-[1,5'-bibenzo[d]imidazol]-3(2H)-yl)methyl)cyclohexyl)nicotinamide;

5-chloro-N-((1r,4r)-4-((2-oxo-3-(quinoxalin-6-yl)-2,3-dihydro-1H-benzo[d]imidazol-1-yl)methyl)cyclohexyl)-2-(trifluoromethyl)nicotinamide;

5-chloro-2-methyl-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide;

5-chloro-N-((1r,4r)-4-((3-(1,3-dimethyl-1H-pyrrolo[2,3-b]pyridin-5-yl)-2-oxo-2,3-dihydro-1H-benzo[d]imidazol-1-yl)methyl)cyclohexyl)-2-methylnicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-(2-fluoroethyl)picolinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-(2,2-difluoroethyl)picolinamide;

5-chloro-N-((1r,4r)-4-((3-(6-((2-hydroxyethyl)thio)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-morpholinopyridin-3-yl)-2-oxo-2,3-dihydro-1H-benzo[d]imidazol-1-yl)methyl)cyclohexyl)nicotinamide;

5-chloro-N-((1r,4r)-4-((3-(2,4-dichlorophenyl)-2-oxo-2,3-dihydro-1H-imidazo[4,5-b]pyridin-1-yl)methyl)cyclohexyl)-2-methylnicotinamide;

5-chloro-2-(difluoromethyl)-N-((1r,4r)-4-((3-(imidazo[1,5-a]pyridin-7-yl)-2-oxo-2,3-dihydro-1H-benzo[d]imidazol-1-yl)methyl)cyclohexyl)nicotinamide;

5-chloro-N-((1r,4r)-4-((3-(6-(2-methoxyethoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(6-(2-methoxyethoxy)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(isoquinolin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinolin-8-yl)-2,3-dihydro-1H-benzo[d]imidazol-1-yl)methyl)cyclohexyl)nicotinamide;

5-chloro-2-(difluoromethyl)-N-((1r,4r)-4-((3-(imidazo[1,2-a]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methyl-2H-indazol-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinolin-7-yl)-2,3-dihydro-1H-benzo[d]imidazol-1-yl)methyl)cyclohexyl)nicotinamide;

5-chloro-2-(difluoromethyl)-N-((1r,4r)-4-((3-(isoquinolin-7-yl)-2-oxo-2,3-dihydro-1H-benzo[d]imidazol-1-yl)methyl)cyclohexyl)nicotinamide;

5-chloro-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)-2-(trifluoromethyl)nicotinamide;

5-chloro-N-((1r,4r)-4-((3-(3-methyl-1H-pyrrolo[2,3-b]pyridin-5-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((3-(3-methyl-1H-pyrrolo[2,3-b]pyridin-5-yl)-2-oxo-2,3-dihydro-1H-imidazol[4,5-b]pyridin-1-yl)methyl)cyclohexyl)nicotinamide;

5-chloro-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)-2-(trifluoromethyl)nicotinamide;

5-chloro-2-(difluoromethyl)-N-((1R,4r)-4-((2-oxo-3-(6-(((R)-tetrahydrofuran-3-yl)oxy)pyridin-3-yl)-2,3-dihydro-1H-benzo[d]imidazol-1-yl)methyl)cyclohexyl)nicotinamide 5-chloro-2-(difluoromethyl)-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1S,4r)-4-((2-oxo-3-(6-(((S)-tetrahydrofuran-3-yl)oxy) pyridin-3-yl)-2,3-dihydro-1H-benzo[d]imidazol-1-yl)methyl)cyclohexyl)nicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-methoxypicolinamide;

5-chloro-2-(difluoromethyl)-N-((1r,4r)-4-((3-(6-(2-fluoroethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-morpholinoethoxy)pyridin-3-yl)-2-oxo-2,3-dihydro-1H-benzo[d]imidazol-1-yl)methyl)cyclohexyl)nicotinamide;

N-((1r,4r)-4-((3-(6-(2-amino-2-oxoethoxy)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-methyl-N-((1r,4r)-4-((3-(4-methyl-6-(methylamino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)nicotinamide;

5-chloro-N-((1r,4r)-4-((3-(6-((2,2-difluoroethyl)amino)pyridin-3-yl)-2-oxo-2,3-dihydro-1H-benzo[d]imidazol-1-yl)methyl)cyclohexyl)-2-methylnicotinamide;

5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(((1-methyl-1H-pyrazol-4-yl)methyl)amino)pyri din-3-yl)-2-oxo-2,3-dihydro-1H-benzo[d]imidazol-1-yl)methyl)cyclohexyl)nicotinamide;

N-((1r,4r)-4-((3-(1,5-naphthyridin-3-yl)-2-oxo-2,3-dihydro-1H-benzo[d]imidazol-1-yl) methyl)cyclohexyl)-5-chloro-2-methylnicotinamide;

5-chloro-2-methyl-N-((1r,4r)-4-((2-oxo-3-(quinazolin-7-yl)-2,3-dihydro-1H-benzo[d]imidazol-1-yl)methyl)cyclohexyl)nicotinamide;

5-chloro-2-methyl-N-((1r,4r)-4-((3-(3-morpholinophenyl)-2-oxo-2,3-dihydro-1H-benzo[d]imidazol-1-yl)methyl)cyclohexyl)nicotinamide;

5-chloro-N-((1r,4r)-4-((3-(4-(isoxazol-3-yl)phenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-(1-methyl-1H-pyrazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(4-(1-methyl-1H-pyrazol-3-yl)phenyl)-2-oxo-2,3-dihydro-1H-benzol[d]imidazol-1-yl)methyl)cyclohexyl)nicotinamide;

N-((1r,4r)-4-((3-benzyl-2-oxo-2,3-dihydro-1H-imidazo[4,5-b]pyridin-1-yl)methyl)cyclohexyl)-5-chloro-2-methylnicotinamide;

5-chloro-2-(difluoromethyl)-N-((1r,4r)-4-((3-(2-fluorophenyl)-2-oxo-2,3-dihydro-1H-imidazo[4,5-b]pyridin-1-yl)methyl)cyclohexyl)nicotinamide;

5-chloro-2-methyl-N-((1r,4r)-4-((3-(4-(oxazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(4-(oxazol-2-yl)phenyl)-2-oxo-2,3-dihydro-1H-benzo[d]imidazol-1-yl)methyl)cyclohexyl)nicotinamide;

5-chloro-N-((1r,4r)-4-((3-(2-chloro-4-methylphenyl)-2-oxo-2,3-dihydro-1H-imidazo[4, 5-b]pyridin-1-yl)methyl)cyclohexyl)-2-(difluoromethyl)nicotinamide;

5-chloro-N-((1r,4r)-4-((3-(2-chloro-5-methoxyphenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(2-chloro-5-fluorophenyl)-2-oxo-2,3-dihydro-1H-imidazo[4, 5-b]pyridin-1-yl)methyl)cyclohexyl)-2-(difluoromethyl)nicotinamide;

5-chloro-2-(difluoromethyl)-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide;

5-chloro-2-(difluoromethyl)-N-((1r,4r)-4-((3-(3-methyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(1H-pyrrolo[2,3-b]pyridin-5-yl)-2,3-dihydro-1H-imidazo[4,5-b]pyridin-1-yl)methyl)cyclohexyl)nicotinamide;

5-chloro-2-(difluoromethyl)-N-((1r,4r)-4-((2-oxo-3-(2-phenoxyethyl)-2,3-dihydro-1H-imidazo[4,5-b]pyridin-1-yl)methyl)cyclohexyl)nicotinamide;

5-chloro-N-((1r,4r)-4-((3-(2,4-dichlorophenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(6-(isopropylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)nicotinamide 5-chloro-2-(difluoromethyl)-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)nicotinamide;

5-chloro-N-((1r,4r)-4-((3-(6-((2,2-difluoroethyl)amino)pyridin-3-yl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(4-methyl-6-(methylamino)pyridin-3-yl)-2-oxo-2,3-dihydro-1H-benzo[d]imidazol-1-yl)methyl)cyclohexyl)nicotinamide;

5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide;

N-((1r,4r)-4-((3-(4-(1H-imidazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-pyrazol-5-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-1,2,3-triazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-pyrazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(6-(1H-imidazol-1-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(2-(1H-imidazol-1-yl)pyridin-4-yl)-2-oxo-2,3-dihydro-1H-benzo[d]imidazol-1-yl)methyl)cyclohexyl)-5-chloro-2-methylnicotinamide;

5-chloro-2-(difluoromethyl)-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

N-((1r,4r)-4-((3-(4-(1H-imidazol-1-yl)pyridin-2-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(5-morpholinopyridin-3-yl)-2-oxo-2,3-dihydro-1H-benzol[d]imidazol-1-yl)methyl)cyclohexyl)nicotinamide;

5-chloro-2-(difluoromethyl)-N-((1r,4r)-4-((3-(6-(2-methoxyethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(oxetan-3-yloxy)pyridin-3-yl)-2-oxo-2,3-dihydro-1H-benzol[d]imidazol-1-yl)methyl)cyclohexyl)nicotinamide;

5-chloro-2-methyl-N-((1r,4r)-4-((2-oxo-3-(6-propionamidopyridin-3-yl)-2,3-dihydro-1H-benzo[d]imidazol-1-yl)methyl)cyclohexyl)nicotinamide;

5-chloro-N-((1r,4r)-4-((3-(6-((3,3-difluoropropyl)amino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(oxetan-3-ylamino)pyridin-3-yl)-2-oxo-2,3-dihydro-1H-benzol[d]imidazol-1-yl)methyl)cyclohexyl)nicotinamide;

5-chloro-2-methyl-N-((1r,4r)-4-((2-oxo-3-(5-(pyrrolidin-1-yl)pyridin-3-yl)-2,3-dihydro-1H-benzo[d]imidazol-1-yl)methyl)cyclohexyl)nicotinamide;

5-chloro-N-((1r,4r)-4-((3-(5-(dimethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5-methoxypyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(oxazol-5-yl)pyridin-3-yl)-2-oxo-2,3-dihydro-1H-benzo[d]imidazol-1-yl)methyl)cyclohexyl)nicotinamide;

5-chloro-N-((1r,4r)-4-((3-(5-(2-methoxyethoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(methylamino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(3-(oxazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(5-(oxazol-5-yl)pyridin-2-yl)-2-oxo-2,3-dihydro-1H-benzo[d]imidazol-1-yl)methyl)cyclohexyl)nicotinamide;

5-(3-(((1r,4r)-4-(2-chloro-5-(trifluoromethyl)benzamido)cyclohexyl)methyl)-2-oxo-2,3-dihydro-1H-benzol[d]imidazol-1-yl)-N-methylpicolinamide;

N-methyl-5-(3-(((1r,4r)-4-(2-methyl-5-(trifluoromethyl)nicotinamido)cyclohexyl)methyl)-2-oxo-2,3-dihydro-1H-benzo[d]imidazol-1-yl)picolinamide;

N-methyl-5-(3-(((1r,4r)-4-(5-methyl-2-(trifluoromethyl)benzamido)cyclohexyl)methyl)-2-oxo-2,3-dihydro-1H-benzo[d]imidazol-1-yl)picolinamide;

5-chloro-2-(difluoromethyl)-N-((1r,4r)-4-((3-(6-(ethylamino)pyridin-3-yl)-2-oxo-2,3-dihydro-1H-benzol[d]imidazol-1-yl)methyl)cyclohexyl)nicotinamide;

5-chloro-2-(difluoromethyl)-N-((1r,4r)-4-((3-(1,3-dimethyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinoxalin-6-yl)-2,3-dihydro-1H-benzo[d]imidazol-1-yl)methyl)cyclohexyl)nicotinamide;

5-chloro-N-((1r,4r)-4-((3-(3-chloropyridin-4-yl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(2-(hydroxymethyl)-1-methyl-1H-indol-5-yl)-2-oxo-2,3-dihydro-1H-benzol[d]imidazol-1-yl)methyl)cyclohexyl)-2-methylnicotinamide;

5-chloro-2-(difluoromethyl)-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide;

5-chloro-N-((1r,4r)-4-((3-(2-cyanophenyl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(6-(2-(methylamino)-2-oxoethoxy)pyridin-3-yl)-2-oxo-2,3-dihydro-1H-benzo[d]imidazol-1-yl)methyl)cyclohexyl)nicotinamide 5-chloro-2-(difluoromethyl)-N-((1r,4r)-4-((2-oxo-3-(6-(2-oxoazetidin-1-yl)pyridin-3-yl)-2,3-dihydro-1H-benzol[d]imidazol-1-yl)methyl)cyclohexyl)nicotinamide;

5-chloro-N-((1r,4r)-4-((3-(6-(cyclopropanecarboxamido)pyridin-3-yl)-2-oxo-2,3-dihydro-1H-benzol[d]imidazol-1-yl)methyl)cyclohexyl)-2-(difluoromethyl)nicotinamide;

N-((1S,4r)-4-((3-(6-(((S)-1-amino-1-oxopropan-2-yl)oxy)pyridin-3-yl)-2-oxo-2,3-dihydro-1H-benzo[d]imidazol-1-yl)methyl)cyclohexyl)-5-chloro-2-(difluoromethyl)nicotinamide;

N-((1R,4r)-4-((3-(6-(((R)-1-amino-1-oxopropan-2-yl)oxy)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((2-oxo-3-(6-(3-oxomorpholino)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(p-tolyl)-2,3-dihydro-1H-imidazo[4,5-b]pyrazin-1-yl)methyl)cyclohexyl)nicotinamide;

5-chloro-N-((1r,4r)-4-((3-(2-cyano-5-methoxyphenyl)-2-oxo-2,3-dihydro-1H-imidazo[4,5-b]pyridin-1-yl)methyl)cyclohexyl)-2-(difluoromethyl)nicotinamide;

N-((1r,4r)-4-((3-(6-acetamidopyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((2-oxo-3-(6-(2-oxopiperidin-1-yl)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-propionamidopyridin-3-yl)-2,3-dihydro-1H-benzo[d]imidazol-1-yl)methyl)cyclohexyl)nicotinamide;

N-((1r,4r)-4-((3-(6-(1H-1,2,3-triazol-1-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-(2H-1,2,3-triazol-2-yl)pyridin-3-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(1-(pyridin-3-yl)piperidin-4-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(isopropylamino)pyridin-3-yl)-2-oxo-2,3-dihydro-1H-benzol[d]imidazol-1-yl)methyl)cyclohexyl)nicotinamide;

5-chloro-2-(difluoromethyl)-N-((1r,4r)-4-((3-(6-((2,2-difluoropropyl)amino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(3-(oxazol-2-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(1-methyl-1H-imidazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(4-(thiazol-2-yl)phenyl)-2,3-dihydro-1H-benzo[d]imidazol-1-yl)methyl)cyclohexyl)nicotinamide;

5-chloro-2-methyl-N-((1r,4r)-4-((3-(2-morpholinopyridin-4-yl)-2-oxo-2,3-dihydro-1H-benzo[d]imidazol-1-yl)methyl)cyclohexyl)nicotinamide;

N-((1r,4r)-4-((3-(6-(1H-imidazol-1-yl)pyridin-2-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(2-(oxazol-5-yl)pyridin-4-yl)-2-oxo-2,3-dihydro-1H-benzo[d]imidazol-1-yl)methyl)cyclohexyl)nicotinamide;

5-chloro-N-((1r,4r)-4-((3-(5-chloro-6-(methylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((2-oxo-3-(6-(2-oxoimidazolidin-1-yl)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(3-methyl-2-oxoimidazolidin-1-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methylbenzo[d]thiazol-5-yl)-2-oxo-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzol[d]imidazol-1-yl)-N-methylpyrazine-2-carboxamide;

5-(3-(((1r,4r)-4-(5-chloro-2-(difluoromethyl)nicotinamido)cyclohexyl)methyl)-7-methyl-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-5-methoxy-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-5-methyl-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-5-fluoro-2-oxo-2,3-dihydro-1H-benzo[d]imidazol-1-yl)-N-methylpicolinamide;

5-(3-(((1r,4r)-4-(5-chloro-2-(trifluoromethoxy)benzamido)cyclohexyl)methyl)-2-oxo-2,3-dihydro-1H-benzol[d]imidazol-1-yl)-N-methylpicolinamide;

N-methyl-5-(3-(((1r,4r)-4-(2-methyl-5-(trifluoromethyl)benzamido)cyclohexyl)methyl)-2-oxo-2,3-dihydro-1H-benzo[d]imidazol-1-yl)picolinamide;

5-(3-(((1r,4r)-4-(5-chloro-2-(difluoromethoxy)benzamido)cyclohexyl)methyl)-2-oxo-2,3-dihydro-1H-benzo[d]imidazol-1-yl)-N-methylpicolinamide;

5-(3-(((1r,4r)-4-(2-amino-5-chloronicotinamido)cyclohexyl)methyl)-2-oxo-2,3-dihydro-1H-benzo[d]imidazol-1-yl)-N-methylpicolinamide;

5-(3-(((1r,4r)-4-(5-bromo-2-(trifluoromethyl)nicotinamido)cyclohexyl)methyl)-2-oxo-2,3-dihydro-1H-benzo[d]imidazol-1-yl)-N-methylpicolinamide;

N-((1r,4r)-4-((3-(2-(2H-1,2,3-triazol-2-yl)pyridin-4-yl)-2-oxo-2,3-dihydro-1H-benzo[d]imidazol-1-yl)methyl)cyclohexyl)-5-chloro-2-methylnicotinamide;

N-((1r,4r)-4-((3-(1H-1,2,3-triazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(3-(2H-1,2,3-triazol-2-yl)phenyl)-2-oxo-2,3-dihydro-benzo[d]imidazol-1-yl)methyl)cyclohexyl)-5-chloro-2-methylnicotinamide;

N-((1r,4r)-4-((3-(3-(1H-imidazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(6-(1H-1,2,3-triazol-1-yl)pyridin-2-yl)-2-oxo-2,3-dihydro-1H-benzo[d]imidazol-1-yl)methyl)cyclohexyl)-5-chloro-2-methylnicotinamide;

N-((1r,4r)-4-((3-(3-(1H-pyrazol-1-yl)phenyl)-2-oxo-2,3-dihydro-1H-benzo[d]imidazol-1-yl)methyl)cyclohexyl)-5-chloro-2-methylnicotinamide;

5-(3-(((1r,4r)-4-(2,5-dichloronicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-(difluoromethyl)nicotinamide;

5-chloro-N-((1r,4r)-4-((3-(5-methyl-6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(4-methyl-6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(6-((2,2,2-trifluoroethyl)amino)pyridin-3-yl)-2,3-dihydro-1H-benzol[d]imidazol-1-yl)methyl)cyclohexyl)-2-(trifluoromethyl)nicotinamide;

5-chloro-2-(difluoromethyl)-N-((1r,4r)-4-((3-(1-methyl-1H-indazol-5-yl)-2-oxo-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-4-fluoro-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-2-oxo-2,3-dihydro-1H-benzol[d]imidazol-1-yl)-N-(2-fluoroethyl)picolinamide;

5-(3-(((1r,4r)-4-(5-chloro-2-(difluoromethyl)nicotinamido)cyclohexyl)methyl)-2-oxo-2,3-dihydro-1H-benzol[d]imidazol-1-yl)-N-(oxetan-3-yl)picolinamide;

5-(3-(((1r,4r)-4-(5-chloro-2-(difluoromethyl)nicotinamido)cyclohexyl)methyl)-2-oxo-2,3-dihydro-1H-benzol[d]imidazol-1-yl)-N-ethylpicolinamide;

5-chloro-N-((1r,4r)-4-((3-(5-fluoro-6-(methylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(3-methoxyazetidin-1-yl)pyridin-3-yl)-2-oxo-2,3-dihydro-1H-benzo[d]imidazol-1-yl)methyl)cyclohexyl)nicotinamide;

3-chloro-5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-2-oxo-2,3-dihydro-1H-benzol[d]imidazol-1-yl)-N,6-dimethylpicolinamide;

N-((1r,4r)-4-((3-(6-(methylcarbamoyl)pyridin-3-yl)-2-oxo-2,3-dihydro-1H-benzo[d]imidazol-1-yl)methyl)cyclohexyl)-2-(2,2,2-trifluoroethyl)-2H-indazole-3-carboxamide;

5-chloro-2-(difluoromethyl)-N-((1r,4r)-4-((3-(4-methyl-6-(2-oxoimidazolidin-1-yl)pyridin-3-yl)-2-oxo-2,3-dihydro-1H-benzo[d]imidazol-1-yl)methyl)cyclohexyl)nicotinamide;

N-((1r,4r)-4-((3-(6-acetamido-4-methylpyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(4-methyl-6-propionamidopyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(4-methyl-6-(2-oxopyrrolidin-1-yl)pyridin-3-yl)-2-oxo-2,3-dihydro-1H-benzo[d]imidazol-1-yl)methyl)cyclohexyl)nicotinamide 5-(3-(((1r,4r)-4-(5-chloro-2-(difluoromethyl)nicotinamido)cyclohexyl)methyl)-6-fluoro-2-oxo-2,3-dihydro-1H-benzo[d]imidazol-1-yl)-N-methylpicolinamide;

5-chloro-2-(difluoromethyl)-N-((1r,4r)-4-((3-(5-(2-hydroxyethoxy)pyrazin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)nicotinamide;

5-(3-(((1r,4r)-4-(5-chloro-2-(cyclopropylamino)nicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(3-morpholinophenyl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(4-(1-methyl-1H-imidazol-2-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(oxazol-4-yl)phenyl)-2-oxo-2,3-dihydro-1H-benzo[d]imidazol-1-yl)methyl)cyclohexyl)nicotinamide;

N-((1r,4r)-4-((3-(4-(1H-imidazol-1-yl)phenyl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(2-(1H-imidazol-1-yl)pyridin-4-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-(methylamino)pyridin-4-yl)-2-oxo-2,3-dihydro-1H-benzo[d]imidazol-1-yl)methyl)cyclohexyl)nicotinamide;

5-chloro-2-methyl-N-((1r,4r)-4-((3-(5-(methylamino)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(3-methyl-1H-indazol-6-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(3-methyl-1H-indazol-5-yl)-2-oxo-2,3-di hydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-4-meth yl-2-oxo-2,3-dihydro-1H-benzo[d]imidazol-1-yl)-N-methylpicolinamide;

5-chloro-2-(difluoromethyl)-N-((1r,4r)-4-((1-(3-methyl-1H-pyrrolo[2,3-b]pyridin-5-yl)-2-oxo-1H-imidazo[4,5-b]pyridin-3(2H)-yl)methyl)cyclohexyl)nicotinamide;

5-chloro-2-methyl-N-((1r,4r)-4-((3-(4-(1-methyl-1H-pyrazol-4-yl)phenyl)-2-oxo-2,3-dihydro-1H-benzol[d]imidazol-1-yl)methyl)cyclohexyl)nicotinamide;

5-chloro-2-methyl-N-((1r,4r)-4-((2-oxo-3-(4-(thiazol-5-yl)phenyl)-2,3-dihydro-1H-benzo[d]imidazol-1-yl)methyl)cyclohexyl)nicotinamide;

N-((1r,4r)-4-((3-(4-(1H-pyrazol-4-yl)phenyl)-2-oxo-2,3-dihydro-1H-benzo[d]imidazol-1-yl)methyl)cyclohexyl)-5-chloro-2-methylnicotinamide;

5-(3-(((1r,4r)-4-(5-chloro-2-(fluoromethyl)nicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(3-methylbenzo[d]isoxazol-6-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((2-oxo-3-(6-(7-oxo-2-oxa-6-azaspiro[3.4]octan-6-yl)pyridin-3-yl)-2,3-dihydro-1H-benzo[d]imidazol-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-cyclopropylpicolinamide;

5-chloro-2-methyl-N-((1r,4r)-4-((3-(3-methylbenzo[d]isoxazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methyl-2-oxo-2,3-dihydrobenzo[d]oxazol-5-yl)-2-oxo-2,3-dihydro-1H-benzo[d]imidazol-1-yl)methyl)cyclohexyl)nicotinamide;

5-chloro-N-((1r,4r)-4-((3-(1-(2-(dimethylamino)ethyl)-3-methyl-1H-indazol-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(3-methyl-1-(2-morpholinoethyl)-1H-indazol-5-yl)-2-oxo-2,3-dihydro-1H-benzo[d]imidazol-1-yl)methyl)cyclohexyl)nicotinamide;

5-chloro-N-((1r,4r)-4-((3-(6-methoxypyridin-3-yl)-2-oxo-3,4-dihydroquinazolin-1(2H)-yl)methyl)cyclohexyl)-2-methylnicotinamide;

N-((1r,4r)-4-((3-(3-aminobenzo[d]isoxazol-5-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2-fluorophenyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)-2-methylnicotinamide;

6-(3-(((1r,4r)-4-(5-chloro-2-methylnicotinamido)cyclohexyl)methyl)-2-oxo-2,3-dihydro-1H-benzo[d]imidazol-1-yl)-N-(2-hydroxyethyl)benzo[d]isoxazole-3-carboxamide;

5-chloro-N-((1r,4r)-4-((3-(4-cyanopyridazin-3-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(methylamino)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-((2-hydroxyethyl)(methyl)amino)pyridin-3-yl)-2-oxo-2,3-dihydro-1H-benzol[d]imidazol-1-yl)methyl)cyclohexyl)-2-(trifluoromethyl)nicotinamide;

5-chloro-N-((1r,4r)-4-((3-(6-morpholinopyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(6-(4-methylpiperazin-1-yl)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(4,6-dimethylpyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2,3-dimethylpyridin-4-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((3-(2-methyl-2H-indazol-4-yl)-2-oxo-2,3-dihydro-1H-benzo[d]imidazol-1-yl)methyl)cyclohexyl)nicotinamide;

5-chloro-N-((1r,4r)-4-((3-(4-chlorophenyl)-2-oxo-2,3-dihydro-1H-imidazo[4,5-b]pyridin-1-yl)methyl)cyclohexyl)-2-(difluoromethyl)nicotinamide;

5-chloro-2-(difluoromethyl)-N-((1r,4r)-4-((2-oxo-3-(1,2,3,4-tetrahydroisoquinolin-7-yl)-2,3-dihydro-1H-benzo[d]imidazol-1-yl)methyl)cyclohexyl)nicotinamide;

N-((1r,4r)-4-((3-(2-acetyl-1,2,3,4-tetrahydroisoquinolin-7-yl)-2-oxo-2,3-dihydro-1H-benzo[d]imidazol-1-yl)methyl)cyclohexyl)-5-chloro-2-(difluoromethyl)nicotinamide;

5-chloro-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1S,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)-2-(trifluoromethyl)nicotinamide;

5-chloro-2-methyl-N-((1R,4r)-4-((2-oxo-3-(6-(((R)-tetrahydrofuran-3-yl)oxy)pyridin-3-yl)-2,3-dihydro-1H-benzo[d]imidazol-1-yl)methyl)cyclohexyl)nicotinamide;

5-chloro-2-methyl-N-((1S,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)nicotinamide;

5-chloro-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-methylquinolin-3-yl)-2-oxo-2,3-dihydro-1H-imidazo[4,5-b]pyridin-1-yl)methyl)cyclohexyl)nicotinamide;

5-chloro-N-((1r,4r)-4-((3-(2-chloro-4-fluorophenyl)-2-oxo-2,3-dihydro-1H-imidazo[4, 5-b]pyridin-1-yl)methyl)cyclohexyl)-2-(difluoromethyl)nicotinamide;

5-chloro-N-((1r,4r)-4-((3-(3-chloro-4-methylphenyl)-2-oxo-2,3-dihydro-1H-imidazo[4, 5-b]pyridin-1-yl)methyl)cyclohexyl)-2-(difluoromethyl)nicotinamide;

5-chloro-N-((1r,4r)-4-((3-(6-((2,2-difluoropropyl)amino)pyridin-3-yl)-2-oxo-2,3-dihydro-1H-benzo[d]imidazol-1-yl)methyl)cyclohexyl)-2-methylnicotinamide;

5-chloro-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-chloro-4-methylphenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(2-chloro-5-methoxyphenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(6-(2-methoxyacetamido)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(dimethylamino)pyridin-3-yl)-2-oxo-2,3-dihydro-1H-imidazo[4,5-b]pyridin-1-yl)methyl)cyclohexyl)nicotinamide;

5-chloro-N-((1r,4r)-4-((3-(2-cyanophenyl)-2-oxo-2,3-dihydro-1H-imidazo[4,5-b]pyridin-1-yl)methyl)cyclohexyl)-2-(difluoromethyl)nicotinamide;

5-chloro-2-(difluoromethyl)-N-((1r,4r)-4-((3-(6-(2-hydroxyacetamido)pyridin-3-yl)-2-oxo-2,3-dihydro-1H-benzo[d]imidazol-1-yl)methyl)cyclohexyl)nicotinamide;

N-((1r,4r)-4-((3-(2-(1H-pyrazol-1-yl)pyridin-4-yl)-2-oxo-2,3-dihydro-1H-benzo[d]imidazol-1-yl)methyl)cyclohexyl)-5-chloro-2-methylnicotinamide;

N-((1r,4r)-4-((3-(6-(1H-pyrazol-1-yl)pyridin-2-yl)-2-oxo-2,3-dihydro-1H-benzo[d]imidazol-1-yl)methyl)cyclohexyl)-5-chloro-2-methylnicotinamide;

5-chloro-N-((1r,4r)-4-((6-fluoro-3-(6-(methylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((5-fluoro-3-(6-(methylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((5-fluoro-3-(6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(2-cyano-4-fluorophenyl)-2-oxo-2,3-dihydro-1H-benzo[d]imidazol-1-yl)methyl)cyclohexyl)-2-(difluoromethyl)nicotinamide;

5-(3-(((1r,4r)-4-(5-chloro-2-(difluoromethyl)nicotinamido)cyclohexyl)methyl)-7-fluoro-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-7-methoxy-2-oxo-2,3-dihydro-1H-benzo[d]imidazol-1-yl)-N-methylpicolinamide;

5-chloro-N-((1r,4r)-4-((1-(2-chlorophenyl)-2-oxo-1H-imidazo[4,5-b]pyridin-3(2H)-yl) methyl)cyclohexyl)-2-(difluoromethyl)nicotinamide;

5-chloro-N-((1r,4r)-4-((1-(2-chloro-5-methoxyphenyl)-2-oxo-1H-imidazo[4,5-c]pyridin-3(2H)-yl)methyl)cyclohexyl)-2-(difluoromethyl)nicotinamide;

5-chloro-N-((1r,4r)-4-((1-(2-chloro-5-fluorophenyl)-2-oxo-1H-imidazo[4,5-c]pyridin-3(2H)-yl)methyl)cyclohexyl)-2-(difluoromethyl)nicotinamide;

N-((1r,4r)-4-((3-(4-(1H-1,2,3-triazol-4-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-1,2,3-triazol-1-yl)phenyl)-2-oxo-2,3-dihydro-1H-imidazo[4,5-b]pyridin-1-yl)methyl)cyclohexyl)-5-chloro-2-(difluoromethyl)nicotinamide;

5-chloro-2-methyl-N-((1r,4r)-4-((3-(4-(oxazol-4-yl)phenyl)-2-oxo-2,3-dihydro-1H-benzo[d]imidazol-1-yl)methyl)cyclohexyl)nicotinamide;

N-((1r,4r)-4-((3-(5-(1H-pyrazol-1-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-(1H-pyrazol-1-yl)pyridin-3-yl)-2-oxo-2,3-dihydro-1H-benzo[d]imidazol-1-yl)methyl)cyclohexyl)-5-chloro-2-methylnicotinamide;

5-chloro-2-(difluoromethyl)-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-fluoro-6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((2-oxo-3-(6-(2-oxoimidazolidin-1-yl)pyridin-3-yl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)-2-(trifluoromethyl)nicotinamide;

N-((1r,4r)-4-((3-(6-acetamidopyridin-3-yl)-2-oxo-2,3-dihydro-1H-benzo[d]imidazol-1-yl)methyl)cyclohexyl)-5-chloro-2-(trifluoromethyl)nicotinamide;

5-chloro-N-((1r,4r)-4-((2-oxo-3-(6-propionamidopyridin-3-yl)-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((3-(6-(3-methylureido)pyridin-3-yl)-2-oxo-2,3-dihydro-1H-benzol[d]imidazol-1-yl)methyl)cyclohexyl)nicotinamide;

5-chloro-2-methyl-N-((1r,4r)-4-((3-(2-methylbenzo[d]thiazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(4-(methylamino)phenyl)-2-oxo-2,3-dihydro-1H-benzo[d]imidazol-1-yl)methyl)cyclohexyl)nicotinamide;

5-chloro-N-((1r,4r)-4-((3-(5-(dimethylamino)pyridin-2-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(5-(dimethylamino)pyridin-2-yl)-2-oxo-2,3-dihydro-1H-benzo[d]imidazol-1-yl)methyl)cyclohexyl)nicotinamide;

5-chloro-N-((1r,4r)-4-((3-(2-(dimethylamino)pyridin-4-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(2-(dimethylamino)pyridin-4-yl)-2-oxo-2,3-dihydro-1H-benzo[d]imidazol-1-yl)methyl)cyclohexyl)nicotinamide;

5-chloro-2-methyl-N-((1r,4r)-4-((3-(3-(1-methyl-1H-pyrazol-3-yl)phenyl)-2-oxo-2,3-dihydro-1H-benzol[d]imidazol-1-yl)methyl)cyclohexyl)nicotinamide;

5-chloro-2-methyl-N-((1r,4r)-4-((3-(5-(1-methyl-1H-pyrazol-3-yl)pyridin-3-yl)-2-oxo-2,3-dihydro-1H-benzo[d]imidazol-1-yl)methyl)cyclohexyl)nicotinamide;

N-((1r,4r)-4-((3-(5-(1H-pyrazol-1-yl)pyridin-2-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-(1-methyl-1H-pyrazol-3-yl)pyridin-4-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(1-methyl-1H-pyrazol-4-yl)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(1-methyl-1H-pyrazol-4-yl)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-urei-dopyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(dimethyl-amino)pyridin-2-yl)-2-oxo-2,3-dihydro-1H-benzo[d]imi-dazol-1-yl)methyl)cyclohexyl)nicotinamide;

5-chloro-2-(difluoromethyl)-N-((1r,4r)-4-((3-(5-(methyl-amino)pyridin-2-yl)-2-oxo-2,3-dihydro-1H-benzo[d]imi-dazol-1-yl)methyl)cyclohexyl)nicotinamide;

5-chloro-2-(difluoromethyl)-N-((1r,4r)-4-((3-(2-(methyl-amino)pyridin-4-yl)-2-oxo-2,3-dihydro-1H-benzo[d]imi-dazol-1-yl)methyl)cyclohexyl)nicotinamide;

5-chloro-2-(difluoromethyl)-N-((1r,4r)-4-((3-(6-(methyl-amino)pyridin-2-yl)-2-oxo-2,3-dihydro-1H-benzo[d]imi-dazol-1-yl)methyl)cyclohexyl)nicotinamide;

5-chloro-N-((1r,4r)-4-((3-(2-(dimethylamino)pyridin-4-yl)-2-oxo-2,3-dihydro-1H-benzo[d]imidazol-1-yl)methyl)cy-clohexyl)-2-(trifluoromethyl)nicotinamide;

5-chloro-N-((1r,4r)-4-((3-(6-((2-methoxyethyl)amino)pyri-din-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-(methylamino)pyridin-4-yl)-2-oxo-2,3-dihydro-1H-benzo[d]imidazol-1-yl)methyl)cy-clohexyl)-2-(trifluoromethyl)nicotinamide;

5-chloro-2-(difluoromethyl)-N-((1r,4r)-4-((3-(1-(2-hy-droxyethyl)-1H-pyrrolo[2,3-b]pyridin-5-yl)-2-oxo-2,3-dihydro-1H-benzo[d]imidazol-1-yl)methyl)cyclohexyl)nicotinamide;

N-((1r,4r)-4-((3-(4-(1H-imidazol-4-yl)phenyl)-2-oxo-2,3-dihydro-1H-benzo[d]imidazol-1-yl)methyl)cyclohexyl)-5-chloro-2-methylnicotinamide;

5-chloro-N-((1r,4r)-4-((7-fluoro-3-(6-(methylamino)pyri-din-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(2-hy-droxy-2-methylpropanamido)pyridin-3-yl)-2-oxo-2,3-di-hydro-1H-benzo[d]imidazol-1-yl)methyl)cyclohexyl)nicotinamide;

5-chloro-2-(difluoromethyl)-N-((1R,4r)-4-((3-(6-((R)-2-hy-droxypropanamido)pyridin-3-yl)-2-oxo-2,3-dihydro-1H-benzo[d]imidazol-1-yl)methyl)cyclohexyl)nicotinamide;

5-chloro-2-(difluoromethyl)-N-((1S,4r)-4-((3-(6-((S)-2-hy-droxypropanamido)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((7-fluoro-3-(6-(methylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(1,2-dimethyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-N-((1r,4r)-4-((1-(2-chloro-5-methoxyphenyl)-2-oxo-1H-imidazo[4,5-b]pyridin-3(2H)-yl)methyl)cyclo-hexyl)-2-(difluoromethyl)nicotinamide;

5-chloro-N-((1r,4r)-4-((1-(2-chloro-5-fluorophenyl)-2-oxo-1H-imidazo[4,5-b]pyridin-3(2H)-yl)methyl)cyclohexyl)-2-(difluoromethyl)nicotinamide;

5-chloro-2-(difluoromethyl)-N-((1r,4r)-4-((1-(4-fluoro-3-methoxyphenyl)-2-oxo-1H-imidazo[4,5-b]pyridin-3(2H)-yl)methyl)cyclohexyl)nicotinamide;

5-chloro-2-methyl-N-((1r,4r)-4-((3-(3-(1-methyl-1H-pyra-zol-4-yl)phenyl)-2-oxo-2,3-dihydro-1H-benzo[d]imi-dazol-1-yl)methyl)cyclohexyl)nicotinamide;

5-chloro-2-methyl-N-((1r,4r)-4-((3-(5-(1-methyl-1H-pyra-zol-4-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-(1-methyl-1H-pyra-zol-4-yl)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(3-(1-methyl-1H-pyrazol-4-yl)phenyl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-(1-methyl-1H-pyrazol-4-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-methoxy-pyridin-3-yl)-2-oxo-2,3-dihydro-1H-benzo[d]imidazol-1-yl)methyl)cyclohexyl)nicotinamide;

N-((1r,4r)-4-((3-(4-(2H-1,2,3-triazol-2-yl)phenyl)-2-oxo-2,3-dihydro-1H-benzo[d]imidazol-1-yl)methyl)cyclo-hexyl)-5-chloro-2-(difluoromethyl)nicotinamide;

N-((1r,4r)-4-((3-(6-(2H-1,2,3-triazol-2-yl)pyridin-3-yl)-2-oxo-2,3-dihydro-1H-benzo[d]imidazol-1-yl)methyl)cy-clohexyl)-5-chloro-2-(difluoromethyl)nicotinamide;

5-chloro-2-(difluoromethyl)-N-((1r,4r)-4-((3-(2-mor-pholinopyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-(oxazol-5-yl)pyridin-4-yl)-2-oxo-2,3-dihydro-1H-benzo[d]imida-zol-1-yl)methyl)cyclohexyl)nicotinamide;

5-chloro-2-(difluoromethyl)-N-((1r,4r)-4-((3-(5-(oxazol-2-yl)pyridin-3-yl)-2-oxo-2,3-dihydro-1H-benzol[d]imida-zol-1-yl)methyl)cyclohexyl)nicotinamide;

5-chloro-2-methyl-N-((1r,4r)-4-((3-(5-(oxazol-2-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-(3-methyl-2-oxoimi-dazolidin-1-yl)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(2-(2-oxoimidazolidin-1-yl)pyridin-4-yl)-2,3-dihydro-1H-benzo[d]imidazol-1-yl)methyl)cyclohexyl)nicotinamide;

5-chloro-N-((1r,4r)-4-((3-(5-(methylamino)pyridin-2-yl)-2-oxo-2,3-dihydro-1H-benzo[d]imidazol-1-yl)methyl)cy-clohexyl)-2-(trifluoromethyl)nicotinamide;

5-chloro-N-((1r,4r)-4-((3-(2-chloro-5-methoxyphenyl)-2-oxo-2,3-dihydro-1H-imidazo[4,5-c]pyridin-1-yl)methyl)cyclohexyl)-2-(difluoromethyl)nicotinamide;

5-chloro-2-(difluoromethyl)-N-((1r,4r)-4-((3-(3-fluorophe-nyl)-2-oxo-2,3-dihydro-1H-imidazo[4,5-c]pyridin-1-yl)methyl)cyclohexyl)nicotinamide;

N-((1r,4r)-4-((3-(6-(1H-imidazol-2-yl)pyridin-3-yl)-2-oxo-2,3-dihydro-1H-benzo[d]imidazol-1-yl)methyl)cyclo-hexyl)-5-chloro-2-methylnicotinamide;

N-((1r,4r)-4-((3-(3-(1H-pyrazol-4-yl)phenyl)-2-oxo-2,3-di-hydro-1H-benzo[d]imidazol-1-yl)methyl)cyclohexyl)-5-chloro-2-methylnicotinamide;

N-((1r,4r)-4-((3-(3-(1H-pyrazol-4-yl)phenyl)-2-oxo-2,3-di-hydro-1H-benzo[d]imidazol-1-yl)methyl)cyclohexyl)-5-chloro-2-(difluoromethyl)nicotinamide;

N-((1r,4r)-4-((3-(2-(1H-pyrazol-4-yl)pyridin-4-yl)-2-oxo-2,3-dihydro-1H-benzo[d]imidazol-1-yl)methyl)cyclo-hexyl)-5-chloro-2-methylnicotinamide;

5-chloro-2-(difluoromethyl)-N-((1r,4r)-4-((3-(2-(1-methyl-1H-pyrazol-4-yl)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(3-(1-methyl-1H-pyrazol-3-yl)phenyl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-(1-methyl-1H-pyrazol-3-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-(1-methyl-1H-pyrazol-3-yl)pyridin-4-yl)-2-oxo-2,3-dihydro-1H-benzo[d]imidazol-1-yl)methyl)cyclohexyl)nicotinamide;

N-((1r,4r)-4-((3-(5-(1H-pyrazol-1-yl)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-N-((1r,4r)-4-((6-fluoro-3-(6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((5-fluoro-3-(6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((2-oxo-3-(2-(2-oxopyrrolidin-1-yl)pyridin-4-yl)-2,3-dihydro-1H-benzo[d]imidazol-1-yl)methyl)cyclohexyl)nicotinamide;

5-chloro-2-(difluoromethyl)-N-((1r,4r)-4-((3-(2-(3-methyl-2-oxoimidazolidin-1-yl)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(1,2-dimethyl-1H-pyrrolo[2,3-b]pyridin-5-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(2-(hydroxymethyl)-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(3-fluoro-4-methoxyphenyl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(6-(3-hydroxypropyl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(6-(2-hydroxyethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(6-((2-hydroxyethyl)amino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(2-(2-hydroxyethoxy)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-((2-hydroxyethyl)amino)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(5-(2-hydroxyethoxy)pyridin-2-yl)-2-oxo-2,3-dihydro-1H-benzo[d]imidazol-1-yl)methyl)cyclohexyl)nicotinamide;

5-chloro-N-((1r,4r)-4-((3-(2-chloro-5-fluorophenyl)-2-oxo-2,3-dihydro-1H-imidazo[4,5-c]pyridin-1-yl)methyl)cyclohexyl)-2-(difluoromethyl)nicotinamide;

5-chloro-2-(difluoromethyl)-N-((1r,4r)-4-((3-(3-fluoro-4-methoxyphenyl)-2-oxo-2,3-dihydro-1H-imidazo[4,5-c]pyridin-1-yl)methyl)cyclohexyl)nicotinamide;

5-chloro-2-(difluoromethyl)-N-((1r,4r)-4-((1-(2-fluoro-5-methoxyphenyl)-2-oxo-1H-imidazo[4,5-b]pyridin-3(2H)-yl)methyl)cyclohexyl)nicotinamide;

5-chloro-N-((1r,4r)-4-((3-(2-chlorophenyl)-2-oxo-2,3-dihydro-1H-imidazo[4,5-c]pyridin-1-yl)methyl)cyclohexyl)-2-(difluoromethyl)nicotinamide;

5-chloro-2-(difluoromethyl)-N-((1r,4r)-4-((1-(3-fluoro-4-methoxyphenyl)-2-oxo-1H-imidazo[4,5-b]pyridin-3(2H)-yl)methyl)cyclohexyl)nicotinamide;

5-chloro-2-(difluoromethyl)-N-((1r,4r)-4-((3-(2-fluoro-5-methoxyphenyl)-2-oxo-2,3-dihydro-1H-imidazo[4,5-c]pyridin-1-yl)methyl)cyclohexyl)nicotinamide;

5-chloro-2-(difluoromethyl)-N-((1r,4r)-4-((1-(3-fluoro-4-methoxyphenyl)-2-oxo-1H-imidazo[4,5-c]pyridin-3(2H)-yl)methyl)cyclohexyl)nicotinamide;

5-chloro-2-(difluoromethyl)-N-((1r,4r)-4-((3-(2-fluoro-5-methoxyphenyl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((1-(2-fluoro-5-methoxyphenyl)-2-oxo-1H-imidazo[4,5-c]pyridin-3(2H)-yl)methyl)cyclohexyl)nicotinamide;

4-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide;

4-(3-(((1r,4r)-4-(5-chloro-2-methylnicotinamido)cyclohexyl)methyl)-2-oxo-2,3-dihydro-1H-benzo[d]imidazol-1-yl)-N-methylpicolinamide;

4-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(1-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(1-(2-hydroxyethyl)-3-methyl-1H-pyrrolo[2,3-b]pyridin-5-yl)-2-oxo-2,3-dihydro-1H-benzo[d]imidazol-1-yl)methyl)cyclohexyl) nicotinamide;

5-chloro-2-(difluoromethyl)-N-((1r,4r)-4-((3-(2-(hydroxymethyl)-1-methyl-1H-pyrrolo[2,3-b]pyridin-5-yl)-2-oxo-2,3-dihydro-1H-benzo[d]imidazol-1-yl)methyl)cyclohexyl) nicotinamide;

N-((1r,4r)-4-((3-(6-(1H-imidazol-2-yl)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(2-(hydroxymethyl)-1-methyl-1H-indol-5-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(5-(3-methyl-2-oxoimidazolidin-1-yl)pyridin-2-yl)-2-oxo-2,3-dihydro-1H-benzo[d]imidazol-1-yl)methyl)cyclohexyl) nicotinamide;

5-chloro-2-(difluoromethyl)-N-((1r,4r)-4-((6-fluoro-2-oxo-3-(6-(2-oxoimidazolidin-1-yl)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

N-((1r,4r)-4-((3-(2-(1H-pyrazol-4-yl)pyridin-4-yl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(3-(5-methyl-1,2,4-oxadiazol-3-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(5-methyl-1,2,4-oxadiazol-3-yl)phenyl)-2-oxo-2,3-dihydro-1H-benzol[d]imidazol-1-yl)methyl)cyclohexyl)nicotinamide;

5-chloro-2-(difluoromethyl)-N-((1r,4r)-4-((3-(3-(5-methyl-1,3,4-oxadiazol-2-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(5-methyl-1,3,4-oxadiazol-2-yl)phenyl)-2-oxo-2,3-dihydro-1H-benzol[d]imidazol-1-yl)methyl)cyclohexyl)nicotinamide;

N-((1r,4r)-4-((3-(3-(1,3,4-oxadiazol-2-yl)phenyl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(3-(1,3,4-oxadiazol-2-yl)phenyl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2-chlorophenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-chlorophenyl)-2-oxo-1H-imidazo[4,5-c]pyridin-3(2H)-yl) methyl)cyclohexyl)-2-(trifluoromethyl)nicotinamide;

5-chloro-N-((1r,4r)-4-((1-(2-chlorophenyl)-2-oxo-1H-imidazo[4,5-b]pyridin-3(2H)-yl) methyl)cyclohexyl)-2-(trifluoromethyl)nicotinamide;

5-chloro-N-((1r,4r)-4-((3-(2-chloro-5-methoxyphenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-chloro-5-methoxyphenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-chloro-5-methoxyphenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(3-fluoro-4-methoxyphenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(3-fluoro-4-methoxyphenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(3-fluoro-4-methoxyphenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(3-fluoro-4-methoxyphenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(2-chloro-5-fluorophenyl)-2-oxo-2,3-dihydro-1H-imidazo[4, 5-c]pyridin-1-yl)cyclohexyl)-2-(trifluoromethyl)nicotinamide;

5-chloro-N-((1r,4r)-4-((1-(2-chloro-5-fluorophenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-chloro-5-fluorophenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(2-fluoro-5-methoxyphenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(2-fluoro-5-methoxyphenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-fluoro-5-methoxyphenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-fluoro-5-methoxyphenyl)-2-oxo-1H-imidazo[4,5-b]pyridin-3(2H)-yl)methyl)cyclohexyl)-2-(trifluoromethyl)nicotinamide;

5-chloro-2-(difluoromethyl)-N-((1r,4r)-4-((2-oxo-3-(5-(2-oxopyrrolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((1-(3-fluorophenyl)-2-oxo-1H-imidazo[4,5-b]pyridin-3(2H)-yl)methyl)cyclohexyl)nicotinamide;

N-((1r,4r)-4-((3-(4-(1H-imidazol-5-yl)phenyl)-2-oxo-2,3-dihydro-1H-benzo[d]imidazol-1-yl)methyl)cyclohexyl)-5-chloro-2-(difluoromethyl)nicotinamide;

5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((2-oxo-3-(5-(2-oxopyrrolidin-1-yl)pyridin-2-yl)-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxoimidazolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-(2-oxoimidazolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(3-methyl-2-oxoimidazolidin-1-yl)pyridin-2-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxopyrrolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-(2-oxopyrrolidin-1-yl)pyridin-2-yl)-2,3-dihydro-1H-benzo[d]imidazol-1-yl)methyl)cyclohexyl)nicotinamide;

5-chloro-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((6-fluoro-3-(5-(2-hydroxyethoxy)pyrazin-2-yl)-2-oxo-2,3-dihydro-1H-benzo[d]imidazol-1-yl)methyl)cyclohexyl)nicotinamide; and 5-chloro-2-(difluoromethyl)-N-((1r,4r)-4-((3-(2-(hydroxymethyl)-1H-indol-5-yl)-2-oxo-2,3-dihydro-1H-imidazo[4,5-b]pyridin-1-yl)methyl)cyclohexyl)nicotinamide;

or a pharmaceutically acceptable salt thereof or a prodrug thereof;

[8] A use of a compound described in any one of [1] to [7] or a pharmaceutically acceptable salt, prodrug, solvate or composition thereof for the manufacture of a medicament for the treatment of a condition or disorder in which CRHR1 and/or CRHR2 are involved;

[9] The use as described in [8], wherein said condition or disorder is selected from the group consisting of: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart disease, and combinations thereof;

[10] The use as described in [9], wherein the heart disease is selected from the group consisting of: acute and chronic heart failure, cardiovascular disease, hyper tension, myocardial infarction, coronary artery disease, and abdominal aortic aneurysm.

[11] A method for the treatment of a condition or disorder in which CRHR1 and/or CRHR2 are involved, in an animal, including a human, which comprises administering to the animal in need of such treatment a therapeutically effective amount of a compound or a prodrug thereof or a pharmaceutically acceptable salt thereof, as described in any one of [1] to [7];

[12] The method as described in [11], wherein said condition or disorder is selected from the group consisting of: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart disease, and combinations thereof;

[13] The method as described in [12], wherein the heart disease is selected from the group consisting of: acute and chronic heart failure, cardiovascular disease, hyper tension, myocardial infarction, coronary artery disease, and abdominal aortic aneurysm;

[14] A pharmaceutical composition comprising a compound or a pharmaceutically acceptable salt thereof or a prodrug thereof, as described in any one of [1] to [7], and a pharmaceutically acceptable carrier;

[15] The pharmaceutical composition as described in [14], further comprising another pharmacologically active agent;

[16] A compound described in any one of [1] to [7] or a prodrug thereof or a pharmaceutically acceptable salt for use in the treatment of a condition or disorder in which CRHR1 and/or CRHR2 are involved;

[17] A process for preparing a pharmaceutical composition, wherein the process comprises mixing a compound described in any one of [1] to [7] or a pharmaceutically acceptable salt thereof or a prodrug thereof and a pharmaceutically acceptable carrier or excipient;

[18] An assay process for identifying a compound which has CRHR1 and/or CRHR2 antagonistic activity, comprising administering of a compound described in any one of [1] to [7] to mice loaded exogenous CRHR2 agonist within 1 week and investigating cardiovascular functions; and

[19] An assay process for identifying a compound which has CRHR1 and/or CRHR2 antagonistic activity, comprising administering of a compound described in any one of [1] to [7] to mice infused urocortin 2 within 2 days and measuring cardiac function by echocardiography.

Advantageous Effects of Invention

The compounds showed activities against both CRHR1 and CRHR2. In particular, the fused cyclic urea derivatives of the present invention show excellent antagonistic activities against the CRHR2 over the compounds with close chemical structure, leading to better pharmacological profiles. The fused cyclic urea derivatives of the present invention show good selectivity against other receptors than CRHR1 and CRHR2, leading to improvements in the side-effect profile. The fused cyclic urea derivatives of the present invention are therefore useful in the treatment of a wide range of disorders.

Therefore, according to a further aspect of the invention, we provide a compound of formula (I) and (II), or a salt thereof, for the treatment or alleviation of treatment of any state with increased endogenous level of CRH or in which the HPA (hypothalamic pituitary axis) is dysregulated, or of various diseases induced or facilitated by CRH.

Compounds of the invention are in particular useful for the treatment or prevention of gastrointestinal disorders including irritable bowel syndrome with or without diarrhea, inflammatory bowel diseases, post-operative ileus, reflux disease and infectious diarrhea.

Compounds of the invention are also in particular useful for the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include fatigue syndrome and dysthymic disorder with early or late onset and with or without atypical features, neurotic depression, post traumatic stress disorders, post operative stress and social phobia; dementia of the Alzheimer type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganized schizophrenia, catatonic schizophrenia, undifferentiated schizophrenia, residual schizophrenia.

Compounds of the invention are also useful in the treatment or prevention of neurodegenerative diseases such as Alzheimer's disease, Parkinson's disease, Huntington's disease, senile dementia of the Alzheimer's type, and multi-infarct dementia.

Compounds of the invention are useful as analgesics. In particular, they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmenorrhea; menstrual pain; meningitis; arachnoiditis; musculoskeletal pain; low back pain e.g. spinal stenosis; prolapsed disc; sciatica; angina; ankylosing spondylitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa, bulimia, obesity and metabolic syndrome.

Compounds of the invention are also useful in the treatment of sleep disorders including dyssomnia, insomnia, sleep apnea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative hypnotic, amphetamine or amphetamine-related drugs (e.g. dextroamphetamine, methylamphetamine) addiction or a combination thereof.

Compounds of the invention are also useful as anti-inflammatory agents. In particular, they are useful in the treatment of inflammation in asthma, influenza, chronic bronchitis and rheumatoid arthritis; in the treatment of inflammatory diseases of the gastrointestinal tract such as Crohn's disease, ulcerative colitis, postoperative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of fertility problems, sexual dysfunctions and pre-term birth and non-inflammatory urogenital disorders such as overactive bladder and related urinary incontinence.

Compounds of the invention are also useful in the treatment of allergic disorders, in particular allergic disorders of the skin such as urticaria, and allergic disorders of the airways such as rhinitis.

Compounds of the invention are also useful in the treatment of mast cell activation disorders such as mastocytosis.

Compounds of the invention are also useful the treatment of Cushing's syndrome induced by drugs such as steroids or cancer such as pituitary adenoma.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intracranial pressure; decreased intracranial pressure (e.g. altitude sickness); opioid analgesics, such as morphine; and gastro-oesophageal reflux disease, acid indigestion, over-indulgence of food or drink, acid stomach, sour stomach, regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome; skin disorders such as psoriasis, pruritus and sunburn; vasospastic diseases such as angina, vascular headache and Reynaud's disease; cerebral ischemia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospasm, hypoglycemia, hypoxia, anoxia, perinatal asphyxia, and cardiac arrest.

Compounds of the invention are useful for hair growth.

Compounds of the invention are useful for heart disease including acute and chronic heart failure, cardiovascular disease, hyper tension, myocardial infarction, coronary artery disease, and abdominal aortic aneurysm.

The utility of the agents of the invention in the above indicated diseases can be confirmed in a range of standard tests. Examples of such tests may include, but are not limited to, the following:

(1) The anxiolytic activity of the agents of the invention can be confirmed in the mouse elevated plus-maze [see, for example, Rodgers R. J., Behavioural Pharmacology 8:477-496 (1997) where the relevance of the elevated plus-maze is discussed on p. 486; for the method, see Rodgers R. J. et al. Ethology and Psychopharmacology (Eds S J Cooper and CA Hendrie), pp 9-44 (1994), J. Wiley, Chichester]. (2) The analgesic activity of the agents of the invention can be confirmed in rat visceral hyperalgesia models following colorectal distension [see for example Schwetz I, Am J Physiology 286: G683-G691 (2004); for the method, see Ness T. J., Brain Research 450:153-169 (1988)]. (3) The anti-diarrheal activity of the agents of the invention can be confirmed in rat defecation models during stress or CRF challenge [see for example, Maillot C., Gastroenterology 119:1569-1579 (2002)]. (4) The hair growth activity of the agents of the invention can be confirmed in the method described in WO 2007/149938. (5) The anti-heart disease activity of the agents of the invention can be confirmed in the method described in this specification and the literature, e.g. Drug Discovery Today Volume 20, Number 7, 906-914 (2015). (6) Other activities of the agents of the invention can be confirmed in the method described in literatures known by a person skilled in the art including well-known art and commonly used art.

Novartis discloses structurally close arts in WO2011/092293 and WO2011/095450. The compounds of present invention show much better activities than those of the close arts.

Namely the present invention is characterized by —B—$R^3$ substituent on the fused cyclic urea ring in the above formula (I) or (II). The structurally closest compounds are synthesized and are described as reference compounds in the present application. The difference between the present invention and the structurally closest art is further well brought out as follows.

The CRHR2 antagonistic activities of the representative chemical structures in the present invention and the structurally close arts are summarized in the following Tables 1-1 and 1-2.

The reference compound of Example 2.46 in the structurally close art, WO2011/092293, shows the inhibitory activity against CRHR2 with 3 microM, whereas the compound of Example 2 in the present invention, where phenyl group is introduced to the terminal ethyl group of Example 2.46, has inhibitory activities against CRHR2 with 0.18 microM. The reference compound of Example 2.50 in the structurally close art, WO2011/092293, shows the inhibitory activity against CRHR2 with 13 microM, whereas the compound of Example 1 in the present invention, where phenyl group is introduced to the terminal methyl group of Example 2.50, has inhibitory activities against CRHR2 with 0.39 microM. The reference compound (A) with cyclohexyl group falls into the claim of the structurally close art, WO2011/092293, shows the inhibitory activity against CRHR2 with 3.1 microM, whereas the compound of Example 156 in the present invention, where cyclohexyl group of the reference compound (A) is replaced with pyridyl group, has inhibitory activities against CRHR2 with 0.28 microM. In addition the compound of Example 30 with methoxy group on the pyridiyl group in the present invention has inhibitory activities against CRHR2 with 0.06 microM. Further the compound of Example 128 with pyrazolopyridyl group in the present invention has inhibitory activities against CRHR2 with 0.28 microM, which shows better activity comparing with the reference compound (A) of the structurally close art, WO2011/092293. Then the compound of Example 148 with methyl-introduced pyrropyridyl group in the present invention has inhibitory activities against CRHR2 with 0.06 microM.

Therefore the compound of the present invention, which has —B—$R^3$ substituent on the bi-cyclic imidazolinone ring in the above formula (I) or (II) shows excellent activity against CRHR2 comparing with the corresponding compound of the structurally close arts.

TABLE 1-1

| Literature/Present invention | Chemical structure | CRHR2 ($IC_{50}$) |
|---|---|---|
| WO2011/092293 | Example 2.46 | 3.0 microM |
| Present invention | Example 2 | 0.18 microM |
| WO2011/092293 | Example 2.50 | 13 microM |
| Present invention | Example 1 | 0.39 microM |

TABLE 1-1-continued
| Literature/Present invention | Chemical structure | CRHR2 (IC$_{50}$) |
|---|---|---|
| WO2011/092293 | 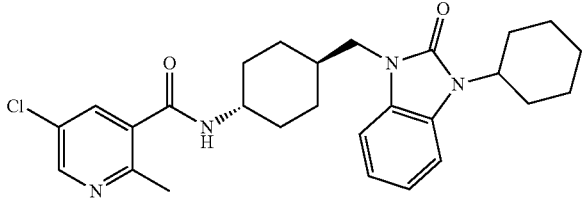<br>Reference compound (A) | 3.1 microM |
TABLE 1-2
| Present invention | Chemical structure | CRHR2 (IC$_{50}$) |
|---|---|---|
| Present invention | 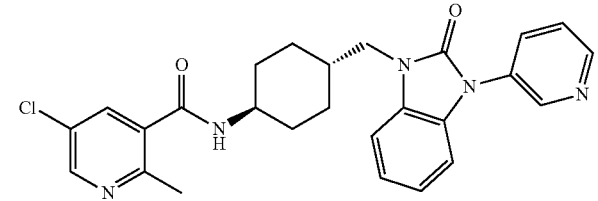<br>Example 156 | 0.28 microM |
| Present invention | 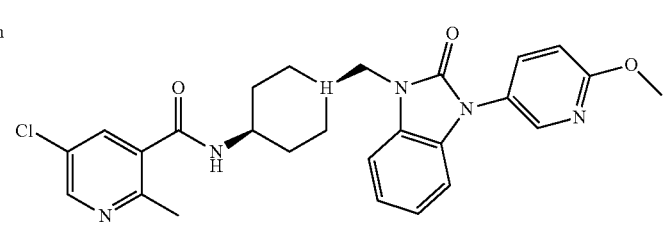<br>Example 30 | 0.06 microM |
| Present invention | 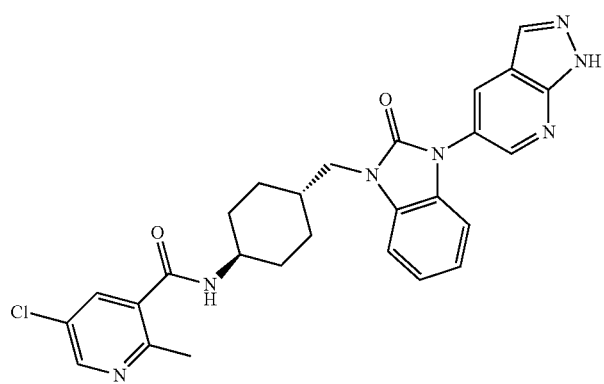<br>Example 128 | 0.28 microM |
| Present invention | 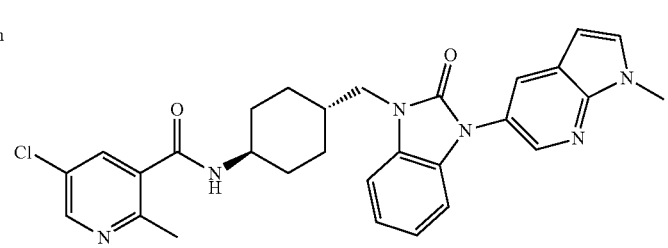<br>Example 148 | 0.06 microM |

Examples of conditions or disorders mediated by CRHR1 and/or CRHR2 include, but are not limited to, CRHR1 and/or CRHR2 related diseases. The compounds of the present invention show the CRHR1 and CRHR2 antagonistic activity. The compounds of the present invention may show less toxicity, good absorption and distribution, good solubility, less protein binding affinity other than CRHR1 and/or CRHR2, less drug-drug interaction, good metabolic stability, reduced inhibitory activity at HERG channel, and/or reduced QT prolongation.

DESCRIPTION OF EMBODIMENTS

As appreciated by those of skill in the art, "halogen" as used herein is intended to include fluoro, chloro, bromo and iodo. Similarly, 1-6, as in $C_{1-6}$ is defined to identify the number as having 1, 2, 3, 4, 5, or 6. According to the definition, for example, $C_6$, as in $C_{1-6}$alkyl is defined to identify the alkyl group as having 1, 2, 3, 4, 5, or 6 carbons. Similarly, $C_{2-6}$alkenyl is defined to identify the alkenyl group as having 2, 3, 4, 5, or 6 carbons. A group which is designated as being independently substituted with substituents may be independently substituted with multiple numbers of such substituents.

The term "alkyl", as used herein, means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

The term "alkoxy", as used herein, means an —O-alkyl such as, but not limited to, methoxy, ethoxy, propoxy, 2-propoxy, butoxy (including all isomeric forms), and the like.

The term "cycloalkyl", as used herein, means a mono- or bi-cyclic ring such as, but not limited to, cyclopropyl, cyclobutyl, cyclopentyl, cyclohexyl, cycloheptyl, norbornyl, adamantyl groups, and the like. In this specification, preferable cycloalkyl is $C_{3-7}$ mono cycloalkyl, more preferable cycloalkyl is $C_{3-6}$ mono cycloalkyl, further preferable cycloalkyl is $C_{3-5}$ mono cycloalkyl.

The term "aryl", as used herein, means unsaturated or partially saturated mono- or bi-cyclic 5-15 membered ring which consists of carbon atoms. Examples of such aryl include, but are not limited to, phenyl, naphthyl, indanyl, indenyl, 1,2,3,4-tetrahydronaphthyl, 1,2-dihydronaphthyl, 2,3-dihydro-1H-indenyl, cyclohexenyl, cyclopentenyl, (1S,4S)-bicyclo[2.2.2]oct-2-enyl, and (1R,4S)-bicyclo[2.2.1]hept-2-enyl and the like. In this specification, preferable aryl is 6-10 membered unsaturated aryl, more preferable aryl is 6-8 membered unsaturated aryl.

The term "heteroaryl" as used herein, means unsaturated and partially saturated mono- or bi-cyclic 5-15 membered ring, preferably mono- or bi-cyclic 5-10 membered ring, which may contain 1-4 heteroatoms selected from O, N, and S.

Examples of such heteroaryl include, but are not limited to, thiophenyl, thiazolyl, isoxazolyl, pyrazolyl, pyrazyl, tetrazolyl, furanyl, pyrrolyl, imidazolyl, oxazolyl, isothiazolyl, triazolyl, thiadiazolyl, pyridyl, pyrimidyl, pyridazinyl, pyrazinyl, pyranyl, triazinyl, 3,6-dihydro-2H-pyran, 1,2,3,6-tetrahydropyridyl, benzofuranyl, benzothiophenyl, benzotriazolyl, benzoxazolyl, indolyl, indazolyl, benzoimidazolyl, pyrrolopyridyl, 2,3-dihydro-pyrrolo[2,3-b]pyridyl, 2,3-dihydro-1H-pyrrolo[2,3-c]pyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinoxalyl, quinazolinyl, phthalazinyl, quinoxalinyl, naphthyridinyl, pyridopyrimidinyl, 2,3-dihydro-[1,4]dioxino[2,3-b]pyridyl, 2,3-dihydro-[1,4]dioxino[2,3-c]pyridyl and N-oxides thereof and S-oxides thereof and the like. In this specification, preferable heteroaryl is 5-6 membered mono heteroaryl, more preferable heteroaryl is 5-6 membered N-containing mono heteroaryl.

The term "heterocyclyl" as used herein includes both unsaturated and saturated heterocyclic moieties, wherein the unsaturated heterocyclic moieties (i.e. "heteroaryl") include, but not limited to, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, 3,6-dihydro-2H-pyranyl, 1,2,3,6-tetrahydropyridinyl, tetrahydro-2H-thiopyran 1,1-dioxide, and N-oxides thereof, and wherein the saturated heterocyclic moieties include, but not limited to, azetidinyl, 1,4-dioxanyl, hexahydroazepinyl, piperazinyl, piperidinyl, pyridin-2-onyl, pyrrolidinyl, morpholinyl, tetrahydrofuranyl, tetrahydropyranyl, thiomorpholinyl, triazolopyrimidyl, tetrahydrothienyl, pyrrolidinonyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, 1,4-oxazepanyl, and N-oxides thereof and S-oxides thereof. In this specification, preferable heterocyclyl is 3-6 membered saturated mono heterocyclyl, which may contain 1-4 heteroatoms selected from O, N, and S, more preferable heterocyclyl is 5-6 membered saturated mono heterocyclyl.

The term "7 to 11 membered spiro-ring", as used herein, means a twisted structure of two rings (a ring system), in which 2 rings are linked together by one common carbon atom, examples of which are shown below, but not limited to.

[Chem. 4]

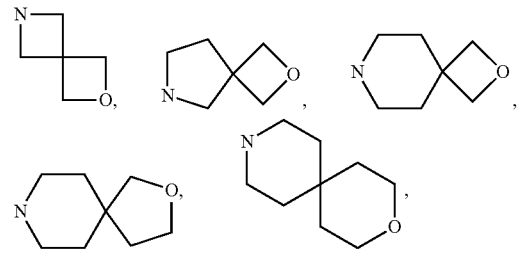

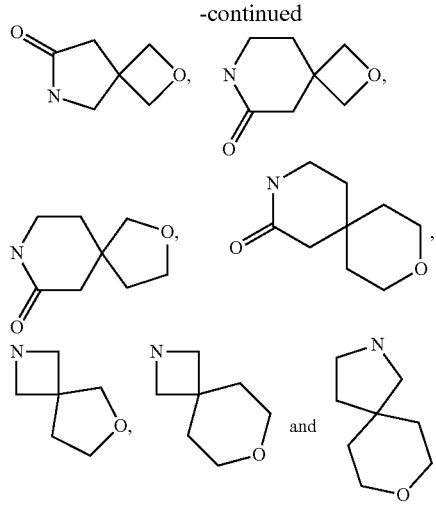

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 2007).

The term "treating" or "treatment", as used herein, includes prohibiting, restraining, slowing, stopping, or reversing the progression or severity of an existing symptom or disorder. As used herein, the term "preventing" or "to prevent" includes prohibiting, restraining, or inhibiting the incidence or occurrence of a symptom or disorder.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I) or (II).

Compounds of formula (I) or (II) can form acid addition salts thereof. It will be appreciated that for use in medicine the salts of the compounds of formula (I) or (II) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g., but not limited to, hydrochloric, hydrobromic, sulfuric, nitric or phosphoric acid; and organic acids e.g., but not limited to, succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) or (II) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases such as choline, arginine, benzathine, diethylamine, glycine, lysine, meglumine, olamine, 2-amino-2-methylpropan-1-ol, benethamine, tert-butylamine, epolamine, ethylenediamine, hydrabamine, morpholine, piperazine, procaine, triethanolamine, diethanolamine, monoethanolamine, triisopropanolamine, and tromethamine.

Also within the scope of the invention are so-called "prodrugs" of the compounds of formula (I) or (II). Thus certain derivatives of compounds of formula (I) or (II) which may have little or no pharmacological activity themselves can, when administered into or onto the body, be converted into compounds of formula (I) or (II) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

The term "CRHR2 agonist", as used herein, includes but are not limited to, urocortin 2, urocortin 1, urocortin 3, sauvagine, CRF, and CRF peptide family containing CRF analogs.

Prodrugs in accordance with the invention can, for example, be produced by replacing appropriate functionalities present in the compounds of formula (I) or (II) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) or (II) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the formula (I) or (II) contains an amino group, a fused cyclic urea derivative prepared by reacting with a suitable acid halide or a suitable acid anhydride is exemplified as a prodrug. A particularly preferred fused cyclic urea derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Salts and solvates having non-pharmaceutically acceptable counter-ions or associated solvents are within the scope of the present invention, for example, for use as intermediates in the preparation of other compounds of formula (I) or (II) and their pharmaceutically acceptable salts.

Compounds of formula (I) or (II) may have polymorphs in crystalline form, which are within the scope of the present invention.

Additionally, compounds of formula (I) or (II) may be administered as prodrugs. As used herein, a "prodrug" of a compound of formula (I) or (II) is a functional derivative of the compound which, upon administration to a patient, eventually liberates the compound of formula (I) or (II) in vivo. Administration of a compound of formula (I) or (II) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I) or (II), there may be one or more chiral carbon atoms. In such cases, compounds of formula (I) or (II) exist as stereoisomers. The invention extends to all optical isomers such as stereoisomeric forms of the compounds of formula (I) or (II) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2H$, $^3H$, $^{11}C$, $^{13}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{123}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, certain compounds exhibit unexpected properties, such as with respect to duration of action and/or metabolism, such as favorable metabolic stability, favorable oral bioavailability or absorption, and/or decreased drug-drug interactions.

A skilled physician will be able to determine the appropriate situation in which subjects are susceptible to or at risk of, for example, stroke as well as suffering from stroke for administration by methods of the present invention.

CRHR1 and/or CRHR2 have been implicated in a wide range of biological functions. This has suggested a potential role for these receptors in a variety of disease processes in humans or other species. The compounds of the present invention have utility in treating, preventing, ameliorating, controlling or reducing the risk of a variety of disorders associated with CRHR1 and/or CRHR2, including one or more of the following conditions or diseases: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart failure, and the like.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range of 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A CRHR1 and CRHR2 antagonist may be usefully combined with another pharmacologically active compound, or with two or more other pharmacologically active compounds, particularly in the treatment of inflammatory, pain and urological diseases or disorders. For example, a CRHR1 and CRHR2 antagonist, particularly a compound of formula (I) and (II), or a prodrug thereof or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, or pentazocine;

a nonsteroidal antiinflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, or zomepirac;

a barbiturate sedative, e.g. amobarbital, aprobarbital, butabarbital, butalbital, mephobarbital, metharbital, methohexital, pentobarbital, phenobarbital, secobarbital, talbutal, thiamylal, or thiopental;

a benzodiazepine having a sedative action, e.g. chlordiazepoxide, clorazepate, diazepam, flurazepam, lorazepam, oxazepam, temazepam, or triazolam;

an H1 antagonist having a sedative action, e.g. diphenhydramine, pyrilamine, promethazine, chlorpheniramine, or chlorcyclizine;

a sedative such as glutethimide, meprobamate, methaqualone, or dichloralphenazone;

a skeletal muscle relaxant, e.g. baclofen, carisoprodol, chlorzoxazone, cyclobenzaprine, methocarbamol, or orphenadrine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil, or (−)-(R)-6-{2-[4-(3-fluorophenyl)-4-hydroxy-1-piperidinyl]-1-hydroxyethyl-3,4-dihydro-2 (1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinol-2-yl)-5-(2-pyridyl)quinazoline;

a tricyclic antidepressant, e.g. desipramine, imipramine, amitriptyline, or nortriptyline;

an anticonvulsant, e.g. carbamazepine, lamotrigine, topiramate, or valproate;

a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-

(4-methylphenyl)-7H-[1,4]diazocino[2,1-g][1,7]-naphthyridine-6, 13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant, or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospiumchloride, darifenacin, solifenacin, temiverine, or ipratropium;

a COX-2 selective inhibitor, e.g. celecoxib, rofecoxib, parecoxib, valdecoxib, deracoxib, etoricoxib, or lumiracoxib;

a coal-tar analgesic, e.g. paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark), or sarizotan;

a vanilloid receptor agonist (e.g. resiniferatoxin) or antagonist (e.g. capsazepine);

a transient receptor potential cation channel subtype (V1, V2, V3, V4, M8, M2, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan, or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594), or nicotine;

Tramadol (registered trademark);

a PDEV inhibitor, such as 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino [2′,1′:6,1]pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, or 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (3-(aminomethyl)bicyclo[3.2.0]hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl)cyclohexyl)methyl)-4H-[1,2,4]oxadiazol-5-one, C-[1-((1H-tetrazol-5-yl)methyl)cycloheptyl]methylamine, (3S,4S)-(1-(aminomethyl)-3,4-dimethylcyclopentyl) acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, or (3R,4R,5R)-3-amino-4,5-dimethyloctanoic acid;

a cannabinoid;

a metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, or trazodone;

a noradrenaline (norepinephrine) reuptake inhibitor, such as maprotiline, lofepramine, mirtazapine, oxaprotiline, fezolamine, tomoxetine, mianserin, bupropion, bupropion metabolite hydroxybupropion, nomifensine, or viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran, or imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide, or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057), or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-meth yl-2-quinolone (ZD-2138), or 2,3,5-trimethyl-6-(3-pyridylmethyl)-1,4-benzoquinone (CV-6504);

a sodium channel blocker, such as lidocaine;

a calcium channel blocker, such as ziconotide, zonisamide, or mibefradil;

a 5-HT3 antagonist, such as ondansetron;

a chemotherapy drug such as oxaliplatin, 5-fluorouracil, leucovorin, or paclitaxel;

a calcitonin gene related peptide (CGRP) antagonist;

a bradykinin (BK1 and BK2) antagonist;

a voltage gated sodium dependent channel blocker ($Na_{v1.7}$, $Na_{v1.8}$);

a voltage dependent calcium channel blocker (N-type, T-type);
a P2X (ion channel type ATP receptor) antagonist;
an acid-sensing ion channel (ASIC1a, ASIC3) antagonist;
an angiotensin-converting enzyme (ACE) inhibitors, such as AT2 antagonist;
an Angiotensin receptor blockers (ARBs);
a direct renin inhibitors (DRIs);
mineralocorticoid receptor antagonists (MRAs);
funny channel (If channel) inhibitor, such as ivabradine;
a Chemokine CCR2B receptor antagonist;
a Cathepsin (B, S, K) inhibitor;
a signal receptor agonist or antagonist;
cardiac sarcomere modulators, such as omecamtiv mecarbil (OM), or MYK-491, Mavacamten,
soluble guanylate cyclase (sGC) stimulators, such as vericiguat,
apelin receptor agonists,
a drugs for heart failure, such as Entresto (registered trademark) which is a combination of sacubitril and valsartan,
or the pharmaceutically acceptable salts, or the solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrated compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or (II) or pharmaceutically acceptable salt thereof and a sterile vehicle. Formulations for injection may be presented in unit dosage form e.g. in ampoules or in multi-dose, utilising a compound of formula (I) or (II) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

Compounds of formula (I) or (II) or pharmaceutically acceptable salts thereof may also be formulated in rectal compositions such as suppositories or retention enemas, e.g. containing conventional suppository bases such as cocoa butter or other glycerides.

Compounds of formula (I) or (II) or pharmaceutically acceptable salts may also be formulated as depot preparations. Such long acting formulations may be administered by implantation (for example subcutaneously or intramuscularly) or by intramuscular injection. Thus, for example, the compounds of formula (I) or (II) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, compounds formula (I) or (II) or pharmaceutically acceptable salts thereof may be formulated as solutions for administration via a suitable metered or unitary dose device or alternatively as a powder mix with a suitable carrier for administration using a suitable delivery device. Thus compounds of formula (I) or (II) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) or (II) and pharmaceutically acceptable salts thereof may be formulated for topical administration in the form of ointments, creams, gels, lotions, pack, tape, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

BINAP tri-o-tolylphosphine, triphenylarsine, 2,2'-bis(diphenylphosphino)-1,1'-binaphthyl
Boc tert-Butoxycarbonyl
JohnPhos 2-(di-tert-butylphosphino)biphenyl
CDI 1,1'-Carbonyldiimidazole
CyJohnPhos 2-(dichlorohexylphosphino)biphenyl
DABCO 1,4-diazabicyclo[2.2.2]octane DavePhos 2-(dicyclohexylphosphino)-2'-(dimethylamino)biphenyl
dba dibenzylideneacetone
DBN 1,5-diazabicyclo[4.3.0]non-5-ene
DBU 1,8-Diazabicyclo[5.4.0]undec-7-ene
DCM Dichloromethane
DIEA N,N-Diisopropylethylamine
DME 1,2-Dimethoxyethane
DMEDA N,N'-Dimethylethylenediamine
DMF N,N-Dimethylformamide
DMA N,N-Dimethylacetamide
DMAP N,N-Dimethyl-4-aminopyridine
DMSO Dimethyl sulfoxide
EDC 1-Ethyl-3-(3-dimethylaminopropyl)carbodiimide Hydrochloride
ESI Electrospray ionization
EtOAc Ethyl acetate
EtOH Ethanol
Ex Example
HOBT 1-Hydroxybenzotriazole
HATU O-(7-Aza-1H-benzotriazol-1-yl)-N,N,N',N'-tetramethyluronium hexafluorophosphate
HBTU O-(Benzotriazol-1-yl)-N,N,N',N'-tetramethyluronium hexafluorophosphate
HPLC High-Performance liquid chromatography
IPE Diisopropyl ether
Ir[dF(CF$_3$)ppy]$_2$(dtbbpy)PF$_6$ [4,4'-bis(1,1-dimethylethyl)-2,2'-bipyridine-N$^1$,N$^{1'}$]bis[3,5-difluoro-2-[5-(trifluoromethyl)-2-pyridinyl-N]phenyl-C]iridium(III) hexafluorophosphate
LC Liquid chromatography
LG Leaving group
tR Retention time
MeCN Acetonitrile
MeOH Methanol
MHz Megahertz
Ms Methanesulfonyl
MS Mass spectrometry
MS 4A Molecular sieves 4 angstrom
NMP N-methylpyrrolidone
NMR Nuclear magnetic resonance
Pd(dppf)Cl$_2$ [1,1-Bis(diphenylphosphino)ferrocene]dichloropalladium(II)
Pd(PPh$_3$)$_4$ Tetrakis(triphenylphospine)palladium(0)
rt Room temperature
SFC Supercritical fluid chromatography
SPhos 2-dicyclohexylphosphino-2',6'-dimethoxybiphenyl
tBuXPhos 2-di-tert-butylphosphino-2',4',6'-triisopropylbiphenyl
T3P (trademark) Propylphosphonic acid anhydride (Cyclic Trimer)
TEA Triethylamine
TFA Trifluoroacetic Acid
THF Tetrahydrofuran
THP Tetrahydropyranyl
TLC Thin layer chromatography
TMEDA N,N,N',N'-tetramethylethylenediamine
TosMIC p-Toluenesulfonylmethyl isocianide
UV Ultraviolet
XPhos 2-Dicyclohexylphosphino-2',4',6'-triisopropylbiphenyl
Xantphos 4,5-Bis(diphenylphosphino)-9,9-dimethylxanthene The term of "base" is likewise no particular restriction on the nature of the bases used, and any base commonly used in reactions of this type may equally be used here. Examples of such bases include, but not limited to: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium tert-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(tert-butyl)-4-methylpyridine, quinoline, N,N-dimethylaniline, N,N-diethylaniline, N,N-dimethyl-4-aminopyridine (DMAP), 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DMAP, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and 1,4-dioxane; aromatic hydrocarbons, such as benzene, toluene and nitrobenzene; amides, such as, DMF, DMA, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane and chloroform are preferred.

The invention is illustrated in the following non-limiting examples in which, unless stated otherwise: all reagents are commercially available, all operations are carried out at room or ambient temperature, that is, in the range of about 18-25° C.; microwave reactions are carried out using Biotage Initiator or Biotage Initiator+; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 F$_{254}$ precoated TLC plates or Merck NH$_2$ F$_{254}$ precoated HPTLC plates), mass spectrometry or NMR. Yields are given for illustrative purposes only. Flash column chromatography is carried out using Biotage SNAP KP-Sil, Biotage SNAP Isolute NH2, Merck silica gel 60 (230-400 mesh ASTM), Fuji Silysia Chromatorex (registered trademark) NH-DM1020 and NH-DM2035, Wako Wakogel C300-HG, Yamazen Hi-FLASH column, or YMC DispoPack-SIL. The pre-purification for the HPLC (preparative LC-MS) is carried out using a strong cation exchange cartridge (ISOLUTE (registered trademark) SCX-2, 1 g/6 mL, Biotage), or strong anion exchange cartridge (ISOLUTE (registered trademark) PE-AX, 1 g/6 mL, Biotage). The purification of compounds using HPLC (preparative LC-MS) or SFC (preparative SFC-MS) is performed by the following apparatus and conditions.

HPLC:
Apparatus: Waters MS-trigger AutoPurification (registered trademark) system
Column: Waters XBridge C8, 19 mm×50 mm, 5 micrometer particle or Waters XBridge C18, 19 mm×50 mm, 5 micrometer particle
Mobile phase 1: (A) 0.05% (v/v) ammonia aqueous solution, (B) MeOH or MeCN
Mobile phase 2: (A) 0.05% (v/v) formic acid aqueous solution, (B) MeOH or MeCN
Mobile phase 3: (A) 10 mM ammonium formate aqueous solution, (B) MeCN/water=90/10 (v/v)
Flow rate: 20 mL/min
Gradient: A/B (95/5) to A/B (5/95) in 5 or 7 or 10 min SFC:
Apparatus: Waters Prep15 SFC system with ACQUITY QDa Detector
Column: Waters Torus 2-PIC, 10 mm×150 mm, 5 micrometer particle; Waters Torus DEA, 10 mm×150 mm, 5 micrometer particle; Waters Torus DIOL, 10 mm×150 mm, 5 micrometer particle; Waters Torus 1-AA, 10 mm×150 mm, 5 micrometer particle
Mobile phase: (A) Carbon dioxide ($CO_2$), (B) MeOH or 10 mM ammonia in MeOH
Flow rate: 15 mL/min
Gradient: A/B (95/5) to A/B (60/40) in 7 or 10 min
Temperature: 40° C.
Pressure: 120 bar (1740 psi)

Mass spectral data (ESI) are obtained by Waters Alliance HPLC system with ZQ mass spectrometer and UV detector. NMR data are determined by 400 MHz (JEOL JNM-ECZ400S) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (moles), mmol (millimoles).

Each prepared compound is generally named by ChemBioDraw (Ultra, version 12.0, CambridgeSoft).

Conditions for Determining HPLC Retention Time:
QC Method:
Apparatus: Waters Acquity Ultra Performance LC with PDA Detector and ZQ mass spectrometer
Column: YMC Triart C18, 2.1×100 mm, 1.9 micrometer particle
Column Temperature: 60° C.
PDA detection: 200-400 nm scan
MS Detection: ESI Positive/Negative Mode
Mobile Phase:
A: 10 mM ammonium acetate aqueous solution
B: acetonitrile

| Time (min) | A (%) | B (%) |
|---|---|---|
| 0 | 90 | 10 |
| 0.05 | 90 | 10 |
| 1.9 | 5 | 95 |
| 2.5 | 5 | 95 |
| 2.51 | 90 | 10 |
| run time | | 3 min |
| Flow rate | | 0.75 mL/min |

All of the compounds of the formula (I) and (II) can be prepared by the procedures described in the general methods presented below or by the specific methods described in the Example synthesis part and Intermediate synthesis part, or by routine modifications thereof. The present invention also encompasses any one or more of these processes for preparing the compound of formula (I) and (II), in addition to any novel intermediates used therein.

In the following general methods, descriptors ($R^1$, $R^2$, $R^3$, $R^4$, $R^5$, $R^6$, A, B, X, p, q, $Y^1$, $Y^2$, $Y^3$, and $Y^4$) are as previously defined for the compound of the formula (I) and (II) unless otherwise stated. All starting materials in the following general syntheses may be commercially available or obtained by the conventional methods known to those skilled in the art, otherwise noted in the Intermediate synthesis part.

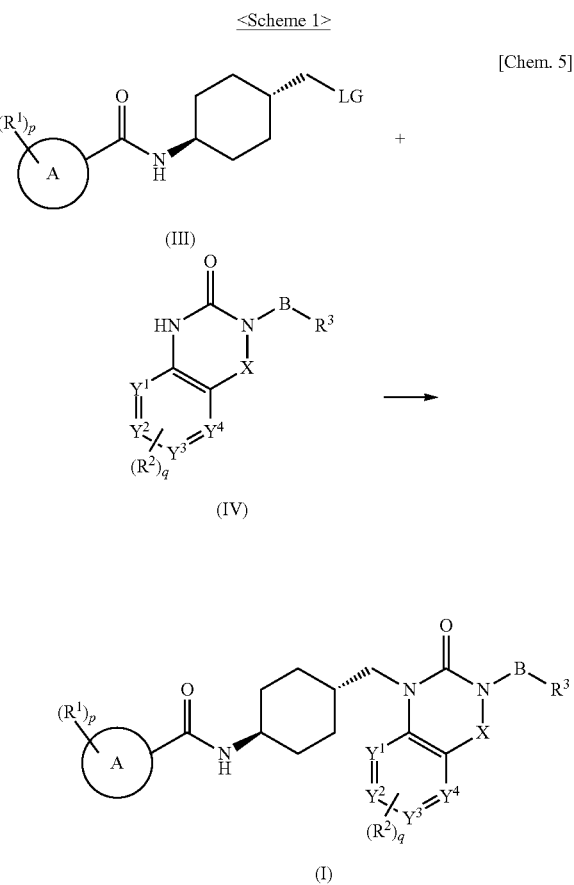

In Scheme 1, a compound of formula (I) can be prepared by the substitution reaction of a compound of formula (III) with a compound of formula (IV) in the presence of a suitable base in an inert solvent. LG is a suitable leaving group such as O-trifluoromethanesulfonate, O-tosylate, O-mesylate, iodide, bromide, chloride, fluoride. Examples of suitable base include, but not limited to, such as sodium hydride, potassium carbonate, cesium carbonate, potassium tert-butoxide, triethyl amine, pyridine, and N,N-diisopropylethylamine. Examples of suitable organic solvent include such as THF, 1,4-dioxane, DMF, DMSO, MeCN, DMA, NMP, toluene. The reaction can be carried out at a temperature from about −20 to 200° C., more preferably from about 0 to 100° C. Reaction times are, in general, from about 30 minutes to 48 hours, more preferably from about 1 hour to 24 hours.

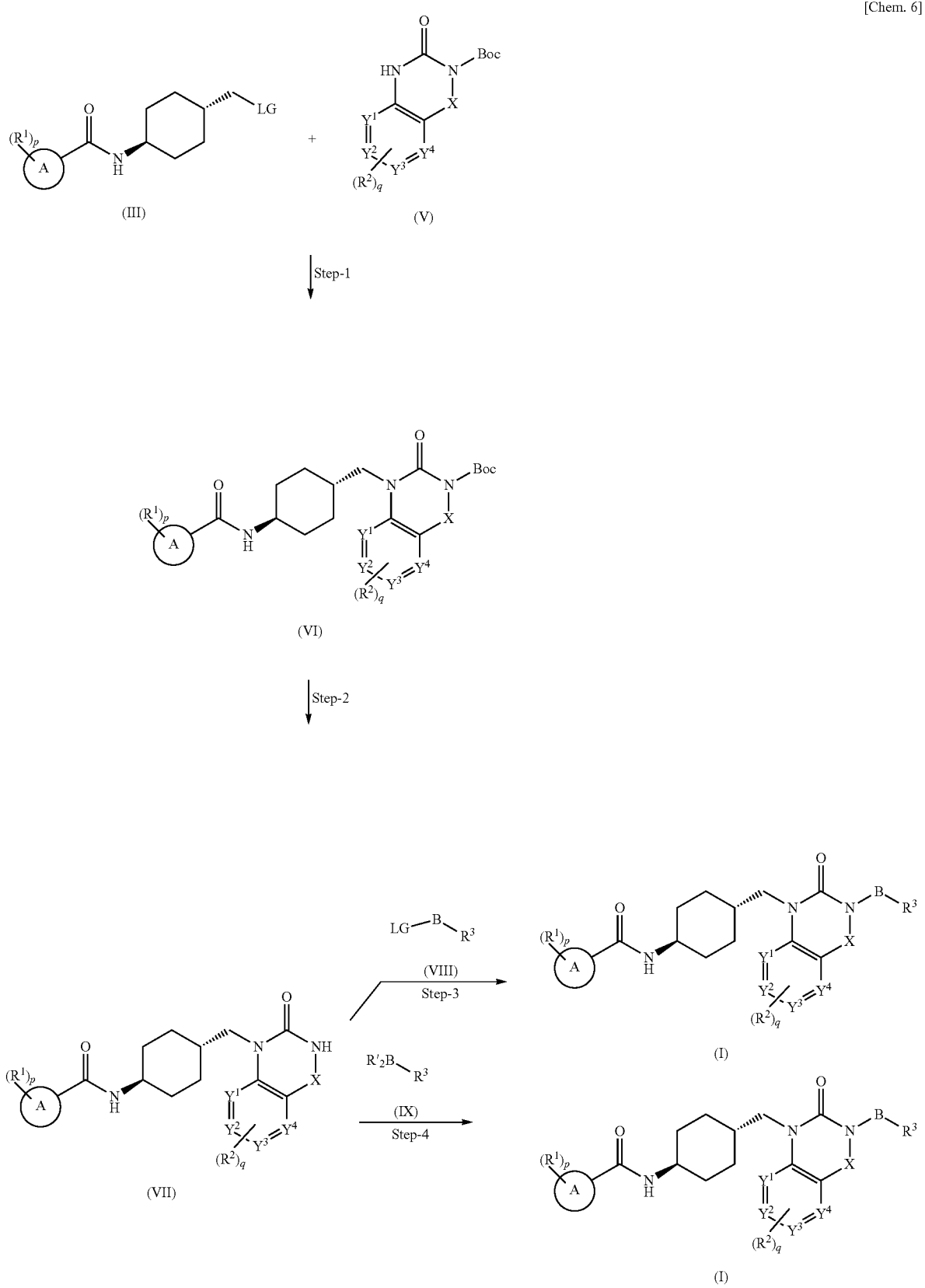

All compounds in Scheme 2, X is bond.

In Step-1 of Scheme 2, a compound of formula (VI) can be prepared a compound of formula (III) and a compound of formula (V) in the substitution reaction conditions by the similar general protocol in Scheme 1.

In Step-2 of Scheme 2, deprotection of Boc group by usual acidic treatment (for example, hydrogen chloride in 1,4-dioxane, TFA-DCM) to afford a compound of formula (VII).

In Step-3 of Scheme 2, a compound of formula (I) can be prepared from a compound of formula (VII) and a compound of formula (VIII) by the similar general protocol in Scheme 1.

In Step-3 of Scheme 2, when B is a chemical bond, a compound of formula (I) can be prepared by cross coupling reaction of a compound of formula (VII) with a compound of formula (VIII) under coupling conditions in suitable organic solvents in the presence of a suitable transition metal catalyst and in the presence or absence of a base. Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(I) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bis(acetonitrile)dichloropalladium(II), bis(dibenzylideneacetone)palladium(0), tris(dibenzylideneacetone)dipalladium (0), [1,1'-bis(diphenylphosphino)ferrocene]palladium(II) dichloride and bis(di-tert-butyl(4-dimethylaminophenyl)phosphine)dichloropalladium(II). Preferred catalysts are tetrakis(triphenylphosphine)palladium(0), bis(triphenylphosphine)palladium(II) chloride, palladium(II) acetate, palladium(II) chloride, bis(acetonitrile)dichloropalladium (0), bis(dibenzylideneacetone)palladium(0), tris(dibenzylideneacetone)dipalladium(0), [1,1-bis(diphenylphosphino)ferrocene]palladium(II) dichloride and bis(di-tert-butyl(4-dimethylaminophenyl)phosphine)dichloropalla-dium(II). Examples of suitable organic solvent include: THF; 1,4-dioxane; DMF; MeCN; DMSO; DMA; alcohols, such as methanol or ethanol; halogenated hydrocarbons, such as DCM, 1,2-dichloroethane, chloroform or carbon tetrachloride; and diethylether. Example of suitable base include: tripotassium phosphate, sodium bicarbonate, sodium carbonate, cesium carbonate and potassium carbonate. This reaction can be carried out in the presence of a suitable additive agent. Examples of such additive agents include: 4,5-Bis(diphenylphosphino)-9,9-dimethylxanthene (Xantphos), triphenylphosphine, tri-tert-butylphosphine, 1,1'-bis(diphenylphosphino)ferrocene, tri-2-furylphosphine, trio-tolylphosphine, triphenylarsine, 2,2'-bis(diphenylphosphino)-1,1'-binaphthyl (BINAP), 2-(dichlorohexylphosphino)biphenyl (CyJohnPhos), 2-(dicyclohexylphosphino)-2'-(dimethylamino)biphenyl (DavePhos), 2-dicyclohexylphosphino-2',4',6'-triisopropylbiphenyl (XPhos), 2-dicyclohexylphosphino-2',6'-dimethoxybiphenyl (SPhos), 2-di-tert-butylphosphino-2',4',6'-triisopropylbiphenyl (tBuXPhos), 2-(di-tert-butylphosphino)biphenyl (JohnPhos), N,N'-dimethylethylenediamine (DMEDA), N,N,N',N'-tetramethylethylenediamine (TMEDA), 2,2'-bipyridine, 1,10-phenanthroline. The reaction can be carried out at a temperature from about 50 to 200° C., more preferably from about 80 to 150° C. Reaction times are, in general, from about 5 minutes to 48 hours, more preferably from about 30 minutes to 24 hours. In an alternative case, the reaction can be carried out with microwave system. The reaction can be carried out at a temperature in the range from about 100 to 200° C., preferably in the range from about 120 to 160° C. Reaction times are, in general, from about 10 minutes to 3 hours, preferably from about 15 minutes to 1 hour.

In Step-4 of Scheme 2, when B is a chemical bond, a compound of formula (I) can be prepared from a compound of formula (VII) and a suitable boronic acid or borate of formula (IX) and a suitable copper salt and in the presence or absence of a base and in the presence or absence of a dehydrating reagent in an inert solvent. In a representation of $BR'_s$, R' means OH, O-low alkyl or fluorine, and s is 2 or 3, B is boron atom. As the concrete representation of substituent, $B(OH)_2$, $B(O\text{-lower alkyl})_2$, $B(\text{lower alkyl})_2$, potassium trifluoroborate $(BF_3^-)(BF_3K)$ are described, but when $B(O\text{-lower alkyl})_2$ may form the cyclic ring between the lower alkyl groups. Example of a suitable copper salt include, copper(0), copper(1) acetate, copper(1) bromide, copper(1) chloride, copper(1) iodide, copper(I) oxide, copper(II) trifluoromethanesulfonate, copper(II) acetate, copper (II) bromide, copper(II) chloride, copper(II) iodide, copper (II) oxide, copper(II) trifluoromethanesulfonate. Examples of a suitable base include, but not limited to, such as triethyl amine, pyridine, and N,N-diisopropylethylamine. Examples of suitable organic solvent include such as DCM, dichloroethane, MeOH, EtOH, THF, 1,4-dioxane, DMF, MeCN, DMA, toluene. Examples of a suitable dehydrating agent include, but not limited to, such as MS 4A, magnesium sulfate, sodium sulfate. The reaction can be carried out at a temperature from about −20 to 150° C., more preferably from about 0 to 100° C. Reaction times are, in general, from about 30 minutes to 7 days, more preferably from about 1 hour to 24 hours.

If a compound of formula (VIII) or (IX) has a protecting group, a deprotecting step is needed to afford a compound of formula (I). The deprotecting step can be carried out by the conventional methods known to those skilled in the art (typical protecting groups described in "Protective Groups in Organic Synthesis Forth Edition" edited by T. W. Greene et al. (John Wiley & Sons, 2007).

<Scheme 3>

[Chem. 7]

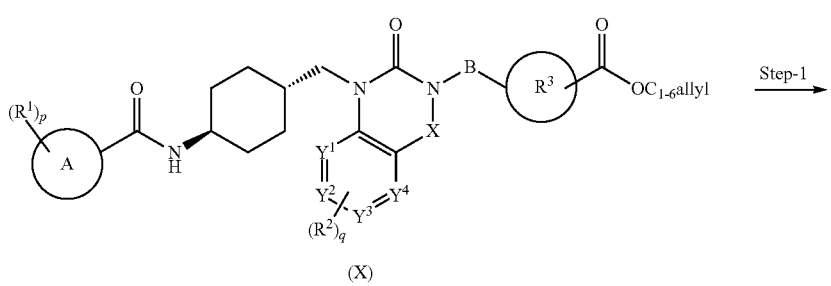

(X)

Step-1

-continued

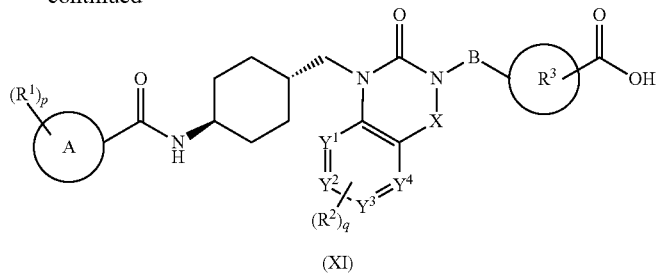

(XI)

Step-2

R⁵R⁶NH (XII) Step-3

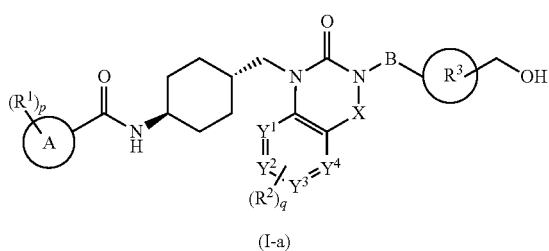

(I-a)

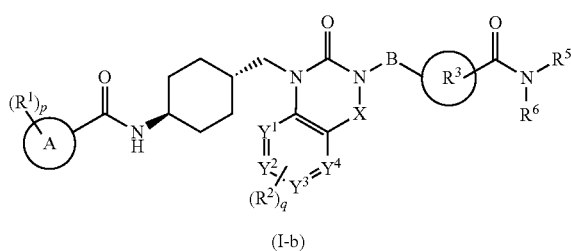

(I-b)

In Scheme 3, a compound of formula (X) can be prepared by the similar general protocol in Scheme 1.

In Step-1 of Scheme 3, a compound of formula (XI) can be prepared by the hydrolysis of a compound of formula (X). The hydrolysis can be carried out by the conventional procedures. In a typical procedure, the hydrolysis is conducted under basic conditions, e.g. in the presence of sodium hydroxide, potassium hydroxide or lithium hydroxide. Suitable solvents include, for example: alcohols such as water, methanol, ethanol, propanol, butanol, 2-methoxyethanol, and ethylene glycol; ethers such as THF, DME, and 1,4-dioxane; amides such as DMF and hexamethylphosphorictriamide; and sulfoxides such as DMSO. Preferred solvents are water, methanol, ethanol, propanol, THF, DME, 1,4-dioxane, DMF, and DMSO. This reaction can be carried out at a temperature in the range from about 20 to 100° C. for from about 5 minutes to 24 hours.

In Step-2 of Scheme 3, a compound of formula (I-a) can be prepared by the reduction of a compound of formula (XI). In a typical procedure, the reduction is conducted by using a reducing agent such as lithium aluminum hydride, borane, lithium borohydride, sodium borohydride in an inert solvent. Suitable solvents include, ethers such as THF, DME, and 1,4-dioxanel. This reaction can be carried out at a temperature in the range from about −80 to 100° C. for from about 5 minutes to 24 hours. In an alternative case, before the reduction of a compound of formula (XI) by using sodium borohydride in alcohols (such as water, MeOH, EtOH), a compound of formula (XI) can be reacted with a reagent (such as CDI, isobutyl chloroformate) for activating carboxylic acid moiety in the presence or absence of base (such as TEA, pyridine, DIEA) in an inert solvent (for example, THF, 1,4-dioxane).

In Step-3 of Scheme 3, a compound of formula (I-b) can be prepared from a compound of formula (XI) by the condensation with a compound of formula (XII) using a suitable condensation reagent such as HBTU, HATU, T3P (registered trademark), EDC, and EDC-HOBT, preferably under the presence of a base such as triethylamine, N,N-diisopropylethylamine, DMAP, DABCO, and DBU in a suitable solvent such as THF, DME, 1,4-dioxane, DMF, DMA, and DCM. This reaction can be carried out at a temperature in the range from about 5 to 60° C. for from about 1 hour to 48 hours.

<Scheme 4>

[Chem. 8]

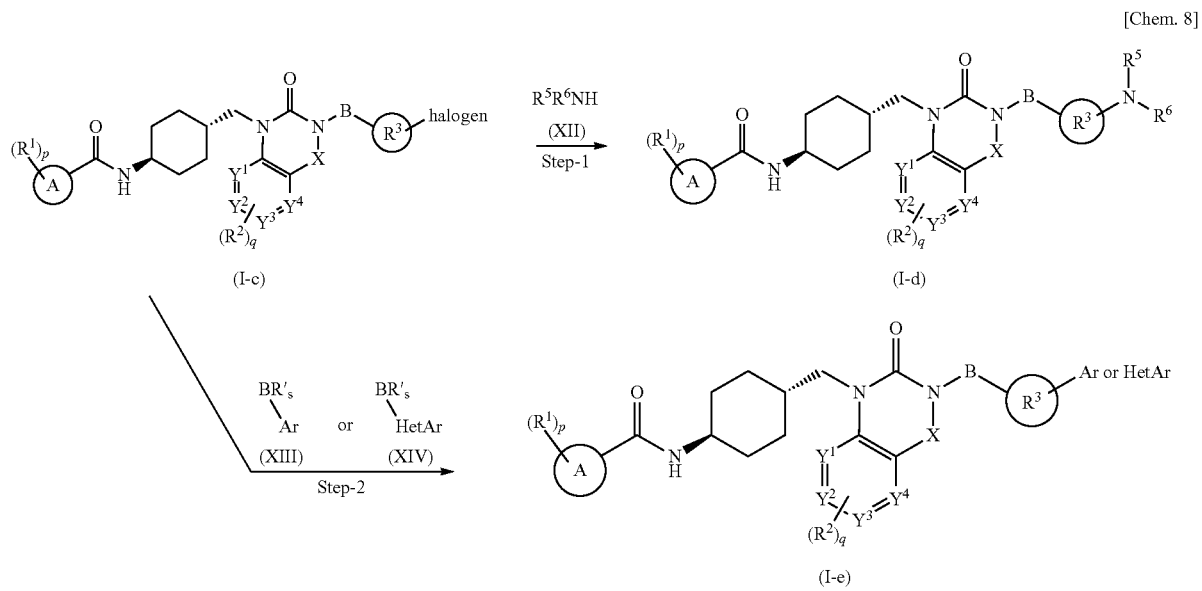

In Scheme 4, a compound of formula (I-c) can be prepared by the similar general protocol in Scheme 1.

In Step-1 of Scheme 4, a compound of formula (I-d) can be prepared from a compound of formula (I-c) and nucleophile (XII) by substitution reaction in the presence of a suitable base in an inert solvent. Examples of a suitable base include, but not limited to, such as sodium hydride, potassium carbonate, cesium carbonate, potassium tert-butoxide, triethyl amine, pyridine, DBU, and N,N-diisopropylethylamine. Examples of suitable organic solvent include such as THF, 1,4-dioxane, DMF, DMSO, MeCN, DMA, 2-propanol, NMP, toluene. The reaction can be carried out at a temperature from about −20 to 200° C., more preferably from about 0 to 100° C. Reaction times are, in general, from about 30 minutes to 48 hours, more preferably from about 1 hour to 24 hours. In an alternative case, the reaction can be carried out with microwave system. The reaction can be carried out at a temperature in the range from about 100 to 300° C. Reaction times are, in general, from about 10 minutes to 3 hours, preferably from about 15 minutes to 1 hour. As well, when $R^4$ is O-substituent (such as —O—$C_{1-6}$ alkyl, —O—$C_{3-7}$ cycloalkyl, and —O-heterocyclyl), a compound of formula (II) can be prepared similar manner in Step-1 of Scheme 4 by using suitable alcohol instead of nucleophile (XII).

In Step-2 of Scheme 4, a compound of formula (I-e) can be prepared by cross coupling reaction of a compound of formula (I-c) with a suitable boronic acid or borate of formula (XIII) and (XIV) in suitable organic solvents and in the presence of a suitable transition metal catalyst and in the presence or absence of a base and in the presence or absence of water. In a representation of BR′$_s$, R′ means OH, O-low alkyl or fluorine, and s is 2 or 3, B is boron atom. As the concrete representation of substituent, B(OH)$_2$, B(O-lower alkyl)$_2$, B(lower alkyl)$_2$, potassium trifluoroborate (BF$_3$)(BF$_3$K) are described, but when B(O-lower alkyl)$_2$ may form the cyclic ring between the lower alkyl groups. Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bis(acetonitrile)dichloropalladium(II), bis(dibenzylideneacetone)palladium(0), tris(dibenzylideneacetone)dipalladium(0), [1,1′-bis(diphenylphosphino)ferrocene]palladium(II) dichloride and bis(di-tert-butyl(4-dimethylaminophenyl)phosphine)dichloropalladium(II). Preferred catalysts are tetrakis(triphenylphosphine)palladium(0), bis(triphenylphosphine)palladium(II) chloride, palladium(II) acetate, palladium(II) chloride, bis(acetonitrile)dichloropalladium (0), bis(dibenzylideneacetone)palladium(0), tris(dibenzylideneacetone)dipalladium(0), [1,1-bis(diphenylphosphino)ferrocene]palladium(II) dichloride and bis(di-tert-butyl(4-dimethylaminophenyl)phosphine)dichloropalladium(II). Examples of suitable organic solvent include: THF; 1,4-dioxane; DMF; MeCN; alcohols, such as methanol or ethanol; halogenated hydrocarbons, such as DCM, 1,2-dichloroethane, chloroform or carbon tetrachloride; and diethyl ether. Example of suitable base include: tripotassium phosphate, sodium bicarbonate, sodium carbonate and potassium carbonate. This reaction can be carried out in the presence of a suitable additive agent. Examples of such additive agents include: 4,5-Bis(diphenylphosphino)-9,9-dimethylxanthene, triphenylphosphine, tritert-butylphosphine, 1,1′-bis(diphenylphosphino)ferrocene, tri-2-furylphosphine, trio-tolylphosphine, 2-(dichlorohexyl- phosphino)biphenyl, triphenylarsine. The reaction can be carried out at a temperature from about 50 to 200° C., more preferably from about 80 to 150° C. Reaction times are, in general, from about 5 minutes to 48 hours, more preferably from about 30 minutes to 24 hours. In an alternative case, the reaction can be carried out with microwave system. The reaction can be carried out at a temperature in the range from about 100 to 200° C., preferably in the range from about 120 to 160° C. Reaction times are, in general, from about 10 minutes to 3 hours, preferably from about 15 minutes to 1 hour.

As well, when R⁴ is unsaturated substituent (such as alkenyl, cycloalkeyl, partially saturated heterocyclic ring), a compound of formula (I) can be prepared similar manner in Step-2 of Scheme 4. Furthermore, the unsaturated substituent can be transformed to saturated substituent (such as alkyl, cycloalkyl, saturated heterocyclic ring) by a general hydrogenation. A general hydrogenation can be carried out in the presence of a suitable transition metal catalyst under hydrogen atmosphere in suitable organic solvents. Examples of suitable transition metal catalysts include: platinum (IV) oxide, palladium on carbon, palladium-fibroin, palladium hydroxide, ruthenium on carbon. Examples of suitable organic solvent include such as THF, 1,4-dioxane, EtOAc, MeOH, EtOH, DMF, DMSO, MeCN, DMA, toluene. The reaction can be carried out at a temperature from about 0 to 100° C. Reaction times are, in general, from about 30 minutes to 48 hours, more preferably from about 1 hour to 24 hours.

If a compound of formula (XII), (XIII), or (XIV) has a protecting group, deprotecting step is needed to afford a compound of formula (I-d) and (I-e). The deprotecting step can be carried out by the conventional methods known to those skilled in the art (typical protecting groups described in "Protective Groups in Organic Synthesis Forth Edition" edited by T. W. Greene et al. (John Wiley & Sons, 2007).

ladium(II) dichloride and bis(di-tert-butyl(4-dimethylaminophenyl)phosphine)dichloropalladium(II). Preferred catalysts are tetrakis(triphenylphosphine)palladium(0), bis(triphenylphosphine)palladium(II) chloride, palladium(II) acetate, palladium(II) chloride, bis(acetonitrile)dichloropalladium(0), bis(dibenzylideneacetone)palladium(0), tris(dibenzylideneacetone)dipalladium(0), [1,1-bis(diphenylphosphino)ferrocene]palladium(II) dichloride and bis(di-tert-butyl(4-dimethylaminophenyl)phosphine)dichloropalladium(II). Examples of suitable organic solvent include: THF; 1,4-dioxane; DMF; DMSO; DMA; MeCN; alcohols, such as methanol or ethanol; halogenated hydrocarbons, such as DCM, 1,2-dichloroethane, chloroform or carbon tetrachloride; and diethylether. Example of suitable base include: tripotassium phosphate, sodium bicarbonate, sodium carbonate, cesium carbonate and potassium carbonate.

This reaction can be carried out in the presence of a suitable additive agent. Examples of such additive agents include: 4,5-Bis(diphenylphosphino)-9,9-dimethylxanthene (Xantphos), triphenylphosphine, tri-tert-butylphosphine, 1,1'-bis(diphenylphosphino)ferrocene, tri-2-furylphosphine, trio-tolylphosphine, triphenylarsine, 2,2'-bis(diphenylphosphino)-1,1'-binaphthyl (BINAP), 2-(dichlorohexylphosphino)biphenyl (CyJohnPhos), 2-(dicyclohexylphosphino)-

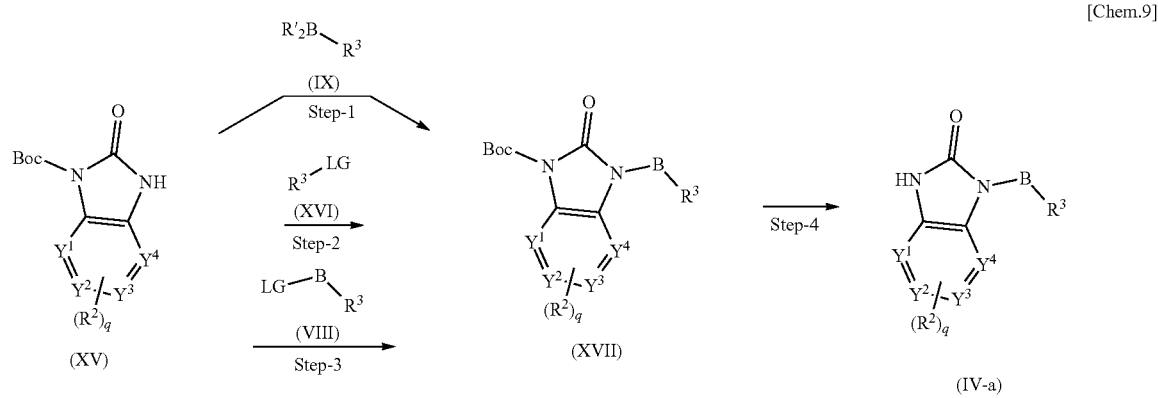

<Scheme 5>

[Chem.9]

In Step-1 of Scheme 5, a compound of formula (XVII) can be prepared from a compound of formula (XV) and a suitable boronic acid or borate of formula (IX) by the similar general protocol in Step 4 of Scheme 2.

In Step-2 of Scheme 5, when B is a chemical bond, a compound of formula (XVII) can be prepared by cross coupling reaction of a compound of formula (XV) with a compound of formula (XVI) under coupling conditions in suitable organic solvents in the presence of a suitable transition metal catalyst and in the presence or absence of a base. Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bis(acetonitrile)dichloropalladium(II), bis(dibenzylideneacetone)palladium(0), tris(dibenzylideneacetone)dipalladium(0), [1,1'-bis(diphenylphosphino)ferrocene]pal- 2'-(dimethylamino)biphenyl (DavePhos), 2-dicyclohexylphosphino-2',4',6'-triisopropylbiphenyl (XPhos), 2-dicyclohexylphosphino-2',6'-dimethoxybiphenyl (SPhos), 2-di-tert-butylphosphino-2',4',6'-triisopropylbiphenyl (tBuXPhos), 2-(di-tert-butylphosphino)biphenyl (JohnPhos), N,N'-dimethylethylenediamine (DMEDA), N,N,N',N'-tetramethylethylenediamine (TMEDA), 2,2'-bipyridine, 1,10-phenanthroline.

The reaction can be carried out at a temperature from about 50 to 200° C., more preferably from about 80 to 150° C. Reaction times are, in general, from about 5 minutes to 48 hours, more preferably from about 30 minutes to 24 hours. In an alternative case, the reaction can be carried out with microwave system. The reaction can be carried out at a temperature in the range from about 100 to 200° C., preferably in the range from about 120 to 160° C. Reaction times are, in general, from about 10 minutes to 3 hours, preferably from about 15 minutes to 1 hour.

In Step-3 of Scheme 5, a compound of formula (XVII) can be prepared from a compound of formula (XV) and a compound of formula (VIII) by the similar general protocol in Scheme 1.

In Step-4 of Scheme 5, deprotection of Boc group in a compound of formula (XVII) by usual acidic treatment (for example, hydrogen chloride in 1,4-dioxane, TFA-DCM) to afford a compound of formula (IV).

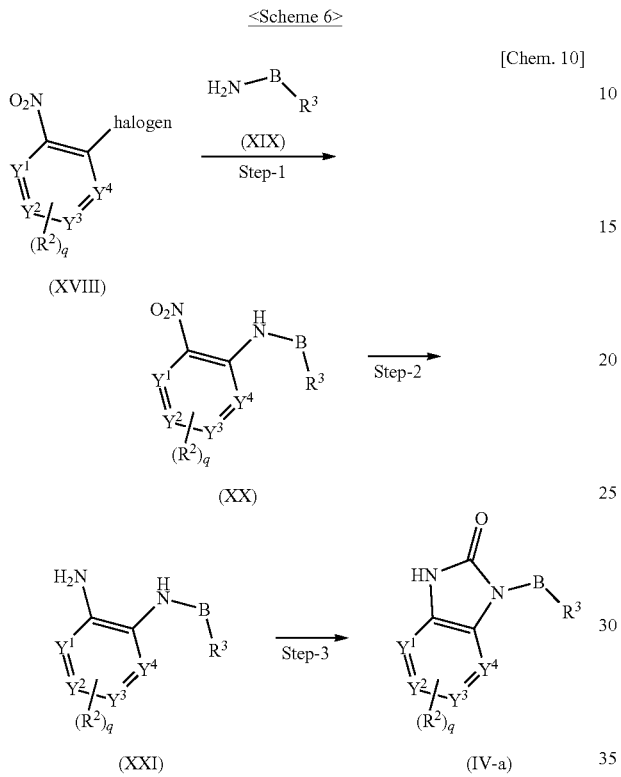

<Scheme 6>
[Chem. 10]

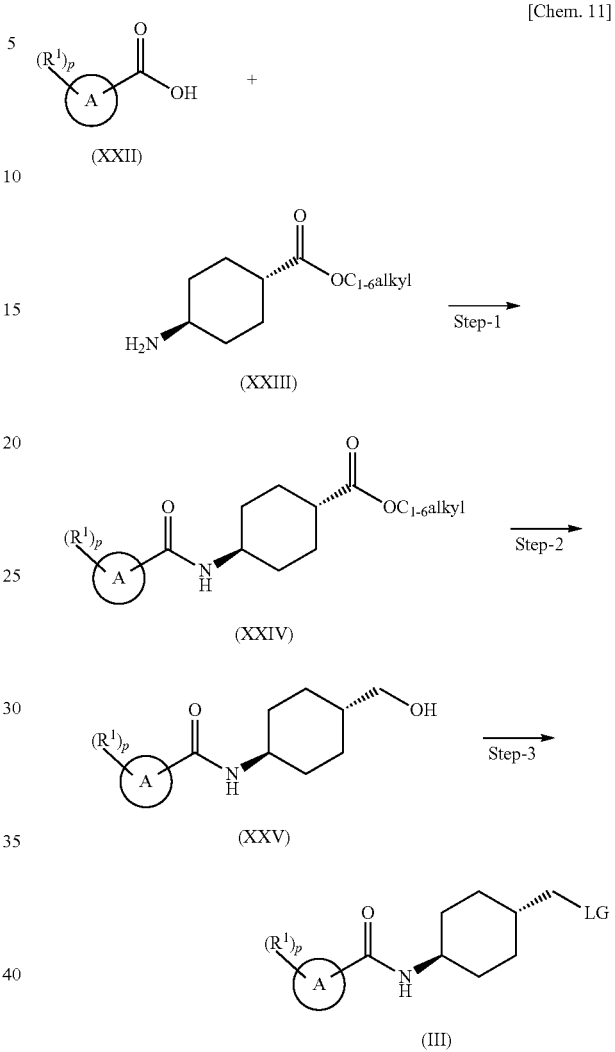

<Scheme 7>
[Chem. 11]

In Step-1 of Scheme 6, a compound of formula (XX) can be prepared from a compound of formula (XVIII) and a compound of formula (XIX) by the similar general protocol in Scheme 1. In alternative, a compound of formula (XX) can be prepared from a compound of formula (XVIII) and a compound of formula (XIX) by the similar general protocol of cross coupling reaction described in Step-2 of Scheme 5.

In Step-2 of Scheme 6, a compound of formula (XXI) can be prepared from a compound of formula (XX) by the similar general hydrogenation described in Step-2 of Scheme 4.

In alternative, a compound of formula (XXI) can be prepared from a compound of formula (XX) and suitable reducing agent (for example, iron, SnCl$_2$, zinc, osmium on carbon) and in the presence or absence acid (for example, acetic acid, hydrochloric acid, ammonium chloride) in suitable organic solvents (for example, MeOH, EtOH, water).

In Step-3 of Scheme 6, a compound of formula (IV-a) can be prepared from a compound of formula (XXI) reacted with CDI, phosgene, diphosgene, triphosgene or N,N'-disuccinimidyl carbonate, in suitable organic solvents in the presence or absence of a base. Examples of a suitable base include, but not limited to, such as triethyl amine, pyridine, DMAP, and N,N-diisopropylethylamine. Examples of suitable organic solvent include such as THF, 1,4-dioxane, DMF, DMSO, MeCN, DMA, toluene, DCM. The reaction can be carried out at a temperature from about −20 to 100° C., more preferably from about 0 to 50° C. Reaction times are, in general, from about 5 minutes to 48 hours, more preferably from about 1 hour to 24 hours.

In Step-1 of Scheme 7, a compound of formula (XXIV) can be prepared from a compound of formula (XXII) and a compound of formula (XXIII) by the similar general protocol in Step 3 of Scheme 3.

In Step-2 of Scheme 7, a compound of formula (XXV) can be prepared from a compound of formula (XXIV) by the similar general protocol in Step 2 of Scheme 3.

In Step-3 of Scheme 7, when LG is O-mesylate, a compound of formula (III) can be prepared by mesylation of a compound of formula (XXV) with Ms$_2$O or MsCl in suitable organic solvents in the presence of a base. Examples of a suitable base include, but not limited to, such as sodium hydride, potassium carbonate, cesium carbonate, potassium tert-butoxide, triethyl amine, pyridine, and N,N-diisopropylethylamine. Examples of suitable organic solvent include such as DCM, THF, 1,4-dioxane, DMF, DMSO, MeCN, DMA, toluene. The reaction can be carried out at a temperature from about −20 to 100° C., more preferably from about 0 to 50° C. Reaction times are, in general, from about 5 minutes to 48 hours, more preferably from about 1 hour to 24 hours.

Scheme 8

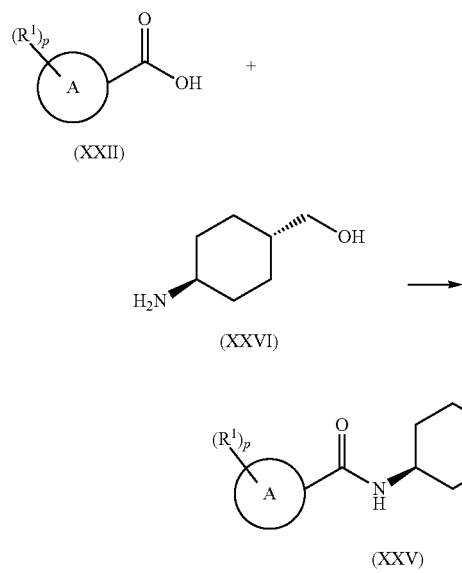

In Scheme 8, a compound of formula (XXV) can be prepared from a compound of formula (XXII) and a compound of formula (XXVI) by the similar general protocol in Step 3 of Scheme 3.

In Step-1 of Scheme 9, a compound of formula (XXVIII) can be prepared from a compound of formula (XXVII) and a compound of formula (IV) by the similar general protocol in Scheme 1.

In Step-2 of Scheme 9, deprotection of Boc group by usual acidic treatment (for example, hydrogen chloride in 1,4-dioxane, TFA-DCM) to afford a compound of formula (XXIX).

In Step-3 of Scheme 9, a compound of formula (I) can be prepared from a compound of formula (XXII) and a compound of formula (XXIX) by the similar general protocol in Step-3 of Scheme 3.

Scheme 9

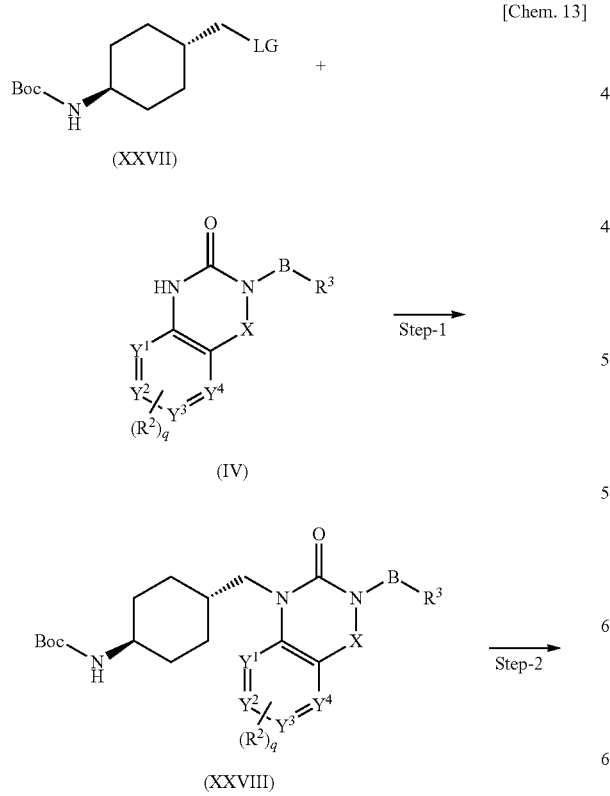

Scheme 10

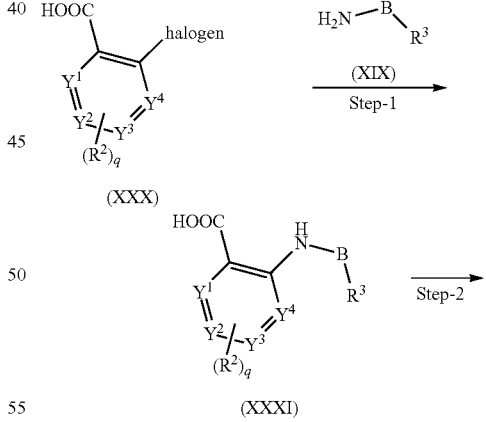

In Step-1 of Scheme 10, a compound of formula (XXXI) can be prepared from a compound of formula (XXX) and a compound of formula (XIX) by the similar general protocol in Scheme 1. In alternative, a compound of formula (XXXI) can be prepared from a compound of formula (XXX) and a compound of formula (XIX) by the similar general protocol of cross coupling reaction described in Step-2 of Scheme 5. In alternative, a compound of formula (XXXI) can be prepared from a compound of formula (XXX) and a compound of formula (XIX) in the presence or absence of suitable acid in an inert solvent. Example of suitable acid include, but not limited to, p-toluenesulfonic acid, benzensulfonic acid, acetic acid, TFA. Examples of suitable organic solvent include such as water, THF, 1,4-dioxane, DMF, DMSO, MeCN, DMA, toluene. The reaction can be carried out at a temperature from about −20 to 200° C., more preferably from about 20 to 100° C. Reaction times are, in general, from about 5 minutes to 48 hours, more preferably from about 1 hour to 24 hours.

In Step-2 of Scheme 10, a compound of formula (IV-a) can be prepared from a compound of formula (XXXI) under Curtius rearrangement conditions. The Curtius rearrangement can be carried out by the conventional procedures. In a typical procedure, the Curtius rearrangement can be conducted by using a suitable reagent such as diphenylphosphoryl azide in the presence or absence suitable base (such as TEA, DIEA, and pyridine) in an inert solvent (such as toluene, THF, and 1,4-dioxane). The reaction can be carried out at a temperature from about −20 to 200° C., more preferably from about 20 to 100° C. Reaction times are, in general, from about 5 minutes to 48 hours, more preferably from about 1 hour to 24 hours.

<Scheme 11>

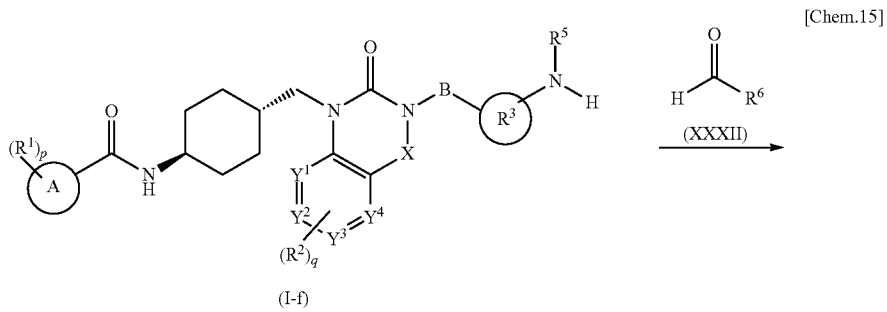

(I-f)

[Chem.15]

(XXXII)

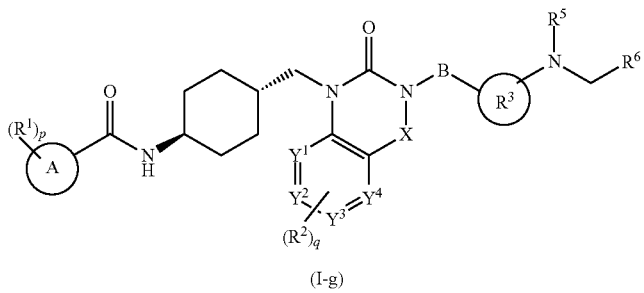

(I-g)

$R^6 = H$

In Scheme 11, a compound of formula (I-g) can be prepared from a compound of formula (1-f) and a compound of formula (XXXII) under reductive amination conditions. The reductive amination can be carried out by the conventional procedures. In a typical procedure, the reductive amination can be conducted by using a suitable reducing reagent such as sodium borohydride, sodium triacetoxyborohydride, and sodium cyanoborohydride in the presence or absence suitable acid (such as acetic acid) in an inert solvent (such as DCM, 1,2-dichloroethane). The reaction can be carried out at a temperature from about −20 to 200° C., more preferably from about 0 to 30° C. Reaction times are, in general, from about 5 minutes to 48 hours, more preferably from about 1 hour to 24 hours.

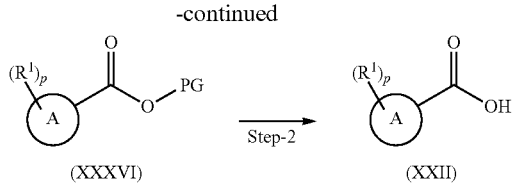

In Step-1 of Scheme 13, a compound of formula (XXXVI) can be prepared from a compound of formula (XXIV) and a compound of formula (XXXVI) by the similar general protocol in Scheme 12.

<Scheme 12>

[Chem. 16]

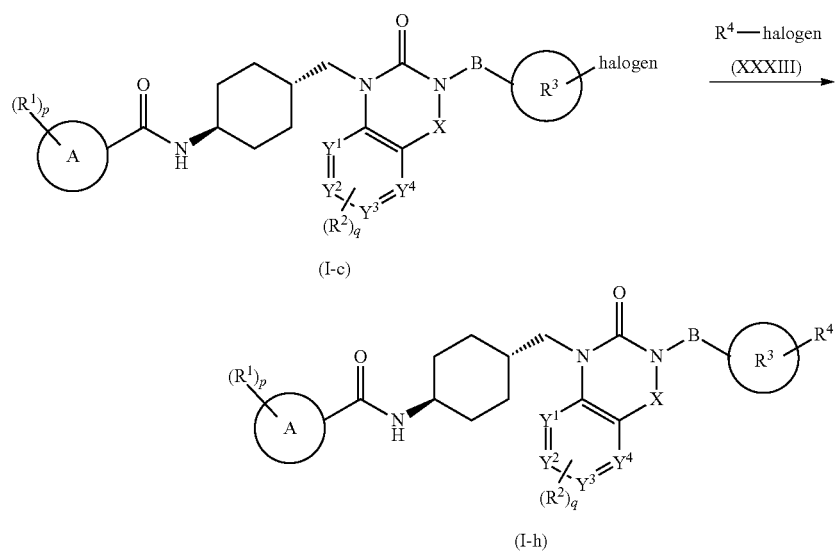

In Scheme 12, a compound of formula (I-h) can be prepared from a compound of formula (1-c) and a compound of formula (XXXIII) under photochemical reaction conditions. The photochemical reaction can be carried out by the conventional procedures. In a typical procedure, iridium catalyst (such as Ir(dF(CF$_3$)ppy)$_2$(dtbbpy)PF$_6$), nickel catalyst (such as NiCl$_2$-glyme, Ni(BF$_4$)$_2$, nickel(II) acetate, and nickel(II) acetylacetonate), ligand (such as 4,4'-di-tert-butyl-2,2'-dipyridine), additive (such as tris(trimethylsilyl)silane), and base (such as 2,6-lutidine, LiOH, and Na$_2$CO$_3$) in an inert solvent (such as DME, MeCN, 1,4-dioxane, and DMA) irradiated with Blue LED lamp. The reaction can be carried out at a temperature from about −20 to 100° C., more preferably from about 10 to 50° C. Reaction times are, in general, from about 5 minutes to 72 hours, more preferably from about 1 hour to 24 hours.

<Scheme 13>

[Chem.17]

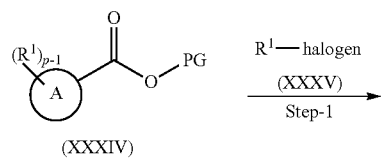

In Step-2 of Scheme 13, a compound of formula (XXII) can be prepared from a compound of formula (XXXVI) by the similar general protocol in Step-1 of Scheme 3.

Intermediate Synthesis Part

Each chemical structure of Intermediate synthesis part is described as a free-base.

Mesylate-1: ((1r,4r)-4-(5-chloro-2-methylnicotinamido)cyclohexyl)methyl methanesulfonate <Step-1>: (1r,4r)-methyl 4-(5-chloro-2-methylnicotinamido)cyclohexanecarboxylate A mixture of 5-chloro-2-methylnicotinic acid (5.23 g, 30.5 mmol), (1r,4r)-methyl 4-aminocyclohexanecarboxylate hydrochloride (5.90 g, 30.5 mmol), HOBt (9.34 g, 61.0 mmol), EDC (11.7 g, 61.0 mmol), and TEA (17 mL, 122 mmol) in DCM (200 mL) is stirred at room temperature overnight. To the mixture is added saturated aqueous sodium bicarbonate. The resultant mixture is extracted with EtOAc. The organic phase is washed with water and brine, dried over MgSO$_4$, filtered and concentrated in vacuo. The resultant residue is purified by column chromatography on silica-gel eluting with 0-70% EtOAc in n-hexane to give 8.55 g (90% yield) of the title compound as a white solid.

$^1$H-NMR (400 MHz, CDCl$_3$) delta 8.50 (1H, d, J=2.3 Hz), 7.62 (1H, d, J=2.7 Hz), 5.57 (1H, d, J=8.2 Hz), 4.00-3.91

(1H, m), 3.69 (3H, s), 2.62 (3H, s), 2.29 (1H, tt, J=12.3, 3.6 Hz), 2.21-2.18 (2H, m), 2.11-2.07 (2H, m), 1.68-1.56 (5H, m), 1.28-1.22 (2H, m). MS (ESI) m/z: 311.2 (M+H)$^+$.

<Step-2>:5-chloro-N-((1r,4r)-4-(hydroxymethyl) cyclohexyl)-2-methylnicotinamide

To a solution of (1r,4r)-methyl 4-(5-chloro-2-methylnicotinamido)cyclohexanecarboxylate (8.55 g, 27.5 mmol, Step-1 of Mesylate-1) in THF (180 mL) is added lithium aluminum hydride (1.57 g, 41.3 mmol) portion wise at 0° C. The reaction mixture is stirred at 0° C. After 1 hr the reaction is quenched with water (150 mL) and Rochelle salt (75 g). The resultant mixture is stirred at room temperature for 1 day. The resultant mixture is extracted with EtOAc, dried over MgSO$_4$, filtered and concentrated in vacuo to give 7.49 g (96% yield) of the title compound as a white solid.
$^1$H-NMR (400 MHz, CDCl$_3$) delta 8.50 (1H, d, J=2.3 Hz), 7.62 (1H, d, J=2.3 Hz), 5.58 (1H, d, J=7.8 Hz), 4.03-3.85 (1H, m), 3.54-3.46 (2H, m), 2.62 (3H, s), 2.22-2.11 (2H, m), 1.96-1.86 (2H, m), 1.60-1.44 (1H, m), 1.35 (1H, br s), 1.31-1.08 (4H, m). MS (ESI) m/z: 283.2 (M+H)$^+$.

<Step-3>: ((1r,4r)-4-(5-chloro-2-methylnicotinamido)cyclohexyl)methyl methanesulfonate To a mixture of 5-chloro-N-((1r,4r)-4-(hydroxymethyl) cyclohexyl)-2-methylnicotinamide (10.2 g, 35.9 mmol, Step-2 of Mesylate-1) and TEA (15 mL) in DCM (120 mL)/THF (60 mL) is added portionwise methanesulfonic anhydride (14.1 g, 81 mmol) at room temperature. The mixture is stirred at room temperature for 18 hrs. To the resultant mixture is added methanesulfonic anhydride (3.13 g, 18.0 mmol) and stirred at room temperature. After 1 hr, to the mixture is added methanesulfonic anhydride (3.13 g, 18.0 mmol) and stirred at room temperature. After 1.5 hrs, the reaction is quenched with saturated aqueous sodium bicarbonate (100 mL) and extracted with DCM (3×150 mL). The combined organic phase is dried over sodium sulfate, filtered and concentrated in vacuo. The residual solid is purified by column chromatography on silica-gel eluting with 0-100% EtOAc in DCM to give 10.5 g (81% yield) of the title compound as a white solid.
$^1$H-NMR (400 MHz, CDCl$_3$) delta 8.50 (1H, d, J=2.3 Hz), 7.62 (1H, d, J=2.3 Hz), 5.61 (1H, d, J=7.8 Hz), 4.07 (2H, d, J=6.6 Hz), 4.01-3.85 (1H, m), 3.02 (3H, s), 2.62 (3H, s), 2.24-2.15 (2H, m), 1.98-1.89 (2H, m), 1.85-1.71 (1H, m), 1.32-1.18 (4H, m). MS (ESI) m/z: 361.1 (M+H)$^+$.

Mesylate-2: ((1r,4r)-4-(2-ethyl-2H-indazole-3-carboxamido)cyclohexyl)methylmethanesulfonate <Step-1>: ethyl 2-ethyl-2H-indazole-3-carboxylate A mixture of 1H-indazole-3-carboxylic acid (500 mg, 3.08 mmol), iodoethane (1.44 g, 9.25 mmol) in DMSO (5 mL) is stirred at 80° C. for 5 hrs. The mixture is diluted with water. The mixture is extracted with EtOAc:n-hexane (1:1). The organic layer is dried over sodium sulfate, filtered and concentrated. The residue is purified by column chromatography on silica-gel eluting with 0-25% EtOAc in n-hexane to give 265 mg (39% yield) of the title compound as a pale yellow oil.
$^1$H-NMR (400 MHz, CDCl$_3$) delta 8.04 (1H, dt, J=8.7, 1.4 Hz), 7.79 (1H, dt, J=8.7, 1.4H), 7.32-7.25 (1H, m), 7.38-7.33 (1H, m), 4.96 (2H, q, J=7.3 Hz), 4.50 (2H, q, J=7.3 Hz), 1.58 (3H, t, J=7.3 Hz), 1.51 (3H, t, J=7.3 Hz). MS (ESI) m/z: 219.4 (M+H)$^+$.

<Step-2>: 2-ethyl-2H-indazole-3-carboxylic acid

A mixture of ethyl 2-ethyl-2H-indazole-3-carboxylate (265 mg, 1.21 mmol, Step-1 of Mesylate-2) and 2 M aqueous sodium hydroxide solution (2 mL) in THF (1 mL) and MeOH (1 mL) is stirred at 50° C. for 2 hrs. The mixture is acidified with 2 M hydrochloric acid. The mixture is extracted with EtOAc. The organic layer is dried over sodium sulfate and filtered. The filtrate is concentrated to give 224 mg (97% yield) of the title compound as a yellow solid.
MS (ESI) m/z: 189.3 (M−H)$^-$.

<Step-3>: (1r,4r)-methyl 4-(2-ethyl-2H-indazole-3-carboxamido)cyclohexanecarboxylate To a mixture of 2-ethyl-2H-indazole-3-carboxylic acid (224 mg, 1.18 mmol, Step-2 of Mesylate-2), (1r,4r)-methyl 4-aminocyclohexanecarboxylate hydrochloride (228 mg, 1.18 mmol), and TEA (0.66 mL, 4.71 mmol) in DCM (2 mL) is added 1.7 M T3P (registered trademark) in EtOAc (1.39 mL, 2.36 mmol) at rt. The mixture is stirred at rt for 1 hr. The mixture is quenched with saturated aqueous sodium bicarbonate. The mixture is extracted with EtOAc. The organic layer is dried over sodium sulfate, filtered and concentrated. The residue is purified by column chromatography on silica-gel eluting with 0-70% EtOAc in n-hexane to give 210 mg (54% yield) of the title compound as a pale yellow solid.
$^1$H-NMR (400 MHz, CDCl$_3$) delta 7.79 (1H, d, J=8.7 Hz), 7.63 (1H, d, J=8.7 Hz), 7.38-7.32 (1H, m), 7.28-7.22 (1H, m), 6.00 (1H, br d, J=7.8 Hz), 4.87 (2H, q, J=7.3 Hz), 4.12-3.98 (1H, m), 3.70 (3H, s), 2.38-2.24 (3H, m), 2.18-2.09 (2H, m), 1.73-1.53 (2H, m), 1.59 (3H, t, J=7.3 Hz), 1.42-1.30 (2H, m). MS (ESI) m/z: 330.3 (M+H)$^+$.

<Step-4>: 2-ethyl-N-((1r,4r)-4-(hydroxymethyl) cyclohexyl)-2H-indazole-3-carboxamide To a mixture of (1r,4r)-methyl 4-(2-ethyl-2H-indazole-3-carboxamido)cyclohexanecarboxylate (210 mg, 0.64 mmol, Step-3 of Mesylate-2) in THF (4 mL) is added lithium aluminum hydride (36 mg, 0.96 mmol) at 0° C. The mixture is stirred at 0° C. for 1 hr. The mixture is acidified with 2 M hydrochloric acid and extracted with EtOAc. The organic layer is dried over sodium sulfate and filtered. The filtrate is concentrated to give 192 mg (quantitative yield) of the title compound as a pale yellow solid.
$^1$H-NMR (400 MHz, CDCl$_3$) delta 7.79 (1H, dd, J=8.7, 0.9 Hz), 7.65 (1H, dd, J=8.7, 0.9 Hz), 7.37-7.31 (1H, m), 6.02 (1H, br d, J=7.8 Hz), 4.87 (2H, q, J=7.3 Hz), 4.09-3.97 (1H, m), 3.52 (2H, d, J=5.9 Hz), 2.29-2.22 (2H, m), 1.99-1.91 (2H, m), 1.59 (3H, t, J=7.3 Hz), 1.60-1.51 (1H, m), 1.41-1.30 (3H, m), 1.27-1.13 (2H, m). MS (ESI) m/z: 302.3 (M+H)$^+$.

<Step-5>: ((1r,4r)-4-(2-ethyl-2H-indazole-3-carboxamido)cyclohexyl)methyl methanesulfonate To a mixture of 2-ethyl-N-((1r,4r)-4-(hydroxymethyl)cyclohexyl)-2H-indazole-3-carboxamide (192 mg, 0.64 mmol, Step-4 of Mesylate-2) and TEA (0.18 mL, 1.27 mmol) in DCM (3 mL) is added methanesulfonic anhydride (166 mg, 0.96 mmol) at rt. The mixture is stirred at rt for 1 hr. The mixture is quenched with saturated aqueous sodium bicarbonate. The mixture is extracted with DCM. The organic layer is dried over sodium sulfate and filtered. The filtrate is concentrated to give 253 mg (quantitative yield) of the title compound as a pale orange solid.

$^1$H-NMR (400 MHz, CDCl$_3$) delta 7.79 (1H, dd, J=8.7, 0.9 Hz), 7.63 (1H, d, J=8.7 Hz), 7.38-7.30 (1H, m), 7.29-7.21 (1H, m), 6.02 (1H, d, J=7.3 Hz), 4.87 (2H, q, J=7.3 Hz), 4.09 (2H, d, J=6.4 Hz), 4.05-3.96 (1H, m), 3.03 (3H, s), 2.28 (2H, br d, J=12.3 Hz), 1.98 (2H, br d, J=12.3 Hz), 1.91-1.63 (1H, m), 1.59 (3H, t, J=7.3 Hz), 1.45-1.18 (4H, m). MS (ESI) m/z: 380.2 (M+H)$^+$.

Mesylate-3: ((1r,4r)-4-(5-chloro-2-(trifluoromethyl) nicotinamido)cyclohexyl)methyl methanesulfonate <Step-1>: 5-chloro-N-((1r,4r)-4-(hydroxymethyl) cyclohexyl)-2-(trifluoromethyl)nicotinamide A mixture of 5-chloro-2-(trifluoromethyl)nicotinic acid (2.28 g, 6.84 mmol), ((1r,4r)-4-aminocyclohexyl)methanol hydrochloride (1.47 g, 8.89 mmol), HBTU (3.89 g, 10.3 mmol), and TEA (3.81 mL, 27.4 mmol) in DMF (35 mL) is stirred at room temperature overnight. To the mixture is added water. The resultant mixture is extracted with EtOAc (×2). The organic phase is washed with 0.5 M HCl, water, then saturated aqueous sodium bicarbonate. The organic layer is dried over MgSO$_4$, filtered and concentrated. The resultant residue is purified by column chromatography on silica-gel eluting with 30-75% EtOAc in n-hexane to give 1.62 g (70% yield) of the title compound as a pale yellow solid.

$^1$H-NMR (400 MHz, DMSO-d$_6$) delta 8.87 (1H, d, J=2.3 Hz), 8.57 (1H, d, J=7.8 Hz), 8.22 (1H, d, J=2.3 Hz), 4.40 (1H, t, J=5.5 Hz), 3.69-3.57 (1H, m), 3.22 (1H, t, J=5.5 Hz), 1.91 (2H, br d, J=11.9 Hz), 1.77 (2H, br d, J=11.9 Hz), 1.38-1.26 (1H, m), 1.29-1.14 (2H, m), 1.03-0.99 (2H, m).

MS (ESI) m/z: 337.4 (M+H)$^+$.

<Step-2>: ((1r,4r)-4-(5-chloro-2-(trifluoromethyl) nicotinamido)cyclohexyl)methyl methanesulfonate To a mixture of 5-chloro-N-((1r,4r)-4-(hydroxymethyl) cyclohexyl)-2-(trifluoromethyl)nicotinamide (1.62 g, 4.81 mmol, Step-1 of Mesylate-3) and TEA (2.34 mL, 16.9 mmol) in DCM (10 mL)/THF (20 mL) is added portionwise methanesulfonic anhydride (1.26 g, 7.22 mmol) at 0° C. The mixture is stirred at room temperature for 1.5 hrs. The mixture is quenched with saturated aqueous sodium bicarbonate and extracted with DCM (×2). The combined organic phase is dried over MgSO$_4$, filtered and concentrated. The residual solid is purified by column chromatography on silica-gel eluting with 10-80% EtOAc in n-hexane to give 1.89 g (95% yield) of the title compound as an off-white solid.

$^1$H-NMR (400 MHz, CDCl$_3$) delta 8.69 (1H, d, J=2.3 Hz), 7.89 (1H, d, J=2.3 Hz), 5.64 (1H, d, J=7.8 Hz), 4.07 (2H, d, J=6.4 Hz), 4.00-3.89 (1H, m), 3.02 (3H, s), 2.23-2.14 (2H, m), 1.99-1.88 (2H, m), 1.85-1.68 (1H, m), 1.33-1.15 (4H, m).

MS (ESI) m/z: 415.4 (M+H)$^+$.

Mesylate-4: ((1r,4r)-4-(5-chloro-2-(difluoromethyl) nicotinamido)cyclohexyl)methyl methanesulfonate <Step-1>: 5-chloro-2-(difluoromethyl)-N-((1r,4r)-4-(hydroxymethyl)cyclohexyl)nicotinamide A mixture of 5-chloro-2-(difluoromethyl)nicotinic acid (500 mg, 2.41 mmol), ((1r,4r)-4-aminocyclohexyl)methanol hydrochloride (599 mg, 3.61 mmol), HBTU (1.37 g, 3.61 mmol), and TEA (1.68 mL, 12.0 mmol) in DCM (10 mL) is stirred at room temperature overnight. To the mixture is added saturated aqueous sodium bicarbonate. The resultant mixture is extracted with EtOAc. The organic layer is dried over sodium sulfate, filtered and concentrated. The resultant residue is purified by column chromatography on silica-gel eluting with 0-70% EtOAc in n-hexane to give 768 mg (quantitative yield) of the title compound as a pale yellow solid.

$^1$H-NMR (400 MHz, DMSO-d$_6$) delta 8.83 (1H, d, J=2.3 Hz), 8.64 (1H, d, J=7.8 Hz), 8.15 (1H, d, J=2.3 Hz), 7.15 (1H, t, J=54.0 Hz), 4.40 (1H, t, J=5.5 Hz), 3.70-3.60 (1H, m), 3.22 (2H, t, J=5.5 Hz), 1.99-1.88 (2H, m), 1.82-1.72 (2H, m), 1.40-1.13 (3H, m), 1.17-0.90 (2H, m).

MS (ESI) m/z: 319.3 (M+H)$^+$.

<Step-2>: ((1r,4r)-4-(5-chloro-2-(difluoromethyl) nicotinamido)cyclohexyl)methyl methanesulfonate To a mixture of 5-chloro-2-(difluoromethyl)-N-((1r,4r)-4-(hydroxymethyl)cyclohexyl)nicotinamide (768 mg, 2.41 mmol, Step-1 of Mesylate-4) and TEA (1.00 mL, 7.23 mmol) in DCM (4 mL)/THF (4 mL) is added portionwise methanesulfonic anhydride (630 mg, 3.61 mmol) at 0° C. The mixture is stirred at room temperature for 1 hr. The mixture is quenched with saturated aqueous sodium bicarbonate and extracted with DCM. The organic layer is dried over sodium sulfate, filtered and concentrated. The residual solid is purified by column chromatography on silica-gel eluting with 0-60% EtOAc in n-hexane to give 777 mg (81% yield) of the title compound as a pale yellow solid.

$^1$H-NMR (400 MHz, DMSO-d$_6$) delta 8.84 (1H, d, J=2.3 Hz), 8.67 (1H, d, J=7.8 Hz), 8.16 (1H, d, J=2.3 Hz), 7.15 (1H, t, J=54.0 Hz), 4.04 (2H, d, J=6.4 Hz), 3.75-3.62 (1H, m), 3.17 (3H, s), 1.95 (2H, br d, J=11.4 Hz), 1.80 (2H, br d, J=11.4 Hz), 1.72-1.61 (1H, m), 1.36-1.22 (2H, m), 1.18-1.14 (2H, m).

MS (ESI) m/z: 397.2 (M+H)$^+$.

Intermediate-1: 1-((tetrahydro-2H-pyran-4-yl) methyl)-1H-benzo[d]imidazol-2(3H)-one <Step-1>: tert-butyl 2-oxo-3-((tetrahydro-2H-pyran-4-yl)methyl)-2,3-dihydro-1H-benzo[d]imidazole-1-carboxylate To a mixture of tert-butyl 2-oxo-2,3-dihydro-1H-benzo [d]imidazole-1-carboxylate (100 mg, 0.43 mmol), 4-(iodomethyl)tetrahydro-2H-pyran (193 mg, 0.85 mmol), and cesium carbonate (278 mg, 0.85 mmol) in DMSO (1 mL) is stirred at 80° C. for 5 hrs. The mixture is diluted with water, extracted with EtOAc. The organic layer is concentrated. The residue is purified by column chromatography on silica-gel eluting with 0-80% EtOAc in n-hexane to give 113 mg (80% yield) of the title compound as a pale yellow gum.

$^1$H-NMR (400 MHz, CDCl$_3$) delta 7.83 (1H, dd, J=7.8, 0.9 Hz), 7.20 (1H, td, J=7.8, 0.9 Hz), 7.12 (1H, td, J=7.8, 0.9 Hz), 6.96 (1H, dd, J=7.8, 0.9 Hz), 3.97 (2H, dd, J=11.4, 2.7 Hz), 3.73 (2H, d, J=7.3 Hz), 3.33 (2H, td, J=11.9, 2.3 Hz), 2.22-2.08 (1H, m), 1.68 (9H, s), 1.65-1.55 (2H, m), 1.52-1.39 (2H, m). MS (ESI) m/z: 332.9 (M+H)$^+$.

<Step-2>: 1-((tetrahydro-2H-pyran-4-yl)methyl)-1H-benzo[d]imidazol-2(3H)-one

A solution of tert-butyl 2-oxo-3-((tetrahydro-2H-pyran-4-yl)methyl)-2,3-dihydro-1H-benzo[d]imidazole-1-carboxylate (113 mg, 0.34 mmol, Step-1 of Intermediate-1) in 4 M HCl in 1,4-dioxane (1 mL) is stirred at room temperature for 1 hr. The mixture is concentrated to give 79 mg (quantitative yield) of the title compound as a pale yellow solid.

MS (ESI) m/z: 233.0 (M+H)$^+$.

Intermediate-2: 3-((3-(((1r,4r)-4-(5-chloro-2-methyl-nicotinamido)cyclohexyl)methyl)-2-oxo-2,3-di-hydro-1H-benzo[d]imidazol-1-yl)methyl)benzoic acid <Step-1>: tert-butyl 3-(3-(methoxycarbonyl)ben-zyl)-2-oxo-2,3-dihydro-1H-benzo[d]imidazole-1-carboxylate The title compound is prepared in 91% yield (372 mg, a pale yellow gum) by the similar manner to Step-1 of Intermediate-1 using methyl 3-(bromomethyl)benzoate in place of 4-(iodomethyl)tetrahydro-2H-pyran.

MS (ESI) m/z: 383.1 (M+H)$^+$.

<Step-2>: methyl 3-((2-oxo-2,3-dihydro-1H-benzo [d]imidazol-1-yl)methyl)benzoate The title compound is prepared in quantitative yield (368 mg, a pale yellow solid) by the similar manner to Step-2 of Intermediate-1 using tert-butyl 3-(3-(methoxycarbonyl)ben-zyl)-2-oxo-2,3-dihydro-1H-benzo[d]imidazole-1-carboxy-late (372 mg, 0.97 mmol, Step-1 of Intermediate-2).

$^1$H-NMR (400 MHz, DMSO-d$_6$) delta 10.98 (1H, br s), 7.88 (1H, s), 7.83 (1H, d, J=7.8 Hz), 7.58 (1H, d, J=7.8 Hz), 7.47 (1H, t, J=7.8 Hz), 7.03-6.88 (4H, m), 5.06 (2H, s), 3.80 (3H, s). MS (ESI) m/z: 283.2 (M+H)$^+$.

<Step-3>: methyl 3-((3-(((1r,4r)-4-(5-chloro-2-methylnicotinamido)cyclohexyl)methyl)-2-oxo-2,3-dihydro-1H-benzo[d]imidazol-1-yl)methyl)benzoate A mixture of ((r,4r)-4-(5-chloro-2-methylnicotinamido) cyclohexyl)methyl methanesulfonate (100 mg, 0.28 mmol, Mesylate-1), methyl 3-((2-oxo-2,3-dihydro-1H-benzo[d] imidazol-1-yl)methyl)benzoate (78 mg, 0.28 mmol, Step-2 of Intermediate-2), and cesium carbonate (181 mg, 0.55 mmol) in DMSO (0.5 mL) is stirred at 80° C. for 2 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) to give 86 mg (57% yield) of the title compound as a yellow gum.

MS (ESI) m/z: 547.2 (M+H)$^+$.

<Step-4>: 3-((3-(((1r,4r)-4-(5-chloro-2-methylnicoti-namido)cyclohexyl)methyl)-2-oxo-2,3-dihydro-1H-benzo[d]imidazol-1-yl)methyl)benzoic acid A mixture of methyl 3-((3-(((1r,4r)-4-(5-chloro-2-meth-ylnicotinamido)cyclohexyl)methyl)-2-oxo-2,3-dihydro-1H-benzo[d]imidazol-1-yl)methyl)benzoate (86 mg, 0.16 mmol, Step-3 of Intermediate-2) and 2 M aqueous sodium hydrox-ide solution (0.5 mL) in THF (1 mL) and MeOH (1 mL) is stirred at 50° C. for 2 hrs. The mixture is neutralized with 2 M hydrochloric acid. The mixture is extracted with EtOAc. The organic layer is dried over sodium sulfate and filtered. The filtrate is concentrated to give 88 mg (quantitative yield) of the title compound as a yellow gum.

MS (ESI) m/z: 533.1 (M+H)$^+$.

Intermediate-3: 2-((3-(((1r,4r)-4-(5-chloro-2-methyl-nicotinamido)cyclohexyl)methyl)-2-oxo-2,3-di-hydro-1H-benzo[d]imidazol-1-yl)methyl)benzoic acid <Step-1>: tert-butyl 3-(2-(methoxycarbonyl)ben-zyl)-2-oxo-2,3-dihydro-1H-benzo[d]imidazole-1-carboxylate The title compound is prepared in quantitative yield (408 mg, a pale yellow gum) by the similar manner to Step-1 of Intermediate-1 using methyl 2-(chloromethyl)benzoate in place of 4-(iodomethyl)tetrahydro-2H-pyran.

$^1$H-NMR (400 MHz, CDCl$_3$) delta 8.05 (1H, dd, J=7.8, 1.8 Hz), 7.88 (1H, dd, J=7.8, 1.8 Hz), 7.39 (1H, td, J=7.8, 1.8 Hz), 7.32 (1H, td, J=7.8, 1.8 Hz), 7.17-7.08 (2H, m), 7.05 (1H, d, J=7.8 Hz), 6.80 (1H, dd, J=7.8, 1.8 Hz), 5.54 (2H, s), 3.97 (3H, s), 7.70 (9H, s). MS (ESI) m/z: 383.3 (M+H)$^+$.

<Step-2>: methyl 2-((2-oxo-2,3-dihydro-1H-benzo [d]imidazol-1-yl)methyl)benzoate The title compound is prepared in quantitative yield (301 mg, a pale yellow solid) by the similar manner to Step-2 of Intermediate-1 using tert-butyl 3-(2-(methoxycarbonyl)ben-zyl)-2-oxo-2,3-dihydro-1H-benzo[d]imidazole-1-carboxy-late (408 mg, 1.07 mmol, Step-1 of Intermediate-3).

MS (ESI) m/z: 283.2 (M+H)$^+$.

<Step-3>: methyl 2-((3-(((1r,4r)-4-(5-chloro-2-methylnicotinamido)cyclohexyl)methyl)-2-oxo-2,3-dihydro-1H-benzo[d]imidazol-1-yl)methyl)benzoate A mixture of ((r,4r)-4-(5-chloro-2-methylnicotinamido) cyclohexyl)methyl methanesulfonate (150 mg, 0.42 mmol, Mesylate-1), methyl 2-((2-oxo-2,3-dihydro-1H-benzo[d] imidazol-1-yl)methyl)benzoate (117 mg, 0.42 mmol, Step-2 of Intermediate-3), and cesium carbonate (271 mg, 0.83 mmol) in DMSO (0.5 mL) is stirred at 80° C. for 2 hrs. The mixture is diluted with water. The mixture is extracted with EtOAc. The organic layer is concentrated. The residue is purified by column chromatography on silica-gel eluting with 0-100% EtOAc in n-hexane to give 111 mg (49% yield) of the title compound as a pale yellow solid.

$^1$H-NMR (400 MHz, CDCl$_3$) delta 8.48 (1H, d, J=2.3 Hz), 8.05 (1H, dd, J=7.8, 1.8 Hz), 7.61 (1H, d, J=2.3 Hz), 7.38 (1H, td, J=7.8, 1.8 Hz), 7.32 (1H, td, J=7.8, 1.4 Hz), 7.11 (1H, td, J=7.8, 1.4 Hz), 7.05-6.96 (3H, m), 6.83 (1H, d, J=7.8 Hz), 5.62 (1H, d, J=8.2 Hz), 5.55 (2H, s), 3.97 (3H, s), 4.00-3.90 (1H, m), 3.82 (2H, d, J=6.9 Hz), 2.61 (3H, s), 2.20-2.10 (2H, m), 2.01-1.83 (3H, m), 1.40-1.14 (4H, m). MS (ESI) m/z: 547.2 (M+H)$^+$.

<Step-4>: 2-((3-(((1r,4r)-4-(5-chloro-2-methylnicoti-namido)cyclohexyl)methyl)-2-oxo-2,3-dihydro-1H-benzo[d]imidazol-1-yl)methyl)benzoic acid The title compound is prepared in quantitative yield (108 mg, a pale yellow solid) by the similar manner to Step-4 of Intermediate-2 using methyl 2-((3-(((1r,4r)-4-(5-chloro-2-methylnicotinamido)cyclohexyl)methyl)-2-oxo-2,3-di-hydro-1H-benzo[d]imidazol-1-yl)methyl)benzoate (111 mg, 0.20 mmol, Step-3 of Intermediate-3).

MS (ESI) m/z: 533.2 (M+H)$^+$.

Intermediate-4: 1-(4-fluorophenyl)-1H-benzo[d]imidazol-2(3H)-one

<Step-1>: tert-butyl 3-(4-fluorophenyl)-2-oxo-2,3-dihydro-1H-benzo[d]imidazole-1-carboxylate A mixture of tert-butyl 2-oxo-2,3-dihydro-1H-benzo[d]imidazole-1-carboxylate (150 mg, 0.64 mmol), (4-fluorophenyl)boronic acid (134 mg, 0.96 mmol), MS 4A (150 mg), copper (II) acetate (233 mg, 1.28 mmol), and pyridine (0.16 mL, 1.92 mmol) in DCM (3 mL) is stirred at room temperature for 2 days. The mixture is filtered by using Celite pad. The filtrate is concentrated. The residue is purified by column chromatography on silica-gel eluting with 0-25% EtOAc in n-hexane to give 77 mg (37% yield) of the title compound as a pale yellow gum.
MS (ESI) m/z: 329.1 (M+H)$^+$.

<Step-2>: 1-(4-fluorophenyl)-1H-benzo[d]imidazol-2(3H)-one

The title compound is prepared in 99% yield (53 mg, a pale yellow solid) by the similar manner to Step-2 of Intermediate-1 using tert-butyl 3-(4-fluorophenyl)-2-oxo-2,3-dihydro-1H-benzo[d]imidazole-1-carboxylate (77 mg, 0.24 mmol, Step-1 of Intermediate-4).
$^1$H-NMR (400 MHz, DMSO-$d_6$) delta 11.16 (1H, s), 7.58 (2H, dd, J=9.2, 5.0 Hz), 7.40 (2H, t, J=9.2 Hz), 7.09-7.06 (2H, m), 7.05-6.98 (1H, m), 6.98-6.94 (1H, m). MS (ESI) m/z: 229.2 (M+H)$^+$.

Intermediate-5: 1-(3-fluorophenyl)-1H-benzo[d]imidazol-2(3H)-one

<Step-1>: tert-butyl 3-(3-fluorophenyl)-2-oxo-2,3-dihydro-1H-benzo[d]imidazole-1-carboxylate The title compound is prepared in 75% yield (105 mg, a pale yellow gum) by the similar manner to Step-1 of Intermediate-4 using methyl (3-fluorophenyl)boronic acid in place of (4-fluorophenyl)boronic acid.
MS (ESI) m/z: 329.2 (M+H)$^+$.

<Step-2>: 1-(3-fluorophenyl)-1H-benzo[d]imidazol-2(3H)-one

The title compound is prepared in 97% yield (71 mg, a pale yellow gum) by the similar manner to Step-2 of Intermediate-1 using tert-butyl 3-(3-fluorophenyl)-2-oxo-2,3-dihydro-1H-benzo[d]imidazole-1-carboxylate (105 mg, 0.43 mmol, Step-1 of Intermediate-5).
$^1$H-NMR (400 MHz, DMSO-$d_6$) delta 11.23 (1H, s), 7.65-7.57 (1H, m), 7.48-7.40 (2H, m), 7.29 (1H, td, J=7.8, 1.8 Hz), 7.11-7.00 (4H, m). MS (ESI) m/z: 229.2 (M+H)$^+$.

Intermediate-6: 1-(3-acetylphenyl)-1H-benzo[d]imidazol-2(3H)-one

<Step-1>: tert-butyl 3-(3-acetylphenyl)-2-oxo-2,3-dihydro-1H-benzo[d]imidazole-1-carboxylate The title compound is prepared in 76% yield (115 mg, a pale yellow gum) by the similar manner to Step-1 of Intermediate-4 using methyl (3-acetylphenyl)boronic acid in place of (4-fluorophenyl)boronic acid.
MS (ESI) m/z: 353.2 (M+H)$^+$.

<Step-2>: 1-(3-acetylphenyl)-1H-benzo[d]imidazol-2(3H)-one

The title compound is prepared in 97% yield (80 mg, a pale yellow gum) by the similar manner to Step-2 of Intermediate-1 using tert-butyl 3-(3-acetylphenyl)-2-oxo-2,3-dihydro-1H-benzo[d]imidazole-1-carboxylate (115 mg, 0.33 mmol, Step-1 of Intermediate-6).
MS (ESI) m/z: 253.2 (M+H)$^+$.

Intermediate-7: 1-(4-acetylphenyl)-1H-benzo[d]imidazol-2(3H)-one

<Step-1>: tert-butyl 3-(4-acetylphenyl)-2-oxo-2,3-dihydro-1H-benzo[d]imidazole-1-carboxylate The title compound is prepared in 68% yield (102 mg, a pale yellow gum) by the similar manner to Step-1 of Intermediate-4 using (4-acetylphenyl)boronic acid in place of (4-fluorophenyl)boronic acid.
MS (ESI) m/z: 353.2 (M+H)$^+$.

<Step-2>: 1-(4-acetylphenyl)-1H-benzo[d]imidazol-2(3H)-one

The title compound is prepared in 86% yield (63 mg, a pale yellow gum) by the similar manner to Step-2 of Intermediate-1 using tert-butyl 3-(4-acetylphenyl)-2-oxo-2,3-dihydro-1H-benzo[d]imidazole-1-carboxylate (102 mg, 0.29 mmol, Step-1 of Intermediate-7).
$^1$H-NMR (400 MHz, DMSO-$d_6$) delta 11.28 (1H, s), 8.13 (2H, d, J=8.7 Hz), 7.74 (2H, d, J=8.7 Hz), 7.16-7.00 (4H, m), 2.63 (3H, s). MS (ESI) m/z: 253.2 (M+H)$^+$.

Intermediate-8: 3-(3-(((1r,4r)-4-(5-chloro-2-methylnicotinamido)cyclohexyl)methyl)-2-oxo-2,3-dihydro-1H-benzo[d]imidazol-1-yl)benzoic acid <Step-1>: tert-butyl 3-(3-(ethoxycarbonyl)phenyl)-2-oxo-2,3-dihydro-1H-benzo[d]imidazole-1-carboxylate The title compound is prepared in 60% yield (98 mg, a pale yellow gum) by the similar manner to Step-1 of Intermediate-4 using (3-(ethoxycarbonyl)phenyl)boronic acid in place of (4-fluorophenyl)boronic acid.
MS (ESI) m/z: 383.1 (M+H)$^+$.

<Step-2>: ethyl 3-(2-oxo-2,3-dihydro-1H-benzo[d]imidazol-1-yl)benzoate

The title compound is prepared in 91% yield (66 mg, a pale yellow gum) by the similar manner to Step-2 of Intermediate-1 using tert-butyl 3-(3-(ethoxycarbonyl)phenyl)-2-oxo-2,3-dihydro-1H-benzo[d]imidazole-1-carboxylate (98 mg, 0.26 mmol, Step-1 of Intermediate-8).
MS (ESI) m/z: 283.2 (M+H)$^+$.

<Step-3>: ethyl 3-(3-(((1r,4r)-4-(5-chloro-2-methylnicotinamido)cyclohexyl)methyl)-2-oxo-2,3-dihydro-1H-benzo[d]imidazol-1-yl)benzoate The title compound is prepared in 69% yield (88 mg, a pale yellow gum) by the similar manner to Step-3 of Intermediate-2 using ethyl 3-(2-oxo-2,3-dihydro-1H-benzo

[d]imidazol-1-yl)benzoate (66 mg, 0.23 mmol, Step-2 of Intermediate-8) in place of methyl 3-((2-oxo-2,3-dihydro-1H-benzo[d]imidazol-1-yl)methyl)benzoate.
MS (ESI) m/z: 547.2 (M+H)+.

<Step-4>: 3-(3-(((1r,4r)-4-(5-chloro-2-methylnicotinamido)cyclohexyl)methyl)-2-oxo-2,3-dihydro-1H-benzo[d]imidazol-1-yl)benzoic acid The title compound is prepared in quantitative yield (88 mg, a pale yellow gum) by the similar manner to Step-4 of Intermediate-2 using ethyl 3-(3-(((1r,4r)-4-(5-chloro-2-methylnicotinamido)cyclohexyl)methyl)-2-oxo-2,3-dihydro-1H-benzo[d]imidazol-1-yl)benzoate (88 mg, 0.16 mmol, Step-3 of Intermediate-8).
MS (ESI) m/z: 519.1 (M+H)+.

Intermediate-9: 4-(3-(((1r,4r)-4-(5-chloro-2-methylnicotinamido)cyclohexyl)methyl)-2-oxo-2,3-dihydro-1H-benzo[d]imidazol-1-yl)benzoic acid <Step-1>: tert-butyl 3-(4-(methoxycarbonyl)phenyl)-2-oxo-2,3-dihydro-1H-benzo[d]imidazole-1-carboxylate The title compound is prepared in 32% yield (51 mg, a pale yellow gum) by the similar manner to Step-1 of Intermediate-4 using (4-(methoxycarbonyl)phenyl)boronic acid in place of (4-fluorophenyl)boronic acid.
MS (ESI) m/z: 369.1 (M+H)+.

<Step-2>: methyl 4-(2-oxo-2,3-dihydro-1H-benzo[d]imidazol-1-yl)benzoate

The title compound is prepared in quantitative yield (39 mg, a pale yellow gum) by the similar manner to Step-2 of Intermediate-1 using tert-butyl 3-(4-(methoxycarbonyl)phenyl)-2-oxo-2,3-dihydro-1H-benzo[d]imidazole-1-carboxylate (51 mg, 0.14 mmol, Step-1 of Intermediate-9).
$^1$H-NMR (400 MHz, DMSO-d$_6$) delta 11.29 (1H, s), 8.14 (2H, d, J=8.7 Hz), 7.75 (2H, d, J=8.7 Hz), 7.15 (1H, d, J=8.2 Hz), 7.14-7.09 (2H, m), 7.08-7.01 (1H, m), 3.90 (3H, s). MS (ESI) m/z: 269.2 (M+H)+.

<Step-3>: methyl 4-(3-(((1r,4r)-4-(5-chloro-2-methylnicotinamido)cyclohexyl)methyl)-2-oxo-2,3-dihydro-1H-benzo[d]imidazol-1-yl)benzoate The title compound is prepared in 49% yield (38 mg, a pale yellow gum) by the similar manner to Step-3 of Intermediate-2 using methyl 4-(2-oxo-2,3-dihydro-1H-benzo[d]imidazol-1-yl)benzoate (39 mg, 0.15 mmol, Step-2 of Intermediate-9) in place of methyl 3-((2-oxo-2,3-dihydro-1H-benzo[d]imidazol-1-yl)methyl)benzoate.
MS (ESI) m/z: 533.2 (M+H)+.

<Step-4>: 4-(3-(((1r,4r)-4-(5-chloro-2-methylnicotinamido)cyclohexyl)methyl)-2-oxo-2,3-dihydro-1H-benzo[d]imidazol-1-yl)benzoic acid The title compound is prepared in quantitative yield (37 mg, a pale yellow gum) by the similar manner to Step-4 of Intermediate-2 using methyl 4-(3-(((1r,4r)-4-(5-chloro-2-methylnicotinamido)cyclohexyl)methyl)-2-oxo-2,3-dihydro-1H-benzo[d]imidazol-1-yl)benzoate (38 mg, 0.16 mmol, Step-3 of Intermediate-9).
MS (ESI) m/z: 519.1 (M+H)+.

Intermediate-10: 4-((3-(((1r,4r)-4-(5-chloro-2-methylnicotinamido)cyclohexyl)methyl)-2-oxo-2,3-dihydro-1H-benzo[d]imidazol-1-yl)methyl)benzoic acid <Step-1>: tert-butyl 3-(4-(methoxycarbonyl)benzyl)-2-oxo-2,3-dihydro-1H-benzo[d]imidazole-1-carboxylate The title compound is prepared in 90% yield (368 mg, a pale yellow solid) by the similar manner to Step-1 of Intermediate-1 using methyl 4-(bromomethyl)benzoate in place of 4-(iodomethyl)tetrahydro-2H-pyran.
MS (ESI) m/z: 383.3 (M+H)+.

<Step-2>: methyl 3-((2-oxo-2,3-dihydro-1H-benzo[d]imidazol-1-yl)methyl)benzoate

The title compound is prepared in quantitative yield (308 mg, a pale yellow solid) by the similar manner to Step-2 of Intermediate-1 using tert-butyl 3-(4-(methoxycarbonyl)benzyl)-2-oxo-2,3-dihydro-1H-benzo[d]imidazole-1-carboxylate (368 mg, 0.96 mmol, Step-1 of Intermediate-10).
$^1$H-NMR (400 MHz, DMSO-d$_6$) delta 11.02 (1H, s), 7.92 (2H, d, J=8.7 Hz), 7.43 (2H, d, J=8.7 Hz), 7.03-6.90 (4H, m), 5.09 (2H, s), 3.83 (3H, s). MS (ESI) m/z: 283.2 (M+H)+.

<Step-3>: methyl 4-((3-(((1r,4r)-4-(5-chloro-2-methylnicotinamido)cyclohexyl)methyl)-2-oxo-2,3-dihydro-1H-benzol[d]imidazol-1-yl)methyl)benzoate The title compound is prepared in 77% yield (88 mg, a pale yellow gum) by the similar manner to Step-3 of Intermediate-2 using methyl 4-(2-oxo-2,3-dihydro-1H-benzo[d]imidazol-1-yl)benzoate (59 mg, 0.21 mmol, Step-2 of Intermediate-10) in place of methyl 3-((2-oxo-2,3-dihydro-1H-benzo[d]imidazol-1-yl)methyl)benzoate.
MS (ESI) m/z: 547.2 (M+H)+.

<Step-4>: 4-((3-(((1r,4r)-4-(5-chloro-2-methylnicotinamido)cyclohexyl)methyl)-2-oxo-2,3-dihydro-1H-benzo[d]imidazol-1-yl)methyl)benzoic acid The title compound is prepared in quantitative yield (88 mg, a pale yellow gum) by the similar manner to Step-4 of Intermediate-2 using methyl 4-((3-(((1r,4r)-4-(5-chloro-2-methylnicotinamido)cyclohexyl)methyl)-2-oxo-2,3-dihydro-1H-benzo[d]imidazol-1-yl)methyl)benzoate (88 mg, 0.16 mmol, Step-3 of Intermediate-10).
MS (ESI) m/z: 533.2 (M+H)+.

Intermediate-11: 1-(6-(trifluoromethyl)pyridin-3-yl)-1H-benzo[d]imidazol-2(3H)-one <Step-1>: tert-butyl 2-oxo-3-(6-(trifluoromethyl)pyridin-3-yl)-2,3-dihydro-1H-benzo[d]imidazole-1-carboxylate The title compound is prepared in 25% yield (40 mg, a pale yellow gum) by the similar manner to Step-1 of Intermediate-4 using (6-(trifluoromethyl)pyridin-3-yl)boronic acid in place of (4-fluorophenyl)boronic acid.
MS (ESI) m/z: 380.1 (M+H)+.

<Step-2>:1-(6-(trifluoromethyl)pyridin-3-yl)-1H-benzo[d]imidazol-2(3H)-one

The title compound is prepared in 92% yield (27 mg, a pale yellow solid) by the similar manner to Step-2 of Intermediate-1 using tert-butyl 2-oxo-3-(6-(trifluoromethyl)pyridin-3-yl)-2,3-dihydro-1H-benzo[d]imidazole-1-carboxylate (40 mg, 0.11 mmol, Step-1 of Intermediate-11).
MS (ESI) m/z: 280.1 (M+H)$^+$.

Intermediate-12: 1-(6-methoxypyridin-3-yl)-1H-benzo[d]imidazol-2(3H)-one

<Step-1>: tert-butyl 3-(6-methoxypyridin-3-yl)-2-oxo-2,3-dihydro-1H-benzo[d]imidazole-1-carboxylate The title compound is prepared in 31% yield (45 mg, a pale yellow gum) by the similar manner to Step-1 of Intermediate-4 using 2-methoxy-5-(4,4,5,5-tetramethyl-1,3,2-dioxaborolan-2-yl)pyridine in place of (4-fluorophenyl)boronic acid.
MS (ESI) m/z: 342.1 (M+H)$^+$.

<Step-2>:1-(6-methoxypyridin-3-yl)-1H-benzo[d]imidazol-2(3H)-one

The title compound is prepared in quantitative yield (36 mg, a pale yellow solid) by the similar manner to Step-2 of Intermediate-1 using tert-butyl 2-oxo-3-(6-(trifluoromethyl)pyridin-3-yl)-2,3-dihydro-1H-benzo[d]imidazole-1-carboxylate (45 mg, 0.13 mmol, Step-1 of Intermediate-12).
MS (ESI) m/z: 242.3 (M+H)$^+$.

Intermediate-13: 1-(6-methylpyridin-3-yl)-1H-benzo[d]imidazol-2(3H)-one

<Step-1>:6-methyl-N-(2-nitrophenyl)pyridin-3-amine

To a mixture of 1-fluoro-2-nitrobenzene (250 mg, 1.77 mmol) and 6-methylpyridin-3-amine (192 mg, 1.77 mmol) in THF (3 mL) is added sodium hydride (60% dispersion in mineral oil, 142 mg, 3.54 mmol) at room temperature. The mixture is stirred at room temperature for 1 day. The mixture is diluted with saturated aqueous ammonium chloride. The mixture is extracted with EtOAc. The organic layer is concentrated. The residue is purified by column chromatography on silica-gel eluting with 0-100% EtOAc in n-hexane to give 170 mg (42% yield) of the title compound as a brown gum.
MS (ESI) m/z: 230.3 (M+H)$^+$.

<Step-2>: N$^1$-(6-methylpyridin-3-yl)benzene-1,2-diamine

A mixture of 6-methyl-N-(2-nitrophenyl)pyridin-3-amine (170 mg, 0.74 mmol, Step-1 of Intermediate-13) and palladium-fibroin (20 mg, purchased from WAKO) in THF (2 mL) and MeOH (2 mL) is stirred at room temperature for 1 day under hydrogen atmosphere. Palladium-fibroin and solvent are removed to give 148 mg (quantitative yield) of the title compound as a brown gum.
MS (ESI) m/z: 200.3 (M+H)$^+$.

<Step-3>:1-(6-methylpyridin-3-yl)-1H-benzo[d]imidazol-2(3H)-one

A mixture of N$^1$-(6-methylpyridin-3-yl)benzene-1,2-diamine (148 mg, 0.74 mmol, Step-2 of Intermediate-13) and CDI (164 mg, 1.17 mmol) in 1,4-dioxane (3 mL) is stirred at room temperature for 3 hrs. The mixture is diluted with saturated aqueous sodium bicarbonate. The mixture is extracted with EtOAc. The organic layer is concentrated. The residue is purified by column chromatography on silica-gel eluting with 0-100% EtOAc in n-hexane to give 135 mg (81% yield) of the title compound as a brown solid.
MS (ESI) m/z: 226.3 (M+H)$^+$.

Intermediate-14: 1-(2,6-dimethylpyridin-3-yl)-1H-benzo[d]imidazol-2(3H)-one

<Step-1>:2,6-dimethyl-N-(2-nitrophenyl)pyridin-3-amine

The title compound is prepared in 12% yield (52 mg, a pale yellow gum) by the similar manner to Step-1 of Intermediate-13 using 2,6-dimethylpyridin-3-amine in place of 6-methylpyridin-3-amine.
MS (ESI) m/z: 244.3 (M+H)$^+$.

<Step-2>: N$^1$-(2,6-dimethylpyridin-3-yl)benzene-1,2-diamine

The title compound is prepared in quantitative yield (45 mg, a brown gum) by the similar manner to Step-2 of Intermediate-13 using 2,6-dimethyl-N-(2-nitrophenyl)pyridin-3-amine (52 mg, 0.21 mmol, Step-1 of Intermediate-14) in place of 6-methyl-N-(2-nitrophenyl)pyridin-3-amine.
MS (ESI) m/z: 214.3 (M+H)$^+$.

<Step-3>:1-(2,6-dimethylpyridin-3-yl)-1H-benzo[d]imidazol-2(3H)-one

The title compound is prepared in 81% yield (41 mg, a brown solid) by the similar manner to Step-3 of Intermediate-13 using N$^1$-(2,6-dimethylpyridin-3-yl)benzene-1,2-diamine (45 mg, 0.21 mmol, Step-2 of Intermediate-14) in place of N$^1$-(6-methylpyridin-3-yl)benzene-1,2-diamine.
MS (ESI) m/z: 240.3 (M+H)$^+$.

Intermediate-15: 1-(6-(2,2-difluoroethoxy)pyridin-3-yl)-1H-benzo[d]imidazol-2(3H)-one <Step-1>: tert-butyl 3-(6-fluoropyridin-3-yl)-2-oxo-2,3-dihydro-1H-benzo[d]imidazole-1-carboxylate The title compound is prepared in 82% yield (345 mg, a pale yellow gum) by the similar manner to Step-1 of Intermediate-4 using (6-fluoropyridin-3-yl)boronic acid in place of (4-fluorophenyl)boronic acid.
$^1$H-NMR (400 MHz, CDCl$_3$) delta 8.42 (1H, dd, J=2.7, 1.4 Hz), 8.03-7.91 (2H, m), 7.26-7.17 (2H, m), 7.14 (1H, dd, J=8.7, 3.2 Hz), 6.95 (1H, dd, J=7.9, 3.2 Hz), 1.69 (9H, s).
MS (ESI) m/z: 330.2 (M+H)$^+$.

<Step-2>:1-(6-(2,2-difluoroethoxy)pyridin-3-yl)-1H-benzo[d]imidazol-2(3H)-one

To a mixture of tert-butyl 3-(6-fluoropyridin-3-yl)-2-oxo-2,3-dihydro-1H-benzo[d]imidazole-1-carboxylate (35 mg, 0.11 mmol, Step-1 of Intermediate-15) and 2,2-difluoroethanol (44 mg, 0.53 mmol) in DMF (1 mL) is added potassium tert-butoxide (36 mg, 0.32 mmol) at rt. The mixture is stirred at rt for 3 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) to give 29 mg (94% yield) of the title compound as a yellow solid.

$^1$H-NMR (400 MHz, CDCl$_3$) delta 8.82 (1H, br s), 8.35 (1H, d, J=2.7 Hz), 7.83 (1H, dd, J=8.7, 2.7 Hz), 7.18-7.05 (3H, m), 7.02-6.95 (2H, m), 6.19 (1H, tt, J=55.3, 4.1 Hz), 4.61 (2H, td, J=13.7, 4.1 Hz). MS (ESI) m/z: 292.2 (M+H)$^+$.

Intermediate-16: 1-(6-ethoxypyridin-3-yl)-1H-benzo[d]imidazol-2(3H)-one

To a mixture of tert-butyl 3-(6-fluoropyridin-3-yl)-2-oxo-2,3-dihydro-1H-benzo[d]imidazole-1-carboxylate (35 mg, 0.11 mmol, Step-1 of Intermediate-15) in DMF (1 mL) is added 20% sodium ethanolate in EtOH (108 mg, 0.32 mmol) at rt. The mixture is stirred at rt for 3 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) to give 17 mg (63% yield) of the title compound as a yellow solid.

$^1$H-NMR (400 MHz, CDCl$_3$) delta 8.83 (1H, br s), 8.33 (1H, d, J=2.7 Hz), 7.74 (1H, dd, J=8.7, 2.7 Hz), 7.15-7.05 (3H, m), 6.97 (1H, d, J=7.7 Hz), 6.89 (1H, d, J=8.7 Hz), 4.43 (2H, q, J=6.9 Hz), 1.44 (3H, t, J=6.9 Hz). MS (ESI) m/z: 256.2 (M+H)$^+$.

Intermediate-17: 1-(2-methoxypyrimidin-5-yl)-1H-benzo[d]imidazol-2(3H)-one

<Step-1>: tert-butyl 3-(2-methoxypyrimidin-5-yl)-2-oxo-2,3-dihydro-1H-benzo[d]imidazole-1-carboxylate The title compound is prepared in 34% yield (50 mg, a pale yellow gum) by the similar manner to Step-1 of Intermediate-4 using (2-methoxypyrimidin-5-yl)boronic acid in place of (4-fluorophenyl)boronic acid.

MS (ESI) m/z: 343.3 (M+H)$^+$.

<Step-2>:1-(2-methoxypyrimidin-5-yl)-1H-benzo[d]imidazol-2(3H)-one

The title compound is prepared in quantitative yield (45 mg, a pale yellow solid) by the similar manner to Step-2 of Intermediate-1 using tert-butyl 2-oxo-3-(6-(trifluoromethyl)pyridin-3-yl)-2,3-dihydro-1H-benzo[d]imidazole-1-carboxylate (50 mg, 0.15 mmol, Step-1 of Intermediate-17).

MS (ESI) m/z: 243.3 (M+H)$^+$.

Intermediate-18: 1-(3,4-dimethoxyphenyl)-1H-benzo[d]imidazol-2(3H)-one

<Step-1>: tert-butyl 3-(3,4-dimethoxyphenyl)-2-oxo-2,3-dihydro-1H-benzo[d]imidazole-1-carboxylate The title compound is prepared in 18% yield (28 mg, a pale yellow gum) by the similar manner to Step-1 of Intermediate-4 using (3,4-dimethoxyphenyl)boronic acid in place of (4-fluorophenyl)boronic acid.

MS (ESI) m/z: 371.3 (M+H)$^+$.

<Step-2>:1-(3,4-dimethoxyphenyl)-1H-benzo[d]imidazol-2(3H)-one

The title compound is prepared in 98% yield (20 mg, a pale yellow solid) by the similar manner to Step-2 of Intermediate-1 using tert-butyl 3-(3,4-dimethoxyphenyl)-2-oxo-2,3-dihydro-1H-benzo[d]imidazole-1-carboxylate (28 mg, 0.076 mmol, Step-1 of Intermediate-18).

MS (ESI) m/z: 271.4 (M+H)$^+$.

Intermediate-19: 1-(2-methoxypyridin-4-yl)-1H-benzo[d]imidazol-2(3H)-one

<Step-1>: tert-butyl 3-(2-methoxypyridin-4-yl)-2-oxo-2,3-dihydro-1H-benzo[d]imidazole-1-carboxylate The title compound is prepared in 30% yield (43 mg, a pale yellow gum) by the similar manner to Step-1 of Intermediate-4 using (2-methoxypyridin-4-yl)boronic acid in place of (4-fluorophenyl)boronic acid.

MS (ESI) m/z: 342.3 (M+H)$^+$.

<Step-2>:1-(2-methoxypyridin-4-yl)-1H-benzo[d]imidazol-2(3H)-one

The title compound is prepared in quantitative yield (31 mg, a pale yellow solid) by the similar manner to Step-2 of Intermediate-1 using tert-butyl 3-(2-methoxypyridin-4-yl)-2-oxo-2,3-dihydro-1H-benzo[d]imidazole-1-carboxylate (43 mg, 0.13 mmol, Step-1 of Intermediate-19).

MS (ESI) m/z: 242.3 (M+H)$^+$.

Intermediate-20: 1-(2,4-difluorophenyl)-1H-benzo[d]imidazol-2(3H)-one

<Step-1>:2,4-difluoro-N-(2-nitrophenyl)aniline

To a mixture of 1-fluoro-2-nitrobenzene (200 mg, 1.42 mmol) and 2,4-difluoroaniline (183 mg, 1.42 mmol) in THF (3 mL) is added potassium tert-butoxide (318 mg, 2.83 mmol) at room temperature. The mixture is stirred at room temperature for 1 hr. The mixture is diluted with saturated aqueous ammonium chloride. The mixture is extracted with EtOAc. The organic layer is concentrated. The residue is purified by column chromatography on silica-gel eluting with 0-25% EtOAc in n-hexane to give 240 mg (68% yield) of the title compound as a brown solid.

<Step-2>: N$^1$-(2,4-difluorophenyl)benzene-1,2-diamine

A mixture of 2,4-difluoro-N-(2-nitrophenyl)aniline (225 mg, 0.92 mmol, Step-1 of Intermediate-20) and palladium-fibroin (20 mg, purchased from WAKO) in THF (2 mL) and MeOH (2 mL) is stirred at room temperature for 1 day under hydrogen atmosphere. Palladium-fibroin and solvent are removed to give 211 mg (quantitative yield) of the title compound as a brown solid.

MS (ESI) m/z: 221.3 (M+H)$^+$.

<Step-3>:1-(2,4-difluorophenyl)-1H-benzo[d]imidazol-2(3H)-one

A mixture of N$^1$-(2,4-difluorophenyl)benzene-1,2-diamine (211 mg, 0.92 mmol, Step-2 of Intermediate-20) and CDI (233 mg, 1.44 mmol) in THF (3 mL) is stirred at room temperature for 1 day. The mixture is diluted with saturated aqueous sodium bicarbonate. The mixture is extracted with EtOAc. The organic layer is concentrated. The residue is purified by column chromatography on silica-gel eluting with 0-100% EtOAc in n-hexane to give 154 mg (65% yield) of the title compound as a brown solid.
¹H-NMR (400 MHz, CDCl₃) delta 9.20 (1H, br s), 7.58-7.48 (1H, m), 7.16-7.11 (2H, m), 7.12-7.03 (3H, m), 6.80 (1H, d, J=6.9 Hz). MS (ESI) m/z: 247.3 (M+H)⁺.

Intermediate-21: 1-(4-fluoro-2-methylphenyl)-1H-benzo[d]imidazol-2(3H)-one

<Step-1>:4-fluoro-2-methyl-N-(2-nitrophenyl)aniline

The title compound is prepared in 65% yield (225 mg, a brown oil) by the similar manner to Step-1 of Intermediate-20 using 4-fluoro-2-methylaniline (177 mg, 1.42 mmol) in place of 2,4-difluoroaniline.
MS (ESI) m/z: 247.3 (M+H)⁺.

<Step-2>: $N^1$-(4-fluoro-2-methylphenyl)benzene-1,2-diamine

The title compound is prepared in quantitative yield (198 mg, a brown oil) by the similar manner to Step-2 of Intermediate-20 using 4-fluoro-2-methyl-N-(2-nitrophenyl)aniline (225 mg, 1.07 mmol, Step-1 of Intermediate-21) in place of 2,4-difluoro-N-(2-nitrophenyl)aniline.
MS (ESI) m/z: 217.4 (M+H)⁺.

<Step-3>:1-(4-fluoro-2-methylphenyl)-1H-benzo[d]imidazol-2(3H)-one

The title compound is prepared in 19% yield (42 mg, a brown gum) by the similar manner to Step-3 of Intermediate-20 using $N^1$-(4-fluoro-2-methylphenyl)benzene-1,2-diamine (198 mg, 0.92 mmol, Step-2 of Intermediate-21) in place of $N^1$-(2,4-difluorophenyl)benzene-1,2-diamine.
¹H-NMR (400 MHz, CDCl₃) delta 9.19 (1H, br s), 7.32 (1H, dd, J=8.2, 5.0 Hz), 7.18-7.00 (5H, m), 6.67 (1H, d, J=7.3 Hz), 2.20 (3H, s). MS (ESI) m/z: 243.3 (M+H)⁺.

Intermediate-22: 1-(4-fluoro-3-methoxyphenyl)-1H-benzo[d]imidazol-2(3H)-one

<Step-1>:4-fluoro-3-methoxy-N-(2-nitrophenyl)aniline

The title compound is prepared in 58% yield (215 mg, a brown solid) by the similar manner to Step-1 of Intermediate-20 using 4-fluoro-3-methoxyaniline (200 mg, 1.42 mmol) in place of 2,4-difluoroaniline.
MS (ESI) m/z: 263.1 (M+H)⁺.

<Step-2>: $N^1$-(4-fluoro-3-methoxyphenyl)benzene-1,2-diamine

The title compound is prepared in quantitative yield (190 mg, a brown solid) by the similar manner to Step-2 of Intermediate-20 using 4-fluoro-3-methoxy-N-(2-nitrophenyl)aniline (215 mg, 0.82 mmol, Step-1 of Intermediate-22) in place of 2,4-difluoro-N-(2-nitrophenyl)aniline.
MS (ESI) m/z: 233.3 (M+H)⁺.

<Step-3>:1-(4-fluoro-3-methoxyphenyl)-1H-benzo[d]imidazol-2(3H)-one

The title compound is prepared in 77% yield (162 mg, a brown solid) by the similar manner to Step-3 of Intermediate-20 using $N^1$-(4-fluoro-3-methoxyphenyl)benzene-1,2-diamine (190 mg, 0.82 mmol, Step-2 of Intermediate-22) in place of $N^1$-(2,4-difluorophenyl)benzene-1,2-diamine.
¹H-NMR (400 MHz, CDCl₃) delta 10.00 (1H, br s), 7.30-7.20 (2H, m), 7.20-7.04 (4H, m), 7.01 (1H, d, J=7.8 Hz), 3.93 (3H, s). MS (ESI) m/z: 259.2 (M+H)⁺.

Intermediate-23: 1-(2-methylpyridin-3-yl)-1H-benzo[d]imidazol-2(3H)-one

<Step-1>:2-methyl-N-(2-nitrophenyl)pyridin-3-amine

The title compound is prepared in 52% yield (170 mg, a brown oil) by the similar manner to Step-1 of Intermediate-20 using 2-methylpyridin-3-amine in place of 2,4-difluoroaniline.
MS (ESI) m/z: 230.3 (M+H)⁺.

<Step-2>: $N^1$-(2-methylpyridin-3-yl)benzene-1,2-diamine

The title compound is prepared in quantitative yield (148 mg, a brown oil) by the similar manner to Step-2 of Intermediate-20 using 2-methyl-N-(2-nitrophenyl)pyridin-3-amine (170 mg, 0.74 mmol, Step-1 of Intermediate-23) in place of 2,4-difluoro-N-(2-nitrophenyl)aniline.
MS (ESI) m/z: 200.3 (M+H)⁺.

<Step-3>:1-(2-methylpyridin-3-yl)-1H-benzo[d]imidazol-2(3H)-one

The title compound is prepared in 88% yield (148 mg, a brown gum) by the similar manner to Step-3 of Intermediate-20 using $N^1$-(2-methylpyridin-3-yl)benzene-1,2-diamine (148 mg, 0.47 mmol, Step-2 of Intermediate-23) in place of $N^1$-(2,4-difluorophenyl)benzene-1,2-diamine.
¹H-NMR (400 MHz, CDCl₃) delta 9.01 (1H, br s), 8.67 (1H, dd, J=5.0, 1.8 Hz), 7.70 (1H, dd, J=8.2, 1.8 Hz), 7.35 (1H, dd, J=8.2, 5.0 Hz), 7.18-7.10 (2H, m), 7.08-7.01 (1H, m), 6.67 (1H, d, J=7.8 Hz), 2.47 (3H, s). MS (ESI) m/z: 226.3 (M+H)⁺.

Intermediate-24: 1-(6-(2-((tetrahydro-2H-pyran-2-yl)oxy)ethoxy)pyridin-3-yl)-1H-benzo[d]imidazol-2(3H)-one To a mixture of tert-butyl 3-(6-fluoropyridin-3-yl)-2-oxo-2,3-dihydro-1H-benzo[d]imidazole-1-carboxylate (30 mg, 0.091 mmol, Step-1 of Intermediate-15 and 2-((tetrahydro-2H-pyran-2-yl)oxy)ethanol (67 mg, 0.46 mmol) in DMF (1 mL) is added potassium tert-butoxide (31 mg, 0.27 mmol) at rt. The mixture is stirred at rt for 3 hrs. The mixture is diluted with water and extracted with EtOAc. The organic layer is concentrated. The residue is purified by column chromatography on silica-gel eluting with 0-100% EtOAc in n-hexane to give 24 mg (74% yield) of the title compound as a pale yellow solid.
MS (ESI) m/z: 356.3 (M+H)⁺.

Intermediate-25: 1-(3-methylpyridin-4-yl)-1H-benzo[d]imidazol-2(3H)-one

<Step-1>:3-methyl-N-(2-nitrophenyl)pyridin-4-amine

The title compound is prepared in 56% yield (182 mg, a brown solid) by the similar manner to Step-1 of Intermediate-20 using 3-methylpyridin-4-amine (153 mg, 1.42 mmol) in place of 2,4-difluoroaniline.

$^1$H-NMR (400 MHz, CDCl$_3$) delta 9.27 (1H, br s), 8.45 (1H, s), 8.39 (1H, d, J=5.5 Hz), 8.25 (1H, dd, J=8.7, 1.4 Hz), 7.58-7.44 (2H, m), 7.28 (1H, d, J=5.5 Hz), 7.00 (1H, td, J=7.3, 1.4 Hz), 2.34 (3H, s). MS (ESI) m/z: 230.3 (M+H)$^+$.

<Step-2>: N$^1$-(3-methylpyridin-4-yl)benzene-1,2-diamine

The title compound is prepared in quantitative yield (158 mg, a brown solid) by the similar manner to Step-2 of Intermediate-20 using 3-methyl-N-(2-nitrophenyl)pyridin-4-amine (182 mg, 0.79 mmol, Step-1 of Intermediate-25) in place of 2,4-difluoro-N-(2-nitrophenyl)aniline.

MS (ESI) m/z: 200.3 (M+H)$^+$.

<Step-3>:1-(3-methylpyridin-4-yl)-1H-benzo[d]imidazol-2(3H)-one

The title compound is prepared in 79% yield (141 mg, a pale yellow solid) by the similar manner to Step-3 of Intermediate-20 using N$^1$-(3-methylpyridin-4-yl)benzene-1,2-diamine (158 mg, 0.79 mmol, Step-2 of Intermediate-25) in place of N$^1$-(2,4-difluorophenyl)benzene-1,2-diamine.

$^1$H-NMR (400 MHz, CDCl$_3$) delta 9.21 (1H, br s), 8.73 (1H, br s), 8.65 (1H, d, J=5.0 Hz), 7.34 (1H, d, J=5.0 Hz), 7.20-7.10 (2H, m), 7.07 (1H, t, J=7.7 Hz), 6.75 (1H, d, J=7.7 Hz), 2.29 (3H, s). MS (ESI) m/z: 226.3 (M+H)$^+$.

Intermediate-26: 1-(6-(dimethylamino)pyridin-3-yl)-1H-benzo[d]imidazol-2(3H)-one A mixture of tert-butyl 3-(6-fluoropyridin-3-yl)-2-oxo-2,3-dihydro-1H-benzo[d]imidazole-1-carboxylate (50 mg, 0.15 mmol, Step-1 of Intermediate-15), dimethylamine hydrochloride (62 mg, 0.76 mmol) and DIEA (0.13 mL, 0.76 mmol) in NMP (0.6 mL) is irradiated with microwave at 200° C. for 20 min. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) to give 16 mg (41% yield) of the title compound as a yellow gum.

MS (ESI) m/z: 255.4 (M+H)$^+$.

Intermediate-27: 1-(6-((2-methoxyethyl)(methyl)amino)pyridin-3-yl)-1H-benzo[d]imidazol-2(3H)-one The title compound is prepared in 44% yield (20 mg, a pale yellow gum) by the similar manner to Intermediate-26 using 2-methoxy-N-methylethanamine in place of dimethylamine hydrochloride.

MS (ESI) m/z: 299.4 (M+H)$^+$.

Intermediate-28: 1-(6-morpholinopyridin-3-yl)-1H-benzo[d]imidazol-2(3H)-one

The title compound is prepared in 58% yield (26 mg, a pale yellow gum) by the similar manner to Intermediate-26 using morpholine in place of dimethylamine hydrochloride.

MS (ESI) m/z: 297.4 (M+H)$^+$.

Intermediate-29: 1-(6-(4-methylpiperazin-1-yl)pyridin-3-yl)-1H-benzo[d]imidazol-2(3H)-one The title compound is prepared in 23% yield (11 mg, a pale yellow gum) by the similar manner to Intermediate-26 using 1-methylpiperazine in place of dimethylamine hydrochloride.

MS (ESI) m/z: 310.3 (M+H)$^+$.

Intermediate-30: 1-(2-methylpyridin-4-yl)-1H-benzo[d]imidazol-2(3H)-one

<Step-1>:2-methyl-N-(2-nitrophenyl)pyridin-4-amine

The title compound is prepared in 30% yield (72 mg, an orange solid) by the similar manner to Step-1 of Intermediate-20 using 2-methylpyridin-4-amine in place of 2,4-difluoroaniline.

$^1$H-NMR (400 MHz, CDCl$_3$) delta 9.26 (1H, br s), 8.40 (1H, d, J=5.5 Hz), 8.22 (1H, dd, J=8.2, 1.4 Hz), 7.62-7.49 (2H, m), 7.05-6.95 (3H, m), 2.54 (3H, s). MS (ESI) m/z: 230.3 (M+H)$^+$.

<Step-2>: N$^1$-(2-methylpyridin-4-yl)benzene-1,2-diamine

The title compound is prepared in quantitative yield (63 mg, a brown gum) by the similar manner to Step-2 of Intermediate-20 using 2-methyl-N-(2-nitrophenyl)pyridin-4-amine (72 mg, 0.31 mmol, Step-1 of Intermediate-30) in place of 2,4-difluoro-N-(2-nitrophenyl)aniline.

MS (ESI) m/z: 200.4 (M+H)$^+$.

<Step-3>:1-(2-methylpyridin-4-yl)-1H-benzo[d]imidazol-2(3H)-one

The title compound is prepared in 21% yield (45 mg, a pale yellow solid) by the similar manner to Step-3 of Intermediate-20 using N$^1$-(2-methylpyridin-4-yl)benzene-1,2-diamine (63 mg, 0.31 mmol, Step-2 of Intermediate-30) in place of N$^1$-(2,4-difluorophenyl)benzene-1,2-diamine.

$^1$H-NMR (400 MHz, DMSO-d$_6$) delta 11.32 (1H, br s), 8.59 (1H, d, J=5.5 Hz), 7.53 (1H, d, J=2.3 Hz), 7.47 (1H, dd, J=5.5, 2.3 Hz), 7.27 (1H, dd, J=7.8, 0.9 Hz), 7.15-7.02 (3H, m), 2.56 (3H, s). MS (ESI) m/z: 226.5 (M+H)$^+$.

Intermediate-31: 7-methyl-1-(6-methylpyridin-3-yl)-1H-benzo[d]imidazol-2(3H)-one <Step-1>:6-methyl-N-(2-methyl-6-nitrophenyl)pyridin-3-amine The title compound is prepared in 58% yield (136 mg, an orange gum) by the similar manner to Step-1 of Intermediate-20 using 6-methylpyridin-3-amine (105 mg, 0.97 mmol) and 2-fluoro-1-methyl-3-nitrobenzene (150 mg, 0.97 mmol) in place of 2,4-difluoroaniline and 1-fluoro-2-nitrobenzene.

$^1$H-NMR (400 MHz, CDCl$_3$) delta 8.23 (1H, br s), 8.07 (1H, d, J=2.7 Hz), 7.99 (1H, d, J=7.8 Hz), 7.44 (1H, d, J=7.3 Hz), 7.10 (1H, t, J=7.8 Hz), 7.03 (1H, d, J=8.2 Hz), 6.94 (1H, dd, J=7.3, 5.5 Hz), 2.50 (3H, s), 2.07 (3H, s). MS (ESI) m/z: 244.5 (M+H)$^+$.

\<Step-2\>:6-methyl-N¹-(6-methylpyridin-3-yl)benzene-1,2-diamine

The title compound is prepared in quantitative yield (119 mg, a pale yellow gum) by the similar manner to Step-2 of Intermediate-20 using 6-methyl-N-(2-methyl-6-nitrophenyl)pyridin-3-amine (136 mg, 0.56 mmol, Step-1 of Intermediate-31) in place of 2,4-difluoro-N-(2-nitrophenyl)aniline.
MS (ESI) m/z: 214.6 (M+H)⁺.

\<Step-3\>:7-methyl-1-(6-methylpyridin-3-yl)-1H-benzo[d]imidazol-2(3H)-one

A mixture of 6-methyl-N-(6-methylpyridin-3-yl)benzene-1,2-diamine (119 mg, 0.56 mmol, Step-2 of Intermediate-31) and CDI (271 mg, 1.67 mmol) in THF (3 mL) is stirred at room temperature for 3 hrs. The mixture is diluted with saturated aqueous sodium bicarbonate. The mixture is extracted with EtOAc. The organic layer is concentrated. The residue is purified by a strong anion exchange cartridge (ISOLUTE (registered trademark) SCX-2, 1 g/6 mL, Biotage) to give 195 mg of the title compound as a pale yellow crude oil.
MS (ESI) m/z: 240.5 (M+H)⁺.

Intermediate-32: 1-(6-methoxypyridin-3-yl)-7-methyl-1H-benzo[d]imidazol-2(3H)-one

\<Step-1\>:6-methoxy-N-(2-methyl-6-nitrophenyl)pyridin-3-amine

The title compound is prepared in 21% yield (53 mg, an orange gum) by the similar manner to Step-1 of Intermediate-20 using 6-methoxypyridin-3-amine (120 mg, 0.97 mmol) and 2-fluoro-1-methyl-3-nitrobenzene (150 mg, 0.97 mmol) in place of 2,4-difluoroaniline and 1-fluoro-2-nitrobenzene.
¹H-NMR (400 MHz, CDCl₃) delta 8.38 (1H, br s), 8.01 (1H, dd, J=8.7, 1.4 Hz), 7.74 (1H, d, J=3.2 Hz), 7.38 (1H, d, J=7.3 Hz), 7.13 (1H, dd, J=8.7, 3.2 Hz), 7.01 (1H, dd, J=8.2, 7.3 Hz), 6.68 (1H, d, J=8.7 Hz), 3.90 (3H, s), 2.02 (3H, s).
MS (ESI) m/z: 260.4 (M+H)⁺.

\<Step-2\>: N¹-(6-methoxypyridin-3-yl)-6-methylbenzene-1,2-diamine

The title compound is prepared in quantitative yield (47 mg, a pale yellow gum) by the similar manner to Step-2 of Intermediate-20 using 6-methoxy-N-(2-methyl-6-nitrophenyl)pyridin-3-amine (53 mg, 0.20 mmol, Step-1 of Intermediate-32) in place of 2,4-difluoro-N-(2-nitrophenyl)aniline.
MS (ESI) m/z: 230.5 (M+H)⁺.

\<Step-3\>:1-(6-methoxypyridin-3-yl)-7-methyl-1H-benzo[d]imidazol-2(3H)-one

The title compound is prepared in 105 mg (a pale yellow crude oil) by the similar manner to Step-3 of Intermediate-31 using N¹-(6-methoxypyridin-3-yl)-6-methylbenzene-1,2-diamine (47 mg, 0.20 mmol, Step-2 of Intermediate-32) in place of 6-methyl-N¹-(6-methylpyridin-3-yl)benzene-1,2-diamine.
MS (ESI) m/z: 256.4 (M+H)⁺.

Intermediate-33: 1-(6-(2-(dimethylamino)ethoxy)pyridin-3-yl)-7-methyl-1H-benzo[d]imidazol-2(3H)-one

\<Step-1\>:6-(2-(dimethylamino)ethoxy)-N-(2-methyl-6-nitrophenyl)pyridin-3-amine The title compound is prepared in 12% yield (37 mg, an orange gum) by the similar manner to Step-1 of Intermediate-20 using 6-(2-(dimethylamino)ethoxy)pyridin-3-amine (175 mg, 0.97 mmol) and 2-fluoro-1-methyl-3-nitrobenzene (150 mg, 0.97 mmol) in place of 2,4-difluoroaniline and 1-fluoro-2-nitrobenzene.
¹H-NMR (400 MHz, CDCl₃) delta 8.39 (1H, br s), 8.01 (1H, dd, J=8.2, 0.9 Hz), 7.71 (1H, dd, J=3.2, 0.9 Hz), 7.38 (1H, dd, J=6.8, 0.9 Hz), 7.11 (1H, dd, J=8.7, 2.7 Hz), 7.01 (1H, dd, J=8.2, 0.9 Hz), 6.73 (1H, d, J=8.7 Hz), 4.36 (2H, t, J=5.9 Hz), 2.70 (2H, t, J=5.9 Hz), 2.32 (6H, s), 2.02 (3H, s).
MS (ESI) m/z: 317.5 (M+H)⁺.

\<Step-2\>: N¹-(6-(2-(dimethylamino)ethoxy)pyridin-3-yl)-6-methylbenzene-1,2-diamine The title compound is prepared in quantitative yield (34 mg, a pale yellow gum) by the similar manner to Step-2 of Intermediate-20 using 6-(2-(dimethylamino)ethoxy)-N-(2-methyl-6-nitrophenyl)pyridin-3-amine (37 mg, 0.12 mmol, Step-1 of Intermediate-33) in place of 2,4-difluoro-N-(2-nitrophenyl)aniline.
MS (ESI) m/z: 287.5 (M+H)⁺.

\<Step-3\>: 1-(6-(2-(dimethylamino)ethoxy)pyridin-3-yl)-7-methyl-1H-benzo[d]imidazol-2(3H)-one The title compound is prepared in 50 mg (a pale yellow crude oil) by the similar manner to Step-3 of Intermediate-31 using N¹-(6-(2-(dimethylamino)ethoxy)pyridin-3-yl)-7-methyl-1H-benzo[d]imidazol-2(3H)-one (34 mg, 0.12 mmol, Step-2 of Intermediate-33) in place of 6-methyl-N¹-(6-methylpyridin-3-yl)benzene-1,2-diamine.
MS (ESI) m/z: 313.5 (M+H)⁺.

Intermediate-34: 1-(6-methoxypyridin-3-yl)-4-methyl-1H-benzo[d]imidazol-2(3H)-one

\<Step-1\>:6-methoxy-N-(3-methyl-2-nitrophenyl)pyridin-3-amine

The title compound is prepared in 4% yield (11 mg, an orange gum) by the similar manner to Step-1 of Intermediate-20. 6-Methoxypyridin-3-amine and 1-fluoro-3-methyl-2-nitrobenzene are used instead of 2,4-difluoroaniline and 1-fluoro-2-nitrobenzene.
MS (ESI) m/z: 260.5 (M+H)⁺.

\<Step-2\>: N¹-(6-methoxypyridin-3-yl)-3-methylbenzene-1,2-diamine

The title compound is prepared in quantitative yield (10 mg, a yellow gum) by the similar manner to Step-2 of Intermediate-20 using 6-methoxy-N-(3-methyl-2-nitrophenyl)pyridin-3-amine (11 mg, 0.042 mmol, Step-1 of Intermediate-34) in place of 2,4-difluoro-N-(2-nitrophenyl)aniline.
MS (ESI) m/z: 230.5 (M+H)⁺.

<Step-3>:1-(6-methoxypyridin-3-yl)-4-methyl-1H-benzo[d]imidazol-2(3H)-one

The title compound is prepared in 36% yield (4 mg, a pale yellow oil) by the similar manner to Step-3 of Intermediate-31 using $N^1$-(6-methoxypyridin-3-yl)-3-methylbenzene-1,2-diamine (10 mg, 0.044 mmol, Step-2 of Intermediate-34) in place of $N^1$-(2,4-difluorophenyl)benzene-1,2-diamine.
MS (ESI) m/z: 256.4 (M+H)$^+$.

Intermediate-35: (S)-1-(6-(3-(dimethylamino)pyrrolidin-1-yl)pyridin-3-yl)-1H-benzo[d]imidazol-2(3H)-one The title compound is prepared in 54% yield (21 mg, a pale yellow gum) by the similar manner to Intermediate-26 using (S)—N,N-dimethylpyrrolidin-3-amine in place of dimethylamine hydrochloride.
MS (ESI) m/z: 324.5 (M+H)$^+$.

Intermediate-36: 5-(3-(((1r,4r)-4-(5-chloro-2-methylnicotinamido)cyclohexyl)methyl)-2-oxo-2,3-dihydro-1H-benzo[d]imidazol-1-yl)picolinic acid <Step-1>: methyl 5-((2-nitrophenyl)amino)picolinate A mixture of methyl 5-aminopicolinate (300 mg, 1.97 mmol), 1-bromo-2-nitrobenzene (398 mg, 1.97 mmol), [1,1'-bis(diphenylphosphino)ferrocene]palladium(II) dichloride dichloromethane adduct (161 mg, 0.20 mmol), 1,1'-bis(diphenylphosphino)ferrocene (22 mg, 0.039 mmol), and tripotassium phosphate (837 mg, 3.4 mmol) in toluene (5 mL) is stirred at 100° C. for 1 day. The mixture is diluted with water and extracted with EtOAc. The organic layer is concentrated. The residue is purified by column chromatography on silica-gel eluting with 0-50% EtOAc in n-hexane to give 242 mg (45% yield) of the title compound as a brown gum.
$^1$H-NMR (400 MHz, CDCl$_3$) delta 9.45 (1H, br s), 8.68 (1H, d, J=2.3 Hz), 8.25 (1H, dd, J=8.2, 1.4 Hz), 8.17 (1H, d, J=8.2 Hz), 7.71 (1H, dd, J=8.2, 2.7 Hz), 7.55-7.48 (1H, m), 7.42 (1H, dd, J=8.2, 0.9 Hz), 7.03-6.98 (1H, m), 4.02 (3H, s). MS (ESI) m/z: 274.6 (M+H)$^+$.

<Step-2>: methyl 5-((2-aminophenyl)amino)picolinate

The title compound is prepared in quantitative yield (214 mg, a pale yellow gum) by the similar manner to Step-2 of Intermediate-13 using methyl 5-((2-nitrophenyl)amino)picolinate (242 mg, 0.89 mmol, Step-1 of Intermediate-36) in place of 6-methyl-N-(2-nitrophenyl)pyridin-3-amine.
MS (ESI) m/z: 244.5 (M+H)$^+$.

<Step-3>: methyl 5-(2-oxo-2,3-dihydro-1H-benzo[d]imidazol-1-yl)picolinate

A mixture of methyl 5-((2-aminophenyl)amino)picolinate (215 mg, 0.88 mmol, Step-2 of Intermediate-36) and CDI (358 mg, 2.21 mmol) in THF (3 mL) is stirred at room temperature for 2 hrs. The mixture is diluted with 10% aqueous citric acid. The precipitate is collected and dried to give 220 mg (92% yield) of the title compound as a purple solid.

$^1$H-NMR (400 MHz, CDCl$_3$) delta 11.37 (1H, br s), 8.96 (1H, t, J=1.8 Hz), 8.22 (2H, d, J=1.8 Hz), 7.20-7.00 (4H, m), 3.90 (3H, s). MS (ESI) m/z: 270.4 (M+H)$^+$.

<Step-4>: 5-(3-(((1r,4r)-4-(5-chloro-2-methylnicotinamido)cyclohexyl)methyl)-2-oxo-2,3-dihydro-1H-benzo[d]imidazol-1-yl)picolinic acid A mixture of ((1r,4r)-4-(5-chloro-2-methylnicotinamido)cyclohexyl)methyl methanesulfonate (161 mg, 0.45 mmol, Mesylate-1), methyl 5-(2-oxo-2,3-dihydro-1H-benzo[d]imidazol-1-yl)picolinate (120 mg, 0.45 mmol, Step-3 of Intermediate-36), cesium carbonate (436 mg, 1.33 mmol) in DMSO (2 mL) is stirred at 80° C. for 5 hrs. Then, the mixture is diluted with water and stirred at rt for 30 min. The mixture is acidified with 2 M hydrochloric acid and extracted with DCM. The organic layer is dried over sodium sulfate and filtered. The filtrate is concentrated to give 320 mg (quantitative yield) of the title compound as a yellow solid.
MS (ESI) m/z: 520.5 (M+H)$^+$.

Intermediate-37: 1-(6-((2-hydroxyethyl)(methyl)amino)pyridin-3-yl)-1H-benzo[d]imidazol-2(3H)-one The title compound is prepared in 49% yield (21 mg, a pale yellow gum) by the similar manner to Intermediate-26 using 2-(methylamino)ethanol in place of dimethylamine hydrochloride.
MS (ESI) m/z: 285.5 (M+H)$^+$.

Intermediate-38: 1-(6-(4-(2-hydroxyethyl)piperazin-1-yl)pyridin-3-yl)-1H-benzo[d]imidazol-2(3H)-one The title compound is prepared in 83% yield (43 mg, a pale yellow gum) by the similar manner to Intermediate-26 using 2-(piperazin-1-yl)ethanol in place of dimethylamine hydrochloride.
MS (ESI) m/z: 340.5 (M+H)$^+$.

Intermediate-39: 1-(6-bromopyridin-3-yl)-1H-benzo[d]imidazol-2(3H)-one

<Step-1>: 6-bromo-N-(2-nitrophenyl)pyridin-3-amine

To a mixture of 1-fluoro-2-nitrobenzene (1 g, 7.09 mmol) and 6-bromopyridin-3-amine (1.23 g, 7.09 mmol) in THF (12 mL) is added potassium tert-butoxide (1.59 g, 14.2 mmol) at rt. The mixture is stirred at rt for 1 hr. The reaction mixture is diluted with water. The mixture is extracted with EtOAc and dried over sodium sulfate. The organic layer is concentrated. The residue is purified by column chromatography on silica-gel eluting with 0-50% EtOAc in hexane to give 1.14 g (55% yield) of the desired product as an orange solid.
$^1$H-NMR (400 MHz, CDCl$_3$) delta 9.32 (1H, s), 8.38 (1H, d, J=3.1 Hz), 8.24 (1H, dd, J=8.6, 1.8 Hz), 7.54-7.43 (3H, m), 7.17 (1H, d, J=8.6 Hz), 6.91 (1H, dd, J=8.6, 7.3 Hz).

<Step-2>: $N^1$-(6-bromopyridin-3-yl)benzene-1,2-diamine

A mixture of 6-bromo-N-(2-nitrophenyl)pyridin-3-amine (1.00 g, 3.40 mmol), iron powder (1.14 g, 20.4 mmol) and ammonium chloride (0.546 g, 10.2 mmol) in ethanol (12.75 mL) and water (4.25 mL) is refluxed with stirring for 2 hrs. After cooling to room temperature, the reaction mixture is filtered through a pad of celite, and filtrate is concentrated in vacuo, the residue is poured into 2 M aqueous sodium hydroxide solution and extracted with EtOAc, dried over sodium sulfate then filtrated and concentrated, to give $N^1$-(6-bromopyridin-3-yl)benzene-1,2-diamine (0.845 g, 3.20 mmol, 94% yield).

$^1$H-NMR (400 MHz, CDCl$_3$) delta 7.92 (1H, d, J=3.1 Hz), 7.24 (1H, d, J=8.6 Hz), 7.10-7.06 (2H, m), 6.85 (1H, dd, J=5.5, 3.1 Hz), 6.82 (1H, dd, J=5.5, 1.8 Hz), 6.77 (1H, ddd, J=8.0, 7.3, 1.2 Hz), 5.26 (1H, br), 3.77 (2H, br).

<Step-3>:1-(6-bromopyridin-3-yl)-1H-benzo[d]imidazol-2(3H)-one

To a mixture of $N^1$-(6-bromopyridin-3-yl)benzene-1,2-diamine (0.840 g, 3.18 mmol) and CDI (0.774 g, 4.77 mmol) in THF (30 mL) is stirred at rt for 3 hrs. The reaction mixture is diluted with saturated aqueous sodium bicarbonate and extracted with EtOAc. The resulting solution is dried over sodium sulfate and concentrated. The residue is purified by solidification with isopropyl acetate (25 mL)-ethanol (18 mL) to give desired product (0.686 g, 80% yield) as pale brown solid.

$^1$H-NMR (400 MHz, CDCl$_3$) delta 8.66 (1H, d, J=2.7 Hz), 7.85 (1H, dd, J=8.7, 2.7 Hz), 7.69 (1H, d, J=7.8 Hz), 7.18-7.07 (4H, m). A signal due to NH is not observed.

Intermediate-40: 1-(6-(dimethylamino)pyridazin-3-yl)-1H-benzo[d]imidazol-2(3H)-one <Step-1>:6-chloro-N-(2-nitrophenyl)pyridazin-3-amine A mixture of 6-chloropyridazin-3-amine (750 mg, 5.79 mmol) and 1-fluoro-2-nitrobenzene (1.23 g, 8.68 mmol) in THF is added potassium tert-butoxide (1.30 g, 11.6 mmol) at 0° C. The mixture is stirred at rt for 2 hrs. The mixture is diluted with water and extracted with EtOAc. The organic layer is dried over sodium sulfate and filtered. The filtrate is concentrated to give 547 mg (38% yield) of the title compound as a brown solid.

MS (ESI) m/z: 251.6 (M+H)$^+$.

<Step-2>: $N^1$-(6-chloropyridazin-3-yl)benzene-1,2-diamine

A mixture of 6-chloro-N-(2-nitrophenyl)pyridazin-3-amine (547 mg, 2.18 mmol, Step-1 of Intermediate-40), iron (501 mg, 8.97 mmol) and ammonium chloride (79 mg, 14.9 mmol) in EtOH (3 mL) and water (1 mL) is stirred at 80° C. for 2 hrs. The mixture is filtered by using Celite pad. The mixture is extracted with DCM. The organic layer is dried over sodium sulfate and filtered. The filtrate is concentrated to give 471 mg (98% yield) of the title compound as a brown oil.

<Step-3>:1-(6-chloropyridazin-3-yl)-1H-benzo[d]imidazol-2(3H)-one

The title compound is prepared in 90% yield (472 mg, a pale orange solid) by the similar manner to Step-3 of Intermediate-36 using $N^1$-(6-chloropyridazin-3-yl)benzene-1,2-diamine (471 mg, 2.14 mmol, Step-2 of Intermediate-40) in place of methyl 5-((2-aminophenyl)amino)picolinate.

MS (ESI) m/z: 247.5 (M+H)$^+$.

<Step-4>:1-(6-(dimethylamino)pyridazin-3-yl)-1H-benzo[d]imidazol-2(3H)-one

A mixture of 1-(6-chloropyridazin-3-yl)-1H-benzo[d]imidazol-2(3H)-one (50 mg, 0.20 mmol, Step-3 of Intermediate-40), dimethylamine hydrochloride (165 mg, 2.03 mmol), and DIEA (0.11 mL, 0.61 mmol) in NMP (0.7 mL) is irradiated with microwave at 200° C. for 30 min. The mixture is diluted with water. The mixture is extracted with DCM. The organic layer is concentrated. The residue is purified by column chromatography on silica-gel eluting with 0-100% EtOAc in n-hexane to give 42 mg (81% yield) of the title compound as a brown solid.

MS (ESI) m/z: 256.7 (M+H)$^+$.

Intermediate-41: 1-(6-(4-methylpiperazin-1-yl)pyridazin-3-yl)-1H-benzo[d]imidazol-2(3H)-one The title compound is prepared in 67% yield (42 mg, a brown solid) by the similar manner to Step-4 of Intermediate-40 using 1-methylpiperazine in place of dimethylamine hydrochloride.

MS (ESI) m/z: 311.7 (M+H)$^+$.

Intermediate-42: 1-(6-(2-((tetrahydro-2H-pyran-2-yl)oxy)ethoxy)pyridazin-3-yl)-1H-benzo[d]imidazol-2(3H)-one A mixture of 1-(6-chloropyridazin-3-yl)-1H-benzo[d]imidazol-2(3H)-one (50 mg, 0.20 mmol, Step-3 of Intermediate-40) and 2-((tetrahydro-2H-pyran-2-yl)oxy)ethanol (89 mg, 0.61 mmol) in DMF (5 mL) is added potassium tert-butoxide (227 mg, 2.03 mmol) at rt. The mixture is stirred at 50° C. for 6 hrs. The mixture is diluted with saturated aqueous ammonium chloride and extracted with DCM. The organic layer is dried over sodium sulfate and filtered. The filtrate is concentrated. The residue is purified by column chromatography on silica-gel eluting with 0-100% EtOAc in n-hexane to give 41 mg (57% yield) of the title compound as a brown solid.

MS (ESI) m/z: 355.7 (M−H)$^−$.

Intermediate-43: 1-(2-bromopyridin-4-yl)-1H-benzo[d]imidazol-2(3H)-one

<Step-1>:2-bromo-N-(2-nitrophenyl)pyridin-4-amine

The title compound is prepared in 45% yield (1.40 g, an orange solid) by the similar manner to Step-1 of Intermediate-39 using 2-bromopyridin-4-amine in place of 6-bromopyridin-3-amine.

$^1$H-NMR (400 MHz, CDCl$_3$) delta 9.20 (1H, s), 8.24-8.22 (2H, m), 7.60 (1H, d, J=3.7 Hz), 7.32 (1H, d, J=2.4 Hz), 7.14-7.08 (1H, m), 7.05 (1H, dd, J=5.5, 2.4 Hz).

<Step-2>: $N^1$-(2-bromopyridin-4-yl)benzene-1,2-diamine

A mixture of 2-bromo-N-(2-nitrophenyl)pyridin-4-amine (1.45 g, 4.93 mmol), iron (1.595 g, 28.6 mmol), and ammonium chloride (0.764 g, 14.28 mmol) in ethanol (18 mL) and water (6 mL) is refluxed with stirring for 2 hrs. After cooling to room temperature, the reaction mixture is filtered through a pad of celite, and filtrate is concentrated in vacuo, the residue is poured into 2 M aqueous sodium hydroxide solution and extracted with EtOAc, dried over sodium sulfate then filtrated and concentrated. To give the title compound (1.30 g, 4.92 mmol, 100% yield).

$^1$H-NMR (400 MHz, CDCl$_3$) delta 7.98 (1H, d, J=5.5 Hz), 7.15 (1H, ddd, J=8.0, 7.3, 1.2 Hz), 7.10 (1H, d, J=7.3 Hz), 6.84 (1H, dd, J=8.0, 1.2 Hz), 6.80 (1H, ddd, J=8.0, 7.3, 1.2 Hz), 6.69 (1H, d, J=1.8 Hz), 6.50 (1H, dd, J=5.5, 1.8 Hz), 5.63 (1H, br), 3.77 (2H, br).

<Step-3>:1-(2-bromopyridin-4-yl)-1H-benzo[d]imidazol-2(3H)-one

To a mixture of N$^1$-(2-bromopyridin-4-yl)benzene-1,2-diamine (1.3 g, 4.92 mmol) and CDI (1.04 g, 6.4 mmol) in THF (30 mL) is stirred at rt for 3 hrs. The reaction mixture is diluted with saturated aqueous sodium bicarbonate and extracted with EtOAc. The resulting solution is dried over sodium sulfate and concentrated. The residual solid is purified by repulped with ethyl acetate (10 mL) and ethanol (15 mL) to give the title compound (1.18 g, 89% yield) as a pale brown solid.

$^1$H-NMR (400 MHz, CDCl$_3$) delta 8.53 (1H, d, J=5.5 Hz), 8.34 (1H, br), 7.86 (1H, d, J=1.8 Hz), 7.64 (1H, dd, J=5.5, 1.8 Hz), 7.30-7.26 (1H), 7.23-7.13 (3H, m).

Intermediate-44: 1-(4-(2-(dimethylamino)ethoxy)phenyl)-1H-benzo[d]imidazol-2(3H)-one <Step-1>: N-(4-(2-(dimethylamino)ethoxy)phenyl)-2-nitroaniline The title compound is prepared in 47% yield (64 mg, a brown gum) by the similar manner to Step-1 of Intermediate-20 using 4-(2-(dimethylamino)ethoxy)aniline (81 mg, 0.45 mmol) in place of 2,4-difluoroaniline.

$^1$H-NMR (400 MHz, CDCl$_3$) delta 9.40 (1H, br s), 8.19 (1H, dd, J=8.7, 1.8 Hz), 7.35-7.30 (1H, m), 7.19 (2H, d, J=8.7 Hz), 7.05-6.95 (3H, m), 6.71 (1H, ddd, J=8.7, 7.3, 1.8 Hz), 4.09 (2H, t, J=5.5 Hz), 2.75 (2H, t, J=5.5 Hz), 2.36 (6H, s). MS (ESI) m/z: 302.6 (M+H)$^+$.

<Step-2>: N$^1$-(4-(2-(dimethylamino)ethoxy)phenyl)benzene-1,2-diamine

The title compound is prepared in 99% yield (57 mg, a pale yellow gum) by the similar manner to Step-2 of Intermediate-20 using N-(4-(2-(dimethylamino)ethoxy)phenyl)-2-nitroaniline (64 mg, 0.21 mmol, Step-1 of Intermediate-44) in place of 2,4-difluoro-N-(2-nitrophenyl)aniline.

<Step-3>:1-(4-(2-(dimethylamino)ethoxy)phenyl)-1H-benzo[d]imidazol-2(3H)-one

The title compound is prepared in 83% yield (52 mg, a pale yellow solid) by the similar manner to Step-3 of Intermediate-20 using N$^1$-(4-(2-(dimethylamino)ethoxy)phenyl)benzene-1,2-diamine (57 mg, 0.21 mmol, Step-2 of Intermediate-44) in place of N$^1$-(2,4-difluorophenyl)benzene-1,2-diamine.

MS (ESI) m/z: 298.5 (M+H)$^+$.

Intermediate-45: (R)-tert-butyl 2-(((5-(2-oxo-2,3-dihydro-1H-benzo[d]imidazol-1-yl)pyridin-2-yl)oxy)methyl)morpholine-4-carboxylate A mixture of tert-butyl 3-(6-fluoropyridin-3-yl)-2-oxo-2,3-dihydro-1H-benzo[d]imidazole-1-carboxylate (75 mg, 0.23 mmol, Step-1 of Intermediate-15) and (R)-tert-butyl 2-(hydroxymethyl)morpholine-4-carboxylate (99 mg, 0.46 mmol) in 1,4-dioxane (1 mL) is added sodium hydride (60% dispersion in mineral oil, 36 mg, 0.91 mmol) at rt. The mixture is stirred at rt for 5 hrs. The mixture is diluted with saturated aqueous ammonium chloride and extracted with EtOAc. The organic layer is dried over sodium sulfate and filtered. The filtrate is concentrated. The residue is purified by column chromatography on silica-gel eluting with 0-50% EtOAc in n-hexane to give 46 mg (47% yield) of the title compound as a pale yellow solid.

MS (ESI) m/z: 427.7 (M+H)$^+$.

Intermediate-46: 5-chloro-2-methyl-N-((1S,4r)-4-((3-(6-((S)-morpholin-2-ylmethoxy)pyridin-3-yl)-2-oxo-2,3-dihydro-1H-benzo[d]imidazol-1-yl)methyl)cyclohexyl)nicotinamide <Step-1>: (S)-tert-butyl 2-(((5-(2-oxo-2,3-dihydro-1H-benzo[d]imidazol-1-yl)pyridin-2-yl)oxy)methyl)morpholine-4-carboxylate A mixture of tert-butyl 3-(6-fluoropyridin-3-yl)-2-oxo-2,3-dihydro-1H-benzo[d]imidazole-1-carboxylate (75 mg, 0.23 mmol, Step-1 of Intermediate-15) and (S)-tert-butyl 2-(hydroxymethyl)morpholine-4-carboxylate (99 mg, 0.46 mmol) in 1,4-dioxane (1 mL) is added sodium hydride (60% dispersion in mineral oil, 36 mg, 0.91 mmol) at rt. The mixture is stirred at rt for 5 hrs. The mixture is diluted with saturated aqueous ammonium chloride and extracted with EtOAc. The organic layer is dried over sodium sulfate and filtered. The filtrate is concentrated. The residue is purified by column chromatography on silica-gel eluting with 0-50% EtOAc in n-hexane to give 23 mg (24% yield) of the title compound as a pale yellow solid.

MS (ESI) m/z: 427.7 (M+H)$^+$.

<Step-2>: (S)-tert-butyl 2-(((5-(3-(((1r,4S)-4-(5-chloro-2-methylnicotinamido)cyclohexyl)methyl)-2-oxo-2,3-dihydro-1H-benzo[d]imidazol-1-yl)pyridin-2-yl)oxy)methyl)morpholine-4-carboxylate The title compound is prepared in 75% yield (28 mg, a pale yellow gum) by the similar manner to Step-3 of Intermediate-2 using (S)-tert-butyl 2-(((5-(2-oxo-2,3-dihydro-1H-benzo[d]imidazol-1-yl)pyridin-2-yl)oxy)methyl)morpholine-4-carboxylate (23 mg, 0.054 mmol, Step-1 of Intermediate-46) in place of methyl 3-((2-oxo-2,3-dihydro-1H-benzo[d]imidazol-1-yl)methyl)benzoate.

MS (ESI) m/z: 691.8 (M+H)$^+$.

<Step-3>: 5-chloro-2-methyl-N-((1S,4r)-4-((3-(6-((S)-morpholin-2-ylmethoxy)pyridin-3-yl)-2-oxo-2,3-dihydro-1H-benzo[d]imidazol-1-yl)methyl)cyclohexyl)nicotinamide A solution of (S)-tert-butyl 2-(((5-(3-(((1r,4S)-4-(5-chloro-2-methylnicotinamido)cyclohexyl)methyl)-2-oxo-2,3-dihydro-1H-benzo[d]imidazol-1-yl)pyridin-2-yl)oxy)methyl)morpholine-4-carboxylate (28 mg, 0.041 mmol, Step-2 of Intermediate-46) in DCM (1 mL) and TFA (1 mL) is stirred at rt for 1 hr. The mixture is concentrated. The residue is basified with saturated aqueous sodium bicarbonate and extracted with DCM. The organic layer is dried over sodium sulfate and filtered. The filtrate is concentrated to give 25 mg (quantitative yield) of the title compound as a pale yellow gum.

MS (ESI) m/z: 591.6 (M+H)$^+$.

Intermediate-47: N-((1r,4r)-4-((3-(6-(azetidin-3-yloxy)pyridin-3-yl)-2-oxo-2,3-dihydro-1H-benzo[d]imidazol-1-yl)methyl)cyclohexyl)-5-chloro-2-methylnicotinamide <Step-1>: tert-butyl 3-((5-(2-oxo-2,3-dihydro-1H-benzo[d]imidazol-1-yl)pyridin-2-yl)oxy)azetidine-1-carboxylate The title compound is prepared in 77% yield (67 mg, a pale yellow solid) by the similar manner to Step-1 of Intermediate-46 using tert-butyl 3-hydroxyazetidine-1-carboxylate in place of (S)-tert-butyl 2-(hydroxymethyl)morpholine-4-carboxylate.
MS (ESI) m/z: 383.8 (M+H)+.

<Step-2>: tert-butyl 3-((5-(3-(((1r,4r)-4-(5-chloro-2-methylnicotinamido)cyclohexyl)methyl)-2-oxo-2,3-dihydro-1H-benzo[d]imidazol-1-yl)pyridin-2-yl)oxy)azetidine-1-carboxylate The title compound is prepared in 67% yield (76 mg, a pale yellow gum) by the similar manner to Step-3 of Intermediate-2 using tert-butyl 3-((5-(2-oxo-2,3-dihydro-1H-benzo[d]imidazol-1-yl)pyridin-2-yl)oxy)azetidine-1-carboxylate (67 mg, 0.18 mmol, Step-1 of Intermediate-47) in place of methyl 3-((2-oxo-2,3-dihydro-1H-benzo[d]imidazol-1-yl)methyl)benzoate.
MS (ESI) m/z: 647.6 (M+H)+.

<Step-3>: N((1r,4r)-4-((3-(6-(azetidin-3-yloxy)pyridin-3-yl)-2-oxo-2,3-dihydro-1H-benzo[d]imidazol-1-yl)methyl)cyclohexyl)-5-chloro-2-methylnicotinamide The title compound is prepared in 92% yield (59 mg, a pale yellow gum) by the similar manner to Step-3 of Intermediate-46 using tert-butyl 3-((5-(3-(((1r,4r)-4-(5-chloro-2-methylnicotinamido)cyclohexyl)methyl)-2-oxo-2,3-dihydro-1H-benzo[d]imidazol-1-yl)pyridin-2-yl)oxy)azetidine-1-carboxylate (76 mg, 0.12 mmol, Step-2 of Intermediate-47).
MS (ESI) m/z: 547.5 (M+H)+.

Intermediate-48: N-((1r,4r)-4-((3-(6-(azetidin-3-ylmethoxy)pyridin-3-yl)-2-oxo-2,3-dihydro-1H-benzo [d]imidazol-1-yl)methyl)cyclohexyl)-5-chloro-2-methylnicotinamide <Step-1>: tert-butyl 3-(((5-(2-oxo-2,3-dihydro-1H-benzo[d]imidazol-1-yl)pyridin-2-yl)oxy)methyl)azetidine-1-carboxylate The title compound is prepared in quantitative yield (94 mg, a pale yellow solid) by the similar manner to Step-1 of Intermediate-46 using tert-butyl 3-(hydroxymethyl)azetidine-1-carboxylate in place of (S)-tert-butyl 2-(hydroxymethyl)morpholine-4-carboxylate.
MS (ESI) m/z: 397.8 (M+H)+.

<Step-2>: tert-butyl 3-(((5-(3-(((1r,4r)-4-(5-chloro-2-methylnicotinamido)cyclohexyl)methyl)-2-oxo-2,3-dihydro-1H-benzo[d]imidazol-1-yl)pyridin-2-yl)oxy)methyl)azetidine-1-carboxylate The title compound is prepared in 52% yield (82 mg, a pale yellow gum) by the similar manner to Step-3 of Intermediate-2 using tert-butyl 3-(((5-(2-oxo-2,3-dihydro-1H-benzo[d]imidazol-1-yl)pyridin-2-yl)oxy)methyl)azetidine-1-carboxylate (94 mg, 0.24 mmol, Step-1 of Intermediate-48) in place of methyl 3-((2-oxo-2,3-dihydro-1H-benzo[d]imidazol-1-yl)methyl)benzoate.
MS (ESI) m/z: 661.7 (M+H)+.

<Step-3>: N((1r,4r)-4-((3-(6-(azetidin-3-ylmethoxy)pyridin-3-yl)-2-oxo-2,3-dihydro-1H-benzo[d]imidazol-1-yl)methyl)cyclohexyl)-5-chloro-2-methylnicotinamide The title compound is prepared in quantitative yield (74 mg, a pale yellow gum) by the similar manner to Step-3 of Intermediate-46 using tert-butyl 3-(((5-(3-(((1r,4r)-4-(5-chloro-2-methylnicotinamido)cyclohexyl)methyl)-2-oxo-2,3-dihydro-1H-benzo[d]imidazol-1-yl)pyridin-2-yl)oxy)methyl)azetidine-1-carboxylate (76 mg, 0.12 mmol, Step-2 of Intermediate-48).

Intermediate-49: (S)-1-(6-(3-hydroxypyrrolidin-1-yl)pyridin-3-yl)-1H-benzo[d]imidazol-2(3H)-one The title compound is prepared in 39% yield (25 mg, a brown gum) by the similar manner to Step-4 of Intermediate-40 using (S)-pyrrolidin-3-ol in place of dimethylamine hydrochloride.
MS (ESI) m/z: 297.5 (M+H)+.

Intermediate-50: (R)-1-(6-(3-hydroxypyrrolidin-1-yl)pyridin-3-yl)-1H-benzo[d]imidazol-2(3H)-one The title compound is prepared in 39% yield (25 mg, a brown gum) by the similar manner to Step-4 of Intermediate-40 using (R)-pyrrolidin-3-ol in place of dimethylamine hydrochloride.
MS (ESI) m/z: 297.6 (M+H)+.

Intermediate-51: 1-(6-cyclopropylpyridin-3-yl)-1H-benzo[d]imidazol-2(3H)-one

<Step-1>: 6-bromo-N-(2-nitrophenyl)pyridin-3-amine

To a mixture of 1-fluoro-2-nitrobenzene (2.00 g, 14.2 mmol) and 6-bromopyridin-3-amine (2.45 g, 14.2 mmol) in THF (14 mL) is added potassium tert-butoxide (3.18 g, 28.3 mmol) at 0° C. and stirred at rt. After 1 hr, the reaction mixture is diluted with water and extracted with EtOAc. The organic phase is washed with brine, dried over MgSO$_4$, filtered and concentrated. The residue is purified by column chromatography on silica-gel eluting with 0-50% EtOAc in n-hexane to give 2.77 g (66% yield) of the title compound as an orange solid.
$^1$H-NMR (400 MHz, CDCl$_3$) delta 9.32 (1H, s), 8.38 (1H, d, J=2.7 Hz), 8.24 (1H, dd, J=8.2, 1.6 Hz), 7.53 (1H, d, J=8.2 Hz), 7.50 (1H, dd, J=8.2, 2.7 Hz), 7.45 (1H, t, J=7.8 Hz), 7.17 (1H, d, J=7.8 Hz), 6.91 (1H, t, J=8.2 Hz).

<Step-2>: N$^1$-(6-bromopyridin-3-yl)benzene-1,2-diamine

A mixture of 6-bromo-N-(2-nitrophenyl)pyridin-3-amine (2.77 g, 9.42 mmol), iron (1.58 g, 28.3 mmol) and ammonium chloride (3.1 g, 56.5 mmol) in ethanol (125 mL) and water (50 mL) is refluxed with stirring for 2.5 hr. After cooling to room temperature, the reaction mixture is filtered through a pad of celite, and the filtrate is concentrated in vacuo, the residue is poured into 2 M aqueous sodium hydroxide solution and extracted with EtOAc. The organic phase is dried over sodium sulfate then filtrated and concentrated to give 2.50 g (100% yield) of the title compound as a beige solid.

$^1$H-NMR (400 MHz, CDCl$_3$) delta 7.92 (1H, d, J=2.7 Hz), 7.24 (1H, d, J=8.7 Hz), 7.11-7.04 (2H, m), 6.88-6.80 (2H, m), 6.77 (1H, td, J=7.5, 1.4 Hz), 5.25 (1H, s), 3.76 (2H, s). MS (ESI) m/z: 264.4 (M+H)$^+$.

<Step-3>:1-(6-bromopyridin-3-yl)-1H-benzo[d]imidazol-2(3H)-one

A mixture of N$^1$-(6-bromopyridin-3-yl)benzene-1,2-diamine (2.50 g, 9.47 mmol) and CDI (1.84 g, 11.4 mmol) in THF is stirred at rt. After 3 hrs, CDI (2.0 g, 12.3 mmol) is added to the reaction mixture and stirred at rt overnight. The reaction mixture is diluted with saturated aqueous sodium bicarbonate and extracted with EtOAc. The organic phase is concentrated. The residual solid is washed with EtOAc then collected by filtration to give 1.9 g (69% yield) of the title compound as a beige solid.

$^1$H-NMR (400 MHz, CDCl$_3$) delta 9.19 (1H, br s), 8.66 (1H, dd, J=2.7, 0.9 Hz), 7.85 (1H, dd, J=8.2, 2.7 Hz), 7.69 (1H, d, J=8.2 Hz), 7.21-7.09 (3H, m), 7.08 (1H, d, J=7.3 Hz).

<Step-4>:1-(6-cyclopropylpyridin-3-yl)-1H-benzo[d]imidazol-2(3H)-one

To a mixture of 1-(6-bromopyridin-3-yl)-1H-benzo[d]imidazol-2(3H)-one (30 mg, 0.103 mmol), cyclopropylboronic acid (13.3 mg, 0.155 mmol), bis(di-tert-butyl(4-dimethylaminophenyl)phosphine)dichloropalladium(II) (3.7 mg, 0.0052 mmol) in 1,4-dioxane (0.5 mL) is added 2 M aqueous tripotassium phosphate solution (0.129 mL) and stirred at 150° C. for 10 min under microwave irradiation. After cooled to rt, the organic phase of the reaction mixture is directly purified by column chromatography on silica-gel eluting with 12-80% EtOAc in n-hexane to give 3 mg (12% yield) of the title compound as a pale yellow solid.

MS (ESI) m/z: 252.4 (M+H)$^+$.

Intermediate-52: 1-(6-(tetrahydro-2H-pyran-4-yl)pyridin-3-yl)-1H-benzo[d]imidazol-2(3H)-one <Step-1>: 1-(6-(3,6-dihydro-2H-pyran-4-yl)pyridin-3-yl)-1H-benzo[d]imidazol-2(3H)-one To a mixture of 1-(6-bromopyridin-3-yl)-1H-benzo[d]imidazol-2(3H)-one (30 mg, 0.103 mmol, Step-3 of Intermediate-51), 2-(3,6-dihydro-2H-pyran-4-yl)-4,4,5,5-tetramethyl-1,3,2-dioxaborolane (26.1 mg, 0.124 mmol), bis(di-tert-butyl(4-dimethylaminophenyl)phosphine)dichloropalladium(II) (3.7 mg, 0.0052 mmol) in 1,4-dioxane (0.6 mL) is added 2 M aqueous tripotassium phosphate solution (0.129 mL) and stirred at 120° C. for 10 min under microwave irradiation. After cooled to rt, the organic phase of the reaction mixture is directly purified by column chromatography on silica-gel eluting with 10-100% EtOAc in n-hexane to give 21 mg (69% yield) of the title compound as a beige solid.

MS (ESI) m/z: 294.4 (M+H)$^+$.

<Step-2>: 1-(6-(tetrahydro-2H-pyran-4-yl)pyridin-3-yl)-1H-benzo[d]imidazol-2(3H)-one A solution of 1-(6-(3,6-dihydro-2H-pyran-4-yl)pyridin-3-yl)-1H-benzo[d]imidazol-2(3H)-one (21 mg, 0.072 mmol) in EtOAc (2 mL) and DMF (1 mL) is evacuated and backfilled with N$_2$ gas. To this is added 10% Pd/C (wet) (8 mg). The mixture is evacuated and backfilled with H$_2$ gas and stirred at rt under H$_2$ atmosphere. After 1 h, the reaction mixture is evacuated and backfilled with N$_2$ gas and the mixture is filtered through celite pad. The filtrate is concentrated in vacuo to give 17 mg (80% yield) of the title compound. It is used for a next reaction without further purification.

$^1$H-NMR (400 MHz, CDCl$_3$) delta 9.27 (1H, br s), 8.79 (1H, d, J=2.7 Hz), 7.89 (1H, dd, J=8.2, 2.7 Hz), 7.39 (1H, d, J=8.2 Hz), 7.17-7.13 (2H, m), 7.13-7.05 (2H, m), 4.18-4.11 (2H, m), 3.64-3.55 (2H, m), 3.12-2.99 (1H, m), 2.03-1.89 (4H, m). MS (ESI) m/z: 296.4 (M+H)$^+$.

Intermediate-53: 1-(1-methyl-1H-pyrazol-4-yl)-1H-benzo[d]imidazol-2(3H)-one

<Step-1>:1-methyl-N-(2-nitrophenyl)-1H-pyrazol-4-amine

The title compound is prepared in 29% yield (66 mg, a pale yellow gum) by the similar manner to Step-1 of Intermediate-36 using 1-methyl-1H-pyrazol-4-amine (100 mg, 1.03 mmol) in place of methyl 5-aminopicolinate.

MS (ESI) m/z: 219.5 (M+H)$^+$.

<Step-2>: N$^1$-(1-methyl-1H-pyrazol-4-yl)benzene-1,2-diamine

The title compound is prepared in quantitative yield (57 mg, a pale yellow gum) by the similar manner to Step-2 of Intermediate-13 using 1-methyl-N-(2-nitrophenyl)-1H-pyrazol-4-amine (66 mg, 0.30 mmol, Step-1 of Intermediate-53).

MS (ESI) m/z: 189.5 (M+H)$^+$.

<Step-3>:1-(1-methyl-H-pyrazol-4-yl)-1H-benzo[d]imidazol-2(3H)-one

The title compound is prepared in 69% yield (45 mg, a pale yellow solid) by the similar manner to Step-3 of Intermediate-20 using N$^1$-(1-methyl-1H-pyrazol-4-yl)benzene-1,2-diamine (57 mg, 0.30 mmol, Step-2 in Intermediate-53).

$^1$H-NMR (400 MHz, DMSO-d$_6$) delta 11.10 (1H, br s), 8.15 (1H, s), 7.76 (1H, d, J=0.9 Hz), 7.11-7.00 (4H, m), 3.91 (3H, s). MS (ESI) m/z: 215.4 (M+H)$^+$.

Intermediate-54: 5-chloro-N-((1r,4r)-4-((3-(6-fluoropyridin-3-yl)-2-oxo-2,3-dihydro-1H-benzo[d]imidazol-1-yl)methyl)cyclohexyl)-2-methylnicotinamide A mixture of ((1r,4r)-4-(5-chloro-2-methylnicotinamido)cyclohexyl)methyl methanesulfonate (200 mg, 0.55 mmol, Mesylate-1), tert-butyl 3-(6-fluoropyridin-3-yl)-2-oxo-2,3-dihydro-1H-benzo[d]imidazole-1-carboxylate (183 mg, 0.55 mmol, Step-1 of Intermediate-15), and cesium carbonate (542 mg, 1.66 mmol) in DMSO (1 mL) is stirred at 90° C. for 5 hrs. The mixture is diluted with water. The mixture is extracted with EtOAc. The organic layer is concentrated. The residue is purified by column chromatography on silica-gel eluting with 0-100% EtOAc in n-hexane to give 182 mg (67% yield) of the title compound as a pale yellow solid.

MS (ESI) m/z: 494.4 (M+H)$^+$.

Intermediate-55: 5-chloro-N-((1r,4r)-4-((3-(6-chloropyridazin-3-yl)-2-oxo-2,3-dihydro-1H-benzo[d]imidazol-1-yl)methyl)cyclohexyl)-2-methylnicotinamide The title compound is prepared in 65% yield (49 mg, a pale yellow gum) by the similar manner to Step-3 of Intermediate-2 using 1-(6-chloropyridazin-3-yl)-1H-benzo[d]imidazol-2(3H)-one (34 mg, 0.14 mmol, Step-3 of Intermediate-40) in place of methyl 3-((2-oxo-2,3-dihydro-1H-benzo[d]imidazol-1-yl)methyl)benzoate.

MS (ESI) m/z: 511.4 (M+H)$^+$.

Intermediate-56: tert-butyl 3-(2,3-dihydro-[1,4]dioxino[2,3-b]pyridin-7-yl)-2-oxo-2,3-dihydro-1H-benzo[d]imidazole-1-carboxylate A mixture of tert-butyl 2-oxo-2,3-dihydro-1H-benzo[d]imidazole-1-carboxylate (105 mg, 0.449 mmol), copper (II) acetate (61 mg, 0.336 mmol), pyridine (0.033 mL, 0.404 mmol), 7-(4,4,5,5-tetramethyl-1,3,2-dioxaborolan-2-yl)-2,3-dihydro-[1,4]dioxino[2,3-b]pyridine (59 mg, 0.224 mmol), and MS 4A (100 mg) in DCM (1 mL) is stirred at rt for 2 days. The reaction mixture is filtered through celite pad. The filtrate is concentrated and the resultant residue is purified by column chromatography on silica-gel eluting with 10-100% EtOAc in n-hexane to give 12 mg (14% yield) of the title compound as an off-white solid.

$^1$H-NMR (400 MHz, CDCl$_3$) delta 7.98 (1H, d, J=2.3 Hz), 7.94-7.89 (1H, m), 7.38 (1H, d, J=2.3 Hz), 7.22-7.14 (2H, m), 6.97-6.91 (1H, m), 4.55-4.48 (2H, m), 4.35-4.28 (2H, m), 1.69 (9H, s). MS (ESI) m/z: 370.4 (M+H)$^+$.

Intermediate-57: 5-chloro-N-((1r,4r)-4-((3-(5-chloropyrazin-2-yl)-2-oxo-2,3-dihydro-1H-benzo[d]imidazol-1-yl)methyl)cyclohexyl)-2-methylnicotinamide <Step-1>: 1-(5-chloropyrazin-2-yl)-1H-benzo[d]imidazol-2(3H)-one A mixture of 1H-benzo[d]imidazol-2(3H)-one (225 mg, 1.68 mmol), 2,5-dichloropyrazine (250 mg, 1.68 mmol), and cesium carbonate (820 mg, 2.52 mmol) in DMSO (2 mL) is stirred at 80° C. for 2 hrs. The mixture is diluted with water. The precipitate is collected and washed with diisopropyl ether to give 356 mg (86% yield) of the title compound as a pale yellow solid.

$^1$H-NMR (400 MHz, DMSO-d$_6$) delta 9.31 (1H, d, J=1.4 Hz), 8.77 (1H, d, J=1.4 Hz), 7.90 (1H, d, J=8.2 Hz), 7.18-7.01 (3H, m). A signal due to NH is not observed.

MS (ESI) m/z: 247.2 (M+H)$^+$.

<Step-2>: 5-chloro-N-((1r,4r)-4-((3-(5-chloropyrazin-2-yl)-2-oxo-2,3-dihydro-1H-benzo[d]imidazol-1-yl)methyl)cyclohexyl)-2-methylnicotinamide A mixture of ((1r,4r)-4-(5-chloro-2-methylnicotinamido)cyclohexyl)methyl methanesulfonate (250 mg, 0.69 mmol, Mesylate-1), 1-(5-chloropyrazin-2-yl)-1H-benzo[d]imidazol-2(3H)-one (171 mg, 0.69 mmol, Step-1 of Intermediate-57), and cesium carbonate (677 mg, 2.08 mmol) in DMSO (1 mL) is stirred at 80° C. for 5 hrs. The mixture is diluted with water. The precipitate is collected and dried in vacuo to give 471 mg (quantitative yield) of the title compound as a pale yellow solid.

MS (ESI) m/z: 511.3 (M+H)$^+$.

Intermediate-58: tert-butyl 3-(5,6-dimethoxypyridin-3-yl)-2-oxo-2,3-dihydro-1H-benzo[d]imidazole-1-carboxylate A mixture of tert-butyl 2-oxo-2,3-dihydro-1H-benzo[d]imidazole-1-carboxylate (100 mg, 0.427 mmol), copper (II) acetate (155 mg, 0.854 mmol), TEA (0.298 mL, 2.13 mmol), 2,3-dimethoxy-5-(4,4,5,5-tetramethyl-1,3,2-dioxaborolan-2-yl)pyridine (226 mg, 0.854 mmol), and molecular sieves 4 angstrom (100 mg) in DCM (3 mL) is stirred at rt for 4 days. The reaction mixture is filtered through celite pad. The filtrate is concentrated and the resultant residue is purified by column chromatography on silica-gel eluting with 10-100% EtOAc in n-hexane to give 113 mg (71% yield) of the title compound as a yellow viscous oil.

$^1$H-NMR (400 MHz, CDCl$_3$) delta 7.94-7.90 (1H, m), 7.87 (1H, d, J=2.3 Hz), 7.20-7.16 (3H, m), 6.96-6.93 (1H, m), 4.08 (3H, s), 3.89 (3H, s), 1.70 (9H, s). MS (ESI) m/z: 372.3 (M+H)$^+$.

Intermediate-59: tert-butyl 3-(5,6-dimethylpyridin-3-yl)-2-oxo-2,3-dihydro-1H-benzo[d]imidazole-1-carboxylate The title compound is prepared by the similar manner to Intermediate-58 using 2,3-dimethyl-5-(4,4,5,5-tetramethyl-1,3,2-dioxaborolan-2-yl)pyridine (199 mg, 0.854 mmol) in place of 2,3-dimethoxy-5-(4,4,5,5-tetramethyl-1,3,2-dioxaborolan-2-yl)pyridine.

$^1$H-NMR (400 MHz, CDCl$_3$) delta 8.48 (1H, d, J=2.3 Hz), 7.94-7.92 (1H, m), 7.60 (1H, d, J=2.3 Hz), 7.21-7.14 (2H, m), 6.95-6.94 (1H, m), 2.58 (3H, s), 2.36 (3H, s), 1.69 (9H, s). MS (ESI) m/z: 340.3 (M+H)$^+$.

Intermediate-60: 1-(6-methoxy-5-methylpyridin-3-yl)-1H-benzo[d]imidazol-2(3H)-one <Step-1>: 6-methoxy-5-methylpyridin-3-amine A solution of 2-methoxy-3-methyl-5-nitropyridine (490 mg, 2.91 mmol) in EtOAc (10 mL) is evacuated and backfilled with N$_2$ gas. To this is added 10% Pd/C (wet) (50 mg). The resulting mixture is evacuated and backfilled with H$_2$ and vigorously stirred at rt under H$_2$ atmosphere for 1 h. After evacuated and backfilled with N$_2$, the mixture is filtered through celite pad. The filtrate is concentrated in vacuo to give 394 mg (98% yield) of the title compound as a pale green oil. It is used for a next step without further purification.

$^1$H-NMR (400 MHz, CDCl$_3$) delta 7.50 (1H, d, J=2.3 Hz), 6.87 (1H, d, J=2.3 Hz), 3.88 (3H, s), 3.28 (2H, br s), 2.13 (3H, s).

<Step-2>: 6-methoxy-5-methyl-N-(2-nitrophenyl)pyridin-3-amine

A solution 2-fluoro-nitrobenzene (30 mg, 0.213 mmol) and 6-methoxy-5-methylpyridin-3-amine (29.4 mg, 0.213 mmol) in THF (1 mL) is added potassium tert-butoxide (47.7 mg, 0.425 mmol) and stirred at rt. After 1 h, the reaction mixture is diluted with EtOAc and 0.5 M hydrochloric acid. The resulting mixture is extracted with EtOAc. The organic phase is dried over MgSO$_4$, filtered and concentrated. The crude mixture is purified by column chromatography on silica-gel eluting with 10-90% EtOAc in n-hexane to give 24 mg (44% yield) of the title compound as a beige solid.

$^1$H-NMR (400 MHz, CDCl$_3$) delta 9.27 (1H, s), 8.21 (1H, dd, J=8.7, 1.4 Hz), 7.96 (1H, d, J=2.7 Hz), 7.38-7.32 (2H, m), 6.92 (1H, dd, J=8.7, 0.9 Hz), 6.78-6.73 (1H, m), 3.99 (3H, s), 2.22 (3H, s).

<Step-3>: N$^1$-(6-methoxy-5-methylpyridin-3-yl)benzene-1,2-diamine

A solution of 6-methoxy-5-methyl-N-(2-nitrophenyl)pyridin-3-amine (24 mg, 0.093 mmol) in EtOAc (3 mL) is evacuated and backfilled with N$_2$ gas. To this is added 10% Pd/C (wet) (10 mg). The resulting mixture is evacuated and backfilled with H$_2$ and vigorously stirred at rt under H$_2$ atmosphere for 1 hr. After evacuated and backfilled with N$_2$, the mixture is filtered through celite pad. The filtrate is concentrated in vacuo to give 20 mg (94% yield) of the title compound as a brown oil. It is used for a next step without further purification.

$^1$H-NMR (400 MHz, CDCl$_3$) delta 7.62 (1H, d, J=2.3 Hz), 7.01 (1H, d, J=2.3 Hz), 6.98-6.90 (2H, m), 6.80 (1H, dd, J=7.8, 0.9 Hz), 6.74 (1H, t, J=7.8 Hz), 3.93 (3H, s), 2.15 (3H, s).

<Step-4>:1-(6-methoxy-5-methylpyridin-3-yl)-1H-benzo[d]imidazol-2(3H)-one

The title compound is prepared in 90% yield (20 mg, a beige solid) by the similar manner to Step-3 of Intermediate-51 using N$^1$-(6-methoxy-5-methylpyridin-3-yl)benzene-1,2-diamine (20 mg, 0.087 mmol) in place of N$^1$-(6-bromopyridin-3-yl)benzene-1,2-diamine.

$^1$H-NMR (400 MHz, CDCl$_3$) delta 8.88 (1H, br s), 8.18 (1H, d, J=2.7 Hz), 7.57 (1H, d, J=2.7 Hz), 7.14-7.04 (3H, m), 6.96 (1H, d, J=7.8 Hz), 4.03 (3H, s), 2.27 (3H, s).

Intermediate-61: 7-fluoro-1-(6-methylpyridin-3-yl)-1H-benzo[d]imidazol-2(3H)-one <Step-1>: N-(2-fluoro-6-nitrophenyl)-6-methylpyridin-3-amine The title compound is prepared in 72% yield (112 mg, a yellow solid) by the similar manner to Step-2 of Intermediate-60 using 1,2-difluoro-3-nitrobenzene (100 mg, 0.629 mmol) and 6-methylpyridin-3-amine (68 mg, 0.629 mmol) in place of 2-fluoro-nitrobenzene and 6-methoxy-5-methylpyridin-3-amine, respectively.

$^1$H-NMR (400 MHz, CDCl$_3$) delta 8.72 (1H, br s), 8.28 (1H, t, J=2.7 Hz), 8.03 (1H, dt, J=8.7, 1.4 Hz), 7.32 (1H, ddd, J=12.0, 7.9, 1.4 Hz), 7.22 (1H, dt, J=8.2, 2.7 Hz), 7.10 (1H, d, J=8.2 Hz), 6.96 (1H, td, J=8.2, 4.7 Hz), 2.54 (3H, s).

<Step-2>:7-fluoro-1-(6-methylpyridin-3-yl)-1H-benzo[d]imidazol-2(3H)-one

The title compound is prepared in 78% yield (86 mg) by the similar manner to both Step-3 of Intermediate-60 and Step-3 of Intermediate-51 using N-(2-fluoro-6-nitrophenyl)-6-methylpyridin-3-amine (112 mg, 0.453 mmol) as a starting material for the former step in place of 6-methoxy-5-methyl-N-(2-nitrophenyl)pyridin-3-amine.

$^1$H-NMR (400 MHz, CDCl$_3$) delta 9.66 (1H, s), 8.67 (1H, t, J=2.3 Hz), 7.74 (1H, dt, J=8.7, 2.3 Hz), 7.32 (1H, d, J=8.7 Hz), 7.07 (1H, td, J=8.2, 4.6 Hz), 6.95 (1H, dd, J=8.2, 0.9 Hz), 6.85 (1H, ddd, J=11.2, 8.2, 0.9 Hz), 2.66 (3H, s). MS (ESI) m/z: 244.3 (M+H)$^+$.

Intermediate-62: 6-fluoro-1-(6-methylpyridin-3-yl)-1H-benzo[d]imidazol-2(3H)-one <Step-1>: N-(5-fluoro-2-nitrophenyl)-6-methylpyridin-3-amine The title compound is prepared in 72% yield (112 mg, a yellow solid) by the similar manner to Step-2 of Intermediate-60 using 2,4-difluoro-1-nitrobenzene (100 mg, 0.629 mmol) and 6-methylpyridin-3-amine (68 mg, 0.629 mmol) in place of 2-fluoro-nitrobenzene and 6-methoxy-5-methylpyridin-3-amine, respectively.

$^1$H-NMR (400 MHz, CDCl$_3$) delta 9.52 (1H, br s), 8.48 (1H, d, J=2.7 Hz), 8.28 (1H, dd, J=9.6, 5.9 Hz), 7.52 (1H, dd, J=8.2, 2.7 Hz), 7.26 (1H, d, J=8.2 Hz), 6.65 (1H, dd, J=11.0, 2.7 Hz), 6.52 (1H, ddd, J=9.6, 7.8, 2.3 Hz), 2.62 (3H, s).

<Step-2>:6-fluoro-1-(6-methylpyridin-3-yl)-1H-benzo[d]imidazol-2(3H)-one

The title compound is prepared in 62% yield (86 mg) by the similar manner to both Step-3 of Intermediate-60 and Step-3 of Intermediate-51 using N-(5-fluoro-2-nitrophenyl)-6-methylpyridin-3-amine (112 mg, 0.453 mmol) as a starting material for the former step in place of 6-methoxy-5-methyl-N-(2-nitrophenyl)pyridin-3-amine.

$^1$H-NMR (400 MHz, CDCl$_3$) delta 9.31 (1H, br s), 8.70 (1H, d, J=2.7 Hz), 7.78 (1H, dd, J=8.2, 2.7 Hz), 7.37 (1H, d, J=8.2 Hz), 7.05 (1H, dd, J=8.9, 4.3 Hz), 6.85 (1H, td, J=8.9, 2.3 Hz), 6.77 (1H, dd, J=8.9, 2.3 Hz), 2.67 (3H, s). MS (ESI) m/z: 244.3 (M+H)$^+$.

Intermediate-63: 5-fluoro-1-(6-methylpyridin-3-yl)-1H-benzo[d]imidazol-2(3H)-one <Step-1>: N-(4-fluoro-2-nitrophenyl)-6-methylpyridin-3-amine The title compound is prepared in 23% yield (35 mg, a yellow solid) by the similar manner to Step-2 of Intermediate-60 using 1,4-difluoro-2-nitrobenzene (100 mg, 0.629 mmol) and 6-methylpyridin-3-amine (68 mg, 0.629 mmol) in place of 2-fluoro-nitrobenzene and 6-methoxy-5-methylpyridin-3-amine, respectively.

$^1$H-NMR (400 MHz, CDCl$_3$) delta 9.21 (1H, br s), 8.47 (1H, d, J=2.7 Hz), 7.94 (1H, dd, J=8.9, 2.7 Hz), 7.49 (1H, dd, J=8.5, 2.7 Hz), 7.25-7.16 (2H, m), 7.07 (1H, dd, J=9.6, 4.6 Hz), 2.60 (3H, s).

<Step-2>:5-fluoro-1-(6-methylpyridin-3-yl)-1H-benzo[d]imidazol-2(3H)-one

The title compound is prepared in 72% yield (21 mg) by the similar manner to both Step-3 of Intermediate-60 and Step-3 of Intermediate-51 using N-(4-fluoro-2-nitrophenyl)-6-methylpyridin-3-amine (35 mg, 0.142 mmol) as a starting material for the former step in place of 6-methoxy-5-methyl-N-(2-nitrophenyl)pyridin-3-amine.

$^1$H-NMR (400 MHz, CDCl$_3$) delta 9.06 (1H, br s), 8.70 (1H, d, J=2.7 Hz), 7.79 (1H, dd, J=8.2, 2.7 Hz), 7.36 (1H, d, J=8.2 Hz), 6.94 (1H, dd, J=8.7, 4.6 Hz), 6.90 (1H, dd, J=8.2, 2.3 Hz), 6.81 (1H, ddd, J=10.0, 8.7, 2.3 Hz), 2.66 (3H, s). MS (ESI) m/z: 244.3 (M+H)+.

Intermediate-64: 4-fluoro-1-(6-methylpyridin-3-yl)-1H-benzo[d]imidazol-2(3H)-one <Step-1>: N-(3-fluoro-2-nitrophenyl)-6-methylpyridin-3-amine The title compound is prepared in 72% yield (112 mg, a yellow solid) by the similar manner to Step-2 of Intermediate-60 using 1,3-difluoro-2-nitrobenzene (100 mg, 0.629 mmol) and 6-methylpyridin-3-amine (68 mg, 0.629 mmol) in place of 2-fluoro-nitrobenzene and 6-methoxy-5-methylpyridin-3-amine, respectively.
$^1$H-NMR (400 MHz, CDCl$_3$) delta 8.44 (1H, d, J=2.7 Hz), 8.37 (1H, br s), 7.46 (1H, dd, J=8.2, 2.7 Hz), 7.31-7.23 (1H, m), 7.21 (1H, d, J=8.2 Hz), 6.83 (1H, dt, J=8.7, 1.2 Hz), 6.62 (1H, ddd, J=11.0, 8.2, 1.2 Hz), 2.58 (3H, s).

<Step-2>: 4-fluoro-1-(6-methylpyridin-3-yl)-1H-benzo[d]imidazol-2(3H)-one

The title compound is prepared in 88% yield (97 mg) by the similar manner to both Step-3 of Intermediate-60 and Step-3 of Intermediate-51 using N-(3-fluoro-2-nitrophenyl)-6-methylpyridin-3-amine (112 mg, 0.453 mmol) as a starting material for the former step in place of 6-methoxy-5-methyl-N-(2-nitrophenyl)pyridin-3-amine.
$^1$H-NMR (400 MHz, CDCl$_3$) delta 9.11 (1H, br s), 8.70 (1H, d, J=2.3 Hz), 7.80 (1H, dd, J=8.2, 2.3 Hz), 7.35 (1H, d, J=8.2 Hz), 7.02 (1H, td, J=8.2, 5.0 Hz), 6.94-6.89 (1H, m), 6.83 (1H, dd, J=8.2, 0.9 Hz), 2.66 (3H, s). MS (ESI) m/z: 244.3 (M+H)+.

Intermediate-65: 5-(3-(((1r,4r)-4-(5-chloro-2-methylnicotinamido)cyclohexyl)methyl)-2-oxo-2,3-dihydro-1H-benzo[d]imidazol-1-yl)-2-methylbenzoic acid <Step-1>: methyl 2-methyl-5-((2-nitrophenyl)amino)benzoate A mixture of 1-bromo-2-nitrobenzene (293 mg, 1.45 mmol), methyl 5-amino-2-methylbenzoate (200 mg, 1.21 mmol), [1,1'-bis(diphenylphosphino)ferrocene] dichloropalladium(II) complex with dichloromethane (99 mg, 0.12 mmol), 1,1'-bis(diphenylphosphino)ferrocene (13 mg, 0.024 mmol), and tripotassium phosphate (514 mg, 2.42 mmol) in toluene (3 mL) is stirred at 100° C. for 1 day. The mixture is diluted with water. The mixture is extracted with EtOAc. The organic layer is dried over sodium sulfate, filtered and concentrated. The residue is purified by column chromatography on silica-gel eluting with 0-25% EtOAc in n-hexane to give 246 mg (71% yield) of the title compound as a brown gum.
$^1$H-NMR (400 MHz, CDCl$_3$) delta 9.45 (1H, br s), 8.21 (1H, dd, J=8.2, 1.8 Hz), 7.83 (1H, d, J=2.3 Hz), 7.41-7.28 (3H, m), 7.14 (1H, dd, J=8.7, 1.4 Hz), 6.79 (1H, ddd, J=8.2, 7.3, 1.4 Hz), 3.90 (3H, s), 2.62 (3H, s).

<Step-2>: methyl 5-((2-aminophenyl)amino)-2-methylbenzoate

The title compound is prepared in quantitative yield (246 mg, a brown gum) by the similar manner to Step-2 of Intermediate-20 using methyl 2-methyl-5-((2-nitrophenyl) amino)benzoate (275 mg, 0.96 mmol, Step-1 in Intermediate-65) in place of 2,4-difluoro-N-(2-nitrophenyl)aniline.

<Step-3>: methyl 2-methyl-5-(2-oxo-2,3-dihydro-1H-benzo[d]imidazol-1-yl)benzoate A mixture of methyl 5-((2-aminophenyl)amino)-2-methylbenzoate (246 mg, 0.96 mmol, Step-2 of Intermediate-65) and CDI (233 mg, 1.44 mmol) in THF (3 mL) is stirred at room temperature for 3 hrs. The mixture is concentrated. The residual solid is washed with diisopropyl ether to give 175 mg (65% yield) of the title compound as a pale yellow solid.
$^1$H-NMR (400 MHz, DMSO-d$_6$) delta 11.21 (1H, br s), 7.95 (1H, d, J=2.3 Hz), 7.70-7.62 (1H, m), 7.52 (1H, d, J=8.2 Hz), 7.10-6.95 (4H, m), 3.85 (3H, m), 2.59 (3H, s). MS (ESI) m/z: 283.3 (M+H)+.

<Step-4>: 5-(3-(((1r,4r)-4-(5-chloro-2-methylnicotinamido)cyclohexyl)methyl)-2-oxo-2,3-dihydro-1H-benzo[d]imidazol-1-yl)-2-methylbenzoic acid A mixture of ((r,4r)-4-(5-chloro-2-methylnicotinamido)cyclohexyl)methyl methanesulfonate (224 mg, 0.62 mmol, Mesylate-1), methyl 2-methyl-5-(2-oxo-2,3-dihydro-1H-benzo[d]imidazol-1-yl)benzoate (175 mg, 0.62 mmol, Step-3 of Intermediate-65), and cesium carbonate (606 mg, 1.86 mmol) in DMSO (2 mL) is stirred at 80° C. for 5 hrs. Then, the mixture is diluted with water and stirred at rt for 3 days. The mixture is acidified with 2 M hydrochloric acid. The precipitate is collected and dried in vacuo to give 120 mg (36% yield) of the title compound as a purple solid.
$^1$H-NMR (400 MHz, DMSO-d$_6$) delta 8.53 (1H, d, J=2.7 Hz), 8.41 (1H, d, J=7.8 Hz), 7.96 (1H, d, J=2.3 Hz), 7.79 (1H, d, J=2.3 Hz), 7.65 (1H, dd, J=8.2, 2.3 Hz), 7.51 (1H, d, J=8.2 Hz), 7.34 (1H, d, J=7.8 Hz), 7.19-7.13 (1H, m), 7.10-7.01 (2H, m), 3.77 (2H, d, J=6.9 Hz), 3.78-3.63 (1H, m), 2.60 (3H, s), 2.51 (3H, s), 1.94-1.69 (5H, m), 1.30-1.13 (4H, m). A signal due to COOH is not observed. MS (ESI) m/z: 533.2 (M+H)+.

Intermediate-66: 2-(3-(((1r,4r)-4-(5-chloro-2-methylnicotinamido)cyclohexyl)methyl)-2-oxo-2,3-dihydro-1H-benzo[d]imidazol-1-yl)-5-methylbenzoic acid <Step-1>: ethyl 5-methyl-2-((2-nitrophenyl)amino)benzoate A mixture of 1-bromo-2-nitrobenzene (336 mg, 1.67 mmol), ethyl 2-amino-5-methylbenzoate (249 mg, 1.39 mmol), [1,1'-bis(diphenylphosphino)ferrocene] dichloropalladium(II) complex with dichloromethane (113 mg, 0.14 mmol), 1,1'-bis(diphenylphosphino)ferrocene (15 mg, 0.028 mmol), and tripotassium phosphate (589 mg, 2.77 mmol) in toluene (3 mL) is stirred at 100° C. for 1 day. The mixture is diluted with water. The mixture is extracted with EtOAc. The organic layer is dried over sodium sulfate, filtered and concentrated. The residue is purified by column chromatography on silica-gel eluting with 0-50% EtOAc in n-hexane to give 368 mg (88% yield) of the title compound as a yellow oil.
MS (ESI) m/z: 301.2 (M+H)+.

<Step-2>: ethyl 2-((2-aminophenyl)amino)-5-methylbenzoate

The title compound is prepared in quantitative yield (331 mg, a pale yellow solid) by the similar manner to Step-2 of Intermediate-20 using ethyl 5-methyl-2-((2-nitrophenyl)amino)benzoate (368 mg, 1.22 mmol, Step-1 in Intermediate-66) in place of 2,4-difluoro-N-(2-nitrophenyl)aniline.

<Step-3>: ethyl 5-methyl-2-(2-oxo-2,3-dihydro-1H-benzo[d]imidazol-1-yl)benzoate

The title compound is prepared in 35% yield (166 mg, a pale yellow solid) by the similar manner to Step-3 of Intermediate-20 using ethyl 2-((2-aminophenyl)amino)-5-methylbenzoate (331 mg, 1.22 mmol, Step-2 in Intermediate-66).
$^1$H-NMR (400 MHz, DMSO-$d_6$) delta 11.06 (1H, m), 7.78 (1H, d, J=1.8 Hz), 7.61 (1H, t, J=1.4 Hz), 7.47 (1H, d, J=8.2 Hz), 7.10-6.91 (3H, m), 6.70 (1H, d, J=7.8 Hz), 4.02 (2H, q, J=7.3 Hz), 2.45 (3H, s), 0.95 (3H, t, J=7.3 Hz). MS (ESI) m/z: 297.3 (M+H)$^+$.

<Step-4>: 2-(3-(((1r,4r)-4-(5-chloro-2-methylnicotinamido)cyclohexyl)methyl)-2-oxo-2,3-dihydro-1H-benzo[d]imidazol-1-yl)-5-methylbenzoic acid A mixture of ((r,4r)-4-(5-chloro-2-methylnicotinamido)cyclohexyl)methyl methanesulfonate (224 mg, 0.62 mmol, Mesylate-1), ethyl 5-methyl-2-(2-oxo-2,3-dihydro-1H-benzo[d]imidazol-1-yl)benzoate (166 mg, 0.56 mmol, Step-3 of Intermediate-66), and cesium carbonate (365 mg, 1.12 mmol) in DMSO (2 mL) is stirred at 80° C. for 5 hrs. Then, the mixture is diluted with water and stirred at rt for 3 hrs. The mixture is acidified with 2 M hydrochloric acid. The precipitate is collected and dried in vacuo to give 245 mg (82% yield) of the title compound as a purple solid.
MS (ESI) m/z: 533.2 (M+H)$^+$.

Intermediate-67: 3-(6-methylpyridin-3-yl)-2-oxo-2,3-dihydro-1H-benzo[d]imidazole-5-carbonitrile <Step-1>:3-((6-methylpyridin-3-yl)amino)-4-nitrobenzonitrile The title compound is prepared in 19% yield (27 mg) by the similar manner to Step-2 of Intermediate-60 using 4-fluoro-3-nitrobenzonitrile (94 mg, 0.565 mmol), 6-methylpyridin-3-amine (67 mg, 0.621 mmol) and sodium tert-amylate (124 mg, 1.13 mmol) in place of 2-fluoro-nitrobenzene, 6-methoxy-5-methylpyridin-3-amine and potassium tert-butoxide, respectively.
$^1$H-NMR (400 MHz, CDCl$_3$) delta 9.36 (1H, s), 8.48 (1H, d, J=2.7 Hz), 8.32 (1H, d, J=8.7 Hz), 7.52 (1H, dd, J=8.2, 2.7 Hz), 7.31 (1H, d, J=8.2 Hz), 7.27 (1H, d, J=1.4 Hz), 7.03 (1H, dd, J=8.7, 1.4 Hz), 2.64 (3H, s).

<Step-2>:4-amino-3-((6-methylpyridin-3-yl)amino)benzonitrile

A crude mixture of the title compound, which is prepared by the similar manner to Step-3 of Intermediate-60 using 3-((6-methylpyridin-3-yl)amino)-4-nitrobenzonitrile (27 mg, 0.106 mmol) in place of 6-methoxy-5-methyl-N-(2-nitrophenyl)pyridin-3-amine, is purified by column chromatography on silica-gel eluting with 7-100% EtOAc in n-hexane followed by 0-10% MeOH in EtOAc to give 17 mg (72% yield) of the title compound as a beige solid.
MS (ESI) m/z: 225.3 (M+H)$^+$.

<Step-3>: 3-(6-methylpyridin-3-yl)-2-oxo-2,3-dihydro-1H-benzo[d]imidazole-5-carbonitrile The title compound is prepared in 79% yield (15 mg, a beige solid) by the similar manner to Step-3 of Intermediate-51 using 4-amino-3-((6-methylpyridin-3-yl)amino)benzonitrile (17 mg, 0.076 mmol) in place of N$^1$-(6-bromopyridin-3-yl)benzene-1,2-diamine.
MS (ESI) m/z: 251.2 (M+H)$^+$.

Intermediate-68: 1-(6-methoxy-4-methylpyridin-3-yl)-1H-benzo[d]imidazol-2(3H)-one <Step-1>:6-methoxy-4-methyl-N-(2-nitrophenyl)pyridin-3-amine A mixture of 1-bromo-2-nitrobenzene (227 mg, 1.12 mmol), 6-methoxy-4-methylpyridin-3-amine (155 mg, 1.12 mmol), tris(dibenzylideneacetone)dipalladium(0) (205 mg, 0.224 mmol), XPhos (214 mg, 0.449 mmol), and sodium tert-pentoxide (247 mg, 2.24 mmol) in 1,4-dioxane (5 mL) is stirred at 110° C. overnight. After cooled to rt, the mixture is diluted with EtOAc and water then filtered. The filtrate is extracted with EtOAc. The filtrate is extracted with EtOAc. The organic phase is washed with brine, dried over MgSO$_4$ filtered and concentrated in vacuo. The residue is purified by column chromatography on silica-gel eluting with 0-100% EtOAc in n-hexane to give 300 mg (quantitative yield) of the title compound as a brown solid.
MS (ESI) m/z: 260.3 (M+H)$^+$.

<Step-2>: N$^1$-(6-methoxy-4-methylpyridin-3-yl)benzene-1,2-diamine

A crude mixture of the title compound, which is prepared by the similar manner to Step-3 of Intermediate-60 using 6-methoxy-4-methyl-N-(2-nitrophenyl)pyridin-3-amine (300 mg, 1.157 mmol) in place of 6-methoxy-5-methyl-N-(2-nitrophenyl)pyridin-3-amine, is purified by column chromatography on silica-gel eluting with 7-100% EtOAc in n-hexane to give 170 mg (64% yield) of the title compound as a beige solid.
$^1$H-NMR (400 MHz, CDCl$_3$) delta 7.68 (1H, s), 6.88 (1H, td, J=7.5, 1.4 Hz), 6.79 (1H, dd, J=7.5, 1.4 Hz), 6.71 (1H, td, J=7.5, 1.4 Hz), 6.65-6.61 (2H, m), 4.80 (1H, br s), 3.89 (3H, s), 3.65 (2H, br s), 2.18 (3H, s).

<Step-3>:1-(6-methoxy-4-methylpyridin-3-yl)-1H-benzo[d]imidazol-2(3H)-one

To a solution of N$^1$-(6-methoxy-4-methylpyridin-3-yl)benzene-1,2-diamine (170 mg, 0.741 mmol) in THF (1 mL) is added CDI (120 mg, 0.741 mmol) and stirred at rt for 1 h. The reaction is monitored by TLC and CDI is further added to the reaction mixture until the starting material is completely consumed. After confirmation of disappearance of the starting material by TLC, saturated aqueous sodium bicarbonate is added to the reaction mixture and stirred for 2 min. The resultant mixture is extracted with EtOAc. The organic phase is dried over MgSO$_4$, filtered and concentrated in vacuo. The crude mixture is purified by column chromatography on silica-gel eluting with 30-85% EtOAc in n-hexane to give 164 mg (87% yield) of the title compound as an ivory solid.
$^1$H-NMR (400 MHz, CDCl$_3$) delta 9.88 (1H, br s), 8.15 (1H, s), 7.16 (1H, dd, J=7.5, 1.4 Hz), 7.11 (1H, td, J=7.5, 1.4 Hz), 7.05 (1H, td, J=7.5, 1.4 Hz), 6.80 (1H, s), 6.71 (1H, d, J=7.5 Hz), 3.99 (3H, s), 2.18 (3H, s).

Intermediate-69: 1-(5-methyl-6-(methylamino)pyridin-3-yl)-1H-benzo[d]imidazol-2(3H)-one <Step-1>: N,3-dimethyl-5-nitropyridin-2-amine A mixture of 2-chloro-3-methyl-5-nitropyridine (200 mg, 1.16 mmol), methanamine (1.16 mL, 2.32 mmol) and TEA (0.808 mL, 5.79 mmol) in 2-propanol (3 mL) is stirred at reflux temperature overnight. After cooled to rt, the mixture is concentrated. The residue is dissolved into DCM and EtOAc (ratio 1/1), washed with water and brine, dried over $MgSO_4$, filtered and concentrated in vacuo to give 172 mg (89% yield) of the title compound as a yellow solid.

$^1$H-NMR (400 MHz, $CDCl_3$) delta 8.99 (1H, d, J=2.3 Hz), 8.01 (1H, d, J=2.3 Hz), 4.96 (1H, br s), 3.16 (3H, d, J=5.0 Hz), 2.16 (3H, s).

<Step-2>: $N^2$,3-dimethylpyridine-2,5-diamine

The title compound is prepared in quantitative yield (133 mg, a pale red oil) by the similar manner to Step-1 of Intermediate-60 using N,3-dimethyl-5-nitropyridin-2-amine (155 mg, 0.927 mmol) in place of $N^1$-(6-bromopyridin-3-yl)benzene-1,2-diamine.

$^1$H-NMR (400 MHz, $CDCl_3$) delta 7.64 (1H, d, J=2.7 Hz), 6.80 (1H, d, J=2.7 Hz), 3.79 (1H, s), 3.16 (2H, s), 2.98 (3H, s), 2.05 (3H, s).

<Step-3>: $N^2$,3-dimethyl-$N^5$-(2-nitrophenyl)pyridine-2,5-diamine

A mixture of 1-bromo-2-nitrobenzene (81 mg, 0.400 mmol), $N^2$, 3-dimethylpyridine-2,5-diamine (64 mg, 0.467 mmol), XPhos (63.5 mg, 0.133 mmol), tris(dibenzylideneacetone)dipalladium(0) (61 mg, 0.067 mmol), and $Cs_2CO_3$ (271 mg, 0.832 mmol) in 1,4-dioxane (1 mL) is stirred at 110° C. overnight. After cooled to rt, the reaction mixture is directly purified by column chromatography on silica-gel eluting with 10-100% EtOAc in n-hexane to give 104 mg (quantitative yield) of the title compound.

$^1$H-NMR (400 MHz, $CDCl_3$) delta 9.25 (1H, s), 8.19 (1H, dd, J=8.7, 1.8 Hz), 8.01 (1H, d, J=2.3 Hz), 7.35-7.28 (1H, m), 7.16 (1H, d, J=2.3 Hz), 6.88 (1H, d, J=7.8 Hz), 6.74-6.67 (1H, m), 4.30 (1H, s), 3.09 (3H, d, J=5.0 Hz), 2.12 (3H, s). MS (ESI) m/z: 259.3 (M+H)$^+$.

<Step-4>: $N^5$-(2-aminophenyl)-$N^2$,3-dimethylpyridine-2,5-diamine

A crude mixture of the title compound, which is prepared by the similar manner to Step-3 of Intermediate-60 using $N^2$,3-dimethyl-N-(2-nitrophenyl)pyridine-2,5-diamine (100 mg, 0.387 mmol) in place of 6-methoxy-5-methyl-N-(2-nitrophenyl)pyridin-3-amine, is purified by column chromatography on silica-gel eluting with 7-100% EtOAc in n-hexane to give 51 mg (45% yield) of the title compound as a brown solid.

$^1$H-NMR (400 MHz, $CDCl_3$) delta 7.79 (1H, d, J=2.7 Hz), 6.96 (1H, d, J=2.7 Hz), 6.89-6.82 (2H, m), 6.80-6.75 (1H, m), 6.75-6.69 (1H, m), 4.84 (1H, br s), 3.99 (1H, br s), 3.63 (2H, br s), 3.03 (3H, s), 2.07 (3H, s). MS (ESI) m/z: 229.3 (M+H)$^+$.

<Step-5>: 1-(5-methyl-6-(methylamino)pyridin-3-yl)-1H-benzo[d]imidazol-2(3H)-one To a solution of $N^1$-(6-methoxy-4-methylpyridin-3-yl)benzene-1,2-diamine (51 mg, 0.223 mmol) in THF (1 mL) is added CDI (36 mg, 0.222 mmol) and stirred at rt for 1 h. The reaction is monitored by TLC and CDI is further added to the reaction mixture until the starting material is completely consumed. After confirmation of disappearance of the starting material by TLC, saturated aqueous sodium bicarbonate is added to the reaction mixture and stirred for 2 min. The resultant mixture is diluted with water and DCM, then insoluble substance is collected by filtration to give 44 mg (78% yield) of the title compound as an ivory solid.

$^1$H-NMR (400 MHz, $CDCl_3$) delta 10.40 (1H, s), 8.14 (1H, d, J=2.3 Hz), 7.35 (1H, d, J=2.3 Hz), 7.12-6.96 (3H, m), 6.91 (1H, d, J=7.3 Hz), 4.70 (1H, s), 3.08 (3H, d, J=5.0 Hz), 2.14 (3H, s).

Intermediate-70: 1-(p-tolyl)-1H-imidazo[4,5-b]pyrazin-2(3H)-one

A mixture of 2,3-dichloropyrazine (198 mg, 1.33 mmol), 1-(p-tolyl)urea (200 mg, 1.33 mmol), and tripotassium phosphate (1.13 g, 5.33 mmol) in 1,4-dioxane (1 mL) is stirred at 110° C. for 7 hrs. The mixture is diluted with water, extracted with EtOAc. The organic layer is dried over sodium sulfate and filtered. The filtrate is concentrated. The residual solid is washed with EtOAc to give 62 mg (21% yield) of the title compound as a pale yellow solid.

$^1$H-NMR (400 MHz, DMSO-$d_6$) delta 7.71 (1H, d, J=3.2 Hz), 7.60 (2H, d, J=7.8 Hz), 7.53 (1H, d, J=3.2 Hz), 7.26 (2H, d, J=7.8 Hz), 2.34 (3H, s). A signal due to NH is not observed. MS (ESI) m/z: 227.3 (M+H)$^+$.

Intermediate-71: 3-(6-(dimethylamino)pyridin-3-yl)-1H-imidazo[4,5-b]pyridin-2(3H)-one <Step-1>: $N^2$,$N^2$-dimethyl-$N^5$-(3-nitropyridin-2-yl)pyridine-2,5-diamine A mixture of 2-fluoro-3-nitropyridine (104 mg, 0.73 mmol), $N^2$,$N^2$ dimethylpyridine-2,5-diamine (100 mg, 0.73 mmol), and potassium carbonate (302 mg, 2.19 mmol) in DMF (3 mL) is stirred at rt for 1 day. The mixture is diluted with water. The mixture is extracted with EtOAc. The organic layer is dried over sodium sulfate, filtered and concentrated. The residue is purified by column chromatography on silica-gel eluting with 0-100% EtOAc in n-hexane to give 155 mg (82% yield) of the title compound as a pale yellow gum.

$^1$H-NMR (400 MHz, CDCl3) delta 9.78 (1H, br s), 8.50 (1H, dd, J=8.2, 1.8 Hz), 8.41 (1H, dd, J=4.6, 1.8 Hz), 8.31 (1H, d, J=2.7 Hz), 7.66 (1H, dd, J=9.1, 2.7 Hz), 6.76 (1H, dd, J=8.2, 4.6 Hz), 6.57 (1H, d, J=9.1 Hz), 3.11 (6H, s). MS (ESI) m/z: 260.3 (M+H)$^+$.

<Step-2>: $N^2$-(6-(dimethylamino)pyridin-3-yl)pyridine-2,3-diamine

The title compound is prepared in quantitative yield (137 mg, a brown gum) by the similar manner to Step-2 of Intermediate-13 using $N^2$,$N^2$-dimethyl-$N^5$ (3-nitropyridin-2-yl)pyridine-2,5-diamine (155 mg, 0.60 mmol, Step-1 of Intermediate-71).

MS (ESI) m/z: 230.3 (M+H)$^+$.

<Step-3>:3-(6-(dimethylamino)pyridin-3-yl)-1H-imidazo[4,5-b]pyridin-2(3H)-one

A mixture of methyl $N^2$-(6-(dimethylamino)pyridin-3-yl)pyridine-2,3-diamine (137 mg, 0.60 mmol, Step-2 of Intermediate-71) and CDI (194 mg, 1.20 mmol) in THF (3 mL) is stirred at room temperature for 1 day. The mixture is diluted with water. The precipitate is collected and dried to give 64 mg (45% yield) of the title compound as a gray solid.

$^1$H-NMR (400 MHz, DMSO-d$_6$) delta 11.32 (1H, s), 8.23 (1H, d, J=2.7 Hz), 7.90 (1H, dd, J=9.1, 2.7 Hz), 7.67 (1H, dd, J=5.0, 1.8 Hz), 7.37 (1H, dd, J=7.8, 1.8 Hz), 7.06 (1H, dd, J=7.8, 5.0 Hz), 6.75 (1H, d, J=9.1 Hz), 3.08 (6H, s). MS (ESI) m/z: 256.3 (M+H)$^+$.

Intermediate-72: 1-(6-(dimethylamino)pyridin-3-yl)-1H-imidazo[4,5-c]pyridin-2(3H)-one <Step-1>: $N^2,N^2$-dimethyl-$N^5$-(3-nitropyridin-4-yl)pyridine-2,5-diamine The title compound is prepared in 76% yield (143 mg, a pale yellow gum) by the similar manner to Step-1 of Intermediate-71 using 4-chloro-3-nitropyridine (116 mg, 0.73 mmol) in place of 2-fluoro-3-nitropyridine.

$^1$H-NMR (400 MHz, CDCl$_3$) delta 9.38 (1H, br s), 9.27 (1H, s), 8.21 (1H, d, J=6.4 Hz), 8.10 (1H, d, J=2.7 Hz), 7.35 (1H, dd, J=9.1, 2.7 Hz), 6.70 (1H, d, J=5.9H), 6.59 (1H, d, J=9.1 Hz), 3.15 (6H, s). MS (ESI) m/z: 260.3 (M+H)$^+$.

<Step-2>: $N^5$-(3-aminopyridin-4-yl)-$N^2,N^2$-dimethylpyridine-2,5-diamine

The title compound is prepared in quantitative yield (127 mg, a brown gum) by the similar manner to Step-2 of Intermediate-13 using $N^2,N^2$-dimethyl-$N^5$ (3-nitropyridin-4-yl)pyridine-2,5-diamine (143 mg, 0.55 mmol, Step-1 of Intermediate-72).
MS (ESI) m/z: 230.3 (M+H)$^+$.

<Step-3>:1-(6-(dimethylamino)pyridin-3-yl)-1H-imidazo[4,5-c]pyridin-2(3H)-one

The title compound is prepared in 50% yield (70 mg, a brown solid) by the similar manner to Step-3 of Intermediate-72 using $N^5$-(3-aminopyridin-4-yl)-$N^2,N^2$ dimethylpyridine-2,5-diamine (127 mg, 0.55 mmol, Step-2 of Intermediate-72).

$^1$H-NMR (400 MHz, DMSO-d$_6$) delta 11.37 (1H, br s), 8.27 (1H, s), 8.18 (1H, dd, J=2.7, 0.9 Hz), 8.16 (1H, d, J=5.5 Hz), 7.63 (1H, dd, J=9.1, 2.7 Hz), 6.91 (1H, dd, J=5.5, 0.9 Hz), 6.78 (1H, d, J=9.1 Hz), 3.09 (6H, s). MS (ESI) m/z: 256.3 (M+H)$^+$.

Intermediate-73: 1-(1-methyl-1H-indazol-5-yl)-1H-benzo[d]imidazol-2(3H)-one

<Step-1>:1-methyl-N-(2-nitrophenyl)-1H-indazol-5-amine

A mixture of 1-bromo-2-nitrobenzene (100 mg, 0.495 mmol), 1-methyl-1H-indazol-5-amine (109 mg, 0.743 mmol), Xphos (71 mg, 0.149 mmol) and tris(dibenzylideneacetone)dipalladium(0) (68 mg, 0.074 mmol) in 1,4-dioxane (2 mL) is stirred at 110° C. overnight. After cooled to rt, the mixture is directly purified by column chromatography on silica-gel eluting with 5-90% EtOAc in n-hexane to give 140 mg (quantitative yield) of the title compound as a brown solid.

$^1$H-NMR (400 MHz, CDCl$_3$) delta 9.56 (1H, s), 8.23 (1H, dd, J=8.5, 1.6 Hz), 7.98 (1H, d, J=0.9 Hz), 7.64 (1H, d, J=1.8 Hz), 7.46 (2H, d, J=9.1 Hz), 7.36-7.28 (2H, m), 7.00 (1H, dd, J=8.7, 0.9 Hz), 6.78-6.71 (1H, m), 4.12 (3H, s).

<Step-2>: $N^1$-(1-methyl-1H-indazol-5-yl)benzene-1,2-diamine

A solution of 1-methyl-N-(2-nitrophenyl)-1H-indazol-5-amine (133 mg, 0.495 mmol) in EtOAc is evacuated and backfilled by N$_2$ gas. To the mixture is added 10% Pd/C (wet) (53 mg). The mixture is evacuated and backfilled with H$_2$ gas and vigorously stirred at rt under H$_2$ atmosphere. After 1 hr, the reaction mixture is evacuated and backfilled with N$_2$ gas and the mixture is filtered through celite pad. After the filtrate is concentrated in vacuo, the residue is purified by column chromatography on silica-gel eluting with 10-60% EtOAc in n-hexane to give 105 mg (89% yield) of the title compound as a beige solid.
MS (ESI) m/z: 239.3 (M+H)$^+$.

<Step-3>:1-(1-methyl-1H-indazol-5-yl)-1H-benzo[d]imidazol-2(3H)-one

The title compound is prepared in 73% yield (85 mg, an off-white solid) by the similar manner to Step-3 of Intermediate-20 using $N^1$-(1-methyl-1H-indazol-5-yl)benzene-1,2-diamine (105 mg, 0.441 mmol, Step-2 of Intermediate-73) in place of $N^1$-(2,4-difluorophenyl)benzene-1,2-diamine.

$^1$H-NMR (400 MHz, CDCl$_3$) delta 8.96 (1H, s), 8.06 (1H, s), 7.89 (1H, s), 7.60-7.51 (2H, m), 7.18-7.03 (3H, m), 6.98 (1H, d, J=7.8 Hz), 4.15 (3H, s).

Intermediate-74: 1-(1H-indol-6-yl)-1H-benzo[d]imidazol-2(3H)-one

<Step-1>: N-(2-nitrophenyl)-1H-indol-6-amine

The title compound is prepared in 57% yield (71 mg) by the similar manner to Step-1 of Intermediate-73 using 1H-indol-6-amine (98 mg, 0.743 mmol) in place of 1-methyl-1H-indazol-5-amine.

$^1$H-NMR (400 MHz, CDCl$_3$) delta 9.62 (1H, s), 8.32 (1H, s), 8.21 (1H, dd, J=8.7, 1.4 Hz), 7.67 (1H, d, J=8.2 Hz), 7.34-7.28 (1H, m), 7.28-7.24 (5H, m), 7.13 (1H, dd, J=8.7, 1.4 Hz), 7.05 (1H, dd, J=8.2, 1.8 Hz), 6.74-6.69 (1H, m), 6.61-6.57 (1H, m).

<Step-2>: $N^1$-(1H-indol-6-yl)benzene-1,2-diamine

The title compound is prepared in 54% yield (34 mg) by the similar manner to Step-2 of Intermediate-73 using N-(2-nitrophenyl)-1H-indol-6-amine (71 mg, 0.280 mmol) in place of 1-methyl-N-(2-nitrophenyl)-1H-indazol-5-amine.

$^1$H-NMR (400 MHz, CDCl$_3$) delta 7.89 (1H, s), 7.49 (1H, d, J=8.2 Hz), 7.13 (1H, dd, J=7.8, 1.4 Hz), 7.06-7.03 (1H, m), 7.02-6.97 (1H, m), 6.82 (1H, dd, J=7.8, 1.4 Hz), 6.79-6.71 (2H, m), 6.70-6.68 (1H, m), 6.47-6.44 (1H, m), 5.20 (1H, s), 3.77 (2H, s).

<Step-3>:1-(1H-indol-6-yl)-1H-benzo[d]imidazol-2(3H)-one

The title compound is prepared in 74% yield (28 mg, a beige solid) by the similar manner to Step-3 of Intermediate-20 using $N^1$-(1H-indol-6-yl)benzene-1,2-diamine (34 mg, 0.152 mmol, Step-2 of Intermediate-74) in place of $N^1$-(2,4-difluorophenyl)benzene-1,2-diamine.

Intermediate-75: 1-(6-(3-methoxyazetidin-1-yl)pyridin-3-yl)-1H-benzo[d]imidazol-2(3H)-one <Step-1>:2-(3-methoxyazetidin-1-yl)-5-nitropyridine A mixture of 2-chloro-5-nitropyridine (75 mg, 0.473 mmol), 3-methoxyazetidine hydrochloride (62 mg, 0.568 mmol) and potassium carbonate (372 mg, 2.37 mmol) in DMF is stirred at 50° C. overnight. After cooled to rt, the mixture is diluted with EtOAc and water then extracted with EtOAc. Organic phase is washed with water and brine, dried over MgSO$_4$, filtered and concentrated. The residue is purified by column chromatography on silica-gel eluting with 5-60% EtOAc in n-hexane to give 84 mg (85% yield) of the title compound as a brown solid.
$^1$H-NMR (400 MHz, CDCl$_3$) delta 9.04 (1H, d, J=2.3 Hz), 8.19 (1H, dd, J=9.4, 2.3 Hz), 6.20 (1H, d, J=9.4 Hz), 4.50-4.29 (3H, m), 4.17-4.00 (2H, m), 3.37 (3H, s).

<Step-2>:6-(3-methoxyazetidin-1-yl)pyridin-3-amine

The title compound is prepared in 81% yield (58 mg, a purple solid) by the similar manner to Step-2 of Intermediate-73 using 2-(3-methoxyazetidin-1-yl)-5-nitropyridine (84 mg, 0.400 mmol) in place of 1-methyl-N-(2-nitrophenyl)-1H-indazol-5-amine.
$^1$H-NMR (400 MHz, CDCl$_3$) delta 7.75 (1H, d, J=2.7 Hz), 6.98 (1H, dd, J=8.7, 2.7 Hz), 6.26 (1H, d, J=8.7 Hz), 4.37-4.29 (1H, m), 4.18-4.12 (2H, m), 3.79 (2H, dd, J=8.7, 4.6 Hz), 3.33 (3H, s), 3.26 (2H, s).

<Step-3>: N$^1$-(6-(3-methoxyazetidin-1-yl)pyridin-3-yl)benzene-1,2-diamine

A mixture of 1-bromo-2-nitrobenzene (103 mg, 0.508 mmol), 6-(3-methoxyazetidin-1-yl)pyridin-3-amine (58 mg, 0.324 mmol), cesium carbonate (276 mg, 0.847 mmol), Xphos (81 mg, 0.169 mmol) and tris(dibenzylideneacetone)dipalladium(0) (78 mg, 0.085 mmol) in 1,4-dioxane (2 mL) is stirred at 110° C. overnight. After cooled to rt, the mixture is directly purified by column chromatography on silica-gel eluting with 5-90% EtOAc in n-hexane. The fractions containing 6-(3-methoxyazetidin-1-yl)-N-(2-nitrophenyl)pyridin-3-amine are collected and concentrated. The residue (115 mg) is dissolved into EtOAc (2 mL) and treated with 10% Pd/C (wet) (36 mg) and H$_2$ gas in a similar manner to Step-2 of Intermediate-73 to give the title compound (75 mg, 82% yield) as a brown gum.
$^1$H-NMR (400 MHz, CDCl$_3$) delta 7.89 (1H, d, J=2.7 Hz), 7.12 (1H, dd, J=8.7, 2.7 Hz), 6.92-6.85 (2H, m), 6.78 (1H, dd, J=8.2, 1.4 Hz), 6.76-6.70 (1H, m), 6.31 (1H, d, J=8.7 Hz), 4.90 (1H, s), 4.38-4.32 (1H, m), 4.23-4.16 (2H, m), 3.88-3.82 (2H, m), 3.65 (2H, s), 3.34 (3H, s).

<Step-4>: 1-(6-(3-methoxyazetidin-1-yl)pyridin-3-yl)-1H-benzo[d]imidazol-2(3H)-one The title compound is prepared in 74% yield (61 mg, a beige powder) by the similar manner to Step-3 of Intermediate-20 using N$^1$-(6-(3-methoxyazetidin-1-yl)pyridin-3-yl)benzene-1,2-diamine (75 mg, 0.277 mmol, Step-3 of Intermediate-75) in place of N$^1$-(2,4-difluorophenyl)benzene-1,2-diamine.
$^1$H-NMR (400 MHz, CDCl$_3$) delta 9.39 (1H, s), 8.30 (1H, d, J=2.5 Hz), 7.60 (1H, dd, J=8.9, 2.5 Hz), 7.17-7.02 (3H, m), 6.94 (1H, d, J=7.3 Hz), 6.45 (1H, d, J=8.9 Hz), 4.43-4.36 (1H, m), 4.34-4.26 (2H, m), 3.98 (2H, dd, J=9.6, 4.1 Hz), 3.37 (3H, s).

Intermediate-76: 1-(6-(3-fluoroazetidin-1-yl)pyridin-3-yl)-1H-benzo[d]imidazol-2(3H)-one <Step-1>:2-(3-fluoroazetidin-1-yl)-5-nitropyridine The title compound is prepared in 85% yield (79 mg, a brown solid) by the similar manner to Step-1 of Intermediate-75 using 3-fluoroazetidine hydrochloride (63 mg, 0.568 mmol) in place of 3-methoxyazetidine hydrochloride.
$^1$H-NMR (400 MHz, CDCl$_3$) delta 9.05 (1H, d, J=2.7 Hz), 8.23 (1H, dd, J=9.1, 2.7 Hz), 6.25 (1H, d, J=9.1 Hz), 5.66-5.37 (1H, m), 4.59-4.41 (2H, m), 4.41-4.23 (2H, m).

<Step-2>:6-(3-fluoroazetidin-1-yl)pyridin-3-amine

The title compound is prepared in 93% yield (62 mg, a purple gum) by the similar manner to Step-2 of Intermediate-73 using 2-(3-methoxyazetidin-1-yl)-5-nitropyridine (79 mg, 0.400 mmol) in place of 1-methyl-N-(2-nitrophenyl)-1H-indazol-5-amine.
$^1$H-NMR (400 MHz, CDCl$_3$) delta 7.76 (1H, t, J=1.4 Hz), 7.00 (1H, dd, J=9.1, 2.7 Hz), 6.28 (1H, d, J=9.1 Hz), 5.53-5.29 (1H, m), 4.31-4.17 (2H, m), 4.10-3.96 (2H, m), 3.29 (2H, s).

<Step-3>: N$^1$-(6-(3-fluoroazetidin-1-yl)pyridin-3-yl)benzene-1,2-diamine

The title compound is prepared in 89% yield (78 mg, a brown gum) by the similar manner to Step-3 of Intermediate-75 using 6-(3-fluoroazetidin-1-yl)pyridin-3-amine (62 mg, 0.371 mmol) and 6-(3-fluoroazetidin-1-yl)-N-(2-nitrophenyl)pyridin-3-amine in place of 6-(3-methoxyazetidin-1-yl)pyridin-3-amine and 6-(3-methoxyazetidin-1-yl)-N-(2-nitrophenyl)pyridin-3-amine, respectively.
$^1$H-NMR (400 MHz, CDCl$_3$) delta 7.89 (1H, d, J=2.7 Hz), 7.12 (1H, dd, J=8.9, 2.7 Hz), 6.93-6.88 (2H, m), 6.79 (1H, dd, J=8.0, 1.6 Hz), 6.76-6.71 (1H, m), 6.32 (1H, d, J=8.9 Hz), 5.58-5.29 (1H, m), 4.92 (1H, s), 4.40-4.21 (2H, m), 4.19-3.97 (2H, m), 3.67 (2H, s).

<Step-4>:1-(6-(3-fluoroazetidin-1-yl)pyridin-3-yl)-1H-benzo[d]imidazol-2(3H)-one The title compound is prepared in 83% yield (71 mg, a pink powder) by the similar manner to Step-3 of Intermediate-20 using N$^1$-(6-(3-fluoroazetidin-1-yl)pyridin-3-yl)benzene-1,2-diamine (78 mg, 0.302 mmol, Step-3 of Intermediate-76) in place of N$^1$-(2,4-difluorophenyl)benzene-1,2-diamine.
$^1$H-NMR (400 MHz, CDCl$_3$) delta 10.21 (1H, s), 8.30 (1H, d, J=1.8 Hz), 7.64 (1H, dd, J=8.7, 1.8 Hz), 7.19-6.97 (3H, m), 6.92 (1H, d, J=7.8 Hz), 6.48 (1H, d, J=8.7 Hz), 5.61-5.36 (1H, m), 4.49-4.31 (2H, m), 4.28-4.12 (2H, m).

Intermediate-77: 1-(6-(3,3-difluoroazetidin-1-yl)pyridin-3-yl)-1H-benzo[d]imidazol-2(3H)-one <Step-1>:2-(3,3-difluoroazetidin-1-yl)-5-nitropyridine The title compound is prepared in 84% yield (86 mg, a brown solid) by the similar manner to Step-1 of Intermediate-75 using 3,3-difluoroazetidine hydrochloride (74 mg, 0.57 mmol) in place of 3-methoxyazetidine hydrochloride.

$^1$H-NMR (400 MHz, CDCl$_3$) delta 9.07 (1H, d, J=2.7 Hz), 8.29 (1H, dd, J=9.1, 2.7 Hz), 6.34 (1H, d, J=9.1 Hz), 4.52 (4H, t, J=11.7 Hz).

<Step-2>:6-(3,3-difluoroazetidin-1-yl)pyridin-3-amine

The title compound is prepared in 88% yield (65 mg, a purple solid) by the similar manner to Step-2 of Intermediate-73 using 2-(3,3-difluoroazetidin-1-yl)-5-nitropyridine (86 mg, 0.40 mmol) in place of 1-methyl-N-(2-nitrophenyl)-1H-indazol-5-amine.

$^1$H-NMR (400 MHz, CDCl$_3$) delta 7.76 (1H, d, J=2.3 Hz), 7.01 (1H, dd, J=8.7, 2.3 Hz), 6.32 (1H, dd, J=8.7, 0.9 Hz), 4.27 (4H, t, J=12.1 Hz), 3.34 (2H, s).

<Step-3>: $N^1$-(6-(3,3-difluoroazetidin-1-yl)pyridin-3-yl)benzene-1,2-diamine

The title compound is prepared in 59% yield (55 mg, a brown solid) by the similar manner to Step-3 of Intermediate-75 using 6-(3,3-difluoroazetidin-1-yl)pyridin-3-amine (65 mg, 0.351 mmol) and 6-(3,3-difluoroazetidin-1-yl)-N-(2-nitrophenyl)pyridin-3-amine in place of 6-(3-methoxyazetidin-1-yl)pyridin-3-amine and 6-(3-methoxyazetidin-1-yl)-N-(2-nitrophenyl)pyridin-3-amine, respectively.

$^1$H-NMR (400 MHz, CDCl$_3$) delta 7.89 (1H, d, J=2.3 Hz), 7.12 (1H, dd, J=8.7, 2.3 Hz), 6.96-6.91 (2H, m), 6.79 (1H, dd, J=8.2, 1.4 Hz), 6.77-6.71 (1H, m), 6.37 (1H, d, J=8.7 Hz), 4.96 (1H, s), 4.31 (4H, t, J=12.1 Hz), 3.69 (2H, s).

<Step-4>: 1-(6-(3,3-difluoroazetidin-1-yl)pyridin-3-yl)-1H-benzo[d]imidazol-2(3H)-one The title compound is prepared in 70% yield (42 mg, a purple powder) by the similar manner to Step-3 of Intermediate-20 using $N^1$-(6-(3,3-difluoroazetidin-1-yl)pyridin-3-yl)benzene-1,2-diamine (55 mg, 0.199 mmol, Step-3 of Intermediate-77) in place of $N^1$-(2,4-difluorophenyl)benzene-1,2-diamine.

$^1$H-NMR (400 MHz, CDCl$_3$) delta 10.11 (1H, s), 8.35 (1H, d, J=2.7 Hz), 7.70 (1H, dd, J=8.7, 2.7 Hz), 7.13-7.00 (3H, m), 6.93 (1H, d, J=7.8 Hz), 6.55 (1H, d, J=8.7 Hz), 4.43 (4H, t, J=12.1 Hz).

Intermediate-78: 1-(6-(oxetan-3-ylamino)pyridin-3-yl)-1H-benzo[d]imidazol-2(3H)-one <Step-1>:5-nitro-N-(oxetan-3-yl)pyridin-2-amine A mixture of 2-chloro-5-nitropyridine (75 mg, 0.473 mmol), oxetan-3-amine (45 mg, 0.615 mmol) and triethylamine (0.330 mL, 2.37 mmol) in 2-propanol (1 mL) is stirred at 70° C. overnight then at 120° C. for 1 hr under microwave irradiation. After the reaction mixture is concentrated, the residue is dissolved into EtOAc, washed with water and brine, dried over MgSO$_4$, filtered and concentrated. The residue is purified by column chromatography on silica-gel eluting with 5-90% EtOAc in n-hexane to give 84 mg (85% yield) of the title compound as a brown solid.

$^1$H-NMR (400 MHz, CDCl$_3$) delta 9.01 (1H, d, J=2.7 Hz), 8.22 (1H, dd, J=9.1, 2.7 Hz), 6.39 (1H, d, J=9.1 Hz), 5.63 (1H, s), 5.19-5.07 (1H, m), 5.04 (2H, t, J=6.6 Hz), 4.58 (2H, t, J=6.6 Hz).

<Step-2>: $N^2$-(oxetan-3-yl)pyridine-2,5-diamine

The title compound is prepared in quantitative yield (50 mg, a red gum) by the similar manner to Step-2 of Intermediate-73 using 5-nitro-N-(oxetan-3-yl)pyridin-2-amine (55 mg, 0.282 mmol) in place of 1-methyl-N-(2-nitrophenyl)-1H-indazol-5-amine.

$^1$H-NMR (400 MHz, CDCl$_3$) delta 7.68 (1H, d, J=2.7 Hz), 6.95 (1H, dd, J=8.7, 2.7 Hz), 6.27 (1H, d, J=8.7 Hz), 4.99 (2H, t, J=6.9 Hz), 4.62-4.44 (3H, m), 3.25 (2H, s).

<Step-3>: $N^5$-(2-nitrophenyl)-$N^2$-(oxetan-3-yl)pyridine-2,5-diamine

The title compound is prepared in 21% yield (20 mg) by the similar manner to Step-3 of Intermediate-69 using $N^2$-(oxetan-3-yl)pyridine-2,5-diamine (50 mg, 0.30 mmol) in place of $N^2$,3-dimethyl-$N^5$-(2-nitrophenyl)pyridine-2,5-diamine.

$^1$H-NMR (400 MHz, CDCl$_3$) delta 9.24 (1H, s), 8.20 (1H, dd, J=8.7, 2.3 Hz), 8.05 (1H, d, J=2.3 Hz), 7.41-7.31 (2H, m), 6.87 (1H, d, J=8.7 Hz), 6.74 (1H, t, J=7.8 Hz), 6.45 (1H, d, J=8.7 Hz), 5.15-4.92 (4H, m), 4.59 (2H, t, J=5.5 Hz).

<Step-4>: $N^5$-(2-aminophenyl)-$N^2$-(oxetan-3-yl)pyridine-2,5-diamine

The title compound is prepared in 39% yield (7 mg) by the similar manner to Step-2 of Intermediate-73 using N-(2-nitrophenyl)-$N^2$-(oxetan-3-yl)pyridine-2,5-diamine (20 mg, 0.070 mmol) in place of 1-methyl-N-(2-nitrophenyl)-1H-indazol-5-amine.

$^1$H-NMR (400 MHz, CDCl$_3$) delta 7.79 (1H, d, J=2.3 Hz), 7.08 (1H, dd, J=8.7, 2.3 Hz), 6.94-6.84 (2H, m), 6.78 (1H, dd, J=8.2, 1.4 Hz), 6.73 (1H, td, J=7.7, 1.4 Hz), 6.33 (1H, d, J=8.7 Hz), 5.00 (2H, t, J=6.6 Hz), 4.96-4.84 (2H, m), 4.70 (1H, d, J=6.9 Hz), 4.54 (2H, t, J=6.6 Hz).

<Step-5>:1-(6-(oxetan-3-ylamino)pyridin-3-yl)-1H-benzo[d]imidazol-2(3H)-one

To a solution of N-(2-aminophenyl)-$N^2$-(oxetan-3-yl)pyridine-2,5-diamine (7 mg, 0.027 mmol) in THF is added CDI (5 mg, 0.031 mmol) is stirred at rt for 1 hr. Further CDI is added until the starting material is completely consumed. After confirmation of disappearance of starting material, the reaction mixture is diluted with saturated aqueous sodium bicarbonate. The mixture is extracted with EtOAc. The organic layer is dried over MgSO$_4$, filtered and concentrated to give the title compound which is used without further purification.

MS (ESI) m/z: 283.2 (M+H)$^+$.

Intermediate-79: tert-butyl 3-(1-methyl-1H-pyrrolo[2,3-b]pyridin-5-yl)-2-oxo-2,3-dihydro-1H-benzo[d]imidazole-1-carboxylate The title compound is prepared in 57% yield (80 mg, an off-white solid) by the similar manner to Intermediate-58 using 1-methyl-5-(4,4,5,5-tetramethyl-1,3,2-dioxaborolan-2-yl)-1H-pyrrolo[2,3-b]pyridine (100 mg, 0.908 mmol) in place of 2,3-dimethoxy-5-(4,4,5,5-tetramethyl-1,3,2-dioxaborolan-2-yl)pyridine.

$^1$H-NMR (400 MHz, CDCl$_3$) delta 8.40 (1H, d, J=2.3 Hz), 8.00 (1H, d, J=2.3 Hz), 7.94 (1H, dd, J=7.3, 1.8 Hz), 7.30

(1H, d, J=3.7 Hz), 7.21-7.11 (2H, m), 6.87 (1H, dd, J=7.5, 1.1 Hz), 6.52 (1H, d, J=3.7 Hz), 3.95 (3H, s), 1.70 (9H, s).

Intermediate-80: 1-(benzo[d]oxazol-6-yl)-1H-benzo[d]imidazol-2(3H)-one

<Step-1>: N-(2-nitrophenyl)benzo[d]oxazol-6-amine

The title compound is prepared in 49% yield (62 mg) by the similar manner to Step-1 of Intermediate-73 using benzo[d]oxazol-6-amine (100 mg, 0.743 mmol) in place of 1-methyl-1H-indazol-5-amine.

$^1$H-NMR (400 MHz, CDCl$_3$) delta 9.58 (1H, s), 8.24 (1H, dd, J=8.7, 1.8 Hz), 8.12 (1H, s), 7.82 (1H, d, J=8.2 Hz), 7.54 (1H, d, J=1.8 Hz), 7.43-7.36 (1H, m), 7.31 (1H, dd, J=8.2, 1.8 Hz), 7.22 (1H, dd, J=8.7, 0.9 Hz), 6.86-6.79 (1H, m).

<Step-2>: N$^1$-(benzo[d]oxazol-6-yl)benzene-1,2-diamine

The title compound is prepared in 51% yield (28 mg) by the similar manner to Step-2 of Intermediate-73 using N-(2-nitrophenyl)benzo[d]oxazol-6-amine (62 mg, 0.243 mmol) in place of 1-methyl-N-(2-nitrophenyl)-1H-indazol-5-amine.

$^1$H-NMR (400 MHz, CDCl$_3$) delta 7.91 (1H, s), 7.59 (1H, d, J=9.1 Hz), 7.14 (2H, dd, J=7.8, 1.4 Hz), 7.07 (2H, td, J=7.8, 1.4 Hz), 6.86-6.81 (3H, m), 6.79 (1H, td, J=7.8, 1.4 Hz), 5.36 (1H, s), 3.80 (2H, s).

<Step-3>: 1-(benzo[d]oxazol-6-yl)-1H-benzo[d]imidazol-2(3H)-one

The title compound is prepared in 51% yield (16 mg, an off-white solid) by the similar manner to Step-3 of Intermediate-20 using N$^1$-(benzo[d]oxazol-6-yl)benzene-1,2-diamine (28 mg, 0.124 mmol, Step-2 of Intermediate-80) in place of N$^1$-(2,4-difluorophenyl)benzene-1,2-diamine.

$^1$H-NMR (400 MHz, CDCl$_3$) delta 9.04 (1H, s), 8.21 (1H, s), 7.96 (1H, d, J=8.2 Hz), 7.86 (1H, d, J=1.8 Hz), 7.59 (1H, dd, J=8.7, 1.8 Hz), 7.19-7.14 (2H, m), 7.11-7.06 (2H, m).

Intermediate-81: tert-butyl 3-(1-methyl-1H-pyrrolo[3,2-b]pyridin-6-yl)-2-oxo-2,3-dihydro-1H-benzo[d]imidazole-1-carboxylate <Step-1>: 1-methyl-6-(4,4,5,5-tetramethyl-1,3,2-dioxaborolan-2-yl)-1H-pyrrolo[3,2-b]pyridine A mixture of 6-bromo-1-methyl-1H-pyrrolo[3,2-b]pyridine (90 mg, 0.426 mmol), 4,4,4',4',5,5,5',5'-octamethyl-2,2'-bi(1,3,2-dioxaborolane) (162 mg, 0.640 mmol), potassium acetate (126 mg, 1.28 mmol) and Pd(dppf)Cl$_2$ (31 mg, 0.043 mmol) in 1,4-dioxane (2 mL) is stirred at 130° C. for 30 min. After cooled to rt, the mixture is directly purified by column chromatography on silica-gel eluting with 10-90% EtOAc in n-hexane to give 30 mg of the title compound with impurities. This is used for the next step without further purification.

$^1$H-NMR (400 MHz, CDCl$_3$) delta 8.83 (1H, d, J=1.4 Hz), 8.06 (1H, s), 7.33 (1H, d, J=3.2 Hz), 6.71 (1H, dd, J=3.2, 0.9 Hz), 3.84 (3H, s), 1.39 (12H, s).

<Step-2>: tert-butyl 3-(1-methyl-H-pyrrolo[3,2-b]pyridin-6-yl)-2-oxo-2,3-dihydro-1H-benzo[d]imidazole-1-carboxylate The title compound is prepared in 17% yield (7 mg) by the similar manner to Intermediate-58 using 1-methyl-6-(4,4,5,5-tetramethyl-1,3,2-dioxaborolan-2-yl)-1H-pyrrolo[3,2-b]pyridine (30 mg, 0.116 mmol, Step-1 of Intermediate-81) in place of 2,3-dimethoxy-5-(4,4,5,5-tetramethyl-1,3,2-dioxaborolan-2-yl)pyridine.

$^1$H-NMR (400 MHz, CDCl$_3$) delta 8.55 (1H, d, J=1.8 Hz), 7.94 (1H, dd, J=7.1, 2.1 Hz), 7.81 (1H, d, J=1.8 Hz), 7.41 (1H, d, J=3.2 Hz), 7.22-7.12 (2H, m), 6.95 (1H, dd, J=6.9, 2.1 Hz), 6.78 (1H, d, J=3.2 Hz), 3.83 (3H, s), 1.70 (9H, s).

MS (ESI) m/z: 365.1 (M+H)$^+$.

Intermediate-82: tert-butyl 2-oxo-3-(1-((2-(trimethylsilyl)ethoxy)methyl)-1H-pyrrolo[3,2-b]pyridin-6-yl)-2,3-dihydro-1H-benzo[d]imidazole-1-carboxylate The title compound is prepared in 65% yield in 2 steps by the similar manner to Step-1 and Step-2 of Intermediate-81 using 6-bromo-1-((2-(trimethylsilyl)ethoxy)methyl)-1H-pyrrolo[3,2-b]pyridine in place of 6-bromo-1-methyl-1H-pyrrolo[3,2-b]pyridine.

MS (ESI) m/z: 481.1 (M+H)$^+$.

Intermediate-83: tert-butyl 7-(3-(tert-butoxycarbonyl)-2-oxo-2,3-dihydro-1H-benzo[d]imidazol-1-yl)-2H-pyrido[3,2-b][1,4]oxazine-4(3H)-carboxylate The title compound is prepared in 17% yield in 2 steps by the similar manner to Step-1 and Step-2 of Intermediate-81 using tert-butyl 7-bromo-2H-pyrido[3,2-b][1,4]oxazine-4(3H)-carboxylate in place of 6-bromo-1-methyl-1H-pyrrolo[3,2-b]pyridine.

$^1$H-NMR (400 MHz, CDCl$_3$) delta 8.22 (1H, d, J=2.3 Hz), 7.91-7.90 (1H, m), 7.39 (1H, d, J=2.3 Hz), 7.18-7.16 (2H, m), 7.00-6.99 (1H, m), 4.31 (2H, t, J=4.6 Hz), 3.99 (2H, t, J=4.6 Hz), 1.69 (9H, s), 1.57 (9H, s).

Intermediate-84: 1-(1-methyl-1H-pyrazolo[3,4-b]pyridin-5-yl)-1H-benzo[d]imidazol-2(3H)-one A mixture of tert-butyl 2-oxo-2,3-dihydro-1H-benzo[d]imidazole-1-carboxylate (149 mg, 0.637 mmol), copper (II) acetate (347 mg, 1.91 mmol), TEA (0.266 mL, 1.91 mmol), 1-methyl-5-(4,4,5,5-tetramethyl-1,3,2-dioxaborolan-2-yl)-1H-pyrazolo[3,4-b]pyridine (165 mg, 0.637 mmol), and molecular sieves 4 A (100 mg) in DMF (0.5 mL) is stirred at 90° C. for 7 hrs. The reaction mixture is filtered through celite pad. The filtrate is concentrated and the resultant residue is purified by column chromatography on silica-gel eluting with 2-20% MeOH in DCM to give 27 mg (16% yield) of the title compound as a yellow solid.

$^1$H-NMR (400 MHz, CDCl$_3$) delta 8.72 (1H, s), 8.24 (1H, d, J=1.6 Hz), 8.10 (1H, s), 7.16-7.05 (4H, m), 6.97 (1H, d, J=7.5 Hz), 4.23 (3H, s).

MS (ESI) m/z: 266.2 (M+H)$^+$.

Intermediate-85: tert-butyl 3-(3-methyl-2-oxo-2,3-dihydrobenzo[d]oxazol-6-yl)-2-oxo-2,3-dihydro-1H-benzo[d]imidazole-1-carboxylate The title compound is prepared in 58% yield in 2 steps by the similar manner to Step-1 and Step-2 of Intermediate-81 using 6-bromo-3-methylbenzo[d]oxazol-2(3H)-one in place of 6-bromo-1-methyl-H-pyrrolo[3,2-b]pyridine.

$^1$H-NMR (400 MHz, CDCl$_3$) delta 7.93-7.91 (1H, m), 7.37 (1H, d, J=1.8 Hz), 7.34 (1H, dd, J=8.2, 1.8 Hz), 7.20-7.15 (2H, m), 7.10 (1H, d, J=8.2 Hz), 6.91-6.90 (1H, m), 3.47 (3H, s), 1.69 (9H, s).

MS (ESI) m/z: 382.2 (M+H)$^+$.

Intermediate-86: tert-butyl 2-oxo-3-(quinoxalin-6-yl)-2,3-dihydro-1H-benzo[d]imidazole-1-carboxylate The title compound (orange oil) is prepared in 72% yield in 2 steps by the similar manner to Step-1 and Step-2 of Intermediate-81 using 6-bromoquinoxaline in place of 6-bromo-1-methyl-1H-pyrrolo[3,2-b]pyridine.

$^1$H-NMR (400 MHz, CDCl$_3$) delta 8.92 (2H, d, J=1.4 Hz), 8.31-8.27 (2H, m), 8.02-7.97 (2H, m), 7.24-7.18 (2H, m), 7.16-7.13 (1H, m), 1.71 (9H, s).
MS (ESI) m/z: 363.1 (M+H)$^+$.

Intermediate-87: N-methyl-5-(2-oxo-2,3-dihydro-1H-benzo[d]imidazol-1-yl)picolinamide A mixture of methyl 5-(2-oxo-2,3-dihydro-1H-benzo[d]imidazol-1-yl)picolinate (9.00 g, 33.4 mmol, Step-3 of Intermediate-36) and 40% methylamine in MeOH (300 mL) is stirred at room temperature for 2 hrs. The mixture is concentrated. The residual solid is washed with EtOAc to give 8.27 g (92% yield) of the title compound as a pale pink solid.

$^1$H-NMR (400 MHz, DMSO-d$_6$) delta 11.19 (1H, br s), 8.87 (1H, t, J=1.4 Hz), 8.85 (1H, q, J=5.0 Hz), 8.24-8.18 (2H, m), 7.19-7.10 (3H, m), 7.10-7.00 (1H, m), 2.86 (3H, d, J=5.0 Hz).
MS (ESI) m/z: 269.2 (M+H)$^+$.

Intermediate-88: 1-(chroman-3-yl)-1H-benzo[d]imidazol-2(3H)-one

<Step-1>: N-(2-nitrophenyl)chroman-3-amine

To a mixture of chroman-3-amine hydrochloride (105 mg, 0.567 mmol), 1-fluoro-2-nitrobenzene (80 mg, 0.567 mmol) and potassium carbonate (157 mg, 1.134 mmol) in DMF (2 mL) is stirred at 90° C. for 25 hrs. The mixture is poured into water, extracted with EtOAc. The organic layer is washed with water, dried over sodium sulfate, filtered and concentrated. The residue is purified by column chromatography on silica-gel eluting with 0-10% EtOAc in n-hexane to give 102 mg (67% yield) of the title compound as a yellow solid.

$^1$H-NMR (400 MHz, CDCl$_3$) delta 8.21 (1H, br s), 8.20 (1H, dd, J=8.7, 1.6 Hz), 7.55-7.45 (1H, m), 7.19-7.13 (1H, m), 7.12-7.06 (1H, m), 6.99 (1H, d, J=8.7 Hz), 6.96-6.88 (2H, m), 6.74-6.68 (1H, m), 4.38-4.33 (1H, m), 4.22-4.13 (1H, m), 4.12-4.05 (1H, m), 3.25 (1H, dd, J=16.0, 4.7 Hz), 2.96 (1H, dd, J=16.0, 6.7 Hz). MS (ESI) m/z: 271.2 (M+H)$^+$.

<Step-2>: N$^1$-(chroman-3-yl)benzene-1,2-diamine

A solution of N-(2-nitrophenyl)chroman-3-amine (102 mg, 0.377 mmol, Step-1 of Intermediate-88) in MeOH (2 mL) and THF (4 mL) is evacuated and backfilled with N$_2$ gas. To this is added 10% Pd/C (10 mg). The mixture is evacuated and backfilled with H$_2$ gas and stirred at rt under H$_2$ atmosphere. After 1 hr, the reaction mixture is evacuated and backfilled with N$_2$ gas and the mixture is filtered through celite pad. The filtrate is concentrated in vacuo to give 91 mg (99% yield) of the title compound.

$^1$H-NMR (400 MHz, DMSO-d$_6$) delta 7.11-7.05 (2H, m), 6.84 (1H, td, J=7.3, 1.4 Hz), 6.80-6.76 (1H, m), 6.61 (1H, dd, J=7.4, 1.4 Hz), 6.56 (1H, dd, J=7.3, 1.6 Hz), 6.51 (1H, td, J=7.4, 1.6 Hz), 6.45 (1H, td, J=7.3, 1.4 Hz), 4.50 (2H, s), 4.34 (1H, d, J=7.1 Hz), 4.28-4.23 (1H, m), 3.86-3.78 (2H, m), 3.11-3.04 (1H, m), 2.78 (1H, dd, J=15.8, 8.1 Hz). MS (ESI) m/z: 241.2 (M+H)$^+$.

<Step-3>: 1-(chroman-3-yl)-1H-benzo[d]imidazol-2(3H)-one

To a mixture of N$^1$-(chroman-3-yl)benzene-1,2-diamine (91 mg, 0.377 mmol) and CDI (123 mg, 0.757 mmol) in THF (2 mL) is stirred at rt for 19 hrs. The reaction mixture is poured into water and extracted with EtOAc. The organic layer is washed with water, dried over sodium sulfate, filtered and concentrated. The residue is purified by column chromatography on silica-gel eluting with 0-50% EtOAc in n-hexane. The residue is purified by solidification with IPE (5 mL). The obtained solid is washed with IPE to give 86 mg (85% yield) of the title compound as a pale yellow solid.

$^1$H-NMR (400 MHz, CDCl$_3$) delta 9.01 (1H, br s), 7.21-7.15 (1H, m), 7.13-7.04 (5H, m), 6.97-6.91 (2H, m), 4.92-4.83 (1H, m), 4.70 (1H, t, J=10.5 Hz), 4.37 (1H, ddd, J=10.5, 4.1, 2.0 Hz), 3.78 (1H, dd, J=16.1, 11.1 Hz), 3.12-3.05 (1H, m). MS (ESI) m/z: 267.2 (M+H)$^+$.

Intermediate-89: tert-butyl 1',2'-dimethyl-2-oxo-1'H-[1,5'-bibenzo[d]imidazole]-3(2H)-carboxylate The title compound (beige solid) is prepared in quantitative yield (182 mg, beige solid) by the similar manner to Step-1 and Step-2 of Intermediate-81 using 5-bromo-1,2-dimethyl-1H-benzo[d]imidazole in place of 6-bromo-1-methyl-1H-pyrrolo[3,2-b]pyridine.
MS (ESI) m/z: 379.2 (M+H)$^+$.

Intermediate-90: tert-butyl 1',3'-dimethyl-2,2'-dioxo-2',3'-dihydro-1'H-[1,5'-bibenzo[d]imidazole]-3(2H)-carboxylate The title compound (brown solid) is prepared in 30% yield in 2 steps by the similar manner to Step-1 and Step-2 of Intermediate-81 using 5-bromo-1,3-dimethyl-1H-benzo[d]imidazol-2(3H)-one in place of 6-bromo-1-methyl-1H-pyrrolo[3,2-b]pyridine.

$^1$H-NMR (400 MHz, CDCl$_3$) delta 7.95-7.91 (1H, m), 7.20-7.13 (3H, m), 7.10 (1H, d, J=1.8 Hz), 7.08 (1H, d, J=8.2 Hz), 6.92-6.88 (1H, m), 3.48 (3H, s), 3.43 (3H, s), 1.69 (9H, s).
MS (ESI) m/z: 395.2 (M+H)$^+$.

Intermediate-91: tert-butyl 3-(3-methyl-1-((2-(trimethylsilyl)ethoxy)methyl)-1H-indazol-5-yl)-2-oxo-2,3-dihydro-1H-benzo[d]imidazole-1-carboxylate The title compound is prepared in 23% yield in 2 steps by the similar manner to Step-1 and Step-2 of Intermediate-81 using 5-bromo-3-methyl-1-((2-(trimethylsilyl)ethoxy)methyl)-1H-indazole in place of 6-bromo-1-methyl-1H-pyrrolo[3,2-b]pyridine.
MS (ESI) m/z: 495.2 (M+H)$^+$.

Intermediate-92: 1-(3-methylbenzo[d]isoxazol-6-yl)-1H-benzo[d]imidazol-2(3H)-one The title compound is prepared in 20% yield in 2 steps by the similar manner to Step-1 and Step-2 of Intermediate-81 using 6-bromo-3-methylbenzo[d]isoxazole in place of 6-bromo-1-methyl-1H-pyrrolo[3,2-b]pyridine.
MS (ESI) m/z: 466.2 (M+H)$^+$.

Intermediate-93: 1-(3-methyl-1-(tetrahydro-2H-pyran-2-yl)-1H-pyrazolo[4,3-b]pyridin-6-yl)-1H-benzo[d]imidazol-2(3H)-one The title compound (brown gum) is prepared in 51% yield in 2 steps by the similar manner to Step-1 and Step-2 of Intermediate-81 using 6-bromo-3-methyl-1-(tetrahydro-2H-pyran-2-yl)-1H-pyrazolo[4,3-b]pyridine in place of 6-bromo-1-methyl-H-pyrrolo[3,2-b]pyridine.

MS (ESI) m/z: 450.3 (M+H)+.

Intermediate-94: 1-(2,3-dihydro-1H-inden-2-yl)-1H-benzo[d]imidazol-2(3H)-one <Step-1>: 5-bromo-N-(2-nitrophenyl)-2,3-dihydro-1H-inden-2-amine A mixture of 1-fluoro-2-nitrobenzene (50 mg, 0.354 mmol), 5-bromo-2,3-dihydro-1H-inden-2-amine hydrobromide (104 mg, 0.354 mmol) and potassium carbonate (171 mg, 1.24 mmol) in DMA (1 mL) is stirred at 80° C. for 6 hrs. After cooled to rt, the reaction mixture is diluted with EtOAc, washed with water, dried over MgSO$_4$, filtered and concentrated. The residue is purified by column chromatography on silica-gel eluting with 5-40% EtOAc in n-hexane to give 118 mg (quantitative yield) of the title compound as a yellow oil.

$^1$H-NMR (400 MHz, CDCl$_3$) delta 8.24 (1H, d, J=5.9 Hz), 8.19 (1H, dd, J=8.7, 1.4 Hz), 7.48 (1H, ddd, J=8.7, 7.8, 1.4 Hz), 7.39 (1H, s), 7.33 (1H, dd, J=7.8, 1.8 Hz), 7.12 (1H, d, J=8.2 Hz), 6.94 (1H, d, J=7.8 Hz), 6.72-6.66 (1H, m), 4.55-4.45 (1H, m), 3.44 (2H, td, J=16.1, 7.2 Hz), 2.97 (2H, td, J=17.2, 5.0 Hz).

<Step-2>: N$^1$-(2,3-dihydro-1H-inden-2-yl)benzene-1,2-diamine

A solution of 5-bromo-N-(2-nitrophenyl)-2,3-dihydro-1H-inden-2-amine (118 mg, 0.354 mmol, Step-1 of Intermediate-94) in EtOAc (1 mL) in a round bottle flask is evacuated and backfilled with N$_2$ gas (three times). To this is added 10% Pd on carbon (38 mg). The resultant mixture is evacuated and backfilled with hydrogen gas and vigorously stirred at rt for 1 hr. To the reaction mixture is added 1 M hydrochloric acid (0.1 mL) and stirring is continued for 1.5 hrs. After replacing H$_2$ with N$_2$, the mixture is filtered through celite pad and the filtrate is concentrated. The residual oil is purified by column chromatography on silica-gel eluting with 2-40% EtOAc in n-hexane to give 31 mg (50%) of the title compound as a purple oil.

$^1$H-NMR (400 MHz, CDCl$_3$) delta 7.25-7.20 (2H, m), 7.20-7.15 (2H, m), 6.88-6.82 (1H, m), 6.77 (1H, d, J=7.3 Hz), 6.74-6.67 (2H, m), 4.37-4.31 (1H, m), 3.70-3.30 (4H, m), 2.92 (2H, dd, J=16.0, 4.6 Hz).

MS (ESI) m/z: 225.3 (M+H)+.

<Step-3>: 1-(2,3-dihydro-1H-inden-2-yl)-1H-benzo[d]imidazol-2(3H)-one

To a solution of N$^1$-(2,3-dihydro-1H-inden-2-yl)benzene-1,2-diamine (40 mg, 0.178 mmol, Step-2 of Intermediate-94) in THF (1.5 mL) is added CDI (31 mg, 0.191 mmol) and stirred at rt for 2 days. The reaction mixture is diluted with EtOAc, washed with water, dried over MgSO$_4$, filtered and concentrated. The residue is purified by column chromatography on silica-gel eluting with 5-90% EtOAc in n-hexane to give 26 mg (54%) of the title compound as a beige solid.

$^1$H-NMR (400 MHz, CDCl$_3$) delta 8.43-8.24 (1H, m), 7.31-7.21 (4H, m), 7.09-7.04 (1H, m), 7.02 (1H, dd, J=7.8, 0.9 Hz), 6.93 (1H, td, J=7.5, 1.4 Hz), 6.68 (1H, d, J=8.7 Hz), 5.58-5.47 (1H, m), 3.50 (2H, dd, J=16.7, 7.5 Hz), 3.43 (2H, dd, J=16.5, 9.6 Hz).

MS (ESI) m/z: 251.2 (M+H)+.

Intermediate-:95 1-(2,3-dimethyl-2H-indazol-5-yl)-1H-benzo[d]imidazol-2(3H)-one <Step-1>: 5-bromo-2,3-dimethyl-2H-indazole To a solution of 5-bromo-3-methyl-1H-indazole (116 mg, 0.551 mmol) in THF (1 mL) and DMF (1 mL) is added NaH (60% in oil, 26 mg, 0.661 mmol) at 0° C. and stirred for 20 min. To the reaction mixture is added iodomethane (0.041 mL, 0.661 mmol) at 0° C. and stirred for 15 min. The reaction is quenched by adding ice-water and the resultant mixture is extracted with EtOAc. The organic phase is washed with water, dried over MgSO$_4$, filtered and concentrated under reduced pressure. The residue is purified by column chromatography on silica-gel eluting with 10-70% EtOAc in n-hexane to give 20 mg (16%) of the title compound as a white solid.

$^1$H-NMR (400 MHz, CDCl$_3$) delta 7.70 (1H, d, J=1.8 Hz), 7.49 (1H, d, J=9.1 Hz), 7.29 (1H, dd, J=9.1, 1.8 Hz), 4.08 (3H, s), 2.56 (3H, s).

<Step-2>: 1-(2,3-dimethyl-2H-indazol-5-yl)-1H-benzo[d]imidazol-2(3H)-one

A mixture of 1H-benzo[d]imidazol-2(3H)-one (60 mg, 0.444 mmol), 5-bromo-2,3-dimethyl-2H-indazole (20 mg, 0.089 mmol, Step-1 of Intermediate-95), copper(I) iodide (42 mg, 0.222 mmol), N$^1$,N$^2$-dimethylethane-1,2-diamine (0.048 mL, 0.444 mmol) and Cs$_2$CO$_3$ (217 mg, 0.666 mmol) in DMA (1 mL) is stirred at 100° C. overnight then at 150° C. for 16 hrs. After cooled to rt, the reaction mixture is diluted with EtOAc, washed with 28% ammonia aqueous solution, dried over MgSO$_4$, filtered and concentrated. The residue is purified by column chromatography on silica-gel eluting with 0-10% methanol in EtOAc to give 9 mg (36%) of the title compound.

$^1$H-NMR (400 MHz, CDCl$_3$) delta 10.02 (1H, s), 7.78 (1H, d, J=8.9 Hz), 7.74 (1H, d, J=2.1 Hz), 7.35 (1H, dd, J=8.9, 2.1 Hz), 7.15 (1H, dd, J=7.3, 1.1 Hz), 7.10 (1H, td, J=7.3, 1.1 Hz), 7.05 (1H, td, J=7.3, 1.1 Hz), 6.98 (1H, d, J=7.3 Hz), 4.16 (3H, s), 2.64 (3H, s).

MS (ESI) m/z: 279.3 (M+H)+.

Intermediate-96: 1-(imidazo[1,2-a]pyridin-6-yl)-1H-benzo[d]imidazol-2(3H)-one The title compound is prepared in 18% yield (10 mg) by the similar manner to Step-2 of Intermediate-95 using 6-bromoimidazo[1,2-a]pyridine (44 mg, 0.222 mmol) in place of 5-bromo-2,3-dimethyl-2H-indazole.

$^1$H-NMR (400 MHz, CDCl$_3$) delta 9.76 (1H, br s), 8.49 (1H, d, J=1.4 Hz), 7.80 (1H, d, J=9.6 Hz), 7.76 (1H, s), 7.70 (1H, s), 7.34 (1H, dd, J=9.6, 1.8 Hz), 7.20-7.07 (3H, m), 7.03 (1H, d, J=7.3 Hz).

MS (ESI) m/z: 251.3 (M+H)+.

Intermediate-97: 1-(quinazolin-5-yl)-1H-benzo[d]imidazol-2(3H)-one

The title compound is prepared in 10% yield (6 mg) by the similar manner to Step-2 of Intermediate-95 using 5-bromoquinazoline (46 mg, 0.222 mmol) in place of 5-bromo-2,3-dimethyl-2H-indazole.

$^1$H-NMR (400 MHz, CDCl$_3$) delta 9.43 (1H, s), 9.33 (1H, s), 8.88 (1H, s), 8.22 (1H, d, J=7.8 Hz), 8.09 (1H, t, J=7.8 Hz), 7.78 (1H, d, J=7.8 Hz), 7.22-7.00 (3H, m), 6.74 (1H, d, J=7.8 Hz).

MS (ESI) m/z: 263.3 (M+H)$^+$.

Intermediate-98: 3-(2,3-dihydro-1H-inden-5-yl)-1H-imidazo[4,5-b]pyridin-2(3H)-one <Step-1>: 2-((2,3-dihydro-1H-inden-5-yl)amino)nicotinic acid A mixture of 2-chloronicotinic acid (150 mg, 0.95 mmol), 2,3-dihydro-1H-inden-5-amine (127 mg, 0.95 mmol), and p-toluenesulfonic acid monohydrate (91 mg, 0.47 mmol) in water (3 mL) is stirred at 100° C. for 1 day. The mixture is concentrated to give the title compound as a crude. The crude is used next step without purification.

MS (ESI) m/z: 255.3 (M+H)$^+$.

<Step-2>: 3-(2,3-dihydro-1H-inden-5-yl)-1H-imidazo[4,5-b]pyridin-2(3H)-one

A mixture of 2-((2,3-dihydro-1H-inden-5-yl)amino)nicotinic acid (crude, 0.95 mmol, Step-1 of Intermediate-98), diphenylphosphoryl azide (0.31 mL, 1.43 mmol), and TEA (0.27 mL, 1.90 mmol) in 1,4-dioxane (3 mL) is stirred at 100° C. for 3 hrs. The mixture is quenched with saturated aqueous sodium bicarbonate and extracted with DCM. The organic layer is dried over sodium sulfate, filtered and concentrated. The residue is purified by column chromatography on silica-gel eluting with 0-75% EtOAc in n-hexane to give 140 mg (59% yield in 2 steps) of the title compound as a pale yellow solid.

$^1$H-NMR (400 MHz, CDCl$_3$) delta 10.31-10.02 (1H, m), 8.07 (1H, dd, J=5.0, 1.4 Hz), 7.46 (1H, s), 7.43-7.32 (3H, m), 7.03 (1H, dd, J=7.3, 5.0 Hz), 3.08-2.90 (4H, m), 2.19-2.18 (2H, m).

MS (ESI) m/z: 252.2 (M+H)$^+$.

Intermediate-99: 3-(4-methoxyphenyl)-1H-imidazo[4,5-b]pyridin-2(3H)-one

<Step-1>: 2-((4-methoxyphenyl)amino)nicotinic acid

A mixture of 2-chloronicotinic acid (150 mg, 0.95 mmol), 4-methoxyaniline (117 mg, 0.95 mmol), and p-toluenesulfonic acid monohydrate (91 mg, 0.47 mmol) in water (3 mL) is stirred at 100° C. for 1 day. The mixture is concentrated to give the title compound as a crude. The crude is used next step without purification.

MS (ESI) m/z: 245.3 (M+H)$^+$.

<Step-2>: 3-(4-methoxyphenyl)-1H-imidazo[4,5-b]pyridin-2(3H)-one

A mixture of 2-((4-methoxyphenyl)amino)nicotinic acid (crude, 0.95 mmol, Step-1 of Intermediate-99), diphenylphosphoryl azide (0.31 mL, 1.43 mmol), and TEA (0.27 mL, 1.90 mmol) in 1,4-dioxane (3 mL) is stirred at 100° C. for 3 hrs. The mixture is quenched with saturated aqueous sodium bicarbonate. The precipitate is collected and washed with diisopropyl ether to give 101 mg (44% yield in 2 steps) of the title compound as a pale yellow solid.

$^1$H-NMR (400 MHz, CDCl$_3$) delta 9.69 (1H, br s), 8.07 (1H, dd, J=5.0, 1.4 Hz), 7.57 (2H, d, J=9.1 Hz), 7.35 (1H, dd, J=7.8, 1.4 Hz), 7.08 (2H, d, J=9.1 Hz), 7.11-7.02 (1H, m), 3.87 (3H, s).

MS (ESI) m/z: 242.3 (M+H)$^+$.

Intermediate-100: 1-(1,3-dimethyl-1H-indazol-6-yl)-1H-benzo[d]imidazol-2(3H)-one The title compound is prepared in 45% yield (41 mg, brown solid) by the similar manner to Intermediate-84 using 1,3-dimethyl-6-(4,4,5,5-tetramethyl-1,3,2-dioxaborolan-2-yl)-1H-indazole (111 mg, 0.33 mmol) in place of 1-methyl-5-(4,4,5,5-tetramethyl-1,3,2-dioxaborolan-2-yl)-1H-pyrazolo[3,4-b]pyridine.

$^1$H-NMR (400 MHz, CDCl$_3$) delta 7.79 (1H, d, J=8.5 Hz), 7.54 (1H, s), 7.26 (1H, m), 7.16-7.04 (4H, m), 6.97 (1H, d, J=7.5 Hz), 4.02 (3H, s), 2.61 (3H, s).

MS (ESI) m/z: 279.2 (M+H)$^+$.

Intermediate-101: N-methyl-5-(7-methyl-2-oxo-2,3-dihydro-1H-benzo[d]imidazol-1-yl)picolinamide <Step-1>: methyl 5-((2-methyl-6-nitrophenyl)amino)picolinate A mixture of 2-bromo-1-methyl-3-nitrobenzene (142 mg, 0.66 mmol), methyl 5-aminopicolinate (100 mg, 0.66 mmol), Pd$_2$(dba)$_3$ (48 mg, 0.053 mmol), Xantphos (61 mg, 0.11 mmol), and K$_3$PO$_4$ (279 mg, 1.31 mmol) in 1,4-dioxane (3 mL) is stirred at 80° C. for 1 day. The mixture is diluted with water and extracted with EtOAc. The organic layer is dried over sodium sulfate, filtered and concentrated. The residue is purified by column chromatography on silica-gel eluting with 0-50% EtOAc in n-hexane to give 170 mg (90% yield) of the title compound as an orange gum.

$^1$H-NMR (400 MHz, CDCl$_3$) delta 8.22 (1H, d, J=2.3 Hz), 8.05-7.93 (3H, m), 7.54 (1H, d, J=7.8 Hz), 7.31-7.23 (1H, m), 6.90 (1H, dd, J=8.2, 2.3 Hz), 3.97 (3H, s), 2.17 (3H, s).

MS (ESI) m/z: 288.3 (M+H)$^+$.

<Step-2>: methyl 5-((2-amino-6-methylphenyl)amino)picolinate

The title compound is prepared in quantitative yield (152 mg, brown gum) by the similar manner to Step-2 of Intermediate-20 using methyl 5-((2-methyl-6-nitrophenyl)amino)picolinate (170 mg, 0.59 mmol, Step-1 of Intermediate-101) in place of 2,4-difluoro-N-(2-nitrophenyl)aniline.

MS (ESI) m/z: 258.3 (M+H)$^+$.

<Step-3>: methyl 5-(7-methyl-2-oxo-2,3-dihydro-1H-benzo[d]imidazol-1-yl)picolinate The title compound is prepared in quantitative yield (167 mg, brown solid) by the similar manner to Step-3 of Intermediate-20 using methyl 5-((2-amino-6-methylphenyl)amino)picolinate (152 mg, 0.59 mmol, Step-2 of Intermediate-101) in place of N$^1$-(2,4-difluorophenyl)benzene-1,2-diamine.

MS (ESI) m/z: 284.2 (M+H)$^+$.

<Step-4>: N-methyl-5-(7-methyl-2-oxo-2,3-dihydro-1H-benzo[d]imidazol-1-yl)picolinamide The title compound is prepared in quantitative yield (166 mg, brown solid) by the similar manner to Intermediate-87 using methyl 5-(7-methyl-2-oxo-2,3-dihydro-1H-benzo[d]imidazol-1-yl)picolinate (Step-3 of Intermediate-101) in place of methyl 5-(2-oxo-2,3-dihydro-1H-benzo[d]imidazol-1-yl)picolinate.
MS (ESI) m/z: 283.1 (M+H)$^+$.

Intermediate-102: 5-(6-fluoro-2-oxo-2,3-dihydro-1H-benzo[d]imidazol-1-yl)-N-methylpicolinamide <Step-1>: methyl 5-((5-fluoro-2-nitrophenyl)amino)picolinate The title compound is prepared in 16% yield (32 mg, orange gum) by the similar manner to Step-1 of Intermediate-101 using 2-bromo-4-fluoro-1-nitrobenzene in place of 2-bromo-1-methyl-3-nitrobenzene.
$^1$H-NMR (400 MHz, CDCl$_3$) delta 9.69 (1H, br s), 8.70 (1H, d, J=2.3 Hz), 8.32 (1H, dd, J=9.2, 5.9 Hz), 8.21 (1H, d, J=8.7 Hz), 7.76 (1H, dd, J=8.2, 2.7 Hz), 6.99 (1H, dd, J=10.5, 2.7 Hz), 6.72-6.64 (1H, ddd, J=9.2, 8.7, 2.7 Hz), 4.04 (3H, s).
MS (ESI) m/z: 292.2 (M+H)$^+$.

<Step-2>: methyl 5-((2-amino-5-fluorophenyl)amino)picolinate

The title compound is prepared in 97% yield (27 mg, pale yellow gum) by the similar manner to Step-2 of Intermediate-88 using methyl 5-((5-fluoro-2-nitrophenyl)amino)picolinate (31 mg, 0.11 mmol, Step-1 of Intermediate-102) in place of N-(2-nitrophenyl)chroman-3-amine.
MS (ESI) m/z: 262.2 (M+H)$^+$.

<Step-3>: methyl 5-(6-fluoro-2-oxo-2,3-dihydro-1H-benzo[d]imidazol-1-yl)picolinate A mixture of methyl 5-((2-amino-5-fluorophenyl)amino)picolinate (27 mg, 0.10 mmol, Step-2 of Intermediate-102) and CDI (34 mg, 0.21 mmol) in THF (3 mL) is stirred at room temperature for 1 day. The mixture is quenched with 1 M hydrochloric acid. The precipitate is collected and washed with diisopropyl ether to give 17 mg (57% yield) of the title compound as a gray solid.
MS (ESI) m/z: 288.2 (M+H)$^+$.

<Step-4>: 5-(6-fluoro-2-oxo-2,3-dihydro-1H-benzo[d]imidazol-1-yl)-N-methylpicolinamide The title compound is prepared in 95% yield (16 mg, gray solid) by the similar manner to Intermediate-87 using methyl 5-(6-fluoro-2-oxo-2,3-dihydro-1H-benzo[d]imidazol-1-yl)picolinate (17 mg, 0.059 mmol, Step-3 of Intermediate-102) in place of methyl 5-(2-oxo-2,3-dihydro-1H-benzo[d]imidazol-1-yl)picolinate.
$^1$H-NMR (400 MHz, DMSO-d$_6$) delta 8.90-8.80 (2H, m), 8.23-8.16 (2H, m), 7.13-7.05 (2H, m), 6.97-6.90 (1H, m), 2.86 (3H, d, J=5.0 Hz). A signal due to NH is not observed.
MS (ESI) m/z: 287.1 (M+H)$^+$.

Intermediate-103: 5-(5-methoxy-2-oxo-2,3-dihydro-1H-benzo[d]imidazol-1-yl)-N-methylpicolinamide <Step-1>: methyl 5-((4-methoxy-2-nitrophenyl)amino)picolinate The title compound is prepared in 41% yield (82 mg, orange gum) by the similar manner to Step-1 of Intermediate-101 using 1-bromo-4-methoxy-2-nitrobenzene (153 mg, 0.66 mmol) in place of 2-bromo-1-methyl-3-nitrobenzene.
$^1$H-NMR (400 MHz, CDCl$_3$) delta 9.09 (1H, s), 8.60 (1H, d, J=2.3 Hz), 8.12 (1H, d, J=8.7 Hz), 7.68 (1H, d, J=2.7 Hz), 7.60 (1H, dd, J=8.2, 2.7 Hz), 7.42 (1H, d, J=9.1 Hz), 7.18 (1H, dd, J=9.1, 2.7 Hz), 4.01 (3H, s), 3.87 (3H, s).
MS (ESI) m/z: 304.2 (M+H)$^+$.

<Step-2>: methyl 5-((2-amino-4-methoxyphenyl)amino)picolinate

The title compound is prepared in quantitative yield (74 mg, brown gum) by the similar manner to Step-2 of Intermediate-20 using methyl methyl 5-((4-methoxy-2-nitrophenyl)amino)picolinate (82 mg, 0.27 mmol, Step-1 of Intermediate-103) in place of 2,4-difluoro-N-(2-nitrophenyl)aniline.
MS (ESI) m/z: 274.2 (M+H)$^+$.

<Step-3>: methyl 5-(5-methoxy-2-oxo-2,3-dihydro-1H-benzo[d]imidazol-1-yl)picolinate The title compound is prepared in 42% yield (34 mg, gray solid) by the similar manner to Step-3 of Intermediate-102 using methyl 5-((2-amino-4-methoxyphenyl)amino)picolinate (74 mg, 0.27 mmol, Step-2 of Intermediate-103) in place of methyl 5-((2-amino-5-fluorophenyl)amino)picolinate.
$^1$H-NMR (400 MHz, DMSO-d$_6$) delta 11.35 (1H, br s), 8.98 (1H, t, J=1.8 Hz), 8.22 (2H, d, J=1.8 Hz), 7.15 (1H, d, J=8.7 Hz), 6.69 (1H, d, J=2.7 Hz), 6.64 (1H, dd, J=8.7, 2.7 Hz), 3.92 (3H, s), 3.76 (3H, s).
MS (ESI) m/z: 300.2 (M+H)$^+$.

<Step-4>: 5-(5-methoxy-2-oxo-2,3-dihydro-1H-benzo[d]imidazol-1-yl)-N-methylpicolinamide The title compound is prepared in 97% yield (34 mg, gray solid) by the similar manner to Intermediate-87 using methyl 5-(5-methoxy-2-oxo-2,3-dihydro-1H-benzo[d]imidazol-1-yl)picolinate (34 mg, 0.11 mmol, Step-3 of Intermediate-103) in place of methyl 5-(2-oxo-2,3-dihydro-1H-benzo[d]imidazol-1-yl)picolinate.
MS (ESI) m/z: 299.1 (M+H)$^+$.

Intermediate-104: 6-bromo-3-(cyclopropylmethyl)benzo[d]oxazol-2(3H)-one

To a stirred solution of 6-bromobenzo[d]oxazol-2(3H)-one (100 mg, 0.467 mmol) and (bromomethyl)cyclopropane (0.054 mL, 0.561 mmol) in DMF (1.8 mL) and THF (0.2 mL) is added NaH (60% in oil, 22 mg, 0.561 mmol) at 0° C. and stirred at rt for 15 min. To the reaction mixture is added sodium iodide (30 mg, 0.200 mmol) and stirred at rt overnight. After the reaction mixture is diluted with EtOAc then the reaction is quenched by adding ice-water. The resultant mixture is extracted with EtOAc. The organic phase is dried over MgSO$_4$, filtered and concentrated under reduced pressure. The residue is purified by column chromatography on silica-gel eluting with 5-25% EtOAc in n-hexane to give 99 mg (79%) of the title compound as a colorless oil.
¹H-NMR (400 MHz, CDCl₃) delta 7.38 (1H, d, J=1.8 Hz), 7.33 (1H, dd, J=8.2, 1.8 Hz), 6.91 (1H, d, J=8.2 Hz), 3.70 (2H, d, J=7.3 Hz), 1.28-1.16 (1H, m), 0.65-0.58 (2H, m), 0.46-0.40 (2H, m).

Intermediate-105: N,4-dimethyl-5-(2-oxo-2,3-dihydro-1H-benzo[d]imidazol-1-yl)picolinamide <Step-1>: methyl 4-methyl-5-((2-nitrophenyl)amino)picolinate The title compound is prepared in 66% yield (solid) by the similar manner to Step-1 of Intermediate-101 using 1-bromo-2-nitrobenzene in place of 2-bromo-1-methyl-3-nitrobenzene, and methyl 5-amino-4-methylpicolinate in place of methyl 5-aminopicolinate, respectively.
¹H-NMR (400 MHz, CDCl₃) delta 9.34 (1H, s), 8.72 (1H, s), 8.26 (1H, dd, J=8.5, 1.6 Hz), 8.11 (1H, s), 7.45 (1H, ddd, J=8.6, 7.2, 1.6 Hz), 7.09 (1H, dd, J=8.5, 1.1 Hz), 6.93 (1H, ddd, J=8.4, 6.8, 1.2 Hz), 4.02 (3H, s), 2.40 (3H, s).
MS (ESI) m/z: 288.1 (M+H)⁺.

<Step-2>: methyl 5-((2-aminophenyl)amino)-4-methylpicolinate

The title compound is prepared in nearly quantitative yield (solid) by the similar manner to Step-2 of Intermediate-88 using methyl 4-methyl-5-((2-nitrophenyl)amino)picolinate (Step-1 of Intermediate-105) in place of N-(2-nitrophenyl)chroman-3-amine.
¹H-NMR (400 MHz, CDCl₃) delta 7.94 (1H, s), 7.91 (1H, s), 7.12-7.06 (2H, m), 6.89 (1H, d, J=7.3 Hz), 6.81 (1H, td, J=7.6, 1.2 Hz), 5.55 (1H, br), 3.94 (3H, s), 3.00 (2H, br), 2.33 (3H, s).
MS (ESI) m/z: 258.2 (M+H)⁺.

<Step-3>: methyl 4-methyl-5-(2-oxo-2,3-dihydro-1H-benzo[d]imidazol-1-yl)picolinate To a mixture of methyl 5-((2-aminophenyl)amino)-4-methylpicolinate (611 mg, 2.38 mmol, Step-2 of Intermediate-105) in MeCN (20 mL) is added CDI (2.44 g, 15.04 mmol) and stirred at rt overnight. The mixture is diluted with 1 M hydrochloric acid and saturated aqueous sodium bicarbonate, extracted with DCM and passed through sodium sulfate. The solvent is removed under vacuum, the title compound is prepared in nearly quantitative yields (672 mg, solid).
¹H-NMR (400 MHz, CDCl₃) delta 10.23 (1H, br), 8.74 (1H, s), 8.24 (1H, s), 7.21-7.12 (2H, m), 7.07 (1H, td, J=7.5, 1.8 Hz), 6.72 (1H, d, J=7.8 Hz), 4.07 (3H, s), 2.39 (3H, s).
MS (ESI) m/z: 284.1 (M+H)⁺.

<Step-4>: N,4-dimethyl-5-(2-oxo-2,3-dihydro-1H-benzo[d]imidazol-1-yl)picolinamide The title compound is prepared in 95% yield (solid) by the similar manner to Intermediate-87 using methyl 4-methyl-5-(2-oxo-2,3-dihydro-1H-benzo[d]imidazol-1-yl)picolinate (Step-3 of Intermediate-105) in place of methyl 5-(2-oxo-2,3-dihydro-1H-benzo[d]imidazol-1-yl)picolinate.
¹H-NMR (400 MHz, CDCl₃) delta 10.32 (1H, s), 8.53 (1H, s), 8.29 (1H, s), 8.04 (1H, brd, J=5.0 Hz), 7.21-7.10 (2H, m), 7.06 (1H, td, J=7.5, 1.8 Hz), 6.69 (1H, d, J=7.8 Hz), 3.08 (3H, d, J=5.0 Hz), 2.35 (3H, s).
MS (ESI) m/z: 283.1 (M+H)⁺.

Intermediate-106: 3-(benzo[d]thiazol-6-yl)-1H-imidazo[4,5-b]pyridin-2(3H)-one

The title compound (solid) is prepared in quantitative yield in 2 steps by the similar manner to Step-1 and Step-2 of Intermediate-99 using benzo[d]thiazol-6-amine in place of 4-methoxyaniline.
MS (ESI) m/z: 269.1 (M+H)⁺.

Intermediate-107: 1-(3-methyl-1-(tetrahydro-2H-pyran-2-yl)-1H-indazol-6-yl)-1H-benzo[d]imidazol-2(3H)-one <Step-1>: 3-methyl-1-(tetrahydro-2H-pyran-2-yl)-6-(4,4,5,5-tetramethyl-1,3,2-dioxaborolan-2-yl)-1H-indazole A mixture of 6-bromo-3-methyl-1-(tetrahydro-2H-pyran-2-yl)-1H-indazole (136 mg, 0.461 mmol), bis(pinacolato)diboron (234 mg, 0.921 mmol), potassium acetate (90 mg, 0.921 mmol), palladium (II) acetate (10 mg, 0.046 mmol), and 2-(dicyclohexylphosphino)biphenyl (32 mg, 0.092 mmol) in 1,4-dioxane (0.5 mL) is stirred overnight at 80° C. The reaction mixture is concentrated and the resultant residue is purified by column chromatography on silica-gel eluting with 6-50% EtOAc in n-hexane to give 127 mg (81% yield) of the title compound as a brown gum.
¹H-NMR (400 MHz, CDCl₃) delta 7.95 (1H, s), 7.63 (1H, dd, J=8.0, 1.0 Hz), 7.55 (1H, d, J=8.0 Hz), 5.71 (1H, dd, J=10.0, 2.5 Hz), 4.11-4.05 (1H, m), 3.77 (1H, td, J=11.5, 2.5 Hz), 2.68-2.60 (1H, m), 2.57 (3H, s), 2.18-2.09 (1H, m), 2.02-1.92 (1H, m), 1.86-1.68 (2H, m), 1.66-1.58 (1H, m), 1.38 (12H, s).
MS (ESI) m/z: 343.2 (M+H)⁺.

<Step-2>: 1-(3-methyl-1-(tetrahydro-2H-pyran-2-yl)-1H-indazol-6-yl)-1H-benzo[d]imidazol-2(3H)-one The title compound is prepared in quantitative yield by the similar manner to Intermediate-84 using 3-methyl-1-(tetrahydro-2H-pyran-2-yl)-6-(4,4,5,5-tetramethyl-1,3,2-dioxaborolan-2-yl)-1H-indazole in place of 1-methyl-5-(4,4,5,5-tetramethyl-1,3,2-dioxaborolan-2-yl)-1H-pyrazolo[3,4-b]pyridine.
MS (ESI) m/z: 349.2 (M+H)⁺.

Intermediate-108: 1'-methyl-1'H-[1,5'-bibenzo[d]imidazol]-2(3H)-one

The title compound is prepared in 21% yield (40 mg, brown solid) by the similar manner to Intermediate-84 using 1-methyl-5-(4,4,5,5-tetramethyl-1,3,2-dioxaborolan-2-yl)-1H-benzo[d]imidazole (184 mg, 0.714 mmol) in place of 1-methyl-5-(4,4,5,5-tetramethyl-1,3,2-dioxaborolan-2-yl)-1H-pyrazolo[3,4-b]pyridine
¹H-NMR (400 MHz, CDCl₃) delta 7.98 (1H, s), 7.95 (1H, s), 7.56 (1H, d, J=8.2 Hz), 7.50 (1H, d, J=8.2 Hz), 7.17-6.96 (5H, m), 3.92 (3H, s).
MS (ESI) m/z: 265.2 (M+H)⁺.

Intermediate-109: 3'-methyl-3'H-[1,5'-bibenzo[d]imidazol]-2(3H)-one

The title compound is prepared in 55% yield (64 mg, brown solid) by the similar manner to Intermediate-84 using 1-methyl-6-(4,4,5,5-tetramethyl-1,3,2-dioxaborolan-2-yl)-1H-benzo[d]imidazole (114 mg, 0.441 mmol) in place of 1-methyl-5-(4,4,5,5-tetramethyl-1,3,2-dioxaborolan-2-yl)-1H-pyrazolo[3,4-b]pyridine $^1$H-NMR (400 MHz, CDCl$_3$) delta 7.97 (1H, s), 7.95 (1H, d, J=8.0 Hz), 7.62 (1H, d, J=2.0 Hz), 7.42 (1H, dd, J=8.0, 2.0 Hz), 7.17-6.98 (5H, m), 3.89 (3H, s).

MS (ESI) m/z: 265.2 (M+H)$^+$.

Intermediate-110: 1-(5-bromo-2,3-dihydro-1H-inden-2-yl)-1H-imidazo[4,5-c]pyridin-2(3H)-one <Step-1>: N$^4$-(5-bromo-2,3-dihydro-1H-inden-2-yl)pyridine-3,4-diamine A mixture of 4-chloro-3-nitropyridine (25 mg, 0.16 mmol), 5-bromo-2,3-dihydro-1H-inden-2-amine hydrobromide (46 mg, 0.16 mmol), TEA (0.078 mL, 0.57 mmol) in MeOH (1 mL) is stirred overnight at 60° C. After the reaction mixture is cooled down to rt, tin(II) chloride (269 mg, 1.42 mmol) is added and stirred for 1 hr at rt. The mixture is purified by column chromatography on amino-functional silica gel eluting with 100% EtOAc to give 31 mg (64% yield) of the title compound as a brown gum.

MS (ESI) m/z: 304.1 (M+H)$^+$.

<Step-2>: 1-(5-bromo-2,3-dihydro-1H-inden-2-yl)-1H-imidazo[4,5-c]pyridin-2(3H)-one A mixture of N$^4$-(5-bromo-2,3-dihydro-1H-inden-2-yl)pyridine-3,4-diamine (31 mg, 0.10 mmol, Step-1 of Intermediate-110) and CDI (164 mg, 1.01 mmol) in MeCN (1 mL) is stirred for 2 days at rt. After the reaction mixture is concentrated, the residue is added with water. The resultant mixture is extracted with EtOAc and concentrated. The resultant residue is purified by column chromatography on silica-gel eluting with 24-100% EtOAc in n-hexane followed by 100% MeOH to give 34 mg (quantitative yield) of the title compound as a brown solid.

MS (ESI) m/z: 330.1 (M+H)$^+$.

Intermediate-111: 3-(3-methyl-1-(tetrahydro-2H-pyran-2-yl)-1H-indazol-5-yl)-1H-imidazo[4,5-b]pyridin-2(3H)-one The title compound (brown gum) is prepared in 81% yield in 2 steps by the similar manner to Step-1 and Step-2 of Intermediate-110 using 3-methyl-1-(tetrahydro-2H-pyran-2-yl)-1H-indazol-5-amine and 2-fluoro-3-nitropyridine in place of 5-bromo-2,3-dihydro-1H-inden-2-amine and 4-chloro-3-nitropyridine.

MS (ESI) m/z: 350.3 (M+H)$^+$.

Intermediate-112: 1-(4-(pyridin-4-yloxy)phenyl)-1H-benzo[d]imidazol-2(3H)-one

<Step-1>: 2-nitro-N-(4-(pyridin-4-yloxy)phenyl)aniline

A mixture of 1-bromo-2-nitrobenzene (163 mg, 0.81 mmol), 4-(pyridin-4-yloxy)aniline (150 mg, 0.81 mmol), Pd$_2$(dba)$_3$ (37 mg, 0.040 mmol), Xantphos (47 mg, 0.081 mmol) and Cs$_2$CO$_3$ (525 mg, 1.61 mmol) in 1,4-dioxane (5 mL) is stirred at 80° C. overnight. The mixture is filtered through a pad of Celite, washed with EtOAc. The filtrate is diluted with H$_2$O, extracted with EtOAc. The organic layer is dried over sodium sulfate, filtered and concentrated in vacuo. The resultant residue is purified by column chromatography on silica-gel eluting with 0-70% EtOAc in n-hexane to give 211 mg (85% yield) of the title compound as a solid.

$^1$H-NMR (400 MHz, CDCl$_3$) delta 9.47 (1H, br s), 8.50 (2H, dd, J=4.6, 1.4 Hz), 8.22 (1H, dd, J=8.6, 1.4 Hz), 7.41 (1H, ddd, J=8.7, 6.8, 2.3 Hz), 7.34 (2H, dd, J=6.8, 2.3 Hz), 7.20 (1H, dd, 8.7, 1.4 Hz), 7.15 (2H, dd, J=6.8, 2.3 Hz), 6.88 (2H, dd, 4.6, 1.4 Hz), 6.81 (1H, ddd, J=8.7, 6.8, 1.4 Hz).

MS (ESI) m/z: 308.1 (M+H)$^+$.

<Step-2>: N$^1$-(4-(pyridin-4-yloxy)phenyl)benzene-1,2-diamine

The title compound is prepared in 94% yield (179 mg) by the similar manner to Step-2 of Intermediate-88 using 2-nitro-N-(4-(pyridin-4-yloxy)phenyl)aniline (212 mg, 0.69 mmol, Step-1 of Intermediate-112) in place of N-(2-nitrophenyl)chroman-3-amine.

$^1$H-NMR (400 MHz, CDCl$_3$) delta 8.42 (2H, dd, J=5.04, 1.8 Hz), 7.13 (1H, dd, J=7.8, 1.4 Hz), 7.04 (1H, td, J=7.8, 1.4 Hz), 6.95 (2H, dd, J=6.9, 2.3 Hz), 6.83 (1H, dd, J=7.8, 1.4 Hz), 6.81 (2H, dd, J=7.8, 1.4 Hz), 6.81-6.80 (1H, m), 6.77 (2H, dd, J=6.9, 2.3 Hz), 5.23 (1H, s), 3.80 (2H, br s). A signal due to NH is not observed.

MS (ESI) m/z: 278.0 (M+H)$^+$.

<Step-3>:1-(4-(pyridin-4-yloxy)phenyl)-1H-benzo[d]imidazol-2(3H)-one

The title compound is prepared in 95% yield (186 mg) by the similar manner to Step-3 of Intermediate-20 using N$^1$-(4-(pyridin-4-yloxy)phenyl)benzene-1,2-diamine (179 mg, 0.64 mmol, Step-2 of Intermediate-112) in place of N$^1$-(2,4-difluorophenyl)benzene-1,2-diamine.

$^1$H-NMR (400 MHz, DMSO-d$_6$) delta 8.49 (2H, dd, J=4.6, 1.4 Hz), 7.62 (2H, dd, J=6.4, 1.8 Hz), 7.35 (2H, dd, J=6.4, 1.8 Hz), 7.07-7.05 (2H, m), 7.03-7.01 (2H, m), 7.00 (2H, dd, J=4.6, 1.4 Hz). A signal due to NH is not observed.

MS (ESI) m/z: 303.9 (M+H)$^+$.

Intermediate-113: 1-(((1r,4r)-4-aminocyclohexyl)methyl)-3-(6-methoxypyridin-3-yl)-1H-benzo[d]imidazol-2(3H)-one <Step-1>: ((1r,4r)-4-((tert-butoxycarbonyl)amino)cyclohexyl)methyl methanesulfonate To a mixture of tert-butyl ((1r,4r)-4-(hydroxymethyl)cyclohexyl)carbamate (1.0 g, 4.4 mmol) and pyridine (690 mg, 8.7 mmol) is added methanesulfonic anhydride (990 mg, 5.7 mmol) at 0° C. and stirred at rt overnight. The mixture is added water and extracted with DCM, and passed through sodium sulfate. The solvent is removed under vacuum, the title compound is prepared in nearly quantitative yields (1.37 g, solid).

$^1$H-NMR (400 MHz, CDCl$_3$) delta 4.39 (1H, br), 4.03 (2H, d, J=6.9 Hz), 3.50-3.26 (1H, m), 3.00 (3H, s), 2.18-1.97 (2H, m), 1.95-1.79 (2H, m), 1.79-1.64 (1H, m), 1.44 (9H, s), 1.22-1.03 (4H, m).

MS (ESI) m/z: 308.0 (M+H)$^+$.

<Step-2>: tert-butyl ((1r,4r)-4-((3-(6-methoxypyridin-3-yl)-2-oxo-2,3-dihydro-1H-benzo[d]imidazol-1-yl) methyl)cyclohexyl)carbamate The title compound is prepared in 95% yield (solid) by the similar manner to Intermediate-54 using ((1r,4r)-4-((tert-butoxycarbonyl)amino)cyclohexyl)methyl methanesulfonate (Step-1 of Intermediate-113) and Intermediate-12 in place of Mesylate-1 and tertbutyl-3-(6-fluoropyridin-3-yl)-2-oxo-2,3-dihydro-1H-benzo[d]imidazole-1-carboxylate $^1$H-NMR (400 MHz, CDCl$_3$) delta 8.34 (1H, d, J=2.3 Hz), 7.75 (1H, dd, J=8.7, 2.7 Hz), 7.19-6.99 (4H, m), 6.90 (1H, d, J=8.7 Hz), 4.44-4.24 (1H, m), 4.00 (3H, s), 3.77 (2H, d, J=6.9 Hz), 3.41 (1H, br), 2.03 (2H, brd, J=11.9 Hz), 1.96-1.73 (3H, m), 1.43 (9H, s), 1.35-1.16 (2H, m), 1.16-0.98 (2H, m).

MS (ESI) m/z: 453.1 (M+H)$^+$.

<Step-3>: 1-(((1r,4r)-4-aminocyclohexyl)methyl)-3-(6-methoxypyridin-3-yl)-1H-benzo[d]imidazol-2(3H)-one ((1r,4r)-4-((3-(6-methoxypyridin-3-yl)-2-oxo-2,3-dihydro-1H-benzo[d]imidazol-1-yl)methyl)cyclohexyl)carbamate (1.92 g, 4.24 mmol, Step-2 of Intermediate-113) in 4 M HCl in 1,4-dioxane (30 mL) is stirred at rt for 1 hr. The solvent is removed under vacuum, the title compound is prepared in nearly quantitative yields (1.66 g, HCl salt).

$^1$H-NMR (400 MHz, CDCl$_3$) delta 8.26 (1H, d, J=2.3 Hz), 7.71-7.62 (1H, m), 7.12-7.03 (1H, m), 7.02-6.90 (3H, m), 6.85-6.78 (1H, m), 3.90 (3H, d, J=3.2 Hz), 3.70 (2H, brd, J=6.9 Hz), 2.57 (1H, br), 1.87-1.66 (5H, m), 1.28-0.82 (4H, m). A signal due to NH$_2$ is not observed.

MS (ESI) m/z: 353.0 (M+H)$^+$.

Intermediate-114: N-methyl-5-(5-methyl-2-oxo-2,3-dihydro-1H-benzo[d]imidazol-1-yl)picolinamide The title compound (brown solid) is prepared in 76% yield in 4 steps by the similar manner to Step-1, Step-2, Step-3, and Step-4 of Intermediate-102 using 1-bromo-4-methyl-2-nitrobenzene in place of 2-bromo-4-fluoro-1-nitrobenzene.

$^1$H-NMR (400 MHz, DMSO-d$_6$) delta 8.86 (1H, t, J=1.8 Hz), 8.84 (1H, br q, J=5.0 Hz), 8.19 (2H, d, J=1.8 Hz), 7.06 (1H, d, J=8.2 Hz), 6.93 (1H, s), 6.87 (1H, d, J=8.2 Hz), 2.85 (3H, d, J=5.0 Hz), 2.34 (3H, s). A signal due to NH is not observed.

MS (ESI) m/z: 283.3 (M+H)$^+$.

Intermediate-115: 5-(5-fluoro-2-oxo-2,3-dihydro-1H-benzo[d]imidazol-1-yl)-N-methylpicolinamide The title compound (gray solid) is prepared in 63% yield in 4 steps by the similar manner to Step-1, Step-2, Step-3, and Step-4 of Intermediate-102 using 1-bromo-4-fluoro-2-nitrobenzene in place of 2-bromo-4-fluoro-1-nitrobenzene.

$^1$H-NMR (400 MHz, DMSO-d$_6$) delta 8.86 (1H, t, J=1.8 Hz), 8.85 (1H, q, J=5.0 Hz), 8.19 (2H, d, J=1.8 Hz), 7.14 (1H, dd, J=8.7, 4.6 Hz), 6.99 (1H, dd, J=8.7, 2.3 Hz), 6.87 (1H, ddd, J=10.1, 8.7, 2.3 Hz), 2.85 (3H, d, J=5.0 Hz). A signal due to NH is not observed.

MS (ESI) m/z: 287.3 (M+H)$^+$.

Intermediate-116: 1-(1-(2-(methoxymethoxy)ethyl)-3-methyl-1H-indazol-5-yl)-1H-benzo[d]imidazol-2(3H)-one <Step-1>: 1-(2-(methoxymethoxy)ethyl)-3-methyl-5-nitro-1H-indazole A mixture of 3-methyl-5-nitro-1H-indazole (2.00 g, 11.29 mmol), 2-iodoethanol (2.91 g, 16.93 mmol) and Cs$_2$CO$_3$ (6.62 g, 20.32 mmol) in DMF (10 mL) is stirred at 100° C. overnight. The mixture is added water and extracted with EtOAc/Hexane=4/1 and passed through sodium sulfate. The solvent is removed under vacuum, the mixture of 2-(3-methyl-5-nitro-1H-indazol-1-yl)ethanol and 2-(3-methyl-5-nitro-2H-indazol-2-yl)ethanol is obtained. Next, the mixture in DCM (20 mL) is added DIEA (7.30 g, 56.4 mmol) and chloromethyl methyl ether (2.73 g, 33.9 mmol) at 0° C., and stirred at rt overnight. The mixture is added water, extracted with DCM and passed through sodium sulfate. The solvent is removed under vacuum, the crude product is purified by column chromatography on silica-gel eluting with 0-50% EtOAc in n-hexane, the title compound is prepared in 66% yield (1.97 g, solid).

$^1$H-NMR (400 MHz, CDCl$_3$) delta 8.64 (1H, d, J=1.8 Hz), 8.24 (1H, dd, J=9.1, 2.3 Hz), 7.49 (1H, d, J=9.1 Hz), 4.55 (2H, t, J=5.3 Hz), 4.51 (2H, s), 3.97 (2H, t, J=5.3 Hz), 3.15 (3H, s), 2.63 (3H, s).

MS (ESI) m/z: 266.0 (M+H)$^+$.

<Step-2>: 1-(2-(methoxymethoxy)ethyl)-3-methyl-1H-indazol-5-amine

To a mixture of 1-(2-(methoxymethoxy)ethyl)-3-methyl-5-nitro-1H-indazole (1.97 g, 7.43 mmol, Step-1 of Intermediate-116) in MeOH (30 mL) is added Os/C (100 mg) and hydrazine monohydrate (5.58 g, 111 mmol), and stirred at 60° C. for 4 hrs. The mixture is passed through celite and the solvent is removed under vacuum, the title compound is prepared in 89% yield (1.56 g, solid).

$^1$H-NMR (400 MHz, CDCl$_3$) delta 7.23 (1H, dd, J=8.2, 1.4 Hz), 6.84 (1H, dd, J=8.7, 1.8 Hz), 6.83 (1H, d, J=1.2 Hz), 4.51 (2H, s), 4.43 (2H, t, J=5.5 Hz), 3.92 (2H, t, J=5.5 Hz), 3.65 (2H, br), 3.18 (3H, s), 2.47 (3H, s).

MS (ESI) m/z: 236.0 (M+H)$^+$.

<Step-3>: 1-(2-(methoxymethoxy)ethyl)-3-methyl-N-(2-nitrophenyl)-1H-indazol-5-amine The title compound is prepared in 96% yield (solid) by the similar manner to Step-1 of Intermediate-101 using 1-(2-(methoxymethoxy)ethyl)-3-methyl-1H-indazol-5-amine (Step-2 of Intermediate-116) and 1-bromo-2-nitrobenzene in place of methyl 5-aminopicolinate and 2-bromo-1-methyl-3-nitrobenzene.

$^1$H-NMR (400 MHz, CDCl$_3$) delta 9.55 (1H, s), 8.22 (1H, dd, J=8.8, 1.2 Hz), 7.57-7.51 (1H, m), 7.49 (1H, d, J=9.2 Hz), 7.33 (1H, ddd, J=9.2, 6.8, 0.8 Hz), 7.27 (1H, dd, J=9.2, 1.6 Hz), 6.99 (1H, dd, J=8.7, 1.0 Hz), 6.73 (1H, ddd, J=8.0, 6.8.1.6 Hz), 4.55 (2H, s), 4.53 (2H, t, J=5.6 Hz), 3.99 (2H, t, J=5.5 Hz), 3.22 (3H, s), 2.56 (3H, s).

MS (ESI) m/z: 356.9 (M+H)$^+$.

<Step-4>: N$^1$-(1-(2-(methoxymethoxy)ethyl)-3-methyl-1H-indazol-5-yl)benzene-1,2-diamine A mixture of 1-(2-(methoxymethoxy)ethyl)-3-methyl-N-(2-nitrophenyl)-1H-indazol-5-amine (2.26 g, 6.34 mmol, Step-3 of Intermediate-116) and Os/C (100 mg) in MeOH (30 mL) is added hydrazine monohydrate (6.64 g, 133 mmol), and stirred at 60° C. overnight. The mixture is passed through celite and the solvent is removed under vacuum. The mixture is diluted with water and extracted with EtOAc, and passed through sodium sulfate. The solvent is removed under vacuum, the title compound is prepared in nearly quantitative yield (2.09 g, solid).

$^1$H-NMR (400 MHz, CDCl$_3$) delta 7.30 (1H, d, J=8.2 Hz), 7.09-6.93 (3H, m), 6.89 (1H, d, J=1.4 Hz), 6.81 (1H, dd, J=7.8, 1.4 Hz), 6.75 (1H, td, J=7.5, 1.4 Hz), 5.24 (1H, s), 4.53 (2H, s), 4.46 (2H, t, J=5.7 Hz), 3.93 (2H, t, J=5.7 Hz), 3.76 (2H, br), 3.21 (3H, s), 2.46 (3H, s).

MS (ESI) m/z: 326.9 (M+H)$^+$.

<Step-5>: 1-(1-(2-(methoxymethoxy)ethyl)-3-methyl-1H-indazol-5-yl)-1H-benzo[d]imidazol-2(3H)-one The title compound is prepared in 87% yield (solid) by the similar manner to Step-3 of Intermediate-105 using N$^1$-(1-(2-(methoxymethoxy)ethyl)-3-methyl-1H-indazol-5-yl)benzene-1,2-diamine (2.09 g, 6.40 mmol, Step-4 of Intermediate-116) in place of methyl 5-((2-aminophenyl)amino)-4-methylpicolinate.

$^1$H-NMR (400 MHz, CDCl$_3$) delta 10.38 (1H, br), 7.80 (1H, d, J=1.8 Hz), 7.59 (1H, d, J=9.6 Hz), 7.49 (1H, dd, J=9.1, 1.8 Hz), 7.19-7.02 (3H, m), 6.95 (1H, d, J=7.3 Hz), 4.57 (4H, t, J=4.8 Hz), 4.00 (2H, t, J=5.5 Hz), 3.26 (3H, s), 2.59 (3H, s).

MS (ESI) m/z: 352.9 (M+H)$^+$.

Intermediate-117: 3-(2-chlorophenyl)-1H-imidazo[4,5-b]pyridin-2(3H)-one

The title compound (pale yellow solid) is prepared in 96% yield in 2 steps by the similar manner to Step-1 and Step-2 of Intermediate-98 using 2-chloroaniline in place of 2,3-dihydro-1H-inden-5-amine.

MS (ESI) m/z: 246.3 (M+H)$^+$.

Intermediate-118: 5-(7-fluoro-2-oxo-2,3-dihydro-1H-benzo[d]imidazol-1-yl)-N-methylpicolinamide <Step-1>: methyl 5-((2-fluoro-6-nitrophenyl)amino)picolinate A mixture of methyl 5-aminopicolinate (105 mg, 0.69 mmol), 1,2-difluoro-3-nitrobenzene (105 mg, 0.66 mmol) and Cs$_2$CO$_3$ (428 mg, 1.31 mmol) in DMSO (3 mL) is stirred at room temperature for 5 hrs. The mixture is diluted with H$_2$O, extracted with EtOAc three times. The organic layer is dried over sodium sulfate, filtered and concentrated in vacuo. The resultant residue is purified by column chromatography on silica-gel eluting with 0-60% EtOAc in n-hexane to give 52 mg (27% yield) of the title compound as a yellow solid.

MS (ESI) m/z: 292.0 (M+H)$^+$.

<Step-2>: methyl 5-((2-amino-6-fluorophenyl)amino)picolinate

The title compound is prepared in quantitative yield (49 mg) by the similar manner to Step-2 of Intermediate-88 using methyl 5-((2-fluoro-6-nitrophenyl)amino)picolinate (52 mg, 0.18 mmol, Step-1 of Intermediate-118) in place of N-(2-nitrophenyl)chroman-3-amine.

MS (ESI) m/z:262.1 (M+H)$^+$.

<Step-3>: methyl 5-(7-fluoro-2-oxo-2,3-dihydro-1H-benzo[d]imidazol-1-yl)picolinate The title compound is prepared in 44% yield (24 mg) by the similar manner to Step-3 of Intermediate-20 using methyl methyl 5-((2-amino-6-fluorophenyl)amino)picolinate (49 mg, 0.18 mmol, Step-2 of Intermediate-118) in place of N$^1$-(2,4-difluorophenyl)benzene-1,2-diamine.

MS (ESI) m/z: 288.0 (M+H)$^+$.

<Step-4>: 5-(7-fluoro-2-oxo-2,3-dihydro-1H-benzo[d]imidazol-1-yl)-N-methylpicolinamide The title compound is prepared in quantitative yield (24 mg) by the similar manner to Intermediate-87 using methyl 5-(7-fluoro-2-oxo-2,3-dihydro-1H-benzo[d]imidazol-1-yl)picolinate (24 mg, 0.083 mmol, Step-3 of Intermediate-118) in place of methyl 5-(2-oxo-2,3-dihydro-1H-benzo[d]imidazol-1-yl)picolinate.

MS (ESI) m/z: 287.1 (M+H)$^+$.

Intermediate-119: 1-(2-(1-methyl-1H-pyrazol-4-yl)ethyl)-1H-benzo[d]imidazol-2(3H)-one The title compound is prepared in 54% yield in 3 steps by the similar manner to Step-1, Step-2, and Step-3 of Intermediate-118 using 1-fluoro-2-nitrobenzene and 2-(1-methyl-1H-pyrazol-4-yl)ethanamine in place of 1,2-difluoro-3-nitrobenzene and methyl 5-aminopicolinate.

MS (ESI) m/z: 243.1 (M+H)$^+$.

Intermediate-120: 1-(2,3-dihydro-1H-inden-4-yl)-1H-imidazo[4,5-c]pyridin-2(3H)-one The title compound (pale yellow solid) is prepared in 39% yield in 2 steps by the similar manner to Step-1 and Step-2 of Intermediate-98 using 4-chloronicotinic acid and 2,3-dihydro-1H-inden-4-amine in place of 2-chloronicotinic acid and 2,3-dihydro-1H-inden-5-amine.

$^1$H-NMR (400 MHz, DMSO-d$_6$) delta 11.38 (1H, br s), 8.29 (1H, s), 8.15 (1H, d, J=5.0 Hz), 7.38 (1H, d, J=7.3 Hz), 7.33 (1H, t, J=7.3 Hz), 7.21 (1H, d, J=7.3 Hz), 6.77 (1H, d, J=5.0 Hz), 3.03-2.95 (2H, m), 2.82-2.71 (1H, m), 2.65-2.53 (1H, m), 2.09-1.93 (2H, m).

MS (ESI) m/z: 252.3 (M+H)$^+$.

Intermediate-121: 5-(3-(((1r,4r)-4-aminocyclohexyl)methyl)-2-oxo-2,3-dihydro-1H-benzo[d]imidazol-1-yl)-N-methylpicolinamide The title compound (solid) is prepared in 92% yield in 2 steps by the similar manner to Step-2 and Step-3 of Intermediate-113 using Intermediate-87 in place of Intermediate-12.

$^1$H-NMR (400 MHz, CDCl$_3$) delta 8.84 (1H, d, J=1.8 Hz), 8.37 (1H, d, J=8.7 Hz), 8.10 (1H, dd, J=8.5, 2.5 Hz), 8.01 (1H, br d, J=4.6 Hz), 7.25-7.01 (4H, m), 3.80 (2H, d, J=6.8 Hz), 3.07 (3H, d, J=5.6 Hz), 2.78-2.53 (1H, m), 1.98-1.66 (5H, m), 1.33-0.88 (4H, m). A signal due to NH$_2$ is not observed.

MS (ESI) m/z: 380.1 (M+H)$^+$.

Intermediate-122: 3-(2,4-dimethoxybenzyl)-1H-imidazo[4,5-b]pyridin-2(3H)-one

<Step-1>: N-(2,4-dimethoxybenzyl)-3-nitropyridin-2-amine

To a mixture of (2,4-dimethoxyphenyl)methanamine (2.53 g, 15.14 mmol), 2-chloro-3-nitropyridine (2.0 g, 12.61 mmol), and TEA (5.27 mL, 37.8 mmol) in DMF (65 mL) is stirred at rt for 4 hrs. The mixture is stirred at 50° C. for 2.5 hrs. The mixture is poured into water, extracted with EtOAc.

The organic layer is washed with water, dried over sodium sulfate, filtered and concentrated. The residue is purified by column chromatography on silica-gel eluting with 0-15% EtOAc in n-hexane to give 3.11 g (85% yield) of the title compound as a yellow solid.

$^1$H-NMR (400 MHz, CDCl$_3$) delta 8.68 (1H, br s), 8.43 (1H, dd, J=4.3, 1.8 Hz), 8.40 (1H, dd, J=8.2, 1.8 Hz), 7.27-7.23 (1H, m), 6.61 (1H, dd, J=8.2, 4.3 Hz), 6.49 (1H, d, J=2.5 Hz), 6.43 (1H, dd, J=8.2, 2.5 Hz), 4.78 (2H, d, J=5.7 Hz), 3.88 (3H, s), 3.80 (3H, s).

MS (ESI) m/z: 290.4 (M+H)$^+$.

<Step-2>: N$^2$-(2,4-dimethoxybenzyl)pyridine-2,3-diamine

A solution of N-(2,4-dimethoxybenzyl)-3-nitropyridin-2-amine (3.11 g, 10.75 mmol, Step-1 of Intermediate-122) in EtOAc (90 mL) is evacuated and backfilled with N$_2$ gas. To this is added 10% Pd/C (311 mg) and 5% Pt-alumina (311 mg). The mixture is evacuated and backfilled with H$_2$ gas and stirred at rt under H$_2$ atmosphere. After 1.5 hrs, the reaction mixture is evacuated and backfilled with N$_2$ gas and the mixture is filtered through celite pad. The filtrate is concentrated in vacuo to give 2.75 g (99% yield) of the title compound.

$^1$H-NMR (400 MHz, CDCl$_3$) delta 7.78 (1H, dd, J=5.0, 1.6 Hz), 7.30-7.21 (1H, m), 6.84 (1H, dd, J=7.3, 1.6 Hz), 6.53 (1H, dd, J=7.3, 5.0 Hz), 6.49 (1H, d, J=2.3 Hz), 6.45 (1H, dd, J=8.1, 2.3 Hz), 4.61-4.47 (3H, m), 3.84 (3H, s), 3.80 (3H, s), 3.18 (2H, br s).

MS (ESI) m/z: 260.4 (M+H)$^+$.

<Step-3>:3-(2,4-dimethoxybenzyl)-1H-imidazo[4,5-b]pyridin-2(3H)-one

To a mixture of N$^2$-(2,4-dimethoxybenzyl)pyridine-2,3-diamine (2.66 g, 10.27 mmol, Step-2 of Intermediate-122) and CDI (3.33 g, 20.55 mmol) in THF (75 mL) is stirred at rt for 16 hrs. The mixture is poured into saturated aqueous sodium bicarbonate, extracted with EtOAc. The organic layer is washed with water, dried over sodium sulfate, filtered and concentrated. The obtained solid is washed with IPE. The residue is poured into EtOAc and saturated aqueous citric acid. The precipitated is collected by filter, washed with EtOAc (10 mL) and dried to give 2.23 g (76% yield) of the title compound as a beige solid.

$^1$H-NMR (400 MHz, CDCl$_3$) delta 9.28 (1H, br s), 8.05 (1H, dd, J=5.2, 1.4 Hz), 7.31-7.22 (1H, m), 7.02-6.94 (2H, m), 6.45 (1H, d, J=2.5 Hz), 6.37 (1H, dd, J=8.4, 2.3 Hz), 5.17 (2H, s), 3.83 (3H, s), 3.76 (3H, m).

MS (ESI) m/z: 286.4 (M+H)$^+$.

Intermediate-123: 5-bromo-2-ethyl-2H-pyrazolo[3,4-b]pyridine

A mixture of 5-bromo-1H-pyrazolo[3,4-b]pyridine (100 mg, 0.505 mmol), iodoethane (0.045 mL, 0.555 mmol) and cesium carbonate (411 mg, 1.26 mmol) in DMF (2 mL) is stirred at rt overnight. The reaction mixture is diluted with EtOAc, washed with water, dried over MgSO$_4$, filtered and concentrated. The residue is purified by column chromatography on silica-gel eluting with 5-25% EtOAc in n-hexane to give 15 mg (13%) of the title compound as a pale yellow solid.

$^1$H-NMR (400 MHz, CDCl$_3$) delta 8.67 (1H, d, J=2.3 Hz), 8.17 (1H, d, J=2.3 Hz), 7.90 (1H, s), 4.51 (2H, q, J=7.3 Hz), 1.66 (3H, t, J=7.3 Hz).

Intermediate-124: 1-(2-chlorophenyl)-1H-imidazo[4,5-b]pyridin-2(3H)-one

<Step-1>: 1-(3-bromopyridin-2-yl)-3-(2-chlorophenyl)urea

A mixture of 1-chloro-2-isocyanatobenzene (107 mg, 0.69 mmol) and 3-bromopyridin-2-amine (100 mg, 0.58 mmol) in THF (3 mL) is stirred at room temperature for 1 day. The mixture is concentrated to give the title compound as a crude. The crude is used next step without purification.

MS (ESI) m/z: 326.3 (M+H)$^+$.

<Step-2>:1-(2-chlorophenyl)-1H-imidazo[4,5-b]pyridin-2(3H)-one

A mixture of 1-(3-bromopyridin-2-yl)-3-(2-chlorophenyl)urea (crude, 0.58 mmol, Step-1 of Intermediate-124), CuI (132 mg, 0.69 mmol), and 1,10-phenanthroline (125 mg, 0.69 mmol) in DMSO (1 mL) is stirred at 100° C. for 1 day. The mixture is diluted with 28% aqueous ammonia solution. The precipitate is collected and washed with diisopropyl ether to give 142 mg (quantitative yield in 2 steps) of the title compound as a brown solid.

MS (ESI) m/z: 246.4 (M+H)$^+$.

Intermediate-125: 1-(2-(trifluoromethyl)phenyl)-1H-imidazo[4,5-b]pyridin-2(3H)-one The title compound (pale yellow solid) is prepared in 56% yield in 2 steps by the similar manner to Step-1 and Step-2 of Intermediate-124 using 1-isocyanato-2-(trifluoromethyl)benzene in place of 1-chloro-2-isocyanatobenzene.

MS (ESI) m/z: 280.4 (M+H)$^+$.

Intermediate-126: 5-(6-methoxy-2-oxo-2,3-dihydro-1H-benzo[d]imidazol-1-yl)-N-methylpicolinamide The title compound (gray solid) is prepared in 27% yield in 4 steps by the similar manner to Step-1, Step-2, Step-3, and Step-4 of Intermediate-102 using 2-iodo-4-methoxy-1-nitrobenzene in place of 2-bromo-4-fluoro-1-nitrobenzene.

$^1$H-NMR (400 MHz, DMSO-d$_6$) delta 10.28 (1H, br s), 8.86 (1H, t, J=1.8 Hz), 8.84 (1H, q, J=5.0 Hz), 8.20 (2H, d, J=2.3 Hz), 7.01 (1H, d, J=8.7 Hz), 6.75-6.65 (2H, m), 3.71 (3H, s), 2.85 (3H, d, J=5.0 Hz).

MS (ESI) m/z: 299.5 (M+H)$^+$.

Intermediate-127: 1-(((1r,4r)-4-aminocyclohexyl)methyl)-3-(6-methylpyridin-3-yl)-1H-benzo[d]imidazol-2(3H)-one The title compound is prepared in 88% yield in 2 steps by the similar manner to Step-2 and Step-3 of Intermediate-113 using Intermediate-13 in place of Intermediate-12.

$^1$H-NMR (400 MHz, DMSO-d$_6$) delta 8.91 (1H, d J=2.3 Hz), 8.39 (1H, dd, J=8.7, 2.3 Hz), 8.03 (2H, br s), 7.82 (1H, d, J=8.2 Hz), 7.34 (1H, d, J=7.8 Hz), 7.20-7.15 (2H, m), 7.11-7.06 (1H, m), 3.74 (2H, d, J=6.9 Hz), 2.91 (1H, br s), 2.70 (3H, s), 1.94-1.92 (2H, m), 1.76-1.73 (3H, m), 1.29-1.12 (4H, m).

MS (ESI) m/z: 337.2 (M+H)$^+$.

Intermediate-128: 1-(((1r,4r)-4-aminocyclohexyl)methyl)-3-(pyridin-4-ylmethyl)-1H-benzo[d]imidazol-2(3H)-one The title compound is prepared in quantitative yield in 2 steps by the similar manner to Step-2 and Step-3 of Intermediate-113 using 1-(pyridin-4-ylmethyl)-1H-benzo[d]imidazol-2(3H)-one in place of Intermediate-12.

Intermediate-129: 1-(((1r,4r)-4-aminocyclohexyl) methyl)-3-(pyridin-2-ylmethyl)-1H-benzo[d]imidazol-2(3H)-one The title compound is prepared in quantitative yield in 2 steps by the similar manner to Step-2 and Step-3 of Intermediate-113 using 1-(pyridin-2-ylmethyl)-1H-benzo[d]imidazol-2(3H)-one in place of Intermediate-12.
MS (ESI) m/z: 337.2 (M+H)+.

Intermediate-130: 1-(((1r,4r)-4-aminocyclohexyl) methyl)-3-(pyridin-3-ylmethyl)-1H-benzo[d]imidazol-2(3H)-one The title compound is prepared in quantitative yield in 2 steps by the similar manner to Step-2 and Step-3 of Intermediate-113 using 1-(pyridin-3-ylmethyl)-1H-benzo[d]imidazol-2(3H)-one in place of Intermediate-12.
MS (ESI) m/z: 337.2 (M+H)+.

Intermediate-131: 1-(((1r,4r)-4-aminocyclohexyl) methyl)-3-(2-oxo-2-phenylethyl)-1H-benzo[d]imidazol-2(3H)-one The title compound (white solid) is prepared in 46% yield in 2 steps by the similar manner to Step-2 and Step-3 of Intermediate-113 using 1-(2-oxo-2-phenylethyl)-1H-benzo[d]imidazol-2(3H)-one in place of Intermediate-12.

Intermediate-132: 5-chloro-N-((1r,4r)-4-((2-oxo-2,3-dihydro-1H-benzo[d]imidazol-1-yl)methyl)cyclohexyl)-2-(trifluoromethyl)nicotinamide The title compound (solid) is prepared in 61% yield in 2 steps by the similar manner to Step-1 and Step-2 of Example 9 using Mesylate-3 in place of Mesylate-1.
1H-NMR (400 MHz, DMSO-$d_6$) delta 10.76 (1H, s), 8.79 (1H, d, J=1.8 Hz), 8.51 (1H, d, J=7.8 Hz), 8.16 (1H, d, J=2.3 Hz), 7.12-7.03 (1H, m), 6.97-6.87 (3H, m), 3.67-3.51 (1H, m), 3.57 (2H, d, J=6.9 Hz), 1.89-1.76 (2H, m), 1.76-1.51 (3H, m), 1.20-1.00 (4H, m).
MS (ESI) m/z: 453.2 (M+H)+.

Intermediate-133: 5-bromo-2-ethyl-3-methyl-2H-pyrazolo[3,4-b]pyridine

To a solution of 5-bromo-3-methyl-1H-pyrazolo[3,4-b]pyridine (100 mg, 0.472 mmol) in THF (2 mL) is added 1.9 M solution of sodium bis(trimethylsilyl)amide in THF (0.37 mL, 0.707 mmol) at 0° C. and stirred for 5 min. To this is added iodoethane (0.057 mL) at 0° C. and stirred for 30 min then at rt for 4 hrs. The reaction is quenched by adding saturated aqueous ammonium chloride solution. The resultant mixture is extracted with EtOAc. The organic phase is washed with brine, dried over MgSO4, filtered and concentrated. The residue is purified by column chromatography on silica-gel eluting with 5-90% EtOAc in n-hexane to give 94 mg (83%) of the title compound as a brown gum.
1H-NMR (400 MHz, CDCl3) delta 8.63 (1H, d, J=2.3 Hz), 8.07 (1H, d, J=2.3 Hz), 4.42 (2H, q, J=7.3 Hz), 2.59 (3H, s), 1.58 (3H, t, J=7.3 Hz).

Intermediate-134: 1-(5-(methylamino)pyrazin-2-yl)-1H-benzo[d]imidazol-2(3H)-one

A mixture of 1-(5-chloropyrazin-2-yl)-1H-benzo[d]imidazol-2(3H)-one (50 mg, 0.20 mmol, Step-1 of Intermediate-57), methanamine hydrochloride (68 mg, 1.01 mmol), DIEA (262 mg, 2.03 mmol) and DBU (154 mg, 1.01 mmol) in NMP (2 mL) is irradiated with micro-wave at 220° C. for 30 min, and the mixture is diluted with saturated aqueous sodium bicarbonate, extracted with EtOAc. The organic layer is concentrated in vacuo. The residue is purified by a strong anion exchange cartridge (ISOLUTE (registered trademark) SCX-2, 1 g/6 mL, Biotage) to give 48 mg (99% yield) of the title compound as a solid.
1H-NMR (400 MHz, CDCl3) delta 8.57 (1H, d, J=1.8 Hz), 7.89 (1H, d, J=1.4 Hz), 7.44-7.41 (1H, m), 7.15-7.08 (3H, m), 4.84 (1H, br s), 3.07 (3H, d, J=5.5 Hz).
MS (ESI) m/z: 256.5 (M+H)+.

Intermediate-135: (S)-1-(6-((tetrahydrofuran-3-yl) amino)pyridin-3-yl)-1H-benzo[d]imidazol-2(3H)-one <Step-1>: 1-(6-fluoropyridin-3-yl)-1H-benzo[d] imidazol-2(3H)-one A mixture of tert-butyl 3-(6-fluoropyridin-3-yl)-2-oxo-2, 3-dihydro-1H-benzo[d]imidazole-1-carboxylate (840 mg, 2.55 mmol, step-1 of Intermediate-15) in 4 M HCl-dioxane (30 mL) is stirred at room temperature for 3 hrs. The mixture is concentrated. The residue is suspended in diisopropyl ether and the precipitate is collected by filtration. This solid is washed with diisopropyl ether, dried in vacuo to give 350 mg (60% yield) of the title compound as a pale yellow solid.
1H-NMR (400 MHz, DMSO-$d_6$) delta 11.10 (1H, br s), 8.47 (1H, dd, J=2.7, 0.9 Hz), 8.22 (1H, ddd, J=8.6, 6.8, 2.7 Hz), 7.41 (1H, dd, J=8.6, 3.2 Hz), 7.11-7.07 (2H, m), 7.06-7.02 (2H, m).
MS (ESI) m/z: 230.2 (M+H)+.

<Step-2>: (S)-1-(6-((tetrahydrofuran-3-yl)amino) pyridin-3-yl)-1H-benzo[d]imidazol-2(3H)-one A mixture of 1-(6-fluoropyridin-3-yl)-1H-benzo[d]imidazol-2(3H)-one (35 mg, 0.15 mmol, Step-1 of Intermediate-135), (S)-tetrahydrofuran-3-amine hydrochloride (189 mg, 1.53 mmol), DIEA (197 mg, 1.53 mmol) and DBU (116 mg, 0.76 mmol) in 2-propanol (1 mL) is stirred at 120° C. overnight. The mixture is diluted with H2O, extracted with EtOAc. The organic layer is dried over sodium sulfate, filtered and concentrated in vacuo. The resultant residue is purified by column chromatography on amine-gel eluting with 50-100% EtOAc in n-hexane to give 22 mg (48% yield) of the title compound.
1H-NMR (400 MHz, CDCl3) delta 8.93 (1H, br s), 8.28 (1H, d, J=2.7 Hz), 7.59 (1H, dd, J=8.6, 2.7 Hz), 7.14-7.06 (3H, m), 6.97 (1H, d, J=7.3 Hz), 6.56 (1H, d, J=9.1 Hz), 4.91 (1H, d, J=7.3 Hz), 4.53-4.49 (1H, m), 4.06-4.00 (2H, m), 3.91 (1H, td, J=8.7, 5.5 Hz), 3.79 (1H, dd, J=9.1, 2.7 Hz), 2.42-2.33 (1H, m), 1.97-1.94 (1H, m).
MS (ESI) m/z: 297.4 (M+H)+.

Intermediate-136: (R)-1-(6-((tetrahydrofuran-3-yl) amino)pyridin-3-yl)-1H-benzo[d]imidazol-2(3H)-one The title compound is prepared in 50% yield (23 mg) by the similar manner to Step-2 of Intermediate-135 using (R)-tetrahydrofuran-3-amine hydrochloride (189 mg, 1.53 mmol) in place of (S)-tetrahydrofuran-3-amine hydrochloride.

¹H-NMR (400 MHz, CDCl₃) delta 9.21 (1H, br s), 8.28 (1H, d, J=2.3 Hz), 7.59 (1H, dd, J=8.7, 2.3 Hz), 7.14-7.06 (3H, m), 6.97 (1H, d, J=7.3 Hz), 6.56 (1H, d, J=8.7 Hz), 4.93 (1H, d, J=7.3 Hz), 4.55-4.46 (1H, m), 4.05-4.01 (2H, m), 3.91 (1H, td, J=8.2, 5.5 Hz), 3.79 (1H, dd, J=9.1, 2.7 Hz), 2.42-2.33 (1H, m), 1.97-1.94 (1H, m).

MS (ESI) m/z: 297.4 (M+H)⁺.

Intermediate-137: 3-(2-oxo-2,3-dihydro-1H-benzo[d]imidazol-1-yl)isonicotinonitrile A mixture of 1H-benzo[d]imidazol-2(3H)-one (50 mg, 0.37 mmol), 3-fluoroisonicotinonitrile (46 mg, 0.37 mmol), and Cs₂CO₃ (364 mg, 1.12 mmol) in DMSO (1 mL) is stirred at rt for 1 day. The mixture is diluted with water and extracted with EtOAc. The organic layer is dried over sodium sulfate, filtered and concentrated. The residue is purified by column chromatography on silica-gel eluting with 0-70% EtOAc in n-hexane to give 24 mg (27% yield) of the title compound as a pale yellow solid.

¹H-NMR (400 MHz, DMSO-d₆) delta 11.44 (1H, br s), 9.04 (1H, s), 8.95 (1H, d, J=5.0 Hz), 8.16 (1H, d, J=5.0 Hz), 7.14 (2H, d, J=4.1 Hz), 7.09-7.01 (1H, m), 6.98 (1H, d, J=7.8 Hz).

MS (ESI) m/z: 237.4 (M+H)⁺.

Intermediate-138: 2-(2-oxo-2,3-dihydro-1H-benzo[d]imidazol-1-yl)nicotinonitrile

The title compound is prepared in 36% yield (32 mg, pale yellow solid) by the similar manner to Intermediate-137 using 2-chloronicotinonitrile (52 mg, 0.37 mmol) in place of 3-fluoroisonicotinonitrile.

¹H-NMR (400 MHz, DMSO-d₆) delta 11.40 (1H, br s), 8.92 (1H, dd, J=5.0, 1.8 Hz), 8.60 (1H, dd, J=7.7, 1.8 Hz), 7.73 (1H, dd, J=7.7, 5.0 Hz), 7.20-7.10 (3H, m), 7.08-7.02 (1H, m).

MS (ESI) m/z: 237.4 (M+H)⁺.

Intermediate-139: 1-(thiazol-4-ylmethyl)-1H-benzo[d]imidazol-2(3H)-one

The title compound (pale yellow solid) is prepared in quantitative yield in 2 steps by the similar manner to Step-1 and Step-2 of Intermediate-1 using 4-(chloromethyl)thiazole in place of 4-(iodomethyl)tetrahydro-2H-pyran.

MS (ESI) m/z: 232.2 (M+H)⁺.

Intermediate-140: 1-(2-(trifluoromethyl)pyridin-3-yl)-1H-benzo[d]imidazol-2(3H)-one <Step-1>: N¹-(2-nitrophenyl)-2-(trifluoromethyl)pyridin-3-amine The title compound is prepared in 95% yield (200 mg, yellow solid) by the similar manner to Step-1 of Intermediate-101 using 1-bromo-2-nitrobenzene (150 mg, 0.74 mmol) and 2-(trifluoromethyl)pyridin-3-amine (120 mg, 0.74 mmol) in place of 2-bromo-1-methyl-3-nitrobenzene and methyl 5-aminopicolinate.

¹H-NMR (400 MHz, CDCl₃) delta 9.58 (1H, br s), 8.52 (1H, d, J=4.6 Hz), 8.26 (1H, dd, J=8.2, 1.4 Hz), 7.91 (1H, d, J=8.7 Hz), 7.52 (1H, dd, J=8.2, 4.6 Hz), 7.46 (1H, td, J=8.2, 1.4 Hz), 7.12 (1H, dd, J=8.7, 0.9 Hz), 6.97 (1H, ddd, J=8.7, 8.2, 1.4 Hz).

MS (ESI) m/z: 284.2 (M+H)⁺.

<Step-2>: N¹-(2-(trifluoromethyl)pyridin-3-yl)benzene-1,2-diamine

The title compound is prepared in quantitative yield (181 mg, brown solid) by the similar manner to Step-2 of Intermediate-88 using N-(2-nitrophenyl)-2-(trifluoromethyl)pyridin-3-amine (200 mg, 0.71 mmol, Step-1 of Intermediate-140) in place of N-(2-nitrophenyl)chroman-3-amine.

¹H-NMR (400 MHz, CDCl₃) delta 8.09 (1H, d, J=4.1 Hz), 7.23 (1H, dd, J=8.2, 4.1 Hz), 7.15 (1H, td, J=7.8, 1.4 Hz), 7.08 (1H, d, J=7.8 Hz), 6.96 (1H, d, J=8.2 Hz), 6.83 (1H, dd, J=6.8, 1.4 Hz), 6.78 (1H, td, J=7.8, 1.4 Hz), 5.82 (1H, br s), 3.80 (2H, br s).

MS (ESI) m/z: 254.1 (M+H)⁺.

<Step-3>: 1-(2-(trifluoromethyl)pyridin-3-yl)-1H-benzo[d]imidazol-2(3H)-one

To a solution of N¹-(2-(trifluoromethyl)pyridin-3-yl)benzene-1,2-diamine (100 mg, 0.40 mmol) in THF is added CDI (192 mg, 1.19 mmol) at room temperature. The mixture is stirred overnight. The mixture is diluted with 2 M aqueous sodium hydroxide solution, extracted with EtOAc. The organic layer is dried over sodium sulfate, filtered and concentrated in vacuo. The resultant residue is purified by column chromatography on silica-gel eluting with 40-100% EtOAc in n-hexane to give 89 mg (81% yield) of the title compound as a brown solid.

¹H-NMR (400 MHz, CDCl₃) delta 9.37 (1H, br s), 8.90 (1H, d, J=4.5 Hz), 7.90 (1H, d, J=7.8 Hz), 7.75 (1H, dd, J=7.8, 4.5 Hz), 7.14 (2H, d, J=4.1 Hz), 7.08-7.01 (1H, m), 6.62 (1H, d, J=7.87 Hz).

MS (ESI) m/z: 280.0 (M+H)⁺.

Intermediate-141: 5-chloro-2-(2-methoxyethyl)nicotinic acid

<Step-1>: benzyl 2-bromo-5-chloronicotinate

A mixture of 2,5-dichloronicotinic acid (500 mg, 2.60 mmol), (bromomethyl)benzene (534 mg, 3.13 mmol), and K₂CO₃ (1.08 g, 7.81 mmol) in MeCN (10 mL) is stirred at rt for 1 day. The mixture is concentrated. The residue is diluted with water and extracted with EtOAc. The organic layer is dried over sodium sulfate, filtered and concentrated. The residue is purified by column chromatography on silica-gel eluting with 0-5% EtOAc in n-hexane to give 409 mg (48% yield) of the title compound as a pale yellow oil.

¹H-NMR (400 MHz, CDCl₃) delta 8.44 (1H, d, J=2.3 Hz), 8.05 (1H, d, J=2.7 Hz), 7.49-7.45 (2H, m), 7.45-7.36 (3H, m), 5.39 (2H, s).

MS (ESI) m/z: 328.25 (M+H)⁺.

<Step-2>: benzyl 5-chloro-2-(2-methoxyethyl)nicotinate

A mixture of benzyl 2-bromo-5-chloronicotinate (100 mg, 0.31 mmol, Step-1 of Intermediate-141), 1-bromo-2-methoxyethane (213 mg, 1.53 mmol), nickel(II) chloride ethylene glycol dimethyl ether complex (7 mg, 0.031 mmol), Ir[dF(CF₃)ppy]₂(dtbbpy)PF₆ (3 mg, 0.0031 mmol), 4,4'-di-tert-butyl-2,2'-bipyridine (8 mg, 0.031 mmol), tris(trimethylsilyl)silane (228 mg, 0.92 mmol), and 2,6-lutidine (66 mg, 0.61 mmol) in DME (4 mL) is stirred under blue LED irradiation for 1 day. The mixture is diluted with water and extracted with EtOAc. The organic layer is dried over sodium sulfate, filtered and concentrated. The residue is purified by column chromatography on silica-gel eluting with 0-10% EtOAc in n-hexane to give 46 mg (49% yield) of the title compound as a pale yellow gum.

$^1$H-NMR (400 MHz, CDCl$_3$) delta 8.61 (1H, d, J=2.3 Hz), 8.14 (1H, d, J=2.3 Hz), 7.48-7.35 (5H, m), 5.36 (2H, s), 3.73 (2H, t, J=6.8 Hz), 3.46 (2H, t, J=6.8 Hz), 3.29 (3H, s).

MS (ESI) m/z: 306.4 (M+H)$^+$.

<Step-3>: 5-chloro-2-(2-methoxyethyl)nicotinic acid

The title compound is prepared in 71% yield (23 mg, pale yellow gum) by the similar manner to Step-4 of Intermediate-2 using benzyl 5-chloro-2-(2-methoxyethyl)nicotinate (46 mg, 0.15 mmol, Step-2 of Intermediate-141) in place of methyl 3-((3-(((1r,4r)-4-(5-chloro-2-methylnicotinamido)cyclohexyl)methyl)-2-oxo-2,3-dihydro-1H-benzo[d]imidazol-1-yl)methyl)benzoate.

MS (ESI) m/z: 216.4 (M+H)$^+$.

Intermediate-142: 5-chloro-2-cyclobutylnicotinic acid

The title compound (pale yellow gum) is prepared in 35% yield in 2 steps by the similar manner to Step-2 and Step-3 of Intermediate-141 using bromocyclobutane in place of 1-bromo-2-methoxyethane.

MS (ESI) m/z:212.4 (M+H)$^+$.

Intermediate-143: 5-chloro-2-(methoxymethyl)nicotinic acid

<Step-1>:5-chloro-2-(hydroxymethyl)nicotinic acid

A mixture of 3-chlorofuro[3,4-b]pyridin-5 (7H)-one (100 mg, 0.59 mmol, Step-1 of Intermediate-143) and 2 M aqueous sodium hydroxide solution (0.60 mL, 1.20 mmol) in MeOH (3 mL) is stirred at 60° C. for 1 hr. The mixture is concentrated, diluted with 2 M hydrochloric acid (0.60 mL, 1.20 mmol) and water to afford pale yellow solid. The precipitate is collected by filtration, washed with water, and dried in vacuo at 50° C. to give 51 mg (46% yield) of the title compound as a yellow solid.

$^1$H-NMR (400 MHz, DMSO-d$_6$) delta 8.50 (1H, d, J=2.3 Hz), 8.20 (1H, d, J=2.3 Hz), 4.81 (2H, s).

MS (ESI) m/z: 188.0 (M+H)$^+$.

<Step-2>: 5-chloro-2-(methoxymethyl)nicotinic acid

To a solution of 5-chloro-2-(hydroxymethyl)nicotinic acid (30 mg, 0.16 mmol) in DMF (0.5 mL) is added sodium hydride (60% dispersion in mineral oil, 18 mg, 0.40 mmol) at 0° C. The mixture is stirred at room temperature for 10 min. Then, to the mixture is added iodomethane (0.025 mL, 0.40 mmol) and stirred for 3 days. The mixture is diluted with saturated aqueous ammonium chloride, extracted with EtOAc, concentrated. To the residue in THF (1 mL) and methanol (1 mL) is added 2 M aqueous sodium hydroxide solution (0.16 mL, 0.32 mmol). The mixture is stirred at 60° C. for 1 hr. The mixture is neutralized with 2 M hydrochloric acid, concentrated. The residue is diluted with water, extracted with EtOAc, concentrated, purified by a strong anion exchange cartridge (ISOLUTE (registered trademark) PE-AX, 1 g/6 mL, Biotage) to give 30 mg (93% yield) of the title compound as a yellow solid.

MS (ESI) m/z: 202.4 (M+H)$^+$.

Intermediate-144: 1-(4,6-dimethylpyridin-3-yl)-1H-benzo[d]imidazol-2(3H)-one

<Step-1>: 4,6-dimethyl-N-(2-nitrophenyl)pyridin-3-amine

The title compound is prepared in quantitative yield (301 mg, orange gum) by the similar manner to Step-1 of Intermediate-101 using 4,6-dimethylpyridin-3-amine (151 mg, 1.24 mmol) and 1-bromo-2-nitrobenzene (300 mg, 1.49 mmol) in place of methyl 5-aminopicolinate and 2-bromo-1-methyl-3-nitrobenzene.

$^1$H-NMR (400 MHz, CDCl$_3$) delta 9.20 (1H, br s), 8.39 (1H, s), 8.23 (1H, d, J=8.7 Hz), 7.34 (1H, dd, J=8.7, 7.3 Hz), 7.14 (1H, s), 6.78 (1H, dd, J=8.7, 7.3 Hz), 6.68 (1H, d, J=8.7 Hz), 2.57 (3H, s), 2.32 (3H, s).

MS (ESI) m/z: 244.5 (M+H)$^+$.

<Step-2>: N$^1$-(4,6-dimethylpyridin-3-yl)benzene-1,2-diamine

The title compound is prepared in 95% yield (252 mg, pale yellow gum) by the similar manner to Step-2 of Intermediate-88 using 4,6-dimethyl-N-(2-nitrophenyl)pyridin-3-amine (306 mg, 1.24 mmol, Step-1 of Intermediate-144) in place of N-(2-nitrophenyl)chroman-3-amine.

$^1$H-NMR (400 MHz, CDCl$_3$) delta 7.93 (1H, s), 6.99-6.92 (1H, m), 6.96 (1H, s), 6.86-6.79 (2H, m), 6.73 (1H, ddd, J=7.8, 7.3, 1.8 Hz), 4.87 (1H, br s), 3.70 (2H, br s), 2.46 (3H, s), 2.20 (3H, s).

MS (ESI) m/z: 214.4 (M+H)$^+$.

<Step-3>: methyl 5-(6-fluoro-2-oxo-2,3-dihydro-1H-benzo[d]imidazol-1-yl)picolinate To a mixture of N$^1$-(4,6-dimethylpyridin-3-yl)benzene-1,2-diamine (252 mg, 1.18 mmol, Step-2 of Intermediate-144), pyridine (0.48 mL, 5.91 mmol) in THF (2 mL) is added triphosgene (438 mg, 1.48 mmol) at 0° C. The mixture is stirred at rt for 1 hr. The mixture is quenched with saturated aqueous sodium bicarbonate and extracted with EtOAc. The organic layer is dried over sodium sulfate, filtered and concentrated. The residue is purified by column chromatography on silica-gel eluting with 0-100% EtOAc in n-hexane to give 246 mg (87% yield) of the title compound as a pale yellow solid.

$^1$H-NMR (400 MHz, DMSO-d$_6$) delta 11.17 (1H, br s), 8.36 (1H, s), 7.37 (1H, s), 7.10-7.02 (2H, m), 6.97 (1H, dd, J=7.8, 1.8 Hz), 6.64 (1H, d, J=7.8 Hz), 2.52 (3H, s), 2.07 (3H, s).

MS (ESI) m/z: 240.5 (M+H)$^+$.

Intermediate-145: 1-(2,3-dimethylpyridin-4-yl)-1H-benzo[d]imidazol-2(3H)-one

The title compound (pale yellow solid) is prepared in 44% yield in 3 steps by the similar manner to Step-1, Step-2, and Step-3 of Intermediate-144 using 2,3-dimethylpyridin-4-amine (243 mg, 1.24 mmol) in place of 4,6-dimethylpyridin-3-amine.

$^1$H-NMR (400 MHz, DMSO-d$_6$) delta 11.21 (1H, br s), 8.43 (1H, d, J=5.5 Hz), 7.26 (1H, d, J=5.0 Hz), 7.13-7.04

(2H, m), 6.98 (1H, dd, J=6.8, 1.8 Hz), 6.68 (1H, d, J=7.8 Hz), 2.56 (3H, s), 2.03 (3H, s).
MS (ESI) m/z: 240.5 (M+H)$^+$.

Intermediate-146: 1-(6-(methylamino)pyridin-3-yl)-1H-benzo[d]imidazol-2(3H)-one

The title compound is prepared in 80% yield (21 mg) by the similar manner to Step-2 of Intermediate-135 (25 mg, 0.11 mmol) using 2 M methanamine in methanol (0.55 mL, 1.09 mmol) in place of (S)-tetrahydrofuran-3-amine hydrochloride.
MS (ESI) m/z: 241.4 (M+H)$^+$.

Intermediate-147: 1-(3-chloropyridin-4-yl)-1H-benzo[d]imidazol-2(3H)-one

<Step-1>: ethyl 2-((3-chloropyridin-4-yl)amino)benzoate

The title compound is prepared in quantitative yield (orange gum) by the similar manner to Step-1 of Intermediate-101 using 3-chloropyridin-4-amine and ethyl 2-iodobenzoate in place of methyl 5-aminopicolinate and 2-bromo-1-methyl-3-nitrobenzene.
$^1$H-NMR (400 MHz, CDCl$_3$) delta 9.89 (1H, br s), 8.48 (1H, s), 8.24 (1H, d, J=5.5 Hz), 8.08 (1H, dd, J=7.8, 1.4 Hz), 7.59-7.48 (2H, m), 7.36 (1H, d, J=5.5 Hz), 7.06 (1H, ddd, J=8.2, 6.9, 1.4 Hz), 4.41 (2H, q, J=7.3 Hz), 1.42 (3H, t, J=7.3 Hz).
MS (ESI) m/z: 277.5 (M+H)$^+$.

<Step-2>: 2-((3-chloropyridin-4-yl)amino)benzoic acid

The title compound is quantitative yield (pale yellow solid) by the similar manner to Step-4 of Intermediate-2 using ethyl 2-((3-chloropyridin-4-yl)amino)benzoate (Step-1 of Intermediate-147) in place of methyl 3-((3-(((1r,4r)-4-(5-chloro-2-methylnicotinamido)cyclohexyl)methyl)-2-oxo-2,3-dihydro-1H-benzo[d]imidazol-1-yl)methyl)benzoate.
MS (ESI) m/z: 249.5 (M+H)$^+$.

<Step-3>: 1-(3-chloropyridin-4-yl)-1H-benzo[d]imidazol-2(3H)-one

The title compound is prepared in 31% yield (pale yellow solid) by the similar manner to Step-2 of Intermediate-98 using 2-((3-chloropyridin-4-yl)amino)benzoic acid (Step-2 of Intermediate-147) in place of 2-((2,3-dihydro-1H-inden-5-yl)amino)nicotinic acid.
$^1$H-NMR (400 MHz, CDCl$_3$) delta 9.40-9.18 (1H, m), 8.69 (1H, s), 8.71 (1H, d, J=5.0 Hz), 7.51 (1H, d, J=5.0 Hz), 7.16 (2H, d, J=4.1 Hz), 7.12-7.06 (1H, m), 6.77 (1H, d, J=7.8 Hz).
MS (ESI) m/z: 246.3 (M+H)$^+$.

Intermediate-148: 1-(2,5-dimethylpyridin-4-yl)-1H-benzo[d]imidazol-2(3H)-one

The title compound (pale yellow gum) is prepared in 46% yield in 3 steps by the similar manner to Step-1, Step-2, and Step-3 of Intermediate-144 using 2,5-dimethylpyridin-4-amine in place of 4,6-dimethylpyridin-3-amine.

$^1$H-NMR (400 MHz, CDCl$_3$) delta 10.15 (1H, br s), 8.60 (1H, s), 7.20 (1H, s), 7.19-7.11 (2H, m), 7.06 (1H, td, J=7.2, 1.4 Hz), 6.74 (1H, d, J=7.8 Hz), 2.62 (3H, s), 2.22 (3H, s).
MS (ESI) m/z: 240.4 (M+H)$^+$.

Intermediate-149: 1-(quinolin-8-yl)-1H-benzo[d]imidazol-2(3H)-one

The title compound (pale yellow solid) is prepared in 25% yield in 3 steps by the similar manner to Step-1, Step-2, and Step-3 of Intermediate-144 using quinolin-8-amine in place of 4,6-dimethylpyridin-3-amine.
$^1$H-NMR (400 MHz, DMSO-d$_6$) delta 11.08 (1H, br s), 8.82 (1H, dd, J=4.1, 1.8 Hz), 8.53 (1H, dd, J=8.2, 1.4 Hz), 8.18 (1H, dd, J=8.2, 1.4 Hz), 7.93 (1H, dd, J=7.3, 1.4 Hz), 7.80 (1H, t, J=7.8 Hz), 7.62 (1H, dd, J=8.2, 4.1 Hz), 7.09 (1H, d, 7.8 Hz), 7.02 (1H, td, J=7.8, 0.9 Hz), 6.87 (1H, td, J=7.8, 0.9 Hz), 6.40 (1H, d, J=7.8 Hz).
MS (ESI) m/z: 262.4 (M+H)$^+$.

Intermediate-150: 1-(isoquinolin-4-yl)-1H-benzo[d]imidazol-2(3H)-one

The title compound (pale yellow solid) is prepared in 25% yield in 3 steps by the similar manner to Step-1, Step-2, and Step-3 of Intermediate-144 using isoquinolin-4-amine in place of 4,6-dimethylpyridin-3-amine.
$^1$H-NMR (400 MHz, DMSO-d$_6$) delta 11.33 (1H, br s), 9.51 (1H, s), 8.64 (1H, s), 8.33 (1H, dd, J=5.9, 2.7 Hz), 7.85-7.76 (2H, m), 7.52 (1H, dd, J=6.9, 2.7 Hz), 7.16 (1H, d, J=7.8 Hz), 7.93 (1H, td, J=7.8, 1.4 Hz), 6.94 (1H, td, J=7.8, 1.4 Hz), 6.57 (1H, d, J=7.8 Hz).
MS (ESI) m/z: 262.4 (M+H)$^+$.

Intermediate-151: N,4-dimethyl-5-(7-methyl-2-oxo-2,3-dihydro-1H-benzo[d]imidazol-1-yl)picolinamide <Step-1>: methyl 4-methyl-5-((2-methyl-6-nitrophenyl)amino)picolinate The title compound is prepared in 34% yield (61 mg, brown gum) by the similar manner to Step-1 of Intermediate-101 using methyl 5-amino-4-methylpicolinate (100 mg, 0.602 mmol) in place of methyl 5-aminopicolinate.
MS (ESI) m/z: 302.4 (M+H)$^+$.

<Step-2>: methyl 5-((2-amino-6-methylphenyl)amino)-4-methylpicolinate

A mixture of methyl 4-methyl-5-((2-methyl-6-nitrophenyl)amino)picolinate (61 mg, 0.20 mmol, Step-1 of Intermediate-151), tin(II) chloride (347 mg, 1.83 mmol) in MeOH (1 mL) is stirred for 1 hr at rt. The mixture is purified by column chromatography on amino-functional silica gel eluting with 100% MeOH to give 60 mg (quantitative yield) of the title compound as a brown solid.
MS (ESI) m/z: 272.5 (M+H)$^+$.

<Step-3>: methyl 4-methyl-5-(7-methyl-2-oxo-2,3-dihydro-1H-benzo[d]imidazol-1-yl)picolinate The title compound is prepared in 59% yield (39 mg, yellow solid) by the similar manner to Step-3 of Intermediate-105 using methyl 5-((2-amino-6-methylphenyl)amino)-4-methylpicolinate (60 mg, 0.22 mmol, Step-2 of Intermediate-151) in place of methyl 5-((2-aminophenyl)amino)-4-methylpicolinate.
MS (ESI) m/z: 298.4 (M+H)$^+$.

<Step-4>: N,4-dimethyl-5-(7-methyl-2-oxo-2,3-dihydro-1H-benzo[d]imidazol-1-yl)picolinamide The title compound is prepared in quantitative yield (43 mg, brown solid) by the similar manner to Intermediate-87 using methyl 4-methyl-5-(7-methyl-2-oxo-2,3-dihydro-1H-benzo[d]imidazol-1-yl)picolinate (39 mg, 0.13 mmol, Step-3 of Intermediate-151) in place of methyl 5-(2-oxo-2,3-dihydro-1H-benzo[d]imidazol-1-yl)picolinate.
MS (ESI) m/z: 297.4 (M+H)$^+$.

Intermediate-152: 2-(oxetan-3-yl)-5-(4,4,5,5-tetramethyl-1,3,2-dioxaborolan-2-yl)-2H-benzo[d][1,2,3]triazole <Step-1>: 5-bromo-2-(oxetan-3-yl)-2H-benzo[d][1,2,3]triazole and 5-bromo-1-(oxetan-3-yl)-1H-benzo[d][1,2,3]triazole A mixture of 5-bromo-1H-benzo[d][1,2,3]triazole (100 mg, 0.505 mmol), 3-iodooxetane (111 mg, 0.606 mmol), cesium carbonate (247 mg, 0.757 mmol) in DMF (1 mL) is stirred overnight at 100° C. The mixture is added with saturated aqueous ammonium chloride. The resultant mixture is extracted with DCM and concentrated. The mixture is purified by column chromatography on silica-gel eluting with 4-66% EtOAc in n-hexane to give 22 mg (17% yield, more polar) of 5-bromo-2-(oxetan-3-yl)-2H-benzo[d][1,2,3]triazole as a pale yellow solid and 61 mg (48% yield, less polar) of 5-bromo-1-(oxetan-3-yl)-1H-benzo[d][1,2,3]triazole as a colorless gum.

5-bromo-2-(oxetan-3-yl)-2H-benzo[d][1,2,3]triazole:
$^1$H-NMR (400 MHz, CDCl$_3$) delta 8.32-8.25 (1H, m), 7.74 (1H, dd, J=8.9, 1.0 Hz), 7.65 (1H, dd, J=8.9, 1.6 Hz), 6.11-5.99 (1H, m), 5.33-5.22 (4H, m).
MS (ESI) m/z: 254.3 (M+H)$^+$.

5-bromo-1-(oxetan-3-yl)-1H-benzo[d][1,2,3]triazole:
$^1$H-NMR (400 MHz, CDCl$_3$) delta 8.11-8.05 (1H, m), 7.78 (1H, d, J=8.7 Hz), 7.54-7.46 (1H, m), 6.10-5.95 (1H, m), 5.31 (2H, t, J=7.0 Hz), 5.19 (2H, t, J=7.0 Hz).

<Step-2>: 2-(oxetan-3-yl)-5-(4,4,5,5-tetramethyl-1,3,2-dioxaborolan-2-yl)-2H-benzo[d][1,2,3]triazole To a mixture of 5-bromo-2-(oxetan-3-yl)-2H-benzo[d][1,2,3]triazole (21 mg, 0.083 mmol, Step-1 of Intermediate-152), 4,4,4',4',5,5,5',5'-octamethyl-2,2'-bi(1,3,2-dioxaborolane) (25 mg, 0.099 mmol), Pd(dppf)Cl$_2$ (7 mg, 0.00827 mmol) and potassium acetate (24 mg, 0.248 mmol) in 1,4-dioxane (1.5 mL) is stirred at 80° C. for 1 hr. The mixture is concentrated. The residue is purified by column chromatography on silica-gel eluting with 0-50% EtOAc in n-hexane to give 17 mg (65% yield) of the title compound as pale yellow oil.
MS (ESI) m/z: 302.4 (M+H)$^+$.

Intermediate-153: 1-(oxetan-3-yl)-5-(4,4,5,5-tetramethyl-1,3,2-dioxaborolan-2-yl)-1H-benzo[d][1,2,3]triazole The title compound is prepared in 69% yield (36 mg, pale yellow solid) by the similar manner to Step-2 of Intermediate-152 using 5-bromo-1-(oxetan-3-yl)-1H-benzo[d][1,2,3]triazole (44 mg, 0.173 mmol, Step-1 of Intermediate-152) in place of 5-bromo-2-(oxetan-3-yl)-2H-benzo[d][1,2,3]triazole.
MS (ESI) m/z: 302.4 (M+H)$^+$.

Intermediate-154: 1-(isoquinolin-5-yl)-1H-benzo[d]imidazol-2(3H)-one

The title compound is prepared in 80% yield in 3 steps by the similar manner to Step-1, Step-2, and Step-3 of Intermediate-140 using isoquinolin-5-amine in place of 2-(trifluoromethyl)pyridin-3-amine.
MS (ESI) m/z: 262.4 (M+H)$^+$.

Intermediate-155: 1-(quinolin-6-yl)-1H-benzo[d]imidazol-2(3H)-one

The title compound is prepared in 84% yield in 3 steps by the similar manner to Step-1, Step-2, and Step-3 of Intermediate-140 using quinolin-6-amine in place of 2-(trifluoromethyl)pyridin-3-amine.
MS (ESI) m/z: 262.3 (M+H)$^+$.

Intermediate-156: 1-(quinolin-5-yl)-1H-benzo[d]imidazol-2(3H)-one

The title compound is prepared in 82% yield in 3 steps by the similar manner to Step-1, Step-2, and Step-3 of Intermediate-140 using quinolin-5-amine in place of 2-(trifluoromethyl)pyridin-3-amine.
MS (ESI) m/z: 262.3 (M+H)$^+$.

Intermediate-157: 1-(quinolin-3-yl)-1H-benzo[d]imidazol-2(3H)-one

The title compound is prepared in quantitative yield in 3 steps by the similar manner to Step-1, Step-2, and Step-3 of Intermediate-140 using quinolin-3-amine in place of 2-(trifluoromethyl)pyridin-3-amine.
MS (ESI) m/z: 262.4 (M+H)$^+$.

Intermediate-158: 1-(1-methyl-H-indazol-4-yl)-1H-benzo[d]imidazol-2(3H)-one

The title compound is prepared in quantitative yield in 3 steps by the similar manner to Step-1, Step-2, and Step-3 of Intermediate-140 using 1-methyl-H-indazol-4-amine in place of 2-(trifluoromethyl)pyridin-3-amine.
$^1$H-NMR (400 MHz, CDCl$_3$) delta 7.56 (1H, d, J=0.9 Hz), 7.73 (1H, d, J=8.7 Hz), 7.54 (1H, dd, J=8.7, 7.3 Hz), 7.23 (1H, d, J=7.3 Hz), 7.08 (1H, td, J=7.8, 0.9 Hz), 7.04 (1H, dd, J=7.8, 0.9 Hz), 6.95 (1H, dd, J=7.8, 1.8 Hz), 6.78 (1H, d, J=7.8 Hz), 4.09 (3H, s). A signal due to NH is not observed.
MS (ESI) m/z: 265.4 (M+H)$^+$.

Intermediate-159: 5-chloro-2-(2,2-difluoroethyl)nicotinic acid

The title compound (pale yellow gum) is prepared in 47% yield in 2 steps by the similar manner to Step-2 and Step-3 of Intermediate-141 using 1,1-difluoro-2-iodoethane in place of 1-bromo-2-methoxyethane.
MS (ESI) m/z: 222.3 (M+H)$^+$.

Intermediate-160: 1-(imidazo[1,2-a]pyridin-5-yl)-1H-benzo[d]imidazol-2(3H)-one

The title compound (pale brown solid) is prepared in 36% yield in 3 steps by the similar manner to Step-1, Step-2, and Step-3 of Intermediate-144 using imidazo[1,2-a]pyridin-5-amine in place of 4,6-dimethylpyridin-3-amine.
MS (ESI) m/z: 251.3 (M+H)$^+$.

Intermediate-161: 1-(quinolin-6-yl)-1H-imidazo[4,5-b]pyridin-2(3H)-one

The title compound is prepared in 63% yield in 3 steps by the similar manner to Step-1, Step-2, and Step-3 of Intermediate-112 using 3-bromo-2-nitropyridine and quinolin-6-amine in place of 4-(pyridin-4-yloxy)aniline and 1-bromo-2-nitrobenzene.
$^1$H-NMR (400 MHz, DMSO-d$_6$) delta 11.97 (1H, br s), 8.97 (1H, dd, J=4.1, 1.8 Hz), 8.48 (1H, dd, J=8.7, 1.4 Hz), 8.22 (1H, d, J=2.3 Hz), 8.18 (1H, d, J=9.1 Hz), 8.04 (1H, dd, J=5.0, 1.4 Hz), 7.97 (1H, dd, J=8.7, 2.3 Hz), 7.62 (1H, dd, J=8.2, 1.4 Hz), 7.49 (1H, dd, J=7.8, 1.4 Hz), 7.07 (1H, dd, J=7.8, 5.0 Hz).
MS (ESI) m/z: 263.3 (M+H)$^+$.

Intermediate-162: 1-(quinolin-3-yl)-1H-imidazo[4,5-b]pyridin-2(3H)-one

The title compound is prepared in 63% yield in 3 steps by the similar manner to Step-1, Step-2, and Step-3 of Intermediate-112 using 3-bromo-2-nitropyridine and quinolin-3-amine in place of 4-(pyridin-4-yloxy)aniline and 1-bromo-2-nitrobenzene.
$^1$H-NMR (400 MHz, DMSO-d$_6$) delta 12.00 (1H, br s), 9.12 (1H, d, J=2.3 Hz), 8.63 (1H, d, J=2.7 Hz), 8.10 (2H, t, J=6.8 Hz), 8.05 (1H, dd, J=5.5, 1.4 Hz), 7.85 (1H, ddd, J=8.3, 6.8, 1.4 Hz), 7.71 (1H, ddd, J=8.3, 7.8, 0.9 Hz), 7.53 (1H, dd, J=8.3, 1.4 Hz), 7.08 (1H, dd, J=8.3, 5.5 Hz).
MS (ESI) m/z: 263.3 (M+H)$^+$.

Intermediate-163: 3-(quinolin-6-yl)-1H-imidazo[4,5-b]pyridin-2(3H)-one

The title compound is prepared in quantitative yield in 2 steps by the similar manner to Step-1 and Step-2 of Intermediate-99 using quinolin-6-amine in place of 4-methoxyaniline.
$^1$H-NMR (400 MHz, DMSO-d$_6$) delta 9.26 (1H, d, J=2.7 Hz), 8.71 (1H, d, J=2.3 Hz), 8.10 (1H, dd, J=5.1, 1.4 Hz), 8.08 (1H, d, J=4.1 Hz), 7.94 (1H, dd, J=5.1, 1.4 Hz), 7.82 (1H, ddd, J=8.2, 6.9, 1.4 Hz), 7.68 (1H, ddd, J=8.2, 7.3, 1.4 Hz), 7.41 (1H, dd, J=7.3, 1.4 Hz), 7.11 (1H, dd, J=7.3, 5.5 Hz). A signal due to NH is not observed.
MS (ESI) m/z: 263.3 (M+H)$^+$.

Intermediate-164: 1-(2-chlorophenyl)-1H-imidazo[4,5-c]pyridin-2(3H)-one

The title compound (pale yellow solid) is prepared in 48% yield in 2 steps by the similar manner to Step-1 and Step-2 of Intermediate-98 using 2-chloroaniline and 4-chloronicotinic acid in place of 2,3-dihydro-1H-inden-5-amine and 2-chloronicotinic acid.
$^1$H-NMR (400 MHz, CDCl$_3$) delta 9.33 (1H br s), 8.44 (1H, s), 8.31 (1H, d, J=5.0 Hz), 7.69-7.62 (1H, m), 7.55-7.50 (3H, m), 6.71 (1H, dd, J=5.5, 0.9 Hz).
MS (ESI) m/z: 246.3 (M+H)$^+$.

Intermediate-165: 5-chloro-2-(difluoromethyl)-N-((1r,4r)-4-((2-oxo-2,3-dihydro-1H-benzo[d]imidazol-1-yl)methyl)cyclohexyl)nicotinamide The title compound (pale yellow solid) is prepared in 86% yield in 2 steps by the similar manner to Step-1 and Step-2 of Example 9 using Mesylate-4 in place of Mesylate-1.

$^1$H-NMR (400 MHz, DMSO-d$_6$) delta 10.81 (1H, s), 8.82 (1H, d, J=2.3 Hz), 8.63 (1H, d, J=7.8 Hz), 8.14 (1H, s), 7.30-6.90 (4H, m), 3.75-3.61 (3H, m), 1.95-1.85 (2H, m), 2.82-2.70 (1H, m), 2.70-2.60 (2H, m), 1.20-1.10 (4H, m). A signal due to NH is not observed.
MS (ESI) m/z: 435.3 (M+H)$^+$.

Intermediate-166: 1-(quinolin-4-yl)-1H-benzo[d]imidazol-2(3H)-one

The title compound is prepared in 98% yield in 3 steps by the similar manner to Step-1, Step-2, and Step-3 of Intermediate-140 using quinolin-4-amine in place of 2-(trifluoromethyl)pyridin-3-amine.
$^1$H-NMR (400 MHz, DMSO-d$_6$) delta 9.10 (1H, d, J=4.6 Hz), 8.19 (1H, d, J=8.2 Hz), 7.86 (1H, ddd, J=8.2, 5.9, 1.8 Hz), 7.71 (1H, d, J=4.6 Hz), 7.65-7.60 (2H, m), 7.18-7.07 (2H, m), 6.96 (1H, td, J=7.8, 1.4 Hz), 6.65 (1H, d, J=7.8 Hz). A signal due to NH is not observed.
MS (ESI) m/z: 262.3 (M+H)$^+$.

Intermediate-167: 1-(isoquinolin-6-yl)-1H-benzo[d]imidazol-2(3H)-one

The title compound is prepared in 20% yield in 3 steps by the similar manner to Step-1, Step-2, and Step-3 of Intermediate-140 using isoquinolin-6-amine in place of 2-(trifluoromethyl)pyridin-3-amine.
MS (ESI) m/z: 262.3 (M+H)$^+$.

Intermediate-168: 1-(4-(hydroxymethyl)phenyl)-1H-benzo[d]imidazol-2(3H)-one

The title compound (off-white solid) is prepared in 13% yield in 2 steps by the similar manner to Step-1 and Step-2 of Intermediate-4 using (4-(hydroxymethyl)phenyl)boronic acid in place of (4-fluorophenyl)boronic acid.
MS (ESI) m/z: 241.0 (M+H)$^+$.

Intermediate-169: 3-(p-tolyl)-1H-imidazo[4,5-b]pyridin-2(3H)-one

The title compound (pale yellow solid) is prepared in 78% yield in 2 steps by the similar manner to Step-1 and Step-2 of Intermediate-98 using p-toluidine in place of 2,3-dihydro-1H-inden-5-amine.
$^1$H-NMR (400 MHz, DMSO-d$_6$) delta 11.35 (1H, s), 7.92 (1H, dd, J=5.0, 1.4 Hz), 7.52 (2H, d, J=8.2 Hz), 7.39 (1H, dd, J=7.8, 1.4 Hz), 7.33 (2H, d, J=8.2 Hz), 7.08 (1H, dd, J=7.8, 5.0 Hz), 2.38 (3H, s).
MS (ESI) m/z: 226.3 (M+H)$^+$.

Intermediate-170: 1-(1,8-naphthyridin-3-yl)-1H-benzo[d]imidazol-2(3H)-one

<Step-1>: N-(2-nitrophenyl)-1,8-naphthyridin-3-amine

The title compound is prepared in 8% yield (20 mg) by the similar manner to Step-1 of Intermediate-112 using 1,8-naphthyridin-3-amine (144 mg, 0.99 mmol) in place of 4-(pyridin-4-yloxy)aniline.
MS (ESI) m/z: 267.3 (M+H)$^+$.

<Step-2>: N$^1$-(1,8-naphthyridin-3-yl)benzene-1,2-diamine

The title compound is prepared in quantitative yield (44 mg) by the similar manner to Step-2 of Intermediate-88 using methyl N-(2-nitrophenyl)-1,8-naphthyridin-3-amine (20 mg, 0.075 mmol, Step-1 of Intermediate-170) in place of N-(2-nitrophenyl)chroman-3-amine.
MS (ESI) m/z: 237.3 (M+H)+.

<Step-3>: methyl 4-methyl-5-(2-oxo-2,3-dihydro-1H-benzo[d]imidazol-1-yl)picolinate To a solution of $N^1$-(1,8-naphthyridin-3-yl)benzene-1,2-diamine (50 mg, 0.21 mmol) in THF (2 mL) is added di(1H-1,2,4-triazol-1-yl)methanone (104 mg, 0.64 mmol) at room temperature. The mixture is stirred overnight. To the mixture is added saturated aqueous sodium bicarbonate, extracted with EtOAc, dried over sodium sulfate, filtered and concentrated. The residue is purified by column chromatography on silica-gel eluting with 50-90% EtOAc in n-hexane to give 20 mg (36% yield) of the title compound.
MS (ESI) m/z: 266.3 (M+H)+.

Intermediate-171: 1-(quinazolin-6-yl)-1H-benzo[d]imidazol-2(3H)-one

The title compound is prepared in 17% yield in 3 steps by the similar manner to Step-1, Step-2, and Step-3 of Intermediate-170 using quinazolin-6-amine in place of 1,8-naphthyridin-3-amine.
$^1$H-NMR (400 MHz, DMSO-$d_6$) delta 9.28 (1H, d, J=2.8 Hz), 9.12 (1H, d, J=2.8 Hz), 8.71 (1H, d, J=2.8 Hz), 8.57 (1H, dd, J=8.2, 1.8 Hz), 7.71 (1H, d, J=7.8 Hz), 7.21 (1H, d, J=7.8 Hz), 7.11 (2H, d, J=4.1 Hz), 7.07-7.02 (1H, m). A signal due to NH is not observed.
MS (ESI) m/z: 263.3 (M+H)+.

Intermediate-172: 1-(quinolin-7-yl)-1H-benzo[d]imidazol-2(3H)-one

The title compound is prepared in 87% yield in 3 steps by the similar manner to Step-1, Step-2, and Step-3 of Intermediate-140 using quinolin-7-amine in place of 2-(trifluoromethyl)pyridin-3-amine.
$^1$H-NMR (400 MHz, DMSO-$d_6$) delta 9.73 (1H, br s), 8.89 (1H, dd, J=4.6, 1.4 Hz), 8.32 (1H, d, J=2.3 Hz), 8.25 (1H, dd, J=8.2, 0.9 Hz), 8.01 (1H, d, J=8.7 Hz), 7.86 (1H, dd, J=8.7, 2.3 Hz), 7.49 (1H, dd, J=8.2, 4.1 Hz), 7.24 (1H, dd, J=7.3, 1.4 Hz), 7.18-7.06 (3H, m).
MS (ESI) m/z: 262.0 (M+H)+.

Intermediate-173: 1-(isoquinolin-7-yl)-1H-benzo[d]imidazol-2(3H)-one

The title compound is prepared in 30% yield in 3 steps by the similar manner to Step-1, Step-2, and Step-3 of Intermediate-140 using isoquinolin-7-amine in place of 2-(trifluoromethyl)pyridin-3-amine.
$^1$H-NMR (400 MHz, DMSO-$d_6$) delta 9.40 (1H, s), 8.55 (1H, d, J=5.5 Hz), 8.32 (1H, d, J=1.8 Hz), 8.13 (1H, d, J=8.7 Hz), 7.96 (1H, dd, J=8.7, 1.8 Hz), 7.90 (1H, d, J=5.5 Hz), 7.14 (1H, d, J=7.8 Hz), 7.12-7.08 (2H, m), 7.05-7.00 (1H, m). A signal due to NH is not observed.
MS (ESI) m/z: 262.0 (M+H)+.

Intermediate-174: 3-(4-fluoro-3-methoxyphenyl)-1H-imidazo[4,5-b]pyridin-2(3H)-one The title compound (pale yellow solid) is prepared in quantitative yield in 2 steps by the similar manner to Step-1 and Step-2 of Intermediate-99 using 4-fluoro-3-methoxyaniline in place of 4-methoxyaniline.
$^1$H-NMR (400 MHz, DMSO-$d_6$) delta 11.40 (1H, br s), 7.94 (1H, dd, J=5.5, 1.4 Hz), 7.47 (1H, dd, J=7.7, 2.3 Hz), 7.42-7.33 (2H, m), 7.26-7.18 (1H, m), 7.09 (1H, dd, J=7.7, 5.5 Hz), 3.84 (3H, s).
MS (ESI) m/z: 260.3 (M+H)+.

Intermediate-175: 3-(4-acetylphenyl)-1H-imidazo[4,5-b]pyridin-2(3H)-one

The title compound (pale yellow solid) is prepared in 83% yield in 2 steps by the similar manner to Step-1 and Step-2 of Intermediate-99 using 1-(4-aminophenyl)ethanone in place of 4-methoxyaniline.
$^1$H-NMR (400 MHz, DMSO-$d_6$) delta 11.53 (1H, br s), 8.12 (2H, d, J=8.9 Hz), 7.98 (1H, dd, J=5.0, 1.4 Hz), 7.95 (2H, d, J=8.9 Hz), 7.44 (1H, dd, J=7.8, 1.4 Hz), 7.14 (1H, dd, J=7.8, 5.0 Hz), 2.63 (3H, s).
MS (ESI) m/z: 254.2 (M+H)+.

Intermediate-176: 3-(3-(cyclopentyloxy)-4-methoxyphenyl)-1H-imidazo[4,5-b]pyridin-2(3H)-one The title compound (pale yellow solid) is prepared in 8% yield in 2 steps by the similar manner to Step-1 and Step-2 of Intermediate-98 using 3-(cyclopentyloxy)-4-methoxyaniline in place of 2,3-dihydro-1H-inden-5-amine.
$^1$H-NMR (400 MHz, DMSO-$d_6$) delta 11.30 (1H, s), 7.92 (1H, dd, J=5.5, 1.4 Hz), 7.37 (1H, dd, J=7.8, 1.4 Hz), 7.19 (1H, d, J=2.3 Hz), 7.13 (1H, dd, J=7.8, 2.7 Hz), 7.09-7.04 (2H, m), 4.75 (1H, br s), 3.80 (3H, s), 2.92-2.80 (2H, m), 2.80-2.68 (4H, m), 2.62-2.52 (2H, m).
MS (ESI) m/z: 326.3 (M+H)+.

Intermediate-177: 3-(4-ethoxyphenyl)-1H-imidazo[4,5-b]pyridin-2(3H)-one

The title compound (pale yellow solid) is prepared in 16% yield in 2 steps by the similar manner to Step-1 and Step-2 of Intermediate-98 using 4-ethoxyaniline in place of 2,3-dihydro-1H-inden-5-amine.
$^1$H-NMR (400 MHz, DMSO-$d_6$) delta 11.30 (1H, br s), 7.91 (1H, dd, J=5.5, 1.4 Hz), 7.50 (2H, d, J=9.2 Hz), 7.37 (1H, dd, J=7.3, 1.4 Hz), 7.10-7.03 (3H, m), 4.08 (2H, q, J=6.9 Hz), 1.36 (3H, t, J=6.9 Hz).
MS (ESI) m/z:256.3 (M+H)+.

Intermediate-178: 5-(3-(((1r,4r)-4-(5-chloro-2-methylnicotinamido)cyclohexyl)methyl)-2-oxo-2,3-dihydro-1H-benzo[d]imidazol-1-yl)-1-methyl-1H-indole-2-carboxylic acid <Step-1>: ethyl 1-methyl-5-(2-oxo-2,3-dihydro-1H-benzo[d]imidazol-1-yl)-1H-indole-2-carboxylate The title compound (black solid) is prepared in 26% yield in 3 steps by the similar manner to Step-1, Step-2, and Step-3 of Intermediate-179 using ethyl 6-amino-1-methyl-1H-indole-2-carboxylate (336 mg, 1.54 mmol) in place of quinoxalin-6-amine.
MS (ESI) m/z: 336.4 (M+H)+.

<Step-2>: 5-(3-(((1r,4r)-4-(5-chloro-2-methylnicotinamido)cyclohexyl)methyl)-2-oxo-2,3-dihydro-1H-benzo[d]imidazol-1-yl)-1-methyl-1H-indole-2-carboxylicacid The title compound (off-white solid) is prepared in quantitative yield in 2 steps by the similar manner to Step-3 and Step-4 of Intermediate-3 using ethyl 1-methyl-5-(2-oxo-2,3-dihydro-1H-benzo[d]imidazol-1-yl)-1H-indole-2-carboxylate (93 mg, 0.28 mmol, Step-1 of Intermediate-178) in place of methyl 2-((2-oxo-2,3-dihydro-1H-benzo[d]imidazol-1-yl)methyl)benzoate.

$^1$H-NMR (400 MHz, DMSO-$d_6$) delta 8.53 (1H, d, J=2.7 Hz), 8.40 (1H, d, J=8.2 Hz), 7.82 (1H, d, J=1.8 Hz), 7.79 (1H, d, J=2.7 Hz), 7.75 (1H, d, J=9.1 Hz), 7.43 (1H, dd, J=9.1, 1.8 Hz), 7.33 (1H, d, J=8.2 Hz), 7.33 (1H, d, J=8.2 Hz), 7.31 (1H, s), 7.13 (1H, td, J=7.8, 0.9 Hz), 7.04 (1H, td, J=7.8, 0.9 Hz), 6.94 (1H, d, J=7.3 Hz), 4.09 (3H, s), 3.79 (2H, d, J=6.9 Hz), 3.71 (1H, br s), 2.47 (3H, s), 1.95-1.73 (5H, m), 1.28-1.17 (4H, m).

MS (ESI) m/z: 572.0 (M+H)$^+$.

Intermediate-179: 1-(quinoxalin-6-yl)-1H-benzo[d]imidazol-2(3H)-one

<Step-1>: N-(2-nitrophenyl)quinoxalin-6-amine

The title compound is prepared in 93% yield (244 mg, red solid) by the similar manner to Step-1 of Intermediate-101 using 1-bromo-2-nitrobenzene (200 mg, 0.99 mmol) and quinoxalin-6-amine (144 mg, 0.99 mmol) in place of 2-bromo-1-methyl-3-nitrobenzene and methyl 5-aminopicolinate.

MS (ESI) m/z: 267.4 (M+H)$^+$.

<Step-2>: N$^1$-(quinoxalin-6-yl)benzene-1,2-diamine

The title compound is prepared in quantitative yield (230 mg, black solid) by the similar manner to Step-2 of Intermediate-88 using N-(2-nitrophenyl)quinoxalin-6-amine (244 mg, 0.92 mmol, Step-1 of Intermediate-179) in place of N-(2-nitrophenyl)chroman-3-amine.

MS (ESI) m/z: 239.3 (M+H)$^+$.

<Step-3>:1-(quinoxalin-6-yl)-1H-benzo[d]imidazol-2(3H)-one

The title compound is prepared in quantitative yield (255 mg, off-white solid) by the similar manner to Step-3 of Intermediate-20 using N$^1$ (quinoxalin-6-yl)benzene-1,2-diamine (230 mg, 0.97 mmol, Step-2 of Intermediate-179) in place of N$^1$-(2,4-difluorophenyl)benzene-1,2-diamine.

$^1$H-NMR (400 MHz, DMSO-$d_6$) delta 11.34 (1H, br s), 9.03 (1H, d, J=4.1 Hz), 9.02 (1H, d, J=4.1 Hz), 8.28 (1H, d, J=9.1 Hz), 8.27 (1H, d, J=2.3 Hz), 8.11 (1H, dd, J=9.1, 2.3 Hz), 7.22 (1H, d, J=7.8 Hz), 7.15-7.12 (2H, m), 7.09-7.04 (1H, m).

MS (ESI) m/z: 263.0 (M+H)$^+$.

Intermediate-180: 5-(3-(((1r,4r)-4-(5-chloro-2-(trifluoromethyl)nicotinamido)cyclohexyl)methyl)-2-oxo-2,3-dihydro-1H-benzo[d]imidazol-1-yl)picolinic acid The title compound is prepared in 90% yield (solid) by the similar manner to Step-4 of Intermediate-36 using Mesylate-3 in place of Mesylate-1.

$^1$H-NMR (400 MHz, DMSO-$d_6$) delta 8.98 (1H, br), 8.87 (1H, d, J=1.8 Hz), 8.58 (1H, d, J=7.8 Hz), 8.30-8.18 (3H, m), 7.39 (1H, d, J=7.8 Hz), 7.31-7.17 (2H, m), 7.12 (1H, t, J=7.5 Hz), 3.80 (2H, d, J=6.4 Hz), 3.75-3.60 (1H, br), 2.00-1.60 (5H, m), 1.33-1.05 (4H, m).

MS (ESI) m/z: 573.9 (M+H)$^+$.

Intermediate-181: 3-(2,4-dichlorophenyl)-1H-imidazo[4,5-b]pyridin-2(3H)-one

The title compound (pale yellow solid) is prepared in 11% yield in 2 steps by the similar manner to Step-1 and Step-2 of Intermediate-98 using 2,4-dichloroaniline in place of 2,3-dihydro-1H-inden-5-amine.

MS (ESI) m/z: 280.2 (M+H)$^+$.

Intermediate-182: 1-(imidazo[1,5-a]pyridin-7-yl)-1H-benzo[d]imidazol-2(3H)-one

The title compound is prepared in quantitative yield (138 mg, green solid) by the similar manner to Step-2 of Intermediate-95 using 7-bromoimidazo[1,5-a]pyridine (98 mg, 0.50 mmol) in place of 5-bromo-2,3-dimethyl-2H-indazole.

MS (ESI) m/z: 251.3 (M+H)$^+$.

Intermediate-183: 1-(6-(2-methoxyethoxy)pyridin-3-yl)-1H-benzo[d]imidazol-2(3H)-one To a mixture of 1-(6-fluoropyridin-3-yl)-1H-benzo[d]imidazol-2(3H)-one (60 mg, 0.26 mmol, Step-1 of intermediate-135), 2-methoxyethanol (60 mg. 0.79 mmol) in DMF (2 mL) is added potassium tert-butoxide (88 mg, 0.79 mmol) at room temperature. The mixture is stirred at 80° C. overnight. The mixture is diluted with H$_2$O, extracted with EtOAc, dried over sodium sulfate, filtered and concentrated. The residue is purified by column chromatography on silica-gel eluting with 40-100% EtOAc in n-hexane to give 37 mg (50% yield) of the title compound.

MS (ESI) m/z: 286.0 (M+H)$^+$.

Intermediate-184: 1-(2-methyl-2H-indazol-4-yl)-1H-benzo[d]imidazol-2(3H)-one

The title compound is prepared in 80% yield in 3 steps by the similar manner to Step-1, Step-2, and Step-3 of Intermediate-140 using 2-methyl-2H-indazol-4-amine (109 mg, 0.74 mmol) in place of 2-(trifluoromethyl)pyridin-3-amine.

$^1$H-NMR (400 MHz, DMSO-$d_6$) delta 8.13 (1H, s), 7.67 (1H, dd, J=8.7, 0.9 Hz), 7.36 (1H, dd, J=8.7, 7.3 Hz), 7.12 (1H, 1H, d, J=7.6 Hz), 7.09-7.02 (2H, m), 6.95 (1H, ddd, J=8.7, 7.3, 1.4 Hz), 6.77 (1H, d, J=7.6 Hz), 4.12 (3H, s). A signal due to NH is not observed.

MS (ESI) m/z: 265.4 (M+H)$^+$.

Intermediate-185: 1-(1-((2-(trimethylsilyl)ethoxy)methyl)-1H-pyrrolo[2,3-b]pyridin-5-yl)-1H-benzo[d]imidazol-2(3H)-one The title compound is prepared in 80% yield in 3 steps by the similar manner to Step-1, Step-2, and Step-3 of Intermediate-179 using 1-((2-(trimethylsilyl)ethoxy)methyl)-1H-pyrrolo[2,3-b]pyridin-5-amine in place of quinoxalin-6-amine.

$^1$H-NMR (400 MHz, CDCl$_3$) delta 9.23 (1H, br s), 8.48 (1H, d, J=2.3 Hz), 8.07 (1H, d, J=2.3 Hz), 7.47 (1H, d, J=2.3 Hz), 7.16-7.04 (3H, m), 6.96 (1H, d, J=7.8 Hz), 6.60 (1H, d, J=3.7 Hz), 5.73 (2H, s), 3.60 (2H, t, J=8.2 Hz), 0.95 (2H, t, J=8.2 Hz), −0.03 (9H, s).

MS (ESI) m/z: 381.3 (M+H)$^+$.

Intermediate-186: 1-(3-methyl-1-((2-(trimethylsilyl) ethoxy)methyl)-1H-pyrrolo[2,3-b]pyridin-5-yl)-1H-benzo[d]imidazol-2(3H)-one The title compound is prepared in 85% yield in 3 steps by the similar manner to Step-1, Step-2, and Step-3 of Intermediate-179 using 3-methyl-1-((2-(trimethylsilyl)ethoxy) methyl)-1H-pyrrolo[2,3-b]pyridin-5-amine in place of quinoxalin-6-amine.

$^1$H-NMR (400 MHz, CDCl$_3$) delta 9.63 (1H, br s), 8.44 (1H, d, J=2.3 Hz), 8.01 (1H, d, J=2.3 Hz), 7.23 (1H, d, J=0.9 Hz), 7.17-7.04 (3H, m), 6.94 (1H, d, J=7.8 Hz), 5.67 (2H, s), 3.57 (2H, t, J=8.2 Hz), 2.33 (3H, d, J=0.9 Hz), 0.95 (2H, t, J=8.2 Hz), 0.03 (9H, s).

MS (ESI) m/z: 395.3 (M+H)$^+$.

Intermediate-187: 3-(3-methyl-1-((2-(trimethylsilyl) ethoxy)methyl)-1H-pyrrolo[2,3-b]pyridin-5-yl)-1H-imidazo[4,5-b]pyridin-2(3H)-one <Step-1>: 3-methyl-N-(3-nitropyridin-2-yl)-1-((2-(trimethylsilyl)ethoxy)methyl)-1H-pyrrolo[2,3-b]pyridin-5-amine The title compound is prepared in 68% yield (175 mg) by the similar manner to Step-1 of Intermediate-101 using 3-methyl-1-((2-(trimethylsilyl)ethoxy)methyl)-1H-pyrrolo[2,3-b]pyridin-5-amine (190 mg, 1.11 mmol, Step-2 of Intermediate-229) and 2-bromo-3-nitropyridine (132 mg, 0.65 mmol) in place of 2-bromo-1-methyl-3-nitrobenzene and methyl 5-aminopicolinate.

MS (ESI) m/z: 400.3 (M+H)$^+$.

<Step-2>: N$^2$-(3-methyl-1-((2-(trimethylsilyl) ethoxy)methyl)-1H-pyrrolo[2,3-b]pyridin-5-yl)pyridine-2,3-diamine The title compound is prepared in quantitative yield (204 mg) by the similar manner to Step-2 of Intermediate-88 using 3-methyl-N-(3-nitropyridin-2-yl)-1-((2-(trimethylsilyl)ethoxy)methyl)-1H-pyrrolo[2,3-b]pyridin-5-amine (175 mg, 0.79 mmol, Step-1 of Intermediate-187) in place of N-(2-nitrophenyl)chroman-3-amine.

MS (ESI) m/z: 370.0 (M+H)$^+$.

<Step-3>: 3-(3-methyl-1-((2-(trimethylsilyl)ethoxy) methyl)-1H-pyrrolo[2,3-b]pyridin-5-yl)-1H-imidazo [4,5-b]pyridin-2(3H)-one The title compound is prepared in quantitative yield (188 mg) by the similar manner to Step-3 of Intermediate-170 using N$^2$-(3-methyl-1-((2-(trimethylsilyl)ethoxy)methyl)-1H-pyrrolo[2,3-b]pyridin-5-yl)pyridine-2,3-diamine (176 mg, 0.48 mmol, Step-2 of Intermediate-187) in place of N$^1$-(1,8-naphthyridin-3-yl)benzene-1,2-diamine.

$^1$H-NMR (400 MHz, CDCl$_3$) delta 10.28 (1H, br s), 8.55 (1H, d J=2.3 Hz), 8.09 (1H, d, J=2.3 Hz), 8.06 (1H, dd, J=5.0, 1.4 Hz), 7.37 (1H, dd, J=7.8, 1.4 Hz), 7.21 (1H, d, J=1.4 Hz), 7.06 (1H, dd, J=7.8, 5.0 Hz), 5.65 (2H, s), 3.56 (2H, dd, J=8.2, 7.8 Hz), 2.34 (3H, d, J=1.4 Hz), 0.94 (2H, dd, J=8.2, 7.8 Hz), −0.02 (9H, s).

MS (ESI) m/z: 395.9 (M+H)$^+$.

Intermediate-188: (R)-1-(6-((tetrahydrofuran-3-yl) oxy)pyridin-3-yl)-1H-benzo[d]imidazol-2(3H)-one The title compound is prepared in 85% yield (55 mg) by the similar manner to Intermediate-24 using (R)-tetrahydrofuran-3-ol (38 mg, 0.44 mmol) in place of 2-((tetrahydro-2H-pyran-2-yl)oxy)ethanol.

MS (ESI) m/z: 298.3 (M+H)$^+$.

Intermediate-189: 1-(6-(2-hydroxy-2-methylpropoxy)pyridin-3-yl)-1H-benzo[d]imidazol-2(3H)-one The title compound is prepared in 69% yield (45 mg) by the similar manner to Intermediate-24 using 2-methylpropane-1,2-diol (39 mg, 0.44 mmol) in place of 2-((tetrahydro-2H-pyran-2-yl)oxy)ethanol.

MS (ESI) m/z: 300.3 (M+H)$^+$.

Intermediate-190: (S)-1-(6-((tetrahydrofuran-3-yl) oxy)pyridin-3-yl)-1H-benzo[d]imidazol-2(3H)-one The title compound is prepared in 80% yield (52 mg) by the similar manner to Intermediate-24 using (S)-tetrahydrofuran-3-ol (38 mg, 0.44 mmol) in place of 2-((tetrahydro-2H-pyran-2-yl)oxy)ethanol.

MS (ESI) m/z: 298.2 (M+H)$^+$.

Intermediate-191: 5-chloro-2-(difluoromethyl)-N-((1r,4r)-4-((3-(6-fluoropyridin-3-yl)-2-oxo-2,3-dihydro-1H-benzo[d]imidazol-1-yl)methyl)cyclohexyl)nicotinamide The title compound is prepared in 96% yield (solid) by the similar manner to Intermediate-54 using Mesylate-4 in place of Mesylate-1.

$^1$H-NMR (400 MHz, CDCl$_3$) delta 8.64 (1H, d, J=2.3 Hz), 8.46 (1H, br d, J=1.6 Hz), 8.04 (1H, ddd, J=8.8, 6.6, 2.8 Hz), 7.91 (1H, d, J=2.3 Hz), 7.20 (1H, td, J=7.7, 1.1 Hz), 7.17-7.04 (4H, m), 6.86 (1H, t, J=54.8 Hz), 6.01 (1H, d, J=7.3 Hz), 4.06-3.88 (1H, m), 3.81 (2H, d, J=7.3 Hz), 2.15 (2H, d, J=9.6 Hz), 2.04-1.81 (3H, m), 1.41-1.11 (4H, m).

MS (ESI) m/z: 529.9 (M+H)$^+$.

Intermediate-192: 5-chloro-N-((1r,4r)-4-((3-(6-fluoro-4-methylpyridin-3-yl)-2-oxo-2,3-dihydro-1H-benzo[d]imidazol-1-yl)methyl)cyclohexyl)-2-methylnicotinamide <Step-1>: 6-fluoro-4-methyl-N-(2-nitrophenyl)pyridin-3-amine A mixture of 1-fluoro-2-nitrobenzene (100 mg, 0.505 mmol), 6-fluoro-4-methylpyridin-3-amine (111 mg, 0.606 mmol), potassium t-butoxide (247 mg, 0.757 mmol) in THF (1 mL) is stirred for 1 hr at rt. The mixture is added with saturated aqueous ammonium chloride. The resultant mixture is extracted with EtOAc. The organic layer is dried over MgSO$_4$, filtered and concentrated in vacuo to give 390 mg of the title compound as a crude. The compound is used for the next reaction without further purification.

MS (ESI) m/z: 248.3 (M+H)$^+$.

<Step-2>: N$^1$-(6-fluoro-4-methylpyridin-3-yl)benzene-1,2-diamine

The title compound is prepared in 82% yield (256 mg, brown solid) by the similar manner to Step-2 of Intermediate-151 using 6-fluoro-4-methyl-N-(2-nitrophenyl)pyridin-3-amine (354 mg, Step-1 of Intermediate-192) in place of methyl 4-methyl-5-((2-methyl-6-nitrophenyl)amino)picolinate.

MS (ESI) m/z: 218.3 (M+H)$^+$.

<Step-3>: 1-(6-fluoro-4-methylpyridin-3-yl)-1H-benzo[d]imidazol-2(3H)-one

The title compound is prepared in 21% yield (60 mg, brown solid) by the similar manner to Step-3 of Intermediate-105 using N$^1$-(6-fluoro-4-methylpyridin-3-yl)benzene-1,2-diamine (256 mg, 1.18 mmol, Step-2 of Intermediate-192) in place of methyl 5-((2-aminophenyl)amino)-4-methylpicolinate.

MS (ESI) m/z: 244.3 (M+H)$^+$.

<Step-4>: 5-chloro-N-((1r,4r)-4-((3-(6-fluoro-4-methylpyridin-3-yl)-2-oxo-2,3-dihydro-1H-benzo[d]imidazol-1-yl)methyl)cyclohexyl)-2-methylnicotinamide A mixture of ((r,4r)-4-(5-chloro-2-methylnicotinamido)cyclohexyl)methyl methanesulfonate (20 mg, 0.055 mmol, Mesylate-1), 1-(6-fluoro-4-methylpyridin-3-yl)-1H-benzo[d]imidazol-2(3H)-one (14 mg, 0.055 mmol, Step-3 of Intermediate-192), and cesium carbonate (45 mg, 0.139 mmol) in DMSO (1 mL) is stirred overnight at 80° C. The mixture is diluted with saturated aqueous sodium chloride. The mixture is extracted with THF. The organic layer is concentrated. The resultant mixture is washed with water followed by diisopropyl ether to give 30 mg (quantitative yield) of the title compound as a brown gum.

MS (ESI) m/z: 508.2 (M+H)$^+$.

Intermediate-193: 1-(6-((2,2,2-trifluoroethyl)amino)pyridin-3-yl)-1H-benzo[d]imidazol-2(3H)-one <Step-1>: N$^5$-(2-nitrophenyl)-N$^2$-(2,2,2-trifluoroethyl)pyridine-2,5-diamine The title compound is prepared in 52% yield (134 mg, brown solid) by the similar manner to Step-1 of Intermediate-73 using N$^2$-(2,2,2-trifluoroethyl)pyridine-2,5-diamine (157 mg, 0.821 mmol) in place of 1-methyl-1H-indazol-5-amine.

$^1$H-NMR (400 MHz, CDCl$_3$) delta 9.25 (1H, s), 8.20 (1H, dd, J=8.7, 2.5 Hz), 8.08 (1H, d, J=2.5 Hz), 7.44-7.30 (2H, m), 6.88 (1H, dd, J=8.5, 1.1 Hz), 6.82-6.67 (1H, m), 6.59 (1H, d, J=8.7 Hz), 4.26-3.99 (2H, m).

MS (ESI) m/z: 313.2 (M+H)$^+$.

<Step-2>: N$^5$-(2-aminophenyl)-N$^2$-(2,2,2-trifluoroethyl)pyridine-2,5-diamine The title compound is prepared in 73% yield (88 mg, brown gum) by the similar manner to Step-2 of Intermediate-151 using N-(2-nitrophenyl)-N$^2$ (2,2,2-trifluoroethyl)pyridine-2,5-diamine (134 mg, 0.429 mmol, Step-1 of Intermediate-193) in place of methyl 4-methyl-5-((2-methyl-6-nitrophenyl)amino)picolinate.

MS (ESI) m/z: 283.3 (M+H)$^+$.

<Step-3>: 1-(6-((2,2,2-trifluoroethyl)amino)pyridin-3-yl)-1H-benzo[d]imidazol-2(3H)-one A mixture of N$^5$-(2-aminophenyl)-N$^2$-(2,2,2-trifluoroethyl)pyridine-2,5-diamine (88 mg, 0.31 mmol, Step-2 of Intermediate-193) and CDI (76 mg, 0.47 mmol) in MeCN (1 mL) is stirred overnight at rt. After the reaction mixture is concentrated, the resultant mixture is washed with water followed by diisopropyl ether to give 37 mg (39% yield) of the title compound as a brown solid.

MS (ESI) m/z: 309.2 (M+H)$^+$.

Intermediate-194: 1-(6-((2,2-difluoroethyl)amino)pyridin-3-yl)-1H-benzo[d]imidazol-2(3H)-one The title compound (brown solid) is prepared in 28% yield in 3 steps by the similar manner to Step-1, Step-2, and Step-3 of Intermediate-193 using N$^2$-(2,2-difluoroethyl)pyridine-2,5-diamine in place of N$^2$-(2,2,2-trifluoroethyl)pyridine-2,5-diamine.

MS (ESI) m/z: 291.2 (M+H)$^+$.

Intermediate-195: 1-(1,5-naphthyridin-3-yl)-1H-benzo[d]imidazol-2(3H)-one

The title compound is prepared in 51% yield in 3 steps by the similar manner to Step-1, Step-2, and Step-3 of Intermediate-102 using 1,5-naphthyridin-3-amine and 1-bromo-2-nitrobenzene in place of 2-bromo-4-fluoro-1-nitrobenzene and methyl 5-aminopicolinate.

$^1$H-NMR (400 MHz, DMSO-d$_6$) delta 11.40 (1H, br s), 9.25 (1H, d, J=2.7 Hz), 9.09 (1H, dd, J=4.1, 1.8 Hz), 8.61 (1H, d, J=1.8 Hz), 8.53 (1H, d, J=8.2 Hz), 7.87 (1H, dd, J=8.2, 4.1 Hz), 7.23 (1H, d, J=7.8 Hz), 7.15-7.13 (2H, m), 7.09-7.03 (1H, m).

MS (ESI) m/z: 263.0 (M+H)$^+$.

Intermediate-196: 1-(quinazolin-7-yl)-1H-benzo[d]imidazol-2(3H)-one

The title compound is prepared in 76% yield in 3 steps by the similar manner to Step-1, Step-2, and Step-3 of Intermediate-102 using quinazolin-7-amine and 1-bromo-2-nitrobenzene in place of 2-bromo-4-fluoro-1-nitrobenzene and methyl 5-aminopicolinate.

$^1$H-NMR (400 MHz, DMSO-d$_6$) delta 11.34 (1H, br s), 9.68 (1H, s), 9.35 (1H, s), 8.37 (1H, d, J=8.7 Hz), 8.17 (1H, d, J=2.3 Hz), 8.04 (1H, dd, J=8.7, 2.3 Hz), 7.27-2.24 (1H, m), 7.15-70.13 (2H, m), 7.09-7.05 (1H, m).

MS (ESI) m/z: 263.0 (M+H)$^+$.

Intermediate-197: 3-(2-fluorophenyl)-1H-imidazo[4,5-b]pyridin-2(3H)-one

The title compound (pale yellow solid) is prepared in 65% yield in 2 steps by the similar manner to Step-1 and Step-2 of Intermediate-98 using 2-fluoroaniline in place of 2,3-dihydro-1H-inden-5-amine.

$^1$H-NMR (400 MHz, DMSO-d$_6$) delta 11.44 (1H, s), 7.90 (1H, dd, J=5.0, 1.4 Hz), 7.62-7.53 (2H, m), 7.50-7.35 (3H, m), 7.09 (1H, dd, J=7.8, 5.0 Hz).

MS (ESI) m/z: 230.3 (M+H)$^+$.

Intermediate-198: 3-(2-chloro-4-methylphenyl)-1H-imidazo[4,5-b]pyridin-2(3H)-one <Step-1>: N-(2-chloro-4-methylphenyl)-3-nitropyridin-2-amine The title compound is prepared in 73% yield (135 mg) by the similar manner to Step-1 of Intermediate-112 using 2-bromo-3-nitropyridine (150 mg, 0.74 mmol) and 2-chloro- 4-methylaniline (105 mg, 0.74 mmol) in place of 1-bromo-2-nitrobenzene and 4-(pyridin-4-yloxy)aniline.
MS (ESI) m/z: 264.0 (M+H)$^+$.

<Step-2>: $N^2$-(2-chloro-4-methylphenyl)pyridine-2,3-diamine

The title compound is prepared in 73% yield (135 mg) by the similar manner to Step-2 of Intermediate-43 using N-(2-chloro-4-methylphenyl)-3-nitropyridin-2-amine (194 mg, 0.94 mmol, Step-1 of Intermediate-198) in place of 2-bromo-N-(2-nitrophenyl)pyridin-4-amine.
MS (ESI) m/z: 233.9 (M+H)$^+$.

<Step-3>: 3-(2-chloro-4-methylphenyl)-1H-imidazo[4,5-b]pyridin-2(3H)-one

The title compound is prepared in 50% yield (89 mg) by the similar manner to Step-3 of Intermediate-20 using $N^2$-(2-chloro-4-methylphenyl)pyridine-2,3-diamine (135 mg, 0.84 mmol, Step-2 of Intermediate-198) in place of $N^1$-(2,4-difluorophenyl)benzene-1,2-diamine.
$^1$H-NMR (400 MHz, DMSO-d$_6$) delta 11.37 (1H, br s), 7.85 (1H, dd, J=5.5, 1.4 Hz), 7.52 (1H, d, J=1.4 Hz), 7.45 (1H, d, J=7.8 Hz), 7.28 (1H, dd, J=7.3, 1.4 Hz), 7.32 (1H, dd, J=7.3, 1.4 Hz), 7.06 (1H, dd, J=7.3, 5.5), 2.40 (3H, s).
MS (ESI) m/z: 259.9 (M+H)$^+$.

Intermediate-199: 3-(2-chloro-5-methoxyphenyl)-1H-imidazo[4,5-b]pyridin-2(3H)-one The title compound is prepared in 6% yield in 3 steps by the similar manner to Step-1, Step-2, and Step-3 of Intermediate-198 using 2-chloro-5-methoxyaniline in place of 2-chloro-4-methylaniline.
$^1$H-NMR (400 MHz, DMSO-d$_6$) delta 11.39 (1H, br s), 7.86 (1H, d, J=5.0, 1.4 Hz), 7.58 (1H, d, J=8.7 Hz), 7.39 (1H, dd, J=7.8, 1.4 Hz), 7.23 (1H, dd, J=3.2 Hz), 7.14 (1H, dd, J=8.7, 3.2 Hz), 7.07 (1H, dd, J=7.8, 5.0 Hz), 3.79 (3H, s).
MS (ESI) m/z: 275.9 (M+H)$^+$.

Intermediate-200: 3-(2-chloro-5-fluorophenyl)-1H-imidazo[4,5-b]pyridin-2(3H)-one The title compound is prepared in 24% yield in 3 steps by the similar manner to Step-1, Step-2, and Step-3 of Intermediate-198 using 2-chloro-5-fluoroaniline in place of 2-chloro-4-methylaniline.
$^1$H-NMR (400 MHz, CDCl$_3$) delta 11.46 (1H, br s), 7.88 (1H, dd, J=7.8, 5.5 Hz), 7.77 (1H, dd, J=8.7, 5.5 Hz), 7.67 (1H, ddd, J=9.1, 5.5, 2.7 Hz), 7.48 (1H, ddd, J=9.1, 5.5, 2.7 Hz), 7.41 (1H, dd, J=7.8, 1.4 Hz), 7.09 (1H, dd, J=7.8, 5.5 Hz).
MS (ESI) m/z: 263.8 (M+H)$^+$.

Intermediate-201: 3-(1-((2-(trimethylsilyl)ethoxy)methyl)-1H-pyrrolo[2,3-b]pyridin-5-yl)-1H-imidazo[4,5-b]pyridin-2(3H)-one The title compound is prepared in 85% yield in 3 steps by the similar manner to Step-1, Step-2, and Step-3 of Intermediate-187 using 1-((2-(trimethylsilyl)ethoxy)methyl)-1H-pyrrolo[2,3-b]pyridin-5-amine in place of 3-methyl-1-((2-(trimethylsilyl)ethoxy)methyl)-1H-pyrrolo[2,3-b]pyridin-5-amine.
MS (ESI) m/z: 381.9 (M+H)$^+$.

Intermediate-202: 3-(2-phenoxyethyl)-1H-imidazo[4,5-b]pyridin-2(3H)-one

<Step-1>: 3-nitro-N-(2-phenoxyethyl)pyridin-2-amine

A mixture of 2-chloro-3-nitropyridine (150 mg, 0.95 mmol), 2-phenoxyethanamine (130 mg, 0.95 mmol), and DIEA (0.50 mL, 2.84 mmol) is stirred at 70° C. for 3 hrs. The mixture is diluted with saturated aqueous sodium bicarbonate and extracted with EtOAc. The organic layer is dried over sodium sulfate, filtered and concentrated. The residue is purified by column chromatography on silica-gel eluting with 0-40% EtOAc in n-hexane to give 181 mg (74% yield) of the title compound as a yellow solid.
$^1$H-NMR (400 MHz, CDCl$_3$) delta 8.55 (1H, br s), 8.45-8.40 (2H, m), 7.32-7.25 (2H, m), 7.00-6.91 (3H, m), 6.68 (1H, dd, J=8.2, 5.0 Hz), 4.22 (2H, t, J=5.5 Hz), 4.07 (2H, q, J=5.5 Hz).
MS (ESI) m/z: 260.2 (M+H)$^+$.

<Step-2>: $N^2$-(2-phenoxyethyl)pyridine-2,3-diamine

The title compound is prepared in quantitative yield (160 mg, pale brown gum) by the similar manner to Step-2 of Intermediate-88 using 3-nitro-N-(2-phenoxyethyl)pyridin-2-amine (181 mg, 0.70 mmol, Step-1 of Intermediate-202) in place of N-(2-nitrophenyl)chroman-3-amine.
MS (ESI) m/z: 230.3 (M+H)$^+$.

<Step-3>: 3-(2-phenoxyethyl)-1H-imidazo[4,5-b]pyridin-2(3H)-one

The title compound is prepared in 16% yield (32 mg, pale yellow solid) by the similar manner to Step-3 of Intermediate-170 using $N^2$-(2-phenoxyethyl)pyridine-2,3-diamine (160 mg, 0.70 mmol, Step-2 of Intermediate-202) in place of $N^1$-(1,8-naphthyridin-3-yl)benzene-1,2-diamine.
$^1$H-NMR (400 MHz, DMSO-d$_6$) delta 11.15 (1H, s), 7.93 (1H, d, J=5.0 Hz), 7.30-7.21 (3H, m), 7.00 (1H, dd, J=7.8, 5.0 Hz), 6.95-6.85 (3H, m), 4.32 (2H, t, J=5.5 Hz), 4.20 (2H, t, J=5.5 Hz).
MS (ESI) m/z: 256.3 (M+H)$^+$.

Intermediate-203: 1-(6-(isopropylamino)pyridin-3-yl)-1H-benzo[d]imidazol-2(3H)-one The title compound (brown solid) is prepared in 19% yield in 3 steps by the similar manner to Step-1, Step-2, and Step-3 of Intermediate-193 using $N^2$-isopropylpyridine-2,5-diamine in place of $N^2$-(2,2,2-trifluoroethyl)pyridine-2,5-diamine.
MS (ESI) m/z: 269.3 (M+H)$^+$.

Intermediate-204: 5-chloro-2-(difluoromethyl)-N-((1r,4r)-4-((3-(6-fluoro-4-methylpyridin-3-yl)-2-oxo-2,3-dihydro-1H-benzo[d]imidazol-1-yl)methyl)cyclohexyl)nicotinamide A mixture of ((r,4r)-4-(5-chloro-2-(difluoromethyl)nicotinamido)cyclohexyl)methyl methanesulfonate (20 mg, 0.050 mmol, Mesylate-4), methyl 1-(6-fluoro-4-methylpyridin-3-yl)-1H-benzo[d]imidazol-2(3H)-one (12 mg, 0.050 mmol, Step-3 of Intermediate-192), and cesium carbonate (32 mg, 0.097 mmol) in DMSO (1 mL) is stirred for 4.5 hrs at 100° C. The mixture is diluted with saturated aqueous sodium chloride. The mixture is extracted with THF. The organic layer is concentrated. The resultant mixture is dissolved in DCM and washed with water. The organic layer is dried over MgSO$_4$, filtered and concentrated in vacuo to give 31 mg of the title compound as a crude. The compound is used for the next reaction without further purification.

MS (ESI) m/z: 544.2 (M+H)$^+$.

Intermediate-205: 1-(6-((3,3-difluoropropyl)amino)pyridin-3-yl)-1H-benzo[d]imidazol-2(3H)-one <Step-1>: N$^2$-(3,3-difluoropropyl)-N-(2-nitrophenyl)pyridine-2,5-diamine The title compound is prepared in 94% yield (37 mg, brown gum) by the similar manner to Step-1 of Intermediate-73 using N$^2$-(3,3-difluoropropyl)pyridine-2,5-diamine (24 mg, 0.13 mmol) in place of 1-methyl-1H-indazol-5-amine.

MS (ESI) m/z: 309.2 (M+H)$^+$.

<Step-2>: N$^5$-(2-aminophenyl)-N$^2$-(3,3-difluoropropyl)pyridine-2,5-diamine

The title compound is prepared in 92% yield (31 mg, brown gum) by the similar manner to Step-2 of Intermediate-151 using N$^2$-(3,3-difluoropropyl)-N$^5$-(2-nitrophenyl)pyridine-2,5-diamine (37 mg, 0.12 mmol) in place of methyl 4-methyl-5-((2-methyl-6-nitrophenyl)amino)picolinate.

MS (ESI) m/z: 279.3 (M+H)$^+$.

<Step-3>: 1-(6-((3,3-difluoropropyl)amino)pyridin-3-yl)-1H-benzo[d]imidazol-2(3H)-one A mixture of N-(2-aminophenyl)-N$^2$-(3,3-difluoropropyl) pyridine-2,5-diamine (31 mg, 0.11 mmol, Step-2 of Intermediate-205) and CDI (27 mg, 0.17 mmol) in MeCN (1 mL) is stirred for 1 hr at rt. After the reaction mixture is concentrated, the residue is added with water. The resultant mixture is extracted with EtOAc and concentrated. The resultant residue is purified by column chromatography on silica-gel eluting with 24-100% EtOAc in n-hexane to give 14 mg (42% yield) of the title compound as a brown gum.

MS (ESI) m/z: 305.2 (M+H)$^+$.

Intermediate-206: 3-(3-chloropyridin-4-yl)-1H-imidazo[4,5-b]pyridin-2(3H)-one

<Step-1>: N-(3-chloropyridin-4-yl)-3-nitropyridin-2-amine

The title compound is prepared in 76% yield (141 mg) by the similar manner to Step-1 of Intermediate-101 using 2-bromo-3-nitropyridine (150 mg, 0.74 mmol) and 3-chloropyridin-4-amine (95 mg, 0.74 mmol) in place of methyl 5-aminopicolinate and 2-bromo-1-methyl-3-nitrobenzene.

$^1$H-NMR (400 MHz, CDCl$_3$) delta 10.9 (1H, br s), 8.78 (1H, d, J=5.5 Hz), 8.65 8.59 (3H, m), 8.44 (1H, d, J=5.5 Hz), 7.11-7.05 (1H, m).

MS (ESI) m/z: 250.9 (M+H)$^+$.

<Step-2>: N$^2$-(3-chloropyridin-4-yl)pyridine-2,3-diamine

The title compound is prepared in 33% yield (41 mg) by the similar manner to Step-2 of Intermediate-43 using N-(3-chloropyridin-4-yl)-3-nitropyridin-2-amine (141 mg, 0.56 mmol, Step-1 of Intermediate-206) in place of 2-bromo-N-(2-nitrophenyl)pyridin-4-amine.

MS (ESI) m/z: 220.9 (M+H)$^+$.

<Step-3>:3-(3-chloropyridin-4-yl)-1H-imidazo[4,5-b]pyridin-2(3H)-one

The title compound is prepared in quantitative yield (46 mg) by the similar manner to Step-3 of Intermediate-170 using N$^2$-(3-chloropyridin-4-yl)pyridine-2,3-diamine (41 mg, 0.19 mmol, Step-2 of Intermediate-206) in place of N$^1$-(1,8-naphthyridin-3-yl)benzene-1,2-diamine.

MS (ESI) m/z: 246.9 (M+H)$^+$.

Intermediate-207: N-((1r,4r)-4-((3-(6-bromopyridin-3-yl)-2-oxo-2,3-dihydro-1H-benzo[d]imidazol-1-yl)methyl)cyclohexyl)-5-chloro-2-(difluoromethyl)nicotinamide The title compound is prepared in 86% yield (solid) by the similar manner to Intermediate-54 using Mesylate-4 in place of Mesylate-1, and Intermediate-39 in place of tert-butyl 3-(6-fluoropyridin-3-yl)-2-oxo-2,3-dihydro-1H-benzo[d]imidazole-1-carboxylate, respectively.

$^1$H-NMR (400 MHz, CDCl$_3$) delta 8.68-8.61 (2H, m), 7.92 (1H, d, J=2.3 Hz), 7.84 (1H, dd, J=8.7, 2.7 Hz), 7.66 (1H, d, J=8.2 Hz), 7.25-7.16 (1H, m), 7.12 (2H, d, J=4.0 Hz), 7.08 (1H, d, J=7.3 Hz), 6.86 (1H, t, J=54.7 Hz), 5.97 (1H, d, J=7.8 Hz), 4.04-3.88 (1H, m), 3.81 (2H, d, J=6.9 Hz), 2.21-2.09 (2H, m), 2.02-1.80 (3H, m), 1.41-1.14 (4H, m).

MS (ESI) m/z: 591.9 (M+H)$^+$.

Intermediate-208: 4-methoxy-2-(2-oxo-1H-imidazo[4,5-b]pyridin-3(2H)-yl)benzonitrile <Step-1>: 4-methoxy-2-((3-nitropyridin-2-yl)amino)benzonitrile A mixture of 2-fluoro-3-nitropyridine (90 mg, 0.63 mmol), 2-amino-4-methoxybenzonitrile (94 mg, 0.63 mmol), and Cs$_2$CO$_3$ (619 mg, 1.90 mmol) in DMSO (3 mL) is stirred at rt for 1 day. The mixture is diluted with water and extracted with EtOAc. The organic layer is dried over sodium sulfate, filtered and concentrated. The residue is purified by column chromatography on silica-gel eluting with 0-50% EtOAc in n-hexane to give 62 mg (36% yield) of the title compound as an orange solid.

MS (ESI) m/z: 271.3 (M+H)$^+$.

<Step-2>:2-((3-aminopyridin-2-yl)amino)-4-methoxybenzonitrile

The title compound is prepared in quantitative yield (55 mg, pale yellow gum) by the similar manner to Step-2 of Intermediate-88 using 4-methoxy-2-((3-nitropyridin-2-yl)amino)benzonitrile (62 mg, 0.23 mmol, Step-1 of Intermediate-208) in place of N-(2-nitrophenyl)chroman-3-amine.

MS (ESI) m/z: 241.3 (M+H)$^+$.

<Step-3>:4-methoxy-2-(2-oxo-1H-imidazo[4,5-b]pyridin-3(2H)-yl)benzonitrile

The title compound is prepared in quantitative yield (61 mg, pale yellow gum) by the similar manner to Step-3 of Intermediate-20 using 2-((3-aminopyridin-2-yl)amino)-4- methoxybenzonitrile (55 mg, 0.23 mmol, Step-2 of Intermediate-208) in place of $N^1$-(2,4-difluorophenyl)benzene-1,2-diamine.

$^1$H-NMR (400 MHz, DMSO-$d_6$) delta 11.52 (1H, s), 7.99 (1H, d, J=8.7 Hz), 7.92 (1H, dd, J=5.0, 1.4 Hz), 7.45 (1H, dd, J=7.8, 1.4 Hz), 7.34 (1H, d, J=2.7 Hz), 7.26 (1H, dd, J=8.7, 2.7 Hz), 7.13 (1H, dd, J=7.8, 5.0 Hz), 3.88 (3H, s).

MS (ESI) m/z: 267.3 (M+H)$^+$.

Intermediate-209: 1-(1-(pyridin-3-yl)piperidin-4-yl)-1H-benzo[d]imidazol-2(3H)-one A mixture of 1-(piperidin-4-yl)-1H-benzo[d]imidazol-2(3H)-one (200 mg, 0.921 mmol), 3-iodopyridine (189 mg, 0.921 mmol), potassium t-butoxide (207 mg, 1.84 mmol), palladium (II) acetate (41 mg, 0.18 mmol), and 4,5-bis(diphenylphosphino)-9,9-dimethylxanthene (107 mg, 0.184 mmol) in 1,4-dioxane (2 mL) is stirred for 1 day at 100° C. The reaction mixture is concentrated and the resultant residue is purified by column chromatography on amino-functional silica gel eluting with 0-30% MeOH in EtOAc to give 27 mg (10% yield) of the title compound as a brown gum.

MS (ESI) m/z: 295.3 (M+H)$^+$.

Intermediate-210: 1-(6-((2,2-difluoropropyl)amino)pyridin-3-yl)-1H-benzo[d]imidazol-2(3H)-one The title compound (brown solid) is prepared in 38% yield in 3 steps by the similar manner to Step-1, Step-2, and Step-3 of Intermediate-193 using $N^2$ (2,2-difluoropropyl)pyridine-2,5-diamine in place of $N^2$ (2,2,2-trifluoroethyl)pyridine-2,5-diamine.

MS (ESI) m/z: 305.2 (M+H)$^+$.

Intermediate-211: 5-(4-bromopyridin-2-yl)oxazole

To a solution of 4-bromopicolinaldehyde (0.25 g, 1.34 mmol) in MeOH (20 mL) is added potassium carbonate (0.557 g, 4.03 mmol) and TosMIC (0.315 g, 1.61 mmol). The resulting mixture is stirred at room temperature for 3 hrs. The reaction mixture is evaporated to dryness, diluted with water and extracted with EtOAc twice. The combined organics are washed with water and brine, dried over sodium sulfate, filtered and evaporated. The residue is purified by column chromatography on silica-gel eluting with 30% EtOAc in n-hexane to give 196 mg (65% yield) of the title compound.

$^1$H-NMR (400 MHz, CDCl$_3$) delta 8.45 (1H, d, J=5.5 Hz), 7.99 (1H, s), 7.85 (1H, d, J=1.8 Hz), 7.73 (1H, s), 7.41 (1H, dd, J=5.5, 1.8 Hz).

Intermediate-212: 1-(5-chloro-6-(methylamino)pyridin-3-yl)-1H-benzo[d]imidazol-2(3H)-one <Step-1>: tert-butyl 3-(5-chloro-6-fluoropyridin-3-yl)-2-oxo-2,3-dihydro-1H-benzo[d]imidazole-1-carboxylate The title compound is prepared in 11% yield (17 mg, pale yellow gum) by the similar manner to Step-1 of Intermediate-4 using (5-chloro-6-fluoropyridin-3-yl)boronic acid (75 mg, 0.43 mmol) in place of (4-fluorophenyl)boronic acid.

$^1$H-NMR (400 MHz, CDCl$_3$) delta 8.31 (1H, dd, J=2.5, 1.6 Hz), 8.08 (1H, dd, J=7.8, 2.5 Hz), 7.96 (1H, dd, J=7.3, 1.8 Hz), 7.25-7.18 (2H, m), 6.98 (1H, dd, J=6.4, 2.7 Hz), 1.69 (9H, s).

<Step-2>: 1-(5-chloro-6-(methylamino)pyridin-3-yl)-1H-benzo[d]imidazol-2(3H)-one A mixture of tert-butyl 3-(5-chloro-6-fluoropyridin-3-yl)-2-oxo-2,3-dihydro-1H-benzo[d]imidazole-1-carboxylate (17 mg, 0.046 mmol, Step-1 of Intermediate-212), methylamine hydrochloride (39 mg, 0.58 mmol), and DIEA (0.101 mL, 0.581 mmol) in NMP (0.5 mL) is stirred for 35 min at 220° C. under microwave irradiation. The reaction mixture is added with water. The resultant mixture is extracted with EtOAc/THF (50:50) and concentrated. The resultant residue is purified by a strong anion exchange cartridge (ISOLUTE (registered trademark) SCX-2, 1 g/6 mL, Biotage) to give 11 mg (85% yield) of the title compound as a brown solid.

MS (ESI) m/z: 275.1 (M+H)$^+$.

Intermediate:213 1-(1,3-dimethyl-1H-pyrrolo[2,3-b]pyridin-5-yl)-1H-benzo[d]imidazol-2(3H)-one The title compound is prepared in 72% yield in 3 steps by the similar manner to Step-1, Step-2, and Step-3 of Intermediate-179 using 1,3-dimethyl-1H-pyrrolo[2,3-b]pyridin-5-amine in place of quinoxalin-6-amine.

$^1$H-NMR (400 MHz, DMSO-$d_6$) delta 11.15 (1H, br s), 8.30 (1H, d, J=2.3 Hz), 8.06 (1H, d, J=2.3 Hz), 7.41 (1H, d, J=0.9 Hz), 7.10-7.03 (2H, m), 6.98 (1H, td, J=7.8, 1.8 Hz), 6.85 (1H, d, J=7.8 Hz), 3.82 (3H, s), 2.27 (3H, d, J=0.9 Hz).

MS (ESI) m/z: 279.3 (M+H)$^+$.

Intermediate-214: 5-chloro-2-(difluoromethyl)-N-((1r,4r)-4-((2-oxo-2,3-dihydro-1H-imidazo[4,5-b]pyridin-1-yl)methyl)cyclohexyl)nicotinamide A mixture of ((1r,4r)-4-(5-chloro-2-(difluoromethyl)nicotinamido)cyclohexyl)methyl methanesulfonate (500 mg, 1.26 mmol, Mesylate-4), 3-(2,4-dimethoxybenzyl)-1H-imidazo[4,5-b]pyridin-2(3H)-one (359 mg, 1.26 mmol, Intermediate-122) and cesium carbonate (1.23 g, 3.78 mmol) in DMSO (5 mL) is stirred at 80° C. overnight. The mixture is diluted with water (30 mL) to afford suspension. The precipitate is collected by filtration, washed with diisopropyl ether (10 mL) and dried in vacuo. The solid in TFA (20 mL) is stirred at 75° C. overnight. The mixture is concentrated, purified by column chromatography on amino-functional silica-gel eluting with 50-85% EtOAc in n-hexane to give 420 mg (76% yield) of the title compound as a brown solid.

$^1$H-NMR (400 MHz, DMSO-$d_6$) delta 11.51 (1H, br s), 8.80 (1H, d, J=2.3 Hz), 8.62 (1H, br d, J=7.8 Hz), 8.12 (1H, d, J=2.3 Hz), 7.87 (1H, dd, J=5.1, 1.4 Hz), 7.46 (1H, dd, J=7.8, 1.4 Hz), 7.11 (1H, t, J=53 Hz), 6.98 (1H, dd, J=5.1, 2.7 Hz), 3.70-3.62 (1H, m), 3.63 (2H, d, J=6.9 Hz), 1.91-1.84 (2H, m), 1.80-1.69 (1H, m), 1.69-1.59 (2H, m), 1.23-1.04 (4H, m).

MS (ESI) m/z: 435.8 (M+H)$^+$.

Intermediate-215: N-methyl-5-(2-oxo-2,3-dihydro-1H-benzo[d]imidazol-1-yl)pyrazine-2-carboxamide <Step-1>: tert-butyl 3-(5-(methoxycarbonyl)pyrazin-2-yl)-2-oxo-2,3-dihydro-1H-benzo[d]imidazole-1-carboxylate A mixture of methyl 5-chloropyrazine-2-carboxylate (100 mg, 0.58 mmol), tert-butyl 2-oxo-2,3-dihydro-1H-benzo[d]imidazole-1-carboxylate (136 mg, 0.58 mmol), and Cs$_2$CO$_3$ (283 mg, 0.87 mmol) in DMSO (3 mL) is stirred at rt for 1 day. The mixture is diluted with 10% aqueous citric acid solution. The precipitate is collected and washed with diisopropyl ether to give 178 mg (83% yield) of the title compound as a pale yellow solid.
MS (ESI) m/z: 371.2 (M+H)+.

<Step-2>: N-methyl-5-(2-oxo-2,3-dihydro-1H-benzo[d]imidazol-1-yl)pyrazine-2-carboxamide The title compound is prepared in 57% yield (74 mg, pale pink solid) by the similar manner to Intermediate-87 using tert-butyl 3-(5-(methoxycarbonyl)pyrazin-2-yl)-2-oxo-2,3-dihydro-1H-benzo[d]imidazole-1-carboxylate (178 mg, 0.48 mmol, Step-1 of Intermediate-215) in place of methyl 5-(2-oxo-2,3-dihydro-1H-benzo[d]imidazol-1-yl)picolinate.
1H-NMR (400 MHz, DMSO-$d_6$) delta 9.51 (1H, d, J=1.4 Hz), 9.12 (1H, d, J=1.4 Hz), 8.88 (1H, q, J=5.0 Hz), 8.09 (1H, dd, J=7.8, 1.4 Hz), 7.19 (1H, dd, J=7.8, 1.4 Hz), 7.11 (2H, d, J=7.8 Hz), 2.85 (3H, d, J=5.0 Hz). A signal due to NH is not observed.
MS (ESI) m/z: 270.2 (M+H)+.

Intermediate-216: 1-(6-(cyclopropylamino)pyridin-3-yl)-1H-benzo[d]imidazol-2(3H)-one The title compound (brown solid) is prepared in 30% yield in 3 steps by the similar manner to Step-1, Step-2, and Step-3 of Intermediate-193 using $N^2$ cyclopropylpyridine-2,5-diamine in place of $N^2$ (2,2,2-trifluoroethyl)pyridine-2,5-diamine.
MS (ESI) m/z: 267.2 (M+H)+.

Intermediate-217: 1-(4-methyl-6-(methylamino)pyridin-3-yl)-1H-benzo[d]imidazol-2(3H)-one The title compound is prepared in 52% yield (26 mg, brown gum) by the similar manner to Step-2 of Intermediate-212 using 1-(6-fluoro-4-methylpyridin-3-yl)-1H-benzo[d]imidazol-2(3H)-one (13 mg, 0.053 mmol, Step-3 of Intermediate-192) in place of tert-butyl 3-(5-chloro-6-fluoropyridin-3-yl)-2-oxo-2,3-dihydro-1H-benzo[d]imidazole-1-carboxy late.
MS (ESI) m/z: 255.2 (M+H)+.

Intermediate-218: 3-(1-methyl-1H-indazol-5-yl)-1H-imidazo[4,5-b]pyridin-2(3H)-one The title compound (off-white solid) is prepared in 74% yield in 2 steps by the similar manner to Step-1 and Step-2 of Intermediate-98 using 1-methyl-1H-indazol-5-amine in place of 2,3-dihydro-1H-inden-5-amine.
1H-NMR (400 MHz, DMSO-$d_6$) delta 11.30 (1H, br s), 8.12 (1H, s), 7.94 (1H, d, J=1.4 Hz), 7.89 (1H, dd, J=5.1, 1.4 Hz) 7.74 (1H, d, J=8.7 Hz), 7.57 (1H, dd, J=8.7, 1.8 Hz), 7.37 (1H, dd, J=7.8, 1.4 Hz), 7.06 (1H, dd, J=7.8, 2.3 Hz), 408 (3H, s).
MS (ESI) m/z: 265.9 (M+H)+.

Intermediate-219: 5-(4-fluoro-2-oxo-2,3-dihydro-1H-benzo[d]imidazol-1-yl)-N-methylpicolinamide The title compound is prepared in 52% yield in 4 steps by the similar manner to Step-1, Step-2, Step-3 and Step-4 of Intermediate-101 using 1-bromo-3-fluoro-2-nitrobenzene in place of 2-bromo-1-methyl-3-nitrobenzene.
1H-NMR (400 MHz, DMSO-$d_6$) delta 11.91 (1H, br s), 8.86 (1H, t, J=1.4 Hz), 8.84 (1H, br d, J=5.0 Hz), 8.20 (2H, d, J=1.4 Hz), 7.08-6.97 (3H, m), 2.85 (3H, d, J=5.0 Hz).
MS (ESI) m/z: 287.3 (M+H)+.

Intermediate-220: 5-(3-(((1r,4r)-4-(5-chloro-2-(difluoromethyl)nicotinamido)cyclohexyl)methyl)-2-oxo-2,3-dihydro-1H-benzo[d]imidazol-1-yl)picolinic acid <Step-1>: methyl 5-(3-(((1r,4r)-4-(5-chloro-2-(difluoromethyl)nicotinamido)cyclohexyl)methyl)-2-oxo-2,3-dihydro-1H-benzo[d]imidazol-1-yl)picolinate The title compound (solid) is prepared in 75% yield by the similar manner to Step-3 and Step-4 of Intermediate-3 using Mesylate-4 and methyl 5-(2-oxo-2,3-dihydro-1H-benzo[d]imidazol-1-yl)picolinate (102 mg, 0.38 mmol, Step-3 of Intermediate-36) in place of Mesylate-1 and methyl 2-((2-oxo-2,3-dihydro-1H-benzo[d]imidazol-1-yl)methyl)benzoate.
1H-NMR (400 MHz, CDCl$_3$) delta 9.04 (1H, d, J=2.3 Hz), 8.64 (1H, d, J=2.3 Hz), 8.33 (1H, d, J=8.7 Hz), 8.18 (1H, dd, J=8.5, 2.5 Hz), 7.92 (1H, d, J=2.3 Hz), 7.26-7.19 (2H, m), 7.19-7.06 (2H, m), 6.85 (1H, t, J=54.7 Hz), 5.89 (1H, d, J=7.3 Hz), 4.06 (3H, s), 4.03-3.90 (1H, m), 3.83 (2H, d, J=6.9 Hz), 2.17 (2H, br d, J=11.9 Hz), 2.05-1.82 (3H, m), 1.42-1.16 (4H, m).
MS (ESI) m/z: 569.8 (M+H)+.

<Step-2>: 5-(3-(((1r,4r)-4-(5-chloro-2-(difluoromethyl)nicotinamido)cyclohexyl)methyl)-2-oxo-2,3-dihydro-1H-benzo[d]imidazol-1-yl)picolinic acid A mixture of Step-1 of Intermediate-220 (162 mg, 0.28 mmol) in MeOH (3 mL) is added 2 M aqueous sodium hydroxide solution (2 mL) and stirred at rt for 2 hr. The mixture is added 2 M hydrochloric acid, the solid is precipitated. The precipitated solid is collected and washed with water, the title compound is prepared in 84% yield (133 mg, solid).
1H-NMR (400 MHz, DMSO-$d_6$) delta 8.98 (1H, t, J=1.6 Hz), 8.83 (1H, d, J=2.3 Hz), 8.68 (1H, d, J=7.8 Hz), 8.25 (2H, d, J=1.4 Hz), 8.16 (1H, d, J=2.3 Hz), 7.40 (1H, d, J=7.8 Hz), 7.35 (1H, br), 7.28-7.17 (2H, m), 7.15 (1H, t, J=54.0 Hz), 7.15-7.07 (1H, m), 3.80 (2H, d, J=7.3 Hz), 3.77-3.65 (1H, m), 2.02-1.68 (5H, m), 1.37-1.11 (4H, m).
MS (ESI) m/z: 555.8 (M+H)+.

Intermediate-221: 3-chloro-N-methyl-5-(2-oxo-2,3-dihydro-1H-benzo[d]imidazol-1-yl)picolinamide <Step-1>: methyl 3-chloro-5-((2-nitrophenyl)amino)picolinate A mixture of 1-bromo-2-nitrobenzene (50 mg, 0.248 mmol), methyl 5-amino-3-chloropicolinate (46 mg, 0.248 mmol), Pd$_2$(dba)$_3$ (11 mg, 0.012 mmol), Xantphos (14 mg, 0.025 mmol) and K$_3$PO$_4$ (105 mg, 0.495 mmol) in 1,4-dioxane (3 mL) is stirred at 80° C. for 1 hr. The reaction mixture is poured into water and extracted EtOAc. The organic layer is dried over sodium sulfate, filtered and concentrated. The residue is purified by column chromatography on silica-gel eluting with 0-33% EtOAc in n-hexane to give 58 mg (76% yield) of the title compound as a yellow solid.
1H-NMR (400 MHz, CDCl$_3$) delta 9.38 (1H, br s), 8.53 (1H, d, J=2.4 Hz), 8.26 (1H, dd, J=8.4, 1.6 Hz), 7.71 (1H, d, J=2.4 Hz), 7.60-7.52 (1H, m), 7.47-7.42 (1H, m), 7.09-7.03 (1H, m), 4.02 (3H, s). MS (ESI) m/z: 308.1 (M+H)$^+$.

<Step-2>: methyl 5-((2-aminophenyl)amino)-3-chloropicolinate

A mixture of methyl 3-chloro-5-((2-nitrophenyl)amino) picolinate (58 mg, 0.189 mmol, Step-1 of Intermediate-221) in MeOH (3 mL) is evacuated and backfilled with N$_2$ gas. To this is added 5% platinum on alumina (10 mg). The mixture is evacuated and backfilled with H$_2$ gas and stirred at rt under H$_2$ atmosphere. After 2.5 hrs, the reaction mixture is evacuated and backfilled with N$_2$ gas and the mixture is filtered through celite pad. The filtrate is concentrated in vacuo to give 52 mg (99% yield) of the title compound as red brown oil.

$^1$H-NMR (400 MHz, CDCl$_3$) delta 8.12 (1H, d, J=2.4 Hz), 7.19-7.09 (2H, m), 6.91 (1H, d, J=2.4 Hz), 6.88-6.78 (2H, m), 5.77 (1H, br s), 3.95 (3H, s), 3.78 (2H, br s).
MS (ESI) m/z: 278.2 (M+H)$^+$.

<Step-3>: methyl 3-chloro-5-(2-oxo-2,3-dihydro-1H-benzo[d]imidazol-1-yl)picolinate A mixture of methyl 5-((2-aminophenyl)amino)-3-chloropicolinate (52 mg, 0.189 mmol, Step-2 of Intermediate-221), CDI (91 mg, 0.562 mmol) in THF (3 mL) is stirred at rt for 14 hrs. The mixture is concentrated. The residual solid is suspended with IPE (10 mL). The precipitate is collected by filtration, washed with IPE to give 25 mg (44% yield) of the title compound as a beige solid.

$^1$H-NMR (400 MHz, DMSO-d$_6$) delta 11.43 (1H, br s), 8.87 (1H, d, J=1.8 Hz), 8.39 (1H, d, J=1.8 Hz), 7.57 (1H, s), 7.25 (1H, d, J=7.6 Hz), 7.18-7.03 (2H, m), 3.93 (3H, s). MS (ESI) m/z: 304.1 (M+H)$^+$.

<Step-4>: 3-chloro-N-methyl-5-(2-oxo-2,3-dihydro-1H-benzo[d]imidazol-1-yl)picolinamide The title compound is prepared in 99% yield (24 mg, pale orange solid) by the similar manner to Intermediate-87 using methyl 3-chloro-5-(2-oxo-2,3-dihydro-1H-benzo[d]imidazol-1-yl)picolinate (25 mg, 0.082 mmol, Step-3 of Intermediate-221) in place of methyl 5-(2-oxo-2,3-dihydro-1H-benzo[d]imidazol-1-yl)picolinate.

$^1$H-NMR (400 MHz, DMSO-d$_6$) delta 8.81 (1H, d, J=2.0 Hz), 8.74-8.66 (1H, m), 8.32 (1H, d, J=2.0 Hz), 7.21-7.02 (4H, m), 2.81 (3H, d, J=4.8 Hz). MS (ESI) m/z: 303.1 (M+H)$^+$. A signal due to NH is not observed.

Intermediate-222: N,6-dimethyl-5-(2-oxo-2,3-dihydro-1H-benzo[d]imidazol-1-yl)picolinamide <Step-1>: methyl 6-methyl-5-((2-nitrophenyl)amino)picolinate A mixture of 1-bromo-2-nitrobenzene (50 mg, 0.248 mmol), methyl 5-amino-6-methylpicolinate (41 mg, 0.248 mmol), Pd$_2$(dba)$_3$ (11 mg, 0.012 mmol), Xantphos (14 mg, 0.025 mmol) and K$_3$PO$_4$ (105 mg, 0.495 mmol) in 1,4-dioxane (3 mL) is stirred at 100° C. for 1.5 hrs. The reaction mixture is poured into water and extracted EtOAc. The organic layer is dried over sodium sulfate, filtered and concentrated. The residue is purified by column chromatography on silica-gel eluting with 0-50% EtOAc in n-hexane to give 53 mg (75% yield) of the title compound as an orange solid.

$^1$H-NMR (400 MHz, CDCl$_3$) delta 9.40 (1H, br s), 8.26 (1H, dd, J=8.4, 1.2 Hz), 8.05 (1H, d, J=8.0 Hz), 7.78 (1H, d, J=8.4 Hz), 7.53-7.46 (1H, m), 7.19 (1H, dd, J=8.4, 1.2 Hz), 7.01-6.93 (1H, m), 4.02 (3H, s), 2.68 (3H, s). MS (ESI) m/z: 288.2 (M+H)$^+$.

<Step-2>: methyl 5-((2-aminophenyl)amino)-6-methylpicolinate

A solution of methyl 6-methyl-5-((2-nitrophenyl)amino) picolinate (53 mg, 0.184 mmol, Step-1 of Intermediate-222) in MeOH (3 mL) is evacuated and backfilled with N$_2$ gas. To this is added 10% Pd/C (10 mg). The mixture is evacuated and backfilled with H$_2$ gas and stirred at rt under H$_2$ atmosphere. After 2 hrs, the reaction mixture is evacuated and backfilled with N$_2$ gas and the mixture is filtered through celite pad. The filtrate is concentrated in vacuo to give 47 mg (99% yield) of the title compound.

$^1$H-NMR (400 MHz, CDCl$_3$) delta 7.87 (1H, d, J=8.8 Hz), 7.17-7.07 (2H, m), 6.87-6.75 (3H, m), 5.45 (1H, br s), 3.96 (3H, s), 3.75 (2H, br s), 2.64 (3H, s). MS (ESI) m/z: 258.2 (M+H)$^+$.

<Step-3>: methyl 6-methyl-5-(2-oxo-2,3-dihydro-1H-benzo[d]imidazol-1-yl)picolinate A mixture of methyl 5-((2-aminophenyl)amino)-6-methylpicolinate (47 mg, 0.184 mmol, Step-2 of Intermediate-222), CDI (89 mg, 0.548 mmol) in THF (3 mL) is stirred at rt for 16 hrs. The mixture is concentrated. The residue is poured into IPE (3 mL) and THF (3 mL). The mixture is concentrated. The residual solid is suspended with IPE (10 mL). The obtained solid is washed with IPE to give 51 mg (99% yield) of the title compound as a beige solid.

$^1$H-NMR (400 MHz, DMSO-d$_6$) delta 11.30 (1H, br s), 8.11-8.04 (2H, m), 7.14-7.07 (2H, m), 7.03-6.96 (1H, s), 6.73 (1H, d, J=7.6 Hz), 3.93 (3H, s), 2.37 (3H, s). MS (ESI) m/z: 284.2 (M+H)$^+$.

<Step-4>: N,6-dimethyl-5-(2-oxo-2,3-dihydro-1H-benzo[d]imidazol-1-yl)picolinamide The title compound is prepared in 99% yield (51 mg, red brown oil) by the similar manner to Intermediate-87 using methyl 6-methyl-5-(2-oxo-2,3-dihydro-1H-benzo[d]imidazol-1-yl)picolinate (51 mg, 0.180 mmol, Step-3 of Intermediate-222) in place of methyl 5-(2-oxo-2,3-dihydro-1H-benzo[d]imidazol-1-yl)picolinate.

$^1$H-NMR (400 MHz, DMSO-d$_6$) delta 12.01 (1H, br s), 8.78-8.73 (1H, m), 8.05-7.98 (2H, m), 7.17-7.07 (2H, m), 7.03-6.97 (1H, m), 6.72 (1H, d, J=7.6 Hz), 2.86 (3H, d, J=4.8 Hz), 2.38 (3H, s). MS (ESI) m/z: 283.2 (M+H)$^+$.

Intermediate-223: 2-(2,2,2-trifluoroethyl)-2H-indazole-3-carboxylic acid

<Step-1>: methyl 2-(2,2,2-trifluoroethyl)-2H-indazole-3-carboxylate

A mixture of methyl 1H-indazole-3-carboxylate (260 mg, 1.45 mmol), 2,2,2-trifluoroethyl trifluoromethanesulfonate (411 mg, 1.77 mmol) and K$_2$CO$_3$ (408 mg, 2.95 mmol) in DMF (4 mL) is stirred at 60° C. for 3 hrs. The reaction mixture is diluted with water, extracted with EtOAc. The organic layer is dried over MgSO$_4$, filtered and concentrated. The residue is purified by column chromatography on silica-gel eluting with 10% EtOAc in n-hexane to give the title compound as an off-white solid (229 mg, 60% yield).
MS (ESI) m/z: 259.1 (M+H)+.

<Step-2>: 2-(2,2,2-trifluoroethyl)-2H-indazole-3-carboxylic acid

The title compound is prepared in quantitative yield (110 mg, off-white solid) by the similar manner to Step-4 of Intermediate-2 using methyl 2-(2,2,2-trifluoroethyl)-2H-indazole-3-carboxylate (113 mg, 0.44 mmol, Step-1 of Intermediate-223) in place of methyl 3-((3-(((1r,4r)-4-(5-chloro-2-methylnicotinamido)cyclohexyl)methyl)-2-oxo-2,3-dihydro-1H-benzo[d]imidazol-1-yl)methyl)benzoate 3-methyl-5-nitro-1H-pyrrolo[2,3-b]pyridine.
MS (ESI) m/z: 245.1 (M+H)+.

Intermediate-224: N-((1r,4r)-4-((3-(6-bromo-4-methylpyridin-3-yl)-2-oxo-2,3-dihydro-1H-benzo[d]imidazol-1-yl)methyl)cyclohexyl)-5-chloro-2-(difluoromethyl)nicotinamide <Step-1>: 6-bromo-4-methyl-N-(2-nitrophenyl)pyridin-3-amine To a mixture of 6-bromo-4-methylpyridin-3-amine (1.0 g, 5.4 mmol), 1-fluoro-2-nitrobenzene (777 mg, 5.5 mmol) in THF (30 mL) is added potassium tert-butoxide (1.2 g, 10.7 mmol) at 0° C., and stirred at rt overnight. The solvent is removed under vacuum, the mixture is added saturated aqueous ammonium chloride and extracted with EtOAc, and passed through sodium sulfate. The solvent is removed under vacuum, the solid is triturated with isopropyl ether and filtered, the title compound is prepared in 81% yield (1.33 g, solid).
$^1$H-NMR (400 MHz, CDCl$_3$) delta 9.17 (1H, s), 8.32 (1H, s), 8.24 (1H, dd, J=7.2, 1.2 Hz), 7.48 (1H, s), 7.41 (1H, ddd, J=8.4, 6.8, 1.6 Hz), 6.86 (1H, ddd, J=8.8, 6.8, 0.8 Hz), 6.78 (1H, dd, J=8.7, 1.4 Hz), 2.27 (3H, s).
MS (ESI) m/z: 307.8 (M+H)+.

<Step-2>: N$^1$-(6-bromo-4-methylpyridin-3-yl)benzene-1,2-diamine

A mixture of 6-bromo-4-methyl-N-(2-nitrophenyl)pyridin-3-amine (1.33 g, 4.3 mmol, Step-1 of Intermediate-224), Fe (723 mg, 13.0 mmol), ammonium chloride (693 mg, 13.0 mmol) in ethanol (30 mL) and H$_2$O (10 mL) is stirred at 90° C. overnight. The mixture is passed through celite and washed with DCM. The solvent is added water and extracted with DCM, and passed through sodium sulfate. The solvent are removed under vacuum, the crude product is triturated with isopropyl ether and filtered, the title compound is prepared in 84% yield (1.01 g, solid).
$^1$H-NMR (400 MHz, CDCl$_3$) delta 7.66 (1H, s), 7.22 (1H, s), 7.17-6.89 (2H, m), 6.86-6.67 (2H, m), 4.97 (1H, s), 3.63 (2H, br), 2.23 (3H, s).
MS (ESI) m/z: 277.9 (M+H)+.

<Step-3>:1-(6-bromo-4-methylpyridin-3-yl)-1H-benzo[d]imidazol-2(3H)-one

To a mixture of N$^1$-(6-bromo-4-methylpyridin-3-yl)benzene-1,2-diamine (1.01 g, 3.6 mmol) in THF (20 mL) is added CDI (942 mg, 5.8 mmol) and stirred at rt for 2 days. The solvent is removed under vacuum, the mixture is added saturated aqueous ammonium chloride, extracted with DCM and passed through sodium sulfate. The solvent is removed under vacuum, the residue is washed with isopropyl ether and filtered, the title compound is prepared in 75% yield (826 mg, solid).
$^1$H-NMR (400 MHz, CDCl$_3$) delta 10.50 (1H, s), 8.38 (1H, s), 7.60 (1H, s), 7.20-7.11 (2H, m), 7.11-7.03 (1H, td, J=7.3, 1.8 Hz), 6.72 (1H, d, J=7.8 Hz), 2.26 (3H, s).
MS (ESI) m/z: 303.8 (M+H)+.

<Step-4>: N((1r,4r)-4-((3-(6-bromo-4-methylpyridin-3-yl)-2-oxo-2,3-dihydro-1H-benzo[d]imidazo 1-1-yl)methyl)cyclohexyl)-5-chloro-2-(difluoromethyl)nicotinamide The title compound (solid) is prepared in 80% yield by the similar manner to Intermediate-207 using 1-(6-bromo-4-methylpyridin-3-yl)-1H-benzo[d]imidazol-2(3H)-one (Step-3 of Intermediate-224) in place of Intermediate-39.
$^1$H-NMR (400 MHz, CDCl$_3$) delta 8.64 (1H, d, J=2.3 Hz), 8.33 (1H, s), 7.92 (1H, d, J=2.3 Hz), 7.56 (1H, s), 7.22-7.14 (1H, m), 7.12-7.04 (2H, m), 6.86 (1H, t, J=54.8 Hz), 6.78-6.72 (1H, m), 5.97 (1H, d, J=8.2 Hz), 4.05-3.88 (1H, m), 3.83 (2H, d, J=6.9 Hz), 2.21 (3H, s), 2.20-2.08 (2H, m), 2.05-1.81 (3H, m), 1.42-1.16 (4H, m).
MS (ESI) m/z: 605.8 (M+H)+.

Intermediate-225: 1-(5-(2-((tetrahydro-2H-pyran-2-yl)oxy)ethoxy)pyrazin-2-yl)-1H-benzo[d]imidazol-2(3H)-one The title compound is prepared in quantitative yield (pale yellow solid) by the similar manner to Intermediate-42 using 1-(5-chloropyrazin-2-yl)-1H-benzo[d]imidazol-2(3H)-one (Step-1 of Intermediate-57) in place of 1-(6-chloropyridazin-3-yl)-1H-benzo[d]imidazol-2(3H)-one.
MS (ESI) m/z: 357.1 (M+H)+.

Intermediate-226: 5-chloro-N-((1r,4r)-4-((3-(2-chloropyridin-4-yl)-2-oxo-2,3-dihydro-1H-benzo[d]imidazol-1-yl)methyl)cyclohexyl)-2-methylnicotinamide <Step-1>: tert-butyl 3-(2-chloropyridin-4-yl)-2-oxo-2,3-dihydro-1H-benzo[d]imidazole-1-carboxylate A mixture of tert-butyl 2-oxo-2,3-dihydro-1H-benzo[d]imidazole-1-carboxylate (28 mg, 0.12 mmol), copper (II) acetate (54 mg, 0.30 mmol), pyridine (0.029 mL, 0.36 mmol), and (2-chloropyridin-4-yl)boronic acid (47 mg, 0.30 mmol) in 1,2-dichloroethane (2 mL) is stirred overnight at 60° C. The reaction mixture is concentrated and the resultant residue is purified by column chromatography on silica-gel eluting with 4-100% EtOAc in n-hexane to give 5.2 mg (13% yield) of the title compound as a pale yellow solid.
MS (ESI) m/z: 346.1 (M+H)+.

<Step-2>: 5-chloro-N-((1r,4r)-4-((3-(2-chloropyridin-4-yl)-2-oxo-2,3-dihydro-1H-benzo[d]imidazol-1-yl)methyl)cyclohexyl)-2-methylnicotinamide A mixture of ((r,4r)-4-(5-chloro-2-methylnicotinamido)cyclohexyl)methyl methanesulfonate (14 mg, 0.038 mmol, Mesylate-1), tert-butyl 3-(2-chloropyridin-4-yl)-2-oxo-2,3-dihydro-1H-benzo[d]imidazole-1-carboxylate (5.2 mg, 0.14 mmol, Step-1 of Intermediate-226), and cesium carbonate (24 mg, 0.074 mmol) in DMSO (1 mL) is stirred for 2 hrs at 100° C. The mixture is diluted with saturated aqueous sodium chloride. The mixture is extracted with THF. After the organic layer is concentrated, the resultant residue is purified by a strong anion exchange cartridge (ISOLUTE (registered trademark) SCX-2, 1 g/6 mL, Biotage) to give 17 mg of the title compound as a crude. The compound is used for the next reaction without further purification.

MS (ESI) m/z: 510.0 (M+H)+.

Intermediate-227: 3-methyl-1-(tetrahydro-2H-pyran-2-yl)-6-(4,4,5,5-tetramethyl-1,3,2-dioxaborolan-2-yl)-1H-indazole A mixture of 6-bromo-3-methyl-1-(tetrahydro-2H-pyran-2-yl)-1H-indazole (136 mg, 0.46 mmol), bis(pinacolato) diboron (234 mg, 0.92 mmol), potassium acetate (90 mg, 0.92 mmol), palladium (II) acetate (10 mg, 0.046 mmol) and 2-(dicyclohexylphosphino)biphenyl (32 mg, 0.092 mmol) in 1,4-dioxane (0.5 mL) is stirred overnight at 80° C. The reaction mixture is concentrated and the resultant residue is purified by column chromatography on silica-gel eluting with 6-50% EtOAc in n-hexane to give 127 mg (81% yield) of the title compound as a colorless syrup.

MS (ESI) m/z: 342.9 (M+H)+.

Intermediate-228: N-methyl-5-(4-methyl-2-oxo-2,3-dihydro-1H-benzo[d]imidazol-1-yl)picolinamide The title compound is prepared in 36% yield in 4 steps by the similar manner to Step-1, Step-2, Step-3 and Step-4 of Intermediate-101 using 1-bromo-3-methyl-2-nitrobenzene in place of 2-bromo-1-methyl-3-nitrobenzene.

$^1$H-NMR (400 MHz, DMSO-$d_6$) delta 11.41 (1H, br s), 8.86 (1H, t, J=5.0 Hz), 8.83 (1H, br s), 8.19 (2H, d, J=1.8 Hz), 6.97-6.92 (3H. m), 2.85 (3H, d, J=5.0 Hz), 2.35 (3H, s).

MS (ESI) m/z: 283.3 (M+H)+.

Intermediate-229: 1-(3-methyl-1-((2-(trimethylsilyl)ethoxy)methyl)-1H-pyrrolo[2,3-b]pyridin-5-yl)-1H-imidazo[4,5-b]pyridin-2(3H)-one <Step-1>: 3-methyl-5-nitro-1-((2-(trimethylsilyl)ethoxy)methyl)-1H-pyrrolo[2,3-b]pyridine To a solution of 3-methyl-5-nitro-1H-pyrrolo[2,3-b]pyridine (300 mg, 1.84 mmol) in DMF (7 mL) is added sodium hydride (60% dispersion in mineral oil, 73.6 mg, 1.84 mmol) at 0° C. and stirred. After 30 min, to the mixture is added 2-(trimethylsilyl)ethoxymethyl chloride (0.49 mL, 2.76 mmol) and stirred at room temperature for 2 hrs. The reaction is quenched with saturated aqueous ammonium chloride (10 mL), extracted with EtOAc. The organic phase is dried over sodium sulfate, filtered and concentrated. The residue is purified by column chromatography on silica-gel eluting with 40-100% EtOAc in n-hexane to give 400 mg (70% yield) of the title compound.

$^1$H-NMR (400 MHz, CDCl$_3$) delta 9.21 (1H, d, J=2.3 Hz), 8.71 (1H, d, J=2.3 Hz), 7.23 (1H, s), 5.66 (2H, s), 3.54-3.50 (2H, m), 2.37 (3H, s), 0.94-0.89 (2H, m), −0.07 (9H, s).

MS (ESI) m/z: 308.3 (M+H)+.

<Step-2>: 3-methyl-1-((2-(trimethylsilyl)ethoxy)methyl)-1H-pyrrolo[2,3-b]pyridin-5-amine A mixture of 3-methyl-5-nitro-1-((2-(trimethylsilyl)ethoxy)methyl)-1H-pyrrolo[2,3-b]pyridine (400 mg. 1.30 mmol, Step-1 of Intermediate-229) and 10% Pd/C (143 mg) in MeOH (2 mL) is stirred under H$_2$ atmosphere for 4 hrs. The mixture is filtered through a pad of celite, and the filtrate is concentrated to give 350 mg (97% yield) of the title compound.

MS (ESI) m/z: 278.3 (M+H)+.

<Step-3>: 1-(3-methyl-1-((2-(trimethylsilyl)ethoxy)methyl)-1H-pyrrolo[2,3-b]pyridin-5-yl)-1H-imidazo[4,5-b]pyridin-2(3H)-one The title compound is prepared in 33% yield in 3 steps by the similar manner to Step-1, Step-2, and Step-3 of Intermediate-187 using 3-bromo-2-nitropyridine in place of 2-bromo-3-nitropyridine.

MS (ESI) m/z: 395.9 (M+H)+.

Intermediate-230: 4-(4-bromophenyl)-1-((2-(trimethylsilyl)ethoxy)methyl)-1H-pyrazole The title compound is prepared in 65% yield (205 mg, ale yellow oil) by the similar manner to Step-1 of Intermediate-229 using 4-(4-bromophenyl)-1H-pyrazole (100 mg, 0.45 mmol) in place of 3-methyl-5-nitro-1H-pyrrolo[2,3-b]pyridine.

$^1$H-NMR (400 MHz, CDCl$_3$) delta 7.77 (2H, d, J=3.7 Hz), 7.47 (2H, d, J=6.4 Hz), 7.34 (2H, d, J=6.4 Hz), 5.43 (2H, s), 3.78 (2H, dd, J=9.1, 8.2 Hz), 0.90 (2H, dd, J=9.1, 8.2 Hz), −0.03 (9H, s).

MS (ESI) m/z: 354.8 (M+H)+.

Intermediate-231: 5-chloro-2-(fluoromethyl)nicotinic acid

<Step-1>: benzyl 5-chloro-2-(hydroxymethyl)nicotinate

A mixture of 3-chlorofuro[3,4-b]pyridin-5 (7H)-one (113 mg, 0.67 mmol) and 2 M aqueous sodium hydroxide solution (0.18 mL, 0.36 mmol) in water (0.18 mL) is stirred at 80° C. for 2 hrs. After cooling, the mixture is concentrated. To the residue in DMF (1 mL) is added benzyl bromide (0.050 mL, 0.42 mmol) at 0° C. The mixture is stirred at room temperature overnight. The mixture is neutralized with 2 M hydrochloric acid, diluted with water, extracted with EtOAc. The organic phase is dried over sodium sulfate, filtered and concentrated. The residue is purified by column chromatography on silica-gel eluting with 50-100% EtOAc in n-hexane to give 50 mg (27% yield) of the title compound as a brown solid.

MS (ESI) m/z: 277.9 (M+H)+.

<Step-2>: benzyl 5-chloro-2-(fluoromethyl)nicotinate

To a solution of benzyl 5-chloro-2-(hydroxymethyl)nicotinate (10 mg, 0.022 mmol, Step-1 of Intermediate-231) in DCM (1 mL) is added bis(2-methoxyethyl)aminosulfur trifluoride (0.012 mL, 0.067 mmol) at 0° C., stirred for 0.5 hr. The mixture is diluted with saturated aqueous sodium bicarbonate, extracted with EtOAc. The organic phase is dried over sodium sulfate, filtered and concentrated to give 11 mg (quantitative yield) of the title compound as a brown solid.

$^1$H-NMR (400 MHz, CDCl$_3$) delta 8.74 (1H, d, J=2.3 Hz), 8.28 (1H, dd, J=2.3, 0.9 Hz), 7.47-7.38 (5H, m), 5.81 (2H, d, J=46.7 Hz), 5.39 (2H, s).

MS (ESI) m/z: 279.9 (M+H)+.

<Step-3>: 5-chloro-2-(fluoromethyl)nicotinic acid

The title compound is prepared in quantitative yield (8.5 mg, off-white solid) by the similar manner to Step-4 of Intermediate-2 using benzyl 5-chloro-2-(fluoromethyl)nicotinate (10 mg, 0.023 mmol, Step-2 of Intermediate-231) in place of methyl 3-((3-(((1r,4r)-4-(5-chloro-2-methylnicotinamido)cyclohexyl)methyl)-2-oxo-2,3-dihydro-1H-benzo[d]imidazol-1-yl)methyl)benzoate 3-methyl-5-nitro-1H-pyrrolo[2,3-b]pyridine.
MS (ESI) m/z: 189.9 (M+H)$^+$.

Intermediate-232: 1-(3-methylbenzo[d]isoxazol-5-yl)-1H-benzo[d]imidazol-2(3H)-one The title compound (solid) is prepared in 85% yield in 3 steps by the similar manner to Step-3, Step-4 and Step-5 of Intermediate-116 using 3-methylbenzo[d]isoxazol-5-amine in place of 1-(2-(methoxymethoxy)ethyl)-3-methyl-1H-indazol-5-amine (Step-2 of Intermediate-116).
$^1$H-NMR (400 MHz, CDCl$_3$) delta 8.22 (1H, brd, J=5.5 Hz), 7.86-7.83 (1H, m), 7.73-7.70 (1H, m), 7.19-7.02 (3H, m), 6.98 (1H, d, J=7.3 Hz), 6.51 (1H, dd, J=5.0, 1.4 Hz), 2.62 (3H, s).
MS (ESI) m/z: 266.3 (M+H)$^+$.

Intermediate-233: 3-(6-methoxypyridin-3-yl)-3,4-dihydroquinazolin-2 (1H)-one

<Step-1>: 6-methoxy-N-(2-nitrobenzyl)pyridin-3-amine

To a mixture of 2-nitrobenzaldehyde (50 mg, 0.329 mmol), 6-methoxypyridin-3-amine (49 mg, 0.394 mmol) and acetic acid (0.019 mL, 0.329 mmol) in DCM (2 mL) is added sodium triacetoxyborohydride (105 mg, 0.493 mmol) and stirred at rt overnight. The reaction mixture is washed with 2 M aqueous sodium hydroxide solution, dried over MgSO$_4$, filtered and concentrated. The residue is purified by column chromatography on silica-gel eluting with 5-80% EtOAc in n-hexane to give 67 mg (79% yield) of the title compound as a brown viscous oil.
$^1$H-NMR (400 MHz, CDCl$_3$) delta 8.06 (1H, dd, J=8.2, 1.4 Hz), 7.64 (1H, dd, J=7.5, 1.1 Hz), 7.58 (1H, td, J=7.5, 1.4 Hz), 7.51 (1H, d, J=3.2 Hz), 7.47-7.41 (1H, m), 6.95 (1H, dd, J=8.7, 3.2 Hz), 6.60 (1H, d, J=9.6 Hz), 4.67 (2H, s), 4.08 (1H, br s), 3.84 (3H, s).

<Step-2>: N-(2-aminobenzyl)-6-methoxypyridin-3-amine

A solution of the product of Step-1 of Intermediate-233 (42 mg, 0.162 mmol) in EtOAc is evacuated and backfilled with N$_2$ gas (three times). To this is added Pt-alumina (5%) (10 mg). Then the mixture is evacuated and backfilled with H$_2$ gas and stirred vigorously at rt for 1 hr. After the reaction mixture is evacuated and backfilled with N$_2$ gas, the mixture is filtered through celite pad. The filtrate is concentrated. The resultant residue is purified by column chromatography on silica-gel eluting with 0-10% MeOH in EtOAc to give 37 mg (quantitative yield) of the title compound as a yellow gum.
$^1$H-NMR (400 MHz, CDCl$_3$) delta 7.69 (1H, d, J=2.7 Hz), 7.18-7.12 (2H, m), 7.07 (1H, dd, J=8.7, 3.2 Hz), 6.78-6.70 (2H, m), 6.65 (1H, d, J=8.7 Hz), 4.22-4.15 (4H, m), 3.88 (3H, s), 3.41 (1H, s).

<Step-3>:3-(6-methoxypyridin-3-yl)-3,4-dihydroquinazolin-2 (1H)-one

To a solution of the product of Step-2 of Intermediate-233 (37 mg, 0.161 mmol) in THF (1 mL) is added CDI (49 mg, 0.302 mmol) and stirred at rt overnight. To the reaction mixture is added CDI (92 mg, 0.568 mmol) and stirred at rt for 1 hr. To this is added CDI (102 mg, 0.629 mmol) and stirred at rt for 30 min. To this is added further CDI (102 mg, 0.629 mmol) and stirred at rt for 30 min. The mixture is diluted with saturated sodium hydrogen carbonate aqueous solution. The mixture is extracted with EtOAc. The organic layer is dried over MgSO$_4$, filtered and concentrated. The resultant residue is purified by column chromatography on silica-gel eluting with 15-50% EtOAc in n-hexane to give 30 mg (73%) of the title compound as an ivory solid.
$^1$H-NMR (400 MHz, CDCl$_3$) delta 8.18 (1H, d, J=2.7 Hz), 7.63 (1H, dd, J=8.9, 3.0 Hz), 7.26-7.20 (1H, m), 7.10-7.08 (2H, m), 7.03-6.97 (1H, m), 6.79 (1H, d, J=8.2 Hz), 6.74 (1H, d, J=7.3 Hz), 4.81 (2H, s), 3.95 (3H, s).

Intermediate-234: 3-(4-chlorophenyl)-1H-imidazo[4,5-b]pyridin-2(3H)-one

The title compound (pale yellow solid) is prepared in 66% yield in 2 steps by the similar manner to Step-1 and Step-2 of Intermediate-98 using 4-chloroaniline in place of 2,3-dihydro-1H-inden-5-amine.
MS (ESI) m/z: 246.2 (M+H)$^+$.

Intermediate-235: tert-butyl 7-(3-(((1r,4r)-4-(5-chloro-2-(difluoromethyl)nicotinamido)cyclohexyl)methyl)-2-oxo-2,3-dihydro-1H-benzo[d]imidazol-1-yl)-3,4-dihydroisoquinoline-2 (1H)-carboxylate <Step-1>: tert-butyl 7-(2-oxo-2,3-dihydro-1H-benzo[d]imidazol-1-yl)-3,4-dihydroisoquinoline-2 (1H)-carboxylate The title compound is prepared in 52% yield (188 mg, pale yellow solid) by the similar manner to Step-2 of Intermediate-95 using tert-butyl 7-bromo-3,4-dihydroisoquinoline-2 (1H)-carboxylate (310 mg, 0.99 mmol) in place of 5-bromo-2,3-dimethyl-2H-indazole.
$^1$H-NMR (400 MHz, CDCl$_3$) delta 7.38-7.30 (3H, m), 7.18-6.97 (4H, m), 4.67 (2H, br s), 3.70 (2H, br s), 2.91 (2H, br s), 1.51 (9H, s). A signal due to NH is not observed.
MS (ESI) m/z: 367.2 (M+H)$^+$.

<Step-2>: tert-butyl 7-(3-(((1r,4r)-4-(5-chloro-2-(difluoromethyl)nicotinamido)cyclohexyl)methyl)-2-oxo-2,3-dihydro-1H-benzo[d]imidazol-1-yl)-3,4-dihydroisoquinoline-2 (1H)-carboxylate The title compound is prepared in 97% yield (138 mg, pale yellow solid) by the similar manner to Step-2 of Intermediate-57 using Mesylate-4 (85 mg, 0.21 mmol) and tert-butyl 7-(2-oxo-2,3-dihydro-1H-benzo[d]imidazol-1-yl)-3,4-dihydroisoquinoline-2 (1H)-carboxylate (78 mg, 0.21 mmol, Step-1 of Intermediate-235) in place of Mesylate-1 and 1-(5-chloropyrazin-2-yl)-1H-benzo[d]imidazol-2(3H)-one.
MS (ESI) m/z: 666.4 (M+H)$^+$.

Intermediate-236: 3-(6-methylquinolin-3-yl)-1H-imidazo[4,5-b]pyridin-2(3H)-one

The title compound (gray solid) is prepared in 83% yield in 2 steps by the similar manner to Step-1 and Step-2 of Intermediate-98 using 6-methylquinolin-3-amine in place of 2,3-dihydro-1H-inden-5-amine.

$^1$H-NMR (400 MHz, DMSO-d$_6$) 9.14 (1H, d, J=2.3 Hz), 8.58 (1H, d, J=2.3 Hz), 8.01-7.97 (2H, m), 7.85 (1H, s), 7.66 (1H, dd, J=8.7, 1.8 Hz), 7.46 (1H, dd, J=7.8, 1.4 Hz), 7.15 (1H, dd, J=7.8, 5.0 Hz), 2.54 (3H, s). A signal due to NH is not observed.

MS (ESI) m/z: 277.0 (M+H)$^+$.

Intermediate-237: 3-(2-chloro-4-fluorophenyl)-1H-imidazo[4,5-b]pyridin-2(3H)-one The title compound is prepared in 29% yield in 3 steps by the similar manner to Step-1, Step-2, and Step-3 of Intermediate-198 using 2-chloro-4-fluoroaniline in place of 2-chloro-4-methylaniline.

$^1$H-NMR (400 MHz, CDCl$_3$) delta 11.42 (1H, br s), 7.87 (1H, dd, J=5.5, 1.4 Hz), 7.74 (1H, dd, J=8.7, 3.2 Hz), 7.70 (1H, dd, J=8.6, 5.9 Hz), 7.44 (1H, dd, J=8.7, 3.2 Hz), 7.41 (1H, dd, J=8.7, 3.2 Hz), 7.08 (1H, dd, J=7.8, 2.3 Hz).

MS (ESI) m/z: 263.8 (M+H)$^+$.

Intermediate-238: 3-(3-chloro-4-methylphenyl)-1H-imidazo[4,5-b]pyridin-2(3H)-one The title compound (pale yellow solid) is prepared in 97% yield in 2 steps by the similar manner to Step-1 and Step-2 of Intermediate-98 using 3-chloro-4-methylaniline in place of 2,3-dihydro-1H-inden-5-amine.

$^1$H-NMR (400 MHz, DMSO-d$_6$) delta 11.47 (1H, br s), 7.96 (1H, dd, J=5.0, 1.4 Hz), 7.79 (1H, d, J=2.3 Hz), 7.61 (1H, dd, J=8.2, 2.3 Hz), 7.50 (1H, d, J=8.2 Hz), 7.41 (1H, dd, J=8.7, 1.4 Hz), 7.11 (1H, dd, J=7.8, 5.0 Hz), 2.40 (3H, s).

MS (ESI) m/z: 260.2 (M+H)$^+$.

Intermediate-239: 2-(2-oxo-1H-imidazo[4,5-b]pyridin-3(2H)-yl)benzonitrile

The title compound (pale yellow solid) is prepared in 29% yield in 3 steps by the similar manner to Step-1, Step-2, and Step-3 of Intermediate-208 using 2-aminobenzonitrile in place of 2-amino-4-methoxybenzonitrile.

$^1$H-NMR (400 MHz, DMSO-d$_6$) delta 11.55 (1H, br s), 8.09 (1H, dd, J=7.8, 1.4 Hz), 7.95-7.88 (2H, m), 7.76 (1H, dd, J=7.3, 1.4 Hz), 7.71 (1H, td, J=7.8, 1.4 Hz), 7.46 (1H, dd, J=7.8, 1.4 Hz), 7.14 (1H, dd, J=7.8, 5.0 Hz).

MS (ESI) m/z: 237.4 (M+H)$^+$.

Intermediate-240: 5-fluoro-1-(6-(methylamino)pyridin-3-yl)-1H-benzo[d]imidazol-2(3H)-one The title compound (brown solid) is prepared in 70% yield in 3 steps by the similar manner to Step-1, Step-2, and Step-3 of Intermediate-193 using 1-bromo-4-fluoro-2-nitrobenzene in place of 1-bromo-2-nitrobenzene and N$^2$-methylpyridine-2,5-diamine in place of N$^2$-(2,2,2-trifluoroethyl)pyridine-2,5-diamine.

MS (ESI) m/z: 259.2 (M+H)$^+$.

Intermediate-241: 6-fluoro-1-(6-(methylamino)pyridin-3-yl)-1H-benzo[d]imidazol-2(3H)-one The title compound (brown solid) is prepared in 49% yield in 3 steps by the similar manner to Step-1, Step-2, and Step-3 of Intermediate-193 using 2-bromo-4-fluoro-1-nitrobenzene in place of 1-bromo-2-nitrobenzene and N$^2$-methylpyridine-2,5-diamine in place of N$^2$-(2,2,2-trifluoroethyl)pyridine-2,5-diamine.

MS (ESI) m/z: 259.2 (M+H)$^+$.

Intermediate-242: 5-(7-methoxy-2-oxo-2,3-dihydro-1H-benzo[d]imidazol-1-yl)-N-methylpicolinamide The title compound is prepared in 30% yield in 4 steps by the similar manner to Step-1, Step-2, Step-3 and Step-4 of Intermediate-118 using 2-fluoro-1-methoxy-3-nitrobenzene in place of 1,2-difluoro-3-nitrobenzene.

MS (ESI) m/z: 299.1 (M+H)$^+$.

Intermediate-243: 1-(2-chloro-5-methoxyphenyl)-1H-imidazo[4,5-c]pyridin-2(3H)-one The title compound (pale yellow gum) is prepared in 29% yield in 2 steps by the similar manner to Step-1 and Step-2 of Intermediate-98 using 2-chloro-5-methoxyaniline and 4-chloronicotinic acid in place of 2,3-dihydro-1H-inden-5-amine and 2-chloronicotinic acid.

$^1$H-NMR (400 MHz, DMSO-d$_6$) delta 11.47 (1H, br s), 8.31 (1H, s), 8.17 (1H, d, J=5.5 Hz), 7.63 (1H, d, J=9.1 Hz), 7.28 (1H, d, J=3.2 Hz), 7.18 (1H, dd, J=9.1, 3.2 Hz), 6.75 (1H, d, J=5.5 Hz), 3.81 (3H, s).

MS (ESI) m/z: 276.2 (M+H)$^+$.

Intermediate-244: 1-(2-chloro-5-fluorophenyl)-1H-imidazo[4,5-c]pyridin-2(3H)-one The title compound (pale yellow solid) is prepared in 47% yield in 2 steps by the similar manner to Step-1 and Step-2 of Intermediate-98 using 2-chloro-5-fluoroaniline and 4-chloronicotinic acid in place of 2,3-dihydro-1H-inden-5-amine and 2-chloronicotinic acid.

$^1$H-NMR (400 MHz, DMSO-d$_6$) delta 11.54 (1H, br s), 8.33 (1H, s), 8.18 (1H, d, J=5.5 Hz), 7.82 (1H, dd. J=9.1, 5.5 Hz), 7.74 (1H, dd, J=9.1, 3.2 Hz), 7.52 (1H, ddd, J=9.1, 8.2, 3.2 Hz), 6.81 (1H, dd, J=5.5, 0.9 Hz).

MS (ESI) m/z: 264.2 (M+H)$^+$.

Intermediate-245: N-((1r,4r)-4-((3-(6-bromopyridin-3-yl)-2-oxo-2,3-dihydro-1H-benzol[d]imidazol-1-yl)methyl)cyclohexyl)-5-chloro-2-(trifluoromethyl)nicotinamide The title compound is prepared in 87% yield (solid) by the similar manner to Step-2 of Intermediate-57 using Intermediate-39 and Mesylate-3 in place of 1-(5-chloropyrazin-2-yl)-1H-benzo[d]imidazol-2(3H)-one and Mesylate-1.

$^1$H-NMR (400 MHz, CDCl$_3$) delta 8.67 (1H, d, J=2.3 Hz), 8.64 (1H, d, J=2.7 Hz), 7.88 (1H, d, J=2.4 Hz), 7.84 (1H, dd, J=8.7, 2.7 Hz), 7.66 (1H, d, J=8.4 Hz), 7.24-7.16 (1H, m), 7.14-7.10 (2H, m), 7.08 (1H, d, J=7.6 Hz), 5.69 (1H, d, J=8.2 Hz), 4.02-3.88 (1H, m), 3.81 (2H, d, J=6.9 Hz), 2.15 (2H, br d, J=9.6 Hz), 2.00-1.82 (3H, m), 1.41-1.12 (4H, m).

MS (ESI) m/z: 609.7 (M+H)$^+$.

Intermediate-246: 5-chloro-N-((1r,4r)-4-((3-(6-fluoropyridin-3-yl)-2-oxo-2,3-dihydro-1H-benzo[d]imidazol-1-yl)methyl)cyclohexyl)-2-(trifluoromethyl)nicotinamide The title compound is prepared in 85% yield (112 mg, yellow solid) by the similar manner to Intermediate-54 using Mesylate-3 (100 mg, 0.241 mmol) in place of Mesylate-1.

¹H-NMR (400 MHz, DMSO-d₆) delta 8.66 (1H, d, J=2.3 Hz), 8.37 (1H, d, J=7.8 Hz), 8.28 (1H, d, J=2.3 Hz), 8.07-8.00 (2H, m), 7.22 (1H, dd, J=8.7, 3.2 Hz), 7.15 (1H, d, J=7.8 Hz), 7.01-6.93 (1H, m), 6.91-6.85 (2H, m), 3.57 (2H, d, J=6.9 Hz), 3.54-3.38 (1H, m), 1.75-1.66 (2H, m), 1.66-1.50 (3H, m), 1.11-0.88 (4H, m).

MS (ESI) m/z: 548.2 (M+H)⁺.

Intermediate-247: 4-fluoro-1-(6-(methylamino)pyridin-3-yl)-1H-benzo[d]imidazol-2(3H)-one The title compound (brown solid) is prepared in 57% yield in 3 steps by the similar manner to Step-1, Step-2, and Step-3 of Intermediate-193 using 1-bromo-3-fluoro-2-nitrobenzene in place of 1-bromo-2-nitrobenzene and $N^2$ methylpyridine-2,5-diamine in place of $N^2$-(2,2,2-trifluoroethyl)pyridine-2,5-diamine.

¹H-NMR (400 MHz, DMSO-d₆) delta 11.42 (1H, s), 7.86 (1H, d, J=2.6 Hz), 7.27 (1H, dd, J=8.8, 2.6 Hz), 6.84-6.71 (2H, m), 6.68-6.60 (1H, m), 6.47 (1H, dd, J=7.3, 1.4 Hz), 6.39 (1H, d, J=8.8 Hz), 2.62 (3H, d, J=4.6 Hz).

MS (ESI) m/z: 259.2 (M+H)⁺.

Intermediate-248: 2-methyl-5-(4,4,5,5-tetramethyl-1,3,2-dioxaborolan-2-yl)-1-((2-(trimethylsilyl)ethoxy)methyl)-1H-pyrrolo[2,3-b]pyridine <Step-1>: 5-bromo-2-methyl-1-((2-(trimethylsilyl)ethoxy)methyl)-1H-pyrrolo[2,3-b]pyridine To a solution of 5-bromo-2-methyl-1H-pyrrolo[2,3-b]pyridine (100 mg, 0.47 mmol) in THF (1 mL) and DMF (1 mL) is added sodium hydride (60% dispersion in mineral oil, 20 mg, 0.50 mmol) at 0° C. The mixture is stirred at room temperature for 30 min. To the mixture is added 2-(trimethylsilyl)ethoxymethyl chloride (0.10 mL, 0.57 mmol) at 0° C. The mixture is stirred at room temperature for 30 min. The reaction is diluted with water at 0° C., extracted with EtOAc. The organic phase is dried over sodium sulfate, filtered and concentrated. The residue is purified by column chromatography on silica-gel eluting with 0-15% EtOAc in n-hexane to give 161 mg (quantitative yield) of the title compound.

MS (ESI) m/z: 342.8 (M+H)⁺.

<Step-2>: 2-methyl-5-(4,4,5,5-tetramethyl-1,3,2-dioxaborolan-2-yl)-1-((2-(trimethylsilyl)ethoxy)methyl)-1H-pyrrolo[2,3-b]pyridine A solution of 5-bromo-2-methyl-1-((2-(trimethylsilyl)ethoxy)methyl)-1H-pyrrolo[2,3-b]pyridine (72 mg, 0.19 mmol, Step-1 of Intermediate-248), bis(pinacolato)diboron (57 mg, 0.22 mmol), potassium acetate (55 mg, 0.56 mmol) and [1,1'-bis(diphenylphosphino)ferrocene]palladium(II) dichloride dichloromethane adduct (15 mg, 0.019 mmol) in 1,4-dioxane (2.5 mL) is stirred at 80° C. overnight. The mixture is concentrated. The residue is purified by column chromatography on amine-gel eluting with 0-20% EtOAc in n-hexane to give 13 mg (16% yield) of the title compound as a pale yellow syrup.

Intermediate-249: 1-(2-chloro-5-methoxyphenyl)-1H-imidazo[4,5-b]pyridin-2(3H)-one <Step-1>: N-(2-chloro-5-methoxyphenyl)-2-nitropyridin-3-amine The title compound is prepared in 79% yield (228 mg, pale yellow solid) by the similar manner to Step-1 of Intermediate-101 using 3-bromo-2-nitropyridine (250 mg, 1.23 mmol) and 2-chloro-5-methoxyaniline (162 mg, 1.03 mmol) in place of 2-bromo-1-methyl-3-nitrobenzene and methyl 5-aminopicolinate.

¹H-NMR (400 MHz, CDCl₃) delta 9.16 (1H, br s), 8.07 (1H, dd, J=4.1, 1.4 Hz), 7.63 (1H, dd, J=8.7, 1.4 Hz), 7.43 (1H, d, J=8.7, 4.1 Hz), 7.42 (1H, d, J=9.2 Hz), 6.93 (1H, d, J=2.7 Hz), 6.78 (1H, dd, J=9.2, 2.7 Hz), 3.81 (3H, s).

MS (ESI) m/z: 280.2 (M+H)⁺.

<Step-2>: $N^3$-(2-chloro-5-methoxyphenyl)pyridine-2,3-diamine

The title compound is prepared in quantitative yield (204 mg, brown gum) by the similar manner to Step-2 of Intermediate-20 using methyl N-(2-chloro-5-methoxyphenyl)-2-nitropyridin-3-amine (228 mg, 0.82 mmol, Step-1 of Intermediate-249) in place of 2,4-difluoro-N-(2-nitrophenyl) aniline.

MS (ESI) m/z: 250.2 (M+H)⁺.

<Step-3>:1-(2-chloro-5-methoxyphenyl)-1H-imidazo[4,5-b]pyridin-2(3H)-one

A mixture of $N^3$-(2-chloro-5-methoxyphenyl)pyridine-2,3-diamine (204 mg, 0.82 mmol, Step-2 of Intermediate-249) and CDI (331 mg, 2.04 mmol) in THF (3 mL) is stirred at room temperature for 1 day. The mixture is quenched with 10% aqueous citric acid solution. The precipitate is collected and washed with diisopropyl ether to give 194 mg (96% yield) of the title compound as a pale yellow solid.

¹H-NMR (400 MHz, DMSO-d₆) delta 11.88 (1H, s), 7.99 (1H, dd, J=4.1, 2.3 Hz), 7.62 (1H, d, J=8.7 Hz), 7.29 (1H, d, J=2.7 Hz), 7.16 (1H, dd, J=8.7, 2.7 Hz), 7.01 (1H, s), 7.00 (1H, d, J=2.3 Hz), 3.80 (3H, s).

MS (ESI) m/z: 276.2 (M+H)⁺.

Intermediate-250: 1-(2-chloro-5-fluorophenyl)-1H-imidazo[4,5-b]pyridin-2(3H)-one The title compound (pale yellow solid) is prepared in 82% yield in 3 steps by the similar manner to Step-1, Step-2, and Step-3 of Intermediate-249 using 2-chloro-5-fluoroaniline in place of 2-chloro-5-methoxyaniline.

¹H-NMR (400 MHz, DMSO-d₆) delta 11.95 (1H, s), 8.01 (1H, dd, J=5.0, 1.4 Hz), 7.81 (1H, dd, J=9.1, 5.5 Hz), 7.73 (1H, dd, J=9.1, 3.2 Hz), 7.51 (1H, ddd, J=9.1, 7.8, 3.2 Hz), 7.09 (1H, dd, J=7.8, 1.4 Hz), 7.02 (1H, dd, J=7.8, 5.0 Hz).

MS (ESI) m/z: 264.2 (M+H)⁺.

Intermediate-251: 1-(4-fluoro-3-methoxyphenyl)-1H-imidazo[4,5-b]pyridin-2(3H)-one The title compound (pale yellow solid) is prepared in 76% yield in 3 steps by the similar manner to Step-1, Step-2, and Step-3 of Intermediate-249 using 4-fluoro-3-methoxyaniline in place of 2-chloro-5-methoxyaniline.

¹H-NMR (400 MHz, DMSO-d₆) delta 11.85 (1H, br s), 7.99 (1H, dd, J=5.0, 1.4 Hz), 7.42-7.31 (3H, m), 7.14-7.10 (1H, m), 7.03 (1H, dd, J=7.8, 5.0 Hz), 3.87 (3H, s).

MS (ESI) m/z: 260.2 (M+H)⁺.

Intermediate-252: N-((1r,4r)-4-((3-(2-bromopyridin-4-yl)-2-oxo-2,3-dihydro-1H-benzo[d]imidazol-1-yl)methyl)cyclohexyl)-5-chloro-2-methylnicotinamide <Step-1>: 2-bromo-N-(2-nitrophenyl)pyridin-4-amine The title compound is prepared in 50% yield (208 mg, brown solid) by the similar manner to Step-1 of Intermediate-20 using 2-bromopyridin-4-amine (200 mg, 1.42 mmol) in place of 2,4-difluoroaniline.

$^1$H-NMR (400 MHz, CDCl$_3$) delta 9.20 (1H, s), 8.28-8.19 (2H, m), 7.64-7.56 (2H, m), 7.32 (1H, d, J=2.4 Hz), 7.15-7.07 (1H, m), 7.05 (1H, dd, J=5.7, 2.4 Hz).

MS (ESI) m/z: 296.0 (M+H)$^+$.

<Step-2>: N$^1$-(2-bromopyridin-4-yl)benzene-1,2-diamine

The title compound is prepared in 99% yield (185 mg, orange solid) by the similar manner to Step-2 of Intermediate-151 using 2-bromo-N-(2-nitrophenyl)pyridin-4-amine (208 mg, 0.707 mmol, Step-1 of Intermediate-252) in place of methyl 4-methyl-5-((2-methyl-6-nitrophenyl)amino)picolinate.

MS (ESI) m/z: 264.0 (M+H)$^+$.

<Step-3>: 1-(2-bromopyridin-4-yl)-1H-benzo[d]imidazol-2(3H)-one

The title compound is prepared in 88% yield (178 mg, pale yellow solid) by the similar manner to Step-3 of Intermediate-193 using N$^1$-(2-bromopyridin-4-yl)benzene-1,2-diamine (185 mg, 0.700 mmol, Step-2 of Intermediate-252) in place of N-(2-aminophenyl)-N$^2$ (2,2,2-trifluoroethyl)pyridine-2,5-diamine.

$^1$H-NMR (400 MHz, DMSO-d$_6$) delta 11.24 (1H, s), 8.33 (1H, d, J=5.3 Hz), 7.75 (1H, d, J=1.8 Hz), 7.56 (1H, dd, J=5.3, 1.8 Hz), 7.12 (1H, d, J=8.2 Hz), 7.01-6.79 (3H, m).

MS (ESI) m/z: 292.1 (M+H)$^+$.

<Step-4>: N((1r,4r)-4-((3-(2-bromopyridin-4-yl)-2-oxo-2,3-dihydro-1H-benzo[d]imidazol-1-yl)methyl)cyclohexyl)-5-chloro-2-methylnicotinamide The title compound is prepared in 94% yield (160 mg, pale yellow solid) by the similar manner to Step-3 of Intermediate-3 using 1-(2-bromopyridin-4-yl)-1H-benzo[d]imidazol-2(3H)-one (89 mg, 0.31 mmol, Step-3 of Intermediate-252) in place of methyl 2-((2-oxo-2,3-dihydro-1H-benzo[d]imidazol-1-yl)methyl)benzoate.

$^1$H-NMR (400 MHz, CDCl$_3$) delta 8.52 (1H, d, J=5.4 Hz), 8.49 (1H, d, J=2.3 Hz), 7.88 (1H, d, J=2.0 Hz), 7.64 (1H, dd, J=5.4, 2.0 Hz), 7.61 (1H, d, J=2.3 Hz), 7.32 (1H, d, J=7.8 Hz), 7.25-7.20 (1H, m), 7.16 (1H, t, J=7.8 Hz), 7.09 (1H, d, J=7.8 Hz), 5.54 (1H, d, J=8.2 Hz), 4.01-3.89 (1H, m), 3.81 (2H, d, J=6.9 Hz), 2.61 (3H, s), 2.24-2.10 (2H, m), 1.98-1.86 (3H, m), 1.39-1.12 (4H, m).

MS (ESI) m/z: 556.0 (M+H)$^+$.

Intermediate-253: 3-(2-chloro-5-methoxyphenyl)-1H-imidazo[4,5-c]pyridin-2(3H)-one The title compound (pale yellow solid) is prepared in 82% yield in 3 steps by the similar manner to Step-1, Step-2, and Step-3 of Intermediate-249 using 3-bromo-4-nitropyridine in place of 3-bromo-2-nitropyridine.

$^1$H-NMR (400 MHz, DMSO-d$_6$) delta 11.72 (1H, br s), 8.23 (1H, d, J=5.5 Hz), 7.87 (1H, s), 7.63 (1H, d, J=8.7 Hz), 7.43 (1H, d, J=8.2 Hz), 7.20-7.13 (2H, m), 3.81 (3H, s).

MS (ESI) m/z: 276.2 (M+H)$^+$.

Intermediate-254: 3-(3-fluorophenyl)-1H-imidazo[4,5-c]pyridin-2(3H)-one

The title compound (pale yellow solid) is prepared in 82% yield in 3 steps by the similar manner to Step-1, Step-2, and Step-3 of Intermediate-249 using 2-chloro-5-fluoroaniline and 3-bromo-4-nitropyridine in place of 2-chloro-5-methoxyaniline and 3-bromo-2-nitropyridine.

$^1$H-NMR (400 MHz, DMSO-d$_6$) delta 11.78 (1H, br s), 8.30 (1H, s), 8.26 (1H, d, J=5.0 Hz), 7.66-7.59 (1H, m), 7.53 (1H, dt, J=10.1, 2.3 Hz), 7.50-7.47 (1H, m), 7.31 (1H, td, J=10.1, 2.7 Hz), 7.16 (1H, d, J=4.6 Hz).

MS (ESI) m/z: 230.3 (M+H)$^+$.

Intermediate-255: 5-bromo-2-(1-((2-(trimethylsilyl)ethoxy)methyl)-1H-imidazol-2-yl)pyridine Under an atmosphere of nitrogen at 0° C., a solution of 5-bromo-2-(1H-imidazol-2-yl)pyridine (100 mg, 0.446 mm) in THF (2 mL) is treated with portionwise addition of sodium hydride (60% dispersion in mineral oil, 20 mg, 0.491 mmol). After stirring for 30 min at 0° C., 2-(trimethylsilyl)ethoxymethyl chloride (0.103 mL, 0.580 mmol) is added and the mixture is stirred for 1 hr at 0° C. The reaction mixture is poured into water and is extracted with EtOAc. The organic layers are dried over sodium sulfate, filtered and concentrated under vacuum to afford crude product. The crude product is purified by column chromatography on silica gel eluting with 0-100% EtOAc in n-hexane to give 137 mg (87% yield) of the title compound.

$^1$H-NMR (400 MHz, CDCl$_3$) delta 8.63 (1H, d, J=2.3 Hz), 8.11 (1H, d, J=8.7 Hz), 7.89 (1H, dd, J=8.7, 2.3 Hz), 7.22 (1H, d, J=1.4 Hz), 7.17 (1H, d, J=1.4 Hz), 6.00 (2H, s), 3.56-3.52 (2H, m), 0.91-0.86 (2H, m), −0.07 (9H, s).

Intermediate-256: 4-(3-bromophenyl)-1-((2-(trimethylsilyl)ethoxy)methyl)-1H-pyrazole The title compound is prepared in 64% yield (67 mg) by the similar manner to Intermediate-255 using 4-(3-bromophenyl)-1H-pyrazole (66 mg, 0.291 mmol) in place of 5-bromo-2-(1H-imidazol-2-yl)pyridine.

$^1$H-NMR (400 MHz, CDCl$_3$) delta 7.82 (1H, d, J=0.9 Hz), 7.80 (1H, br), 7.65 (1H, dd, J=1.8, 1.8 Hz), 7.44-7.41 (1H, m), 7.38-7.35 (1H, m), 7.26-7.22 (1H, m), 5.46 (2H, s), 3.62-3.58 (2H, m), 0.95-0.91 (2H, m), −0.01 (9H, s).

Intermediate-257: tert-butyl 4-(4-bromopyridin-2-yl)-1H-pyrazole-1-carboxylate

A mixture of tert-butyl 4-(4,4,5,5-tetramethyl-1,3,2-dioxaborolan-2-yl)-1H-pyrazole-1-carboxylate (100 mg, 0.340 mmol), 2,4-dibromopyridine (81 mg, 0.340 mmol), Pd(PPh$_3$)$_4$ (39 mg, 0.034 mmol) and Cs$_2$CO$_3$ (332 mg, 1.020 mmol) in 1,4-dioxane (3 mL) is stirred at 80° C. for 1 hr. The reaction mixture is poured into water and extracted EtOAc. The organic layer is dried over sodium sulfate, filtered and concentrated. The residue is purified by column chromatography on silica-gel eluting with 0-50% EtOAc in n-hexane to give 23 mg (21% yield) of the title compound as colorless oil.

$^1$H-NMR (400 MHz, CDCl$_3$) delta 8.59 (1H, d, J=0.7 Hz), 8.44-8.41 (1H, m), 8.20 (1H, d, J=0.7 Hz), 7.72-7.69 (1H, m), 7.36 (1H, dd, J=5.3, 1.8 Hz), 1.68 (9H, s). MS (ESI) m/z: 324.0 (M+H)$^+$.

Intermediate-258: 4-bromo-2-(1-methyl-1H-pyrazol-3-yl)pyridine

A mixture of 1-methyl-3-(4,4,5,5-tetramethyl-1,3,2-dioxaborolan-2-yl)-1H-pyrazole (44 mg, 0.211 mmol), 2,4-dibromopyridine (50 mg, 0.211 mmol), Pd(PPh$_3$)$_4$ (24 mg, 0.021 mmol) and Cs$_2$CO$_3$ (206 mg, 0.633 mmol) in 1,4-dioxane (2 mL) is stirred at 80° C. for 1 hr. The reaction mixture is concentrated. The residue is purified by column chromatography on silica-gel eluting with 0-50% EtOAc in n-hexane to give 33 mg (66% yield) of the title compound as pale yellow oil.

$^1$H-NMR (400 MHz, CDCl$_3$) delta 8.42 (1H, d, J=5.2 Hz), 8.11 (1H, d, J=1.6 Hz), 7.42 (1H, d, J=2.2 Hz), 7.35 (1H, dd, J=5.2, 1.6 Hz), 6.86 (1H, d, J=2.2 Hz), 3.99 (3H, s). MS (ESI) m/z: 238.0 (M+H)$^+$.

Intermediate-259: N-((1r,4r)-4-((3-(2-bromopyridin-4-yl)-2-oxo-2,3-dihydro-1H-benzo[d]imidazol-1-yl)methyl)cyclohexyl)-5-chloro-2-(difluoromethyl)nicotinamide The title compound is prepared in 91% yield (165 mg, brown solid) by the similar manner to Step-4 of Intermediate-252 using ((1r,4r)-4-(5-chloro-2-(difluoromethyl)nicotinamido)cyclohexyl)methyl methanesulfonate (122 mg, 0.307 mmol, Mesylate-4) in place of ((1r,4r)-4-(5-chloro-2-methylnicotinamido)cyclohexyl)methyl methanesulfonate.

$^1$H-NMR (400 MHz, CDCl$_3$) delta 8.64 (1H, d, J=2.3 Hz), 8.51 (1H, d, J=5.4 Hz), 7.92 (1H, d, J=2.3 Hz), 7.87 (1H, d, J=2.0 Hz), 7.64 (1H, dd, J=5.4, 2.0 Hz), 7.32 (1H, d, J=7.8 Hz), 7.25-7.21 (1H, m), 7.16 (1H, t, J=7.8 Hz), 7.08 (1H, d, J=6.9 Hz), 6.84 (1H, t, J=54.7 Hz), 5.86 (1H, d, J=7.3 Hz), 4.04-3.88 (1H, m), 3.80 (2H, d, J=6.9 Hz), 2.16 (2H, d, J=11.0 Hz), 2.00-1.83 (3H, m), 1.39-1.10 (4H, m).
MS (ESI) m/z: 592.0 (M+H)$^+$.

Intermediate-260: 3-(3-fluoro-4-methoxyphenyl)-1H-imidazo[4,5-b]pyridin-2(3H)-one The title compound is prepared in quantitative yield in 2 steps by the similar manner to Step-1 and Step-2 of Intermediate-99 using 3-fluoro-4-methoxyaniline in place of 4-methoxyaniline.

$^1$H-NMR (400 MHz, DMSO-d$_6$) delta 7.73 (1H, dd, J=13.3, 2.3 Hz), 7.67-7.63 (2H, m), 7.24 (1H, t, J=9.6 Hz), 7.11 (1H, dd, J=7.3, 1.4 Hz), 6.86 (1H, dd, J=7.3, 5.0 Hz), 3.87 (3H, s). A signal due to NH is not observed.
MS (ESI) m/z: 260.1 (M+H)$^+$.

Intermediate-261: 1-(6-(3-((tetrahydro-2H-pyran-2-yl)oxy)propyl)pyridin-3-yl)-1H-benzo[d]imidazol-2(3H)-one <Step-1>: 1-(6-(3-((tetrahydro-2H-pyran-2-yl)oxy)prop-1-yn-1-yl)pyridin-3-yl)-1H-benzo[d]imidazol-2(3H)-one A mixture of 1-(6-bromopyridin-3-yl)-1H-benzo[d]imidazol-2(3H)-one (50 mg, 0.17 mmol, Intermediate-39), 2-(prop-2-yn-1-yloxy)tetrahydro-2H-pyran (48 mg, 0.35 mmol), CuI (7 mg, 0.034 mmol), [1,1'-bis(diphenylphosphino)ferrocene]palladium(II) dichloride dichloromethane adduct (28 mg, 0.034 mmol) and TEA (0.096 mL, 0.69 mmol) in DMF (3 mL) is stirred at 65° C. for 1 day. The mixture is diluted with water, extracted with EtOAc. The organic phase is dried over sodium sulfate, filtered and concentrated to give the title compound as a crude. The crude is used next step without purification.
MS (ESI) m/z: 349.8 (M+H)$^+$.

<Step-2>: 1-(6-(3-((tetrahydro-2H-pyran-2-yl)oxy)propyl)pyridin-3-yl)-1H-benzo[d]imidazol-2(3H)-one A mixture of 1-(6-(3-((tetrahydro-2H-pyran-2-yl)oxy)prop-1-yn-1-yl)pyridin-3-yl)-1H-benzo[d]imidazol-2(3H)-one (crude, 0.17 mmol, Step-1 of Intermediate-261) and 10% Pd/C (37 mg) in MeOH (1 mL) and THF (0.5 mL) is stirred under H$_2$ atmosphere for 3 hrs. The mixture is filtered through a pad of celite and the filtrate is concentrated to give the title compound as a crude. The crude is used next step without purification.
MS (ESI) m/z: 353.9 (M+H)$^+$.

Intermediate-262: 5-chloro-2-(difluoromethyl)-N-((1r,4r)-4-((6-fluoro-3-(6-fluoropyridin-3-yl)-2-oxo-2,3-dihydro-1H-benzo[d]imidazol-1-yl)methyl)cyclohexyl)nicotinamide The title compound is prepared in 31% in 4 steps by the similar manner to Step-1, Step-2, Step-3, and Step-4 of Intermediate-224 using 6-fluoropyridin-3-amine and 1,4-difluoro-2-nitrobenzene in place of 6-bromo-4-methylpyridin-3-amine and 1-fluoro-2-nitrobenzene.

$^1$H-NMR (400 MHz, CDCl$_3$) delta 8.64 (1H, d, J=2.3 Hz), 8.44 (1H, br d, J=1.4 Hz), 8.02 (1H, ddd, J=8.4, 6.8, 2.8 Hz), 7.92 (1H, d, J=1.8 Hz), 7.13 (1H, dd, J=8.7, 3.2 Hz), 6.98 (1H, dd, J=9.1, 4.1 Hz), 6.89-6.77 (2H, m), 6.85 (1H, t, J=54.4 Hz), 5.97 (1H, d, J=7.3 Hz), 4.09-3.88 (1H, m), 3.78 (2H, d, J=6.9 Hz), 2.17 (2H, d, J=10.5 Hz), 2.04-1.80 (3H, m), 1.43-1.11 (4H, m).
MS (ESI) m/z: 547.8 (M+H)$^+$.

Intermediate-263: 5-chloro-N-((1r,4r)-4-((3-(2-chloropyridin-4-yl)-6-fluoro-2-oxo-2,3-dihydro-1H-benzo[d]imidazol-1-yl)methyl)cyclohexyl)-2-(difluoromethyl)nicotinamide <Step-1>: 1-(2-chloropyridin-4-yl)-5-fluoro-1H-benzo[d]imidazol-2(3H)-one The title compound is prepared in 37% yield in 3 steps by the similar manner to Step-1, Step-2, and Step-3 of Intermediate-193 using 2-chloropyridin-4-amine and 1-bromo-4-fluoro-2-nitrobenzene in place of N$^2$ (2,2,2-trifluoroethyl)pyridine-2,5-diamine and 1-bromo-2-nitrobenzene.

$^1$H-NMR (400 MHz, DMSO-d$_6$) delta 11.43 (1H, s), 8.36 (1H, d, J=5.5 Hz), 7.62 (1H, d, J=1.6 Hz), 7.53 (1H, dd, J=5.5, 1.6 Hz), 7.15 (1H, dd, J=8.7, 4.6 Hz), 6.79 (1H, dd, J=8.7, 2.3 Hz), 6.76-6.66 (1H, m).
MS (ESI) m/z: 264.1 (M+H)$^+$.

<Step-2>: 5-chloro-N-((1r,4r)-4-((3-(2-chloropyridin-4-yl)-6-fluoro-2-oxo-2,3-dihydro-1H-benzo[d]imidazol-1-yl)methyl)cyclohexyl)-2-(difluoromethyl)nicotinamide The title compound is prepared in 97% yield by the similar manner to Step-3 of Intermediate-3 using 1-(2- chloropyridin-4-yl)-5-fluoro-1H-benzo[d]imidazol-2(3H)-one (Step-1 of Intermediate-263) and Mesylate-4 in place of methyl 2-((2-oxo-2,3-dihydro-1H-benzo[d]imidazol-1-yl)methyl)benzoate and Mesylate-1.
MS (ESI) m/z: 564.0 (M+H)$^+$.

Intermediate-264: 5-chloro-2-(difluoromethyl)-N-((1r,4r)-4-((6-fluoro-2-oxo-2,3-dihydro-1H-benzo[d]imidazol-1-yl)methyl)cyclohexyl)nicotinamide <Step-1>: tert-butyl 5-fluoro-2-oxo-2,3-dihydro-1H-benzo[d]imidazole-1-carboxylate The title compound is prepared by the similar manner to Step-3 of Intermediate-193 using tert-butyl (2-amino-4-fluorophenyl)carbamate in place of N-(2-aminophenyl)-N$^2$-(2,2,2-trifluoroethyl)pyridine-2,5-diamine.
$^1$H-NMR (400 MHz, DMSO-d$_6$) delta 11.21 (1H, s), 7.42 (1H, dd, J=8.8, 4.8 Hz), 6.73-6.68 (1H, m), 6.65 (1H, dd, J=8.8, 2.3 Hz), 1.38 (9H, s).
MS (ESI) m/z: 251.2 (M–H)$^-$.

<Step-2>: 5-chloro-2-(difluoromethyl)-N-((1r,4r)-4-((6-fluoro-2-oxo-2,3-dihydro-1H-benzo[d]imidazol-1-yl)methyl)cyclohexyl)nicotinamide The title compound is prepared in 2 steps by the similar manner to Step-1 and Step-2 of Example 9 using tert-butyl 5-fluoro-2-oxo-2,3-dihydro-1H-benzo[d]imidazole-1-carboxylate (Step-1 of Intermediate-264) and Masylate-4 in place of tert-butyl 2-oxo-2,3-dihydro-1H-benzo[d]imidazole-1-carboxylate and Mesylate-1.
MS (ESI) m/z: 551.1 (M–H)$^-$.

Intermediate-265: N-((1r,4r)-4-((3-(5-bromopyridin-2-yl)-2-oxo-2,3-dihydro-1H-benzo[d]imidazol-1-yl)methyl)cyclohexyl)-5-chloro-2-(difluoromethyl)nicotinamide The title compound (pale yellow solid) is prepared in in 29% yield 4 steps by the similar manner to Step-1, Step-2, Step-3, and Step-4 of Intermediate-224 using 5-bromopyridin-2-amine in place of 6-bromo-4-methylpyridin-3-amine.
MS (ESI) m/z: 592.0 (M+H)$^+$.

Intermediate-266: 3-(2-chloro-5-fluorophenyl)-1H-imidazo[4,5-c]pyridin-2(3H)-one The title compound (pale yellow solid) is prepared in 11% yield in 3 steps by the similar manner to Step-1, Step-2, and Step-3 of Intermediate-198 using 2-chloro-5-fluoroaniline and 3-bromo-4-nitropyridine in place of 2-chloro-4-methylaniline and 2-bromo-3-nitropyridine.
MS (ESI) m/z: 264.1 (M+H)$^+$.

Intermediate-267: 3-(3-fluoro-4-methoxyphenyl)-1H-imidazo[4,5-c]pyridin-2(3H)-one The title compound (pale yellow solid) is prepared in 72% yield in 3 steps by the similar manner to Step-1, Step-2, and Step-3 of Intermediate-249 using 3-bromo-4-nitropyridine and 3-fluoro-4-methoxyaniline in place of 3-bromo-2-nitropyridine and 2-chloro-5-methoxyaniline.
$^1$H-NMR (400 MHz, DMSO-d$_6$) delta 11.64 (1H, br s), 8.24 (1H, d, J=5.0 Hz), 8.18 (1H, s), 7.53 (1H, dd, J=12.4, 1.8 Hz), 7.41-7.31 (2H, m), 7.13 (1H, d, J=5.5 Hz), 3.92 (3H, s).
MS (ESI) m/z: 260.2 (M+H)$^+$.

Intermediate-268: 1-(2-fluoro-5-methoxyphenyl)-1H-imidazo[4,5-b]pyridin-2(3H)-one The title compound (pale yellow solid) is prepared in 31% yield in 3 steps by the similar manner to Step-1, Step-2, and Step-3 of Intermediate-249 using 2-fluoro-5-methoxyaniline in place of 2-chloro-5-methoxyaniline.
$^1$H-NMR (400 MHz, DMSO-d$_6$) delta 11.43 (1H, br s), 7.90 (1H, dd, J=5.0, 1.4 Hz), 7.43-7.34 (2H, m), 7.17 (1H, dd, J=5.9, 3.2 Hz), 7.13-7.07 (2H, m), 3.78 (3H, s).
MS (ESI) m/z: 260.2 (M+H)$^+$.

Intermediate-269: 3-(2-chlorophenyl)-1H-imidazo[4,5-c]pyridin-2(3H)-one

The title compound (pale yellow solid) is prepared in 14% yield in 3 steps by the similar manner to Step-1, Step-2, and Step-3 of Intermediate-198 using 2-chloroaniline and 3-bromo-4-nitropyridine in place of 2-chloro-4-methylaniline and 2-bromo-3-nitropyridine.
MS (ESI) m/z: 246.1 (M+H)$^+$.

Intermediate-270: 1-(3-fluoro-4-methoxyphenyl)-1H-imidazo[4,5-b]pyridin-2(3H)-one The title compound (pale yellow solid) is prepared in 49% yield in 3 steps by the similar manner to Step-1, Step-2, and Step-3 of Intermediate-249 using 3-fluoro-4-methoxyaniline in place of 2-chloro-5-methoxyaniline.
$^1$H-NMR (400 MHz, DMSO-d$_6$) delta 11.39 (1H, br s), 7.94 (1H, dd, J=5.1, 1.4 Hz), 7.58 (1H, dd, J=12.6, 2.4 Hz), 7.49-7.45 (1H, m), 7.39 (1H, dd, J=7.7, 1.4 Hz), 7.31 (1H, J=9.1 Hz), 7.09 (1H, dd, J=7.7, 5.3 Hz), 3.90 (3H, s).
MS (ESI) m/z: 260.2 (M+H)$^+$.

Intermediate-271: 3-(2-fluoro-5-methoxyphenyl)-1H-imidazo[4,5-c]pyridin-2(3H)-one The title compound (pale yellow solid) is prepared in 55% yield in 3 steps by the similar manner to Step-1, Step-2, and Step-3 of Intermediate-249 using 3-bromo-4-nitropyridine and 2-fluoro-5-methoxyaniline in place of 3-bromo-2-nitropyridine and 2-chloro-5-methoxyaniline.
$^1$H-NMR (400 MHz, DMSO-d$_6$) delta 11.72 (1H, br s), 8.24 (1H, d, J=5.0 Hz), 8.02 (1H, s), 7.43 (1H, t, J=9.6 Hz), 7.24 (1H, dd, J=6.4, 3.2 Hz), 7.17-7.08 (2H, m), 3.79 (3H, s).
MS (ESI) m/z: 260.2 (M+H)$^+$.

Intermediate-272: 1-(3-fluoro-4-methoxyphenyl)-1H-imidazo[4,5-c]pyridin-2(3H)-one The title compound (pale yellow solid) is prepared in quantitative yield in 2 steps by the similar manner to Step-1 and Step-2 of Intermediate-98 using 3-fluoro-4-methoxyaniline and 4-chloronicotinic acid in place of 2,3-dihydro-1H-inden-5-amine and 2-chloronicotinic acid.
MS (ESI) m/z: 260.2 (M+H)$^+$.

Intermediate-273: 3-(2-fluoro-5-methoxyphenyl)-1H-imidazo[4,5-b]pyridin-2(3H)-one The title compound (pale yellow solid) is prepared in 85% yield in 2 steps by the similar manner to Step-1 and Step-2 of Intermediate-98 using 2-fluoro-5-methoxyaniline in place of 2,3-dihydro-1H-inden-5-amine.
MS (ESI) m/z: 260.2 (M+H)+.

Intermediate-274: 1-(2-fluoro-5-methoxyphenyl)-1H-imidazo[4,5-c]pyridin-2(3H)-one The title compound (pale yellow solid) is prepared in 89% yield in 2 steps by the similar manner to Step-1 and Step-2 of Intermediate-98 using 2-fluoro-5-methoxyaniline and 4-chloronicotinic acid in place of 2,3-dihydro-1H-inden-5-amine and 2-chloronicotinic acid.
MS (ESI) m/z: 260.2 (M+H)+.

Intermediate-275: N-methyl-4-(2-oxo-2,3-dihydro-1H-benzo[d]imidazol-1-yl)picolinamide The title compound is prepared in 29% yield by the similar manner to Intermediate-137 using 4-chloro-N-methylpicolinamide in place of 3-fluoroisonicotinonitrile. The reaction is carried out at 120° C.
$^1$H-NMR (400 MHz, DMSO-$d_6$) delta 11.43 (1H, s), 8.89 (1H, br dd, J=9.2, 4.0 Hz), 8.78 (1H, d, J=5.5 Hz), 8.29 (1H, d, J=1.8 Hz), 7.89 (1H, dd, J=5.3, 2.1 Hz), 7.32 (1H, d, J=7.8 Hz), 7.21-7.06 (3H, m), 2.86 (3H, d, J=4.6 Hz).
MS (ESI) m/z: 269.0 (M+H)+.

Intermediate-276: 1-(3-fluorophenyl)-1H-imidazo[4,5-b]pyridin-2(3H)-one

The title compound is prepared in 3 steps by the similar manner to Step-1, Step-2, and Step-3 of Intermediate-249 using 3-fluoroaniline in place of 2-chloro-5-methoxyaniline.
MS (ESI) m/z: 230.2 (M+H)+.

Intermediate-277: N-((1r,4r)-4-((3-(5-bromopyridin-2-yl)-2-oxo-2,3-dihydro-1H-benzo[d]imidazol-1-yl)methyl)cyclohexyl)-5-chloro-2-methylnicotinamide The title compound (pale yellow solid) is prepared in 16% yield in 4 steps by the similar manner to Step-1, Step-2, Step-3, and Step-4 of Intermediate-252 using 5-bromopyridin-2-amine in place of 2-bromopyridin-4-amine.
$^1$H-NMR (400 MHz, DMSO-$d_6$) delta 8.52 (1H, d, J=2.3 Hz), 8.32 (1H, d, J=2.6 Hz), 8.19 (1H, d, J=7.8 Hz), 8.05 (1H, dd, J=8.8, 2.6 Hz), 7.91 (1H, d, J=8.8 Hz), 7.78 (1H, d, J=6.9 Hz), 7.57 (1H, d, J=2.3 Hz), 7.15 (1H, d, J=7.3 Hz), 7.04-6.96 (1H, m), 6.96-6.84 (1H, m), 3.58 (2H, d, J=6.9 Hz), 3.50 (1H, s), 2.25 (3H, s), 1.77-1.47 (5H, m), 1.09-0.91 (4H, m).
MS (ESI) m/z: 556.0 (M+H)+.

Intermediate-278: N-((1r,4r)-4-((3-(6-bromopyridin-2-yl)-2-oxo-2,3-dihydro-1H-benzo[d]imidazol-1-yl)methyl)cyclohexyl)-5-chloro-2-methylnicotinamide The title compound (pale yellow solid) is prepared in 31% yield in 4 steps by the similar manner to Step-1, Step-2, Step-3, and Step-4 of Intermediate-252 using 6-bromopyridin-2-amine in place of 2-bromopyridin-4-amine.
$^1$H-NMR (400 MHz, DMSO-$d_6$) delta 8.33 (1H, d, J=2.7 Hz), 8.20 (1H, d, J=8.2 Hz), 8.01 (1H, d, J=8.2 Hz), 7.83-7.77 (1H, m), 7.76 (1H, d, J=7.8 Hz), 7.59 (1H, d, J=2.3 Hz), 7.43 (1H, d, J=7.8 Hz), 7.18 (1H, d, J=6.9 Hz), 7.04 (1H, td, J=7.8, 1.4 Hz), 6.98 (1H, td, J=7.7, 1.2 Hz), 3.60 (2H, d, J=7.3 Hz), 3.56-3.42 (1H, m), 2.26 (3H, s), 1.77-1.46 (5H, m), 1.10-0.93 (4H, m).
MS (ESI) m/z: 556.0 (M+H)+.

Intermediate-279: N-((1r,4r)-4-((3-(6-bromopyridin-2-yl)-2-oxo-2,3-dihydro-1H-benzo[d]imidazol-1-yl)methyl)cyclohexyl)-5-chloro-2-(difluoromethyl)nicotinamide The title compound (brown solid) is prepared in 46% yield in 4 steps by the similar manner to Step-1, Step-2, Step-3, and Step-4 of Intermediate-224 using 6-bromopyridin-2-amine in place of 6-bromo-4-methylpyridin-3-amine.
$^1$H-NMR (400 MHz, DMSO-$d_6$) delta 8.62 (1H, d, J=2.3 Hz), 8.44 (1H, d, J=7.8 Hz), 8.01 (1H, d, J=8.2 Hz), 7.94 (1H, d, J=2.3 Hz), 7.83-7.70 (2H, m), 7.42 (1H, d, J=7.3 Hz), 7.17 (1H, d, J=6.9 Hz), 7.11-6.75 (3H, m), 3.59 (2H, d, J=7.3 Hz), 3.54-3.42 (1H, m), 1.76-1.45 (5H, m), 1.11-0.90 (4H, m).
MS (ESI) m/z: 592.0 (M+H)+.

Intermediate-280: 5-chloro-N-((1r,4r)-4-((3-(5-chloropyrazin-2-yl)-6-fluoro-2-oxo-2,3-dihydro-1H-benzo[d]imidazol-1-yl)methyl)cyclohexyl)-2-(difluoromethyl)nicotinamide The title compound is prepared by the similar manner to Step-1 of Intermediate-57 using 5-chloro-2-(difluoromethyl)-N-((1r,4r)-4-((6-fluoro-2-oxo-2,3-dihydro-1H-benzo[d]imidazol-1-yl)methyl)cyclohexyl)nicotinamide (Intermediate-264) in place of 1H-benzo[d]imidazol-2(3H)-one.

Example Synthesis Part

Each chemical structure of Example synthesis part is described as a free-base.

Representative Procedure for Method A1

The following preparation of Example 1 represents the Method A1.

Example 1: 5-chloro-2-methyl-N-((1r,4r)-4-((2-oxo-3-phenyl-2,3-dihydro-1H-benzo[d]imidazol-1-yl)methyl)cyclohexyl)nicotinamide

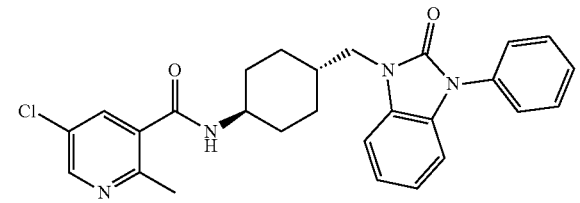

[Chem. 18]

A mixture of ((r,4r)-4-(5-chloro-2-methylnicotinamido)cyclohexyl)methyl methanesulfonate (25 mg, 0.069 mmol, Mesylate-1), 1-phenyl-1H-benzo[d]imidazol-2(3H)-one (15 mg, 0.069 mmol), and cesium carbonate (45 mg, 0.14 mmol) in DMSO (0.5 mL) is stirred at 80° C. for 5 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 7.4 mg (22% yield) of the title compound.

Representative Procedure for Method B

The following preparation of Example 4 represents the Method B.

Example 4: 5-chloro-2-methyl-N-((1r,4r)-4-((3-(3-(methylcarbamoyl)benzyl)-2-oxo-2,3-dihydro-1H-benzo[d]imidazol-1-yl)methyl)cyclohexyl)nicotinamide

[Chem. 19]

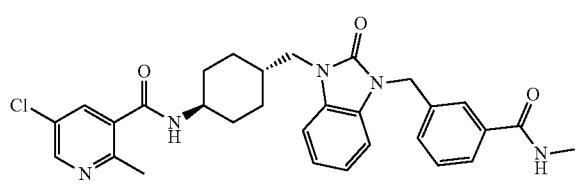

A mixture of 3-((3-(((1r,4r)-4-(5-chloro-2-methylnicotinamido)cyclohexyl)methyl)-2-oxo-2,3-dihydro-1H-benzo[d]imidazol-1-yl)methyl)benzoic acid (22 mg, 0.041 mmol, Intermediate-2), 2 M methanamine in THF (0.5 mL), HBTU (31 mg, 0.083 mmol), and TEA (0.029 mL, 0.21 mmol) in DCM (2 mL) is stirred at room temperature for 1 day. The mixture is diluted with saturated aqueous sodium bicarbonate. The mixture is extracted with EtOAc. The organic layer is dried over sodium sulfate, filtered and concentrated. The residue is purified by amino-functional silica gel column chromatography and then purified by preparative LC-MS to give 2.2 mg (10% yield) of the title compound.

Representative Procedure for Method C1

The following preparation of Example 9 represents the Method C1.

Example 9: 5-chloro-N-((1r,4r)-4-((3-(2-(4-methoxyphenyl)-2-oxoethyl)-2-oxo-2,3-dihydro-1H-benzo[d]imidazol-1-yl)methy)cyclohexyl)-2-methylnicotinamide

[Chem. 20]

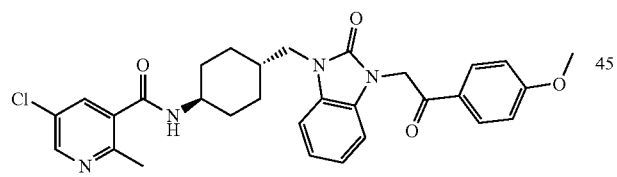

<Step-1>: tert-butyl 3-(((1r,4r)-4-(5-chloro-2-methylnicotinamido)cyclohexyl)methyl)-2-oxo-2,3-dihydro-1H-benzo[d]imidazole-1-carboxylate A mixture of ((r,4r)-4-(5-chloro-2-methylnicotinamido)cyclohexyl)methyl methanesulfonate (500 mg, 1.39 mmol, Mesylate-1), tert-butyl 2-oxo-2,3-dihydro-1H-benzo[d]imidazole-1-carboxylate (325 mg, 1.39 mmol), and cesium carbonate (903 mg, 2.77 mmol) in DMSO (1 mL) is stirred at 80° C. for 6 hrs. The mixture is diluted with water. The mixture is extracted with EtOAc. The organic layer is concentrated. The residue is purified by column chromatography on silica-gel eluting with 0-70% EtOAc in n-hexane to give 487 mg (70% yield) of the title compound as a yellow gum.

$^1$H-NMR (400 MHz, CDCl$_3$) delta 8.47 (1H, d, J=2.3 Hz), 7.84 (1H, dd, J=7.8, 0.9 Hz), 7.60 (1H, d, J=2.3 Hz), 7.21 (1H, td, J=7.8, 0.9 Hz), 7.13 (1H, td, J=7.8, 1.4 Hz), 6.96 (1H, dd, J=7.8, 0.9 Hz), 5.66 (1H, d, J=8.2 Hz), 4.00-3.88 (1H, m), 3.71 (2H, d, J=6.9 Hz), 2.60 (3H, s), 2.17-2.09 (2H, m), 1.98-1.80 (3H, m), 1.68 (9H, s), 1.37-1.12 (4H, m). MS (ESI) m/z: 499.2 (M+H)$^+$.

<Step-2>: 5-chloro-2-methyl-N-((1r,4r)-4-((2-oxo-2,3-dihydro-1H-benzo[d]imidazol-1-yl)meth yl)cyclohexyl)nicotinamide The title compound is prepared in quantitative yield (477 mg, a pale yellow solid) by the similar manner to Step-2 of Intermediate-1 using tert-butyl 3-(((1r,4r)-4-(5-chloro-2-methylnicotinamido)cyclohexyl)methyl)-2-oxo-2,3-dihydro-1H-benzo[d]imidazole-1-carboxylate (487 mg, 0.98 mmol, Step-1 of Example 9).

MS (ESI) m/z: 399.1 (M+H)$^+$.

<Step-3>: 5-chloro-N-((1r,4r)-4-((3-(2-(4-methoxyphenyl)-2-oxoethyl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-2,3-dihydro-1H-benzo[d]imidazol-1-yl)methyl)cyclohexyl) nicotinamide (25 mg, 0.057 mmol, Step-2 of Example 9), 2-bromo-1-(4-methoxyphenyl)ethanone (13 mg, 0.057 mmol), and cesium carbonate (37 mg, 0.12 mmol) in DMSO (0.5 mL) is stirred at rt for 2 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 5.6 mg (18% yield) of the title compound.

Representative Procedure for Method D

The following preparation of Example 11 represents the Method D.

Example 11: 5-chloro-N-((1r,4r)-4-((3-(2-(hydroxymethyl)benzyl)-2-oxo-2,3-dihydro-1H-benzo[d]imidazol-1-yl)methyl)cyclohexyl)-2-methylnicotinamide

[Chem. 21]

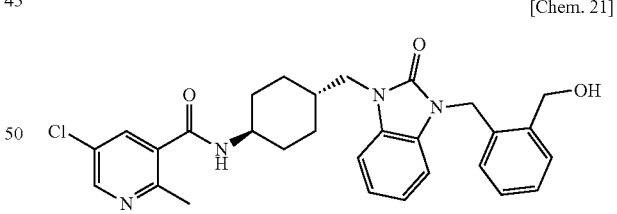

A mixture of 2-((3-(((1r,4r)-4-(5-chloro-2-methylnicotinamido)cyclohexyl)methyl)-2-oxo-2,3-dihydro-1H-benzo[d]imidazol-1-yl)methyl)benzoic acid (34 mg, 0.064 mmol, Intermediate-3) and CDI (16 mg, 0.096 mmol) in THF (1 mL) is stirred at room temperature for 5 hrs. Then, to the mixture is added sodium borohydride (10 mg, 0.26 mmol) in water (0.5 mL) at rt. The mixture is stirred at rt for 1 hr. The mixture is diluted with water. The mixture is extracted with EtOAc. The organic layer is dried over sodium sulfate, filtered and concentrated. The residue is purified by amino-functional silica gel column chromatography and then purified by preparative LC-MS to give 7 mg (21% yield) of the title compound.

Representative Procedure for Method C2

The following preparation of Example 12 represents the Method C2.

Example 12: 5-chloro-N-((1r,4r)-4-((3-(2-(2,4-difluorophenyl)-2-oxoethyl)-2-oxo-2,3-dihydro-1H-benzo[d]imidazol-1-yl)methyl)cyclohexyl)-2-methylnicotinamide

[Chem. 22]

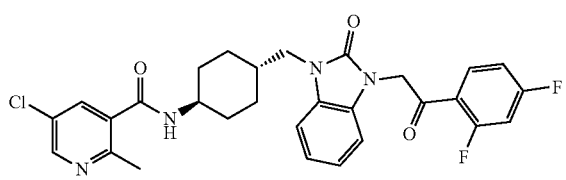

A mixture of 5-chloro-2-methyl-N-((1r,4r)-4-((2-oxo-2,3-dihydro-1H-benzo[d]imidazol-1-yl)methyl)cyclohexyl) nicotinamide (25 mg, 0.057 mmol, Step-2 of Example 9), 2-bromo-1-(2,4-difluorophenyl)ethanone (19 mg, 0.069 mmol) and potassium carbonate (16 mg, 0.12 mmol) in DMF (0.5 mL) is stirred at rt for 5 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 3.2 mg (10% yield) of the title compound.

Representative Procedure for Method E

The following preparation of Example 19 represents the Method E.

Example 19: 5-chloro-N-((1r,4r)-4-((3-(4-(1-hydroxyethyl)phenyl)-2-oxo-2,3-dihydro-1H-benzo[d]imidazol-1-yl)methyl)cyclohexyl)-2-methylnicotinamide

[Chem. 23]

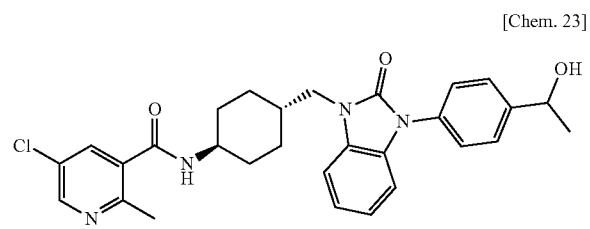 [SMILES: Cc1ncc(Cl)cc1C(=O)N[C@H]1CC[C@H](Cn2c(=O)n(-c3ccc(C(C)O)cc3)c3ccccc32)CC1]

A mixture of N((1r,4r)-4-((3-(4-acetylphenyl)-2-oxo-2,3-dihydro-1H-benzo[d]imidazol-1-yl)methyl)cyclohexyl)-5-chloro-2-methylnicotinamide (20 mg, 0.039 mmol, Example 18) in MeOH (1 mL) is added sodium borohydride (3 mg, 0.077 mmol) at rt. The mixture is stirred at rt for 30 min. The mixture is diluted with water. The mixture is extracted with DCM. The organic layer is dried over sodium sulfate, filtered and concentrated. The residue is purified by preparative LC-MS to give 4.5 mg (22% yield) of the title compound.

Example 40: 2-(2-hydroxyethyl)-N-((1r,4r)-4-((2-oxo-3-(p-tolyl)-2,3-dihydro-1H-benzo[d]imidazol-1-yl)methyl)cyclohexyl)-2H-indazole-3-carboxamide

[Chem. 24]

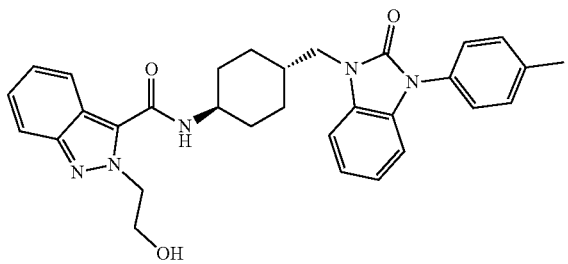

<Step-1>: methyl 2-(2-((tert-butyldimethylsilyl)oxy) ethyl)-2H-indazole-3-carboxylate A mixture of methyl 1H-indazole-3-carboxylate (300 mg, 1.70 mmol), (2-bromoethoxy)(tert-butyl)dimethylsilane (489 mg, 2.04 mmol) in DMSO (5 mL) is stirred at 80° C. for 5 hrs. The mixture is diluted with water. The mixture is extracted with EtOAc:n-hexane (1:1). The organic layer is dried over sodium sulfate, filtered and concentrated. The residue is purified by column chromatography on silica-gel eluting with 0-25% EtOAc in n-hexane to give 163 mg (29% yield) of the title compound as a pale yellow oil.

$^1$H-NMR (400 MHz, CDCl$_3$) delta 8.02 (1H, dt, J=8.7, 0.9 Hz), 7.78 (1H, dt, J=8.7, 0.9 Hz), 7.38-7.33 (1H, m), 7.30-7.25 (1H, m), 5.08 (2H, t, J=5.9 Hz), 4.09 (2H, t, J=5.9 Hz), 4.03 (3H, s), 0.78 (9H, s), −0.13 (6H, s). MS (ESI) m/z: 335.3 (M+H)$^+$.

<Step-2>: 2-(2-((tert-butyldimethylsilyl)oxy)ethyl)-2H-indazole-3-carboxylic acid A mixture of methyl 2-(2-((tert-butyldimethylsilyl)oxy) ethyl)-2H-indazole-3-carboxylate (163 mg, 0.49 mmol, Step-1 of Example 40) and 2 M aqueous sodium hydroxide solution (2 mL) in THF (1 mL) and MeOH (1 mL) is stirred at 50° C. for 2 hrs. The mixture is acidified with 2 M hydrochloric acid. The mixture is extracted with EtOAc. The organic layer is dried over sodium sulfate and filtered. The filtrate is concentrated to give 141 mg (90% yield) of the title compound as a yellow solid.

MS (ESI) m/z:321.3 (M+H)$^+$.

<Step-3>: (1r,4r)-methyl 4-(2-(2-hydroxyethyl)-2H-indazole-3-carboxamido)cyclohexanecarboxylate To a mixture of 2-(2-((tert-butyldimethylsilyl)oxy)ethyl)-2H-indazole-3-carboxylic acid (167 mg, 0.52 mmol, Step-2 of Example 40), (1r,4r)-methyl 4-aminocyclohexanecarboxylate hydrochloride (101 mg, 0.52 mmol), and TEA (0.29 mL, 2.01 mmol) in DCM (2 mL) is added 1.7 M T3P (registered trademark) in EtOAc (0.61 mL, 1.04 mmol) at rt. The mixture is stirred at rt for 1 hr. The mixture is quenched with saturated aqueous sodium bicarbonate. The mixture is extracted with EtOAc. The organic layer is dried over sodium sulfate, filtered and concentrated. The residue is purified by column chromatography on silica-gel eluting with 0-80% EtOAc in n-hexane to give 70 mg (39% yield) of the title compound as a pale yellow solid.
MS (ESI) m/z: 346.3 (M+H)⁺.

<Step-4>: (1r,4r)-methyl 4-(2-(2-((tert-butyldiphenylsilyl)oxy)ethyl)-2H-indazole-3-carboxamido)cyclohexanecarboxylate To a solution of (1r,4r)-methyl 4-(2-(2-hydroxyethyl)-2H-indazole-3-carboxamido)cyclohexanecarboxylate (70 mg, 0.20 mmol, Step-3 of Example 40), DIEA (0.11 mL, 0.61 mmol) and DMAP (2 mg, 0.02 mmol) in DCM (1 mL) is added tert-butylchlorodiphenylsilane (0.08 mL, 0.30 mmol) at rt. The mixture is stirred at rt for 3 days. The mixture is quenched with saturated aqueous sodium bicarbonate. The mixture is extracted with EtOAc. The organic layer is dried over sodium sulfate, filtered and concentrated. The residue is purified by column chromatography on silica-gel eluting with 0-50% EtOAc in n-hexane to give 111 mg (94% yield) of the title compound as a pale yellow solid.

<Step-5>: 2-(2-((tert-butyldiphenylsilyl)oxy)ethyl)-N-((1r,4r)-4-(hydroxymethyl)cyclohexyl)-2H-indazole-3-carboxamide To a mixture of (1r,4r)-methyl 4-(2-(2-((tert-butyldiphenylsilyl)oxy)ethyl)-2H-indazole-3-carboxamido)cyclohexanecarboxylate (111 mg, 0.19 mmol, Step-4 of Example 40) in THF (4 mL) is added lithium aluminum hydride (11 mg, 0.29 mmol) at 0° C. The mixture is stirred at 0° C. for 1 hr. The mixture is acidified with 2 M hydrochloric acid and extracted with EtOAc. The organic layer is dried over sodium sulfate and filtered. The filtrate is concentrated to give 101 mg (96% yield) of the title compound as a pale yellow solid.
¹H-NMR (400 MHz, CDCl₃) delta 7.78 (1H, d, J=8.7 Hz), 7.66 (1H, d, J=8.2 Hz), 7.40-7.31 (7H, m), 7.28-7.17 (5H, m), 5.94 (1H, d, J=5.5 Hz), 5.06 (2H, t, J=5.5 Hz), 4.19 (2H, t, J=5.5 Hz), 3.95-3.82 (1H, m), 3.49 (2H, d, J=6.4 Hz), 2.11-2.00 (2H, m), 1.90-1.80 (2H, m), 1.52-1.40 (1H, m), 1.20-1.08 (4H, m), 0.93 (9H, s). A signal due to OH is not observed. MS (ESI) m/z: 556.4 (M+H)⁺.

<Step-6>: ((1r,4r)-4-(2-(2-((tert-butyldiphenylsilyl)oxy)ethyl)-2H-indazole-3-carboxamido)cyclo hexyl)methylmethanesulfonate To a mixture of 2-(2-((tert-butyldiphenylsilyl)oxy)ethyl)-N-((1r,4r)-4-(hydroxymethyl)cyclohexyl)-2H-indazole-3-carboxamide (101 mg, 0.18 mmol, Step-5 of Example 40), and TEA (0.05 mL, 0.36 mmol) in DCM (3 mL) is added methanesulfonic anhydride (48 mg, 0.27 mmol) at rt. The mixture is stirred at rt for 1 hr. The mixture is quenched with saturated aqueous sodium bicarbonate. The mixture is extracted with DCM. The organic layer is dried over sodium sulfate and filtered. The filtrate is concentrated to give 122 mg (quantitative yield) of the title compound as a pale orange solid.
MS (ESI) m/z: 634.5 (M+H)⁺.

<Step-7>: 2-(2-hydroxyethyl)-N-((1r,4r)-4-((2-oxo-3-(p-tolyl)-2,3-dihydro-1H-benzo[d]imidazol-1-yl)methyl)cyclohexyl)-2H-indazole-3-carboxamide A mixture of ((1r,4r)-4-(2-(2-((tert-butyldiphenylsilyl)oxy)ethyl)-2H-indazole-3-carboxamido)cyclo hexyl)methyl methanesulfonate (30 mg, 0.047 mmol, Step-6 of Example 40), 1-(p-tolyl)-1H-benzo[d]imidazol-2(3H)-one (11 mg, 0.047 mmol), and cesium carbonate (31 mg, 0.095 mmol) in DMSO (0.5 mL) is stirred at 80° C. for 3 hrs. The mixture is diluted with water. The mixture is extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 4.3 mg (17% yield) of the title compound.

Example 50: 5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-methylnicotinamide

[Chem. 25]

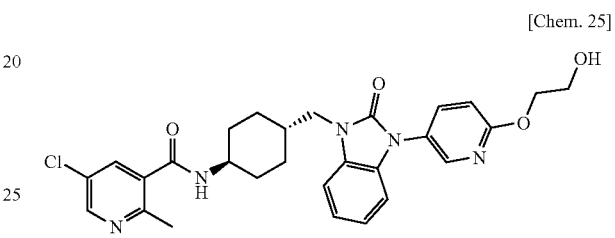

<Step-1>: 5-chloro-2-methyl-N-((1r,4r)-4-((2-oxo-3-(6-(2-((tetrahydro-2H-pyran-2-yl)oxy)ethoxy)pyridin-3-yl)-2,3-dihydro-1H-benzo[d]imidazol-1-yl)methyl)cyclohexyl)nicotinamide A mixture of ((r,4r)-4-(5-chloro-2-methylnicotinamido)cyclohexyl)methyl methanesulfonate (249 mg, 0.69 mmol, Mesylate-1), 1-(6-(2-((tetrahydro-2H-pyran-2-yl)oxy)ethoxy)pyridin-3-yl)-1H-benzo[d]imidazol-2(3H)-one (245 mg, 0.69 mmol, Intermediate-24), and cesium carbonate (449 mg, 1.38 mmol) in DMF (2 mL) is stirred at 80° C. for 1 day. The mixture is diluted with water and extracted with EtOAc. The organic layer is dried over sodium sulfate, filtered and concentrated. The residue is purified by column chromatography on silica-gel eluting with 0-100% EtOAc in n-hexane to give 395 mg (92% yield) of the title compound as a brown solid.
MS (ESI) m/z: 620.4 (M+H)⁺.

<Step-2>: 5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-3-(6-(2-((tetrahydro-2H-pyran-2-yl)oxy)ethoxy)pyridin-3-yl)-2,3-dihydro-1H-benzo[d]imidazol-1-yl)methyl)cyclohexyl)nicotinamide (395 mg, 0.64 mmol, Step-1 of Example 50) and p-toluenesulfonic acid (20 mg, 0.11 mmol) in MeOH (3 mL) and water (1 mL) is stirred at 70° C. for 3 hrs. The mixture is diluted with saturated sodium hydrogen carbonate aqueous solution. The mixture is extracted with DCM. The organic layer is dried over sodium sulfate, filtered and concentrated. The residue is purified by column chromatography on silica-gel eluting with 0-90% EtOAc in DCM to give 207 mg (61% yield) of the title compound as a pale yellow solid.

Example 62: 5-(3-(((1r,4r)-4-(5-chloro-2-methylnicotinamido)cyclohexyl)methyl)-2-oxo-2,3-dihydro-1H-benzo[d]imidazol-1-yl)picolinamide

[Chem. 26]

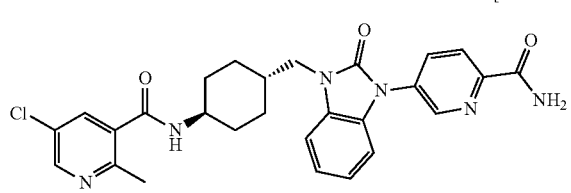

A mixture of 5-(3-(((1r,4r)-4-(5-chloro-2-methylnicotinamido)cyclohexyl)methyl)-2-oxo-2,3-dihydro-1H-benzo[d]imidazol-1-yl)picolinic acid (25 mg, 0.048 mmol, Intermediate-36), ammonia hydrochloride (13 mg, 0.24 mmol), HBTU (55 mg, 0.14 mmol), and TEA (0.034 mL, 0.24 mmol) in DMF (2 mL) is stirred at room temperature for 1 day. The mixture is diluted with saturated sodium hydrogen carbonate aqueous solution. The mixture is extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 7.4 mg (30% yield) of the title compound.

Example 63: 5-(3-(((1r,4r)-4-(5-chloro-2-methylnicotinamido)cyclohexyl)methyl)-2-oxo-2,3-dihydro-1H-benzo[d]imidazol-1-yl)-N-methylpicolinamide

[Chem. 27]

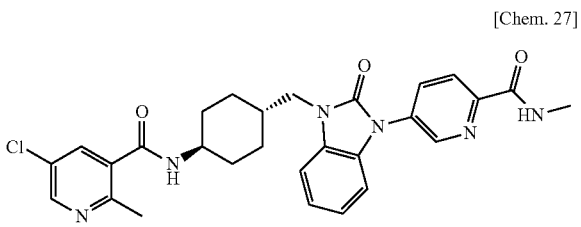 [SMILES: CNC(=O)c1ccc(-n2c(=O)n(C[C@H]3CC[C@H](NC(=O)c4cc(Cl)cnc4C)CC3)c3ccccc32)cn1]

A mixture of 5-(3-(((1r,4r)-4-(5-chloro-2-methylnicotinamido)cyclohexyl)methyl)-2-oxo-2,3-dihydro-1H-benzo[d]imidazol-1-yl)picolinic acid (25 mg, 0.048 mmol, Intermediate-36), methanamine hydrochloride (16 mg, 0.24 mmol), HBTU (55 mg, 0.14 mmol), and TEA (0.034 mL, 0.24 mmol) in DMF (2 mL) is stirred at room temperature for 1 day. The mixture is diluted with saturated sodium hydrogen carbonate aqueous solution. The mixture is extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 3.3 mg (13% yield) of the title compound.

Example 69: 5-chloro-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)-2-methylnicotinamide

[Chem. 28]

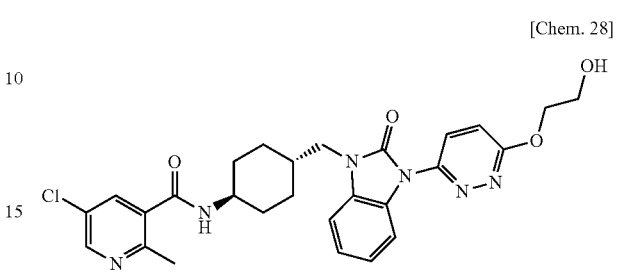

A mixture of ((r,4r)-4-(5-chloro-2-methylnicotinamido)cyclohexyl)methyl methanesulfonate (25 mg, 0.069 mmol, Mesylate-1), 1-(6-(2-((tetrahydro-2H-pyran-2-yl)oxy)ethoxy)pyridazin-3-yl)-1H-benzo[d]imidazol-2(3H)-one (15 mg, 0.069 mmol, Intermediate-42), and cesium carbonate (68 mg, 0.21 mmol) in DMSO (0.5 mL) is stirred at 90° C. for 5 hrs. The mixture is diluted with water and extracted with EtOAc. The organic layer is concentrated. The residual oil and p-toluenesulfonic acid (25 mg) in MeOH (1 mL) and water (1 mL) is stirred at 80° C. for 1 hr. The mixture is diluted with saturated sodium hydrogen carbonate aqueous solution. The mixture is extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 12 mg (32% yield) of the title compound.

Representative Procedure for Method F

The following preparation of Example 70 represents the Method F.

Example 70: 5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide

[Chem. 29]

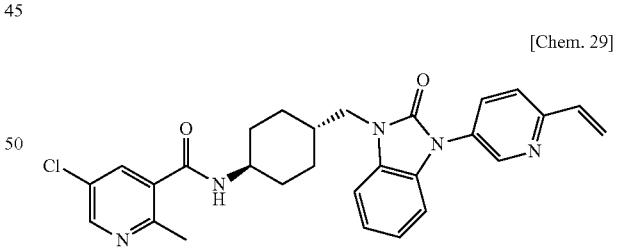

A microwave vial equipped with a stirrer bar is charged with N((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide (100 mg, 0.18 mmol, Example 66), cesium carbonate (176 mg, 0.541 mmol), 4,4,5,5-tetramethyl-2-vinyl-1,3,2-dioxaborolane (36.1 mg, 0.234 mmol), palladium(II)acetate (2.0 mg, 0.009 mmol) and XPhos (8.59 mg, 0.018 mmol), then sealed with a cap lined with a disposable septum. The vial is then evacuated under vacuum and purged with nitrogen atmosphere. Anhydrous THF (1 mL) and water (0.1 mL) are added by syringe and the resulting mixture is stirred and heated at 80° C. for overnight. The reaction mixture is extracted with EtOAc and water. The organic layer is dried (sodium sulfate) and concentrated in vacuo. The residue is purified by a strong anion exchange cartridge (ISOLUTE (registered trademark) SCX-2, 1 g/6 mL, Biotage) to give 85 mg (94% yield) of the title compound.

Representative Procedure for Method G

The following preparation of Example 72 represents the Method G.

Example 72: 5-chloro-N-((1r,4r)-4-((3-(6-ethylpyridin-3-yl)-2-oxo-2,3-dihydro-1H-benzo[d]imidazol-1-yl)methyl)cyclohexyl)-2-methylnicotinamide

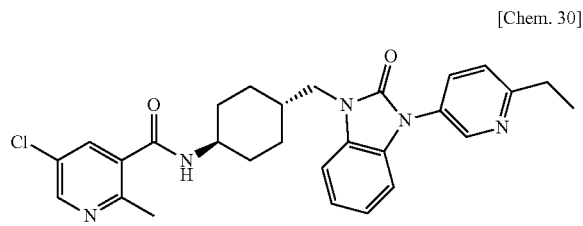 [SMILES: CCc1ccc(-n2c(=O)n(C[C@H]3CC[C@H](NC(=O)c4cc(Cl)cnc4C)CC3)c3ccccc32)cn1]

[Chem. 30]

To an ethanol (1 mL) solution of 5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide (13 mg, 0.026 mmol) is added 5% platinum on alumina (1 mg) and the resulting mixture is stirred at room temperature under hydrogen atmosphere for 3 hrs. The catalyst is filtered off and the filtrate is concentrated. The resulting crude product is purified by a strong anion exchange cartridge (ISOLUTE (registered trademark) SCX-2, 1 g/6 mL, Biotage) and then purified by preparative LC-MS to give 5.7 mg (44% yield) of the title compound.

Example 74: 5-chloro-2-methyl-N-((1R,4r)-4-((3-(6-((R)-morpholin-2-ylmethoxy)pyridin-3-yl)-2-oxo-2,3-dihydro-1H-benzo[d]imidazol-1-yl)methyl)cyclohexyl)nicotinamide <Step-1>: (R)-tert-butyl 2-(((5-(3-(((1r,4R)-4-(5-chloro-2-methylnicotinamido)cyclohexyl)methyl)-2-oxo-2,3-dihydro-1H-benzol[d]imidazol-1-yl)pyridin-2-yl)oxy)methyl)morpholine-4-carboxylate The title compound is prepared in 46% yield (68 mg, a pale yellow gum) by the similar manner to Step-3 of Intermediate-2 using (R)-tert-butyl 2-(((5-(2-oxo-2,3-dihydro-1H-benzo[d]imidazol-1-yl)pyridin-2-yl)oxy)methyl)morpholine-4-carboxylate (46 mg, 0.11 mmol, Intermediate-45) in place of methyl 3-((2-oxo-2,3-dihydro-1H-benzo[d]imidazol-1-yl)methyl)benzoate.

MS (ESI) m/z: 691.8 (M+H)$^+$.

<Step-2>: 5-chloro-2-methyl-N-((1R,4r)-4-((3-(6-((R)-morpholin-2-ylmethoxy)pyridin-3-yl)-2-oxo-2,3-dihydro-1H-benzo[d]imidazol-1-yl)methyl)cyclohexyl)nicotinamide A solution of (R)-tert-butyl 2-(((5-(3-(((1r,4R)-4-(5-chloro-2-methylnicotinamido)cyclohexyl)methyl)-2-oxo-2,3-dihydro-1H-benzo[d]imidazol-1-yl)pyridin-2-yl)oxy)methyl)morpholine-4-carboxylate (28 mg, 0.041 mmol, Step-1 of Example 74) in DCM (1 mL) and TFA (1 mL) is stirred at rt for 1 hr. The mixture is concentrated. The residue is basified with saturated aqueous sodium bicarbonate and extracted with DCM. The organic layer is dried over sodium sulfate and filtered. The filtrate is concentrated. The residue is purified by preparative LC-MS to give 6.2 mg (11% yield) of the title compound.

Representative Procedure for Method H

The following preparation of Example 75 represents the Method H.

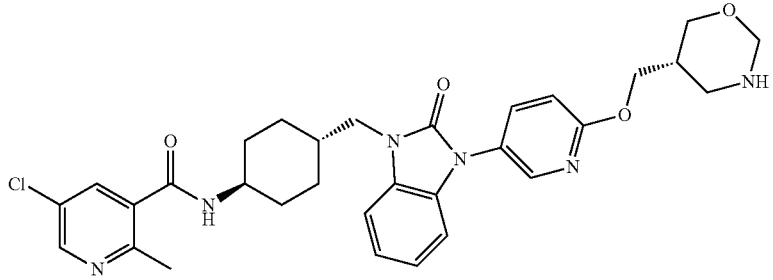

[Chem. 31]

Example 75: 5-chloro-2-methyl-N-((1S,4r)-4-((3-(6-(((S)-4-methylmorpholin-2-yl)methoxy)pyridin-3-yl)-2-oxo-2,3-dihydro-1H-benzo[d]imidazol-1-yl)methyl)cyclohexyl)nicotinamide

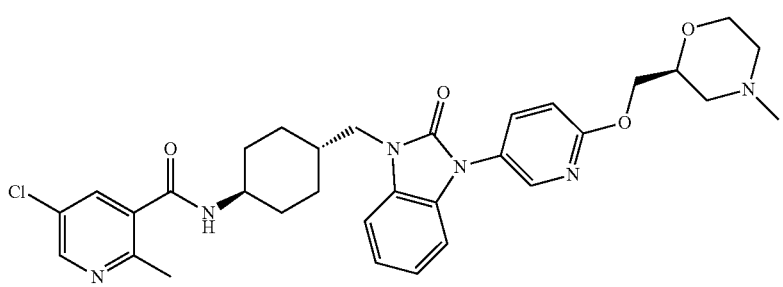

[Chem. 32]

To a mixture of 5-chloro-2-methyl-N-((1S,4r)-4-((3-(6-((S)-morpholin-2-ylmethoxy)pyridin-3-yl)-2-oxo-2,3-dihydro-1H-benzo[d]imidazol-1-yl)methyl)cyclohexyl)nicotinamide (10 mg, 0.017 mmol, Intermediate-46), paraformaldehyde (5 mg) in DCM (2 mL) is added sodium triacetoxyborohydride (18 mg, 0.085 mmol) at rt. The mixture is stirred at rt for 1 day. The mixture is basified with saturated aqueous sodium bicarbonate and extracted with EtOAc. The organic layer is dried over sodium sulfate and filtered. The filtrate is concentrated. The residue is purified by preparative LC-MS to give 6.8 mg (66% yield) of the title compound.

Example 77: N-((1R,4r)-4-((3-(6-(((R)-4-acetylmorpholin-2-yl)methoxy)pyridin-3-yl)-2-oxo-2,3-dihydro-1H-benzo[d]imidazol-1-yl)methyl)cyclohexyl)-5-chloro-2-methylnicotinamide

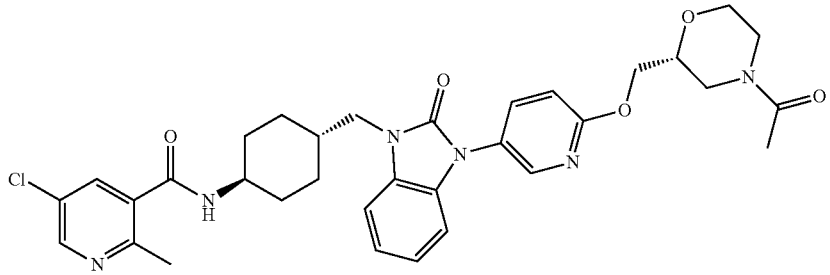

[Chem. 33]

To a mixture of 5-chloro-2-methyl-N-((1R,4r)-4-((3-(6-((R)-morpholin-2-ylmethoxy)pyridin-3-yl)-2-oxo-2,3-dihydro-1H-benzo[d]imidazol-1-yl)methyl)cyclohexyl)nicotinamide (22 mg, 0.037 mmol, Step-2 of Example 74) and TEA (0.025 mL, 0.18 mmol) in DCM (1 mL) is added acetic anhydride (0.01 mL, 0.11 mmol). The mixture is stirred at rt for 1 day. The mixture is basified with saturated aqueous sodium bicarbonate and extracted with DCM. The organic layer is dried over sodium sulfate and filtered. The filtrate is concentrated. The residue is purified by preparative LC-MS to give 8.1 mg (35% yield) of the title compound.

Example 78: N-((1r,4r)-4-((3-(6-((1-acetylazetidin-3-yl)oxy)pyridin-3-yl)-2-oxo-2,3-dihydro-1H-benzo[d]imidazol-1-yl)methyl)cyclohexyl)-5-chloro-2-methylnicotinamide

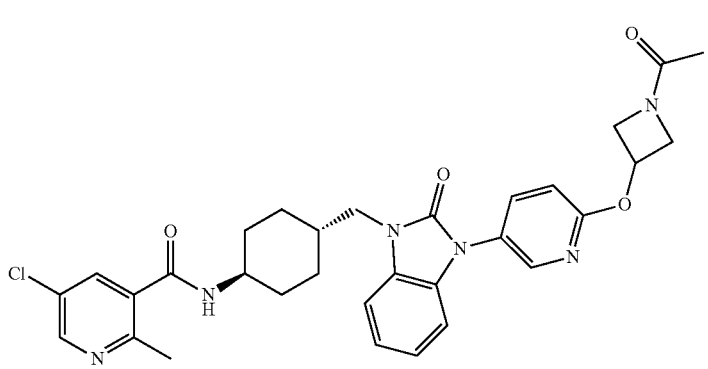

[Chem. 34]

To a mixture of N((1r,4r)-4-((3-(6-(azetidin-3-yloxy)pyridin-3-yl)-2-oxo-2,3-dihydro-1H-benzo[d]imidazol-1-yl)methyl)cyclohexyl)-5-chloro-2-methylnicotinamide (20 mg, 0.037 mmol, Intermediate-47) and TEA (0.025 mL, 0.18 mmol) in DCM (1 mL) is added acetic anhydride (0.01 mL, 0.11 mmol). The mixture is stirred at rt for 1 day. The mixture is basified with saturated aqueous sodium bicarbonate and extracted with DCM. The organic layer is dried over sodium sulfate and filtered. The filtrate is concentrated. The residue is purified by preparative LC-MS to give 6.2 mg (29% yield) of the title compound.

Example 79: N-((1r,4r)-4-((3-(6-((1-acetylazetidin-3-yl)methoxy)pyridin-3-yl)-2-oxo-2,3-dihydro-1H-benzo[d]imidazol-1-yl)methy)cyclohexyl)-5-chloro-2-methylnicotinamide

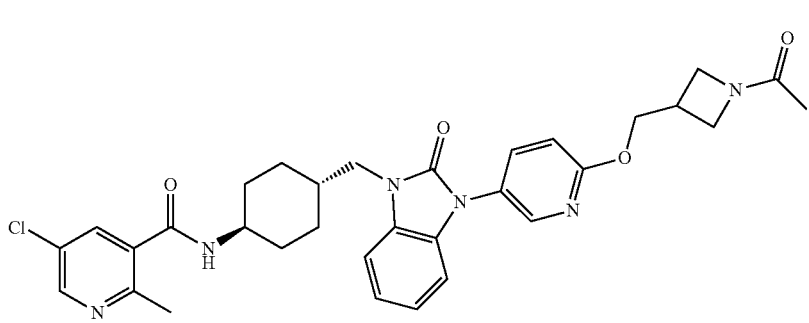

[Chem. 35]

To a mixture of N((1r,4r)-4-((3-(6-(azetidin-3-ylmethoxy)pyridin-3-yl)-2-oxo-2,3-dihydro-1H-benzo[d]imidazol-1-yl)methyl)cyclohexyl)-5-chloro-2-methylnicotinamide (21 mg, 0.037 mmol, Intermediate-48) and TEA (0.025 mL, 0.18 mmol) in DCM (1 mL) is added acetic anhydride (0.01 mL, 0.11 mmol). The mixture is stirred at rt for 1 day. The mixture is basified with saturated aqueous sodium bicarbonate and extracted with DCM. The organic layer is dried over sodium sulfate and filtered. The filtrate is concentrated. The residue is purified by preparative LC-MS to give 3.9 mg (18% yield) of the title compound.

Example 85: 5-chloro-2-methyl-N-((1r,4r)-4-((2-oxo-3-(1',2',3',6'-tetrahydro-[2,4'-bipyridin]-5-yl)-2,3-dihydro-1H-benzo[d]imidazol-1-yl)methyl)cyclohexyl)nicotinamide

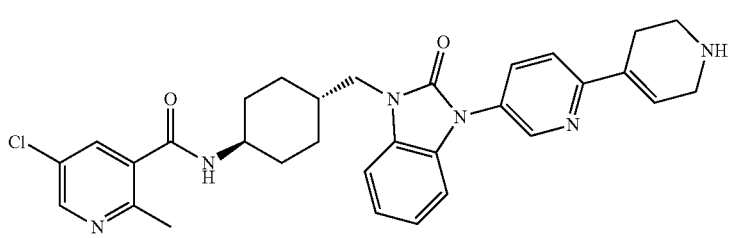

[Chem. 36]

A microwave vial equipped with a stirrer bar is charged with N((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide (20 mg, 0.036 mmol, Example 66), cesium carbonate (35.2 mg, 0.108 mmol), tert-butyl 4-(4,4,5,5-tetramethyl-1,3,2-dioxaborolan-2-yl)-5,6-dihydropyridine-1 (2H)-carboxylat e (14.5 mg, 0.047 mmol), palladium(II)acetate (0.41 mg, 0.0018 mmol) and XPhos (1.72 mg, 0.0036 mmol), then sealed with a cap lined with a disposable septum. The vial is then evacuated under vacuum and purged with nitrogen atmosphere. Anhydrous THF (1 mL) and water (0.1 mL) are added by syringe and the resulting mixture is stirred and heated at 90° C. for over night. The reaction mixture is extracted with EtOAc and water. The organic layer is dried (sodium sulfate) and concentrated in vacuo. The residue is purified by a strong anion exchange cartridge (ISOLUTE (registered trademark) SCX-2, 1 g/6 mL, Biotage) to give tert-butyl 5-(3-(((1r,4r)-4-(5-chloro-2-methylnicotinamido)cyclohexyl)methyl)-2-oxo-2,3-dihydro-1H-benzo[d]imidazol-1-yl)-5',6'-dihydro-[2,4'-bipyridine]-1'(2'H)-carboxylate (22 mg, 0.033 mmol, 93% yield). Then, a solution of tert-butyl 5-(3-(((1r,4r)-4-(5-chloro-2-methylnicotinamido)cyclohexyl)methyl)-2-oxo-2,3-dihydro-1H-benzo[d]imidazol-1-yl)-5',6'-dihydro-[2,4'-bipyridine]-1'(2'H)-carboxylate (22 mg, 0.033 mmol) in 4 M hydrochloric acid in 1,4-dioxane (1 mL) is stirred at rt for 1 hr. The reaction mixture is concentrated and extracted with ethyl acetate—saturated aqueous sodium bicarbonate. The organic layer is washed with brine, dried (sodium sulfate) and concentrated to give the title compound (18 mg, 97% yield).

Representative Procedure for Method A2

The following preparation of Example 86 represents the Method A2.

Example 86: 5-chloro-N-((1r,4r)-4-((3-(6-cyclopropylpyridin-3-yl)-2-oxo-2,3-dihydro-1H-benzo[d]imidazol-1-yl)methyl)cyclohexyl)-2-methylnicotinamide

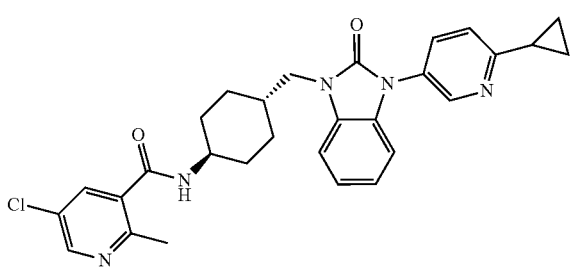

[Chem. 37]

A mixture of Mesylate-1 (4.3 mg, 0.012 mmol), Intermediate-51 (3 mg, 0.012 mmol), cesium carbonate (9.7 mg, 0.030 mmol) in NMP (0.2 mL) is stirred at 80° C. for 4 hrs. After cooled to rt, the mixture is diluted with water and extracted with EtOAc. The organic layer is dried over MgSO$_4$, filtered and concentrated. The residue is purified by preparative LC-MS to give 2.2 mg (36% yield) of the title compound.

Representative procedure for Method I

The following preparation of Example 89 represents the Method I.

Example 89: 5-chloro-2-methyl-N-((1r,4r)-4-((2-oxo-3-(6-phenylpyridin-3-yl)-2,3-dihydro-1H-benzo[d]imidazol-1-yl)methyl)cyclohexyl)nicotinamide

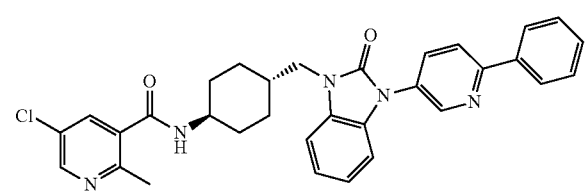

[Chem. 38]

A mixture of N((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide (25 mg, 0.045 mmol, Example 66), phenylboronic acid (11 mg, 0.09 mmol), and [1,1'-bis(diphenylphosphino)ferrocene]dichloropalladium (II), complex with dichloromethane (4 mg, 0.004 mmol) in 1,4-dioxane (0.7 mL) and saturated aqueous sodium bicarbonate (0.7 mL) is stirred at 80° C. for 3 hrs. The mixture is diluted with water. The mixture is extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 9.6 mg (39% yield) of the title compound.

Representative Procedure for Method J

The following preparation of Example 91 represents the Method J.

Example 91: 5-chloro-2-methyl-N-((1r,4r)-4-((3-(6-(methylamino)pyridin-3-yl)-2-oxo-2,3-dihydro-1H-benzo[d]imidazol-1-yl)methyl)cyclohexyl)nicotinamide

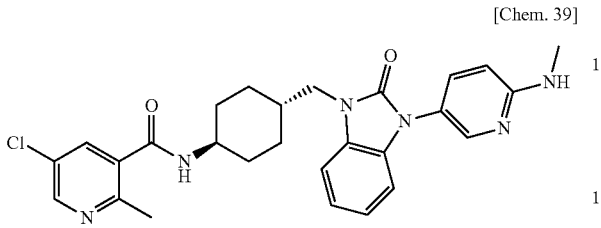

[Chem. 39]

A mixture of 5-chloro-N-((1r,4r)-4-((3-(6-fluoropyridin-3-yl)-2-oxo-2,3-dihydro-1H-benzo[d]imidazol-1-yl)methyl)cyclohexyl)-2-methylnicotinamide (25 mg, 0.051 mmol, Intermediate-54), dimethylamine hydrochloride (27 mg, 0.51 mmol), and DIEA (0.088 mL, 0.51 mmol) in NMP (2 mL) is irradiated with microwave at 220° C. for 30 min. The mixture is diluted with saturated aqueous sodium bicarbonate and extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 10 mg (40% yield) of the title compound.

Representative Procedure for Method K

The following preparation of Example 93 represents the Method K.

Example 93: 5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-methylnicotinamide

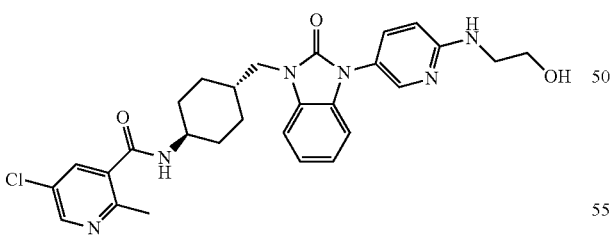

[Chem. 40]

A mixture of Example 66 (15 mg, 0.027 mmol), 2-aminoethanol (5.0 mg, 0.081 mmol) and TEA (0.02 mL, 0.14 mmol) in 2-propanol (0.5 mL) is stirred at 100° C. for 20 min then 150° C. for 3.5 hrs under microwave irradiation. After cooled to rt, the mixture is diluted with EtOAc, washed with water, dried over MgSO$_4$, filtered and concentrated in vacuo. The residue is purified by preparative LC-MS to give 6.8 mg (47% yield) of the title compound.

Example 97: 5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide

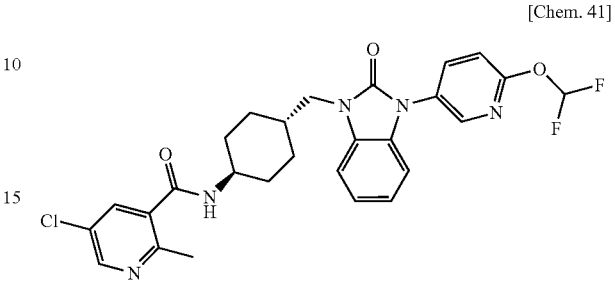

[Chem. 41]

<Step-1>: N((1r,4r)-4-((3-(6-(tert-butoxy)pyridin-3-yl)-2-oxo-2,3-dihydro-1H-benzo[d]imidazol-1-yl)methyl)cyclohexyl)-5-chloro-2-methylnicotinamide A mixture of Example 66 (40 mg, 0.072 mmol) and potassium tert-butoxide (24.3 mg, 0.216 mmol) in 1-methyl-2-pyrrolidone (0.5 mL) is stirred at 80° C. overnight. To the mixture is added potassium tert-butoxide (24.3 mg, 0.216 mmol) and stirred at 90° C. After starting material is completely consumed, the reaction mixture is cooled to rt. The mixture is diluted with EtOAc, washed with 1 M hydrochloric acid, dried over MgSO$_4$, filtered and concentrated in vacuo. The residue is purified by column chromatography on silica-gel eluting with 20-90% EtOAc in n-hexane to give 10 mg (25% yield) of the title compound.
MS (ESI) m/z: 548.5 (M+H)$^+$.

<Step-2>: 5-chloro-2-methyl-N-((1r,4r)-4-((2-oxo-3-(6-oxo-1,6-dihydropyridin-3-yl)-2,3-dihydro-1H-benzo[d]imidazol-1-yl)methyl)cyclohexyl)nicotinamide A solution of N((1r,4r)-4-((3-(6-(tert-butoxy)pyridin-3-yl)-2-oxo-2,3-dihydro-1H-benzo[d]imidazol-1-yl)methyl)cyclohexyl)-5-chloro-2-methylnicotinamide (10 mg, 0.018 mmol) in DCM (0.2 mL) and TFA (0.5 mL) is stirred at rt for 30 min. The reaction mixture is concentrated and the residue is purified by a strong anion exchange cartridge (ISOLUTE (registered trademark) SCX-2, 1 g/6 mL, Biotage) to give the title compound as a crude product (11 mg). It is used for the next Step-3 without further purification.
MS (ESI) m/z: 492.3 (M+H)$^+$.

<Step-3>: 5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-3-(6-oxo-1,6-dihydropyridin-3-yl)-2,3-dihydro-1H-benzo[d]imidazol-1-yl)methyl)cyclohexyl)nicotinamide (10 mg, 0.020 mmol) and sodium chlorodifluoroacetate (4.7 mg, 0.030 mmol) in acetonitrile (1 mL) is stirred at 85° C. overnight. After cooled to rt, the mixture is diluted with EtOAc, washed with water. The organic layer is purified by a strong anion exchange cartridge (ISOLUTE (registered trademark) SCX-2, 1 g/6 mL, Biotage) and then purified by preparative LC-MS to give 3.0 mg (27% yield) of the title compound.

Example 98: N-((1r,4r)-4-((3-(6-acetamidopyridin-3-yl)-2-oxo-2,3-dihydro-1H-benzo[d]imidazol-1-yl)methyl)cyclohexyl)-5-chloro-2-methylnicotinamide

[Chem. 42]

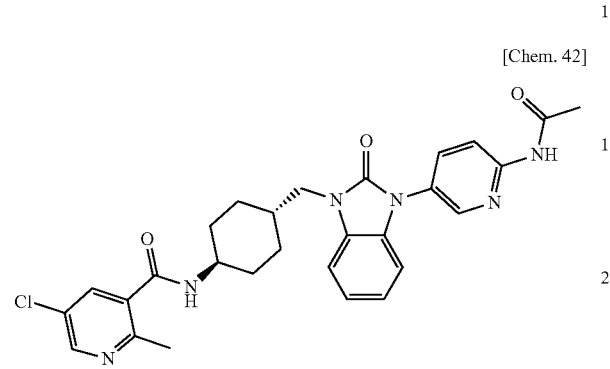

A mixture of Example 66 (20 mg, 0.036 mmol), acetamide (3.2 mg, 0.054 mmol), Xantphos (2 mg, 0.0036 mmol), palladium (II) acetate (1 mg, 0.0044 mmol) and cesium carbonate (23 mg, 0.072 mmol) in 1,4-dioxane (0.5 mL) is stirred at 100° C. overnight. To the mixture are added XPhos (4 mg, 0.0084 mmol) and palladium (II) acetate (1 mg, 0.0044 mmol) and stirred at 100° C. overnight. After cooled to rt, the mixture is diluted with EtOAc and water. The insoluble material is filtered off through celite pad. The filtrate is extracted with EtOAc. The organic layer is purified by a strong anion exchange cartridge (ISOLUTE (registered trademark) SCX-2, 1 g/6 mL, Biotage) and then purified by preparative LC-MS to give 3.0 mg (16% yield) of the title compound.

Representative Procedure for Method L

The following preparation of Example 99 represents the Method L.

Example 99: 5-chloro-N-((1r,4r)-4-((3-(6-(2-(hydroxymethyl)morpholino)pyridin-3-yl)-2-oxo-2,3-dihydro-1H-benzol[d]imidazol-1-yl)methyl)cyclohexyl)-2-methylnicotinamide A mixture of morpholin-2-ylmethanol (22 mg, 0.184 mmol), Intermediate-54 (18 mg, 0.036 mmol), and TEA (0.102 mL, 0.729 mmol) in 2-propanol (0.5 mL) is stirred at 160° C. for 3 hrs under microwave irradiation. After cooled to rt, the mixture is concentrated. The residue is diluted with EtOAc, washed with water, dried over MgSO$_4$, filtered and concentrated. The residue is purified by preparative LC-MS to give 10.4 mg (48% yield) of the title compound.

Example 100: 5-chloro-N-((1r,4r)-4-((3-(6-(difluoromethyl)pyridin-3-yl)-2-oxo-2,3-dihydro-1H-benzo[d]imidazol-1-yl)methyl)cyclohexyl)-2-methylnicotinamide

[Chem. 44]

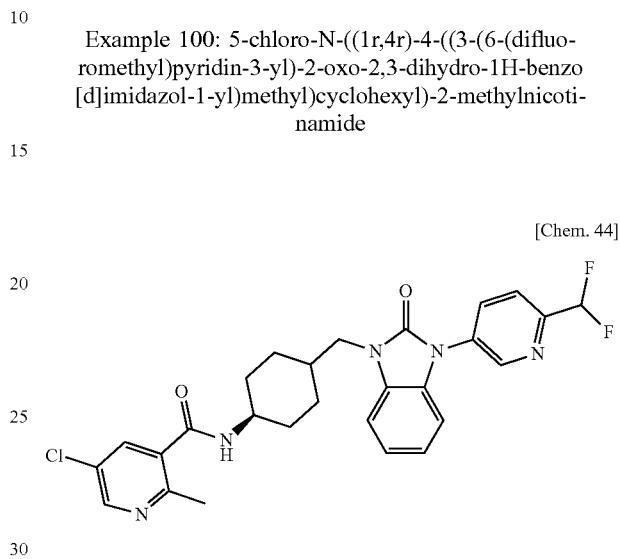

<Step-1>: 5-chloro-N-((1r,4r)-4-((3-(6-formylpyridin-3-yl)-2-oxo-2,3-dihydro-1H-benzo[d]imidazol-1-yl)methyl)cyclohexyl)-2-methylnicotinamide Ozone is bubbled in a solution of Example 70 (100 mg, 0.199 mmol) in DCM (2 mL) at −78° C. until reaction solution turned to pale blue solution. N$_2$ is bubbled to dissipate blue color, and dimethylsulfane (0.087 mL, 1.20 mmol) is added to the reaction mixture and stirred for 20 min at −78° C., then stirred over night at room temperature. After removal of solvent, the residue is extracted with ethyl acetate-water. The organic layer is washed with brine, dried over sodium sulfate filtered and concentrated. The residue is purified by column chromatography on silica-gel eluting with 30-100% EtOAc in n-hexane followed by 0-10% MeOH in EtOAc to give 65 mg (65% yield) of the title compound as a pale yellow solid.

MS (ESI) m/z: 504.5 (M+H)$^+$.

[Chem. 43]

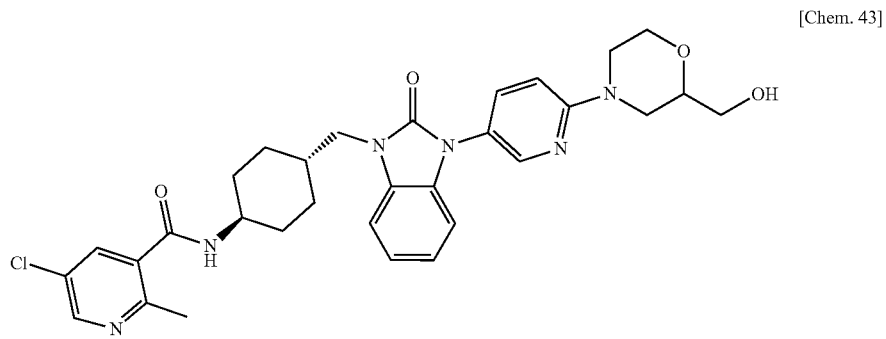 [SMILES: Cc1ncc(Cl)cc1C(=O)N[C@H]1CC[C@H](Cn2c(=O)n(-c3ccc(N4CCOC(CO)C4)nc3)c3ccccc32)CC1]

<Step-2>: 5-chloro-N-((1r,4r)-4-((3-(6-(difluoromethyl)pyridin-3-yl)-2-oxo-2,3-dihydro-1H-benzo[d]imidazol-1-yl)methyl)cyclohexyl)-2-methylnicotinamide To a solution of 5-chloro-N-((1r,4r)-4-((3-(6-formylpyridin-3-yl)-2-oxo-2,3-dihydro-1H-benzo[d]imidazol-1-yl)methyl)cyclohexyl)-2-methylnicotinamide (20 mg, 0.040 mmol) in DCM (0.5 mL) is added deoxofluor (40 microL, 0.217 mmol) at −50° C. and stirred at 0° C. for 30 min then rt overnight. After cooling to 0° C., the reaction is quenched with saturated aqueous sodium bicarbonate. The resulting mixture is extracted with EtOAc. The organic phase is dried over MgSO$_4$, filtered and concentrated. The residue is purified by preparative LC-MS to give 5.8 mg (28% yield) of the title compound.

Example 101: 5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-methylnicotinamide

[Chem. 45]

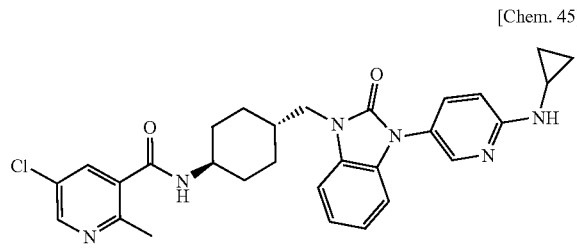

To a mixture of 5-chloro-N-((1r,4r)-4-((3-(6-fluoropyridin-3-yl)-2-oxo-2,3-dihydro-1H-benzo[d]imidazol-1-yl)methyl)cyclohexyl)-2-methylnicotinamide (25 mg, 0.051 mmol, Intermediate-54), and cyclopropylamine (29 mg, 0.51 mmol) in NMP (2 mL) is added sodium hydride (60% dispersion in mineral oil, 22 mg, 0.15 mmol) at room temperature. The mixture is stirred at room temperature for 1 day. The mixture is diluted with water and extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 2.1 mg (8% yield) of the title compound.

Example 102: 5-chloro-2-methyl-N-((1R,4r)-4-((3-(6-(((R)-4-methylmorpholin-3-yl)methoxy)pyridin-3-yl)-2-oxo-2,3-dihydro-1H-benzo[d]imidazol-1-yl)methyl)cyclohexyl)nicotinamide <Step-1>: (R)-tert-butyl 3-(((5-(3-(((1r,4R)-4-(5-chloro-2-methylnicotinamido)cyclohexyl)methyl)-2-oxo-2,3-dihydro-1H-benzol[d]imidazol-1-yl)pyridin-2-yl)oxy)methyl)morpholine-4-carboxylate To a mixture of 5-chloro-N-((1r,4r)-4-((3-(6-fluoropyridin-3-yl)-2-oxo-2,3-dihydro-1H-benzo[d]imidazol-1-yl)methyl)cyclohexyl)-2-methylnicotinamide (25 mg, 0.051 mmol, Intermediate-54), and (S)-tert-butyl 3-(hydroxymethyl)morpholine-4-carboxylate (11 mg, 0.51 mmol) in DMF (2 mL) is added sodium hydride (60% dispersion in mineral oil, 8 mg, 0.20 mmol) at room temperature. The mixture is stirred at room temperature for 1 hr. The mixture is diluted with water and extracted with EtOAc. The organic layer is concentrated. The residue is purified by a strong anion exchange cartridge (ISOLUTE (registered trademark) SCX-2, 1 g/6 mL, Biotage) to give 23 mg (66% yield) of the title compound as a pale yellow gum.
MS (ESI) m/z: 691.6 (M+H)$^+$.

<Step-2>: 5-chloro-2-methyl-N-((1R,4r)-4-((3-(6-((R)-morpholin-3-ylmethoxy)pyridin-3-yl)-2-oxo-2,3-dihydro-1H-benzo[d]imidazol-1-yl)methyl)cyclohexyl)nicotinamide hydrochloride The title compound is prepared in quantitative yield (21 mg, a pale yellow gum) by the similar manner to Step-2 of Intermediate-1 using (R)-tert-butyl 3-(((5-(3-(((1r,4R)-4-(5-chloro-2-methylnicotinamido)cyclohexyl)methyl)-2-oxo-2,3-dihydro-1H-benzo[d]imidazol-1-yl)pyridin-2-yl)oxy)methyl)morpholine-4-carboxylate (23 mg, 0.033 mmol, Step-1 of Example 102).
MS (ESI) m/z: 591.5 (M+H)$^+$.

<Step-3>: 5-chloro-2-methyl-N-((1R,4r)-4-((3-(6-(((R)-4-methylmorpholin-3-yl)methoxy)pyridin-3-yl)-2-oxo-2,3-dihydro-1H-benzo[d]imidazol-1-yl)methyl)cyclohexyl)nicotinamide To a mixture of 5-chloro-2-methyl-N-((1R,4r)-4-((3-(6-((R)-morpholin-3-ylmethoxy)pyridin-3-yl)-2-oxo-2,3-dihydro-1H-benzo[d]imidazol-1-yl)methyl)cyclohexyl)nicotinamide hydrochloride (21 mg, 0.033 mmol, Step-2 of Example 102), paraformaldehyde (10 mg) in DCM (2 mL) is added sodium triacetoxyborohydride (18 mg, 0.085 mmol) at rt. The mixture is stirred at rt for 3 hrs. The mixture is basified with saturated aqueous sodium bicarbonate and extracted with EtOAc. The organic layer is dried over sodium sulfate and filtered. The filtrate is concentrated. The residue is purified by a strong anion exchange cartridge (ISOLUTE (registered trademark) SCX-2, 1 g/6 mL, Biotage) and then purified by preparative LC-MS to give 1.9 mg (9% yield) of the title compound.

[Chem. 46]

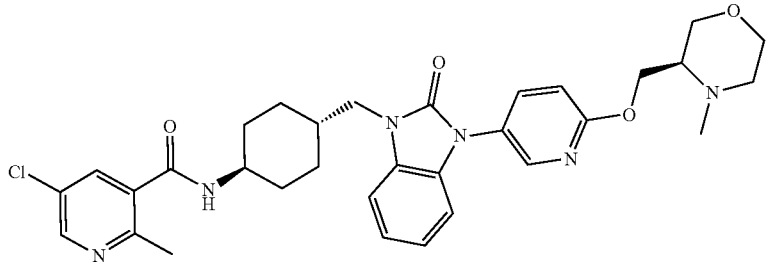

Example 103: 5-chloro-2-methyl-N-((1S,4r)-4-((3-(6-(((S)-4-methylmorpholin-3-yl)methoxy)pyridin-3-yl)-2-oxo-2,3-dihydro-1H-benzo[d]imidazol-1-yl)methyl)cyclohexyl)nicotinamide

[Chem. 47]

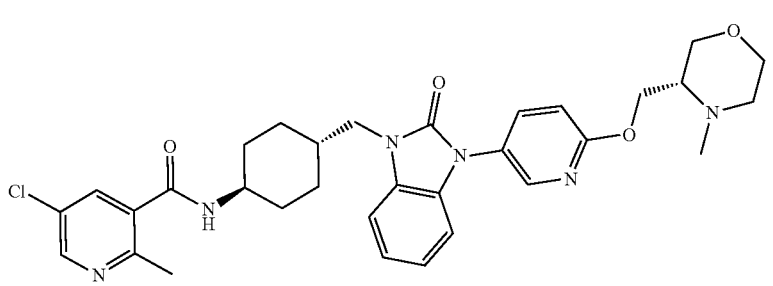

<Step-1>: (S)-tert-butyl 3-(((5-(3-(((1r,4S)-4-(5-chloro-2-methylnicotinamido)cyclohexyl)methyl)-2-oxo-2,3-dihydro-1H-benzo[d]imidazol-1-yl)pyridin-2-yl)oxy)methyl)morpholine-4-carboxylate To a mixture of 5-chloro-N-((1r,4r)-4-((3-(6-fluoropyridin-3-yl)-2-oxo-2,3-dihydro-1H-benzo[d]imidazol-1-yl)methyl)cyclohexyl)-2-methylnicotinamide (25 mg, 0.051 mmol, Intermediate-54), and (R)-tert-butyl 3-(hydroxymethyl)morpholine-4-carboxylate (11 mg, 0.51 mmol) in DMF (2 mL) is added sodium hydride (60% dispersion in mineral oil, 8 mg, 0.20 mmol) at room temperature. The mixture is stirred at room temperature for 1 hr. The mixture is diluted with water and extracted with EtOAc. The organic layer is concentrated. The residue is purified by a strong anion exchange cartridge (ISOLUTE (registered trademark) SCX-2, 1 g/6 mL, Biotage) to give 23 mg (66% yield) of the title compound as a pale yellow gum.
MS (ESI) m/z: 691.6 (M+H)$^+$.

<Step-2>: 5-chloro-2-methyl-N-((1S,4r)-4-((3-(6-((S)-morpholin-3-ylmethoxy)pyridin-3-yl)-2-oxo-2,3-dihydro-1H-benzo[d]imidazol-1-yl)methyl)cyclohexyl)nicotinamide hydrochloride The title compound is prepared in quantitative yield (21 mg, a pale yellow gum) by the similar manner to Step-2 of Intermediate-1 using (S)-tert-butyl 3-(((5-(3-(((1r,4S)-4-(5-chloro-2-methylnicotinamido)cyclohexyl)methyl)-2-oxo-2,3-dihydro-1H-benzo[d]imidazol-1-yl)pyridin-2-yl)oxy)methyl)morpholine-4-carboxylate (23 mg, 0.033 mmol, Step-1 of Example 103).
MS (ESI) m/z: 591.5 (M+H)$^+$.

<Step-3>: 5-chloro-2-methyl-N-((1S,4r)-4-((3-(6-(((S)-4-methylmorpholin-3-yl)methoxy)pyridin-3-yl)-2-oxo-2,3-dihydro-1H-benzo[d]imidazol-1-yl)methyl)cyclohexyl)nicotinamide To a mixture of 5-chloro-2-methyl-N-((1S,4r)-4-((3-(6-((S)-morpholin-3-ylmethoxy)pyridin-3-yl)-2-oxo-2,3-dihydro-1H-benzo[d]imidazol-1-yl)methyl)cyclohexyl)nicotinamide hydrochloride (21 mg, 0.033 mmol, Step-2 of Example 103), paraformaldehyde (10 mg) in DCM (2 mL) is added sodium triacetoxyborohydride (18 mg, 0.085 mmol) at rt. The mixture is stirred at rt for 3 hrs. The mixture is basified with saturated aqueous sodium bicarbonate and extracted with EtOAc. The organic layer is dried over sodium sulfate and filtered. The filtrate is concentrated. The residue is purified by a strong anion exchange cartridge (ISOLUTE (registered trademark) SCX-2, 1 g/6 mL, Biotage) and then purified by preparative LC-MS to give 2.8 mg (14% yield) of the title compound.

Example 104: 5-chloro-2-methyl-N-((1r,4r)-4-((3-(6-(methylamino)pyridazin-3-yl)-2-oxo-2,3-dihydro-1H-benzo[d]imidazol-1-yl)methyl)cyclohexyl)nicotinamide

[Chem. 48]

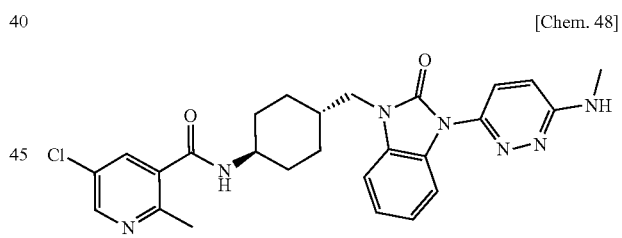

A mixture of 5-chloro-N-((1r,4r)-4-((3-(6-chloropyridazin-3-yl)-2-oxo-2,3-dihydro-1H-benzo[d]imidazol-1-yl)methyl)cyclohexyl)-2-methylnicotinamide (23 mg, 0.045 mmol, Intermediate-55), methanamine hydrochloride (30 mg, 0.45 mmol) and DIEA (0.079 mL, 0.45 mmol) in NMP (2 mL) is irradiated with microwave at 200° C. for 30 min. The mixture is diluted with saturated aqueous sodium bicarbonate and extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 3.2 mg (14% yield) of the title compound.
Representative Procedure for Method M
The following preparation of Example 105 represents the Method M.

Example 105: 5-chloro-N-((1r,4r)-4-((3-(6-((cyclopropylmethyl)amino)pyridin-3-yl)-2-oxo-2,3-dihydro-1H-benzo[d]imidazol-1-yl)methyl)cyclohexyl)-2-methylnicotinamide

[Chem. 49]

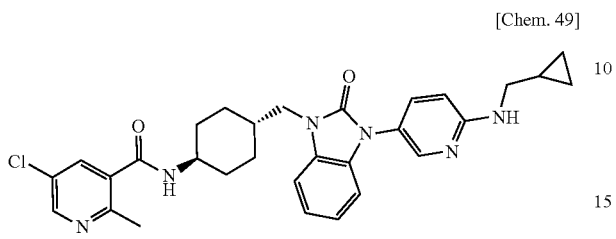

A mixture of 5-chloro-N-((1r,4r)-4-((3-(6-fluoropyridin-3-yl)-2-oxo-2,3-dihydro-1H-benzo[d]imidazol-1-yl)methyl)cyclohexyl)-2-methylnicotinamide (25 mg, 0.051 mmol, Intermediate-54), cyclopropylmethanamine (36 mg, 0.51 mmol), DIEA (0.088 mL, 0.51 mmol), and DBU (0.038 mL, 0.25 mmol) in NMP (2 mL) is irradiated with microwave at 220° C. for 30 min. The mixture is diluted with saturated aqueous sodium bicarbonate and extracted with EtOAc. The organic layer is concentrated. The residue is purified by a strong anion exchange cartridge (ISOLUTE (registered trademark) SCX-2, 1 g/6 mL, Biotage) and then purified by preparative LC-MS to give 5.1 mg (18% yield) of the title compound.

Example 111: 5-chloro-2-methyl-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide

[Chem. 50]

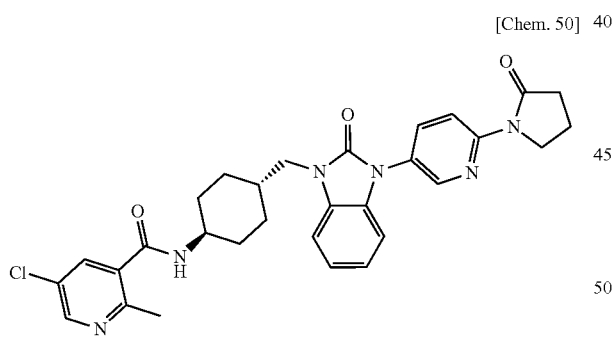

A mixture of Example 66 (20 mg, 0.036 mmol), pyrrolidin-2-one (6.1 mg, 0.072 mmol), XPhos (5.2 mg, 0.011 mmol), tris(dibenzylideneacetone)dipalladium(0) (5.0 mg, 0.0054 mmol) and sodium tert-pentoxide (7.9 mg, 0.072 mmol) in 1,4-dioxane (0.5 mL) is stirred at 100° C. overnight. After cooled to rt, the mixture is diluted with EtOAc and water followed by extraction with EtOAc. The organic layer is purified by a strong anion exchange cartridge (ISOLUTE (registered trademark) SCX-2, 1 g/6 mL, Biotage) and then purified by preparative LC-MS to give 10.4 mg (52% yield) of the title compound.

Representative Procedure for Method N

The following preparation of Example 112 represents the Method N.

Example 112: 5-chloro-N-(4-((3-(6-(cyclopropylmethoxy)pyridin-3-yl)-2-oxo-2,3-dihydro-1H-benzo[d]imidazol-1-yl)methyl)cyclohexyl)-2-methylnicotinamide

[Chem. 51]

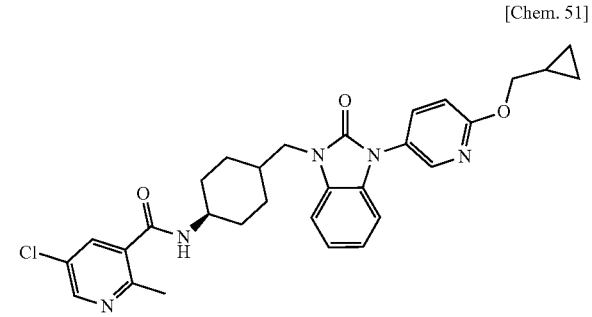

A mixture of Intermediate-54 (20 mg, 0.040 mmol), cyclopropylmethanol (20 mg, 0.277 mmol) and sodium tert-pentoxide (14 mg, 0.127 mmol) in THF is stirred at 90° C. for 11 hrs. After cooled to rt, the mixture is diluted with EtOAc, washed with water and brine, dried over MgSO$_4$, filtered and concentrated. The residue is purified by preparative LC-MS to give 11.1 mg (50% yield) of the title compound.

Example 128: 5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide

[Chem. 52]

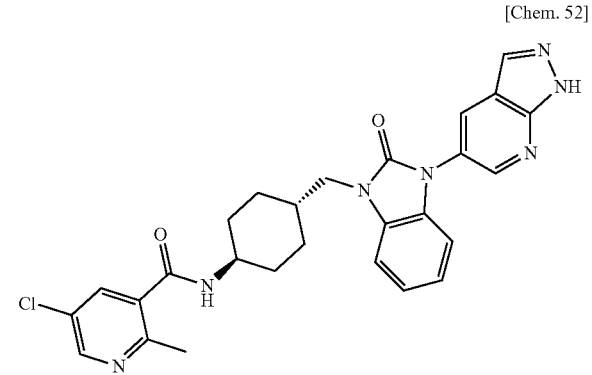 [SMILES: Cc1ncc(Cl)cc1C(=O)N[C@H]1CC[C@H](Cn2c(=O)n(-c3cnc4[nH]ncc4c3)c3ccccc32)CC1]

<Step-1>:5-bromo-1-(tetrahydro-2H-pyran-2-yl)-1H-pyrazolo[3,4-b]pyridine

A mixture of 5-bromo-1H-pyrazolo[3,4-b]pyridine (202 mg, 1.02 mmol), 3,4-dihydro-2H-pyran (0.187 mL, 2.04 mmol) and p-toluenesulfonic acid (19 mg, 0.10 mmol) in toluene (2 mL) is stirred at 100° C. for 4 hrs. After cooling to rt, the mixture is directly purified by column chromatography on silica-gel eluting with 10-60% EtOAc in n-hexane to give 281 mg (98% yield) of the title compound as a pale yellow oil.

$^1$H-NMR (400 MHz, CDCl$_3$) delta 8.61 (1H, d, J=1.8 Hz), 8.21 (1H, d, J=0.9 Hz), 8.17 (1H, dd, J=1.8, 0.9 Hz), 5.70 (1H, dd, J=8.5, 2.5 Hz), 4.04-3.96 (1H, m), 3.81-3.71 (1H, m), 2.54-2.38 (1H, m), 2.22-2.07 (2H, m), 1.88-1.65 (3H, m).

231

<Step-2>: 1-(tetrahydro-2H-pyran-2-yl)-5-(4,4,5,5-tetramethyl-1,3,2-dioxaborolan-2-yl)-1H-pyrazolo[3,4-b]pyridine After degassed with N₂ gas, a mixture of 5-bromo-1-(tetrahydro-2H-pyran-2-yl)-1H-pyrazolo[3,4-b]pyridine (230 mg, 0.815 mmol), bis(pinacolato)diboron (621 mg, 2.45 mmol), Pd(dppf)Cl₂ (60 mg, 0.082 mmol) and potassium acetate (240 mg, 2.45 mmol) in 1,4-dioxane (3 mL) is stirred at 100° C. for 3 hrs. After cooled to rt, the mixture is directly purified by column chromatography on silica-gel eluting with 10-60% EtOAc in n-hexane to give 200 mg (75% yield) of the title compound as a brown oil.
¹H-NMR (400 MHz, CDCl₃) delta 8.89 (1H, d, J=1.4 Hz), 8.51 (1H, d, J=1.4 Hz), 8.08 (1H, d, J=0.9 Hz), 6.18 (1H, dd, J=10.7, 2.5 Hz), 4.17-4.09 (1H, m), 3.89-3.81 (1H, m), 2.75-2.53 (1H, m), 2.20-2.09 (1H, m), 2.02-1.94 (1H, m), 1.88-1.72 (2H, m), 1.69-1.59 (1H, m), 1.37 (12H, s). MS (ESI) m/z: 330.3 (M+H)⁺.

<Step-3>: tert-butyl 2-oxo-3-(1-(tetrahydro-2H-pyran-2-yl)-1H-pyrazolo[3,4-b]pyridin-5-yl)-2,3-dihydro-1H-benzo[d]imidazole-1-carboxylate A mixture of tert-butyl 2-oxo-2,3-dihydro-1H-benzo[d]imidazole-1-carboxylate (100 mg, 0.427 mmol), copper (II) acetate (116 mg, 0.640 mmol), TEA (0.089 mL, 0.640 mmol), 1-(tetrahydro-2H-pyran-2-yl)-5-(4,4,5,5-tetramethyl-1,3,2-dioxaborolan-2-yl)-1H-pyrazolo[3,4-b]pyridine (200 mg, 0.608 mmol) and MS 4A (100 mg) in DCM (3 mL) is stirred at rt for 4 days. To the reaction mixture are added copper (II) acetate (116 mg, 0.640 mmol) and TEA (0.089 mL, 0.640 mmol) and stirred at rt overnight. The mixture is directly purified by column chromatography on amino-functional silica-gel eluting with 5-60% EtOAc in n-hexane to give 127 mg (68% yield) of the title compound as a white solid.
¹H-NMR (400 MHz, CDCl₃) delta 8.67 (1H, d, J=2.3 Hz), 8.20 (1H, d, J=2.3 Hz), 8.16 (1H, s), 7.95 (1H, dd, J=7.5, 1.8 Hz), 7.24-7.14 (2H, m), 6.89 (1H, dd, J=7.3, 1.8 Hz), 6.18 (1H, dd, J=10.5, 2.3 Hz), 4.20-4.10 (1H, m), 3.92-3.79 (1H, m), 2.75-2.60 (1H, m), 2.26-2.11 (1H, m), 2.09-2.00 (1H, m), 1.88-1.77 (2H, m), 1.73-1.61 (10H, m). MS (ESI) m/z: 436.2 (M+H)⁺.

<Step-4>: 5-chloro-2-methyl-N-((1r,4r)-4-((2-oxo-3-(1-(tetrahydro-2H-pyran-2-yl)-1H-pyrazolo[3,4-b]pyridin-5-yl)-2,3-dihydro-1H-benzo[d]imidazol-1-yl)methyl)cyclohexyl)nicotinamide A mixture of Mesylate-1 (100 mg, 0.277 mmol), tert-butyl 2-oxo-3-(1-(tetrahydro-2H-pyran-2-yl)-1H-pyrazolo[3,4-b]pyridin-5-yl)-2,3-dihydro-1H-benzo[d]imidazole-1-carboxylate (127 mg, 0.292 mmol), cesium carbonate (226 mg, 0.693 mmol) in NMP (1 mL) is stirred at 80° C. overnight.

232

To the mixture is added Mesylate-1 (22 mg, 0.061 mmol) and stirred at 80° C. for 16 hrs. After cooled to rt, the mixture is diluted with EtOAc and washed with water. The organic layer is dried over MgSO₄, filtered and concentrated. The residue is purified by column chromatography on silica-gel eluting with 30-100% EtOAc in n-hexane followed by 0-10% MeOH in EtOAc to give 103 mg (62% yield) of the title compound.
¹H-NMR (400 MHz, CDCl₃) delta 8.73 (1H, d, J=2.3 Hz), 8.49 (1H, d, J=2.3 Hz), 8.24 (1H, d, J=2.3 Hz), 8.16 (1H, s), 7.61 (1H, d, J=2.3 Hz), 7.22-7.17 (1H, m), 7.13-7.07 (2H, m), 7.04-7.00 (1H, m), 6.18 (1H, dd, J=10.5, 2.7 Hz), 5.57 (1H, d, J=7.8 Hz), 4.20-4.12 (1H, m), 4.04-3.80 (4H, m), 2.80-2.52 (4H, m), 2.25-2.12 (3H, m), 2.10-1.76 (6H, m), 1.73-1.62 (1H, m), 1.44-1.07 (4H, m). MS (ESI) m/z: 600.4 (M+H)⁺.

<Step-5>: 5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide A solution of 5-chloro-2-methyl-N-((1r,4r)-4-((2-oxo-3-(1-(tetrahydro-2H-pyran-2-yl)-1H-pyrazolo[3,4-b]pyridin-5-yl)-2,3-dihydro-1H-benzo[d]imidazol-1-yl)methyl)cyclohexyl)nicotinamide (103 mg, 0.172 mmol) in DCM (0.5 mL) and TFA (1 mL) is stirred at rt for 1.5 hrs. After the reaction mixture is concentrated, the residue is dissolved into DCM, washed with saturated aqueous sodium bicarbonate, dried over MgSO₄, filtered and concentrated. One third of the resultant residue is purified by preparative LC-MS to give 8.8 mg (29% yield) of the title compound.
Representative Procedure for Method O
The following preparation of Example 130 represents the Method O.

Example 130: 5-chloro-2-methyl-N-((1r,4r)-4-((3-(4-(oxetan-3-ylcarbamoyl)phenyl)-2-oxo-2,3-dihydro-1H-benzo[d]imidazol-1-yl)methyl)cyclohexyl)nicotinamide

[Chem. 53]

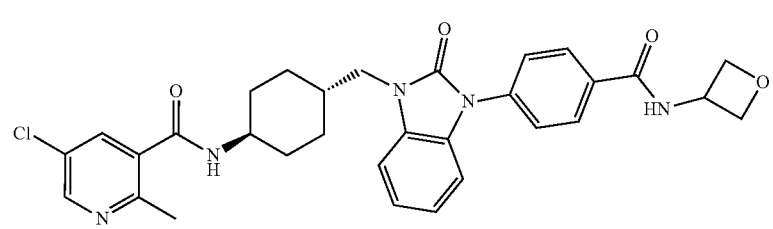

A mixture of 4-(3-(((1r,4r)-4-(5-chloro-2-methylnicotinamido)cyclohexyl)methyl)-2-oxo-2,3-dihydro-1H-benzo[d]imidazol-1-yl)benzoic acid (25 mg, 0.048 mmol, Intermediate-9), oxetan-3-amine (7 mg, 0.096 mmol), HBTU (37 mg, 0.096 mmol), and TEA (0.034 mL, 0.24 mmol) in DMF (1 mL) is stirred at room temperature for 3 hrs. The mixture is diluted with saturated sodium hydrogen carbonate aqueous solution. The mixture is extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 5.9 mg (21% yield) of the title compound.

Example 134: 5-chloro-N-((1r,4r)-4-((3-(6-(3-hydroxypropoxy)pyridin-3-yl)-2-oxo-2,3-dihydro-1H-benzo[d]imidazol-1-yl)methyl)cyclohexyl)-2-methylnicotinamide

[Chem. 54]

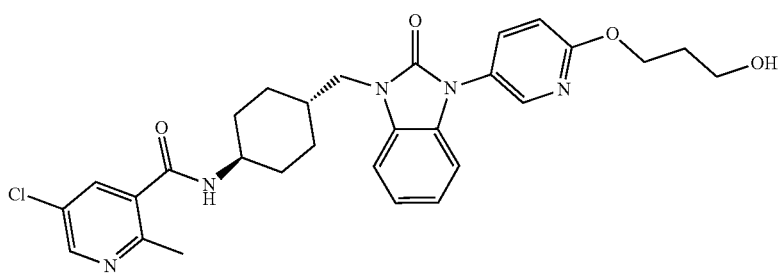

A mixture of Intermediate-54 (15 mg, 0.030 mmol), propane-1,3-diol (3.5 mg, 0.046 mmol) and sodium tert-pentoxide (8.4 mg, 0.076 mmol) in THF (0.5 mL) is stirred at 120° C. for 30 min under microwave irradiation. After cooled to rt, to the reaction mixture is added MeOH to dissolve precipitate. The resulting solution is purified by a strong anion exchange cartridge (ISOLUTE (registered trademark) SCX-2, 1 g/6 mL, Biotage) and then purified by preparative LC-MS to give 6.0 mg (36% yield) of the title compound.

Example 135: 5-chloro-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)-2-methylnicotinamide

[Chem. 55]

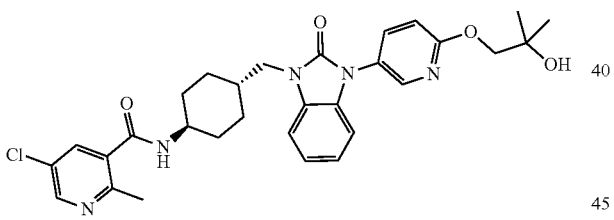

The title compound is prepared in 26% yield (4.3 mg) by the similar manner to Example 134 using 2-methylpropane-1,2-diol (4.1 mg, 0.046 mmol) in place of propane-1,3-diol.

Example 140: 5-chloro-2-methyl-N-((1r,4r)-4-((3-(6-(oxetan-3-yloxy)pyridin-3-yl)-2-oxo-2,3-dihydro-1H-benzo[d]imidazol-1-yl)methyl)cyclohexyl)nicotinamide

[Chem. 56]

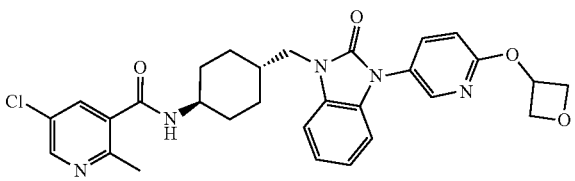

The title compound is prepared in 65% yield (10.8 mg) by the similar manner to Example 134 using oxetan-3-ol (3.4 mg, 0.046 mmol) in place of propane-1,3-diol.

Example 143: N-((1r,4r)-4-((3-(6-aminopyridin-3-yl)-2-oxo-2,3-dihydro-1H-benzo[d]imidazol-1-yl)methyl)cyclohexyl)-5-chloro-2-methylnicotinamide

[Chem. 57]

<Step-1>: N-((1r,4r)-4-((3-(6-azidopyridin-3-yl)-2-oxo-2,3-dihydro-1H-benzo[d]imidazol-1-yl)methyl)cyclohexyl)-5-chloro-2-methylnicotinamide A mixture of Intermediate-54 (15 mg, 0.030 mmol) and sodium azide (4.0 mg, 0.061 mmol) in DMSO is stirred at 100° C. overnight. After cooled to rt, the mixture is diluted with EtOAc, washed with water, dried over $MgSO_4$, filtered and concentrated. The residue is purified by column chromatography on silica-gel eluting with 30-100% EtOAc in n-hexane to give 10 mg (64% yield) of the title compound as a beige solid.
$^1$H-NMR (400 MHz, $CDCl_3$) delta 9.22-9.20 (1H, m), 8.49 (1H, d, J=2.7 Hz), 8.20 (1H, dd, J=9.6, 0.9 Hz), 8.00 (1H, dd, J=9.6, 1.8 Hz), 7.62 (1H, d, J=2.7 Hz), 7.31-7.24 (1H, m), 7.21-7.17 (2H, m), 7.14 (1H, d, J=7.8 Hz), 5.63 (1H, d, J=7.8 Hz), 4.06-3.90 (1H, m), 3.85 (2H, d, J=6.9 Hz), 2.61 (3H, s), 2.23-2.12 (2H, m), 2.04-1.82 (3H, m), 1.47-1.11 (4H, m).

<Step-2>: N((1r,4r)-4-((3-(6-aminopyridin-3-yl)-2-oxo-2,3-dihydro-1H-benzo[d]imidazol-1-yl)methyl)cyclohexyl)-5-chloro-2-methylnicotinamide A mixture of triphenylphosphine (6.1 mg, 0.023 mmol) and N((1r,4r)-4-((3-(6-azidopyridin-3-yl)-2-oxo-2,3-dihydro-1H-benzo[d]imidazol-1-yl)methyl)cyclohexyl)-5-chloro-2-methylnicotinamide (10 mg, 0.019 mmol) in THF (1 mL) and water (0.1 mL) is stirred at rt overnight. To this is added 2 M hydrochloric acid and stirred at rt for 5 hrs. To the reaction mixture is added 2 M aqueous sodium hydroxide solution to neutralize the mixture. The resultant mixture is extracted with EtOAc. The organic phase is dried over MgSO$_4$, filtered and concentrated. The residue is purified by preparative LC-MS to give 4.6 mg (48% yield) of the title compound.

Example 149: 5-chloro-N-((1r,4r)-4-((3-(6-methoxy-2-methylpyridin-3-yl)-2-oxo-2,3-dihydro-1H-benzo[d]imidazol-1-yl)methyl)cyclohexyl)-2-methylnicotinamide

[Chem. 58]

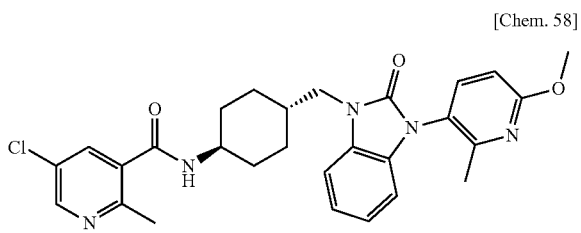 [SMILES: COc1ccc(-n2c(=O)n(C[C@H]3CC[C@H](NC(=O)c4cc(Cl)cnc4C)CC3)c3ccccc32)c(C)n1]

<Step-1>:6-fluoro-2-methyl-N-(2-nitrophenyl)pyridin-3-amine

The title compound is prepared in 64% yield (562 mg, an orange solid) by the similar manner to Step-1 of Intermediate-20 using 6-fluoro-2-methylpyridin-3-amine (500 mg, 3.96 mmol) in place of 2,4-difluoroaniline.

$^1$H-NMR (400 MHz, CDCl$_3$) delta 9.20 (1H, s), 8.25 (1H, dd, J=8.5, 1.6 Hz), 7.68 (1H, t, J=7.8 Hz), 7.42-7.36 (1H, m), 6.88 (1H, dd, J=7.8, 3.7 Hz), 6.85-6.80 (1H, m), 6.65 (1H, dd, J=8.7, 1.4 Hz), 2.45 (3H, s).

<Step-2>: N$^1$-(6-fluoro-2-methylpyridin-3-yl)benzene-1,2-diamine

The title compound is prepared in quantitative yield (494 mg) by the similar manner to Step-2 of Intermediate-20 using 4-fluoro-2-methyl-N-(2-nitrophenyl)aniline (562 mg, 2.27 mmol, Step-1 of Example 149) in place of 2,4-difluoro-N-(2-nitrophenyl)aniline.

$^1$H-NMR (400 MHz, CDCl$_3$) delta 7.03 (1H, td, J=7.5, 1.4 Hz), 6.98 (1H, dd, J=8.7, 6.9 Hz), 6.91 (1H, dd, J=7.5, 1.4 Hz), 6.82 (1H, dd, J=7.5, 1.4 Hz), 6.76 (1H, td, J=7.5, 1.4 Hz), 6.63 (1H, dd, J=8.7, 3.7 Hz), 4.92 (1H, s), 3.73 (2H, s), 2.46 (3H, s).

<Step-3>:1-(6-fluoro-2-methylpyridin-3-yl)-1H-benzo[d]imidazol-2(3H)-one

The title compound is prepared in 92% yield (511 mg, an off-white powder) by the similar manner to Step-3 of Intermediate-20 using N$^1$-(6-fluoro-2-methylpyridin-3-yl)benzene-1,2-diamine (494 mg, 2.27 mmol, Step-2 of Example 149) in place of N$^1$-(2,4-difluorophenyl)benzene-1,2-diamine.

$^1$H-NMR (400 MHz, CDCl$_3$) delta 9.19 (1H, s), 7.78 (1H, dd, J=8.5, 7.3 Hz), 7.18-7.12 (2H, m), 7.10-7.05 (1H, m), 6.97 (1H, dd, J=8.5, 3.2 Hz), 6.67 (1H, d, J=7.3 Hz), 2.40 (3H, s).

<Step-4>: 5-chloro-N-((1r,4r)-4-((3-(6-fluoro-2-methylpyridin-3-yl)-2-oxo-2,3-dihydro-1H-benzo[d]imidazol-1-yl)methyl)cyclohexyl)-2-methylnicotinamide A mixture of Mesylate-1 (50 mg, 0.139 mmol), 1-(6-fluoro-2-methylpyridin-3-yl)-1H-benzo[d]imidazol-2(3H)-one (40 mg, 0.166 mmol), cesium carbonate (113 mg, 0.346 mmol) in NMP (0.5 mL) is stirred at 80° C. for 5 hrs. After cooled to rt, the mixture is diluted with water and extracted with EtOAc. The organic layer is dried over MgSO$_4$, filtered and concentrated. The residue is purified by column chromatography on silica-gel eluting with 30-100% EtOAc in n-hexane followed by 0-10% MeOH in EtOAc to give 42 mg (60% yield) of the title compound as a beige solid.

$^1$H-NMR (400 MHz, CDCl$_3$) delta 8.49 (1H, d, J=2.3 Hz), 7.75 (1H, t, J=7.8 Hz), 7.61 (1H, d, J=2.3 Hz), 7.21-7.16 (1H, m), 7.12-7.05 (2H, m), 6.95 (1H, dd, J=7.8, 3.4 Hz), 6.71-6.67 (1H, m), 5.56 (1H, d, J=7.8 Hz), 4.05-3.89 (1H, m), 3.84 (2H, d, J=6.9 Hz), 2.61 (3H, s), 2.36 (3H, s), 2.22-2.10 (2H, m), 2.03-1.82 (3H, m), 1.43-1.14 (4H, m).

<Step-5>: 5-chloro-N-((1r,4r)-4-((3-(6-methoxy-2-methylpyridin-3-yl)-2-oxo-2,3-dihydro-1H-benzo[d]imidazol-1-yl)methyl)cyclohexyl)-2-methylnicotinamide A mixture of 5-chloro-N-((1r,4r)-4-((3-(6-fluoro-2-methylpyridin-3-yl)-2-oxo-2,3-dihydro-1H-benzo[d]imidazol-1-yl)methyl)cyclohexyl)-2-methylnicotinamide (20 mg, 0.039 mmol) and sodium methoxide (4.3 mg, 0.079 mmol) in MeOH is stirred at 120° C. for 30 min then 150° C. for 30 min. After cooled to rt, the mixture is purified by a strong anion exchange cartridge (ISOLUTE (registered trademark) SCX-2, 1 g/6 mL, Biotage) and then purified by preparative LC-MS to give 9.1 mg (44% yield) of the title compound.

Example 150: 5-chloro-2-methyl-N-((1r,4r)-4-((3-(2-methyl-6-(methylamino)pyridin-3-yl)-2-oxo-2,3-dihydro-1H-benzo[d]imidazol-1-yl)methyl)cyclohexyl)nicotinamide

[Chem. 59]

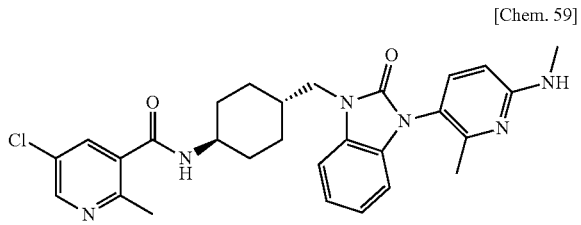 [SMILES: CNc1ccc(-n2c(=O)n(C[C@H]3CC[C@H](NC(=O)c4cc(Cl)cnc4C)CC3)c3ccccc32)c(C)n1]

A mixture of 5-chloro-N-((1r,4r)-4-((3-(6-fluoro-2-methylpyridin-3-yl)-2-oxo-2,3-dihydro-1H-benzo[d]imidazol-1-yl)methyl)cyclohexyl)-2-methylnicotinamide (20 mg, 0.039 mmol, Step-4 of Example 149), 2 M methylamine in THF (0.039 mL, 0.079 mmol), DBU (0.030 mL, 0.197 mmol), TEA (0.027 mL, 0.197 mmol) in 2-propanol (0.5 mL) is stirred at 160° C. for 3 hrs under microwave irradiation. After cooled to rt, the mixture is concentrated. The residue is dissolved into EtOAc, washed with water, dried over MgSO$_4$, filtered and concentrated. The residue is purified by preparative LC-MS to give 5.1 mg (25% yield) of the title compound.

Example 152: 5-chloro-N-((1r,4r)-4-((3-(2,3-di-hydro-1H-pyrrolo[2,3-b]pyridin-5-yl)-2-oxo-2,3-dihydro-1H-benzo[d]imidazol-1-yl)methyl)cyclo-hexyl)-2-methylnicotinamide

[Chem. 60]

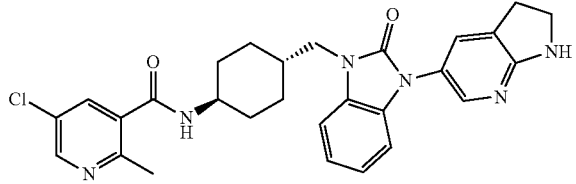

<Step-1>: tert-butyl 3-(1-(tert-butoxycarbonyl)-2,3-dihydro-1H-pyrrolo[2,3-b]pyridin-5-yl)-2-oxo-2,3-dihydro-1H-benzo[d]imidazole-1-carboxylate The title compound is prepared in 31% yield (60 mg, a colorless viscous oil) by the similar manner to Intermediate-58 using tert-butyl 5-(4,4,5,5-tetramethyl-1,3,2-dioxaborolan-2-yl)-2,3-dihydro-1H-pyrrolo[2,3-b]pyridine-1-carboxylate (222 mg, 0.640 mmol) in place of 2,3-dimethoxy-5-(4,4,5,5-tetramethyl-1,3,2-dioxaborolan-2-yl)pyridine.

$^1$H-NMR (400 MHz, CDCl$_3$) delta 8.32 (1H, d, J=2.3 Hz), 7.93-7.89 (1H, m), 7.59-7.56 (1H, m), 7.21-7.08 (2H, m), 6.96-6.91 (1H, m), 4.15-4.08 (2H, m), 3.13 (2H, t, J=8.5 Hz), 1.69 (9H, s), 1.58 (9H, s).

<Step-2>: tert-butyl 5-(3-(((1r,4r)-4-(5-chloro-2-methylnicotinamido)cyclohexyl)methyl)-2-oxo-2,3-dihydro-1H-benzo[d]imidazol-1-yl)-2,3-dihydro-1H-pyrrolo[2,3-b]pyridine-1-carboxylate The title compound is prepared in 49% yield (40 mg, a beige solid) by the similar manner to the Step-4 of Example-149 using 3-(1-(tert-butoxycarbonyl)-2,3-dihydro-1H-pyrrolo[2,3-b]pyridin-5-yl)-2-oxo-2,3-dihydro-1H-benzo[d]imidazole-1-carboxylate (60 mg, 0.133 mmol) in place of 1-(6-fluoro-2-methylpyridin-3-yl)-1H-benzo[d]imidazol-2(3H)-one.

MS (ESI) m/z: 617.2 (M+H)$^+$.

<Step-3>: 5-chloro-N-((1r,4r)-4-((3-(2,3-dihydro-1H-pyrrolo[2,3-b]pyridin-5-yl)-2-oxo-2,3-dihydro-1H-benzo[d]imidazol-1-yl)methyl)cyclohexyl)-2-methylnicotinamide After a solution of tert-butyl 5-(3-(((1r,4r)-4-(5-chloro-2-methylnicotinamido)cyclohexyl)methyl)-2-oxo-2,3-dihydro-1H-benzo[d]imidazol-1-yl)-2,3-dihydro-1H-pyrrolo[2,3-b]pyridine-1-carboxylate (40 mg, 0.065 mmol) in DCM (0.5 mL) and TFA (1 mL) is stirred at rt for 30 min, the reaction mixture is concentrated. The residual oil is purified by column chromatography on silica-gel eluting with 50-100% EtOAc in n-hexane followed by 0-10% MeOH in EtOAc to give 19 mg (57% yield) of the title compound as a white solid.

$^1$H-NMR (400 MHz, CDCl$_3$) delta 8.48 (1H, d, J=2.3 Hz), 7.93 (1H, d, J=2.3 Hz), 7.61 (1H, d, J=2.3 Hz), 7.36 (1H, d, J=2.3 Hz), 7.14 (1H, td, J=7.7, 0.9 Hz), 7.10-7.02 (2H, m), 6.98 (1H, dd, J=7.7, 0.9 Hz), 5.67 (1H, d, J=8.2 Hz), 4.68 (1H, s), 4.05-3.87 (1H, m), 3.79 (2H, d, J=6.9 Hz), 3.72 (2H, t, J=8.5 Hz), 3.14 (2H, t, J=8.5 Hz), 2.22-2.09 (2H, m), 2.03-1.83 (3H, m), 1.44-1.12 (4H, m).

Example 154: 5-chloro-2-methyl-N-((1r,4r)-4-((3-(1-methyl-2,3-dihydro-1H-pyrrolo[2,3-b]pyridin-5-yl)-2-oxo-2,3-dihydro-1H-benzo[d]imidazol-1-yl)methyl)cyclohexyl)nicotinamide

[Chem. 61]

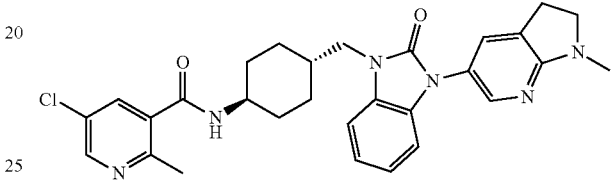

A mixture of Example 152 (10 mg, 0.019 mmol), formic acid (0.2 mL) and 37% formaline (0.2 mL) is stirred at 80° C. overnight. After cooled to rt, the mixture is concentrated. The residue is purified by a strong anion exchange cartridge (ISOLUTE (registered trademark) SCX-2, 1 g/6 mL, Biotage) and then purified by preparative LC-MS to give 6.9 mg (67% yield) of the title compound.

Example 155: N-((1r,4r)-4-((3-(1-acetyl-2,3-dihydro-1H-pyrrolo[2,3-b]pyridin-5-yl)-2-oxo-2,3-dihydro-1H-benzo[d]imidazol-1-yl)methyl)cyclohexyl)-5-chloro-2-methylnicotinamide

[Chem. 62]

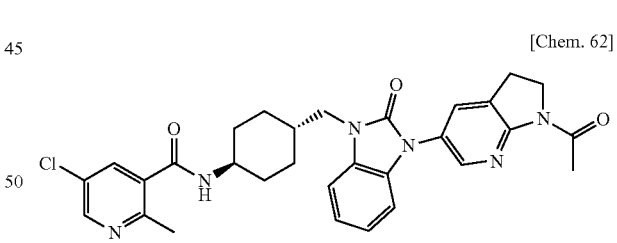

A mixture of Example 152 (7 mg, 0.014 mmol), acetic anhydride (0.010 mL, 0.106 mmol) and DMAP (0.5 mg, 0.004 mmol) in pyridine is stirred at rt overnight. After the reaction mixture is concentrated, the resultant residue is dissolved into EtOAc, washed with water, dried over MgSO$_4$, filtered and concentrated. The residue is purified by preparative LC-MS to give 5.1 mg (67% yield) of the title compound.

Representative Procedure for Method O

The following preparation of Example 158 represents the Method O.

Example 158: 5-chloro-2-methyl-N-((1r,4r)-4-((2-oxo-3-(1H-pyrrolo[3,2-b]pyridin-6-yl)-2,3-dihydro-1H-benzo[d]imidazol-1-yl)methyl)cyclohexyl)nicotinamide

[Chem. 63]

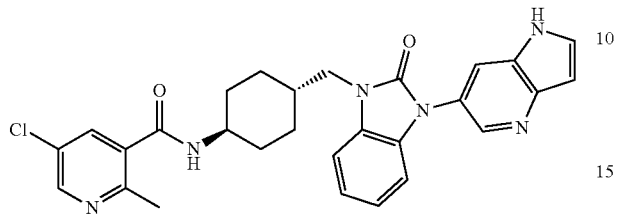

<Step-1>: 5-chloro-2-methyl-N-((1r,4r)-4-((2-oxo-3-(1-((2-(trimethylsilyl)ethoxy)methyl)-1H-pyrrolo[3,2-b]pyridin-6-yl)-2,3-dihydro-1H-benzo[d]imidazol-1-yl)methyl)cyclohexyl)nicotinamide A mixture of Mesylate-1 (8.3 mg, 0.023 mmol), Intermediate-82 (30 mg, 0.062 mmol) and $Cs_2CO_3$ (16 mg, 0.048 mmol) in DMSO (0.5 mL) is stirred at 80° C. for 5 hrs. After cooled to rt, the mixture is diluted with EtOAc, washed with water, dried over $MgSO_4$, filtered and concentrated. The residue is purified by column chromatography on silica-gel eluting with 0-10% MeOH in EtOAc to give 40 mg (quantitative yield) of the title compound.

MS (ESI) m/z: 645.2 $(M+H)^+$.

<Step-2>: 5-chloro-2-methyl-N-((1r,4r)-4-((2-oxo-3-(1H-pyrrolo[3,2-b]pyridin-6-yl)-2,3-dihydro-1H-benzo[d]imidazol-1-yl)methyl)cyclohexyl)nicotinamide To a solution of 5-chloro-2-methyl-N-((1r,4r)-4-((2-oxo-3-(1-((2-(trimethylsilyl)ethoxy)methyl)-1H-pyrrolo[3,2-b]pyridin-6-yl)-2,3-dihydro-1H-benzo[d]imidazol-1-yl)methyl)cyclohexyl)nicotinamide (30 mg, 0.046 mmol) in DCM (0.5 mL) is added TFA (1 mL) at rt and stirred. After 30 min the reaction mixture is concentrated. The residue is purified by a strong anion exchange cartridge (ISOLUTE (registered trademark) SCX-2, 1 g/6 mL, Biotage) and then purified by preparative LC-MS to give 7.8 mg (33% yield) of the title compound.

Example 159: 5-chloro-N-((1r,4r)-4-((3-(3,4-dihydro-2H-pyrido[3,2-b][1,4]oxazin-7-yl)-2-oxo-2,3-dihydro-1H-benzo[d]imidazol-1-yl)methyl)cyclohexyl)-2-methylnicotinamide

[Chem. 64]

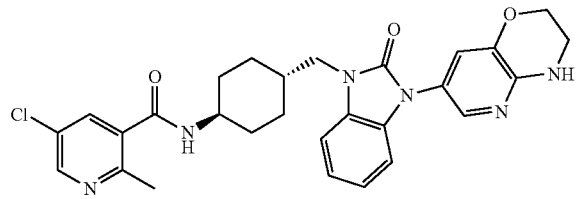

The title compound is prepared in 37% yield for 2 steps by the similar manner to Step-1 and Step-2 of Example 158 using Intermediate-83 in place of Intermediate-82.

Representative Procedure for Method P

The following preparation of Example 161 represents the Method P.

Example 161: 5-chloro-N-((1r,4r)-4-((3-(6-(3-(dimethylamino)azetidin-1-yl)pyridin-3-yl)-2-oxo-2,3-dihydro-1H-benzo[d]imidazol-1-yl)methyl)cyclohexyl)-2-methylnicotinamide

[Chem. 65]

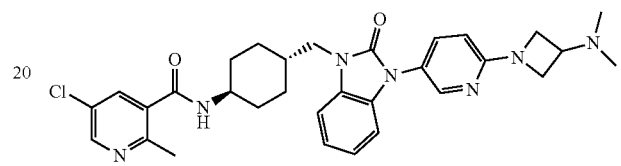

A mixture of Intermediate-54 (15 mg, 0.030 mmol), N,N-dimethylazetidin-3-amine dihydrochloride (7.9 mg, 0.046 mmol), DBU (0.014 mL, 0.091 mmol) and DIEA (0.016 mL, 0.091 mmol) in 2-propanol (0.5 mL) is stirred at 120° C. for 1 hr under microwave irradiation. To this are added N,N-dimethylazetidin-3-amine dihydrochloride (2.0 mg, 0.012 mmol), DBU (0.014 mL, 0.091 mmol) and DIEA (0.016 mL, 0.091 mmol) and stirred at 120° C. for 1 hr under microwave irradiation. To this are added N,N-dimethylazetidin-3-amine dihydrochloride (2.0 mg, 0.012 mmol), DBU (0.014 mL, 0.091 mmol) and DIEA (0.016 mL, 0.091 mmol) and stirred at 120° C. for 30 min under microwave irradiation. The resultant mixture is diluted with EtOAc, washed with water, dried over $MgSO_4$, filtered and concentrated. The residue is purified by preparative LC-MS to give 8.1 mg (46% yield) of the title compound.

Example 172: 5-chloro-2-methyl-N-((1r,4r)-4-((3-(3-methyl-1H-pyrazolo[4,3-b]pyridin-6-yl)-2-oxo-2,3-dihydro-1H-benzo[d]imidazol-1-yl)methyl)cyclohexyl)nicotinamide

[Chem. 66]

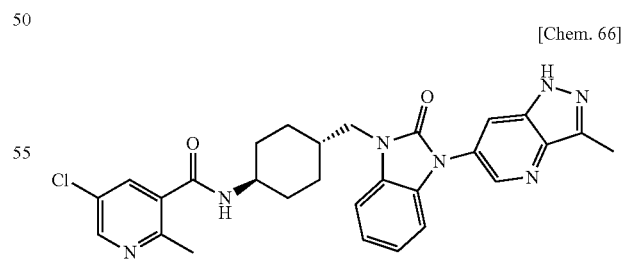

The title compound is prepared in 43% yield for 2 steps by the similar manner to Step-1 and Step-2 of Example 158 using Intermediate-93 in place of Intermediate-82.

Representative Procedure for Method Q

The following preparation of Example 173 represents the Method Q.

Example 173: 5-(3-(((1r,4r)-4-(5-chloro-2-methylnicotinamido)cyclohexyl)methyl)-2-oxo-2,3-dihydro-1H-benzo[d]imidazol-1-yl)-N-(1-methyl-1H-pyrazol-3-yl)picolinamide

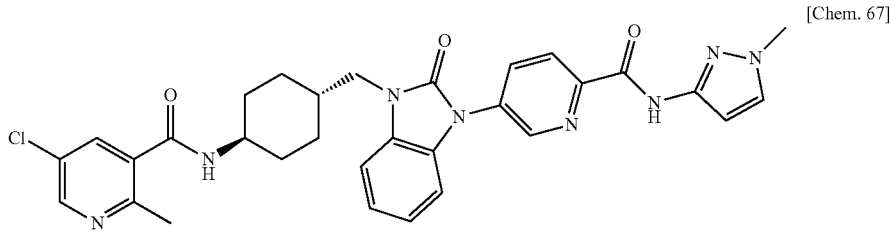 [SMILES: Cc1ncc(Cl)cc1C(=O)N[C@H]1CC[C@H](Cn2c(=O)n(-c3ccc(C(=O)Nc4ccn(C)n4)nc3)c3ccccc32)CC1]

[Chem. 67]

To a mixture of 5-(3-(((1r,4r)-4-(5-chloro-2-methylnicotinamido)cyclohexyl)methyl)-2-oxo-2,3-dihydro-1H-benzo[d]imidazol-1-yl)picolinic acid (20 mg, 0.038 mmol, Intermediate-36), 1-methyl-1H-pyrazol-3-amine (5.6 mg, 0.058 mmol) and DIEA (0.027 mL, 0.15 mmol) in DMF (1 mL) is added HATU (29 mg, 0.077 mmol). The mixture is stirred at room temperature overnight. The mixture is diluted with water and extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 7.8 mg (33% yield) of the title compound.

MS (ESI) m/z: 599.2 (M+H)$^+$.

Example 188: N-((1r,4r)-4-((3-(2-acetylisoindolin-5-yl)-2-oxo-2,3-dihydro-1H-benzo[d]imidazol-1-yl)methyl)cyclohexyl)-5-chloro-2-methylnicotinamide

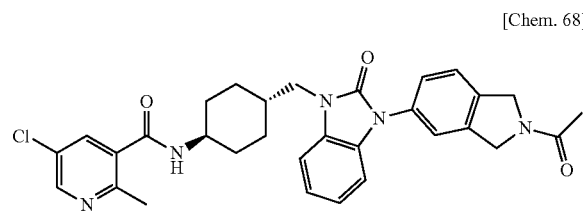 [SMILES: CC(=O)N1Cc2ccc(-n3c(=O)n(C[C@H]4CC[C@H](NC(=O)c5cc(Cl)cnc5C)CC4)c4ccccc43)cc2C1]

[Chem. 68]

\<Step-1\>: 5-bromo-2-((2-nitrophenyl)sulfonyl)isoindoline

A mixture of 5-bromoisoindoline hydrochloride (500 mg, 2.13 mmol), 2-nitrobenzenesulfonyl chloride (709 mg, 3.20 mmol) and potassium carbonate (884 mg, 6.40 mmol) in MeCN (3 mL) is stirred for 1 hr at rt. After the reaction mixture is concentrated, the residue is added with saturated aqueous ammonium chloride. The resultant mixture is washed with water to give 996 mg of the title compound as a pale yellow solid. The compound is used for the next reaction without further purification.

MS (ESI) m/z: 382.9 (M+H)$^+$.

\<Step-2\>: 2-((2-nitrophenyl)sulfonyl)-5-(4,4,5,5-tetramethyl-1,3,2-dioxaborolan-2-yl)isoindoline The title compound is prepared in 72% yield in 2 steps (663 mg, brown solid) by the similar manner to Step-1 of Intermediate-107 using 5-bromo-2-((2-nitrophenyl)sulfonyl)isoindoline (Step-1 of Example 188) in place of 6-bromo-3-methyl-1-(tetrahydro-2H-pyran-2-yl)-1H-indazole.

$^1$H-NMR (400 MHz, CDCl$_3$) delta 8.05-8.00 (1H, m), 7.73 (1H, d, J=8.0 Hz), 7.71-7.66 (3H, m), 7.64-7.60 (1H, m), 7.24 (1H, d, J=8.0 Hz), 4.85-4.79 (4H, m), 1.34 (12H, s).

MS (ESI) m/z: 431.1 (M+H)$^+$.

\<Step-3\>: 1-(2-((2-nitrophenyl)sulfonyl)isoindolin-5-yl)-1H-benzo[d]imidazol-2(3H)-one The title compound is prepared in 31% yield (205 mg, brown gum) by the similar manner to Intermediate-84 using 2-((2-nitrophenyl)sulfonyl)-5-(4,4,5,5-tetramethyl-1,3,2-dioxaborolan-2-yl)isoindoline (361 mg, 1.51 mmol, Step-2 of Example 188) in place of 1-methyl-5-(4,4,5,5-tetramethyl-1,3,2-dioxaborolan-2-yl)-1H-pyrazolo[3,4-b]pyridine.

MS (ESI) m/z: 437.0 (M+H)$^+$.

\<Step-4\>: 5-chloro-2-methyl-N-((1r,4r)-4-((3-(2-((2-nitrophenyl)sulfonyl)isoindolin-5-yl)-2-oxo-2,3-dihydro-1H-benzo[d]imidazol-1-yl)methyl)cyclohexyl)nicotinamide The title compound is prepared in 38% yield (64 mg, brown gum) by the similar manner to Step-3 of Intermediate-3 using 1-(2-((2-nitrophenyl)sulfonyl)isoindolin-5-yl)-1H-benzo[d]imidazol-2(3H)-one (104 mg, 0.074 mmol, Step-3 of Example 188) in place of methyl 2-((2-oxo-2,3-dihydro-1H-benzo[d]imidazol-1-yl)methyl)benzoate.

MS (ESI) m/z: 701.3 (M+H)$^+$.

\<Step-5\>: 5-chloro-N-((1r,4r)-4-((3-(isoindolin-5-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((3-(2-((2-nitrophenyl)sulfonyl)isoindolin-5-yl)-2-oxo-2,3-dihydro-1H-benzo[d]imidazol-1-yl)methyl)cyclohexyl)nicotinamide (48 mg, 0.068 mmol, Step-4 of Example 188), 1-dodecanethiol (0.033 mL, 0.14 mmol) and DBU (0.021 mL, 0.14 mmol) in MeCN (0.5 mL) is stirred for 2 hrs at rt. The mixture is purified by a strong anion exchange cartridge (ISOLUTE (registered trademark) SCX-2, 1 g/6 mL, Biotage) to give 26 mg (75% yield) of the title compound as a brown solid.

MS (ESI) m/z: 516.3 (M+H)$^+$.

243

<Step-6>: N((1r,4r)-4-((3-(2-acetylisoindolin-5-yl)-2-oxo-2,3-dihydro-1H-benzo[d]imidazol-1-yl)methyl)cyclohexyl)-5-chloro-2-methylnicotinamide A mixture of 5-chloro-N-((1r,4r)-4-((3-(isoindolin-5-yl)-2-oxo-2,3-dihydro-1H-benzo[d]imidazol-1-yl)methyl)cyclohexyl)-2-methylnicotinamide (57 mg, 0.11 mmol, Step-5 of Example 188), acetic anhydride (0.016 mL, 0.17 mmol) and TEA (0.023 mL, 0.17 mmol) in DCM is stirred for 2 hrs at rt. After the reaction mixture is concentrated, the resultant residue is purified by a strong anion exchange cartridge (ISOLUTE (registered trademark) SCX-2, 1 g/6 mL, Biotage) and column chromatography on amino-functional silica gel eluting with 2-100% MeOH in DCM. The residue is purified by preparative LC-MS to give 3.5 mg (6% yield) of the title compound.

Representative Procedure for Method R

The following preparation of Example 195 represents the Method R.

Example 195: 5-chloro-N-((1r,4r)-4-((3-(3-(cyclopropylmethyl)-2-oxo-2,3-dihydrobenzo[d]oxazol-6-yl)-2-oxo-2,3-dihydro-1H-benzo[d]imidazol-1-yl)methyl)cyclohexyl)-2-methylnicotinamide

[Chem. 69]

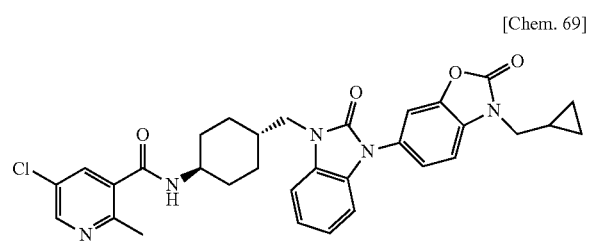 [SMILES: Cc1ncc(Cl)cc1C(=O)N[C@H]1CC[C@H](Cn2c(=O)n(-c3ccc4c(c3)oc(=O)n4CC3CC3)c3ccccc32)CC1]

A mixture of Intermediate-104 (15 mg, 0.056 mmol), the product of Step-2 of Example 9 (15 mg, 0.038 mmol), copper(I) iodide (11 mg, 0.056 mmol), $N^1,N^2$ dimethylethane-1,2-diamine (0.012 mL, 0.113 mmol) and $Cs_2CO_3$ (49 mg, 0.150 mmol) in DMA (0.3 mL) is stirred at 100° C. overnight. After cooled to rt, the reaction mixture is diluted with EtOAc, washed with 28% ammonia aqueous solution, dried over $MgSO_4$, filtered and concentrated. The residue is purified by preparative LC-MS to give 6.2 mg (28% yield) of the title compound.

Example 197: N-((1r,4r)-4-((3-(3-amino-1H-indazol-6-yl)-2-oxo-2,3-dihydro-1H-benzo[d]imidazol-1-yl)methyl)cyclohexyl)-5-chloro-2-methylnicotinamide

[Chem. 70]

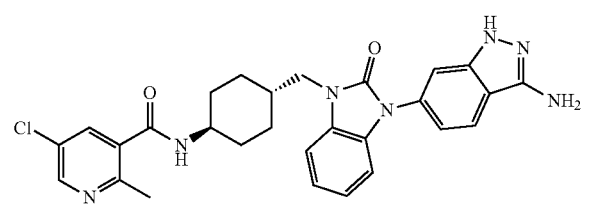

244

<Step-1>: 5-chloro-N-((1r,4r)-4-((3-(4-cyano-3-fluorophenyl)-2-oxo-2,3-dihydro-1H-benzo[d]imidazol-1-yl)methyl)cyclohexyl)-2-methylnicotinamide The title compound is prepared in 72% yield (47 mg) by the similar manner to Example 195 using 4-bromo-2-fluorobenzonitrile (38 mg, 0.188 mmol) in place of Intermediate-104. In addition, the purification is carried out by column chromatography on silica gel eluting with 20-100% EtOAc in n-hexane instead of preparative LC-MS.

$^1$H-NMR (400 MHz, CDCl$_3$) delta 8.49 (1H, d, J=2.3 Hz), 7.79 (1H, dd, J=8.5, 7.1 Hz), 7.64-7.58 (2H, m), 7.28-7.07 (5H, m), 5.57 (1H, d, J=7.8 Hz), 4.01-3.88 (1H, m), 3.81 (2H, d, J=6.9 Hz), 2.61 (3H, s), 2.16 (2H, d, J=10.1 Hz), 2.01-1.85 (3H, m), 1.40-1.10 (4H, m).

MS (ESI) m/z: 518.3 (M+H)$^+$.

<Step-2>: N((1r,4r)-4-((3-(3-amino-1H-indazol-6-yl)-2-oxo-2,3-dihydro-1H-benzo[d]imidazol-1-yl)methyl)cyclohexyl)-5-chloro-2-methylnicotinamide A mixture of 5-chloro-N-((1r,4r)-4-((3-(4-cyano-3-fluorophenyl)-2-oxo-2,3-dihydro-1H-benzo[d]imidazol-1-yl)methyl)cyclohexyl)-2-methylnicotinamide (20 mg, 0.039 mmol) and hydrazine hydrate (0.010 mL, 0.193 mmol) in EtOH (0.5 mL) is stirred at 150° C. for 20 min under microwave irradiation. To this is added hydrazine hydrate (0.010 mL, 0.193 mmol) stirred at 150° C. for 20 min under microwave irradiation. After cooled to rt, water is added to it and stirred for 1 min. The precipitate is collected by filtration, dried in vacuo, and purified by preparative LC-MS to give 4.6 mg (22% yield) of the title compound.

Example 198: N-((1r,4r)-4-((3-(3-aminobenzo[d]isoxazol-6-yl)-2-oxo-2,3-dihydro-1H-benzo[d]imidazol-1-yl)methyl)cyclohexyl)-5-chloro-2-methylnicotinamide

[Chem. 71]

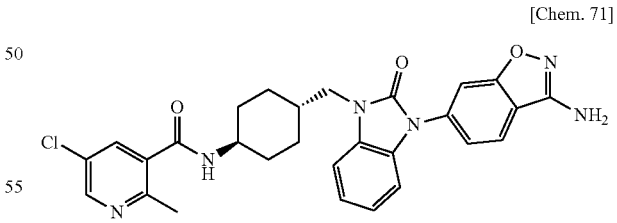

A mixture of the product of Step-1 of Example 197 (20 mg, 0.039 mmol), N-hydroxyacetamide (8.7 mg, 0.116 mmol) and $K_2CO_3$ in DMF (0.5 mL) and water (0.1 mL) is stirred at 80° C. for 2 hrs. After cooled to rt, the mixture is diluted with EtOAc, washed with water, dried over $MgSO_4$, filtered and concentrated. The residue is purified by preparative LC-MS to give 5.9 mg (29% yield) of the title compound.

Example 205: 5-chloro-2-methyl-N-((1r,4r)-4-((3-(3-methyl-1H-indazol-6-yl)-2-oxo-2,3-dihydro-1H-benzo[d]imidazol-1-yl)methyl)cyclohexyl)nicotinamide

[Chem. 72]

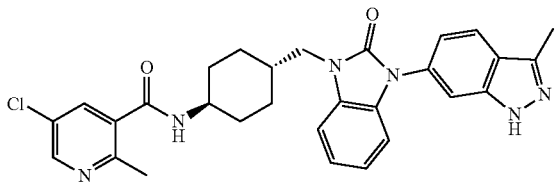

<Step-1>: 5-chloro-2-methyl-N-((1r,4r)-4-((3-(3-methyl-1-(tetrahydro-2H-pyran-2-yl)-1H-indazol-6-yl)-2-oxo-2,3-dihydro-1H-benzo[d]imidazol-1-yl)methyl)cyclohexyl)nicotinamide The title compound is prepared in 75% yield (83 mg, yellow gum) by the similar manner to Step-3 of Intermediate-3 using 1-(3-methyl-1-(tetrahydro-2H-pyran-2-yl)-1H-indazol-6-yl)-1H-benzo[d]imidazol-2(3H)-one (85 mg, 0.18 mmol, Step-2 of Intermediate-107) in place of methyl 2-((2-oxo-2,3-dihydro-1H-benzo[d]imidazol-1-yl)methyl)benzoate.
MS (ESI) m/z: 613.3 (M+H)⁺.

<Step-2>: 5-chloro-2-methyl-N-((1r,4r)-4-((3-(3-methyl-1H-indazol-6-yl)-2-oxo-2,3-dihydro-1H-benzo[d]imidazol-1-yl)methyl)cyclohexyl)nicotinamide 5-chloro-2-methyl-N-((1r,4r)-4-((3-(3-methyl-1-(tetrahydro-2H-pyran-2-yl)-1H-indazol-6-yl)-2-oxo-2,3-dihydro-1H-benzo[d]imidazol-1-yl)methyl)cyclohexyl)nicotinamide (28 mg, 0.045 mmol, Step-1 of Example 205) in TFA (1 mL) is stirred overnight at rt. After the reaction mixture is concentrated, the resultant residue is purified by preparative LC-MS to give 4.8 mg (20% yield) of the title compound.

Example 210: 5-chloro-N-((1r,4r)-4-((3-(3-chloro-1H-indazol-6-yl)-2-oxo-2,3-dihydro-1H-benzo[d]imidazol-1-yl)methyl)cyclohexyl)-2-methylnicotinamide

[Chem. 73]

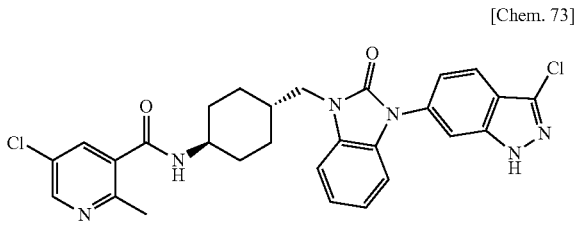 [SMILES: Cc1ncc(Cl)cc1C(=O)N[C@H]1CC[C@H](Cn2c(=O)n(-c3ccc4c(Cl)n[nH]c4c3)c3ccccc32)CC1]

<Step-1>: 6-bromo-3-chloro-1-(tetrahydro-2H-pyran-2-yl)-1H-indazole

A mixture of 6-bromo-3-chloro-1H-indazole (100 mg, 0.432 mmol), 4-methylbenzenesulfonic acid hydrate (3.6 mg, 0.019 mmol) and 3,4-dihydro-2H-pyran (0.028 mL, 0.302 mmol) in toluene (2 mL) is stirred at 80° C. for 2 hrs. After cooled to rt, the mixture is purified by column chromatography on silica-gel eluting with 0-70% EtOAc in n-hexane to give 104 mg (76%) of the title compound as a white solid.
¹H-NMR (400 MHz, CDCl₃) delta 7.77 (1H, d, J=1.4 Hz), 7.52 (1H, d, J=8.7 Hz), 7.33 (1H, dd, J=8.7, 1.4 Hz), 5.61 (1H, dd, J=9.1, 2.7 Hz), 4.06-3.97 (1H, m), 3.80-3.68 (1H, m), 2.57-2.41 (1H, m), 2.20-2.01 (2H, m), 1.83-1.62 (3H, m).

<Step-2>: 5-chloro-N-((1r,4r)-4-((3-(3-chloro-1-(tetrahydro-2H-pyran-2-yl)-1H-indazol-6-yl)-2-oxo-2,3-dihydro-1H-benzo[d]imidazol-1-yl)methyl)cyclohexyl)-2-methylnicotinamide The title compound is prepared in 42% yield (10 mg) by the similar manner to Example 195 using 6-bromo-3-chloro-1-(tetrahydro-2H-pyran-2-yl)-1H-indazole (24 mg, 0.075 mmol) in place of Intermediate-104. In addition, the purification is carried out by column chromatography on silica gel eluting with 0-10% MeOH in EtOAc instead of preparative LC-MS.
¹H-NMR (400 MHz, CDCl₃) delta 8.48 (1H, d, J=2.3 Hz), 7.87-7.75 (2H, m), 7.61 (1H, d, J=2.3 Hz), 7.40 (1H, dd, J=8.7, 1.4 Hz), 7.25-7.05 (4H, m), 5.69 (1H, dd, J=9.1, 2.7 Hz), 5.63 (1H, d, J=8.2 Hz), 4.08-3.65 (5H, m), 2.70-2.48 (4H, m), 2.23-1.90 (7H, m), 1.84-1.55 (3H, m), 1.50-1.15 (4H, m).
MS (ESI) m/z: 631.3 (M−H)⁻.

<Step-3>: 5-chloro-N-((1r,4r)-4-((3-(3-chloro-1H-indazol-6-yl)-2-oxo-2,3-dihydro-1H-benzo[d]imidazol-1-yl)methyl)cyclohexyl)-2-methylnicotinamide The title compound is prepared in 92% yield (8 mg) by the similar manner to Step-2 of Example 158 using the product of Step-2 of Example 210 (10 mg, 0.016 mmol) in place of the product of Step-1 of Example 158.

Representative Procedure for Method S
The following preparation of Example 212 represents the Method S.

Example 212: 5-chloro-2-methyl-N-((1r,4r)-4-((3-(3-methyl-1H-indazol-5-yl)-2-oxo-2,3-dihydro-1H-imidazo[4,5-b]pyridin-1-yl)methyl)cyclohexyl)nicotinamide

[Chem. 74]

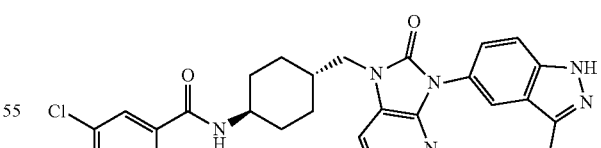

<Step-1>: 5-chloro-2-methyl-N-((1r,4r)-4-((3-(3-methyl-1-(tetrahydro-2H-pyran-2-yl)-1H-indazol-5-yl)-2-oxo-2,3-dihydro-1H-imidazo[4,5-b]pyridin-1-yl)methyl)cyclohexyl)nicotinamide The title compound is prepared in 18% yield (15 mg, brown solid) by the similar manner to Step-3 of Intermediate-3 using 3-(3-methyl-1-(tetrahydro-2H-pyran-2-yl)-1H-indazol-5-yl)-1H-imidazo[4,5-b]pyridin-2(3H)-one (48 mg, 0.13 mmol, Intermediate-111) in place of methyl 2-((2-oxo-2,3-dihydro-1H-benzo[d]imidazol-1-yl)methyl)benzoate.

MS (ESI) m/z: 614.3 (M+H)⁺.

<Step-2>: 5-chloro-2-methyl-N-((1r,4r)-4-((3-(3-methyl-1H-indazol-5-yl)-2-oxo-2,3-dihydro-1H-imidazo[4,5-b]pyridin-1-yl)methyl)cyclohexyl)nicotinamide 5-chloro-2-methyl-N-((1r,4r)-4-((3-(3-methyl-1-(tetrahydro-2H-pyran-2-yl)-1H-indazol-5-yl)-2-oxo-2,3-dihydro-1H-imidazo[4,5-b]pyridin-1-yl)methyl)cyclohexyl)nicotinamide (15 mg, 0.024 mmol, Step-1 of Example 212) in TFA (1 mL) is stirred for 2 hrs at rt. After the reaction mixture is concentrated, the resultant residue is purified by preparative LC-MS to give 5.1 mg (40% yield) of the title compound.

Representative Procedure for Method T

The following preparation of Example 215 represents the Method T.

Example 215: 5-chloro-2-methyl-N-((1r,4r)-4-((3-(3-methyl-2-oxo-2,3-dihydrooxazolo[4,5-b]pyridin-6-yl)-2-oxo-2,3-dihydro-1H-benzo[d]imidazol-1-yl)methyl)cyclohexyl)nicotinamide

[Chem. 75]

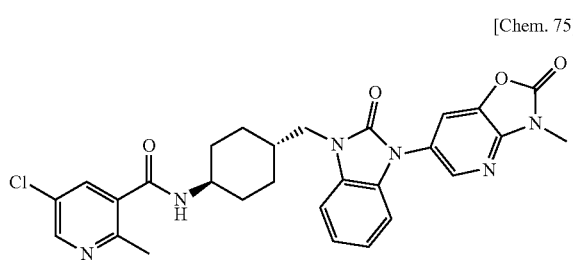

A mixture of 5-chloro-2-methyl-N-((1r,4r)-4-((2-oxo-2,3-dihydro-1H-benzo[d]imidazol-1-yl)methyl)cyclohexyl)nicotinamide (15 mg, 0.038 mmol, Step-2 of Example 9), 3-methyl-6-(4,4,5,5-tetramethyl-1,3,2-dioxaborolan-2-yl)oxazolo[4,5-b]pyridin-2(3H)one (10 mg, 0.038 mmol), copper acetate (17 mg, 0.094 mmol) and TEA (0.016 mL, 0.113 mmol) in MeCN (2 mL) is stirred at 100° C. for 2 hrs. The mixture is filtered through celite pad. The filtrate is concentrated in vacuo. The residue is purified by a strong anion exchange cartridge (ISOLUTE (registered trademark) SCX-2, 1 g/6 mL, Biotage) and then purified by preparative LC-MS to give 6.2 mg (30% yield) of the title compound.

MS (ESI) m/z: 547.2 (M+H)⁺.

Example 218: N-((1r,4r)-4-((3-(2-acetyl-1,2,3,4-tetrahydroisoquinolin-6-yl)-2-oxo-2,3-dihydro-1H-benzo[d]imidazol-1-yl)methyl)cyclohexyl)-5-chloro-2-methylnicotinamide

[Chem. 76]

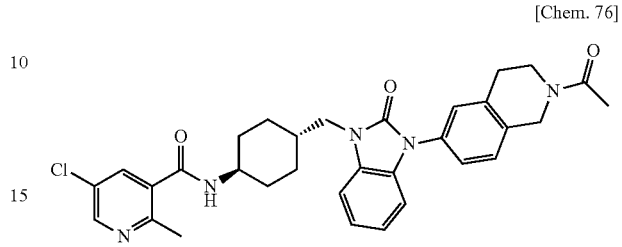

<Step-1>: tert-butyl 6-(2-oxo-2,3-dihydro-1H-benzo[d]imidazol-1-yl)-3,4-dihydroisoquinoline-2 (1H)-carboxylate The title compound is prepared in 84% yield in 3 steps by the similar manner to Step-1, Step-2, and Step-3 of Intermediate-112 using tert-butyl 6-amino-3,4-dihydroisoquinoline-2 (1H)-carboxylate in place of 4-(pyridin-4-yloxy)aniline.

¹H-NMR (400 MHz, DMSO-d₆) delta 11.12 (1H, br s), 7.37-7.31 (3H, m), 7.07-7.04 (2H, m), 7.00-6.97 (2H, m), 4.57 (2H, s), 3.59 (2H, t, J=5.9 Hz), 2.85 (2H. t. J=5.9 Hz), 1.44 (9H, s).

MS (ESI) m/z: 365.9 (M+H)⁺.

<Step-2>: tert-butyl 6-(3-(((1r,4r)-4-(5-chloro-2-methylnicotinamido)cyclohexyl)methyl)-2-oxo-2,3-dihydro-1H-benzo[d]imidazol-1-yl)-3,4-dihydroisoquinoline-2 (1H)-carboxylate The title compound is prepared in 87% yield (151 mg) by the similar manner to Step-3 of Intermediate-3 using tert-butyl 6-(2-oxo-2,3-dihydro-1H-benzo[d]imidazol-1-yl)-3,4-dihydroisoquinoline-2 (1H)-carboxylate (101 mg, 0.28 mmol, Step-1 of Example 218) in place of methyl 2-((2-oxo-2,3-dihydro-1H-benzo[d]imidazol-1-yl)methyl)benzoate.

MS (ESI) m/z: 630.1 (M+H)⁺.

<Step-3>: 5-chloro-2-methyl-N-((1r,4r)-4-((2-oxo-3-(1,2,3,4-tetrahydroisoquinolin-6-yl)-2,3-dihydro-1H-benzo[d]imidazol-1-yl)methyl)cyclohexyl)nicotinamide To a solution of tert-butyl 6-(3-(((1r,4r)-4-(5-chloro-2-methylnicotinamido)cyclohexyl)methyl)-2-oxo-2,3-dihydro-1H-benzo[d]imidazol-1-yl)-3,4-dihydroisoquinoline-2 (1H)-carboxylate (164 mg, 0.25 mmol, Step-2 of Example 218) in 1,4-dioxane (1 mL) is added 4 M HCl in 1,4-dioxane (5 mL) at room temperature. The mixture is stirred at room temperature for 1 hr. The mixture is concentrated to give 142 mg (quantitative yield) of the title compound.

MS (ESI) m/z: 530.0 (M+H)⁺.

<Step-4>: N((1r,4r)-4-((3-(2-acetyl-1,2,3,4-tetrahydroisoquinolin-6-yl)-2-oxo-2,3-dihydro-1H-benzo[d]imidazol-1-yl)methyl)cyclohexyl)-5-chloro-2-methylnicotinamide To a mixture of 5-chloro-2-methyl-N-((1r,4r)-4-((2-oxo-3-(1,2,3,4-tetrahydroisoquinolin-6-yl)-2,3-dihydro-1H-benzo[d]imidazol-1-yl)methyl)cyclohexyl)nicotinamide (25 mg, 0.042 mmol, Step-3 of Example 218) and TEA (0.035 mL, 0.25 mmol) in dichloromethane (2 mL) is added acetic anhydride (0.012 mL, 0.13 mmol) at room temperature. The mixture is stirred at room temperature overnight. The mixture is quenched with saturated aqueous sodium bicarbonate, extracted with EtOAc. The organic layer is concentrated. The residue is purified by preparative LC-MS to give 8.3 mg (33% yield) of the title compound.

MS (ESI) m/z: 572.2 (M+H)+.

Representative Procedure for Method U

The following preparation of Example 219 represents the Method U.

Example 219: 5-chloro-N-((1r,4r)-4-((3-(2-cyanophenyl)-2-oxo-2,3-dihydro-1H-benzo[d]imidazol-1-yl)methyl)cyclohexyl)-2-methylnicotinamide

[Chem. 77]

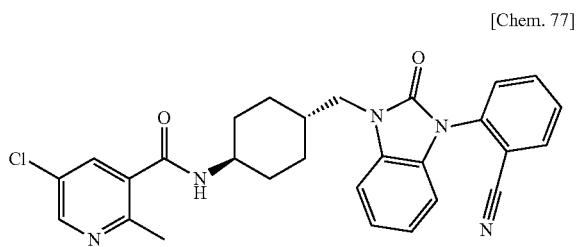 [SMILES: Cc1ncc(Cl)cc1C(=O)N[C@H]1CC[C@H](Cn2c(=O)n(-c3ccccc3C#N)c3ccccc32)CC1]

A mixture of 5-chloro-2-methyl-N-((1r,4r)-4-((2-oxo-2,3-dihydro-1H-benzo[d]imidazol-1-yl)methyl)cyclohexyl)nicotinamide (25 mg, 0.063 mmol, Step-2 of Ex 9), 2-fluorobenzonitrile (11 mg, 0.094 mmol) and Cs₂CO₃ (41 mg, 0.125 mmol) in DMSO (1 mL) is stirred at 100° C. for 4 hr. The mixture is added water and extracted with EtOAc. The organic layer is dried over sodium sulfate, filtered and concentrated. The solvent is removed under vacuum, the crude product is purified by preparative LC-MS to give 7.9 mg (25% yield) of the title compound.

Example 222: 5-chloro-N-((1r,4r)-4-((3-(3-chloro-1H-indazol-5-yl)-2-oxo-2,3-dihydro-1H-benzo[d]imidazol-1-yl)methyl)cyclohexyl)-2-methylnicotinamide

[Chem. 78]

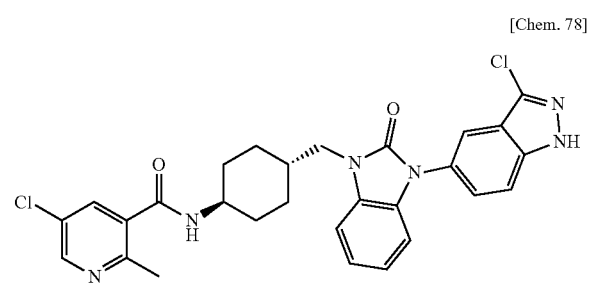 [SMILES: Cc1ncc(Cl)cc1C(=O)N[C@H]1CC[C@H](Cn2c(=O)n(-c3ccc4[nH]nc(Cl)c4c3)c3ccccc32)CC1]

<Step-1>: 5-bromo-3-chloro-1-(tetrahydro-2H-pyran-2-yl)-1H-indazole

The title compound is prepared in 84% yield (115 mg, colorless oil) by the similar manner to Step-1 of Example 210 using 5-bromo-3-chloro-1H-indazole (100 mg, 0.432 mmol) in place of 6-bromo-3-chloro-1H-indazole.

¹H-NMR (400 MHz, CDCl₃) delta 7.82 (1H, dd, J=1.8, 0.9 Hz), 7.51 (1H, dd, J=9.1, 1.8 Hz), 7.46 (1H, dd, J=9.1, 0.9 Hz), 5.64 (1H, dd, J=8.7, 2.7 Hz), 4.01-3.95 (1H, m), 3.76-3.68 (1H, m), 2.55-2.44 (1H, m), 2.20-2.02 (2H, m), 1.82-1.60 (3H, m).

<Step-2>: 5-chloro-N-((1r,4r)-4-((3-(3-chloro-1-(tetrahydro-2H-pyran-2-yl)-1H-indazol-5-yl)-2-oxo-2,3-dihydro-1H-benzo[d]imidazol-1-yl)methyl)cyclohexyl)-2-methylnicotinamide The title compound is prepared in 43% yield (32 mg, beige gum) by the similar manner to Step-2 of Example 210 using 5-bromo-3-chloro-1-(tetrahydro-2H-pyran-2-yl)-1H-indazole (59 mg, 0.188 mmol) and N¹,N¹,N²,N²-tetramethylethane-1,2-diamine (0.066 mL, 0.439 mmol) in place of 6-bromo-3-chloro-1-(tetrahydro-2H-pyran-2-yl)-1H-indazole and N¹,N² dimethylethane-1,2-diamine, respectively.

¹H-NMR (400 MHz, CDCl₃) delta 8.49 (1H, d, J=2.3 Hz), 7.84 (1H, d, J=1.8 Hz), 7.73 (1H, d, J=8.2 Hz), 7.63-7.58 (2H, m), 7.17 (1H, td, J=7.5, 1.4 Hz), 7.12-7.02 (3H, m), 5.72 (1H, dd, J=8.9, 2.5 Hz), 5.57 (1H, d, J=8.2 Hz), 4.06-3.90 (2H, m), 3.84 (2H, d, J=6.9 Hz), 3.80-3.70 (1H, m), 2.67-2.45 (4H, m), 2.22-2.08 (4H, m), 2.02-1.88 (3H, m), 1.83-1.63 (3H, m), 1.44-1.15 (4H, m).

MS (ESI) m/z: 631.3 (M−H)⁻.

<Step-3>: 5-chloro-N-((1r,4r)-4-((3-(3-chloro-1H-indazol-5-yl)-2-oxo-2,3-dihydro-1H-benzo[d]imidazol-1-yl)methyl)cyclohexyl)-2-methylnicotinamide The title compound is prepared in 27% yield (3.5 mg) by the similar manner to Step-3 of Example 210 using the product of Step-2 of Example 222 in place of the product of Step-2 of Example 210.

Example 224: 5-chloro-2-methyl-N-((1r,4r)-4-((2-oxo-3-(3-oxo-3,4-dihydro-2H-pyrido[3,2-b][1,4]oxazin-7-yl)-2,3-dihydro-1H-benzo[d]imidazol-1-yl)methyl)cyclohexyl)nicotinamide

[Chem. 79]

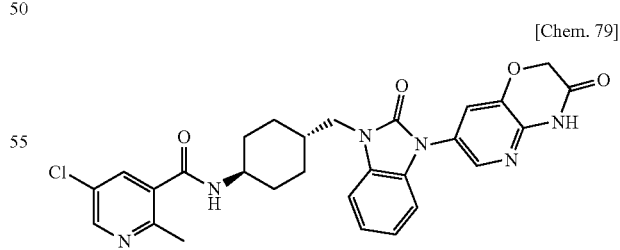

<Step-1>: 7-bromo-4-((2-(trimethylsilyl)ethoxy)methyl)-2H-pyrido[3,2-b][1,4]oxazin-3(4H)-one A mixture of 7-bromo-2H-pyrido[3,2-b][1,4]oxazin-3(4H)-one (300 mg, 1.31 mmol), (2-(chloromethoxy)ethyl)trimethylsilane (0.279 mL, 1.57 mmol) and Cs₂CO₃ (854 mg, 2.62 mmol) in DMF (4 mL) is stirred at 70° C. for 2 hrs. After cooled to rt, the reaction mixture is diluted with EtOAc, washed with water, dried over MgSO$_4$, filtered and concentrated. The residue is purified by column chromatography on silica-gel eluting with 5-100% EtOAc in n-hexane to give 215 mg (46%) of the title compound as a colorless oil. 1H-NMR (400 MHz, CDCl$_3$) delta 8.12 (1H, d, J=2.1 Hz), 7.41 (1H, d, J=2.1 Hz), 5.56 (2H, s), 4.70 (2H, s), 3.72-3.67 (2H, m), 1.00-0.94 (2H, m), −0.02 (9H, s).

<Step-2>: 7-(4,4,5,5-tetramethyl-1,3,2-dioxaborolan-2-yl)-4-((2-(trimethylsilyl)ethoxy)methyl)-2H-pyrido[3,2-b][1,4]oxazin-3 (4H)-one A mixture of 7-bromo-4-((2-(trimethylsilyl)ethoxy)methyl)-2H-pyrido[3,2-b][1,4]oxazin-3 (4H)-one (100 mg, 0.278 mmol, Step-1 of Example 224), 4,4,4',4',5,5,5',5'-octamethyl-2,2'-bi(1,3,2-dioxaborolane) (85 mg, 0.334 mmol), Pd(dppf)Cl$_2$-DCM adduct (23 mg, 0.028 mmol) and potassium acetate (82 mg, 0.835 mmol) in 1,4-dioxane (2 mL) is stirred at 120° C. for 20 min under microwave irradiation. The mixture is concentrated in vacuo. The residue is purified by column chromatography on silica-gel eluting with 0-33% EtOAc in n-hexane to give 99 mg (88% yield) of the title compound as yellow oil.

H-NMR (400 MHz, CDCl$_3$) delta 8.40 (1H, d, J=1.4 Hz), 7.59 (1H, d, J=1.4 Hz), 5.62 (2H, s), 4.66 (2H, s), 3.75-3.66 (2H, m), 1.34 (12H, s), 0.99-0.93 (2H, m), 0.02 (9H, s). MS (ESI) m/z: 407.4 (M+H)$^+$.

<Step-3>: 5-chloro-2-methyl-N-((1r,4r)-4-((2-oxo-3-(3-oxo-3,4-dihydro-2H-pyrido[3,2-b][1,4]oxazin-7-yl)-2,3-dihydro-1H-benzo[d]imidazol-1-yl)methyl)cyclohexyl)nicotinamide A mixture of 5-chloro-2-methyl-N-((1r,4r)-4-((2-oxo-2,3-dihydro-1H-benzo[d]imidazol-1-yl)methyl)cyclohexyl)nicotinamide (15 mg, 0.038 mmol, Step-2 of Example 9), 7-(4,4,5,5-tetramethyl-1,3,2-dioxaborolan-2-yl)-4-((2-(trimethylsilyl)ethoxy)methyl)-2H-pyrido[3,2-b][1,4] oxazin-3 (4H)-one (23 mg, 0.056 mmol, Step-2 of Example 224), copper(II) acetate (17 mg, 0.094 mmol) and TEA (0.016 mL, 0.113 mmol) in DMA (2 mL) is stirred at 100° C. for 2 hrs. To the mixture is added copper acetate (17 mg, 0.094 mmol) and TEA (0.016 mL, 0.113 mmol) and the mixture is stirred at 100° C. for 2 hrs. The mixture is filtered through celite pad. The filtrate is concentrated in vacuo. The residue is purified by column chromatography on silica-gel eluting with 0-66% EtOAc in n-hexane to give 14 mg of 5-chloro-2-methyl-N-((1r,4r)-4-((2-oxo-3-(3-oxo-4-((2-(trimethylsilyl)ethoxy)methyl)-3,4-dihydro-2H-pyrido[3,2-b][1,4]oxazin-7-yl)-2,3-dihydro-1H-benzo[d]imidazol-1-yl)methyl)cyclohexyl)nicotinamide. This is dissolved in DCM (1.5 mL). To the mixture is added TFA (0.5 mL) and the mixture is stirred at rt for 1.5 hrs. The mixture is concentrated. The residue is dissolved in DCM (3 mL). The organic layer is washed with water, dried over sodium sulfate, filtered and concentrated and then purified by preparative LC-MS to give 3.3 mg (16% yield) of the title compound.

MS (ESI) m/z: 547.3 (M+H)$^+$.

Example 230: 5-chloro-N-((1r,4r)-4-((3-(1-(2-hydroxyethyl)-3-methyl-1H-indazol-5-yl)-2-oxo-2,3-dihydro-1H-benzo[d]imidazol-1-yl)methyl)cyclohexyl)-2-methylnicotinamide

[Chem. 80]

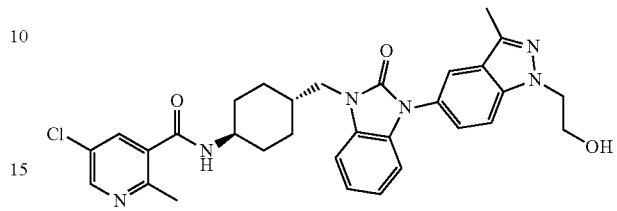

<Step-1>: 5-chloro-N-((1r,4r)-4-((3-(1-(2-(methoxymethoxy)ethyl)-3-methyl-1H-indazol-5-yl)-2-oxo-2,3-dihydro-1H-benzo[d]imidazol-1-yl)methyl)cyclohexyl)-2-methylnicotinamide The title compound is prepared in 92% yield (oil) by the similar manner to Step-3 of Intermediate-3 using 1-(1-(2-(methoxymethoxy)ethyl)-3-methyl-1H-indazol-5-yl)-1H-benzo[d]imidazol-2(3H)-one (Intermediate-116) in place of methyl 2-((2-oxo-2,3-dihydro-1H-benzo[d]imidazol-1-yl)methyl)benzoate.

$^1$H-NMR (400 MHz, CDCl$_3$) delta 8.39 (1H, d, J=2.3 Hz), 7.75 (1H, d, J=1.4 Hz), 7.55 (1H, d, J=2.3 Hz), 7.52 (1H, d, J=8.2 Hz), 7.41 (1H, dd, J=8.7, 1.8 Hz), 7.16 (1H, td, J=7.5, 1.5 Hz), 7.10-7.04 (2H, m), 7.03-6.98 (1H, m), 6.36 (1H, d, J=8.2 Hz), 4.56-4.51 (4H, m), 3.98 (2H, t, J=5.5 Hz), 3.98-3.86 (1H, m), 3.81 (2H, d, J=6.9 Hz), 3.22 (3H, s), 2.56 (3H, s), 2.53 (3H, s), 2.16-2.04 (2H, m), 2.01-1.82 (3H, m), 1.40-1.14 (4H, m)

MS (ESI) m/z: 617.1 (M+H)$^+$.

<Step-2>: 5-chloro-N-((1r,4r)-4-((3-(1-(2-hydroxyethyl)-3-methyl-1H-indazol-5-yl)-2-oxo-2,3-dihydro-1H-benzo[d]imidazol-1-yl)methyl)cyclohexyl)-2-methylnicotinamide A mixture of 5-chloro-N-((1r,4r)-4-((3-(1-(2-(methoxymethoxy)ethyl)-3-methyl-1H-indazol-5-yl)-2-oxo-2,3-dihydro-1H-benzo[d]imidazol-1-yl)methyl)cyclohexyl)-2-methylnicotinamide (30 mg, 0.049 mmol, Step-1 of Ex 230) in 4 M HCl/1,4-dioxane (1 mL) is stirred at rt for 1 hr. The solvent is removed by flowing N$_2$ gas, the crude product is purified by preparative LC-MS to give 8.8 mg (32% yield) of the title compound.

Example 241: 5-chloro-N-((1r,4r)-4-((3-(2-cyanobenzyl)-2-oxo-2,3-dihydro-1H-benzo[d]imidazol-1-yl)methyl)cyclohexyl)-2-methylnicotinamide

[Chem. 81]

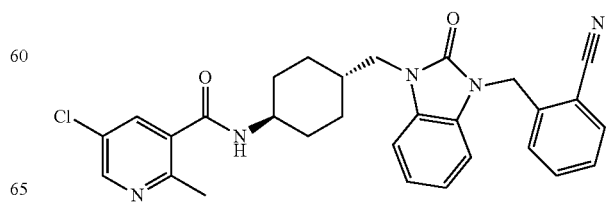

A mixture of 5-chloro-2-methyl-N-((1r,4r)-4-((2-oxo-2,3-dihydro-1H-benzo[d]imidazol-1-yl)methyl)cyclohexyl)nicotinamide (20 mg, 0.050 mmol, Step-2 of Ex 9), 2-(bromomethyl)benzonitrile (11 mg, 0.055 mmol) and Cs$_2$CO$_3$ (33 mg, 0.10 mmol) in DMSO (1 mL) is stirred at 80° C. for 6 hr. The mixture is added water and extracted with EtOAc. The organic layer is dried over sodium sulfate, filtered and concentrated. The solvent is removed under vacuum, the crude product is purified by preparative LC-MS to give 7.6 mg (30% yield, solid) of the title compound.

Example 242: 5-chloro-N-((1r,4r)-4-((3-(3-cyanobenzyl)-2-oxo-2,3-dihydro-1H-benzo[d]imidazol-1-yl)methyl)cyclohexyl)-2-methylnicotinamide

[Chem. 82]

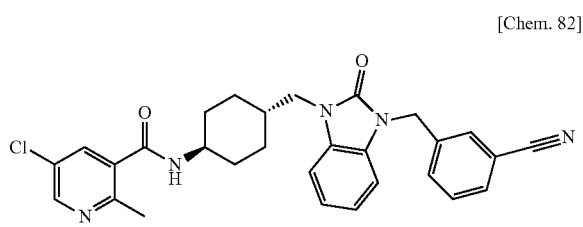 [SMILES: Cc1ncc(Cl)cc1C(=O)N[C@H]1CC[C@H](Cn2c(=O)n(Cc3cccc(C#N)c3)c3ccccc32)CC1]

The title compound is prepared in 33% yield (solid) by the similar manner to Ex 241 using 3-(bromomethyl)benzonitrile in place of 2-(bromomethyl)benzonitrile.

Example 243: 6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxamide <Step-1>: methyl 6-(4,4,5,5-tetramethyl-1,3,2-dioxaborolan-2-yl)benzo[d]isoxazole-3-carboxylate The title compound is prepared in 54% yield (1.15 g, yellow solid) by the similar manner to Step-1 of Intermediate-107 using methyl 6-bromobenzo[d]isoxazole-3-carboxylate (716 mg) in place of 6-bromo-3-methyl-1-(tetrahydro-2H-pyran-2-yl)-1H-indazole.

$^1$H-NMR (400 MHz, CDCl$_3$) delta 8.14-8.09 (2H, m), 7.84 (1H, d, J=8.2 Hz), 4.10 (3H, s), 1.38 (12H, s).
MS (ESI) m/z: 304.3 (M+H)$^+$.

<Step-2>: methyl 6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxylate A mixture of 5-chloro-2-methyl-N-((1r,4r)-4-((2-oxo-2,3-dihydro-1H-benzo[d]imidazol-1-yl)methyl)cyclohexyl)nicotinamide (137 mg, 0.345 mmol, Step-2 of Example 9), copper(II) acetate (125 mg, 0.689 mmol), TEA (0.096 mL, 0.69 mmol) and methyl 6-(4,4,5,5-tetramethyl-1,3,2-dioxaborolan-2-yl)benzo[d]isoxazole-3-carboxylate (288 mg, 0.517 mmol, Step-1 of Example 243) in MeCN (3.4 mL) is stirred overnight at 60° C. The reaction mixture is concentrated and the resultant residue is purified by column chromatography on silica-gel eluting with 24-100% EtOAc in n-hexane to give 80 mg (40% yield) of the title compound as a brown gum.

$^1$H-NMR (400 MHz, CDCl$_3$) delta 8.49 (1H, d, J=2.5 Hz), 8.27 (1H, d, J=8.7 Hz), 7.95 (1H, d, J=1.8 Hz), 7.73 (1H, dd, J=8.7, 1.8 Hz), 7.61 (1H, d, J=2.5 Hz), 7.25-7.18 (2H, m), 7.17-7.07 (2H, m), 5.57 (1H, d, J=7.8 Hz), 4.12 (3H, s), 4.02-3.90 (1H, m), 3.84 (2H, d, J=6.9 Hz), 2.61 (3H, s), 2.21-2.12 (2H, m), 1.99-1.87 (3H, m), 1.44-1.15 (4H, m).
MS (ESI) m/z: 574.4 (M+H)$^+$.

<Step-3>: 6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxamide A mixture of methyl 6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxylate (10 mg, 0.017 mmol, Step-2 of Example 243) and 2 M ammonia in MeOH (0.5 mL) is stirred overnight at rt. After the reaction mixture is concentrated, the resultant residue is purified by preparative LC-MS to give 4.8 mg (51% yield) of the title compound.

Example 244: 6-(3-(((1r,4r)-4-(5-chloro-2-methylnicotinamido)cyclohexyl)methyl)-2-oxo-2,3-dihydro-1H-benzo[d]imidazol-1-yl)-N-methylbenzo[d]isoxazole-3-carboxamide

[Chem. 83]

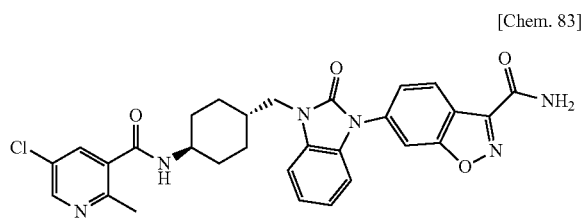 [SMILES: Cc1ncc(Cl)cc1C(=O)N[C@H]1CC[C@H](Cn2c(=O)n(-c3ccc4c(C(N)=O)noc4c3)c3ccccc32)CC1]

[Chem. 84]

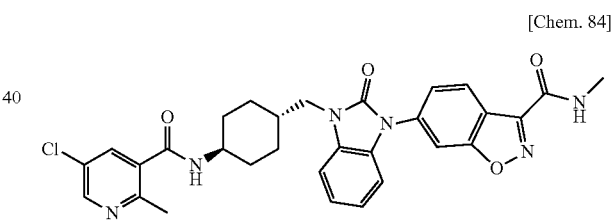

The title compound is prepared in 36% yield (3.5 mg) by the similar manner to Step-3 of Example 243 using 2 M methylamine in THF (0.5 mL) in place of 2 M ammonia in MeOH.

Example 245: 6-(3-(((1r,4r)-4-(5-chloro-2-methylnicotinamido)cyclohexyl)methyl)-2-oxo-2,3-dihydro-1H-benzol[d]imidazol-1-yl)-N,N-dimethylbenzo[d]isoxazole-3-carboxamide

[Chem. 85]

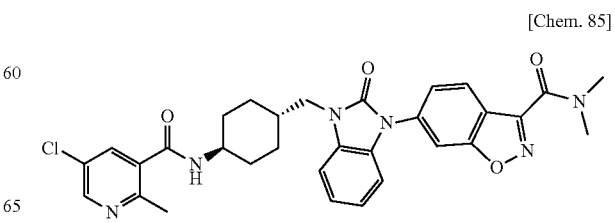

Example 253: 5-chloro-N-((1r,4r)-4-((3-(1-(2-hydroxyethyl)-1H-pyrazolo[3,4-b]pyridin-5-yl)-2-oxo-2,3-dihydro-1H-benzo[d]imidazol-1-yl)methyl)cyclohexyl)-2-methylnicotinamide The title compound is prepared in 54% yield (5.4 mg) by the similar manner to Step-3 of Example 243 using 2 M dimethylamine in THF (0.5 mL) in place of 2 M ammonia in MeOH.

[Chem. 86]

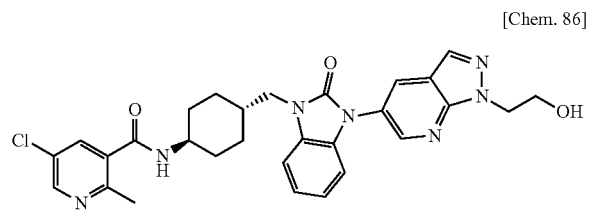 [SMILES: Cc1ncc(Cl)cc1C(=O)N[C@H]1CC[C@H](Cn2c(=O)n(-c3cnc4c(cnn4CCO)c3)c3ccccc32)CC1]

<Step-1>: 5-bromo-1-(2-((tert-butyldimethylsilyl)oxy)ethyl)-1H-pyrazolo[3,4-b]pyridine A mixture of 5-bromo-1H-pyrazolo[3,4-b]pyridine (100 mg, 0.505 mmol), (2-bromoethoxy)(tert-butyl)dimethylsilane (0.119 mL, 0.555 mmol) and $Cs_2CO_3$ (411 mg, 1.26 mmol) in DMF (2 mL) is stirred at rt overnight. The reaction mixture is diluted with EtOAc, washed with water, dried over $MgSO_4$, filtered and concentrated. The residue is purified by column chromatography on silica-gel eluting with 5-25% EtOAc in n-hexane to give 119 mg (66%) of the title compound as a colorless oil.

1H-NMR (400 MHz, CDCl3) delta 8.55 (1H, d, J=2.1 Hz), 8.17 (1H, d, J=2.1 Hz), 7.96 (1H, s), 4.63 (2H, t, J=5.7 Hz), 4.08 (2H, t, J=5.7 Hz), 0.73 (9H, s), −0.15 (6H, s).

<Step-2>: 5-chloro-N-((1r,4r)-4-((3-(1-(2-hydroxyethyl)-1H-pyrazolo[3,4-b]pyridin-5-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-2,3-dihydro-1H-benzo[d]imidazol-1-yl)methyl)cyclohexyl)nicotinamide (20 mg, 0.050 mmol, Step-2 of Example 9), 5-bromo-1-(2-((tert-butyldimethylsilyl)oxy)ethyl)-1H-pyrazolo[3,4-b]pyridine (36 mg, 0.100 mmol, Step-1 of Example 253), $N^1,N^2$-dimethylethane-1,2-diamine (0.030 mL, 0.276 mmol), $Cs_2CO_3$ (65 mg, 0.201 mmol) and CuI (24 mg, 0.125 mmol) in DMA (1.5 mL) is stirred at 100° C. for 2 hrs. The mixture is poured into 28% aqueous ammonia solution (3 mL), extracted with EtOAc. The organic layer is washed with water, dried over sodium sulfate, filtered and concentrated. The residue is purified by column chromatography on silica-gel eluting with 0-90% EtOAc in n-hexane to give 32 mg of N((1r,4r)-4-((3-(1-(2-((tert-butyldimethylsilyl)oxy)ethyl)-1H-pyrazolo[3,4-b]pyridin-5-yl)-2-oxo-2,3-dihydro-1H-benzo[d]imidazol-1-yl)methyl)cyclohexyl)-5-chloro-2-methylnicotinamide. This is dissolved in DCM (1.5 mL). To the mixture is added TFA (0.5 mL) and the mixture is stirred at rt for 0.5 hrs. The mixture is concentrated. The residue is dissolved in DCM (5 mL). The organic layer is washed with water, dried over sodium sulfate, filtered and concentrated and then purified by preparative LC-MS to give 9.0 mg (32% yield) of the title compound.

Example 260: 5-chloro-N-((1r,4r)-4-((3-(3-methyl-1H-indazol-5-yl)-2-oxo-2,3-dihydro-1H-benzo[d]imidazol-1-yl)methyl)cyclohexyl)-2-(trifluoromethyl)nicotinamide

[Chem. 87]

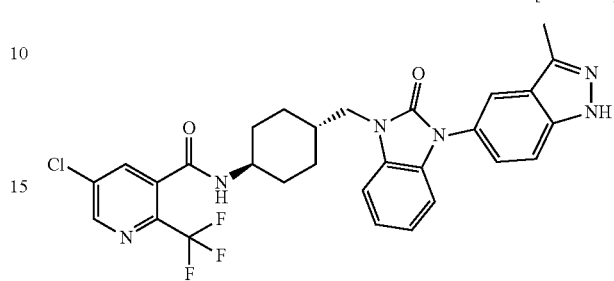

<Step-1>: 5-chloro-N-((1r,4r)-4-((3-(3-methyl-1-(tetrahydro-2H-pyran-2-yl)-1H-indazol-5-yl)-2-oxo-2,3-dihydro-1H-benzo[d]imidazol-1-yl)methyl)cyclohexyl)-2-(trifluoromethyl)nicotinamide A mixture of Intermediate-132 (32 mg, 0.071 mmol), 5-bromo-3-methyl-1-(tetrahydro-2H-pyran-2-yl)-1H-indazole (31 mg, 0.11 mmol), CuI (27 mg, 0.14 mmol), DMEDA (13 mg, 0.14 mmol) and $Cs_2CO_3$ (45 mg, 0.21 mmol) in DMA (1 mL) is stirred at 130° C. for 6 hrs under $N_2$ condition. To the mixture is added water, extracted with EtOAc and passed through sodium sulfate/amino-functional silica gel. The solvent is removed under vacuum, the title compound is obtained as a crude solid. The title compound is used next step without further purification.

MS (ESI) m/z: 667.5 (M+H)+.

<Step-2>: 5-chloro-N-((1r,4r)-4-((3-(3-methyl-1H-indazol-5-yl)-2-oxo-2,3-dihydro-1H-benzo[d]imidazol-1-yl)methyl)cyclohexyl)-2-(trifluoromethyl)nicotinamide A mixture of 5-chloro-N-((1r,4r)-4-((3-(3-methyl-1-(tetrahydro-2H-pyran-2-yl)-1H-indazol-5-yl)-2-oxo-2,3-dihydro-1H-benzo[d]imidazol-1-yl)methyl)cyclohexyl)-2-(trifluoromethyl)nicotinamide (Step-1 of Ex 260) is added DCM/TFA=1/1 (1 mL) and stirred at rt for 2 hrs. The solvent is removed by flowing $N_2$ gas, the crude product is purified by preparative LC-MS to give 6.0 mg (15% yield, total: 2 steps) of the title compound.

Example 261: 5-chloro-N-((1r,4r)-4-((3-(3-(hydroxymethyl)benzo[d]isoxazol-6-yl)-2-oxo-2,3-dihydro-1H-benzo[d]imidazol-1-yl)methyl)cyclohexyl)-2-methylnicotinamide

[Chem. 88]

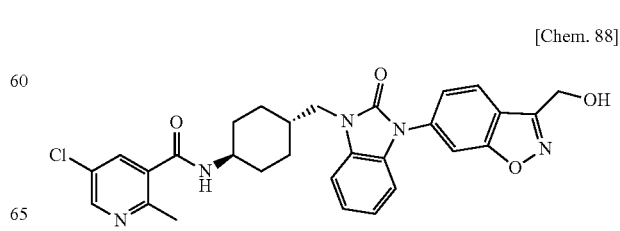

A mixture of methyl 6-(3-(((1r,4r)-4-(5-chloro-2-methyl-nicotinamido)cyclohexyl)methyl)-2-oxo-2,3-dihydro-1H-benzo[d]imidazol-1-yl)benzo[d]isoxazole-3-carboxylate (40 mg, 0.070 mmol, Step-2 of Example 243), sodium borohydride (42 mg, 1.11 mmol) and lithium chloride (71 mg, 1.67 mmol) in THF is stirred for 4 hrs at rt. The reaction mixture is added with saturated aqueous ammonium chloride. The resultant mixture is extracted with EtOAc and concentrated. The resultant residue is purified by a strong anion exchange cartridge (ISOLUTE (registered trademark) SCX-2, 1 g/6 mL, Biotage). The residue is purified by preparative LC-MS to give 5.1 mg (13% yield) of the title compound.

Example 263: N-((1r,4r)-4-((3-(2-aminobenzo[d]oxazol-5-yl)-2-oxo-2,3-dihydro-1H-benzo[d]imidazol-1-yl)methyl)cyclohexyl)-5-chloro-2-methylnicotinamide

[Chem. 89]

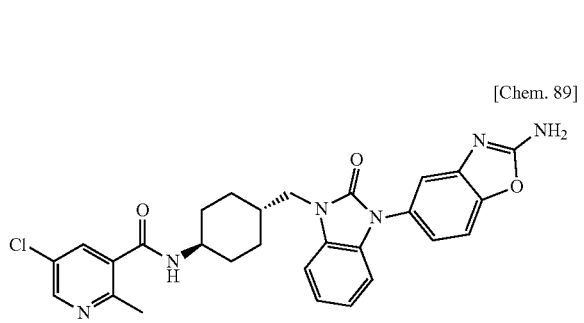 [SMILES: Cc1ncc(Cl)cc1C(=O)N[C@H]1CC[C@H](Cn2c(=O)n(-c3ccc4oc(N)nc4c3)c3ccccc32)CC1]

<Step-1>:5-bromo-N-(2,4-dimethoxybenzyl)benzo[d]oxazol-2-amine

To a stirred solution of 5-bromo-2-chlorobenzo[d]oxazole (50 mg, 0.215 mmol) in THF (1 mL) are added (2,4-dimethoxyphenyl)methanamine (72 mg, 0.430 mmol) and TEA (0.090 mL, 0.645 mmol) at rt and stirred for 1 hr. The reaction mixture is diluted with water, extracted with EtOAc. The organic phase is dried over MgSO$_4$, filtered and concentrated. The residue is purified by column chromatography on silica-gel eluting with 5-50% EtOAc in n-hexane to give 30 mg (38%) of the title compound as an ivory solid.
1H-NMR (400 MHz, CDCl$_3$) delta 7.46 (1H, d, J=1.8 Hz), 7.26 (1H, d, J=8.2 Hz), 7.12 (1H, dd, J=8.2, 1.8 Hz), 7.07 (1H, d, J=8.2 Hz), 6.48 (1H, d, J=2.3 Hz), 6.44 (1H, dd, J=8.2, 2.3 Hz), 5.46 (1H, t, J=5.9 Hz), 4.56 (2H, d, J=5.9 Hz), 3.85 (3H, s), 3.80 (3H, s).

<Step-2>: N((1r,4r)-4-((3-(2-aminobenzo[d]oxazol-5-yl)-2-oxo-2,3-dihydro-1H-benzo[d]imidazol-1-yl)methyl)cyclohexyl)-5-chloro-2-methylnicotinamide A mixture of 5-chloro-2-methyl-N-((1r,4r)-4-((2-oxo-2,3-dihydro-1H-benzo[d]imidazol-1-yl)methyl)cyclohexyl)nicotinamide (40 mg, 0.100 mmol, Step-2 of Example 9), 5-bromo-N-(2,4-dimethoxybenzyl)benzo[d]oxazol-2-amine (44 mg, 0.120 mmol, Step-1 of Example 263), N$^1$,N$^2$-dimethylethane-1,2-diamine (0.060 mL, 0.552 mmol), Cs$_2$CO$_3$ (131 mg, 0.402 mmol) and CuI (48 mg, 0.250 mmol) in DMA (1.5 mL) is stirred at 110° C. for 21 hrs. The mixture is poured into 28% aqueous ammonia solution (5 mL), extracted with EtOAc. The organic layer is washed with water, dried over sodium sulfate, filtered and concentrated. The residue is purified by column chromatography on amino-functional silica gel eluting with 0-90% EtOAc in n-hexane to give 14 mg of 5-chloro-N-((1r,4r)-4-((3-(2-((2,4-dimethoxybenzyl)amino)benzo[d]oxazol-5-yl)-2-oxo-2,3-dihydro-1H-benzo[d]imidazol-1-yl)methyl)cyclohexyl)-2-methylnicotinamide. This is dissolved in DCM (1.5 mL). To the mixture is added TFA (1.5 mL) and the mixture is stirred at 45° C. for 1.5 hrs. The mixture is concentrated. The residue is purified by a strong anion exchange cartridge (ISOLUTE (registered trademark) SCX-2, 1 g/6 mL, Biotage) and then purified by preparative LC-MS to give 4.1 mg (38% yield) of the title compound.

Example 271: 5-chloro-2-methyl-N-((1r,4r)-4-((3-(3-methyl-1H-pyrazolo[3,4-b]pyridin-5-yl)-2-oxo-2,3-dihydro-1H-benzo[d]imidazol-1-yl)methyl)cyclohexyl)nicotinamide

[Chem. 90]

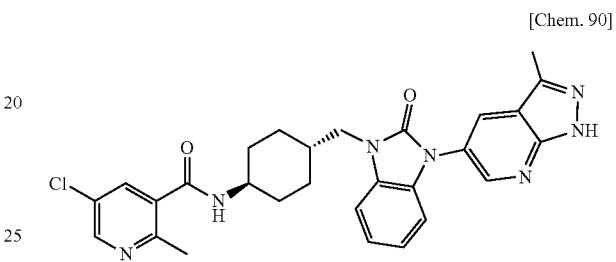

The title compound is prepared in 21% yield in 2 steps by the similar manner to Step-1 and Step-2 of Example 260 using 5-bromo-3-methyl-1-(tetrahydro-2H-pyran-2-yl)-1H-pyrazolo[3,4-b]pyridine and 5-chloro-2-methyl-N-((1r,4r)-4-((2-oxo-2,3-dihydro-1H-benzo[d]imidazol-1-yl)methyl)cyclohexyl)nicotinamide (Step-2 of Example 9) in place of 5-bromo-3-methyl-1-(tetrahydro-2H-pyran-2-yl)-1H-indazole and 5-chloro-N-((1r,4r)-4-((2-oxo-2,3-dihydro-1H-benzo[d]imidazol-1-yl)methyl)cyclohex yl)-2-(trifluoromethyl)nicotinamide.

Example 273: 5-chloro-N-((1r,4r)-4-((3-(2-cyano-5-(dimethylamino)phenyl)-2-oxo-2,3-dihydro-1H-benzo[d]imidazol-1-yl)methyl)cyclohexyl)-2-methylnicotinamide

[Chem. 91]

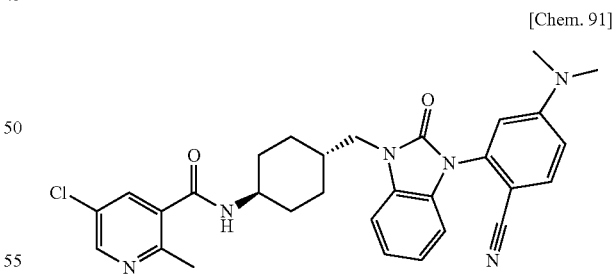

A solution of Ex 307 (30 mg, 0.052 mmol), dimethylamine hydrochloride (8.5 mg, 0.10 mmol), Pd$_2$(dba)$_3$ (2.4 mg, 0.0026 mmol), Xantphos (1.5 mg, 0.0026 mmol) and Cs$_2$CO$_3$ (51 mg, 0.16 mmol) in 1,4-dioxane (1 mL) is stirred at 100° C. for 12 hrs. To the mixture is added water, extracted with EtOAc and passed through sodium sulfate/amino-functional silica gel. The solvent is removed under vacuum, the crude product is purified by a strong anion exchange cartridge (ISOLUTE (registered trademark) SCX-2, 1 g/6 mL, Biotage) and then purified by preparative LC-MS to give 3.6 mg (13% yield) of the title compound.

Example 276: 5-chloro-N-((1r,4r)-4-((3-(1-(2-hydroxyethyl)-1H-benzo[d][1,2,3]triazol-5-yl)-2-oxo-2,3-dihydro-1H-benzo[d]imidazol-1-yl)methyl)cyclohexyl)-2-methylnicotinamide

[Chem. 92]

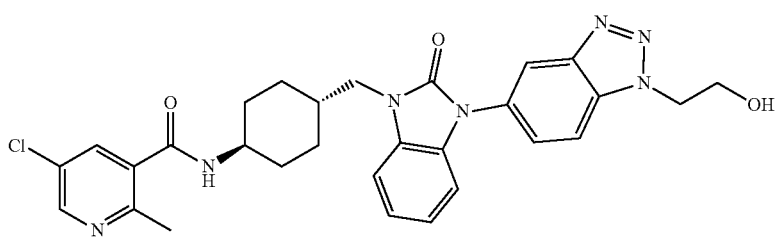

<Step-1>: 5-bromo-1-(2-((tert-butyldimethylsilyl)oxy)ethyl)-1H-benzo[d][1,2,3]triazole Sodium hydride (60%, dispersion in mineral oil) (45 mg, 1.14 mmol) and (2-bromoethoxy)(tert-butyl)dimethylsilane (0.243 mL, 1.14 mmol) is added to the solution of 5-bromo-1H-benzo[d][1,2,3]triazole (150 mg, 0.757 mmol) in DMF at 0° C. After that the reaction mixture is warmed up to 60° C. and stirred overnight at the same temperature. The reaction mixture is added with saturated aqueous ammonium chloride. The resultant mixture is extracted with DCM and concentrated. The resultant residue is purified by column chromatography on silica-gel eluting with 8-50% EtOAc in n-hexane to give 79 mg (29% yield) of the title compound as a pale yellow gum.

$^1$H-NMR (400 MHz, CDCl$_3$) delta 8.04 (1H, d, J=1.8 Hz), 7.74 (1H, d, J=9.4 Hz), 7.45 (1H, dd, J=9.4, 1.8 Hz), 4.80 (2H, t, J=5.7 Hz), 4.25 (2H, t, J=5.7 Hz), 0.77 (9H, s), −0.09 (6H, s).

MS (ESI) m/z: 356.4 (M+H)$^+$.

<Step-2>: 5-chloro-N-((1r,4r)-4-((3-(1-(2-hydroxyethyl)-1H-benzo[d][1,2,3]triazol-5-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-2,3-dihydro-1H-benzo[d]imidazol-1-yl)methyl)cyclohexyl)nicotinamide (15 mg, 0.038 mmol, Step-2 of Example 9), 5-bromo-1-(2-((tert-butyldimethylsilyl)oxy)ethyl)-1H-benzo[d][1,2,3]triazole (20 mg, 0.056 mmol, Step-1 of Example 276), N$^1$,N$^2$-dimethylethane-1,2-diamine (0.022 mL, 0.207 mmol), Cs$_2$CO$_3$ (49 mg, 0.150 mmol) and CuI (18 mg, 0.094 mmol) in DMA (1.5 mL) is stirred at 100° C. for 4.5 hrs. The mixture is poured into 28% aqueous ammonia solution (3 mL), extracted with EtOAc. The organic layer is washed with water, dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 2.2 mg (10% yield) of the title compound.

Example 279: 5-chloro-N-((1r,4r)-4-((3-(6-cyclobutylpyridin-3-yl)-2-oxo-2,3-dihydro-1H-benzo[d]imidazol-1-yl)methyl)cyclohexyl)-2-methylnicotinamide

[Chem. 93]

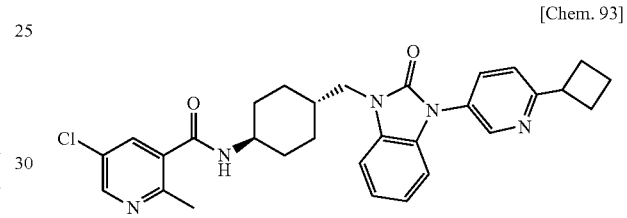

A mixture of N((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide (30 mg, 0.054 mmol, Example 66), bromocyclobutane (37 mg, 0.27 mmol), nickel (II) chloride ethylene glycol dimethyl ether complex (1.2 mg, 0.0054 mmol), Ir[dF(CF$_3$)ppy]$_2$(dtbbpy)PF$_6$ (0.6 mg, 0.00054 mmol), 4,4'-di-tert-butyl-2,2'-bipyridine (1.5 mg, 0.0054 mmol), tris(trimethylsilyl)silane (40 mg, 0.16 mmol), and 2,6-lutidine (12 mg, 0.11 mmol) in DME (0.3 mL) is stirred under blue LED irradiation for 3 days. The mixture is diluted with water and extracted with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 2.4 mg (8% yield) of the title compound.

Example 301: 5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-(trifluoromethyl)nicotinamide

[Chem. 94]

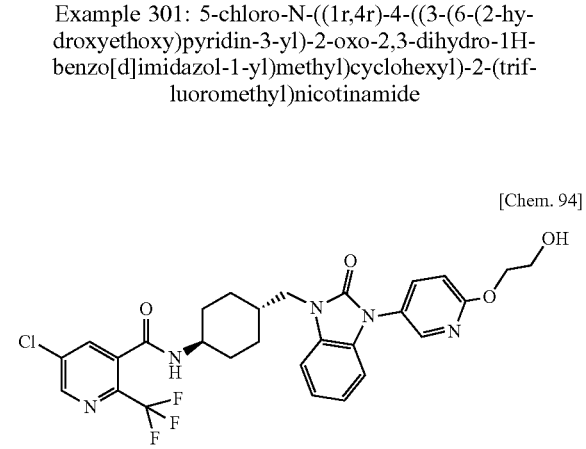

The title compound is prepared in 25% yield in 2 steps by the similar manner to Step-1 and Step-2 of Example 50 using Mesylate-3 in place of Mesylate-1.

Example 305: 5-chloro-2-methyl-N-((1r,4r)-4-((2-oxo-3-(4-oxo-3,4-dihydroquinazolin-7-yl)-2,3-dihydro-1H-benzo[d]imidazol-1-yl)methyl)cyclohexyl)nicotinamide

[Chem. 95]

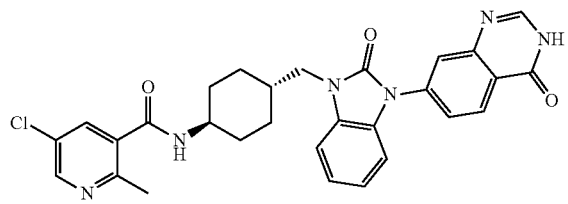

<Step-1>: 7-bromo-4-((4-methoxybenzyl)oxy)quinazoline

A mixture of 7-bromoquinazolin-4-ol (100 mg, 0.444 mmol), Cs$_2$CO$_3$ (434 mg, 1.33 mmol) and 1-(chloromethyl)-4-methoxybenzene (0.073 mL, 0.533 mmol) in THF (2 mL) is stirred at rt overnight. To the reaction mixture are added Cs$_2$CO$_3$ (200 mg, 0.614 mmol) and 1-(chloromethyl)-4-methoxybenzene (0.073 mL, 0.533 mmol) and stirred at rt for 2 hrs. The reaction mixture is diluted with EtOAc and water, then the resultant mixture is extracted with EtOAc. The organic phase is washed with brine, dried over MgSO$_4$, filtered and concentrated. The residue is purified by column chromatography on silica-gel eluting with 5-50% EtOAc in n-hexane to give 145 mg (95%) of the title compound as a white solid.

$^1$H-NMR (400 MHz, CDCl$_3$) delta 8.17 (1H, d, J=8.2 Hz), 8.09 (1H, s), 7.87 (1H, d, J=1.8 Hz), 7.60 (1H, dd, J=8.2, 1.8 Hz), 7.30 (2H, d, J=8.7 Hz), 6.88 (2H, d, J=8.7 Hz), 5.11 (2H, s), 3.79 (3H, s).
MS (ESI) m/z: 345.3 (M+H)$^+$.

<Step-2>: 5-chloro-N-((1r,4r)-4-((3-(4-((4-methoxybenzyl)oxy)quinazolin-7-yl)-2-oxo-2,3-dihydro-1H-benzo[d]imidazol-1-yl)methyl)cyclohexyl)-2-methylnicotinamide The title compound is prepared in quantitative yield (50 mg, yellow gum) by the similar manner to Step-2 of Example 210 using 7-bromo-4-((4-methoxybenzyl)oxy)quinazoline (39 mg, 0.113 mmol, Step-1 of Example 305) in place of 6-bromo-3-chloro-1-(tetrahydro-2H-pyran-2-yl)-1H-indazole.

$^1$H-NMR (400 MHz, CDCl$_3$) delta 8.50-8.44 (2H, m), 8.14 (1H, s), 7.93 (1H, d, J=2.3 Hz), 7.80 (1H, dd, J=8.7, 2.3 Hz), 7.61 (1H, d, J=2.3 Hz), 7.33 (2H, d, J=8.7 Hz), 7.28-7.23 (1H, m), 7.22-7.16 (1H, m), 7.14-7.04 (2H, m), 6.90 (2H, d, J=8.7 Hz), 5.58 (1H, d, J=8.2 Hz), 5.16 (2H, s), 4.02-3.88 (1H, m), 3.83 (2H, d, J=6.9 Hz), 3.80 (3H, s), 2.61 (3H, s), 2.20-2.10 (2H, m), 2.03-1.82 (3H, m), 1.41-1.15 (4H, m).
MS (ESI) m/z: 633.7 (M+H)$^+$.

<Step-3>: 5-chloro-2-methyl-N-((1r,4r)-4-((2-oxo-3-(4-oxo-3,4-dihydroquinazolin-7-yl)-2,3-dihydro-1H-benzo[d]imidazol-1-yl)methyl)cyclohexyl)nicotinamide TFA (1 mL) is added to the product of Step-2 of Example 305 (50 mg, 0.075 mmol) and refluxed for 1.5 hrs. After cooled to rt, the mixture is concentrated. The residue is purified by a strong anion exchange cartridge (ISOLUTE (registered trademark) SCX-2, 1 g/6 mL, Biotage) and then purified by preparative LC-MS to give 4.6 mg (11% yield) of the title compound.

Example 308: 5-chloro-N-((1r,4r)-4-((3-(4-cyano-6-methylpyridin-3-yl)-2-oxo-2,3-dihydro-1H-benzo[d]imidazol-1-yl)methyl)cyclohexyl)-2-methylnicotinamide

[Chem. 96]

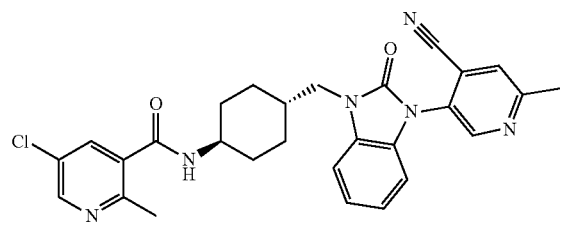

<Step-1>: N((1r,4r)-4-((3-(6-bromo-4-cyanopyridin-3-yl)-2-oxo-2,3-dihydro-1H-benzo[d]imidazol-1-yl)methyl)cyclohexyl)-5-chloro-2-methylnicotinamide The title compound is prepared in 91% yield (132 mg, solid) by the similar manner to Ex 219 using 2-bromo-5-fluoroisonicotinonitrile (66 mg, 0.33 mmol) in place of 2-fluorobenzonitrile.

$^1$H-NMR (400 MHz, CDCl$_3$) delta 8.70 (1H, s), 8.48 (1H, d, J=2.3 Hz), 7.94 (1H, s), 7.60 (1H, d, J=2.3 Hz), 7.24 (1H, dd, J=7.8, 1.4 Hz), 7.18-7.08 (2H, m), 6.94 (1H, d, J=7.3 Hz), 5.70 (1H, d, J=7.8 Hz), 4.02-3.89 (1H, m), 3.84 (2H, br), 2.60 (3H, s), 2.22-2.08 (2H, m), 2.02-1.83 (3H, m), 1.42-1.15 (4H, m) MS (ESI) m/z: 581.1 (M+H)$^+$.

<Step-2>: 5-chloro-N-((1r,4r)-4-((3-(4-cyano-6-methylpyridin-3-yl)-2-oxo-2,3-dihydro-1H-benzo[d]imidazol-1-yl)methyl)cyclohexyl)-2-methylnicotinamide A mixture of N((1r,4r)-4-((3-(6-bromo-4-cyanopyridin-3-yl)-2-oxo-2,3-dihydro-1H-benzo[d]imidazol-1-yl)methyl)cyclohexyl)-5-chloro-2-methylnicotinamide (30 mg, 0.052 mmol, Step-1 of Ex 308), 2,4,6-trimethyl-1,3,5,2,4,6-trioxatriborinane (10 mg, 0.078 mmol), Pd(PPh$_3$)$_4$ (12 mg, 0.010 mmol), K$_2$CO$_3$ (14 mg, 0.103 mmol) in 1,4-dioxane/H$_2$O=2/1 (3 mL) is stirred at 100° C. overnight. The mixture is added water, extracted with EtOAc and passed through sodium sulfate/amino-functional silica gel. The solvent is removed under vacuum, the crude product is purified by a strong anion exchange cartridge (ISOLUTE (registered trademark) SCX-2, 1 g/6 mL, Biotage) and then purified by preparative LC-MS to give 2.8 mg (11% yield) of the title compound.

Example 310: 5-chloro-N-((1r,4r)-4-((3-(4-cyano-6-((2-methoxyethyl)amino)pyridin-3-yl)-2-oxo-2,3-dihydro-1H-benzo[d]imidazol-1-yl)methyl)cyclohexyl)-2-methylnicotinamide

[Chem. 97]

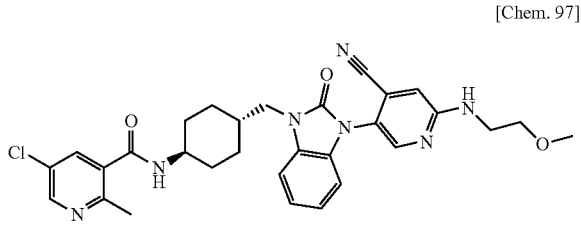 [SMILES: COCCNc1cc(C#N)c(-n2c(=O)n(C[C@H]3CC[C@H](NC(=O)c4cc(Cl)cnc4C)CC3)c3ccccc32)cn1]

A mixture of N((1r,4r)-4-((3-(6-bromo-4-cyanopyridin-3-yl)-2-oxo-2,3-dihydro-1H-benzo[d]imidazol-1-yl)methyl)cyclohexyl)-5-chloro-2-methylnicotinamide (30 mg, 0.052 mmol, Step-1 of Ex 308), 2-methoxyethanamine (19 mg, 0.26 mmol), Pd$_2$(dba)$_3$ (9.5 mg, 0.010 mmol), Xantphos (6.0 mg, 0.010 mmol) and Cs$_2$CO$_3$ (34 mg, 0.10 mmol) in 1,4-dioxane (2 mL) is stirred at 100° C. overnight. The solvent is removed under vacuum, the crude product is purified by a strong anion exchange cartridge (ISOLUTE (registered trademark) SCX-2, 1 g/6 mL, Biotage) and then purified by preparative LC-MS to give 2.0 mg (6.7% yield) of the title compound.

Example 319: N-((1r,4r)-4-((3-(4-aminopyrido[3,2-d]pyrimidin-7-yl)-2-oxo-2,3-dihydro-1H-benzo[d]imidazol-1-yl)methyl)cyclohexyl)-5-chloro-2-methylnicotinamide

[Chem. 98]

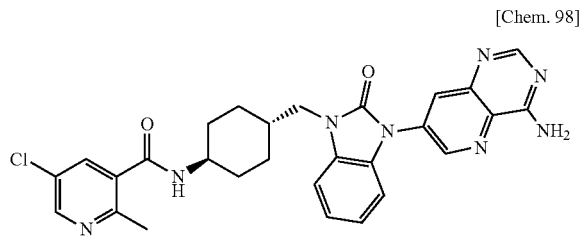 [SMILES: Cc1ncc(Cl)cc1C(=O)N[C@H]1CC[C@H](Cn2c(=O)n(-c3cnc4c(N)ncnc4c3)c3ccccc32)CC1]

<Step-1>:7-bromo-N-(2,4-dimethoxybenzyl)pyrido[3,2-d]pyrimidin-4-amine

A mixture of 7-bromo-4-chloropyrido[3,2-d]pyrimidine (100 mg, 0.409 mmol), (2,4-dimethoxyphenyl)methanamine (103 mg, 0.614 mmol) and K$_2$CO$_3$ (170 mg, 1.23 mmol) in DMF (2 mL) is stirred at rt for 2 hrs. The reaction mixture is diluted with EtOAc and water. Insoluble material, which is the title compound, is collected by filtration. Then the filtrate is washed with water and brine, dried over MgSO$_4$, filtered and concentrated. The residue is purified by column chromatography on silica-gel eluting with 5-100% EtOAc in n-hexane to give the title compound as a white solid (66 mg, 43% combined yield).

$^1$H-NMR (400 MHz, CDCl$_3$) delta 8.66 (1H, d, J=2.3 Hz), 8.63 (1H, s), 8.23 (1H, d, J=1.8 Hz), 7.49 (1H, br s), 7.30 (1H, d, J=8.2 Hz), 6.50 (1H, d, J=2.3 Hz), 6.45 (1H, dd, J=8.2, 2.3 Hz), 4.78 (2H, d, J=5.9 Hz), 3.88 (3H, s), 3.80 (3H, s).

<Step-2>: 5-chloro-N-((1r,4r)-4-((3-(4-((2,4-dimethoxybenzyl)amino)pyrido[3,2-d]pyrimidin-7-yl)-2-oxo-2,3-dihydro-1H-benzo[d]imidazol-1-yl)methyl)cyclohexyl)-2-methylnicotinamide The title compound is prepared in 62% yield (30 mg, beige solid) by the similar manner to Step-2 of Example 210 using 7-bromo-N-(2,4-dimethoxybenzyl)pyrido[3,2-d]pyrimidin-4-amine (40 mg, 0.105 mmol), which is the product of Step-1 of Example 319, in place of 6-bromo-3-chloro-1-(tetrahydro-2H-pyran-2-yl)-1H-indazole. In addition, this reaction is carried out at 150° C.

MS (ESI) m/z: 693.7 (M+H)$^+$.

<Step-3>: N((1r,4r)-4-((3-(4-aminopyrido[3,2-d]pyrimidin-7-yl)-2-oxo-2,3-dihydro-1H-benzo[d]imidazol-1-yl)methyl)cyclohexyl)-5-chloro-2-methylnicotinamide The title compound is prepared in 23% yield (5.5 mg) by the similar manner to Step-3 of Example 305 using the product of Step-2 of Example 319 (30 mg, 0.043 mmol) in place of the product of Step-2 of Example 305.

Example 348: 5-chloro-2-methyl-N-((1r,4r)-4-((2-oxo-3-(3-phenyl-1H-indazol-5-yl)-2,3-dihydro-1H-benzo[d]imidazol-1-yl)methyl)cyclohexyl)nicotinamide

[Chem. 99]

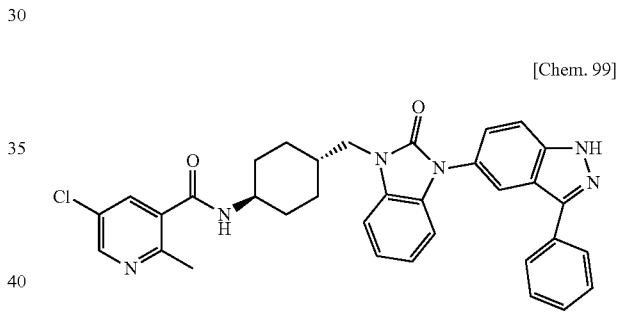

<Step-1>:5-bromo-3-phenyl-1-(tetrahydro-2H-pyran-2-yl)-1H-indazole

A mixture of 5-bromo-3-phenyl-1H-indazole (50 mg, 0.18 mmol), 3,4-dihydro-2H-pyran (0.025 mL, 0.28 mmol) and p-toluenesulfonic acid (3 mg, 0.02 mmol) in toluene (1 mL) is stirred for 8 hrs at 80° C. The reaction mixture is purified by column chromatography on silica-gel eluting with 4-33% EtOAc in n-hexane to give 64 mg (98% yield) of the title compound as a pale yellow gum.

$^1$H-NMR (400 MHz, CDCl$_3$) delta 8.13 (1H, d, J=1.4 Hz), 7.95-7.88 (2H, m), 7.58-7.45 (4H, m), 7.45-7.38 (1H, m), 5.76 (1H, dd, J=9.1, 2.7 Hz), 4.10-3.99 (1H, m), 3.82-3.70 (1H, m), 2.70-2.53 (1H, m), 2.27-2.08 (2H, m), 1.88-1.60 (3H, m).

MS (ESI) m/z: 357.2 (M+H)$^+$.

<Step-2>: 5-chloro-2-methyl-N-((1r,4r)-4-((2-oxo-3-(3-phenyl-1H-indazol-5-yl)-2,3-dihydro-1H-benzo[d]imidazol-1-yl)methyl)cyclohexyl)nicotinamide A mixture of 5-chloro-2-methyl-N-((1r,4r)-4-((2-oxo-2,3-dihydro-1H-benzo[d]imidazol-1-yl)methyl)cyclohexyl)nicotinamide (15 mg, 0.038 mmol, Step-2 of Example 9), 5-bromo-3-phenyl-1-(tetrahydro-2H-pyran-2-yl)-1H-indazole (16 mg, 0.045 mmol, Step-1 of Example 348), $N^1,N^2$-dimethylethane-1,2-diamine (0.022 mL, 0.207 mmol), $Cs_2CO_3$ (49 mg, 0.150 mmol) and CuI (18 mg, 0.094 mmol) in DMA (1.5 mL) is stirred at 120° C. for 1.5 hrs. The mixture is poured into 28% aqueous ammonia solution (3 mL), extracted with EtOAc. The organic layer is washed with water, dried over sodium sulfate, filtered and concentrated. The residue is purified by a strong anion exchange cartridge (ISOLUTE (registered trademark) SCX-2, 1 g/6 mL, Biotage) to give 12 mg of 5-chloro-2-methyl-N-((1r,4r)-4-((2-oxo-3-(3-phenyl-1-(tetrahydro-2H-pyran-2-yl)-1H-indazol-5-yl)-2,3-dihydro-1H-benzo[d]imidazol-1-yl)methyl)cyclohexyl)nicotinamide. This is dissolved in DCM (1 mL). To the mixture is added TFA (1 mL) and the mixture is stirred at rt for 1.5 hrs. The mixture is concentrated. The residue is purified by a strong anion exchange cartridge (ISOLUTE (registered trademark) SCX-2, 1 g/6 mL, Biotage) and then purified by preparative LC-MS to give 8.8 mg (40% yield) of the title compound.

MS (ESI) m/z: 591.5 $(M+H)^+$.

Example 355: 5-chloro-N-((1r,4r)-4-((3-(2-ethyloxazolo[4,5-b]pyridin-6-yl)-2-oxo-2,3-dihydro-1H-benzo[d]imidazol-1-yl)methyl)cyclohexyl)-2-methylnicotinamide

[Chem. 100]

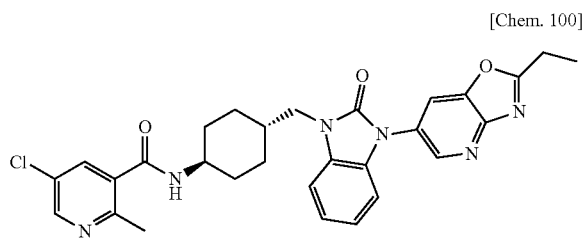 [SMILES: CCc1nc2ncc(-n3c(=O)n(C[C@H]4CC[C@H](NC(=O)c5cc(Cl)cnc5C)CC4)c4ccccc43)cc2o1]

\<Step-1\>:5-bromo-N-(4-methoxybenzyl)-3-((4-methoxybenzyl)oxy)pyridin-2-amine

A mixture of 2-amino-5-bromopyridin-3-ol (200 mg, 1.058 mmol), 1-(chloromethyl)-4-methoxybenzene (365 mg, 2.328 mmol) and potassium carbonate (731 mg, 5.29 mmol) in THF (3 mL) is stirred at rt for 3 days. The mixture is stirred at 50° C. for 1 hr. The reaction mixture is poured into water and extracted EtOAc. The organic layer is washed with brine, dried over sodium sulfate, filtered and concentrated. The residue is purified by column chromatography on silica-gel eluting with 0-60% EtOAc in n-hexane to give 82 mg (18% yield) of the title compound.

MS (ESI) m/z: 429.3, 431.2 $(M+H)^+$.

\<Step-2\>: 5-chloro-N-((1r,4r)-4-((3-(6-((4-methoxybenzyl)amino)-5-((4-methoxybenzyl)oxy)pyri din-3-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-2,3-dihydro-1H-benzo[d]imidazol-1-yl)methyl)cyclohexyl)nicotinamide (55 mg, 0.138 mmol, Step-2 of Example 9), 5-bromo-N-(4-methoxybenzyl)-3-((4-methoxybenzyl)oxy)pyridin-2-amine (77 mg, 0.179 mmol, Step-1 of Example 355), $N^1,N^2$-dimethylethane-1,2-diamine (0.037 mL, 0.345 mmol), $Cs_2CO_3$ (180 mg, 0.552 mmol) and CuI (53 mg, 0.276 mmol) in DMA (1 mL) is stirred at 100° C. for 15 hrs. The mixture is poured into 28% aqueous ammonia solution, extracted with EtOAc. The organic layer is dried over sodium sulfate, filtered and concentrated. The residue is purified by column chromatography on silica-gel eluting with 0-90% EtOAc in n-hexane to give 90 mg (87% yield, pale yellow gum) of the title compound.

$^1$H-NMR (400 MHz, $CDCl_3$) delta 8.49 (1H, d, J=2.3 Hz), 7.91 (1H, d, J=1.8 Hz), 7.61 (1H, d, J=2.3 Hz), 7.35-7.24 (4H, m), 7.19-6.97 (5H, m), 6.93-6.84 (4H, m), 5.56 (1H, d, J=7.8 Hz), 5.34 (1H, t, J=6.0 Hz), 4.99 (2H, s), 4.64 (2H, d, J=6.0 Hz), 4.01-3.91 (1H, m), 3.85-3.78 (2H, m), 3.82 (3H, s), 3.80 (3H, s), 2.61 (3H, s), 2.21-2.13 (2H, m), 2.01-1.88 (3H, m), 1.41-1.15 (4H, m). MS (ESI) m/z: 747.7 $(M+H)^+$.

\<Step-3\>: N((1r,4r)-4-((3-(6-amino-5-hydroxypyridin-3-yl)-2-oxo-2,3-dihydro-1H-benzo[d]imidazol-1-yl)methyl)cyclohexyl)-5-chloro-2-methylnicotinamide A mixture of 5-chloro-N-((1r,4r)-4-((3-(6-((4-methoxybenzyl)amino)-5-((4-methoxybenzyl)oxy)pyri din-3-yl)-2-oxo-2,3-dihydro-1H-benzo[d]imidazol-1-yl)methyl)cyclohexyl)-2-methylnicotinamide (90 mg, 0.120 mmol, Step-2 of Example 355) is dissolved in DCM (0.5 mL). To the mixture is added TFA (1.0 mL) and the mixture is stirred at rt for 3 hrs. The reaction mixture is concentrated. The residue is purified by a strong anion exchange cartridge (ISOLUTE (registered trademark) SCX-2, 1 g/6 mL, Biotage) to give 50 mg (82% yield) of the title compound.

$^1$H-NMR (400 MHz, DMSO-$d_6$) delta 9.93 (1H, br s), 8.53 (1H, d, J=2.3 Hz), 8.39 (1H, d, J=8.2 Hz), 7.79 (1H, d, J=2.3 Hz), 7.56 (1H, d, J=2.3 Hz), 7.29 (1H, d, J=7.8 Hz), 7.10 (1H, td, J=7.8, 0.9 Hz), 7.03 (1H, td, J=7.8, 0.9 Hz), 6.94-6.89 (2H, m), 5.80 (2H, s), 3.78-3.65 (1H, m), 3.75 (2H, d, J=6.8 Hz), 1.97-1.68 (5H, m), 1.31-1.14 (4H, m). MS (ESI) m/z: 507.4 $(M+H)^+$.

\<Step-4\>: 5-chloro-N-((1r,4r)-4-((3-(2-ethyloxazolo[4,5-b]pyridin-6-yl)-2-oxo-2,3-dihydro-1H-benzo[d]imidazol-1-yl)methyl)cyclohexyl)-2-methylnicotinamide A mixture of N((1r,4r)-4-((3-(6-amino-5-hydroxypyridin-3-yl)-2-oxo-2,3-dihydro-1H-benzo[d]imidazol-1-yl)methyl)cyclohexyl)-5-chloro-2-methylnicotinamide (15 mg, 0.030 mmol, Step-3 of Example 355) and 4-methylbenzenesulfonic acid hydrate (0.6 mg, 0.003 mmol) in 1,1,1-trimethoxypropane (0.5 mL) is stirred at 120° C. for 0.5 hr under microwave irradiation. The mixture is poured into water, extracted with EtOAc. The organic layer is dried over sodium sulfate, filtered and concentrated. The residue is purified by preparative LC-MS to give 3.2 mg (20% yield) of the title compound.

Example 356: 5-chloro-2-methyl-N-((1r,4r)-4-((3-(2-methyloxazolo[4,5-b]pyridin-6-yl)-2-oxo-2,3-dihydro-1H-benzo[d]imidazol-1-yl)methyl)cyclohexyl)nicotinamide

[Chem. 101]

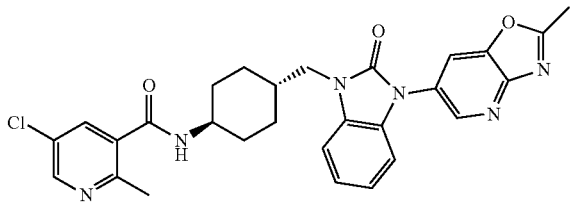

The title compound is prepared in 26% yield (4.0 mg) by the similar manner to Step-4 of Example 355 using 1,1,1-trimethoxyethane in place of 1,1,1-trimethoxypropane.

Example 357: 5-chloro-N-((1r,4r)-4-((3-(6-(2-hydroxyethoxy)-4-methylpyridin-3-yl)-2-oxo-2,3-dihydro-1H-benzo[d]imidazol-1-yl)methyl)cyclohexyl)-2-(trifluoromethyl)nicotinamide

[Chem. 102]

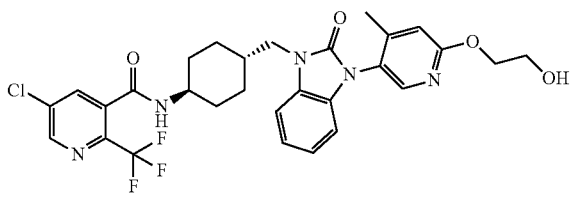

<Step-1>: 1-(6-(2-hydroxyethoxy)-4-methylpyridin-3-yl)-1H-benzo[d]imidazol-2(3H)-one A mixture of 1-(6-fluoro-4-methylpyridin-3-yl)-1H-benzo[d]imidazol-2(3H)-one (80 mg, 0.33 mmol, Step-3 of Intermediate-192), 2-((tetrahydro-2H-pyran-2-yl)oxy)ethanol (0.134 mL, 0.987 mmol) and potassium tert-butoxide (111 mg, 0.987 mmol) in DMF (1 mL) is stirred for 2 hrs at rt. The reaction mixture is added with saturated aqueous ammonium chloride. The resultant mixture is extracted with EtOAc. The organic layer is dried over MgSO$_4$, filtered and concentrated in vacuo. The resultant residue is purified by column chromatography on silica-gel eluting with 12-100% EtOAc in n-hexane to give 64 mg (69% yield) of the title compound as a pale brown gum.
MS (ESI) m/z: 286.3 (M+H)$^+$.

<Step-2>: tert-butyl 3-(6-(2-((tert-butoxycarbonyl)oxy)ethoxy)-4-methylpyridin-3-yl)-2-oxo-2,3-dihydro-1H-benzo[d]imidazole-1-carboxylate A mixture of 1-(6-(2-hydroxyethoxy)-4-methylpyridin-3-yl)-1H-benzo[d]imidazol-2(3H)-one (64 mg, 0.23 mmol, Step-1 of Example 357), di-tert-butyl dicarbonate (0.465 mL, 2.03 mmol) and potassium tert-butoxide (228 mg, 2.03 mmol) in DMF (1 mL) is stirred for 2 hrs at rt. The reaction mixture is added with saturated aqueous ammonium chloride. The resultant mixture is extracted with EtOAc and the organic layer is concentrated. The resultant residue is purified by column chromatography on silica-gel eluting with 4-50% EtOAc in n-hexane to give 35 mg (32% yield) of the title compound as a pale yellow gum.
$^1$H-NMR (400 MHz, CDCl$_3$) delta 8.04 (1H, s), 7.90 (1H, dd, J=7.1, 2.1 Hz), 7.21-7.09 (2H, m), 6.81 (1H, s), 6.67-6.59 (1H, m), 4.64-4.51 (2H, m), 4.46-4.39 (2H, m), 2.13 (3H, s), 1.69 (9H, s), 1.51 (9H, s).
MS (ESI) m/z: 486.5 (M+H)$^+$.

<Step-3>: tert-butyl (2-((5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-4-methylpyridin-2-yl)oxy)ethyl) carbonate A mixture of ((r,4r)-4-(5-chloro-2-(trifluoromethyl)nicotinamido)cyclohexyl)methyl methanesulfonate (20 mg, 0.056 mmol, Mesylate-3), tert-butyl 3-(6-(2-((tert-butoxycarbonyl)oxy)ethoxy)-4-methylpyridin-3-yl)-2-oxo-2,3-dihydro-1H-benzo[d]imidazole-1-carboxylate (11 mg, 0.028 mmol, Step-2 of Example 357) and cesium carbonate (23 mg, 0.069 mmol) in DMSO (1 mL) is stirred overnight at 100° C. The reaction mixture is added with water. The resultant mixture is extracted with EtOAc and the organic layer is concentrated. The resultant residue is purified by column chromatography on silica-gel eluting with 12-100% EtOAc in n-hexane to give 15 mg (61% yield) of the title compound as a pale yellow gum.
MS (ESI) m/z: 704.5 (M+H)$^+$.

<Step-4>: 5-chloro-N-((1r,4r)-4-((3-(6-(2-hydroxyethoxy)-4-methylpyridin-3-yl)-2-oxo-2,3-dihydro-1H-benzo[d]imidazol-1-yl)methyl)cyclohexyl)-2-(trifluoromethyl)nicotinamide tert-butyl (2-((5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-4-methylpyridin-2-yl)oxy)ethyl) carbonate (15 mg, 0.022 mmol, Step-3 of Example 357) in TFA (1 mL) is stirred for 1 hr at rt. After the reaction mixture is concentrated, the resultant residue is purified by preparative LC-MS to give 8.3 mg (62% yield) of the title compound.

Example 365: 5-chloro-2-(difluoromethyl)-N-((1r,4r)-4-((3-(6-(2-hydroxyethoxy)pyridin-3-yl)-2-oxo-2,3-dihydro-1H-benzo[d]imidazol-1-yl)methyl)cyclohexyl)nicotinamide

[Chem. 103]

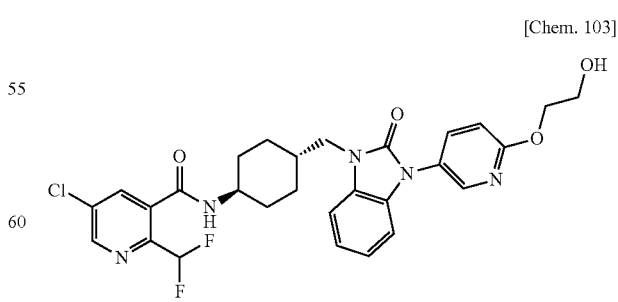

The title compound is prepared in 30% yield (8.7 mg) by the similar manner to Example 69 using Mesylate-4 (20 mg, 0.050 mmol) and Intermediate-24 (18 mg, 0.050 mmol) in place of Mesylate-1 and 1-(6-(2-((tetrahydro-2H-pyran-2-yl)oxy)ethoxy)pyridazin-3-yl)-1H-benzo[d]imidazol-2(3H)-one.

Example 369: 5-chloro-N-((1r,4r)-4-((3-(3-cyanopyrazin-2-yl)-2-oxo-2,3-dihydro-1H-benzo[d]imidazol-1-yl)methyl)cyclohexyl)-2-(difluoromethyl)nicotinamide

[Chem. 104]

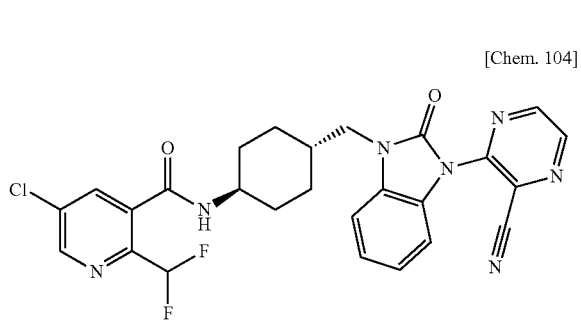 [SMILES: N#Cc1nccnc1-n1c(=O)n(C[C@H]2CC[C@H](NC(=O)c3cc(Cl)cnc3C(F)F)CC2)c2ccccc21]

A mixture of 5-chloro-2-(difluoromethyl)-N-((1r,4r)-4-((2-oxo-2,3-dihydro-1H-benzo[d]imidazol-1-yl)methyl)cyclohexyl)nicotinamide (25 mg, 0.057 mmol, Intermediate-165), 3-chloropyrazine-2-carbonitrile (12 mg, 0.086 mmol), and $Cs_2CO_3$ (56 mg, 0.17 mmol) in DMSO (0.5 mL) is stirred at rt for 3 hrs. The mixture is diluted with water and extracted with EtOAc. The organic layer is dried over sodium sulfate, filtered and concentrated. The residue is purified by preparative SFC-MS to give 2.6 mg (8% yield) of the title compound.

Example 385: 5-chloro-2-(difluoromethyl)-N-((1r,4r)-4-((3-(1-(2-hydroxyethyl)-1H-benzo[d][1,2,3]triazol-5-yl)-2-oxo-2,3-dihydro-1H-benzo[d]imidazol-1-yl)methyl)cyclohexyl)nicotinamide

[Chem. 105]

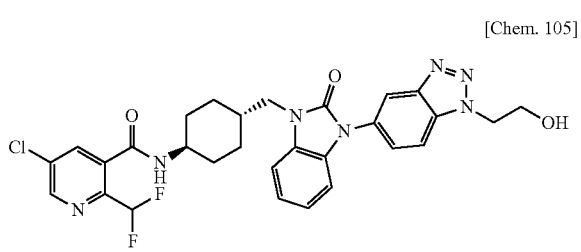 [SMILES: O=C(N[C@H]1CC[C@H](Cn2c(=O)n(-c3ccc4c(c3)nnn4CCO)c3ccccc32)CC1)c1cc(Cl)cnc1C(F)F]

A mixture of 5-chloro-2-(difluoromethyl)-N-((1r,4r)-4-((2-oxo-2,3-dihydro-1H-benzo[d]imidazol-1-yl)methyl)cyclohexyl)nicotinamide (15 mg, 0.034 mmol, Intermediate-165), 5-bromo-1-(2-((tert-butyldimethylsilyl)oxy)ethyl)-1H-benzo[d][1,2,3]triazole (15 mg, 0.041 mmol, Step-1 of Example 276), $N^1,N^2$-dimethylethane-1,2-diamine (0.020 mL, 0.190 mmol), $Cs_2CO_3$ (45 mg, 0.138 mmol) and CuI (16 mg, 0.086 mmol) in DMA (1.5 mL) is stirred at 100° C. for 15 hrs. The mixture is poured into 28% aqueous ammonia solution (3 mL), extracted with EtOAc. The organic layer is washed with water, dried over sodium sulfate, filtered and concentrated. The residue is purified by a strong anion exchange cartridge (ISOLUTE (registered trademark) SCX-2, 1 g/6 mL, Biotage) to remove impurity and then purified by preparative LC-MS to give 4.0 mg (19.47% yield) of the title compound.

Representative Procedure for Method V

The following preparation of Example 408 represents the Method V.

Example 408: 5-chloro-2-methyl-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide

[Chem. 106]

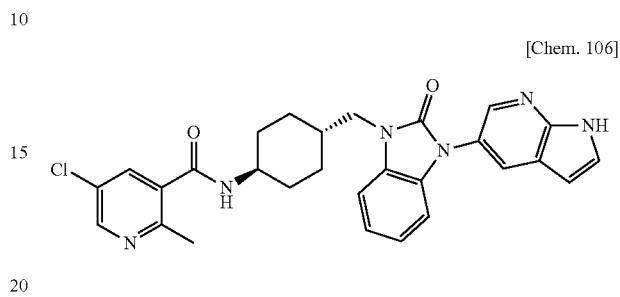

<Step-1>: 5-chloro-2-methyl-N-((1r,4r)-4-((2-oxo-3-(1-((2-(trimethylsilyl)ethoxy)methyl)-1H-pyrrolo[2,3-b]pyridin-5-yl)-2,3-dihydro-1H-benzo[d]imidazol-1-yl)methyl)cyclohexyl)nicotinamide The title compound is prepared in 64% yield (24 mg) by the similar manner to Step-3 of Intermediate-3 using 1-(1-((2-(trimethylsilyl)ethoxy)methyl)-1H-pyrrolo[2,3-b]pyridin-5-yl)-1H-benzo[d]imidazol-2(3H)-one (21 mg, 0.055 mmol, Intermediate-185) in place of methyl 2-((2-oxo-2,3-dihydro-1H-benzo[d]imidazol-1-yl)methyl)benzoate.

MS (ESI) m/z: 645.1 (M+H)$^+$.

<Step-2>: 5-chloro-2-methyl-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide To a solution of 5-chloro-2-methyl-N-((1r,4r)-4-((2-oxo-3-(1-((2-(trimethylsilyl)ethoxy)methyl)-1H-pyrrolo[2,3-b]pyridin-5-yl)-2,3-dihydro-1H-benzo[d]imidazol-1-yl)methyl)cyclohexyl)nicotinamide (24 mg, 0.047 mmol, Step-1 of Example 408) in dichloromethane (0.5 mL) is added TFA (1.5 mL). The mixture is stirred at room temperature for 3 hrs. The mixture is concentrated. The residue in 28% aqueous ammonia solution (0.5 mL) and 2 M ammonia in methanol (1.5 mL) is stirred at room temperature overnight. The mixture is concentrated. The residue is purified by a strong anion exchange cartridge (ISOLUTE (registered trademark) SCX-2, 1 g/6 mL, Biotage) and then purified by preparative LC-MS to give 3 mg (11% yield) of the title compound.

Example 412: 5-chloro-N-((1r,4r)-4-((3-(6-((2-hydroxyethyl)thio)pyridin-3-yl)-2-oxo-2,3-dihydro-1H-benzo[d]imidazol-1-yl)methyl)cyclohexyl)-2-methylnicotinamide

[Chem. 107]

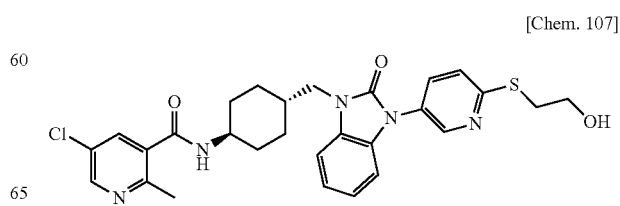

A mixture of Intermediate-54 (53 mg, 0.11 mmol), 2-mercaptoethanol (25 mg, 0.32 mmol) and Cs$_2$CO$_3$ (105 mg, 0.32 mmol) in DMSO (1 mL) is stirred at 50° C. for 2 hrs. To the mixture is added water, extracted with EtOAc and passed through sodium sulfate/amino-functional silica gel. The solvent is removed under vacuum, the crude product is purified by preparative SFC-MS to give 6.7 mg (11% yield) of the title compound.

Representative Procedure for Method W

The following preparation of Example 432 represents the Method W.

Example 432: 5-chloro-2-(difluoromethyl)-N-((1r,4r)-4-((3-(6-(2-fluoroethoxy)pyridin-3-yl)-2-oxo-2,3-dihydro-1H-benzo[d]imidazol-1-yl)methyl)cyclohexyl)nicotinamide

[Chem. 108]

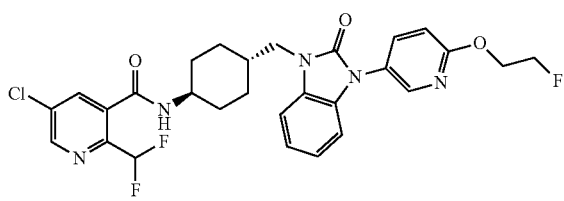

To a mixture of Intermediate-191 (15 mg, 0.028 mmol), 2-fluoroethanol (5.4 mg, 0.085 mmol) in DMF (1 mL) is added potassium tert-butoxide (9.5 mg, 0.085 mmol) and stirred at rt overnight. To the mixture is added water, extracted with EtOAc and passed through sodium sulfate/amino-functional silica gel. The solvent is removed under vacuum, the crude product is purified by preparative SFC-MS to give 9.9 mg (61% yield) of the title compound.

Example 438: 5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-methylnicotinamide

[Chem. 109]

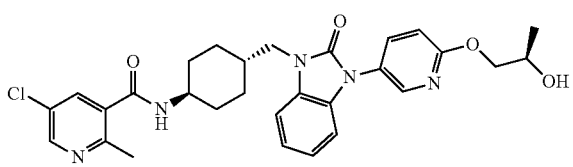

<Step-1>: (R)-1-(6-(2-(methoxymethoxy)propoxy)pyridin-3-yl)-1H-benzo[d]imidazol-2(3H)-one The title compound is prepared in 57% yield (43 mg) by the similar manner to Intermediate-183 using (R)-2-(methoxymethoxy)propan-1-ol (52 mg, 0.44 mmol) in place of 2-methoxyethanol.
MS (ESI) m/z: 329.9 (M+H)$^+$.

<Step-2>: 5-chloro-N-((1R,4r)-4-((3-(6-((R)-2-(methoxymethoxy)propoxy)pyridin-3-yl)-2-oxo-2,3-dihydro-1H-benzo[d]imidazol-1-yl)methyl)cyclohexyl)-2-methylnicotinamide The title compound is prepared in quantitative yield (23 mg) by the similar manner to Step-3 of Intermediate-3 using (R)-1-(6-(2-(methoxymethoxy)propoxy)pyridin-3-yl)-1H-benzo[d]imidazol-2(3H)-one (14 mg, 0.042 mmol, Step-1 of Example 438) in place of methyl 2-((2-oxo-2,3-dihydro-1H-benzo[d]imidazol-1-yl)methyl)benzoate.
MS (ESI) m/z: 594.1 (M+H)$^+$.

<Step-3>: 5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-methylnicotinamide A mixture of 5-chloro-N-((1R,4r)-4-((3-(6-((R)-2-(methoxymethoxy)propoxy)pyridin-3-yl)-2-oxo-2,3-dihydro-1H-benzo[d]imidazol-1-yl)methyl)cyclohexyl)-2-methylnicotinamide (23 mg, 0.042 mmol, Step-2 of Example 438) and TFA (1 mL) is stirred at room temperature for 2 hrs. The mixture is concentrated. The residue is purified by a strong anion exchange cartridge (ISOLUTE (registered trademark) SCX-2, 1 g/6 mL, Biotage) and then purified by preparative SFC-MS to give 3.4 mg (32% yield) of the title compound.

Example 439: 5-chloro-2-(difluoromethyl)-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)nicotinamide

[Chem. 110]

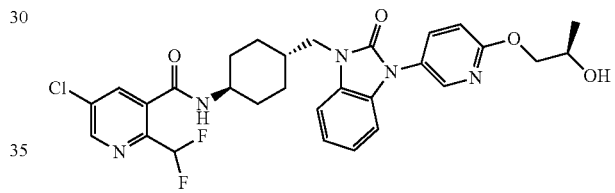

The title compound is prepared in 30% yield in 2 steps by the similar manner to Step-2 and Step-3 of Example 438 using Mesylate-4 in place of Mesylate-1.

Example 440: 5-chloro-2-(difluoromethyl)-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)nicotinamide

[Chem. 111]

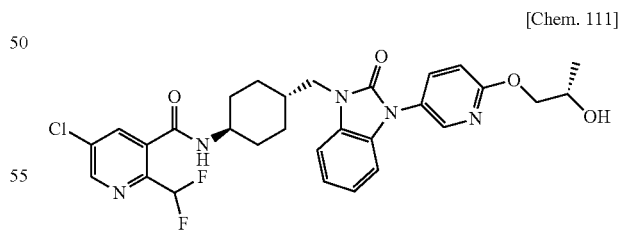

<Step-1>: (S)-1-(6-(2-(methoxymethoxy)propoxy)pyridin-3-yl)-1H-benzo[d]imidazol-2(3H)-one The title compound is prepared in 63% yield (45 mg) by the similar manner to Intermediate-183 using (S)-2-(methoxymethoxy)propan-1-ol (52 mg, 0.44 mmol) in place of 2-methoxyethanol.
MS (ESI) m/z: 330.0 (M+H)$^+$.

<Step-2>: 5-chloro-2-(difluoromethyl)-N-((1S,4r)-4-((3-(6-((S)-2-(methoxymethoxy)propoxy)pyridin-3-yl)-2-oxo-2,3-dihydro-1H-benzo[d]imidazol-1-yl)methyl)cyclohexyl)nicotinamide The title compound is prepared in 41% yield (10 mg) by the similar manner to Step-3 of Intermediate-3 using (S)-1-(6-(2-(methoxymethoxy)propoxy)pyridin-3-yl)-1H-benzo[d]imidazol-2(3H)-one (14 mg, 0.042 mmol, Step-1 of Example 440) and Mesylate-4 (17 mg, 0.042 mmol) in place of methyl 2-((2-oxo-2,3-dihydro-1H-benzo[d]imidazol-1-yl)methyl)benzoate and Mesylate-1.
MS (ESI) m/z: 694.1 (M+H)+.

<Step-3>:5-chloro-2-(difluoromethyl)-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)nicotinamide The title compound is prepared in 55% yield (5.3 mg) by the similar manner to Step-3 of Example 438 using 5-chloro-2-(difluoromethyl)-N-((1S,4r)-4-((3-(6-((S)-2-(methoxymethoxy)propoxy)pyridin-3-yl)-2-oxo-2,3-dihydro-1H-benzo[d]imidazol-1-yl)methyl)cyclohexyl)nicotinamide (10 mg, 0.016 mmol, Step-2 of Example 440) in place of 5-chloro-N-((1R,4r)-4-((3-(6-((R)-2-(methoxymethoxy)propoxy)pyridin-3-yl)-2-oxo-2, 3-dihydro-1H-benzo[d]imidazol-1-yl)methyl)cyclohexyl)-2-methylnicotinamide.

Example 441: 5-chloro-2-methyl-N-((1r,4r)-4-((3-(6-(((1-methyl-1H-pyrazol-4-yl)methyl)amino)pyridin-3-yl)-2-oxo-2,3-dihydro-1H-benzo[d]imidazol-1-yl)methyl)cyclohexyl)nicotinamide

[Chem. 112]

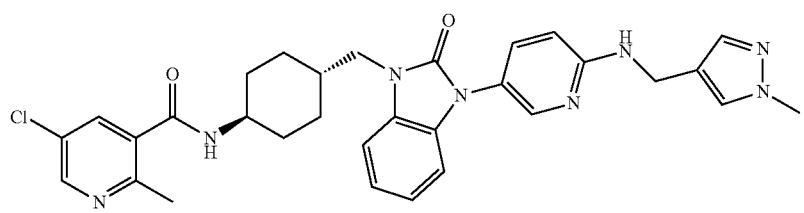

A mixture of N((1r,4r)-4-((3-(6-aminopyridin-3-yl)-2-oxo-2,3-dihydro-1H-benzo[d]imidazol-1-yl)methyl)cyclohexyl)-5-chloro-2-methylnicotinamide (22 mg, 0.045 mmol, Example 143), 1-methyl-1H-pyrazole-4-carbaldehyde (4.93 mg, 0.045 mmol) and acetic acid (0.003 mL, 0.045 mmol) in DCM (5 mL) is stirred at 40° C. for 3 hrs. After cooling to rt, sodium triacetoxy borohydride (18.99 mg, 0.09 mmol) is added. The resulting mixture is stirred at rt for 2 hrs. Then, the mixture is poured onto water, and the aqueous layer is extracted with EtOAc. The combined organic layer is dried over MgSO4 and concentrated in vacuo to give crude product. The residue is purified by a strong anion exchange cartridge (ISOLUTE (registered trademark) SCX-2, 1 g/6 mL, Biotage) and then purified by preparative SFC-MS to give 5.3 mg (20% yield) of the title compound.

Example 466: 5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide

[Chem. 113]

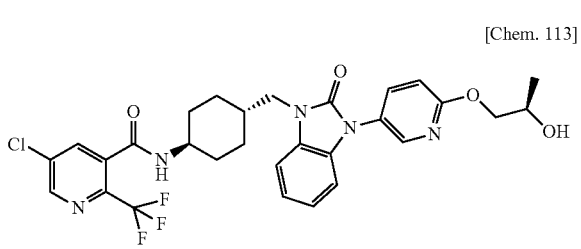 [SMILES: C[C@@H](O)COc1ccc(-n2c(=O)n(C[C@H]3CC[C@H](NC(=O)c4cc(Cl)cnc4C(F)(F)F)CC3)c3ccccc32)cn1]

The title compound is prepared in 29% yield in 2 steps by the similar manner to Step-2 and Step-3 of Example 438 using Mesylate-3 in place of Mesylate-1.

Example 467: 5-chloro-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide

[Chem. 114]

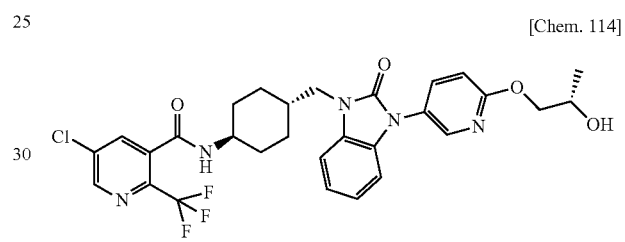

The title compound is prepared in 23% yield in 2 steps by the similar manner to Step-2 and Step-3 of Example 440 using Mesylate-3 in place of Mesylate-4.

Example 479: 5-chloro-2-methyl-N-((1r,4r)-4-((2-oxo-3-(6-propionamidopyridin-3-yl)-2,3-dihydro-1H-benzo[d]imidazol-1-yl)methyl)cyclohexyl)nicotinamide

[Chem. 115]

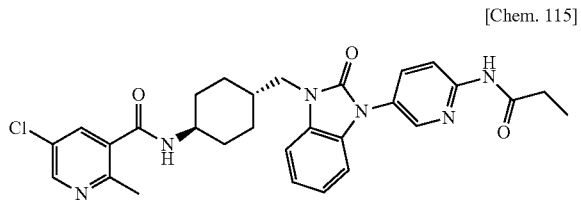 [SMILES: CCC(=O)Nc1ccc(-n2c(=O)n(C[C@H]3CC[C@H](NC(=O)c4cc(Cl)cnc4C)CC3)c3ccccc32)cn1]

To a mixture of Ex 143 (20 mg, 0.041 mmol) and DIEA (15.8 mg, 0.12 mmol) in DCM (1 mL) is added propionyl chloride (7.5 mg, 0.081 mmol) and stirred at rt for 1 hr. The solvent is removed under vacuum, the crude product is purified by a strong anion exchange cartridge (ISOLUTE (registered trademark) SCX-2, 1 g/6 mL, Biotage) and then purified by preparative LC-MS to give 2.5 mg (11% yield) of the title compound.

Example 487: 5-chloro-2-methyl-N-((1r,4r)-4-((3-(5-(methylamino)pyridin-3-yl)-2-oxo-2,3-dihydro-1H-benzo[d]imidazol-1-yl)methyl)cyclohexyl)nicotinamide

[Chem. 116]

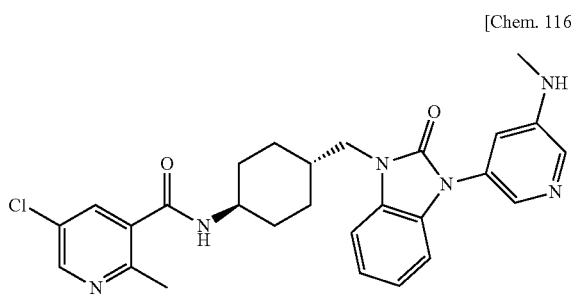 [SMILES: CNc1cncc(-n2c(=O)n(C[C@H]3CC[C@H](NC(=O)c4cc(Cl)cnc4C)CC3)c3ccccc32)c1]

A mixture of 5-chloro-2-methyl-N-((1r,4r)-4-((2-oxo-2,3-dihydro-1H-benzo[d]imidazol-1-yl)methyl)cyclohexyl) nicotinamide (15 mg, 0.038 mmol, Step-2 of Example 9), tert-butyl (5-bromopyridin-3-yl)(methyl)carbamate (11 mg, 0.038 mmol), $N^1,N^2$ dimethylethane-1,2-diamine (0.022 mL, 0.207 mmol), $Cs_2CO_3$ (49 mg, 0.150 mmol) and CuI (18 mg, 0.094 mmol) in DMA (1.5 mL) is stirred at 110° C. for 3.5 hrs. The mixture is poured into 28% aqueous ammonia solution (3 mL), extracted with EtOAc. The organic layer is washed with water, dried over sodium sulfate, filtered and concentrated. The residue is purified by a strong anion exchange cartridge (ISOLUTE (registered trademark) SCX-2, 1 g/6 mL, Biotage) to give 22 mg of tert-butyl (5-(3-(((1r,4r)-4-(5-chloro-2-methylnicotinamido)cyclohexyl)methyl)-2-oxo-2,3-dihydro-1H-benzo[d]imidazol-1-yl)pyridin-3-yl)(methyl)carbamate.

This is dissolved in DCM (1 mL). To the mixture is added TFA (1 mL) and the mixture is stirred at rt for 0.5 hrs. The mixture is concentrated. The residue is purified by a strong anion exchange cartridge (ISOLUTE (registered trademark) SCX-2, 1 g/6 mL, Biotage) and then purified by preparative LC-MS to give 9.8 mg (52% yield) of the title compound.

MS (ESI) m/z: 505.1 (M+H)⁺.

Representative Procedure for Method X

The following preparation of Example 489 represents the Method X.

Example 489: 5-chloro-2-methyl-N-((1r,4r)-4-((3-(5-(oxazol-5-yl)pyridin-2-yl)-2-oxo-2,3-dihydro-1H-benzo[d]imidazol-1-yl)methyl)cyclohexyl)nicotinamide

[Chem. 117]

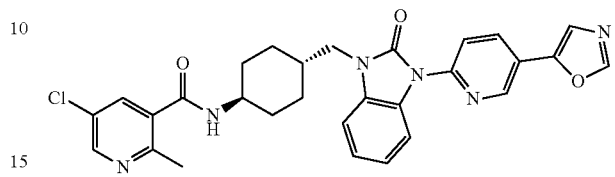

A mixture of 5-chloro-2-methyl-N-((1r,4r)-4-((2-oxo-2,3-dihydro-1H-benzo[d]imidazol-1-yl)methyl)cyclohexyl) nicotinamide (15 mg, 0.038 mmol, Step-2 of Example 9), 5-(6-chloropyridin-3-yl)oxazole (7 mg, 0.038 mmol), $Pd_2(dba)_3$ (7 mg, 0.0075 mmol), Xantphos (9 mg, 0.015 mmol) and $Cs_2CO_3$ (25 mg, 0.075 mmol) in 1,4-dioxane (1.5 mL) is stirred at 120° C. for 4.0 hrs. The mixture is stirred at 130° C. for 1.5 hrs. The mixture is concentrated. The residue is purified by a strong anion exchange cartridge (ISOLUTE (registered trademark) SCX-2, 1 g/6 mL, Biotage) and then purified by preparative LC-MS to give 4.2 mg (21% yield) of the title compound.

Representative Procedure for Method Y

The following preparation of Example 498 represents the Method Y.

Example 498: 5-chloro-2-(difluoromethyl)-N-((1r,4r)-4-((2-oxo-3-(6-(2-oxopyrrolidin-1-yl)pyridin-3-yl)-2,3-dihydro-1H-benzo[d]imidazol-1-yl)methyl) cyclohexyl)nicotinamide

[Chem. 118]

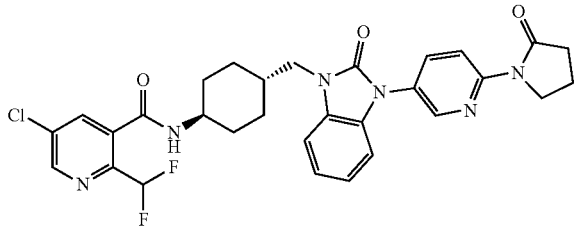

A mixture of Intermediate-209 (20 mg, 0.034 mmol), pyrrolidin-2-one (8.64 mg, 0.102 mmol), CuI (0.65 mg, 0.0034 mmol), DMEDA (0.60 mg, 0.0068 mmol) and $K_2CO_3$ (33.1 mg, 0.10 mmol) in 1,4-dioxane (1 mL) is stirred at 100° C. for 4 hrs. To the mixture is added water and extracted with EtOAc, and passed through sodium sulfate/amino-functional silica gel. The solvent is removed by flowing $N_2$ gas, the crude product is purified by preparative SFC-MS to give 4.0 mg (20% yield) of the title compound.

Example 500: 5-chloro-2-(difluoromethyl)-N-((1r,4r)-4-((3-(6-(2-(methylamino)-2-oxoethoxy)pyridin-3-yl)-2-oxo-2,3-dihydro-1H-benzo[d]imidazol-1-yl)methyl)cyclohexyl)nicotinamide

[Chem. 119]

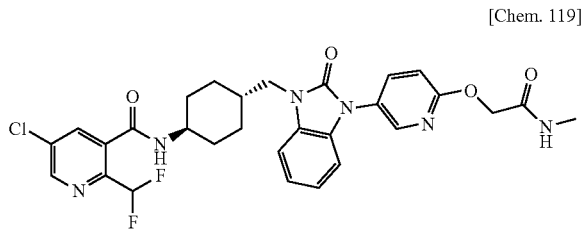 [SMILES: CNC(=O)COc1ccc(-n2c(=O)n(C[C@H]3CC[C@H](NC(=O)c4cc(Cl)cnc4C(F)F)CC3)c3ccccc32)cn1]

<Step-1>: ethyl 2-((5-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-2-yl)oxy)acetate A solution of Intermediate-191 (50 mg, 0.094 mmol), ethyl 2-hydroxyacetate (30 mg 0.28 mmol) and potassium tert-butoxide (32 mg, 0.28 mmol) in THF (2 mL) is stirred at rt for 2 hrs. The solvent is removed by flowing $N_2$ gas, the title compound is obtained as a crude solid. The title compound is used next step without further purification.

$^1$H-NMR (400 MHz, CDCl$_3$) delta 8.62 (1H, d, J=2.3 Hz), 8.27 (1H, d, J=2.3 Hz), 7.89 (1H, d, J=2.3 Hz), 7.78 (1H, dd, J=8.9, 2.5 Hz), 7.17 (1H, td, J=7.5, 1.1 Hz), 7.11-6.99 (4H, m), 6.89 (1H, t, J=54.4 Hz), 6.29 (1H, d, J=8.2 Hz), 4.93 (2H, s), 4.25 (2H, q, J=7.2 Hz), 4.00-3.86 (1H, m), 3.79 (2H, d, J=6.9 Hz), 2.12 (2H, brd, J=10.1 Hz), 2.01-1.78 (3H, m), 1.37-1.14 (7H, m).
MS (ESI) m/z: 614.0 (M+H)$^+$.

<Step-2>: 2-((5-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-2-yl)oxy)acetic acid To a mixture of ethyl 2-((5-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-2-yl)oxy)acetate (Step-1 of Ex 500) in MeOH (2 mL) is added 2 M aqueous sodium hydroxide solution (1 mL) and stirred at rt for 2 hrs. To the mixture is added 2 M hydrochloric acid (1 mL), the solid is precipitated. The precipitated solid is collected, the title compound is prepared in 80% yield (44 mg, solid, total: 2 steps).

$^1$H-NMR (400 MHz, DMSO-d$_6$) delta 8.83 (1H, d, J=2.7 Hz), 8.67 (1H, d, J=7.8 Hz), 8.33 (1H, d, J=2.7 Hz), 8.16 (1H, d, J=2.3 Hz), 7.95 (1H, dd, J=8.7, 2.7 Hz), 7.34 (1H, d, J=7.8 Hz), 7.21-6.91 (5H, m), 4.90 (2H, s), 3.78 (2H, d, J=6.9 Hz), 3.7-3.64 (1H, m), 2.01-1.87 (2H, m), 1.87-1.67 (3H, m), 1.31-1.13 (4H, m).
MS (ESI) m/z: 585.9 (M+H)$^+$.

<Step-3>: 5-chloro-2-(difluoromethyl)-N-((1r,4r)-4-((3-(6-(2-(methylamino)-2-oxoethoxy)pyridin-3-yl)-2-oxo-2,3-dihydro-1H-benzo[d]imidazol-1-yl)methyl)cyclohexyl)nicotinamide A mixture of 2-((5-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-2-yl)oxy)acetic acid (12 mg, 0.020 mmol, Step-2 of Ex 500), methanamine hydrochloride (4.2 mg, 0.061 mmol), HBTU (12 mg, 0.033 mmol) and DIEA (7.9 mg, 0.061 mmol) in DMF (1 mL) is stirred at rt overnight. To the mixture is added saturated aqueous sodium bicarbonate, extracted with EtOAc and passed through sodium sulfate. The solvent is removed by flowing $N_2$ gas, the crude product is purified by preparative SFC-MS to give 6.5 mg (53% yield) of the title compound.

Example 552: 5-chloro-N-((1r,4r)-4-((3-(5-fluoro-6-(methylamino)pyridin-3-yl)-2-oxo-2,3-dihydro-1H-benzo[d]imidazol-1-yl)methyl)cyclohexyl)-2-methylnicotinamide

[Chem. 120]

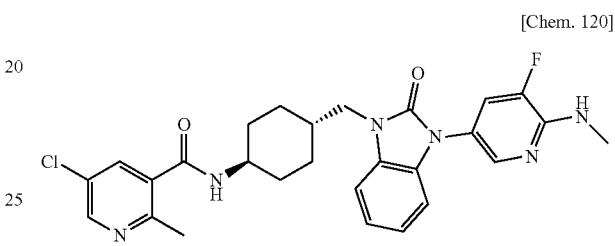

A mixture of 5-chloro-2-methyl-N-((1r,4r)-4-((2-oxo-2,3-dihydro-1H-benzo[d]imidazol-1-yl)methyl)cyclohexyl)nicotinamide (25 mg, 0.063 mmol, Step-2 of Example 9), 5-bromo-3-fluoro-N-methylpyridin-2-amine (39 mg, 0.19 mmol), CuI (1.2 mg, 0.0063 mmol), DMEDA (1.1 mg, 0.013 mmol) and K$_2$CO$_3$ (26 mg, 0.19 mmol) in 1,4-dioxane (1 mL) is stirred at 100° C. overnight. The mixture is added water and 25% aqueous ammonia solution, extracted with EtOAc and passed through sodium sulfate/amino-functional silica gel. The solvent is removed by flowing $N_2$ gas, the crude product is purified by preparative SFC-MS to give 24 mg (73% yield) of the title compound.

Example 553: 5-chloro-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)-2-methylnicotinamide

[Chem. 121]

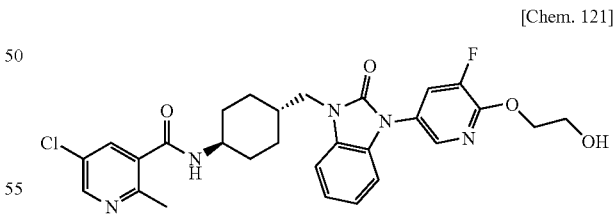

<Step-1>: 5-bromo-3-fluoro-2-(2-((tetrahydro-2H-pyran-2-yl)oxy)ethoxy)pyridine

A mixture of 5-bromo-2,3-difluoropyridine (200 mg, 1.03 mmol), 2-((tetrahydro-2H-pyran-2-yl)oxy)ethanol (166 mg, 1.13 mmol) and Cs$_2$CO$_3$ (504 mg, 1.55 mmol) in DMF (2 mL) is stirred at rt overnight. To the mixture is added saturated aqueous ammonium chloride, extracted with EtOAc/n-hexane=4/1 and passed through sodium sulfate.

The solvent is removed under vacuum, the crude product is purified by column chromatography on silica-gel eluting with 0-20% EtOAc in n-hexane, the title compound is prepared in 82% yield (270 mg, oil).

$^1$H-NMR (400 MHz, CDCl$_3$) delta 7.97 (1H, d, J=1.8 Hz), 7.48 (1H, dd, J=9.4, 2.1 Hz), 4.71 (1H, t, J=3.6 Hz), 4.61-4.49 (2H, m), 4.13-4.02 (1H, m), 3.94-3.77 (2H, m), 3.57-3.47 (1H, m), 1.89-1.67 (2H, m), 1.67-1.44 (4H, m).

MS (ESI) m/z: 319.8 (M+H)$^+$.

<Step-2>: 5-chloro-N-((1r,4r)-4-((3-(5-fluoro-6-(2-((tetrahydro-2H-pyran-2-yl)oxy)ethoxy)pyridin-3-yl)-2-oxo-2,3-dihydro-1H-benzo[d]imidazol-1-yl)methyl)cyclohexyl)-2-methylnicotinamide A mixture of 5-chloro-2-methyl-N-((1r,4r)-4-((2-oxo-2,3-dihydro-1H-benzo[d]imidazol-1-yl)methyl)cyclohexyl)nicotinamide (25 mg, 0.063 mmol, Step-2 of Example 9), 5-bromo-3-fluoro-2-(2-((tetrahydro-2H-pyran-2-yl)oxy)ethoxy)pyridine (30 mg, 0.094 mmol, Step-1 of Ex 553), CuI (1.2 mg, 0.0063 mmol), DMEDA (1.1 mg, 0.013 mmol) and K$_2$CO$_3$ (26 mg, 0.19 mmol) in 1,4-dioxane (1 mL) is stirred at 100° C. overnight. To the mixture is added water and 25% aqueous ammonia solution, extracted with EtOAc and passed through sodium sulfate/amino-functional silica gel. The solvent is removed by flowing N$_2$ gas, the title compound is prepared as a crude product (38 mg, solid). The product is used next step without further purification.

MS (ESI) m/z: 638.0 (M+H)$^+$.

<Step-3>: 5-chloro-N-((1r,4r)-4-((3-(5-fluoro-6-(2-hydroxyethoxy)pyridin-3-yl)-2-oxo-2,3-dihydro-1H-benzol[d]imidazol-1-yl)methyl)cyclohexyl)-2-methylnicotinamide To the mixture of 5-chloro-N-((1r,4r)-4-((3-(5-fluoro-6-(2-((tetrahydro-2H-pyran-2-yl)oxy)ethoxy)pyridin-3-yl)-2-oxo-2,3-dihydro-1H-benzo[d]imidazol-1-yl)methyl)cyclohexyl)-2-methylnicotinamide (38 mg, crude, Step-2 of Ex 553) in DCM (1 mL) is added TFA (1 mL) and stirred at rt for 1 hr. The solvent is removed by flowing N$_2$ gas, the crude product is purified by a strong anion exchange cartridge (ISOLUTE (registered trademark) SCX-2, 1 g/6 mL, Biotage) and then purified by preparative SFC-MS to give 25 mg (72% yield, total: 2 steps) of the title compound.

Example 563: 5-chloro-2-(difluoromethyl)-N-((1r,4r)-4-((3-(5-(2-hydroxyethoxy)pyrazin-2-yl)-2-oxo-2,3-dihydro-1H-benzo[d]imidazol-1-yl)methyl)cyclohexyl)nicotinamide

[Chem. 122]

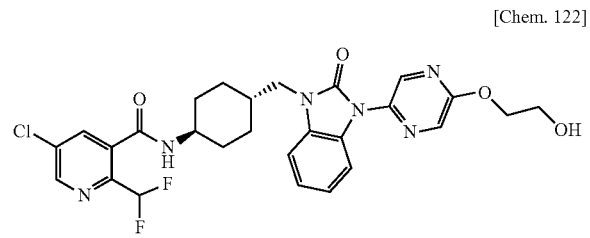 [SMILES: O=C(N[C@H]1CC[C@H](Cn2c(=O)n(-c3cnc(OCCO)cn3)c3ccccc32)CC1)c1cc(Cl)cnc1C(F)F]

The title compound is prepared in 33% yield (9.4 mg) by the similar manner to Example 69 using Mesylate-4 (20 mg, 0.050 mmol) and Intermediate-225 (18 mg, 0.050 mmol) in place of Mesylate-1 and 1-(6-(2-((tetrahydro-2H-pyran-2-yl)oxy)ethoxy)pyridazin-3-yl)-1H-benzo[d]imidazol-2(3H)-one.

Example 564: 5-chloro-2-(difluoromethyl)-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)nicotinamide

[Chem. 123]

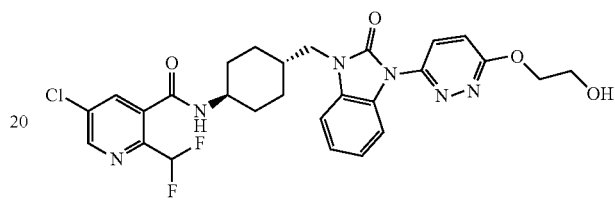

The title compound is prepared in 30% yield (8.6 mg) by the similar manner to Example 69 using Mesylate-4 (20 mg, 0.050 mmol) in place of Mesylate-1.

Example 573: 5-chloro-2-methyl-N-((1r,4r)-4-((3-(2-(methylamino)pyridin-4-yl)-2-oxo-2,3-dihydro-1H-benzo[d]imidazol-1-yl)methyl)cyclohexyl)nicotinamide

[Chem. 124]

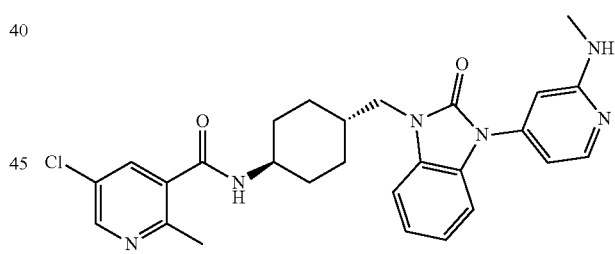

A mixture of 5-chloro-N-((1r,4r)-4-((3-(2-chloropyridin-4-yl)-2-oxo-2,3-dihydro-1H-benzo[d]imidazol-1-yl)methyl)cyclohexyl)-2-methylnicotinamide (17 mg, Step-2 of Intermediate-226), methylamine hydrochloride (25 mg, 0.37 mmol), and DIEA (0.066 mL, 0.37 mmol) in NMP (0.5 mL) is stirred for 140 min at 220° C. under microwave irradiation. The mixture is diluted with saturated aqueous sodium chloride. The mixture is extracted with THF. The resultant residue is purified by a strong anion exchange cartridge (ISOLUTE (registered trademark) SCX-2, 1 g/6 mL, Biotage). The resultant residue is purified by preparative LC-MS to give 1.6 mg (8% yield in 2 steps from Step-2 of Intermediate-226) of the title compound.

Example 574: 5-chloro-2-methyl-N-((1r,4r)-4-((3-(5-(methylamino)pyridin-2-yl)-2-oxo-2,3-dihydro-1H-benzo[d]imidazol-1-yl)methyl)cyclohexyl)nicotinamide

[Chem. 125]

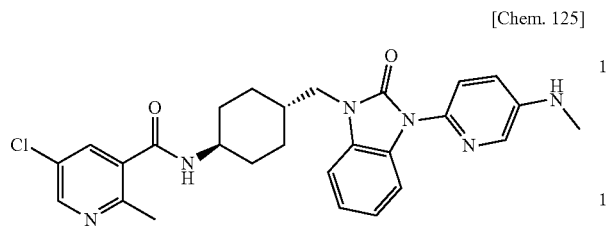

<Step-1>: 5-chloro-2-methyl-N-((1r,4r)-4-((3-(5-nitropyridin-2-yl)-2-oxo-2,3-dihydro-1H-benzo[d]imidazol-1-yl)methyl)cyclohexyl)nicotinamide A mixture of 5-chloro-2-methyl-N-((1r,4r)-4-((2-oxo-2,3-dihydro-1H-benzo[d]imidazol-1-yl)methyl)cyclohexyl)nicotinamide (30 mg, 0.075 mmol, Step-2 of Example 9), 2-fluoro-5-nitropyridine (14 mg, 0.098 mmol), and cesium carbonate (49 mg, 0.15 mmol) in DMSO (1 mL) is stirred for 2 hrs at 100° C. The mixture is diluted with saturated aqueous ammonium chloride. The precipitate is collected and washed with water followed by diisopropyl ether to give 34 mg (86% yield) of the title compound as a pale yellow solid.
MS (ESI) m/z: 521.2 (M+H)$^+$.

<Step-2>: N((1r,4r)-4-((3-(5-aminopyridin-2-yl)-2-oxo-2,3-dihydro-1H-benzo[d]imidazol-1-yl)methyl)cyclohexyl)-5-chloro-2-methylnicotinamide A mixture of 5-chloro-2-methyl-N-((1r,4r)-4-((3-(5-nitropyridin-2-yl)-2-oxo-2,3-dihydro-1H-benzo[d]imidazol-1-yl)methyl)cyclohexyl)nicotinamide (34 mg, 0.064 mmol, Step-1 of Example 574), tin(II) chloride (110 mg, 0.58 mmol) in MeOH (1 mL) is stirred for 2 days at rt. The mixture is purified by column chromatography on amino-functional silica gel eluting with 100% MeOH to give 37 mg of the title compound as a crude. The compound is used for the next reaction without further purification.
MS (ESI) m/z: 491.1 (M+H)$^+$.

<Step-3>: 5-chloro-2-methyl-N-((1r,4r)-4-((3-(5-(methylamino)pyridin-2-yl)-2-oxo-2,3-dihydro-1H-benzo[d]imidazol-1-yl)methyl)cyclohexyl)nicotinamide A mixture of N((1r,4r)-4-((3-(5-aminopyridin-2-yl)-2-oxo-2,3-dihydro-1H-benzo[d]imidazol-1-yl)methyl)cyclohexyl)-5-chloro-2-methylnicotinamide (19 mg, Step-2 of Example 574) and TFA (0.002 mL, 0.003 mmol) in triethyl orthoformate (0.5 mL) is stirred for 6 hrs at 140° C. After the mixture is concentrated, EtOH (1 mL) and sodium borohydride (7.3 mg, 0.19 mmol) are added to the resultant residue. The reaction mixture is stirred for 2 days at rt. After the mixture is concentrated, the resultant residue is purified by a strong anion exchange cartridge (ISOLUTE (registered trademark) SCX-2, 1 g/6 mL, Biotage). The resultant residue is purified by preparative LC-MS to give 4.0 mg (25% yield in 2 steps) of the title compound.

Example 575: 5-chloro-2-(difluoromethyl)-N-((1r,4r)-4-((3-(3-methyl-1H-indazol-6-yl)-2-oxo-2,3-dihydro-1H-imidazo[4,5-b]pyridin-1-yl)methyl)cyclohexyl)nicotinamide

[Chem. 126]

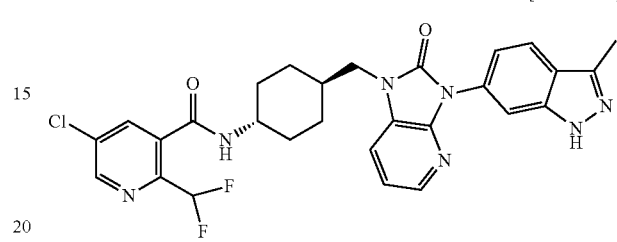

A solution of 5-chloro-2-(difluoromethyl)-N-((1r,4r)-4-((2-oxo-2,3-dihydro-1H-imidazo[4,5-b]pyridin-1-yl)methyl)cyclohexyl)nicotinamide (20 mg, 0.046 mmol, Intermediate-214), 3-methyl-1-(tetrahydro-2H-pyran-2-yl)-6-(4,4,5,5-tetramethyl-1,3,2-dioxaborolan-2-yl)-1H-indazole (16 mg, 0.046 mmol, Intermediate-227), copper(II) acetate (20 mg, 0.11 mmol) and TEA (0.019 mL, 0.14 mmol) in DMA (1 mL) is stirred at 100° C. overnight. The mixture is filtered through a pad of celite. The filtrate is diluted with water, extracted with EtOAc. The organic phase is dried over sodium sulfate, filtered through short column of amino-functional silica gel, concentrated. To the residue in dichloromethane (0.5 mL) is added TFA (1.5 mL). The mixture is stirred at room temperature for 3 hrs. The mixture is concentrated. The residue is purified by a strong anion exchange cartridge (ISOLUTE (registered trademark) SCX-2, 1 g/6 mL, Biotage), concentrated. The residue is purified by preparative LC-MS to give 7.8 mg (26% yield) of the title compound.
MS (ESI) m/z: 566.0 (M+H)$^+$.

Example 581: N-((1r,4r)-4-((3-(4-(1H-pyrazol-4-yl)phenyl)-2-oxo-2,3-dihydro-1H-benzo[d]imidazol-1-yl)methyl)cyclohexyl)-5-chloro-2-methylnicotinamide

[Chem. 127]

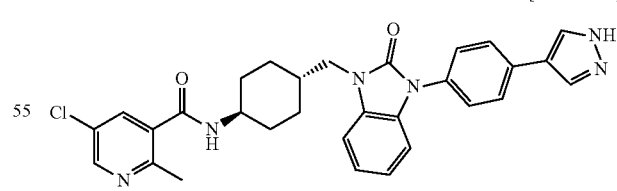

A mixture of 5-chloro-2-methyl-N-((1r,4r)-4-((2-oxo-2,3-dihydro-1H-benzo[d]imidazol-1-yl)methyl)cyclohexyl)nicotinamide (20 mg, 0.050 mmol, Step-2 of Example 9), 4-(4-bromophenyl)-1-((2-(trimethylsilyl)ethoxy)methyl)-1H-pyrazole (18 mg, 0.050 mmol, Intermediate-230), $N^1,N^2$-dimethylethane-1,2-diamine (0.030 mL, 0.28 mmol), cesium carbonate (65 mg, 0.20 mmol) and CuI (24 mg, 0.13 mmol) in DMA (1.5 mL) is stirred at 120° C. overnight. The reaction is quench with 28% aqueous ammonia solution, extracted with EtOAc. The organic layer is washed with water, dried over sodium sulfate, filtered and concentrated. To the residue in DCM (0.5 mL) is added TFA (1 mL) and the mixture is stirred at rt for 2.5 hrs. The mixture is concentrated. The residue is purified by a strong anion exchange cartridge (ISOLUTE (registered trademark) SCX-2, 1 g/6 mL, Biotage) and then purified by preparative LC-MS to give 7.7 mg (28% yield) of the title compound.

MS (ESI) m/z: 541.0 (M+H)$^+$.

Example 588: 5-chloro-N-((1r,4r)-4-((3-(1-(2-(dimethylamino)ethyl)-3-methyl-1H-indazol-5-yl)-2-oxo-2,3-dihydro-1H-benzo[d]imidazol-1-yl)methyl)cyclohexyl)-2-methylnicotinamide

[Chem. 128]

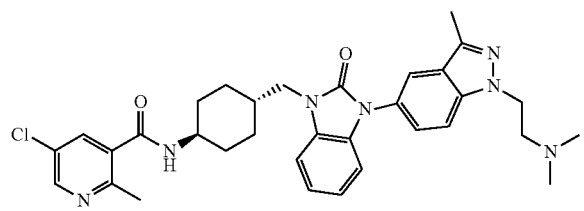

<Step-1>: 2-(5-(3-(((1r,4r)-4-(5-chloro-2-methylnicotinamido)cyclohexyl)methyl)-2-oxo-2,3-dihydro-1H-benzo[d]imidazol-1-yl)-3-methyl-1H-indazol-1-yl)ethyl methanesulfonate To a mixture of Example 230 (226 mg, 0.39 mmol) in DCM (4 mL) is added methanesulfonic anhydride (124 mg, 0.71 mmol) and stirred at rt for 2 hr. The mixture is added water, extracted with DCM and passed through sodium sulfate. The solvent is removed under vacuum, the title compound is prepared in 91% as a crude product (233 mg, solid). The product is used next step without further purification.

MS (ESI) m/z: 651.2 (M+H)$^+$.

<Step-2>: 5-chloro-N-((1r,4r)-4-((3-(1-(2-(dimethylamino)ethyl)-3-methyl-1H-indazol-5-yl)-2-oxo-2,3-dihydro-1H-benzo[d]imidazol-1-yl)methyl)cyclohexyl)-2-methylnicotinamide A mixture of 2-(5-(3-(((1r,4r)-4-(5-chloro-2-methylnicotinamido)cyclohexyl)methyl)-2-oxo-2,3-dihydro-1H-benzo[d]imidazol-1-yl)-3-methyl-1H-indazol-1-yl)ethyl methanesulfonate (25 mg, 0.038 mmol, Step-1 of Ex 588) and 2 M ammonia in THF (2 mL) is stirred at 80° C. overnight. The solvent is removed by flowing N$_2$ gas, the crude product is purified by preparative LC-MS to give 8.5 mg (37% yield) of the title compound.

Example 589: 5-chloro-2-methyl-N-((1r,4r)-4-((3-(3-methyl-1-(2-morpholinoethyl)-1H-indazol-5-yl)-2-oxo-2,3-dihydro-1H-benzo[d]imidazol-1-yl)methyl)cyclohexyl)nicotinamide

[Chem. 129]

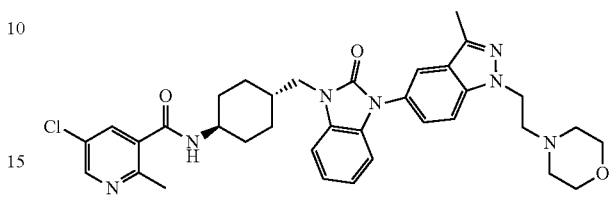

The title compound is prepared in 26% yield (solid) by the similar manner to Step-2 of Example 588 using morpholine in place of dimethylamine.

Example 591: N-((1r,4r)-4-((3-(3-aminobenzo[d]isoxazol-5-yl)-2-oxo-2,3-dihydro-1H-benzo[d]imidazol-1-yl)methyl)cyclohexyl)-5-chloro-2-methylnicotinamide

[Chem. 130]

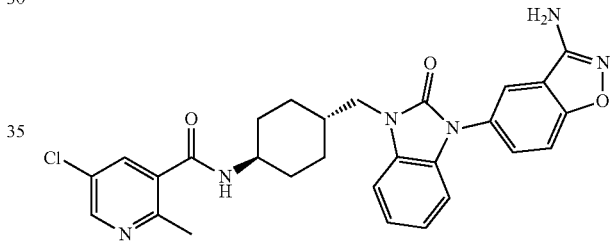

<Step-1>:2-fluoro-5-((2-nitrophenyl)amino)benzonitrile

A mixture of 1-bromo-2-nitrobenzene (163 mg, 0.808 mmol), 5-amino-2-fluorobenzonitrile (110 mg, 0.808 mmol), Pd$_2$(dba)$_3$ (22 mg, 0.024 mmol), Xantphos (28 mg, 0.048 mmol) and cesium carbonate (527 mg, 1.616 mmol) in 1,4-dioxane (6 mL) is stirred at 100° C. for 1.5 hrs. The reaction mixture is poured into water and extracted EtOAc. The organic layer is dried over sodium sulfate, filtered and concentrated. The residue is purified by column chromatography on silica-gel eluting with 0-33% EtOAc in n-hexane to give 170 mg (81% yield) of the title compound as an orange solid.

$^1$H-NMR (400 MHz, CDCl$_3$) delta 9.35 (1H, br s), 8.24 (1H, dd, J=8.6, 1.4 Hz), 7.57-7.42 (3H, m), 7.32-7.21 (1H, m), 7.10 (1H, dd, J=8.6, 1.4 Hz), 6.93-6.86 (1H, m). MS (ESI) m/z: 256.3 (M−H)$^−$.

<Step-2>:5-((2-aminophenyl)amino)-2-fluorobenzonitrile

A solution of 2-fluoro-5-((2-nitrophenyl)amino)benzonitrile (170 mg, 0.661 mmol, Step-1 of Example 591) in MeOH (7 mL) and THF (7 mL) is evacuated and backfilled with N$_2$ gas. To this is added 10% Pd/C (35 mg). The mixture is evacuated and backfilled with $H_2$ gas and stirred at rt under $H_2$ atmosphere. After 1 hr, the reaction mixture is evacuated and backfilled with $N_2$ gas and the mixture is filtered through celite pad. The filtrate is concentrated in vacuo to give 146 mg (97% yield) of the title compound as a brown solid.

$^1$H-NMR (400 MHz, CDCl$_3$) delta 7.12-6.97 (3H, m), 6.92-6.87 (1H, m), 6.85-6.76 (3H, m), 5.26 (1H, br s). A signal due to NH$_2$ is not observed.

MS (ESI) m/z: 228.3 (M+H)$^+$.

<Step-3>:2-fluoro-5-(2-oxo-2,3-dihydro-1H-benzo[d]imidazol-1-yl)benzonitrile

A mixture of 5-((2-aminophenyl)amino)-2-fluorobenzonitrile (146 mg, 0.643 mmol, Step-2 of Example 591), CDI (208 mg, 1.285 mmol) in THF (5 mL) is stirred at rt for 3.5 hrs. The reaction mixture is poured into water and extracted EtOAc. The organic layer is dried over sodium sulfate, filtered and concentrated. The residual solid is suspended with IPE (5 mL). The obtained solid is washed with IPE and EtOAc/n-hexane to give 100 mg (62% yield) of the title compound as a beige solid.

$^1$H-NMR (400 MHz, CDCl$_3$) delta 8.85 (1H, br s), 7.91-7.83 (2H, m), 7.42 (1H, t, J=8.6 Hz), 7.21-7.10 (3H, m), 7.07-7.03 (1H, m). MS (ESI) m/z: 254.3 (M+H)$^+$.

<Step-4>: 5-chloro-N-((1r,4r)-4-((3-(3-cyano-4-fluorophenyl)-2-oxo-2,3-dihydro-1H-benzo[d]imidazol-1-yl)methyl)cyclohexyl)-2-methylnicotinamide A mixture of ((1r,4r)-4-(5-chloro-2-methylnicotinamido)cyclohexyl)methyl methanesulfonate (114 mg, 0.316 mmol, Mesylate-1), 2-fluoro-5-(2-oxo-2,3-dihydro-1H-benzo[d]imidazol-1-yl)benzonitrile (80 mg, 0.316 mmol, Step-3 of Example 591), and cesium carbonate (309 mg, 0.948 mmol) in DMSO (6 mL) is stirred at 80° C. for 15 hrs. The reaction mixture is poured into water and extracted EtOAc. The organic layer is dried over sodium sulfate, filtered and concentrated. The residue is purified by column chromatography on silica-gel eluting with 0-80% EtOAc in n-hexane to give 80 mg (49% yield) of the title compound as colorless oil.

$^1$H-NMR (400 MHz, CDCl$_3$) delta 8.49 (1H, d, J=2.4 Hz), 7.90-7.82 (2H, m), 7.61 (1H, d, J=2.4 Hz), 7.40 (1H, t, J=8.6 Hz), 7.30-7.05 (4H, m), 5.56 (1H, d, J=8.0 Hz), 4.01-3.90 (1H, m), 3.81 (2H, d, J=6.8 Hz), 2.61 (3H, s), 2.21-2.13 (2H, m), 2.02-1.87 (3H, m), 1.41-1.15 (4H, m). MS (ESI) m/z: 518.3 (M+H)$^+$.

<Step-5>: N((1r,4r)-4-((3-(3-aminobenzo[d]isoxazol-5-yl)-2-oxo-2,3-dihydro-1H-benzo[d]imidazo 1-1-yl)methyl)cyclohexyl)-5-chloro-2-methylnicotinamide A mixture of 5-chloro-N-((1r,4r)-4-((3-(3-cyano-4-fluorophenyl)-2-oxo-2,3-dihydro-1H-benzo[d]imidazol-1-yl)methyl)cyclohexyl)-2-methylnicotinamide (50 mg, 0.097 mmol, Step-4 of Example 591), N-hydroxyacetamide (22 mg, 0.290 mmol) and potassium carbonate (80 mg, 0.579 mmol) in DMF/water (5/1, 1.8 mL) is stirred at 80° C. for 2 hrs. The reaction mixture is poured into water and extracted EtOAc. The organic layer is washed with water, dried over sodium sulfate, filtered and concentrated. The residue is purified by preparative LC-MS to give 8.3 mg (16% yield) of the title compound.

Example 594: 6-(3-(((1r,4r)-4-(5-chloro-2-methylnicotinamido)cyclohexyl)methyl)-2-oxo-2,3-dihydro-1H-benzo[d]imidazol-1-yl)-N-(2-hydroxyethyl)benzo[d]isoxazole-3-carboxamide

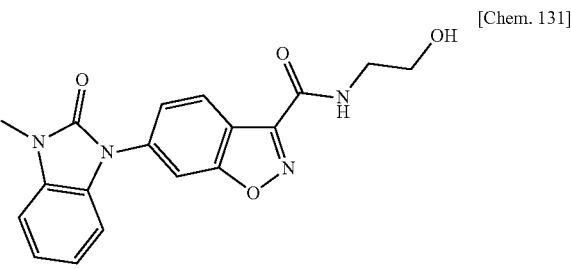

[Chem. 131]

The title compound is prepared in 48% yield (9.8 mg) by the similar manner to Step-3 of Example 243 using 2-aminoethanol (53 mg, 0.872 mmol) in place of ammonia.

Example 595: 5-chloro-N-((1r,4r)-4-((3-(4-cyanopyridazin-3-yl)-2-oxo-2,3-dihydro-1H-benzo[d]imidazol-1-yl)methyl)cyclohexyl)-2-(trifluoromethyl)nicotinamide

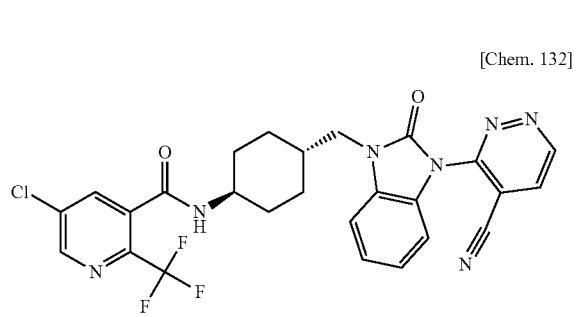 [SMILES: N#Cc1ccnnc1-n1c(=O)n(C[C@H]2CC[C@H](NC(=O)c3cc(Cl)cnc3C(F)(F)F)CC2)c2ccccc21]

[Chem. 132]

The title compound is prepared in 24% yield (7.4 mg) by the similar manner to Example 369 using 3-chloropyridazine-4-carbonitrile (12 mg, 0.083 mmol) and 5-chloro-N-((1r,4r)-4-((2-oxo-2,3-dihydro-1H-benzo[d]imidazol-1-yl)methyl)cyclohex yl)-2-(trifluoromethyl)nicotinamide (25 mg, 0.055 mmol, Intermediate-132) in place of 3-chloropyrazine-2-carbonitrile and Intermediate-165.

Example 604: 5-chloro-2-(difluoromethyl)-N-((1r,4r)-4-((2-oxo-3-(1,2,3,4-tetrahydroisoquinolin-7-yl)-2,3-dihydro-1H-benzo[d]imidazol-1-yl)methyl)cyclohexyl)nicotinamide

[Chem. 133]

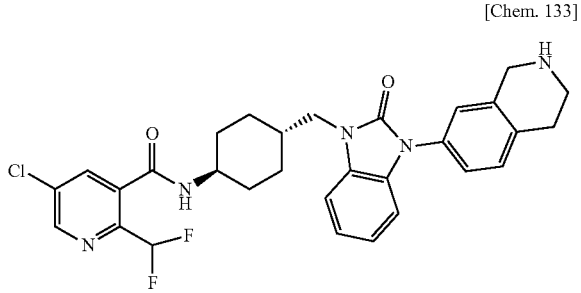 [SMILES: O=C(N[C@H]1CC[C@H](Cn2c(=O)n(-c3ccc4c(c3)CNCC4)c3ccccc32)CC1)c1cc(Cl)cnc1C(F)F]

A mixture of tert-butyl 7-(3-(((1r,4r)-4-(5-chloro-2-(difluoromethyl)nicotinamido)cyclohexyl)methyl)-2-oxo-2,3-dihydro-1H-benzo[d]imidazol-1-yl)-3,4-dihydroisoquinoline-2(1H)-carboxylate (138 mg, 0.21 mmol, Intermediate-235) and 4 M hydrogen chloride in 1,4-dioxane (2 mL) in MeOH (1 mL) is stirred at rt for 1 hr. The mixture is concentrated to give 125 mg (quantitative yield) of the title compound (HCl salt) as a pale yellow solid. This solid (25 mg) is purified by preparative LC-MS to give 2.3 mg (9% yield) of the title compound.

Example 605: N-((1r,4r)-4-((3-(2-acetyl-1,2,3,4-tetrahydroisoquinolin-7-yl)-2-oxo-2,3-dihydro-1H-benzo[d]imidazol-1-yl)methyl)cyclohexyl)-5-chloro-2-(difluoromethyl)nicotinamide

[Chem. 134]

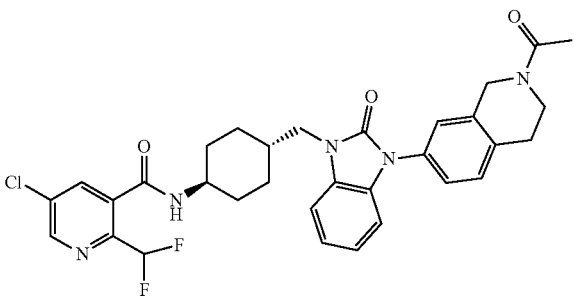

To a mixture of 5-chloro-2-(difluoromethyl)-N-((1r,4r)-4-((2-oxo-3-(1,2,3,4-tetrahydroisoquinolin-7-yl)-2,3-dihydro-1H-benzo[d]imidazol-1-yl)methyl)cyclohexyl)nicotinamide (HCl salt, 30 mg, 0.050 mmol, Example 604) and TEA (0.028 mL, 0.20 mmol) in DCM (1 mL) is added acetyl chloride (8 mg, 0.10 mmol) at 0° C. The mixture is stirred at 0° C. for 30 min. Then, the mixture is quenched with saturated aqueous sodium bicarbonate and extracted with EtOAc. The organic layer is dried over sodium sulfate, filtered and concentrated. The residue is purified by preparative LC-MS to give 8.8 mg (29% yield) of the title compound.

Example 610: 5-chloro-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)-2-methylnicotinamide

[Chem. 135]

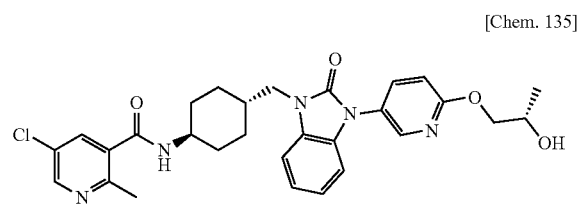 [SMILES: Cc1ncc(Cl)cc1C(=O)N[C@H]1CC[C@H](Cn2c(=O)n(-c3ccc(OC[C@H](C)O)nc3)c3ccccc32)CC1]

The title compound is prepared in 53% yield in 2 steps by the similar manner to Step-2 and Step-3 of Example 440 using Mesylate-1 in place of Mesylate-4.

Example 618: 5-chloro-2-(difluoromethyl)-N-((1r,4r)-4-((3-(6-(2-methoxyacetamido)pyridin-3-yl)-2-oxo-2,3-dihydro-1H-benzo[d]imidazol-1-yl)methyl)cyclohexyl)nicotinamide

[Chem. 136]

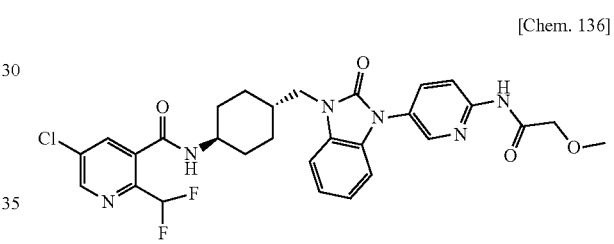

The title compound is prepared in 15% yield (solid) by the similar manner to Ex 498 using 2-methoxyacetamide in place of pyrrolidin-2-one.

Example 633: N-((1r,4r)-4-((3-(4-(1H-1,2,3-triazol-4-yl)phenyl)-2-oxo-2,3-dihydro-1H-benzo[d]imidazol-1-yl)methyl)cyclohexyl)-5-chloro-2-methylnicotinamide

[Chem. 137]

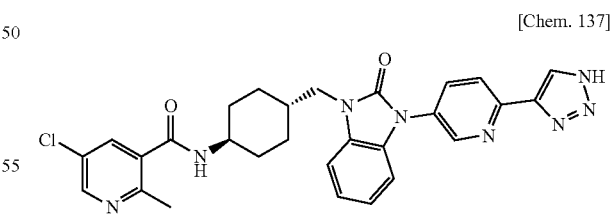

A mixture of 5-chloro-2-methyl-N-((1r,4r)-4-((2-oxo-2,3-dihydro-1H-benzo[d]imidazol-1-yl)methyl)cyclohexyl)nicotinamide (15 mg, 0.038 mmol, Step-2 of Example 9), 4-(4-bromophenyl)-1-((2-(trimethylsilyl)ethoxy)methyl)-1H-1,2,3-triazole (13 mg, 0.038 mmol), $N^1,N^2$-dimethylethane-1,2-diamine (0.022 mL, 0.207 mmol), cesium carbonate (49 mg, 0.150 mmol) and CuI (18 mg, 0.094 mmol) in DMA (1.5 mL) is stirred at 120° C. for 7.5 hrs. The mixture is poured into 28% aqueous ammonia solution (3 mL), extracted with EtOAc. The organic layer is washed with water, dried over sodium sulfate, filtered and concentrated. The residue is purified by a strong anion exchange cartridge (ISOLUTE(registered trademark) SCX-2, 1 g/6 mL, Biotage) to give 17 mg of 5-chloro-2-methyl-N-((1r,4r)-4-((2-oxo-3-(4-(1-((2-(trimethylsilyl)ethoxy)methyl)-1H1,2,3-triazol-4-yl)phenyl)-2,3-dihydro-1H-benzo[d]imidazol-1-yl)methyl)cyclohexyl)nicotinamide.

This is dissolved in DCM (1 mL). To the mixture is added TFA (1 mL) and the mixture is stirred at rt for 2.5 hrs. The mixture is concentrated. The residue is purified by a strong anion exchange cartridge (ISOLUTE (registered trademark) SCX-2, 1 g/6 mL, Biotage) and then purified by preparative LC-MS to give 3.8 mg (19% yield) of the title compound.

Example 638: 5-chloro-2-(difluoromethyl)-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)nicotinamide

[Chem. 138]

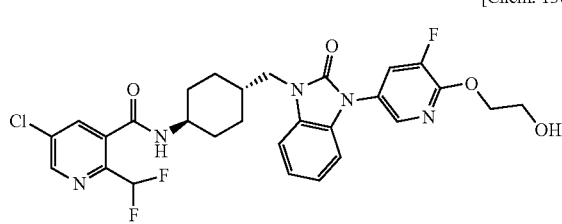

The title compound is prepared in 32% yield (solid, total: 2 steps) by the similar manner to Ex 553 using Intermediate-165 in place of 5-chloro-2-methyl-N-((1r,4r)-4-((2-oxo-2,3-dihydro-1H-benzo[d]imidazol-1-yl)methyl)cyclohexyl)nicotinamide (Step-2 of Example 9).

Example 639: 5-chloro-2-(difluoromethyl)-N-((1r,4r)-4-((3-(5-fluoro-6-(methylamino)pyridin-3-yl)-2-oxo-2,3-dihydro-1H-benzo[d]imidazol-1-yl)methyl)cyclohexyl)nicotinamide

[Chem. 139]

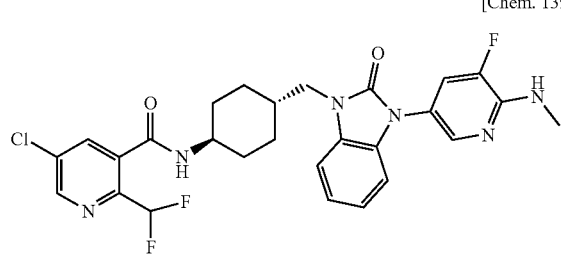

The title compound is prepared in 34% yield (solid) by the similar manner to Ex 552 using Intermediate-165 in place of 5-chloro-2-methyl-N-((1r,4r)-4-((2-oxo-2,3-dihydro-1H-benzo[d]imidazol-1-yl)methyl)cyclohexyl)nicotinamide (Step-2 of Example 9).

Example 646: 5-chloro-2-methyl-N-((1r,4r)-4-((3-(4-(methylamino)phenyl)-2-oxo-2,3-dihydro-1H-benzo[d]imidazol-1-yl)methyl)cyclohexyl)nicotinamide

[Chem. 140]

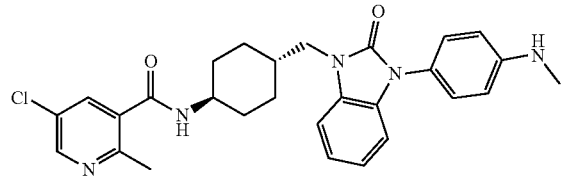

<Step-1>: 5-chloro-2-methyl-N-((1r,4r)-4-((3-(4-nitrophenyl)-2-oxo-2,3-dihydro-1H-benzo[d]imidazol-1-yl)methyl)cyclohexyl)nicotinamide A mixture of 5-chloro-2-methyl-N-((1r,4r)-4-((2-oxo-2,3-dihydro-1H-benzo[d]imidazol-1-yl)methyl)cyclohexyl)nicotinamide (19 mg, 0.047 mmol, Step-2 of Example 9), 1-bromo-4-nitrobenzene (10 mg, 0.047 mmol), $N^1,N^2$-dimethylethane-1,2-diamine (0.028 mL, 0.26 mmol), cesium carbonate (62 mg, 0.19 mmol) and CuI (23 mg, 0.12 mmol) in DMA (1 mL) is stirred overnight at 100° C. The mixture is poured into 28% aqueous ammonia solution, extracted with EtOAc. The organic layer is concentrated. The resultant residue is purified by column chromatography on silica-gel eluting with 24-100% EtOAc in n-hexane to give 12 mg (50% yield) of the title compound as a yellow solid.

$^1$H-NMR (400 MHz, CDCl$_3$) delta 8.49 (1H, d, J=2.3 Hz), 8.41 (2H, d, J=9.1 Hz), 7.84 (2H, d, J=9.1 Hz), 7.61 (1H, d, J=2.3 Hz), 7.26-7.20 (2H, m), 7.18-7.07 (2H, m), 5.55 (1H, d, J=8.2 Hz), 4.05-3.88 (1H, m), 3.83 (2H, d, J=6.9 Hz), 2.61 (3H, s), 2.16 (2H, m), 2.02-1.86 (3H, m), 1.43-1.28 (2H, m), 1.27-1.13 (2H, m).

MS (ESI) m/z: 520.1 (M+H)$^+$.

<Step-2>: N((1r,4r)-4-((3-(4-aminophenyl)-2-oxo-2,3-dihydro-1H-benzo[d]imidazol-1-yl)methyl)cyclohexyl)-5-chloro-2-methylnicotinamide The title compound is prepared as a crude (18 mg) by the similar manner to Step-2 of Example 574 using 5-chloro-2-methyl-N-((1r,4r)-4-((3-(4-nitrophenyl)-2-oxo-2,3-dihydro-1H-benzo[d]imidazol-1-yl)methyl)cyclohexyl)nicotinamide (12 mg, 0.024 mmol, Step-1 of Example 646) in place of 5-chloro-2-methyl-N-((1r,4r)-4-((3-(5-nitropyridin-2-yl)-2-oxo-2,3-dihydro-1H-benzo[d]imidazol-1-yl)methyl)cyclohexyl)nicotinamide.

MS (ESI) m/z: 490.1 (M+H)$^+$.

<Step-3>: 5-chloro-2-methyl-N-((1r,4r)-4-((3-(4-(methylamino)phenyl)-2-oxo-2,3-dihydro-1H-benzo[d]imidazol-1-yl)methyl)cyclohexyl)nicotinamide The title compound is prepared in 14% yield in 2 steps (1.7 mg) by the similar manner to Step-3 of Example 574 using N((1r,4r)-4-((3-(4-aminophenyl)-2-oxo-2,3-dihydro-1H-benzo[d]imidazol-1-yl)methyl)cyclohexyl)-5-chloro-2-methylnicotinamide (18 mg, Step-2 of Example 646) in place of N-((1r,4r)-4-((3-(5-aminopyridin-2-yl)-2-oxo-2,3-dihydro-1H-benzo[d]imidazol-1-yl) methyl)cyclohexyl)-5-chloro-2-methylnicotinamide.

Example 658: 5-chloro-2-(difluoromethyl)-N-((1r, 4r)-4-((2-oxo-3-(6-ureidopyridin-3-yl)-2,3-dihydro-1H-benzo[d]imidazol-1-yl)methyl)cyclohexyl)nicotinamide

[Chem. 141]

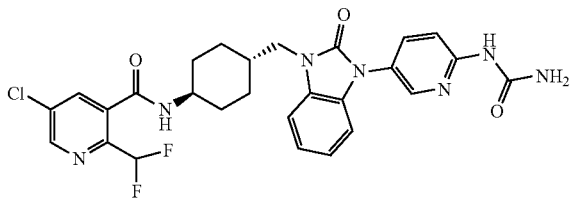

A mixture of Intermediate-207 (30 mg, 0.051 mmol), ethyl carbamate (14 mg, 0.15 mmol), CuI (1.0 mg, 0.0051 mmol), DMEDA (0.9 mg, 0.010 mmol) and $K_2CO_3$ (21 mg, 0.15 mmol) in 1,4-dioxane (1 mL) is stirred at 100° C. overnight. The mixture is added 28% aqueous ammonia solution and water, extracted with EtOAc and passed through sodium sulfate/amino-functional silica gel. The solvent is removed by flowing $N_2$ gas, ethyl (5-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-2-yl)carbamate is obtained as a crude solid. The mixture is added DMF (1 mL) and $NH_4Cl$ (190 mg, 10.5 mmol), and stirred at 140° C. for 10 hrs. The mixture is added water, extracted with EtOAc and passed through sodium sulfate/amino-functional silica gel. The solvent is removed by flowing $N_2$ gas, the crude product is purified by preparative LC-MS to give 4.2 mg (15% yield, total: 2 steps) of the title compound.

Example 660: 5-chloro-2-(difluoromethyl)-N-((1r, 4r)-4-((3-(5-(methylamino)pyridin-2-yl)-2-oxo-2, 3-dihydro-1H-benzo[d]imidazol-1-yl)methyl)cyclohexyl)nicotinamide

[Chem. 142]

<Step-1>: tert-butyl (6-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-3-yl)(methyl)carbamate A mixture of 5-chloro-2-(difluoromethyl)-N-((1r,4r)-4-((2-oxo-2,3-dihydro-1H-benzo[d]imidazol-1-yl)methyl)cyclohexyl)nicotinamide (16 mg, 0.038 mmol, Intermediate-165), tert-butyl (6-bromopyridin-3-yl)(methyl)carbamate (11 mg, 0.038 mmol), $N^1,N^2$ dimethylethane-1,2-diamine (0.022 mL, 0.21 mmol), cesium carbonate (49 mg, 0.15 mmol) and CuI (18 mg, 0.094 mmol) in DMA (1 mL) is stirred overnight at 100° C. The mixture is poured into 28% aqueous ammonia solution, extracted with EtOAc. The organic layer is concentrated. The resultant residue is dissolved in DCM and washed with water. The solvent is removed to give 27 mg of the title compound as a crude. The compound is used for the next reaction without further purification.

MS (ESI) m/z: 641.2 $(M+H)^+$.

<Step-2>: 5-chloro-2-(difluoromethyl)-N-((1r,4r)-4-((3-(5-(methylamino)pyridin-2-yl)-2-oxo-2,3-dihydro-1H-benzo[d]imidazol-1-yl)methyl)cyclohexyl)nicotinamide tert-butyl (6-(3-(((1r,4r)-4-(5-chloro-2-(difluoromethyl)nicotinamido)cyclohexyl)methyl)-2-oxo-2,3-dihydro-1H-benzo[d]imidazol-1-yl)pyridin-3-yl)(methyl)carbamate (27 mg, Step-1 of Example 660) in TFA (1 mL) is stirred for 1 hr at rt. After the reaction mixture is concentrated, the resultant residue is purified by preparative LC-MS to give 5.7 mg (28% yield in 2 steps) of the title compound.

Example 661: 5-chloro-2-(difluoromethyl)-N-((1r, 4r)-4-((3-(2-(methylamino)pyridin-4-yl)-2-oxo-2, 3-dihydro-1H-benzo[d]imidazol-1-yl)methyl)cyclohexyl)nicotinamide

[Chem. 143]

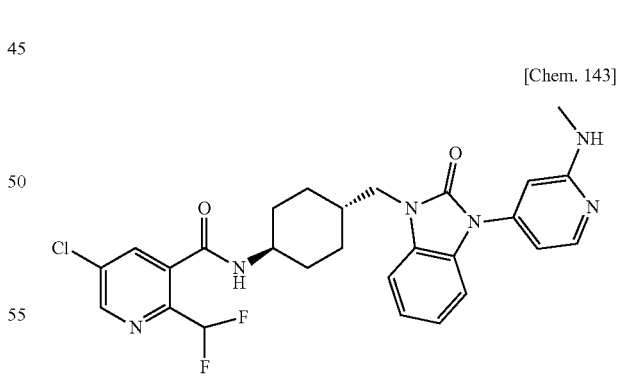

The title compound is prepared in 24% yield (5.0 mg) by the similar manner to Example 660 using tert-butyl (4-bromopyridin-2-yl)(methyl)carbamate (11 mg, 0.038 mmol) in place of tert-butyl (6-bromopyridin-3-yl)(methyl)carbamate.

Example 662: 5-chloro-2-(difluoromethyl)-N-((1r,4r)-4-((3-(6-(methylamino)pyridin-2-yl)-2-oxo-2,3-dihydro-1H-benzo[d]imidazol-1-yl)methyl)cyclohexyl)nicotinamide

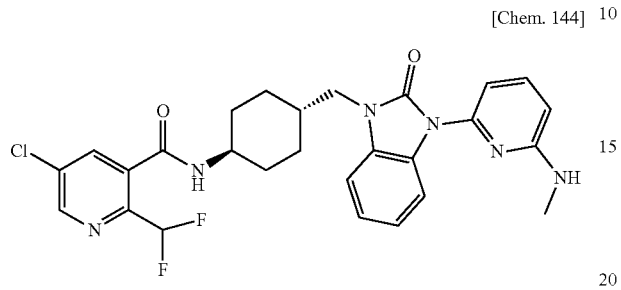

[Chem. 144]

The title compound is prepared in 33% yield (6.7 mg) by the similar manner to Example 660 using tert-butyl (6-bromopyridin-2-yl)(methyl)carbamate (11 mg, 0.038 mmol) in place of tert-butyl (6-bromopyridin-3-yl)(methyl)carbamate.

Example 665: 5-chloro-N-((1r,4r)-4-((3-(2-(methylamino)pyridin-4-yl)-2-oxo-2,3-dihydro-1H-benzo[d]imidazol-1-yl)methyl)cyclohexyl)-2-(trifluoromethyl)nicotinamide

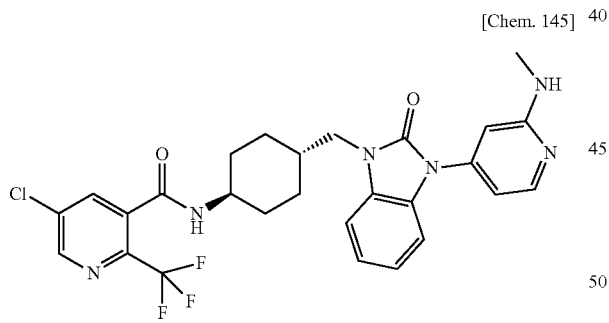

[Chem. 145]

The title compound is prepared in 20% yield (4.2 mg) by the similar manner to Example 660 using 5-chloro-N-((1r,4r)-4-((2-oxo-2,3-dihydro-1H-benzo[d]imidazol-1-yl)methyl)cyclohex yl)-2-(trifluoromethyl)nicotinamide (17 mg, 0.038 mmol, Intermediate-132) in place of 5-chloro-2-(difluoromethyl)-N-((1r,4r)-4-((2-oxo-2,3-dihydro-1H-benzo[d]imidazol-1-yl)methyl)cyclohexyl)nicotinamide and tert-butyl (4-bromopyridin-2-yl)(methyl)carbamate (11 mg, 0.038 mmol) in place of tert-butyl (6-bromopyridin-3-yl)(methyl)carbamate.

Example 666: 5-chloro-2-(difluoromethyl)-N-((1r,4r)-4-((3-(1-(2-hydroxyethyl)-1H-pyrrolo[2,3-b]pyridin-5-yl)-2-oxo-2,3-dihydro-1H-benzo[d]imidazol-1-yl)methyl)cyclohexyl)nicotinamide

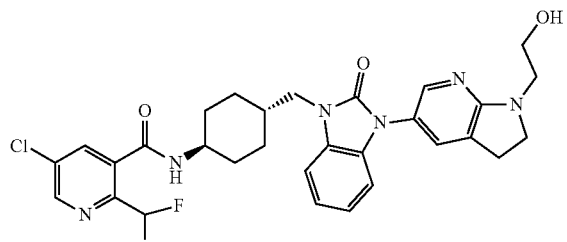

[Chem. 146]

<Step-1>: 5-chloro-2-(difluoromethyl)-N-((1r,4r)-4-((2-oxo-3-(1-((2-(trimethylsilyl)ethoxy)meth yl)-1H-pyrrolo[2,3-b]pyridin-5-yl)-2,3-dihydro-1H-benzo[d]imidazol-1-yl)methyl)cyclohexyl)nicotinamide The title compound is prepared in 86% yield (74 mg) by the similar manner to Step-3 of Intermediate-3 using 1-(1-((2-(trimethylsilyl)ethoxy)methyl)-1H-pyrrolo[2,3-b]pyridin-5-yl)-1H-benzo[d]imidazol-2(3H)-one (48 mg, 0.13 mmol, Intermediate-185) and Mesylate-4 (50 mg, 0.13 mmol) in place of methyl 2-((2-oxo-2,3-dihydro-1H-benzo[d]imidazol-1-yl)methyl)benzoate and Mesylate-1.

MS (ESI) m/z: 681.1 (M+H)$^+$.

<Step-2>: 5-chloro-2-(difluoromethyl)-N-((1r,4r)-4-((2-oxo-3-(1H-pyrrolo[2,3-b]pyridin-5-yl)-2, 3-dihydro-1H-benzo[d]imidazol-1-yl)methyl)cyclohexyl)nicotinamide To a solution of 5-chloro-2-(difluoromethyl)-N-((1r,4r)-4-((2-oxo-3-(1H-pyrrolo[2,3-b]pyridin-5-yl)-2, 3-dihydro-1H-benzo[d]imidazol-1-yl)methyl)cyclohexyl)nicotinamide (60 mg, 0.047 mg, Step-1 of Example 666) in dichloromethane (0.5 mL) is added TFA (1.5 mL). The mixture is stirred at room temperature for 3 hrs. The mixture is concentrated. The residue in 28% aqueous ammonia solution (0.5 mL) and 2 M ammonia in methanol (1.5 mL). The mixture is stirred at room temperature overnight. The mixture is concentrated to give 60 mg (quantitative yield) of the title compound.

MS (ESI) m/z: 550.9 (M+H)$^+$.

<Step-3>: 5-chloro-2-(difluoromethyl)-N-((1r,4r)-4-((3-(1-(2-hydroxyethyl)-1H-pyrrolo[2,3-b]pyridin-5-yl)-2-oxo-2,3-dihydro-1H-benzo[d]imidazol-1-yl)methyl)cyclohexyl)nicotinamide To a solution of 5-chloro-2-(difluoromethyl)-N-((1r,4r)-4-((2-oxo-3-(1H-pyrrolo[2,3-b]pyridin-5-yl)-2, 3-dihydro-1H-benzo[d]imidazol-1-yl)methyl)cyclohexyl)nicotinamide (15 mg, 0.027 mmol, Step-2 of Example 666) in DMF (1 mL) is added sodium hydride (60% dispersion in mineral oil, 1.1 mg, 0.040 mmol) at 0° C. The mixture is stirred at room temperature for 30 min. To the mixture is added (2-bromoethoxy)(tert-butyl)dimethylsilane (6.4 mg, 0.027 mmol). The mixture is stirred at room temperature for 2 hrs. The reaction is quenched with saturated aqueous ammonium chloride (10 mL), extracted with EtOAc. The organic phase is dried over sodium sulfate, filtered and concentrated. The residue is purified by a strong anion exchange cartridge (ISOLUTE (registered trademark) SCX-2, 1 g/6 mL, Biotage) and then purified by preparative SFC-MS to give 2.2 mg (14% yield) of the title compound.

Example 667: N-((1r,4r)-4-((3-(4-(1H-imidazol-4-yl)phenyl)-2-oxo-2,3-dihydro-1H-benzo[d]imidazol-1-yl)methyl)cyclohexyl)-5-chloro-2-methylnicotinamide

[Chem. 147]

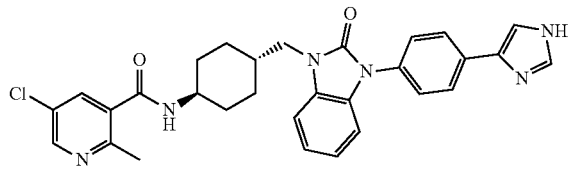

The title compound is prepared in 22% yield (6.1 mg) by the similar manner to Example 633 using 4-(4-bromophenyl)-1-((2-(trimethylsilyl)ethoxy)methyl)-1H-imidazole (18 mg, 0.050 mmol) in place of 4-(4-bromophenyl)-1-((2-(trimethylsilyl)ethoxy)methyl)-1H-1,2,3-triazole.

Example 673: 5-chloro-2-(difluoromethyl)-N-((1r,4r)-4-((3-(2-methyl-1H-pyrrolo[2,3-b]pyridin-5-yl)-2-oxo-2,3-dihydro-1H-benzo[d]imidazol-1-yl)methyl)cyclohexyl)nicotinamide

[Chem. 148]

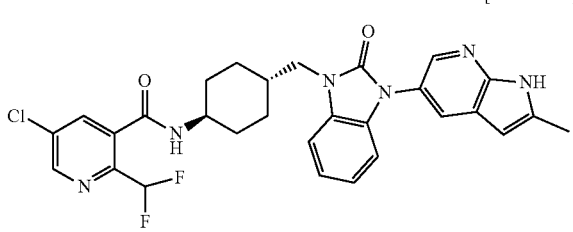

A solution of 5-chloro-2-(difluoromethyl)-N-((1r,4r)-4-((2-oxo-2,3-dihydro-1H-benzo[d]imidazol-1-yl)methyl)cyclohexyl)nicotinamide (20 mg, 0.046 mmol, Intermediate-165), 2-methyl-5-(4,4,5,5-tetramethyl-1,3,2-dioxaborolan-2-yl)-1-((2-(trimethylsilyl)ethoxy) methyl)-1H-pyrrolo[2,3-b]pyridine (13 mg, 0.032 mmol, Intermediate-248), copper (II) acetate (20 mg, 0.11 mmol), TEA (0.018 mL, 0.13 mmol) in DMA (1 mL) is stirred at 100° C. overnight. The mixture is filtered through a pad of celite. The filtrate is diluted with water (5 mL), extracted with EtOAc. The organic phase is dried over sodium sulfate, filtered through short column of amino-functional silica gel, concentrated. The residue in dichloromethane (0.5 mL) is added TFA (1.5 mL, 19.5 mmol). The mixture is stirred at room temperature for 3 hrs. The mixture is concentrated. The residue in 28% aqueous ammonia solution (0.5 mL) and 2 M ammonia in methanol (1.5 mL) is stirred at room temperature overnight. The mixture is concentrated. The residue is purified by a strong anion exchange cartridge (ISOLUTE (registered trademark) SCX-2, 1 g/6 mL, Biotage), concentrated. The residue is purified by preparative LC-MS to give 3.2 mg (18% yield) of the title compound.

Example 674: 5-chloro-2-(difluoromethyl)-N-((1r,4r)-4-((3-(1,2-dimethyl-1H-pyrrolo[2,3-b]pyridin-5-yl)-2-oxo-2,3-dihydro-1H-benzo[d]imidazol-1-yl)methyl)cyclohexyl)nicotinamide

[Chem. 149]

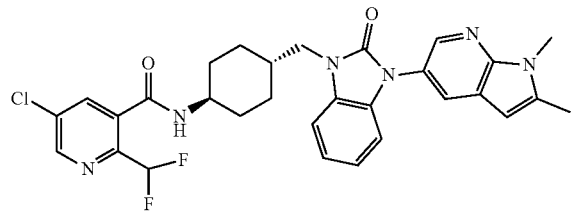

<Step-1>: 1,2-dimethyl-5-(4,4,5,5-tetramethyl-1,3,2-dioxaborolan-2-yl)-1H-pyrrolo[2,3-b]pyridine The title compound is prepared in 49% yield (60 mg, pale yellow gum) by the similar manner to Step-1 of Intermediate-81 using 5-bromo-1,2-dimethyl-1H-pyrrolo[2,3-b]pyridine (101 mg, 0.45 mmol) in place of 6-bromo-1-methyl-1H-pyrrolo[3,2-b]pyridine.

<Step-2>: 5-chloro-2-(difluoromethyl)-N-((1r,4r)-4-((3-(1,2-dimethyl-1H-pyrrolo[2,3-b]pyridin-5-yl)-2-oxo-2,3-dihydro-1H-benzo[d]imidazol-1-yl)methyl)cyclohexyl)nicotinamide A solution of 5-chloro-2-(difluoromethyl)-N-((1r,4r)-4-((2-oxo-2,3-dihydro-1H-benzo[d]imidazol-1-yl)methyl)cyclohexyl)nicotinamide (20 mg, 0.046 mmol, Intermediate-165), 1,2-dimethyl-5-(4,4,5,5-tetramethyl-1,3,2-dioxaborolan-2-yl)-1H-pyrrolo[2,3-b]pyridin e (18 mg, 0.046 mmol, Step-1 of Example 674), copper (II) acetate (20 mg, 0.11 mmol), TEA (0.018 mL, 0.13 mmol) in DMA (1 mL) is stirred at 100° C. overnight. The mixture is filtered through a pad of celite. The filtrate is diluted with water, extracted with EtOAc. The organic phase is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 3.8 mg (14% yield) of the title compound.

Example 692: 5-chloro-N-((1r,4r)-4-((3-(5-(methylamino)pyridin-2-yl)-2-oxo-2,3-dihydro-1H-benzo[d]imidazol-1-yl)methyl)cyclohexyl)-2-(trifluoromethyl)nicotinamide

[Chem. 150]

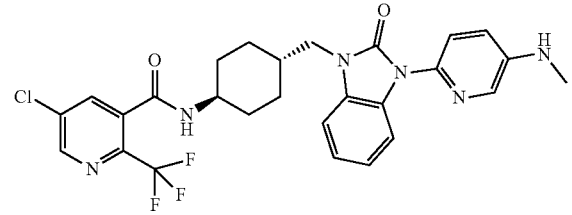

The title compound is prepared in 26% yield (5.5 mg) by the similar manner to Example 665 using tert-butyl (6-bromopyridin-3-yl)(methyl)carbamate (11 mg, 0.038 mmol) in place of tert-butyl (4-bromopyridin-2-yl)(methyl)carbamate.

Example 695: N-((1r,4r)-4-((3-(6-(1H-imidazol-2-yl)pyridin-3-yl)-2-oxo-2,3-dihydro-1H-benzo[d]imidazol-1-yl)methyl)cyclohexyl)-5-chloro-2-methylnicotinamide

[Chem. 151]

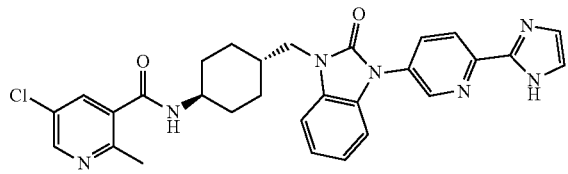

The title compound is prepared in 23% yield (4.7 mg) by the similar manner to Example 581 using 5-bromo-2-(1-((2-(trimethylsilyl)ethoxy)methyl)-1H-imidazol-2-yl)pyridine (13.3 mg, 0.038 mmol, Intermediate-255) in place of 4-(4-bromophenyl)-1-((2-(trimethylsilyl)ethoxy)methyl)-1H-pyrazole.

Example 696: N-((1r,4r)-4-((3-(3-(1H-pyrazol-4-yl)phenyl)-2-oxo-2,3-dihydro-1H-benzo[d]imidazol-1-yl)methyl)cyclohexyl)-5-chloro-2-methylnicotinamide

[Chem. 152]

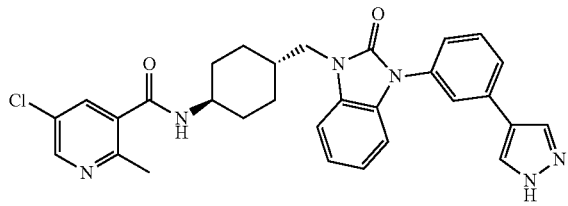

The title compound is prepared in 10% yield (2.0 mg) by the similar manner to Example 581 using 4-(3-bromophenyl)-1-((2-(trimethylsilyl)ethoxy)methyl)-1H-pyrazole (14.6 mg, 41 mmol, Intermediate-256) in place of 4-(4-bromophenyl)-1-((2-(trimethylsilyl)ethoxy)methyl)-1H-pyrazole.

Example 697: N-((1r,4r)-4-((3-(3-(1H-pyrazol-4-yl)phenyl)-2-oxo-2,3-dihydro-1H-benzo[d]imidazol-1-yl)methyl)cyclohexyl)-5-chloro-2-(difluoromethyl)nicotinamide

[Chem. 153]

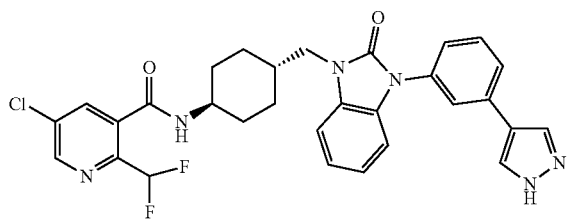

The title compound is prepared in 12% yield (2.5 mg) by the similar manner to Example 581 using 4-(3-bromophenyl)-1-((2-(trimethylsilyl)ethoxy)methyl)-1H-pyrazole (14.6 mg, 0.041 mmol, Intermediate-256) and Intermediate-165 in place of 4-(4-bromophenyl)-1-((2-(trimethylsilyl)ethoxy)methyl)-1H-pyrazole and 5-chloro-2-methyl-N-((1r,4r)-4-((2-oxo-2,3-dihydro-1H-benzo[d]imidazol-1-yl)methyl)cyclohexyl)nicotinamide.

Example 698: N-((1r,4r)-4-((3-(2-(1H-pyrazol-4-yl)pyridin-4-yl)-2-oxo-2,3-dihydro-1H-benzo[d]imidazol-1-yl)methyl)cyclohexyl)-5-chloro-2-methylnicotinamide

[Chem. 154]

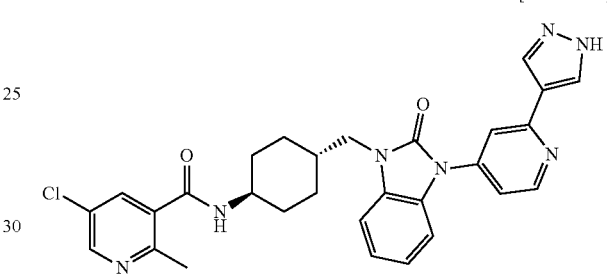

The title compound is prepared by the similar manner to Example 660 using tert-butyl 4-(4-bromopyridin-2-yl)-1H-pyrazole-1-carboxylate (Intermediate-257) in place of tert-butyl (6-bromopyridin-3-yl)(methyl)carbamate.

Example 708: 5-chloro-2-(difluoromethyl)-N-((1r,4r)-4-((3-(1,2-dimethyl-1H-pyrrolo[2,3-b]pyridin-5-yl)-2-oxo-2,3-dihydro-1H-imidazo[4,5-b]pyridin-1-yl)methyl)cyclohexyl)nicotinamide

[Chem. 155]

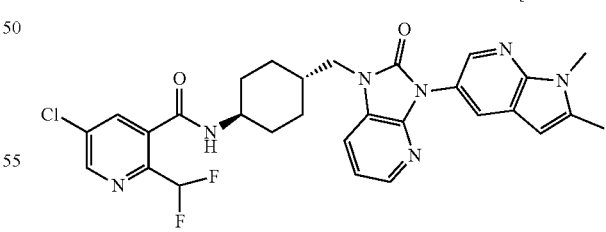

The title compound is prepared in 7% yield (1.8 mg) by the similar manner to Step-2 of Example 674 using 5-chloro-2-(difluoromethyl)-N-((1r,4r)-4-((2-oxo-2,3-dihydro-1H-imidazo[4,5-b]pyridin-1-yl)methyl)cyclohexyl)nicotinamide (20 mg, 0.046 mmol, Intermediate-214) in place of Intermediate-165.

Example 709: 5-chloro-2-(difluoromethyl)-N-((1r,4r)-4-((3-(2-(hydroxymethyl)-1H-pyrrolo[2,3-b]pyridin-5-yl)-2-oxo-2,3-dihydro-1H-benzo[d]imidazol-1-yl)methyl)cyclohexyl)nicotinamide

[Chem. 156]

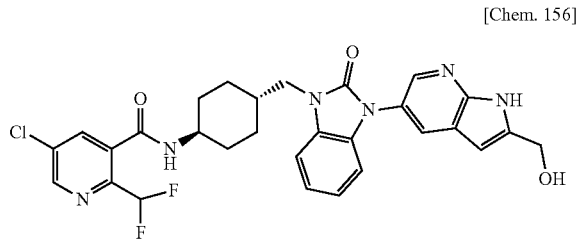 [SMILES: O=C(N[C@H]1CC[C@H](Cn2c(=O)n(-c3cnc4[nH]c(CO)cc4c3)c3ccccc32)CC1)c1cc(Cl)cnc1C(F)F]

<Step-1>: methyl 5-(4,4,5,5-tetramethyl-1,3,2-dioxaborolan-2-yl)-1-((2-(trimethylsilyl)ethoxy)methyl)-1H-pyrrolo[2,3-b]pyridine-2-carboxylate The title compound is prepared in 57% yield in 2 steps by the similar manner to Step-1 and Step-2 of Intermediate-248 using methyl 5-bromo-1H-pyrrolo[2,3-b]pyridine-2-carboxylate in place of 5-bromo-2-methyl-1H-pyrrolo[2,3-b]pyridine.
MS (ESI) m/z: 432.9 (M+H)⁺.

<Step-2>: methyl 5-(3-(((1r,4r)-4-(5-chloro-2-(difluoromethyl)nicotinamido)cyclohexyl)methyl)-2-oxo-2,3-dihydro-1H-benzo[d]imidazol-1-yl)-1-((2-(trimethylsilyl)ethoxy)methyl)-1H-pyrrolo[2,3-b]pyridine-2-carboxylate The title compound is prepared in 57% yield (65 mg, brown solid) in by the similar manner to Step-2 of Example 674 using methyl methyl 5-(4,4,5,5-tetramethyl-1,3,2-dioxaborolan-2-yl)-1-((2-(trimethylsilyl)ethoxy)methyl)-1H-pyrrolo[2,3-b]pyridine-2-carboxylate (40 mg, 0.092 mmol, Step-1 of Example 709) in place of 5-bromo-2-methyl-1H-pyrrolo[2,3-b]pyridine.
MS (ESI) m/z: 739.0 (M+H)⁺.

<Step-3>: 5-(3-(((1r,4r)-4-(5-chloro-2-(difluoromethyl)nicotinamido)cyclohexyl)methyl)-2-oxo-2,3-dihydro-1H-benzo[d]imidazol-1-yl)-1-((2-(trimethylsilyl)ethoxy)methyl)-1H-pyrrolo[2,3-b]pyridine-2-carboxylicacid To a mixture of methyl 5-(3-(((1r,4r)-4-(5-chloro-2-(difluoromethyl)nicotinamido)cyclohexyl)methyl)-2-oxo-2,3-dihydro-1H-benzo[d]imidazol-1-yl)-1-((2-(trimethylsilyl)ethoxy)methyl)-1H-pyrrolo[2,3-b]pyridine-2-carboxylate (65 mg, 0.088 mmol, Step-2 of Example 709) in MeOH (1.5 mL) and THF (1.5 mL) is added 2 M aqueous sodium hydroxide solution (0.13 mL, 0.26 mmol). The mixture is stirred at 60° C. for 1.5 hrs. The mixture is neutralized with 2 M hydrochloric acid, and concentrated. The residue is diluted water, extracted with EtOAc. The organic layer is dried over sodium sulfate and filtered. The filtrate is concentrated to give 35 mg (55% yield) of the title compound as a brown solid.
MS (ESI) m/z: 725.0 (M+H)⁺.

<Step-4>: 5-chloro-2-(difluoromethyl)-N-((1r,4r)-4-((3-(2-(hydroxymethyl)-1-((2-(trimethylsilyl)ethoxy)methyl)-1H-pyrrolo[2,3-b]pyridin-5-yl)-2-oxo-2,3-dihydro-1H-benzo[d]imidazol-1-yl)methyl)cyclohexyl)nicotinamide To a solution of 5-(3-(((1r,4r)-4-(5-chloro-2-(difluoromethyl)nicotinamido)cyclohexyl)methyl)-2-oxo-2,3-dihydro-1H-benzol[d]imidazol-1-yl)-1-((2-(trimethylsilyl)ethoxy)methyl)-1H-pyrrolo[2,3-b]pyridine-2-carboxylic acid (35 mg, 0.048 mmol, Step-3 of Example 709) in THF (2 mL) is added CDI (31 mg, 0.19 mmol) at room temperature. The mixture is stirred at room temperature for 1 hr. Then, to the mixture is added sodium borohydride (11 mg, 0.29 mmol) in water (0.2 ml) at rt. The mixture is stirred at room temperature for 3 hrs. The mixture is quenched with saturated aqueous ammonium chloride, extracted with EtOAc. The organic layer is concentrated to give 27 mg (78% yield) of the title compound as a brown solid.
MS (ESI) m/z: 711.0 (M+H)⁺.

<Step-5>: 5-chloro-2-(difluoromethyl)-N-((1r,4r)-4-((3-(2-(hydroxymethyl)-1H-pyrrolo[2,3-b]pyridin-5-yl)-2-oxo-2,3-dihydro-1H-benzo[d]imidazol-1-yl)methyl)cyclohexyl)nicotinamide The title compound is prepared in 6% yield (1.7 mg) by the similar manner to Step-2 of Example 408 using 5-chloro-2-(difluoromethyl)-N-((1r,4r)-4-((3-(2-(hydroxymethyl)-1-((2-(trimethylsilyl)ethoxy)methyl)-1H-pyrrolo[2,3-b]pyridin-5-yl)-2-oxo-2,3-dihydro-1H-benzo[d]imidazol-1-yl)methyl)cyclohexyl)nicotinamide (27 mg, 0.038 mmol, Step-4 of Example 709) in place of 5-chloro-2-methyl-N-((1r,4r)-4-((2-oxo-3-(1-((2-(trimethylsilyl)ethoxy)methyl)-1H-pyrrolo[2,3-b]pyridin-5-yl)-2,3-dihydro-1H-benzo[d]imidazol-1-yl)methyl)cyclohexyl)nicotinamide.

Example 711: 5-chloro-2-(difluoromethyl)-N-((1r,4r)-4-((3-(6-(3-hydroxypropyl)pyridin-3-yl)-2-oxo-2,3-dihydro-1H-benzo[d]imidazol-1-yl)methyl)cyclohexyl)nicotinamide

[Chem. 157]

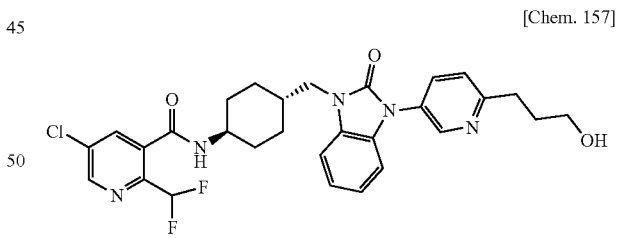

A mixture of ((r,4r)-4-(5-chloro-2-(difluoromethyl)nicotinamido)cyclohexyl)methyl methanesulfonate (20 mg, 0.050 mmol, Mesylate-4), 1-(6-(3-((tetrahydro-2H-pyran-2-yl)oxy)propyl)pyridin-3-yl)-1H-benzo[d]imidazol-2(3H)-one (18 mg, 0.050 mmol, Intermediate-261) and cesium carbonate (49 mg, 0.15 mmol) in DMSO (1 mL) is stirred at 80° C. for 1 day. The mixture is diluted with water, extracted with EtOAc. The organic phase is dried over sodium sulfate, filtered and concentrated. The residue in TFA (2 mL) is stirred at room temperature for 1 hr. The mixture is concentrated. The residue is purified by a strong anion exchange cartridge (ISOLUTE (registered trademark) SCX-2, 1 g/6 mL, Biotage) and then purified by preparative LC-MS to give 4.9 mg (17% yield) of the title compound.

Example 712: 5-chloro-2-(difluoromethyl)-N-((1r,4r)-4-((6-fluoro-3-(6-(2-hydroxyethoxy)pyridin-3-yl)-2-oxo-2,3-dihydro-1H-benzo[d]imidazol-1-yl)methyl)cyclohexyl)nicotinamide

[Chem. 158]

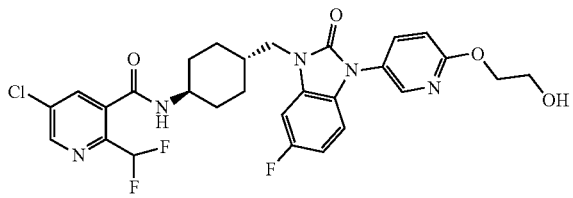

<Step-1>: 5-chloro-2-(difluoromethyl)-N-((1r,4r)-4-((6-fluoro-2-oxo-3-(6-(2-((tetrahydro-2H-pyran-2-yl)oxy)ethoxy)pyridin-3-yl)-2,3-dihydro-1H-benzo[d]imidazol-1-yl)methyl)cyclohexyl)nicotinamide The title compound is prepared by the similar manner to Step-1 of Intermediate-42 using Intermediate-262 in place of 1-(6-chloropyridazin-3-yl)-1H-benzo[d]imidazol-2(3H)-one.
MS (ESI) m/z: 674.0 (M+H)⁺.

<Step-2>: 5-chloro-2-(difluoromethyl)-N-((1r,4r)-4-((6-fluoro-3-(6-(2-hydroxyethoxy)pyridin-3-yl)-2-oxo-2,3-dihydro-1H-benzo[d]imidazol-1-yl)methyl)cyclohexyl)nicotinamide The title compound is prepared in 37% yield by the similar manner to Step-2 of Example 260 using 5-chloro-2-(difluoromethyl)-N-((1r,4r)-4-((6-fluoro-2-oxo-3-(6-(2-((tetrahydro-2H-pyran-2-yl)oxy)ethoxy)pyridin-3-yl)-2,3-dihydro-1H-benzo[d]imidazol-1-yl)methyl)cyclohexyl)nicotinamide (Step-1 of Example 712) in place of 5-chloro-N-((1r,4r)-4-((3-(3-methyl-1-(tetrahydro-2H-pyran-2-yl)-1H-indazol-5-yl)-2-oxo-2,3-dihydro-1H-benzo[d]imidazol-1-yl)methyl)cyclohexyl)-2-(trifluoromethyl)nicotinamide.

Example 714: 5-chloro-2-(difluoromethyl)-N-((1r,4r)-4-((6-fluoro-3-(2-(2-hydroxyethoxy)pyridin-4-yl)-2-oxo-2,3-dihydro-1H-benzo[d]imidazol-1-yl)methyl)cyclohexyl)nicotinamide

[Chem. 159]

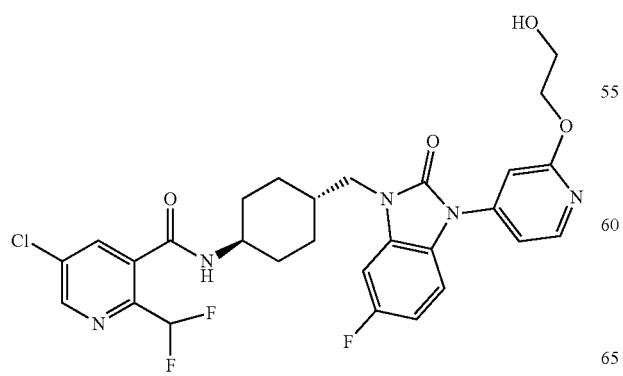

The title compound is prepared in 2 steps by the similar manner to Step-1 and Step-2 of Example 712 using Intermediate-263 in place of Intermediate-262.

Example 715: 5-chloro-2-(difluoromethyl)-N-((1r,4r)-4-((3-(5-((2-hydroxyethyl)amino)pyridin-2-yl)-2-oxo-2,3-dihydro-1H-benzo[d]imidazol-1-yl)methyl)cyclohexyl)nicotinamide

[Chem. 160]

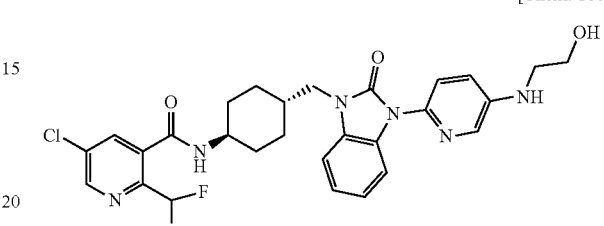

<Step-1>: tert-butyl (6-bromopyridin-3-yl)(2-((tert-butyldimethylsilyl)oxy)ethyl)carbamate The title compound is prepared in 52% yield (41 mg, colorless gum) by the similar manner to Step-1 of Example 276 using tert-butyl (6-bromopyridin-3-yl)carbamate (50 mg, 0.18 mmol) in place of 5-bromo-1H-benzo[d][1,2,3]triazole.
¹H-NMR (400 MHz, CDCl₃) delta 8.35 (1H, d, J=2.7 Hz), 7.61-7.53 (1H, m), 7.41 (1H, d, J=9.1 Hz), 3.80 (2H, t, J=5.3 Hz), 3.71 (2H, t, J=5.3 Hz), 1.44 (9H, s), 0.86 (9H, s), 0.03 (6H, s).
MS (ESI) m/z: 433.0 (M+H)⁺.

<Step-2>: 5-chloro-2-(difluoromethyl)-N-((1r,4r)-4-((3-(5-((2-hydroxyethyl)amino)pyridin-2-yl)-2-oxo-2,3-dihydro-1H-benzo[d]imidazol-1-yl)methyl)cyclohexyl)nicotinamide The title compound is prepared in 2 steps by the similar manner to Step-1 and Step-2 of Example 660 using tert-butyl (6-bromopyridin-3-yl)(2-((tert-butyldimethylsilyl)oxy)ethyl)carbamate (Step-1 of Example 715) in place of tert-butyl (6-bromopyridin-3-yl)(methyl)carbamate.

Example 716: 5-chloro-2-(difluoromethyl)-N-((1r,4r)-4-((6-fluoro-3-(5-(2-hydroxyethoxy)pyridin-2-yl)-2-oxo-2,3-dihydro-1H-benzo[d]imidazol-1-yl)methyl)cyclohexyl)nicotinamide

[Chem. 161]

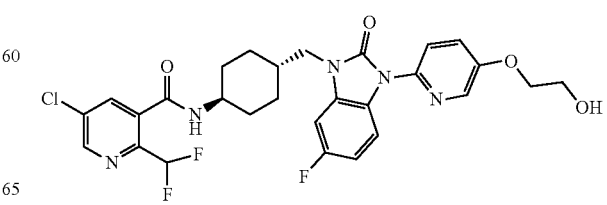

The title compound is prepared in 2 steps by the similar manner to Step-1 and Step-2 of Example 260 using Intermediate-264 and 2-bromo-5-(2-((tetrahydro-2H-pyran-2-yl)oxy)ethoxy)pyridine in place of Intermediate-132 and 5-bromo-3-methyl-1-(tetrahydro-2H-pyran-2-yl)-1H-indazole.

Example 731: 5-chloro-2-(difluoromethyl)-N-((1r,4r)-4-((3-(1-(2-hydroxyethyl)-3-methyl-1H-pyrrolo[2,3-b]pyridin-5-yl)-2-oxo-2,3-dihydro-1H-benzo[d]imidazol-1-yl)methyl)cyclohexyl)nicotinamide

[Chem. 162]

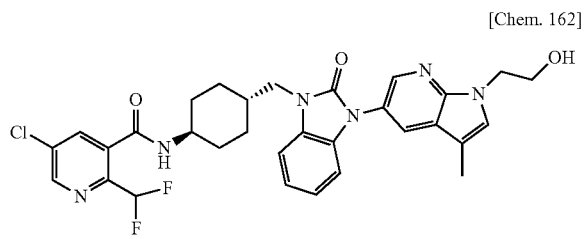 [SMILES: Cc1cn(CCO)c2ncc(-n3c(=O)n(C[C@H]4CC[C@H](NC(=O)c5cc(Cl)cnc5C(F)F)CC4)c4ccccc43)cc12]

The title compound is prepared by the similar manner to Step-3 of Example 666 using Example 456 in place of 5-chloro-2-(difluoromethyl)-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide.

Example 732: 5-chloro-2-(difluoromethyl)-N-((1r,4r)-4-((3-(2-(hydroxymethyl)-1-methyl-1H-pyrrolo[2,3-b]pyridin-5-yl)-2-oxo-2,3-dihydro-1H-benzo[d]imidazol-1-yl)methyl)cyclohexyl)nicotinamide

[Chem. 163]

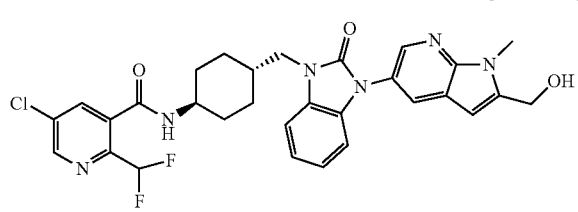

The title compound is prepared in 4 steps by the similar manner to Step-1, Step-2, Step-3, and Step-4 of Example 709 using methyl 5-bromo-1-methyl-1H-pyrrolo[2,3-b]pyridine-2-carboxylate in place of methyl 5-bromo-1H-pyrrolo[2,3-b]pyridine-2-carboxylate.

Example 733: N-((1r,4r)-4-((3-(6-(1H-imidazol-2-yl)pyridin-3-yl)-2-oxo-2,3-dihydro-1H-benzo[d]imidazol-1-yl)methyl)cyclohexyl)-5-chloro-2-(difluoromethyl)nicotinamide

[Chem. 164]

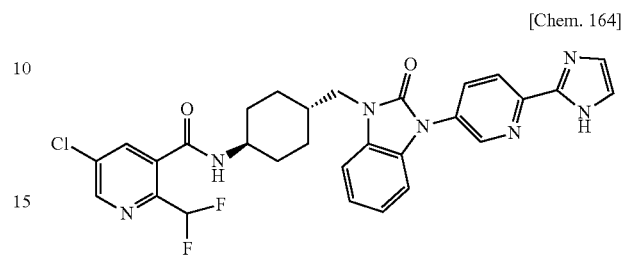

The title compound is prepared by the similar manner to Example 581 using 5-bromo-2-(1-((2-(trimethylsilyl)ethoxy)methyl)-1H-imidazol-2-yl)pyridine (Intermediate-255) and Intermediate-165 in place of 4-(4-bromophenyl)-1-((2-(trimethylsilyl)ethoxy)methyl)-1H-pyrazole and Step-2 of Example 9.

Example 734: 5-chloro-2-(difluoromethyl)-N-((1r,4r)-4-((3-(2-(hydroxymethyl)-1-methyl-1H-indol-5-yl)-2-oxo-2,3-dihydro-1H-imidazo[4,5-b]pyridin-1-yl)methyl)cyclohexyl)nicotinamide

[Chem. 165]

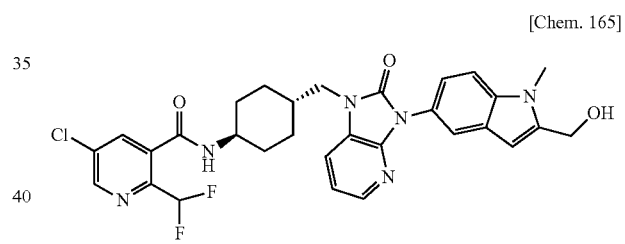

<Step-1>: ethyl 1-methyl-5-(2-oxo-1H-imidazo[4,5-b]pyridin-3(2H)-yl)-1H-indole-2-carboxylate The title compound is prepared in 3 steps by the similar manner to Step-1, Step-2, and Step-3 of Intermediate-249 using 2-bromo-3-nitropyridine and ethyl 5-amino-1-methyl-1H-indole-2-carboxylate in place of 3-bromo-2-nitropyridine and 2-chloro-5-methoxyaniline.

$^1$H-NMR (400 MHz, DMSO-$d_6$) delta 11.36 (1H, br s), 7.91 (1H, dd, J=5.0, 1.8 Hz), 7.89 (1H, d, J=1.8 Hz), 7.73 (1H, d, J=8.7 Hz), 7.53 (1H, dd, J=8.7, 1.8 Hz), 7.39 (1H, dd, J=7.8, 1.4 Hz), 7.36 (1H, s), 7.08 (1H, dd, J=7.8, 5.0 Hz), 4.35 (2H, q, J=7.3 Hz), 4.09 (3H, s), 1.36 (3H, t, J=7.3 Hz). MS (ESI) m/z: 336.9 (M+H)$^+$.

<Step-2>: ethyl 5-(1-(((1r,4r)-4-(5-chloro-2-(difluoromethyl)nicotinamido)cyclohexyl)methyl)-2-oxo-1H-imidazo[4,5-b]pyridin-3(2H)-yl)-1-methyl-1H-indole-2-carboxylate The title compound is prepared by the similar manner to Step-3 of Intermediate-3 using ethyl 1-methyl-5-(2-oxo-1H-imidazo[4,5-b]pyridin-3(2H)-yl)-1H-indole-2-carboxylate (Step-1 of Example 734) and Mesylate-4 in place of methyl 2-((2-oxo-2,3-dihydro-1H-benzo[d]imidazol-1-yl)methyl)benzoate and Mesylate-1.

<Step-3>: 5-chloro-2-(difluoromethyl)-N-((1r,4r)-4-((3-(2-(hydroxymethyl)-1-methyl-H-indol-5-yl)-2-oxo-2,3-dihydro-1H-imidazo[4,5-b]pyridin-1-yl)methyl)cyclohexyl)nicotinamide The title compound is prepared in 2 steps by the similar manner to Step-3 and Step-4 of Example 709 using ethyl 5-(1-(((1r,4r)-4-(5-chloro-2-(difluoromethyl)nicotinamido)cyclohexyl)methyl)-2-oxo-1H-imidazo[4,5-b]pyridin-3(2H)-yl)-1-methyl-1H-indole-2-carboxylate (Step-2 of Example 734) in place of methyl 5-(3-(((1r,4r)-4-(5-chloro-2-(difluoromethyl)nicotinamido)cyclohexyl)methyl)-2-oxo-2,3-dihydro-1H-benzo[d]imidazol-1-yl)-1-((2-(trimethylsilyl)ethoxy)methyl)-1H-pyrrolo[2,3-b]pyridine-2-carboxylate.

Example 738: 5-chloro-2-(difluoromethyl)-N-((1r,4r)-4-((3-(2-methyl-1H-pyrrolo[2,3-b]pyridin-5-yl)-2-oxo-2,3-dihydro-1H-imidazo[4,5-b]pyridin-1-yl)methyl)cyclohexyl)nicotinamide

[Chem. 166]

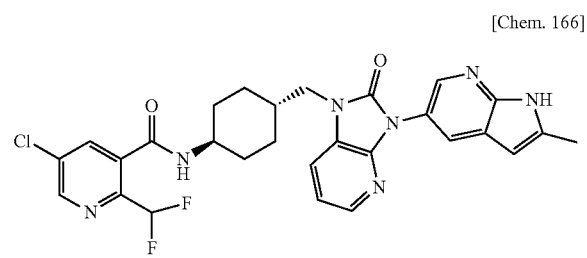 [SMILES: Cc1cc2cc(-n3c(=O)n(C[C@H]4CC[C@H](NC(=O)c5cc(Cl)cnc5C(F)F)CC4)c4cccnc43)cnc2[nH]1]

The title compound is prepared by the similar manner to Example 673 using Intermediate-214 in place of Intermediate-165.

Example 740: N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-methylnicotinamide

[Chem. 167]

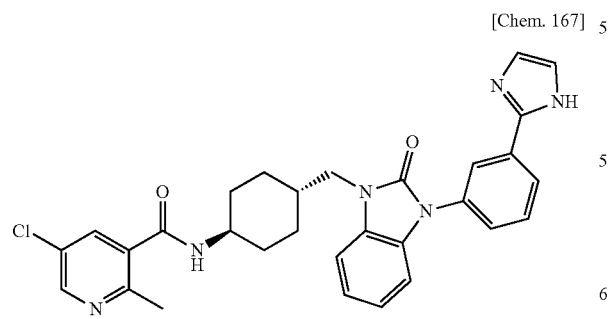

The title compound is prepared by the similar manner to Example 581 using 2-(3-bromophenyl)-1-((2-(trimethylsilyl)ethoxy)methyl)-1H-imidazole in place of 4-(4-bromophenyl)-1-((2-(trimethylsilyl)ethoxy)methyl)-1H-pyrazole.

Example 741: N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide

[Chem. 168]

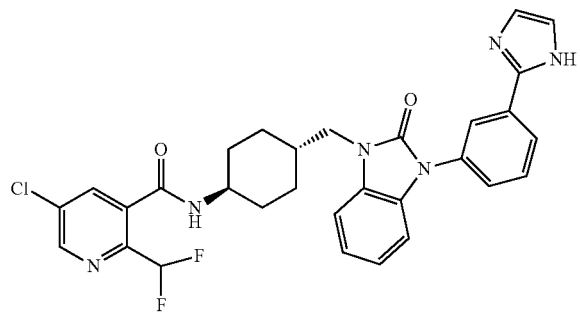

The title compound is prepared by the similar manner to Example 581 using 2-(3-bromophenyl)-1-((2-(trimethylsilyl)ethoxy)methyl)-1H-imidazole and Intermediate-165 in place of 4-(4-bromophenyl)-1-((2-(trimethylsilyl)ethoxy)methyl)-1H-pyrazole and Step-2 of Example 9.

Example 742: N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-methylnicotinamide

[Chem. 169]

The title compound is prepared by the similar manner to Example 581 using 2-(4-bromophenyl)-1-((2-(trimethylsilyl)ethoxy)methyl)-1H-imidazole in place of 4-(4-bromophenyl)-1-((2-(trimethylsilyl)ethoxy)methyl)-1H-pyrazole.

Example 743: N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide

[Chem. 170]

The title compound is prepared by the similar manner to Example 581 using 2-(4-bromophenyl)-1-((2-(trimethylsilyl)ethoxy)methyl)-1H-imidazole and Intermediate-165 in place of 4-(4-bromophenyl)-1-((2-(trimethylsilyl)ethoxy)methyl)-1H-pyrazole and Step-2 of Example 9.

Example 769: N-((1r,4r)-4-((3-(4-(1H-imidazol-5-yl)phenyl)-2-oxo-2,3-dihydro-1H-benzo[d]imidazol-1-yl)methyl)cyclohexyl)-5-chloro-2-(difluoromethyl)nicotinamide

[Chem. 171]

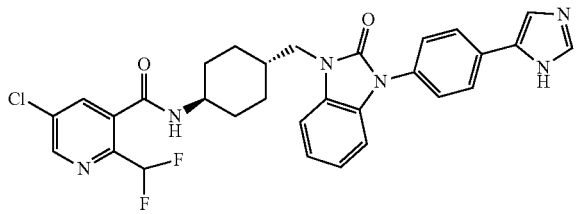

The title compound is prepared by the similar manner to Example 667 using Intermediate-165 in place of Step-2 of Example 9.

Example 778: 5-chloro-2-(difluoromethyl)-N-((1r,4r)-4-((6-fluoro-3-(5-(2-hydroxyethoxy)pyrazin-2-yl)-2-oxo-2,3-dihydro-1H-benzo[d]imidazol-1-yl)methyl)cyclohexyl)nicotinamide

[Chem. 172]

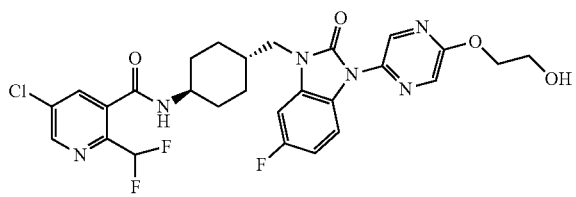

The title compound is prepared in 2 steps by the similar manner to Step-1 and Step-2 of Example 712 using Intermediate-280 in place of Intermediate-262.

Example 779: 5-chloro-2-(difluoromethyl)-N-((1r,4r)-4-((3-(2-(hydroxymethyl)-1H-indol-5-yl)-2-oxo-2,3-dihydro-1H-imidazo[4,5-b]pyridin-1-yl)methyl)cyclohexyl)nicotinamide

[Chem. 173]

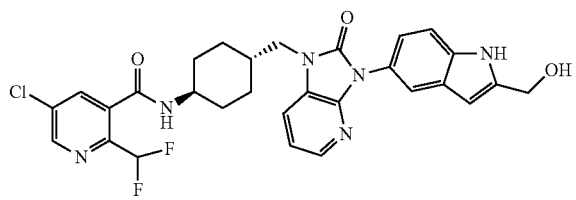

<Step-1>: ethyl 5-amino-1-((2-(trimethylsilyl)ethoxy)methyl)-1H-indole-2-carboxylate The title compound is prepared in 2 steps by the similar manner to Step-1 and Step-2 of Intermediate-229 using ethyl 5-nitro-1H-indole-2-carboxylate in place of 3-methyl-5-nitro-1H-pyrrolo[2,3-b]pyridine.

MS (ESI) m/z: 452.8 (M+H)$^+$.

<Step-2>: ethyl 5-(2-oxo-1H-imidazo[4,5-b]pyridin-3(2H)-yl)-1-((2-(trimethylsilyl)ethoxy)methyl)-1H-indole-2-carboxylate The title compound is prepared in 3 steps by the similar manner to Step-1, Step-2, and Step-3 of Intermediate-249 using 2-bromo-3-nitropyridine and ethyl 5-amino-1-((2-(trimethylsilyl)ethoxy)methyl)-1H-indole-2-carboxylate (Step-1 of Example 779) in place of 3-bromo-2-nitropyridine and 2-chloro-5-methoxyaniline.

<Step-3>: ethyl 5-(1-(((1r,4r)-4-(5-chloro-2-(difluoromethyl)nicotinamido)cyclohexyl)methyl)-2-oxo-1H-imidazo[4,5-b]pyridin-3(2H)-yl)-1-((2-(trimethylsilyl)ethoxy)methyl)-1H-indole-2-carboxylate The title compound is prepared by the similar manner to Step-3 of Intermediate-3 using ethyl 5-(2-oxo-1H-imidazo[4,5-b]pyridin-3(2H)-yl)-1-((2-(trimethylsilyl)ethoxy)methyl)-1H-indole-2-carboxylate (Step-2 of Example 779) and Mesylate-4 in place of methyl 2-((2-oxo-2,3-dihydro-1H-benzo[d]imidazol-1-yl)methyl)benzoate and Mesylate-1.

<Step-4>: 5-chloro-2-(difluoromethyl)-N-((1r,4r)-4-((3-(2-(hydroxymethyl)-1H-indol-5-yl)-2-oxo-2,3-dihydro-1H-imidazo[4,5-b]pyridin-1-yl)methyl)cyclohexyl)nicotinamide The title compound is prepared in 3 steps by the similar manner to Step-3, Step-4, and Step-5 of Example 709 using ethyl 5-(1-(((1r,4r)-4-(5-chloro-2-(difluoromethyl)nicotinamido)cyclohexyl)methyl)-2-oxo-1H-imidazo[4,5-b]pyridin-3(2H)-yl)-1-((2-(trimethylsilyl)ethoxy)methyl)-1H-indole-2-carboxylate (Step-3 of Example 779) in place of methyl 5-(3-(((1r,4r)-4-(5-chloro-2-(difluoromethyl)nicotinamido)cyclohexyl)methyl)-2-oxo-2,3-dihydro-1H-benzo[d]imidazol-1-yl)-1-((2-(trimethylsilyl)ethoxy)methyl)-1H-pyrrolo[2,3-b]pyridine-2-carboxylate.

The other examples in Table 2 are prepared according to the representative procedure (Method A to Y) described in the example synthesis part using reactants shown in Table 2. The reactants are commercially available materials or obtained by conventional methods known to those skilled in the art, unless otherwise noted in the synthesis part. Each chemical structure of Example is described as a free-base in Table 2.

The observed MS (positive or negative mode) and retention time by LC-MS of all examples are described in Tables 3-1 to 3-12.

The $^1$H-NMR data of selected examples are described in Tables 4-1 to 4-2.

TABLE 2

| Ex. | Structure | Name | Reactants | Method |
|---|---|---|---|---|
| 1 | 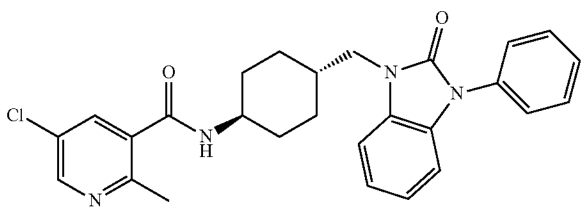 [SMILES: Cc1ncc(Cl)cc1C(=O)N[C@H]1CC[C@H](Cn2c(=O)n(-c3ccccc3)c3ccccc32)CC1] | 5-chloro-2-methyl-N-((1r,4r)-4-((2-oxo-3-phenyl-2,3-dihydro-1H-benzo[d]imidazol-1-yl)methyl)cyclohexyl)nicotinamide | (1-phenyl-benzimidazol-2-one), Mesylate-1 | A1 |
| 2 | 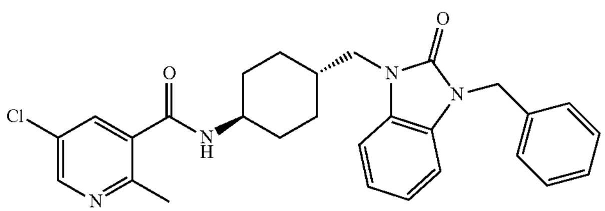 [SMILES: Cc1ncc(Cl)cc1C(=O)N[C@H]1CC[C@H](Cn2c(=O)n(Cc3ccccc3)c3ccccc32)CC1] | N-((1r,4r)-4-((3-benzyl-2-oxo-2,3-dihydro-1H-benzo[d]imidazol-1-yl)methyl)cyclohexyl)-5-chloro-2-methylnicotinamide | (1-benzyl-benzimidazol-2-one), Mesylate-1 | A1 |
| 3 | 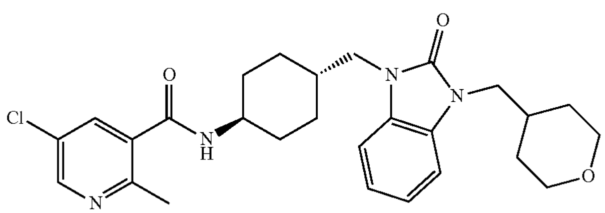 [SMILES: Cc1ncc(Cl)cc1C(=O)N[C@H]1CC[C@H](Cn2c(=O)n(CC3CCOCC3)c3ccccc32)CC1] | 5-chloro-2-methyl-N-((1r,4r)-4-((2-oxo-3-((tetrahydro-2H-pyran-4-yl)methyl)-2,3-dihydro-1H-benzo[d]imidazol-1-yl)methyl)cyclohexyl)nicotinamide | Intermediate-1, Mesylate-1 | A1 |
| 4 | 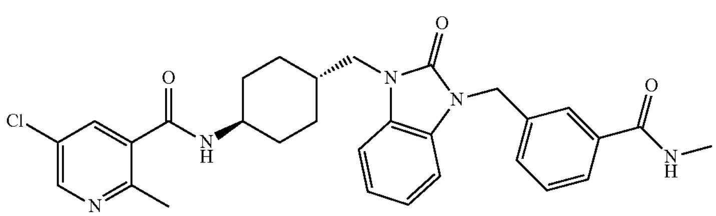 [SMILES: CNC(=O)c1cccc(Cn2c(=O)n(C[C@H]3CC[C@H](NC(=O)c4cc(Cl)cnc4C)CC3)c3ccccc32)c1] | 5-chloro-2-methyl-N-((1r,4r)-4-((3-(3-(methylcarbamoyl)benzyl)-2-oxo-2,3-dihydro-1H-benzo[d]imidazol-1-yl)methyl)cyclohexyl)nicotinamide | Intermediate-2, 2 M methanamine in THF | B |

TABLE 2-continued

| Ex. | Structure | Name | Reactants | Method |
|---|---|---|---|---|
| 5 | 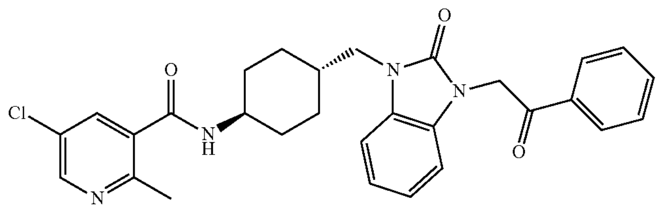 [SMILES: Cc1ncc(Cl)cc1C(=O)N[C@H]1CC[C@H](Cn2c(=O)n(CC(=O)c3ccccc3)c3ccccc32)CC1] | 5-chloro-2-methyl-N-((1r,4r)-4-((2-oxo-3-(2-oxo-2-phenylethyl)-2,3-dihydro-1H-benzo[d]imidazol-1-yl)methyl)cyclohexyl)nicotinamide | ; Mesylate-1 | A1 |
| 6 | 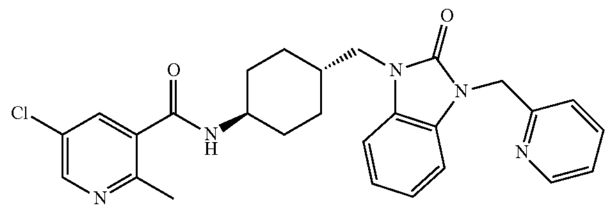 [SMILES: Cc1ncc(Cl)cc1C(=O)N[C@H]1CC[C@H](Cn2c(=O)n(Cc3ccccn3)c3ccccc32)CC1] | 5-chloro-2-methyl-N-((1r,4r)-4-((2-oxo-3-(pyridin-2-ylmethyl)-2,3-dihydro-1H-benzo[d]imidazol-1-yl)methyl)cyclohexyl)nicotinamide | ; Mesylate-1 | A1 |
| 7 | 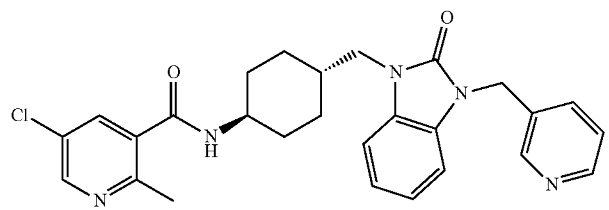 [SMILES: Cc1ncc(Cl)cc1C(=O)N[C@H]1CC[C@H](Cn2c(=O)n(Cc3cccnc3)c3ccccc32)CC1] | 5-chloro-2-methyl-N-((1r,4r)-4-((2-oxo-3-(pyridin-3-ylmethyl)-2,3-dihydro-1H-benzo[d]imidazol-1-yl)methyl)cyclohexyl)nicotinamide | ; Mesylate-1 | A1 |
| 8 | 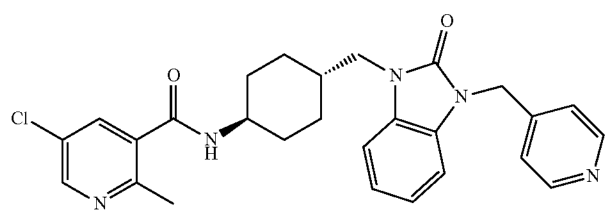 [SMILES: Cc1ncc(Cl)cc1C(=O)N[C@H]1CC[C@H](Cn2c(=O)n(Cc3ccncc3)c3ccccc32)CC1] | 5-chloro-2-methyl-N-((1r,4r)-4-((2-oxo-3-(pyridin-4-ylmethyl)-2,3-dihydro-1H-benzo[d]imidazol-1-yl)methyl)cyclohexyl)nicotinamide | ; Mesylate-1 | A1 |

TABLE 2-continued

| Ex. | Structure | Name | Reactants | Method |
|---|---|---|---|---|
| 9 | 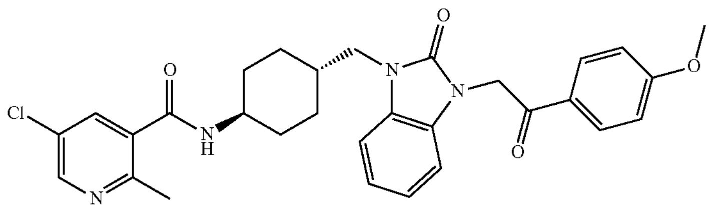 [SMILES: COc1ccc(C(=O)Cn2c(=O)n(C[C@H]3CC[C@H](NC(=O)c4cc(Cl)cnc4C)CC3)c3ccccc32)cc1] | 5-chloro-N-((1r,4r)-4-((3-(2-(4-methoxyphenyl)-2-oxoethyl)-2-oxo-2,3-dihydro-1H-benzo[d]imidazol-1-yl)methyl)cyclohexyl)-2-methylnicotinamide | (4-methoxyphenyl bromoacetyl); Step-2 of Ex 9 | C1 |
| 10 | 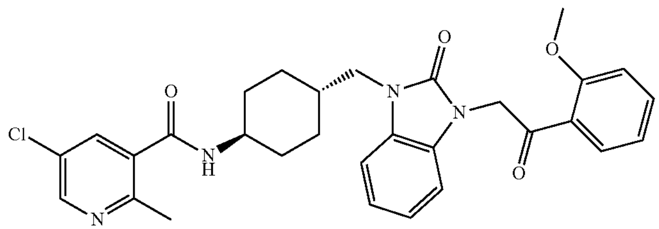 [SMILES: COc1ccccc1C(=O)Cn1c(=O)n(C[C@H]2CC[C@H](NC(=O)c3cc(Cl)cnc3C)CC2)c2ccccc21] | 5-chloro-N-((1r,4r)-4-((3-(2-(2-methoxyphenyl)-2-oxoethyl)-2-oxo-2,3-dihydro-1H-benzo[d]imidazol-1-yl)methyl)cyclohexyl)-2-methylnicotinamide | (2-methoxyphenyl bromoacetyl); Step-2 of Ex 9 | C1 |
| 11 | 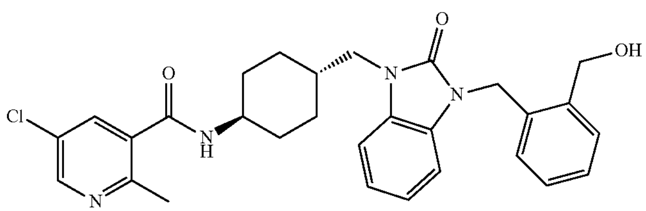 [SMILES: Cc1ncc(Cl)cc1C(=O)N[C@H]1CC[C@H](Cn2c(=O)n(Cc3ccccc3CO)c3ccccc32)CC1] | 5-chloro-N-((1r,4r)-4-((3-(2-(hydroxymethyl)benzyl)-2-oxo-2,3-dihydro-1H-benzo[d]imidazol-1-yl)methyl)cyclohexyl)-2-methylnicotinamide | Intermediate-3 | D |
| 12 | 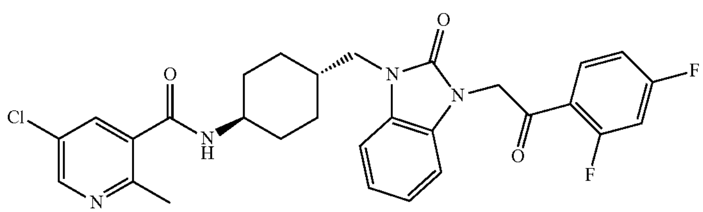 [SMILES: Cc1ncc(Cl)cc1C(=O)N[C@H]1CC[C@H](Cn2c(=O)n(CC(=O)c3ccc(F)cc3F)c3ccccc32)CC1] | 5-chloro-N-((1r,4r)-4-((3-(2-(2,4-difluorophenyl)-2-oxoethyl)-2-oxo-2,3-dihydro-1H-benzo[d]imidazol-1-yl)methyl)cyclohexyl)-2-methylnicotinamide | (2,4-difluorophenyl bromoacetyl); Step-2 of Ex 9 | C2 |
| 13 | 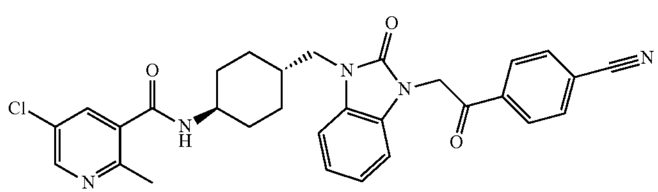 [SMILES: Cc1ncc(Cl)cc1C(=O)N[C@H]1CC[C@H](Cn2c(=O)n(CC(=O)c3ccc(C#N)cc3)c3ccccc32)CC1] | 5-chloro-N-((1r,4r)-4-((3-(2-(4-cyanophenyl)-2-oxoethyl)-2-oxo-2,3-dihydro-1H-benzo[d]imidazol-1-yl)methyl)cyclohexyl)-2-methylnicotinamide | (4-cyanophenyl bromoacetyl) | C2 |

TABLE 2-continued

| Ex. | Structure | Name | Reactants | Method |
|---|---|---|---|---|
| 14 | 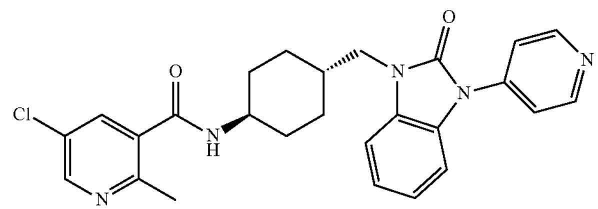 [SMILES: Cc1ncc(Cl)cc1C(=O)N[C@H]1CC[C@H](Cn2c(=O)n(-c3ccncc3)c3ccccc32)CC1] | 5-chloro-2-methyl-N-((1r,4r)-4-((2-oxo-3-(pyridin-4-yl)-2,3-dihydro-1H-benzo[d]imidazol-1-yl)methyl)cyclohexyl)nicotinamide | Mesylate-1 | A1 |
| 15 | 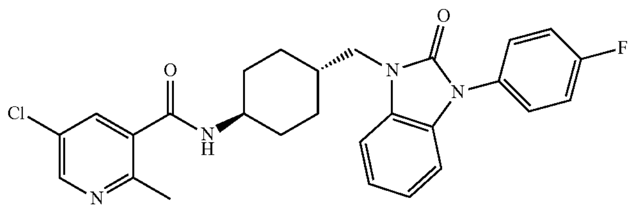 [SMILES: Cc1ncc(Cl)cc1C(=O)N[C@H]1CC[C@H](Cn2c(=O)n(-c3ccc(F)cc3)c3ccccc32)CC1] | 5-chloro-N-((1r,4r)-4-((3-(4-fluorophenyl)-2-oxo-2,3-dihydro-1H-benzo[d]imidazol-1-yl)methyl)cyclohexyl)-2-methylnicotinamide | Intermediate-4, Mesylate-1 | A1 |
| 16 | 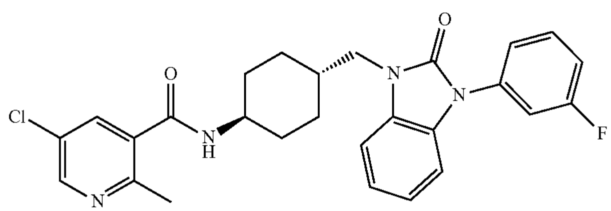 [SMILES: Cc1ncc(Cl)cc1C(=O)N[C@H]1CC[C@H](Cn2c(=O)n(-c3cccc(F)c3)c3ccccc32)CC1] | 5-chloro-N-((1r,4r)-4-((3-(3-fluorophenyl)-2-oxo-2,3-dihydro-1H-benzo[d]imidazol-1-yl)methyl)cyclohexyl)-2-methylnicotinamide | Intermediate-5, Mesylate-1 | A1 |
| 17 | 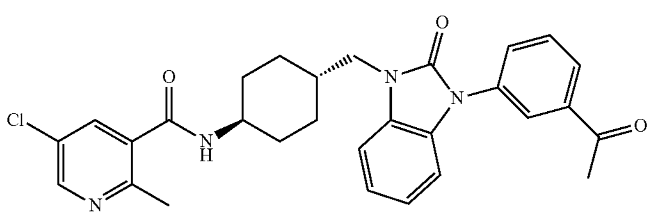 [SMILES: CC(=O)c1cccc(-n2c(=O)n(C[C@H]3CC[C@H](NC(=O)c4cc(Cl)cnc4C)CC3)c3ccccc32)c1] | N-((1r,4r)-4-(3-(3-acetylphenyl)-2-oxo-2,3-dihydro-1H-benzo[d]imidazol-1-yl)methyl)cyclohexyl)-5-chloro-2-methylnicotinamide | Intermediate-6, Mesylate-1 | A1 |

TABLE 2-continued

| Ex. | Structure | Name | Reactants | Method |
|---|---|---|---|---|
| 18 | 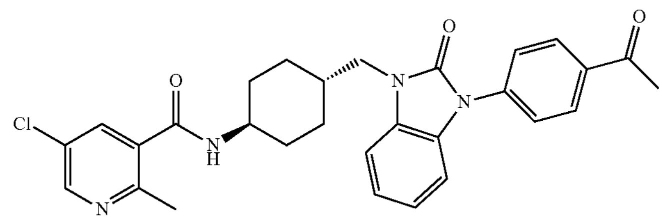 [SMILES: CC(=O)c1ccc(-n2c(=O)n(C[C@H]3CC[C@H](NC(=O)c4cc(Cl)cnc4C)CC3)c3ccccc32)cc1] | N-((1r,4r)-4-((3-(4-acetylphenyl)-2-oxo-2,3-dihydro-1H-benzo[d]imidazol-1-yl)methyl)cyclohexyl)-5-chloro-2-methylnicotinamide | Intermediate-7, Mesylate-1 | A1 |
| 19 | 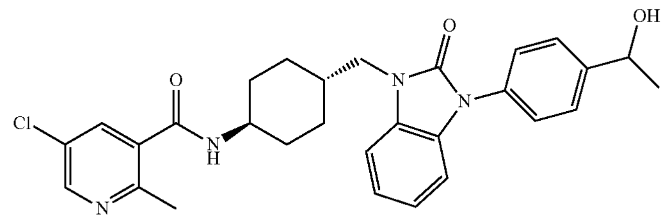 [SMILES: Cc1ncc(Cl)cc1C(=O)N[C@H]1CC[C@H](Cn2c(=O)n(-c3ccc(C(C)O)cc3)c3ccccc32)CC1] | 5-chloro-N-((1r,4r)-4-((3-(4-(1-hydroxyethyl)phenyl)-2-oxo-2,3-dihydro-1H-benzo[d]imidazol-1-yl)methyl)cyclohexyl)-2-methylnicotinamide | Example 18 | E |
| 20 | 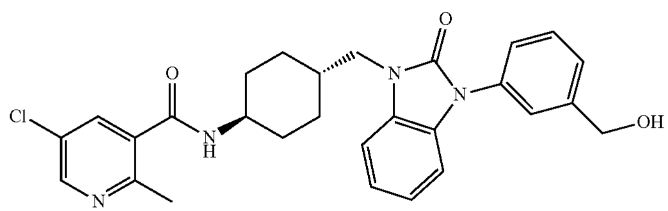 [SMILES: Cc1ncc(Cl)cc1C(=O)N[C@H]1CC[C@H](Cn2c(=O)n(-c3cccc(CO)c3)c3ccccc32)CC1] | 5-chloro-N-((1r,4r)-4-((3-(3-(hydroxymethyl)phenyl)-2-oxo-2,3-dihydro-1H-benzo[d]imidazol-1-yl)methyl)cyclohexyl)-2-methylnicotinamide | Intermediate-8 | D |
| 21 | 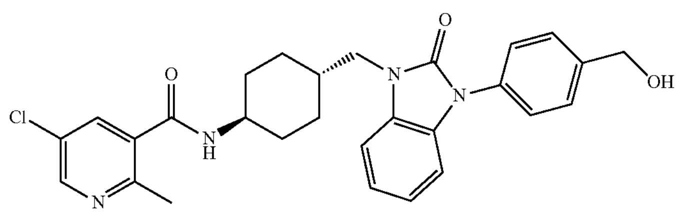 [SMILES: Cc1ncc(Cl)cc1C(=O)N[C@H]1CC[C@H](Cn2c(=O)n(-c3ccc(CO)cc3)c3ccccc32)CC1] | 5-chloro-N-((1r,4r)-4-((3-(4-(hydroxymethyl)phenyl)-2-oxo-2,3-dihydro-1H-benzo[d]imidazol-1-yl)methyl)cyclohexyl)-2-methylnicotinamide | Intermediate-9 | D |

TABLE 2-continued

| Ex. | Structure | Name | Reactants | Method |
|---|---|---|---|---|
| 22 | 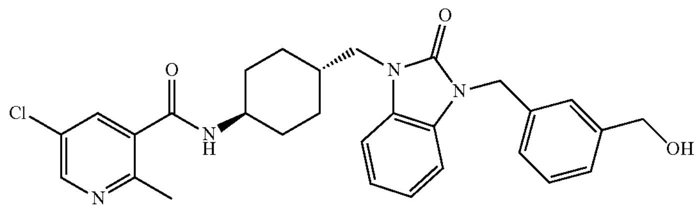 [SMILES: Cc1ncc(Cl)cc1C(=O)N[C@H]1CC[C@H](Cn2c(=O)n(Cc3cccc(CO)c3)c3ccccc32)CC1] | 5-chloro-N-((1r,4r)-4-((3-(3-(hydroxymethyl)benzyl)-2-oxo-2,3-dihydro-1H-benzo[d]imidazol-1-yl)methyl)cyclohexyl)-2-methylnicotinamide | Intermediate-2 | D |
| 23 | 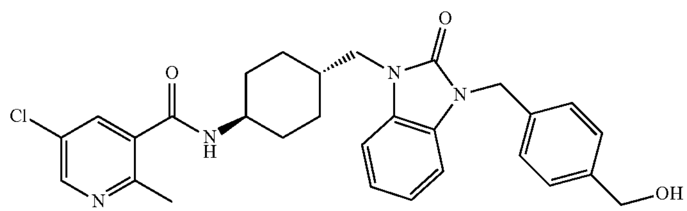 [SMILES: Cc1ncc(Cl)cc1C(=O)N[C@H]1CC[C@H](Cn2c(=O)n(Cc3ccc(CO)cc3)c3ccccc32)CC1] | 5-chloro-N-((1r,4r)-4-((3-(4-(hydroxymethyl)benzyl)-2-oxo-2,3-dihydro-1H-benzo[d]imidazol-1-yl)methyl)cyclohexyl)-2-methylnicotinamide | Intermediate-10 | D |
| 24 | 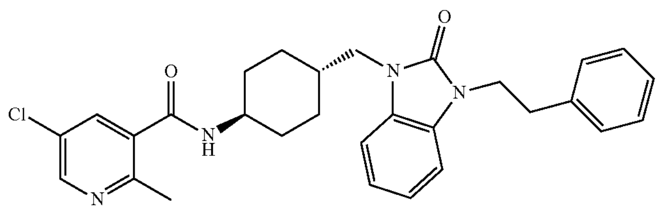 [SMILES: Cc1ncc(Cl)cc1C(=O)N[C@H]1CC[C@H](Cn2c(=O)n(CCc3ccccc3)c3ccccc32)CC1] | 5-chloro-2-methyl-N-((1r,4r)-4-((2-oxo-3-phenethyl-2,3-dihydro-1H-benzo[d]imidazol-1-yl)methyl)cyclohexyl)nicotinamide | , Mesylate-1 | A1 |
| 25 | 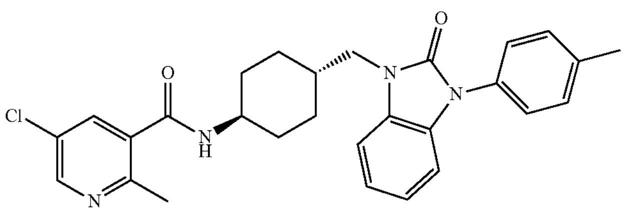 [SMILES: Cc1ccc(-n2c(=O)n(C[C@H]3CC[C@H](NC(=O)c4cc(Cl)cnc4C)CC3)c3ccccc32)cc1] | 5-chloro-2-methyl-N-((1r,4r)-4-((2-oxo-3-(p-tolyl)-2,3-dihydro-1H-benzo[d]imidazol-1-yl)methyl)cyclohexyl)nicotinamide | , Mesylate-1 | A1 |

TABLE 2-continued

| Ex. | Structure | Name | Reactants | Method |
|---|---|---|---|---|
| 26 | 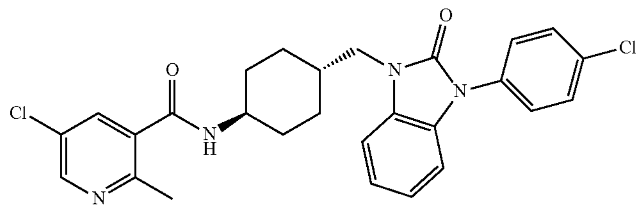 | 5-chloro-N-((1r,4r)-4-((3-(4-chlorophenyl)-2-oxo-2,3-dihydro-1H-benzo[d]imidazol-1-yl)methyl)cyclohexyl)-2-methylnicotinamide |  , Mesylate-1 | A1 |
| 27 | 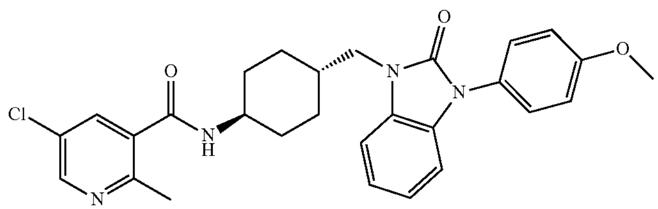 [SMILES: COc1ccc(-n2c(=O)n(C[C@H]3CC[C@H](NC(=O)c4cc(Cl)cnc4C)CC3)c3ccccc32)cc1] | 5-chloro-N-((1r,4r)-4-((3-(4-methoxyphenyl)-2-oxo-2,3-dihydro-1H-benzo[d]imidazol-1-yl)methyl)cyclohexyl)-2-methylnicotinamide |  , Mesylate-1 | A1 |
| 28 | 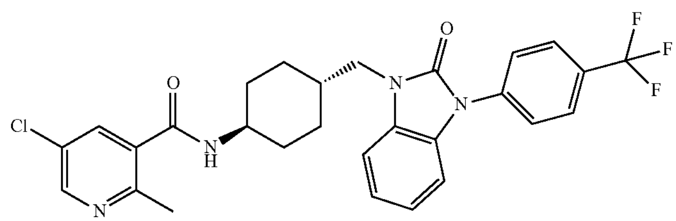 [SMILES: Cc1ncc(Cl)cc1C(=O)N[C@H]1CC[C@H](Cn2c(=O)n(-c3ccc(C(F)(F)F)cc3)c3ccccc32)CC1] | 5-chloro-2-methyl-N-((1r,4r)-4-((2-oxo-3-(4-(trifluoromethyl)phenyl)-2,3-dihydro-1H-benzo[d]imidazol-1-yl)methyl)cyclohexyl)nicotinamide |  , Mesylate-1 | A1 |
| 29 | 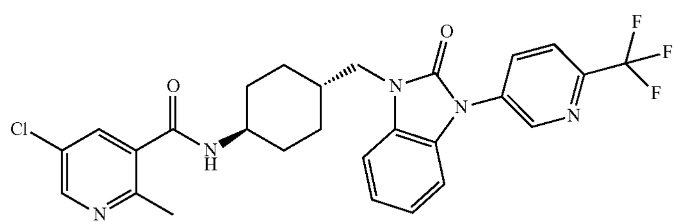 [SMILES: Cc1ncc(Cl)cc1C(=O)N[C@H]1CC[C@H](Cn2c(=O)n(-c3ccc(C(F)(F)F)nc3)c3ccccc32)CC1] | 5-chloro-2-methyl-N-((1r,4r)-4-((2-oxo-3-(6-(trifluoromethyl)pyridin-3-yl)-2,3-dihydro-1H-benzo[d]imidazol-1-yl)methyl)cyclohexyl)nicotinamide | Intermediate-11, Mesylate-1 | A1 |

TABLE 2-continued

| Ex. | Structure | Name | Reactants | Method |
|---|---|---|---|---|
| 30 | 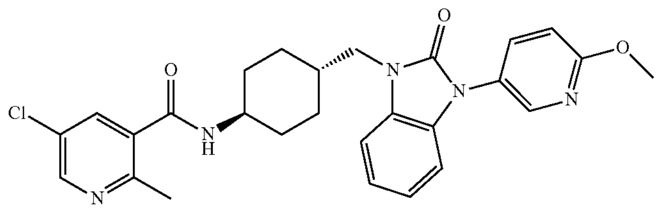 | 5-chloro-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide | Intermediate-12, Mesylate-1 | A1 |
| 31 | 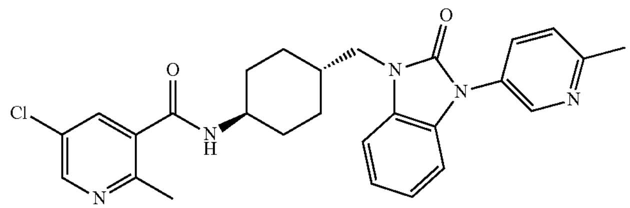 | 5-chloro-2-methyl-N-((1r,4r)-4-((3-(6-methylpyridin-3-yl)-2-oxo-2,3-dihydro-1H-benzo[d]imidazol-1-yl)methyl)cyclohexyl)nicotinamide | Intermediate-13, Mesylate-1 | A1 |
| 32 | 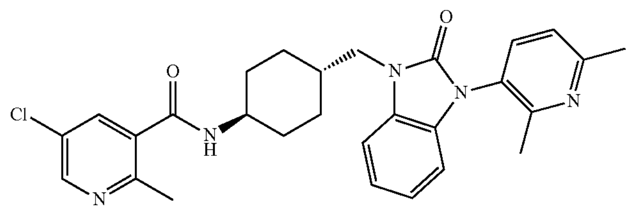 [SMILES: Cc1ccc(-n2c(=O)n(C[C@H]3CC[C@H](NC(=O)c4cc(Cl)cnc4C)CC3)c3ccccc32)c(C)n1] | 5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-methylnicotinamide | Intermediate-14, Mesylate-1 | A1 |
| 33 | 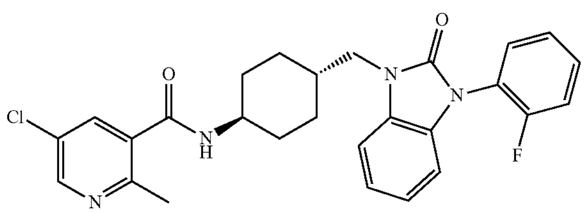 [SMILES: Cc1ncc(Cl)cc1C(=O)N[C@H]1CC[C@H](Cn2c(=O)n(-c3ccccc3F)c3ccccc32)CC1] | 5-chloro-N-((1r,4r)-4-((3-(2-fluorophenyl)-2-oxo-2,3-dihydro-1H-benzo[d]imidazol-1-yl)methyl)cyclohexyl)-2-methylnicotinamide | , Mesylate-1 | A1 |

TABLE 2-continued

| Ex. | Structure | Name | Reactants | Method |
|---|---|---|---|---|
| 34 | 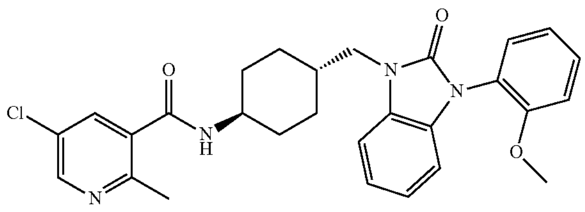 [SMILES: COc1ccccc1-n1c(=O)n(C[C@H]2CC[C@H](NC(=O)c3cc(Cl)cnc3C)CC2)c2ccccc21] | 5-chloro-N-((1r,4r)-4-((3-(2-methoxyphenyl)-2-oxo-2,3-dihydro-1H-benzo[d]imidazol-1-yl)methyl)cyclohexyl)-2-methylnicotinamide | , Mesylate-1 | A1 |
| 35 | 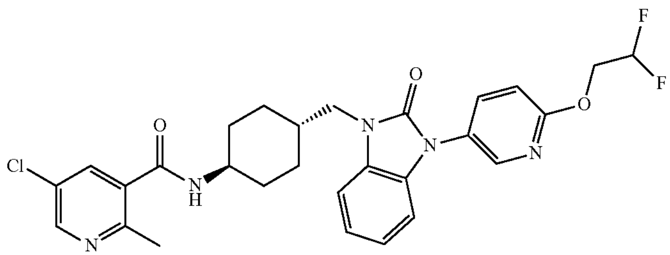 [SMILES: Cc1ncc(Cl)cc1C(=O)N[C@H]1CC[C@H](Cn2c(=O)n(-c3ccc(OCC(F)F)nc3)c3ccccc32)CC1] | 5-chloro-N-((1r,4r)-4-((3-(6-(2,2-difluoroethoxy)pyridin-3-yl)-2-oxo-2,3-dihydro-1H-benzo[d]imidazol-1-yl)methyl)cyclohexyl)-2-methylnicotinamide | Intermediate-15, Mesylate-1 | A1 |
| 36 | 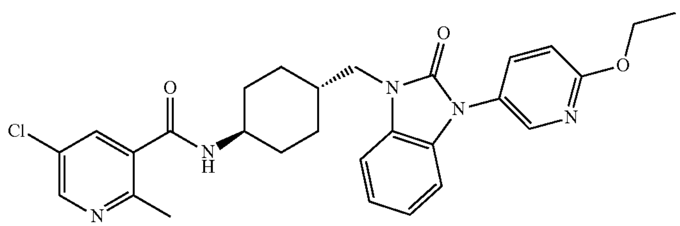 [SMILES: CCOc1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-ethoxypyridin-3-yl)-2-oxo-2,3-dihydro-1H-benzo[d]imidazol-1-yl)methyl)cyclohexyl)-2-methylnicotinamide | Intermediate-16, Mesylate-1 | A1 |
| 37 | 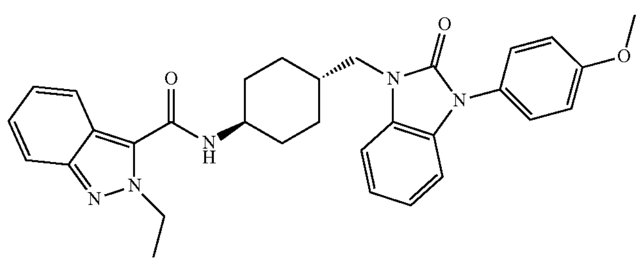 [SMILES: CCn1nc2ccccc2c1C(=O)N[C@H]1CC[C@H](Cn2c(=O)n(-c3ccc(OC)cc3)c3ccccc32)CC1] | 2-ethyl-N-((1r,4r)-4-((3-(4-methoxyphenyl)-2-oxo-2,3-dihydro-1H-benzo[d]imidazol-1-yl)methyl)cyclohexyl)-2H-indazole-3-carboxamide | , Mesylate-2 | A1 |

TABLE 2-continued

| Ex. | Structure | Name | Reactants | Method |
|---|---|---|---|---|
| 38 | 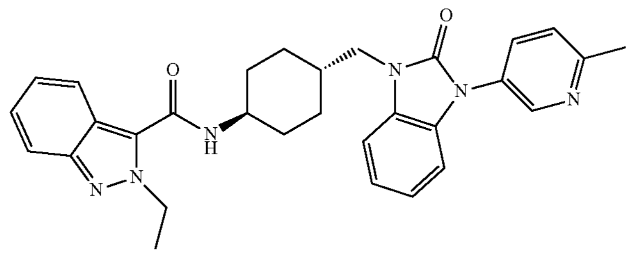 [SMILES: CCn1nc2ccccc2c1C(=O)N[C@H]1CC[C@H](Cn2c(=O)n(-c3ccc(C)nc3)c3ccccc32)CC1] | 2-ethyl-N-((1r,4r)-4-((3-(6-methylpyridin-3-yl)-2-oxo-2,3-dihydro-1H-benzo[d]imidazol-1-yl)methyl)cyclohexyl)-2H-indazole-3-carboxamide | Intermediate-13, Mesylate-2 | A1 |
| 39 | 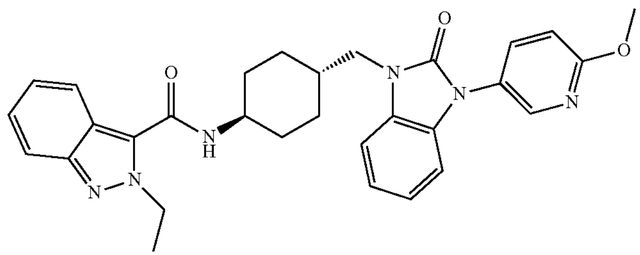 [SMILES: CCn1nc2ccccc2c1C(=O)N[C@H]1CC[C@H](Cn2c(=O)n(-c3ccc(OC)nc3)c3ccccc32)CC1] | 2-ethyl-N-((1r,4r)-4-((3-(6-methoxypyridin-3-yl)-2-oxo-2,3-dihydro-1H-benzo[d]imidazol-1-yl)methyl)cyclohexyl)-2H-indazole-3-carboxamide | Intermediate-12, Mesylate-2 | A1 |
| 40 | 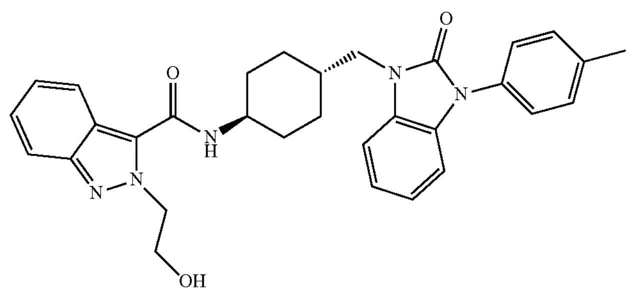 [SMILES: Cc1ccc(-n2c(=O)n(C[C@H]3CC[C@H](NC(=O)c4c5ccccc5nn4CCO)CC3)c3ccccc32)cc1] | 2-(2-hydroxyethyl)-N-((1r,4r)-4-((2-oxo-3-(p-tolyl)-2,3-dihydro-1H-benzo[d]imidazol-1-yl)methyl)cyclohexyl)-2H-indazole-3-carboxamide | see Example synthesis part | |

TABLE 2-continued

| Ex. | Structure | Name | Reactants | Method |
|---|---|---|---|---|
| 41 | 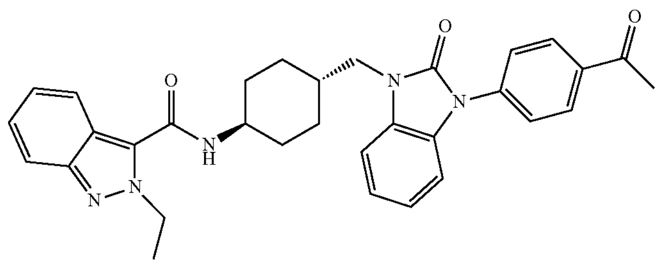 [SMILES: CCn1nc2ccccc2c1C(=O)N[C@H]1CC[C@H](Cn2c(=O)n(-c3ccc(C(C)=O)cc3)c3ccccc32)CC1] | N-((1r,4r)-4-((3-(4-acetylphenyl)-2-oxo-2,3-dihydro-1H-benzo[d]imidazol-1-yl)methyl)cyclohexyl)-2-ethyl-2H-indazole-3-carboxamide | Intermediate-7, Mesylate-2 | A1 |
| 42 | 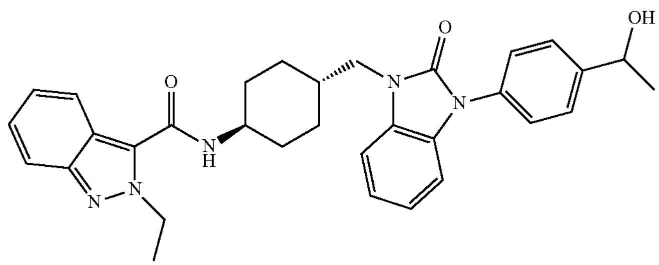 [SMILES: CCn1nc2ccccc2c1C(=O)N[C@H]1CC[C@H](Cn2c(=O)n(-c3ccc(C(C)O)cc3)c3ccccc32)CC1] | 2-ethyl-N-((1r,4r)-4-((3-(4-(1-hydroxyethyl)phenyl)-2-oxo-2,3-dihydro-1H-benzo[d]imidazol-1-yl)methyl)cyclohexyl)-2H-indazole-3-carboxamide | Example 41 | E |
| 43 | 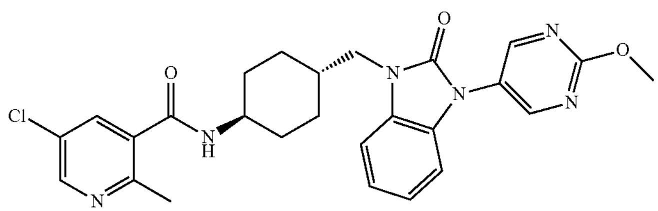 [SMILES: COc1ncc(-n2c(=O)n(C[C@H]3CC[C@H](NC(=O)c4cc(Cl)cnc4C)CC3)c3ccccc32)cn1] | 5-chloro-N-((1r,4r)-4-((3-(2-methoxypyrimidin-5-yl)-2-oxo-2,3-dihydro-1H-benzo[d]imidazol-1-yl)methyl)cyclohexyl)-2-methylnicotinamide | Intermediate-17, Mesylate-1 | A1 |
| 44 | 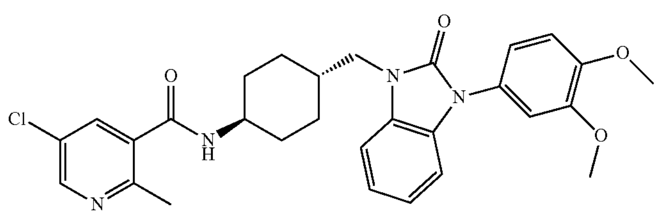 [SMILES: COc1ccc(-n2c(=O)n(C[C@H]3CC[C@H](NC(=O)c4cc(Cl)cnc4C)CC3)c3ccccc32)cc1OC] | 5-chloro-N-((1r,4r)-4-((3-(3,4-dimethoxyphenyl)-2-oxo-2,3-dihydro-1H-benzo[d]imidazol-1-yl)methyl)cyclohexyl)-2-methylnicotinamide | Intermediate-18, Mesylate-1 | A1 |

TABLE 2-continued

| Ex. | Structure | Name | Reactants | Method |
|---|---|---|---|---|
| 45 | 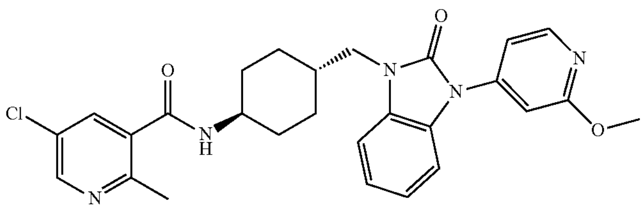 [SMILES: COc1cc(-n2c(=O)n(C[C@H]3CC[C@H](NC(=O)c4cc(Cl)cnc4C)CC3)c3ccccc32)ccn1] | 5-chloro-N-((1r,4r)-4-((3-(2-methoxypyridin-4-yl)-2-oxo-2,3-dihydro-1H-benzo[d]imidazol-1-yl)methyl)cyclohexyl)-2-methylnicotinamide | Intermediate-19, Mesylate-1 | A1 |
| 46 | 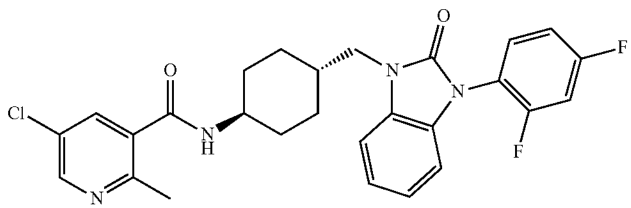 [SMILES: Cc1ncc(Cl)cc1C(=O)N[C@H]1CC[C@H](Cn2c(=O)n(-c3ccc(F)cc3F)c3ccccc32)CC1] | 5-chloro-N-((1r,4r)-4-((3-(2,4-difluorophenyl)-2-oxo-2,3-dihydro-1H-benzo[d]imidazol-1-yl)methyl)cyclohexyl)-2-methylnicotinamide | Intermediate-20, Mesylate-1 | A1 |
| 47 | 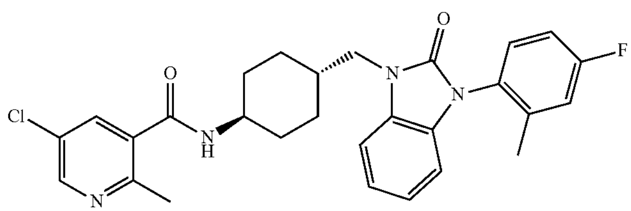 [SMILES: Cc1cc(F)ccc1-n1c(=O)n(C[C@H]2CC[C@H](NC(=O)c3cc(Cl)cnc3C)CC2)c2ccccc21] | 5-chloro-N-((1r,4r)-4-((3-(4-fluoro-2-methylphenyl)-2-oxo-2,3-dihydro-1H-benzo[d]imidazol-1-yl)methyl)cyclohexyl)-2-methylnicotinamide | Intermediate-21, Mesylate-1 | A1 |
| 48 | 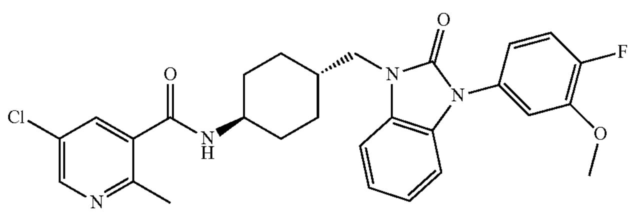 [SMILES: COc1cc(-n2c(=O)n(C[C@H]3CC[C@H](NC(=O)c4cc(Cl)cnc4C)CC3)c3ccccc32)ccc1F] | 5-chloro-N-((1r,4r)-4-((3-(4-fluoro-3-methoxyphenyl)-2-oxo-2,3-dihydro-1H-benzo[d]imidazol-1-yl)methyl)cyclohexyl)-2-methylnicotinamide | Intermediate-22, Mesylate-1 | A1 |
| 49 | 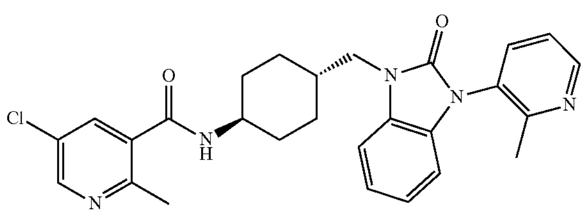 [SMILES: Cc1ncc(Cl)cc1C(=O)N[C@H]1CC[C@H](Cn2c(=O)n(-c3cccnc3C)c3ccccc32)CC1] | 5-chloro-2-methyl-N-((1r,4r)-4-((3-(2-methylpyridin-3-yl)-2-oxo-2,3-dihydro-1H-benzo[d]imidazol-1-yl)methyl)cyclohexyl)nicotinamide | Intermediate-23, Mesylate-1 | A1 |

TABLE 2-continued

| Ex. | Structure | Name | Reactants | Method |
|---|---|---|---|---|
| 50 | 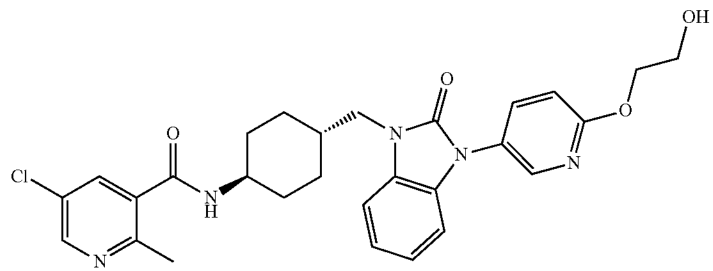 [SMILES: Cc1ncc(Cl)cc1C(=O)N[C@H]1CC[C@H](Cn2c(=O)n(-c3ccc(OCCO)nc3)c3ccccc32)CC1] | 5-chloro-N-((1r,4r)-4-(3-(6-(2-hydroxyethoxy)pyridin-3-yl)-2-oxo-2,3-dihydro-1H-benzo[d]imidazol-1-yl)methyl)cyclohexyl)-2-methylnicotinamide | see Example synthesis part | |
| 51 | 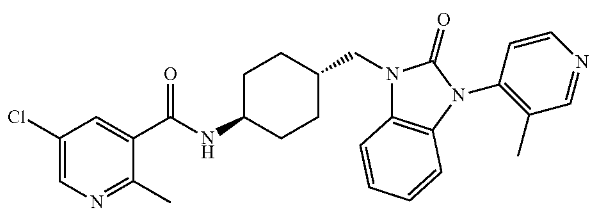 [SMILES: Cc1cnccc1-n1c(=O)n(C[C@H]2CC[C@H](NC(=O)c3cc(Cl)cnc3C)CC2)c2ccccc21] | 5-chloro-2-methyl-N-((1r,4r)-4-((3-(3-methylpyridin-4-yl)-2-oxo-2,3-dihydro-1H-benzo[d]imidazol-1-yl)methyl)cyclohexyl)nicotinamide | Intermediate-25, Mesylate-1 | A1 |
| 52 | 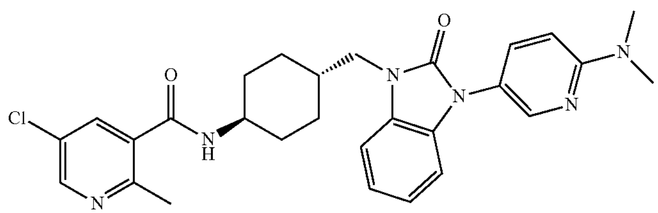 | 5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-methylnicotinamide | Intermediate-26, Mesylate-1 | A1 |
| 53 | 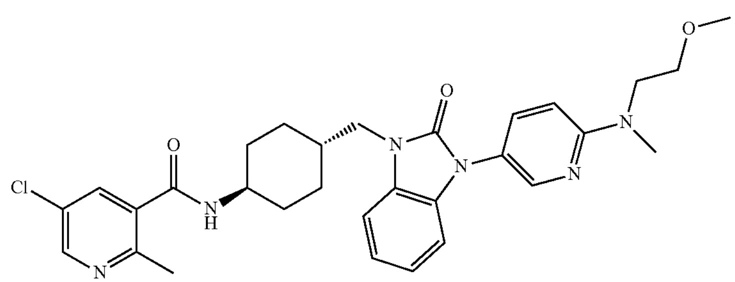 [SMILES: COCCN(C)c1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-((2-methoxyethyl)(methyl)amino)pyridin-3-yl)-2-oxo-2,3-dihydro-1H-benzo[d]imidazol-1-yl)methyl)cyclohexyl)-2-methylnicotinamide | Intermediate-27, Mesylate-1 | A1 |

TABLE 2-continued

| Ex. | Structure | Name | Reactants | Method |
|---|---|---|---|---|
| 54 | 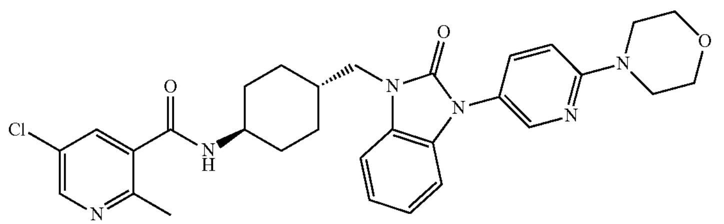 [SMILES: Cc1ncc(Cl)cc1C(=O)N[C@H]1CC[C@H](Cn2c(=O)n(-c3ccc(N4CCOCC4)nc3)c3ccccc32)CC1] | 5-chloro-2-methyl-N-((1r,4r)-4-((3-(6-morpholinopyridin-3-yl)-2-oxo-2,3-dihydro-1H-benzo[d]imidazol-1-yl)methyl)cyclohexyl)nicotinamide | Intermediate-28, Mesylate-1 | A1 |
| 55 | 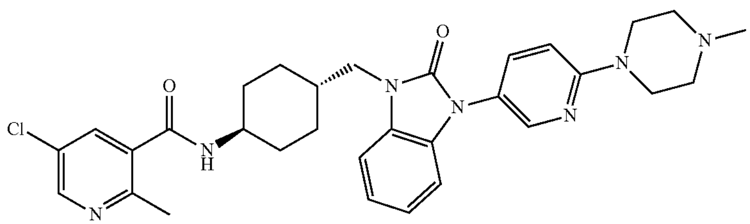 [SMILES: Cc1ncc(Cl)cc1C(=O)N[C@H]1CC[C@H](Cn2c(=O)n(-c3ccc(N4CCN(C)CC4)nc3)c3ccccc32)CC1] | 5-chloro-2-methyl-N-((1r,4r)-4-((3-(6-(4-methylpiperazin-1-yl)pyridin-3-yl)-2-oxo-2,3-dihydro-1H-benzo[d]imidazol-1-yl)methyl)cyclohexyl)nicotinamide | Intermediate-29, Mesylate-1 | A1 |
| 56 | 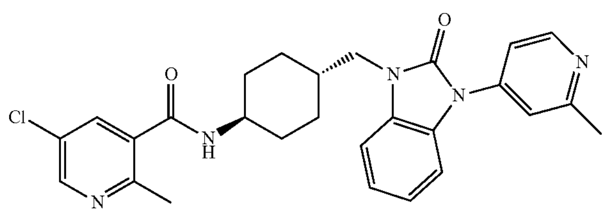 | 5-chloro-2-methyl-N-((1r,4r)-4-((3-(2-methylpyridin-4-yl)-2-oxo-2,3-dihydro-1H-benzo[d]imidazol-1-yl)methyl)cyclohexyl)nicotinamide | Intermediate-30, Mesylate-1 | A1 |
| 57 | 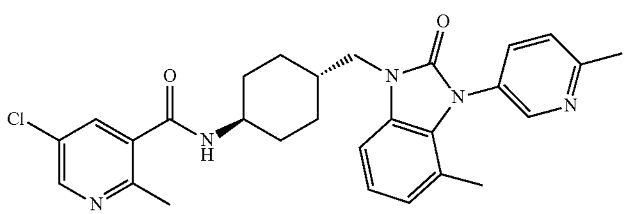 [SMILES: Cc1ccc(-n2c(=O)n(C[C@H]3CC[C@H](NC(=O)c4cc(Cl)cnc4C)CC3)c3cccc(C)c32)cn1] | 5-chloro-2-methyl-N-((1r,4r)-4-((4-methyl-3-(6-methylpyridin-3-yl)-2-oxo-2,3-dihydro-1H-benzo[d]imidazol-1-yl)methyl)cyclohexyl)nicotinamide | Intermediate-31, Mesylate-1 | A1 |

TABLE 2-continued

| Ex. | Structure | Name | Reactants | Method |
|---|---|---|---|---|
| 58 | 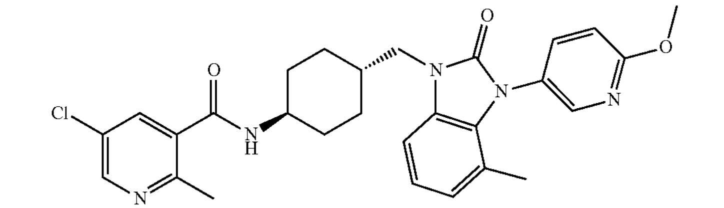 [SMILES: COc1ccc(-n2c(=O)n(C[C@H]3CC[C@H](NC(=O)c4cc(Cl)cnc4C)CC3)c3cccc(C)c32)cn1] | 5-chloro-N-((1r,4r)-4-((3-(6-methoxypyridin-3-yl)-4-methyl-2-oxo-2,3-dihydro-1H-benzo[d]imidazol-1-yl)methyl)cyclohexyl)-2-methylnicotinamide | Intermediate-32, Mesylate-1 | A1 |
| 59 | 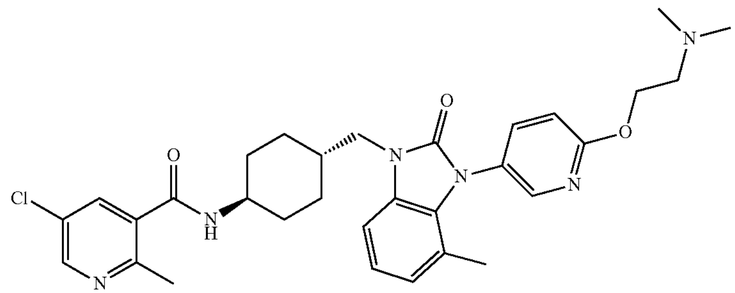 [SMILES: Cc1ncc(Cl)cc1C(=O)N[C@H]1CC[C@H](Cn2c(=O)n(-c3ccc(OCCN(C)C)nc3)c3c(C)cccc32)CC1] | 5-chloro-N-((1r,4r)-4-((3-(6-(2-(dimethylamino)ethoxy)pyridin-3-yl)-4-methyl-2-oxo-2,3-dihydro-1H-benzo[d]imidazol-1-yl)methyl)cyclohexyl)-2-methylnicotinamide | Intermediate-33, Mesylate-1 | A1 |
| 60 | 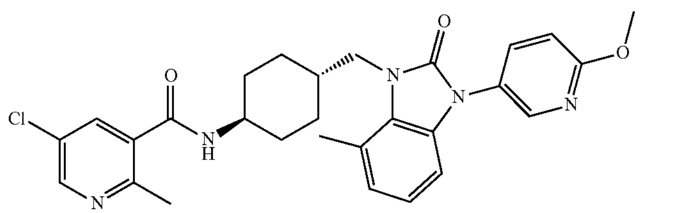 [SMILES: COc1ccc(-n2c(=O)n(C[C@H]3CC[C@H](NC(=O)c4cc(Cl)cnc4C)CC3)c3c(C)cccc32)cn1] | 5-chloro-N-((1r,4r)-4-((3-(6-methoxypyridin-3-yl)-7-methyl-2-oxo-2,3-dihydro-1H-benzo[d]imidazol-1-yl)methyl)cyclohexyl)-2-methylnicotinamide | Intermediate-34, Mesylate-1 | A1 |
| 61 | 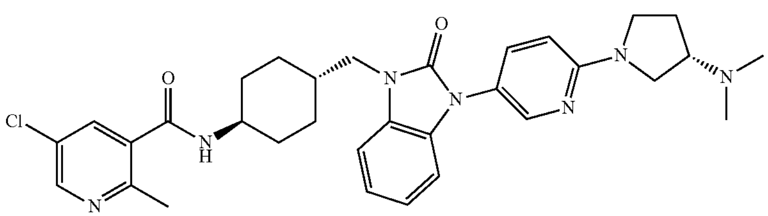 [SMILES: Cc1ncc(Cl)cc1C(=O)N[C@H]1CC[C@H](Cn2c(=O)n(-c3ccc(N4CC[C@H](N(C)C)C4)nc3)c3ccccc32)CC1] | 5-chloro-N-((1S,4r)-4-(3-((S)-3-(dimethylamino)pyrrolidin-1-yl)pyridin-3-yl)-2-oxo-2,3-dihydro-1H-benzo[d]imidazol-1-yl)methyl)cyclohexyl)-2-methylnicotinamide | Intermediate-35, Mesylate-1 | A1 |

TABLE 2-continued

| Ex. | Structure | Name | Reactants | Method |
|---|---|---|---|---|
| 62 | 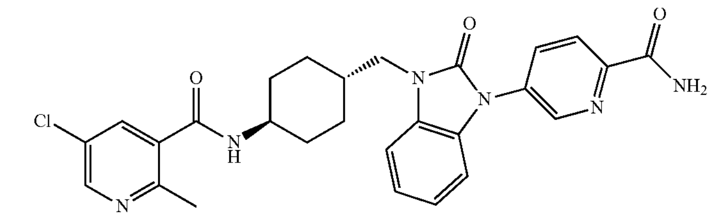 [SMILES: Cc1ncc(Cl)cc1C(=O)N[C@H]1CC[C@H](Cn2c(=O)n(-c3ccc(C(N)=O)nc3)c3ccccc32)CC1] | 5-(3-(((1r,4r)-4-(5-chloro-2-methyl)nicotinamido)cyclohexyl)methyl)-2-oxo-2,3-dihydro-1H-benzo[d]imidazol-1-yl)picolinamide | see Example synthesis part | |
| 63 | 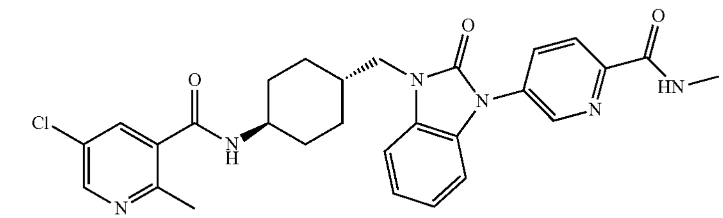 [SMILES: CNC(=O)c1ccc(-n2c(=O)n(C[C@H]3CC[C@H](NC(=O)c4cc(Cl)cnc4C)CC3)c3ccccc32)cn1] | 5-(3-(((1r,4r)-4-(5-chloro-2-methyl)nicotinamido)cyclohexyl)methyl)-2-oxo-2,3-dihydro-1H-benzo[d]imidazol-1-yl)-N-methylpicolinamide | see Example synthesis part | |
| 64 | 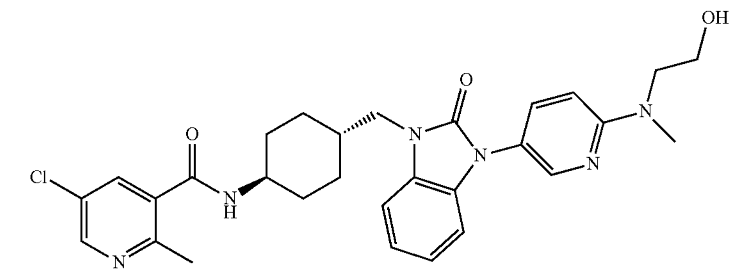 [SMILES: Cc1ncc(Cl)cc1C(=O)N[C@H]1CC[C@H](Cn2c(=O)n(-c3ccc(N(C)CCO)nc3)c3ccccc32)CC1] | 5-chloro-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)-2-methylnicotinamide | Intermediate-37, Mesylate-1 | A1 |
| 65 | 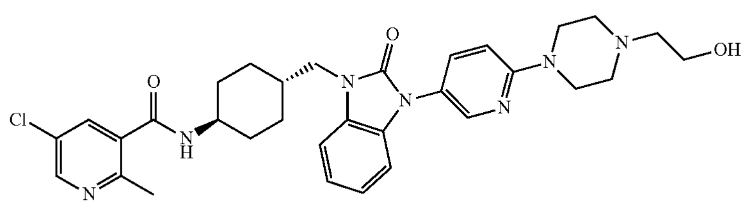 [SMILES: Cc1ncc(Cl)cc1C(=O)N[C@H]1CC[C@H](Cn2c(=O)n(-c3ccc(N4CCN(CCO)CC4)nc3)c3ccccc32)CC1] | 5-chloro-N-((1r,4r)-4-((3-(6-(4-(2-hydroxyethyl)piperazin-1-yl)pyridin-3-yl)-2-oxo-2,3-dihydro-1H-benzo[d]imidazol-1-yl)methyl)cyclohexyl)-2-methylnicotinamide | Intermediate-38, Mesylate-1 | A1 |

TABLE 2-continued

| Ex. | Structure | Name | Reactants | Method |
|---|---|---|---|---|
| 66 | 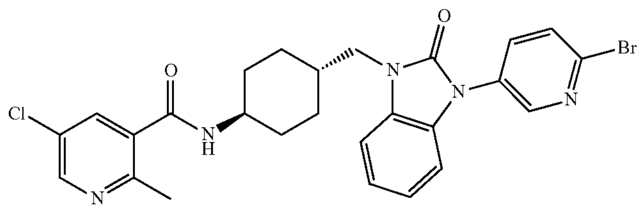 [SMILES: Cc1ncc(Cl)cc1C(=O)N[C@H]1CC[C@H](Cn2c(=O)n(-c3ccc(Br)nc3)c3ccccc32)CC1] | N-((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide | Intermediate-39, Mesylate-1 | A1 |
| 67 | 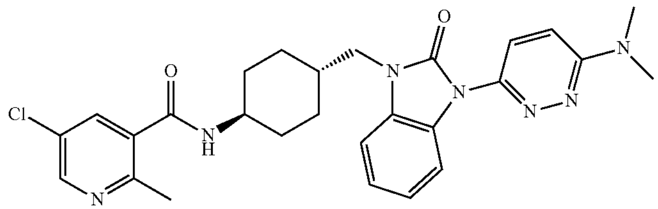 | 5-chloro-N-((1r,4r)-4-((3-(6-(dimethylamino)pyridazin-3-yl)-2-oxo-2,3-dihydro-1H-benzo[d]imidazol-1-yl)methyl)cyclohexyl)-2-methylnicotinamide | Intermediate-40, Mesylate-1 | A1 |
| 68 | 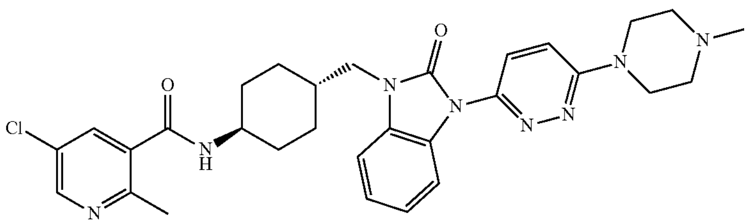 [SMILES: Cc1ncc(Cl)cc1C(=O)N[C@H]1CC[C@H](Cn2c(=O)n(-c3ccc(N4CCN(C)CC4)nn3)c3ccccc32)CC1] | 5-chloro-2-methyl-N-((1r,4r)-4-((3-(6-(4-methylpiperazin-1-yl)pyridazin-3-yl)-2-oxo-2,3-dihydro-1H-benzo[d]imidazol-1-yl)methyl)cyclohexyl)nicotinamide | Intermediate-41, Mesylate-1 | A1 |
| 69 | 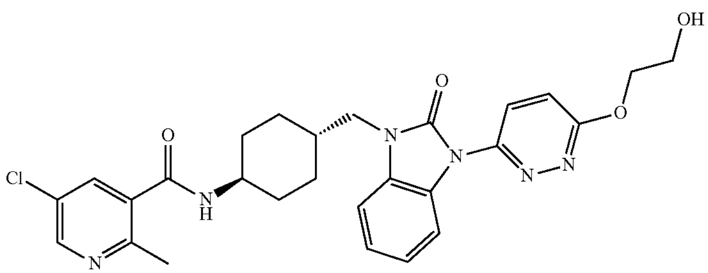 [SMILES: Cc1ncc(Cl)cc1C(=O)N[C@H]1CC[C@H](Cn2c(=O)n(-c3ccc(OCCO)nn3)c3ccccc32)CC1] | 5-chloro-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 70 | 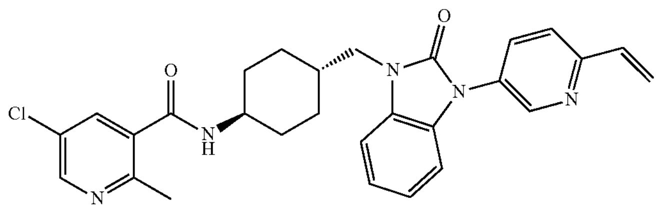 [SMILES: C=Cc1ccc(-n2c(=O)n(C[C@H]3CC[C@H](NC(=O)c4cc(Cl)cnc4C)CC3)c3ccccc32)cn1] | 5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide | Ex 66, (pinacol vinylboronate) | F |
| 71 | 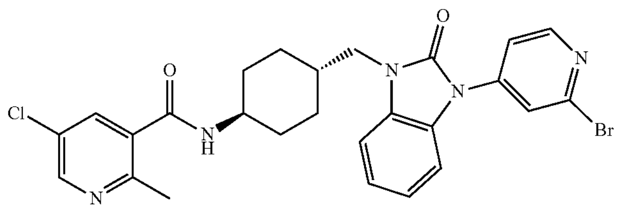 [SMILES: Cc1ncc(Cl)cc1C(=O)N[C@H]1CC[C@H](Cn2c(=O)n(-c3ccnc(Br)c3)c3ccccc32)CC1] | N-((1r,4r)-4-((3-(2-bromopyridin-4-yl)-2-oxo-2,3-dihydro-1H-benzo[d]imidazol-1-yl)methyl)cyclohexyl)-5-chloro-2-methylnicotinamide | Intermediate-43, Mesylate-1 | A1 |
| 72 | 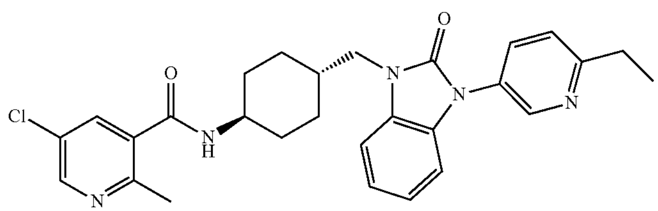 [SMILES: CCc1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-ethylpyridin-3-yl)-2-oxo-2,3-dihydro-1H-benzo[d]imidazol-1-yl)methyl)cyclohexyl)-2-methylnicotinamide | Ex 70 | G |
| 73 | 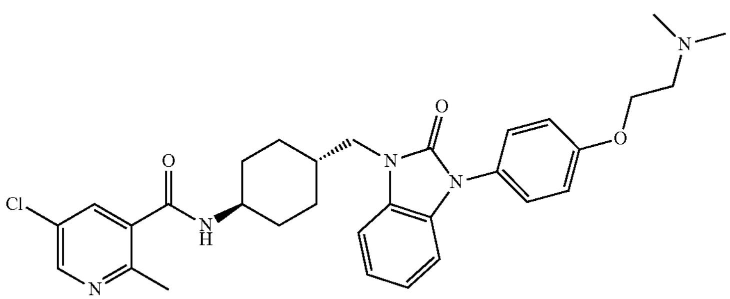 [SMILES: Cc1ncc(Cl)cc1C(=O)N[C@H]1CC[C@H](Cn2c(=O)n(-c3ccc(OCCN(C)C)cc3)c3ccccc32)CC1] | 5-chloro-N-((1r,4r)-4-((3-(4-(2-(dimethylamino)ethoxy)phenyl)-2-oxo-2,3-dihydro-1H-benzo[d]imidazol-1-yl)methyl)cyclohexyl)-2-methylnicotinamide | Intermediate-44, Mesylate-1 | A1 |

TABLE 2-continued

| Ex. | Structure | Name | Reactants | Method |
|---|---|---|---|---|
| 74 | 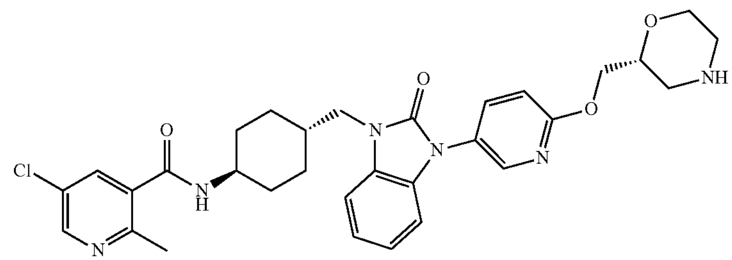 [SMILES: Cc1ncc(Cl)cc1C(=O)N[C@H]1CC[C@H](Cn2c(=O)n(-c3ccc(OC[C@H]4CNCCO4)nc3)c3ccccc32)CC1] | 5-chloro-2-methyl-N-((1R,4r)-4-((3-(6-((R)-morpholin-2-yl-methoxy)pyridin-3-yl)-2-oxo-2,3-dihydro-1H-benzo[d]imidazol-1-yl)methyl)cyclohexyl)nicotinamide | see Example synthesis part | |
| 75 | 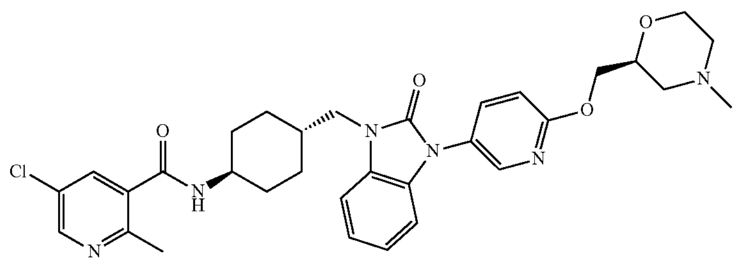 [SMILES: Cc1ncc(Cl)cc1C(=O)N[C@H]1CC[C@H](Cn2c(=O)n(-c3ccc(OC[C@@H]4CN(C)CCO4)nc3)c3ccccc32)CC1] | 5-chloro-2-methyl-N-((1S,4r)-4-((3-(6-(((S)-4-methylmorpholin-2-yl)methoxy)pyridin-3-yl)-2-oxo-2,3-dihydro-1H-benzo[d]imidazol-1-yl)methyl)cyclohexyl)nicotinamide | Intermediate-46 | H |
| 76 | 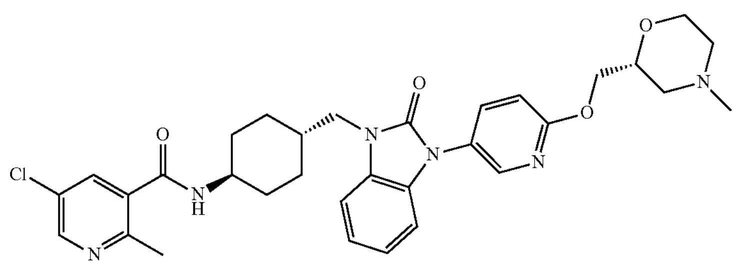 [SMILES: Cc1ncc(Cl)cc1C(=O)N[C@H]1CC[C@H](Cn2c(=O)n(-c3ccc(OC[C@H]4CN(C)CCO4)nc3)c3ccccc32)CC1] | 5-chloro-2-methyl-N-((1R,4r)-4-((3-(6-(((R)-4-methylmorpholin-2-yl)methoxy)pyridin-3-yl)-2-oxo-2,3-dihydro-1H-benzo[d]imidazol-1-yl)methyl)cyclohexyl)nicotinamide | Ex 74 | H |
| 77 | 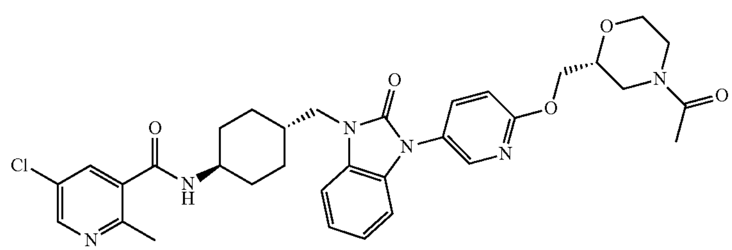 [SMILES: CC(=O)N1CCO[C@@H](COc2ccc(-n3c(=O)n(C[C@H]4CC[C@H](NC(=O)c5cc(Cl)cnc5C)CC4)c4ccccc43)cn2)C1] | N-((1R,4r)-4-((3-(6-(((R)-4-acetylmorpholin-2-yl)methoxy)pyridin-3-yl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 78 | 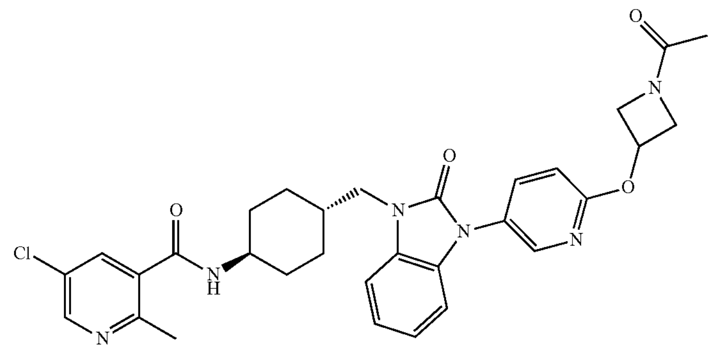 [SMILES: CC(=O)N1CC(Oc2ccc(-n3c(=O)n(C[C@H]4CC[C@H](NC(=O)c5cc(Cl)cnc5C)CC4)c4ccccc43)cn2)C1] | N-((1r,4r)-4-(3-(6-((1-acetylazetidin-3-yl)oxy)pyridin-3-yl)-2-oxo-2,3-dihydro-1H-benzo[d]imidazol-1-yl)methyl)cyclohexyl)-5-chloro-2-methylnicotinamide | see Example synthesis part | |
| 79 | 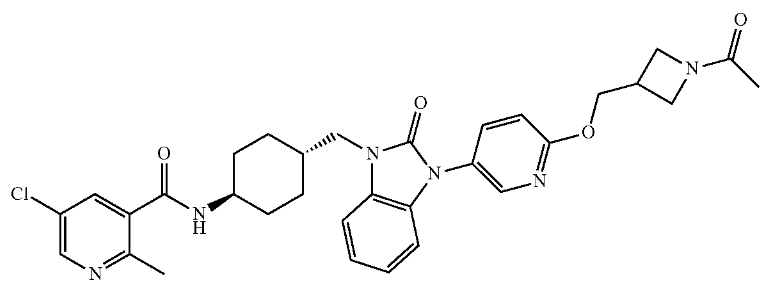 [SMILES: CC(=O)N1CC(COc2ccc(-n3c(=O)n(C[C@H]4CC[C@H](NC(=O)c5cc(Cl)cnc5C)CC4)c4ccccc43)cn2)C1] | N-((1r,4r)-4-(3-(6-((1-acetylazetidin-3-yl)methoxy)pyridin-3-yl)-2-oxo-2,3-dihydro-1H-benzo[d]imidazol-1-yl)methyl)cyclohexyl)-5-chloro-2-methylnicotinamide | see Example synthesis part | |
| 80 | 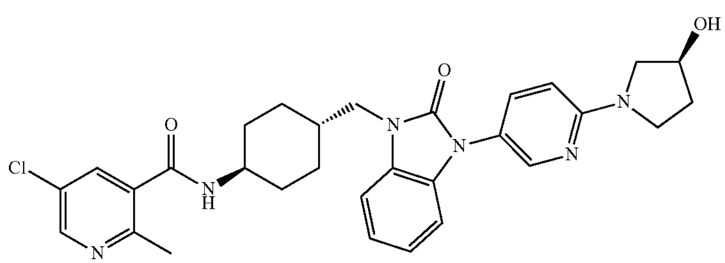 [SMILES: Cc1ncc(Cl)cc1C(=O)N[C@H]1CC[C@H](Cn2c(=O)n(-c3ccc(N4CC[C@H](O)C4)nc3)c3ccccc32)CC1] | 5-chloro-N-((1S,4r)-4-(3-(6-((S)-3-hydroxypyrrolidin-1-yl)pyridin-3-yl)-2-oxo-2,3-dihydro-1H-benzo[d]imidazol-1-yl)methyl)cyclohexyl)-2-methylnicotinamide | Intermediate-49, Mesylate-1 | A1 |

TABLE 2-continued

| Ex. | Structure | Name | Reactants | Method |
|---|---|---|---|---|
| 81 | 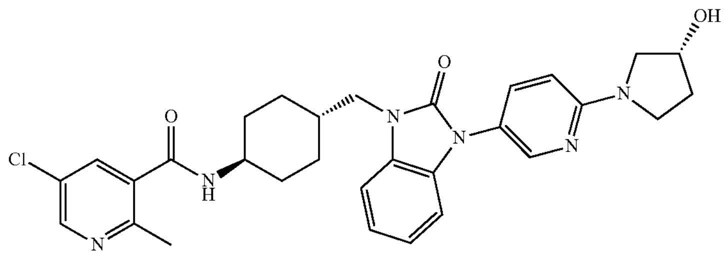 [SMILES: Cc1ncc(Cl)cc1C(=O)N[C@H]1CC[C@H](Cn2c(=O)n(-c3ccc(N4CC[C@@H](O)C4)nc3)c3ccccc32)CC1] | 5-chloro-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)-2-methylnicotinamide | Intermediate-50, Mesylate-1 | A1 |
| 82 | 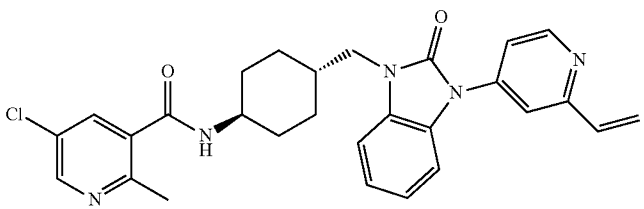 [SMILES: C=Cc1cc(-n2c(=O)n(C[C@H]3CC[C@H](NC(=O)c4cc(Cl)cnc4C)CC3)c3ccccc32)ccn1] | 5-chloro-2-methyl-N-((1r,4r)-4-((2-oxo-3-(2-vinylpyridin-4-yl)-2,3-dihydro-1H-benzo[d]imidazol-1-yl)methyl)cyclohexyl)nicotinamide | Ex 71, (vinyl pinacol boronate) | F |
| 83 | 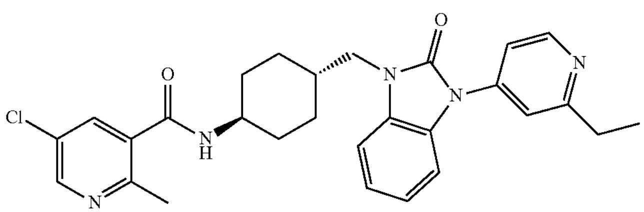 [SMILES: CCc1cc(-n2c(=O)n(C[C@H]3CC[C@H](NC(=O)c4cc(Cl)cnc4C)CC3)c3ccccc32)ccn1] | 5-chloro-N-((1r,4r)-4-((3-(2-ethylpyridin-4-yl)-2-oxo-2,3-dihydro-1H-benzo[d]imidazol-1-yl)methyl)cyclohexyl)-2-methylnicotinamide | Ex 82 | G |
| 84 | 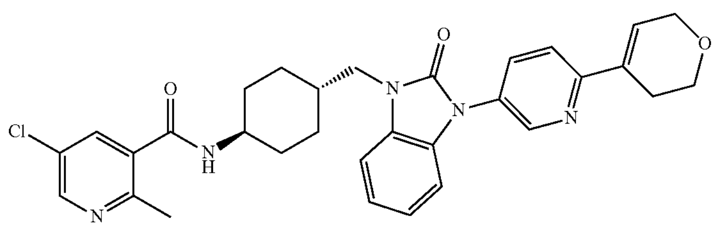 [SMILES: Cc1ncc(Cl)cc1C(=O)N[C@H]1CC[C@H](Cn2c(=O)n(-c3ccc(C4=CCOCC4)nc3)c3ccccc32)CC1] | 5-chloro-N-((1r,4r)-4-((3-(6-(3,6-dihydro-2H-pyran-4-yl)pyridin-3-yl)-2-oxo-2,3-dihydro-1H-benzo[d]imidazol-1-yl)methyl)cyclohexyl)-2-methylnicotinamide | Ex 66, (dihydropyran pinacol boronate) | F |

TABLE 2-continued

| Ex. | Structure | Name | Reactants | Method |
|---|---|---|---|---|
| 85 | 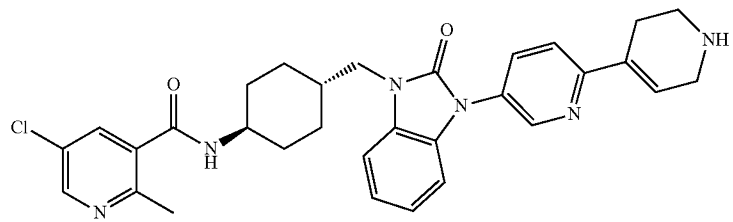 [SMILES: Cc1ncc(Cl)cc1C(=O)N[C@H]1CC[C@H](Cn2c(=O)n(-c3ccc(C4=CCNCC4)nc3)c3ccccc32)CC1] | 5-chloro-2-methyl-N-((1r,4r)-4-((2-oxo-3-(1',2',3',6'-tetrahydro-[2,4'-bipyridin]-5-yl)-2,3-dihydro-1H-benzo[d]imidazol-1-yl)methyl)cyclohexyl)nicotinamide | see Example synthesis part | |
| 86 | 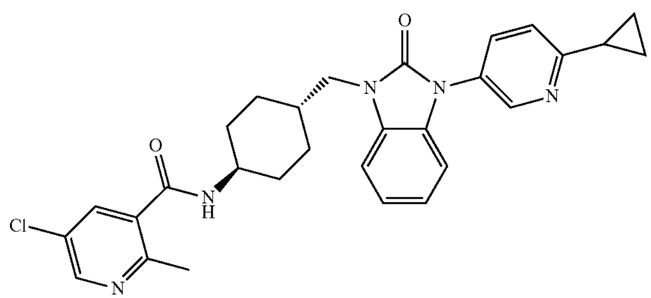 [SMILES: Cc1ncc(Cl)cc1C(=O)N[C@H]1CC[C@H](Cn2c(=O)n(-c3ccc(C4CC4)nc3)c3ccccc32)CC1] | 5-chloro-N-((1r,4r)-4-((3-(6-cyclopropylpyridin-3-yl)-2-oxo-2,3-dihydro-1H-benzo[d]imidazol-1-yl)methyl)cyclohexyl)-2-methylnicotinamide | Intermediate-51, Mesylate-1 | A2 |
| 87 | 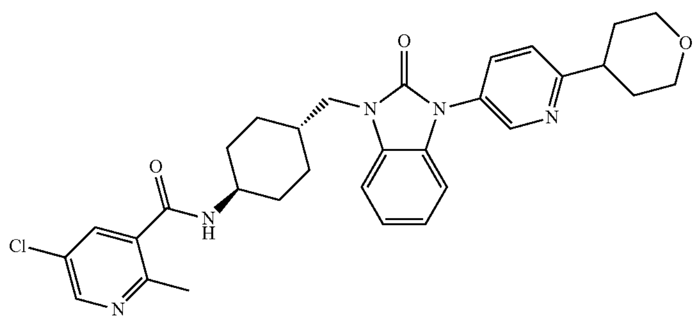 [SMILES: Cc1ncc(Cl)cc1C(=O)N[C@H]1CC[C@H](Cn2c(=O)n(-c3ccc(C4CCOCC4)nc3)c3ccccc32)CC1] | 5-chloro-2-methyl-N-((1r,4r)-4-((2-oxo-3-(6-(tetrahydro-2H-pyran-4-yl)pyridin-3-yl)-2,3-dihydro-1H-benzo[d]imidazol-1-yl)methyl)cyclohexyl)nicotinamide | Intermediate-52, Mesylate-1 | A2 |
| 88 | 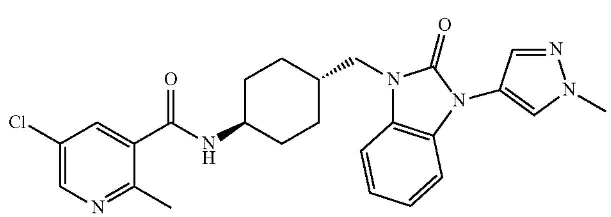 [SMILES: Cc1ncc(Cl)cc1C(=O)N[C@H]1CC[C@H](Cn2c(=O)n(-c3cnn(C)c3)c3ccccc32)CC1] | 5-chloro-2-methyl-N-((1r,4r)-4-((3-(1-methyl-1H-pyrazol-4-yl)-2-oxo-2,3-dihydro-1H-benzo[d]imidazol-1-yl)methyl)cyclohexyl)nicotinamide | Intermediate-53, Mesylate-1 | A1 |

TABLE 2-continued

| Ex. | Structure | Name | Reactants | Method |
|---|---|---|---|---|
| 89 | 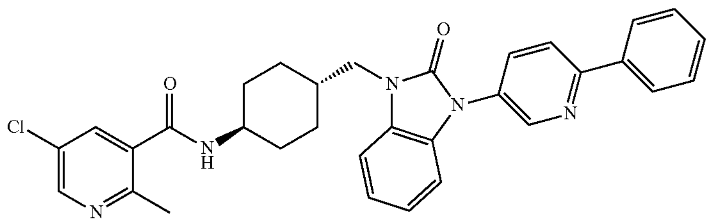 [SMILES: Cc1ncc(Cl)cc1C(=O)N[C@H]1CC[C@H](Cn2c(=O)n(-c3ccc(-c4ccccc4)nc3)c3ccccc32)CC1] | 5-chloro-2-methyl-N-((1r,4r)-4-((2-oxo-3-(6-phenylpyridin-3-yl)-2,3-dihydro-1H-benzo[d]imidazol-1-yl)methyl)cyclohexyl)nicotinamide | Ex 66, (HO)₂B-Ph | I |
| 90 | 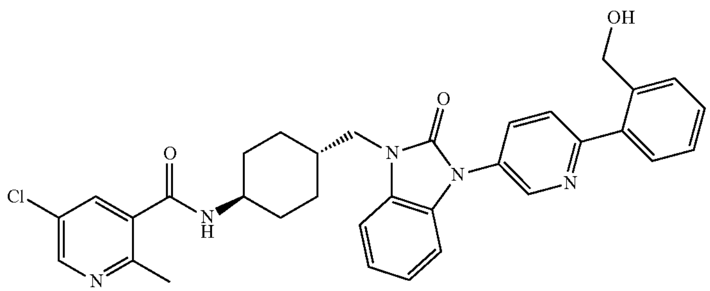 [SMILES: Cc1ncc(Cl)cc1C(=O)N[C@H]1CC[C@H](Cn2c(=O)n(-c3ccc(-c4ccccc4CO)nc3)c3ccccc32)CC1] | 5-chloro-N-((1r,4r)-4-((3-(6-(2-(hydroxymethyl)phenyl)pyridin-3-yl)-2-oxo-2,3-dihydro-1H-benzo[d]imidazol-1-yl)methyl)cyclohexyl)-2-methylnicotinamide | Ex 66, (benzoxaborole) | I |
| 91 | 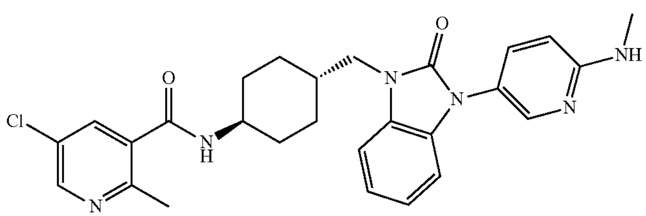 [SMILES: CNc1ccc(-n2c(=O)n(C[C@H]3CC[C@H](NC(=O)c4cc(Cl)cnc4C)CC3)c3ccccc32)cn1] | 5-chloro-2-methyl-N-((1r,4r)-4-((3-(6-(methylamino)pyridin-3-yl)-2-oxo-2,3-dihydro-1H-benzo[d]imidazol-1-yl)methyl)cyclohexyl)nicotinamide | Intermediate-54, methanamine hydrochloride | J |
| 92 | 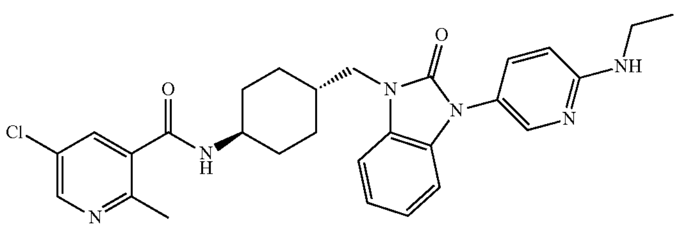 [SMILES: CCNc1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-(ethylamino)pyridin-3-yl)-2-oxo-2,3-dihydro-1H-benzo[d]imidazol-1-yl)methyl)cyclohexyl)-2-methylnicotinamide | Intermediate-54, ethanamine hydrochloride | J |

TABLE 2-continued

| Ex. | Structure | Name | Reactants | Method |
|---|---|---|---|---|
| 93 | 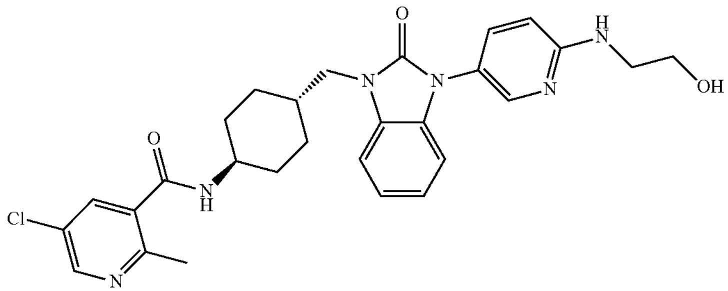 [SMILES: Cc1ncc(Cl)cc1C(=O)N[C@H]1CC[C@H](Cn2c(=O)n(-c3ccc(NCCO)nc3)c3ccccc32)CC1] | 5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-methylnicotinamide | Ex 66, H₂N~~OH | K |
| 94 | 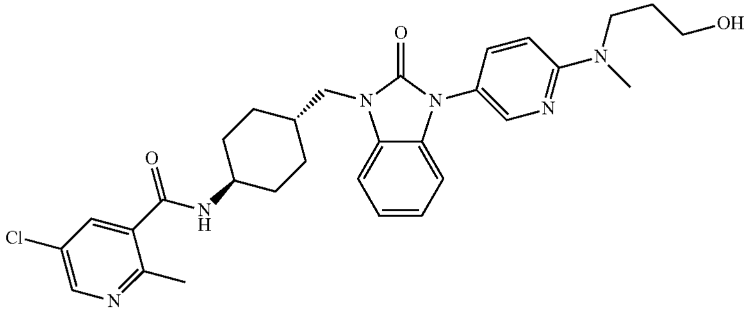 [SMILES: Cc1ncc(Cl)cc1C(=O)N[C@H]1CC[C@H](Cn2c(=O)n(-c3ccc(N(C)CCCO)nc3)c3ccccc32)CC1] | 5-chloro-N-((1r,4r)-4-((3-(6-((3-hydroxypropyl)(methyl)amino)pyridin-3-yl)-2-oxo-2,3-dihydro-1H-benzo[d]imidazol-1-yl)methyl)cyclohexyl)-2-methylnicotinamide | Ex 66, CH₃NH-propyl-OH | K |
| 95 | 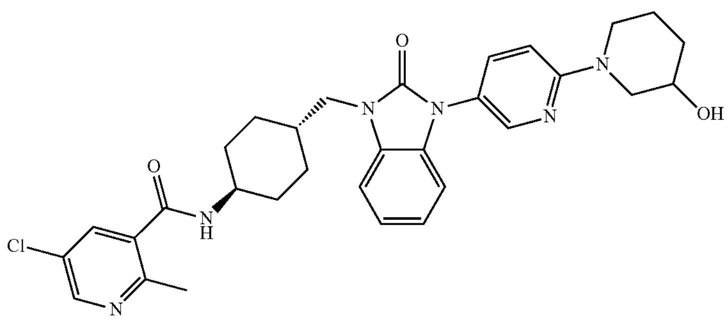 [SMILES: Cc1ncc(Cl)cc1C(=O)N[C@H]1CC[C@H](Cn2c(=O)n(-c3ccc(N4CCCC(O)C4)nc3)c3ccccc32)CC1] | 5-chloro-N-((1r,4r)-4-((3-(6-(3-hydroxypiperidin-1-yl)pyridin-3-yl)-2-oxo-2,3-dihydro-1H-benzo[d]imidazol-1-yl)methyl)cyclohexyl)-2-methylnicotinamide | Ex 66, 3-hydroxypiperidine | K |

TABLE 2-continued

| Ex. | Structure | Name | Reactants | Method |
|---|---|---|---|---|
| 96 | 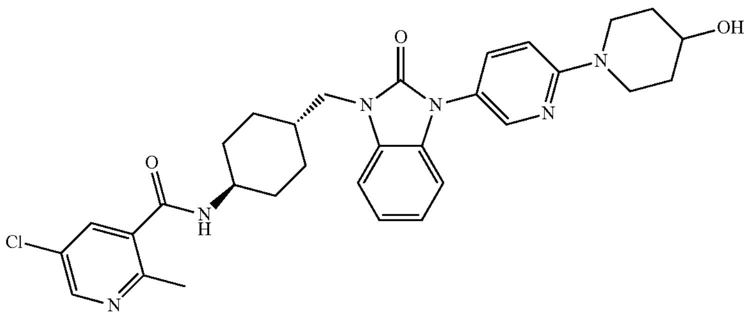 [SMILES: Cc1ncc(Cl)cc1C(=O)N[C@H]1CC[C@H](Cn2c(=O)n(-c3ccc(N4CCC(O)CC4)nc3)c3ccccc32)CC1] | 5-chloro-N-((1r,4r)-4-((3-(6-(4-hydroxypiperidin-1-yl)pyridin-3-yl)-2-oxo-2,3-dihydro-1H-benzo[d]imidazol-1-yl)methyl)cyclohexyl)-2-methylnicotinamide | Ex 66, [4-hydroxypiperidine] | K |
| 97 | 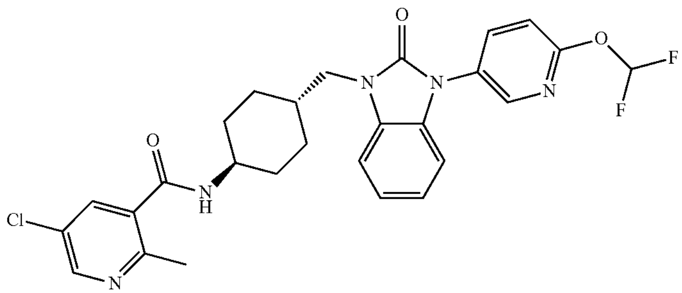 [SMILES: Cc1ncc(Cl)cc1C(=O)N[C@H]1CC[C@H](Cn2c(=O)n(-c3ccc(OC(F)F)nc3)c3ccccc32)CC1] | 5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide | see Example synthesis part | |
| 98 | 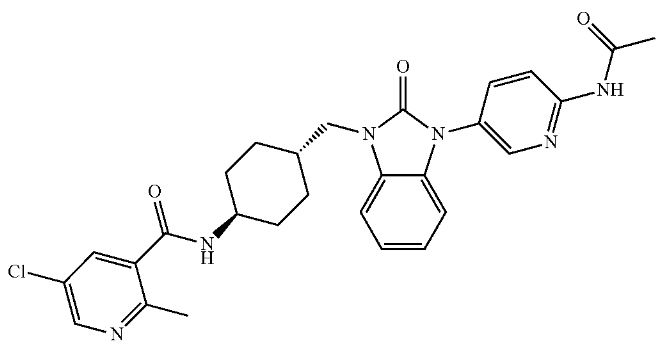 [SMILES: CC(=O)Nc1ccc(-n2c(=O)n(C[C@H]3CC[C@H](NC(=O)c4cc(Cl)cnc4C)CC3)c3ccccc32)cn1] | N-((1r,4r)-4-((3-(6-acetamidopyridin-3-yl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 99 | 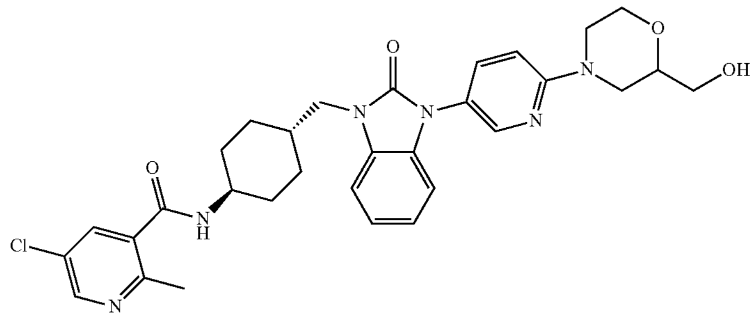 [SMILES: Cc1ncc(Cl)cc1C(=O)N[C@H]1CC[C@H](Cn2c(=O)n(-c3ccc(N4CCOC(CO)C4)nc3)c3ccccc32)CC1] | 5-chloro-N-((1r,4r)-4-((3-(6-(2-(hydroxymethyl)morpholino)pyridin-3-yl)-2-oxo-2,3-dihydro-1H-benzo[d]imidazol-1-yl)methyl)cyclohexyl)-2-methylnicotinamide | Intermediate-54, | L |
| 100 | 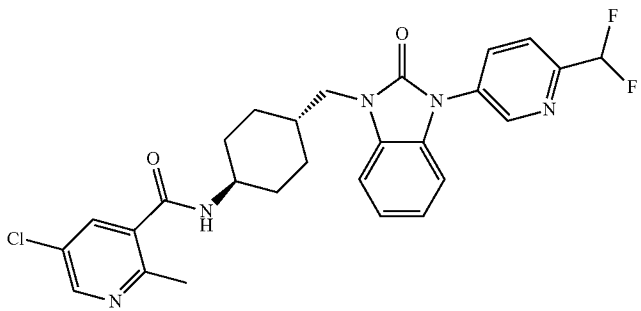 [SMILES: Cc1ncc(Cl)cc1C(=O)N[C@H]1CC[C@H](Cn2c(=O)n(-c3ccc(C(F)F)nc3)c3ccccc32)CC1] | 5-chloro-N-(4-((3-(6-(difluoromethyl)pyridin-3-yl)-2-oxo-2,3-dihydro-1H-benzo[d]imidazol-1-yl)methyl)cyclohexyl)-2-methylnicotinamide | see Example synthesis part | 100 |
| 101 | 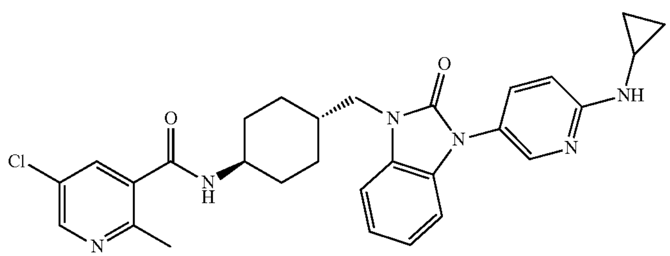 [SMILES: Cc1ncc(Cl)cc1C(=O)N[C@H]1CC[C@H](Cn2c(=O)n(-c3ccc(NC4CC4)nc3)c3ccccc32)CC1] | 5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 102 | 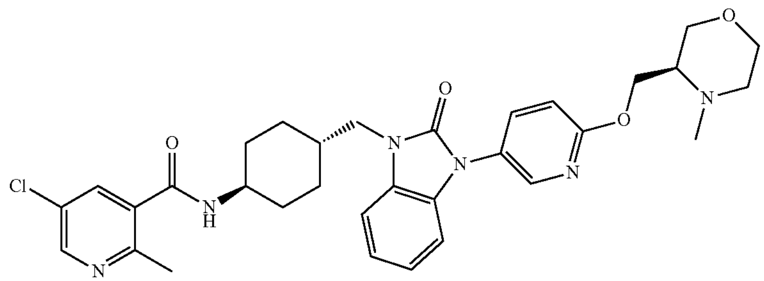 [SMILES: Cc1ncc(Cl)cc1C(=O)N[C@H]1CC[C@H](Cn2c(=O)n(-c3ccc(OC[C@H]4COCCN4C)nc3)c3ccccc32)CC1] | 5-chloro-2-methyl-N-((1R,4r)-4-((3-(6-(((R)-4-methylmorpholin-3-yl)methoxy)pyridin-3-yl)-2-oxo-2,3-dihydro-1H-benzo[d]imidazol-1-yl)methyl)cyclohexyl)nicotinamide | see Example synthesis part | |
| 103 | 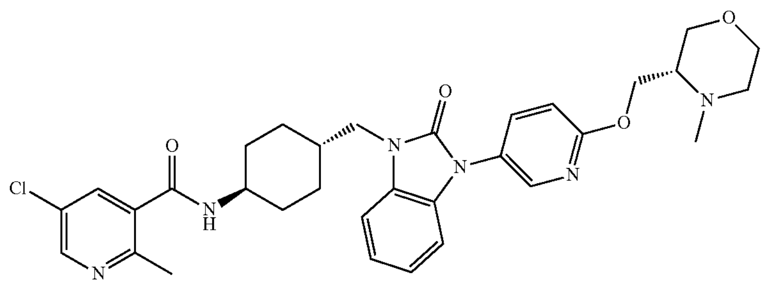 [SMILES: Cc1ncc(Cl)cc1C(=O)N[C@H]1CC[C@H](Cn2c(=O)n(-c3ccc(OC[C@@H]4COCCN4C)nc3)c3ccccc32)CC1] | 5-chloro-2-methyl-N-((1S,4r)-4-((3-(6-(((S)-4-methylmorpholin-3-yl)methoxy)pyridin-3-yl)-2-oxo-2,3-dihydro-1H-benzo[d]imidazol-1-yl)methyl)cyclohexyl)nicotinamide | see Example synthesis part | |
| 104 | 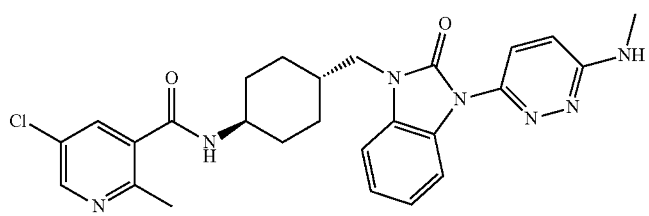 [SMILES: CNc1ccc(-n2c(=O)n(C[C@H]3CC[C@H](NC(=O)c4cc(Cl)cnc4C)CC3)c3ccccc32)nn1] | 5-chloro-2-methyl-N-((1r,4r)-4-((3-(6-(methylamino)pyridazin-3-yl)-2-oxo-2,3-dihydro-1H-benzo[d]imidazol-1-yl)methyl)cyclohexyl)nicotinamide | see Example synthesis part | |
| 105 | 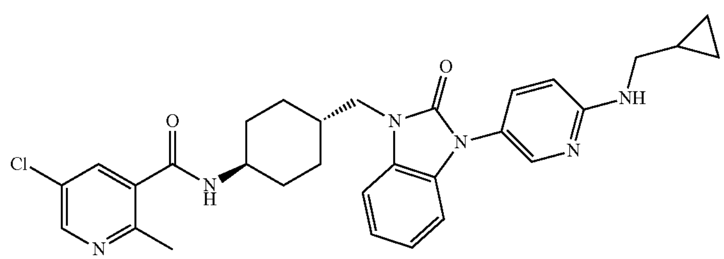 [SMILES: Cc1ncc(Cl)cc1C(=O)N[C@H]1CC[C@H](Cn2c(=O)n(-c3ccc(NCC4CC4)nc3)c3ccccc32)CC1] | 5-chloro-N-((1r,4r)-4-((3-(6-(((cyclopropylmethyl)amino)pyridin-3-yl)-2-oxo-2,3-dihydro-1H-benzo[d]imidazol-1-yl)methyl)cyclohexyl)-2-methylnicotinamide | Intermediate-54, cyclopropylmethylamine | M |

TABLE 2-continued

| Ex. | Structure | Name | Reactants | Method |
|---|---|---|---|---|
| 106 | 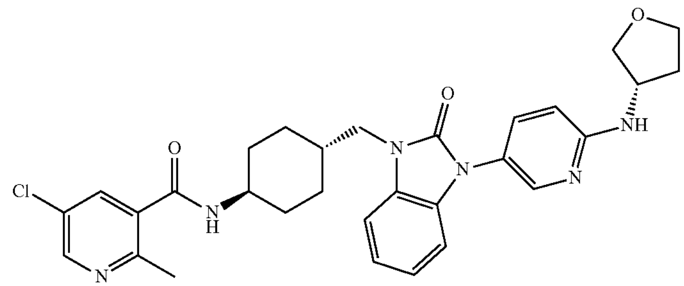 [SMILES: Cc1ncc(Cl)cc1C(=O)N[C@H]1CC[C@H](Cn2c(=O)n(-c3ccc(N[C@H]4CCOC4)nc3)c3ccccc32)CC1] | 5-chloro-2-methyl-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)nicotinamide | Intermediate-54, (S)-tetrahydrofuran-3-amine | M |
| 107 | 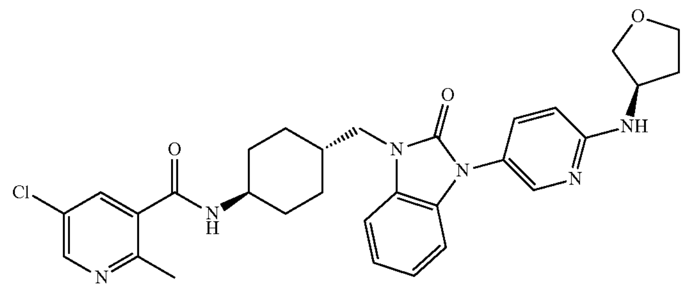 [SMILES: Cc1ncc(Cl)cc1C(=O)N[C@H]1CC[C@H](Cn2c(=O)n(-c3ccc(N[C@@H]4CCOC4)nc3)c3ccccc32)CC1] | 5-chloro-2-methyl-N-((1R,4R)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide | Intermediate-54, (R)-tetrahydrofuran-3-amine | M |
| 108 | 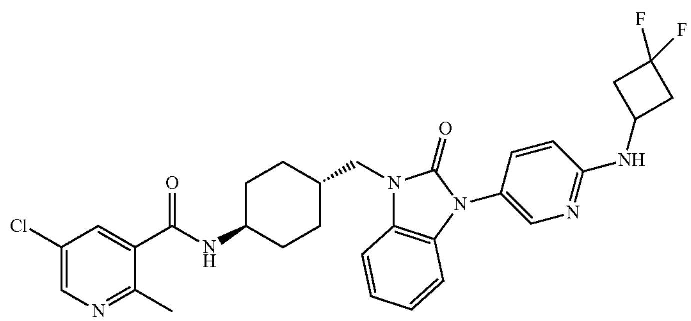 [SMILES: Cc1ncc(Cl)cc1C(=O)N[C@H]1CC[C@H](Cn2c(=O)n(-c3ccc(NC4CC(F)(F)C4)nc3)c3ccccc32)CC1] | 5-chloro-N-((1r,4r)-4-(3-(6-(((3,3-difluorocyclobutyl)amino)pyridin-3-yl)-2-oxo-2,3-dihydro-1H-benzo[d]imidazol-1-yl)methyl)cyclohexyl)-2-methylnicotinamide | Intermediate-54, 3,3-difluorocyclobutanamine hydrochloride | M |

TABLE 2-continued

| Ex. | Structure | Name | Reactants | Method |
|---|---|---|---|---|
| 109 | 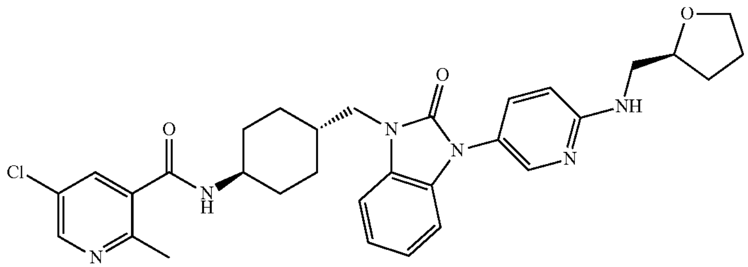 [SMILES: Cc1ncc(Cl)cc1C(=O)N[C@H]1CC[C@H](Cn2c(=O)n(-c3ccc(NC[C@@H]4CCCO4)nc3)c3ccccc32)CC1] | 5-chloro-2-methyl-N-((1S,4r)-4-((2-oxo-3-(6-((((S)-tetrahydrofuran-2-yl)methyl)amino)pyridin-3-yl)-2,3-dihydro-1H-benzo[d]imidazol-1-yl)methyl)cyclohexyl)nicotinamide | Intermediate-54, (S)-tetrahydrofuran-2-ylmethanamine | M |
| 110 | 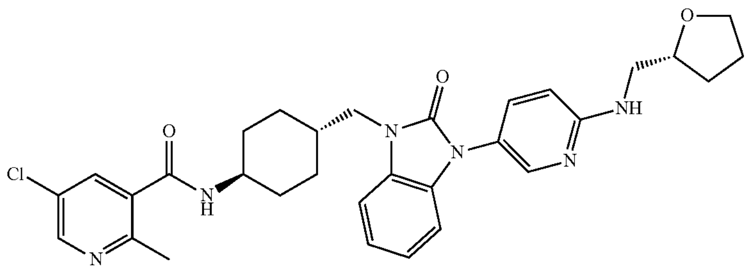 [SMILES: Cc1ncc(Cl)cc1C(=O)N[C@H]1CC[C@H](Cn2c(=O)n(-c3ccc(NC[C@H]4CCCO4)nc3)c3ccccc32)CC1] | 5-chloro-2-methyl-N-((1R,4r)-4-((2-oxo-3-(6-((((R)-tetrahydrofuran-2-yl)methyl)amino)pyridin-3-yl)-2,3-dihydro-1H-benzo[d]imidazol-1-yl)methyl)cyclohexyl)nicotinamide | Intermediate-54, (R)-tetrahydrofuran-2-ylmethanamine | M |
| 111 | 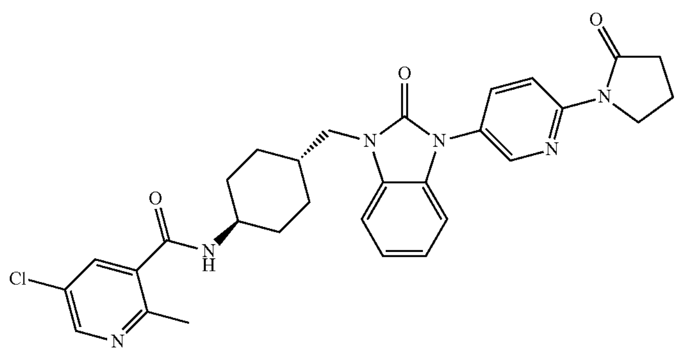 [SMILES: Cc1ncc(Cl)cc1C(=O)N[C@H]1CC[C@H](Cn2c(=O)n(-c3ccc(N4CCCC4=O)nc3)c3ccccc32)CC1] | 5-chloro-2-methyl-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 112 | 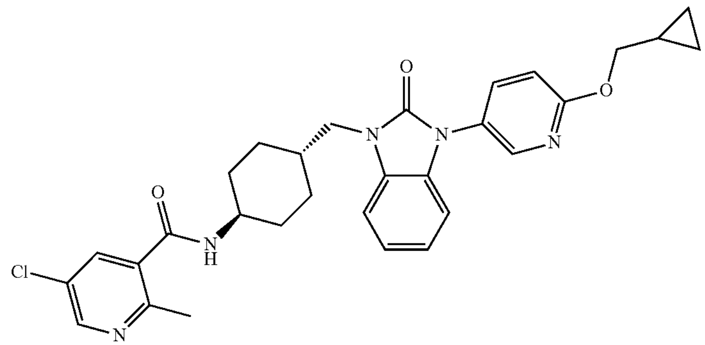 [SMILES: Cc1ncc(Cl)cc1C(=O)N[C@H]1CC[C@H](Cn2c(=O)n(-c3ccc(OCC4CC4)nc3)c3ccccc32)CC1] | 5-chloro-N-(4-((3-(6-(cyclopropylmethoxy)pyridin-3-yl)-2-oxo-2,3-dihydro-1H-benzo[d]imidazol-1-yl)methyl)cyclohexyl)-2-methylnicotinamide | Intermediate-54, cyclopropylmethanol | N |
| 113 | 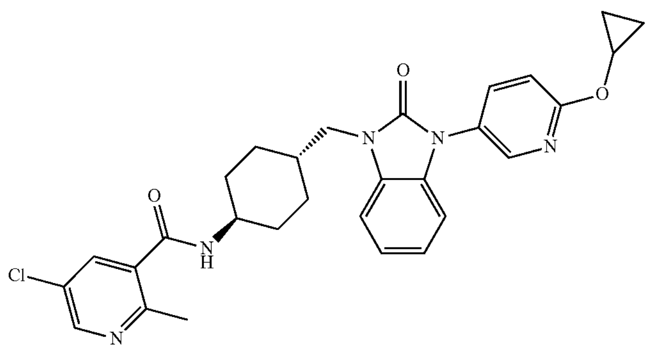 [SMILES: Cc1ncc(Cl)cc1C(=O)N[C@H]1CC[C@H](Cn2c(=O)n(-c3ccc(OC4CC4)nc3)c3ccccc32)CC1] | 5-chloro-N-(4-((3-(6-cyclopropoxypyridin-3-yl)-2-oxo-2,3-dihydro-1H-benzo[d]imidazol-1-yl)methyl)cyclohexyl)-2-methylnicotinamide | Intermediate-54, cyclopropanol | N |
| 114 | 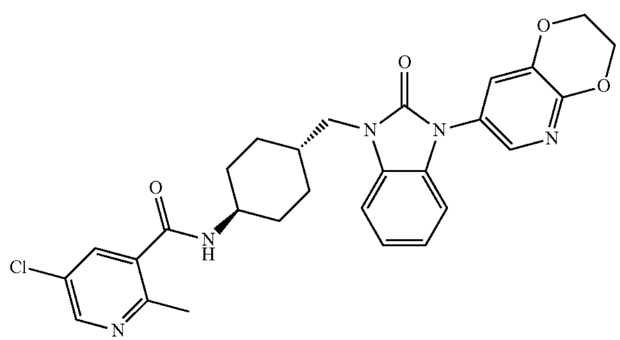 [SMILES: Cc1ncc(Cl)cc1C(=O)N[C@H]1CC[C@H](Cn2c(=O)n(-c3cnc4c(c3)OCCO4)c3ccccc32)CC1] | 5-chloro-N-((1r,4r)-4-((3-(2,3-dihydro-[1,4]dioxino[2,3-b]pyridin-7-yl)-2-oxo-2,3-dihydro-1H-benzo[d]imidazol-1-yl)methyl)cyclohexyl)-2-methylnicotinamide | Intermediate-56, Mesylate-1 | A1 |

TABLE 2-continued

| Ex. | Structure | Name | Reactants | Method |
|---|---|---|---|---|
| 115 | 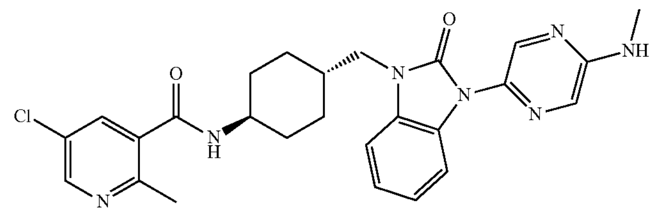 [SMILES: CNc1cnc(-n2c(=O)n(C[C@H]3CC[C@H](NC(=O)c4cc(Cl)cnc4C)CC3)c3ccccc32)cn1] | 5-chloro-2-methyl-N-((1r,4r)-4-((3-(5-(methylamino)pyrazin-2-yl)-2-oxo-2,3-dihydro-1H-benzo[d]imidazol-1-yl)methyl)cyclohexyl)nicotinamide | Intermediate-57, methanamine hydrochloride | M |
| 116 | 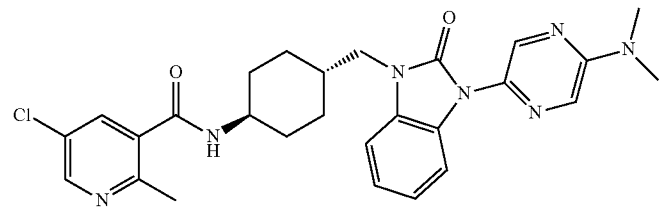 [SMILES: Cc1ncc(Cl)cc1C(=O)N[C@H]1CC[C@H](Cn2c(=O)n(-c3cnc(N(C)C)cn3)c3ccccc32)CC1] | 5-chloro-N-((1r,4r)-4-(3-(5-(dimethylamino)pyrazin-2-yl)-2-oxo-2,3-dihydro-1H-benzo[d]imidazol-1-yl)methyl)cyclohexyl)-2-methylnicotinamide | Intermediate-57, dimethylamine hydrochloride | M |
| 117 | 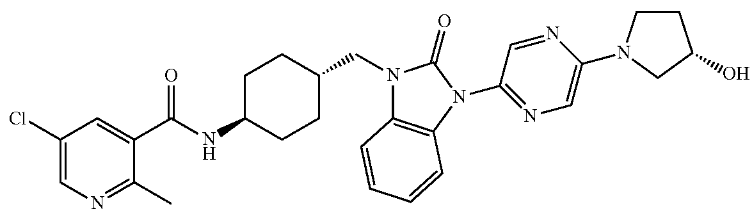 [SMILES: Cc1ncc(Cl)cc1C(=O)N[C@H]1CC[C@H](Cn2c(=O)n(-c3cnc(N4CC[C@H](O)C4)cn3)c3ccccc32)CC1] | 5-chloro-N-((1S,4r)-4-((3-(5-((S)-3-hydroxypyrrolidin-1-yl)pyrazin-2-yl)-2-oxo-2,3-dihydro-1H-benzo[d]imidazol-1-yl)methyl)cyclohexyl)-2-methylnicotinamide | Intermediate-57, | M |
| 118 | 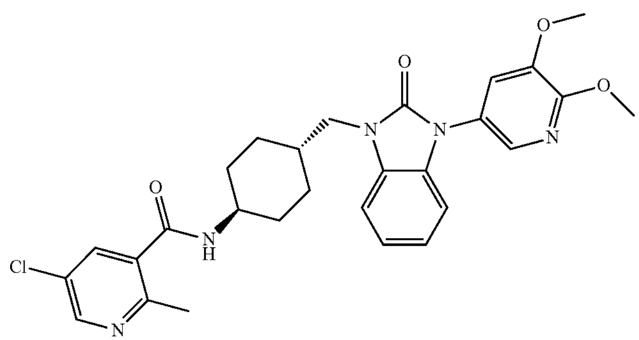 [SMILES: COc1cc(-n2c(=O)n(C[C@H]3CC[C@H](NC(=O)c4cc(Cl)cnc4C)CC3)c3ccccc32)cnc1OC] | 5-chloro-N-((1r,4r)-4-((3-(5,6-dimethoxypyridin-3-yl)-2-oxo-2,3-dihydro-1H-benzo[d]imidazol-1-yl)methyl)cyclohexyl)-2-methylnicotinamide | Intermediate-58, Mesylate-1 | A2 |

TABLE 2-continued

| Ex. | Structure | Name | Reactants | Method |
|---|---|---|---|---|
| 119 | 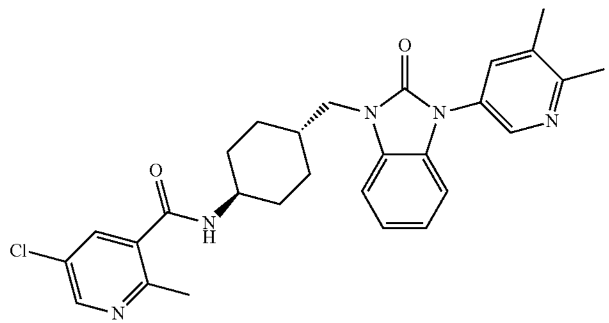 [SMILES: Cc1cc(-n2c(=O)n(C[C@H]3CC[C@H](NC(=O)c4cc(Cl)cnc4C)CC3)c3ccccc32)cnc1C] | 5-chloro-N-((1r,4r)-4-((3-(5,6-dimethylpyridin-3-yl)-2-oxo-2,3-dihydro-1H-benzo[d]imidazol-1-yl)methyl)cyclohexyl)-2-methylnicotinamide | Intermediate-59, Mesylate-1 | A2 |
| 120 | 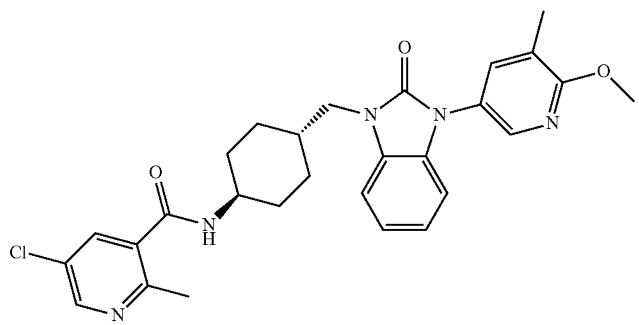 [SMILES: COc1ncc(-n2c(=O)n(C[C@H]3CC[C@H](NC(=O)c4cc(Cl)cnc4C)CC3)c3ccccc32)cc1C] | 5-chloro-N-((1r,4r)-4-((3-(6-methoxy-5-methylpyridin-3-yl)-2-oxo-2,3-dihydro-1H-benzo[d]imidazol-1-yl)methyl)cyclohexyl)-2-methylnicotinamide | Intermediate-60, Mesylate-1 | A2 |
| 121 | 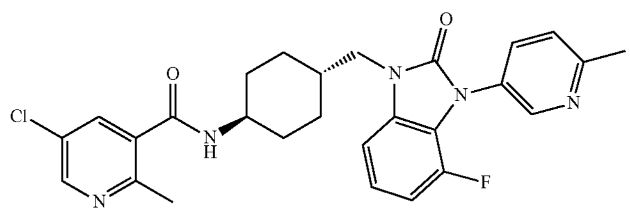 | 5-chloro-N-((1r,4r)-4-((4-fluoro-3-(6-methylpyridin-3-yl)-2-oxo-2,3-dihydro-1H-benzo[d]imidazol-1-yl)methyl)cyclohexyl)-2-methylnicotinamide | Intermediate-61, Mesylate-1 | A2 |

TABLE 2-continued

| Ex. | Structure | Name | Reactants | Method |
|---|---|---|---|---|
| 122 | 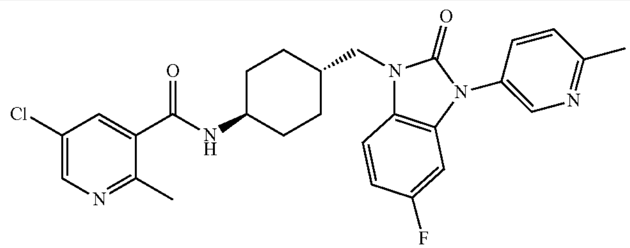 [SMILES: Cc1ccc(-n2c(=O)n(C[C@H]3CC[C@H](NC(=O)c4cc(Cl)cnc4C)CC3)c3ccc(F)cc32)cn1] | 5-chloro-N-((1r,4r)-4-((5-fluoro-3-(6-methylpyridin-3-yl)-2-oxo-2,3-dihydro-1H-benzo[d]imidazol-1-yl)methyl)cyclohexyl)-2-methylnicotinamide | Intermediate-62, Mesylate-1 | A2 |
| 123 | 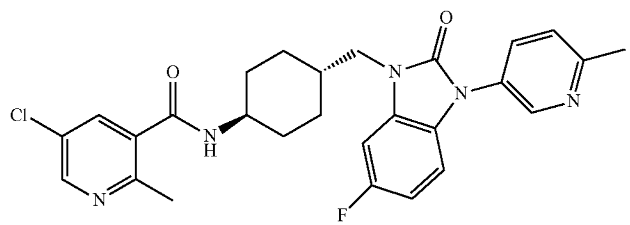 [SMILES: Cc1ccc(-n2c(=O)n(C[C@H]3CC[C@H](NC(=O)c4cc(Cl)cnc4C)CC3)c3cc(F)ccc32)cn1] | 5-chloro-N-((1r,4r)-4-((6-fluoro-3-(6-methylpyridin-3-yl)-2-oxo-2,3-dihydro-1H-benzo[d]imidazol-1-yl)methyl)cyclohexyl)-2-methylnicotinamide | Intermediate-63, Mesylate-1 | A2 |
| 124 | 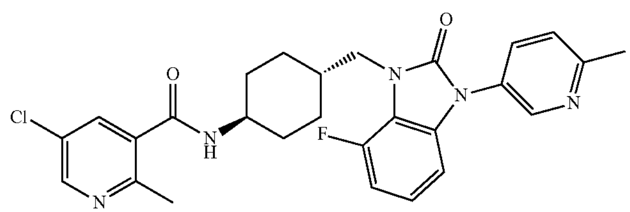 [SMILES: Cc1ccc(-n2c(=O)n(C[C@H]3CC[C@H](NC(=O)c4cc(Cl)cnc4C)CC3)c3c(F)cccc32)cn1] | 5-chloro-N-((1r,4r)-4-((7-fluoro-3-(6-methylpyridin-3-yl)-2-oxo-2,3-dihydro-1H-benzo[d]imidazol-1-yl)methyl)cyclohexyl)-2-methylnicotinamide | Intermediate-64, Mesylate-1 | A2 |
| 125 | 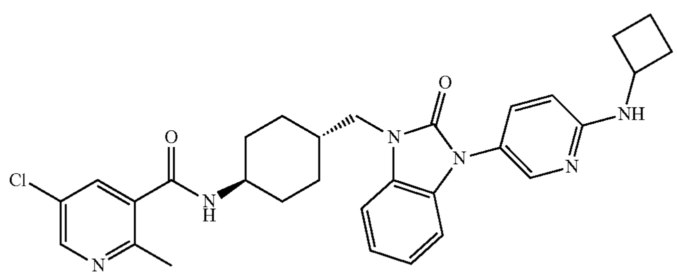 [SMILES: Cc1ncc(Cl)cc1C(=O)N[C@H]1CC[C@H](Cn2c(=O)n(-c3ccc(NC4CCC4)nc3)c3ccccc32)CC1] | 5-chloro-N-((1r,4r)-4-((3-(6-(cyclobutylamino)pyridin-3-yl)-2-oxo-2,3-dihydro-1H-benzo[d]imidazol-1-yl)methyl)cyclohexyl)-2-methylnicotinamide | Intermediate-54, cyclobutanamine | L |

TABLE 2-continued

| Ex. | Structure | Name | Reactants | Method |
|---|---|---|---|---|
| 126 | 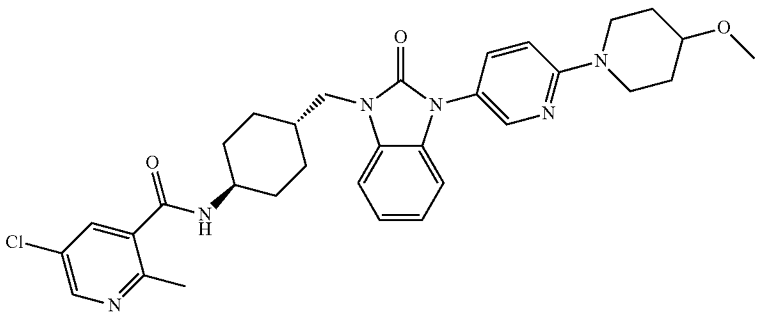 [SMILES: COC1CCN(c2ccc(-n3c(=O)n(C[C@H]4CC[C@H](NC(=O)c5cc(Cl)cnc5C)CC4)c4ccccc43)cn2)CC1] | 5-chloro-N-((1r,4r)-4-((3-(6-(4-methoxypiperidin-1-yl)pyridin-3-yl)-2-oxo-2,3-dihydro-1H-benzo[d]imidazol-1-yl)methyl)cyclohexyl)-2-methylnicotinamide | Intermediate-54, | L |
| 127 | 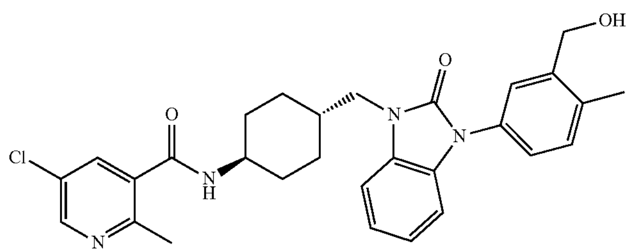 [SMILES: Cc1ccc(-n2c(=O)n(C[C@H]3CC[C@H](NC(=O)c4cc(Cl)cnc4C)CC3)c3ccccc32)cc1CO] | 5-chloro-N-((1r,4r)-4-((3-(3-(hydroxymethyl)-4-methylphenyl)-2-oxo-2,3-dihydro-1H-benzo[d]imidazol-1-yl)methyl)cyclohexyl)-2-methylnicotinamide | Intermediate-65 | D |
| 128 | 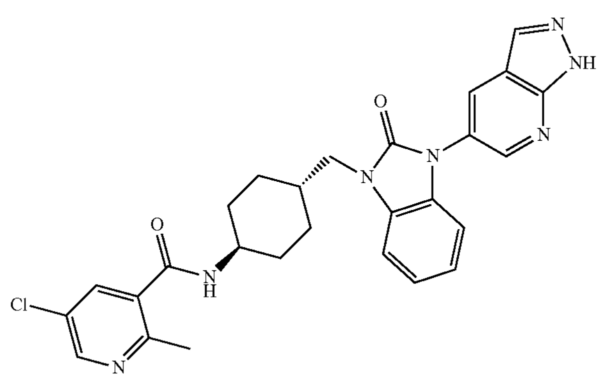 [SMILES: Cc1ncc(Cl)cc1C(=O)N[C@H]1CC[C@H](Cn2c(=O)n(-c3cnc4[nH]ncc4c3)c3ccccc32)CC1] | 5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 129 | 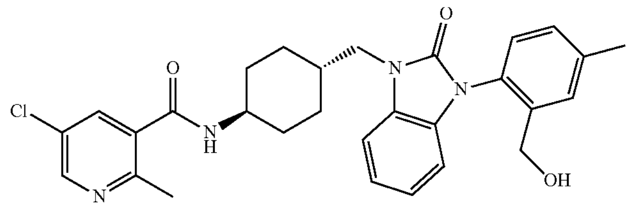 [SMILES: Cc1ccc(-n2c(=O)n(C[C@H]3CC[C@H](NC(=O)c4cc(Cl)cnc4C)CC3)c3ccccc32)c(CO)c1] | 5-chloro-N-((1r,4r)-4-((3-(2-(hydroxymethyl)-4-methylphenyl)-2-oxo-2,3-dihydro-1H-benzo[d]imidazol-1-yl)methyl)cyclohexyl)-2-methylnicotinamide | Intermediate-66 | D |
| 130 | 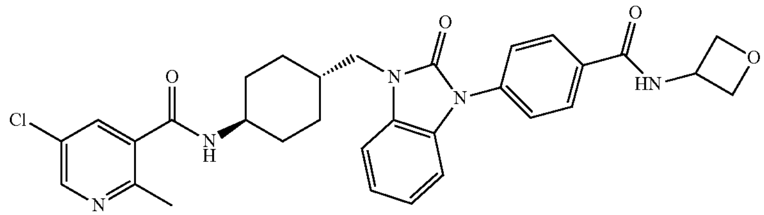 [SMILES: Cc1ncc(Cl)cc1C(=O)N[C@H]1CC[C@H](Cn2c(=O)n(-c3ccc(C(=O)NC4COC4)cc3)c3ccccc32)CC1] | 5-chloro-2-methyl-N-((1r,4r)-4-((3-(4-(oxetan-3-ylcarbamoyl)phenyl)-2-oxo-2,3-dihydro-1H-benzo[d]imidazol-1-yl)methyl)cyclohexyl)nicotinamide | see Example synthesis part | |
| 131 | 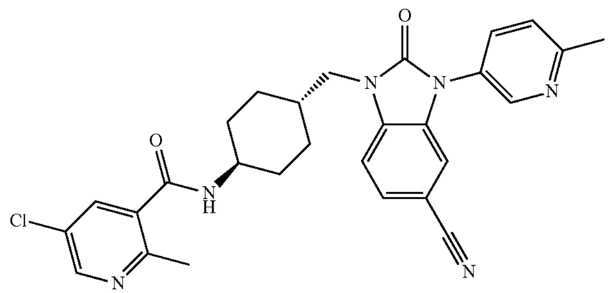 [SMILES: Cc1ccc(-n2c(=O)n(C[C@H]3CC[C@H](NC(=O)c4cc(Cl)cnc4C)CC3)c3ccc(C#N)cc32)cn1] | 5-chloro-N-((1r,4r)-4-((5-cyano-3-(6-methylpyridin-3-yl)-2-oxo-2,3-dihydro-1H-benzo[d]imidazol-1-yl)methyl)cyclohexyl)-2-methylnicotinamide | Intermediate-67, Mesylate-1 | A2 |
| 132 | 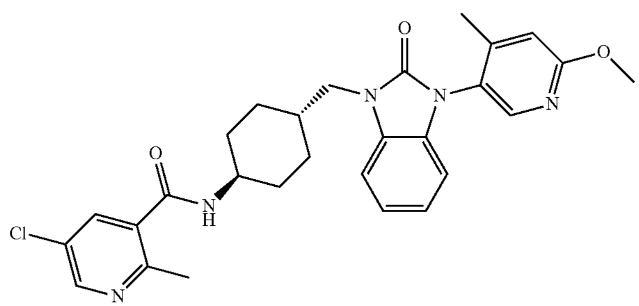 [SMILES: COc1cc(C)c(-n2c(=O)n(C[C@H]3CC[C@H](NC(=O)c4cc(Cl)cnc4C)CC3)c3ccccc32)cn1] | 5-chloro-N-((1r,4r)-4-((3-(6-methoxy-4-methylpyridin-3-yl)-2-oxo-2,3-dihydro-1H-benzo[d]imidazol-1-yl)methyl)cyclohexyl)-2-methylnicotinamide | Intermediate-68, Mesylate-1 | A2 |

TABLE 2-continued

| Ex. | Structure | Name | Reactants | Method |
|---|---|---|---|---|
| 133 | 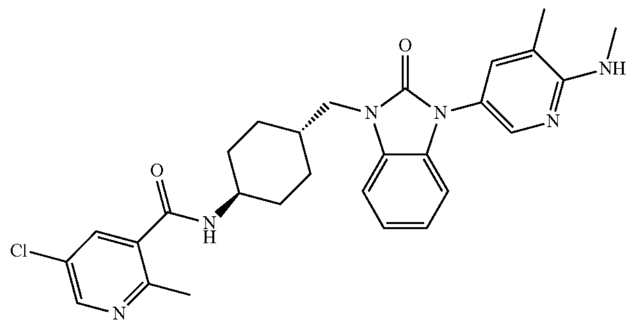 [SMILES: CNc1ncc(-n2c(=O)n(C[C@H]3CC[C@H](NC(=O)c4cc(Cl)cnc4C)CC3)c3ccccc32)cc1C] | 5-chloro-2-methyl-N-((1r,4r)-4-(3-(5-methyl-6-(methylamino)pyridin-3-yl)-2-oxo-2,3-dihydro-1H-benzo[d]imidazol-1-yl)methyl)cyclohexyl)nicotinamide | Intermediate-69, Mesylate-1 | A2 |
| 134 | 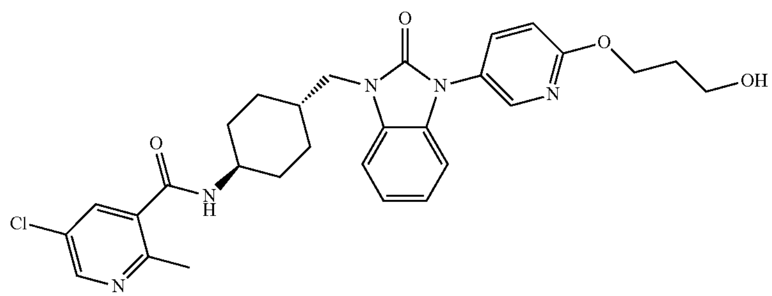 [SMILES: Cc1ncc(Cl)cc1C(=O)N[C@H]1CC[C@H](Cn2c(=O)n(-c3ccc(OCCCO)nc3)c3ccccc32)CC1] | 5-chloro-N-((1r,4r)-4-(3-(6-(3-hydroxypropoxy)pyridin-3-yl)-2-oxo-2,3-dihydro-1H-benzo[d]imidazol-1-yl)methyl)cyclohexyl)-2-methylnicotinamide | see Example synthesis part | |
| 135 | 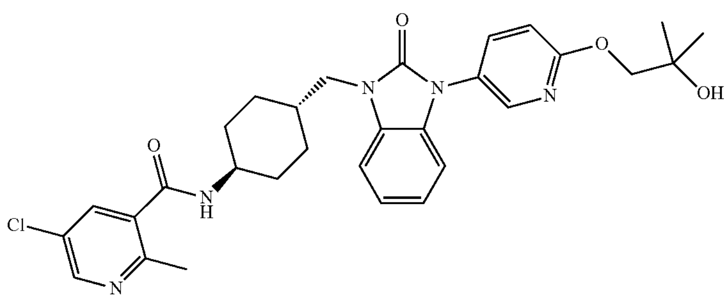 [SMILES: Cc1ncc(Cl)cc1C(=O)N[C@H]1CC[C@H](Cn2c(=O)n(-c3ccc(OCC(C)(C)O)nc3)c3ccccc32)CC1] | 5-chloro-N-((1r,4r)-4-(3-(6-(2-hydroxy-2-methylpropoxy)pyridin-3-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 136 | 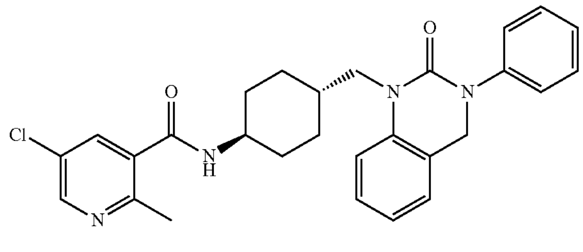 [SMILES: Cc1ncc(Cl)cc1C(=O)N[C@H]1CC[C@H](CN2C(=O)N(c3ccccc3)Cc3ccccc32)CC1] | 5-chloro-2-methyl-N-((1r,4r)-4-((2-oxo-3-phenyl-3,4-dihydroquinazolin-1(2H)-yl)methyl)cyclohexyl)nicotinamide | Mesylate-1 | A1 |
| 137 | 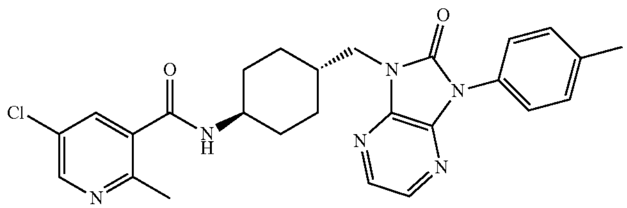 [SMILES: Cc1ccc(-n2c(=O)n(C[C@H]3CC[C@H](NC(=O)c4cc(Cl)cnc4C)CC3)c3nccnc32)cc1] | 5-chloro-2-methyl-N-((1r,4r)-4-((2-oxo-3-(p-tolyl)-2,3-dihydro-1H-imidazo[4,5-b]pyrazin-1-yl)methyl)cyclohexyl)nicotinamide | Intermediate-70 Mesylate-1 | A1 |
| 138 | 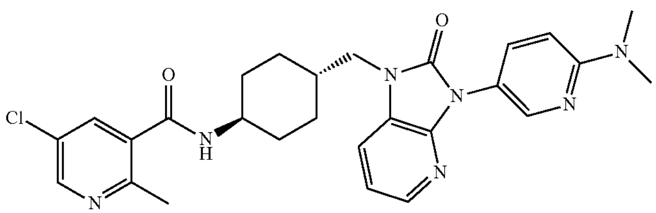 [SMILES: Cc1ncc(Cl)cc1C(=O)N[C@H]1CC[C@H](Cn2c(=O)n(-c3ccc(N(C)C)nc3)c3ncccc32)CC1] | 5-chloro-N-((1r,4r)-4-((3-(6-(dimethylamino)pyridin-3-yl)-2-oxo-2,3-dihydro-1H-imidazo[4,5-b]pyridin-1-yl)methyl)cyclohexyl)-2-methylnicotinamide | Intermediate-71 Mesylate-1 | A1 |
| 139 | 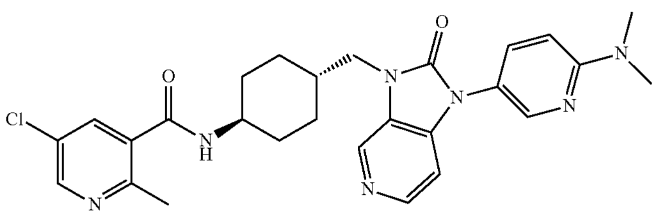 [SMILES: Cc1ncc(Cl)cc1C(=O)N[C@H]1CC[C@H](Cn2c(=O)n(-c3ccc(N(C)C)nc3)c3ccncc32)CC1] | 5-chloro-N-((1r,4r)-4-((1-(6-(dimethylamino)pyridin-3-yl)-2-oxo-1H-imidazo[4,5-c]pyridin-3(2H)-yl)methyl)cyclohexyl)-2-methylnicotinamide | Intermediate-72 Mesylate-1 | A1 |

TABLE 2-continued

| Ex. | Structure | Name | Reactants | Method |
|---|---|---|---|---|
| 140 | 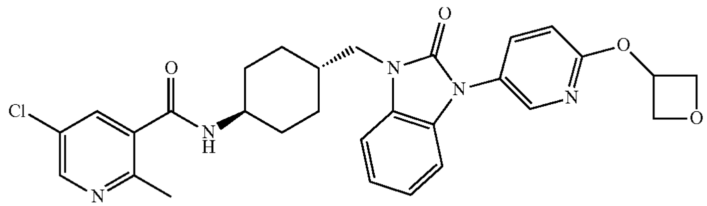 [SMILES: Cc1ncc(Cl)cc1C(=O)N[C@H]1CC[C@H](Cn2c(=O)n(-c3ccc(OC4COC4)nc3)c3ccccc32)CC1] | 5-chloro-2-methyl-N-((1r,4r)-4-((3-(6-(oxetan-3-yloxy)pyridin-3-yl)-2-oxo-2,3-dihydro-1H-benzo[d]imidazol-1-yl)methyl)cyclohexyl)nicotinamide | see Example synthesis part | |
| 141 | 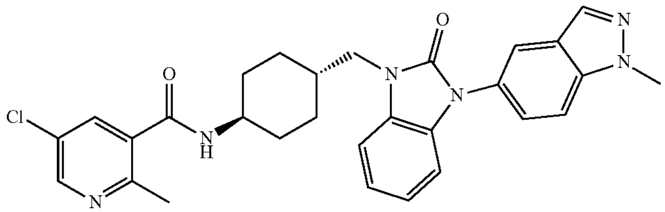 [SMILES: Cc1ncc(Cl)cc1C(=O)N[C@H]1CC[C@H](Cn2c(=O)n(-c3ccc4c(cnn4C)c3)c3ccccc32)CC1] | 5-chloro-2-methyl-N-((1r,4r)-4-((3-(1-methyl-1H-indazol-5-yl)-2-oxo-2,3-dihydro-1H-benzo[d]imidazol-1-yl)methyl)cyclohexyl)nicotinamide | Intermediate-73 Mesylate-1 | A2 |
| 142 | 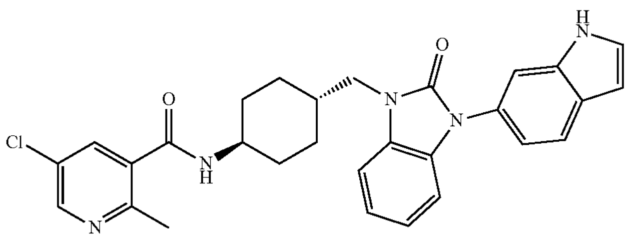 [SMILES: Cc1ncc(Cl)cc1C(=O)N[C@H]1CC[C@H](Cn2c(=O)n(-c3ccc4cc[nH]c4c3)c3ccccc32)CC1] | N-((1r,4r)-4-((3-(1H-indol-6-yl)-2-oxo-2,3-dihydro-1H-benzo[d]imidazol-1-yl)methyl)cyclohexyl)-5-chloro-2-methylnicotinamide | Intermediate-74 Mesylate-1 | A2 |
| 143 | 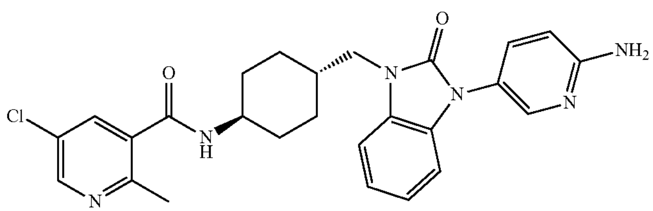 [SMILES: Cc1ncc(Cl)cc1C(=O)N[C@H]1CC[C@H](Cn2c(=O)n(-c3ccc(N)nc3)c3ccccc32)CC1] | N-((1r,4r)-4-((3-(6-aminopyridin-3-yl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 144 | 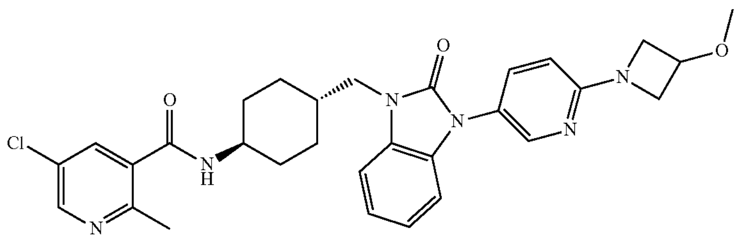 [SMILES: COC1CN(c2ccc(-n3c(=O)n(C[C@H]4CC[C@H](NC(=O)c5cc(Cl)cnc5C)CC4)c4ccccc43)cn2)C1] | 5-chloro-N-((1r,4r)-4-((3-(6-(3-methoxyazetidin-1-yl)pyridin-3-yl)-2-oxo-2,3-dihydro-1H-benzo[d]imidazol-1-yl)methyl)cyclohexyl)-2-methylnicotinamide | Intermediate-75<br>Mesylate-1 | A2 |
| 145 | 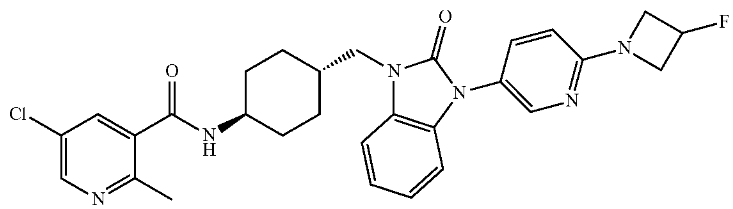 [SMILES: Cc1ncc(Cl)cc1C(=O)N[C@H]1CC[C@H](Cn2c(=O)n(-c3ccc(N4CC(F)C4)nc3)c3ccccc32)CC1] | 5-chloro-N-((1r,4r)-4-((3-(6-(3-fluoroazetidin-1-yl)pyridin-3-yl)-2-oxo-2,3-dihydro-1H-benzo[d]imidazol-1-yl)methyl)cyclohexyl)-2-methylnicotinamide | Intermediate-76<br>Mesylate-1 | A2 |
| 146 | 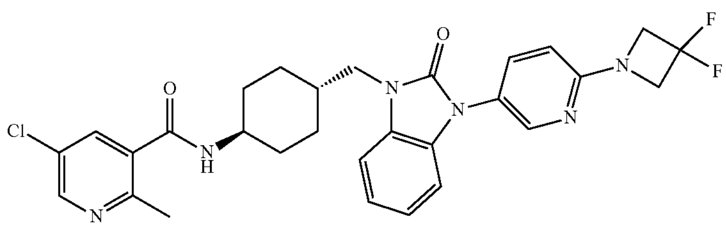 [SMILES: Cc1ncc(Cl)cc1C(=O)N[C@H]1CC[C@H](Cn2c(=O)n(-c3ccc(N4CC(F)(F)C4)nc3)c3ccccc32)CC1] | 5-chloro-N-((1r,4r)-4-((3-(6-(3,3-difluoroazetidin-1-yl)pyridin-3-yl)-2-oxo-2,3-dihydro-1H-benzo[d]imidazol-1-yl)methyl)cyclohexyl)-2-methylnicotinamide | Intermediate-77<br>Mesylate-1 | A2 |
| 147 | 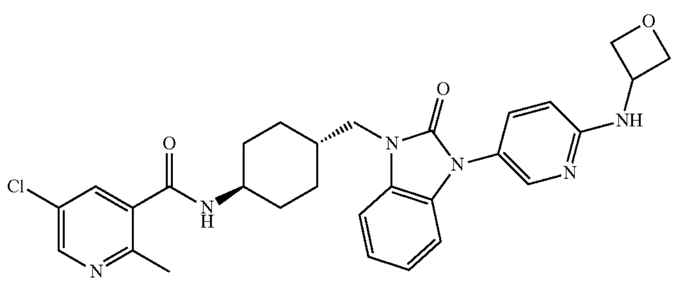 [SMILES: Cc1ncc(Cl)cc1C(=O)N[C@H]1CC[C@H](Cn2c(=O)n(-c3ccc(NC4COC4)nc3)c3ccccc32)CC1] | 5-chloro-2-methyl-N-((1r,4r)-4-((3-(6-((oxetan-3-yl)amino)pyridin-3-yl)-2-oxo-2,3-dihydro-1H-benzo[d]imidazol-1-yl)methyl)cyclohexyl)nicotinamide | Intermediate-78<br>Mesylate-1 | A1 |

TABLE 2-continued

| Ex. | Structure | Name | Reactants | Method |
|---|---|---|---|---|
| 148 | 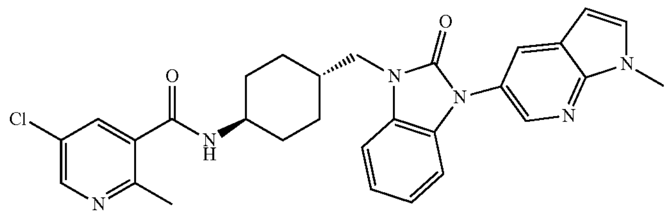 [SMILES: Cc1ncc(Cl)cc1C(=O)N[C@H]1CC[C@H](Cn2c(=O)n(-c3cnc4c(ccn4C)c3)c3ccccc32)CC1] | 5-chloro-2-methyl-N-((1r,4r)-4-(3-(1-methyl-1H-pyrrolo[2,3-b]pyridin-5-yl)-2-oxo-2,3-dihydro-1H-benzo[d]imidazol-1-yl)methyl)cyclohexyl)nicotinamide | Intermediate-79 Mesylate-1 | A2 |
| 149 | 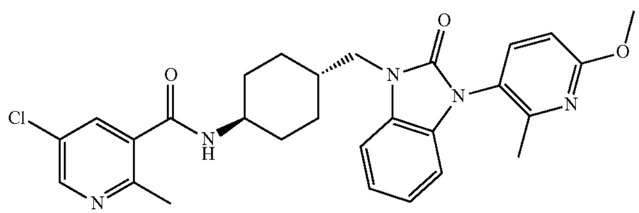 [SMILES: COc1ccc(-n2c(=O)n(C[C@H]3CC[C@H](NC(=O)c4cc(Cl)cnc4C)CC3)c3ccccc32)c(C)n1] | 5-chloro-N-((1r,4r)-4-((3-(6-methoxy-2-methylpyridin-3-yl)-2-oxo-2,3-dihydro-1H-benzo[d]imidazol-1-yl)methyl)cyclohexyl)-2-methylnicotinamide | see Example synthesis part | |
| 150 | 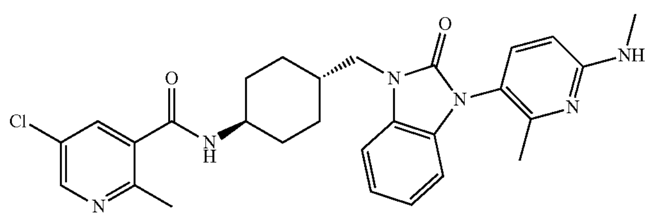 [SMILES: CNc1ccc(-n2c(=O)n(C[C@H]3CC[C@H](NC(=O)c4cc(Cl)cnc4C)CC3)c3ccccc32)c(C)n1] | 5-chloro-2-methyl-N-((1r,4r)-4-((3-(2-methylaminopyridin-3-yl)-2-oxo-2,3-dihydro-1H-benzo[d]imidazol-1-yl)methyl)cyclohexyl)nicotinamide | see Example synthesis part | |
| 151 | 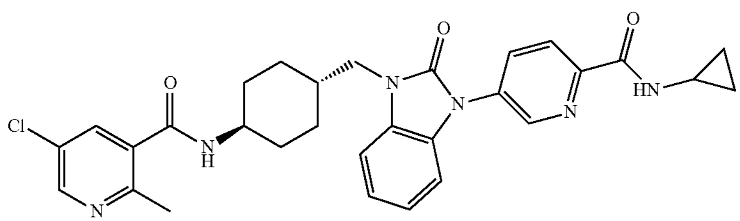 [SMILES: Cc1ncc(Cl)cc1C(=O)N[C@H]1CC[C@H](Cn2c(=O)n(-c3ccc(C(=O)NC4CC4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-cyclopropylpicolinamide | Intermediate-36 | Q |

TABLE 2-continued

| Ex. | Structure | Name | Reactants | Method |
|---|---|---|---|---|
| 152 | 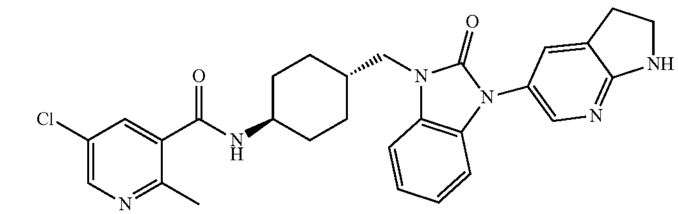 [SMILES: Cc1ncc(Cl)cc1C(=O)N[C@H]1CC[C@H](Cn2c(=O)n(-c3cnc4c(c3)CCN4)c3ccccc32)CC1] | 5-chloro-N-((1r,4r)-4-((3-(2,3-dihydro-1H-pyrrolo[2,3-b]pyridin-5-yl)-2-oxo-2,3-dihydro-1H-benzo[d]imidazol-1-yl)methyl)cyclohexyl)-2-methylnicotinamide | see Example synthesis part | |
| 153 | 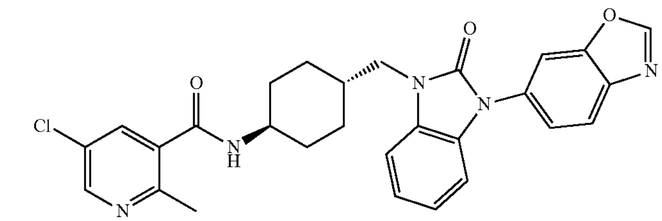 [SMILES: Cc1ncc(Cl)cc1C(=O)N[C@H]1CC[C@H](Cn2c(=O)n(-c3ccc4ncoc4c3)c3ccccc32)CC1] | N-((1r,4r)-4-((3-(benzo[d]oxazol-6-yl)-2-oxo-2,3-dihydro-1H-benzo[d]imidazol-1-yl)methyl)cyclohexyl)-5-chloro-2-methylnicotinamide | Intermediate-80 Mesylate-1 | A1 |
| 154 | 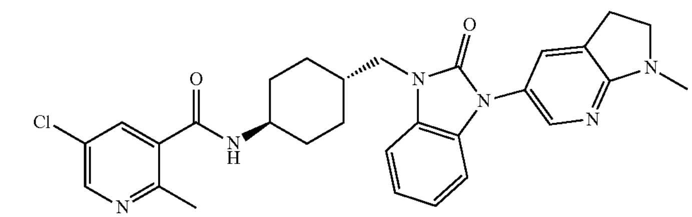 [SMILES: Cc1ncc(Cl)cc1C(=O)N[C@H]1CC[C@H](Cn2c(=O)n(-c3cnc4c(c3)CCN4C)c3ccccc32)CC1] | 5-chloro-2-methyl-N-((1r,4r)-4-((3-(1-methyl-2,3-dihydro-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |
| 155 | 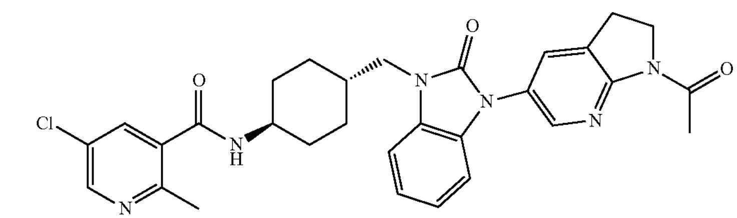 [SMILES: CC(=O)N1CCc2cc(-n3c(=O)n(C[C@H]4CC[C@H](NC(=O)c5cc(Cl)cnc5C)CC4)c4ccccc43)cnc21] | N-((1r,4r)-4-((3-(1-acetyl-2,3-dihydro-1H-pyrrolo[2,3-b]pyridin-5-yl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 156 | 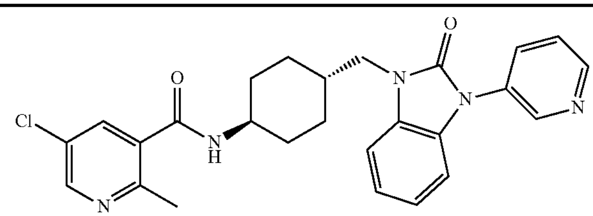 | 5-chloro-2-methyl-N-((1r,4r)-4-((2-oxo-3-(pyridin-3-yl)-2,3-dihydro-1H-benzo[d]imidazol-1-yl)methyl)cyclohexyl)nicotinamide | | A1 |
| 157 | 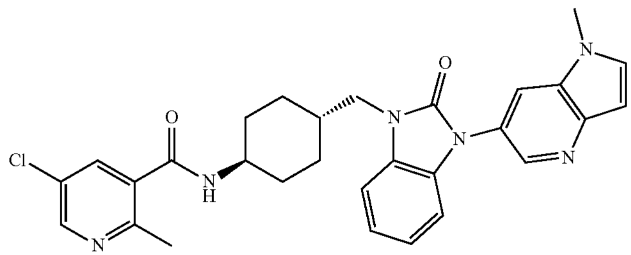 [SMILES: Cc1ncc(Cl)cc1C(=O)N[C@H]1CC[C@H](Cn2c(=O)n(-c3cnc4ccn(C)c4c3)c3ccccc32)CC1] | 5-chloro-2-methyl-N-((1r,4r)-4-((3-(1-methyl-1H-pyrrolo[3,2-b]pyridin-6-yl)-2-oxo-2,3-dihydro-1H-benzo[d]imidazol-1-yl)methyl)cyclohexyl)nicotinamide | Intermediate-81, Mesylate-1 | A1 |
| 158 | 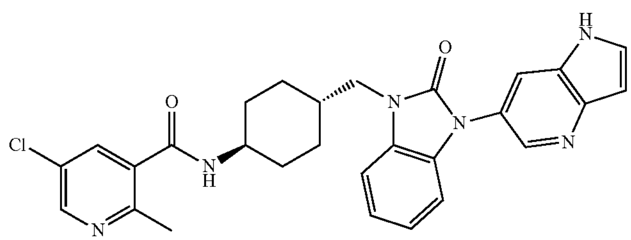 [SMILES: Cc1ncc(Cl)cc1C(=O)N[C@H]1CC[C@H](Cn2c(=O)n(-c3cnc4cc[nH]c4c3)c3ccccc32)CC1] | 5-chloro-2-methyl-N-((1r,4r)-4-((2-oxo-3-(1H-pyrrolo[3,2-b]pyridin-6-yl)-2,3-dihydro-1H-benzo[d]imidazol-1-yl)methyl)cyclohexyl)nicotinamide | Intermediate-82, Mesylate-1 | O |
| 159 | 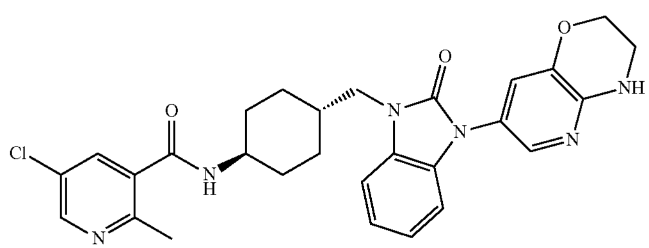 [SMILES: Cc1ncc(Cl)cc1C(=O)N[C@H]1CC[C@H](Cn2c(=O)n(-c3cnc4c(c3)OCCN4)c3ccccc32)CC1] | 5-chloro-N-((1r,4r)-4-(3-(3,4-dihydro-2H-pyrido[3,2-b][1,4]oxazin-7-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 160 | 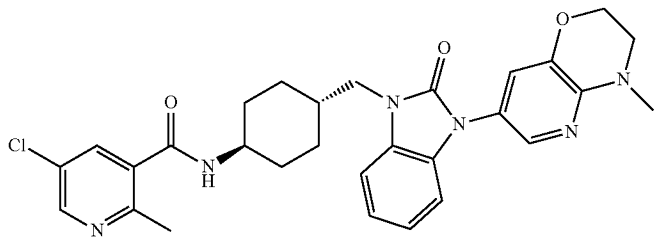 [SMILES: Cc1ncc(Cl)cc1C(=O)N[C@H]1CC[C@H](Cn2c(=O)n(-c3cnc4c(c3)OCCN4C)c3ccccc32)CC1] | 5-chloro-2-methyl-N-((1r,4r)-4-(3-(4-methyl-3,4-dihydro-2H-pyrido[3,2-b][1,4]oxazin-7-yl)-2-oxo-2,3-dihydro-1H-benzo[d]imidazol-1-yl)methyl)cyclohexyl)nicotinamide | Ex 159 | H |
| 161 | 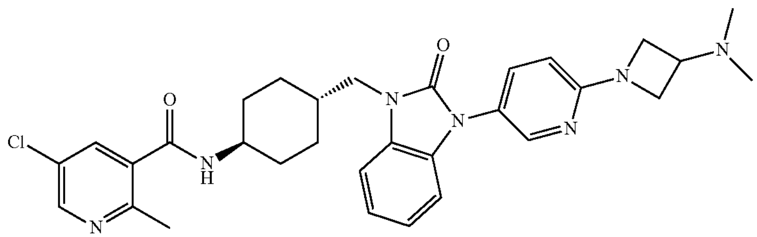 [SMILES: Cc1ncc(Cl)cc1C(=O)N[C@H]1CC[C@H](Cn2c(=O)n(-c3ccc(N4CC(N(C)C)C4)nc3)c3ccccc32)CC1] | 5-chloro-N-((1r,4r)-4-(3-(6-(3-(dimethylamino)azetidin-1-yl)pyridin-3-yl)-2-oxo-2,3-dihydro-1H-benzo[d]imidazol-1-yl)methyl)cyclohexyl)-2-methylnicotinamide | Intermediate-54, | P |
| 162 | 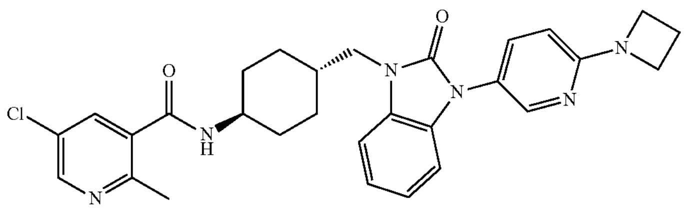 [SMILES: Cc1ncc(Cl)cc1C(=O)N[C@H]1CC[C@H](Cn2c(=O)n(-c3ccc(N4CCC4)nc3)c3ccccc32)CC1] | N-((1r,4r)-4-(3-(6-(azetidin-1-yl)pyridin-3-yl)-2-oxo-2,3-dihydro-1H-benzo[d]imidazol-1-yl)methyl)cyclohexyl)-5-chloro-2-methylnicotinamide | Intermediate-54, | P |
| 163 | 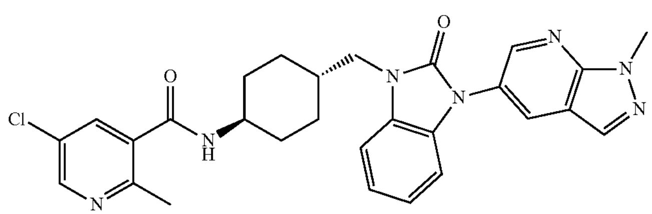 [SMILES: Cc1ncc(Cl)cc1C(=O)N[C@H]1CC[C@H](Cn2c(=O)n(-c3cnc4c(cnn4C)c3)c3ccccc32)CC1] | 5-chloro-2-methyl-N-((1r,4r)-4-(3-(1-methyl-1H-pyrazolo[3,4-b]pyridin-5-yl)-2-oxo-2,3-dihydro-1H-benzo[d]imidazol-1-yl)methyl)cyclohexyl)nicotinamide | Intermediate-84, Mesylate-1 | A1 |

TABLE 2-continued

| Ex. | Structure | Name | Reactants | Method |
|---|---|---|---|---|
| 164 | 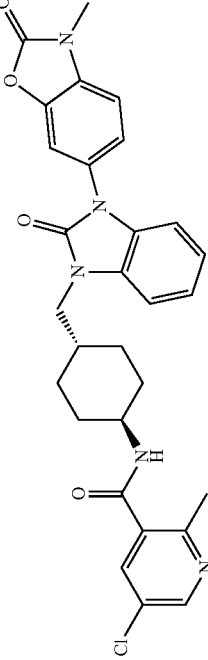 | 5-chloro-2-methyl-N-((1r,4r)-4-((3-(3-methyl-2-oxo-2,3-dihydrobenzo[d]oxazol-6-yl)-2-oxo-2,3-dihydro-1H-benzo[d]imidazol-1-yl)methyl)cyclohexyl)nicotinamide | Intermediate-85, Mesylate-1 | A1 |
| 165 | 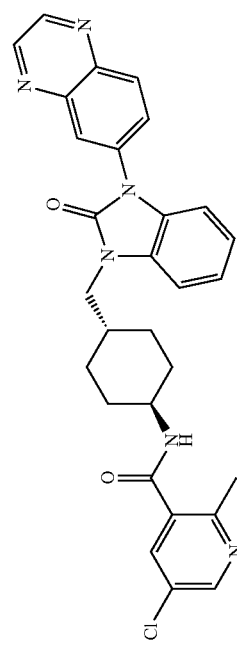 | 5-chloro-2-methyl-N-((1r,4r)-4-((2-oxo-3-(quinoxalin-6-yl)-2,3-dihydro-1H-benzo[d]imidazol-1-yl)methyl)cyclohexyl)nicotinamide | Intermediate-86, Mesylate-1 | A1 |
| 166 | 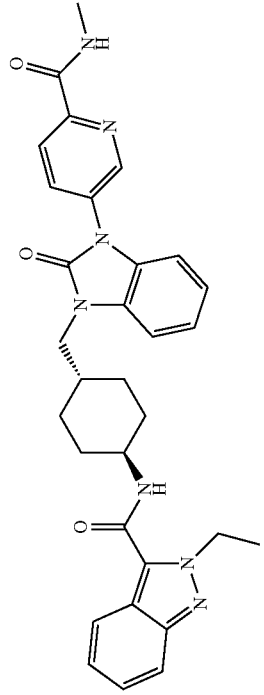 | 2-ethyl-N-((1r,4r)-4-((3-(6-(methylcarbamoyl)pyridin-3-yl)-2-oxo-2,3-dihydro-1H-benzo[d]imidazol-1-yl)methyl)cyclohexyl)-2H-indazole-3-carboxamide | Intermediate-87, Mesylate-1 | A1 |
| 167 | 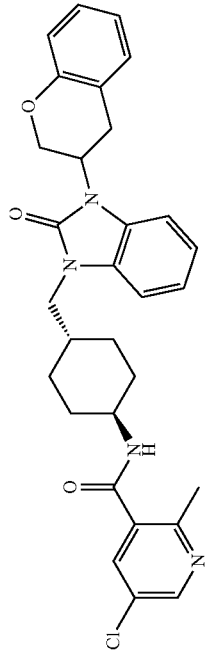 | 5-chloro-N-((1r,4r)-4-((3-(chroman-3-yl)-2-oxo-2,3-dihydro-1H-benzo[d]imidazol-1-yl)methyl)cyclohexyl)-2-methylnicotinamide | Intermediate-88, Mesylate-1 | A1 |

TABLE 2-continued

| Ex. | Structure | Name | Reactants | Method |
|---|---|---|---|---|
| 168 | 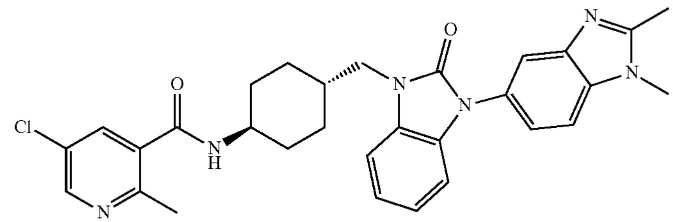 [SMILES: Cc1ncc(Cl)cc1C(=O)N[C@H]1CC[C@H](Cn2c(=O)n(-c3ccc4c(c3)nc(C)n4C)c3ccccc32)CC1] | 5-chloro-N-((1r,4r)-4-((1',2'-dimethyl-2-oxo-1H-[1,5'-bibenzo[d]imidazol]-3(2H)-yl)methyl)cyclohexyl)-2-methylnicotinamide | Intermediate-89, Mesylate-1 | A1 |
| 169 | 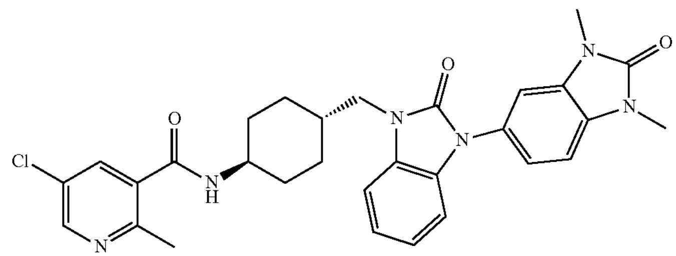 [SMILES: Cc1ncc(Cl)cc1C(=O)N[C@H]1CC[C@H](Cn2c(=O)n(-c3ccc4c(c3)n(C)c(=O)n4C)c3ccccc32)CC1] | 5-chloro-N-((1r,4r)-4-((1,3'-dimethyl-2,2'-dioxo-2',3'-dihydro-1H-[1,5'-bibenzo[d]imidazol]-3(2H)-yl)methyl)cyclohexyl)-2-methylnicotinamide | Intermediate-90, Mesylate-1 | A1 |
| 170 | 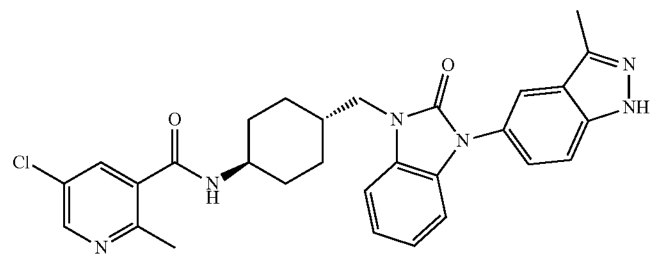 [SMILES: Cc1ncc(Cl)cc1C(=O)N[C@H]1CC[C@H](Cn2c(=O)n(-c3ccc4[nH]nc(C)c4c3)c3ccccc32)CC1] | 5-chloro-2-methyl-N-((1r,4r)-4-((3-(3-methyl-1H-indazol-5-yl)-2-oxo-2,3-dihydro-1H-benzo[d]imidazol-1-yl)methyl)cyclohexyl)nicotinamide | Intermediate-91, Mesylate-1 | O |
| 171 | 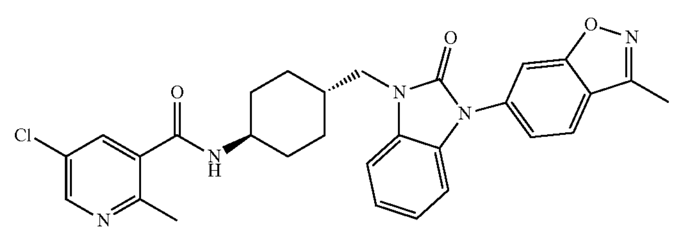 [SMILES: Cc1ncc(Cl)cc1C(=O)N[C@H]1CC[C@H](Cn2c(=O)n(-c3ccc4c(C)noc4c3)c3ccccc32)CC1] | 5-chloro-2-methyl-N-((1r,4r)-4-((3-(3-methylbenzo[d]isoxazol-6-yl)-2-oxo-2,3-dihydro-1H-benzo[d]imidazol-1-yl)methyl)cyclohexyl)nicotinamide | Intermediate-92, Mesylate-1 | A1 |

TABLE 2-continued

| Ex. | Structure | Name | Reactants | Method |
|---|---|---|---|---|
| 172 | 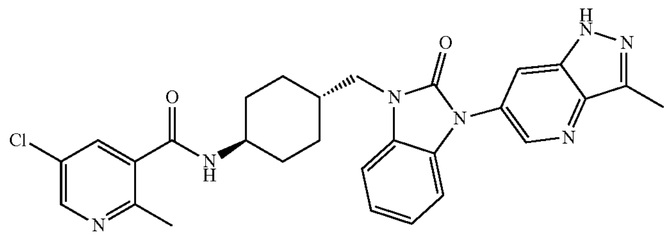 [SMILES: Cc1ncc(Cl)cc1C(=O)N[C@H]1CC[C@H](Cn2c(=O)n(-c3cnc4c(C)n[nH]c4c3)c3ccccc32)CC1] | 5-chloro-2-methyl-N-((1r,4r)-4-(3-(3-methyl-1H-pyrazolo[4,3-b]pyridin-6-yl)-2-oxo-2,3-dihydro-1H-benzo[d]imidazol-1-yl)methyl)cyclohexyl)nicotinamide | see Example synthesis part | |
| 173 | 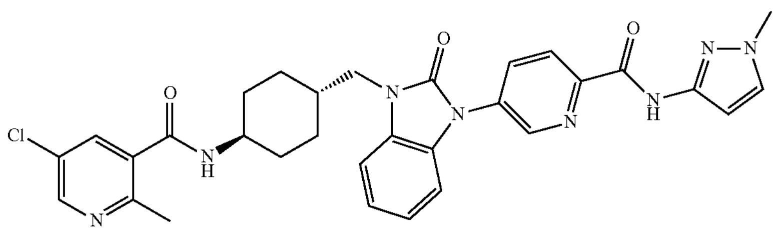 [SMILES: Cc1ncc(Cl)cc1C(=O)N[C@H]1CC[C@H](Cn2c(=O)n(-c3ccc(C(=O)Nc4ccn(C)n4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(1-methyl-1H-pyrazol-3-yl)picolinamide | Intermediate-36, | Q |
| 174 | 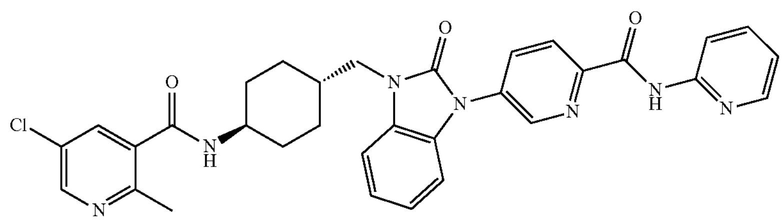 [SMILES: Cc1ncc(Cl)cc1C(=O)N[C@H]1CC[C@H](Cn2c(=O)n(-c3ccc(C(=O)Nc4ccccn4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-2-yl)picolinamide | Intermediate-36, | Q |
| 175 | 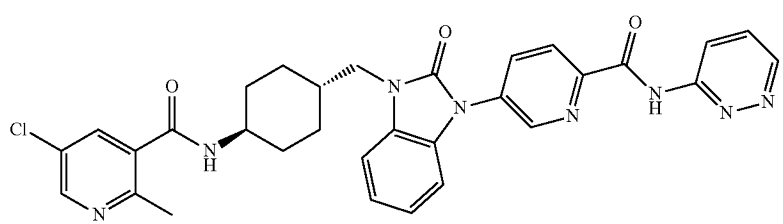 [SMILES: Cc1ncc(Cl)cc1C(=O)N[C@H]1CC[C@H](Cn2c(=O)n(-c3ccc(C(=O)Nc4cccnn4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(pyridazin-3-yl)picolinamide | Intermediate-36, | Q |

TABLE 2-continued

| Ex. | Structure | Name | Reactants | Method |
|---|---|---|---|---|
| 176 | 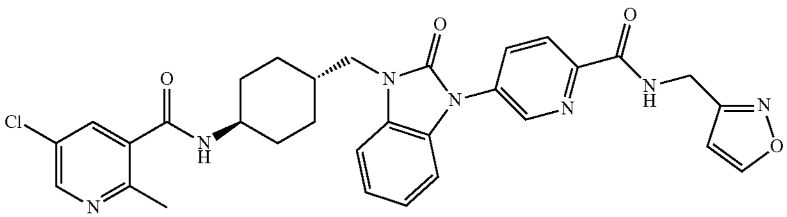 [SMILES: Cc1ncc(Cl)cc1C(=O)N[C@H]1CC[C@H](Cn2c(=O)n(-c3ccc(C(=O)NCc4ccon4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(isoxazol-3-ylmethyl)picolinamide | Intermediate-36, | Q |
| 177 | 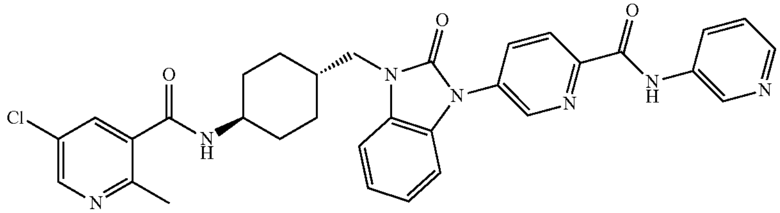 [SMILES: Cc1ncc(Cl)cc1C(=O)N[C@H]1CC[C@H](Cn2c(=O)n(-c3ccc(C(=O)Nc4cccnc4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-3-yl)picolinamide | Intermediate-36, | Q |
| 178 | 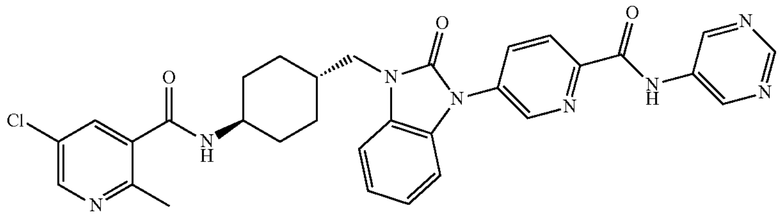 [SMILES: Cc1ncc(Cl)cc1C(=O)N[C@H]1CC[C@H](Cn2c(=O)n(-c3ccc(C(=O)Nc4cncnc4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(pyrimidin-5-yl)picolinamide | Intermediate-36, | Q |
| 179 | 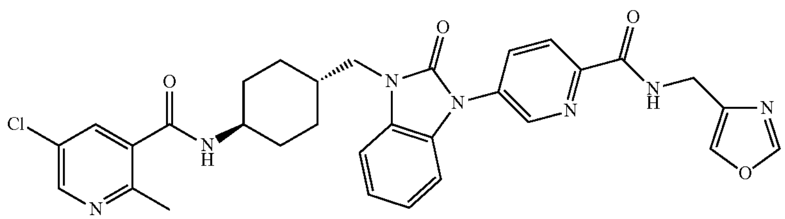 [SMILES: Cc1ncc(Cl)cc1C(=O)N[C@H]1CC[C@H](Cn2c(=O)n(-c3ccc(C(=O)NCc4cocn4)nc3)c3ccccc32)CC1] | 5-(3-(((1r,4r)-4-(5-chloro-2-methylnicotinamido)cyclohexyl)methyl)-2-oxo-2,3-dihydro-1H-benzo[d]imidazol-1-yl)-N-(oxazol-4-ylmethyl)picolinamide | Intermediate-36, | Q |

TABLE 2-continued

| Ex. | Structure | Name | Reactants | Method |
|-----|-----------|------|-----------|--------|
| 180 | 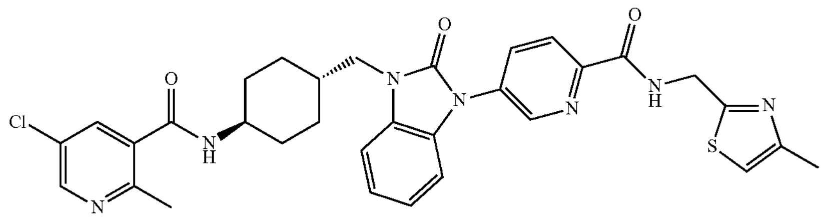 [SMILES: Cc1csc(CNC(=O)c2ccc(-n3c(=O)n(C[C@H]4CC[C@H](NC(=O)c5cc(Cl)cnc5C)CC4)c4ccccc43)cn2)n1] | 5-(3-((1r,4r)-4-(5-chloro-2-methylnicotinamido)cyclohexyl)methyl)-2-oxo-2,3-dihydro-1H-benzo[d]imidazol-1-yl)-N-((4-methylthiazol-2-yl)methyl)picolinamide | Intermediate-36, (4-methylthiazol-2-yl)methanamine | Q |
| 181 | 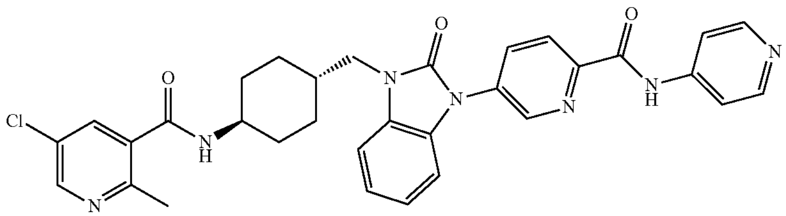 [SMILES: Cc1ncc(Cl)cc1C(=O)N[C@H]1CC[C@H](Cn2c(=O)n(-c3ccc(C(=O)Nc4ccncc4)nc3)c3ccccc32)CC1] | 5-(3-((1r,4r)-4-(5-chloro-2-methylnicotinamido)cyclohexyl)methyl)-2-oxo-2,3-dihydro-1H-benzo[d]imidazol-1-yl)-N-(pyridin-4-yl)picolinamide | Intermediate-36, pyridin-4-amine | Q |
| 182 | 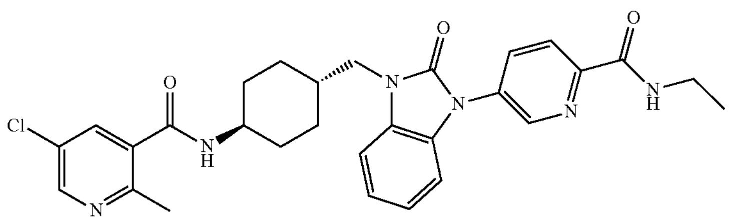 [SMILES: CCNC(=O)c1ccc(-n2c(=O)n(C[C@H]3CC[C@H](NC(=O)c4cc(Cl)cnc4C)CC3)c3ccccc32)cn1] | 5-(3-((1r,4r)-4-(5-chloro-2-methylnicotinamido)cyclohexyl)methyl)-2-oxo-2,3-dihydro-1H-benzo[d]imidazol-1-yl)-N-ethylpicolinamide | Intermediate-36, ethylamine | Q |
| 183 | 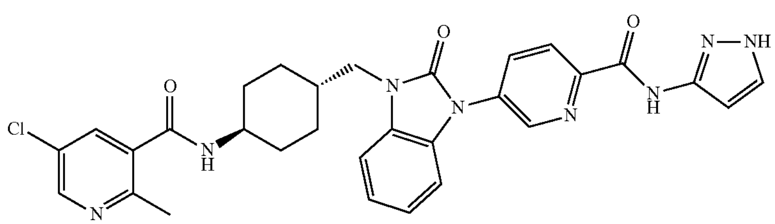 [SMILES: Cc1ncc(Cl)cc1C(=O)N[C@H]1CC[C@H](Cn2c(=O)n(-c3ccc(C(=O)Nc4cc[nH]n4)nc3)c3ccccc32)CC1] | 5-(3-((1r,4r)-4-(5-chloro-2-methylnicotinamido)cyclohexyl)methyl)-2-oxo-2,3-dihydro-1H-benzo[d]imidazol-1-yl)-N-(1H-pyrazol-3-yl)picolinamide | Intermediate-36, 1H-pyrazol-3-amine | Q |

TABLE 2-continued

| Ex. | Structure | Name | Reactants | Method |
|---|---|---|---|---|
| 184 | 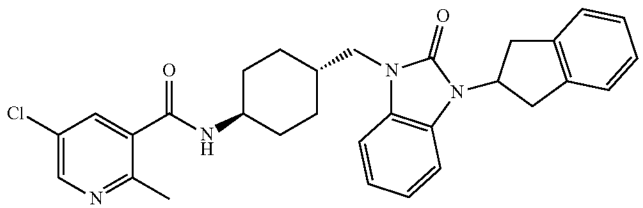 [SMILES: Cc1ncc(Cl)cc1C(=O)N[C@H]1CC[C@H](Cn2c(=O)n(C3Cc4ccccc4C3)c3ccccc32)CC1] | 5-chloro-N-((1r,4r)-4-((3-(2,3-dihydro-1H-inden-2-yl)-2-oxo-2,3-dihydro-1H-benzo[d]imidazol-1-yl)methyl)cyclohexyl)-2-methylnicotinamide | Intermediate-94, Mesylate-1 | A1 |
| 185 | 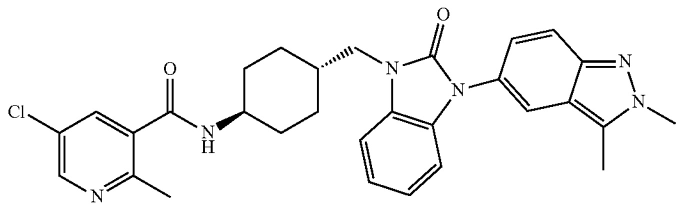 [SMILES: Cc1ncc(Cl)cc1C(=O)N[C@H]1CC[C@H](Cn2c(=O)n(-c3ccc4nn(C)c(C)c4c3)c3ccccc32)CC1] | 5-chloro-N-((1r,4r)-4-((3-(2,3-dimethyl-2H-indazol-5-yl)-2-oxo-2,3-dihydro-1H-benzo[d]imidazol-1-yl)methyl)cyclohexyl)-2-methylnicotinamide | Intermediate-95, Mesylate-1 | A1 |
| 186 | 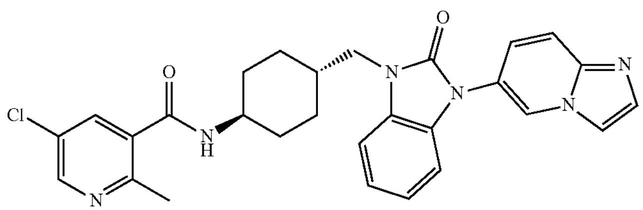 [SMILES: Cc1ncc(Cl)cc1C(=O)N[C@H]1CC[C@H](Cn2c(=O)n(-c3ccc4nccn4c3)c3ccccc32)CC1] | 5-chloro-N-((1r,4r)-4-((3-(imidazol[1,2-a]pyridin-6-yl)-2-oxo-2,3-dihydro-1H-benzo[d]imidazol-1-yl)methyl)cyclohexyl)-2-methylnicotinamide | Intermediate-96, Mesylate-1 | A1 |
| 187 | 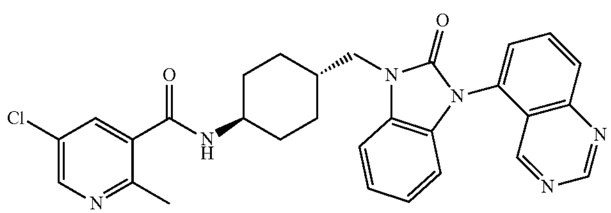 [SMILES: Cc1ncc(Cl)cc1C(=O)N[C@H]1CC[C@H](Cn2c(=O)n(-c3cccc4ncncc34)c3ccccc32)CC1] | 5-chloro-2-methyl-N-((1r,4r)-4-((2-oxo-3-(quinazolin-5-yl)-2,3-dihydro-1H-benzo[d]imidazol-1-yl)methyl)cyclohexyl)nicotinamide | Intermediate-97, Mesylate-1 | A1 |
| 188 | 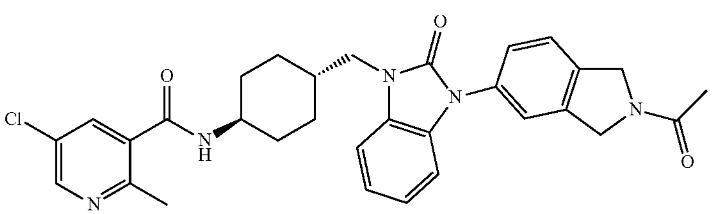 [SMILES: CC(=O)N1Cc2ccc(-n3c(=O)n(C[C@H]4CC[C@H](NC(=O)c5cc(Cl)cnc5C)CC4)c4ccccc43)cc2C1] | N-((1r,4r)-4-((3-(2-acetylisoindolin-5-yl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 189 | 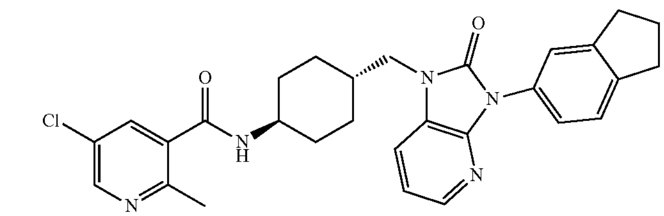 [SMILES: Cc1ncc(Cl)cc1C(=O)N[C@H]1CC[C@H](Cn2c(=O)n(-c3ccc4c(c3)CCC4)c3ncccc32)CC1] | 5-chloro-N-((1r,4r)-4-((3-(2,3-dihydro-1H-inden-5-yl)-2-oxo-2,3-dihydro-1H-imidazo[4,5-b]pyridin-1-yl)methyl)cyclohexyl)-2-methylnicotinamide | Intermediate-98, Mesylate-1 | A1 |
| 190 | 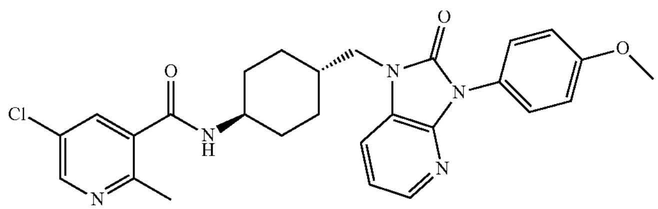 | 5-chloro-N-((1r,4r)-4-((3-(4-methoxyphenyl)-2-oxo-2,3-dihydro-1H-imidazo[4,5-b]pyridin-1-yl)methyl)cyclohexyl)-2-methylnicotinamide | Intermediate-99, Mesylate-1 | A1 |
| 191 | 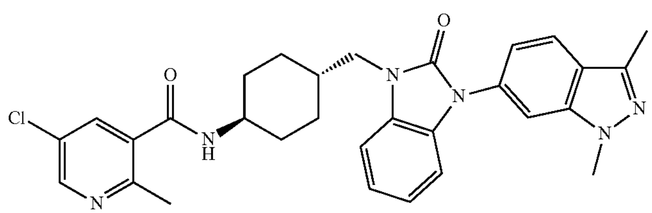 [SMILES: Cc1ncc(Cl)cc1C(=O)N[C@H]1CC[C@H](Cn2c(=O)n(-c3ccc4c(C)nn(C)c4c3)c3ccccc32)CC1] | 5-chloro-N-((1r,4r)-4-((3-(1,3-dimethyl-1H-indazol-6-yl)-2-oxo-2,3-dihydro-1H-benzo[d]imidazol-1-yl)methyl)cyclohexyl)-2-methylnicotinamide | Intermediate-100, Mesylate-1 | A1 |
| 192 | 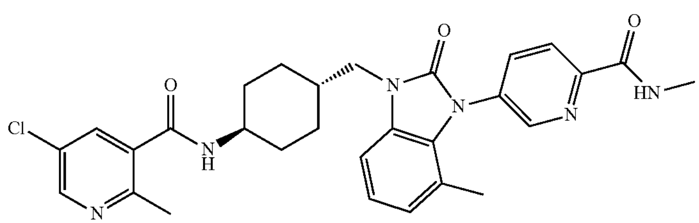 [SMILES: CNC(=O)c1ccc(-n2c(=O)n(C[C@H]3CC[C@H](NC(=O)c4cc(Cl)cnc4C)CC3)c3cccc(C)c32)cn1] | 5-(3-(((1r,4r)-4-(5-chloro-2-methylnicotinamido)cyclohexyl)methyl)-7-methyl-2-oxo-2,3-dihydro-1H-benzo[d]imidazol-1-yl)-N-methylpicolinamide | Intermediate-101, Mesylate-1 | A1 |

TABLE 2-continued

| Ex. | Structure | Name | Reactants | Method |
|---|---|---|---|---|
| 193 | 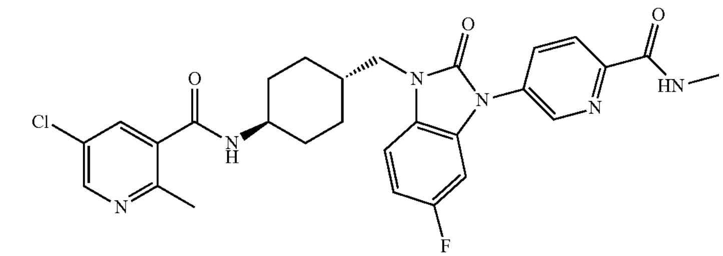 [SMILES: CNC(=O)c1ccc(-n2c(=O)n(C[C@H]3CC[C@H](NC(=O)c4cc(Cl)cnc4C)CC3)c3ccc(F)cc32)cn1] | 5-(3-((1r,4r)-4-(5-chloro-2-methylnicotinamido)cyclohexyl)methyl)-6-fluoro-2-oxo-2,3-dihydro-1H-benzo[d]imidazol-1-yl)-N-methylpicolinamide | Intermediate-102, Mesylate-1 | A1 |
| 194 | 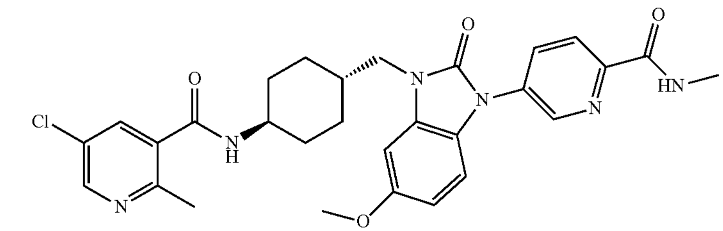 [SMILES: CNC(=O)c1ccc(-n2c(=O)n(C[C@H]3CC[C@H](NC(=O)c4cc(Cl)cnc4C)CC3)c3cc(OC)ccc32)cn1] | 5-(3-((1r,4r)-4-(5-chloro-2-methylnicotinamido)cyclohexyl)methyl)-5-methoxy-2-oxo-2,3-dihydro-1H-benzo[d]imidazol-1-yl)-N-methylpicolinamide | Intermediate-103, Mesylate-1 | A1 |
| 195 | 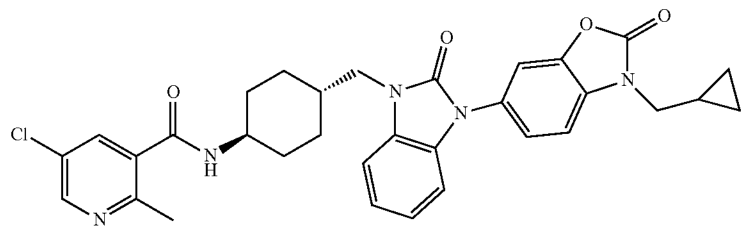 [SMILES: Cc1ncc(Cl)cc1C(=O)N[C@H]1CC[C@H](Cn2c(=O)n(-c3ccc4c(c3)oc(=O)n4CC3CC3)c3ccccc32)CC1] | 5-chloro-N-((1r,4r)-4-((3-(cyclopropylmethyl)-2-oxo-2,3-dihydrobenzo[d]oxazol-6-yl)-2-oxo-2,3-dihydro-1H-benzo[d]imidazol-1-yl)methyl)cyclohexyl)-2-methylnicotinamide | Intermediate-104, Step-2 of Ex 9 | R |
| 196 | 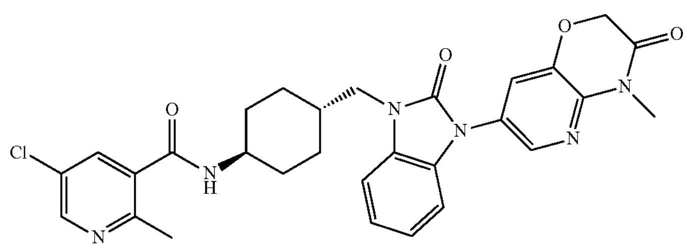 [SMILES: Cc1ncc(Cl)cc1C(=O)N[C@H]1CC[C@H](Cn2c(=O)n(-c3cnc4c(c3)OCC(=O)N4C)c3ccccc32)CC1] | 5-chloro-2-methyl-N-((1r,4r)-4-((3-(4-methyl-3-oxo-3,4-dihydro-2H-pyrido[3,2-b][1,4]oxazin-7-yl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 197 | 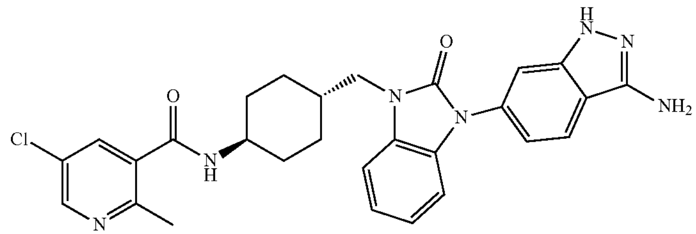 [SMILES: Cc1ncc(Cl)cc1C(=O)N[C@H]1CC[C@H](Cn2c(=O)n(-c3ccc4c(N)n[nH]c4c3)c3ccccc32)CC1] | N-((1r,4r)-4-((3-(3-amino-1H-indazol-6-yl)-2-oxo-2,3-dihydro-1H-benzo[d]imidazol-1-yl)methyl)cyclohexyl)-5-chloro-2-methylnicotinamide | see Example synthesis part | |
| 198 | 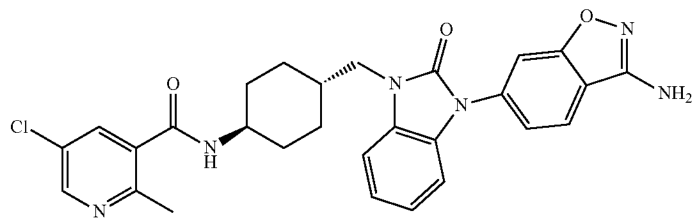 [SMILES: Cc1ncc(Cl)cc1C(=O)N[C@H]1CC[C@H](Cn2c(=O)n(-c3ccc4c(N)noc4c3)c3ccccc32)CC1] | N-((1r,4r)-4-((3-(3-aminobenzo[d]isoxazol-6-yl)-2-oxo-2,3-dihydro-1H-benzo[d]imidazol-1-yl)methyl)cyclohexyl)-5-chloro-2-methylnicotinamide | see Example synthesis part | |
| 199 | 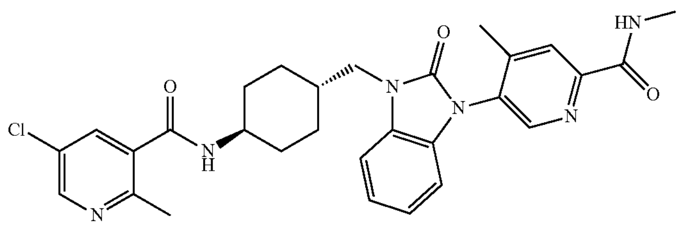 [SMILES: CNC(=O)c1cc(C)c(-n2c(=O)n(C[C@H]3CC[C@H](NC(=O)c4cc(Cl)cnc4C)CC3)c3ccccc32)cn1] | 5-(3-((1r,4r)-4-(5-chloro-2-methylnicotinamido)cyclohexyl)methyl)-2-oxo-2,3-dihydro-1H-benzo[d]imidazol-1-yl)-N,4-dimethylpicolinamide | Intermediate-105, Mesylate-1 | A1 |
| 200 | 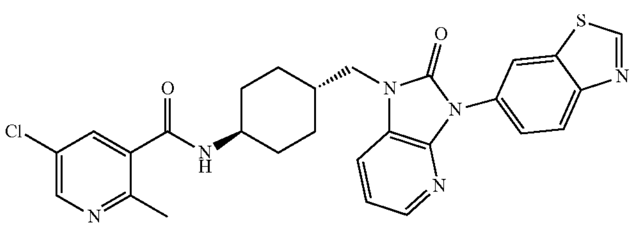 [SMILES: Cc1ncc(Cl)cc1C(=O)N[C@H]1CC[C@H](Cn2c(=O)n(-c3ccc4ncsc4c3)c3ncccc32)CC1] | N-((1r,4r)-4-(3-(benzo[d]thiazol-6-yl)-2-oxo-2,3-dihydro-1H-imidazo[4,5-b]pyridin-1-yl)methyl)cyclohexyl)-5-chloro-2-methylnicotinamide | Intermediate-106, Mesylate-1 | A1 |

TABLE 2-continued

| Ex. | Structure | Name | Reactants | Method |
|---|---|---|---|---|
| 201 | 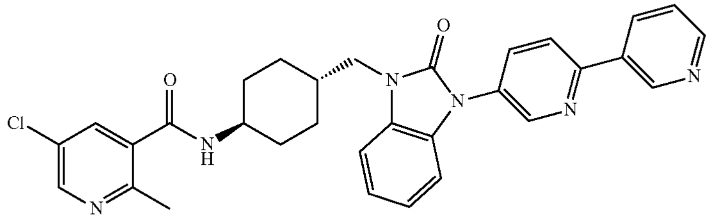 | N-((1r,4r)-4-((3-([2,3'-bipyridin]-5-yl)-2-oxo-2,3-dihydro-1H-benzo[d]imidazol-1-yl)methyl)cyclohexyl)-5-chloro-2-methylnicotinamide | Ex 66, [pyridin-3-yl boronic acid pinacol ester] | I |
| 202 | 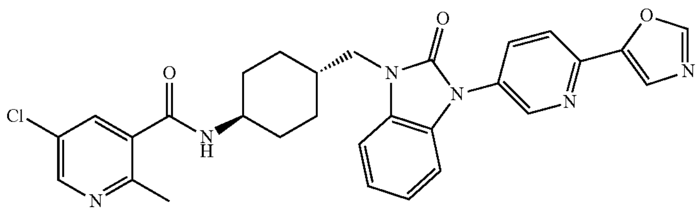 | 5-chloro-2-methyl-N-(((1r,4r)-4-((3-(6-(oxazol-5-yl)pyridin-3-yl)-2-oxo-2,3-dihydro-1H-benzo[d]imidazol-1-yl)methyl)cyclohexyl)nicotinamide | Ex 66, [oxazol-5-yl boronic acid pinacol ester] | I |
| 203 | 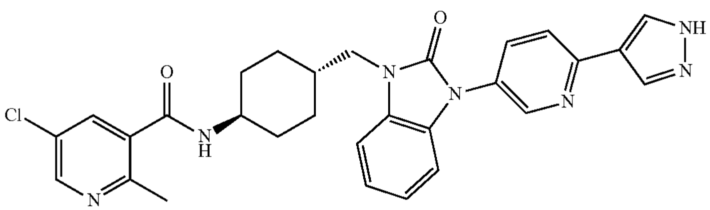 [SMILES: Cc1ncc(Cl)cc1C(=O)N[C@H]1CC[C@H](Cn2c(=O)n(-c3ccc(-c4cn[nH]c4)nc3)c3ccccc32)CC1] | N-((1r,4r)-4-((3-(6-(1H-pyrazol-4-yl)pyridin-3-yl)-2-oxo-2,3-dihydro-1H-benzo[d]imidazol-1-yl)methyl)cyclohexyl)-5-chloro-2-methylnicotinamide | Ex 66, [1H-pyrazol-4-yl boronic acid pinacol ester] | I |
| 204 | 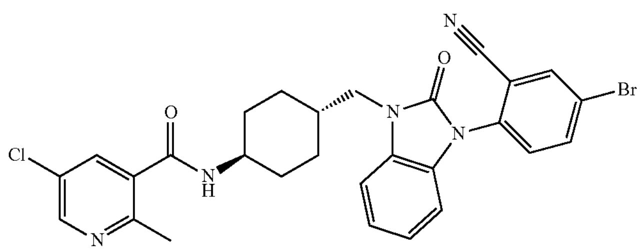 [SMILES: Cc1ncc(Cl)cc1C(=O)N[C@H]1CC[C@H](Cn2c(=O)n(-c3ccc(Br)cc3C#N)c3ccccc32)CC1] | N-((1r,4r)-4-((3-(4-bromo-2-cyanophenyl)-2-oxo-2,3-dihydro-1H-benzo[d]imidazol-1-yl)methyl)cyclohexyl)-5-chloro-2-methylnicotinamide | 5-bromo-2-fluorobenzonitrile, Step-2 of Ex 9 | R |

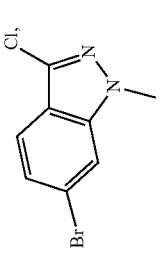

TABLE 2-continued

| Ex. | Structure | Name | Reactants | Method |
|---|---|---|---|---|
| 209 | 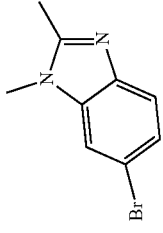 | 5-chloro-N-((1r,4r)-4-((2',3'-dimethyl-2-oxo-3H-[1,5'-bibenzo[d]imidazol]-3(2H)-yl)methyl)cyclohexyl)-2-methylnicotinamide | 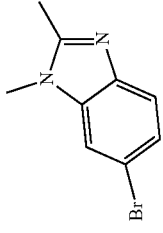  Step-2 of Ex 9 | R |
| 210 | 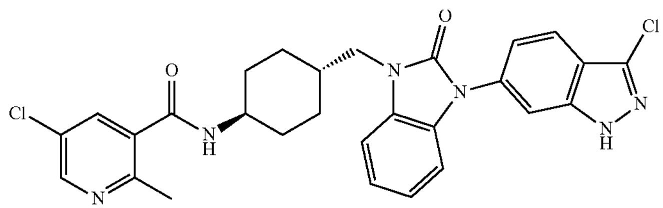 [SMILES: Cc1ncc(Cl)cc1C(=O)N[C@H]1CC[C@H](Cn2c(=O)n(-c3ccc4c(Cl)n[nH]c4c3)c3ccccc32)CC1] | 5-chloro-N-((1r,4r)-4-((3-(3-chloro-1H-indazol-6-yl)-2-oxo-2,3-dihydro-1H-benzo[d]imidazol-1-yl)methyl)cyclohexyl)-2-methylnicotinamide | see Example synthesis part | |
| 211 | 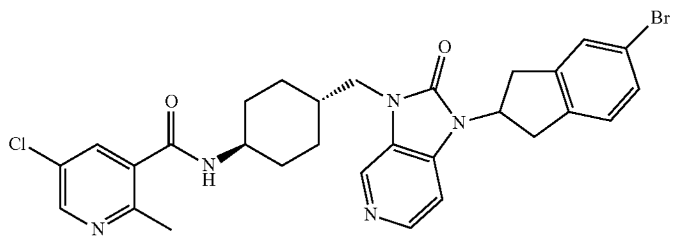 [SMILES: Cc1ncc(Cl)cc1C(=O)N[C@H]1CC[C@H](Cn2c(=O)n(C3Cc4ccc(Br)cc4C3)c3ccncc32)CC1] | N-((1r,4r)-4-((1-(5-bromo-2,3-dihydro-1H-inden-2-yl)-2-oxo-1H-imidazo[4,5-c]pyridin-3(2H)-yl)methyl)cyclohexyl)-5-chloro-2-methylnicotinamide | Intermediate-110, Mesylate-1 | A1 |
| 212 | 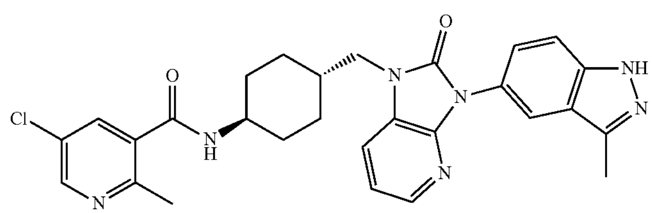 [SMILES: Cc1ncc(Cl)cc1C(=O)N[C@H]1CC[C@H](Cn2c(=O)n(-c3ccc4[nH]nc(C)c4c3)c3ncccc32)CC1] | 5-chloro-2-methyl-N-((1r,4r)-4-((3-(3-methyl-1H-indazol-5-yl)-2-oxo-2,3-dihydro-1H-imidazo[4,5-b]pyridin-1-yl)methyl)cyclohexyl)nicotinamide | Intermediate-111, Mesylate-1 | S |

TABLE 2-continued

| Ex. | Structure | Name | Reactants | Method |
|---|---|---|---|---|
| 213 | 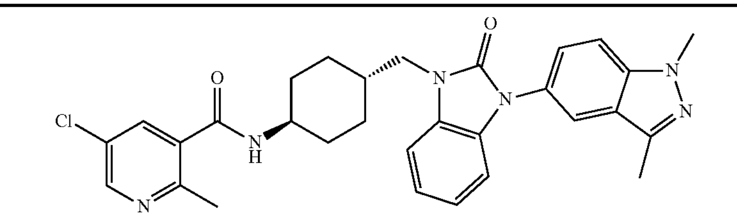 | 5-chloro-N-((1r,4r)-4-((3-(1,3-dimethyl-1H-indazol-5-yl)-2-oxo-2,3-dihydro-1H-benzo[d]imidazol-1-yl)methyl)cyclohexyl)-2-methylnicotinamide | | R |
| 214 | 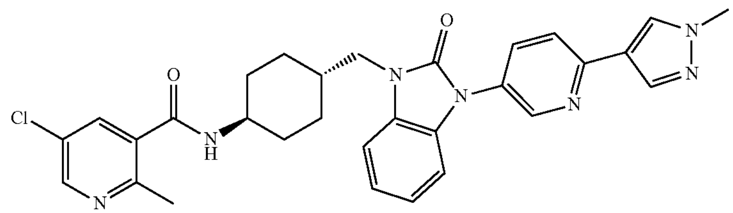 [SMILES: Cc1ncc(Cl)cc1C(=O)N[C@H]1CC[C@H](Cn2c(=O)n(-c3ccc(-c4cnn(C)c4)nc3)c3ccccc32)CC1] | 5-chloro-2-methyl-N-((1r,4r)-4-((3-(6-(1-methyl-1H-pyrazol-4-yl)pyridin-3-yl)-2-oxo-2,3-dihydro-1H-benzo[d]imidazol-1-yl)methyl)cyclohexyl)nicotinamide | Step-2 of Ex 9 Ex 66, | I |
| 215 | 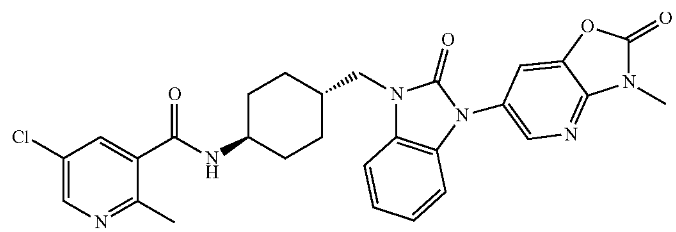 [SMILES: Cc1ncc(Cl)cc1C(=O)N[C@H]1CC[C@H](Cn2c(=O)n(-c3cnc4c(c3)oc(=O)n4C)c3ccccc32)CC1] | 5-chloro-2-methyl-N-((1r,4r)-4-((3-(3-methyl-2-oxo-2,3-dihydrooxazolo[4,5-b]pyridin-6-yl)-2-oxo-2,3-dihydro-1H-benzo[d]imidazol-1-yl)methyl)cyclohexyl)nicotinamide | | T |
| 216 | 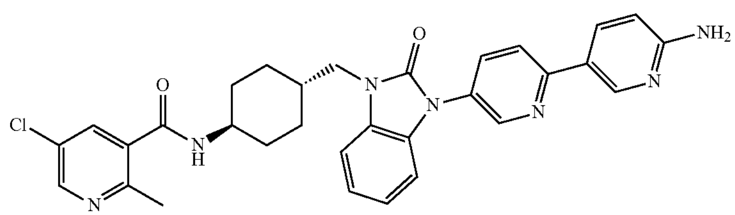 [SMILES: Cc1ncc(Cl)cc1C(=O)N[C@H]1CC[C@H](Cn2c(=O)n(-c3ccc(-c4ccc(N)nc4)nc3)c3ccccc32)CC1] | N-((1r,4r)-4-((3-(6'-amino-[2,3-b]pyridin]-5-yl)-2-oxo-2,3-dihydro-1H-benzo[d]imidazol-1-yl)methyl)cyclohexyl)-5-chloro-2-methylnicotinamide | Step-2 of Ex 9 Ex 66, | I |

TABLE 2-continued

| Ex. | Structure | Name | Reactants | Method |
|---|---|---|---|---|
| 217 | 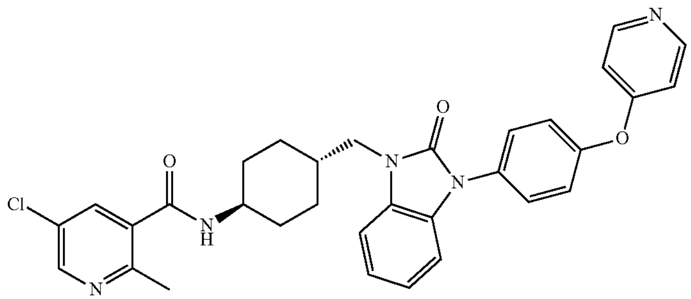 [SMILES: Cc1ncc(Cl)cc1C(=O)N[C@H]1CC[C@H](Cn2c(=O)n(-c3ccc(Oc4ccncc4)cc3)c3ccccc32)CC1] | 5-chloro-2-methyl-N-((1r,4r)-4-((2-oxo-3-(4-(pyridin-4-yloxy)phenyl)-2,3-dihydro-1H-benzo[d]imidazol-1-yl)methyl)cyclohexyl)nicotinamide | Intermediate-112, Mesylate-1 | A1 |
| 218 | 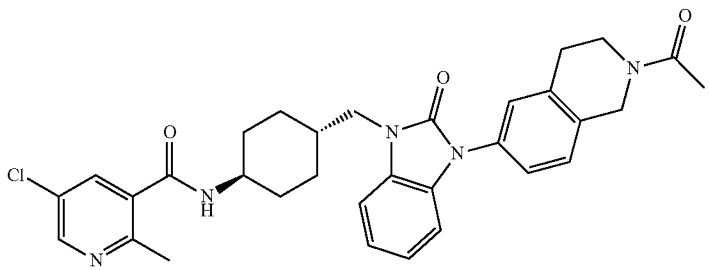 [SMILES: CC(=O)N1CCc2cc(-n3c(=O)n(C[C@H]4CC[C@H](NC(=O)c5cc(Cl)cnc5C)CC4)c4ccccc43)ccc2C1] | N-((1r,4r)-4-((3-(2-acetyl-1,2,3,4-tetrahydroisoquinolin-6-yl)-2-oxo-2,3-dihydro-1H-benzo[d]imidazol-1-yl)methyl)cyclohexyl)-5-chloro-2-methylnicotinamide | see Example synthesis part | |
| 219 | 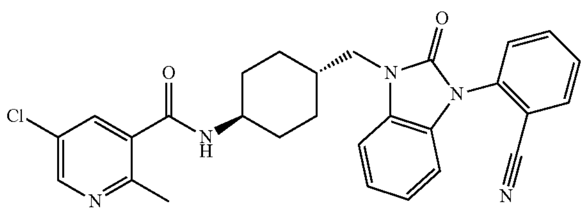 [SMILES: Cc1ncc(Cl)cc1C(=O)N[C@H]1CC[C@H](Cn2c(=O)n(-c3ccccc3C#N)c3ccccc32)CC1] | 5-chloro-N-((1r,4r)-4-((3-(2-cyanophenyl)-2-oxo-2,3-dihydro-1H-benzo[d]imidazol-1-yl)methyl)cyclohexyl)-2-methylnicotinamide | Step-2 of Ex 9 | U |
| 220 | 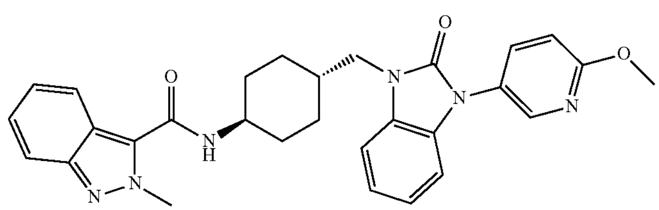 [SMILES: COc1ccc(-n2c(=O)n(C[C@H]3CC[C@H](NC(=O)c4c5ccccc5nn4C)CC3)c3ccccc32)cn1] | N-((1r,4r)-4-((3-(6-methoxypyridin-3-yl)-2-oxo-2,3-dihydro-1H-benzo[d]imidazol-1-yl)methyl)cyclohexyl)-2-methyl-2H-indazole-3-carboxamide | Intermediate-113, | Q |

TABLE 2-continued

| Ex. | Structure | Name | Reactants | Method |
|---|---|---|---|---|
| 221 | 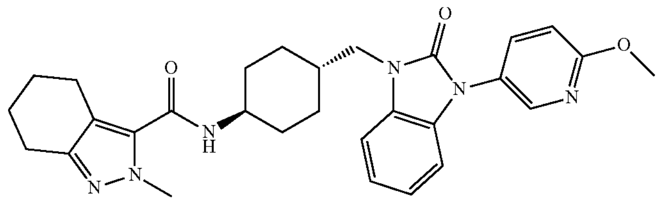 [SMILES: COc1ccc(-n2c(=O)n(C[C@H]3CC[C@H](NC(=O)c4c5c(nn4C)CCCC5)CC3)c3ccccc32)cn1] | N-((1r,4r)-4-((3-(6-methoxy-pyridin-3-yl)-2-oxo-2,3-dihydro-1H-benzo[d]imidazol-1-yl)methyl)cyclohexyl)-2-methyl-4,5,6,7-tetrahydro-2H-indazole-3-carboxamide | Intermediate-113, see Example synthesis part | Q |
| 222 | 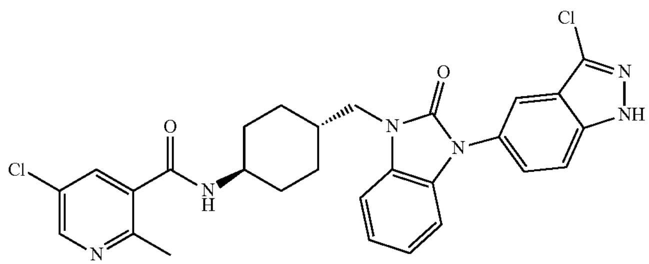 [SMILES: Cc1ncc(Cl)cc1C(=O)N[C@H]1CC[C@H](Cn2c(=O)n(-c3ccc4[nH]nc(Cl)c4c3)c3ccccc32)CC1] | 5-chloro-N-((1r,4r)-4-((3-(3-chloro-1H-indazol-5-yl)-2-oxo-2,3-dihydro-1H-benzo[d]imidazol-1-yl)methyl)cyclohexyl)-2-methylnicotinamide | | |
| 223 | 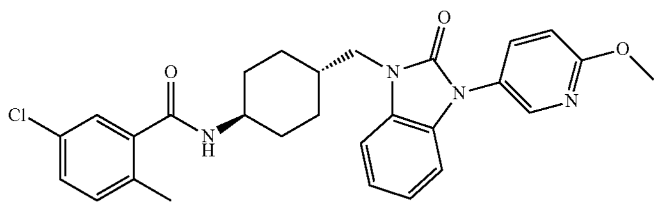 [SMILES: COc1ccc(-n2c(=O)n(C[C@H]3CC[C@H](NC(=O)c4cc(Cl)ccc4C)CC3)c3ccccc32)cn1] | 5-chloro-N-((1r,4r)-4-((3-(6-methoxypyridin-3-yl)-2-oxo-2,3-dihydro-1H-benzo[d]imidazol-1-yl)methyl)cyclohexyl)-2-methylbenzamide | Intermediate-113, see Example synthesis part | Q |
| 224 | 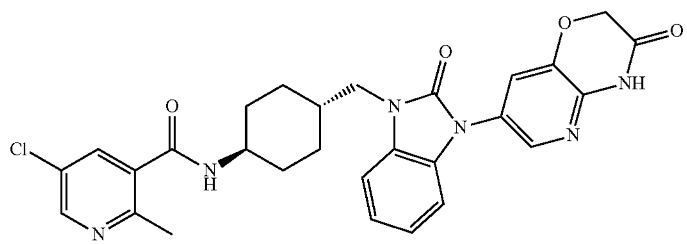 [SMILES: Cc1ncc(Cl)cc1C(=O)N[C@H]1CC[C@H](Cn2c(=O)n(-c3cnc4c(c3)OCC(=O)N4)c3ccccc32)CC1] | 5-chloro-2-methyl-N-((1r,4r)-4-((2-oxo-3-(3-oxo-3,4-dihydro-2H-pyrido[3,2-b][1,4]oxazin-7-yl)-2,3-dihydro-1H-benzo[d]imidazol-1-yl)methyl)cyclohexyl)nicotinamide | | |

TABLE 2-continued

| Ex. | Structure | Name | Reactants | Method |
|---|---|---|---|---|
| 225 | 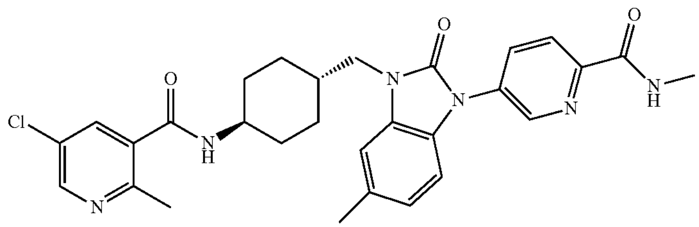 [SMILES: CNC(=O)c1ccc(-n2c(=O)n(C[C@H]3CC[C@H](NC(=O)c4cc(Cl)cnc4C)CC3)c3cc(C)ccc32)cn1] | 5-(3-((1r,4r)-4-(5-chloro-2-methylnicotinamido)cyclohexyl)methyl)-5-methyl-2-oxo-2,3-dihydro-1H-benzo[d]imidazol-1-yl)-N-methylpicolinamide | Intermediate-114, Mesylate-1 | A1 |
| 226 | 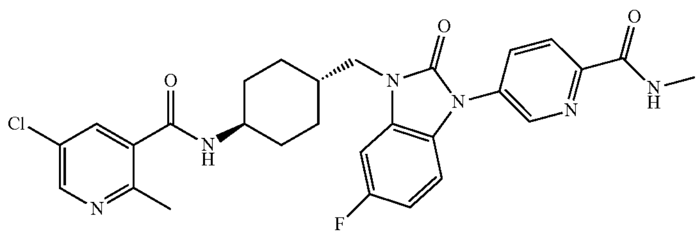 [SMILES: CNC(=O)c1ccc(-n2c(=O)n(C[C@H]3CC[C@H](NC(=O)c4cc(Cl)cnc4C)CC3)c3cc(F)ccc32)cn1] | 5-(3-((1r,4r)-4-(5-chloro-2-methylnicotinamido)cyclohexyl)methyl)-5-fluoro-2-oxo-2,3-dihydro-1H-benzo[d]imidazol-1-yl)-N-methylpicolinamide | Intermediate-115, Mesylate-1 | A1 |
| 227 | 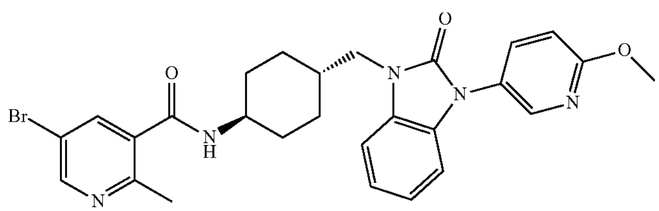 | 5-bromo-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide | Intermediate-113, | Q |
| 228 | 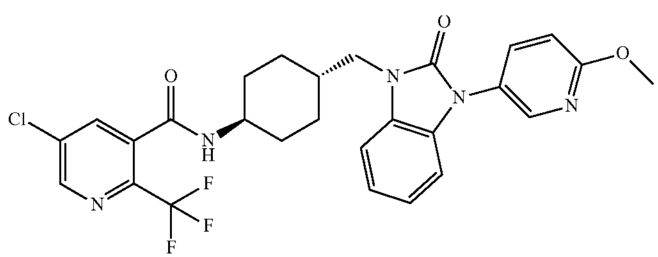 [SMILES: COc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-methoxypyridin-3-yl)-2-oxo-2,3-dihydro-1H-benzo[d]imidazol-1-yl)methyl)cyclohexyl)-2-(trifluoromethyl)nicotinamide | Intermediate-113, | Q |

TABLE 2-continued

| Ex. | Structure | Name | Reactants | Method |
|---|---|---|---|---|
| 229 | 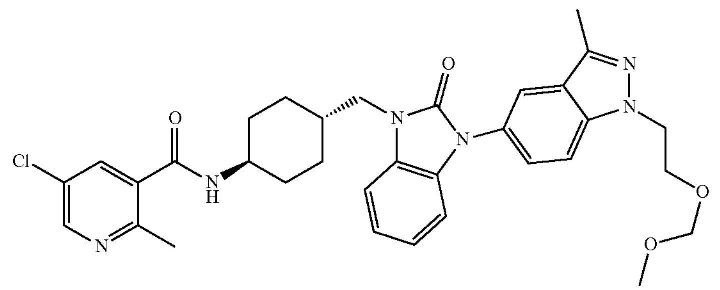 [SMILES: COCOCCn1nc(C)c2cc(-n3c(=O)n(C[C@H]4CC[C@H](NC(=O)c5cc(Cl)cnc5C)CC4)c4ccccc43)ccc21] | 5-chloro-N-((1r,4r)-4-((3-(1-(2-(methoxymethoxy)ethyl)-3-methyl-1H-indazol-5-yl)-2-oxo-2,3-dihydro-1H-benzo[d]imidazol-1-yl)methyl)cyclohexyl)-2-methylnicotinamide | Intermediate-116, Mesylate-1 | A1 |
| 230 | 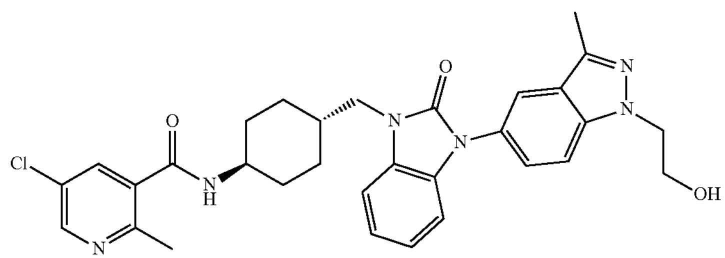 [SMILES: Cc1ncc(Cl)cc1C(=O)N[C@H]1CC[C@H](Cn2c(=O)n(-c3ccc4c(c3)c(C)nn4CCO)c3ccccc32)CC1] | 5-chloro-N-((1r,4r)-4-((3-(1-(2-hydroxyethyl)-3-methyl-1H-indazol-5-yl)-2-oxo-2,3-dihydro-1H-benzo[d]imidazol-1-yl)methyl)cyclohexyl)-2-methylnicotinamide | see Example synthesis part | |
| 231 | 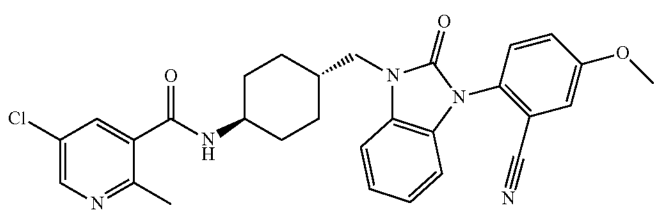 [SMILES: COc1ccc(-n2c(=O)n(C[C@H]3CC[C@H](NC(=O)c4cc(Cl)cnc4C)CC3)c3ccccc32)c(C#N)c1] | 5-chloro-N-((1r,4r)-4-((3-(2-cyano-4-methoxyphenyl)-2-oxo-2,3-dihydro-1H-benzo[d]imidazol-1-yl)methyl)cyclohexyl)-2-methylnicotinamide | Step-2 of Ex 9 | U |
| 232 | 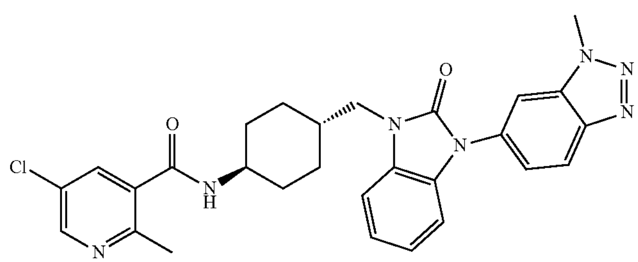 [SMILES: Cc1ncc(Cl)cc1C(=O)N[C@H]1CC[C@H](Cn2c(=O)n(-c3ccc4nnn(C)c4c3)c3ccccc32)CC1] | 5-chloro-2-methyl-N-((1r,4r)-4-((3-(1-methyl-1H-benzo[d][1,2,3]triazol-6-yl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 233 | 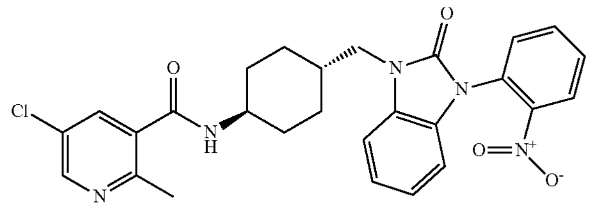 [SMILES: Cc1ncc(Cl)cc1C(=O)N[C@H]1CC[C@H](Cn2c(=O)n(-c3ccccc3[N+](=O)[O-])c3ccccc32)CC1] | 5-chloro-2-methyl-N-((1r,4r)-4-(3-(2-nitrophenyl)-2-oxo-2,3-dihydro-1H-benzo[d]imidazol-1-yl)methyl)cyclohexyl)nicotinamide | Step-2 of Ex 9 | U |
| 234 | 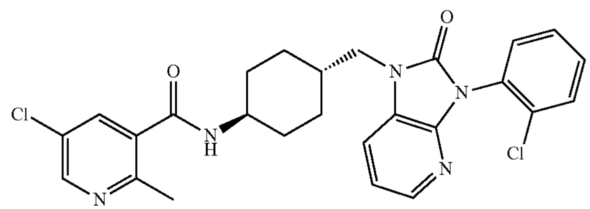 | 5-chloro-N-((1r,4r)-4-(3-(2-chlorophenyl)-2-oxo-2,3-dihydro-1H-imidazo[4,5-b]pyridin-1-yl)methyl)cyclohexyl)-2-methylnicotinamide | Intermediate-117, Mesylate-1 | A1 |
| 235 | 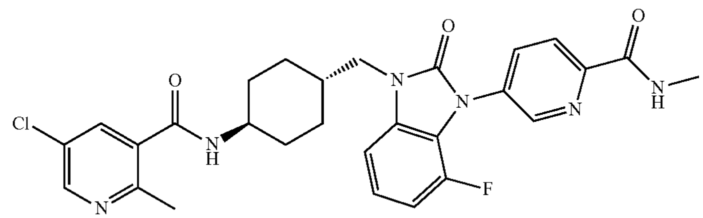 [SMILES: CNC(=O)c1ccc(-n2c(=O)n(C[C@H]3CC[C@H](NC(=O)c4cc(Cl)cnc4C)CC3)c3cccc(F)c32)cn1] | 5-(3-((1r,4r)-4-(5-chloro-2-methylnicotinamido)cyclohexyl)methyl)-7-fluoro-2-oxo-2,3-dihydro-1H-benzo[d]imidazol-1-yl)-N-methylpicolinamide | Intermediate-118, Mesylate-1 | A1 |
| 236 | 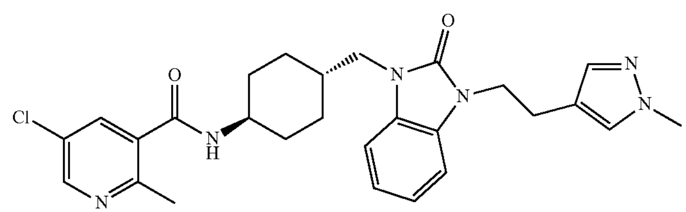 [SMILES: Cc1ncc(Cl)cc1C(=O)N[C@H]1CC[C@H](Cn2c(=O)n(CCc3cnn(C)c3)c3ccccc32)CC1] | 5-chloro-2-methyl-N-((1r,4r)-4-((3-(2-(1-methyl-1H-pyrazol-4-yl)ethyl)-2-oxo-2,3-dihydro-1H-benzo[d]imidazol-1-yl)methyl)cyclohexyl)nicotinamide | Intermediate-119, Mesylate-1 | A1 |

TABLE 2-continued

| Ex. | Structure | Name | Reactants | Method |
|---|---|---|---|---|
| 237 | 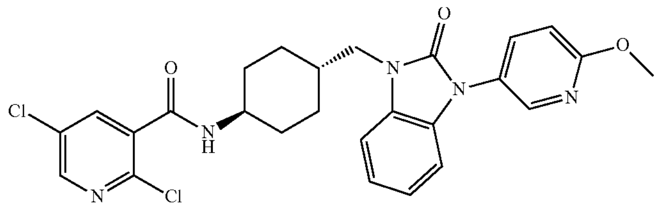 [SMILES: COc1ccc(-n2c(=O)n(C[C@H]3CC[C@H](NC(=O)c4cc(Cl)cnc4Cl)CC3)c3ccccc32)cn1] | 2,5-dichloro-N-((1r,4r)-4-((3-(6-methoxypyridin-3-yl)-2-oxo-2,3-dihydro-1H-benzo[d]imidazol-1-yl)methyl)cyclohexyl)nicotinamide | Intermediate-113, | Q |
| 238 | 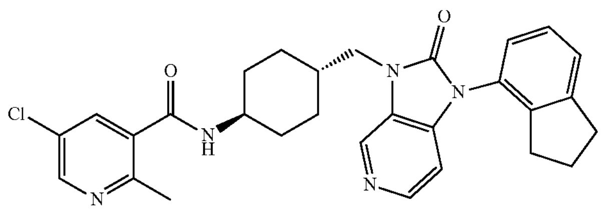 [SMILES: Cc1ncc(Cl)cc1C(=O)N[C@H]1CC[C@H](Cn2c(=O)n(-c3cccc4c3CCC4)c3ccncc32)CC1] | 5-chloro-N-((1r,4r)-4-((1-(2,3-dihydro-1H-inden-4-yl)-2-oxo-1H-imidazol[4,5-c]pyridin-3(2H)-yl)methyl)cyclohexyl)-2-methylnicotinamide | Intermediate-120, Mesylate-1 | A1 |
| 239 | 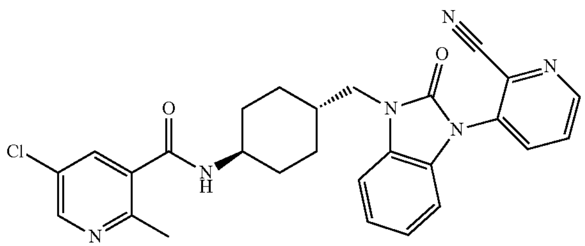 [SMILES: Cc1ncc(Cl)cc1C(=O)N[C@H]1CC[C@H](Cn2c(=O)n(-c3cccnc3C#N)c3ccccc32)CC1] | 5-chloro-N-((1r,4r)-4-((3-(2-cyanopyridin-3-yl)-2-oxo-2,3-dihydro-1H-benzo[d]imidazol-1-yl)methyl)cyclohexyl)-2-methylnicotinamide | Step-2 of Ex 9 | U |
| 240 | 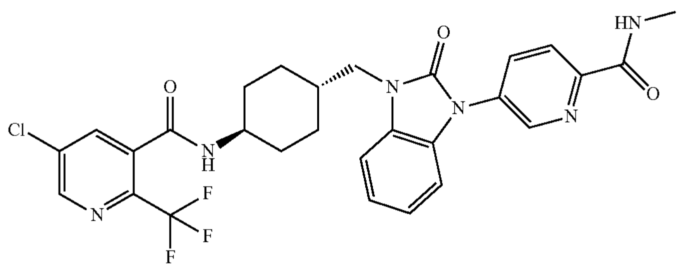 [SMILES: CNC(=O)c1ccc(-n2c(=O)n(C[C@H]3CC[C@H](NC(=O)c4cc(Cl)cnc4C(F)(F)F)CC3)c3ccccc32)cn1] | 5-(3-((1r,4r)-4-(5-chloro-2-(trifluoromethyl)nicotinamido)cyclohexyl)methyl)-2-oxo-2,3-dihydro-1H-benzo[d]imidazol-1-yl)-N-methylpicolinamide | Intermediate-121, | Q |

TABLE 2-continued

| Ex. | Structure | Name | Reactants | Method |
|---|---|---|---|---|
| 241 | 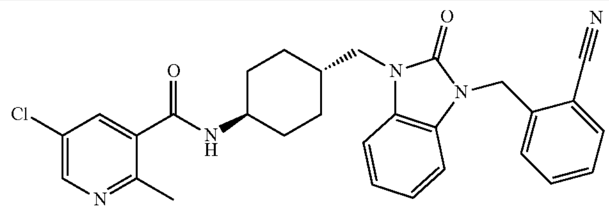 [SMILES: Cc1ncc(Cl)cc1C(=O)N[C@H]1CC[C@H](Cn2c(=O)n(Cc3ccccc3C#N)c3ccccc32)CC1] | 5-chloro-N-((1r,4r)-4-((3-(2-cyanobenzyl)-2-oxo-2,3-dihydro-1H-benzo[d]imidazol-1-yl)methyl)cyclohexyl)-2-methylnicotinamide | see Example synthesis part | |
| 242 | 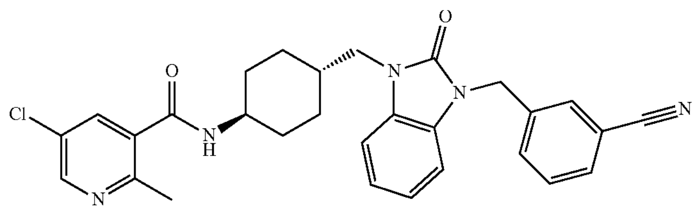 [SMILES: Cc1ncc(Cl)cc1C(=O)N[C@H]1CC[C@H](Cn2c(=O)n(Cc3cccc(C#N)c3)c3ccccc32)CC1] | 5-chloro-N-((1r,4r)-4-((3-(3-cyanobenzyl)-2-oxo-2,3-dihydro-1H-benzo[d]imidazol-1-yl)methyl)cyclohexyl)-2-methylnicotinamide | see Example synthesis part | |
| 243 | 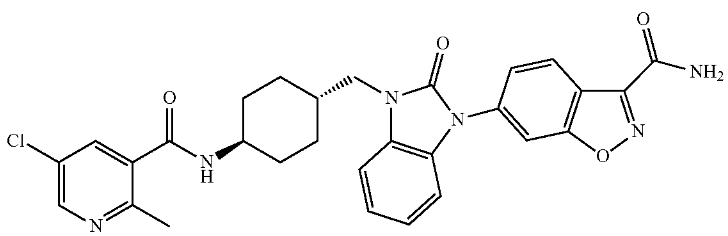 [SMILES: Cc1ncc(Cl)cc1C(=O)N[C@H]1CC[C@H](Cn2c(=O)n(-c3ccc4c(C(N)=O)noc4c3)c3ccccc32)CC1] | 6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxamide | see Example synthesis part | |
| 244 | 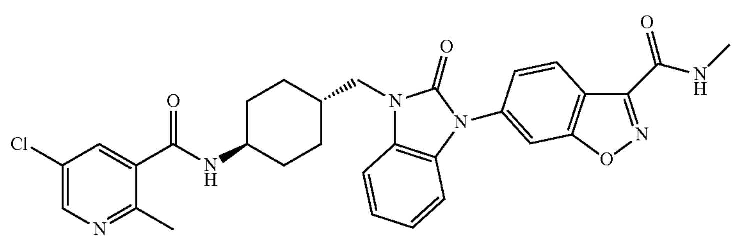 [SMILES: CNC(=O)c1noc2cc(-n3c(=O)n(C[C@H]4CC[C@H](NC(=O)c5cc(Cl)cnc5C)CC4)c4ccccc43)ccc12] | 6-(3-(((1r,4r)-4-(5-chloro-2-methylnicotinamido)cyclohexyl)methyl)-2-oxo-2,3-dihydro-1H-benzo[d]imidazol-1-yl)-N-methylbenzo[d]isoxazole-3-carboxamide | see Example synthesis part | |

TABLE 2-continued

| Ex. | Structure | Name | Reactants | Method |
|---|---|---|---|---|
| 245 | 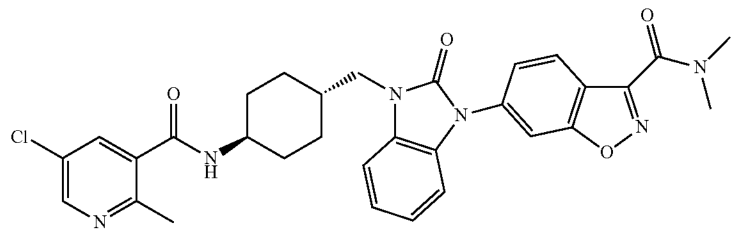 [SMILES: Cc1ncc(Cl)cc1C(=O)N[C@H]1CC[C@H](Cn2c(=O)n(-c3ccc4c(C(=O)N(C)C)noc4c3)c3ccccc32)CC1] | 6-(3-(((1r,4r)-4-(5-chloro-2-methylnicotinamido)cyclohexyl)methyl)-2-oxo-2,3-dihydro-1H-benzo[d]imidazol-1-yl)-N,N-dimethylbenzo[d]isoxazole-3-carboxamide | see Example synthesis part | |
| 246 | 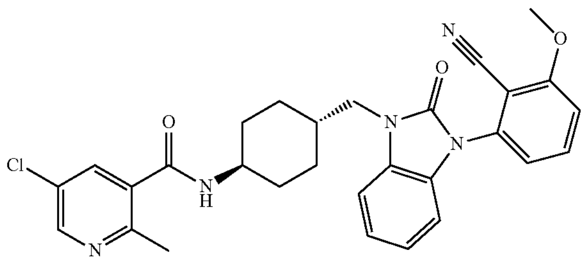 [SMILES: COc1cccc(-n2c(=O)n(C[C@H]3CC[C@H](NC(=O)c4cc(Cl)cnc4C)CC3)c3ccccc32)c1C#N] | 5-chloro-N-((1r,4r)-4-((3-(2-cyano-3-methoxyphenyl)-2-oxo-2,3-dihydro-1H-benzo[d]imidazol-1-yl)methyl)cyclohexyl)-2-methylnicotinamide | Step-2 of Ex 9 | U |
| 247 | 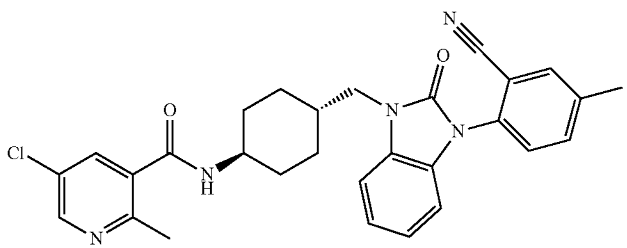 [SMILES: Cc1ccc(-n2c(=O)n(C[C@H]3CC[C@H](NC(=O)c4cc(Cl)cnc4C)CC3)c3ccccc32)c(C#N)c1] | 5-chloro-N-((1r,4r)-4-((3-(2-cyano-4-methylphenyl)-2-oxo-2,3-dihydro-1H-benzo[d]imidazol-1-yl)methyl)cyclohexyl)-2-methylnicotinamide | Step-2 of Ex 9 | U |
| 248 | 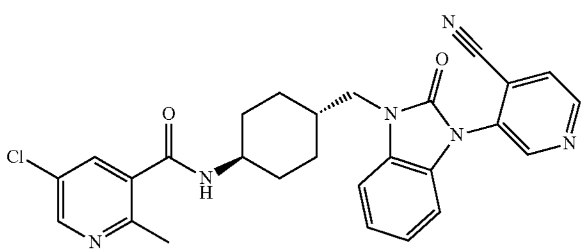 [SMILES: Cc1ncc(Cl)cc1C(=O)N[C@H]1CC[C@H](Cn2c(=O)n(-c3cnccc3C#N)c3ccccc32)CC1] | 5-chloro-N-((1r,4r)-4-((3-(4-cyanopyridin-3-yl)-2-oxo-2,3-dihydro-1H-benzo[d]imidazol-1-yl)methyl)cyclohexyl)-2-methylnicotinamide | Step-2 of Ex 9 | U |

TABLE 2-continued

| Ex. | Structure | Name | Reactants | Method |
|---|---|---|---|---|
| 249 | 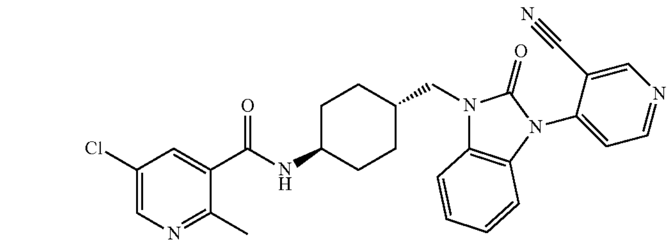 [SMILES: Cc1ncc(Cl)cc1C(=O)N[C@H]1CC[C@H](Cn2c(=O)n(-c3ccncc3C#N)c3ccccc32)CC1] | 5-chloro-N-((1r,4r)-4-((3-(3-cyanopyridin-4-yl)-2-oxo-2,3-dihydro-1H-benzo[d]imidazol-1-yl)methyl)cyclohexyl)-2-methylnicotinamide | 3-cyano-4-chloropyridine; Step-2 of Ex 9 | U |
| 250 | 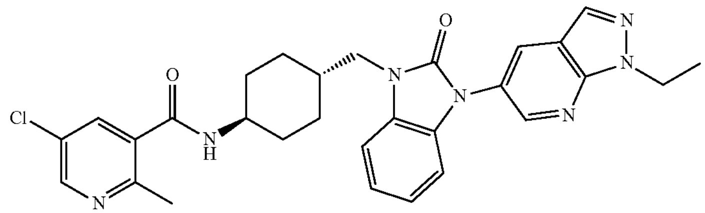 [SMILES: CCn1ncc2cc(-n3c(=O)n(C[C@H]4CC[C@H](NC(=O)c5cc(Cl)cnc5C)CC4)c4ccccc43)cnc21] | 5-chloro-N-((1r,4r)-4-((3-(1-ethyl-1H-pyrazolo[3,4-b]pyridin-5-yl)-2-oxo-2,3-dihydro-1H-benzo[d]imidazol-1-yl)methyl)cyclohexyl)-2-methylnicotinamide | 5-bromo-1-ethyl-1H-pyrazolo[3,4-b]pyridine; Step-2 of Ex 9 | R |
| 251 | 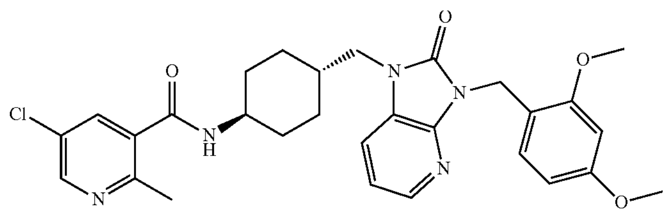 [SMILES: COc1ccc(Cn2c(=O)n(C[C@H]3CC[C@H](NC(=O)c4cc(Cl)cnc4C)CC3)c3cccnc32)c(OC)c1] | 5-chloro-N-((1r,4r)-4-((3-(2,4-dimethoxybenzyl)-2-oxo-2,3-dihydro-1H-imidazo[4,5-b]pyridin-1-yl)methyl)cyclohexyl)-2-methylnicotinamide | Intermediate-122, Mesylate-1 | A1 |
| 252 | 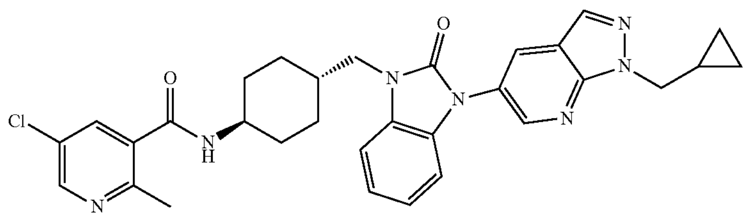 [SMILES: Cc1ncc(Cl)cc1C(=O)N[C@H]1CC[C@H](Cn2c(=O)n(-c3cnc4c(cnn4CC4CC4)c3)c3ccccc32)CC1] | 5-chloro-N-((1r,4r)-4-((3-(1-(cyclopropylmethyl)-1H-pyrazolo[3,4-b]pyridin-5-yl)-2-oxo-2,3-dihydro-1H-benzo[d]imidazol-1-yl)methyl)cyclohexyl)-2-methylnicotinamide | 5-bromo-1-(cyclopropylmethyl)-1H-pyrazolo[3,4-b]pyridine; Step-2 of Ex 9 | R |

TABLE 2-continued

| Ex. | Structure | Name | Reactants | Method |
|---|---|---|---|---|
| 253 | 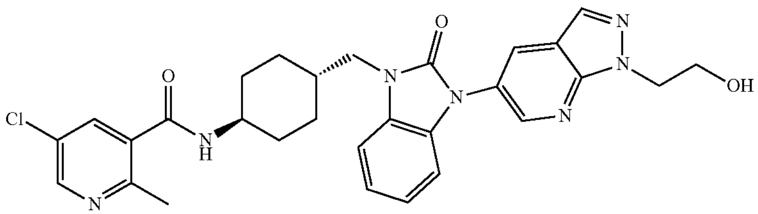 [SMILES: Cc1ncc(Cl)cc1C(=O)N[C@H]1CC[C@H](Cn2c(=O)n(-c3cnc4c(cnn4CCO)c3)c3ccccc32)CC1] | 5-chloro-N-((1r,4r)-4-((3-(1-(2-hydroxyethyl)-1H-pyrazolo[3,4-b]pyridin-5-yl)-2-oxo-2,3-dihydro-1H-benzo[d]imidazol-1-yl)methyl)cyclohexyl)-2-methylnicotinamide | see Example synthesis part | |
| 254 | 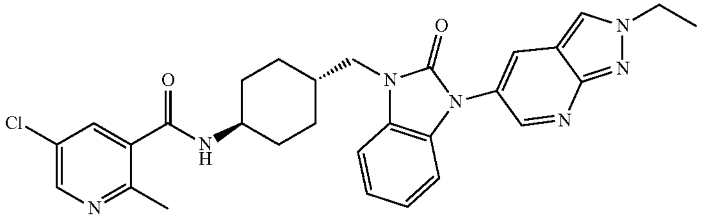 [SMILES: CCn1cc2cc(-n3c(=O)n(C[C@H]4CC[C@H](NC(=O)c5cc(Cl)cnc5C)CC4)c4ccccc43)cnc2n1] | 5-chloro-N-((1r,4r)-4-((3-(2-ethyl-2H-pyrazolo[3,4-b]pyridin-5-yl)-2-oxo-2,3-dihydro-1H-benzo[d]imidazol-1-yl)methyl)cyclohexyl)-2-methylnicotinamide | Intermediate-123, Step-2 of Ex 9 | R |
| 255 | 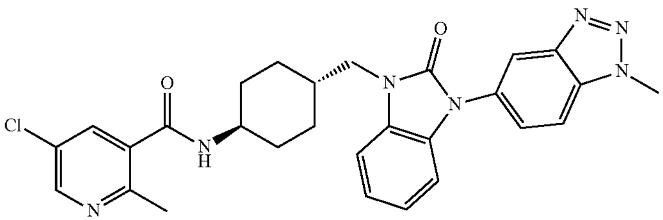 [SMILES: Cc1ncc(Cl)cc1C(=O)N[C@H]1CC[C@H](Cn2c(=O)n(-c3ccc4c(c3)nnn4C)c3ccccc32)CC1] | 5-chloro-2-methyl-N-((1r,4r)-4-((3-(1-methyl-1H-benzo[d][1,2,3]triazol-5-yl)-2-oxo-2,3-dihydro-1H-benzo[d]imidazol-1-yl)methyl)cyclohexyl)nicotinamide | Step-2 of Ex 9 | R |
| 256 | 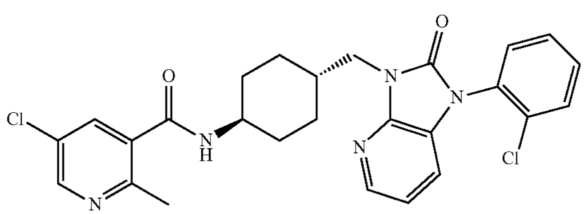 | 5-chloro-N-((1r,4r)-4-((1-(2-chlorophenyl)-2-oxo-1H-imidazo[4,5-b]pyridin-3(2H)-yl)methyl)cyclohexyl)-2-methylnicotinamide | Intermediate-124, Mesylate-1 | A1 |

TABLE 2-continued

| Ex. | Structure | Name | Reactants | Method |
|---|---|---|---|---|
| 257 | 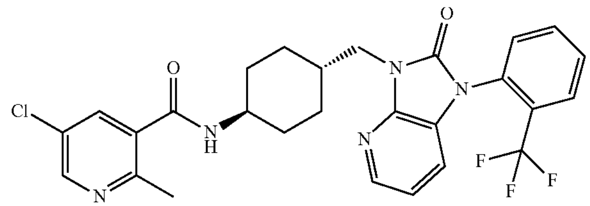 [SMILES: Cc1ncc(Cl)cc1C(=O)N[C@H]1CC[C@H](Cn2c(=O)n(-c3ccccc3C(F)(F)F)c3cccnc32)CC1] | 5-chloro-2-methyl-N-((1r,4r)-4-((2-oxo-1-(2-(trifluoromethyl)phenyl)-1H-imidazo[4,5-b]pyridin-3(2H)-yl)methyl)cyclohexyl)nicotinamide | Intermediate-125, Mesylate-1 | A1 |
| 258 | 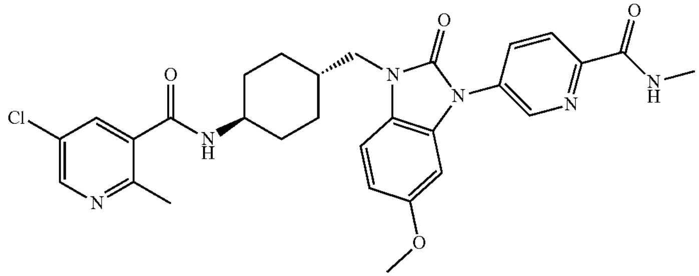 [SMILES: CNC(=O)c1ccc(-n2c(=O)n(C[C@H]3CC[C@H](NC(=O)c4cc(Cl)cnc4C)CC3)c3ccc(OC)cc32)cn1] | 5-(((1r,4r)-4-(5-chloro-2-methylnicotinamido)cyclohexyl)methyl)-6-methoxy-2-oxo-2,3-dihydro-1H-benzo[d]imidazol-1-yl)-N-methylpicolinamide | Intermediate-126, Mesylate-1 | A1 |
| 259 | 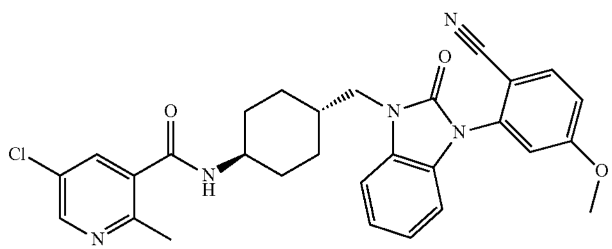 [SMILES: COc1ccc(C#N)c(-n2c(=O)n(C[C@H]3CC[C@H](NC(=O)c4cc(Cl)cnc4C)CC3)c3ccccc32)c1] | 5-chloro-N-((1r,4r)-4-((3-(2-cyano-5-methoxyphenyl)-2-oxo-2,3-dihydro-1H-benzo[d]imidazol-1-yl)methyl)cyclohexyl)-2-methylnicotinamide | | U |
| 260 | 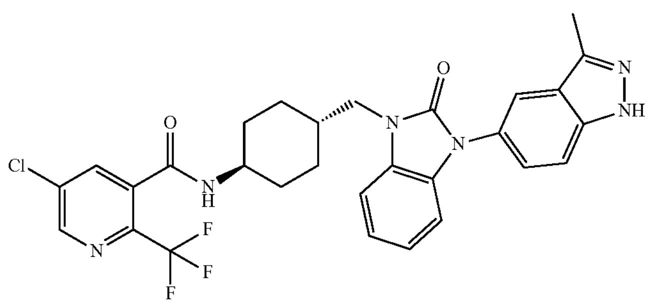 [SMILES: Cc1n[nH]c2ccc(-n3c(=O)n(C[C@H]4CC[C@H](NC(=O)c5cc(Cl)cnc5C(F)(F)F)CC4)c4ccccc43)cc12] | 5-chloro-N-((1r,4r)-4-((3-(3-methyl-1H-indazol-5-yl)-2-oxo-2,3-dihydro-1H-benzo[d]imidazol-1-yl)methyl)cyclohexyl)-2-(trifluoromethyl)nicotinamide | Step-2 of Ex 9 see Example synthesis part | |

TABLE 2-continued

| Ex. | Structure | Name | Reactants | Method |
|---|---|---|---|---|
| 261 | 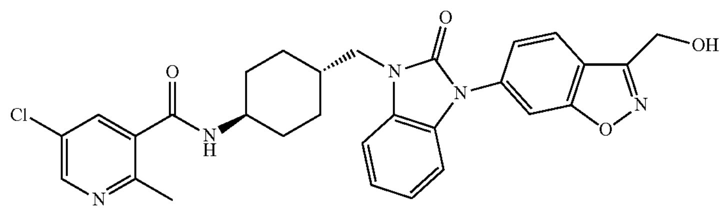 [SMILES: Cc1ncc(Cl)cc1C(=O)N[C@H]1CC[C@H](Cn2c(=O)n(-c3ccc4c(CO)noc4c3)c3ccccc32)CC1] | 5-chloro-N-((1r,4r)-4-((3-(hydroxymethyl)benzo[d]isoxazol-6-yl)-2-oxo-2,3-dihydro-1H-benzo[d]imidazol-1-yl)methyl)cyclohexyl)-2-methylnicotinamide | see Example synthesis part | |
| 262 | 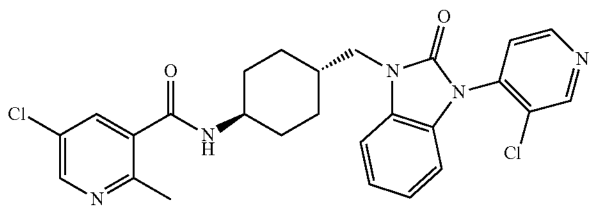 | 5-chloro-N-((1r,4r)-4-((3-(3-chloropyridin-4-yl)-2-oxo-2,3-dihydro-1H-benzo[d]imidazol-1-yl)methyl)cyclohexyl)-2-methylnicotinamide | Step-2 of Ex 9 | R |
| 263 | 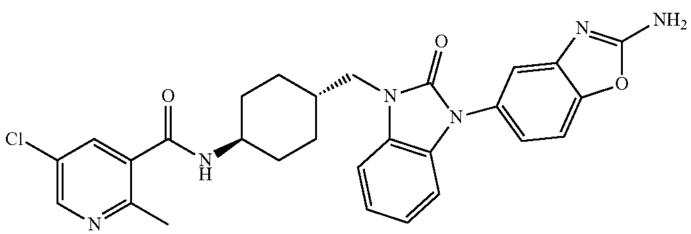 [SMILES: Cc1ncc(Cl)cc1C(=O)N[C@H]1CC[C@H](Cn2c(=O)n(-c3ccc4oc(N)nc4c3)c3ccccc32)CC1] | N-((1r,4r)-4-(3-(2-aminobenzo[d]oxazol-5-yl)-2-oxo-2,3-dihydro-1H-benzo[d]imidazol-1-yl)methyl)cyclohexyl)-5-chloro-2-methylnicotinamide | see Example synthesis part | |
| 264 | 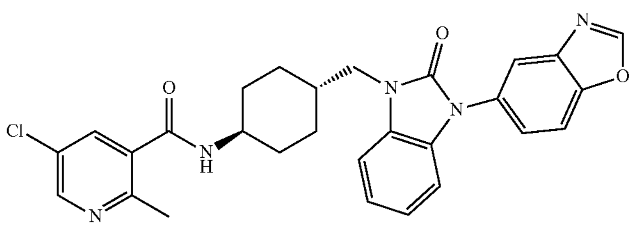 [SMILES: Cc1ncc(Cl)cc1C(=O)N[C@H]1CC[C@H](Cn2c(=O)n(-c3ccc4ocnc4c3)c3ccccc32)CC1] | N-((1r,4r)-4-(3-(benzo[d]oxazol-5-yl)-2-oxo-2,3-dihydro-1H-benzo[d]imidazol-1-yl)methyl)cyclohexyl)-5-chloro-2-methylnicotinamide | Step-2 of Ex 9 | T |

TABLE 2-continued

| Ex. | Structure | Name | Reactants | Method |
|---|---|---|---|---|
| 265 | 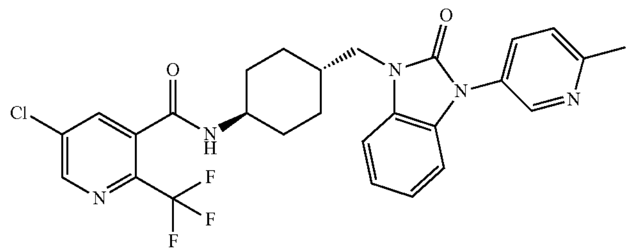 [SMILES: Cc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)nicotinamide | Intermediate-127, | Q |
| 266 | 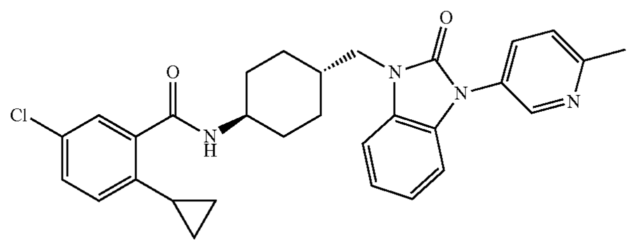 [SMILES: Cc1ccc(-n2c(=O)n(C[C@H]3CC[C@H](NC(=O)c4cc(Cl)ccc4C4CC4)CC3)c3ccccc32)cn1] | 5-chloro-2-cyclopropyl-N-((1r,4r)-4-((3-(6-methylpyridin-3-yl)-2-oxo-2,3-dihydro-1H-benzo[d]imidazol-1-yl)methyl)cyclohexyl)benzamide | Intermediate-127, | Q |
| 267 | 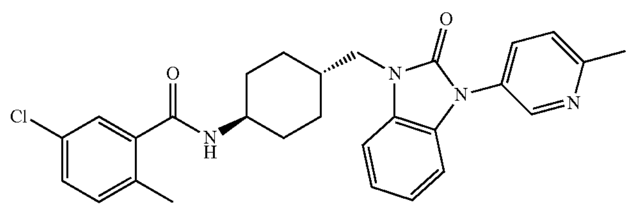 [SMILES: Cc1ccc(-n2c(=O)n(C[C@H]3CC[C@H](NC(=O)c4cc(Cl)ccc4C)CC3)c3ccccc32)cn1] | 5-chloro-2-methyl-N-((1r,4r)-4-((3-(6-methylpyridin-3-yl)-2-oxo-2,3-dihydro-1H-benzo[d]imidazol-1-yl)methyl)cyclohexyl)benzamide | Intermediate-127, | Q |
| 268 | 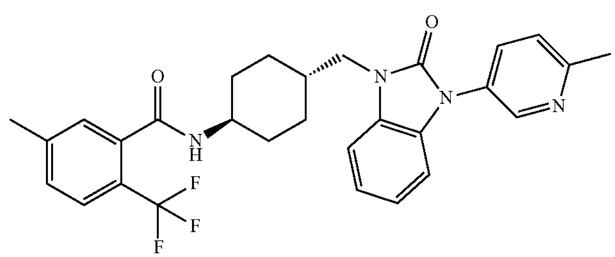 | 5-methyl-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)benzamide | Intermediate-127, | Q |

TABLE 2-continued

| Ex. | Structure | Name | Reactants | Method |
|---|---|---|---|---|
| 269 | 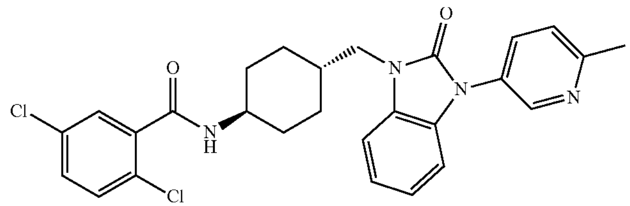 [SMILES: Cc1ccc(-n2c(=O)n(C[C@H]3CC[C@H](NC(=O)c4cc(Cl)ccc4Cl)CC3)c3ccccc32)cn1] | 2,5-dichloro-N-((1r,4r)-4-((3-(6-methylpyridin-3-yl)-2-oxo-2,3-dihydro-1H-benzo[d]imidazol-1-yl)methyl)cyclohexyl)benzamide | Intermediate-127, 2,5-dichlorobenzoic acid | Q |
| 270 | 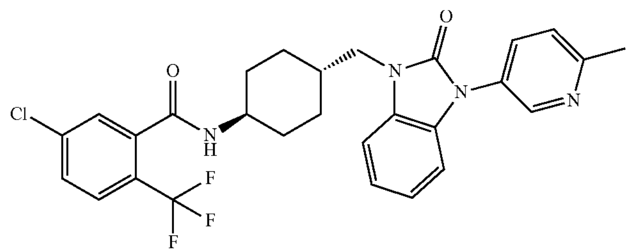 [SMILES: Cc1ccc(-n2c(=O)n(C[C@H]3CC[C@H](NC(=O)c4cc(Cl)ccc4C(F)(F)F)CC3)c3ccccc32)cn1] | 5-chloro-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)benzamide | Intermediate-127, 5-chloro-2-(trifluoromethyl)benzoic acid | Q |
| 271 | 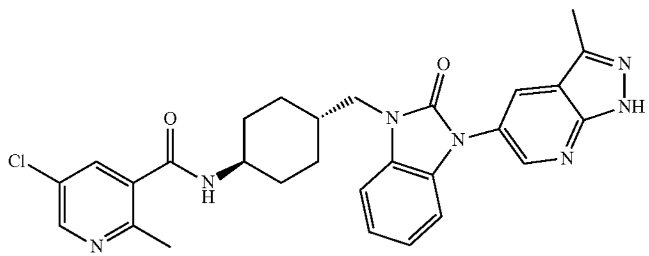 [SMILES: Cc1ncc(Cl)cc1C(=O)N[C@H]1CC[C@H](Cn2c(=O)n(-c3cnc4[nH]nc(C)c4c3)c3ccccc32)CC1] | 5-chloro-2-methyl-N-((1r,4r)-4-((3-(3-methyl-1H-pyrazolo[3,4-b]pyridin-5-yl)-2-oxo-2,3-dihydro-1H-benzo[d]imidazol-1-yl)methyl)cyclohexyl)nicotinamide | see Example synthesis part | |
| 272 | 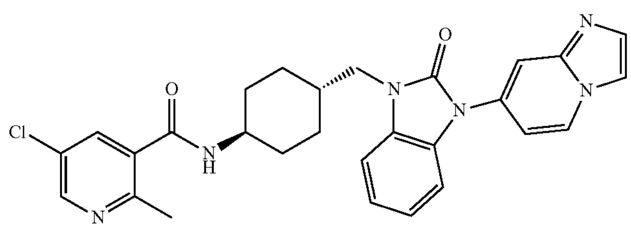 [SMILES: Cc1ncc(Cl)cc1C(=O)N[C@H]1CC[C@H](Cn2c(=O)n(-c3ccn4ccnc4c3)c3ccccc32)CC1] | 5-chloro-N-((1r,4r)-4-(3-(imidazo[1,2-a]pyridin-7-yl)-2-oxo-2,3-dihydro-1H-benzo[d]imidazol-1-yl)methyl)cyclohexyl)-2-methyl-nicotinamide | 7-bromoimidazo[1,2-a]pyridine, Step-2 of Ex 9 | R |

TABLE 2-continued

| Ex. | Structure | Name | Reactants | Method |
|---|---|---|---|---|
| 273 | 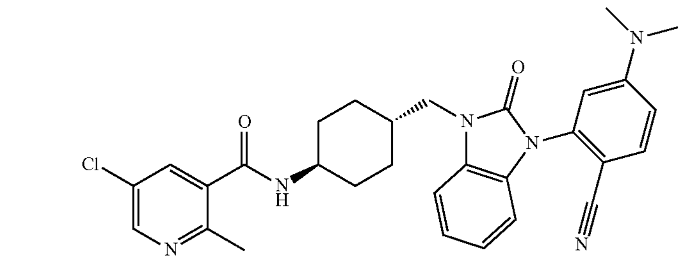 [SMILES: Cc1ncc(Cl)cc1C(=O)N[C@H]1CC[C@H](Cn2c(=O)n(-c3cc(N(C)C)ccc3C#N)c3ccccc32)CC1] | 5-chloro-N-((1r,4r)-4-((3-(2-cyano-5-(dimethylamino)phenyl)-2-oxo-2,3-dihydro-1H-benzo[d]imidazol-1-yl)methyl)cyclohexyl)-2-methylnicotinamide | see Example synthesis part | |
| 274 | 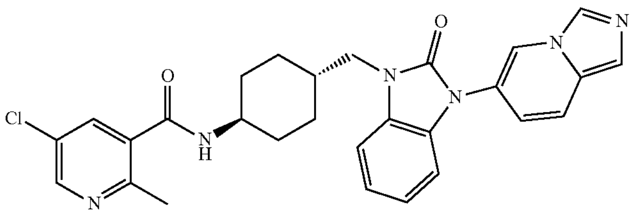 [SMILES: Cc1ncc(Cl)cc1C(=O)N[C@H]1CC[C@H](Cn2c(=O)n(-c3ccc4cncn4c3)c3ccccc32)CC1] | 5-chloro-N-((1r,4r)-4-((3-(imidazo[1,5-a]pyridin-6-yl)-2-oxo-2,3-dihydro-1H-benzo[d]imidazol-1-yl)methyl)cyclohexyl)-2-methylnicotinamide | 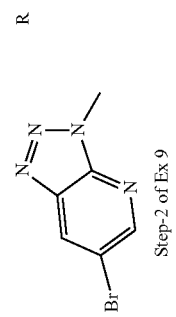 Step-2 of Ex 9 | R |
| 275 | 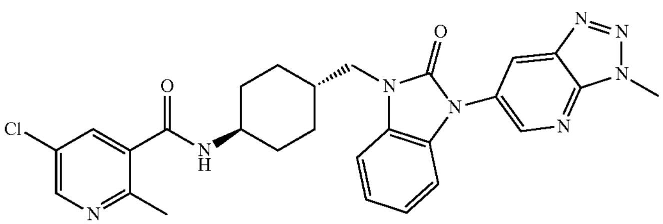 | 5-chloro-2-methyl-N-((1r,4r)-4-((3-(3-methyl-3H-[1,2,3]triazolo[4,5-b]pyridin-6-yl)-2-oxo-2,3-dihydro-1H-benzo[d]imidazol-1-yl)methyl)cyclohexyl)nicotinamide | 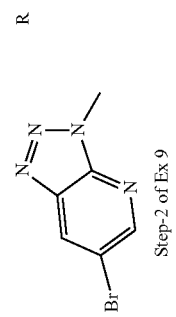 Step-2 of Ex 9 | R |
| 276 | 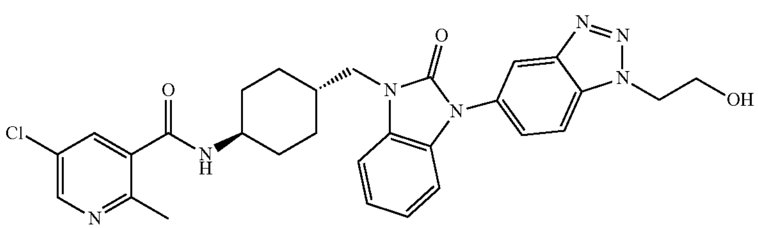 [SMILES: Cc1ncc(Cl)cc1C(=O)N[C@H]1CC[C@H](Cn2c(=O)n(-c3ccc4c(c3)nnn4CCO)c3ccccc32)CC1] | 5-chloro-N-((1r,4r)-4-(3-(1-(2-hydroxyethyl)-1H-benzo[d][1,2,3]triazol-5-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 277 | 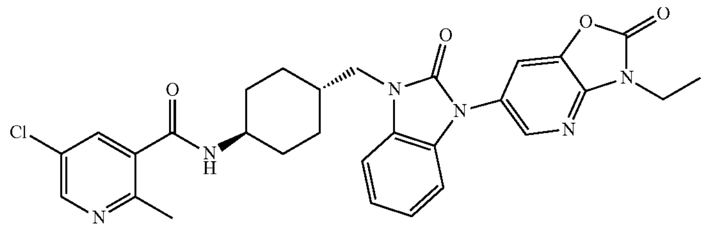 [SMILES: CCn1c(=O)oc2cc(-n3c(=O)n(C[C@H]4CC[C@H](NC(=O)c5cc(Cl)cnc5C)CC4)c4ccccc43)cnc21] | 5-chloro-N-((1r,4r)-4-((3-(3-ethyl-2-oxo-2,3-dihydro-oxazolo[4,5-b]pyridin-6-yl)-2-oxo-2,3-dihydro-1H-benzo[d]imidazol-1-yl)methyl)cyclohexyl)-2-methylnicotinamide | 3-ethyl-6-(4,4,5,5-tetramethyl-1,3,2-dioxaborolan-2-yl)oxazolo[4,5-b]pyridin-2(3H)-one; Step-2 of Ex 9 | T |
| 278 | 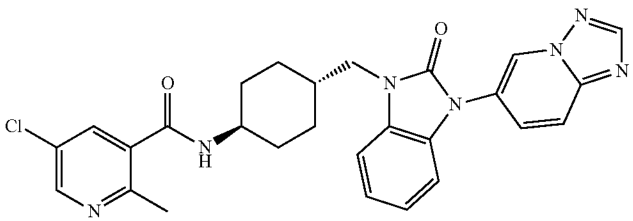 [SMILES: Cc1ncc(Cl)cc1C(=O)N[C@H]1CC[C@H](Cn2c(=O)n(-c3ccc4ncnn4c3)c3ccccc32)CC1] | N-((1r,4r)-4-(3-([1,2,4]triazolo[1,5-a]pyridin-6-yl)-2-oxo-2,3-dihydro-1H-benzo[d]imidazol-1-yl)methyl)-5-chloro-2-methylnicotinamide | 6-bromo-[1,2,4]triazolo[1,5-a]pyridine; Step-2 of Ex 9 | R |
| 279 | 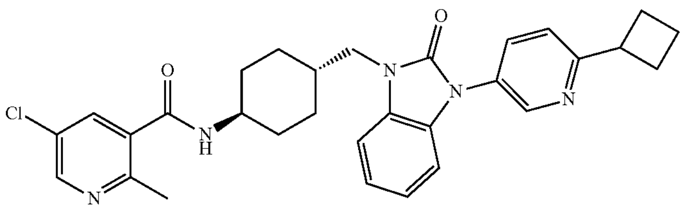 [SMILES: Cc1ncc(Cl)cc1C(=O)N[C@H]1CC[C@H](Cn2c(=O)n(-c3ccc(C4CCC4)nc3)c3ccccc32)CC1] | 5-chloro-N-((1r,4r)-4-((3-(6-cyclobutylpyridin-3-yl)-2-oxo-2,3-dihydro-1H-benzo[d]imidazol-1-yl)methyl)cyclohexyl)-2-methylnicotinamide | see Example synthesis part | |
| 280 | 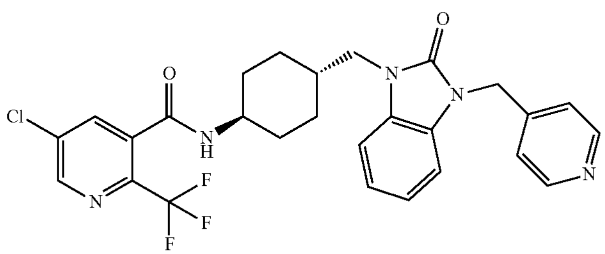 [SMILES: O=C(N[C@H]1CC[C@H](Cn2c(=O)n(Cc3ccncc3)c3ccccc32)CC1)c1cc(Cl)cnc1C(F)(F)F] | 5-chloro-N-((1r,4r)-4-((2-oxo-3-(pyridin-4-ylmethyl)-2,3-dihydro-1H-benzo[d]imidazol-1-yl)methyl)cyclohexyl)-2-(trifluoromethyl)nicotinamide | Intermediate-128, | Q |

TABLE 2-continued

| Ex. | Structure | Name | Reactants | Method |
|---|---|---|---|---|
| 281 | 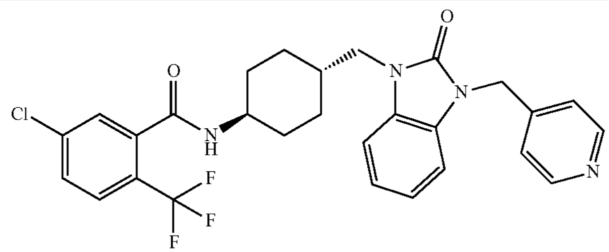 [SMILES: O=C(N[C@H]1CC[C@H](Cn2c(=O)n(Cc3ccncc3)c3ccccc32)CC1)c1cc(Cl)ccc1C(F)(F)F] | 5-chloro-N-((1r,4r)-4-((2-oxo-3-(pyridin-4-ylmethyl)-2,3-dihydro-1H-benzo[d]imidazol-1-yl)methyl)cyclohexyl)-2-(trifluoromethyl)benzamide | Intermediate-128, | Q |
| 282 | 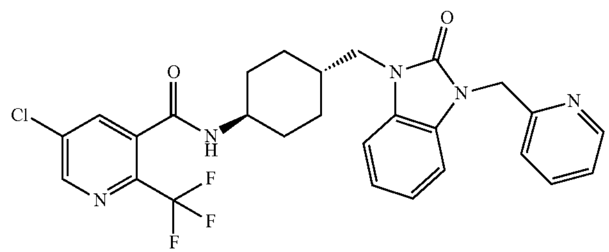 [SMILES: O=C(N[C@H]1CC[C@H](Cn2c(=O)n(Cc3ccccn3)c3ccccc32)CC1)c1cc(Cl)cnc1C(F)(F)F] | 5-chloro-N-((1r,4r)-4-((2-oxo-3-(pyridin-2-ylmethyl)-2,3-dihydro-1H-benzo[d]imidazol-1-yl)methyl)cyclohexyl)-2-(trifluoromethyl)nicotinamide | Intermediate-129, | Q |
| 283 | 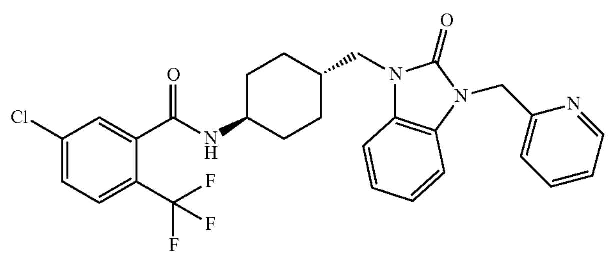 [SMILES: O=C(N[C@H]1CC[C@H](Cn2c(=O)n(Cc3ccccn3)c3ccccc32)CC1)c1cc(Cl)ccc1C(F)(F)F] | 5-chloro-N-((1r,4r)-4-((2-oxo-3-(pyridin-2-ylmethyl)-2,3-dihydro-1H-benzo[d]imidazol-1-yl)methyl)cyclohexyl)-2-(trifluoromethyl)benzamide | Intermediate-129, | Q |
| 284 | 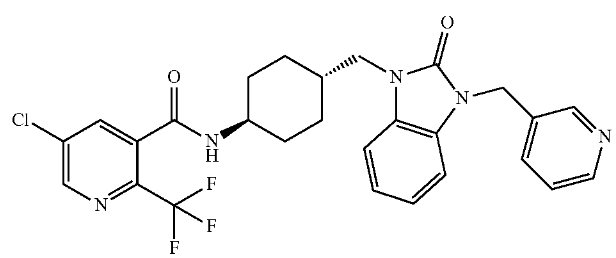 [SMILES: O=C(N[C@H]1CC[C@H](Cn2c(=O)n(Cc3cccnc3)c3ccccc32)CC1)c1cc(Cl)cnc1C(F)(F)F] | 5-chloro-N-((1r,4r)-4-((2-oxo-3-(pyridin-3-ylmethyl)-2,3-dihydro-1H-benzo[d]imidazol-1-yl)methyl)cyclohexyl)-2-(trifluoromethyl)nicotinamide | Intermediate-130, | Q |

TABLE 2-continued

| Ex. | Structure | Name | Reactants | Method |
|---|---|---|---|---|
| 285 | 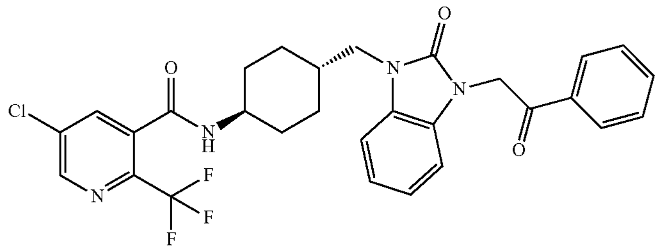 [SMILES: O=C(Cn1c(=O)n(C[C@H]2CC[C@H](NC(=O)c3cc(Cl)cnc3C(F)(F)F)CC2)c2ccccc21)c1ccccc1] | 5-chloro-N-((1r,4r)-4-((2-oxo-3-(2-oxo-2-phenylethyl)-2,3-dihydro-1H-benzo[d]imidazol-1-yl)methyl)cyclohexyl)-2-(trifluoromethyl)nicotinamide | Intermediate-131, | Q |
| 286 | 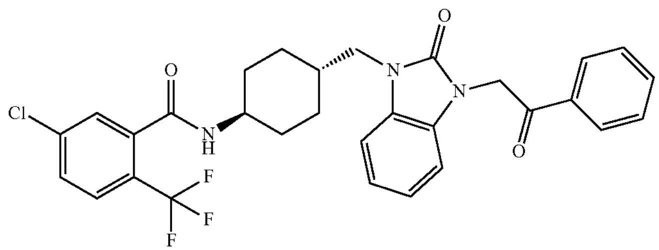 [SMILES: O=C(Cn1c(=O)n(C[C@H]2CC[C@H](NC(=O)c3cc(Cl)ccc3C(F)(F)F)CC2)c2ccccc21)c1ccccc1] | 5-chloro-N-((1r,4r)-4-((2-oxo-3-(2-oxo-2-phenylethyl)-2,3-dihydro-1H-benzo[d]imidazol-1-yl)methyl)cyclohexyl)-2-(trifluoromethyl)benzamide | Intermediate-131, | Q |
| 287 | 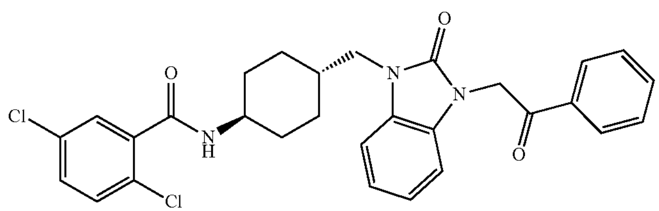 [SMILES: O=C(Cn1c(=O)n(C[C@H]2CC[C@H](NC(=O)c3cc(Cl)ccc3Cl)CC2)c2ccccc21)c1ccccc1] | 2,5-dichloro-N-((1r,4r)-4-((2-oxo-3-(2-oxo-2-phenylethyl)-2,3-dihydro-1H-benzo[d]imidazol-1-yl)methyl)cyclohexyl)benzamide | Intermediate-131, | Q |
| 288 | 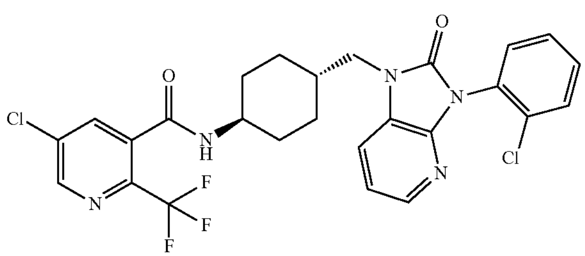 [SMILES: O=C(N[C@H]1CC[C@H](Cn2c(=O)n(-c3ccccc3Cl)c3ncccc32)CC1)c1cc(Cl)cnc1C(F)(F)F] | 5-chloro-N-((1r,4r)-4-((3-(2-chlorophenyl)-2-oxo-2,3-dihydro-1H-imidazo[4,5-b]pyridin-1-yl)methyl)cyclohexyl)-2-(trifluoromethyl)nicotinamide | Intermediate-117, Mesylate-3 | A1 |

TABLE 2-continued

| Ex. | Structure | Name | Reactants | Method |
|---|---|---|---|---|
| 289 | 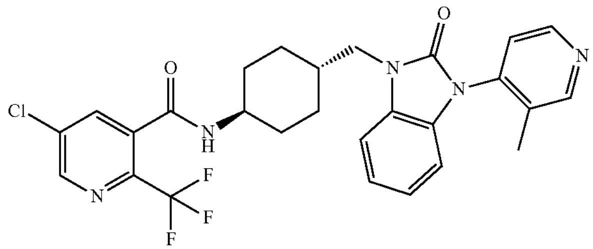 [SMILES: Cc1cnccc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(3-methylpyridin-4-yl)-2-oxo-2,3-dihydro-1H-benzo[d]imidazol-1-yl)methyl)cyclohexyl)-2-(trifluoromethyl)nicotinamide | Intermediate-25, Mesylate-3 | A1 |
| 290 | 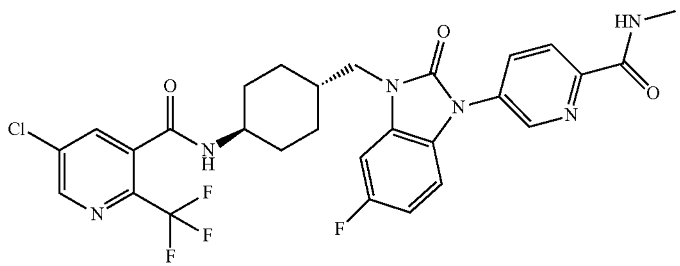 [SMILES: CNC(=O)c1ccc(-n2c(=O)n(C[C@H]3CC[C@H](NC(=O)c4cc(Cl)cnc4C(F)(F)F)CC3)c3cc(F)ccc32)cn1] | 5-(3-((1r,4r)-4-(5-chloro-2-(trifluoromethyl)nicotinamido)cyclohexyl)methyl)-5-fluoro-2-oxo-2,3-dihydro-1H-benzo[d]imidazol-1-yl)-N-methylpicolinamide | Intermediate-115, Mesylate-3 | A1 |
| 291 | 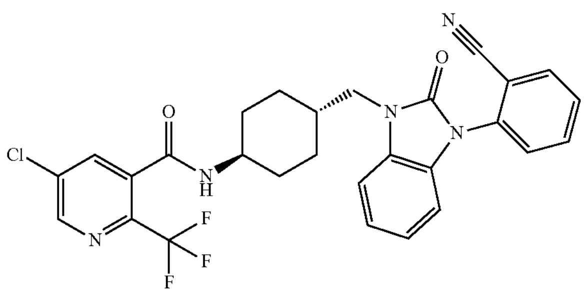 [SMILES: N#Cc1ccccc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(2-cyanophenyl)-2-oxo-2,3-dihydro-1H-benzo[d]imidazol-1-yl)methyl)cyclohexyl)-2-(trifluoromethyl)nicotinamide | 2-fluorobenzonitrile, Intermediate-132 | U |

TABLE 2-continued

| Ex. | Structure | Name | Reactants | Method |
|---|---|---|---|---|
| 292 | 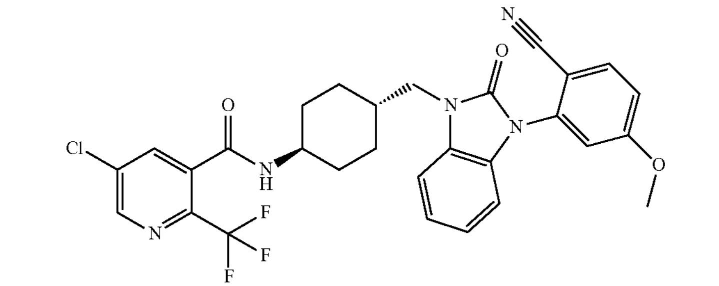 [SMILES: COc1ccc(C#N)c(-n2c(=O)n(C[C@H]3CC[C@H](NC(=O)c4cc(Cl)cnc4C(F)(F)F)CC3)c3ccccc32)c1] | 5-chloro-N-((1r,4r)-4-((3-(2-cyano-5-methoxyphenyl)-2-oxo-2,3-dihydro-1H-benzo[d]imidazol-1-yl)methyl)cyclohexyl)-2-(trifluoromethyl)nicotinamide | Intermediate-132 | U |
| 293 | 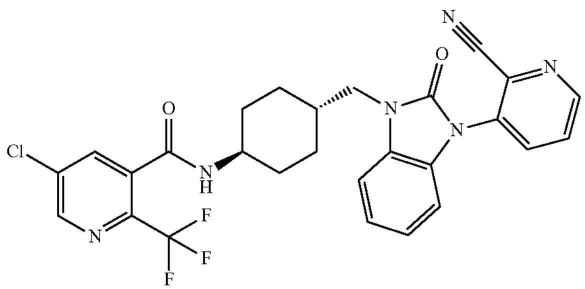 [SMILES: N#Cc1ncccc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(2-cyanopyridin-3-yl)-2-oxo-2,3-dihydro-1H-benzo[d]imidazol-1-yl)methyl)cyclohexyl)-2-(trifluoromethyl)nicotinamide | Intermediate-132 | U |
| 294 | 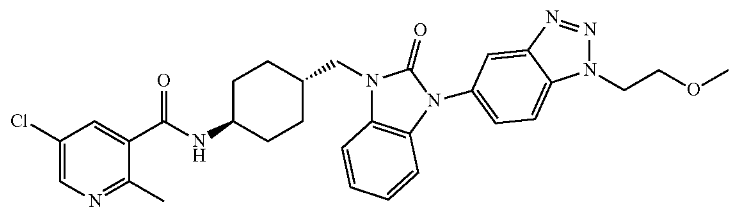 [SMILES: COCCn1nnc2cc(-n3c(=O)n(C[C@H]4CC[C@H](NC(=O)c5cc(Cl)cnc5C)CC4)c4ccccc43)ccc21] | 5-chloro-N-((1r,4r)-4-((3-(1-(2-methoxyethyl)-1H-benzo[d][1,2,3]triazol-5-yl)-2-oxo-2,3-dihydro-1H-benzo[d]imidazol-1-yl)methyl)cyclohexyl)-2-methylnicotinamide | Step-2 of Ex 9 | R |
| 295 | 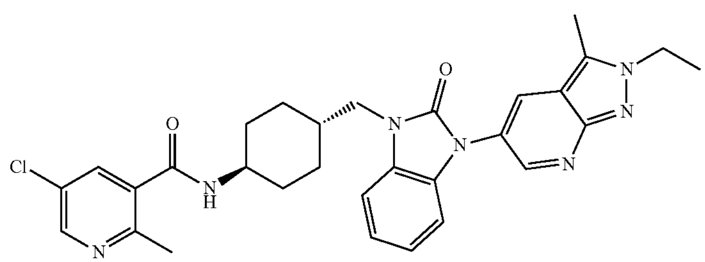 [SMILES: CCn1nc2ncc(-n3c(=O)n(C[C@H]4CC[C@H](NC(=O)c5cc(Cl)cnc5C)CC4)c4ccccc43)cc2c1C] | 5-chloro-N-((1r,4r)-4-((3-(2-ethyl-3-methyl-2H-pyrazolo[3,4-b]pyridin-5-yl)-2-oxo-2,3-dihydro-1H-benzo[d]imidazol-1-yl)methyl)cyclohexyl)-2-methylnicotinamide | Intermediate-133, Step-2 of Ex 9 | R |

TABLE 2-continued

| Ex. | Structure | Name | Reactants | Method |
|---|---|---|---|---|
| 296 | 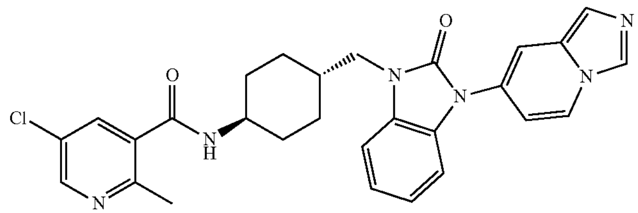 [SMILES: Cc1ncc(Cl)cc1C(=O)N[C@H]1CC[C@H](Cn2c(=O)n(-c3ccn4cncc4c3)c3ccccc32)CC1] | 5-chloro-N-((1r,4r)-4-(3-(imidazo[1,5-a]pyridin-7-yl)-2-oxo-2,3-dihydro-1H-benzo[d]imidazol-1-yl)methyl)cyclohexyl)-2-methylnicotinamide | Step-2 of Ex 9 | R |
| 297 | 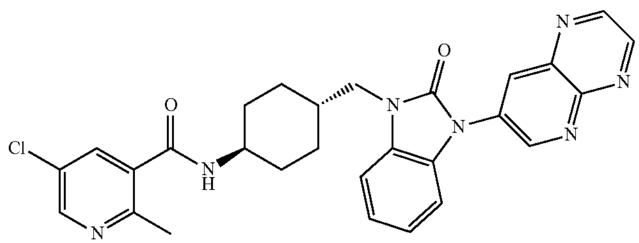 [SMILES: Cc1ncc(Cl)cc1C(=O)N[C@H]1CC[C@H](Cn2c(=O)n(-c3cnc4nccnc4c3)c3ccccc32)CC1] | 5-chloro-2-methyl-N-((1r,4r)-4-((2-oxo-3-(pyrido[2,3-b]pyrazin-7-yl)-2,3-dihydro-1H-benzo[d]imidazol-1-yl)methyl)cyclohexyl)nicotinamide | Step-2 of Ex 9 | T |
| 298 | 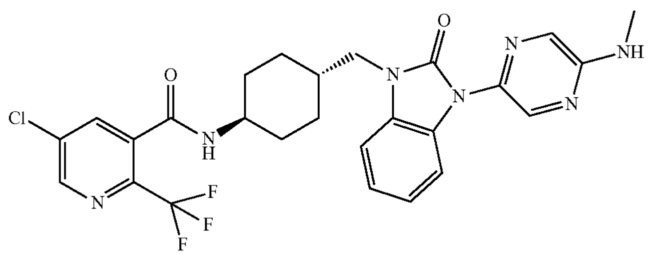 [SMILES: CNc1cnc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-(3-(5-(methylamino)pyrazin-2-yl)-2-oxo-2,3-dihydro-1H-benzo[d]imidazol-1-yl)methyl)cyclohexyl)-2-(trifluoromethyl)nicotinamide | Intermediate-134, Mesylate-3 | A1 |

TABLE 2-continued

| Ex. | Structure | Name | Reactants | Method |
|---|---|---|---|---|
| 299 | 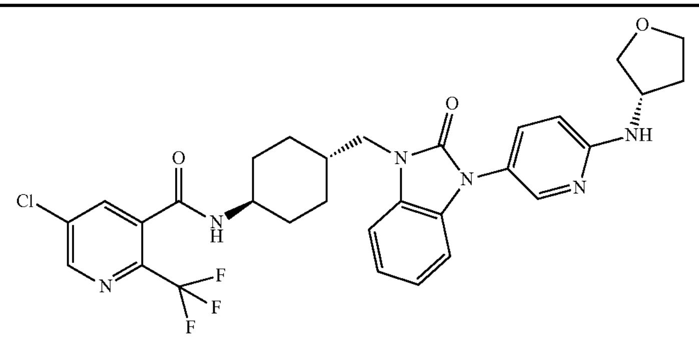 | 5-chloro-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)-2-(trifluoromethyl)nicotinamide | Intermediate-135, Mesylate-3 | A1 |
| 300 | 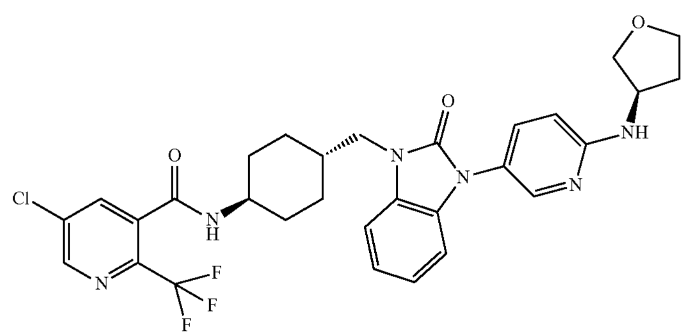 [SMILES: O=C(N[C@H]1CC[C@H](Cn2c(=O)n(-c3ccc(N[C@@H]4CCOC4)nc3)c3ccccc32)CC1)c1cc(Cl)cnc1C(F)(F)F] | 5-chloro-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)-2-(trifluoromethyl)nicotinamide | Intermediate-136, Mesylate-3 | A1 |
| 301 | 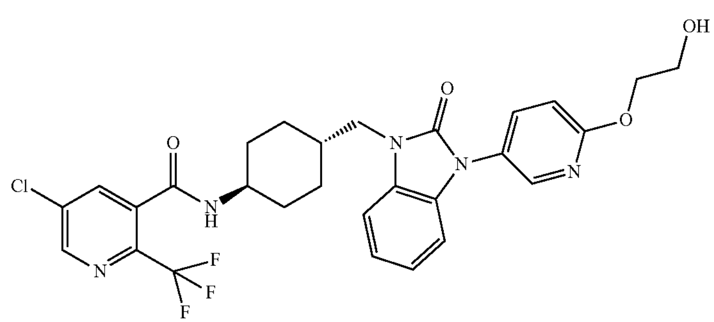 [SMILES: O=C(N[C@H]1CC[C@H](Cn2c(=O)n(-c3ccc(OCCO)nc3)c3ccccc32)CC1)c1cc(Cl)cnc1C(F)(F)F] | 5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-(trifluoromethyl)nicotinamide | see Example synthesis part | |

TABLE 2-continued

| Ex. | Structure | Name | Reactants | Method |
|---|---|---|---|---|
| 302 | 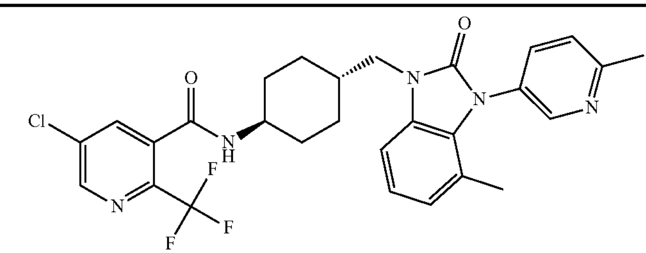 | 5-chloro-N-((1r,4r)-4-((4-methyl-3-(6-methylpyridin-3-yl)-2-oxo-2,3-dihydro-1H-benzo[d]imidazol-1-yl)methyl)cyclohexyl)-2-(trifluoromethyl)nicotinamide | Intermediate-31, Mesylate-3 | A1 |
| 303 | 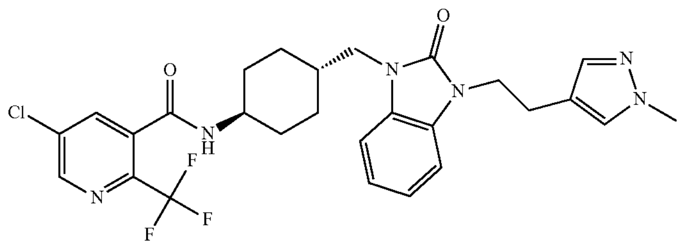 [SMILES: Cn1cc(CCn2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(2-(1-methyl-1H-pyrazol-4-yl)ethyl)-2-oxo-2,3-dihydro-1H-benzo[d]imidazol-1-yl)methyl)cyclohexyl)-2-(trifluoromethyl)nicotinamide | Intermediate-119, Mesylate-3 | A1 |
| 304 | 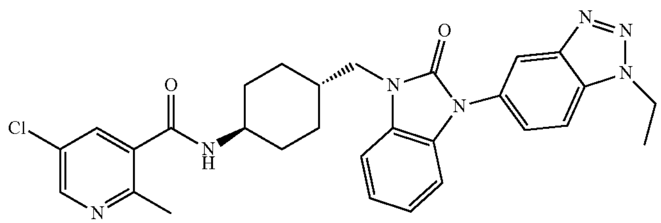 [SMILES: CCn1nnc2cc(-n3c(=O)n(C[C@H]4CC[C@H](NC(=O)c5cc(Cl)cnc5C)CC4)c4ccccc43)ccc21] | 5-chloro-N-((1r,4r)-4-((3-(1-ethyl-1H-benzo[d][1,2,3]triazol-5-yl)-2-oxo-2,3-dihydro-1H-benzo[d]imidazol-1-yl)methyl)cyclohexyl)-2-methylnicotinamide | Step-2 of Ex 9 | R |
| 305 | 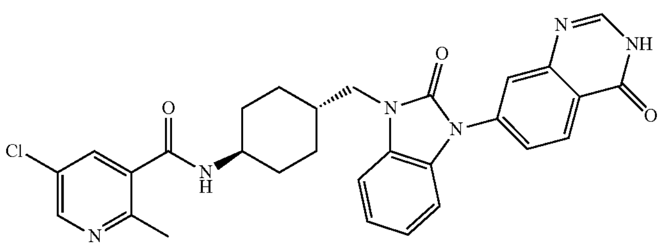 [SMILES: Cc1ncc(Cl)cc1C(=O)N[C@H]1CC[C@H](Cn2c(=O)n(-c3ccc4c(=O)[nH]cnc4c3)c3ccccc32)CC1] | 5-chloro-2-methyl-N-((1r,4r)-4-((2-oxo-3-(4-oxo-3,4-dihydroquinazolin-7-yl)-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 306 | 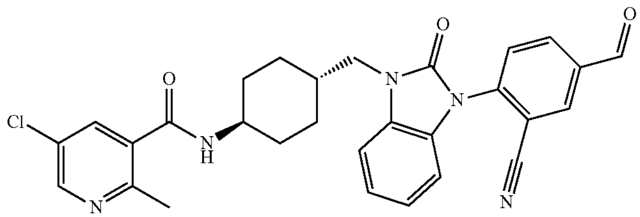 [SMILES: Cc1ncc(Cl)cc1C(=O)N[C@H]1CC[C@H](Cn2c(=O)n(-c3ccc(C=O)cc3C#N)c3ccccc32)CC1] | 5-chloro-N-((1r,4r)-4-((3-(2-cyano-4-formylphenyl)-2-oxo-2,3-dihydro-1H-benzo[d]imidazol-1-yl)methyl)cyclohexyl)-2-methylnicotinamide | (4-fluoro-3-cyanobenzaldehyde); Step-2 of Ex 9 | U |
| 307 | 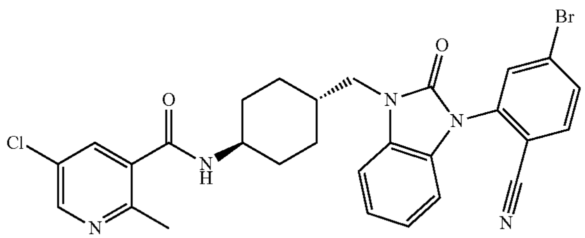 [SMILES: Cc1ncc(Cl)cc1C(=O)N[C@H]1CC[C@H](Cn2c(=O)n(-c3cc(Br)ccc3C#N)c3ccccc32)CC1] | N-((1r,4r)-4-((3-(5-bromo-2-cyanophenyl)-2-oxo-2,3-dihydro-1H-benzo[d]imidazol-1-yl)methyl)cyclohexyl)-5-chloro-2-methylnicotinamide | (4-bromo-2-fluorobenzonitrile); Step-2 of Ex 9 | U |
| 308 | 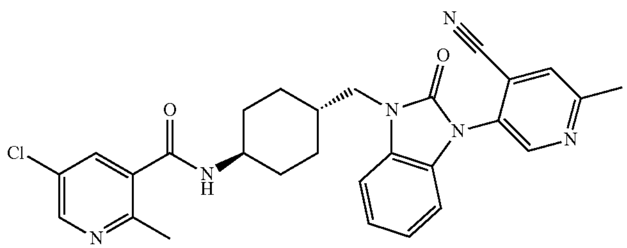 [SMILES: Cc1cc(C#N)c(-n2c(=O)n(C[C@H]3CC[C@H](NC(=O)c4cc(Cl)cnc4C)CC3)c3ccccc32)cn1] | 5-chloro-N-((1r,4r)-4-((3-(4-cyano-6-methylpyridin-3-yl)-2-oxo-2,3-dihydro-1H-benzo[d]imidazol-1-yl)methyl)cyclohexyl)-2-methylnicotinamide | see Example synthesis part | U |
| 309 | 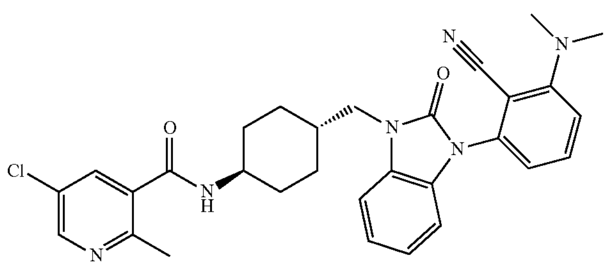 [SMILES: Cc1ncc(Cl)cc1C(=O)N[C@H]1CC[C@H](Cn2c(=O)n(-c3cccc(N(C)C)c3C#N)c3ccccc32)CC1] | 5-choro-N-((1r,4r)-4-((3-(2-cyano-3-(dimethylamino)phenyl)-2-oxo-2,3-dihydro-1H-benzo[d]imidazol-1-yl)methyl)cyclohexyl)-2-methylnicotinamide | (2-(dimethylamino)-6-fluorobenzonitrile); Step-2 of Ex 9 | U |

TABLE 2-continued

| Ex. | Structure | Name | Reactants | Method |
|---|---|---|---|---|
| 310 | 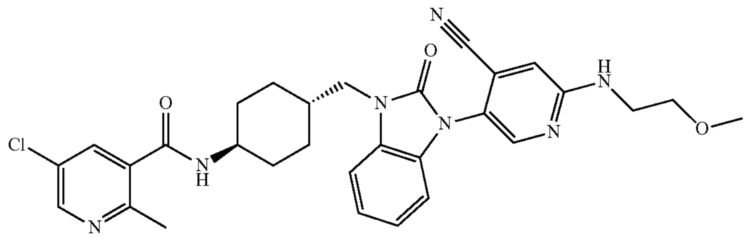 [SMILES: COCCNc1cc(C#N)c(-n2c(=O)n(C[C@H]3CC[C@H](NC(=O)c4cc(Cl)cnc4C)CC3)c3ccccc32)cn1] | 5-chloro-N-((1r,4r)-4-((3-(4-cyano-6-((2-methoxyethyl)amino)pyridin-3-yl)-2-oxo-2,3-dihydro-1H-benzo[d]imidazol-1-yl)methyl)cyclohexyl)-2-methylnicotinamide | see Example synthesis part | |
| 311 | 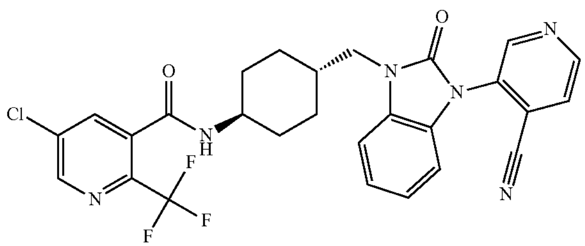 [SMILES: N#Cc1ccncc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(4-cyanopyridin-3-yl)-2-oxo-2,3-dihydro-1H-benzo[d]imidazol-1-yl)methyl)cyclohexyl)-2-(trifluoromethyl)nicotinamide | Intermediate-137, Mesylate-3 | A1 |
| 312 | 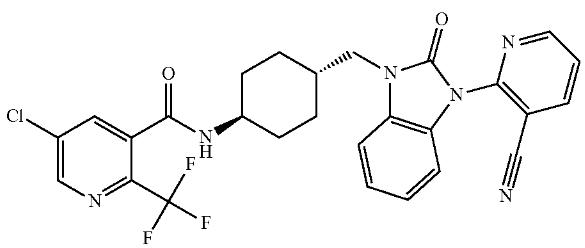 [SMILES: N#Cc1cccnc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(3-cyanopyridin-2-yl)-2-oxo-2,3-dihydro-1H-benzo[d]imidazol-1-yl)methyl)cyclohexyl)-2-(trifluoromethyl)nicotinamide | Intermediate-138, Mesylate-3 | A1 |
| 313 | 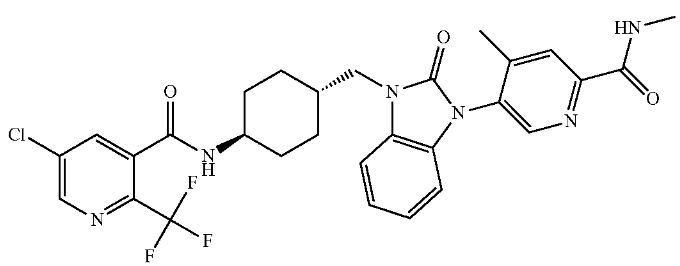 [SMILES: CNC(=O)c1cc(C)c(-n2c(=O)n(C[C@H]3CC[C@H](NC(=O)c4cc(Cl)cnc4C(F)(F)F)CC3)c3ccccc32)cn1] | 5-(3-((1r,4r)-4-(5-chloro-2-(trifluoromethyl)nicotinamido)cyclohexyl)methyl)-2-oxo-2,3-dihydro-1H-benzo[d]imidazol-1-yl)-N,4-dimethylpicolinamide | Intermediate-105, Mesylate-3 | A1 |

TABLE 2-continued

| Ex. | Structure | Name | Reactants | Method |
|---|---|---|---|---|
| 314 | 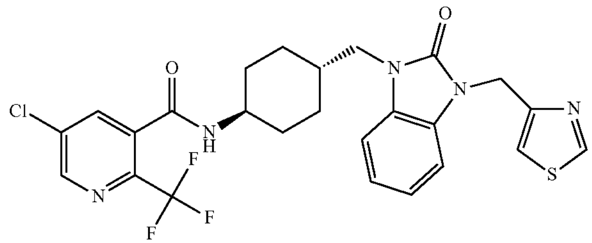 [SMILES: O=C(N[C@H]1CC[C@H](Cn2c(=O)n(Cc3cscn3)c3ccccc32)CC1)c1cc(Cl)cnc1C(F)(F)F] | 5-chloro-N-((1r,4r)-4-((2-oxo-3-(thiazol-4-ylmethyl)-2,3-dihydro-1H-benzo[d]imidazol-1-yl)methyl)cyclohexyl)-2-(trifluoromethyl)nicotinamide | Intermediate-139, Mesylate-3 | A1 |
| 315 | 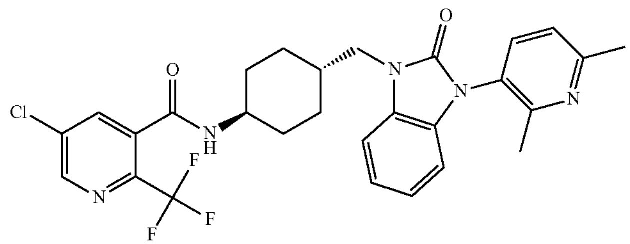 [SMILES: Cc1ccc(-n2c(=O)n(C[C@H]3CC[C@H](NC(=O)c4cc(Cl)cnc4C(F)(F)F)CC3)c3ccccc32)c(C)n1] | 5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-(trifluoromethyl)nicotinamide | Intermediate-14, Mesylate-3 | A1 |
| 316 | 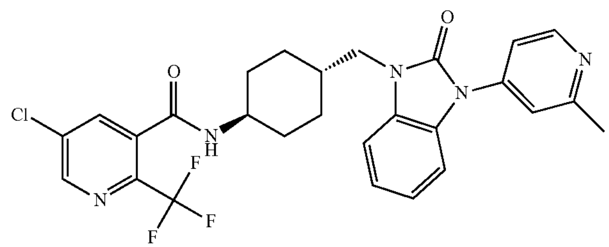 [SMILES: Cc1cc(-n2c(=O)n(C[C@H]3CC[C@H](NC(=O)c4cc(Cl)cnc4C(F)(F)F)CC3)c3ccccc32)ccn1] | 5-chloro-N-((1r,4r)-4-((3-(2-methylpyridin-4-yl)-2-oxo-2,3-dihydro-1H-benzo[d]imidazol-1-yl)methyl)cyclohexyl)-2-(trifluoromethyl)nicotinamide | Intermediate-30, Mesylate-3 | A1 |
| 317 | 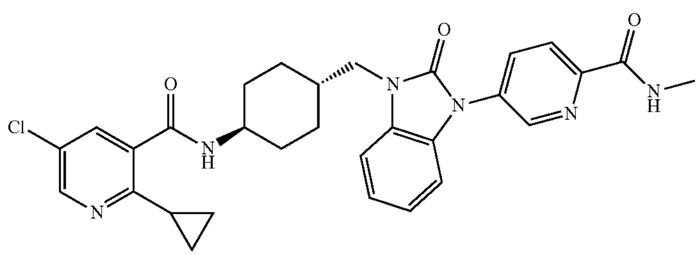 [SMILES: CNC(=O)c1ccc(-n2c(=O)n(C[C@H]3CC[C@H](NC(=O)c4cc(Cl)cnc4C4CC4)CC3)c3ccccc32)cn1] | 5-(3-((1r,4r)-4-(5-chloro-2-cyclopropyl-2-oxo-2,3-dihydro-1H-benzo[d]imidazol-1-yl)-N-methyl-picolinamide | Intermediate-121, | B |

TABLE 2-continued

| Ex. | Structure | Name | Reactants | Method |
|---|---|---|---|---|
| 318 | 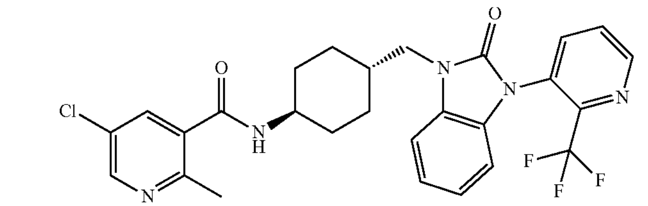 [SMILES: Cc1ncc(Cl)cc1C(=O)N[C@H]1CC[C@H](Cn2c(=O)n(-c3cccnc3C(F)(F)F)c3ccccc32)CC1] | 5-chloro-2-methyl-N-((1r,4r)-4-((2-oxo-3-(2-(trifluoromethyl)pyridin-3-yl)-2,3-dihydro-1H-benzo[d]imidazol-1-yl)methyl)cyclohexyl)nicotinamide | Intermediate-140, Mesylate-3 | A1 |
| 319 | 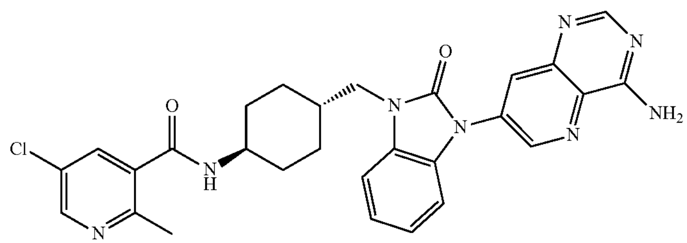 [SMILES: Cc1ncc(Cl)cc1C(=O)N[C@H]1CC[C@H](Cn2c(=O)n(-c3cnc4c(N)ncnc4c3)c3ccccc32)CC1] | N-((1r,4r)-4-((3-(4-aminopyrido[3,2-d]pyrimidin-7-yl)-2-oxo-2,3-dihydro-1H-benzo[d]imidazol-1-yl)methyl)cyclohexyl)-5-chloro-2-methylnicotinamide | see Example synthesis part | |
| 320 | 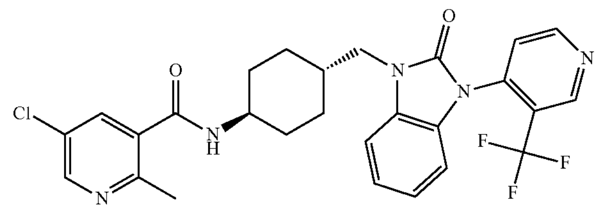 [SMILES: Cc1ncc(Cl)cc1C(=O)N[C@H]1CC[C@H](Cn2c(=O)n(-c3ccncc3C(F)(F)F)c3ccccc32)CC1] | 5-chloro-2-methyl-N-((1r,4r)-4-((2-oxo-3-(3-(trifluoromethyl)pyridin-4-yl)-2,3-dihydro-1H-benzo[d]imidazol-1-yl)methyl)cyclohexyl)nicotinamide | Step-2 of Ex 9 | U |
| 321 | 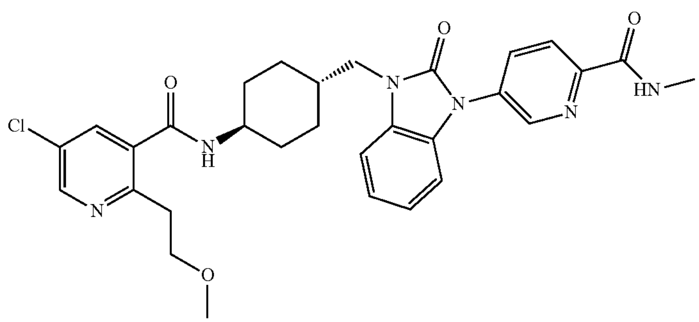 [SMILES: CNC(=O)c1ccc(-n2c(=O)n(C[C@H]3CC[C@H](NC(=O)c4cc(Cl)cnc4CCOC)CC3)c3ccccc32)cn1] | 5-(3-((1r,4r)-4-(5-chloro-2-(2-methoxyethyl)nicotinamido)cyclohexyl)methyl)-2-oxo-2,3-dihydro-1H-benzo[d]imidazol-1-yl)-N-methylpicolinamide | Intermediate-121, Intermediate-141 | B |

TABLE 2-continued

| Ex. | Structure | Name | Reactants | Method |
|---|---|---|---|---|
| 322 | 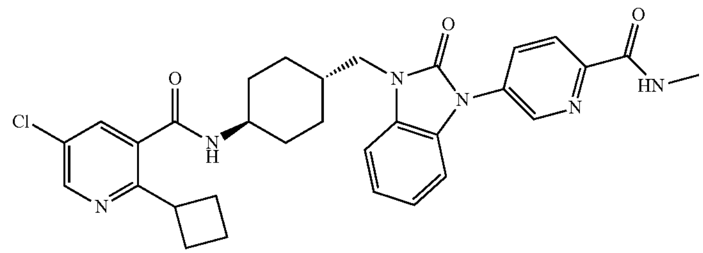 [SMILES: CNC(=O)c1ccc(-n2c(=O)n(C[C@H]3CC[C@H](NC(=O)c4cc(Cl)cnc4C4CCC4)CC3)c3ccccc32)cn1] | 5-(3-((1r,4r)-4-(5-chloro-2-cyclobutylnicotinamido)cyclohexyl)methyl)-2-oxo-2,3-dihydro-1H-benzo[d]imidazol-1-yl)-N-methylpicolinamide | Intermediate-121, Intermediate-142 | B |
| 323 | 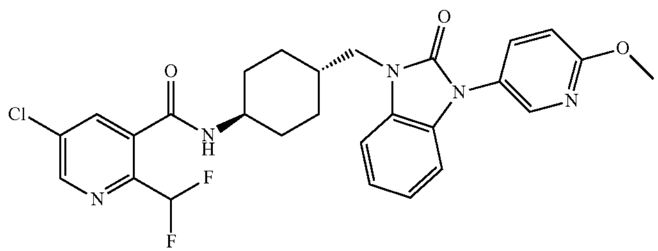 | 5-chloro-2-(difluoromethyl)-N-((1r,4r)-4-((3-(6-methoxypyridin-3-yl)-2-oxo-2,3-dihydro-1H-benzo[d]imidazol-1-yl)methyl)cyclohexyl)nicotinamide | Intermediate-113, | Q |
| 324 | 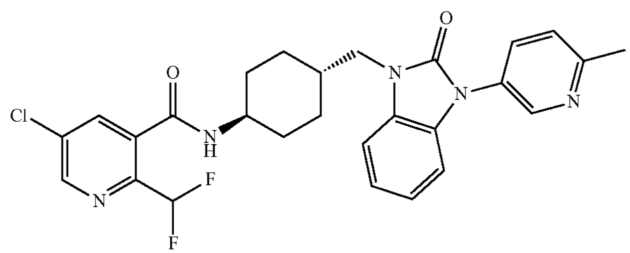 [SMILES: Cc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-methylpyridin-3-yl)-2-oxo-2,3-dihydro-1H-benzo[d]imidazol-1-yl)methyl)cyclohexyl)nicotinamide | Intermediate-127, | Q |
| 325 | 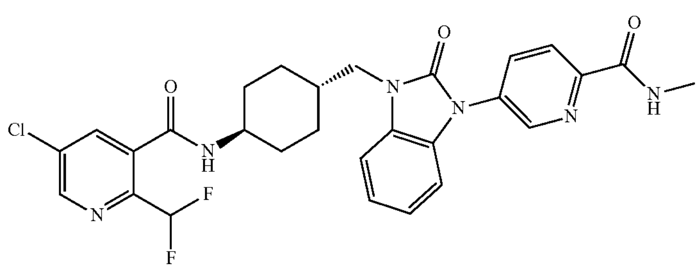 [SMILES: CNC(=O)c1ccc(-n2c(=O)n(C[C@H]3CC[C@H](NC(=O)c4cc(Cl)cnc4C(F)F)CC3)c3ccccc32)cn1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide | Intermediate-121, | Q |

TABLE 2-continued

| Ex. | Structure | Name | Reactants | Method |
|---|---|---|---|---|
| 326 | 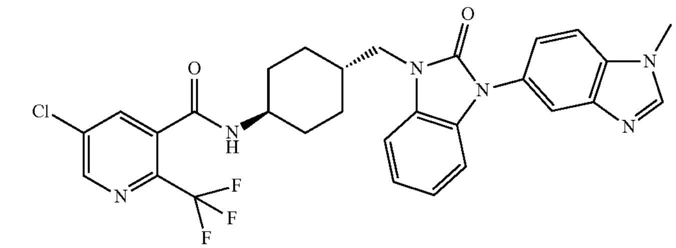 [SMILES: Cn1cnc2cc(-n3c(=O)n(C[C@H]4CC[C@H](NC(=O)c5cc(Cl)cnc5C(F)(F)F)CC4)c4ccccc43)ccc21] | 5-chloro-N-((1r,4r)-4-((1'-methyl-2-oxo-1H-[1,5'-bibenzo[d]imidazol]-3(2H)-yl)methyl)cyclohexyl)-2-(trifluoromethyl)nicotinamide | Intermediate-108, Mesylate-3 | A1 |
| 327 | 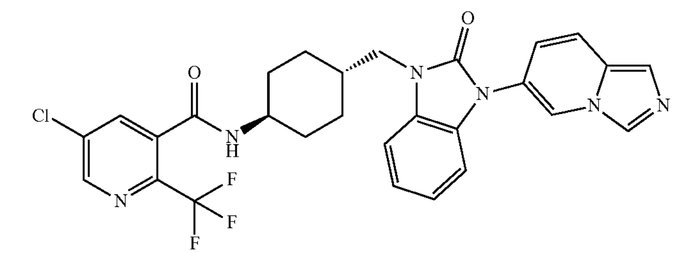 [SMILES: O=C(N[C@H]1CC[C@H](Cn2c(=O)n(-c3ccc4cncn4c3)c3ccccc32)CC1)c1cc(Cl)cnc1C(F)(F)F] | 5-chloro-N-((1r,4r)-4-((3-(imidazo[1,5-a]pyridin-6-yl)-2-oxo-2,3-dihydro-1H-benzo[d]imidazol-1-yl)methyl)cyclohexyl)-2-(trifluoromethyl)nicotinamide | (6-bromoimidazo[1,5-a]pyridine), Intermediate-132 | R |
| 328 | 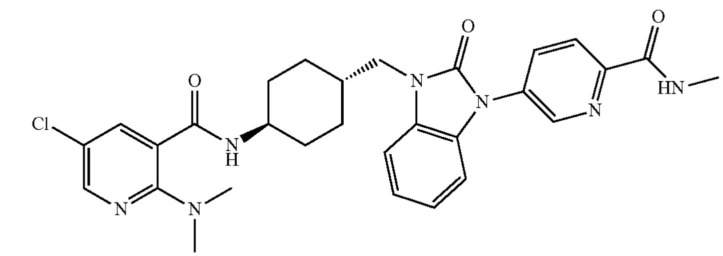 [SMILES: CNC(=O)c1ccc(-n2c(=O)n(C[C@H]3CC[C@H](NC(=O)c4cc(Cl)cnc4N(C)C)CC3)c3ccccc32)cn1] | 5-(3-((1r,4r)-4-(5-chloro-2-(dimethylamino)nicotinamido)cyclohexyl)methyl)-2-oxo-2,3-dihydro-1H-benzo[d]imidazol-1-yl)-N-methylpicolinamide | Intermediate-121, (5-chloro-2-(dimethylamino)nicotinic acid) | B |
| 329 | 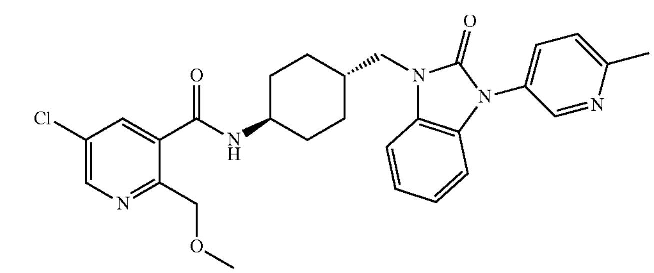 [SMILES: COCc1ncc(Cl)cc1C(=O)N[C@H]1CC[C@H](Cn2c(=O)n(-c3ccc(C)nc3)c3ccccc32)CC1] | 5-chloro-2-(methoxymethyl)-N-((1r,4r)-4-((3-(6-methylpyridin-3-yl)-2-oxo-2,3-dihydro-1H-benzo[d]imidazol-1-yl)methyl)cyclohexyl)nicotinamide | Intermediate-127, Intermediate-143 | Q |

TABLE 2-continued

| Ex. | Structure | Name | Reactants | Method |
|---|---|---|---|---|
| 330 | 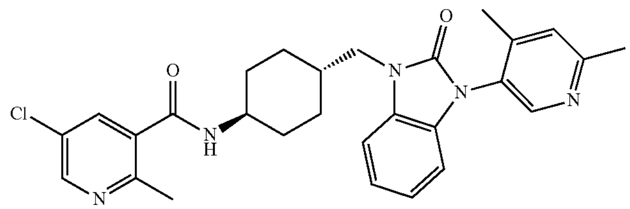 [SMILES: Cc1cc(C)c(-n2c(=O)n(C[C@H]3CC[C@H](NC(=O)c4cc(Cl)cnc4C)CC3)c3ccccc32)cn1] | 5-chloro-N-((1r,4r)-4-((3-(4,6-dimethylpyridin-3-yl)-2-oxo-2,3-dihydro-1H-benzo[d]imidazol-1-yl)methyl)cyclohexyl)-2-methylnicotinamide | Intermediate-144, Mesylate-1 | A1 |
| 331 | 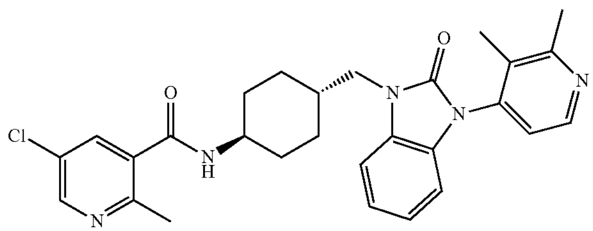 [SMILES: Cc1ncc(Cl)cc1C(=O)N[C@H]1CC[C@H](Cn2c(=O)n(-c3ccnc(C)c3C)c3ccccc32)CC1] | 5-chloro-N-((1r,4r)-4-((3-(2,3-dimethylpyridin-4-yl)-2-oxo-2,3-dihydro-1H-benzo[d]imidazol-1-yl)methyl)cyclohexyl)-2-methylnicotinamide | Intermediate-145, Mesylate-1 | A1 |
| 332 | 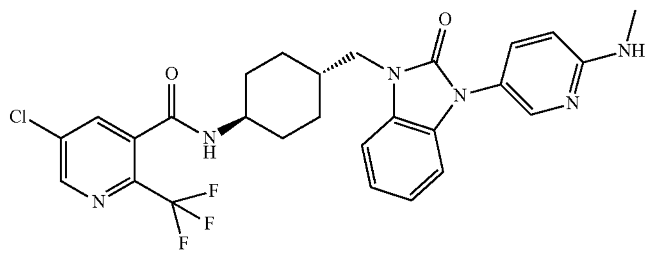 [SMILES: CNc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-(methylamino)pyridin-3-yl)-2-oxo-2,3-dihydro-1H-benzo[d]imidazol-1-yl)methyl)cyclohexyl)-2-(trifluoromethyl)nicotinamide | Intermediate-146, Mesylate-3 | A1 |
| 333 | 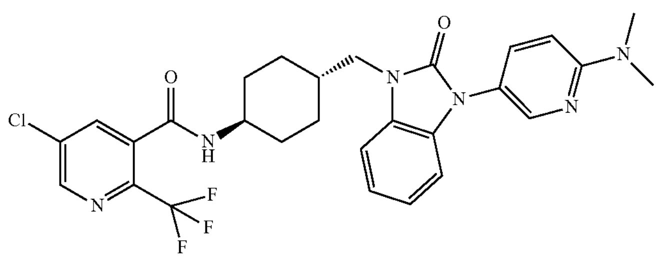 [SMILES: CN(C)c1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-(trifluoromethyl)nicotinamide | Intermediate-26, Mesylate-3 | A1 |

TABLE 2-continued

| Ex. | Structure | Name | Reactants | Method |
|---|---|---|---|---|
| 334 | 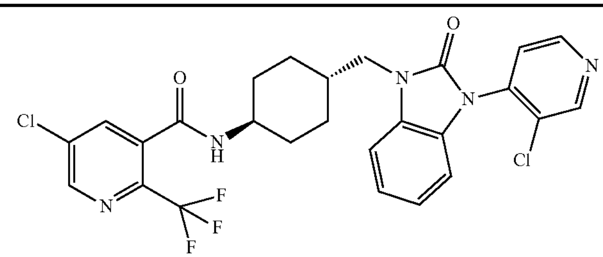 | 5-chloro-N-((1r,4r)-4-((3-(3-chloropyridin-4-yl)-2-oxo-2,3-dihydro-1H-benzo[d]imidazol-1-yl)methyl)cyclohexyl)-2-(trifluoromethyl)nicotinamide | Intermediate-147, Mesylate-3 | A1 |
| 335 | 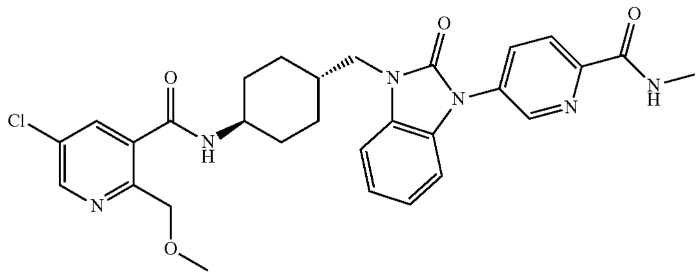 [SMILES: CNC(=O)c1ccc(-n2c(=O)n(C[C@H]3CC[C@H](NC(=O)c4cc(Cl)cnc4COC)CC3)c3ccccc32)cn1] | 5-(3-((1r,4r)-4-(5-chloro-2-(methoxymethyl)nicotinamido)cyclohexyl)methyl)-2-oxo-2,3-dihydro-1H-benzo[d]imidazol-1-yl)-N-methylpicolinamide | Intermediate-121, Intermediate-143 | Q |
| 336 | 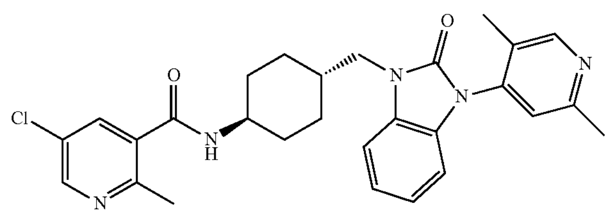 [SMILES: Cc1cc(-n2c(=O)n(C[C@H]3CC[C@H](NC(=O)c4cc(Cl)cnc4C)CC3)c3ccccc32)c(C)cn1] | 5-chloro-N-((1r,4r)-4-((3-(2,5-dimethylpyridin-4-yl)-2-oxo-2,3-dihydro-1H-benzo[d]imidazol-1-yl)methyl)cyclohexyl)-2-methylnicotinamide | Intermediate-148, Mesylate-1 | A1 |
| 337 | 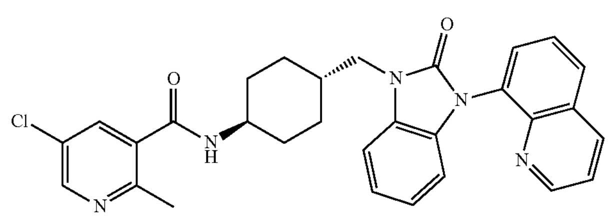 [SMILES: Cc1ncc(Cl)cc1C(=O)N[C@H]1CC[C@H](Cn2c(=O)n(-c3cccc4cccnc34)c3ccccc32)CC1] | 5-chloro-2-methyl-N-((1r,4r)-4-((2-oxo-3-(quinolin-8-yl)-2,3-dihydro-1H-benzo[d]imidazol-1-yl)methyl)cyclohexyl)nicotinamide | Intermediate-149, Mesylate-1 | A1 |

TABLE 2-continued

| Ex. | Structure | Name | Reactants | Method |
|---|---|---|---|---|
| 338 | 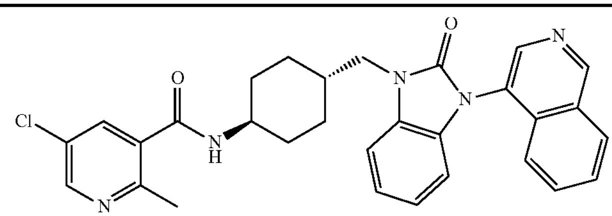 | 5-chloro-N-((1r,4r)-4-((3-(isoquinolin-4-yl)-2-oxo-2,3-dihydro-1H-benzo[d]imidazol-1-yl)methyl)cyclohexyl)-2-methylnicotinamide | Intermediate-150, Mesylate-1 | A1 |
| 339 | 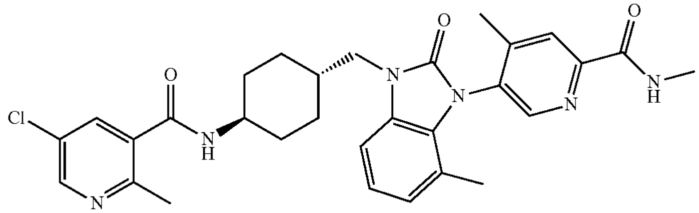 [SMILES: CNC(=O)c1cc(C)c(-n2c(=O)n(C[C@H]3CC[C@H](NC(=O)c4cc(Cl)cnc4C)CC3)c3cccc(C)c32)cn1] | 5-(((1r,4r)-4-(5-chloro-2-methylnicotinamido)cyclohexyl)methyl)-7-methyl-2-oxo-2,3-dihydro-1H-benzo[d]imidazol-1-yl)-N,4-dimethylpicolinamide | Intermediate-151, Mesylate-1 | A1 |
| 340 | 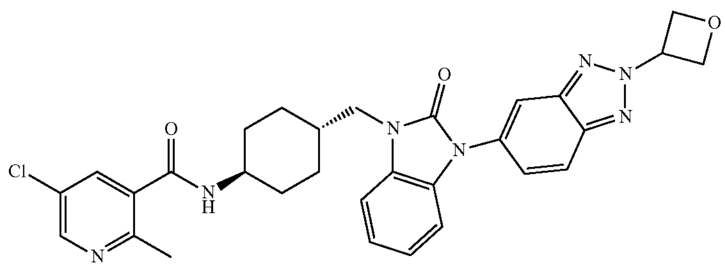 [SMILES: Cc1ncc(Cl)cc1C(=O)N[C@H]1CC[C@H](Cn2c(=O)n(-c3ccc4nn(C5COC5)nc4c3)c3ccccc32)CC1] | 5-chloro-2-methyl-N-((1r,4r)-4-((3-(2-(oxetan-3-yl)-2H-benzo[d][1,2,3]triazol-5-yl)-2-oxo-2,3-dihydro-1H-benzo[d]imidazol-1-yl)methyl)cyclohexyl)nicotinamide | Intermediate-152, Step-2 of Ex 9 | T |
| 341 | 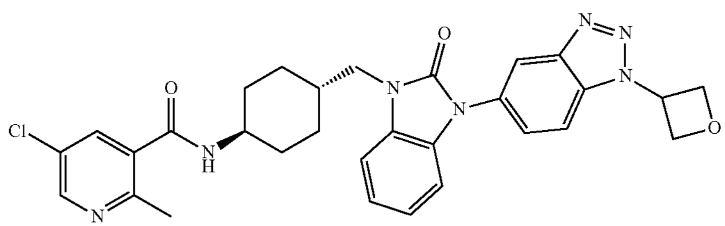 [SMILES: Cc1ncc(Cl)cc1C(=O)N[C@H]1CC[C@H](Cn2c(=O)n(-c3ccc4c(c3)nnn4C3COC3)c3ccccc32)CC1] | 5-chloro-2-methyl-N-((1r,4r)-4-((3-(1-(oxetan-3-yl)-1H-benzo[d][1,2,3]triazol-5-yl)-2-oxo-2,3-dihydro-1H-benzo[d]imidazol-1-yl)methyl)cyclohexyl)nicotinamide | Intermediate-153, Step-2 of Ex 9 | T |

| Ex. | Structure | Name | Reactants | Method |
|---|---|---|---|---|
| 342 | 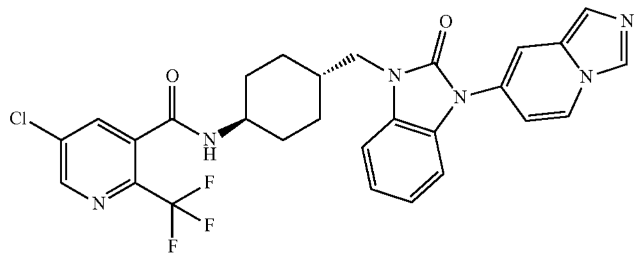 [SMILES: O=C(N[C@H]1CC[C@H](Cn2c(=O)n(-c3ccn4cncc4c3)c3ccccc32)CC1)c1cc(Cl)cnc1C(F)(F)F] | 5-chloro-N-((1r,4r)-4-((3-(imidazo[1,5-a]pyridin-7-yl)-2-oxo-2,3-dihydro-1H-benzo[d]imidazol-1-yl)methyl)cyclohexyl)-2-(trifluoromethyl)nicotinamide | Intermediate-132 | R |
| 343 | 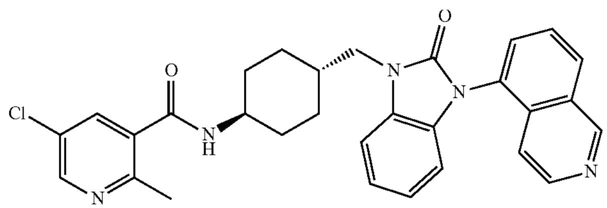 [SMILES: Cc1ncc(Cl)cc1C(=O)N[C@H]1CC[C@H](Cn2c(=O)n(-c3cccc4cnccc34)c3ccccc32)CC1] | 5-chloro-N-((1r,4r)-4-((3-(isoquinolin-5-yl)-2-oxo-2,3-dihydro-1H-benzo[d]imidazol-1-yl)methyl)cyclohexyl)-2-methylnicotinamide | Intermediate-154, Mesylate-1 | A1 |
| 344 | 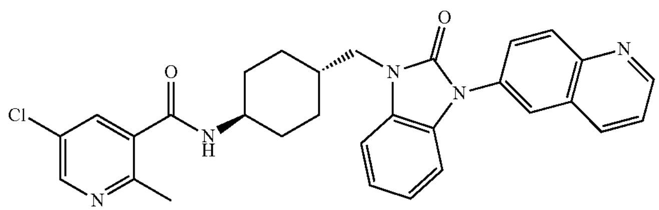 [SMILES: Cc1ncc(Cl)cc1C(=O)N[C@H]1CC[C@H](Cn2c(=O)n(-c3ccc4ncccc4c3)c3ccccc32)CC1] | 5-chloro-2-methyl-N-((1r,4r)-4-((2-oxo-3-(quinolin-6-yl)-2,3-dihydro-1H-benzo[d]imidazol-1-yl)methyl)cyclohexyl)nicotinamide | Intermediate-155, Mesylate-1 | A1 |
| 345 | 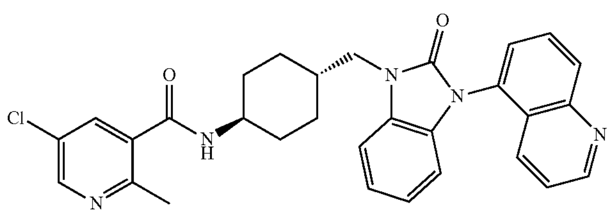 [SMILES: Cc1ncc(Cl)cc1C(=O)N[C@H]1CC[C@H](Cn2c(=O)n(-c3cccc4ncccc34)c3ccccc32)CC1] | 5-chloro-2-methyl-N-((1r,4r)-4-((2-oxo-3-(quinolin-5-yl)-2,3-dihydro-1H-benzo[d]imidazol-1-yl)methyl)cyclohexyl)nicotinamide | Intermediate-156, Mesylate-1 | A1 |

TABLE 2-continued

| Ex. | Structure | Name | Reactants | Method |
|---|---|---|---|---|
| 346 | 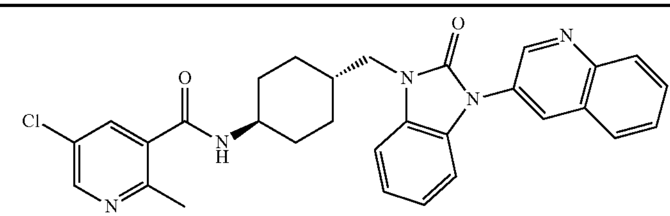 | 5-chloro-2-methyl-N-((1r,4r)-4-((2-oxo-3-(quinolin-3-yl)-2,3-dihydro-1H-benzo[d]imidazol-1-yl)methyl)cyclohexyl)nicotinamide | Intermediate-157, Mesylate-1 | A1 |
| 347 | 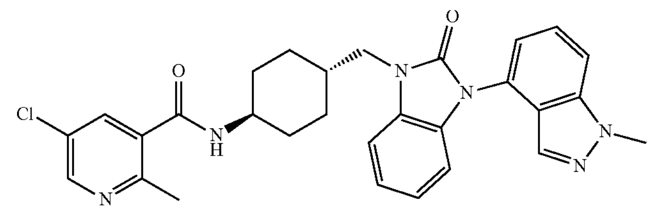 [SMILES: Cc1ncc(Cl)cc1C(=O)N[C@H]1CC[C@H](Cn2c(=O)n(-c3cccc4c3cnn4C)c3ccccc32)CC1] | 5-chloro-2-methyl-N-((1r,4r)-4-((3-(1-methyl-1H-indazol-4-yl)-2-oxo-2,3-dihydro-1H-benzo[d]imidazol-1-yl)methyl)cyclohexyl)nicotinamide | Intermediate-158, Mesylate-1 | A1 |
| 348 | 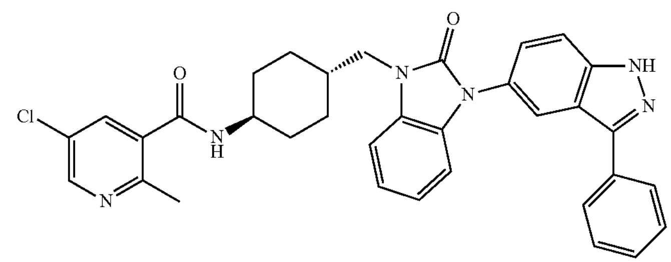 [SMILES: Cc1ncc(Cl)cc1C(=O)N[C@H]1CC[C@H](Cn2c(=O)n(-c3ccc4[nH]nc(-c5ccccc5)c4c3)c3ccccc32)CC1] | 5-chloro-2-methyl-N-((1r,4r)-4-((2-oxo-3-(3-phenyl-1H-indazol-5-yl)-2,3-dihydro-1H-benzo[d]imidazol-1-yl)methyl)cyclohexyl)nicotinamide | see Example synthesis part | |
| 349 | 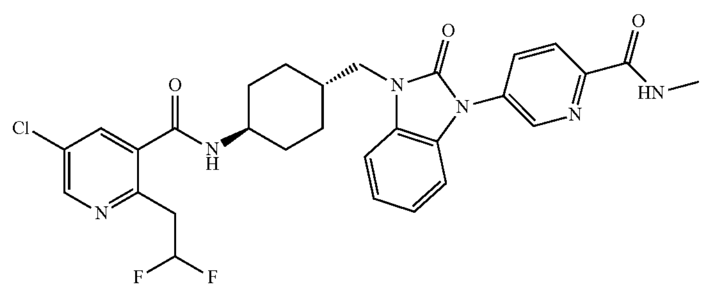 [SMILES: CNC(=O)c1ccc(-n2c(=O)n(C[C@H]3CC[C@H](NC(=O)c4cc(Cl)cnc4CC(F)F)CC3)c3ccccc32)cn1] | 5-(3-((1r,4r)-4-(5-chloro-2-(2,2-difluoroethyl)nicotinamido)cyclohexyl)methyl)-2-oxo-2,3-dihydro-1H-benzo[d]imidazol-1-yl)-N-methylpicolinamide | Intermediate-159, Intermediate-121 | B |

TABLE 2-continued

| Ex. | Structure | Name | Reactants | Method |
|---|---|---|---|---|
| 350 | 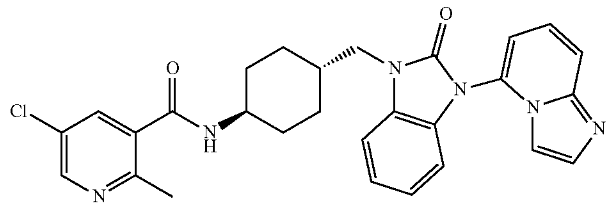 [SMILES: Cc1ncc(Cl)cc1C(=O)N[C@H]1CC[C@H](Cn2c(=O)n(-c3cccc4nccn34)c3ccccc32)CC1] | 5-chloro-N-((1r,4r)-4-((3-(imidazo[1,2-a]pyridin-5-yl)-2-oxo-2,3-dihydro-1H-benzo[d]imidazol-1-yl)methyl)cyclohexyl)-2-methylnicotinamide | Intermediate-160, Mesylate-1 | A1 |
| 351 | 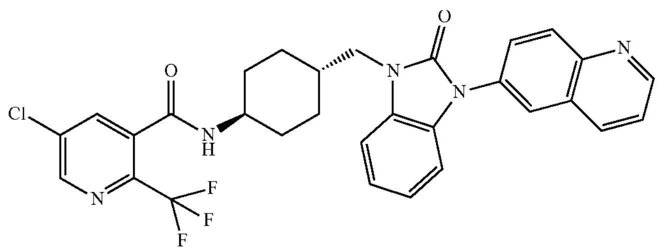 [SMILES: O=C(N[C@H]1CC[C@H](Cn2c(=O)n(-c3ccc4ncccc4c3)c3ccccc32)CC1)c1cc(Cl)cnc1C(F)(F)F] | 5-chloro-N-((1r,4r)-4-((2-oxo-3-(quinolin-6-yl)-2,3-dihydro-1H-benzo[d]imidazol-1-yl)methyl)cyclohexyl)-2-(trifluoromethyl)nicotinamide | Intermediate-155, Mesylate-3 | A1 |
| 352 | 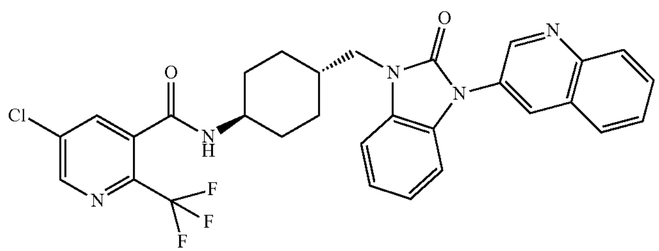 [SMILES: O=C(N[C@H]1CC[C@H](Cn2c(=O)n(-c3cnc4ccccc4c3)c3ccccc32)CC1)c1cc(Cl)cnc1C(F)(F)F] | 5-chloro-N-((1r,4r)-4-((2-oxo-3-(quinolin-3-yl)-2,3-dihydro-1H-benzo[d]imidazol-1-yl)methyl)cyclohexyl)-2-(trifluoromethyl)nicotinamide | Intermediate-157, Mesylate-3 | A1 |
| 353 | 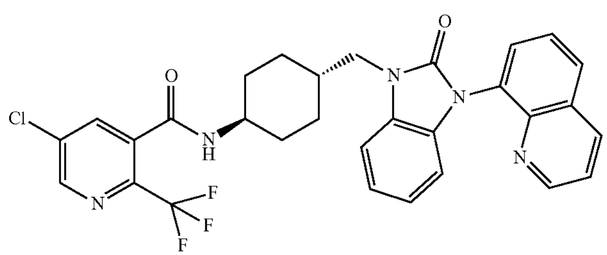 [SMILES: O=C(N[C@H]1CC[C@H](Cn2c(=O)n(-c3cccc4cccnc34)c3ccccc32)CC1)c1cc(Cl)cnc1C(F)(F)F] | 5-chloro-N-((1r,4r)-4-((2-oxo-3-(quinolin-8-yl)-2,3-dihydro-1H-benzo[d]imidazol-1-yl)methyl)cyclohexyl)-2-(trifluoromethyl)nicotinamide | Intermediate-149, Mesylate-3 | A1 |

TABLE 2-continued

| Ex. | Structure | Name | Reactants | Method |
|---|---|---|---|---|
| 354 | 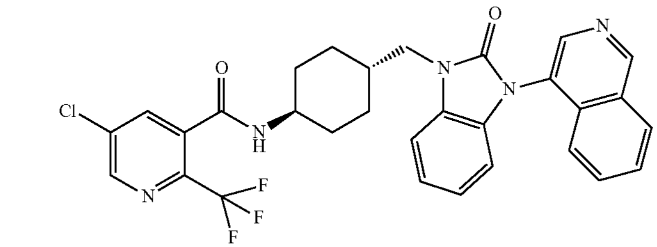 [SMILES: O=C(N[C@H]1CC[C@H](Cn2c(=O)n(-c3cncc4ccccc34)c3ccccc32)CC1)c1cc(Cl)cnc1C(F)(F)F] | 5-chloro-N-((1r,4r)-4-((3-(isoquinolin-4-yl)-2-oxo-2,3-dihydro-1H-benzo[d]imidazol-1-yl)methyl)cyclohexyl)-2-(trifluoromethyl)nicotinamide | Intermediate-150, Mesylate-3 | A1 |
| 355 | 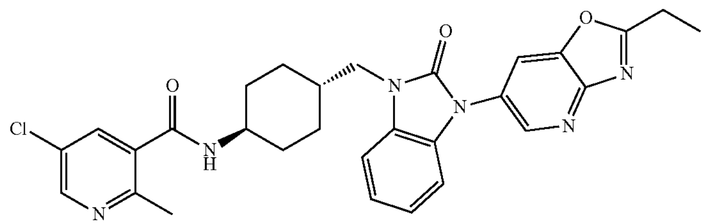 [SMILES: CCc1nc2ncc(-n3c(=O)n(C[C@H]4CC[C@H](NC(=O)c5cc(Cl)cnc5C)CC4)c4ccccc43)cc2o1] | 5-chloro-N-((1r,4r)-4-((3-(2-ethyloxazolo[4,5-b]pyridin-6-yl)-2-oxo-2,3-dihydro-1H-benzo[d]imidazol-1-yl)methyl)cyclohexyl)-2-methylnicotinamide | see Example synthesis part | |
| 356 | 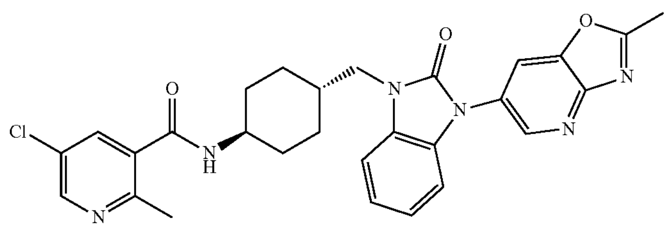 [SMILES: Cc1nc2ncc(-n3c(=O)n(C[C@H]4CC[C@H](NC(=O)c5cc(Cl)cnc5C)CC4)c4ccccc43)cc2o1] | 5-chloro-2-methyl-N-((1r,4r)-4-(3-(2-methyloxazolo[4,5-b]pyridin-6-yl)-2-oxo-2,3-dihydro-1H-benzo[d]imidazol-1-yl)methyl)cyclohexyl)nicotinamide | see Example synthesis part | |
| 357 | 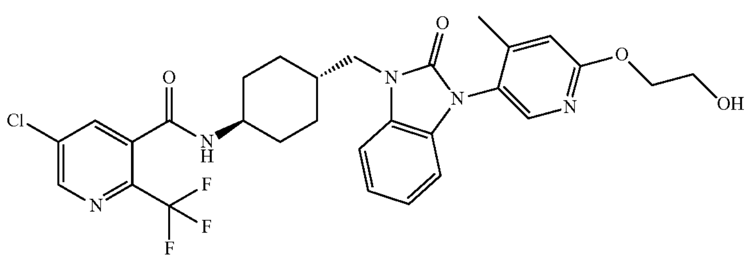 [SMILES: Cc1cc(OCCO)ncc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(6-(2-hydroxyethoxy)-4-methylpyridin-3-yl)-2-oxo-2,3-dihydro-1H-benzo[d]imidazol-1-yl)methyl)cyclohexyl)-2-(trifluoromethyl)nicotinamide | see Example synthesis part | |

TABLE 2-continued

| Ex. | Structure | Name | Reactants | Method |
|---|---|---|---|---|
| 358 | 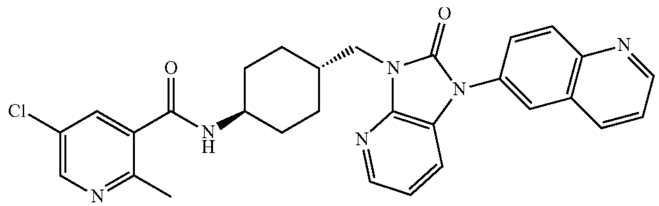 [SMILES: Cc1ncc(Cl)cc1C(=O)N[C@H]1CC[C@H](Cn2c(=O)n(-c3ccc4ncccc4c3)c3cccnc32)CC1] | 5-chloro-2-methyl-N-((1r,4r)-4-((2-oxo-1-(quinolin-6-yl)-1H-imidazo[4,5-b]pyridin-3(2H)-yl)methyl)cyclohexyl)nicotinamide | Intermediate-161, Mesylate-1 | A1 |
| 359 | 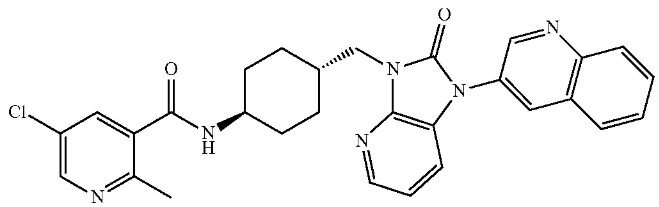 [SMILES: Cc1ncc(Cl)cc1C(=O)N[C@H]1CC[C@H](Cn2c(=O)n(-c3cnc4ccccc4c3)c3cccnc32)CC1] | 5-chloro-2-methyl-N-((1r,4r)-4-((2-oxo-1-(quinolin-3-yl)-1H-imidazo[4,5-b]pyridin-3(2H)-yl)methyl)cyclohexyl)nicotinamide | Intermediate-162, Mesylate-1 | A1 |
| 360 | 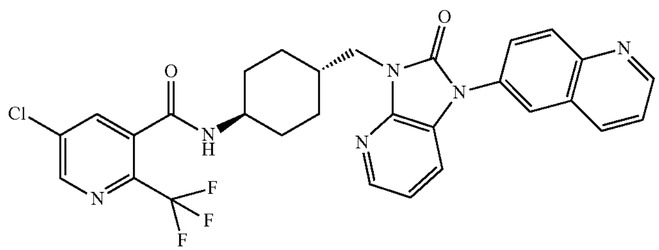 [SMILES: O=C(N[C@H]1CC[C@H](Cn2c(=O)n(-c3ccc4ncccc4c3)c3cccnc32)CC1)c1cc(Cl)cnc1C(F)(F)F] | 5-chloro-N-((1r,4r)-4-((2-oxo-1-(quinolin-6-yl)-1H-imidazo[4,5-b]pyridin-3(2H)-yl)methyl)cyclohexyl)-2-(trifluoromethyl)nicotinamide | Intermediate-161, Mesylate-3 | A1 |
| 361 | 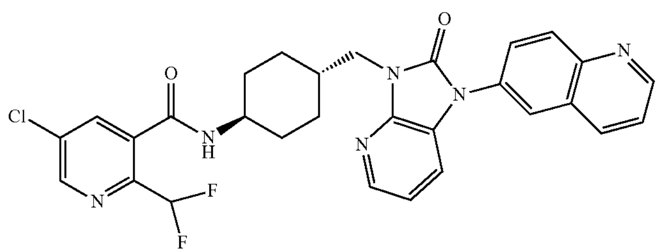 | 5-chloro-2-(difluoromethyl)-N-((1r,4r)-4-((2-oxo-1-(quinolin-6-yl)-1H-imidazo[4,5-b]pyridin-3(2H)-yl)methyl)cyclohexyl)nicotinamide | Intermediate-161, Mesylate-4 | A1 |

| Ex. | Structure | Name | Reactants | Method |
|---|---|---|---|---|
| 362 | 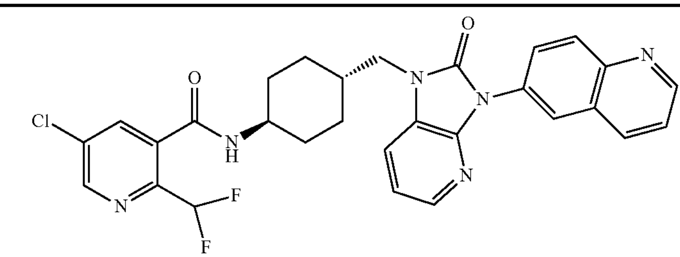 | 5-chloro-2-(difluoromethyl)-N-((1r,4r)-4-((2-oxo-3-(quinolin-6-yl)-2,3-dihydro-1H-imidazo[4,5-b]pyridin-1-yl)methyl)cyclohexyl)nicotinamide | Intermediate-163, Mesylate-4 | A1 |
| 363 | 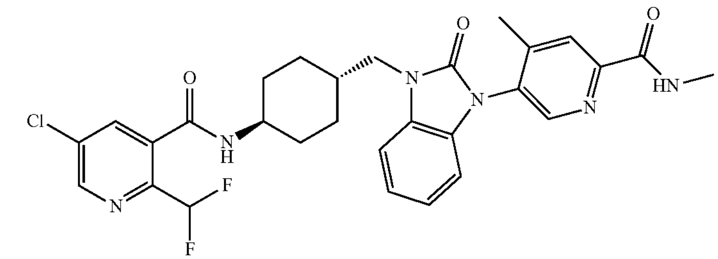 [SMILES: CNC(=O)c1cc(C)c(-n2c(=O)n(C[C@H]3CC[C@H](NC(=O)c4cc(Cl)cnc4C(F)F)CC3)c3ccccc32)cn1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N,4-dimethylpicolinamide | Intermediate-105, Mesylate-4 | A1 |
| 364 | 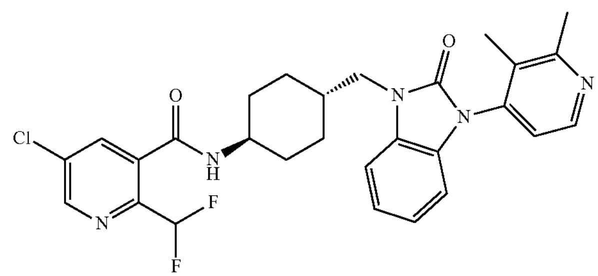 [SMILES: Cc1nccc(-n2c(=O)n(C[C@H]3CC[C@H](NC(=O)c4cc(Cl)cnc4C(F)F)CC3)c3ccccc32)c1C] | 5-chloro-2-(difluoromethyl)-N-((1r,4r)-4-((3-(2,3-dimethylpyridin-4-yl)-2-oxo-2,3-dihydro-1H-benzo[d]imidazol-1-yl)methyl)cyclohexyl)nicotinamide | Intermediate-145, Mesylate-4 | A1 |

TABLE 2-continued

| Ex. | Structure | Name | Reactants | Method |
|---|---|---|---|---|
| 365 | 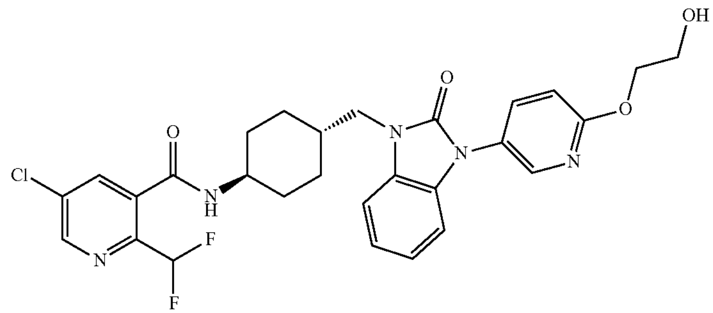 [SMILES: O=C(N[C@H]1CC[C@H](Cn2c(=O)n(-c3ccc(OCCO)nc3)c3ccccc32)CC1)c1cc(Cl)cnc1C(F)F] | 5-chloro-2-(difluoromethyl)-N-((1r,4r)-4-((3-(6-(2-hydroxyethoxy)pyridin-3-yl)-2-oxo-2,3-dihydro-1H-benzo[d]imidazol-1-yl)methyl)cyclohexyl)nicotinamide | see Example synthesis part | |
| 366 | 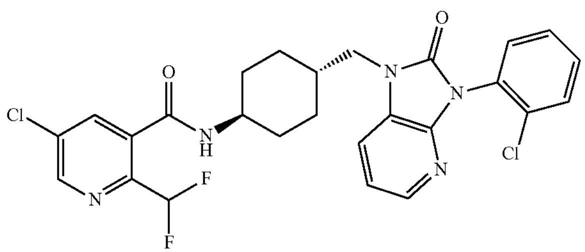 [SMILES: O=C(N[C@H]1CC[C@H](Cn2c(=O)n(-c3ccccc3Cl)c3ncccc32)CC1)c1cc(Cl)cnc1C(F)F] | 5-chloro-N-((1r,4r)-4-((3-(2-chlorophenyl)-2-oxo-2,3-dihydro-1H-imidazo[4,5-b]pyridin-1-yl)methyl)cyclohexyl)-2-(difluoromethyl)nicotinamide | Intermediate-117, Mesylate-4 | A1 |
| 367 | 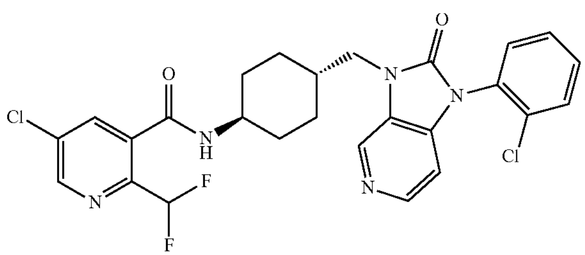 [SMILES: O=C(N[C@H]1CC[C@H](Cn2c(=O)n(-c3ccccc3Cl)c3ccncc32)CC1)c1cc(Cl)cnc1C(F)F] | 5-chloro-N-((1r,4r)-4-((1-(2-chlorophenyl)-2-oxo-1H-imidazo[4,5-c]pyridin-3(2H)-yl)methyl)cyclohexyl)-2-(difluoromethyl)nicotinamide | Intermediate-164, Mesylate-4 | A1 |

TABLE 2-continued

| Ex. | Structure | Name | Reactants | Method |
|---|---|---|---|---|
| 368 | 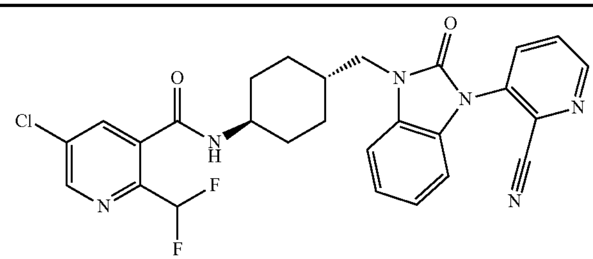 | 5-chloro-N-((1r,4r)-4-((3-(2-cyanopyridin-3-yl)-2-oxo-2,3-dihydro-1H-benzo[d]imidazol-1-yl)methyl)cyclohexyl)-2-(difluoromethyl)nicotinamide | | U |
| 369 | 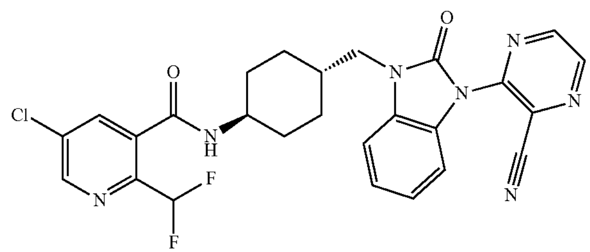 [SMILES: N#Cc1nccnc1-n1c(=O)n(C[C@H]2CC[C@H](NC(=O)c3cc(Cl)cnc3C(F)F)CC2)c2ccccc21] | 5-chloro-N-((1r,4r)-4-((3-(3-cyanopyrazin-2-yl)-2-oxo-2,3-dihydro-1H-benzo[d]imidazol-1-yl)methyl)cyclohexyl)-2-(difluoromethyl)nicotinamide | Intermediate-165<br><br>see Example synthesis part | |
| 370 | 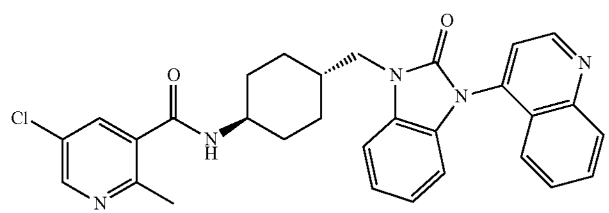 [SMILES: Cc1ncc(Cl)cc1C(=O)N[C@H]1CC[C@H](Cn2c(=O)n(-c3ccnc4ccccc34)c3ccccc32)CC1] | 5-chloro-2-methyl-N-((1r,4r)-4-((2-oxo-3-(quinolin-4-yl)-2,3-dihydro-1H-benzo[d]imidazol-1-yl)methyl)cyclohexyl)nicotinamide | Intermediate-166, Mesylate-1 | A1 |
| 371 | 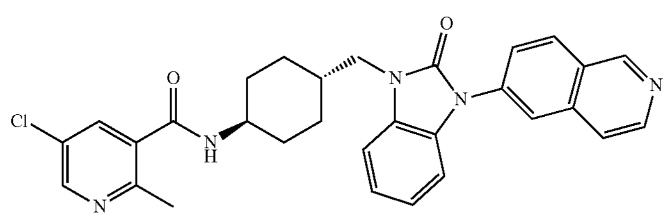 [SMILES: Cc1ncc(Cl)cc1C(=O)N[C@H]1CC[C@H](Cn2c(=O)n(-c3ccc4cnccc4c3)c3ccccc32)CC1] | 5-chloro-N-((1r,4r)-4-((3-(isoquinolin-6-yl)-2-oxo-2,3-dihydro-1H-benzo[d]imidazol-1-yl)methyl)cyclohexyl)-2-methylnicotinamide | Intermediate-167, Mesylate-1 | A1 |

TABLE 2-continued

| Ex. | Structure | Name | Reactants | Method |
|---|---|---|---|---|
| 372 | 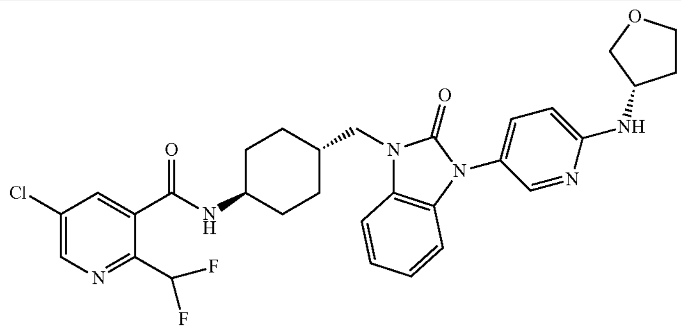 [SMILES: O=C(N[C@H]1CC[C@H](Cn2c(=O)n(-c3ccc(N[C@H]4CCOC4)nc3)c3ccccc32)CC1)c1cc(Cl)cnc1C(F)F] | 5-chloro-2-(difluoromethyl)-N-((1S,4r)-4-(2-oxo-3-(6-(((S)-tetrahydrofuran-3-yl)amino)pyridin-3-yl)-2,3-dihydro-1H-benzo[d]imidazol-1-yl)methyl)cyclohexyl)nicotinamide | Intermediate-135, Mesylate-4 | A1 |
| 373 | 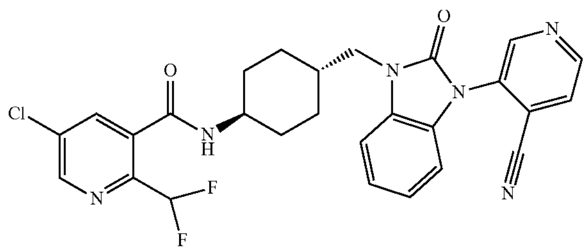 [SMILES: N#Cc1ccncc1-n1c(=O)n(C[C@H]2CC[C@H](NC(=O)c3cc(Cl)cnc3C(F)F)CC2)c2ccccc21] | 5-chloro-N-((1r,4r)-4-(3-(4-cyanopyridin-3-yl)-2-oxo-2,3-dihydro-1H-benzo[d]imidazol-1-yl)methyl)cyclohexyl)-2-(difluoromethyl)nicotinamide | Intermediate-137, Mesylate-4 | A1 |
| 374 | 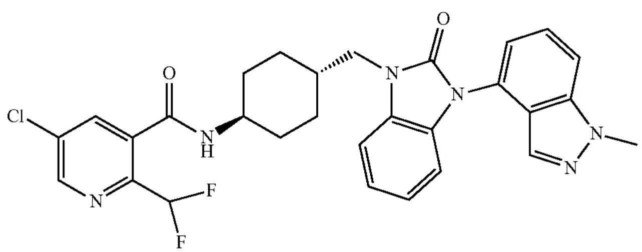 [SMILES: Cn1ncc2c(-n3c(=O)n(C[C@H]4CC[C@H](NC(=O)c5cc(Cl)cnc5C(F)F)CC4)c4ccccc43)cccc21] | 5-chloro-2-(difluoromethyl)-N-((1r,4r)-4-((3-(1-methyl-1H-indazol-4-yl)-2-oxo-2,3-dihydro-1H-benzo[d]imidazol-1-yl)methyl)cyclohexyl)nicotinamide | Intermediate-158, Mesylate-4 | A1 |

TABLE 2-continued

| Ex. | Structure | Name | Reactants | Method |
|---|---|---|---|---|
| 375 | 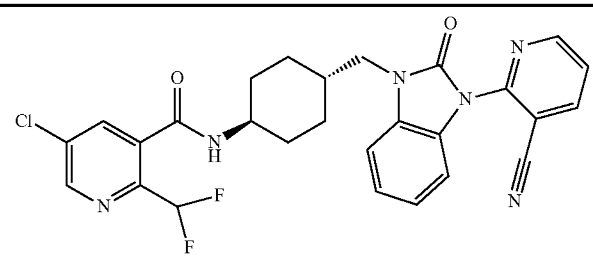 | 5-chloro-N-((1r,4r)-4-((3-(3-cyanopyridin-2-yl)-2-oxo-2,3-dihydro-1H-benzo[d]imidazol-1-yl)methyl)cyclohexyl)-2-(difluoromethyl)nicotinamide | Intermediate-138, Mesylate-4 | A1 |
| 376 | 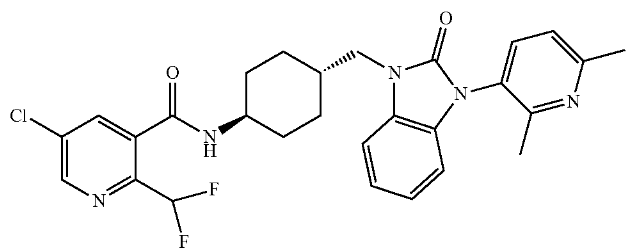 [SMILES: Cc1ccc(-n2c(=O)n(C[C@H]3CC[C@H](NC(=O)c4cc(Cl)cnc4C(F)F)CC3)c3ccccc32)c(C)n1] | 5-chloro-2-(difluoromethyl)-N-((1r,4r)-4-((3-(2,6-dimethyl-pyridin-3-yl)-2-oxo-2,3-dihydro-1H-benzo[d]imidazol-1-yl)methyl)cyclohexyl)nicotinamide | Intermediate-14, Mesylate-4 | A1 |
| 377 | 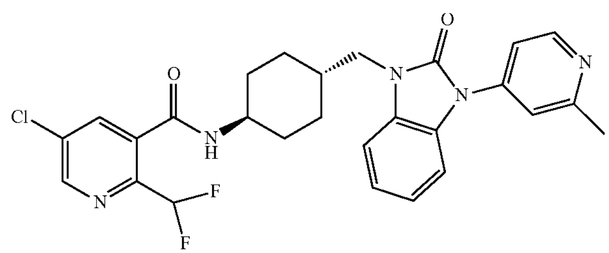 [SMILES: Cc1cc(-n2c(=O)n(C[C@H]3CC[C@H](NC(=O)c4cc(Cl)cnc4C(F)F)CC3)c3ccccc32)ccn1] | 5-chloro-2-(difluoromethyl)-N-((1r,4r)-4-((3-(2-methyl-pyridin-4-yl)-2-oxo-2,3-dihydro-1H-benzo[d]imidazol-1-yl)methyl)cyclohexyl)nicotinamide | Intermediate-30, Mesylate-4 | A1 |
| 378 | 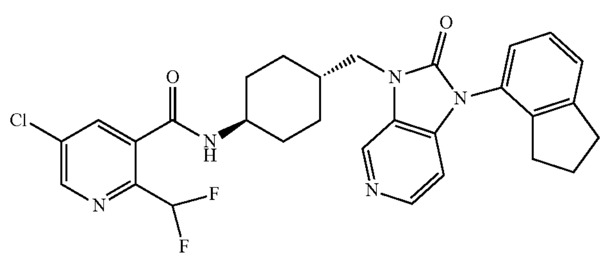 [SMILES: O=C(N[C@H]1CC[C@H](Cn2c(=O)n(-c3cccc4c3CCC4)c3ccncc32)CC1)c1cc(Cl)cnc1C(F)F] | 5-chloro-2-(difluoromethyl)-N-((1r,4r)-4-((1-(2,3-dihydro-1H-inden-4-yl)-2-oxo-1H-imidazo[4,5-c]pyridin-3(2H)-yl)methyl)cyclohexyl)nicotinamide | Intermediate-120, Mesylate-4 | A1 |

TABLE 2-continued

| Ex. | Structure | Name | Reactants | Method |
|---|---|---|---|---|
| 379 | 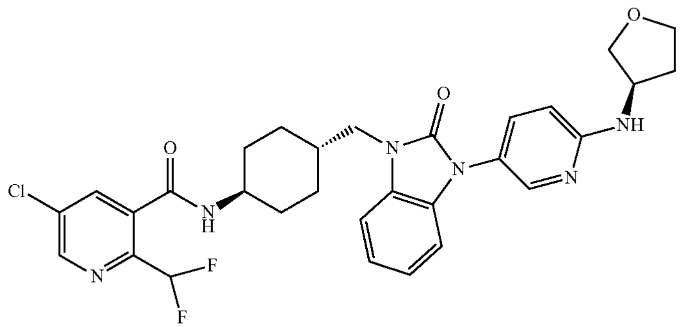 [SMILES: O=C(N[C@H]1CC[C@H](Cn2c(=O)n(-c3ccc(N[C@@H]4CCOC4)nc3)c3ccccc32)CC1)c1cc(Cl)cnc1C(F)F] | 5-chloro-2-(difluoromethyl)-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide | Intermediate-136, Mesylate-4 | A1 |
| 380 | 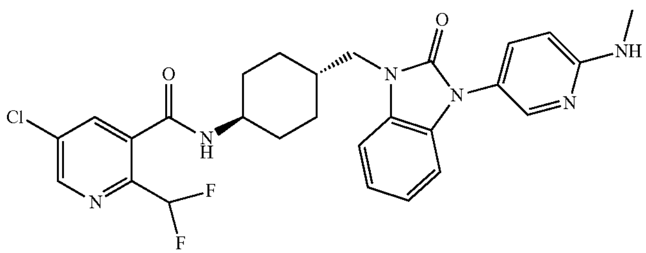 [SMILES: CNc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(methyl-amino)pyridin-3-yl)-2-oxo-2,3-dihydro-1H-benzo[d]imidazol-1-yl)methyl)cyclohexyl)nicotinamide | Intermediate-146, Mesylate-4 | A1 |
| 381 | 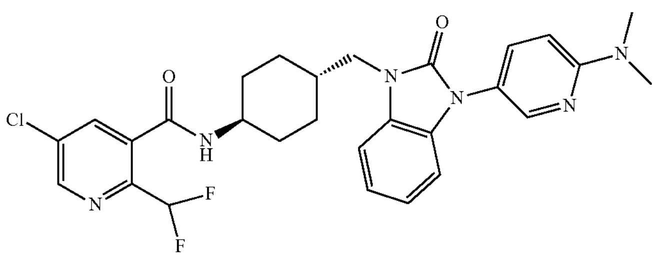 [SMILES: CN(C)c1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(dimethyl-amino)pyridin-3-yl)-2-oxo-2,3-dihydro-1H-benzo[d]imidazol-1-yl)methyl)cyclohexyl)nicotinamide | Intermediate-26, Mesylate-4 | A1 |

TABLE 2-continued

| Ex. | Structure | Name | Reactants | Method |
|---|---|---|---|---|
| 382 | 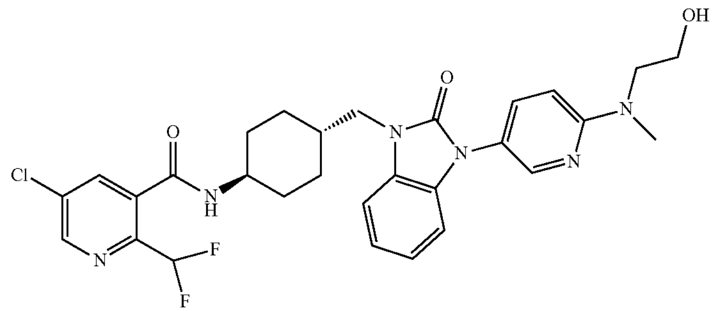 [SMILES: CN(CCO)c1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-(3-(6-((2-hydroxyethyl)(methyl)amino)pyridin-3-yl)-2-oxo-2,3-dihydro-1H-benzo[d]imidazol-1-yl)methyl)cyclohexyl)nicotinamide | Intermediate-37, Mesylate-4 | A1 |
| 383 | 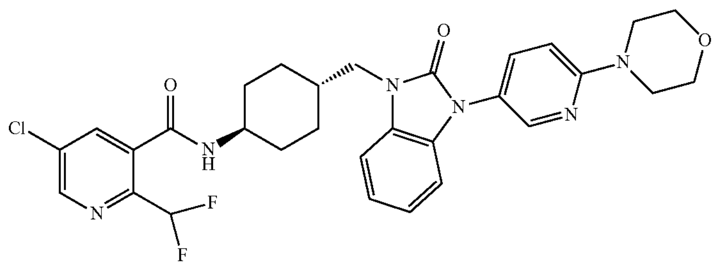 [SMILES: O=C(N[C@H]1CC[C@H](Cn2c(=O)n(-c3ccc(N4CCOCC4)nc3)c3ccccc32)CC1)c1cc(Cl)cnc1C(F)F] | 5-chloro-2-(difluoromethyl)-N-((1r,4r)-4-((3-(6-morpholinopyridin-3-yl)-2-oxo-2,3-dihydro-1H-benzo[d]imidazol-1-yl)methyl)cyclohexyl)nicotinamide | Intermediate-28, Mesylate-4 | A1 |
| 384 | 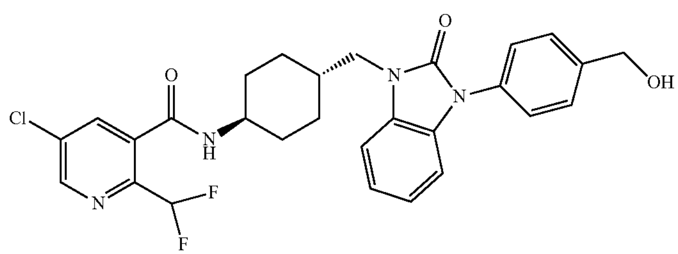 [SMILES: O=C(N[C@H]1CC[C@H](Cn2c(=O)n(-c3ccc(CO)cc3)c3ccccc32)CC1)c1cc(Cl)cnc1C(F)F] | 5-chloro-2-(difluoromethyl)-N-((1r,4r)-4-((3-(4-(hydroxymethyl)phenyl)-2-oxo-2,3-dihydro-1H-benzo[d]imidazol-1-yl)methyl)cyclohexyl)nicotinamide | Intermediate-168, Mesylate-4 | A1 |

TABLE 2-continued

| Ex. | Structure | Name | Reactants | Method |
|---|---|---|---|---|
| 385 | 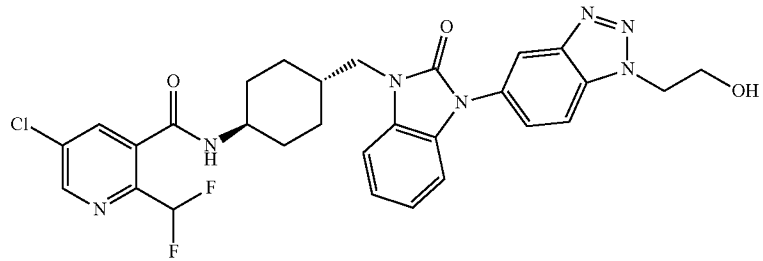 [SMILES: O=C(N[C@H]1CC[C@H](Cn2c(=O)n(-c3ccc4c(c3)nnn4CCO)c3ccccc32)CC1)c1cc(Cl)cnc1C(F)F] | 5-chloro-2-(difluoromethyl)-N-((1r,4r)-4-(3-(1-(2-hydroxyethyl)-1H-benzo[d][1,2,3]triazol-5-yl)-2-oxo-2,3-dihydro-1H-benzo[d]imidazol-1-yl)methyl)cyclohexyl)nicotinamide | see Example synthesis part | |
| 386 | 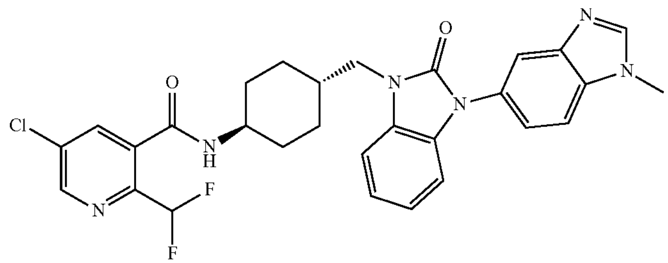 [SMILES: Cn1cnc2cc(-n3c(=O)n(C[C@H]4CC[C@H](NC(=O)c5cc(Cl)cnc5C(F)F)CC4)c4ccccc43)ccc21] | 5-chloro-2-(difluoromethyl)-N-((1r,4r)-4-((1'-methyl-2-oxo-1'H-[1,5'-bibenzo[d]imidazol]-3(2H)-yl)methyl)cyclohexyl)nicotinamide | Intermediate-108, Mesylate-4 | A1 |
| 387 | 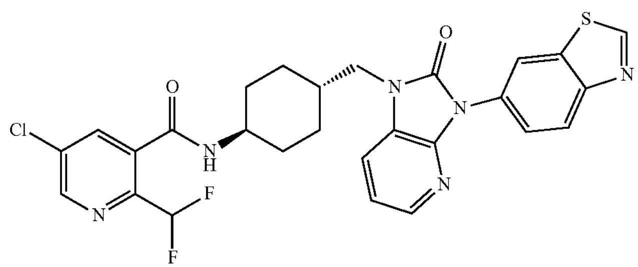 [SMILES: O=C(N[C@H]1CC[C@H](Cn2c(=O)n(-c3ccc4ncsc4c3)c3ncccc32)CC1)c1cc(Cl)cnc1C(F)F] | N-((1r,4r)-4-((3-(benzo[d]thiazol-6-yl)-2-oxo-2,3-dihydro-1H-imidazo[4,5-b]pyridin-1-yl)methyl)cyclohexyl)-5-chloro-2-(difluoromethyl)nicotinamide | Intermediate-106, Mesylate-4 | A1 |
| 388 | 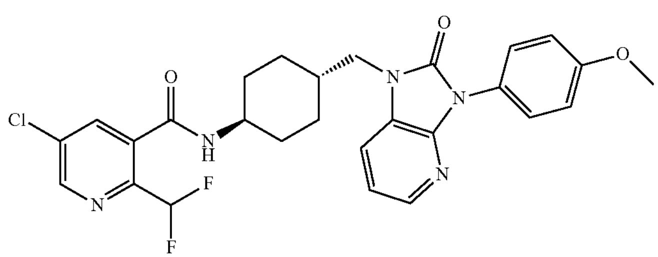 [SMILES: COc1ccc(-n2c(=O)n(C[C@H]3CC[C@H](NC(=O)c4cc(Cl)cnc4C(F)F)CC3)c3cccnc32)cc1] | 5-chloro-2-(difluoromethyl)-N-((1r,4r)-4-((3-(4-methoxyphenyl)-2-oxo-2,3-dihydro-1H-imidazo[4,5-b]pyridin-1-yl)methyl)cyclohexyl)nicotinamide | Intermediate-99, Mesylate-4 | A1 |

TABLE 2-continued

| Ex. | Structure | Name | Reactants | Method |
|---|---|---|---|---|
| 389 | 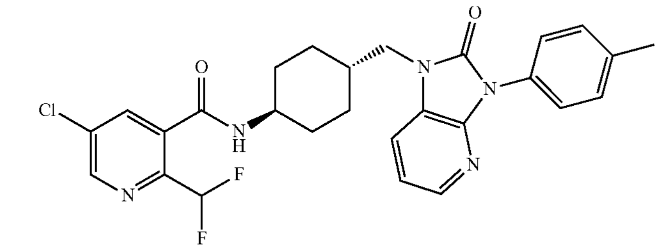 | 5-chloro-2-(difluoromethyl)-N-((1r,4r)-4-((2-oxo-3-(p-tolyl)-2,3-dihydro-1H-imidazo[4,5-b]pyridin-1-yl)methyl)cyclohexyl)nicotinamide | Intermediate-169, Mesylate-4 | A1 |
| 390 | 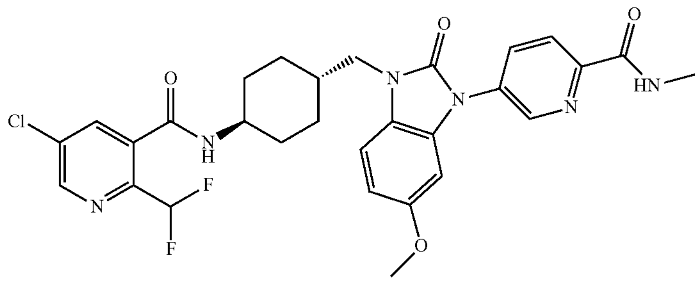 [SMILES: CNC(=O)c1ccc(-n2c(=O)n(C[C@H]3CC[C@H](NC(=O)c4cc(Cl)cnc4C(F)F)CC3)c3ccc(OC)cc32)cn1] | 5-(3-((1r,4r)-4-(5-chloro-2-(difluoromethyl)nicotinamido)cyclohexyl)methyl)-6-methoxy-2-oxo-2,3-dihydro-1H-benzo[d]imidazol-1-yl)-N-methylpicolinamide | Intermediate-126, Mesylate-4 | A1 |
| 391 | 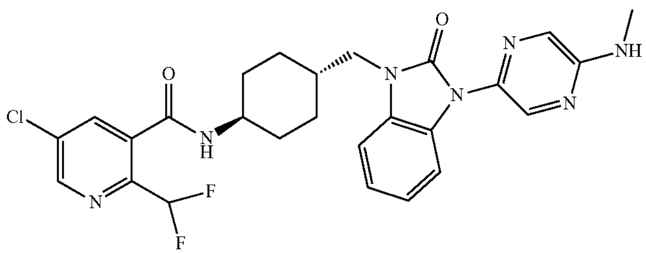 [SMILES: CNc1cnc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(5-(methylamino)pyrazin-2-yl)-2-oxo-2,3-dihydro-1H-benzo[d]imidazol-1-yl)methyl)cyclohexyl)nicotinamide | Intermediate-134, Mesylate-4 | A1 |
| 392 | 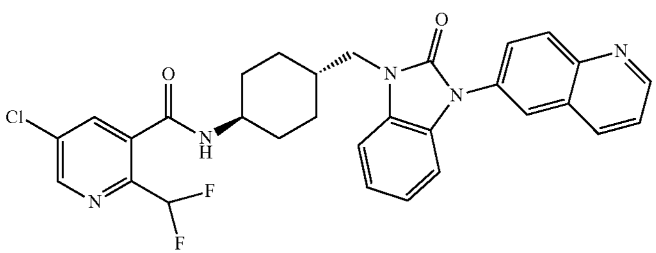 [SMILES: O=C(N[C@H]1CC[C@H](Cn2c(=O)n(-c3ccc4ncccc4c3)c3ccccc32)CC1)c1cc(Cl)cnc1C(F)F] | 5-chloro-2-(difluoromethyl)-N-((1r,4r)-4-((2-oxo-3-(quinolin-6-yl)-2,3-dihydro-1H-benzo[d]imidazol-1-yl)methyl)cyclohexyl)nicotinamide | Intermediate-155, Mesylate-4 | A1 |

TABLE 2-continued

| Ex. | Structure | Name | Reactants | Method |
|---|---|---|---|---|
| 393 | 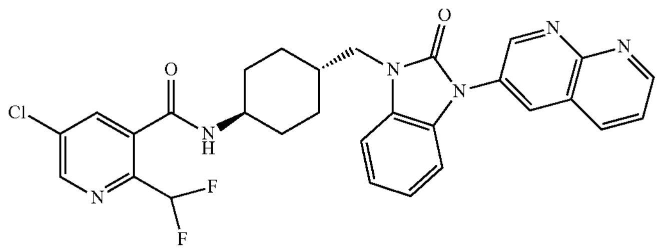 [SMILES: O=C(N[C@H]1CC[C@H](Cn2c(=O)n(-c3cnc4ncccc4c3)c3ccccc32)CC1)c1cc(Cl)cnc1C(F)F] | N-((1r,4r)-4-(3-(1,8-naph-thyridin-3-yl)-2-oxo-2,3-dihydro-1H-benzo[d]imidazol-1-yl)methyl)cyclohexyl)-5-chloro-2-(difluoromethyl)nicotinamide | Intermediate-170, Mesylate-4 | A1 |
| 394 | 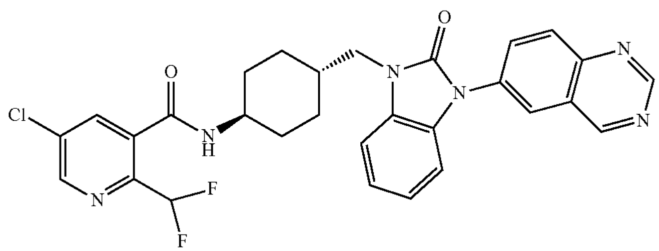 | 5-chloro-2-(difluoromethyl)-N-((1r,4r)-4-((2-oxo-3-(quinazolin-6-yl)-2,3-dihydro-1H-benzo[d]imidazol-1-yl)methyl)cyclohexyl)nicotinamide | Intermediate-171, Mesylate-4 | A1 |
| 395 | 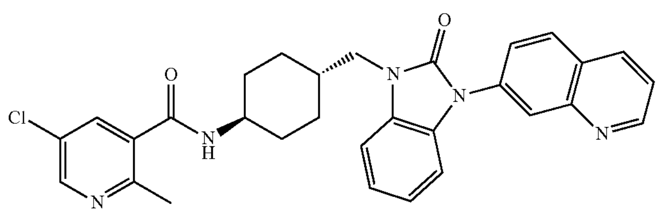 [SMILES: Cc1ncc(Cl)cc1C(=O)N[C@H]1CC[C@H](Cn2c(=O)n(-c3ccc4cccnc4c3)c3ccccc32)CC1] | 5-chloro-2-methyl-N-((1r,4r)-4-((2-oxo-3-(quinolin-7-yl)-2,3-dihydro-1H-benzo[d]imidazol-1-yl)methyl)cyclohexyl)nicotinamide | Intermediate-172, Mesylate-1 | A1 |
| 396 | 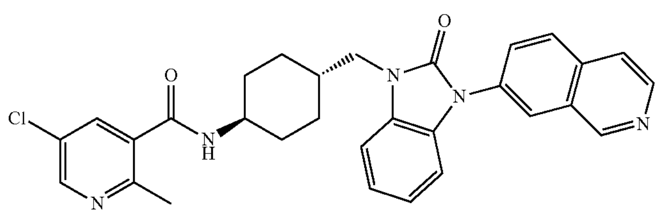 [SMILES: Cc1ncc(Cl)cc1C(=O)N[C@H]1CC[C@H](Cn2c(=O)n(-c3ccc4ccncc4c3)c3ccccc32)CC1] | 5-chloro-N-((1r,4r)-4-((3-(isoquinolin-7-yl)-2-oxo-2,3-dihydro-1H-benzo[d]imidazol-1-yl)methyl)cyclohexyl)-2-methyl-nicotinamide | Intermediate-173, Mesylate-1 | A1 |

TABLE 2-continued

| Ex. | Structure | Name | Reactants | Method |
|---|---|---|---|---|
| 397 | 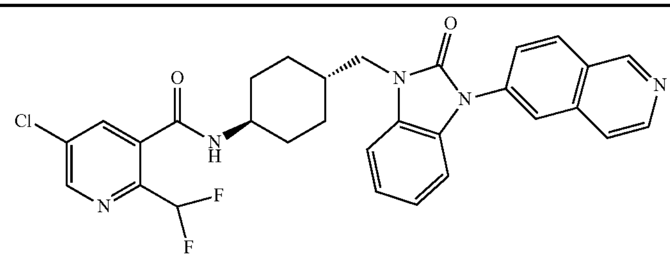 | 5-chloro-2-(difluoromethyl)-N-((1r,4r)-4-(3-(isoquinolin-6-yl)-2-oxo-2,3-dihydro-1H-benzo[d]imidazol-1-yl)methyl)cyclohexyl)nicotinamide | Intermediate-167, Mesylate-4 | A1 |
| 398 | 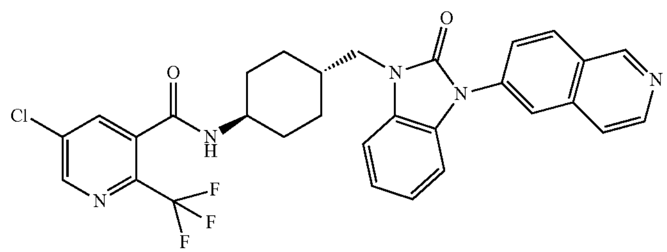 [SMILES: O=C(N[C@H]1CC[C@H](Cn2c(=O)n(-c3ccc4cnccc4c3)c3ccccc32)CC1)c1cc(Cl)cnc1C(F)(F)F] | 5-chloro-N-((1r,4r)-4-(3-(isoquinolin-6-yl)-2-oxo-2,3-dihydro-1H-benzo[d]imidazol-1-yl)methyl)cyclohexyl)-2-(trifluoromethyl)nicotinamide | Intermediate-167, Mesylate-3 | A1 |
| 399 | 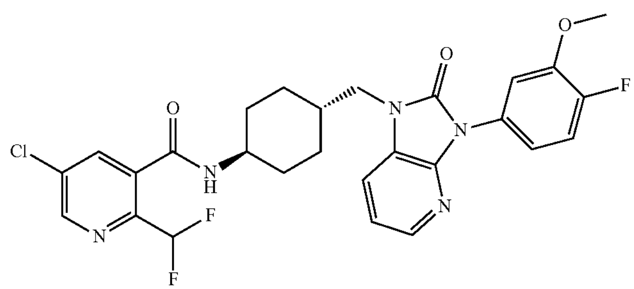 [SMILES: COc1cc(-n2c(=O)n(C[C@H]3CC[C@H](NC(=O)c4cc(Cl)cnc4C(F)F)CC3)c3cccnc32)ccc1F] | 5-chloro-2-(difluoromethyl)-N-((1r,4r)-4-(3-(4-fluoro-3-methoxyphenyl)-2-oxo-2,3-dihydro-1H-imidazo[4,5-b]pyridin-1-yl)methyl)cyclohexyl)nicotinamide | Intermediate-174, Mesylate-4 | A1 |
| 400 | 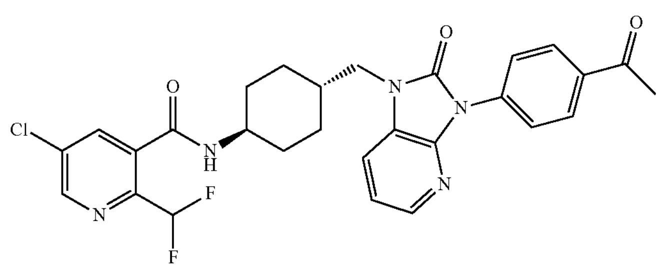 [SMILES: CC(=O)c1ccc(-n2c(=O)n(C[C@H]3CC[C@H](NC(=O)c4cc(Cl)cnc4C(F)F)CC3)c3cccnc32)cc1] | N-((1r,4r)-4-(3-(4-acetylphenyl)-2-oxo-2,3-dihydro-1H-imidazo[4,5-b]pyridin-1-yl)methyl)cyclohexyl)-5-chloro-2-(difluoromethyl)nicotinamide | Intermediate-175, Mesylate-4 | A1 |

TABLE 2-continued

| Ex. | Structure | Name | Reactants | Method |
|---|---|---|---|---|
| 401 | 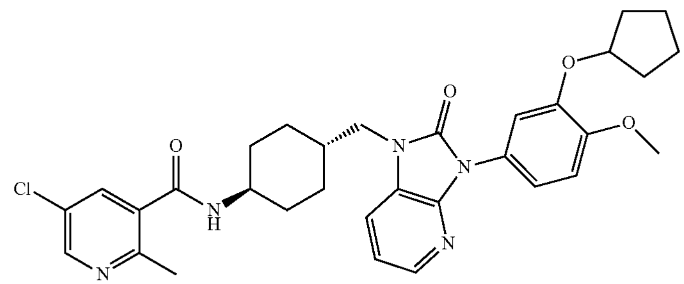 [SMILES: COc1ccc(-n2c(=O)n(C[C@H]3CC[C@H](NC(=O)c4cc(Cl)cnc4C)CC3)c3cccnc32)cc1OC1CCCC1] | 5-chloro-N-((1r,4r)-4-((3-(3-(cyclopentyloxy)-4-methoxyphenyl)-2-oxo-2,3-dihydro-1H-imidazo[4,5-b]pyridin-1-yl)methyl)cyclohexyl)-2-methylnicotinamide | Intermediate-176, Mesylate-1 | A1 |
| 402 | 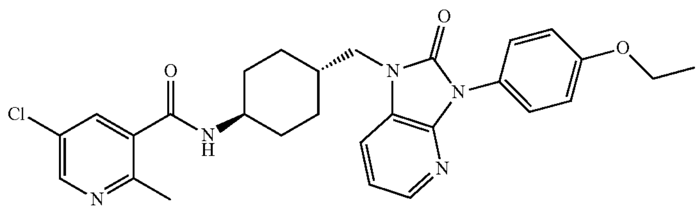 [SMILES: CCOc1ccc(-n2c(=O)n(C[C@H]3CC[C@H](NC(=O)c4cc(Cl)cnc4C)CC3)c3cccnc32)cc1] | 5-chloro-N-((1r,4r)-4-((3-(4-ethoxyphenyl)-2-oxo-2,3-dihydro-1H-imidazo[4,5-b]pyridin-1-yl)methyl)cyclohexyl)-2-methylnicotinamide | Intermediate-177, Mesylate-1 | A1 |
| 403 | 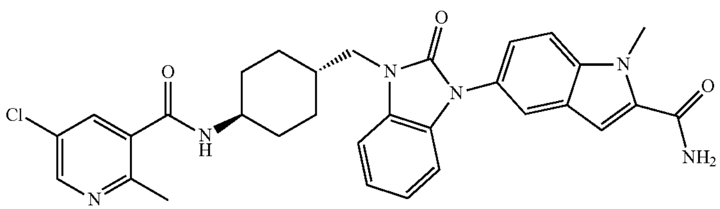 [SMILES: Cc1ncc(Cl)cc1C(=O)N[C@H]1CC[C@H](Cn2c(=O)n(-c3ccc4c(c3)cc(C(N)=O)n4C)c3ccccc32)CC1] | 5-(((1r,4r)-4-(5-chloro-2-methylnicotinamido)cyclohexyl)methyl)-2-oxo-2,3-dihydro-1H-benzo[d]imidazol-1-yl)-1-methyl-1H-indole-2-carboxamide | Intermediate-178, NH$_3$ | Q |
| 404 | 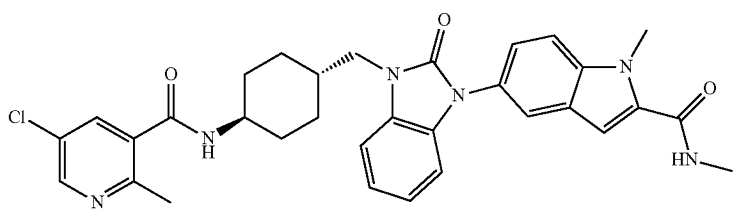 [SMILES: CNC(=O)c1cc2cc(-n3c(=O)n(C[C@H]4CC[C@H](NC(=O)c5cc(Cl)cnc5C)CC4)c4ccccc43)ccc2n1C] | 5-(3-((1r,4r)-4-(5-chloro-2-methylnicotinamido)cyclohexyl)methyl)-2-oxo-2,3-dihydro-1H-benzo[d]imidazol-1-yl)-N,1-dimethyl-1H-indole-2-carboxamide | Intermediate-178, MeNH$_2$ | Q |

TABLE 2-continued

| Ex. | Structure | Name | Reactants | Method |
|---|---|---|---|---|
| 405 | 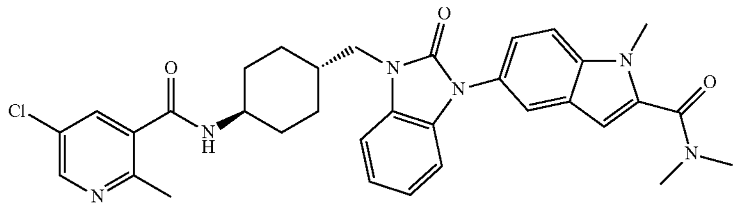 [SMILES: Cc1ncc(Cl)cc1C(=O)N[C@H]1CC[C@H](Cn2c(=O)n(-c3ccc4c(c3)cc(C(=O)N(C)C)n4C)c3ccccc32)CC1] | 5-(3-((1r,4r)-4-(5-chloro-2-methylnicotinamido)cyclohexyl)methyl)-2-oxo-2,3-dihydro-1H-benzo[d]imidazol-1-yl)-N,N,1-trimethyl-1H-indole-2-carboxamide | Intermediate-178, Me$_2$NH | Q |
| 406 | 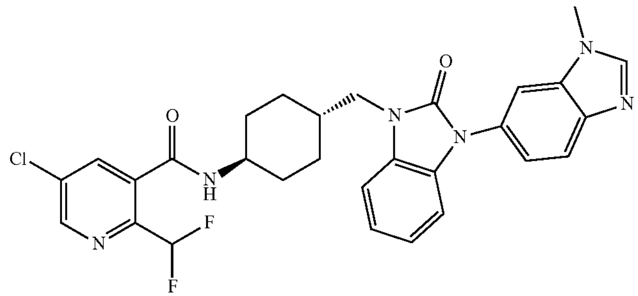 [SMILES: Cn1cnc2ccc(-n3c(=O)n(C[C@H]4CC[C@H](NC(=O)c5cc(Cl)cnc5C(F)F)CC4)c4ccccc43)cc21] | 5-chloro-2-(difluoromethyl)-N-((1r,4r)-4-((3'-methyl-2-oxo-3H-[1,5'-bibenzo[d]imidazol]-3(2H)-yl)methyl)cyclohexyl)nicotinamide | Intermediate-109, Mesylate-4 | A1 |
| 407 | 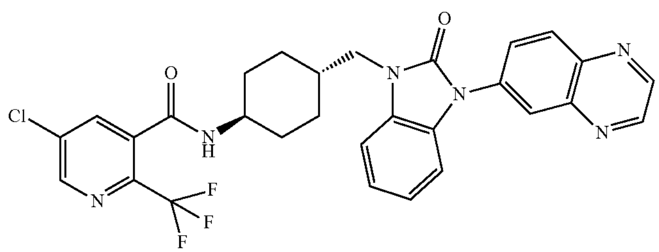 | 5-chloro-N-((1r,4r)-4-(2-oxo-3-(quinoxalin-6-yl)-2,3-dihydro-1H-benzo[d]imidazol-1-yl)methyl)cyclohexyl)-2-(trifluoromethyl)nicotinamide | Intermediate-179, Mesylate-3 | A1 |
| 408 | 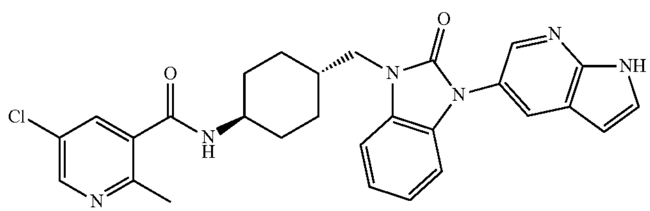 [SMILES: Cc1ncc(Cl)cc1C(=O)N[C@H]1CC[C@H](Cn2c(=O)n(-c3cnc4[nH]ccc4c3)c3ccccc32)CC1] | 5-chloro-2-methyl-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide | see Example synthesis part Method V | |

TABLE 2-continued

| Ex. | Structure | Name | Reactants | Method |
|---|---|---|---|---|
| 409 | 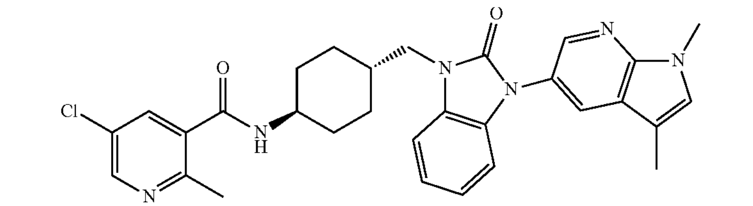 [SMILES: Cc1ncc(Cl)cc1C(=O)N[C@H]1CC[C@H](Cn2c(=O)n(-c3cnc4c(c3)c(C)cn4C)c3ccccc32)CC1] | 5-chloro-N-((1r,4r)-4-(3-(1,3-dimethyl-1H-pyrrolo[2,3-b]pyridin-5-yl)-2-oxo-2,3-dihydro-1H-benzo[d]imidazol-1-yl)methyl)cyclohexyl)-2-methylnicotinamide | Intermediate-213, Mesylate-1 | A1 |
| 410 | 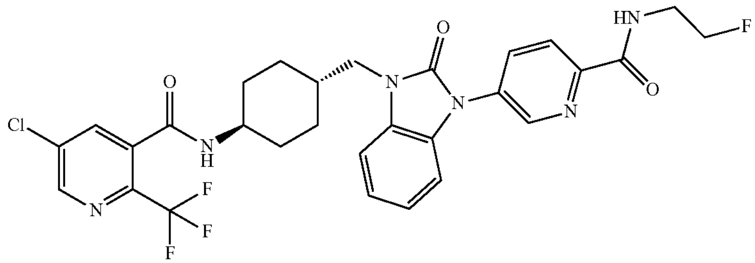 [SMILES: O=C(NCCF)c1ccc(-n2c(=O)n(C[C@H]3CC[C@H](NC(=O)c4cc(Cl)cnc4C(F)(F)F)CC3)c3ccccc32)cn1] | 5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-(2-fluoroethyl)picolinamide | Intermediate-180, H₂N–CH₂–CH₂–F | Q |
| 411 | 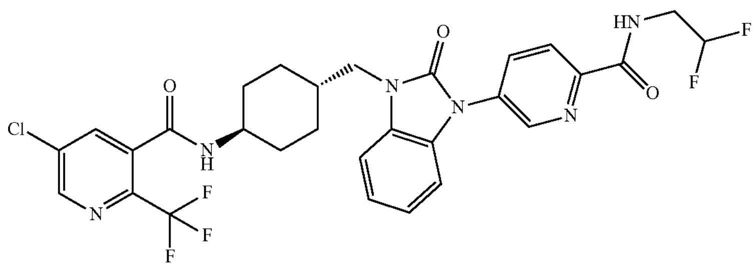 [SMILES: O=C(NCC(F)F)c1ccc(-n2c(=O)n(C[C@H]3CC[C@H](NC(=O)c4cc(Cl)cnc4C(F)(F)F)CC3)c3ccccc32)cn1] | 5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-(2,2-difluoroethyl)picolinamide | Intermediate-180, H₂N–CH₂–CHF₂ | Q |
| 412 | 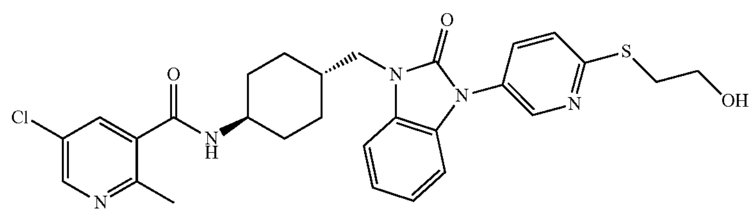 [SMILES: Cc1ncc(Cl)cc1C(=O)N[C@H]1CC[C@H](Cn2c(=O)n(-c3ccc(SCCO)nc3)c3ccccc32)CC1] | 5-chloro-N-((1r,4r)-4-((3-(6-((2-hydroxyethyl)thio)pyridin-3-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 413 | 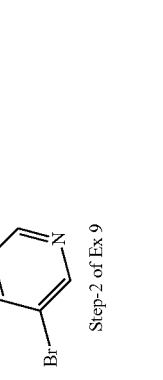 | 5-chloro-2-methyl-N-((1r,4r)-4-((3-(5-morpholinopyridin-3-yl)-2-oxo-2,3-dihydro-1H-benzo[d]imidazol-1-yl)methyl)cyclohexyl)nicotinamide |  Step-2 of Ex 9 | R |
| 414 | 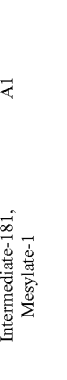 | 5-chloro-N-((1r,4r)-4-((3-(2,4-dichlorophenyl)-2-oxo-2,3-dihydro-1H-imidazo[4,5-b]pyridin-1-yl)methyl)cyclohexyl)-2-methylnicotinamide | Intermediate-181, Mesylate-1 | A1 |
| 415 | 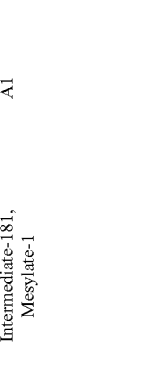 | 5-chloro-2-(difluoromethyl)-N-((1r,4r)-4-((3-(imidazo[1,5-a]pyridin-7-yl)-2-oxo-2,3-dihydro-1H-benzo[d]imidazol-1-yl)methyl)cyclohexyl)nicotinamide | Intermediate-182, Mesylate-4 | A1 |

TABLE 2-continued

| Ex. | Structure | Name | Reactants | Method |
|---|---|---|---|---|
| 416 | 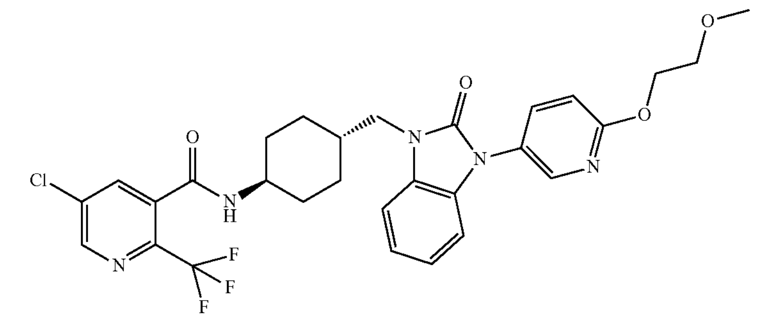 [SMILES: COCCOc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-(2-methoxyethoxy)pyridin-3-yl)-2-oxo-2,3-dihydro-1H-benzo[d]imidazol-1-yl)methyl)cyclohexyl)-2-(trifluoromethyl)nicotinamide | Intermediate-183, Mesylate-3 | A1 |
| 417 | 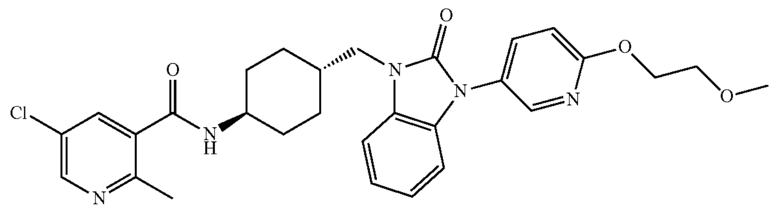 [SMILES: COCCOc1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-(2-methoxyethoxy)pyridin-3-yl)-2-oxo-2,3-dihydro-1H-benzo[d]imidazol-1-yl)methyl)cyclohexyl)-2-methylnicotinamide | Intermediate-183, Mesylate-1 | A1 |
| 418 | 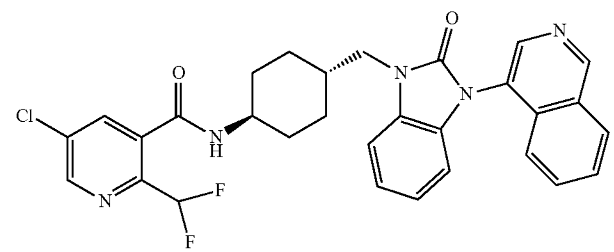 [SMILES: O=C(N[C@H]1CC[C@H](Cn2c(=O)n(-c3cncc4ccccc34)c3ccccc32)CC1)c1cc(Cl)cnc1C(F)F] | 5-chloro-2-(difluoromethyl)-N-((1r,4r)-4-((3-(isoquinolin-4-yl)-2-oxo-2,3-dihydro-1H-benzo[d]imidazol-1-yl)methyl)cyclohexyl)nicotinamide | Intermediate-150, Mesylate-4 | A1 |
| 419 | 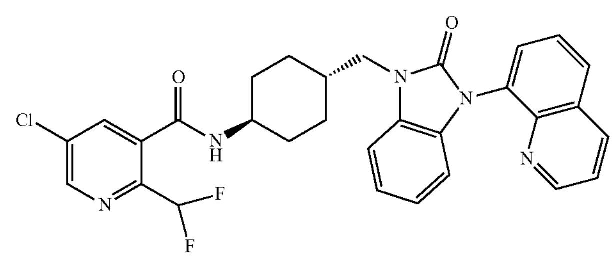 [SMILES: O=C(N[C@H]1CC[C@H](Cn2c(=O)n(-c3cccc4cccnc34)c3ccccc32)CC1)c1cc(Cl)cnc1C(F)F] | 5-chloro-2-(difluoromethyl)-N-((1r,4r)-4-((3-(quinolin-8-yl)-2-oxo-2,3-dihydro-1H-benzo[d]imidazol-1-yl)methyl)cyclohexyl)nicotinamide | Intermediate-149, Mesylate-4 | A1 |

TABLE 2-continued

| Ex. | Structure | Name | Reactants | Method |
|---|---|---|---|---|
| 420 | 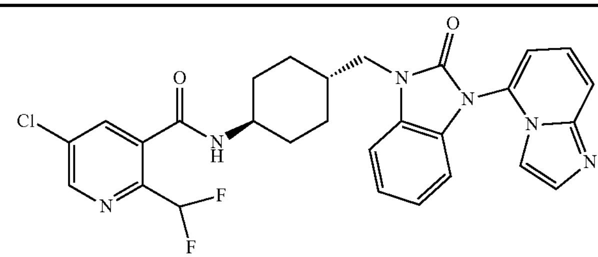 | 5-chloro-2-(difluoromethyl)-N-((1r,4r)-4-((3-(imidazo[1,2-a]pyridin-5-yl)-2-oxo-2,3-dihydro-1H-benzo[d]imidazol-1-yl)methyl)cyclohexyl)nicotinamide | Intermediate-160, Mesylate-4 | A1 |
| 421 | 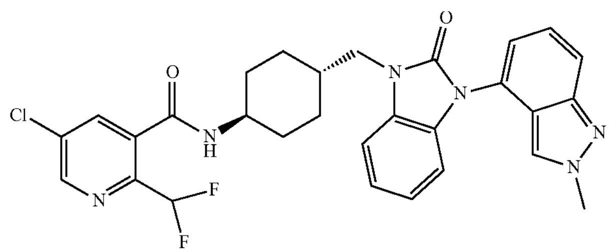 [SMILES: Cn1cc2c(-n3c(=O)n(C[C@H]4CC[C@H](NC(=O)c5cc(Cl)cnc5C(F)F)CC4)c4ccccc43)cccc2n1] | 5-chloro-2-(difluoromethyl)-N-((1r,4r)-4-((3-(2-methyl-2H-indazol-4-yl)-2-oxo-2,3-dihydro-1H-benzo[d]imidazol-1-yl)methyl)cyclohexyl)nicotinamide | Intermediate-184, Mesylate-4 | A1 |
| 422 | 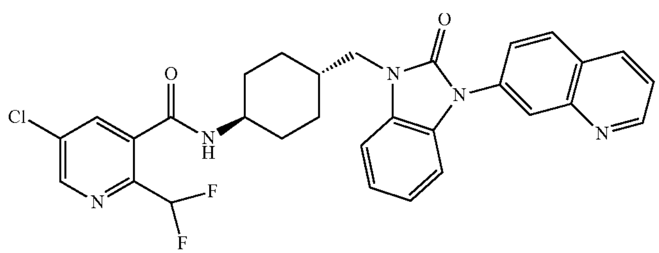 | 5-chloro-2-(difluoromethyl)-N-((1r,4r)-4-((2-oxo-3-(quinolin-7-yl)-2,3-dihydro-1H-benzo[d]imidazol-1-yl)methyl)cyclohexyl)nicotinamide | Intermediate-172, Mesylate-4 | A1 |
| 423 | 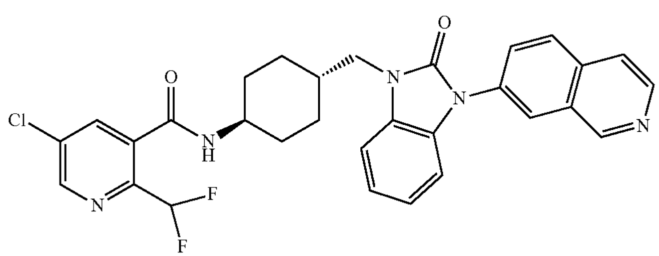 | 5-chloro-2-(difluoromethyl)-N-((1r,4r)-4-((3-(isoquinolin-7-yl)-2-oxo-2,3-dihydro-1H-benzo[d]imidazol-1-yl)methyl)cyclohexyl)nicotinamide | Intermediate-173, Mesylate-4 | A1 |

TABLE 2-continued

| Ex. | Structure | Name | Reactants | Method |
|---|---|---|---|---|
| 424 | 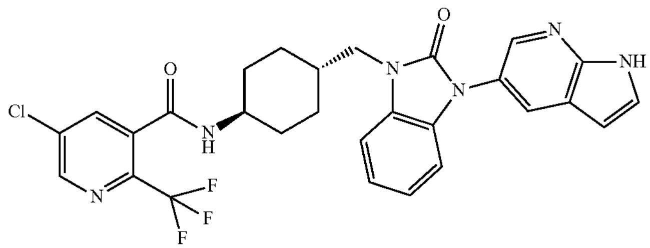 [SMILES: O=C(N[C@H]1CC[C@H](Cn2c(=O)n(-c3cnc4[nH]ccc4c3)c3ccccc32)CC1)c1cc(Cl)cnc1C(F)(F)F] | 5-chloro-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)-2-(trifluoromethyl)nicotinamide | Intermediate-185, Mesylate-3 | V |
| 425 | 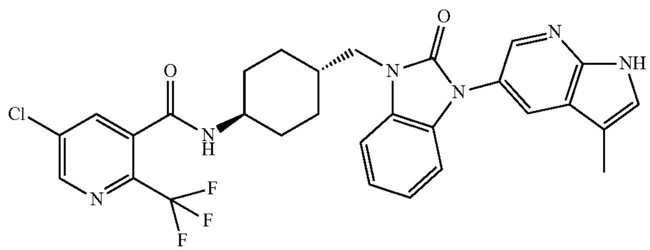 [SMILES: Cc1c[nH]c2ncc(-n3c(=O)n(C[C@H]4CC[C@H](NC(=O)c5cc(Cl)cnc5C(F)(F)F)CC4)c4ccccc43)cc12] | 5-chloro-N-((1r,4r)-4-((3-(3-methyl-1H-pyrrolo[2,3-b]pyridin-5-yl)-2-oxo-2,3-dihydro-1H-benzo[d]imidazol-1-yl)methyl)cyclohexyl)-2-(trifluoromethyl)nicotinamide | Intermediate-186, Mesylate-3 | V |
| 426 | 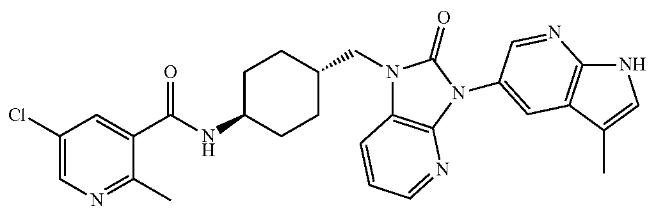 [SMILES: Cc1ncc(Cl)cc1C(=O)N[C@H]1CC[C@H](Cn2c(=O)n(-c3cnc4[nH]cc(C)c4c3)c3ncccc32)CC1] | 5-chloro-2-methyl-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)nicotinamide | Intermediate-187, Mesylate-1 | V |
| 427 | 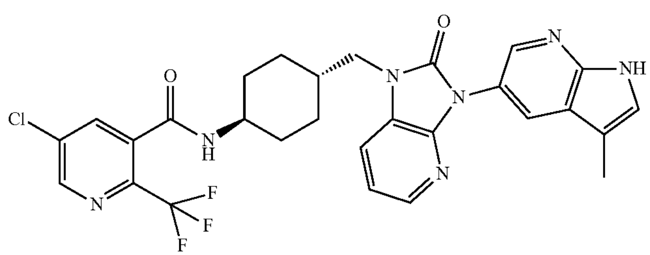 | 5-chloro-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)-2-(trifluoromethyl)nicotinamide | Intermediate-187, Mesylate-3 | V |

TABLE 2-continued

| Ex. | Structure | Name | Reactants | Method |
|---|---|---|---|---|
| 428 | 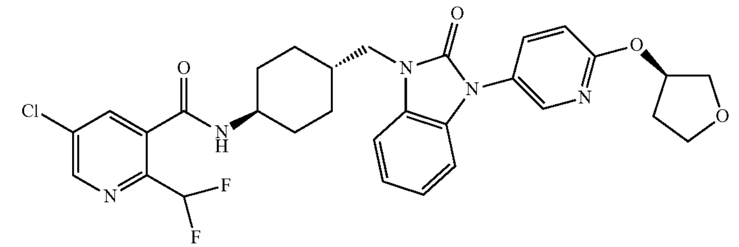 [SMILES: O=C(N[C@H]1CC[C@H](Cn2c(=O)n(-c3ccc(O[C@@H]4CCOC4)nc3)c3ccccc32)CC1)c1cc(Cl)cnc1C(F)F] | 5-chloro-2-(difluoromethyl)-N-((1R,4r)-4-((2-oxo-3-(6-(((R)-tetrahydrofuran-3-yl)oxy)pyridin-3-yl)-2,3-dihydro-1H-benzo[d]imidazol-1-yl)methyl)cyclohexyl)nicotinamide | Intermediate-188, Mesylate-4 | A1 |
| 429 | 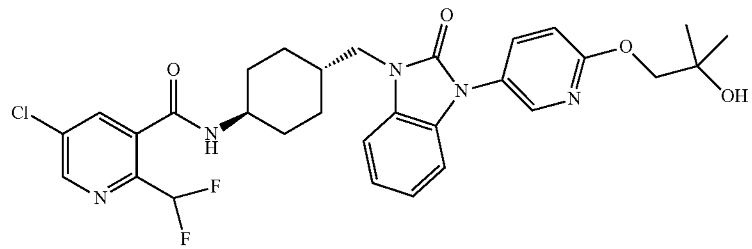 [SMILES: CC(C)(O)COc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)nicotinamide | Intermediate-189, Mesylate-4 | A1 |
| 430 | 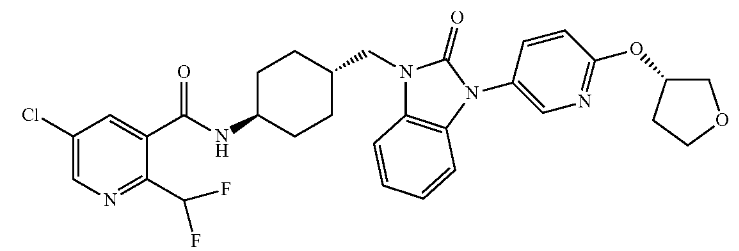 [SMILES: O=C(N[C@H]1CC[C@H](Cn2c(=O)n(-c3ccc(O[C@H]4CCOC4)nc3)c3ccccc32)CC1)c1cc(Cl)cnc1C(F)F] | 5-chloro-2-(difluoromethyl)-N-((1S,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)nicotinamide | Intermediate-190, Mesylate-4 | A1 |
| 431 | 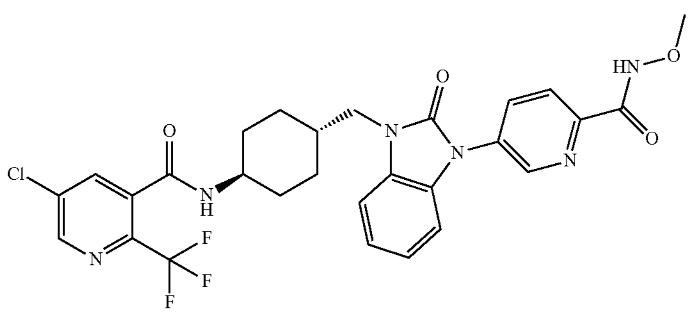 [SMILES: CONC(=O)c1ccc(-n2c(=O)n(C[C@H]3CC[C@H](NC(=O)c4cc(Cl)cnc4C(F)(F)F)CC3)c3ccccc32)cn1] | 5-(3-((1r,4r)-4-(5-chloro-2-(trifluoromethyl)nicotinamido)cyclohexyl)methyl)-2-oxo-2,3-dihydro-1H-benzo[d]imidazol-1-yl)-N-methoxypicolinamide | Intermediate-180, H₂N—O | Q |

TABLE 2-continued

| Ex. | Structure | Name | Reactants | Method |
|---|---|---|---|---|
| 432 | 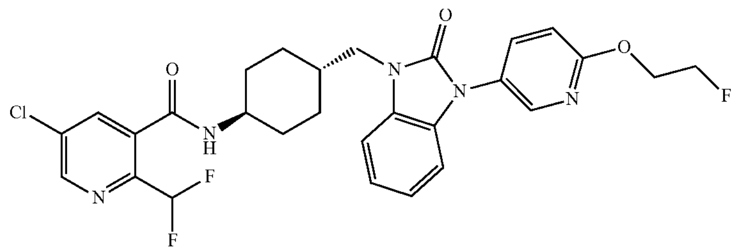 [SMILES: O=C(N[C@H]1CC[C@H](Cn2c(=O)n(-c3ccc(OCCF)nc3)c3ccccc32)CC1)c1cc(Cl)cnc1C(F)F] | 5-chloro-2-(difluoromethyl)-N-((1r,4r)-4-((3-(6-(2-fluoroethoxy)pyridin-3-yl)-2-oxo-2,3-dihydro-1H-benzo[d]imidazol-1-yl)methyl)cyclohexyl)nicotinamide | Intermediate-191, (2-fluoroethanol) | W |
| 433 | 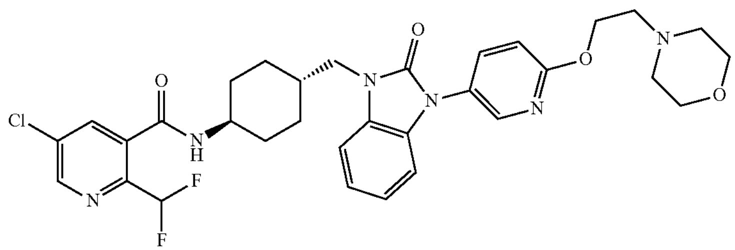 [SMILES: O=C(N[C@H]1CC[C@H](Cn2c(=O)n(-c3ccc(OCCN4CCOCC4)nc3)c3ccccc32)CC1)c1cc(Cl)cnc1C(F)F] | 5-chloro-2-(difluoromethyl)-N-((1r,4r)-4-((3-(6-(2-morpholinoethoxy)pyridin-3-yl)-2-oxo-2,3-dihydro-1H-benzo[d]imidazol-1-yl)methyl)cyclohexyl)nicotinamide | Intermediate-191, (2-morpholinoethanol) | W |
| 434 | 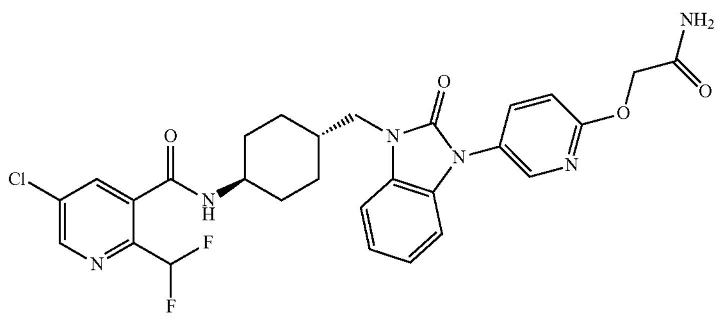 [SMILES: NC(=O)COc1ccc(-n2c(=O)n(C[C@H]3CC[C@H](NC(=O)c4cc(Cl)cnc4C(F)F)CC3)c3ccccc32)cn1] | N-((1r,4r)-4-((3-(6-(2-amino-2-oxoethoxy)pyridin-3-yl)-2-oxo-2,3-dihydro-1H-benzo[d]imidazol-1-yl)methyl)cyclohexyl)-5-chloro-2-(difluoromethyl)nicotinamide | Intermediate-191, (2-hydroxyacetamide) | W |
| 435 | 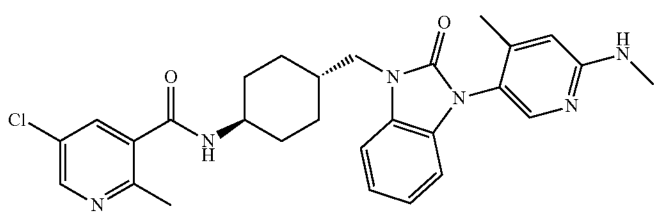 [SMILES: CNc1cc(C)c(-n2c(=O)n(C[C@H]3CC[C@H](NC(=O)c4cc(Cl)cnc4C)CC3)c3ccccc32)cn1] | 5-chloro-2-methyl-N-((1r,4r)-4-((3-(4-methyl-6-(methylamino)pyridin-3-yl)-2-oxo-2,3-dihydro-1H-benzo[d]imidazol-1-yl)methyl)cyclohexyl)nicotinamide | Intermediate-192, H₂N-methyl | J |

TABLE 2-continued

| Ex. | Structure | Name | Reactants | Method |
|---|---|---|---|---|
| 436 | 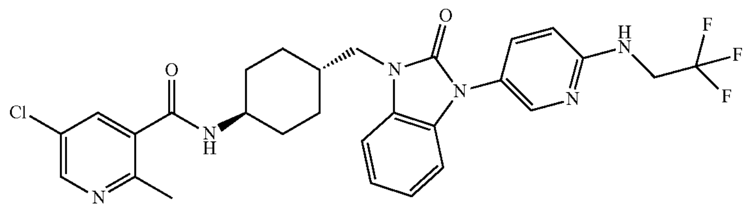 [SMILES: Cc1ncc(Cl)cc1C(=O)N[C@H]1CC[C@H](Cn2c(=O)n(-c3ccc(NCC(F)(F)F)nc3)c3ccccc32)CC1] | 5-chloro-2-methyl-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)nicotinamide | Intermediate-193, Mesylate-1 | A1 |
| 437 | 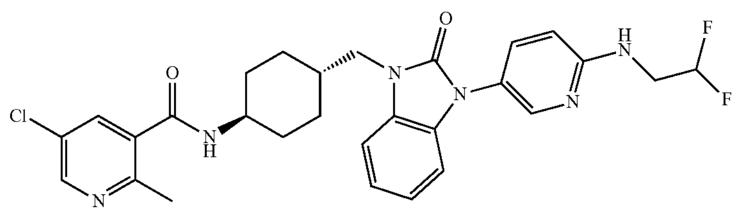 [SMILES: Cc1ncc(Cl)cc1C(=O)N[C@H]1CC[C@H](Cn2c(=O)n(-c3ccc(NCC(F)F)nc3)c3ccccc32)CC1] | 5-chloro-N-((1r,4r)-4-((3-(6-((2,2-difluoroethyl)amino)pyridin-3-yl)-2-oxo-2,3-dihydro-1H-benzo[d]imidazol-1-yl)methyl)cyclohexyl)-2-methylnicotinamide | Intermediate-194, Mesylate-1 | A1 |
| 438 | 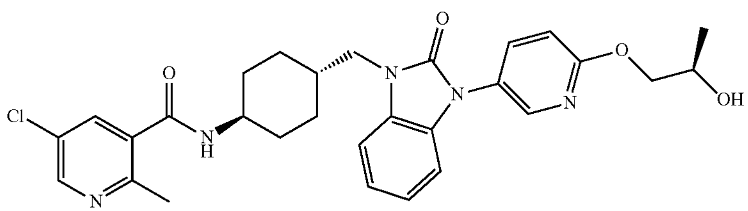 [SMILES: Cc1ncc(Cl)cc1C(=O)N[C@H]1CC[C@H](Cn2c(=O)n(-c3ccc(OC[C@@H](C)O)nc3)c3ccccc32)CC1] | 5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-methylnicotinamide | see Example synthesis part | |
| 439 | 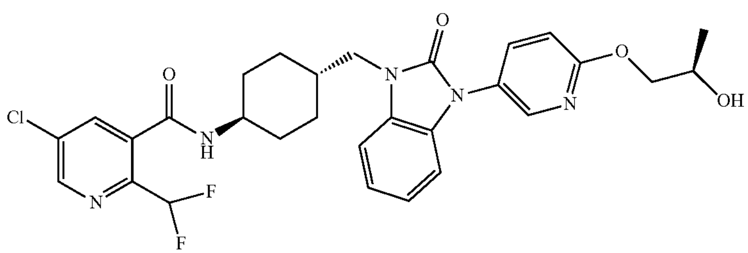 [SMILES: C[C@@H](O)COc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 440 | 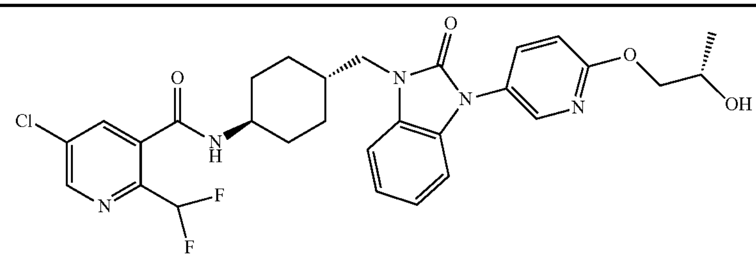 | 5-chloro-2-(difluoromethyl)-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)nicotinamide | see Example synthesis part | |
| 441 | 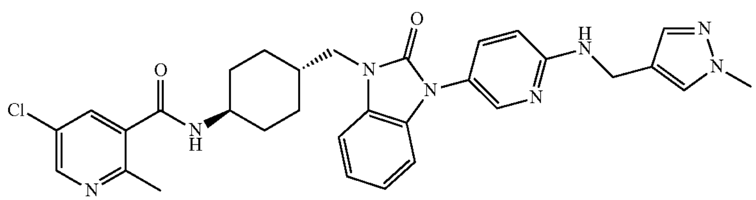 [SMILES: Cc1ncc(Cl)cc1C(=O)N[C@H]1CC[C@H](Cn2c(=O)n(-c3ccc(NCc4cnn(C)c4)nc3)c3ccccc32)CC1] | 5-chloro-2-methyl-N-((1r,4r)-4-((3-(6-(((1-methyl-1H-pyrazol-4-yl)methyl)amino)pyridin-3-yl)-2-oxo-2,3-dihydro-1H-benzo[d]imidazol-1-yl)methyl)cyclohexyl)nicotinamide | see Example synthesis part | |
| 442 | 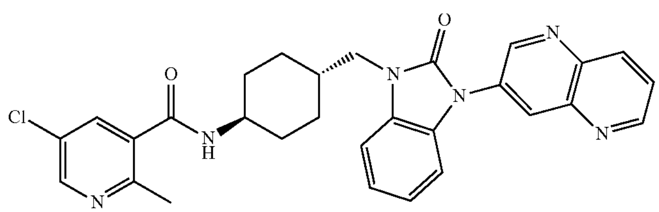 [SMILES: Cc1ncc(Cl)cc1C(=O)N[C@H]1CC[C@H](Cn2c(=O)n(-c3cnc4cccnc4c3)c3ccccc32)CC1] | N-((1r,4r)-4-(3-(1,5-naphthyridin-3-yl)-2-oxo-2,3-dihydro-1H-benzo[d]imidazol-1-yl)methyl)cyclohexyl)-5-chloro-2-methylnicotinamide | Intermediate-195, Mesylate-1 | A1 |
| 443 | 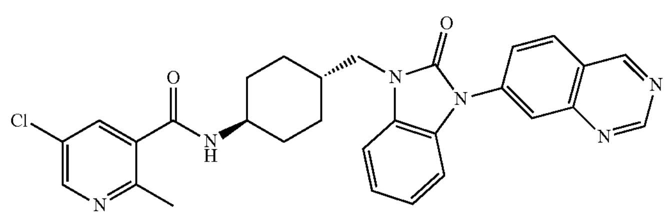 [SMILES: Cc1ncc(Cl)cc1C(=O)N[C@H]1CC[C@H](Cn2c(=O)n(-c3ccc4cncnc4c3)c3ccccc32)CC1] | 5-chloro-2-methyl-N-((1r,4r)-4-((2-oxo-3-(quinazolin-7-yl)-2,3-dihydro-1H-benzo[d]imidazol-1-yl)methyl)cyclohexyl)nicotinamide | Intermediate-196, Mesylate-1 | A1 |

TABLE 2-continued

| Ex. | Structure | Name | Reactants | Method |
|---|---|---|---|---|
| 444 | 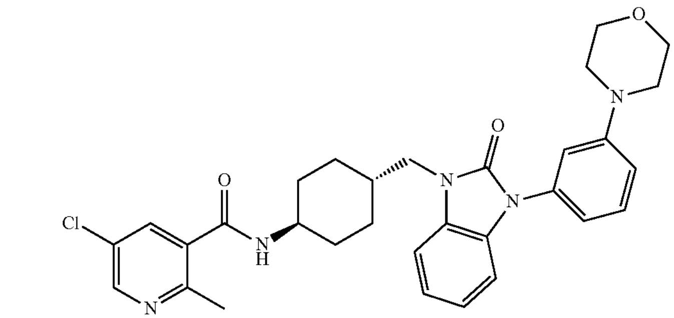 [SMILES: Cc1ncc(Cl)cc1C(=O)N[C@H]1CC[C@H](Cn2c(=O)n(-c3cccc(N4CCOCC4)c3)c3ccccc32)CC1] | 5-chloro-2-methyl-N-((1r,4r)-4-((3-(3-morpholinophenyl)-2-oxo-2,3-dihydro-1H-benzo[d]imidazol-1-yl)methyl)cyclohexyl)nicotinamide | R = 3-morpholinophenyl bromide; Step-2 of Ex 9 | R |
| 445 | 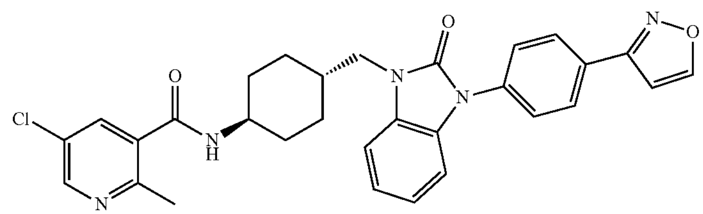 [SMILES: Cc1ncc(Cl)cc1C(=O)N[C@H]1CC[C@H](Cn2c(=O)n(-c3ccc(-c4ccon4)cc3)c3ccccc32)CC1] | 5-chloro-N-((1r,4r)-4-((3-(4-(isoxazol-3-yl)phenyl)-2-oxo-2,3-dihydro-1H-benzo[d]imidazol-1-yl)methyl)cyclohexyl)-2-methylnicotinamide | R = 4-(isoxazol-3-yl)phenyl bromide; Step-2 of Ex 9 | R |
| 446 | 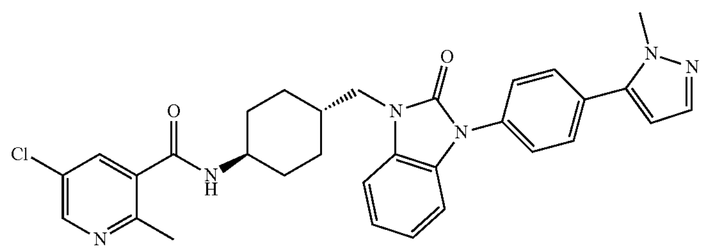 [SMILES: Cc1ncc(Cl)cc1C(=O)N[C@H]1CC[C@H](Cn2c(=O)n(-c3ccc(-c4ccnn4C)cc3)c3ccccc32)CC1] | 5-chloro-N-((1r,4r)-4-((3-(4-(1-methyl-1H-pyrazol-5-yl)phenyl)-2-oxo-2,3-dihydro-1H-benzo[d]imidazol-1-yl)methyl)cyclohexyl)-2-methylnicotinamide | R = 4-(1-methyl-1H-pyrazol-5-yl)phenyl bromide; Step-2 of Ex 9 | R |
| 447 | 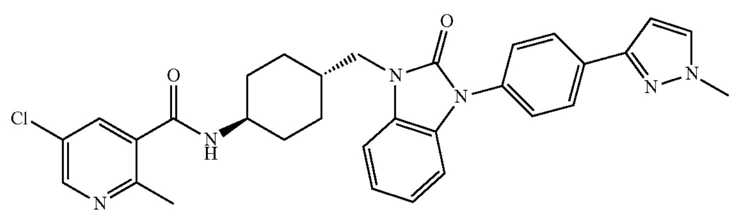 [SMILES: Cc1ncc(Cl)cc1C(=O)N[C@H]1CC[C@H](Cn2c(=O)n(-c3ccc(-c4ccn(C)n4)cc3)c3ccccc32)CC1] | 5-chloro-N-((1r,4r)-4-((3-(4-(1-methyl-1H-pyrazol-3-yl)phenyl)-2-oxo-2,3-dihydro-1H-benzo[d]imidazol-1-yl)methyl)cyclohexyl)-2-methylnicotinamide | R = 4-(1-methyl-1H-pyrazol-3-yl)phenyl bromide; Step-2 of Ex 9 | R |

TABLE 2-continued

| Ex. | Structure | Name | Reactants | Method |
|---|---|---|---|---|
| 448 | 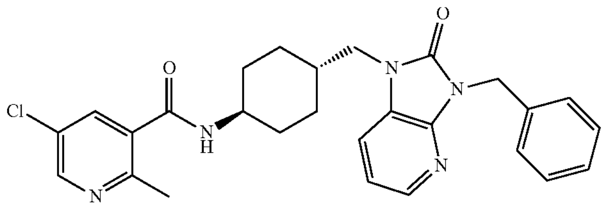 | N-((1r,4r)-4-((3-benzyl-2-oxo-2,3-dihydro-1H-imidazo[4,5-b]pyridin-1-yl)methyl)cyclohexyl)-5-chloro-2-methylnicotinamide | | A1 |
| 449 | 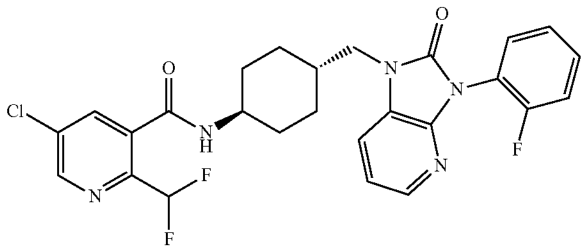 [SMILES: O=C(N[C@H]1CC[C@H](Cn2c(=O)n(-c3ccccc3F)c3ncccc32)CC1)c1cc(Cl)cnc1C(F)F] | 5-chloro-2-(difluoromethyl)-N-((1r,4r)-4-((3-(2-fluorophenyl)-2-oxo-2,3-dihydro-1H-imidazo[4,5-b]pyridin-1-yl)methyl)cyclohexyl)nicotinamide | Mesylate-1 Intermediate-197, Mesylate-4 | A1 |
| 450 | 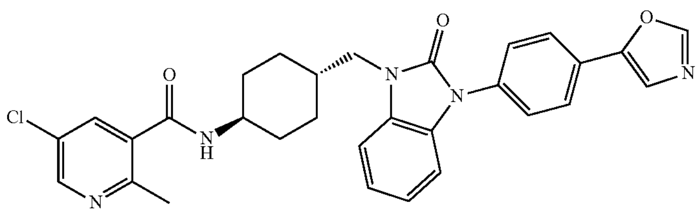 [SMILES: Cc1ncc(Cl)cc1C(=O)N[C@H]1CC[C@H](Cn2c(=O)n(-c3ccc(-c4cnco4)cc3)c3ccccc32)CC1] | 5-chloro-2-methyl-N-((1r,4r)-4-((3-(4-(oxazol-5-yl)phenyl)-2-oxo-2,3-dihydro-1H-benzo[d]imidazol-1-yl)methyl)cyclohexyl)nicotinamide | Step-2 of Ex 9 | R |
| 451 | 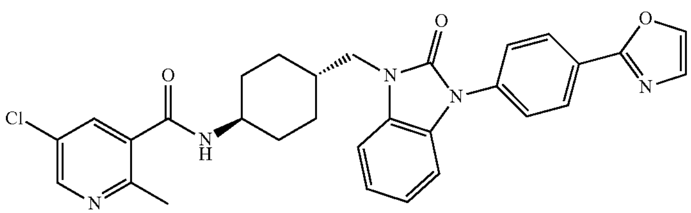 [SMILES: Cc1ncc(Cl)cc1C(=O)N[C@H]1CC[C@H](Cn2c(=O)n(-c3ccc(-c4ncco4)cc3)c3ccccc32)CC1] | 5-chloro-2-methyl-N-((1r,4r)-4-((3-(4-(oxazol-2-yl)phenyl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 452 | 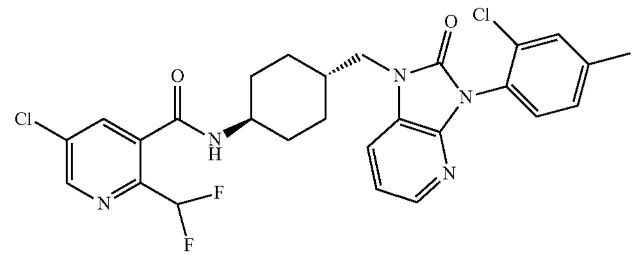 [SMILES: Cc1ccc(-n2c(=O)n(C[C@H]3CC[C@H](NC(=O)c4cc(Cl)cnc4C(F)F)CC3)c3cccnc32)c(Cl)c1] | 5-chloro-N-((1r,4r)-4-((3-(2-chloro-4-methylphenyl)-2-oxo-2,3-dihydro-1H-imidazo[4,5-b]pyridin-1-yl)methyl)cyclohexyl)-2-(difluoromethyl)nicotinamide | Intermediate-198, Mesylate-4 | A1 |
| 453 | 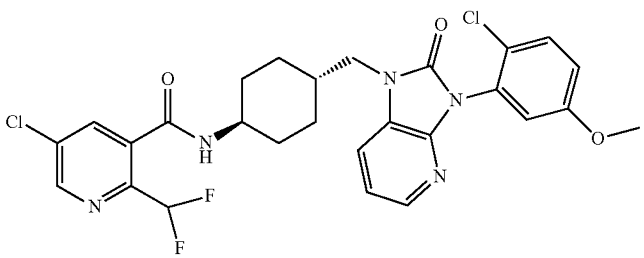 [SMILES: COc1ccc(Cl)c(-n2c(=O)n(C[C@H]3CC[C@H](NC(=O)c4cc(Cl)cnc4C(F)F)CC3)c3cccnc32)c1] | 5-chloro-N-((1r,4r)-4-((3-(2-chloro-5-methoxyphenyl)-2-oxo-2,3-dihydro-1H-imidazo[4,5-b]pyridin-1-yl)methyl)cyclohexyl)-2-(difluoromethyl)nicotinamide | Intermediate-199, Mesylate-4 | A1 |
| 454 | 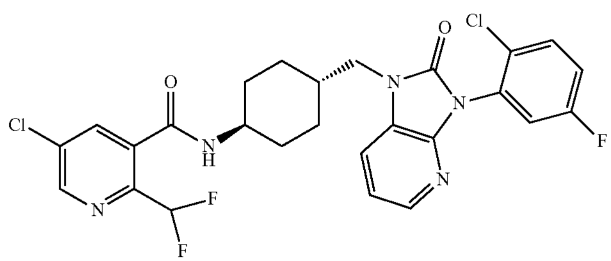 [SMILES: O=C(N[C@H]1CC[C@H](Cn2c(=O)n(-c3cc(F)ccc3Cl)c3ncccc32)CC1)c1cc(Cl)cnc1C(F)F] | 5-chloro-N-((1r,4r)-4-((3-(2-chloro-5-fluorophenyl)-2-oxo-2,3-dihydro-1H-imidazo[4,5-b]pyridin-1-yl)methyl)cyclohexyl)-2-(difluoromethyl)nicotinamide | Intermediate-200, Mesylate-4 | A1 |
| 455 | 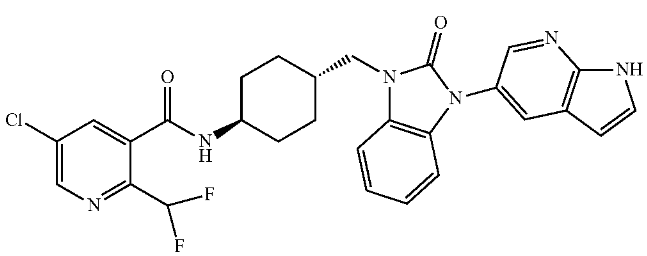 | 5-chloro-2-(difluoromethyl)-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide | Intermediate-185, Mesylate-4 | V |

TABLE 2-continued

| Ex. | Structure | Name | Reactants | Method |
|---|---|---|---|---|
| 456 | 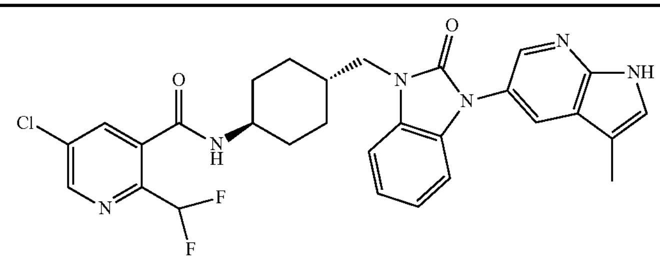 | 5-chloro-2-(difluoromethyl)-N-((1r,4r)-4-(3-(3-methyl-1H-pyrrolo[2,3-b]pyridin-5-yl)-2-oxo-2,3-dihydro-1H-benzo[d]imidazol-1-yl)methyl)cyclohexyl)nicotinamide | Intermediate-186, Mesylate-4 | V |
| 457 | 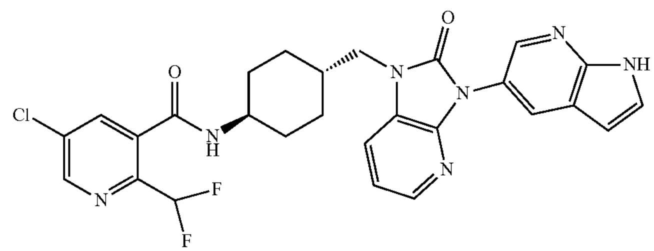 [SMILES: O=C(N[C@H]1CC[C@H](Cn2c(=O)n(-c3cnc4[nH]ccc4c3)c3ncccc32)CC1)c1cc(Cl)cnc1C(F)F] | 5-chloro-2-(difluoromethyl)-N-((1r,4r)-4-((2-oxo-3-(1H-pyrrolo[2,3-b]pyridin-5-yl)-2,3-dihydro-1H-imidazo[4,5-b]pyridin-1-yl)methyl)cyclohexyl)nicotinamide | Intermediate-201, Mesylate-4 | V |
| 458 | 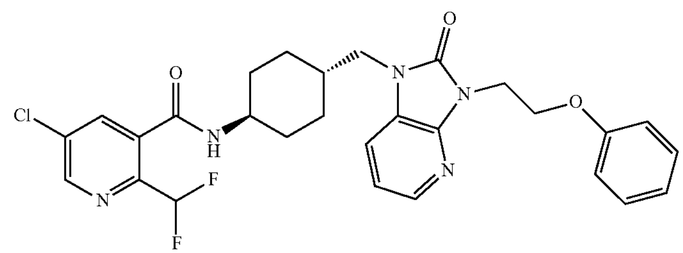 [SMILES: O=C(N[C@H]1CC[C@H](Cn2c(=O)n(CCOc3ccccc3)c3ncccc32)CC1)c1cc(Cl)cnc1C(F)F] | 5-chloro-2-(difluoromethyl)-N-((1r,4r)-4-((2-oxo-3-(2-phenoxyethyl)-2,3-dihydro-1H-imidazo[4,5-b]pyridin-1-yl)methyl)cyclohexyl)nicotinamide | Intermediate-202, Mesylate-4 | A1 |
| 459 | 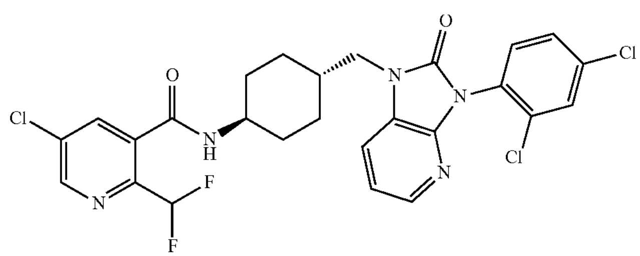 [SMILES: O=C(N[C@H]1CC[C@H](Cn2c(=O)n(-c3ccc(Cl)cc3Cl)c3ncccc32)CC1)c1cc(Cl)cnc1C(F)F] | 5-chloro-N-((1r,4r)-4-((3-(2,4-dichlorophenyl)-2-oxo-2,3-dihydro-1H-imidazo[4,5-b]pyridin-1-yl)methyl)cyclohexyl)-2-(difluoromethyl)nicotinamide | Intermediate-181, Mesylate-4 | A1 |

TABLE 2-continued

| Ex. | Structure | Name | Reactants | Method |
|---|---|---|---|---|
| 460 | 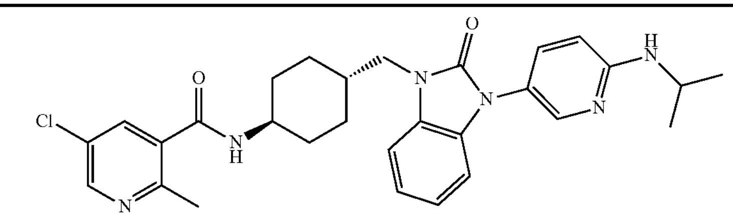 | 5-chloro-N-((1r,4r)-4-((3-(6-(isopropyl)amino)pyridin-3-yl)-2-oxo-2,3-dihydro-1H-benzo[d]imidazol-1-yl)methyl)cyclohexyl)-2-methylnicotinamide | Intermediate-203, Mesylate-1 | A1 |
| 461 | 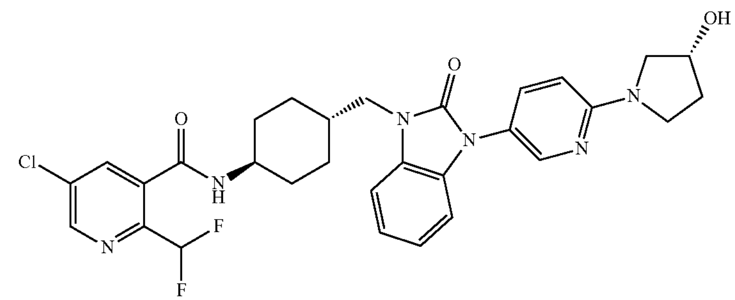 [SMILES: O=C(N[C@H]1CC[C@H](Cn2c(=O)n(-c3ccc(N4CC[C@@H](O)C4)nc3)c3ccccc32)CC1)c1cc(Cl)cnc1C(F)F] | 5-chloro-2-(difluoromethyl)-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)nicotinamide | Intermediate-50, Mesylate-4 | A1 |
| 462 | 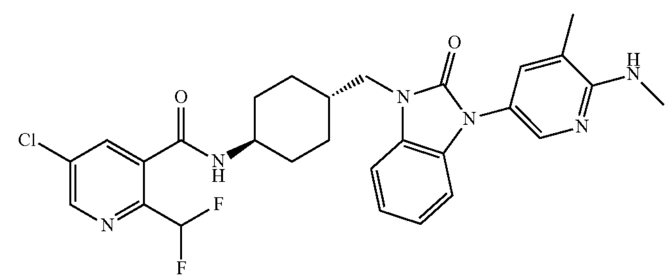 [SMILES: CNc1ncc(-n2c(=O)n(C[C@H]3CC[C@H](NC(=O)c4cc(Cl)cnc4C(F)F)CC3)c3ccccc32)cc1C] | 5-chloro-2-(difluoromethyl)-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide | Intermediate-69, Mesylate-4 | A1 |
| 463 | 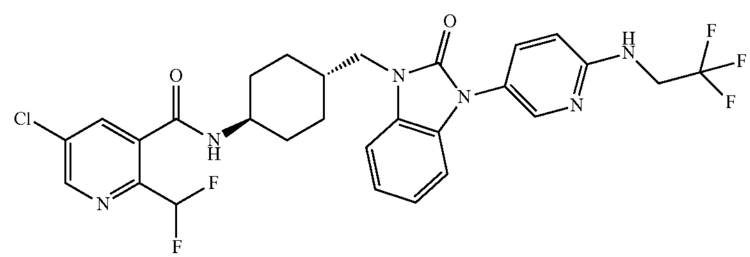 [SMILES: O=C(N[C@H]1CC[C@H](Cn2c(=O)n(-c3ccc(NCC(F)(F)F)nc3)c3ccccc32)CC1)c1cc(Cl)cnc1C(F)F] | 5-chloro-2-(difluoromethyl)-N-((1r,4r)-4-(2-oxo-3-(6-((2,2,2-trifluoroethyl)amino)pyridin-3-yl)-2,3-dihydro-1H-benzo[d]imidazol-1-yl)methyl)cyclohexyl)nicotinamide | Intermediate-193, Mesylate-4 | A1 |

TABLE 2-continued

| Ex. | Structure | Name | Reactants | Method |
|---|---|---|---|---|
| 464 | 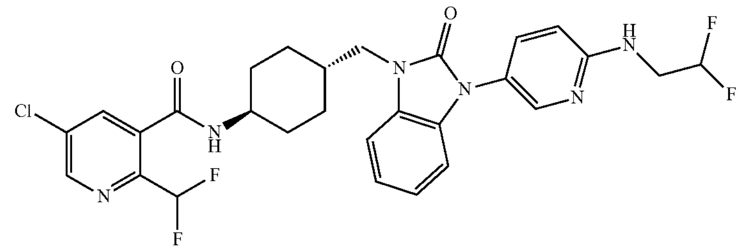 [SMILES: O=C(N[C@H]1CC[C@H](Cn2c(=O)n(-c3ccc(NCC(F)F)nc3)c3ccccc32)CC1)c1cc(Cl)cnc1C(F)F] | 5-chloro-N-((1r,4r)-4-((3-(6-(((2,2-difluoroethyl)amino)pyridin-3-yl)-2-oxo-2,3-dihydro-1H-benzo[d]imidazol-1-yl)methyl)cyclohexyl)-2-(difluoromethyl)nicotinamide | Intermediate-194, Mesylate-4 | A1 |
| 465 | 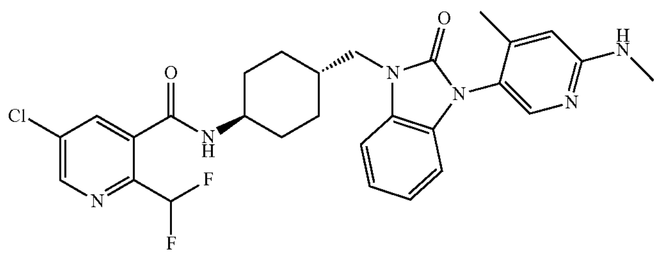 [SMILES: CNc1cc(C)c(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(4-methyl-6-(methylamino)pyridin-3-yl)-2-oxo-2,3-dihydro-1H-benzo[d]imidazol-1-yl)methyl)cyclohexyl)nicotinamide | Intermediate-204, H$_2$N— | J |
| 466 | 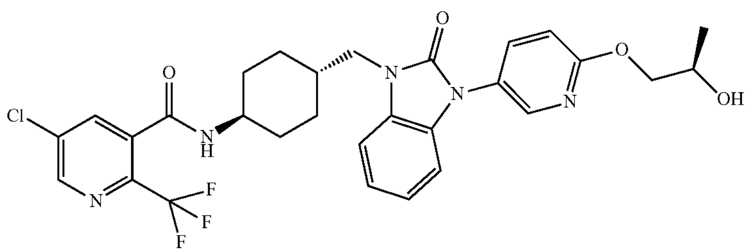 [SMILES: C[C@@H](O)COc1ccc(-n2c(=O)n(C[C@H]3CC[C@H](NC(=O)c4cc(Cl)cnc4C(F)(F)F)CC3)c3ccccc32)cn1] | 5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide | see Example synthesis part | |
| 467 | 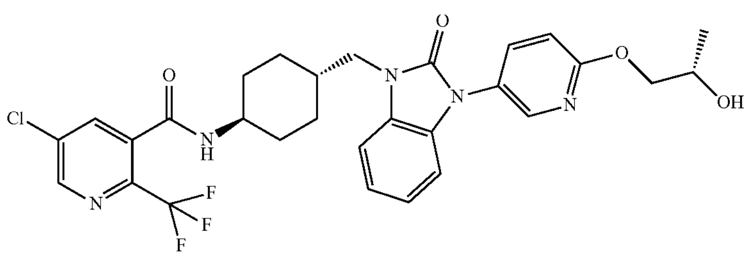 [SMILES: C[C@H](O)COc1ccc(-n2c(=O)n(C[C@H]3CC[C@H](NC(=O)c4cc(Cl)cnc4C(F)(F)F)CC3)c3ccccc32)cn1] | 5-chloro-N-((1S,4r)-4-((3-(6-(((S)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide | see Example synthesis part | |

TABLE 2-continued

| Ex. | Structure | Name | Reactants | Method |
|---|---|---|---|---|
| 468 | 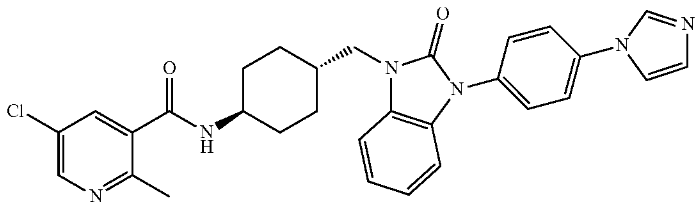 [SMILES: Cc1ncc(Cl)cc1C(=O)N[C@H]1CC[C@H](Cn2c(=O)n(-c3ccc(-n4ccnc4)cc3)c3ccccc32)CC1] | N-((1r,4r)-4-((3-(4-(1H-imidazol-1-yl)phenyl)-2-oxo-2,3-dihydro-1H-benzo[d]imidazol-1-yl)methyl)cyclohexyl)-5-chloro-2-methylnicotinamide | Step-2 of Ex 9 | R |
| 469 | 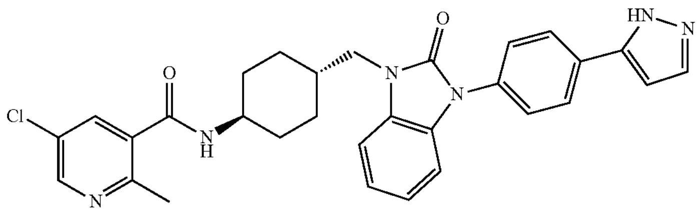 [SMILES: Cc1ncc(Cl)cc1C(=O)N[C@H]1CC[C@H](Cn2c(=O)n(-c3ccc(-c4ccn[nH]4)cc3)c3ccccc32)CC1] | N-((1r,4r)-4-((3-(4-(1H-pyrazol-5-yl)phenyl)-2-oxo-2,3-dihydro-1H-benzo[d]imidazol-1-yl)methyl)cyclohexyl)-5-chloro-2-methylnicotinamide | Step-2 of Ex 9 | R |
| 470 | 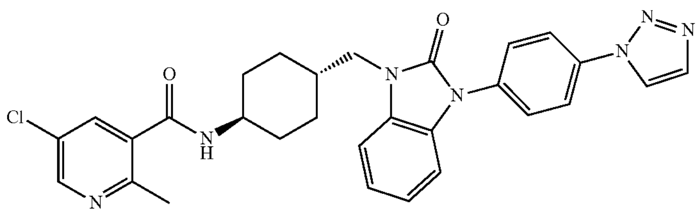 | N-((1r,4r)-4-((3-(4-(1H-1,2,3-triazol-1-yl)phenyl)-2-oxo-2,3-dihydro-1H-benzo[d]imidazol-1-yl)methyl)cyclohexyl)-5-chloro-2-methylnicotinamide | Step-2 of Ex 9 | R |
| 471 | 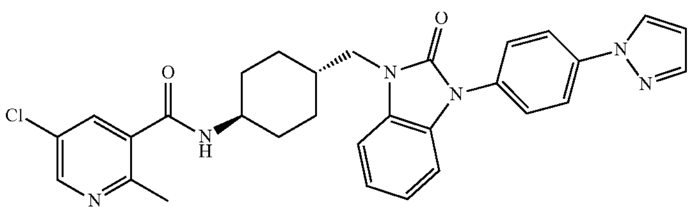 [SMILES: Cc1ncc(Cl)cc1C(=O)N[C@H]1CC[C@H](Cn2c(=O)n(-c3ccc(-n4cccn4)cc3)c3ccccc32)CC1] | N-((1r,4r)-4-((3-(4-(1H-pyrazol-1-yl)phenyl)-2-oxo-2,3-dihydro-1H-benzo[d]imidazol-1-yl)methyl)cyclohexyl)-5-chloro-2-methylnicotinamide | Step-2 of Ex 9 | R |

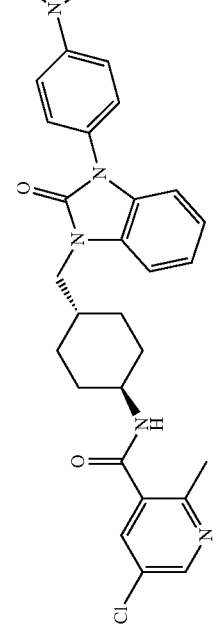

TABLE 2-continued

| Ex. | Structure | Name | Reactants | Method |
|---|---|---|---|---|
| 472 | 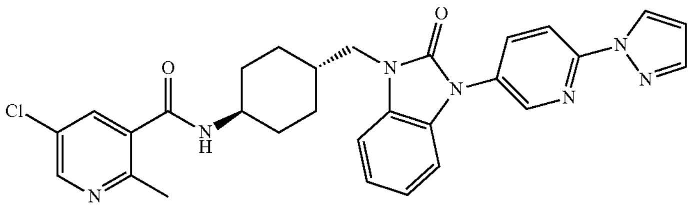 [SMILES: Cc1ncc(Cl)cc1C(=O)N[C@H]1CC[C@H](Cn2c(=O)n(-c3ccc(-n4cccn4)nc3)c3ccccc32)CC1] | N-((1r,4r)-4-((3-(6-(1H-imidazol-1-yl)pyridin-3-yl)-2-oxo-2,3-dihydro-1H-benzo[d]imidazol-1-yl)methyl)cyclohexyl)-5-chloro-2-methylnicotinamide | Step-2 of Ex 9 | R |
| 473 | 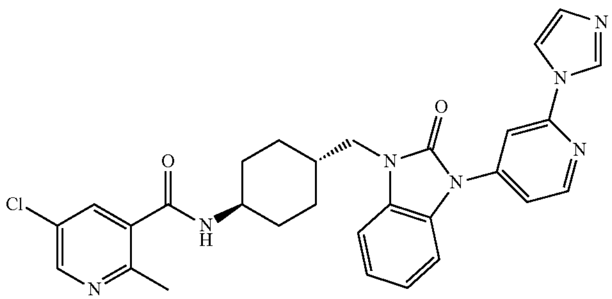 [SMILES: Cc1ncc(Cl)cc1C(=O)N[C@H]1CC[C@H](Cn2c(=O)n(-c3ccnc(-n4ccnc4)c3)c3ccccc32)CC1] | N-((1r,4r)-4-((3-(2-(1H-imidazol-1-yl)pyridin-4-yl)-2-oxo-2,3-dihydro-1H-benzo[d]imidazol-1-yl)methyl)cyclohexyl)-5-chloro-2-methylnicotinamide | Step-2 of Ex 9 | R |
| 474 | 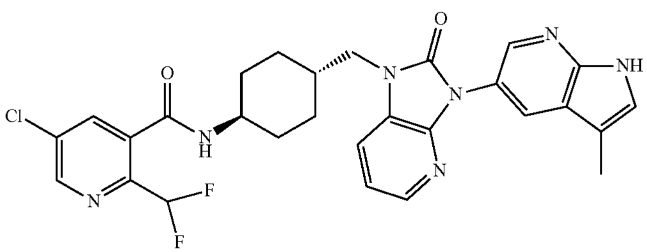 [SMILES: Cc1c[nH]c2ncc(-n3c(=O)n(C[C@H]4CC[C@H](NC(=O)c5cc(Cl)cnc5C(F)F)CC4)c4cccnc43)cc12] | 5-chloro-2-(difluoromethyl)-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)nicotinamide | Intermediate-187, Mesylate-4 | V |

| Ex. | Structure | Name | Reactants | Method |
|---|---|---|---|---|
| 475 | 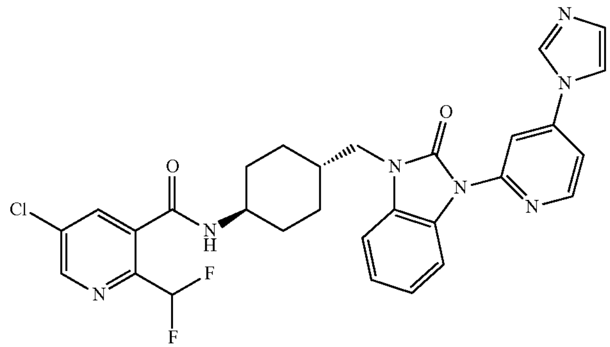 [SMILES: O=C(N[C@H]1CC[C@H](Cn2c(=O)n(-c3cc(-n4ccnc4)ccn3)c3ccccc32)CC1)c1cc(Cl)cnc1C(F)F] | N-((1r,4r)-4-((3-(4-(1H-imidazol-1-yl)pyridin-2-yl)-2-oxo-2,3-dihydro-1H-benzo[d]imidazol-1-yl)methyl)cyclohexyl)-5-chloro-2-(difluoromethyl)nicotinamide | 3-(1H-imidazol-1-yl)chlorobenzene; Intermediate-165 | X |
| 476 | 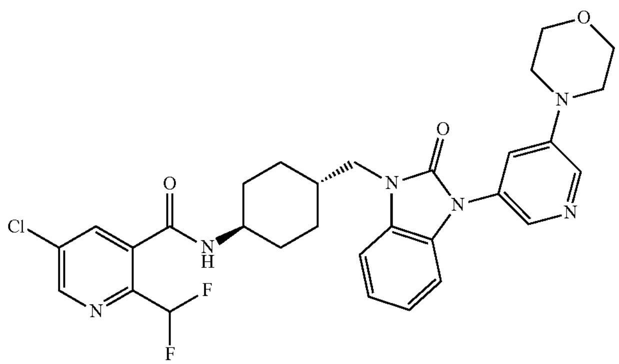 [SMILES: O=C(N[C@H]1CC[C@H](Cn2c(=O)n(-c3cncc(N4CCOCC4)c3)c3ccccc32)CC1)c1cc(Cl)cnc1C(F)F] | 5-chloro-2-(difluoromethyl)-N-((1r,4r)-4-((3-(5-morpholino-pyridin-3-yl)-2-oxo-2,3-dihydro-1H-benzo[d]imidazol-1-yl)methyl)cyclohexyl)nicotinamide | 3-bromo-5-morpholinopyridine; Intermediate-165 | R |
| 477 | 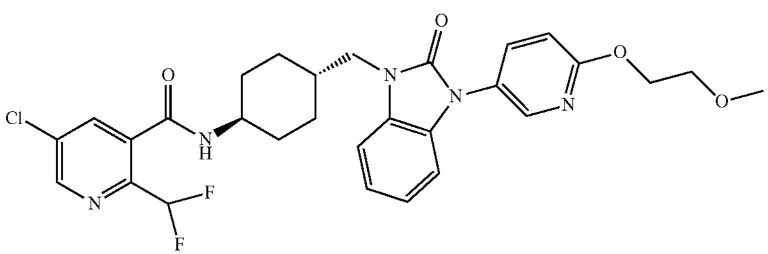 [SMILES: COCCOc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(2-methoxyethoxy)pyridin-3-yl)-2-oxo-2,3-dihydro-1H-benzo[d]imidazol-1-yl)methyl)cyclohexyl)nicotinamide | 2-methoxyethanol; Intermediate-191 | N |

TABLE 2-continued

| Ex. | Structure | Name | Reactants | Method |
|---|---|---|---|---|
| 478 | 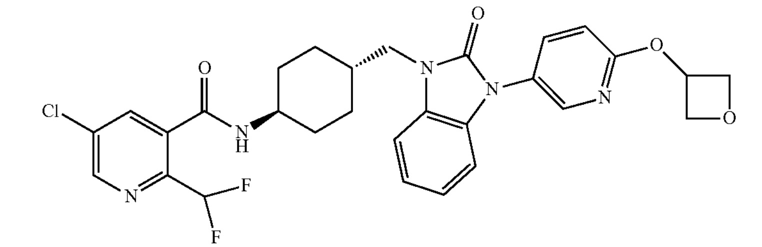 [SMILES: O=C(N[C@H]1CC[C@H](Cn2c(=O)n(-c3ccc(OC4COC4)nc3)c3ccccc32)CC1)c1cc(Cl)cnc1C(F)F] | 5-chloro-2-(difluoromethyl)-N-((1r,4r)-4-((3-(6-(oxetan-3-yloxy)pyridin-3-yl)-2-oxo-2,3-dihydro-1H-benzo[d]imidazol-1-yl)methyl)cyclohexyl)nicotinamide | Intermediate-191 | N |
| 479 | 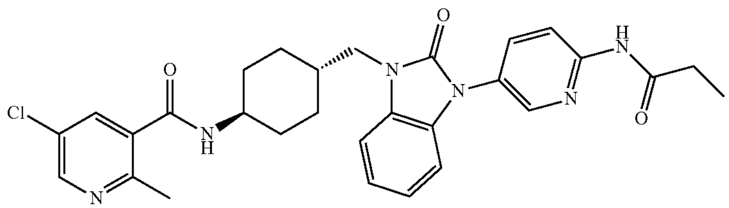 [SMILES: CCC(=O)Nc1ccc(-n2c(=O)n(C[C@H]3CC[C@H](NC(=O)c4cc(Cl)cnc4C)CC3)c3ccccc32)cn1] | 5-chloro-2-methyl-N-((1r,4r)-4-((2-oxo-3-(6-propionamidopyridin-3-yl)-2,3-dihydro-1H-benzo[d]imidazol-1-yl)methyl)cyclohexyl)nicotinamide | see Example synthesis part | |
| 480 | 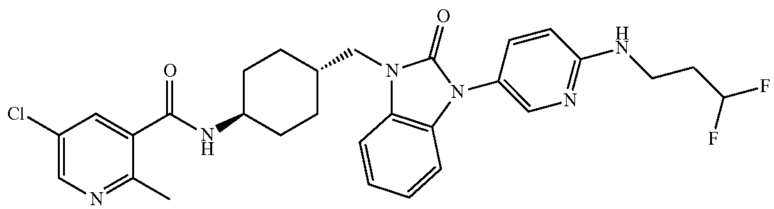 [SMILES: Cc1ncc(Cl)cc1C(=O)N[C@H]1CC[C@H](Cn2c(=O)n(-c3ccc(NCCC(F)F)nc3)c3ccccc32)CC1] | 5-chloro-N-((1r,4r)-4-((3-(6-((3,3-difluoropropyl)amino)pyridin-3-yl)-2-oxo-2,3-dihydro-1H-benzo[d]imidazol-1-yl)methyl)cyclohexyl)-2-methylnicotinamide | Intermediate-205, Mesylate-1 | A1 |
| 481 | 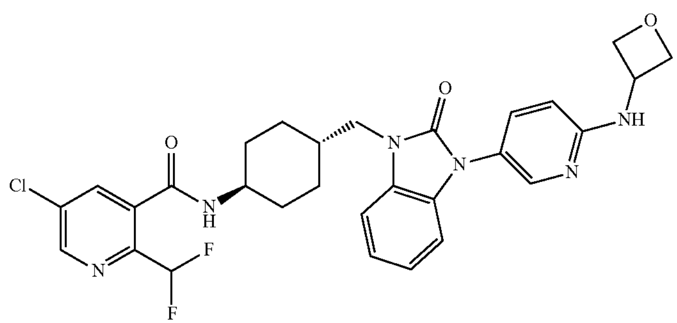 [SMILES: O=C(N[C@H]1CC[C@H](Cn2c(=O)n(-c3ccc(NC4COC4)nc3)c3ccccc32)CC1)c1cc(Cl)cnc1C(F)F] | 5-chloro-2-(difluoromethyl)-N-((1r,4r)-4-((3-(6-(oxetan-3-ylamino)pyridin-3-yl)-2-oxo-2,3-dihydro-1H-benzo[d]imidazol-1-yl)methyl)cyclohexyl)nicotinamide | Intermediate-78, Mesylate-4 | A1 |

TABLE 2-continued

| Ex. | Structure | Name | Reactants | Method |
|---|---|---|---|---|
| 482 | 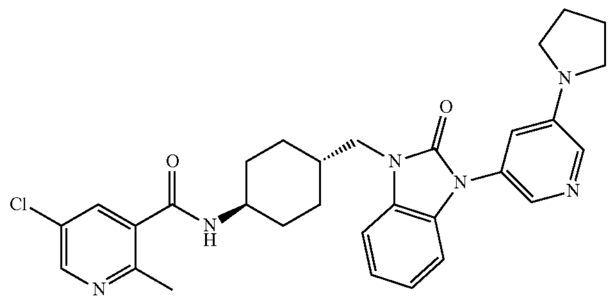 [SMILES: Cc1ncc(Cl)cc1C(=O)N[C@H]1CC[C@H](Cn2c(=O)n(-c3cncc(N4CCCC4)c3)c3ccccc32)CC1] | 5-chloro-2-methyl-N-((1r,4r)-4-((2-oxo-3-(5-(pyrrolidin-1-yl)pyridin-3-yl)-2,3-dihydro-1H-benzo[d]imidazol-1-yl)methyl)cyclohexyl)nicotinamide | Step-2 of Ex 9 | R |
| 483 | 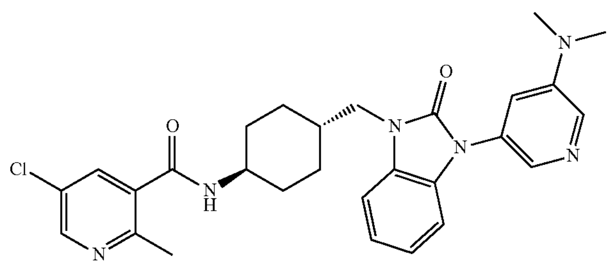 [SMILES: Cc1ncc(Cl)cc1C(=O)N[C@H]1CC[C@H](Cn2c(=O)n(-c3cncc(N(C)C)c3)c3ccccc32)CC1] | 5-chloro-N-((1r,4r)-4-((3-(5-(dimethylamino)pyridin-3-yl)-2-oxo-2,3-dihydro-1H-benzo[d]imidazol-1-yl)methyl)cyclohexyl)-2-methylnicotinamide | Step-2 of Ex 9 | R |
| 484 | 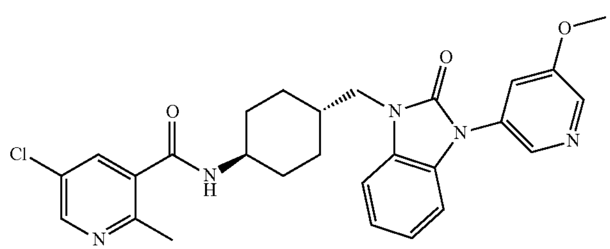 [SMILES: COc1cncc(-n2c(=O)n(C[C@H]3CC[C@H](NC(=O)c4cc(Cl)cnc4C)CC3)c3ccccc32)c1] | 5-chloro-N-((1r,4r)-4-((3-(5-methoxypyridin-3-yl)-2-oxo-2,3-dihydro-1H-benzo[d]imidazol-1-yl)methyl)cyclohexyl)-2-methylnicotinamide | Step-2 of Ex 9 | R |

TABLE 2-continued

| Ex. | Structure | Name | Reactants | Method |
|---|---|---|---|---|
| 485 | 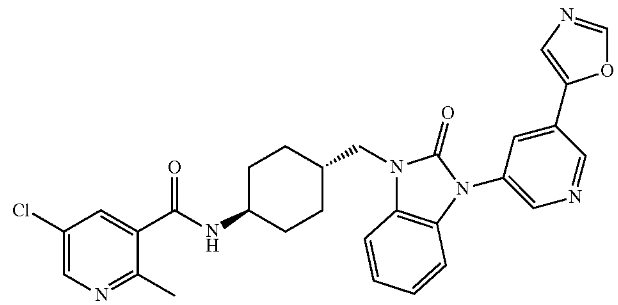 | 5-chloro-2-methyl-N-((1r,4r)-4-((3-(5-(oxazol-5-yl)pyridin-3-yl)-2-oxo-2,3-dihydro-1H-benzo[d]imidazol-1-yl)methyl)cyclohexyl)nicotinamide | Step-2 of Ex 9 | R |
| 486 | 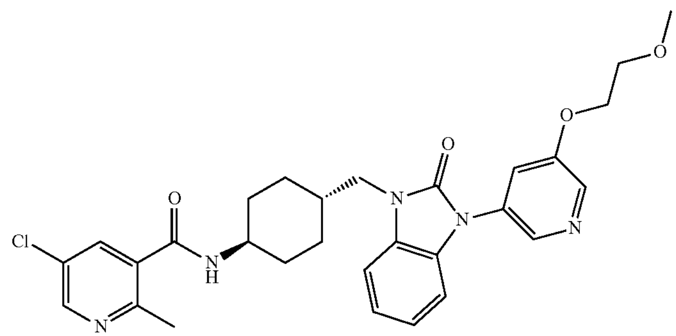 [SMILES: COCCOc1cncc(-n2c(=O)n(C[C@H]3CC[C@H](NC(=O)c4cc(Cl)cnc4C)CC3)c3ccccc32)c1] | 5-chloro-N-((1r,4r)-4-((3-(5-(2-methoxyethoxy)pyridin-3-yl)-2-oxo-2,3-dihydro-1H-benzo[d]imidazol-1-yl)methyl)cyclohexyl)-2-methylnicotinamide | Step-2 of Ex 9 | R |
| 487 | 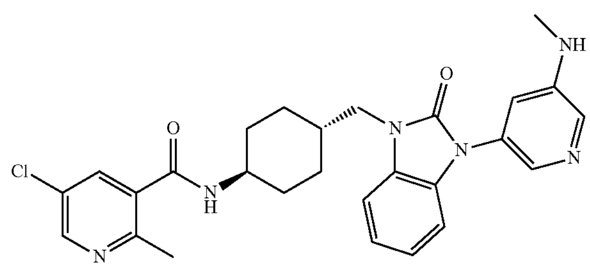 [SMILES: CNc1cncc(-n2c(=O)n(C[C@H]3CC[C@H](NC(=O)c4cc(Cl)cnc4C)CC3)c3ccccc32)c1] | 5-chloro-2-methyl-N-((1r,4r)-4-((3-(5-(methylamino)pyridin-3-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 488 | 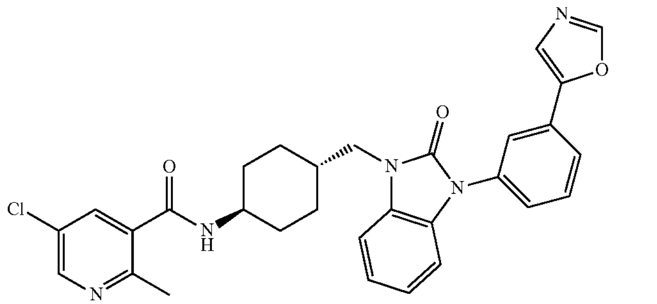 | 5-chloro-2-methyl-N-(((1r,4r)-4-(3-(oxazol-5-yl)phenyl)-2-oxo-2,3-dihydro-1H-benzo[d]imidazol-1-yl)methyl)cyclohexyl)nicotinamide | Step-2 of Ex 9 | R |
| 489 | 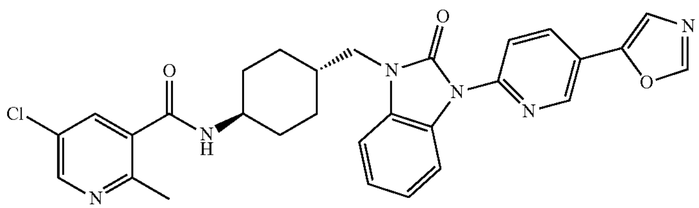 [SMILES: Cc1ncc(Cl)cc1C(=O)N[C@H]1CC[C@H](Cn2c(=O)n(-c3ccc(-c4cnco4)cn3)c3ccccc32)CC1] | 5-chloro-2-methyl-N-(((1r,4r)-4-(5-(oxazol-5-yl)pyridin-2-yl)-2-oxo-2,3-dihydro-1H-benzo[d]imidazol-1-yl)methyl)cyclohexyl)nicotinamide | Step-2 of Ex 9 | X |
| 490 | 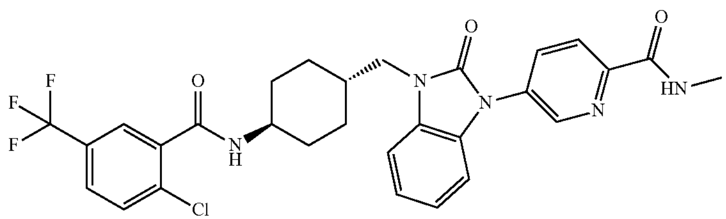 | 5-(3-(((1r,4r)-4-(2-chloro-5-(trifluoromethyl)benzamido)cyclohexyl)methyl)-2-oxo-2,3-dihydro-1H-benzo[d]imidazol-1-yl)-N-methylpicolinamide | Intermediate-121, | Q |
| 491 | 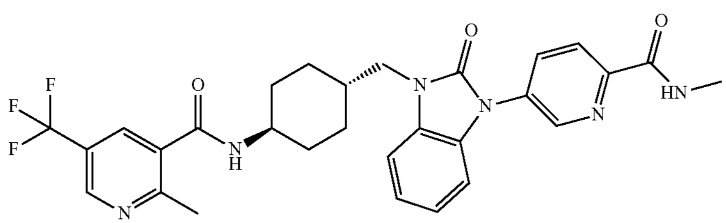 [SMILES: CNC(=O)c1ccc(-n2c(=O)n(C[C@H]3CC[C@H](NC(=O)c4cc(C(F)(F)F)cnc4C)CC3)c3ccccc32)cn1] | N-methyl-5-(3-(((1r,4r)-4-(2-methyl-5-(trifluoromethyl)nicotinamido)cyclohexyl)methyl)-2-oxo-2,3-dihydro-1H-benzo[d]imidazol-1-yl)picolinamide | Intermediate-121, | Q |

TABLE 2-continued

| Ex. | Structure | Name | Reactants | Method |
|---|---|---|---|---|
| 492 | 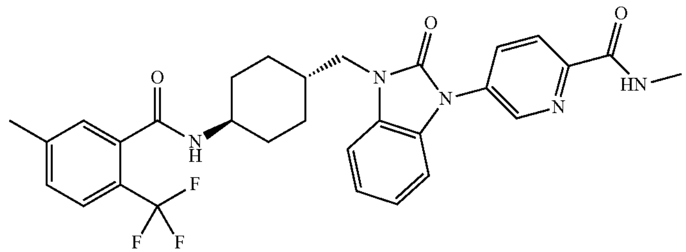 | N-methyl-5-(3-(((1r,4r)-4-(5-methyl-2-(trifluoromethyl)benzamido)cyclohexyl)methyl)-2-oxo-2,3-dihydro-1H-benzo[d]imidazol-1-yl)picolinamide | Intermediate-121, | Q |
| 493 | 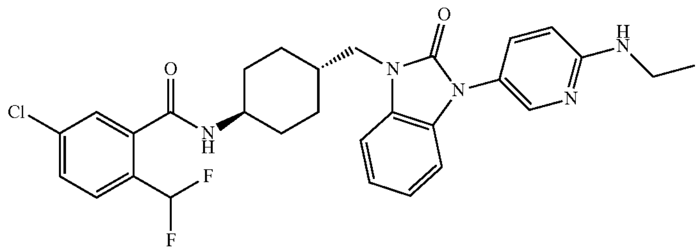 [SMILES: CCNc1ccc(-n2c(=O)n(C[C@H]3CC[C@H](NC(=O)c4cc(Cl)ccc4C(F)F)CC3)c3ccccc32)cn1] | 5-chloro-2-(difluoromethyl)-N-((1r,4r)-4-((3-(6-(ethylamino)pyridin-3-yl)-2-oxo-2,3-dihydro-1H-benzo[d]imidazol-1-yl)methyl)cyclohexyl)nicotinamide | Intermediate-191, | J |
| 494 | 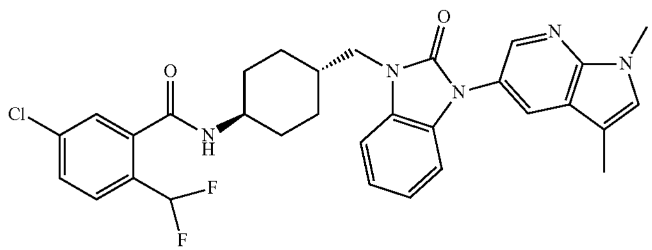 [SMILES: Cc1cn(C)c2ncc(-n3c(=O)n(C[C@H]4CC[C@H](NC(=O)c5cc(Cl)ccc5C(F)F)CC4)c4ccccc43)cc12] | 5-chloro-2-(difluoromethyl)-N-((1r,4r)-4-((3-(1,3-dimethyl-1H-pyrrolo[2,3-b]pyridin-5-yl)-2-oxo-2,3-dihydro-1H-benzo[d]imidazol-1-yl)methyl)cyclohexyl)nicotinamide | Intermediate-213, Mesylate-4 | A1 |
| 495 | 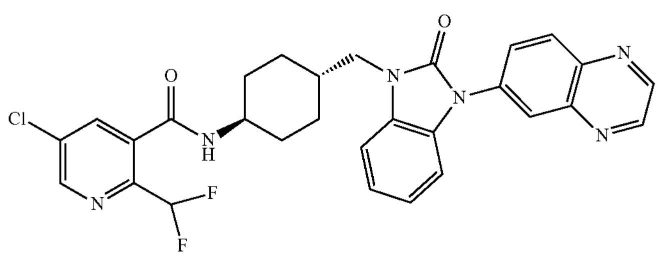 [SMILES: O=C(N[C@H]1CC[C@H](Cn2c(=O)n(-c3ccc4nccnc4c3)c3ccccc32)CC1)c1cc(Cl)cnc1C(F)F] | 5-chloro-2-(difluoromethyl)-N-((1r,4r)-4-((2-oxo-3-(quinoxalin-6-yl)-2,3-dihydro-1H-benzo[d]imidazol-1-yl)methyl)cyclohexyl)nicotinamide | Intermediate-179, Mesylate-4 | A1 |

TABLE 2-continued

| Ex. | Structure | Name | Reactants | Method |
|---|---|---|---|---|
| 496 | 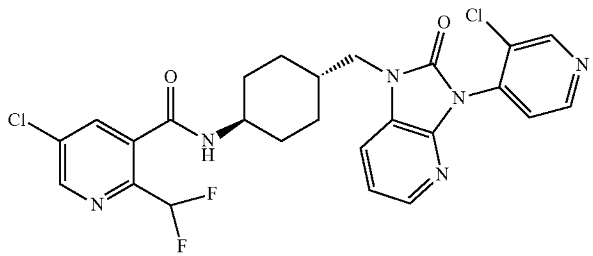 [SMILES: O=C(N[C@H]1CC[C@H](Cn2c(=O)n(-c3ccncc3Cl)c3ncccc32)CC1)c1cc(Cl)cnc1C(F)F] | 5-chloro-N-((1r,4r)-4-((3-(3-chloropyridin-4-yl)-2-oxo-2,3-dihydro-1H-imidazo[4,5-b]pyridin-1-yl)methyl)cyclohexyl)-2-(difluoromethyl)nicotinamide | Intermediate-206, Mesylate-4 | A1 |
| 497 | 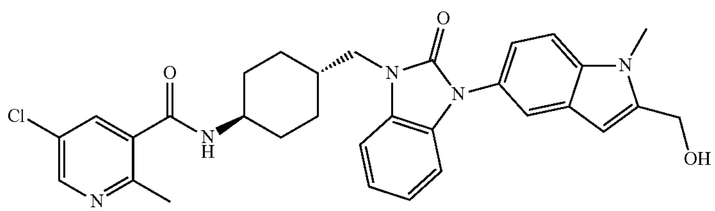 [SMILES: Cc1ncc(Cl)cc1C(=O)N[C@H]1CC[C@H](Cn2c(=O)n(-c3ccc4c(c3)cc(CO)n4C)c3ccccc32)CC1] | 5-chloro-N-((1r,4r)-4-((2-(hydroxymethyl)-1-methyl-1H-indol-5-yl)-2-oxo-2,3-dihydro-1H-benzo[d]imidazol-1-yl)methyl)cyclohexyl)-2-methylnicotinamide | Intermediate-178 | D |
| 498 | 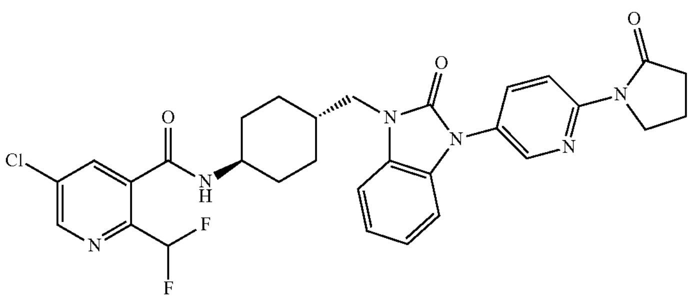 [SMILES: O=C(N[C@H]1CC[C@H](Cn2c(=O)n(-c3ccc(N4CCCC4=O)nc3)c3ccccc32)CC1)c1cc(Cl)cnc1C(F)F] | 5-chloro-2-(difluoromethyl)-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide | Intermediate-207, | Y |
| 499 | 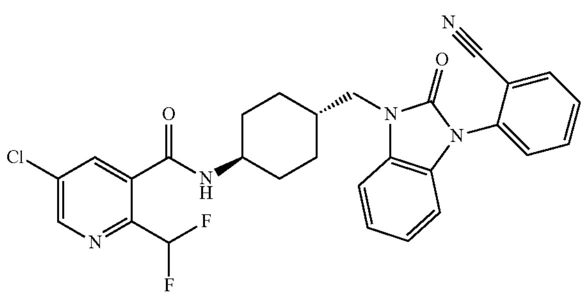 [SMILES: N#Cc1ccccc1-n1c(=O)n(C[C@H]2CC[C@H](NC(=O)c3cc(Cl)cnc3C(F)F)CC2)c2ccccc21] | 5-chloro-N-((1r,4r)-4-((3-(2-cyanophenyl)-2-oxo-2,3-dihydro-1H-benzo[d]imidazol-1-yl)methyl)cyclohexyl)-2-(difluoromethyl)nicotinamide | Intermediate-165 | U |

TABLE 2-continued

| Ex. | Structure | Name | Reactants | Method |
|---|---|---|---|---|
| 500 | 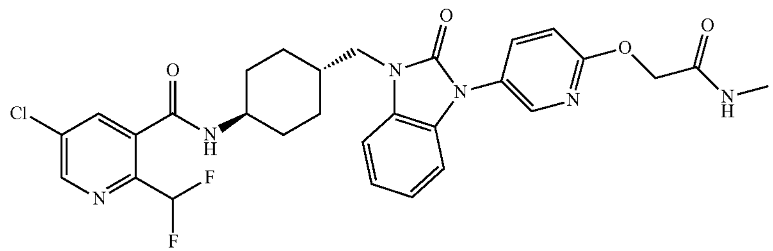 [SMILES: CNC(=O)COc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(2-(methylamino)-2-oxoethoxy)pyridin-3-yl)-2-oxo-2,3-dihydro-1H-benzo[d]imidazol-1-yl)methyl)cyclohexyl)nicotinamide | see Example synthesis part | |
| 501 | 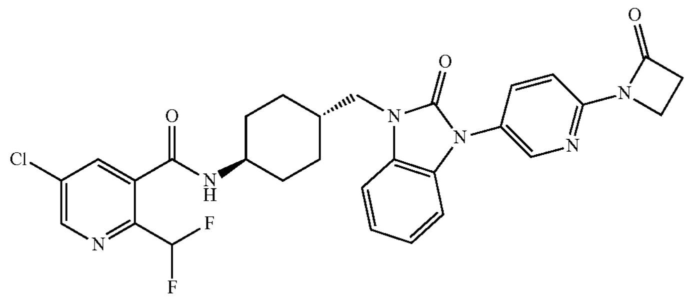 [SMILES: O=C(N[C@H]1CC[C@H](Cn2c(=O)n(-c3ccc(N4CCC4=O)nc3)c3ccccc32)CC1)c1cc(Cl)cnc1C(F)F] | 5-chloro-2-(difluoromethyl)-N-((1r,4r)-4-((3-(6-(2-oxoazetidin-1-yl)pyridin-3-yl)-2,3-dihydro-1H-benzo[d]imidazol-1-yl)methyl)cyclohexyl)nicotinamide | Intermediate-207, | Y |
| 502 | 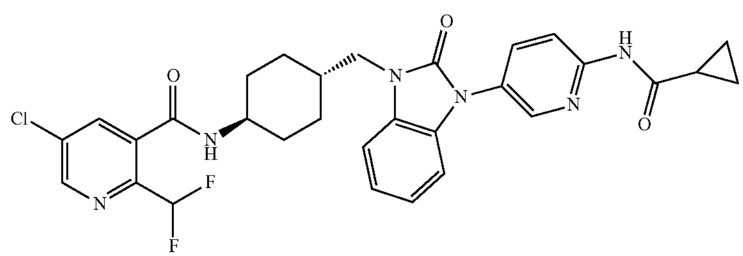 [SMILES: O=C(N[C@H]1CC[C@H](Cn2c(=O)n(-c3ccc(NC(=O)C4CC4)nc3)c3ccccc32)CC1)c1cc(Cl)cnc1C(F)F] | 5-chloro-N-((1r,4r)-4-((3-(6-(cyclopropanecarboxamido)pyridin-3-yl)-2-oxo-2,3-dihydro-1H-benzo[d]imidazol-1-yl)methyl)cyclohexyl)-2-(difluoromethyl)nicotinamide | Intermediate-207, | Y |

TABLE 2-continued

| Ex. | Structure | Name | Reactants | Method |
|---|---|---|---|---|
| 503 | 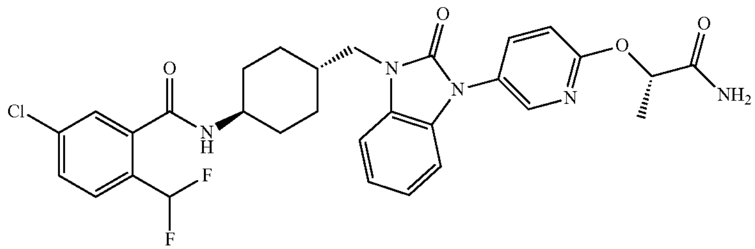 [SMILES: C[C@H](Oc1ccc(-n2c(=O)n(C[C@H]3CC[C@H](NC(=O)c4cc(Cl)ccc4C(F)F)CC3)c3ccccc32)cn1)C(N)=O] | N-((1S,4r)-4-((3-(6-(((S)-1-amino-1-oxopropan-2-yl)oxy)pyridin-3-yl)-2-oxo-2,3-dihydro-1H-benzo[d]imidazol-1-yl)methyl)cyclohexyl)-5-chloro-2-(difluoromethyl)nicotinamide | Intermediate-191, | W |
| 504 | 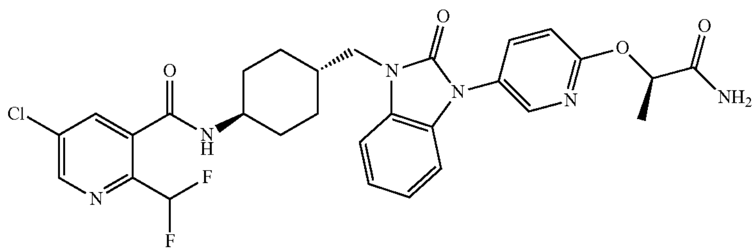 [SMILES: C[C@@H](Oc1ccc(-n2c(=O)n(C[C@H]3CC[C@H](NC(=O)c4cc(Cl)cnc4C(F)F)CC3)c3ccccc32)cn1)C(N)=O] | N-((1R,4r)-4-((3-(6-(((R)-1-amino-1-oxopropan-2-yl)oxy)pyridin-3-yl)-2-oxo-2,3-dihydro-1H-benzo[d]imidazol-1-yl)methyl)cyclohexyl)-5-chloro-2-(difluoromethyl)nicotinamide | Intermediate-191, | W |
| 505 | 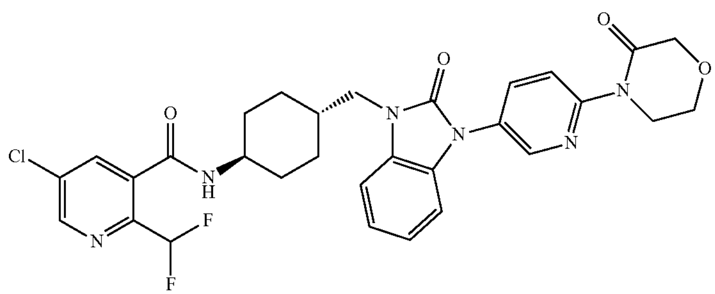 [SMILES: O=C(N[C@H]1CC[C@H](Cn2c(=O)n(-c3ccc(N4CCOCC4=O)nc3)c3ccccc32)CC1)c1cc(Cl)cnc1C(F)F] | 5-chloro-2-(difluoromethyl)-N-((1r,4r)-4-((2-oxo-3-(6-(3-oxomorpholino)pyridin-3-yl)-2,3-dihydro-1H-benzo[d]imidazol-1-yl)methyl)cyclohexyl)nicotinamide | Intermediate-207, | Y |
| 506 | 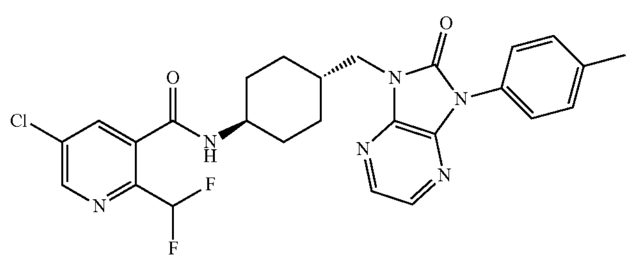 [SMILES: Cc1ccc(-n2c(=O)n(C[C@H]3CC[C@H](NC(=O)c4cc(Cl)cnc4C(F)F)CC3)c3nccnc32)cc1] | 5-chloro-2-(difluoromethyl)-N-((1r,4r)-4-((2-oxo-3-(p-tolyl)-2,3-dihydro-1H-imidazo[4,5-b]pyrazin-1-yl)methyl)cyclohexyl)nicotinamide | Intermediate-70, Mesylate-4 | A1 |

TABLE 2-continued

| Ex. | Structure | Name | Reactants | Method |
|---|---|---|---|---|
| 507 | 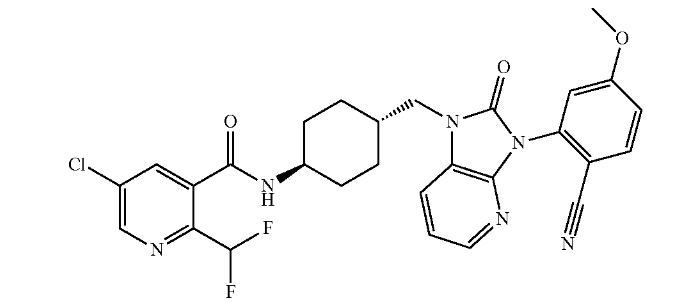 [SMILES: COc1ccc(C#N)c(-n2c(=O)n(C[C@H]3CC[C@H](NC(=O)c4cc(Cl)cnc4C(F)F)CC3)c3cccnc32)c1] | 5-chloro-N-((1r,4r)-4-((3-(2-cyano-5-methoxyphenyl)-2-oxo-2,3-dihydro-1H-imidazo[4,5-b]pyridin-1-yl)methyl)cyclohexyl)-2-(difluoromethyl)nicotinamide | Intermediate-208, Mesylate-4 | A1 |
| 508 | 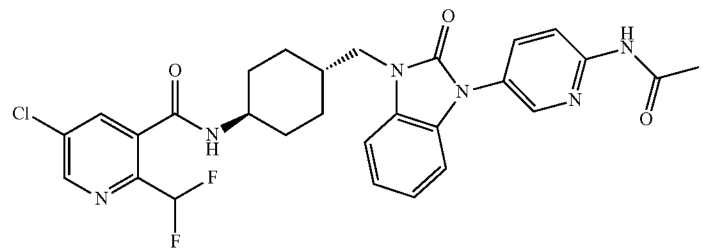 | N-((1r,4r)-4-((3-(6-acetamidopyridin-3-yl)-2-oxo-2,3-dihydro-1H-benzo[d]imidazol-1-yl)methyl)cyclohexyl)-5-chloro-2-(difluoromethyl)nicotinamide | Intermediate-207, (acetamide) | Y |
| 509 | 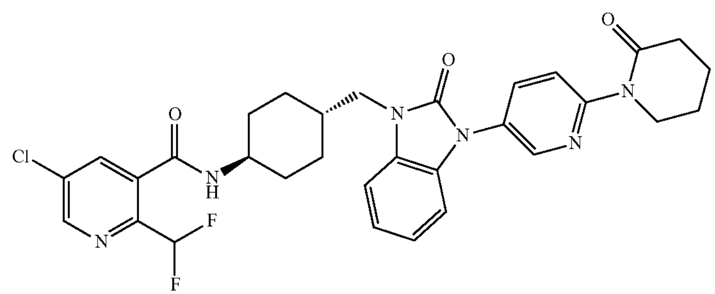 [SMILES: O=C(N[C@H]1CC[C@H](Cn2c(=O)n(-c3ccc(N4CCCCC4=O)nc3)c3ccccc32)CC1)c1cc(Cl)cnc1C(F)F] | 5-chloro-2-(difluoromethyl)-N-((1r,4r)-4-((2-oxo-3-(6-(2-oxopiperidin-1-yl)pyridin-3-yl)-2,3-dihydro-1H-benzo[d]imidazol-1-yl)methyl)cyclohexyl)nicotinamide | Intermediate-207, (2-oxopiperidine) | Y |

TABLE 2-continued

| Ex. | Structure | Name | Reactants | Method |
|---|---|---|---|---|
| 510 | 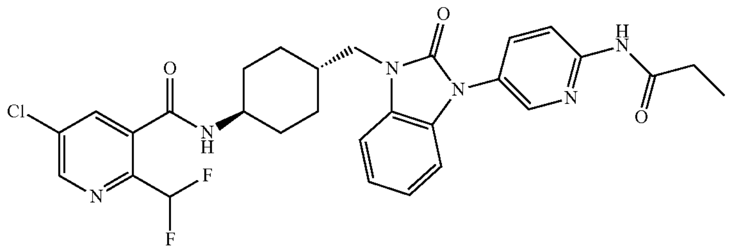 | 5-chloro-2-(difluoromethyl)-N-((1r,4r)-4-((2-oxo-3-(6-propionamidopyridin-3-yl)-2,3-dihydro-1H-benzo[d]imidazol-1-yl)methyl)cyclohexyl)nicotinamide | Intermediate-207, | Y |
| 511 | 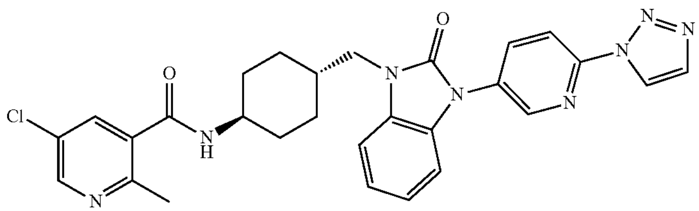 [SMILES: Cc1ncc(Cl)cc1C(=O)N[C@H]1CC[C@H](Cn2c(=O)n(-c3ccc(-n4ccnn4)nc3)c3ccccc32)CC1] | N-((1r,4r)-4-((3-(6-(1H-1,2,3-triazol-1-yl)pyridin-3-yl)-2-oxo-2,3-dihydro-1H-benzo[d]imidazol-1-yl)methyl)cyclohexyl)-5-chloro-2-methylnicotinamide | Step-2 of Ex 9 | R |
| 512 | 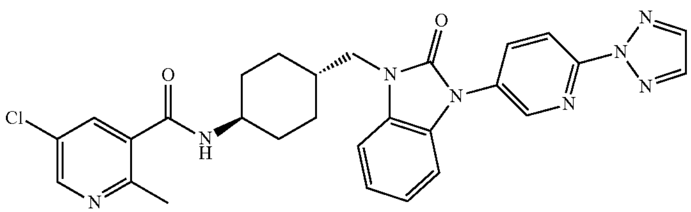 [SMILES: Cc1ncc(Cl)cc1C(=O)N[C@H]1CC[C@H](Cn2c(=O)n(-c3ccc(-n4nccn4)nc3)c3ccccc32)CC1] | N-((1r,4r)-4-((3-(6-(2H-1,2,3-triazol-2-yl)pyridin-3-yl)-2-oxo-2,3-dihydro-1H-benzo[d]imidazol-1-yl)methyl)cyclohexyl)-5-chloro-2-methylnicotinamide | Step-2 of Ex 9 | R |
| 513 | 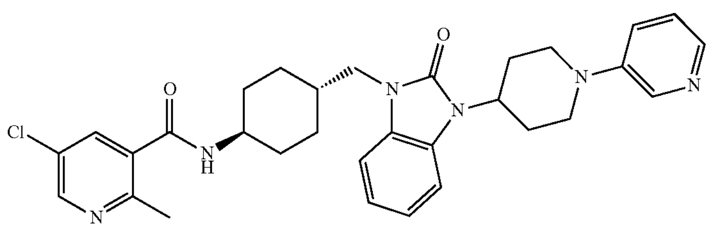 [SMILES: Cc1ncc(Cl)cc1C(=O)N[C@H]1CC[C@H](Cn2c(=O)n(C3CCN(c4cccnc4)CC3)c3ccccc32)CC1] | 5-chloro-2-methyl-N-((1r,4r)-4-((2-oxo-3-(1-(pyridin-3-yl)piperidin-4-yl)-2,3-dihydro-1H-benzo[d]imidazol-1-yl)methyl)cyclohexyl)nicotinamide | Intermediate-209, Mesylate-1 | A1 |

TABLE 2-continued

| Ex. | Structure | Name | Reactants | Method |
|---|---|---|---|---|
| 514 | 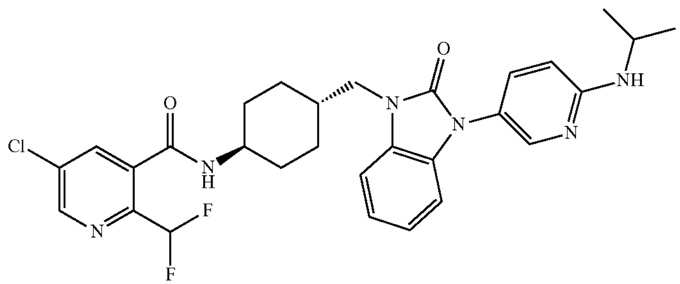 [SMILES: CC(C)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(isopropylamino)pyridin-3-yl)-2-oxo-2,3-dihydro-1H-benzo[d]imidazol-1-yl)methyl)cyclohexyl)nicotinamide | Intermediate-203, Mesylate-4 | A1 |
| 515 | 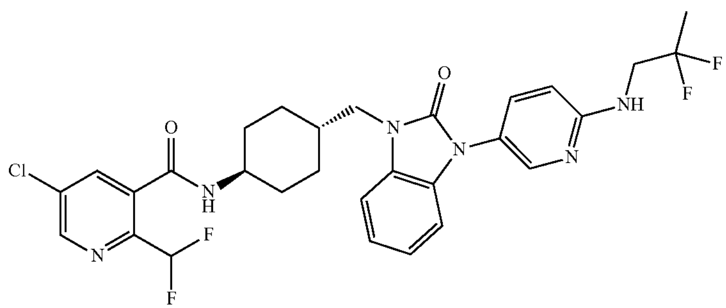 [SMILES: CC(F)(F)CNc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-((2,2-difluoropropyl)amino)pyridin-3-yl)-2-oxo-2,3-dihydro-1H-benzo[d]imidazol-1-yl)methyl)cyclohexyl)nicotinamide | Intermediate-210, Mesylate-4 | A1 |
| 516 | 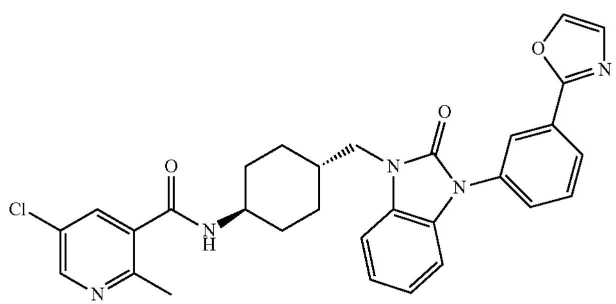 [SMILES: Cc1ncc(Cl)cc1C(=O)N[C@H]1CC[C@H](Cn2c(=O)n(-c3cccc(-c4ncco4)c3)c3ccccc32)CC1] | 5-chloro-2-methyl-N-((1r,4r)-4-((3-(3-(oxazol-2-yl)phenyl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 517 | 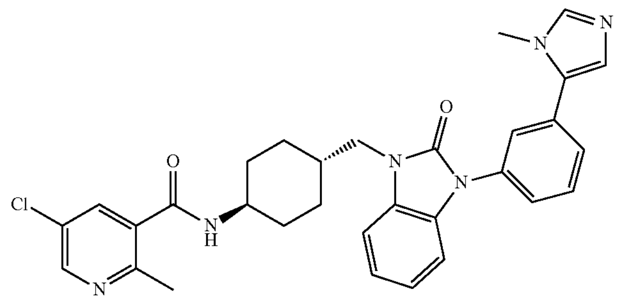 [SMILES: Cc1ncc(Cl)cc1C(=O)N[C@H]1CC[C@H](Cn2c(=O)n(-c3cccc(-c4cncn4C)c3)c3ccccc32)CC1] | 5-chloro-2-methyl-N-((1r,4r)-4-((3-(3-(1-methyl-1H-imidazol-5-yl)phenyl)-2-oxo-2,3-dihydro-1H-benzo[d]imidazol-1-yl)methyl)cyclohexyl)nicotinamide | Step-2 of Ex 9 | R |
| 518 | 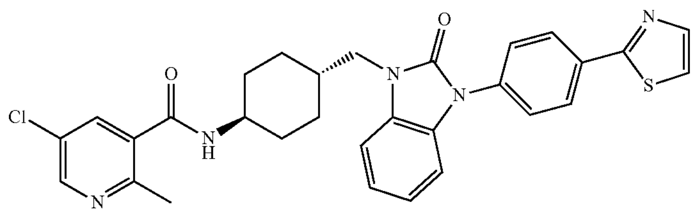 [SMILES: Cc1ncc(Cl)cc1C(=O)N[C@H]1CC[C@H](Cn2c(=O)n(-c3ccc(-c4nccs4)cc3)c3ccccc32)CC1] | 5-chloro-2-methyl-N-((1r,4r)-4-((2-oxo-3-(4-(thiazol-2-yl)phenyl)-2,3-dihydro-1H-benzo[d]imidazol-1-yl)methyl)cyclohexyl)nicotinamide | Step-2 of Ex 9 | R |
| 519 | 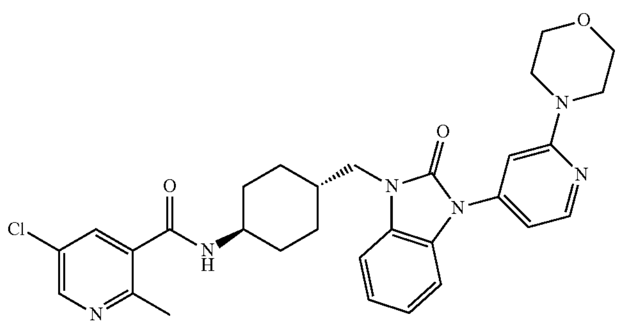 [SMILES: Cc1ncc(Cl)cc1C(=O)N[C@H]1CC[C@H](Cn2c(=O)n(-c3ccnc(N4CCOCC4)c3)c3ccccc32)CC1] | 5-chloro-2-methyl-N-((1r,4r)-4-((3-(2-morpholinopyridin-4-yl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 520 | 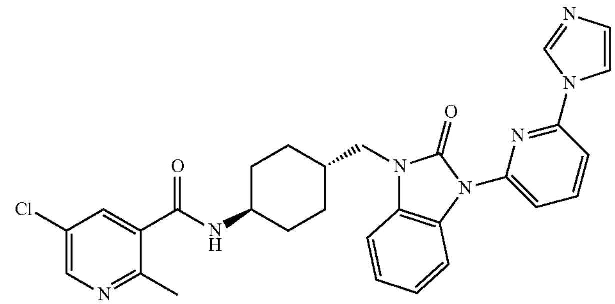 [SMILES: Cc1ncc(Cl)cc1C(=O)N[C@H]1CC[C@H](Cn2c(=O)n(-c3cccc(-n4ccnc4)n3)c3ccccc32)CC1] | N-((1r,4r)-4-((3-(6-(1H-imidazol-1-yl)pyridin-2-yl)-2-oxo-2,3-dihydro-1H-benzo[d]imidazol-1-yl)methyl)cyclohexyl)-5-chloro-2-methyl-nicotinamide | Step-2 of Ex 9 | X |
| 521 | 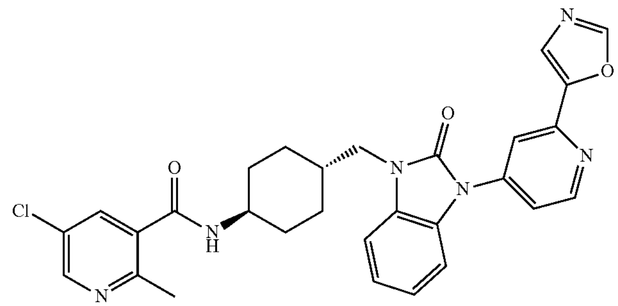 [SMILES: Cc1ncc(Cl)cc1C(=O)N[C@H]1CC[C@H](Cn2c(=O)n(-c3ccnc(-c4cnco4)c3)c3ccccc32)CC1] | 5-chloro-2-methyl-N-((1r,4r)-4-((3-(2-(oxazol-5-yl)pyridin-4-yl)-2-oxo-2,3-dihydro-1H-benzo[d]imidazol-1-yl)methyl)cyclohexyl)nicotinamide | Intermediate-211, Step-2 of Ex 9 | R |
| 522 | 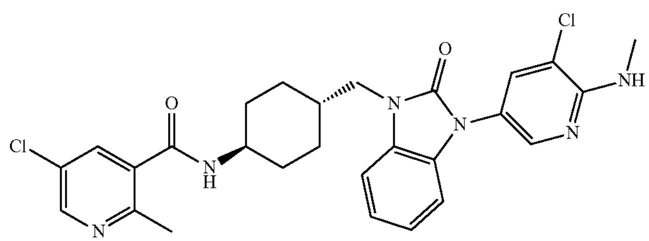 [SMILES: CNc1ncc(-n2c(=O)n(C[C@H]3CC[C@H](NC(=O)c4cc(Cl)cnc4C)CC3)c3ccccc32)cc1Cl] | 5-chloro-N-((1r,4r)-4-((3-(5-chloro-6-(methylamino)pyridin-3-yl)-2-oxo-2,3-dihydro-1H-benzo[d]imidazol-1-yl)methyl)cyclohexyl)-2-methyl-nicotinamide | Intermediate-212, Mesylate-1 | A1 |

TABLE 2-continued

| Ex. | Structure | Name | Reactants | Method |
|---|---|---|---|---|
| 523 | 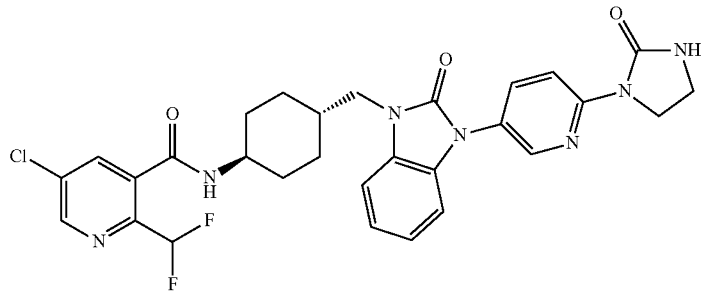 | 5-chloro-2-(difluoromethyl)-N-((1r,4r)-4-((2-oxo-3-(6-(2-oxoimidazolidin-1-yl)pyridin-3-yl)-2,3-dihydro-1H-benzo[d]imidazol-1-yl)methyl)cyclohexyl)nicotinamide | Intermediate-207, | Y |
| 524 | 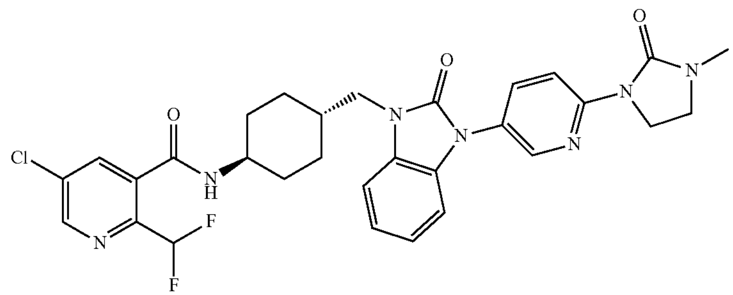 [SMILES: CN1CCN(c2ccc(-n3c(=O)n(C[C@H]4CC[C@H](NC(=O)c5cc(Cl)cnc5C(F)F)CC4)c4ccccc43)cn2)C1=O] | 5-chloro-2-(difluoromethyl)-N-((1r,4r)-4-((3-(6-(3-methyl-2-oxoimidazolidin-1-yl)pyridin-3-yl)-2-oxo-2,3-dihydro-1H-benzo[d]imidazol-1-yl)methyl)cyclohexyl)nicotinamide | Intermediate-207, | Y |
| 525 | 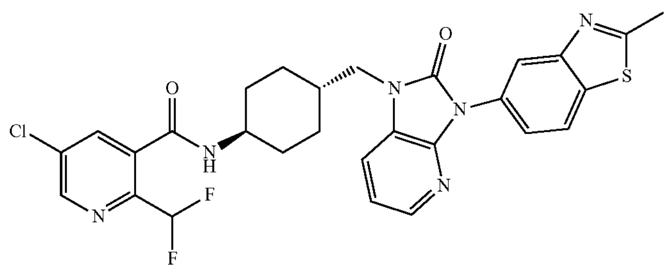 [SMILES: Cc1nc2cc(-n3c(=O)n(C[C@H]4CC[C@H](NC(=O)c5cc(Cl)cnc5C(F)F)CC4)c4cccnc43)ccc2s1] | 5-chloro-2-(difluoromethyl)-N-((1r,4r)-4-((3-(2-methylbenzo[d]thiazol-5-yl)-2-oxo-2,3-dihydro-1H-imidazo[4,5-b]pyridin-1-yl)methyl)cyclohexyl)nicotinamide | Intermediate-214 | R |

TABLE 2-continued

| Ex. | Structure | Name | Reactants | Method |
|---|---|---|---|---|
| 526 | 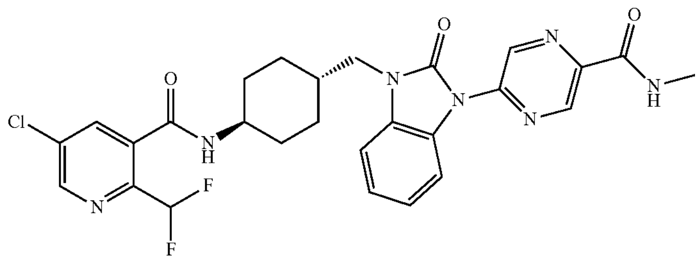 [SMILES: CNC(=O)c1cnc(-n2c(=O)n(C[C@H]3CC[C@H](NC(=O)c4cc(Cl)cnc4C(F)F)CC3)c3ccccc32)cn1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N-methylpyrazine-2-carboxamide | Intermediate-215, Mesylate-4 | A1 |
| 527 | 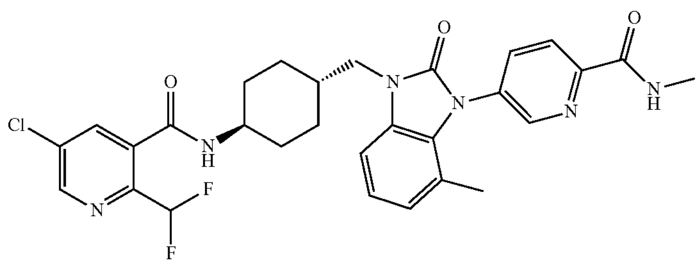 [SMILES: CNC(=O)c1ccc(-n2c(=O)n(C[C@H]3CC[C@H](NC(=O)c4cc(Cl)cnc4C(F)F)CC3)c3cccc(C)c32)cn1] | 5-(3-((1r,4r)-4-(5-chloro-2-(difluoromethyl)nicotinamido)cyclohexyl)methyl)-7-methyl-2-oxo-2,3-dihydro-1H-benzo[d]imidazol-1-yl)-N-methylpicolinamide | Intermediate-101, Mesylate-4 | A1 |
| 528 | 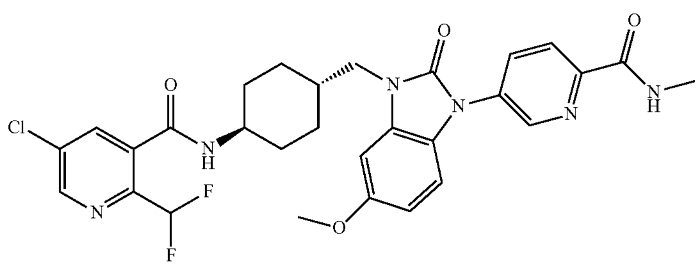 [SMILES: CNC(=O)c1ccc(-n2c(=O)n(C[C@H]3CC[C@H](NC(=O)c4cc(Cl)cnc4C(F)F)CC3)c3cc(OC)ccc32)cn1] | 5-(3-((1r,4r)-4-(5-chloro-2-(difluoromethyl)nicotinamido)cyclohexyl)methyl)-5-methoxy-2-oxo-2,3-dihydro-1H-benzo[d]imidazol-1-yl)-N-methylpicolinamide | Intermediate-103, Mesylate-4 | A1 |
| 529 | 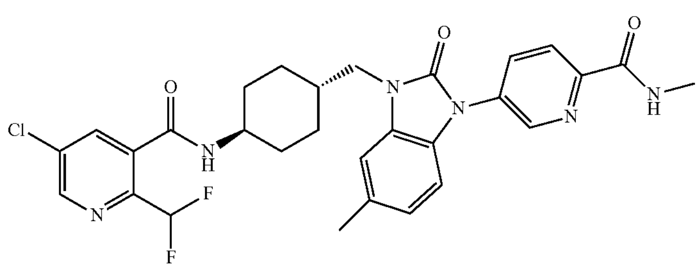 [SMILES: CNC(=O)c1ccc(-n2c(=O)n(C[C@H]3CC[C@H](NC(=O)c4cc(Cl)cnc4C(F)F)CC3)c3cc(C)ccc32)cn1] | 5-(3-((1r,4r)-4-(5-chloro-2-(difluoromethyl)nicotinamido)cyclohexyl)methyl)-5-methyl-2-oxo-2,3-dihydro-1H-benzo[d]imidazol-1-yl)-N-methylpicolinamide | Intermediate-114, Mesylate-4 | A1 |

TABLE 2-continued

| Ex. | Structure | Name | Reactants | Method |
|---|---|---|---|---|
| 530 | 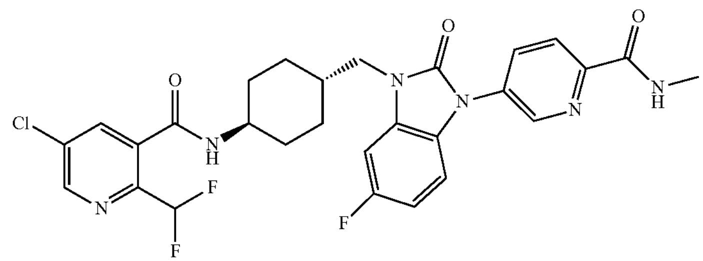 [SMILES: CNC(=O)c1ccc(-n2c(=O)n(C[C@H]3CC[C@H](NC(=O)c4cc(Cl)cnc4C(F)F)CC3)c3cc(F)ccc32)cn1] | 5-(3-(((1r,4r)-4-(5-chloro-2-(difluoromethyl)nicotinamido)cyclohexyl)methyl)-5-fluoro-2-oxo-2,3-dihydro-1H-benzo[d]imidazol-1-yl)-N-methylpicolinamide | Intermediate-115, Mesylate-4 | A1 |
| 531 | 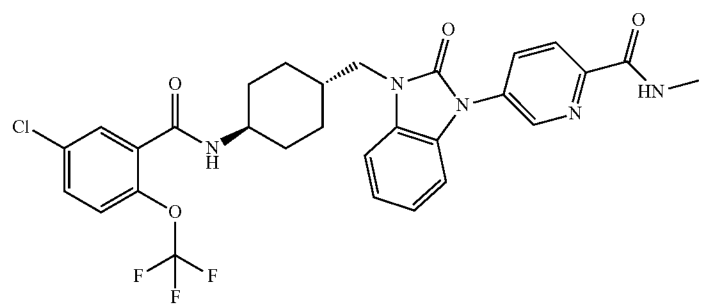 [SMILES: CNC(=O)c1ccc(-n2c(=O)n(C[C@H]3CC[C@H](NC(=O)c4cc(Cl)ccc4OC(F)(F)F)CC3)c3ccccc32)cn1] | 5-(3-(((1r,4r)-4-(5-chloro-2-(trifluoromethoxy)benzamido)cyclohexyl)methyl)-2-oxo-2,3-dihydro-1H-benzo[d]imidazol-1-yl)-N-methylpicolinamide | Intermediate-121, [5-chloro-2-(trifluoromethoxy)benzoic acid] | Q |
| 532 | 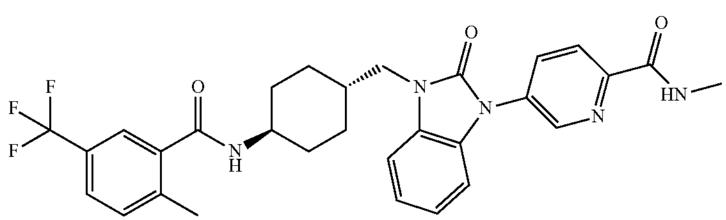 [SMILES: CNC(=O)c1ccc(-n2c(=O)n(C[C@H]3CC[C@H](NC(=O)c4cc(C(F)(F)F)ccc4C)CC3)c3ccccc32)cn1] | N-methyl-5-(3-(((1r,4r)-4-(2-methyl-5-(trifluoromethyl)benzamido)cyclohexyl)methyl)-2-oxo-2,3-dihydro-1H-benzo[d]imidazol-1-yl)picolinamide | Intermediate-121, [2-methyl-5-(trifluoromethyl)benzoic acid] | Q |

TABLE 2-continued

| Ex. | Structure | Name | Reactants | Method |
|---|---|---|---|---|
| 533 | 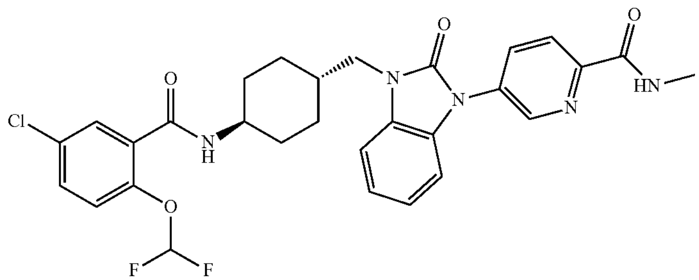 [SMILES: CNC(=O)c1ccc(-n2c(=O)n(C[C@H]3CC[C@H](NC(=O)c4cc(Cl)ccc4OC(F)F)CC3)c3ccccc32)cn1] | 5-(3-(((1r,4r)-4-(5-chloro-2-(difluoromethoxy)benzamido)cyclohexyl)methyl)-2-oxo-2,3-dihydro-1H-benzo[d]imidazol-1-yl)-N-methylpicolinamide | Intermediate-121, (5-chloro-2-(difluoromethoxy)benzoic acid) | Q |
| 534 | 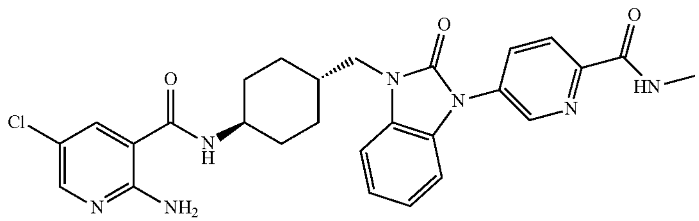 [SMILES: CNC(=O)c1ccc(-n2c(=O)n(C[C@H]3CC[C@H](NC(=O)c4cc(Cl)cnc4N)CC3)c3ccccc32)cn1] | 5-(3-(((1r,4r)-4-(2-amino-5-chloronicotinamido)cyclohexyl)methyl)-2-oxo-2,3-dihydro-1H-benzo[d]imidazol-1-yl)-N-methylpicolinamide | Intermediate-121, (2-amino-5-chloronicotinic acid) | Q |
| 535 | 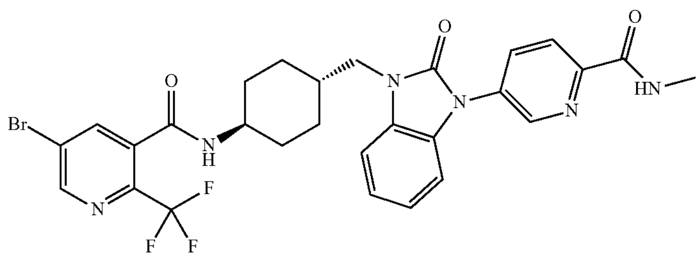 [SMILES: CNC(=O)c1ccc(-n2c(=O)n(C[C@H]3CC[C@H](NC(=O)c4cc(Br)cnc4C(F)(F)F)CC3)c3ccccc32)cn1] | 5-(3-(((1r,4r)-4-(5-bromo-2-(trifluoromethyl)nicotinamido)cyclohexyl)methyl)-2-oxo-2,3-dihydro-1H-benzo[d]imidazol-1-yl)-N-methylpicolinamide | Intermediate-121, (5-bromo-2-(trifluoromethyl)nicotinic acid) | Q |

TABLE 2-continued

| Ex. | Structure | Name | Reactants | Method |
|---|---|---|---|---|
| 536 | 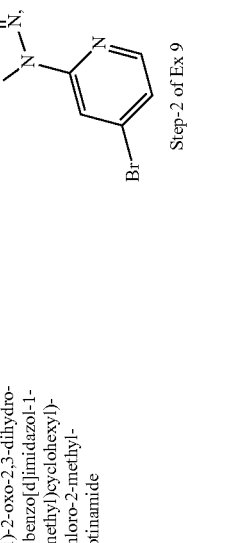 | N-((1r,4r)-4-((3-(2-(2H-1,2,3-triazol-2-yl)pyridin-4-yl)-2-oxo-2,3-dihydro-1H-benzo[d]imidazol-1-yl)methyl)cyclohexyl)-5-chloro-2-methylnicotinamide | 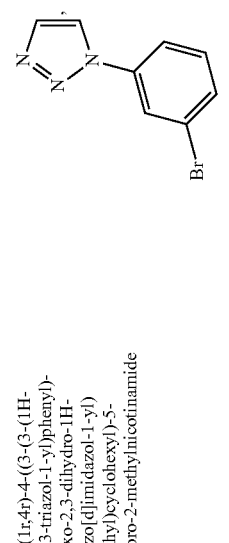 Step-2 of Ex 9 | R |
| 537 | 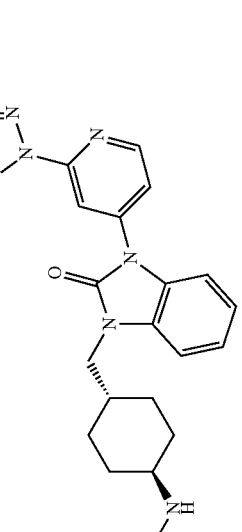 | N-((1r,4r)-4-((3-(3-(1H-1,2,3-triazol-1-yl)phenyl)-2-oxo-2,3-dihydro-1H-benzo[d]imidazol-1-yl)methyl)cyclohexyl)-5-chloro-2-methylnicotinamide | 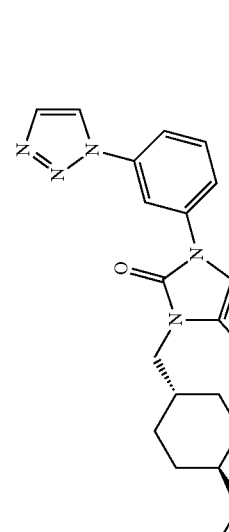 Step-2 of Ex 9 | R |
| 538 | 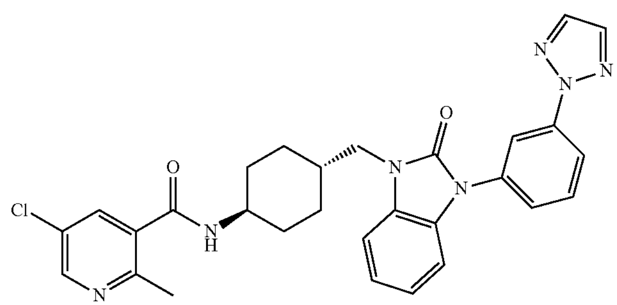 [SMILES: Cc1ncc(Cl)cc1C(=O)N[C@H]1CC[C@H](Cn2c(=O)n(-c3cccc(-n4nccn4)c3)c3ccccc32)CC1] | N-((1r,4r)-4-((3-(3-(2H-1,2,3-triazol-2-yl)phenyl)-2-oxo-2,3-dihydro-1H-benzo[d]imidazol-1-yl)methyl)cyclohexyl)-5-chloro-2-methylnicotinamide |  Step-2 of Ex 9 | R |

TABLE 2-continued

| Ex. | Structure | Name | Reactants | Method |
|---|---|---|---|---|
| 539 | 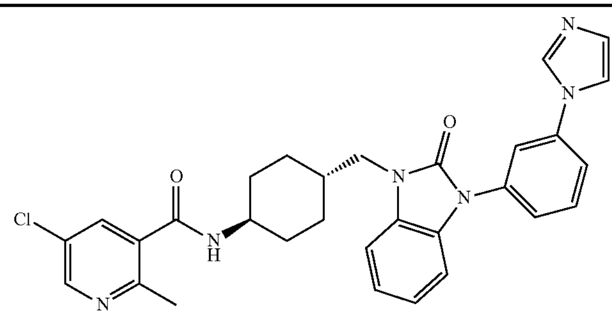 | N-((1r,4r)-4-((3-(3-(1H-imidazol-1-yl)phenyl)-2-oxo-2,3-dihydro-1H-benzo[d]imidazol-1-yl)methyl)cyclohexyl)-5-chloro-2-methylnicotinamide | 3-(1H-imidazol-1-yl)phenyl bromide; Step-2 of Ex 9 | R |
| 540 | 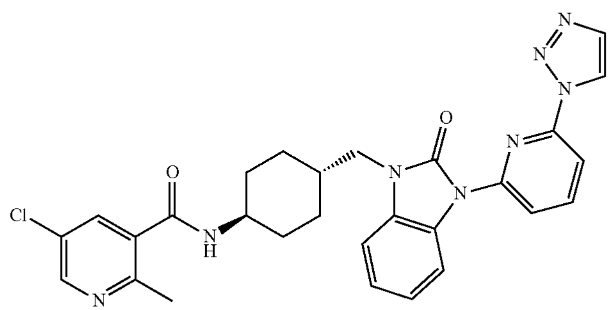 [SMILES: Cc1ncc(Cl)cc1C(=O)N[C@H]1CC[C@H](Cn2c(=O)n(-c3cccc(-n4ccnn4)n3)c3ccccc32)CC1] | N-((1r,4r)-4-((3-(6-(1H-1,2,3-triazol-1-yl)pyridin-2-yl)-2-oxo-2,3-dihydro-1H-benzo[d]imidazol-1-yl)methyl)cyclohexyl)-5-chloro-2-methylnicotinamide | 6-(1H-1,2,3-triazol-1-yl)-2-bromopyridine; Step-2 of Ex 9 | R |
| 541 | 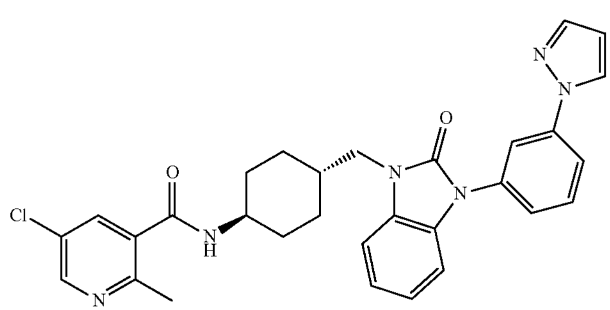 [SMILES: Cc1ncc(Cl)cc1C(=O)N[C@H]1CC[C@H](Cn2c(=O)n(-c3cccc(-n4cccn4)c3)c3ccccc32)CC1] | N-((1r,4r)-4-((3-(3-(1H-pyrazol-1-yl)phenyl)-2-oxo-2,3-dihydro-1H-benzo[d]imidazol-1-yl)methyl)cyclohexyl)-5-chloro-2-methylnicotinamide | 3-(1H-pyrazol-1-yl)phenyl bromide; Step-2 of Ex 9 | R |

TABLE 2-continued

| Ex. | Structure | Name | Reactants | Method |
|---|---|---|---|---|
| 542 | 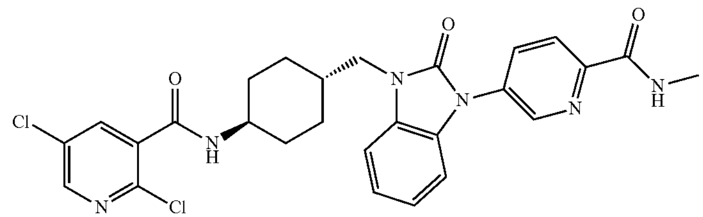 [SMILES: CNC(=O)c1ccc(-n2c(=O)n(C[C@H]3CC[C@H](NC(=O)c4cc(Cl)cnc4Cl)CC3)c3ccccc32)cn1] | 5-(3-(((1r,4r)-4-(2,5-dichloronicotinamido)cyclohexyl)methyl)-2-oxo-2,3-dihydro-1H-benzo[d]imidazol-1-yl)-N-methylpicolinamide | Intermediate-121, | Q |
| 543 | 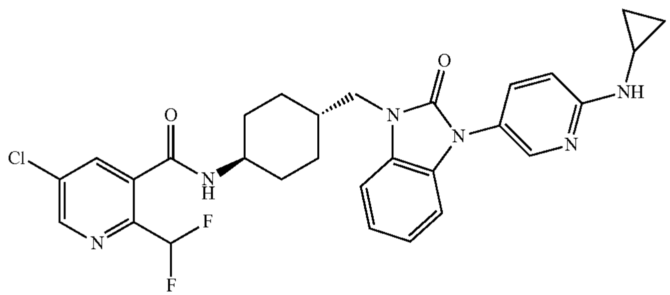 [SMILES: O=C(N[C@H]1CC[C@H](Cn2c(=O)n(-c3ccc(NC4CC4)nc3)c3ccccc32)CC1)c1cc(Cl)cnc1C(F)F] | 5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-(difluoromethyl)nicotinamide | Intermediate-216, Mesylate-4 | A1 |
| 544 | 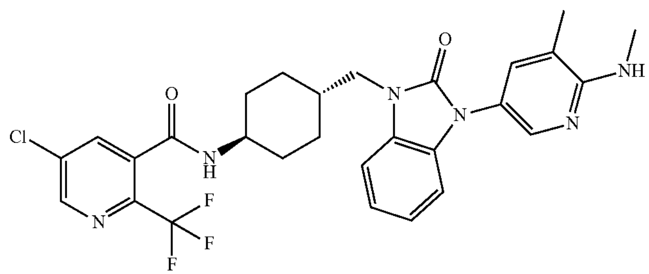 [SMILES: CNc1ncc(-n2c(=O)n(C[C@H]3CC[C@H](NC(=O)c4cc(Cl)cnc4C(F)(F)F)CC3)c3ccccc32)cc1C] | 5-chloro-N-((1r,4r)-4-((3-(5-methyl-6-(methylamino)pyridin-3-yl)-2-oxo-2,3-dihydro-1H-benzo[d]imidazol-1-yl)methyl)cyclohexyl)-2-(trifluoromethyl)nicotinamide | Intermediate-69, Mesylate-3 | A1 |
| 545 | 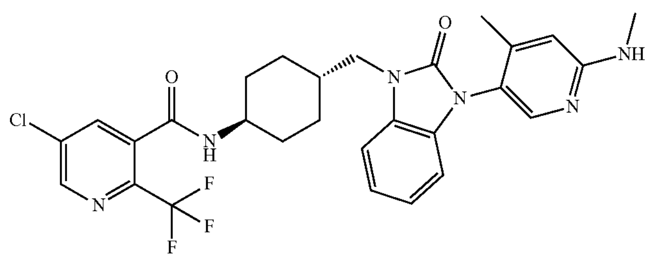 [SMILES: CNc1cc(C)c(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(4-methyl-6-(methylamino)pyridin-3-yl)-2-oxo-2,3-dihydro-1H-benzo[d]imidazol-1-yl)methyl)cyclohexyl)-2-(trifluoromethyl)nicotinamide | Intermediate-217, Mesylate-3 | A1 |

TABLE 2-continued

| Ex. | Structure | Name | Reactants | Method |
|---|---|---|---|---|
| 546 | 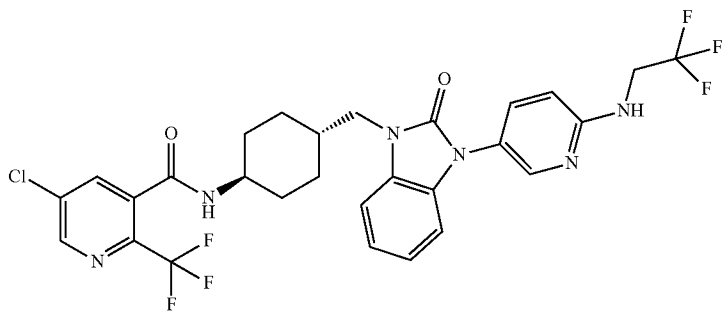 [SMILES: O=C(N[C@H]1CC[C@H](Cn2c(=O)n(-c3ccc(NCC(F)(F)F)nc3)c3ccccc32)CC1)c1cc(Cl)cnc1C(F)(F)F] | 5-chloro-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)-2-(trifluoromethyl)nicotinamide | Intermediate-193, Mesylate-3 | A1 |
| 547 | 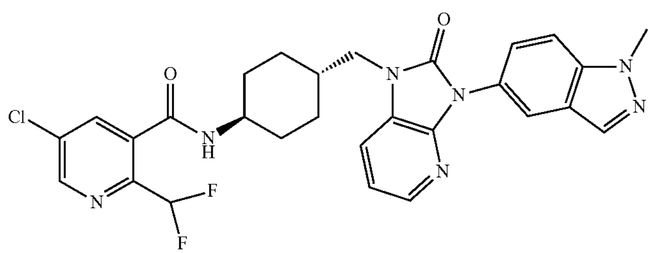 [SMILES: Cn1ncc2cc(-n3c(=O)n(C[C@H]4CC[C@H](NC(=O)c5cc(Cl)cnc5C(F)F)CC4)c4cccnc43)ccc21] | 5-chloro-2-(difluoromethyl)-N-((1r,4r)-4-((3-(1-methyl-1H-indazol-5-yl)-2-oxo-2,3-dihydro-1H-imidazo[4,5-b]pyridin-1-yl)methyl)cyclohexyl)nicotinamide | Intermediate-218, Mesylate-4 | A1 |
| 548 | 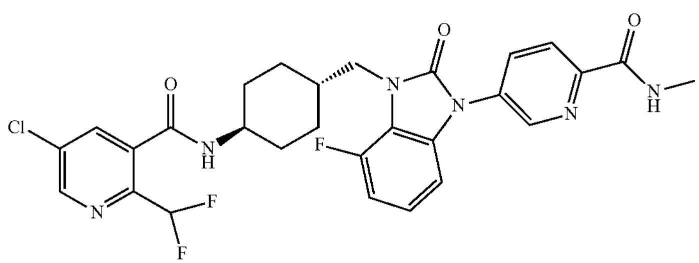 [SMILES: CNC(=O)c1ccc(-n2c(=O)n(C[C@H]3CC[C@H](NC(=O)c4cc(Cl)cnc4C(F)F)CC3)c3c(F)cccc32)cn1] | 5-(3-((1r,4r)-4-(5-chloro-2-(difluoromethyl)nicotinamido)cyclohexyl)methyl)-4-fluoro-2-oxo-2,3-dihydro-1H-benzo[d]imidazol-1-yl)-N-methylpicolinamide | Intermediate-219, Mesylate-4 | A1 |

TABLE 2-continued

| Ex. | Structure | Name | Reactants | Method |
|---|---|---|---|---|
| 549 | 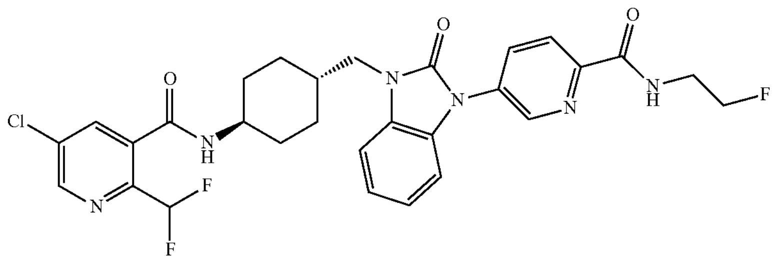 [SMILES: O=C(NCCF)c1ccc(-n2c(=O)n(C[C@H]3CC[C@H](NC(=O)c4cc(Cl)cnc4C(F)F)CC3)c3ccccc32)cn1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N-(2-fluoroethyl)picolinamide | Intermediate-220, H₂N–CH₂CH₂–F | Q |
| 550 | 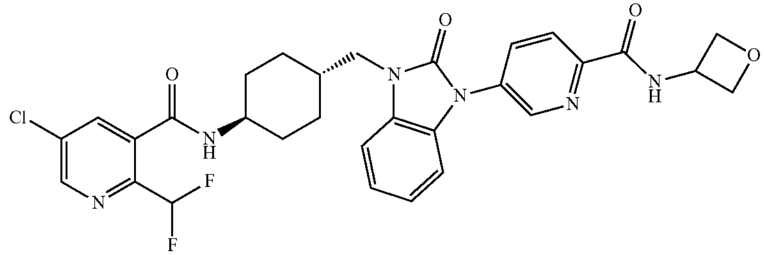 [SMILES: O=C(NC1COC1)c1ccc(-n2c(=O)n(C[C@H]3CC[C@H](NC(=O)c4cc(Cl)cnc4C(F)F)CC3)c3ccccc32)cn1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N-(oxetan-3-yl)picolinamide | Intermediate-220, 3-aminooxetane | Q |
| 551 | 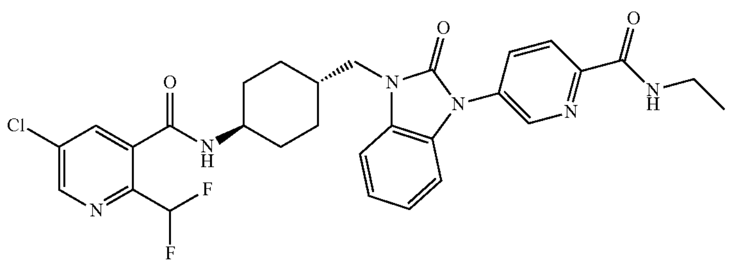 [SMILES: CCNC(=O)c1ccc(-n2c(=O)n(C[C@H]3CC[C@H](NC(=O)c4cc(Cl)cnc4C(F)F)CC3)c3ccccc32)cn1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N-ethylpicolinamide | Intermediate-220, H₂N–CH₂CH₃ | Q |
| 552 | 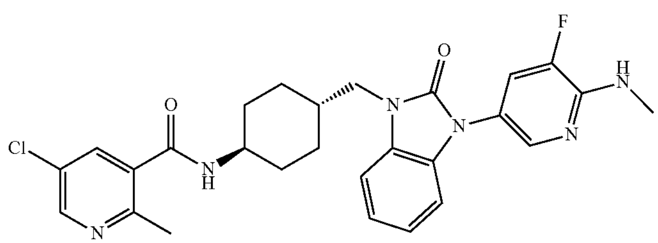 [SMILES: CNc1ncc(-n2c(=O)n(C[C@H]3CC[C@H](NC(=O)c4cc(Cl)cnc4C)CC3)c3ccccc32)cc1F] | 5-chloro-N-((1r,4r)-4-(3-(5-fluoro-6-(methylamino)pyridin-3-yl)-2-oxo-2,3-dihydro-1H-benzo[d]imidazol-1-yl)methyl)cyclohexyl)-2-methylnicotinamide | see Example synthesis part | |

TABLE 2-continued

| Ex. | Structure | Name | Reactants | Method |
|---|---|---|---|---|
| 553 | 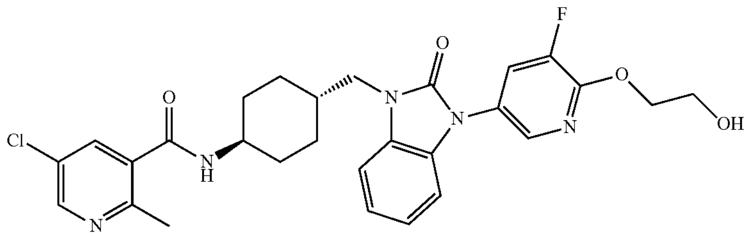 [SMILES: Cc1ncc(Cl)cc1C(=O)N[C@H]1CC[C@H](Cn2c(=O)n(-c3cnc(OCCO)c(F)c3)c3ccccc32)CC1] | 5-chloro-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)-2-methyl-nicotinamide | see Example synthesis part | |
| 554 | 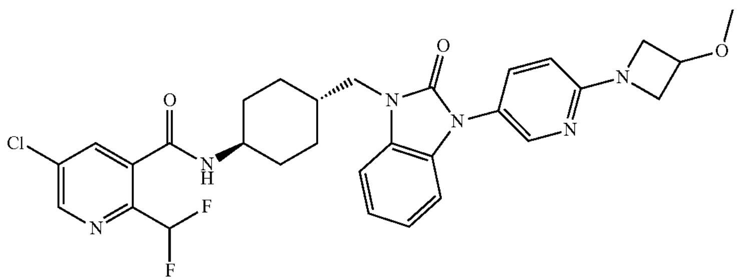 [SMILES: COC1CN(c2ccc(-n3c(=O)n(C[C@H]4CC[C@H](NC(=O)c5cc(Cl)cnc5C(F)F)CC4)c4ccccc43)cn2)C1] | 5-chloro-2-(difluoromethyl)-N-((1r,4r)-4-((3-(6-(3-methoxyazetidin-1-yl)pyridin-3-yl)-2-oxo-2,3-dihydro-1H-benzo[d]imidazol-1-yl)methyl)cyclohexyl)nicotinamide | Intermediate-75, Mesylate-4 | A1 |
| 555 | 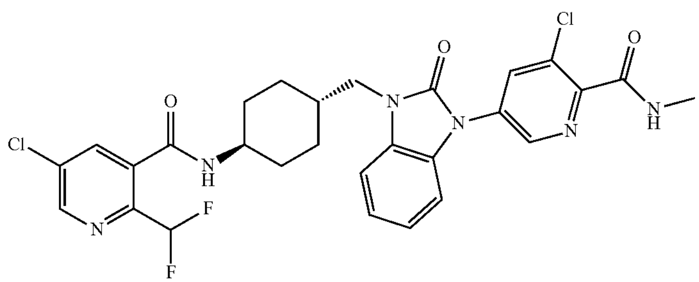 [SMILES: CNC(=O)c1ncc(-n2c(=O)n(C[C@H]3CC[C@H](NC(=O)c4cc(Cl)cnc4C(F)F)CC3)c3ccccc32)cc1Cl] | 3-chloro-5-(3-((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide | Intermediate-221, Mesylate-4 | A1 |

TABLE 2-continued

| Ex. | Structure | Name | Reactants | Method |
|---|---|---|---|---|
| 556 | 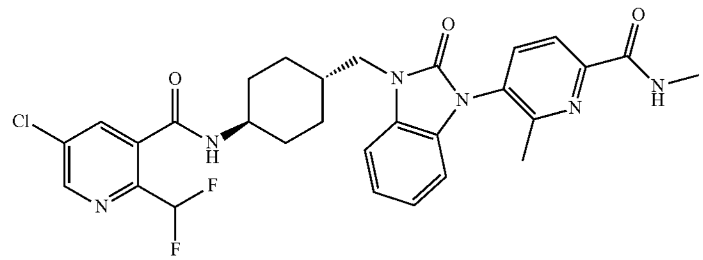 [SMILES: CNC(=O)c1ccc(-n2c(=O)n(C[C@H]3CC[C@H](NC(=O)c4cc(Cl)cnc4C(F)F)CC3)c3ccccc32)c(C)n1] | 5-(3-((1r,4r)-4-(5-chloro-2-(difluoromethyl)nicotinamido)cyclohexyl)methyl)-2-oxo-2,3-dihydro-1H-benzo[d]imidazol-1-yl)-N,6-dimethylpicolinamide | Intermediate-222, Mesylate-4 | A1 |
| 557 | 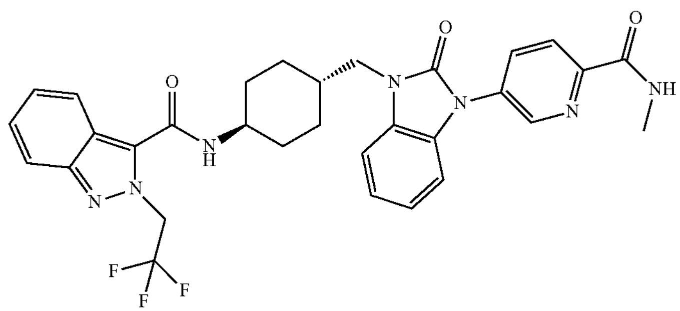 [SMILES: CNC(=O)c1ccc(-n2c(=O)n(C[C@H]3CC[C@H](NC(=O)c4c5ccccc5nn4CC(F)(F)F)CC3)c3ccccc32)cn1] | N-((1r,4r)-4-(3-(6-(methylcarbamoyl)pyridin-3-yl)-2-oxo-2,3-dihydro-1H-benzo[d]imidazol-1-yl)methyl)cyclohexyl)-2-(2,2,2-trifluoroethyl)-2H-indazole-3-carboxamide | Intermediate-121, Intermediate-223 | Q |
| 558 | 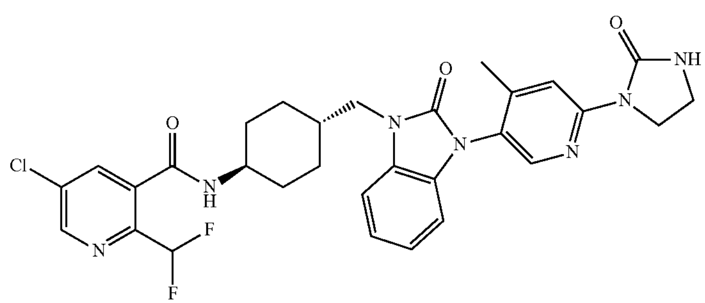 [SMILES: Cc1cc(N2CCNC2=O)ncc1-n1c(=O)n(C[C@H]2CC[C@H](NC(=O)c3cc(Cl)cnc3C(F)F)CC2)c2ccccc21] | 5-chloro-2-(difluoromethyl)-N-((1r,4r)-4-((3-(4-methyl-6-(2-oxoimidazolidin-1-yl)pyridin-3-yl)-2-oxo-2,3-dihydro-1H-benzo[d]imidazol-1-yl)methyl)cyclohexyl)nicotinamide | Intermediate-224, | Y |

TABLE 2-continued

| Ex. | Structure | Name | Reactants | Method |
|---|---|---|---|---|
| 559 | 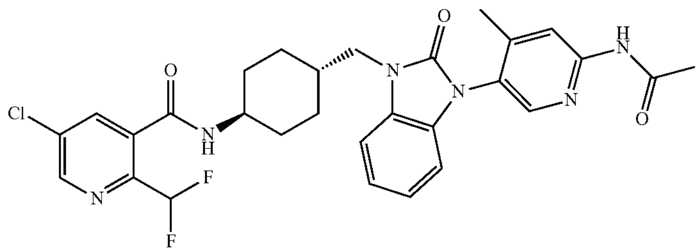 [SMILES: CC(=O)Nc1cc(C)c(-n2c(=O)n(C[C@H]3CC[C@H](NC(=O)c4cc(Cl)cnc4C(F)F)CC3)c3ccccc32)cn1] | N-((1r,4r)-4-((3-(6-acetamido-4-methylpyridin-3-yl)-2-oxo-2,3-dihydro-1H-benzo[d]imidazol-1-yl)methyl)cyclohexyl)-5-chloro-2-(difluoromethyl)nicotinamide | Intermediate-224, acetamide | Y |
| 560 | 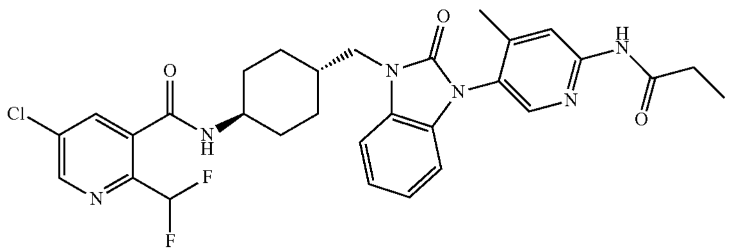 [SMILES: CCC(=O)Nc1cc(C)c(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(4-methyl-6-propionamidopyridin-3-yl)-2-oxo-2,3-dihydro-1H-benzo[d]imidazol-1-yl)methyl)cyclohexyl)nicotinamide | Intermediate-224, propionamide | Y |
| 561 | 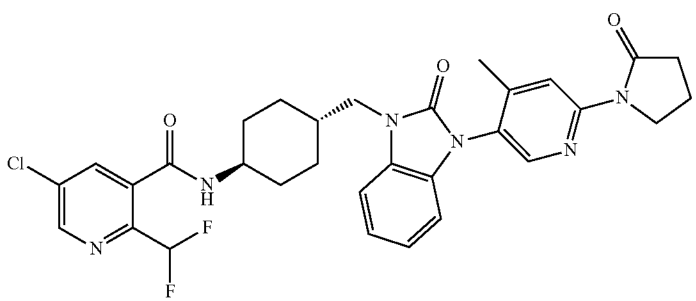 [SMILES: Cc1cc(N2CCCC2=O)ncc1-n1c(=O)n(C[C@H]2CC[C@H](NC(=O)c3cc(Cl)cnc3C(F)F)CC2)c2ccccc21] | 5-chloro-2-(difluoromethyl)-N-((1r,4r)-4-((3-(4-methyl-6-(2-oxopyrrolidin-1-yl)pyridin-3-yl)-2-oxo-2,3-dihydro-1H-benzo[d]imidazol-1-yl)methyl)cyclohexyl)nicotinamide | Intermediate-224, 2-pyrrolidinone | Y |

| Ex. | Structure | Name | Reactants | Method |
|---|---|---|---|---|
| 562 | 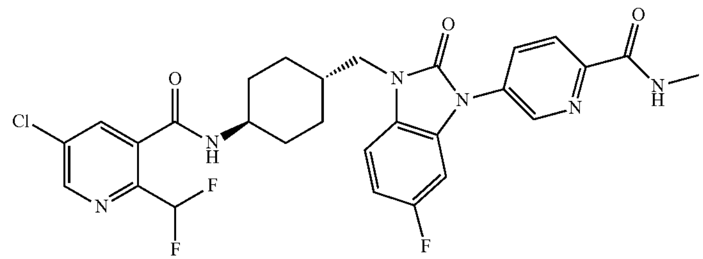 [SMILES: CNC(=O)c1ccc(-n2c(=O)n(C[C@H]3CC[C@H](NC(=O)c4cc(Cl)cnc4C(F)F)CC3)c3ccc(F)cc32)cn1] | 5-(3-((1r,4r)-4-(5-chloro-2-(difluoromethyl)nicotina-mido)cyclohexyl)methyl)-6-fluoro-2-oxo-2,3-dihydro-1H-benzo[d]imidazol-1-yl)-N-methylpicolinamide | Intermediate-102, Mesylate-4 | A1 |
| 563 | 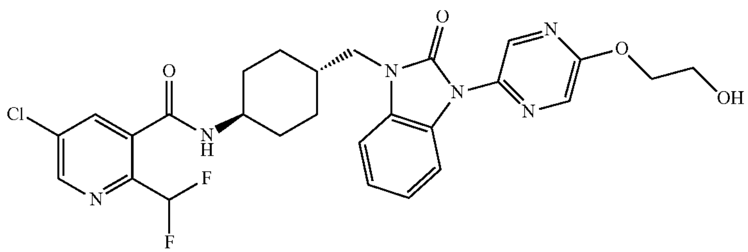 [SMILES: O=C(N[C@H]1CC[C@H](Cn2c(=O)n(-c3cnc(OCCO)cn3)c3ccccc32)CC1)c1cc(Cl)cnc1C(F)F] | 5-chloro-2-(difluoromethyl)-N-((1r,4r)-4-(3-(5-(2-hydroxyethoxy)pyrazin-2-yl)-2-oxo-2,3-dihydro-1H-benzo[d]imidazol-1-yl)methyl)cyclohexyl)nicotinamide | see Example synthesis part | |
| 564 | 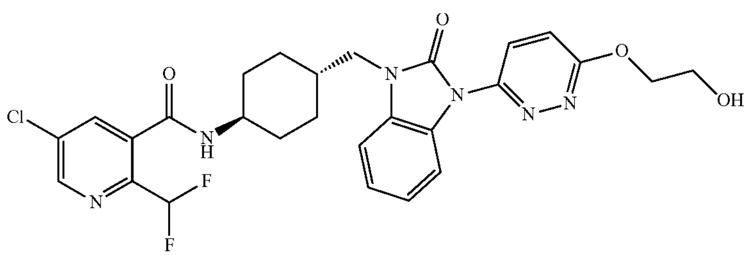 [SMILES: O=C(N[C@H]1CC[C@H](Cn2c(=O)n(-c3ccc(OCCO)nn3)c3ccccc32)CC1)c1cc(Cl)cnc1C(F)F] | 5-chloro-2-(difluoromethyl)-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)nicotinamide | see Example synthesis part | |
| 565 | 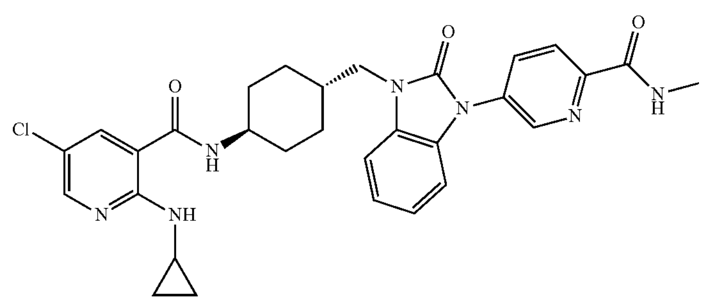 [SMILES: CNC(=O)c1ccc(-n2c(=O)n(C[C@H]3CC[C@H](NC(=O)c4cc(Cl)cnc4NC4CC4)CC3)c3ccccc32)cn1] | 5-(3-((1r,4r)-4-(5-chloro-2-(cyclopropylamino)nicotina-mido)cyclohexyl)methyl)-2-oxo-2,3-dihydro-1H-benzo[d]imidazol-1-yl)-N-methyl-picolinamide | Intermediate-121, | Q |

TABLE 2-continued

| Ex. | Structure | Name | Reactants | Method |
|---|---|---|---|---|
| 566 | 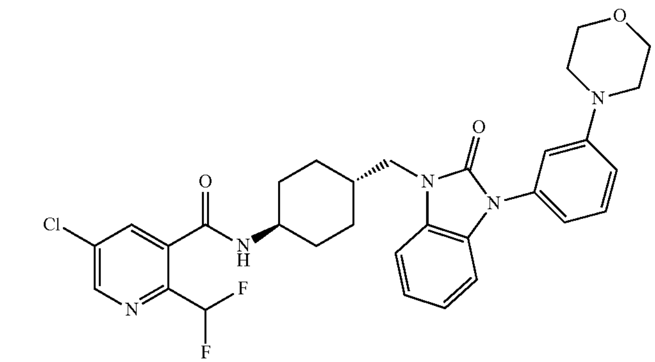 [SMILES: O=C(N[C@H]1CC[C@H](Cn2c(=O)n(-c3cccc(N4CCOCC4)c3)c3ccccc32)CC1)c1cc(Cl)cnc1C(F)F] | 5-chloro-2-(difluoromethyl)-N-((1r,4r)-4-((3-(3-morpholinophenyl)-2-oxo-2,3-dihydro-1H-benzo[d]imidazol-1-yl)methyl)cyclohexyl)nicotinamide | 3-bromophenylmorpholine; Intermediate-165 | R |
| 567 | 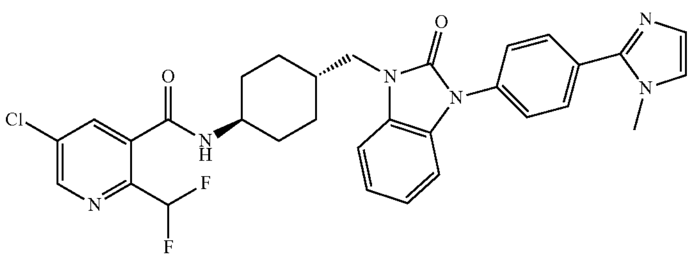 [SMILES: Cn1ccnc1-c1ccc(-n2c(=O)n(C[C@H]3CC[C@H](NC(=O)c4cc(Cl)cnc4C(F)F)CC3)c3ccccc32)cc1] | 5-chloro-2-(difluoromethyl)-N-((1r,4r)-4-((3-(4-(1-methyl-1H-imidazol-2-yl)phenyl)-2-oxo-2,3-dihydro-1H-benzo[d]imidazol-1-yl)methyl)cyclohexyl)nicotinamide | 2-(4-bromophenyl)-1-methyl-1H-imidazole; Intermediate-165 | R |
| 568 | 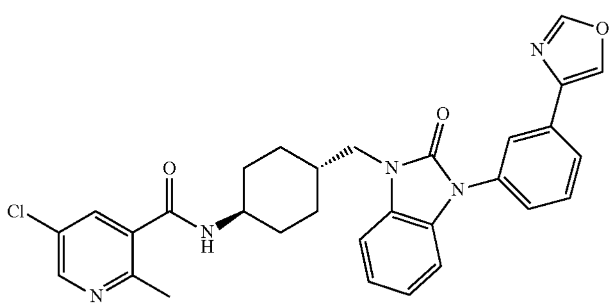 [SMILES: Cc1ncc(Cl)cc1C(=O)N[C@H]1CC[C@H](Cn2c(=O)n(-c3cccc(-c4cocn4)c3)c3ccccc32)CC1] | 5-chloro-2-methyl-N-((1r,4r)-4-((3-(3-(oxazol-4-yl)phenyl)-2-oxo-2,3-dihydro-1H-benzo[d]imidazol-1-yl)methyl)cyclohexyl)nicotinamide | 4-(3-bromophenyl)oxazole; Step-2 of Ex 9 | R |

TABLE 2-continued

| Ex. | Structure | Name | Reactants | Method |
|---|---|---|---|---|
| 569 | 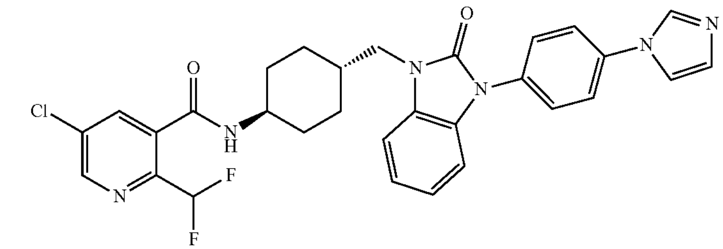 [SMILES: O=C(N[C@H]1CC[C@H](Cn2c(=O)n(-c3ccc(-n4ccnc4)cc3)c3ccccc32)CC1)c1cc(Cl)cnc1C(F)F] | N-((1r,4r)-4-((3-(4-(1H-imidazol-1-yl)phenyl)-2-oxo-2,3-dihydro-1H-benzo[d]imidazol-1-yl)methyl)cyclohexyl)-5-chloro-2-(difluoromethyl)nicotinamide | 1-(4-bromophenyl)-1H-imidazole, Intermediate-165 | R |
| 570 | 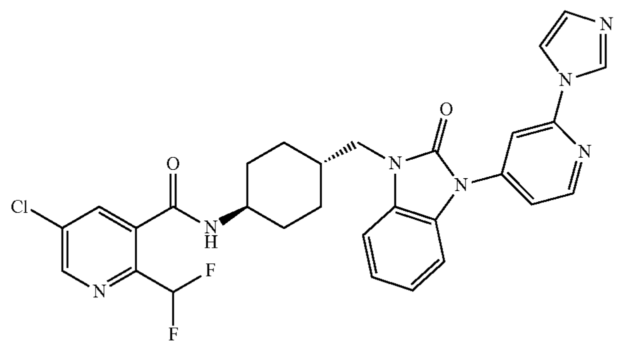 [SMILES: O=C(N[C@H]1CC[C@H](Cn2c(=O)n(-c3ccnc(-n4ccnc4)c3)c3ccccc32)CC1)c1cc(Cl)cnc1C(F)F] | N-((1r,4r)-4-((3-(2-(1H-imidazol-1-yl)pyridin-4-yl)-2-oxo-2,3-dihydro-1H-benzo[d]imidazol-1-yl)methyl)cyclohexyl)-5-chloro-2-(difluoromethyl)nicotinamide | 4-bromo-2-(1H-imidazol-1-yl)pyridine, Intermediate-165 | R |
| 571 | 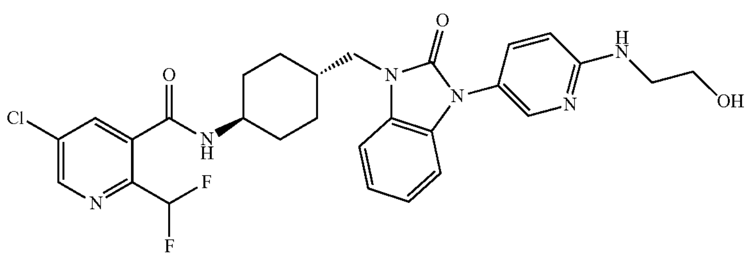 [SMILES: O=C(N[C@H]1CC[C@H](Cn2c(=O)n(-c3ccc(NCCO)nc3)c3ccccc32)CC1)c1cc(Cl)cnc1C(F)F] | 5-chloro-2-(difluoromethyl)-N-((1r,4r)-4-(3-(6-((2-hydroxyethyl)amino)pyridin-3-yl)-2-oxo-2,3-dihydro-1H-benzo[d]imidazol-1-yl)methyl)cyclohexyl)nicotinamide | Intermediate-191, 2-aminoethanol | L |

TABLE 2-continued

| Ex. | Structure | Name | Reactants | Method |
|---|---|---|---|---|
| 572 | 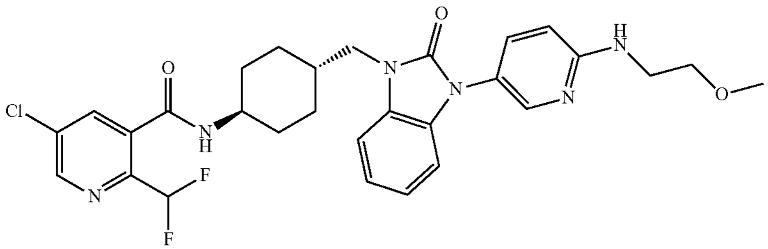 [SMILES: COCCNc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-(3-(6-((2-methoxyethyl)amino)pyridin-3-yl)-2-oxo-2,3-dihydro-1H-benzo[d]imidazol-1-yl)methyl)cyclohexyl)nicotinamide | Intermediate-191, H₂N∼∼O∼ | L |
| 573 | 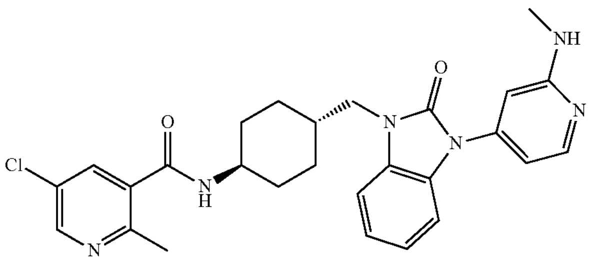 [SMILES: CNc1cc(-n2c(=O)n(C[C@H]3CC[C@H](NC(=O)c4cc(Cl)cnc4C)CC3)c3ccccc32)ccn1] | 5-chloro-2-methyl-N-((1r,4r)-4-((3-(2-(methylamino)pyridin-4-yl)-2-oxo-2,3-dihydro-1H-benzo[d]imidazol-1-yl)methyl)cyclohexyl)nicotinamide | see Example synthesis part | |
| 574 | 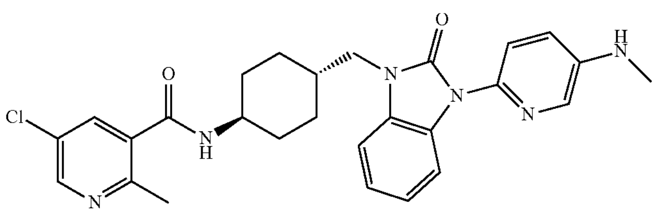 [SMILES: CNc1ccc(-n2c(=O)n(C[C@H]3CC[C@H](NC(=O)c4cc(Cl)cnc4C)CC3)c3ccccc32)nc1] | 5-chloro-2-methyl-N-((1r,4r)-4-((3-(5-(methylamino)pyridin-2-yl)-2-oxo-2,3-dihydro-1H-benzo[d]imidazol-1-yl)methyl)cyclohexyl)nicotinamide | see Example synthesis part | |
| 575 | 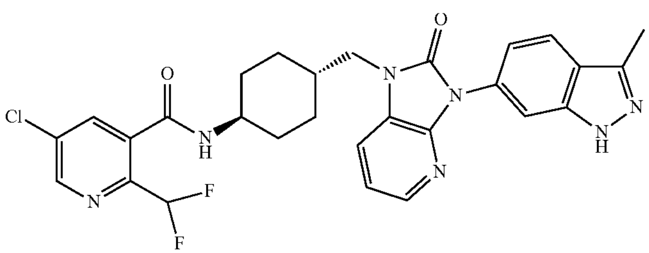 [SMILES: Cc1n[nH]c2cc(-n3c(=O)n(C[C@H]4CC[C@H](NC(=O)c5cc(Cl)cnc5C(F)F)CC4)c4cccnc43)ccc12] | 5-chloro-2-(difluoromethyl)-N-((1r,4r)-4-(3-(3-methyl-1H-indazol-6-yl)-2-oxo-2,3-dihydro-1H-imidazo[4,5-b]pyridin-1-yl)methyl)cyclohexyl)nicotinamide | see Example synthesis part | |

TABLE 2-continued

| Ex. | Structure | Name | Reactants | Method |
|---|---|---|---|---|
| 576 | 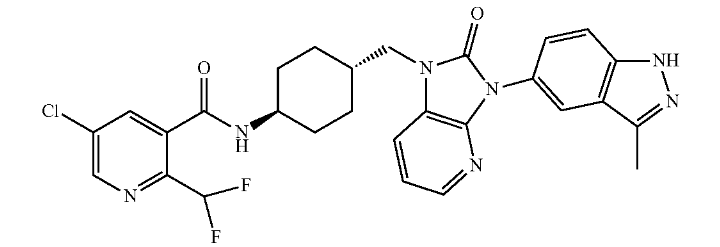 [SMILES: Cc1n[nH]c2ccc(-n3c(=O)n(C[C@H]4CC[C@H](NC(=O)c5cc(Cl)cnc5C(F)F)CC4)c4cccnc43)cc12] | 5-chloro-2-(difluoromethyl)-N-((1r,4r)-4-(3-(3-methyl-1H-indazol-5-yl)-2-oxo-2,3-dihydro-1H-imidazo[4,5-b]pyridin-1-yl)methyl)cyclohexyl)nicotinamide | Intermediate-111, Mesylate-4 | S |
| 577 | 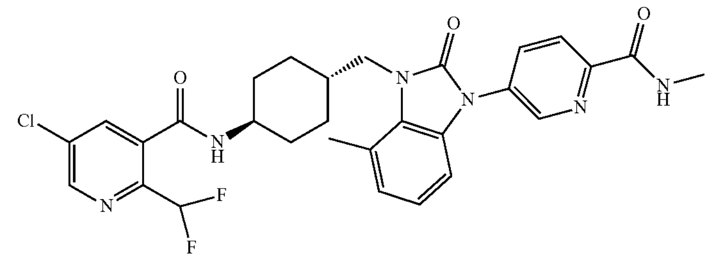 [SMILES: CNC(=O)c1ccc(-n2c(=O)n(C[C@H]3CC[C@H](NC(=O)c4cc(Cl)cnc4C(F)F)CC3)c3c(C)cccc32)cn1] | 5-(3-(((1r,4r)-4-(5-chloro-2-(difluoromethyl)nicotinamido)cyclohexyl)methyl)-4-methyl-2-oxo-2,3-dihydro-1H-benzo[d]imidazol-1-yl)-N-methylpicolinamide | Intermediate-228, Mesylate-4 | A1 |
| 578 | 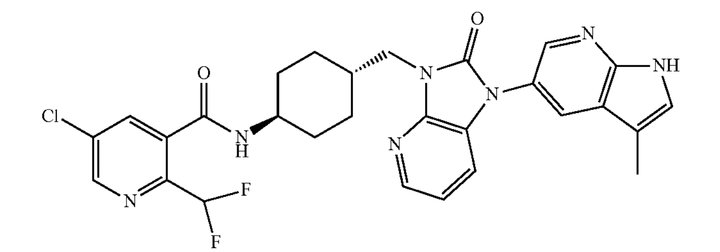 [SMILES: Cc1c[nH]c2ncc(-n3c(=O)n(C[C@H]4CC[C@H](NC(=O)c5cc(Cl)cnc5C(F)F)CC4)c4ncccc43)cc12] | 5-chloro-2-(difluoromethyl)-N-((1r,4r)-4-((1-(3-methyl-1H-pyrrolo[2,3-b]pyridin-5-yl)-2-oxo-1H-imidazo[4,5-b]pyridin-3(2H)-yl)methyl)cyclohexyl)methyl)nicotinamide | Intermediate-229, Mesylate-4 | V |
| 579 | 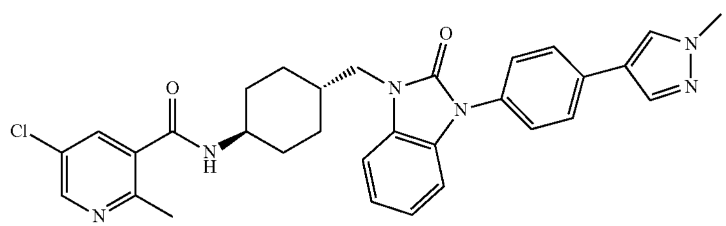 [SMILES: Cc1ncc(Cl)cc1C(=O)N[C@H]1CC[C@H](Cn2c(=O)n(-c3ccc(-c4cnn(C)c4)cc3)c3ccccc32)CC1] | 5-chloro-2-methyl-N-((1r,4r)-4-((3-(4-(1-methyl-1H-pyrazol-4-yl)phenyl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 580 | 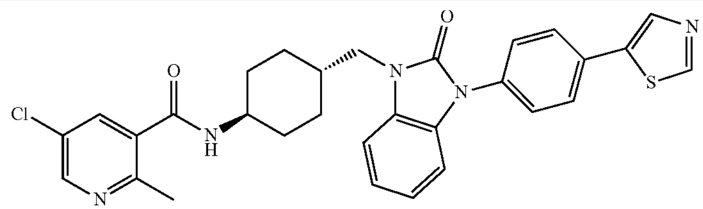 [SMILES: Cc1ncc(Cl)cc1C(=O)N[C@H]1CC[C@H](Cn2c(=O)n(-c3ccc(-c4cncs4)cc3)c3ccccc32)CC1] | 5-chloro-2-methyl-N-((1r,4r)-4-((2-oxo-3-(4-(thiazol-5-yl)phenyl)-2,3-dihydro-1H-benzo[d]imidazol-1-yl)methyl)cyclohexyl)nicotinamide | | R |
| 581 | 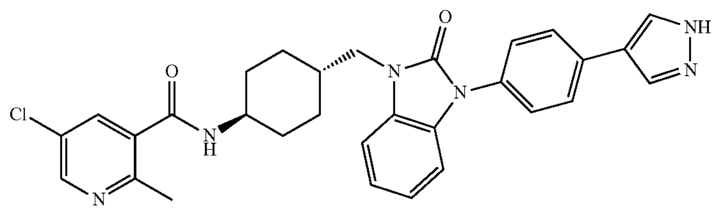 | N-((1r,4r)-4-(3-(4-(1H-pyrazol-4-yl)phenyl)-2-oxo-2,3-dihydro-1H-benzo[d]imidazol-1-yl)methyl)cyclohexyl)-5-chloro-2-methylnicotinamide | Step-2 of Ex 9 see Example synthesis part | |
| 582 | 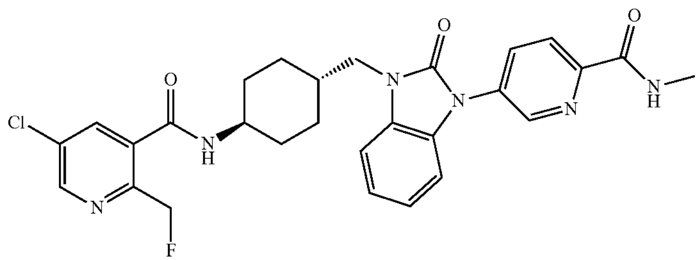 [SMILES: CNC(=O)c1ccc(-n2c(=O)n(C[C@H]3CC[C@H](NC(=O)c4cc(Cl)cnc4CF)CC3)c3ccccc32)cn1] | 5-(3-((1r,4r)-4-(5-chloro-2-(fluoromethyl)nicotinamido)cyclohexyl)methyl)-2-oxo-2,3-dihydro-1H-benzo[d]imidazol-1-yl)-N-methylpicolinamide | Intermediate-121, Intermediate-231 | Q |
| 583 | 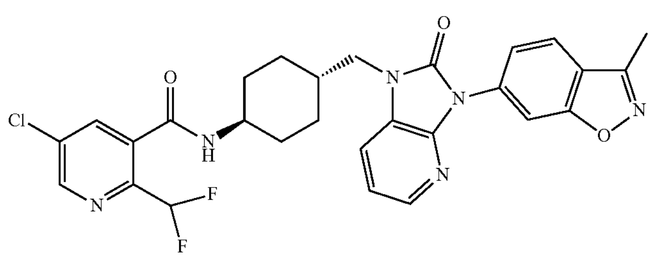 [SMILES: Cc1noc2cc(-n3c(=O)n(C[C@H]4CC[C@H](NC(=O)c5cc(Cl)cnc5C(F)F)CC4)c4cccnc43)ccc12] | 5-chloro-2-(difluoromethyl)-N-((1r,4r)-4-((3-(3-methyl-benzo[d]isoxazol-6-yl)-2-oxo-2,3-dihydro-1H-imidazo[4,5-b]pyridin-1-yl)methyl)cyclohexyl)nicotinamide | Intermediate-214, | T |

| Ex. | Structure | Name | Reactants | Method |
|---|---|---|---|---|
| 584 | 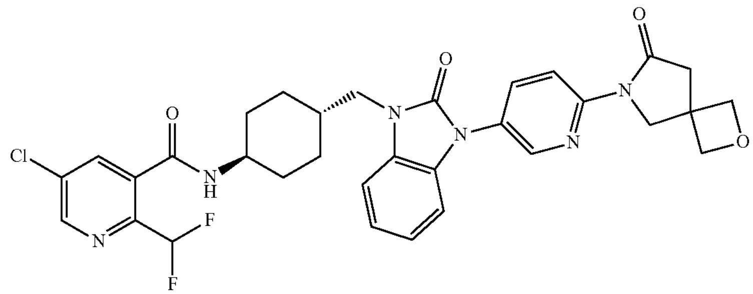 [SMILES: O=C(N[C@H]1CC[C@H](Cn2c(=O)n(-c3ccc(N4CC5(COC5)CC4=O)nc3)c3ccccc32)CC1)c1cc(Cl)cnc1C(F)F] | 5-chloro-2-(difluoromethyl)-N-((1r,4r)-4-((2-oxo-3-(6-(7-oxo-2-oxa-6-azaspiro[3,4]octan-6-yl)pyridin-3-yl)-2,3-dihydro-1H-benzo[d]imidazol-1-yl)methyl)cyclohexyl)nicotinamide | Intermediate-207, | Y |
| 585 | 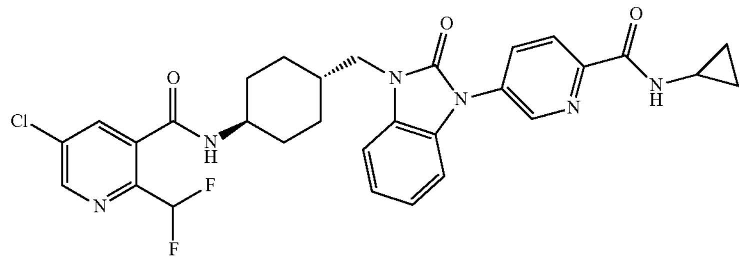 [SMILES: O=C(NC1CC1)c1ccc(-n2c(=O)n(C[C@H]3CC[C@H](NC(=O)c4cc(Cl)cnc4C(F)F)CC3)c3ccccc32)cn1] | 5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-cyclopropylpicolinamide | Intermediate-220, | Q |
| 586 | 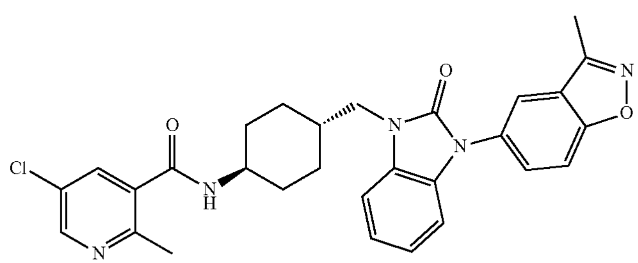 [SMILES: Cc1ncc(Cl)cc1C(=O)N[C@H]1CC[C@H](Cn2c(=O)n(-c3ccc4onc(C)c4c3)c3ccccc32)CC1] | 5-chloro-2-methyl-N-((1r,4r)-4-((3-(3-methylbenzo[d]isoxazol-5-yl)-2-oxo-2,3-dihydro-1H-benzo[d]imidazol-1-yl)methyl)cyclohexyl)nicotinamide | Intermediate-232, Mesylate-1 | A1 |

TABLE 2-continued

| Ex. | Structure | Name | Reactants | Method |
|---|---|---|---|---|
| 587 | 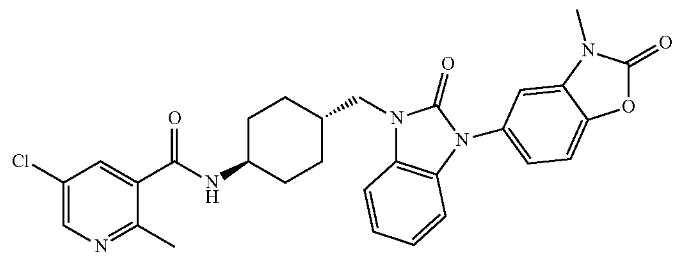 [SMILES: Cc1ncc(Cl)cc1C(=O)N[C@H]1CC[C@H](Cn2c(=O)n(-c3ccc4oc(=O)n(C)c4c3)c3ccccc32)CC1] | 5-chloro-2-methyl-N-((1r,4r)-4-((3-(3-methyl-2-oxo-2,3-dihydrobenzo[d]oxazol-5-yl)-2-oxo-2,3-dihydro-1H-benzo[d]imidazol-1-yl)methyl)cyclohexyl)nicotinamide | Step-2 of Ex 9 | R |
| 588 | 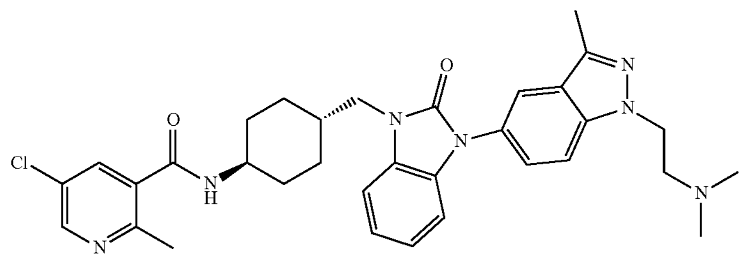 [SMILES: Cc1ncc(Cl)cc1C(=O)N[C@H]1CC[C@H](Cn2c(=O)n(-c3ccc4c(c3)c(C)nn4CCN(C)C)c3ccccc32)CC1] | 5-chloro-N-((1r,4r)-4-(3-(1-(2-(dimethylamino)ethyl)-3-methyl-1H-indazol-5-yl)-2-oxo-2,3-dihydro-1H-benzo[d]imidazol-1-yl)methyl)cyclohexyl)-2-methylnicotinamide | see Example synthesis part | |
| 589 | 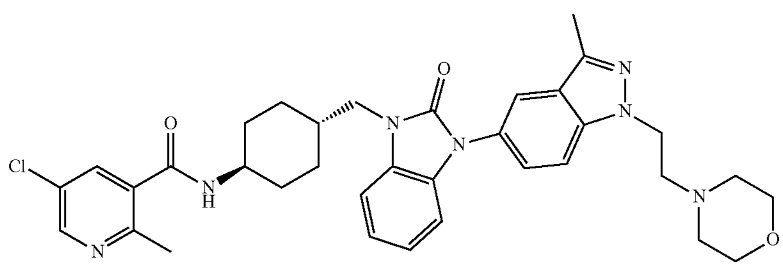 [SMILES: Cc1ncc(Cl)cc1C(=O)N[C@H]1CC[C@H](Cn2c(=O)n(-c3ccc4c(c3)c(C)nn4CCN3CCOCC3)c3ccccc32)CC1] | 5-chloro-2-methyl-N-((1r,4r)-4-((3-(3-methyl-1-(2-morpholinoethyl)-1H-indazol-5-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 590 | 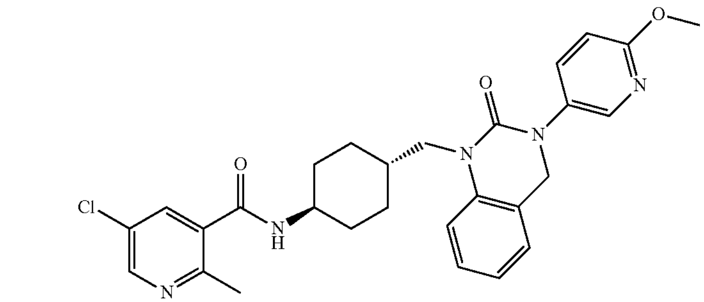 [SMILES: COc1ccc(N2Cc3ccccc3N(C[C@H]3CC[C@H](NC(=O)c4cc(Cl)cnc4C)CC3)C2=O)cn1] | 5-chloro-N-((1r,4r)-4-((3-(6-methoxypyridin-3-yl)-2-oxo-3,4-dihydroquinazolin-1(2H)-yl)methyl)cyclohexyl)-2-methylnicotinamide | Intermediate-233, Mesylate-1 | A1 |
| 591 | 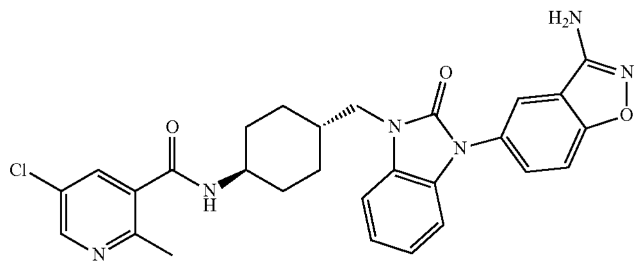 [SMILES: Cc1ncc(Cl)cc1C(=O)N[C@H]1CC[C@H](Cn2c(=O)n(-c3ccc4onc(N)c4c3)c3ccccc32)CC1] | N-((1r,4r)-4-((3-(3-aminobenzo[d]isoxazol-5-yl)-2-oxo-2,3-dihydro-1H-benzo[d]imidazol-1-yl)methyl)cyclohexyl)-5-chloro-2-methylnicotinamide | see Example synthesis part | |
| 592 | 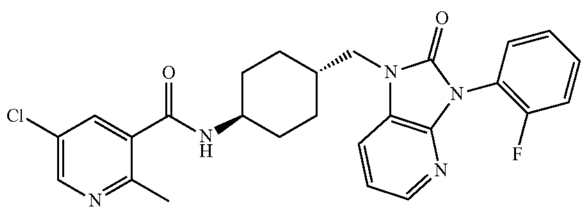 | 5-chloro-N-((1r,4r)-4-((3-(2-fluorophenyl)-2-oxo-2,3-dihydro-1H-imidazo[4,5-b]pyridin-1-yl)methyl)cyclohexyl)-2-methylnicotinamide | Intermediate-197, Mesylate-1 | A1 |
| 593 | 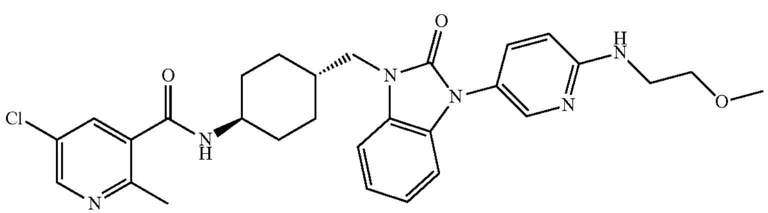 [SMILES: COCCNc1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)-2-methylnicotinamide | Intermediate-54, | L |

TABLE 2-continued

| Ex. | Structure | Name | Reactants | Method |
|---|---|---|---|---|
| 594 | 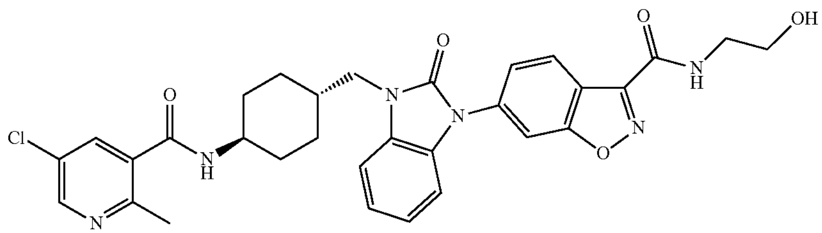 [SMILES: Cc1ncc(Cl)cc1C(=O)N[C@H]1CC[C@H](Cn2c(=O)n(-c3ccc4c(C(=O)NCCO)noc4c3)c3ccccc32)CC1] | 6-(3-((1r,4r)-4-(5-chloro-2-methylnicotinamido)cyclohexyl)methyl)-2-oxo-2,3-dihydro-1H-benzo[d]imidazol-1-yl)-N-(2-hydroxyethyl)benzo[d]isoxazole-3-carboxamide | see Example synthesis part | |
| 595 | 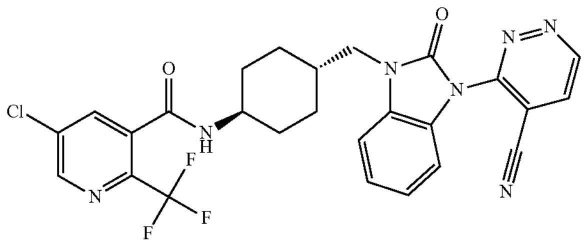 [SMILES: N#Cc1ccnnc1-n1c(=O)n(C[C@H]2CC[C@H](NC(=O)c3cc(Cl)cnc3C(F)(F)F)CC2)c2ccccc21] | 5-chloro-N-((1r,4r)-4-((3-(4-cyanopyridazin-3-yl)-2-oxo-2,3-dihydro-1H-benzo[d]imidazol-1-yl)methyl)cyclohexyl)-2-(trifluoromethyl)nicotinamide | see Example synthesis part | |
| 596 | 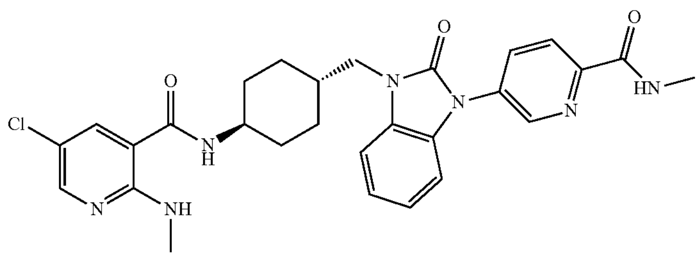 [SMILES: CNC(=O)c1ccc(-n2c(=O)n(C[C@H]3CC[C@H](NC(=O)c4cc(Cl)cnc4NC)CC3)c3ccccc32)cn1] | 5-(3-((1r,4r)-4-(5-chloro-2-(methylamino)nicotinamido)cyclohexyl)methyl)-1H-benzo[d]imidazol-1-yl)-N-methylpicolinamide | Intermediate-121, | Q |
| 597 | 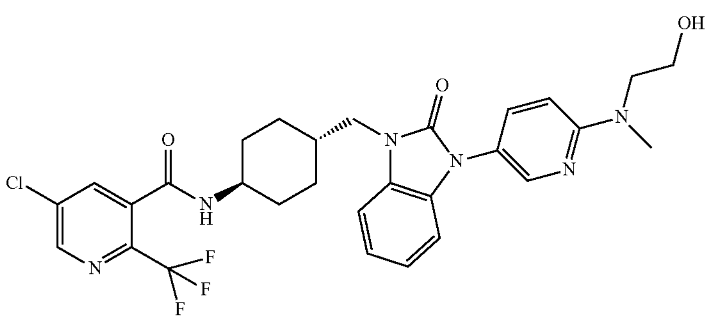 [SMILES: CN(CCO)c1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)-2-(trifluoromethyl)nicotinamide | Intermediate-37, Mesylate-3 | A1 |

TABLE 2-continued

| Ex. | Structure | Name | Reactants | Method |
|---|---|---|---|---|
| 598 | 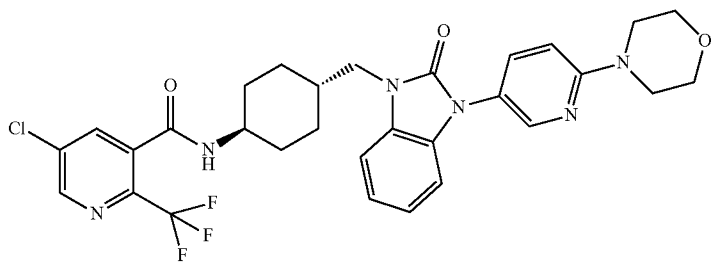 [SMILES: O=C(N[C@H]1CC[C@H](Cn2c(=O)n(-c3ccc(N4CCOCC4)nc3)c3ccccc32)CC1)c1cc(Cl)cnc1C(F)(F)F] | 5-chloro-N-((1r,4r)-4-((3-(6-morpholinopyridin-3-yl)-2-oxo-2,3-dihydro-1H-benzo[d]imidazol-1-yl)methyl)cyclohexyl)-2-(trifluoromethyl)nicotinamide | Intermediate-28, Mesylate-3 | A1 |
| 599 | 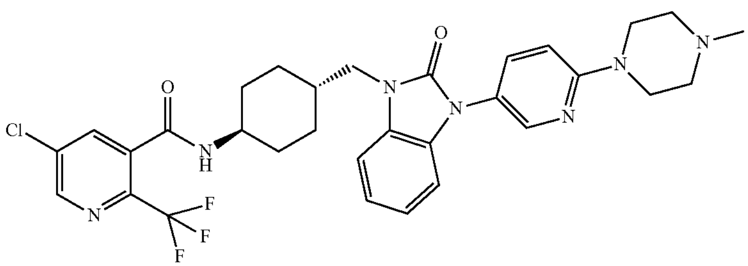 [SMILES: CN1CCN(c2ccc(-n3c(=O)n(C[C@H]4CC[C@H](NC(=O)c5cc(Cl)cnc5C(F)(F)F)CC4)c4ccccc43)cn2)CC1] | 5-chloro-N-((1r,4r)-4-((3-(6-(4-methylpiperazin-1-yl)pyridin-3-yl)-2-oxo-2,3-dihydro-1H-benzo[d]imidazol-1-yl)methyl)cyclohexyl)-2-(trifluoromethyl)nicotinamide | Intermediate-29, Mesylate-3 | A1 |
| 600 | 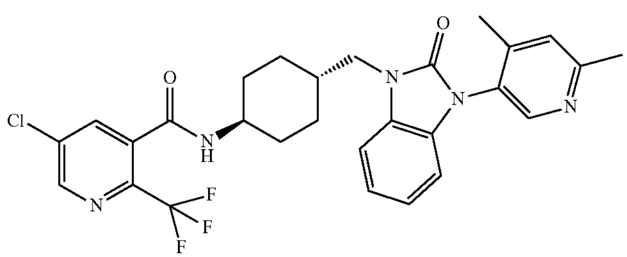 [SMILES: Cc1cc(C)c(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(4,6-dimethylpyridin-3-yl)-2-oxo-2,3-dihydro-1H-benzo[d]imidazol-1-yl)methyl)cyclohexyl)-2-(trifluoromethyl)nicotinamide | Intermediate-144, Mesylate-3 | A1 |

TABLE 2-continued

| Ex. | Structure | Name | Reactants | Method |
|---|---|---|---|---|
| 601 | 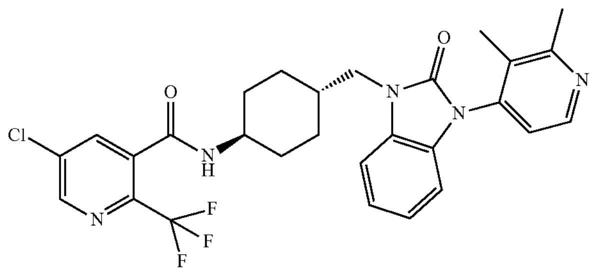 [SMILES: Cc1nccc(-n2c(=O)n(C[C@H]3CC[C@H](NC(=O)c4cc(Cl)cnc4C(F)(F)F)CC3)c3ccccc32)c1C] | 5-chloro-N-((1r,4r)-4-((3-(2,3-dimethylpyridin-4-yl)-2-oxo-2,3-dihydro-1H-benzo[d]imidazol-1-yl)methyl)cyclohexyl)-2-(trifluoromethyl)nicotinamide | Intermediate-145, Mesylate-3 | A1 |
| 602 | 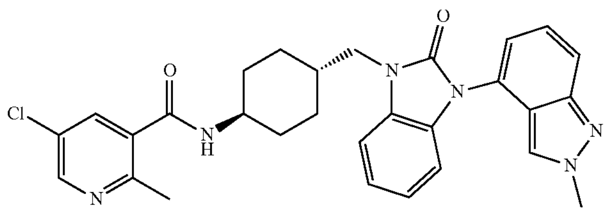 [SMILES: Cc1ncc(Cl)cc1C(=O)N[C@H]1CC[C@H](Cn2c(=O)n(-c3cccc4nn(C)cc34)c3ccccc32)CC1] | 5-chloro-2-methyl-N-((1r,4r)-4-((3-(2-methyl-2H-indazol-4-yl)-2-oxo-2,3-dihydro-1H-benzo[d]imidazol-1-yl)methyl)cyclohexyl)nicotinamide | Intermediate-184, Mesylate-1 | A1 |
| 603 | 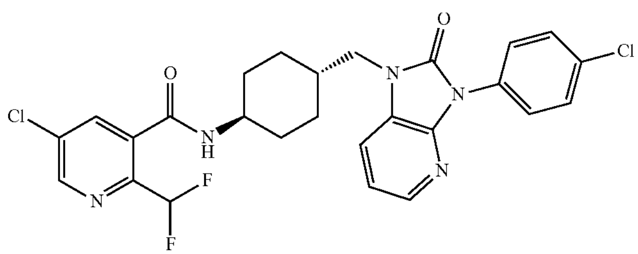 [SMILES: O=C(N[C@H]1CC[C@H](Cn2c(=O)n(-c3ccc(Cl)cc3)c3ncccc32)CC1)c1cc(Cl)cnc1C(F)F] | 5-chloro-N-((1r,4r)-4-((3-(4-chlorophenyl)-2-oxo-2,3-dihydro-1H-imidazo[4,5-b]pyridin-1-yl)methyl)cyclohexyl)-2-(difluoromethyl)nicotinamide | Intermediate-234, Mesylate-4 | A1 |
| 604 | 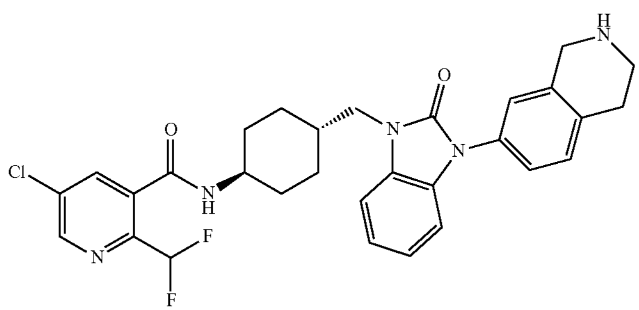 [SMILES: O=C(N[C@H]1CC[C@H](Cn2c(=O)n(-c3ccc4c(c3)CNCC4)c3ccccc32)CC1)c1cc(Cl)cnc1C(F)F] | 5-chloro-2-(difluoromethyl)-N-((1r,4r)-4-((2-oxo-3-(1,2,3,4-tetrahydroisoquinolin-7-yl)-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 605 | 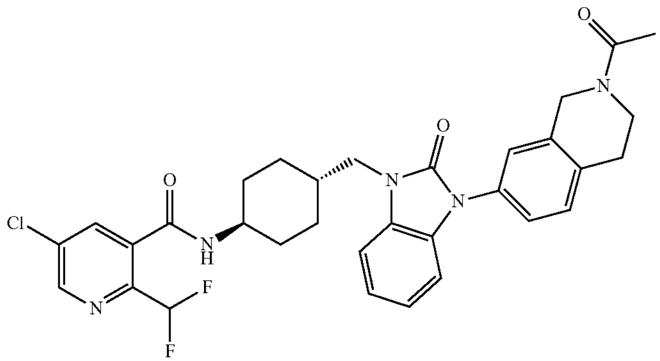 [SMILES: CC(=O)N1CCc2ccc(-n3c(=O)n(C[C@H]4CC[C@H](NC(=O)c5cc(Cl)cnc5C(F)F)CC4)c4ccccc43)cc2C1] | N-((1r,4r)-4-((3-(2-acetyl-1,2,3,4-tetrahydroisoquinolin-7-yl)-2-oxo-2,3-dihydro-1H-benzo[d]imidazol-1-yl)methyl)cyclohexyl)-5-chloro-2-(difluoromethyl)nicotinamide | see Example synthesis part | |
| 606 | 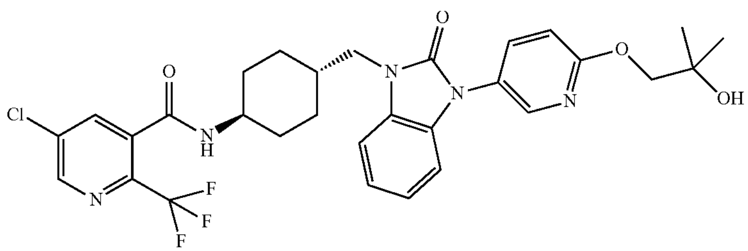 [SMILES: CC(C)(O)COc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)-2-(trifluoromethyl)nicotinamide | Intermediate-189, Mesylate-3 | A1 |
| 607 | 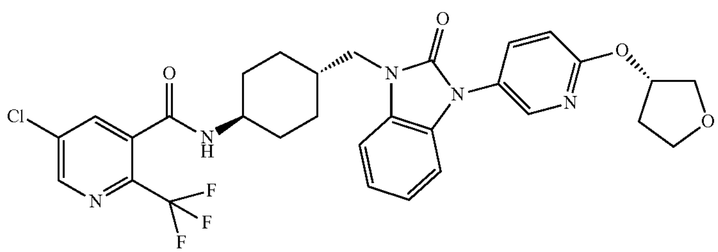 [SMILES: O=C(N[C@H]1CC[C@H](Cn2c(=O)n(-c3ccc(O[C@H]4CCOC4)nc3)c3ccccc32)CC1)c1cc(Cl)cnc1C(F)(F)F] | 5-chloro-N-((1s,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)-2-(trifluoromethyl)nicotinamide | Intermediate-190, Mesylate-3 | A1 |

TABLE 2-continued

| Ex. | Structure | Name | Reactants | Method |
|---|---|---|---|---|
| 608 | 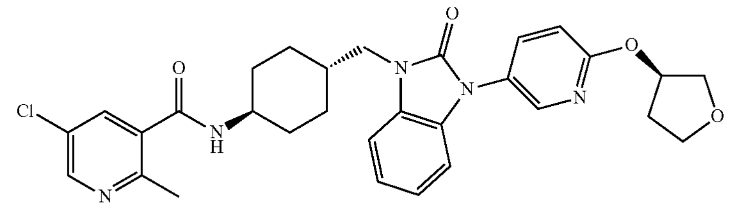 [SMILES: Cc1ncc(Cl)cc1C(=O)N[C@H]1CC[C@H](Cn2c(=O)n(-c3ccc(O[C@@H]4CCOC4)nc3)c3ccccc32)CC1] | 5-chloro-2-methyl-N-((1R,4r)-4-((2-oxo-3-(6-(((R)-tetrahydrofuran-3-yl)oxy)pyridin-3-yl)-2,3-dihydro-1H-benzo[d]imidazol-1-yl)methyl)cyclohexyl)nicotinamide | Intermediate-188, Mesylate-1 | A1 |
| 609 | 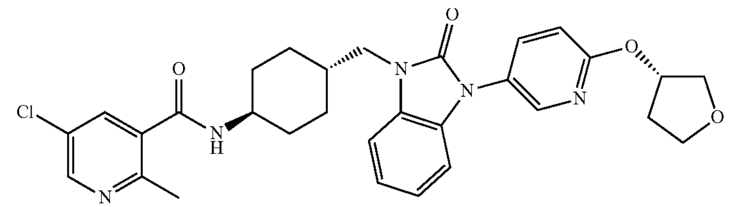 [SMILES: Cc1ncc(Cl)cc1C(=O)N[C@H]1CC[C@H](Cn2c(=O)n(-c3ccc(O[C@H]4CCOC4)nc3)c3ccccc32)CC1] | 5-chloro-2-methyl-N-((1S,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)nicotinamide | Intermediate-190, Mesylate-1 | A1 |
| 610 | 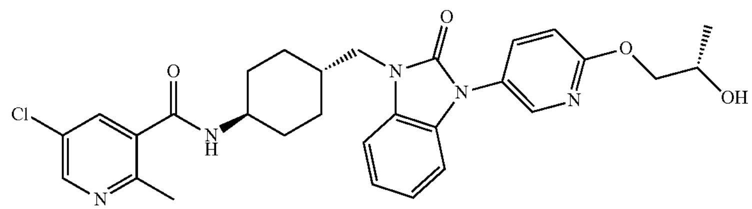 [SMILES: Cc1ncc(Cl)cc1C(=O)N[C@H]1CC[C@H](Cn2c(=O)n(-c3ccc(OC[C@H](C)O)nc3)c3ccccc32)CC1] | 5-chloro-N-((1S,4r)-4-(3-(6-((S)-2-hydroxypropoxy)pyridin-3-yl)-2-oxo-2,3-dihydro-1H-benzo[d]imidazol-1-yl)methyl)cyclohexyl)-2-methylnicotinamide | see Example synthesis part | |
| 611 | 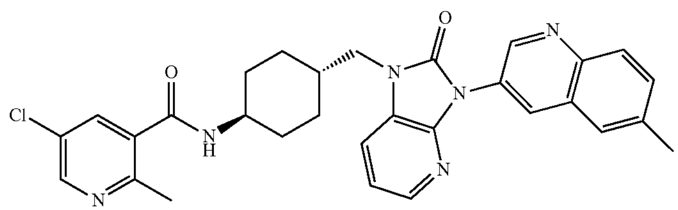 [SMILES: Cc1ccc2ncc(-n3c(=O)n(C[C@H]4CC[C@H](NC(=O)c5cc(Cl)cnc5C)CC4)c4cccnc43)cc2c1] | 5-chloro-2-methyl-N-((1r,4r)-4-((3-(6-methylquinolin-3-yl)-2-oxo-2,3-dihydro-1H-imidazo[4,5-b]pyridin-1-yl)methyl)cyclohexyl)nicotinamide | Intermediate-236, Mesylate-1 | A1 |

TABLE 2-continued

| Ex. | Structure | Name | Reactants | Method |
|---|---|---|---|---|
| 612 | 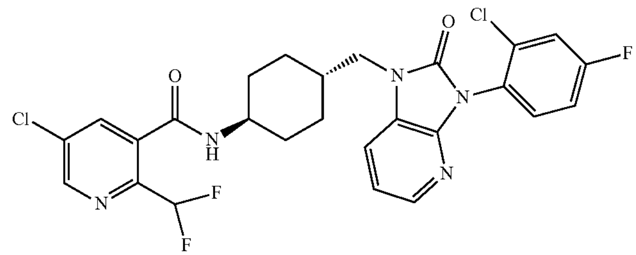 [SMILES: O=C(N[C@H]1CC[C@H](Cn2c(=O)n(-c3ccc(F)cc3Cl)c3ncccc32)CC1)c1cc(Cl)cnc1C(F)F] | 5-chloro-N-((1r,4r)-4-((3-(2-chloro-4-fluorophenyl)-2-oxo-2,3-dihydro-1H-imidazo[4,5-b]pyridin-1-yl)methyl)cyclohexyl)-2-(difluoromethyl)nicotinamide | Intermediate-237, Mesylate-4 | A1 |
| 613 | 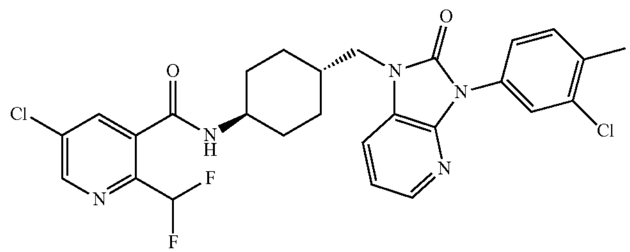 [SMILES: Cc1ccc(-n2c(=O)n(C[C@H]3CC[C@H](NC(=O)c4cc(Cl)cnc4C(F)F)CC3)c3cccnc32)cc1Cl] | 5-chloro-N-((1r,4r)-4-((3-(3-chloro-4-methylphenyl)-2-oxo-2,3-dihydro-1H-imidazo[4,5-b]pyridin-1-yl)methyl)cyclohexyl)-2-(difluoromethyl)nicotinamide | Intermediate-238, Mesylate-4 | A1 |
| 614 | 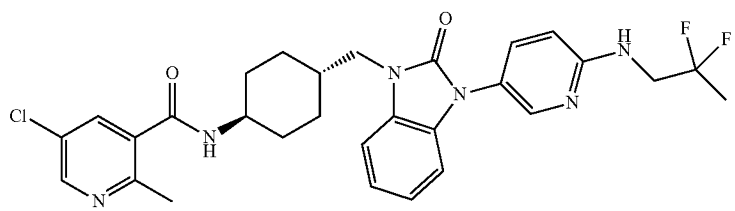 [SMILES: Cc1ncc(Cl)cc1C(=O)N[C@H]1CC[C@H](Cn2c(=O)n(-c3ccc(NCC(C)(F)F)nc3)c3ccccc32)CC1] | 5-chloro-N-((1r,4r)-4-((3-(6-((2,2-difluoropropyl)amino)pyridin-3-yl)-2-oxo-2,3-dihydro-1H-benzo[d]imidazol-1-yl)methyl)cyclohexyl)-2-methylnicotinamide | Intermediate-210, Mesylate-1 | A1 |
| 615 | 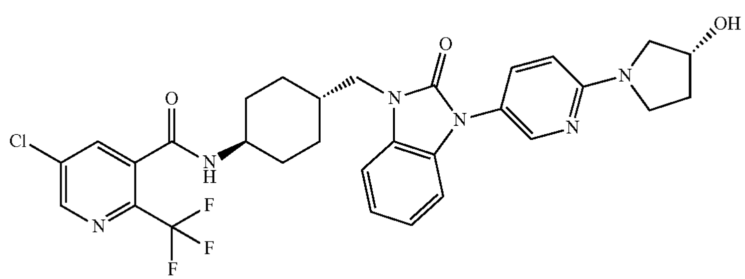 [SMILES: O=C(N[C@H]1CC[C@H](Cn2c(=O)n(-c3ccc(N4CC[C@@H](O)C4)nc3)c3ccccc32)CC1)c1cc(Cl)cnc1C(F)(F)F] | 5-chloro-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)-2-(trifluoromethyl)nicotinamide | Intermediate-50, Mesylate-3 | A1 |

TABLE 2-continued

| Ex. | Structure | Name | Reactants | Method |
|---|---|---|---|---|
| 616 | 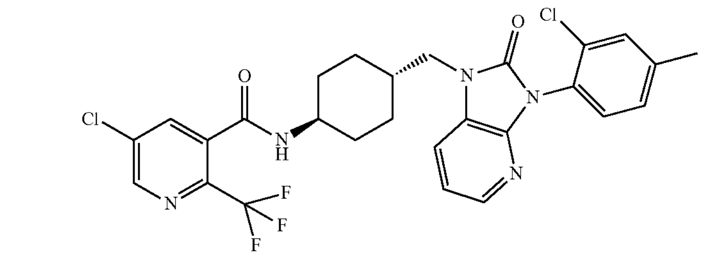 [SMILES: Cc1ccc(-n2c(=O)n(C[C@H]3CC[C@H](NC(=O)c4cc(Cl)cnc4C(F)(F)F)CC3)c3cccnc32)c(Cl)c1] | 5-chloro-N-((1r,4r)-4-((3-(2-chloro-4-methylphenyl)-2-oxo-2,3-dihydro-1H-imidazo[4,5-b]pyridin-1-yl)methyl)cyclohexyl)-2-(trifluoromethyl)nicotinamide | Intermediate-198, Mesylate-3 | A1 |
| 617 | 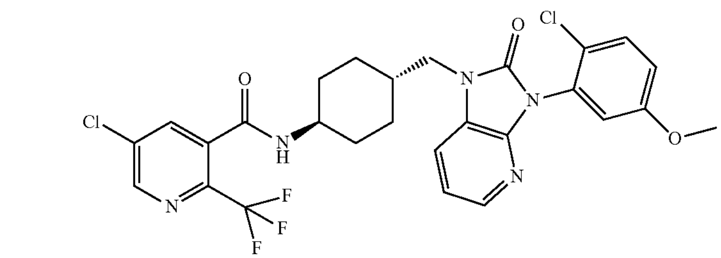 [SMILES: COc1ccc(Cl)c(-n2c(=O)n(C[C@H]3CC[C@H](NC(=O)c4cc(Cl)cnc4C(F)(F)F)CC3)c3cccnc32)c1] | 5-chloro-N-((1r,4r)-4-((3-(2-chloro-5-methoxyphenyl)-2-oxo-2,3-dihydro-1H-imidazo[4,5-b]pyridin-1-yl)methyl)cyclohexyl)-2-(trifluoromethyl)nicotinamide | Intermediate-199, Mesylate-3 | A1 |
| 618 | 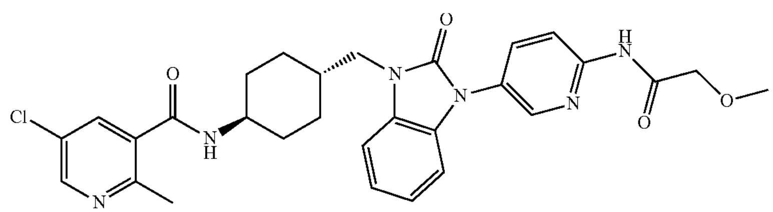 [SMILES: COCC(=O)Nc1ccc(-n2c(=O)n(C[C@H]3CC[C@H](NC(=O)c4cc(Cl)cnc4C)CC3)c3ccccc32)cn1] | 5-chloro-N-((1r,4r)-4-((3-(6-(2-methoxyacetamido)pyridin-3-yl)-2-oxo-2,3-dihydro-1H-benzo[d]imidazol-1-yl)methyl)cyclohexyl)-2-methylnicotinamide | see Example synthesis part | |
| 619 | 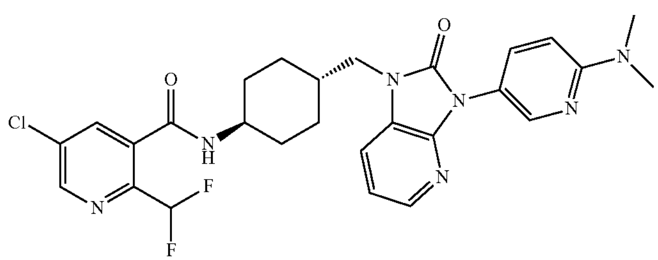 [SMILES: CN(C)c1ccc(-n2c(=O)n(C[C@H]3CC[C@H](NC(=O)c4cc(Cl)cnc4C(F)F)CC3)c3cccnc32)cn1] | 5-chloro-2-(difluoromethyl)-N-((1r,4r)-4-((3-(6-(dimethylamino)pyridin-3-yl)-2-oxo-2,3-dihydro-1H-imidazo[4,5-b]pyridin-1-yl)methyl)cyclohexyl)nicotinamide | Intermediate-71, Mesylate-4 | A1 |

TABLE 2-continued

| Ex. | Structure | Name | Reactants | Method |
|---|---|---|---|---|
| 620 | 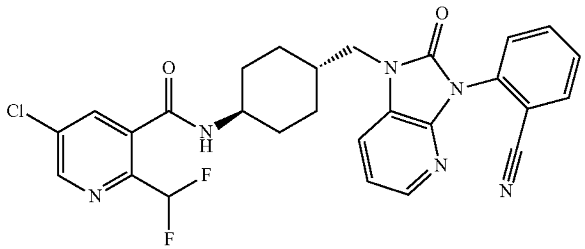 [SMILES: N#Cc1ccccc1-n1c(=O)n(C[C@H]2CC[C@H](NC(=O)c3cc(Cl)cnc3C(F)F)CC2)c2cccnc21] | 5-chloro-N-((1r,4r)-4-((3-(2-cyanophenyl)-2-oxo-2,3-dihydro-1H-imidazo[4,5-b]pyridin-1-yl)methyl)cyclohexyl)-2-(difluoromethyl)nicotinamide | Intermediate-239, Mesylate-4 | A1 |
| 621 | 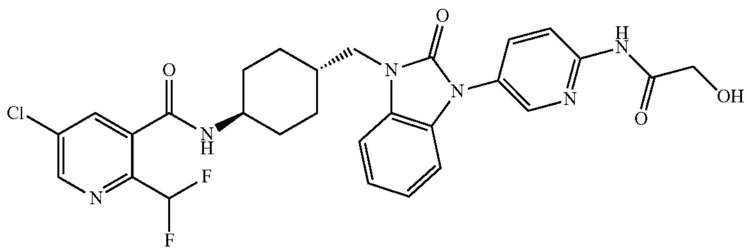 [SMILES: O=C(CO)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(2-hydroxyacetamido)pyridin-3-yl)-2-oxo-2,3-dihydro-1H-benzo[d]imidazol-1-yl)methyl)cyclohexyl)nicotinamide | Intermediate-207, 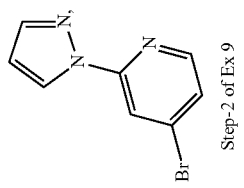 | Y |
| 622 | 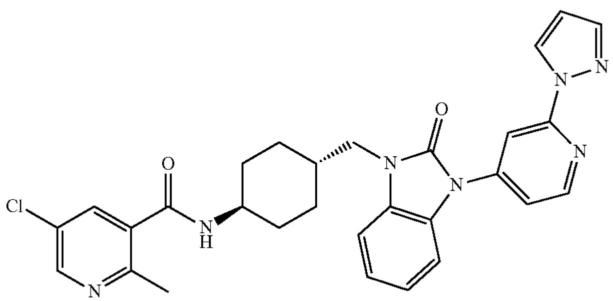 [SMILES: Cc1ncc(Cl)cc1C(=O)N[C@H]1CC[C@H](Cn2c(=O)n(-c3ccnc(-n4cccn4)c3)c3ccccc32)CC1] | N-((1,4r)-4-((3-(2-(1H-pyrazol-1-yl)pyridin-4-yl)-2-oxo-2,3-dihydro-1H-benzo[d]imidazol-1-yl)methyl)cyclohexyl)-5-chloro-2-methylnicotinamide | Step-2 of Ex 9 | R |

TABLE 2-continued

| Ex. | Structure | Name | Reactants | Method |
|---|---|---|---|---|
| 623 | 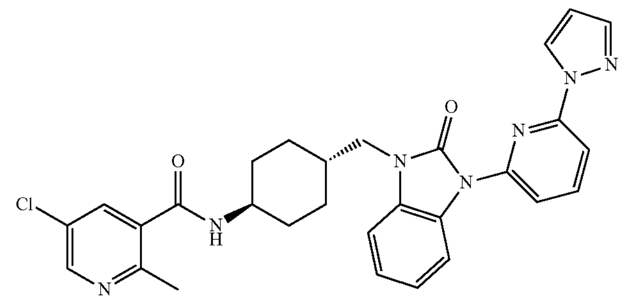 [SMILES: Cc1ncc(Cl)cc1C(=O)N[C@H]1CC[C@H](Cn2c(=O)n(-c3cccc(-n4cccn4)n3)c3ccccc32)CC1] | N-((1r,4r)-4-((3-(6-(1H-pyrazol-1-yl)pyridin-2-yl)-2-oxo-2,3-dihydro-1H-benzo[d]imidazol-1-yl)methyl)cyclohexyl)-5-chloro-2-methylnicotinamide | Step-2 of Ex 9 | R |
| 624 | 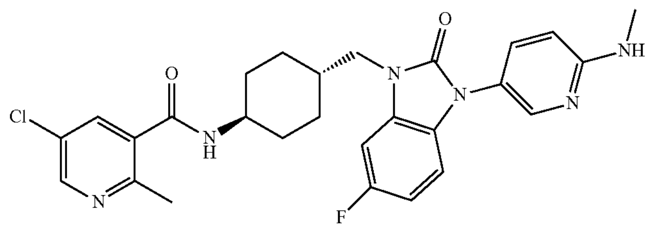 [SMILES: CNc1ccc(-n2c(=O)n(C[C@H]3CC[C@H](NC(=O)c4cc(Cl)cnc4C)CC3)c3cc(F)ccc32)cn1] | 5-chloro-N-((1r,4r)-4-((6-fluoro-3-(6-(methylamino)pyridin-3-yl)-2-oxo-2,3-dihydro-1H-benzo[d]imidazol-1-yl)methyl)cyclohexyl)-2-methylnicotinamide | Intermediate-240, Mesylate-1 | A1 |
| 625 | 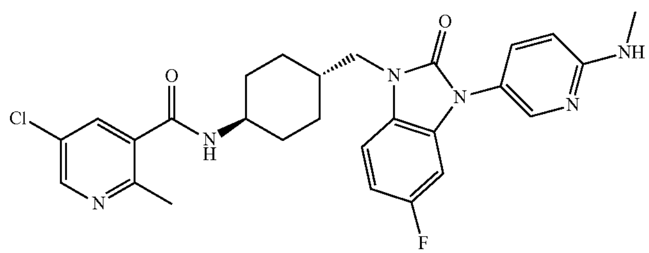 [SMILES: CNc1ccc(-n2c(=O)n(C[C@H]3CC[C@H](NC(=O)c4cc(Cl)cnc4C)CC3)c3ccc(F)cc32)cn1] | 5-chloro-N-((1r,4r)-4-((5-fluoro-3-(6-(methylamino)pyridin-3-yl)-2-oxo-2,3-dihydro-1H-benzo[d]imidazol-1-yl)methyl)cyclohexyl)-2-methylnicotinamide | Intermediate-241, Mesylate-1 | A1 |
| 626 | 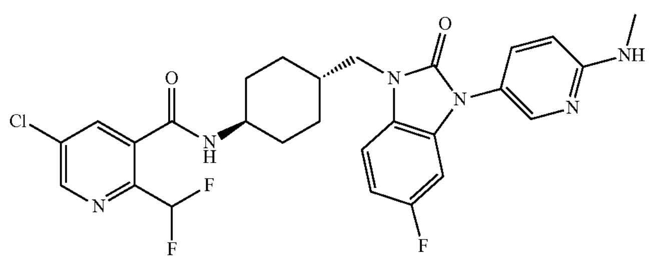 [SMILES: CNc1ccc(-n2c(=O)n(C[C@H]3CC[C@H](NC(=O)c4cc(Cl)cnc4C(F)F)CC3)c3ccc(F)cc32)cn1] | 5-chloro-2-(difluoromethyl)-N-((1r,4r)-4-((5-fluoro-3-(6-(methylamino)pyridin-3-yl)-2-oxo-2,3-dihydro-1H-benzo[d]imidazol-1-yl)methyl)cyclohexyl)nicotinamide | Intermediate-241, Mesylate-4 | A1 |

TABLE 2-continued

| Ex. | Structure | Name | Reactants | Method |
|---|---|---|---|---|
| 627 | 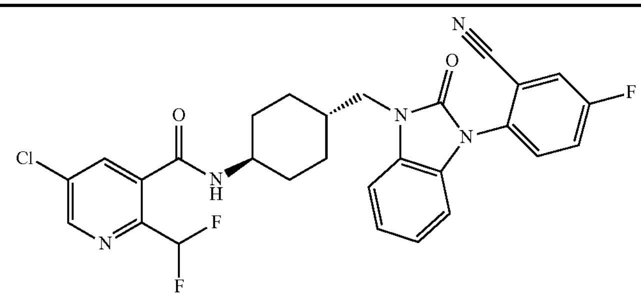 | 5-chloro-N-((1r,4r)-4-((3-(2-cyano-4-fluorophenyl)-2-oxo-2,3-dihydro-1H-benzo[d]imidazol-1-yl)methyl)cyclohexyl)-2-(difluoromethyl)nicotinamide | Intermediate-165 | U |
| 628 | 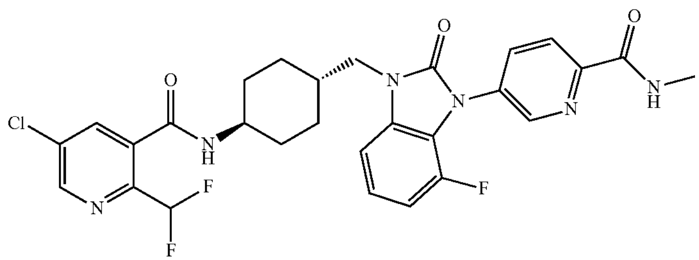 [SMILES: CNC(=O)c1ccc(-n2c(=O)n(C[C@H]3CC[C@H](NC(=O)c4cc(Cl)cnc4C(F)F)CC3)c3cccc(F)c32)cn1] | 5-(3-((1r,4r)-4-(5-chloro-2-(difluoromethyl)nicotinamido)cyclohexyl)methyl)-7-fluoro-2-oxo-2,3-dihydro-1H-benzo[d]imidazol-1-yl)-N-methylpicolinamide | Intermediate-118, Mesylate-4 | A1 |
| 629 | 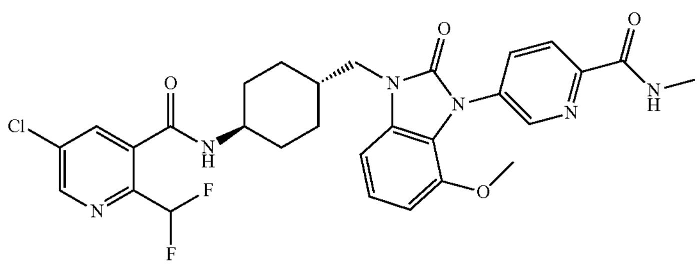 [SMILES: CNC(=O)c1ccc(-n2c(=O)n(C[C@H]3CC[C@H](NC(=O)c4cc(Cl)cnc4C(F)F)CC3)c3cccc(OC)c32)cn1] | 5-(3-((1r,4r)-4-(5-chloro-2-(difluoromethyl)nicotinamido)cyclohexyl)methyl)-7-methoxy-2-oxo-2,3-dihydro-1H-benzo[d]imidazol-1-yl)-N-methylpicolinamide | Intermediate-242, Mesylate-4 | A1 |

TABLE 2-continued

| Ex. | Structure | Name | Reactants | Method |
|---|---|---|---|---|
| 630 | 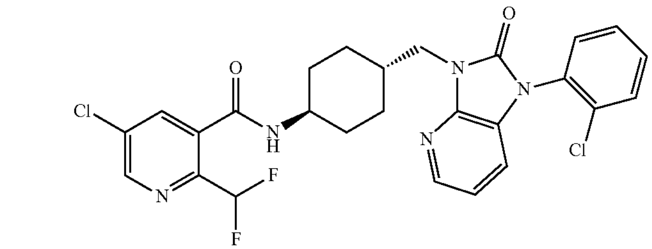 [SMILES: O=C(N[C@H]1CC[C@H](Cn2c(=O)n(-c3ccccc3Cl)c3cccnc32)CC1)c1cc(Cl)cnc1C(F)F] | 5-chloro-N-((1r,4r)-4-((1-(2-chlorophenyl)-2-oxo-1H-imidazo[4,5-b]pyridin-3(2H)-yl)methyl)cyclohexyl)-2-(difluoromethyl)nicotinamide | Intermediate-124, Mesylate-4 | A1 |
| 631 | 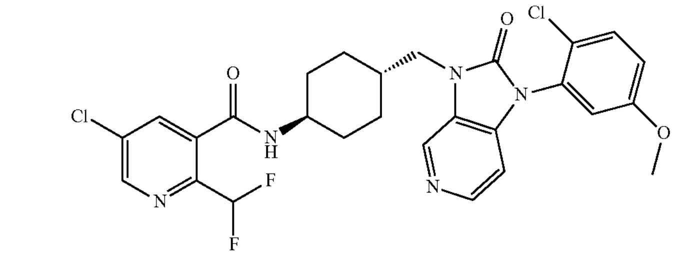 [SMILES: COc1ccc(Cl)c(-n2c(=O)n(C[C@H]3CC[C@H](NC(=O)c4cc(Cl)cnc4C(F)F)CC3)c3cnccc32)c1] | 5-chloro-N-((1r,4r)-4-((1-(2-chloro-5-methoxyphenyl)-2-oxo-1H-imidazo[4,5-c]pyridin-3(2H)-yl)methyl)cyclohexyl)-2-(difluoromethyl)nicotinamide | Intermediate-243, Mesylate-4 | A1 |
| 632 | 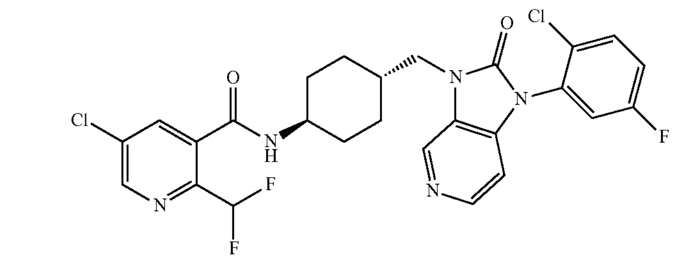 [SMILES: O=C(N[C@H]1CC[C@H](Cn2c(=O)n(-c3cc(F)ccc3Cl)c3ccncc32)CC1)c1cc(Cl)cnc1C(F)F] | 5-chloro-N-((1r,4r)-4-((1-(2-chloro-5-fluorophenyl)-2-oxo-1H-imidazo[4,5-c]pyridin-3(2H)-yl)methyl)cyclohexyl)-2-(difluoromethyl)nicotinamide | Intermediate-244, Mesylate-4 | A1 |
| 633 | 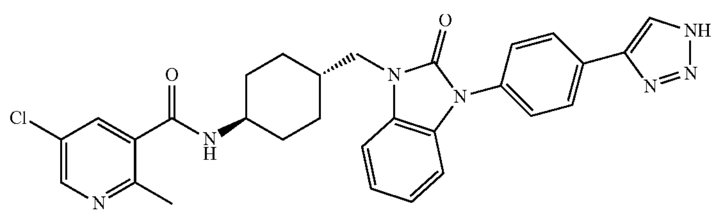 | N-((1r,4r)-4-(3-(4-(1H-1,2,3-triazol-1-yl)phenyl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 634 | 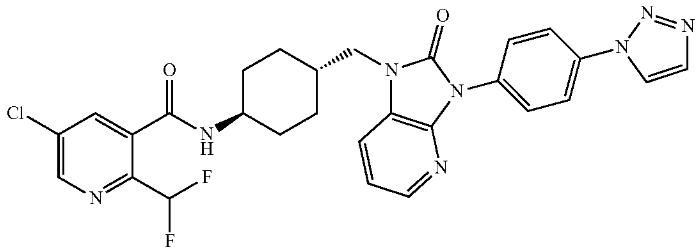 [SMILES: O=C(N[C@H]1CC[C@H](Cn2c(=O)n(-c3ccc(-n4ccnn4)cc3)c3ncccc32)CC1)c1cc(Cl)cnc1C(F)F] | N-((1r,4r)-4-(3-(4-(1H-1,2,3-triazol-1-yl)phenyl)-2-oxo-2,3-dihydro-1H-imidazo[4,5-b]pyridin-1-yl)methyl)cyclohexyl)-5-chloro-2-(difluoromethyl)nicotinamide | Intermediate-214 | R |
| 635 | 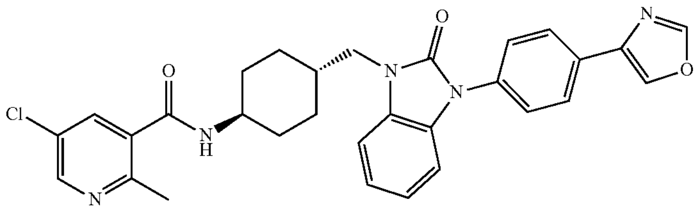 [SMILES: Cc1ncc(Cl)cc1C(=O)N[C@H]1CC[C@H](Cn2c(=O)n(-c3ccc(-c4cocn4)cc3)c3ccccc32)CC1] | 5-chloro-2-methyl-N-((1r,4r)-4-((3-(4-(oxazol-4-yl)phenyl)-2-oxo-2,3-dihydro-1H-benzo[d]imidazol-1-yl)methyl)cyclohexyl)nicotinamide | Step-2 of Ex 9 | R |
| 636 | 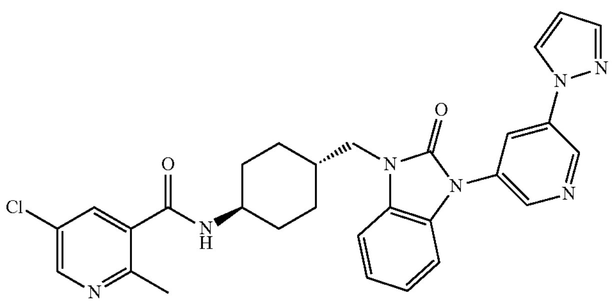 [SMILES: Cc1ncc(Cl)cc1C(=O)N[C@H]1CC[C@H](Cn2c(=O)n(-c3cncc(-n4cccn4)c3)c3ccccc32)CC1] | N-((1r,4r)-4-((3-(5-(1H-pyrazol-1-yl)pyridin-3-yl)-2-oxo-2,3-dihydro-1H-benzo[d]imidazol-1-yl)methyl)cyclohexyl)-5-chloro-2-methylnicotinamide | Step-2 of Ex 9 | R |
| 637 | 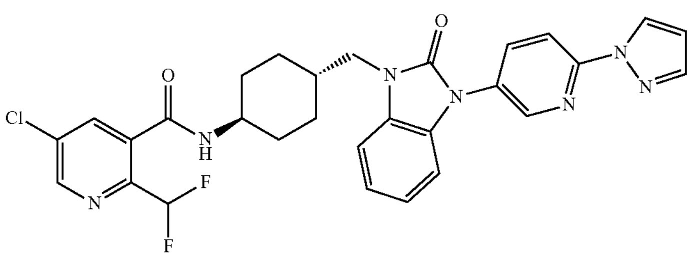 [SMILES: O=C(N[C@H]1CC[C@H](Cn2c(=O)n(-c3ccc(-n4cccn4)nc3)c3ccccc32)CC1)c1cc(Cl)cnc1C(F)F] | N-((1r,4r)-4-((3-(6-(1H-pyrazol-1-yl)pyridin-3-yl)-2-oxo-2,3-dihydro-1H-benzo[d]imidazol-1-yl)methyl)cyclohexyl)-5-chloro-2-(difluoromethyl)nicotinamide | Step-2 of Ex 9 | R |

TABLE 2-continued

| Ex. | Structure | Name | Reactants | Method |
|---|---|---|---|---|
| 638 | 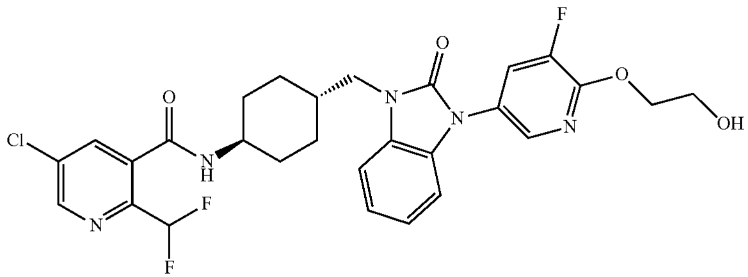 [SMILES: O=C(N[C@H]1CC[C@H](Cn2c(=O)n(-c3cnc(OCCO)c(F)c3)c3ccccc32)CC1)c1cc(Cl)cnc1C(F)F] | 5-chloro-2-(difluoromethyl)-N-((1r,4r)-4-(3-(5-fluoro-6-(2-hydroxyethoxy)pyridin-3-yl)-2-oxo-2,3-dihydro-1H-benzo[d]imidazol-1-yl)methyl)cyclohexyl)nicotinamide | see Example synthesis part | |
| 639 | 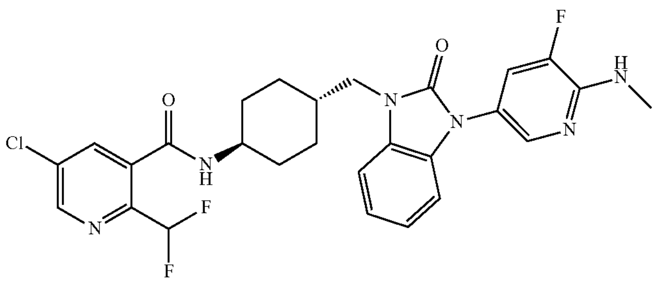 [SMILES: CNc1ncc(-n2c(=O)n(C[C@H]3CC[C@H](NC(=O)c4cc(Cl)cnc4C(F)F)CC3)c3ccccc32)cc1F] | 5-chloro-2-(difluoromethyl)-N-((1r,4r)-4-((3-(5-fluoro-6-(methylamino)pyridin-3-yl)-2-oxo-2,3-dihydro-1H-benzo[d]imidazol-1-yl)methyl)cyclohexyl)nicotinamide | see Example synthesis part | |
| 640 | 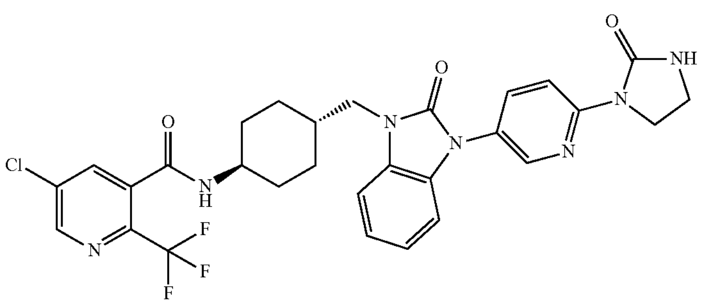 [SMILES: O=C(N[C@H]1CC[C@H](Cn2c(=O)n(-c3ccc(N4CCNC4=O)nc3)c3ccccc32)CC1)c1cc(Cl)cnc1C(F)(F)F] | 5-chloro-N-((1r,4r)-4-((2-oxo-3-(6-(2-oxoimidazolidin-1-yl)pyridin-3-yl)-2,3-dihydro-1H-benzo[d]imidazol-1-yl)methyl)cyclohexyl)-2-(trifluoromethyl)nicotinamide | Intermediate-245, | Y |

TABLE 2-continued

| Ex. | Structure | Name | Reactants | Method |
|---|---|---|---|---|
| 641 | 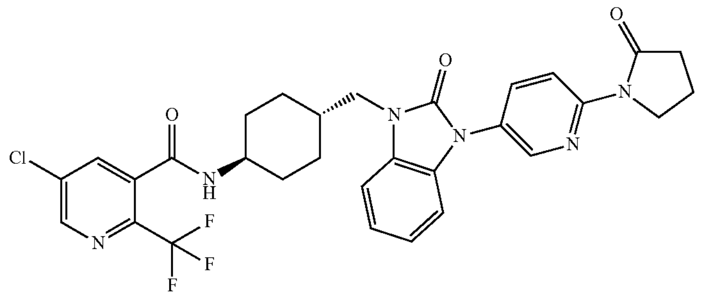 [SMILES: O=C(N[C@H]1CC[C@H](Cn2c(=O)n(-c3ccc(N4CCCC4=O)nc3)c3ccccc32)CC1)c1cc(Cl)cnc1C(F)(F)F] | 5-chloro-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)-2-(trifluoromethyl)nicotinamide | Intermediate-245, | Y |
| 642 | 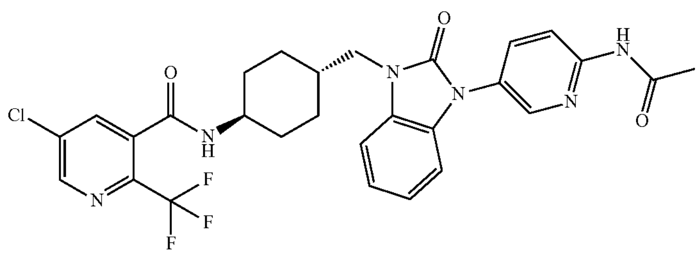 [SMILES: CC(=O)Nc1ccc(-n2c(=O)n(C[C@H]3CC[C@H](NC(=O)c4cc(Cl)cnc4C(F)(F)F)CC3)c3ccccc32)cn1] | N-((1r,4r)-4-((3-(6-acetamidopyridin-3-yl)-2-oxo-2,3-dihydro-1H-benzo[d]imidazol-1-yl)methyl)cyclohexyl)-5-chloro-2-(trifluoromethyl)nicotinamide | Intermediate-245, | Y |
| 643 | 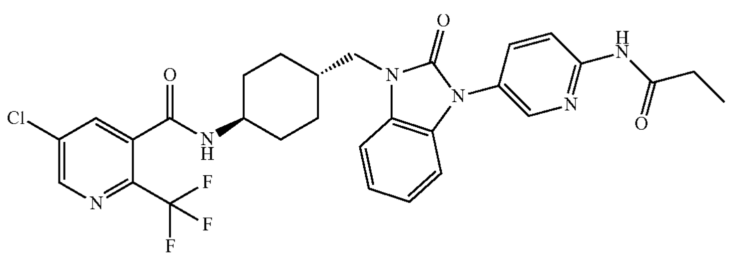 [SMILES: CCC(=O)Nc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((2-oxo-3-(6-propionamidopyridin-3-yl)-2,3-dihydro-1H-benzo[d]imidazol-1-yl)methyl)cyclohexyl)-2-(trifluoromethyl)nicotinamide | Intermediate-245, | Y |
| 644 | 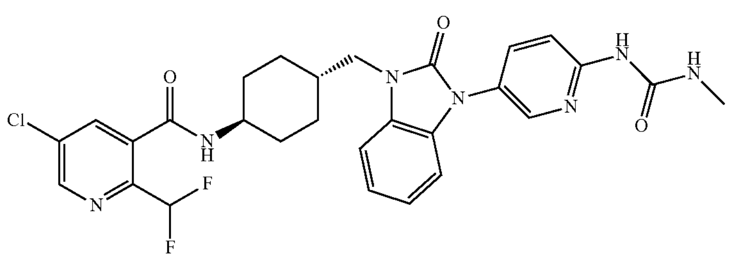 [SMILES: CNC(=O)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((3-(6-(3-methylureido)pyridin-3-yl)-2-oxo-2,3-dihydro-1H-benzo[d]imidazol-1-yl)methyl)cyclohexyl)nicotinamide | Intermediate-207, | Y |

TABLE 2-continued

| Ex. | Structure | Name | Reactants | Method |
|---|---|---|---|---|
| 645 | 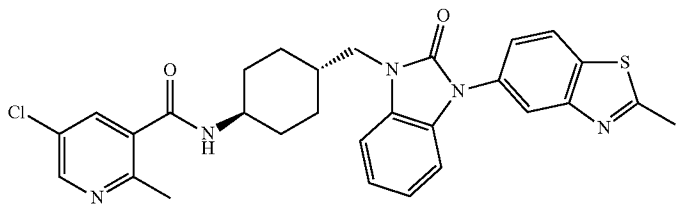 [SMILES: Cc1nc2cc(-n3c(=O)n(C[C@H]4CC[C@H](NC(=O)c5cc(Cl)cnc5C)CC4)c4ccccc43)ccc2s1] | 5-chloro-2-methyl-N-((1r,4r)-4-((3-(2-methylbenzo[d]thiazol-5-yl)-2-oxo-2,3-dihydro-1H-benzo[d]imidazol-1-yl)methyl)cyclohexyl)nicotinamide | (2-methylbenzothiazole with Br); Step-2 of Ex 9 | R |
| 646 | 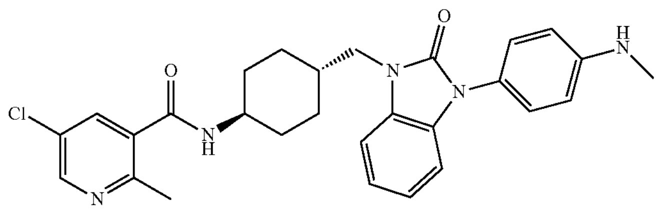 | 5-chloro-2-methyl-N-((1r,4r)-4-((3-(4-(methylamino)phenyl)-2-oxo-2,3-dihydro-1H-benzo[d]imidazol-1-yl)methyl)cyclohexyl)nicotinamide | see Example synthesis part | |
| 647 | 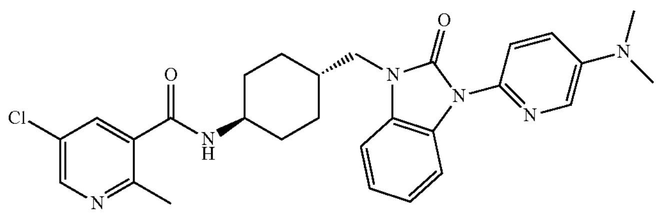 [SMILES: Cc1ncc(Cl)cc1C(=O)N[C@H]1CC[C@H](Cn2c(=O)n(-c3ccc(N(C)C)cn3)c3ccccc32)CC1] | 5-chloro-N-((1r,4r)-4-((3-(5-(dimethylamino)pyridin-2-yl)-2-oxo-2,3-dihydro-1H-benzo[d]imidazol-1-yl)methyl)cyclohexyl)-2-methylnicotinamide | (5-dimethylamino-2-bromopyridine); Step-2 of Ex 9 | R |
| 648 | 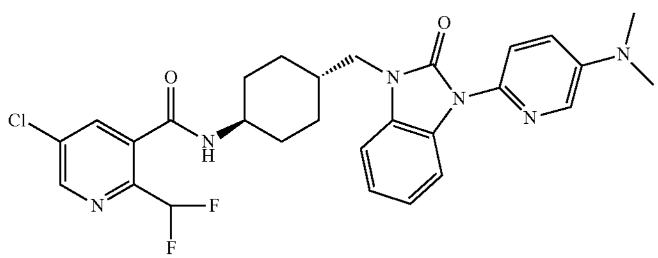 [SMILES: CN(C)c1ccc(-n2c(=O)n(C[C@H]3CC[C@H](NC(=O)c4cc(Cl)cnc4C(F)F)CC3)c3ccccc32)nc1] | 5-chloro-2-(difluoromethyl)-N-((1r,4r)-4-((3-(5-(dimethylamino)pyridin-2-yl)-2-oxo-2,3-dihydro-1H-benzo[d]imidazol-1-yl)methyl)cyclohexyl)nicotinamide | (5-dimethylamino-2-bromopyridine); Intermediate-165 | R |

TABLE 2-continued

| Ex. | Structure | Name | Reactants | Method |
|---|---|---|---|---|
| 649 | 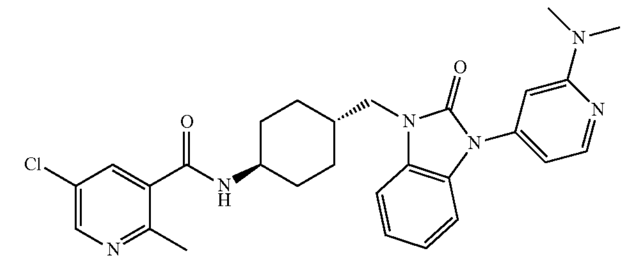 [SMILES: Cc1ncc(Cl)cc1C(=O)N[C@H]1CC[C@H](Cn2c(=O)n(-c3ccnc(N(C)C)c3)c3ccccc32)CC1] | 5-chloro-N-((1r,4r)-4-((3-(2-(dimethyl)amino)pyridin-4-yl)-2-oxo-2,3-dihydro-1H-benzo[d]imidazol-1-yl)methyl)cyclohexyl)-2-methyl-nicotinamide | Step-2 of Ex 9 | R |
| 650 | 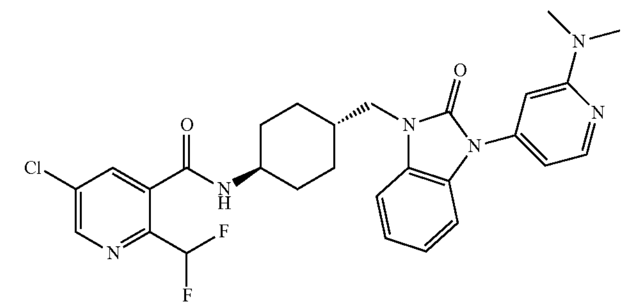 [SMILES: CN(C)c1cc(-n2c(=O)n(C[C@H]3CC[C@H](NC(=O)c4cc(Cl)cnc4C(F)F)CC3)c3ccccc32)ccn1] | 5-chloro-2-(difluoromethyl)-N-((1r,4r)-4-((3-(2-(dimethyl-amino)pyridin-4-yl)-2-oxo-2,3-dihydro-1H-benzo[d]imidazol-1-yl)methyl)cyclohexyl)nicotinamide | Intermediate-165 | R |
| 651 | 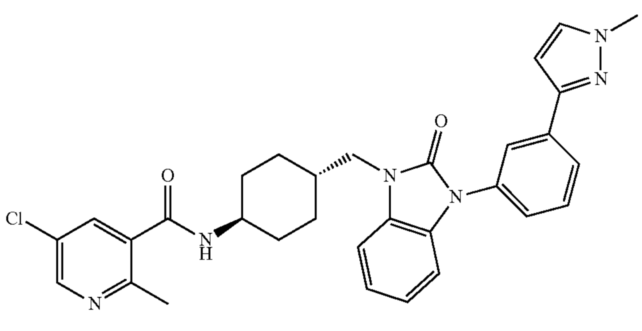 [SMILES: Cc1ncc(Cl)cc1C(=O)N[C@H]1CC[C@H](Cn2c(=O)n(-c3cccc(-c4ccn(C)n4)c3)c3ccccc32)CC1] | 5-chloro-2-methyl-N-((1r,4r)-4-((3-(3-(1-methyl-1H-pyrazol-3-yl)phenyl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 652 | 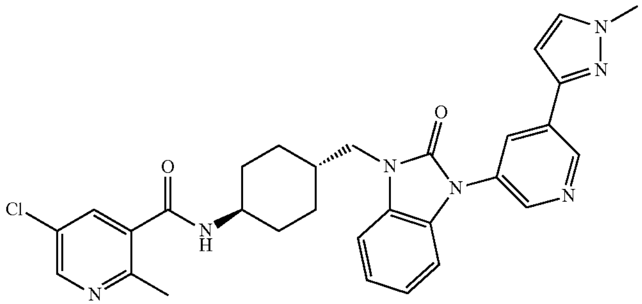 | 5-chloro-2-methyl-N-((1r,4r)-4-((3-(5-(1-methyl-1H-pyrazol-3-yl)pyridin-3-yl)-2-oxo-2,3-dihydro-1H-benzo[d]imidazol-1-yl)methyl)cyclohexyl)nicotinamide | Step-2 of Ex 9 | R |
| 653 | 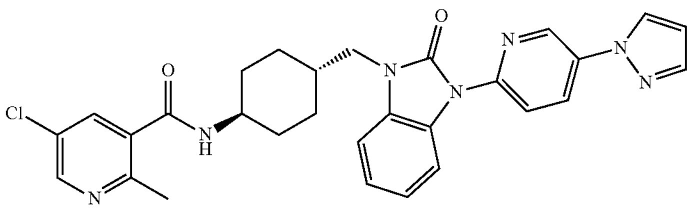 [SMILES: Cc1ncc(Cl)cc1C(=O)N[C@H]1CC[C@H](Cn2c(=O)n(-c3ccc(-n4cccn4)cn3)c3ccccc32)CC1] | N-((1r,4r)-4-(3-(5-(1H-pyrazol-1-yl)pyridin-2-yl)-2-oxo-2,3-dihydro-1H-benzo[d]imidazol-1-yl)methyl)cyclohexyl)-5-chloro-2-methylnicotinamide | Step-2 of Ex 9 | R |
| 654 | 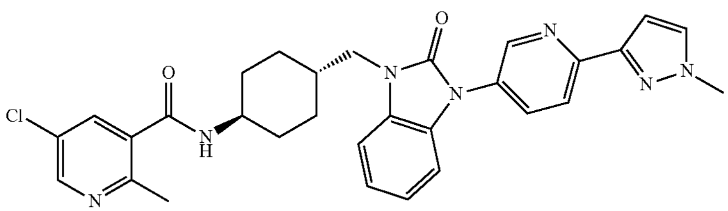 [SMILES: Cc1ncc(Cl)cc1C(=O)N[C@H]1CC[C@H](Cn2c(=O)n(-c3ccc(-c4ccn(C)n4)nc3)c3ccccc32)CC1] | 5-chloro-2-methyl-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)nicotinamide | Step-2 of Ex 9 | R |
| 655 | 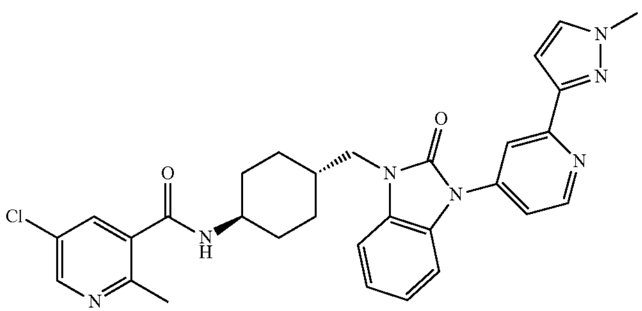 [SMILES: Cc1ncc(Cl)cc1C(=O)N[C@H]1CC[C@H](Cn2c(=O)n(-c3ccnc(-c4ccn(C)n4)c3)c3ccccc32)CC1] | 5-chloro-2-methyl-N-((1r,4r)-4-((3-(2-(1-methyl-1H-pyrazol-3-yl)pyridin-4-yl)-2-oxo-2,3-dihydro-1H-benzo[d]imidazol-1-yl)methyl)cyclohexyl)nicotinamide | Step-2 of Ex 9 | X |

TABLE 2-continued

| Ex. | Structure | Name | Reactants | Method |
|---|---|---|---|---|
| 656 | 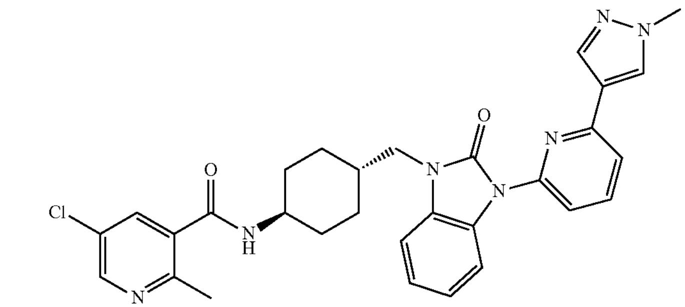 [SMILES: Cc1ncc(Cl)cc1C(=O)N[C@H]1CC[C@H](Cn2c(=O)n(-c3cccc(-c4cnn(C)c4)n3)c3ccccc32)CC1] | 5-chloro-2-methyl-N-((1r,4r)-4-((3-(6-(1-methyl-1H-pyrazol-4-yl)pyridin-2-yl)-2-oxo-2,3-dihydro-1H-benzo[d]imidazol-1-yl)methyl)cyclohexyl)nicotinamide | Step-2 of Ex 9 | R |
| 657 | 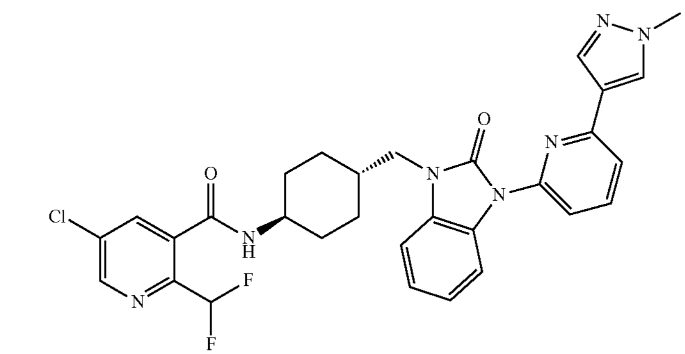 [SMILES: Cn1cc(-c2cccc(-n3c(=O)n(C[C@H]4CC[C@H](NC(=O)c5cc(Cl)cnc5C(F)F)CC4)c4ccccc43)n2)cn1] | 5-chloro-2-(difluoromethyl)-N-((1r,4r)-4-((3-(6-(1-methyl-1H-pyrazol-4-yl)pyridin-2-yl)-2-oxo-2,3-dihydro-1H-benzo[d]imidazol-1-yl)methyl)cyclohexyl)nicotinamide | Intermediate-165 | R |
| 658 | 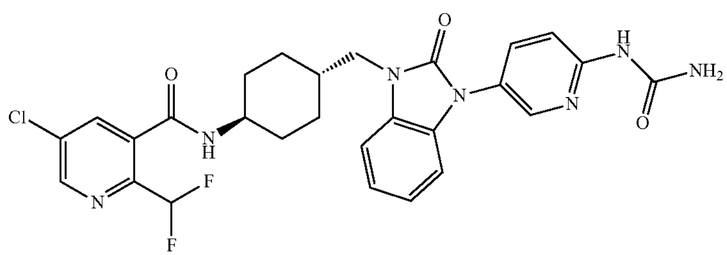 [SMILES: NC(=O)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-((2-oxo-3-(6-ureidopyridin-3-yl)-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 659 | 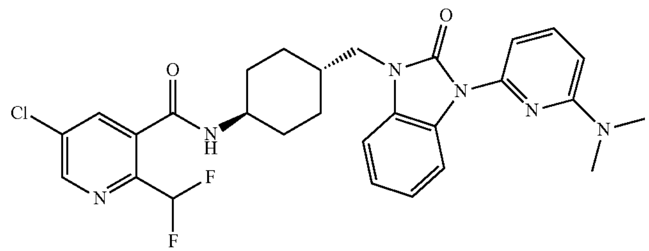 [SMILES: CN(C)c1cccc(-n2c(=O)n(C[C@H]3CC[C@H](NC(=O)c4cc(Cl)cnc4C(F)F)CC3)c3ccccc32)n1] | 5-chloro-2-(difluoromethyl)-N-((1r,4r)-4-(3-(6-(dimethylamino)pyridin-2-yl)-2-oxo-2,3-dihydro-1H-benzo[d]imidazol-1-yl)methyl)cyclohexyl)nicotinamide | 6-bromo-N,N-dimethylpyridin-2-amine; Intermediate-165 | R |
| 660 | 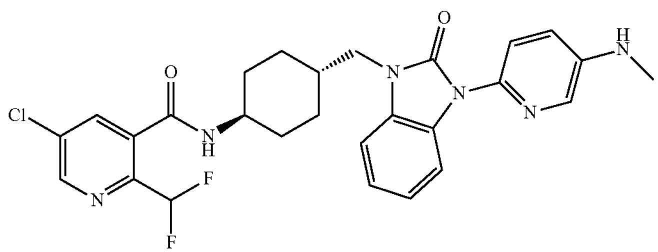 [SMILES: CNc1ccc(-n2c(=O)n(C[C@H]3CC[C@H](NC(=O)c4cc(Cl)cnc4C(F)F)CC3)c3ccccc32)nc1] | 5-chloro-2-(difluoromethyl)-N-((1r,4r)-4-(3-(5-(methylamino)pyridin-2-yl)-2-oxo-2,3-dihydro-1H-benzo[d]imidazol-1-yl)methyl)cyclohexyl)nicotinamide | see Example synthesis part | |
| 661 | 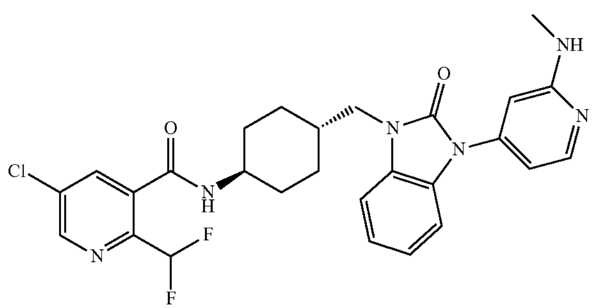 [SMILES: CNc1cc(-n2c(=O)n(C[C@H]3CC[C@H](NC(=O)c4cc(Cl)cnc4C(F)F)CC3)c3ccccc32)ccn1] | 5-chloro-2-(difluoromethyl)-N-((1r,4r)-4-(3-(2-(methylamino)pyridin-4-yl)-2-oxo-2,3-dihydro-1H-benzo[d]imidazol-1-yl)methyl)cyclohexyl)nicotinamide | see Example synthesis part | |
| 662 | 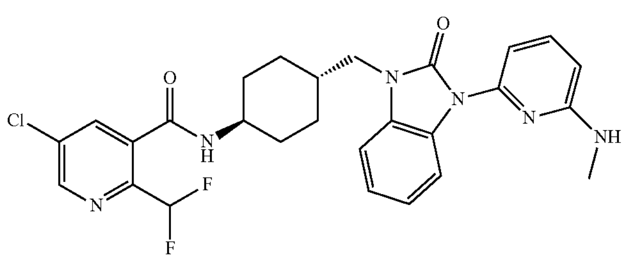 [SMILES: CNc1cccc(-n2c(=O)n(C[C@H]3CC[C@H](NC(=O)c4cc(Cl)cnc4C(F)F)CC3)c3ccccc32)n1] | 5-chloro-2-(difluoromethyl)-N-((1r,4r)-4-(3-(6-(methylamino)pyridin-2-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 663 | 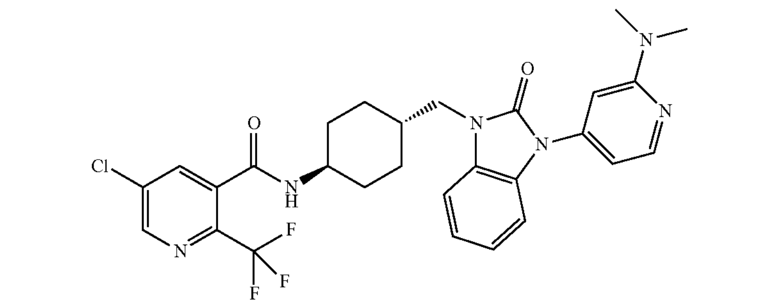 [SMILES: CN(C)c1cc(-n2c(=O)n(C[C@H]3CC[C@H](NC(=O)c4cc(Cl)cnc4C(F)(F)F)CC3)c3ccccc32)ccn1] | 5-chloro-N-((1r,4r)-4-((3-(2-(dimethylamino)pyridin-4-yl)-2-oxo-2,3-dihydro-1H-benzo[d]imidazol-1-yl)methyl)cyclohexyl)-2-(trifluoromethyl)nicotinamide | Intermediate-132 | R |
| 664 | 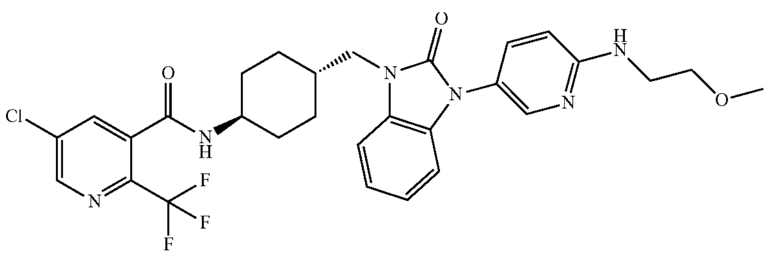 [SMILES: COCCNc1ccc(-n2c(=O)n(C[C@H]3CC[C@H](NC(=O)c4cc(Cl)cnc4C(F)(F)F)CC3)c3ccccc32)cn1] | 5-chloro-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)-2-(trifluoromethyl)nicotinamide | Intermediate-246, | L |
| 665 | 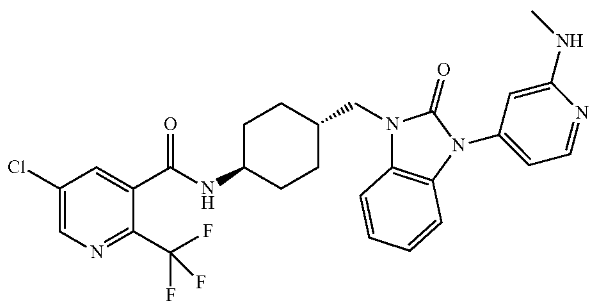 [SMILES: CNc1cc(-n2c(=O)n(C[C@H]3CC[C@H](NC(=O)c4cc(Cl)cnc4C(F)(F)F)CC3)c3ccccc32)ccn1] | 5-chloro-N-((1r,4r)-4-((3-(2-(methylamino)pyridin-4-yl)-2-oxo-2,3-dihydro-1H-benzo[d]imidazol-1-yl)methyl)cyclohexyl)-2-(trifluoromethyl)nicotinamide | see Example synthesis part | |

TABLE 2-continued

| Ex. | Structure | Name | Reactants | Method |
|---|---|---|---|---|
| 666 | 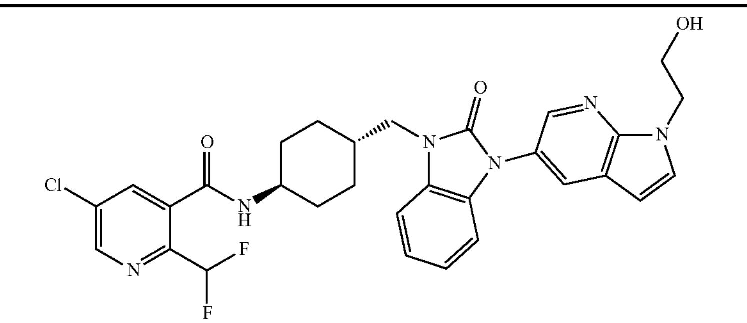 | 5-chloro-2-(difluoromethyl)-N-((1r,4r)-4-(3-(1-(2-hydroxyethyl)-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |
| 667 | 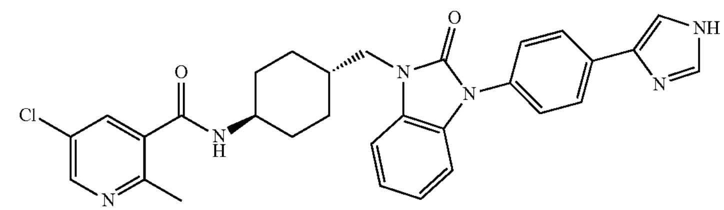 [SMILES: Cc1ncc(Cl)cc1C(=O)N[C@H]1CC[C@H](Cn2c(=O)n(-c3ccc(-c4c[nH]cn4)cc3)c3ccccc32)CC1] | N-((1r,4r)-4-(3-(4-(1H-imidazol-4-yl)phenyl)-2-oxo-2,3-dihydro-1H-benzo[d]imidazol-1-yl)methyl)cyclohexyl)-5-chloro-2-methylnicotinamide | see Example synthesis part | |
| 668 | 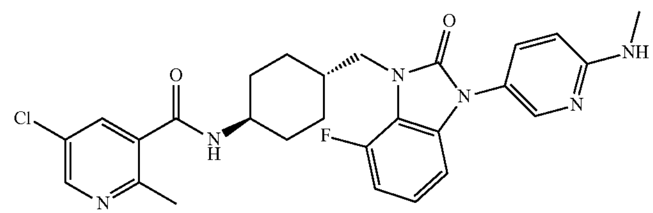 [SMILES: CNc1ccc(-n2c(=O)n(C[C@H]3CC[C@H](NC(=O)c4cc(Cl)cnc4C)CC3)c3c(F)cccc32)cn1] | 5-chloro-N-((1r,4r)-4-((7-fluoro-3-(6-(methylamino)pyridin-3-yl)-2-oxo-2,3-dihydro-1H-benzo[d]imidazol-1-yl)methyl)cyclohexyl)-2-methylnicotinamide | Intermediate-247, Mesylate-1 | A1 |
| 669 | 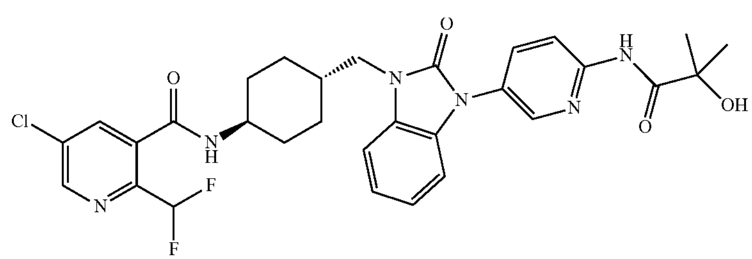 [SMILES: CC(C)(O)C(=O)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1r,4r)-4-(3-(6-(2-hydroxy-2-methylpropanamido)pyridin-3-yl)-2-oxo-2,3-dihydro-1H-benzo[d]imidazol-1-yl)methyl)cyclohexyl)nicotinamide | Intermediate-207, | Y |

TABLE 2-continued

| Ex. | Structure | Name | Reactants | Method |
|---|---|---|---|---|
| 670 | 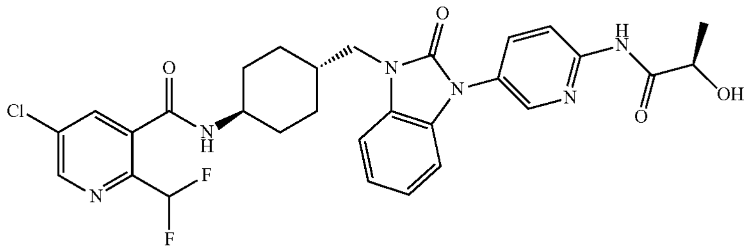 [SMILES: C[C@@H](O)C(=O)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1R,4r)-4-((3-(6-((R)-2-hydroxypropanamido)pyridin-3-yl)-2-oxo-2,3-dihydro-1H-benzo[d]imidazol-1-yl)methyl)cyclohexyl)nicotinamide | Intermediate-207, | Y |
| 671 | 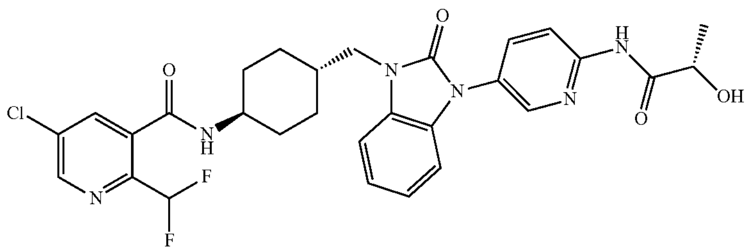 [SMILES: C[C@H](O)C(=O)Nc1ccc(-n2c(=O)n(C[C@H]3CC[C@H](NC(=O)c4cc(Cl)cnc4C(F)F)CC3)c3ccccc32)cn1] | 5-chloro-2-(difluoromethyl)-N-((1S,4r)-4-((3-(6-((S)-2-hydroxypropanamido)pyridin-3-yl)-2-oxo-2,3-dihydro-1H-benzo[d]imidazol-1-yl)methyl)cyclohexyl)nicotinamide | Intermediate-207, | Y |
| 672 | 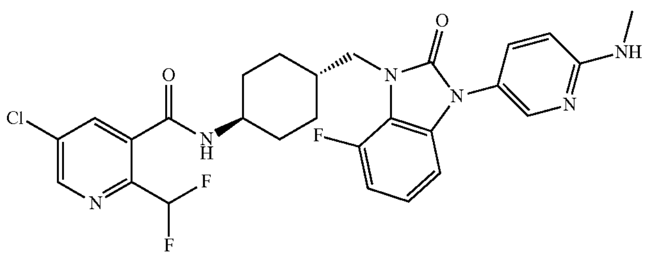 [SMILES: CNc1ccc(-n2c(=O)n(C[C@H]3CC[C@H](NC(=O)c4cc(Cl)cnc4C(F)F)CC3)c3c(F)cccc32)cn1] | 5-chloro-2-(difluoromethyl)-N-((1r,4r)-4-((7-fluoro-3-(6-(methylamino)pyridin-3-yl)-2-oxo-2,3-dihydro-1H-benzo[d]imidazol-1-yl)methyl)cyclohexyl)nicotinamide | Intermediate-247, Mesylate-4 | A1 |
| 673 | 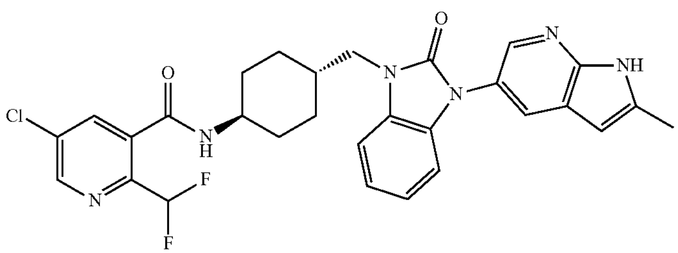 [SMILES: Cc1cc2cc(-n3c(=O)n(C[C@H]4CC[C@H](NC(=O)c5cc(Cl)cnc5C(F)F)CC4)c4ccccc43)cnc2[nH]1] | 5-chloro-2-(difluoromethyl)-N-((1r,4r)-4-((3-(2-methyl-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 674 | 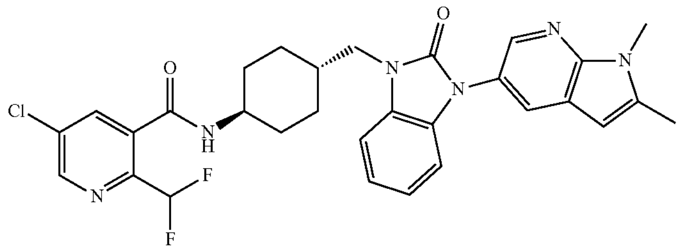 [SMILES: Cc1cc2cc(-n3c(=O)n(C[C@H]4CC[C@H](NC(=O)c5cc(Cl)cnc5C(F)F)CC4)c4ccccc43)cnc2n1C] | 5-chloro-2-(difluoromethyl)-N-((1r,4r)-4-((3-(1,2-dimethyl-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |
| 675 | 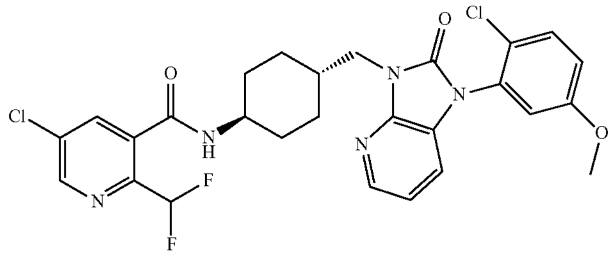 [SMILES: COc1ccc(Cl)c(-n2c(=O)n(C[C@H]3CC[C@H](NC(=O)c4cc(Cl)cnc4C(F)F)CC3)c3ncccc32)c1] | 5-chloro-N-((1r,4r)-4-((1-(2-chloro-5-methoxyphenyl)-2-oxo-1H-imidazo[4,5-b]pyridin-3(2H)-yl)methyl)cyclohexyl)-2-(difluoromethyl)nicotinamide | Intermediate-249, Mesylate-4 | A1 |
| 676 | 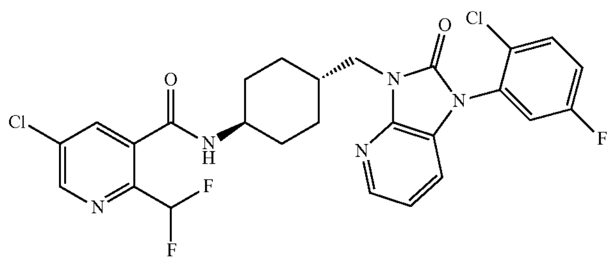 [SMILES: O=C(N[C@H]1CC[C@H](Cn2c(=O)n(-c3cc(F)ccc3Cl)c3cccnc32)CC1)c1cc(Cl)cnc1C(F)F] | 5-chloro-N-((1r,4r)-4-((1-(2-chloro-5-fluorophenyl)-2-oxo-1H-imidazo[4,5-b]pyridin-3(2H)-yl)methyl)cyclohexyl)-2-(difluoromethyl)nicotinamide | Intermediate-250, Mesylate-4 | A1 |

TABLE 2-continued

| Ex. | Structure | Name | Reactants | Method |
|---|---|---|---|---|
| 677 | 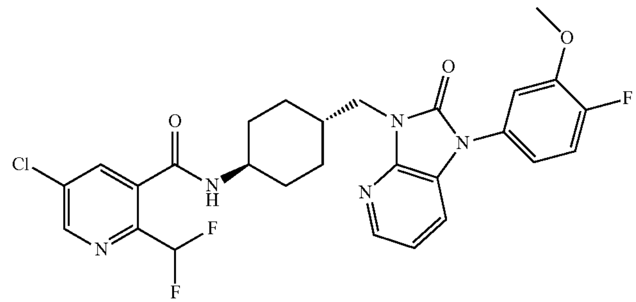 [SMILES: COc1cc(-n2c(=O)n(C[C@H]3CC[C@H](NC(=O)c4cc(Cl)cnc4C(F)F)CC3)c3ncccc32)ccc1F] | 5-chloro-2-(difluoromethyl)-N-((1r,4r)-4-((1-(4-fluoro-3-methoxyphenyl)-2-oxo-1H-imidazo[4,5-b]pyridin-3(2H)-yl)methyl)cyclohexyl)nicotinamide | Intermediate-251, Mesylate-4 | A1 |
| 678 | 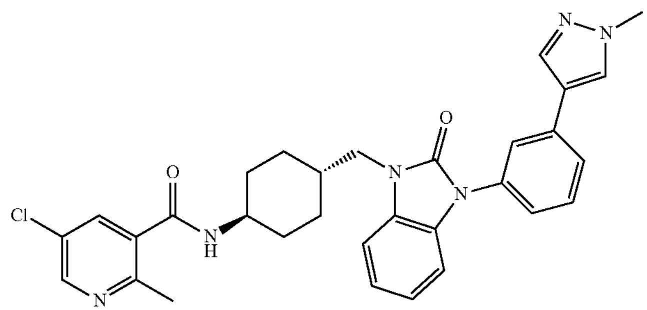 [SMILES: Cc1ncc(Cl)cc1C(=O)N[C@H]1CC[C@H](Cn2c(=O)n(-c3cccc(-c4cnn(C)c4)c3)c3ccccc32)CC1] | 5-chloro-2-methyl-N-((1r,4r)-4-((3-(1-methyl-1H-pyrazol-4-yl)phenyl)-2-oxo-2,3-dihydro-1H-benzo[d]imidazol-1-yl)methyl)cyclohexyl)nicotinamide | Step-2 of Ex 9 | R |
| 679 | 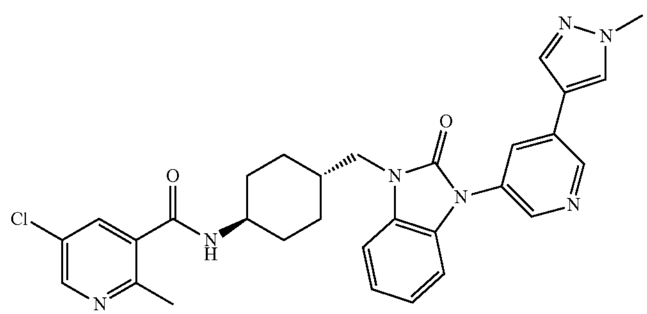 [SMILES: Cc1ncc(Cl)cc1C(=O)N[C@H]1CC[C@H](Cn2c(=O)n(-c3cncc(-c4cnn(C)c4)c3)c3ccccc32)CC1] | 5-chloro-2-methyl-N-((1r,4r)-4-((3-(5-(1-methyl-1H-pyrazol-4-yl)pyridin-3-yl)-2-oxo-2,3-dihydro-1H-benzo[d]imidazol-1-yl)methyl)cyclohexyl)nicotinamide | Step-2 of Ex 9 | R |

TABLE 2-continued

| Ex. | Structure | Name | Reactants | Method |
|---|---|---|---|---|
| 680 | 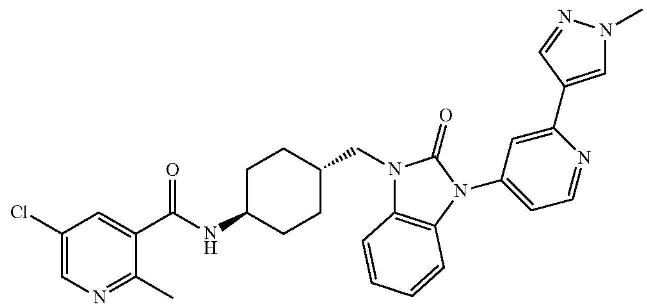 | 5-chloro-2-methyl-N-((1r,4r)-4-((3-(2-(1-methyl-1H-pyrazol-4-yl)pyridin-4-yl)-2-oxo-2,3-dihydro-1H-benzo[d]imidazol-1-yl)methyl)cyclohexyl)nicotinamide | Step-2 of Ex 9 | X |
| 681 | 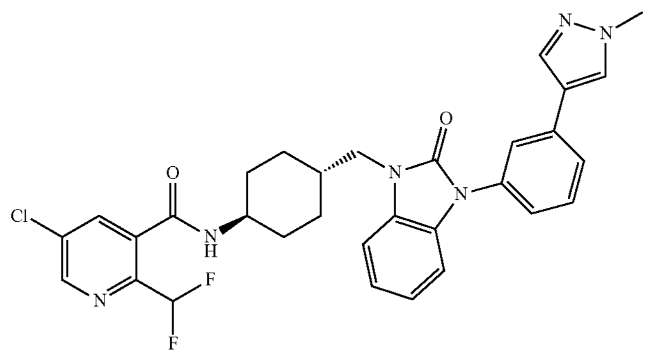 [SMILES: Cn1cc(-c2cccc(-n3c(=O)n(C[C@H]4CC[C@H](NC(=O)c5cc(Cl)cnc5C(F)F)CC4)c4ccccc43)c2)cn1] | 5-chloro-2-(difluoromethyl)-N-((1r,4r)-4-((3-(3-(1-methyl-1H-pyrazol-4-yl)phenyl)-2-oxo-2,3-dihydro-1H-benzo[d]imidazol-1-yl)methyl)cyclohexyl)nicotinamide | Intermediate-165 | R |
| 682 | 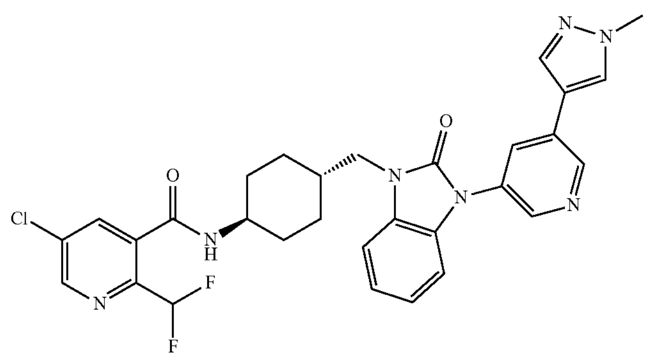 [SMILES: Cn1cc(-c2cncc(-n3c(=O)n(C[C@H]4CC[C@H](NC(=O)c5cc(Cl)cnc5C(F)F)CC4)c4ccccc43)c2)cn1] | 5-chloro-2-(difluoromethyl)-N-((1r,4r)-4-((3-(5-(1-methyl-1H-pyrazol-4-yl)pyridin-3-yl)-2-oxo-2,3-dihydro-1H-benzo[d]imidazol-1-yl)methyl)cyclohexyl)nicotinamide | Intermediate-165 | R |

TABLE 2-continued

| Ex. | Structure | Name | Reactants | Method |
|---|---|---|---|---|
| 683 | 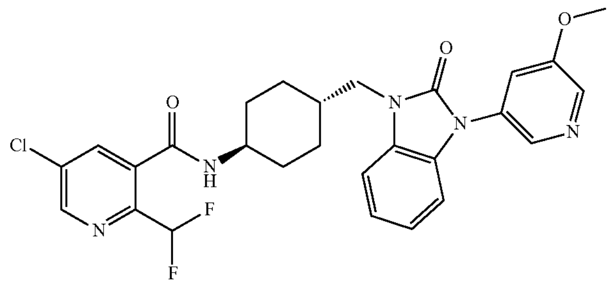 [SMILES: COc1cncc(-n2c(=O)n(C[C@H]3CC[C@H](NC(=O)c4cc(Cl)cnc4C(F)F)CC3)c3ccccc32)c1] | 5-chloro-2-(difluoromethyl)-N-((1r,4r)-4-((3-(5-methoxypyridin-3-yl)-2-oxo-2,3-dihydro-1H-benzo[d]imidazol-1-yl)methyl)cyclohexyl)nicotinamide | 3-bromo-5-methoxypyridine, Intermediate-165 | R |
| 684 | 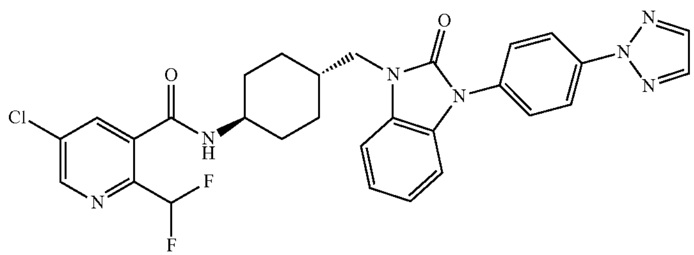 [SMILES: O=C(N[C@H]1CC[C@H](Cn2c(=O)n(-c3ccc(-n4nccn4)cc3)c3ccccc32)CC1)c1cc(Cl)cnc1C(F)F] | N-((1r,4r)-4-((3-(4-(2H-1,2,3-triazol-2-yl)phenyl)-2-oxo-2,3-dihydro-1H-benzo[d]imidazol-1-yl)methyl)cyclohexyl)-5-chloro-2-(difluoromethyl)nicotinamide | 2-(4-bromophenyl)-2H-1,2,3-triazole, Intermediate-165 | R |
| 685 | 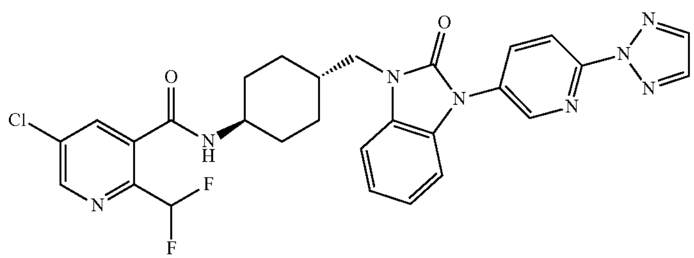 [SMILES: O=C(N[C@H]1CC[C@H](Cn2c(=O)n(-c3ccc(-n4nccn4)nc3)c3ccccc32)CC1)c1cc(Cl)cnc1C(F)F] | N-((1r,4r)-4-((3-(6-(2H-1,2,3-triazol-2-yl)pyridin-3-yl)-2-oxo-2,3-dihydro-1H-benzo[d]imidazol-1-yl)methyl)cyclohexyl)-5-chloro-2-(difluoromethyl)nicotinamide | 2-(5-bromopyridin-2-yl)-2H-1,2,3-triazole, Intermediate-165 | R |

| Ex. | Structure | Name | Reactants | Method |
|---|---|---|---|---|
| 686 | 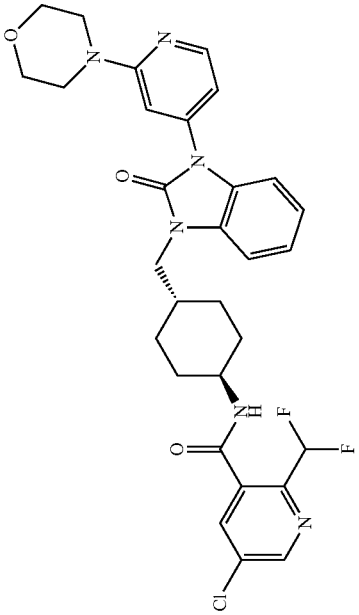 | 5-chloro-2-(difluoromethyl)-N-((1r,4)-4-((3-(2-morpholinopyridin-4-yl)-2-oxo-2,3-dihydro-1H-benzo[d]imidazol-1-yl)methyl)cyclohexyl)nicotinamide | 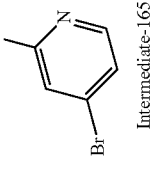<br>Intermediate-165 | R |
| 687 | 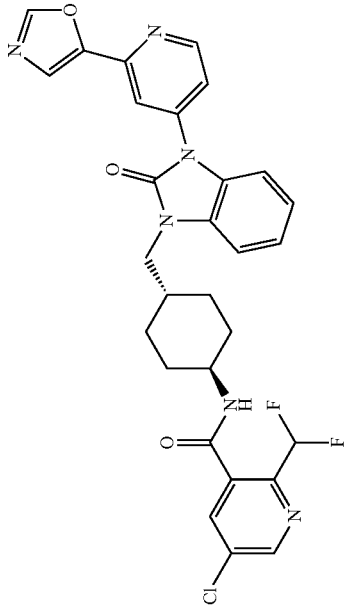 | 5-chloro-2-(difluoromethyl)-N-((1r,4)-4-((3-(2-(oxazol-5-yl)pyridin-4-yl)-2-oxo-2,3-dihydro-1H-benzo[d]imidazol-1-yl)methyl)cyclohexyl)nicotinamide | Intermediate-211, Intermediate-165 | R |
| 688 | 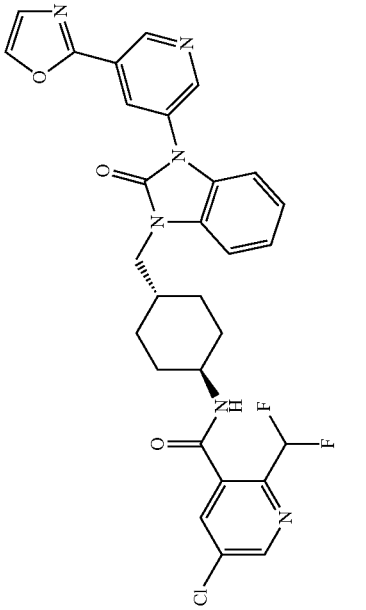 | 5-chloro-2-(difluoromethyl)-N-((1r,4)-4-((3-(5-(oxazol-2-yl)pyridin-3-yl)-2-oxo-2,3-dihydro-1H-benzo[d]imidazol-1-yl)methyl)cyclohexyl)nicotinamide | 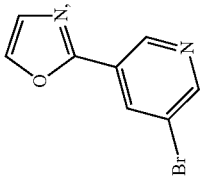<br>Intermediate-165 | R |

TABLE 2-continued

| Ex. | Structure | Name | Reactants | Method |
|---|---|---|---|---|
| 689 | 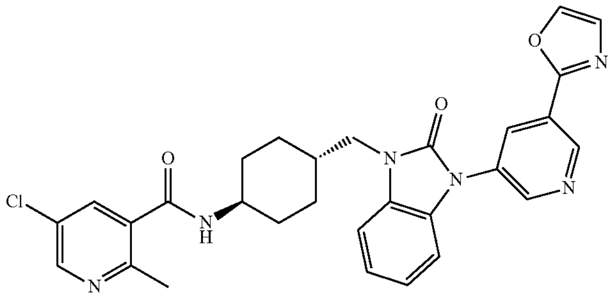 [SMILES: Cc1ncc(Cl)cc1C(=O)N[C@H]1CC[C@H](Cn2c(=O)n(-c3cncc(-c4ncco4)c3)c3ccccc32)CC1] | 5-chloro-2-methyl-N-((1r,4r)-4-((3-(5-(oxazol-2-yl)pyridin-3-yl)-2-oxo-2,3-dihydro-1H-benzo[d]imidazol-1-yl)methyl)cyclohexyl)nicotinamide | Step-2 of Ex 9 | R |
| 690 | 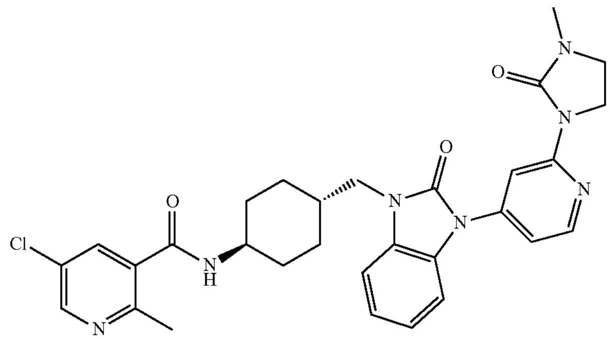 [SMILES: Cc1ncc(Cl)cc1C(=O)N[C@H]1CC[C@H](Cn2c(=O)n(-c3ccnc(N4CCN(C)C4=O)c3)c3ccccc32)CC1] | 5-chloro-2-methyl-N-((1r,4r)-4-((3-(2-(3-methyl-2-oxoimidazolidin-1-yl)pyridin-4-yl)-2-oxo-2,3-dihydro-1H-benzo[d]imidazol-1-yl)methyl)cyclohexyl)nicotinamide | Intermediate-252, | Y |
| 691 | 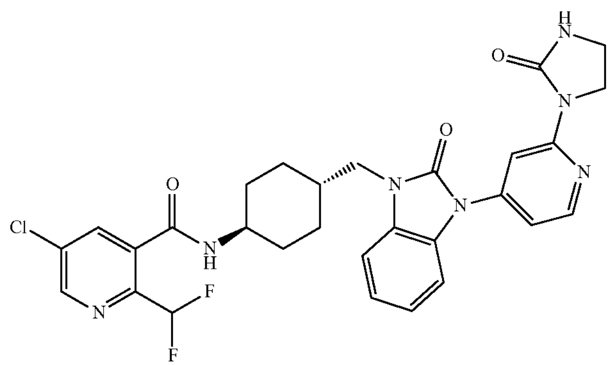 [SMILES: O=C(N[C@H]1CC[C@H](Cn2c(=O)n(-c3ccnc(N4CCNC4=O)c3)c3ccccc32)CC1)c1cc(Cl)cnc1C(F)F] | 5-chloro-2-(difluoromethyl)-N-((1r,4r)-4-((2-oxo-3-(2-(2-oxoimidazolidin-1-yl)pyridin-4-yl)-2,3-dihydro-1H-benzo[d]imidazol-1-yl)methyl)cyclohexyl)nicotinamide | Intermediate-252, | Y |

TABLE 2-continued

| Ex. | Structure | Name | Reactants | Method |
|---|---|---|---|---|
| 692 | 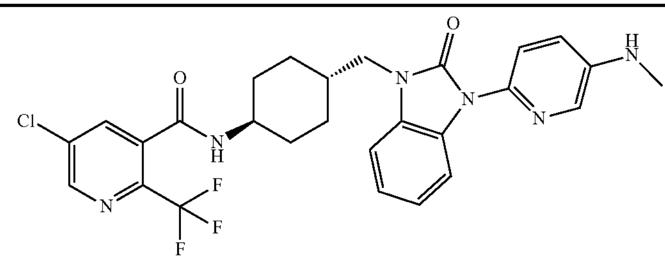 | 5-chloro-N-((1r,4r)-4-((3-(5-(methylamino)pyridin-2-yl)-2-oxo-2,3-dihydro-1H-benzo[d]imidazol-1-yl)methyl)cyclohexyl)-2-(trifluoromethyl)nicotinamide | see Example synthesis part | |
| 693 | 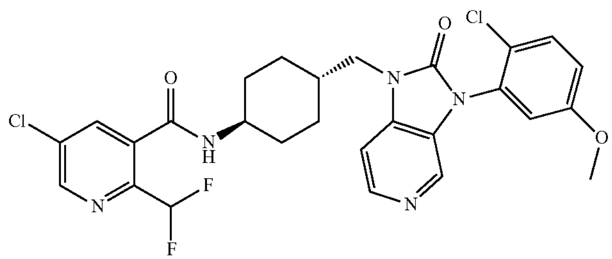 [SMILES: COc1ccc(Cl)c(-n2c(=O)n(C[C@H]3CC[C@H](NC(=O)c4cc(Cl)cnc4C(F)F)CC3)c3ccncc32)c1] | 5-chloro-N-((1r,4r)-4-((3-(2-chloro-5-methoxyphenyl)-2-oxo-2,3-dihydro-1H-imidazo[4,5-c]pyridin-1-yl)methyl)cyclohexyl)-2-(difluoromethyl)nicotinamide | Intermediate-253, Mesylate-4 | A1 |
| 694 | 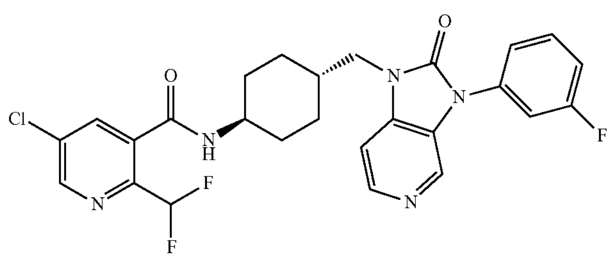 [SMILES: O=C(N[C@H]1CC[C@H](Cn2c(=O)n(-c3cccc(F)c3)c3cnccc32)CC1)c1cc(Cl)cnc1C(F)F] | 5-chloro-2-(difluoromethyl)-N-((1r,4r)-4-((3-(3-fluorophenyl)-2-oxo-2,3-dihydro-1H-imidazo[4,5-c]pyridin-1-yl)methyl)cyclohexyl)nicotinamide | Intermediate-254, Mesylate-4 | A1 |
| 695 | 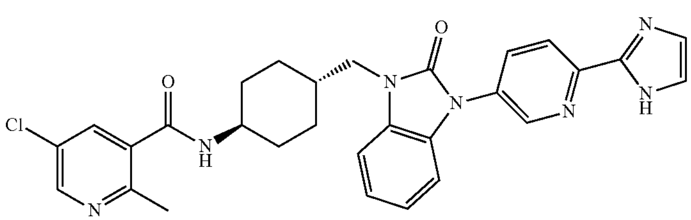 [SMILES: Cc1ncc(Cl)cc1C(=O)N[C@H]1CC[C@H](Cn2c(=O)n(-c3ccc(-c4ncc[nH]4)nc3)c3ccccc32)CC1] | N-((1r,4r)-4-(3-(6-(1H-imidazol-2-yl)pyridin-3-yl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 696 | 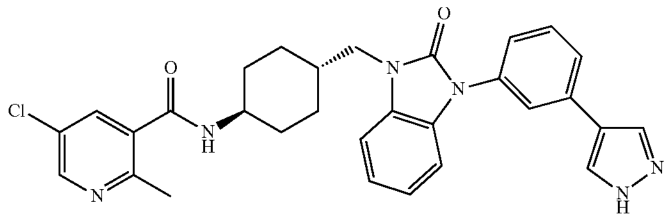 [SMILES: Cc1ncc(Cl)cc1C(=O)N[C@H]1CC[C@H](Cn2c(=O)n(-c3cccc(-c4cn[nH]c4)c3)c3ccccc32)CC1] | N-((1r,4r)-4-((3-(3-(1H-pyrazol-4-yl)phenyl)-2-oxo-2,3-dihydro-1H-benzo[d]imidazol-1-yl)methyl)cyclohexyl)-5-chloro-2-methylnicotinamide | see Example synthesis part | |
| 697 | 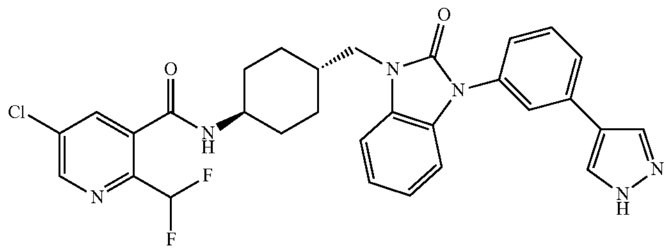 [SMILES: O=C(N[C@H]1CC[C@H](Cn2c(=O)n(-c3cccc(-c4cn[nH]c4)c3)c3ccccc32)CC1)c1cc(Cl)cnc1C(F)F] | N-((1r,4r)-4-((3-(3-(1H-pyrazol-4-yl)phenyl)-2-oxo-2,3-dihydro-1H-benzo[d]imidazol-1-yl)methyl)cyclohexyl)-5-Chloro-2-(difluoromethyl)nicotinamide | see Example synthesis part | |
| 698 | 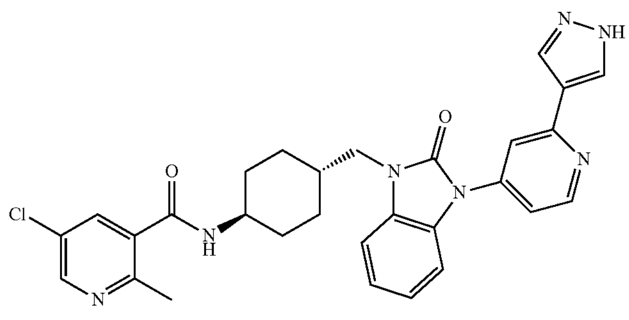 [SMILES: Cc1ncc(Cl)cc1C(=O)N[C@H]1CC[C@H](Cn2c(=O)n(-c3ccnc(-c4cn[nH]c4)c3)c3ccccc32)CC1] | N-((1r,4r)-4-((3-(2-(1H-pyrazol-4-yl)pyridin-4-yl)-2-oxo-2,3-dihydro-1H-benzo[d]imidazol-1-yl)methyl)cyclohexyl)-5-chloro-2-methylnicotinamide | see Example synthesis part | |

| Ex. | Structure | Name | Reactants | Method |
|---|---|---|---|---|
| 699 | 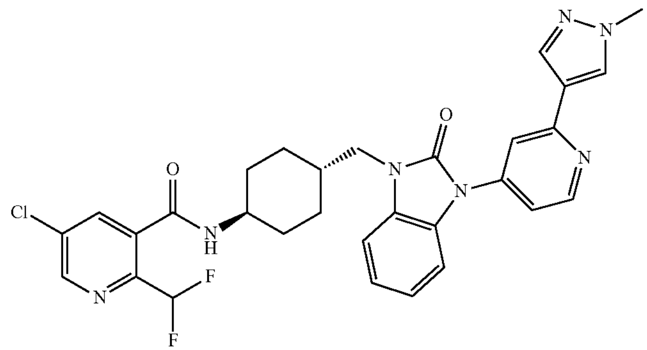 [SMILES: Cn1cc(-c2cc(-n3c(=O)n(C[C@H]4CC[C@H](NC(=O)c5cc(Cl)cnc5C(F)F)CC4)c4ccccc43)ccn2)cn1] | 5-chloro-2-(difluoromethyl)-N-((1r,4r)-4-(3-(2-(1-methyl-1H-pyrazol-4-yl)pyridin-4-yl)-2-oxo-2,3-dihydro-1H-benzo[d]imidazol-1-yl)methyl)cyclohexyl)nicotinamide | Intermediate-165 | R |
| 700 | 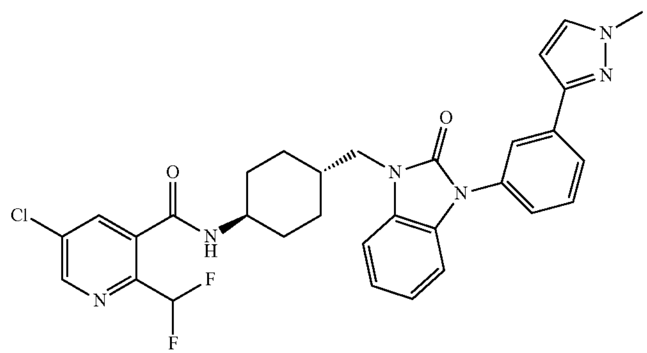 [SMILES: Cn1ccc(-c2cccc(-n3c(=O)n(C[C@H]4CC[C@H](NC(=O)c5cc(Cl)cnc5C(F)F)CC4)c4ccccc43)c2)n1] | 5-chloro-2-(difluoromethyl)-N-((1r,4r)-4-((3-(3-(1-methyl-1H-pyrazol-3-yl)phenyl)-2-oxo-2,3-dihydro-1H-benzo[d]imidazol-1-yl)methyl)cyclohexyl)nicotinamide | Intermediate-165 | R |
| 701 | 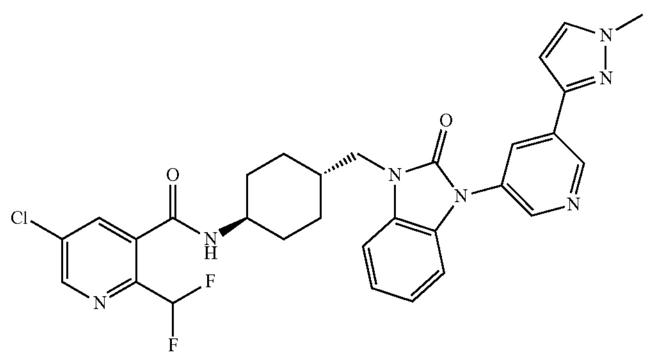 [SMILES: Cn1ccc(-c2cncc(-n3c(=O)n(C[C@H]4CC[C@H](NC(=O)c5cc(Cl)cnc5C(F)F)CC4)c4ccccc43)c2)n1] | 5-chloro-2-(difluoromethyl)-N-((1r,4r)-4-((3-(5-(1-methyl-1H-pyrazol-3-yl)pyridin-3-yl)-2-oxo-2,3-dihydro-1H-benzo[d]imidazol-1-yl)methyl)cyclohexyl)nicotinamide | Intermediate-165 | R |

TABLE 2-continued

| Ex. | Structure | Name | Reactants | Method |
|---|---|---|---|---|
| 702 | 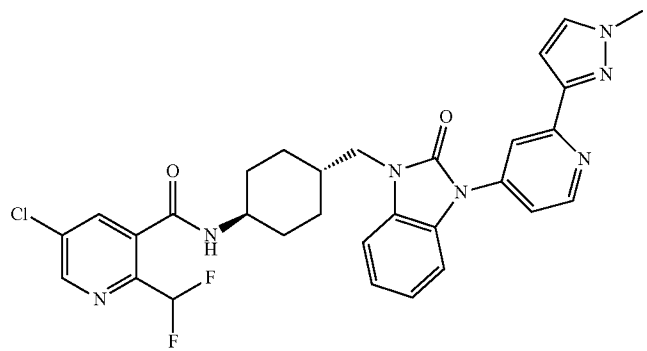 [SMILES: Cn1ccc(-c2cc(-n3c(=O)n(C[C@H]4CC[C@H](NC(=O)c5cc(Cl)cnc5C(F)F)CC4)c4ccccc43)ccn2)n1] | 5-chloro-2-(difluoromethyl)-N-((1r,4r)-4-((3-(2-(1-methyl-1H-pyrazol-3-yl)pyridin-4-yl)-2-oxo-2,3-dihydro-1H-benzo[d]imidazol-1-yl)methyl)cyclohexyl)nicotinamide | Intermediate-258, Intermediate-165 | R |
| 703 | 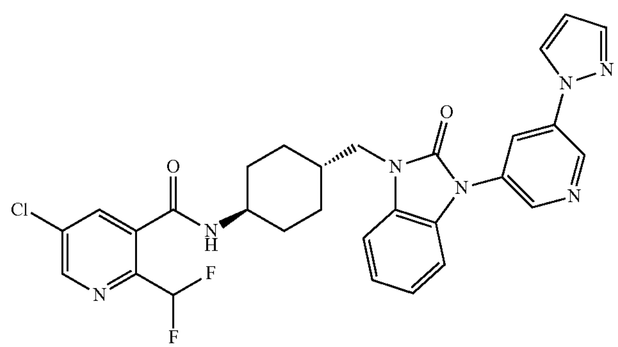 [SMILES: O=C(N[C@H]1CC[C@H](Cn2c(=O)n(-c3cncc(-n4cccn4)c3)c3ccccc32)CC1)c1cc(Cl)cnc1C(F)F] | N-((1r,4r)-4-(3-(5-(1H-pyrazol-1-yl)pyridin-3-yl)-2-oxo-2,3-dihydro-1H-benzo[d]imidazol-1-yl)methyl)cyclohexyl)-5-chloro-2-(difluoromethyl)nicotinamide | Intermediate-165 | R |
| 704 | 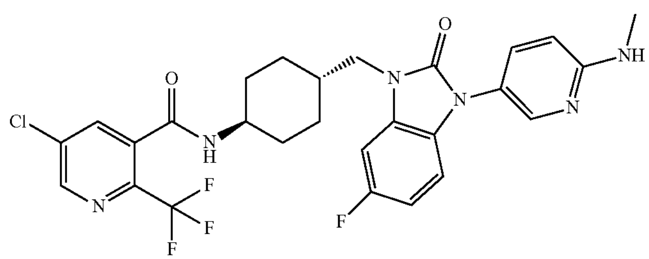 [SMILES: CNc1ccc(-n2c(=O)n(C[C@H]3CC[C@H](NC(=O)c4cc(Cl)cnc4C(F)(F)F)CC3)c3cc(F)ccc32)cn1] | 5-chloro-N-((1r,4r)-4-((6-fluoro-3-(6-(methylamino)pyridin-3-yl)-2-oxo-2,3-dihydro-1H-benzo[d]imidazol-1-yl)methyl)cyclohexyl)-2-(trifluoromethyl)nicotinamide | Intermediate-240, Mesylate-3 | A1 |

TABLE 2-continued

| Ex. | Structure | Name | Reactants | Method |
|---|---|---|---|---|
| 705 | 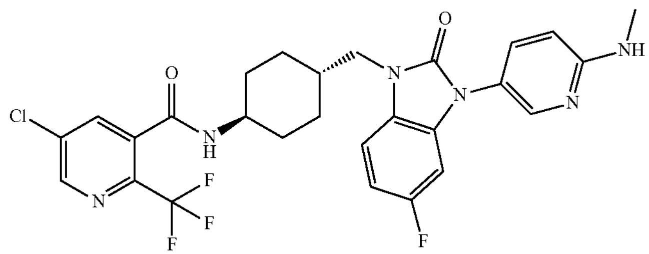 [SMILES: CNc1ccc(-n2c(=O)n(C[C@H]3CC[C@H](NC(=O)c4cc(Cl)cnc4C(F)(F)F)CC3)c3ccc(F)cc32)cn1] | 5-chloro-N-((1r,4r)-4-((5-fluoro-3-(6-(methylamino)pyridin-3-yl)-2-oxo-2,3-dihydro-1H-benzo[d]imidazol-1-yl)methyl)cyclohexyl)-2-(trifluoromethyl)nicotinamide | Intermediate-241, Mesylate-3 | A1 |
| 706 | 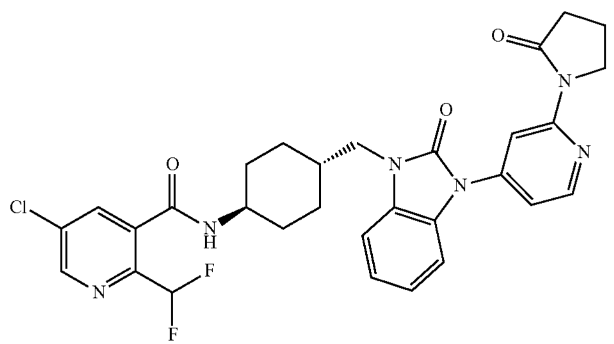 [SMILES: O=C(N[C@H]1CC[C@H](Cn2c(=O)n(-c3ccnc(N4CCCC4=O)c3)c3ccccc32)CC1)c1cc(Cl)cnc1C(F)F] | 5-chloro-2-(difluoromethyl)-N-((1r,4r)-4-((2-oxo-3-(2-(2-oxopyrrolidin-1-yl)pyridin-4-yl)-2,3-dihydro-1H-benzo[d]imidazol-1-yl)methyl)cyclohexyl)nicotinamide | Intermediate-259, | Y |
| 707 | 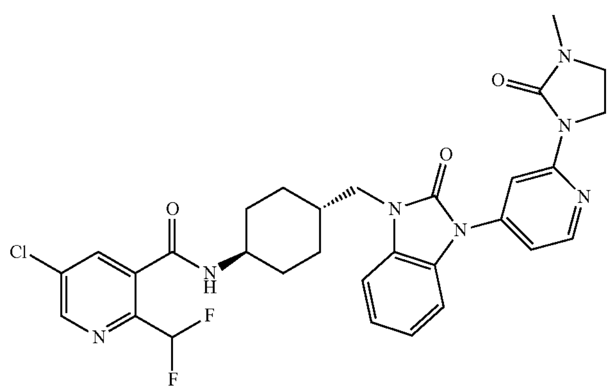 [SMILES: CN1CCN(c2cc(-n3c(=O)n(C[C@H]4CC[C@H](NC(=O)c5cc(Cl)cnc5C(F)F)CC4)c4ccccc43)ccn2)C1=O] | 5-chloro-2-(difluoromethyl)-N-((1r,4r)-4-((3-(2-(3-methyl-2-oxoimidazolidin-1-yl)pyridin-4-yl)-2-oxo-2,3-dihydro-1H-benzo[d]imidazol-1-yl)methyl)cyclohexyl)nicotinamide | Intermediate-259, | Y |

TABLE 2-continued

| Ex. | Structure | Name | Reactants | Method |
|---|---|---|---|---|
| 708 | 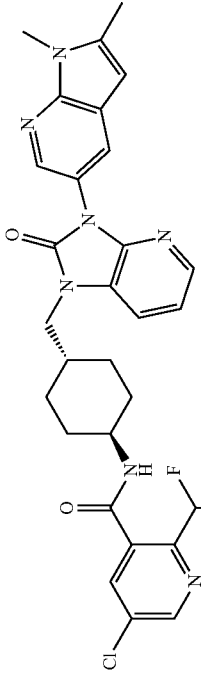 | 5-chloro-2-(difluoromethyl)-N-((1r,4r)-4-(3-(1,2-dimethyl-1H-pyrrolo[2,3-b]pyridin-5-yl)-2-oxo-2,3-dihydro-1H-imidazo[4,5-b]pyridin-1-yl)methyl)cyclohexyl)nicotinamide | see Example synthesis part | |
| 709 | 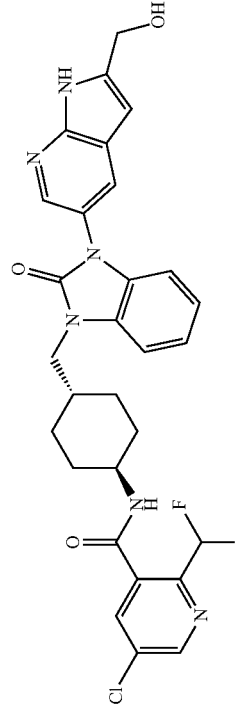 | 5-chloro-2-(difluoromethyl)-N-((1r,4r)-4-(3-(2-(hydroxymethyl)-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |
| 710 | 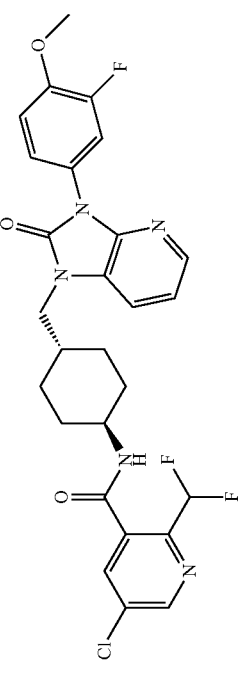 | 5-chloro-2-(difluoromethyl)-N-((1r,4r)-4-(3-(3-fluoro-4-methoxyphenyl)-2-oxo-2,3-dihydro-1H-imidazo[4,5-b]pyridin-1-yl)methyl)cyclohexyl)nicotinamide | Intermediate-260, Mesylate-4 | A1 |
| 711 | 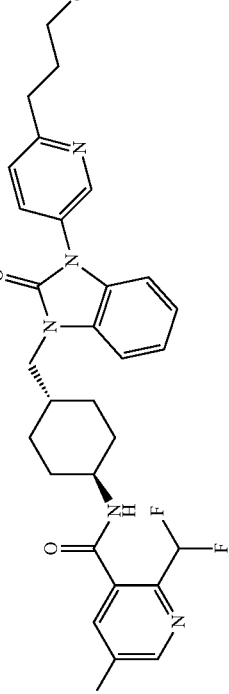 | 5-chloro-2-(difluoromethyl)-N-((1r,4r)-4-(3-(6-(3-hydroxypropyl)pyridin-3-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 712 | 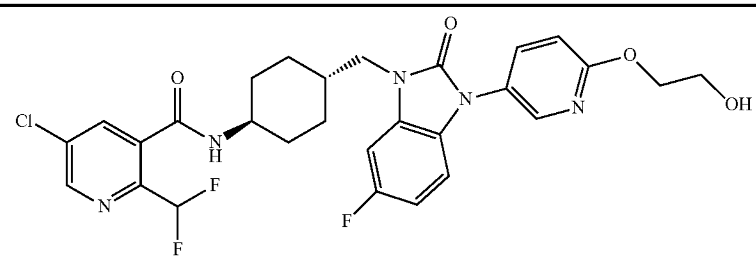 | 5-chloro-2-(difluoromethyl)-N-((1r,4r)-4-((6-fluoro-3-(6-(2-hydroxyethoxy)pyridin-3-yl)-2-oxo-2,3-dihydro-1H-benzo[d]imidazol-1-yl)methyl)cyclohexyl)nicotinamide | see Example synthesis part | |
| 713 | 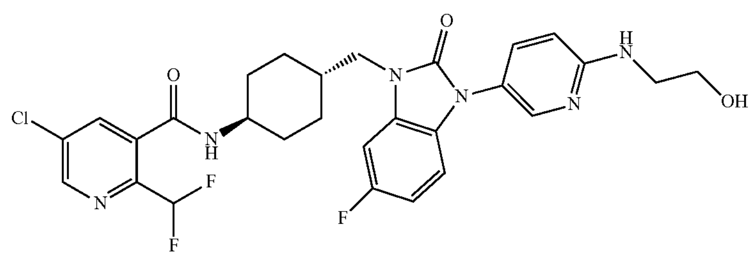 [SMILES: O=C(N[C@H]1CC[C@H](Cn2c(=O)n(-c3ccc(NCCO)nc3)c3ccc(F)cc32)CC1)c1cc(Cl)cnc1C(F)F] | 5-chloro-2-(difluoromethyl)-N-((1r,4r)-4-((6-fluoro-3-(6-((2-hydroxyethyl)amino)pyridin-3-yl)-2-oxo-2,3-dihydro-1H-benzo[d]imidazol-1-yl)methyl)cyclohexyl)nicotinamide | H$_2$N$\sim$OH, Intermediate-262 | K |
| 714 | 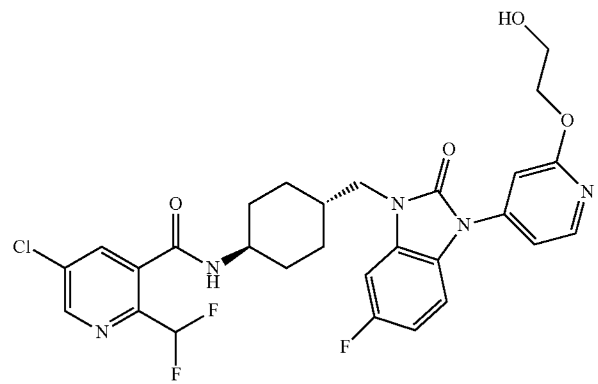 [SMILES: O=C(N[C@H]1CC[C@H](Cn2c(=O)n(-c3ccnc(OCCO)c3)c3ccc(F)cc32)CC1)c1cc(Cl)cnc1C(F)F] | 5-chloro-2-(difluoromethyl)-N-((1r,4r)-4-((6-fluoro-3-(2-(2-hydroxyethoxy)pyridin-4-yl)-2-oxo-2,3-dihydro-1H-benzo[d]imidazol-1-yl)methyl)cyclohexyl)nicotinamide | see Example synthesis part | |

TABLE 2-continued

| Ex. | Structure | Name | Reactants | Method |
|---|---|---|---|---|
| 715 | 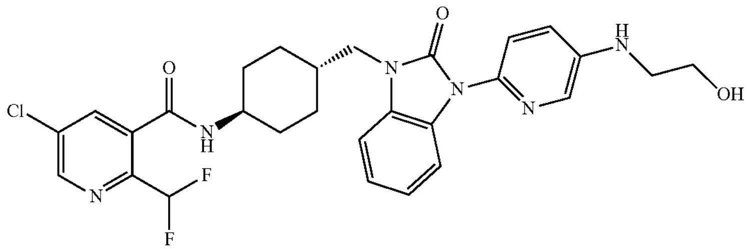 [SMILES: O=C(N[C@H]1CC[C@H](Cn2c(=O)n(-c3ccc(NCCO)cn3)c3ccccc32)CC1)c1cc(Cl)cnc1C(F)F] | 5-chloro-2-(difluoromethyl)-N-((1r,4r)-4-(3-(5-((2-hydroxyethyl)amino)pyridin-2-yl)-2-oxo-2,3-dihydro-1H-benzo[d]imidazol-1-yl)methyl)cyclohexyl)nicotinamide | see Example synthesis part | |
| 716 | 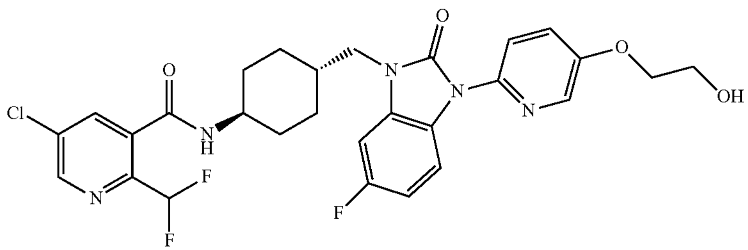 [SMILES: O=C(N[C@H]1CC[C@H](Cn2c(=O)n(-c3ccc(OCCO)cn3)c3ccc(F)cc32)CC1)c1cc(Cl)cnc1C(F)F] | 5-chloro-2-(difluoromethyl)-N-((1r,4r)-4-((6-fluoro-3-(5-(2-hydroxyethoxy)pyridin-2-yl)-2-oxo-2,3-dihydro-1H-benzo[d]imidazol-1-yl)methyl)cyclohexyl)nicotinamide | see Example synthesis part | |
| 717 | 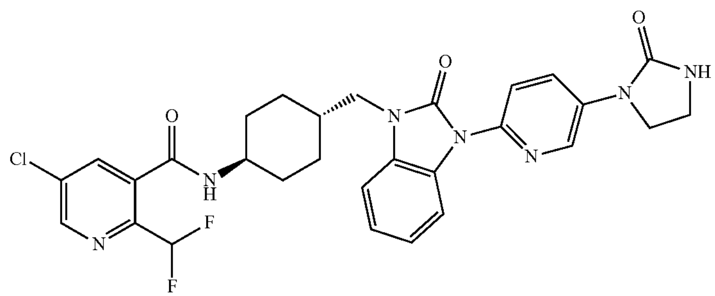 [SMILES: O=C(N[C@H]1CC[C@H](Cn2c(=O)n(-c3ccc(N4CCNC4=O)cn3)c3ccccc32)CC1)c1cc(Cl)cnc1C(F)F] | 5-chloro-2-(difluoromethyl)-N-((1r,4r)-4-((5-(2-oxoimidazolidin-1-yl)pyridin-2-yl)-2-oxo-2,3-dihydro-1H-benzo[d]imidazol-1-yl)methyl)cyclohexyl)nicotinamide | Intermediate-265 | R |
| 718 | 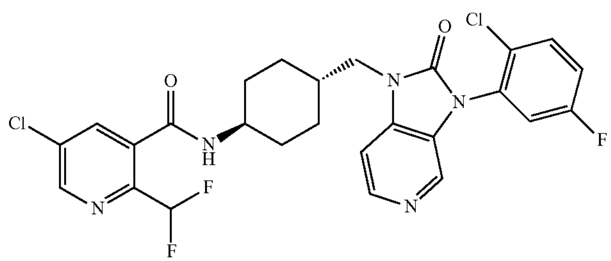 [SMILES: O=C(N[C@H]1CC[C@H](Cn2c(=O)n(-c3cc(F)ccc3Cl)c3cnccc32)CC1)c1cc(Cl)cnc1C(F)F] | 5-chloro-N-((1r,4r)-4-((3-(2-chloro-5-fluorophenyl)-2-oxo-2,3-dihydro-1H-imidazo[4,5-c]pyridin-1-yl)methyl)cyclohexyl)-2-(difluoromethyl)nicotinamide | Intermediate-266, Mesylate-4 | A1 |

TABLE 2-continued

| Ex. | Structure | Name | Reactants | Method |
|---|---|---|---|---|
| 719 | 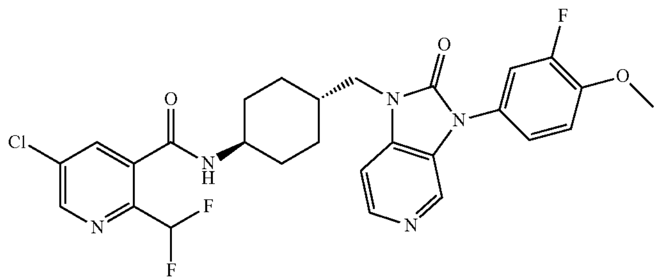 [SMILES: COc1ccc(-n2c(=O)n(C[C@H]3CC[C@H](NC(=O)c4cc(Cl)cnc4C(F)F)CC3)c3ccncc32)cc1F] | 5-chloro-2-(difluoromethyl)-N-((1r,4r)-4-((3-(3-fluoro-4-methoxyphenyl)-2-oxo-2,3-dihydro-1H-imidazo[4,5-c]pyridin-1-yl)methyl)cyclohexyl)nicotinamide | Intermediate-267, Mesylate-4 | A1 |
| 720 | 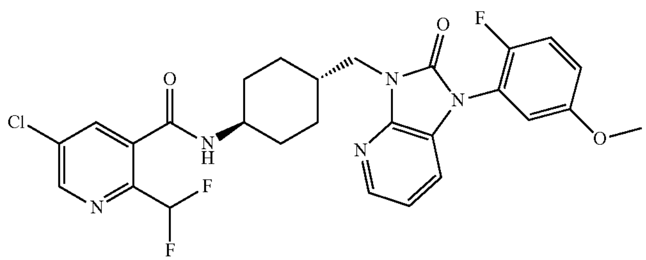 [SMILES: COc1ccc(F)c(-n2c(=O)n(C[C@H]3CC[C@H](NC(=O)c4cc(Cl)cnc4C(F)F)CC3)c3ncccc32)c1] | 5-chloro-2-(difluoromethyl)-N-((1r,4r)-4-((1-(2-fluoro-5-methoxyphenyl)-2-oxo-1H-imidazo[4,5-b]pyridin-3(2H)-yl)methyl)cyclohexyl)nicotinamide | Intermediate-268, Mesylate-4 | A1 |
| 721 | 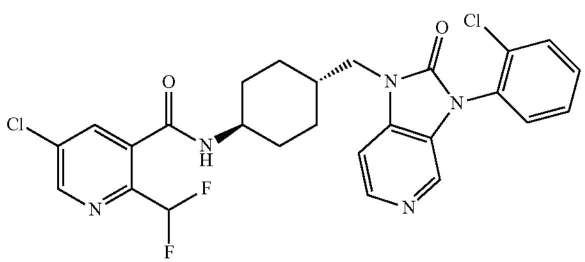 [SMILES: O=C(N[C@H]1CC[C@H](Cn2c(=O)n(-c3ccccc3Cl)c3cnccc32)CC1)c1cc(Cl)cnc1C(F)F] | 5-chloro-N-((1r,4r)-4-((3-(2-chlorophenyl)-2-oxo-2,3-dihydro-1H-imidazo[4,5-c]pyridin-1-yl)methyl)cyclohexyl)-2-(difluoromethyl)nicotinamide | Intermediate-269, Mesylate-4 | A1 |

TABLE 2-continued

| Ex. | Structure | Name | Reactants | Method |
|---|---|---|---|---|
| 722 | 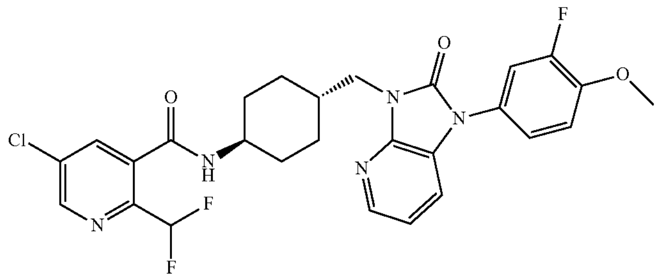 [SMILES: COc1ccc(-n2c(=O)n(C[C@H]3CC[C@H](NC(=O)c4cc(Cl)cnc4C(F)F)CC3)c3ncccc32)cc1F] | 5-chloro-2-(difluoromethyl)-N-((1r,4r)-4-((1-(3-fluoro-4-methoxyphenyl)-2-oxo-1H-imidazo[4,5-b]pyridin-3(2H)-yl)methyl)cyclohexyl)nicotinamide | Intermediate-270, Mesylate-4 | A1 |
| 723 | 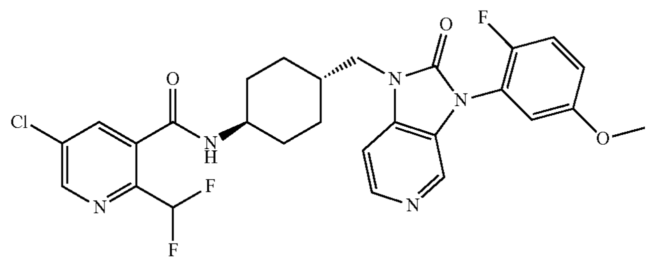 [SMILES: COc1ccc(F)c(-n2c(=O)n(C[C@H]3CC[C@H](NC(=O)c4cc(Cl)cnc4C(F)F)CC3)c3ccncc32)c1] | 5-chloro-2-(difluoromethyl)-N-((1r,4r)-4-((3-(2-fluoro-5-methoxyphenyl)-2-oxo-2,3-dihydro-1H-imidazo[4,5-c]pyridin-1-yl)methyl)cyclohexyl)nicotinamide | Intermediate-271, Mesylate-4 | A1 |
| 724 | 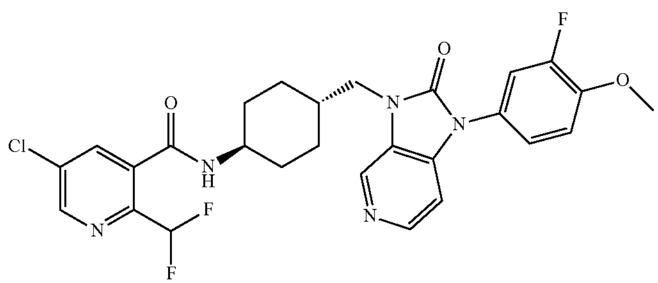 [SMILES: COc1ccc(-n2c(=O)n(C[C@H]3CC[C@H](NC(=O)c4cc(Cl)cnc4C(F)F)CC3)c3cnccc32)cc1F] | 5-chloro-2-(difluoromethyl)-N-((1r,4r)-4-((1-(3-fluoro-4-methoxyphenyl)-2-oxo-1H-imidazo[4,5-c]pyridin-3(2H)-yl)methyl)cyclohexyl)nicotinamide | Intermediate-272, Mesylate-4 | A1 |

TABLE 2-continued

| Ex. | Structure | Name | Reactants | Method |
|---|---|---|---|---|
| 725 | 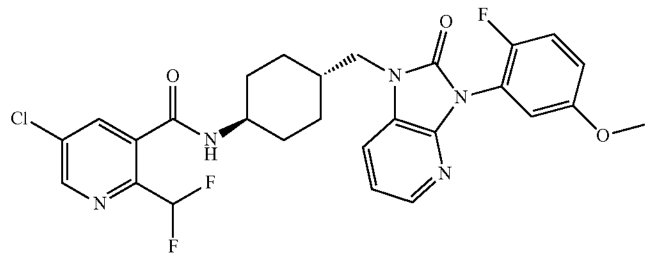 [SMILES: COc1ccc(F)c(-n2c(=O)n(C[C@H]3CC[C@H](NC(=O)c4cc(Cl)cnc4C(F)F)CC3)c3cccnc32)c1] | 5-chloro-2-(difluoromethyl)-N-((1r,4r)-4-(3-(2-fluoro-5-methoxyphenyl)-2-oxo-2,3-dihydro-1H-imidazo[4,5-b]pyridin-1-yl)methyl)cyclohexyl)nicotinamide | Intermediate-273, Mesylate-4 | A1 |
| 726 | 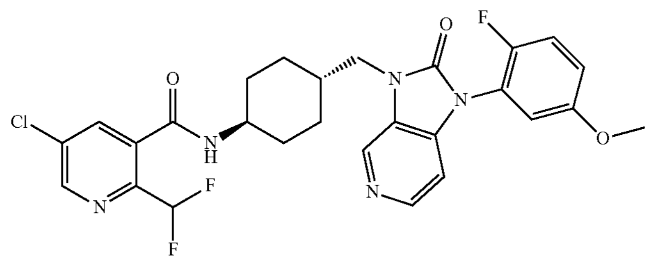 [SMILES: COc1ccc(F)c(-n2c(=O)n(C[C@H]3CC[C@H](NC(=O)c4cc(Cl)cnc4C(F)F)CC3)c3cnccc32)c1] | 5-chloro-2-(difluoromethyl)-N-((1r,4r)-4-((1-(2-fluoro-5-methoxyphenyl)-2-oxo-1H-imidazo[4,5-c]pyridin-3(2H)-yl)methyl)cyclohexyl)nicotinamide | Intermediate-274, Mesylate-4 | A1 |
| 727 | 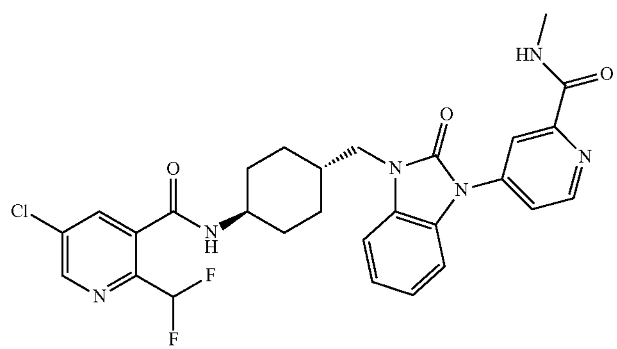 [SMILES: CNC(=O)c1cc(-n2c(=O)n(C[C@H]3CC[C@H](NC(=O)c4cc(Cl)cnc4C(F)F)CC3)c3ccccc32)ccn1] | 4-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide | Intermediate-275, Mesylate-4 | A1 |

TABLE 2-continued

| Ex. | Structure | Name | Reactants | Method |
|---|---|---|---|---|
| 728 | 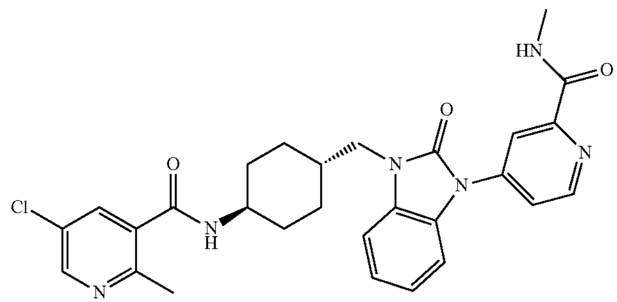 [SMILES: CNC(=O)c1cc(-n2c(=O)n(C[C@H]3CC[C@H](NC(=O)c4cc(Cl)cnc4C)CC3)c3ccccc32)ccn1] | 4-(3-((1r,4r)-4-(5-chloro-2-methylnicotinamido)cyclohexyl)methyl)-2-oxo-2,3-dihydro-1H-benzo[d]imidazol-1-yl)-N-methylpicolinamide | Intermediate-275, Mesylate-1 | A1 |
| 729 | 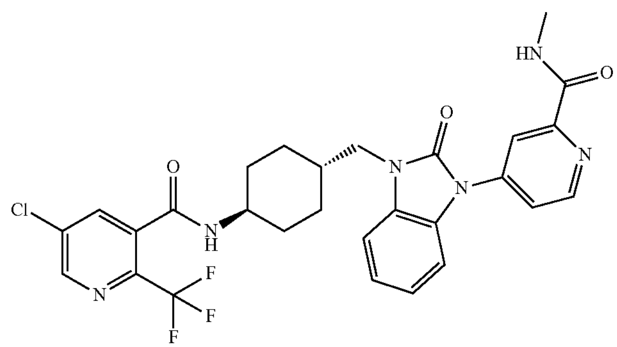 [SMILES: CNC(=O)c1cc(-n2c(=O)n(C[C@H]3CC[C@H](NC(=O)c4cc(Cl)cnc4C(F)(F)F)CC3)c3ccccc32)ccn1] | 4-(3-((1r,4r)-4-(5-chloro-2-(trifluoromethyl)nicotinamido)cyclohexyl)methyl)-2-oxo-2,3-dihydro-1H-benzo[d]imidazol-1-yl)-N-methylpicolinamide | Intermediate-275, Mesylate-3 | A1 |
| 730 | 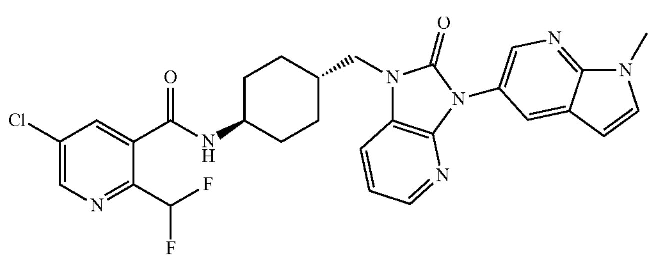 [SMILES: Cn1ccc2cc(-n3c(=O)n(C[C@H]4CC[C@H](NC(=O)c5cc(Cl)cnc5C(F)F)CC4)c4cccnc43)cnc21] | 5-chloro-2-(difluoromethyl)-N-((1r,4r)-4-(3-(1-methyl-1H-pyrrolo[2,3-b]pyridin-5-yl)-2-oxo-2,3-dihydro-1H-imidazol[4,5-b]pyridin-1-yl)methyl)cyclohexyl)nicotinamide | [boronate structure], Intermediate-214 | T |

TABLE 2-continued

| Ex. | Structure | Name | Reactants | Method |
|---|---|---|---|---|
| 731 | 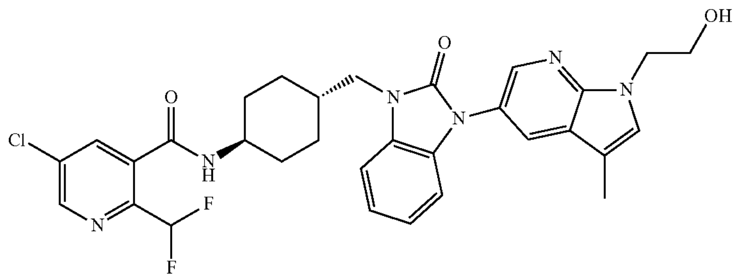 [SMILES: Cc1cn(CCO)c2ncc(-n3c(=O)n(C[C@H]4CC[C@H](NC(=O)c5cc(Cl)cnc5C(F)F)CC4)c4ccccc43)cc12] | 5-chloro-2-(difluoromethyl)-N-((1r,4r)-4-(3-(1-(2-hydroxyethyl)-3-methyl-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |
| 732 | 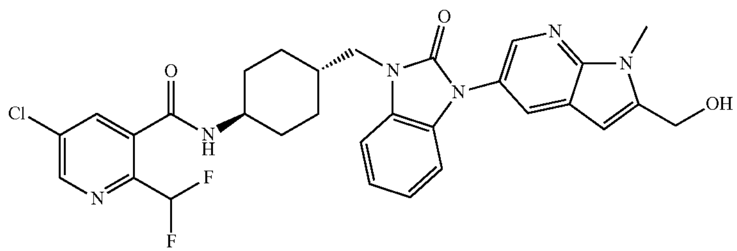 [SMILES: Cn1c(CO)cc2cc(-n3c(=O)n(C[C@H]4CC[C@H](NC(=O)c5cc(Cl)cnc5C(F)F)CC4)c4ccccc43)cnc21] | 5-chloro-2-(difluoromethyl)-N-((1r,4r)-4-((3-(2-(hydroxymethyl)-1-methyl-1H-pyrrolo[2,3-b]pyridin-5-yl)-2-oxo-2,3-dihydro-1H-benzo[d]imidazol-1-yl)methyl)cyclohexyl)nicotinamide | see Example synthesis part | |
| 733 | 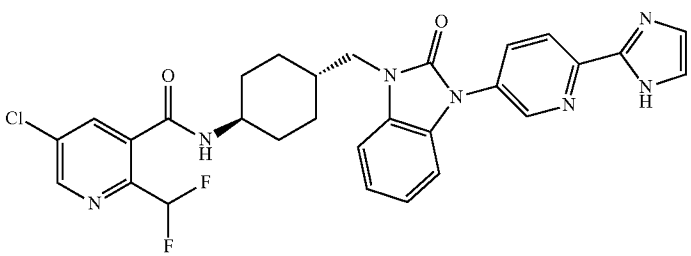 [SMILES: O=C(N[C@H]1CC[C@H](Cn2c(=O)n(-c3ccc(-c4ncc[nH]4)nc3)c3ccccc32)CC1)c1cc(Cl)cnc1C(F)F] | N-((1r,4r)-4-(3-(6-(1H-imidazol-2-yl)pyridin-3-yl)-2-oxo-2,3-dihydro-1H-benzo[d]imidazol-1-yl)methyl)cyclohexyl)-5-chloro-2-(difluoromethyl)nicotinamide | see Example synthesis part | |
| 734 | 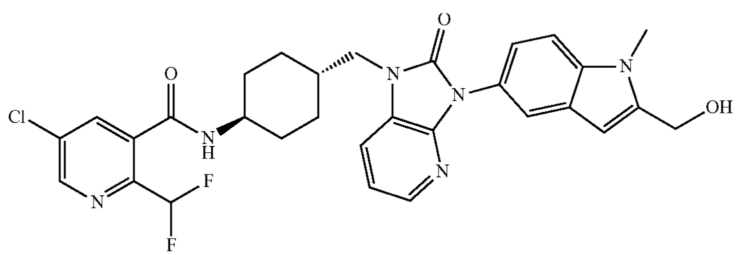 [SMILES: Cn1c(CO)cc2cc(-n3c(=O)n(C[C@H]4CC[C@H](NC(=O)c5cc(Cl)cnc5C(F)F)CC4)c4cccnc43)ccc21] | 5-chloro-2-(difluoromethyl)-N-((1r,4r)-4-((3-(2-(hydroxymethyl)-1-methyl-1H-indol-5-yl)-2-oxo-2,3-dihydro[4,5-b]pyridin-1-yl)methyl)cyclohexyl)nicotinamide | see Example synthesis part | |

TABLE 2-continued

| Ex. | Structure | Name | Reactants | Method |
|---|---|---|---|---|
| 735 | 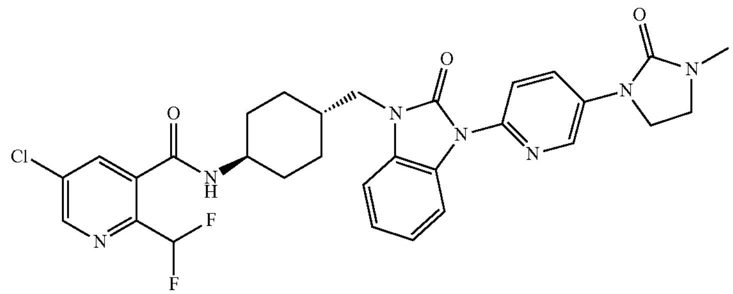 [SMILES: CN1CCN(c2ccc(-n3c(=O)n(C[C@H]4CC[C@H](NC(=O)c5cc(Cl)cnc5C(F)F)CC4)c4ccccc43)nc2)C1=O] | 5-chloro-2-(difluoromethyl)-N-((1r,4r)-4-((3-(5-(3-methyl-2-oxoimidazolidin-1-yl)pyridin-2-yl)-2-oxo-2,3-dihydro-1H-benzo[d]imidazol-1-yl)methyl)cyclohexyl)nicotinamide | Intermediate-265 | R |
| 736 | 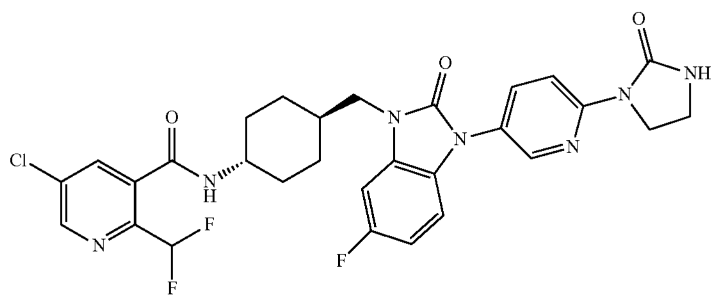 [SMILES: O=C(N[C@H]1CC[C@H](Cn2c(=O)n(-c3ccc(N4CCNC4=O)nc3)c3ccc(F)cc32)CC1)c1cc(Cl)cnc1C(F)F] | 5-chloro-2-(difluoromethyl)-N-((1r,4r)-4-((6-fluoro-2-oxo-3-(6-(2-oxoimidazolidin-1-yl)pyridin-3-yl)-2,3-dihydro-1H-benzo[d]imidazol-1-yl)methyl)cyclohexyl)nicotinamide | Intermediate-262 | U |
| 737 | 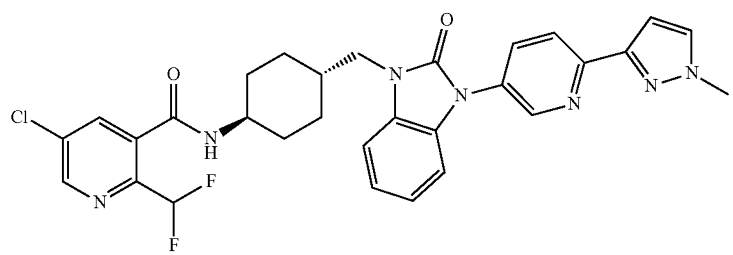 [SMILES: Cn1ccc(-c2ccc(-n3c(=O)n(C[C@H]4CC[C@H](NC(=O)c5cc(Cl)cnc5C(F)F)CC4)c4ccccc43)cn2)n1] | 5-chloro-2-(difluoromethyl)-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)nicotinamide | Intermediate-165 | R |

TABLE 2-continued

| Ex. | Structure | Name | Reactants | Method |
|---|---|---|---|---|
| 738 | 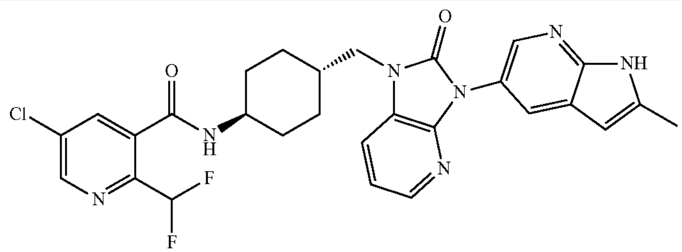 [SMILES: Cc1cc2cc(-n3c(=O)n(C[C@H]4CC[C@H](NC(=O)c5cc(Cl)cnc5C(F)F)CC4)c4cccnc43)cnc2[nH]1] | 5-chloro-2-(difluoromethyl)-N-((1r,4r)-4-((3-(2-methyl-1H-pyrrolo[2,3-b]pyridin-5-yl)-2-oxo-2,3-dihydro-1H-imidazo[4,5-b]pyridin-1-yl)methyl)cyclohexyl)nicotinamide | see Example synthesis part | |
| 739 | 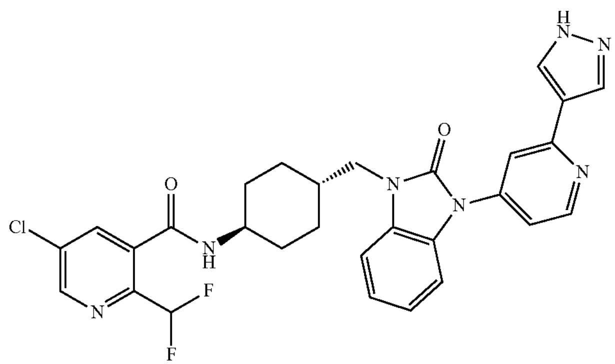 [SMILES: O=C(N[C@H]1CC[C@H](Cn2c(=O)n(-c3ccnc(-c4cn[nH]c4)c3)c3ccccc32)CC1)c1cc(Cl)cnc1C(F)F] | N-((1r,4r)-4-((3-(2-(1H-pyrazol-4-yl)pyridin-4-yl)-2-oxo-2,3-dihydro-1H-benzo[d]imidazol-1-yl)methyl)cyclohexyl)-5-chloro-2-(difluoromethyl)nicotinamide | Intermediate-257, Intermediate-165 | R |
| 740 | 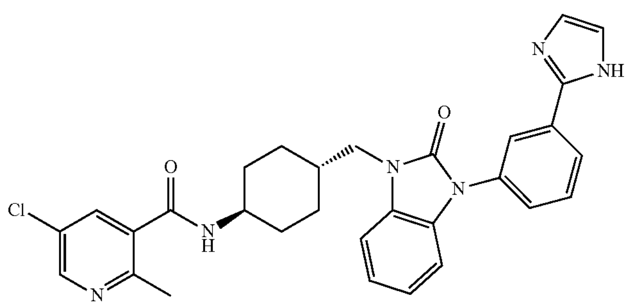 [SMILES: Cc1ncc(Cl)cc1C(=O)N[C@H]1CC[C@H](Cn2c(=O)n(-c3cccc(-c4ncc[nH]4)c3)c3ccccc32)CC1] | N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-methylnicotinamide | see Example synthesis part | |

TABLE 2-continued

| Ex. | Structure | Name | Reactants | Method |
|---|---|---|---|---|
| 741 | 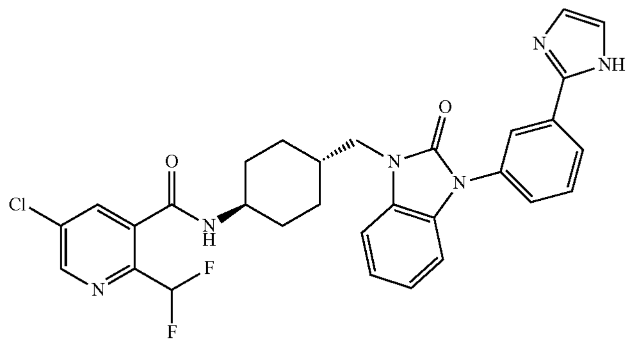 [SMILES: O=C(N[C@H]1CC[C@H](Cn2c(=O)n(-c3cccc(-c4ncc[nH]4)c3)c3ccccc32)CC1)c1cc(Cl)cnc1C(F)F] | N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide | see Example synthesis part | |
| 742 | 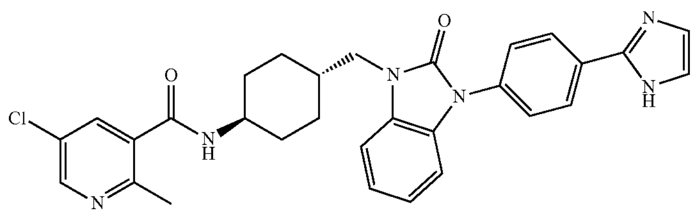 [SMILES: Cc1ncc(Cl)cc1C(=O)N[C@H]1CC[C@H](Cn2c(=O)n(-c3ccc(-c4ncc[nH]4)cc3)c3ccccc32)CC1] | N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-methylnicotinamide | see Example synthesis part | |
| 743 | 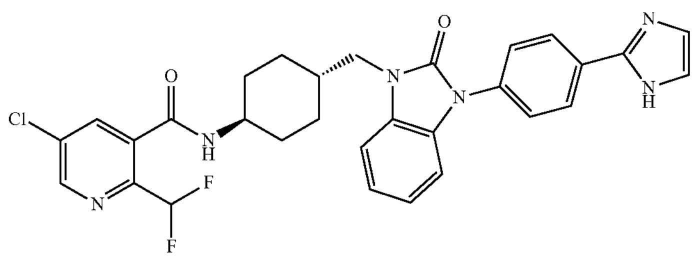 [SMILES: O=C(N[C@H]1CC[C@H](Cn2c(=O)n(-c3ccc(-c4ncc[nH]4)cc3)c3ccccc32)CC1)c1cc(Cl)cnc1C(F)F] | N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide | see Example synthesis part | |

TABLE 2-continued

| Ex. | Structure | Name | Reactants | Method |
|---|---|---|---|---|
| 744 | 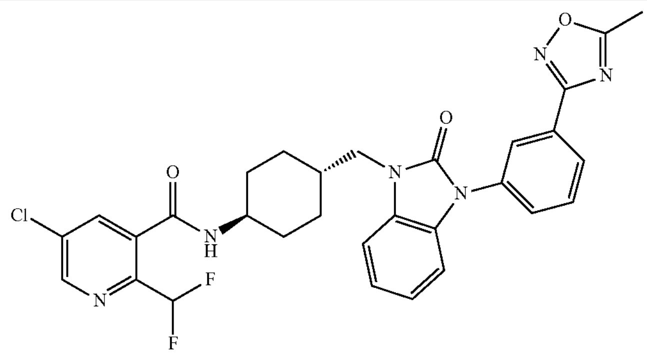 [SMILES: Cc1nc(-c2cccc(-n3c(=O)n(C[C@H]4CC[C@H](NC(=O)c5cc(Cl)cnc5C(F)F)CC4)c4ccccc43)c2)no1] | 5-chloro-2-(difluoromethyl)-N-((1r,4r)-4-(3-(5-methyl-1,2,4-oxadiazol-3-yl)phenyl)-2-oxo-2,3-dihydro-1H-benzo[d]imidazol-1-yl)methyl)cyclohexyl)nicotinamide | Intermediate-165, | R |
| 745 | 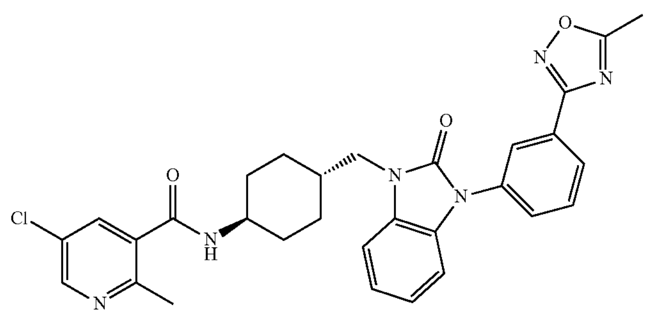 [SMILES: Cc1nc(-c2cccc(-n3c(=O)n(C[C@H]4CC[C@H](NC(=O)c5cc(Cl)cnc5C)CC4)c4ccccc43)c2)no1] | 5-chloro-2-methyl-N-((1r,4r)-4-(3-(5-methyl-1,2,4-oxadiazol-3-yl)phenyl)-2-oxo-2,3-dihydro-1H-benzo[d]imidazol-1-yl)methyl)cyclohexyl)nicotinamide | Step-2 of Ex 9, | R |
| 746 | 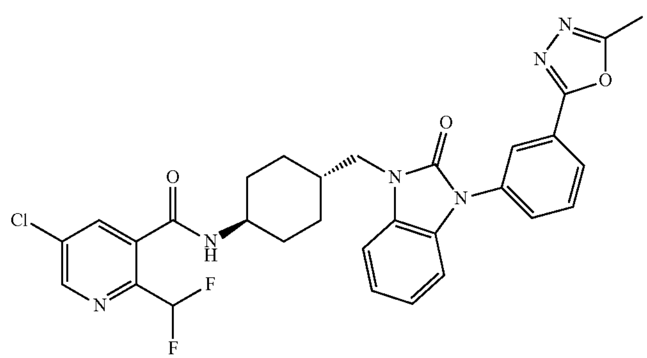 [SMILES: Cc1nnc(-c2cccc(-n3c(=O)n(C[C@H]4CC[C@H](NC(=O)c5cc(Cl)cnc5C(F)F)CC4)c4ccccc43)c2)o1] | 5-chloro-2-(difluoromethyl)-N-((1r,4r)-4-(3-(5-methyl-1,3,4-oxadiazol-2-yl)phenyl)-2-oxo-2,3-dihydro-1H-benzo[d]imidazol-1-yl)methyl)cyclohexyl)nicotinamide | Intermediate-165, | R |

TABLE 2-continued

| Ex. | Structure | Name | Reactants | Method |
|---|---|---|---|---|
| 747 | 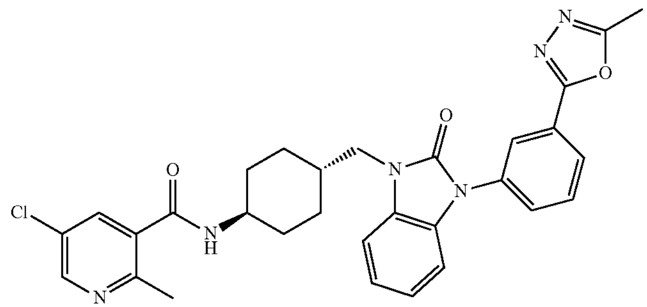 [SMILES: Cc1nnc(-c2cccc(-n3c(=O)n(C[C@H]4CC[C@H](NC(=O)c5cc(Cl)cnc5C)CC4)c4ccccc43)c2)o1] | 5-chloro-2-methyl-N-((1r,4r)-4-((3-(5-methyl-1,3,4-oxadiazol-2-yl)phenyl)-2-oxo-2,3-dihydro-1H-benzo[d]imidazol-1-yl)methyl)cyclohexyl)nicotinamide | Step-2 of Ex 9, | R |
| 748 | 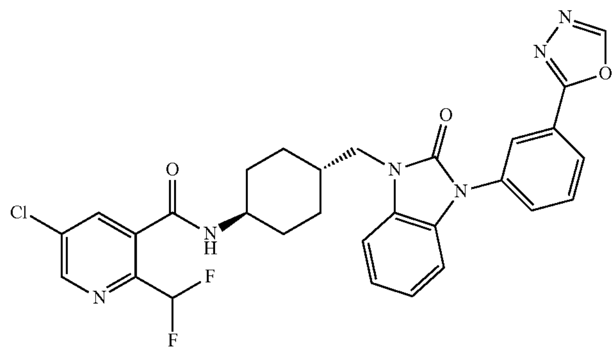 [SMILES: O=C(N[C@H]1CC[C@H](Cn2c(=O)n(-c3cccc(-c4nnco4)c3)c3ccccc32)CC1)c1cc(Cl)cnc1C(F)F] | N-((1r,4r)-4-(3-(3-(1,3,4-oxadiazol-2-yl)phenyl)-2-oxo-2,3-dihydro-1H-benzo[d]imidazol-1-yl)methyl)cyclohexyl)-5-chloro-2-(difluoromethyl)nicotinamide | Intermediate-165, | R |
| 749 | 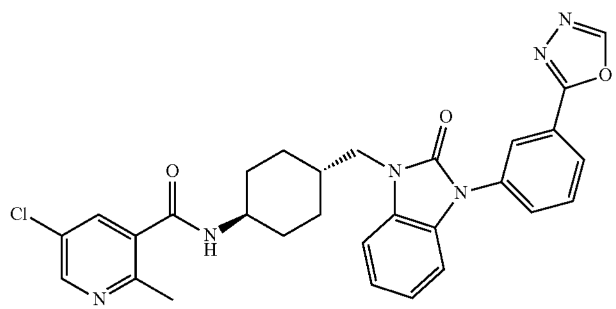 | N-((1r,4r)-4-(3-(3-(1,3,4-oxadiazol-2-yl)phenyl)-2-oxo-2,3-dihydro-1H-benzo[d]imidazol-1-yl)methyl)cyclohexyl)-5-chloro-2-methylnicotinamide | Step-2 of Ex 9, | R |

TABLE 2-continued

| Ex. | Structure | Name | Reactants | Method |
|---|---|---|---|---|
| 750 | 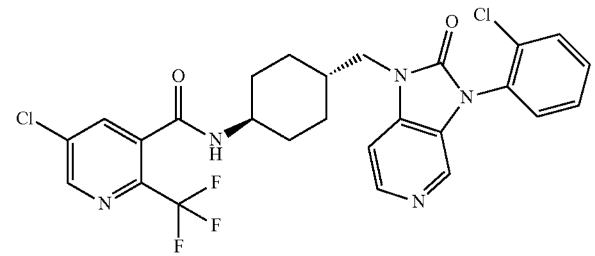 [SMILES: O=C(N[C@H]1CC[C@H](Cn2c(=O)n(-c3ccccc3Cl)c3cnccc32)CC1)c1cc(Cl)cnc1C(F)(F)F] | 5-chloro-N-((1r,4r)-4-((3-(2-chlorophenyl)-2-oxo-2,3-dihydro-1H-imidazo[4,5-c]pyridin-1-yl)methyl)cyclohexyl)-2-(trifluoromethyl)nicotinamide | Intermediate-269, Mesylate-3 | A1 |
| 751 | 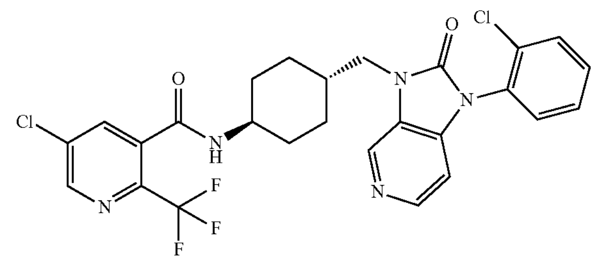 [SMILES: O=C(N[C@H]1CC[C@H](Cn2c(=O)n(-c3ccccc3Cl)c3ccncc32)CC1)c1cc(Cl)cnc1C(F)(F)F] | 5-chloro-N-((1r,4r)-4-((1-(2-chlorophenyl)-2-oxo-1H-imidazo[4,5-c]pyridin-3(2H)-yl)methyl)cyclohexyl)-2-(trifluoromethyl)nicotinamide | Intermediate-164, Mesylate-3 | A1 |
| 752 | 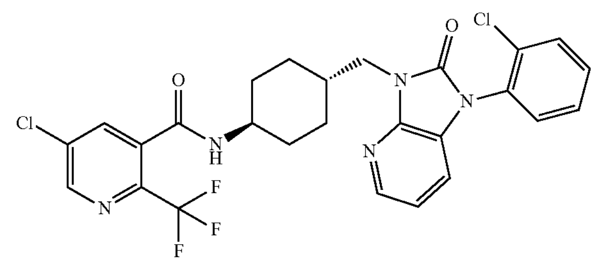 [SMILES: O=C(N[C@H]1CC[C@H](Cn2c(=O)n(-c3ccccc3Cl)c3cccnc32)CC1)c1cc(Cl)cnc1C(F)(F)F] | 5-chloro-N-((1r,4r)-4-(((1-(2-chlorophenyl)-2-oxo-1H-imidazo[4,5-b]pyridin-3(2H)-yl)methyl)cyclohexyl)-2-(trifluoromethyl)nicotinamide | Intermediate-124, Mesylate-3 | A1 |
| 753 | 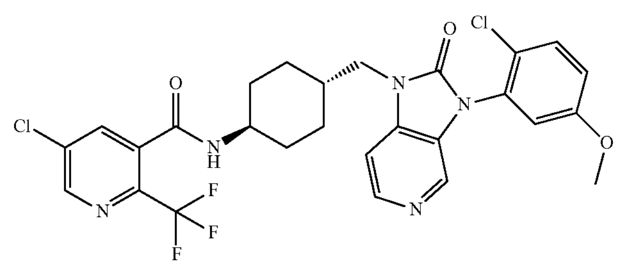 [SMILES: COc1ccc(Cl)c(-n2c(=O)n(C[C@H]3CC[C@H](NC(=O)c4cc(Cl)cnc4C(F)(F)F)CC3)c3ccncc32)c1] | 5-chloro-N-((1r,4r)-4-((3-(2-chloro-5-methoxyphenyl)-2-oxo-2,3-dihydro-1H-imidazo[4,5-c]pyridin-1-yl)methyl)cyclohexyl)-2-(trifluoromethyl)nicotinamide | Intermediate-253, Mesylate-3 | A1 |

TABLE 2-continued

| Ex. | Structure | Name | Reactants | Method |
|---|---|---|---|---|
| 754 | 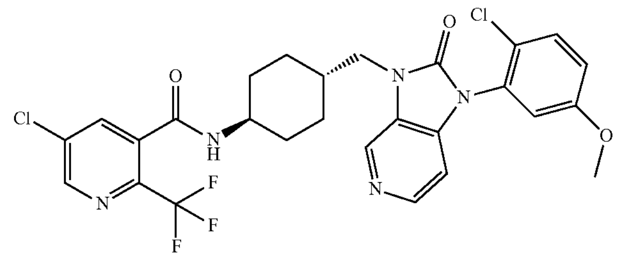 [SMILES: COc1ccc(Cl)c(-n2c(=O)n(C[C@H]3CC[C@H](NC(=O)c4cc(Cl)cnc4C(F)(F)F)CC3)c3cnccc32)c1] | 5-chloro-N-((1r,4r)-4-((1-(2-chloro-5-methoxyphenyl)-2-oxo-1H-imidazo[4,5-c]pyridin-3(2H)-yl)methyl)cyclohexyl)-2-(trifluoromethyl)nicotinamide | Intermediate-243, Mesylate-3 | A1 |
| 755 | 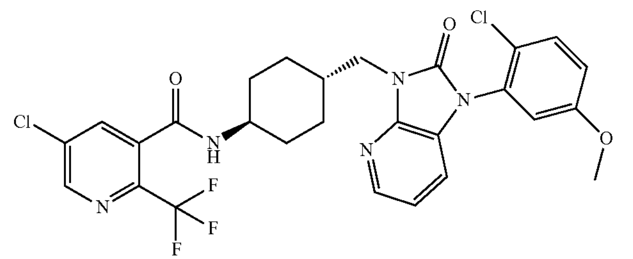 [SMILES: COc1ccc(Cl)c(-n2c(=O)n(C[C@H]3CC[C@H](NC(=O)c4cc(Cl)cnc4C(F)(F)F)CC3)c3ncccc32)c1] | 5-chloro-N-((1r,4r)-4-((1-(2-chloro-5-methoxyphenyl)-2-oxo-1H-imidazo[4,5-b]pyridin-3(2H)-yl)methyl)cyclohexyl)-2-(trifluoromethyl)nicotinamide | Intermediate-249, Mesylate-3 | A1 |
| 756 | 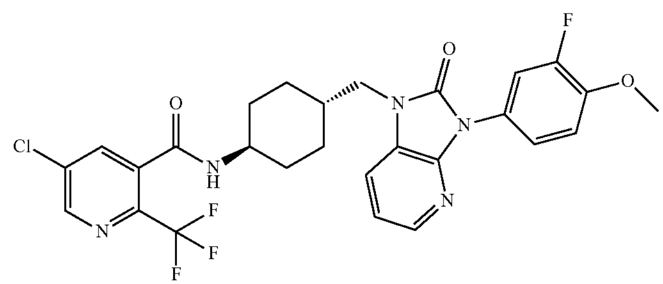 [SMILES: COc1ccc(-n2c(=O)n(C[C@H]3CC[C@H](NC(=O)c4cc(Cl)cnc4C(F)(F)F)CC3)c3cccnc32)cc1F] | 5-chloro-N-((1r,4r)-4-((3-(3-fluoro-4-methoxyphenyl)-2-oxo-2,3-dihydro-1H-imidazo[4,5-b]pyridin-1-yl)methyl)cyclohexyl)-2-(trifluoromethyl)nicotinamide | Intermediate-260, Mesylate-3 | A1 |

| Ex. | Structure | Name | Reactants | Method |
|---|---|---|---|---|
| 757 | 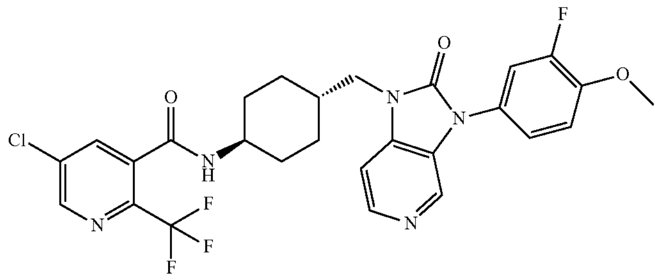 [SMILES: COc1ccc(-n2c(=O)n(C[C@H]3CC[C@H](NC(=O)c4cc(Cl)cnc4C(F)(F)F)CC3)c3ccncc32)cc1F] | 5-chloro-N-((1r,4r)-4-((3-(3-fluoro-4-methoxyphenyl)-2-oxo-2,3-dihydro-1H-imidazo[4,5-c]pyridin-1-yl)methyl)cyclohexyl)-2-(trifluoromethyl)nicotinamide | Intermediate-267, Mesylate-3 | A1 |
| 758 | 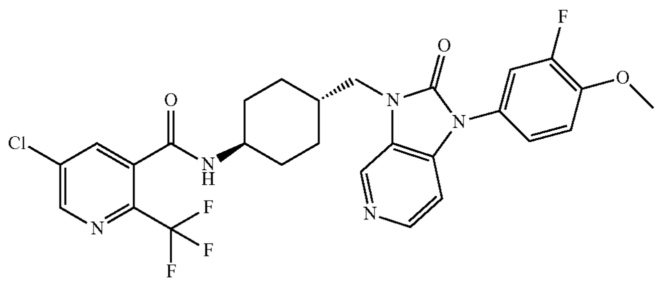 [SMILES: COc1ccc(-n2c(=O)n(C[C@H]3CC[C@H](NC(=O)c4cc(Cl)cnc4C(F)(F)F)CC3)c3cnccc32)cc1F] | 5-chloro-N-((1r,4r)-4-((1-(3-fluoro-4-methoxyphenyl)-2-oxo-1H-imidazo[4,5-c]pyridin-3(2H)-yl)methyl)cyclohexyl)-2-(trifluoromethyl)nicotinamide | Intermediate-272, Mesylate-3 | A1 |
| 759 | 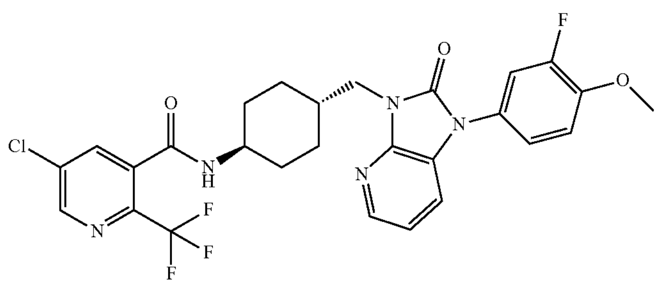 [SMILES: COc1ccc(-n2c(=O)n(C[C@H]3CC[C@H](NC(=O)c4cc(Cl)cnc4C(F)(F)F)CC3)c3ncccc32)cc1F] | 5-chloro-N-((1r,4r)-4-((1-(3-fluoro-4-methoxyphenyl)-2-oxo-1H-imidazo[4,5-b]pyridin-3(2H)-yl)methyl)cyclohexyl)-2-(trifluoromethyl)nicotinamide | Intermediate-270, Mesylate-3 | A1 |

TABLE 2-continued

| Ex. | Structure | Name | Reactants | Method |
|---|---|---|---|---|
| 760 | 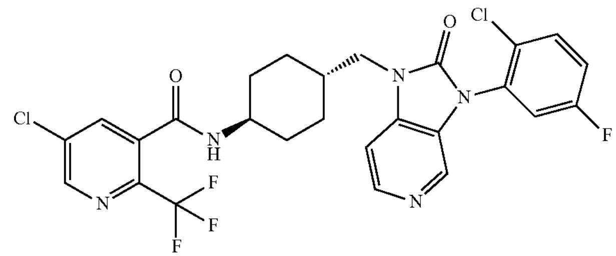 [SMILES: O=C(N[C@H]1CC[C@H](Cn2c(=O)n(-c3cc(F)ccc3Cl)c3cnccc32)CC1)c1cc(Cl)cnc1C(F)(F)F] | 5-chloro-N-((1r,4r)-4-((3-(2-chloro-5-fluorophenyl)-2-oxo-2,3-dihydro-1H-imidazo[4,5-c]pyridin-1-yl)methyl)cyclohexyl)-2-(trifluoromethyl)nicotinamide | Intermediate-266, Mesylate-3 | A1 |
| 761 | 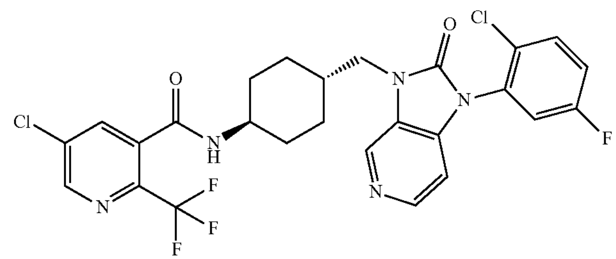 [SMILES: O=C(N[C@H]1CC[C@H](Cn2c(=O)n(-c3cc(F)ccc3Cl)c3ccncc32)CC1)c1cc(Cl)cnc1C(F)(F)F] | 5-chloro-N-((1r,4r)-4-((1-(2-chloro-5-fluorophenyl)-2-oxo-1H-imidazo[4,5-c]pyridin-3(2H)-yl)methyl)cyclohexyl)-2-(trifluoromethyl)nicotinamide | Intermediate-244, Mesylate-3 | A1 |
| 762 | 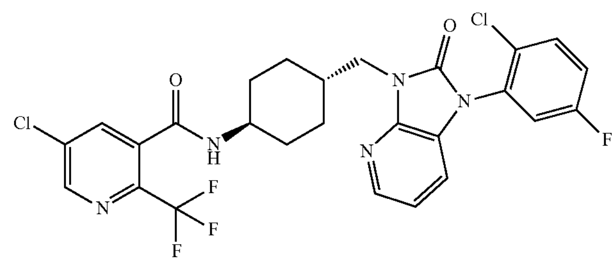 [SMILES: O=C(N[C@H]1CC[C@H](Cn2c(=O)n(-c3cc(F)ccc3Cl)c3cccnc32)CC1)c1cc(Cl)cnc1C(F)(F)F] | 5-chloro-N-((1r,4r)-4-((1-(2-chloro-5-fluorophenyl)-2-oxo-1H-imidazo[4,5-b]pyridin-3(2H)-yl)methyl)cyclohexyl)-2-(trifluoromethyl)nicotinamide | Intermediate-250, Mesylate-3 | A1 |
| 763 | 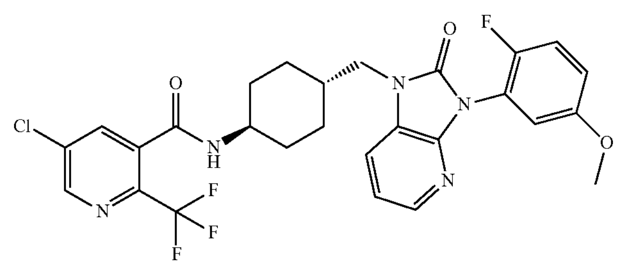 | 5-chloro-N-((1r,4r)-4-((3-(2-fluoro-5-methoxyphenyl)-2-oxo-2,3-dihydro-1H-imidazo[4,5-b]pyridin-1-yl)methyl)cyclohexyl)-2-(trifluoromethyl)nicotinamide | Intermediate-273, Mesylate-3 | A1 |

TABLE 2-continued

| Ex. | Structure | Name | Reactants | Method |
|---|---|---|---|---|
| 764 | 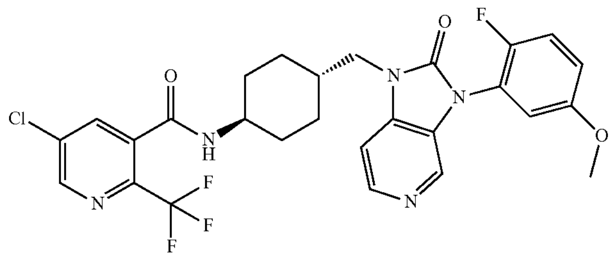 | 5-chloro-N-((1r,4r)-4-((3-(2-fluoro-5-methoxyphenyl)-2-oxo-2,3-dihydro-1H-imidazo[4,5-c]pyridin-1-yl)methyl)cyclohexyl)-2-(trifluoromethyl)nicotinamide | Intermediate-271, Mesylate-3 | A1 |
| 765 | 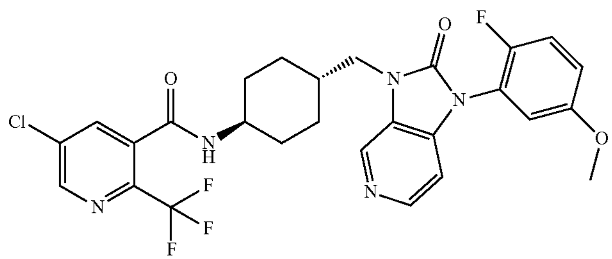 | 5-chloro-N-((1r,4r)-4-((1-(2-fluoro-5-methoxyphenyl)-2-oxo-1H-imidazo[4,5-c]pyridin-3(2H)-yl)methyl)cyclohexyl)-2-(trifluoromethyl)nicotinamide | Intermediate-274, Mesylate-3 | A1 |
| 766 | 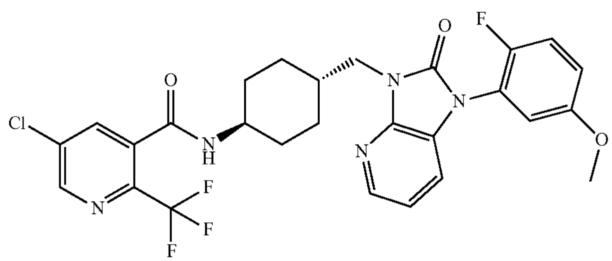 | 5-chloro-N-((1r,4r)-4-((1-(2-fluoro-5-methoxyphenyl)-2-oxo-1H-imidazo[4,5-b]pyridin-3(2H)-yl)methyl)cyclohexyl)-2-(trifluoromethyl)nicotinamide | Intermediate-268, Mesylate-3 | A1 |

TABLE 2-continued

| Ex. | Structure | Name | Reactants | Method |
|---|---|---|---|---|
| 767 | 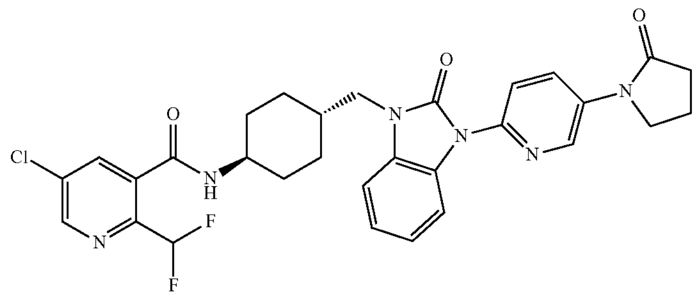 [SMILES: O=C(N[C@H]1CC[C@H](Cn2c(=O)n(-c3ccc(N4CCCC4=O)cn3)c3ccccc32)CC1)c1cc(Cl)cnc1C(F)F] | 5-chloro-2-(difluoromethyl)-N-((1r,4r)-4-((2-oxo-3-(5-(2-oxopyrrolidin-1-yl)pyridin-2-yl)-2,3-dihydro-1H-benzo[d]imidazol-1-yl)methyl)cyclohexyl)nicotinamide | Intermediate-265 | R |
| 768 | 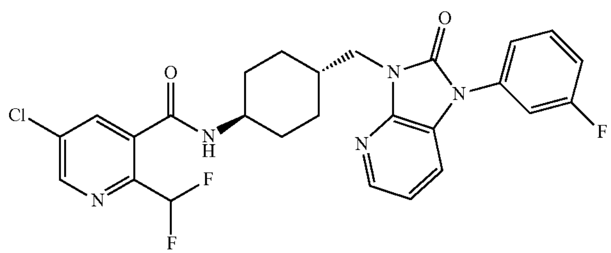 [SMILES: O=C(N[C@H]1CC[C@H](Cn2c(=O)n(-c3cccc(F)c3)c3cccnc32)CC1)c1cc(Cl)cnc1C(F)F] | 5-chloro-2-(difluoromethyl)-N-((1r,4r)-4-((1-(3-fluorophenyl)-2-oxo-1H-imidazo[4,5-b]pyridin-3(2H)-yl)methyl)cyclohexyl)nicotinamide | Intermediate-276, Mesylate-4 | A1 |
| 769 | 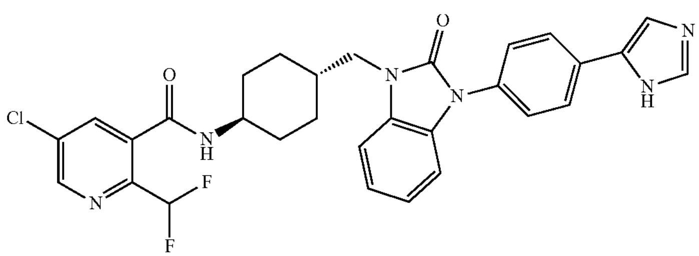 [SMILES: O=C(N[C@H]1CC[C@H](Cn2c(=O)n(-c3ccc(-c4cnc[nH]4)cc3)c3ccccc32)CC1)c1cc(Cl)cnc1C(F)F] | N-((1r,4r)-4-(3-(4-(1H-imidazol-5-yl)phenyl)-2-oxo-2,3-dihydro-1H-benzo[d]imidazol-1-yl)methyl)cyclohexyl)-5-chloro-2-(difluoromethyl)nicotinamide | see Example synthesis part | |
| 770 | 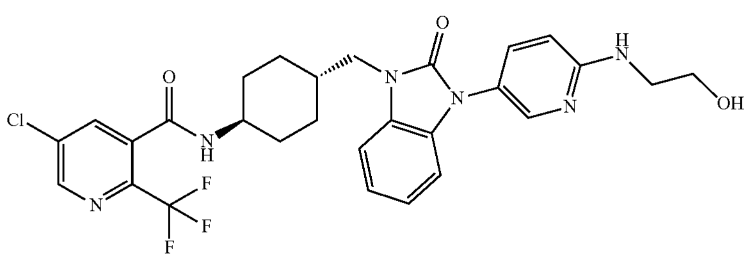 [SMILES: O=C(N[C@H]1CC[C@H](Cn2c(=O)n(-c3ccc(NCCO)nc3)c3ccccc32)CC1)c1cc(Cl)cnc1C(F)(F)F] | 5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-(trifluoromethyl)nicotinamide | Intermediate-246 | K |

TABLE 2-continued

| Ex. | Structure | Name | Reactants | Method |
|---|---|---|---|---|
| 771 | 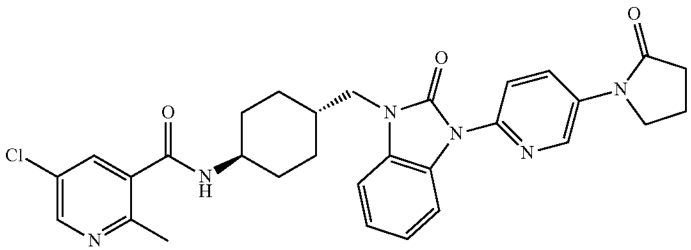 [SMILES: Cc1ncc(Cl)cc1C(=O)N[C@H]1CC[C@H](Cn2c(=O)n(-c3ccc(N4CCCC4=O)cn3)c3ccccc32)CC1] | 5-chloro-2-methyl-N-((1r,4r)-4-((2-oxo-3-(5-(2-oxo-pyrrolidin-1-yl)pyridin-2-yl)-2,3-dihydro-1H-benzo[d]imidazol-1-yl)methyl)cyclohexyl)nicotinamide | Intermediate 277 | R |
| 772 | 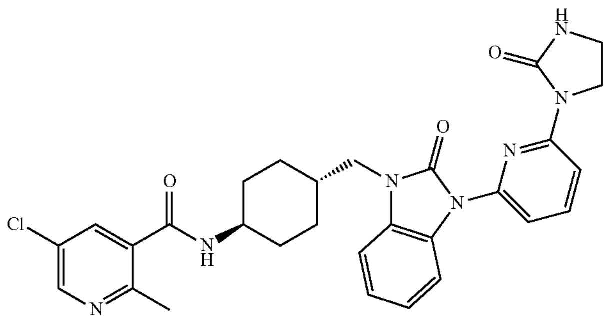 [SMILES: Cc1ncc(Cl)cc1C(=O)N[C@H]1CC[C@H](Cn2c(=O)n(-c3cccc(N4CCNC4=O)n3)c3ccccc32)CC1] | 5-chloro-2-methyl-N-((1r,4r)-4-((2-oxo-3-(6-(2-oxo-imidazolidin-1-yl)pyridin-2-yl)-2,3-dihydro-1H-benzo[d]imidazol-1-yl)methyl)cyclohexyl)nicotinamide | Intermediate 278 | R |
| 773 | 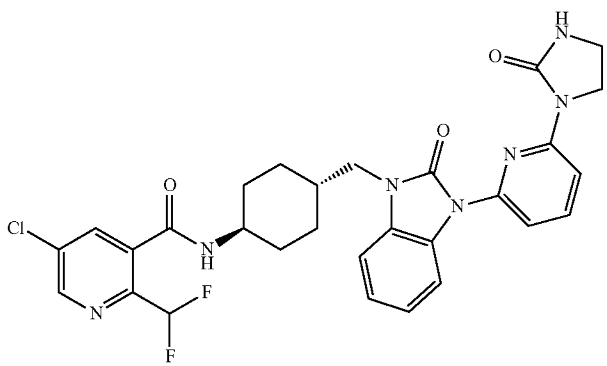 [SMILES: O=C(N[C@H]1CC[C@H](Cn2c(=O)n(-c3cccc(N4CCNC4=O)n3)c3ccccc32)CC1)c1cc(Cl)cnc1C(F)F] | 5-chloro-2-(difluoromethyl)-N-((1r,4r)-4-((2-oxo-3-(6-(2-oxoimidazolidin-1-yl)pyridin-2-yl)-2,3-dihydro-1H-benzo[d]imidazol-1-yl)methyl)cyclohexyl)nicotinamide | Intermediate 279 | R |

TABLE 2-continued

| Ex. | Structure | Name | Reactants | Method |
|---|---|---|---|---|
| 774 | 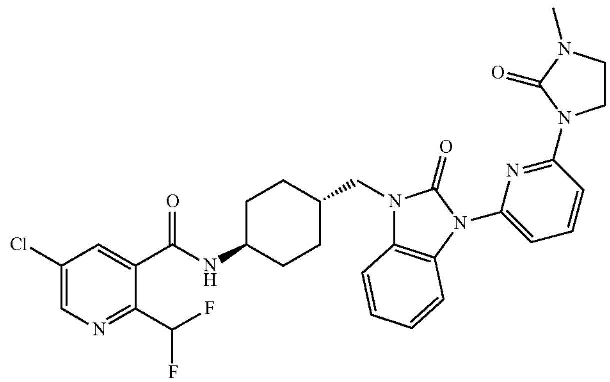 [SMILES: CN1CCN(c2cccc(-n3c(=O)n(C[C@H]4CC[C@H](NC(=O)c5cc(Cl)cnc5C(F)F)CC4)c4ccccc43)n2)C1=O] | 5-chloro-2-(difluoromethyl)-N-((1r,4r)-4-(3-(6-(3-methyl-2-oxoimidazolidin-1-yl)pyridin-2-yl)-2-oxo-2,3-dihydro-1H-benzo[d]imidazol-1-yl)methyl)cyclohexyl)nicotinamide | 1-methylimidazolidin-2-one; Intermediate 279 | R |
| 775 | 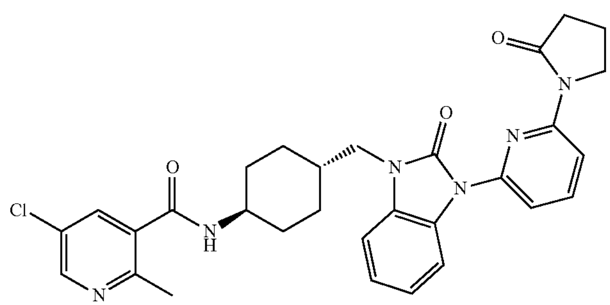 [SMILES: Cc1ncc(Cl)cc1C(=O)N[C@H]1CC[C@H](Cn2c(=O)n(-c3cccc(N4CCCC4=O)n3)c3ccccc32)CC1] | 5-chloro-2-methyl-N-((1r,4r)-4-((2-oxo-3-(6-(2-oxopyrrolidin-1-yl)pyridin-2-yl)-2,3-dihydro-1H-benzo[d]imidazol-1-yl)methyl)cyclohexyl)nicotinamide | pyrrolidin-2-one; Intermediate 278 | R |
| 776 | 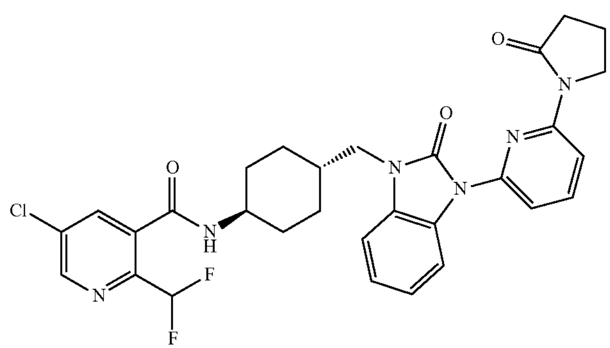 [SMILES: O=C(N[C@H]1CC[C@H](Cn2c(=O)n(-c3cccc(N4CCCC4=O)n3)c3ccccc32)CC1)c1cc(Cl)cnc1C(F)F] | 5-chloro-2-(difluoromethyl)-N-((1r,4r)-4-((2-oxo-3-(6-(2-oxopyrrolidin-1-yl)pyridin-2-yl)-2,3-dihydro-1H-benzo[d]imidazol-1-yl)methyl)cyclohexyl)nicotinamide | pyrrolidin-2-one; Intermediate 279 | R |

TABLE 2-continued

| Ex. | Structure | Name | Reactants | Method |
|---|---|---|---|---|
| 777 | 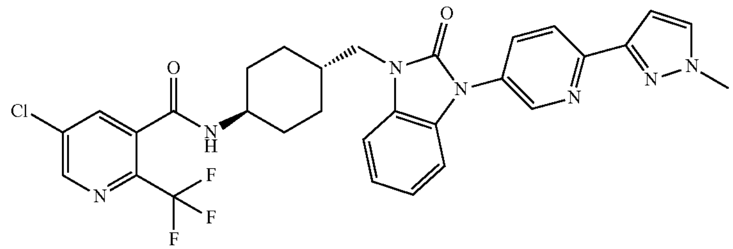 [SMILES: Cn1ccc(-c2ccc(-n3c(=O)n(C[C@H]4CC[C@H](NC(=O)c5cc(Cl)cnc5C(F)(F)F)CC4)c4ccccc43)cn2)n1] | 5-chloro-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)-2-(trifluoromethyl)nicotinamide | Intermediate-132 | R |
| 778 | 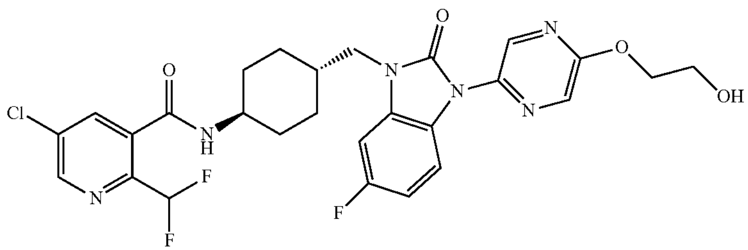 [SMILES: O=C(N[C@H]1CC[C@H](Cn2c(=O)n(-c3cnc(OCCO)cn3)c3ccc(F)cc32)CC1)c1cc(Cl)cnc1C(F)F] | 5-chloro-2-(difluoromethyl)-N-((1r,4r)-4-((6-fluoro-3-(5-(2-hydroxyethoxy)pyrazin-2-yl)-2-oxo-2,3-dihydro-1H-benzo[d]imidazol-1-yl)methyl)cyclohexyl)nicotinamide | see Example synthesis part | |
| 779 | 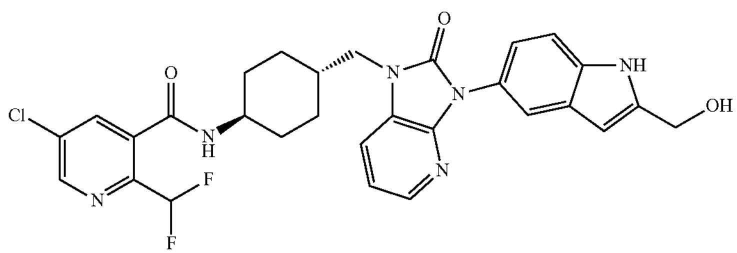 [SMILES: O=C(N[C@H]1CC[C@H](Cn2c(=O)n(-c3ccc4[nH]c(CO)cc4c3)c3ncccc32)CC1)c1cc(Cl)cnc1C(F)F] | 5-chloro-2-(difluoromethyl)-N-((1r,4r)-4-((3-(2-(hydroxymethyl)-1H-indol-5-yl)-2-oxo-2,3-dihydro-1H-imidazo[4,5-b]pyridin-1-yl)methyl)cyclohexyl)nicotinamide | see Example synthesis part | |

TABLE 3-1

| Ex | m/z | tR (min) |
|---|---|---|
| 1 | 475 | 1.90 |
| 2 | 489.1 | 1.88 |
| 3 | 497.1 | 1.66 |
| 4 | 546.1 | 1.55 |
| 5 | 517 | 1.77 |
| 6 | 490 | 1.62 |
| 7 | 490 | 1.55 |
| 8 | 490.1 | 1.53 |
| 9 | 547.1 | 1.78 |
| 10 | 547.1 | 1.82 |
| 11 | 519 | 1.64 |
| 12 | 553 | 1.82 |
| 13 | 542 | 1.72 |
| 14 | 476.1 | 1.59 |
| 15 | 493 | 1.89 |
| 16 | 493 | 1.91 |
| 17 | 517 | 1.79 |
| 18 | 517 | 1.80 |
| 19 | 519.1 | 1.66 |
| 20 | 505 | 1.61 |
| 21 | 505 | 1.59 |
| 22 | 519.1 | 1.60 |
| 23 | 519.1 | 1.58 |
| 24 | 503 | 1.90 |
| 25 | 489 | 1.98 |
| 26 | 509 | 2.00 |
| 27 | 505.1 | 1.87 |
| 28 | 543 | 2.03 |
| 29 | 544 | 1.88 |
| 30 | 506.1 | 1.78 |
| 31 | 490.1 | 1.65 |
| 32 | 504.1 | 1.66 |
| 33 | 493.2 | 1.84 |
| 34 | 505.2 | 1.82 |
| 35 | 556.1 | 1.86 |
| 36 | 520.2 | 1.89 |
| 37 | 524.3 | 2.01 |
| 38 | 509.3 | 1.81 |
| 39 | 525.2 | 1.94 |
| 40 | 524.2 | 1.90 |
| 41 | 536.2 | 1.94 |
| 42 | 538.2 | 1.81 |
| 43 | 507.2 | 1.63 |
| 44 | 535.2 | 1.78 |
| 45 | 506.2 | 1.81 |
| 46 | 511.1 | 1.86 |
| 47 | 507.2 | 1.92 |
| 48 | 523.2 | 1.87 |
| 49 | 490.1 | 1.60 |
| 50 | 536.1 | 1.53 |
| 51 | 490.2 | 1.62 |
| 52 | 519.3 | 1.80 |
| 53 | 563.3 | 1.81 |
| 54 | 561.3 | 1.74 |
| 55 | 574.4 | 1.70 |
| 56 | 490.3 | 1.67 |
| 57 | 504.3 | 1.68 |
| 58 | 520.2 | 1.81 |
| 59 | 577.3 | 1.60 |
| 60 | 520.2 | 1.86 |
| 61 | 588.4 | 1.67 |
| 62 | 519.3 | 1.49 |
| 63 | 533.3 | 1.57 |
| 64 | 549.3 | 1.58 |
| 65 | 604.4 | 1.52 |
| 66 | 554.2 | 1.83 |

TABLE 3-2

| Ex | m/z | tR (min) |
|---|---|---|
| 67 | 520.3 | 1.68 |
| 68 | 575.4 | 1.62 |
| 69 | 537.3 | 1.50 |
| 70 | 502.3 | 1.78 |
| 71 | 554.2 | 1.85 |
| 72 | 504.3 | 1.77 |
| 73 | 562.3 | 1.63 |
| 74 | 591.3 | 1.50 |
| 75 | 605.4 | 1.70 |
| 76 | 605.4 | 1.70 |
| 77 | 633.4 | 1.59 |
| 78 | 589.3 | 1.57 |
| 79 | 603.3 | 1.57 |
| 80 | 561.3 | 1.54 |
| 81 | 561.3 | 1.53 |
| 82 | 502.3 | 1.77 |
| 83 | 504.3 | 1.77 |
| 84 | 558.4 | 1.77 |
| 85 | 557.4 | 1.45 |
| 86 | 516.3 | 1.85 |
| 87 | 560.4 | 1.70 |
| 88 | 479.2 | 1.55 |
| 89 | 552.3 | 1.99 |
| 90 | 582.3 | 1.77 |
| 91 | 505.2 | 1.61 |
| 92 | 519.2 | 1.71 |
| 93 | 535.3 | 1.46 |
| 94 | 563.3 | 1.63 |
| 95 | 575.3 | 1.64 |
| 96 | 575.3 | 1.60 |
| 97 | 542.3 | 1.86 |
| 98 | 533.2 | 1.55 |
| 99 | 591.3 | 1.55 |
| 100 | 526.3 | 1.76 |
| 101 | 531.3 | 1.74 |
| 102 | 605.4 | 1.70 |
| 103 | 605.4 | 1.70 |
| 104 | 506.2 | 1.52 |
| 105 | 545.3 | 1.82 |
| 106 | 561.3 | 1.62 |
| 107 | 561.3 | 1.62 |
| 108 | 581.3 | 1.80 |
| 109 | 575.3 | 1.71 |
| 110 | 575.3 | 1.71 |
| 111 | 559.3 | 1.72 |
| 112 | 546.2 | 2.00 |
| 113 | 532.1 | 1.85 |
| 114 | 534.2 | 1.62 |
| 115 | 506.2 | 1.61 |
| 116 | 520.2 | 1.82 |
| 117 | 562.3 | 1.52 |
| 118 | 536.2 | 1.76 |
| 119 | 504.2 | 1.73 |
| 120 | 520.2 | 1.94 |
| 121 | 508.2 | 1.67 |
| 122 | 508.2 | 1.68 |
| 123 | 508.2 | 1.68 |
| 124 | 508.2 | 1.73 |
| 125 | 545.2 | 1.86 |
| 126 | 589.2 | 1.87 |
| 127 | 519.1 | 1.71 |
| 128 | 516 | 1.50 |
| 129 | 519.1 | 1.75 |
| 130 | 574.1 | 1.57 |
| 131 | 515 | 1.59 |
| 132 | 520.1 | 1.82 |

TABLE 3-3

| Ex | m/z | tR (min) |
|---|---|---|
| 133 | 519.1 | 1.69 |
| 134 | 550.1 | 1.58 |
| 135 | 564.1 | 1.67 |
| 136 | 488.2 | 1.90 |
| 137 | 490.2 | 1.81 |
| 138 | 519.2 | 1.58 |
| 139 | 519.2 | 1.48 |
| 140 | 547.2 | 1.73 |

TABLE 3-3-continued

| Ex | m/z | tR (min) |
|---|---|---|
| 141 | 528.2 | 1.75 |
| 142 | 513.2 | 1.83 |
| 143 | 490.2 | 1.48 |
| 144 | 560.2 | 1.70 |
| 145 | 548.2 | 1.73 |
| 146 | 566.2 | 1.82 |
| 148 | 528.2 | 1.78 |
| 149 | 519.2 | 1.86 |
| 150 | 518.2 | 1.68 |
| 151 | 558.2 | 1.69 |
| 152 | 516.2 | 1.58 |
| 153 | 515.2 | 1.72 |
| 154 | 530.2 | 1.74 |
| 155 | 558.2 | 1.68 |
| 156 | 475.2 | 1.58 |
| 157 | 529.0 | 1.63 |
| 158 | 515.0 | 1.52 |
| 159 | 533.1 | 1.60 |
| 160 | 547.0 | 1.78 |
| 161 | 574.1 | 1.62 |
| 162 | 531.1 | 1.76 |
| 163 | 530.0 | 1.67 |
| 164 | 546.1 | 1.71 |
| 165 | 527.1 | 1.71 |
| 166 | 552.1 | 1.73 |
| 167 | 531.1 | 1.97 |
| 168 | 543.2 | 1.62 |
| 169 | 559.1 | 1.65 |
| 170 | 529.0 | 1.66 |
| 172 | 530.1 | 1.50 |
| 173 | 599.2 | 1.68 |
| 174 | 596.1 | 1.91 |
| 175 | 597.1 | 1.67 |
| 176 | 600.1 | 1.63 |
| 177 | 596.1 | 1.67 |
| 178 | 597.1 | 1.74 |
| 179 | 600.1 | 1.57 |
| 180 | 630.1 | 1.71 |
| 181 | 596.1 | 1.68 |
| 182 | 547.1 | 1.67 |
| 183 | 585.1 | 1.56 |
| 184 | 515.1 | 2.02 |
| 185 | 543.1 | 1.68 |
| 186 | 515.1 | 1.52 |
| 187 | 527.1 | 1.60 |
| 188 | 558.1 | 1.58 |
| 189 | 516.1 | 1.90 |
| 190 | 506.1 | 1.66 |
| 191 | 543.1 | 1.84 |
| 192 | 547.2 | 1.60 |
| 193 | 551.1 | 1.59 |
| 194 | 563.2 | 1.57 |
| 195 | 586.2 | 1.91 |
| 196 | 561.1 | 1.72 |
| 197 | 530.1 | 1.47 |
| 198 | 531.1 | 1.61 |
| 199 | 547.2 | 1.59 |
| 200 | 533.1 | 1.58 |

TABLE 3-4

| Ex | m/z | tR (min) |
|---|---|---|
| 201 | 553.1 | 1.69 |
| 202 | 543.1 | 1.63 |
| 203 | 542.1 | 1.50 |
| 204 | 578.1 | 1.90 |
| 205 | 529.2 | 1.69 |
| 206 | 529.2 | 1.57 |
| 207 | 529.2 | 1.56 |
| 208 | 563.2 | 2.00 |
| 209 | 543.2 | 1.59 |
| 210 | 549.2 | 1.85 |
| 211 | 594.0 | 1.85 |
| 212 | 530.1 | 1.45 |

TABLE 3-4-continued

| Ex | m/z | tR (min) |
|---|---|---|
| 213 | 543.1 | 1.81 |
| 214 | 556.1 | 1.60 |
| 215 | 547.2 | 1.66 |
| 216 | 568.2 | 1.58 |
| 217 | 568.2 | 1.80 |
| 218 | 572.2 | 1.64 |
| 219 | 500.1 | 1.74 |
| 220 | 511.2 | 1.86 |
| 221 | 515.2 | 1.89 |
| 222 | 549.1 | 1.79 |
| 223 | 505.2 | 2.00 |
| 224 | 547.2 | 1.52 |
| 225 | 547.3 | 1.67 |
| 226 | 551.2 | 1.61 |
| 227 | 550.1 | 1.83 |
| 228 | 560.2 | 1.93 |
| 229 | 617.3 | 1.82 |
| 230 | 573.2 | 1.61 |
| 231 | 530.2 | 1.80 |
| 232 | 530.1 | 1.66 |
| 233 | 520.1 | 1.79 |
| 234 | 510.1 | 1.66 |
| 235 | 551.2 | 1.60 |
| 236 | 507.2 | 1.55 |
| 237 | 526.2 | 1.88 |
| 238 | 516.2 | 1.75 |
| 239 | 501.2 | 1.64 |
| 240 | 587.3 | 1.72 |
| 241 | 514.2 | 1.80 |
| 242 | 514.2 | 1.78 |
| 243 | 559.2 | 1.64 |
| 244 | 573.2 | 1.75 |
| 245 | 587.3 | 1.78 |
| 246 | 530.2 | 1.76 |
| 247 | 514.2 | 1.85 |
| 248 | 501.2 | 1.60 |
| 249 | 501.2 | 1.59 |
| 250 | 544.2 | 1.79 |
| 251 | 550.3 | 1.75 |
| 252 | 570.3 | 1.90 |
| 253 | 560.2 | 1.49 |
| 254 | 544.2 | 1.55 |
| 255 | 530.2 | 1.65 |
| 256 | 510.1 | 1.77 |
| 257 | 544.2 | 1.92 |
| 258 | 563.3 | 1.57 |
| 259 | 530.2 | 1.78 |
| 260 | 583.2 | 1.79 |
| 261 | 546.2 | 1.63 |
| 262 | 510.2 | 1.69 |
| 263 | 531.2 | 1.55 |
| 264 | 516.2 | 1.72 |
| 265 | 544.2 | 1.81 |
| 266 | 515.3 | 1.95 |

TABLE 3-5

| Ex | m/z | tR (min) |
|---|---|---|
| 267 | 489.3 | 1.88 |
| 268 | 523.3 | 1.86 |
| 269 | 509.2 | 1.87 |
| 270 | 543.3 | 1.90 |
| 271 | 530.2 | 1.55 |
| 272 | 515.2 | 1.54 |
| 273 | 543.2 | 1.83 |
| 274 | 515.2 | 1.58 |
| 275 | 531.2 | 1.62 |
| 276 | 560.2 | 1.57 |
| 277 | 561.2 | 1.77 |
| 278 | 516.2 | 1.51 |
| 279 | 530.2 | 1.96 |
| 280 | 544.1 | 1.69 |
| 281 | 543.2 | 1.78 |
| 282 | 544.2 | 1.70 |

TABLE 3-5-continued

| Ex | m/z | tR (min) |
|---|---|---|
| 283 | 543.2 | 1.79 |
| 284 | 544.1 | 1.78 |
| 285 | 571.2 | 1.90 |
| 286 | 570.2 | 1.97 |
| 287 | 536.1 | 1.96 |
| 288 | 564.1 | 1.81 |
| 289 | 544.2 | 1.77 |
| 290 | 605.2 | 1.75 |
| 291 | 554.2 | 1.87 |
| 292 | 584.2 | 1.90 |
| 293 | 555.2 | 1.78 |
| 294 | 574.3 | 1.69 |
| 295 | 558.3 | 1.58 |
| 296 | 515.2 | 1.57 |
| 297 | 528.2 | 1.52 |
| 298 | 560.2 | 1.77 |
| 299 | 615.3 | 1.76 |
| 300 | 615.3 | 1.76 |
| 301 | 590.3 | 1.68 |
| 302 | 558.3 | 1.84 |
| 303 | 561.3 | 1.71 |
| 304 | 544.3 | 1.74 |
| 305 | 543.2 | 1.48 |
| 306 | 528.2 | 1.70 |
| 307 | 578.1 | 1.90 |
| 308 | 515.3 | 1.68 |
| 309 | 543.3 | 1.85 |
| 310 | 574.3 | 1.69 |
| 311 | 555.2 | 1.75 |
| 312 | 555.2 | 1.82 |
| 313 | 601.3 | 1.75 |
| 314 | 550.2 | 1.76 |
| 315 | 558.2 | 1.83 |
| 316 | 544.2 | 1.81 |
| 317 | 559.2 | 1.78 |
| 318 | 544.2 | 1.74 |
| 319 | 543.2 | 1.46 |
| 320 | 544.2 | 1.72 |
| 321 | 577.3 | 1.68 |
| 322 | 573.3 | 1.85 |
| 323 | 542.2 | 1.88 |
| 324 | 526.2 | 1.75 |
| 325 | 569.3 | 1.67 |
| 326 | 583.3 | 1.72 |
| 327 | 569.3 | 1.73 |
| 328 | 562.3 | 1.76 |
| 329 | 520.3 | 1.69 |
| 330 | 504.2 | 1.68 |
| 331 | 504.3 | 1.67 |
| 332 | 559.3 | 1.76 |

TABLE 3-6

| Ex | m/z | tR (min) |
|---|---|---|
| 333 | 573.3 | 1.94 |
| 334 | 564.2 | 1.83 |
| 335 | 563.3 | 1.61 |
| 336 | 504.2 | 1.69 |
| 337 | 526.2 | 1.78 |
| 338 | 526.2 | 1.74 |
| 339 | 561.3 | 1.65 |
| 340 | 572.3 | 1.63 |
| 341 | 572.3 | 1.74 |
| 342 | 569.3 | 1.72 |
| 343 | 526.2 | 1.69 |
| 344 | 526.2 | 1.76 |
| 345 | 526.2 | 1.71 |
| 346 | 526.2 | 1.83 |
| 347 | 529.3 | 1.79 |
| 348 | 591.3 | 1.91 |
| 349 | 583.2 | 1.72 |
| 350 | 515.2 | 1.56 |
| 351 | 580.2 | 1.89 |
| 352 | 580.2 | 1.95 |

TABLE 3-6-continued

| Ex | m/z | tR (min) |
|---|---|---|
| 353 | 580.2 | 1.90 |
| 354 | 580.2 | 1.87 |
| 355 | 545.2 | 1.70 |
| 356 | 531.1 | 1.59 |
| 357 | 604.2 | 1.71 |
| 358 | 527.2 | 1.61 |
| 359 | 527.2 | 1.69 |
| 360 | 581.2 | 1.76 |
| 361 | 563.2 | 1.69 |
| 362 | 563.2 | 1.66 |
| 363 | 583.2 | 1.69 |
| 364 | 540.2 | 1.75 |
| 365 | 572.2 | 1.62 |
| 366 | 546.0 | 1.75 |
| 367 | 546.0 | 1.67 |
| 368 | 537.1 | 1.72 |
| 369 | 538.1 | 1.77 |
| 370 | 526.2 | 1.74 |
| 371 | 526.2 | 1.74 |
| 372 | 597.2 | 1.70 |
| 373 | 537.1 | 1.69 |
| 374 | 565.2 | 1.86 |
| 375 | 537.1 | 1.76 |
| 376 | 540.2 | 1.76 |
| 377 | 526.1 | 1.74 |
| 378 | 552.2 | 1.82 |
| 379 | 597.2 | 1.70 |
| 380 | 541.1 | 1.70 |
| 381 | 555.1 | 1.89 |
| 382 | 585.2 | 1.66 |
| 383 | 597.2 | 1.83 |
| 384 | 541.1 | 1.68 |
| 385 | 596.3 | 1.66 |
| 386 | 565.2 | 1.66 |
| 387 | 569.1 | 1.69 |
| 388 | 542.2 | 1.75 |
| 389 | 526.2 | 1.85 |
| 390 | 599.2 | 1.66 |
| 391 | 542.2 | 1.71 |
| 392 | 562.2 | 1.83 |
| 393 | 563.1 | 1.61 |
| 394 | 563.1 | 1.71 |
| 395 | 526.1 | 1.78 |
| 396 | 526.2 | 1.74 |
| 397 | 562.1 | 1.83 |
| 398 | 580.2 | 1.88 |

TABLE 3-7

| Ex | m/z | tR (min) |
|---|---|---|
| 399 | 560.1 | 1.79 |
| 400 | 554.1 | 1.73 |
| 401 | 590.2 | 1.90 |
| 402 | 520.1 | 1.77 |
| 403 | 571.2 | 1.63 |
| 404 | 585.2 | 1.72 |
| 405 | 599.2 | 1.75 |
| 406 | 565.1 | 1.66 |
| 407 | 581.2 | 1.86 |
| 408 | 515.2 | 1.63 |
| 409 | 543.2 | 1.89 |
| 410 | 619.2 | 1.78 |
| 411 | 637.1 | 1.83 |
| 412 | 552.2 | 1.62 |
| 413 | 561.2 | 1.61 |
| 414 | 544.1 | 1.82 |
| 415 | 551.2 | 1.66 |
| 416 | 604.3 | 1.90 |
| 417 | 550.3 | 1.77 |
| 418 | 562.2 | 1.81 |
| 419 | 562.2 | 1.85 |
| 420 | 551.2 | 1.65 |
| 421 | 565.2 | 1.77 |
| 422 | 562.2 | 1.86 |

TABLE 3-7-continued

| Ex | m/z | tR (min) |
|---|---|---|
| 423 | 562.2 | 1.83 |
| 424 | 569.2 | 1.76 |
| 425 | 583.2 | 1.85 |
| 426 | 530.2 | 1.53 |
| 427 | 584.2 | 1.68 |
| 428 | 598.3 | 1.86 |
| 429 | 600.3 | 1.76 |
| 430 | 598.2 | 1.86 |
| 431 | 603.1 | 1.68 |
| 432 | 574.1 | 1.87 |
| 433 | 641.2 | 1.76 |
| 434 | 585.1 | 1.53 |
| 435 | 519.2 | 1.64 |
| 436 | 573.2 | 1.81 |
| 437 | 555.1 | 1.74 |
| 438 | 550.1 | 1.61 |
| 439 | 586.2 | 1.70 |
| 440 | 586.2 | 1.70 |
| 441 | 585.2 | 1.59 |
| 442 | 527.0 | 1.63 |
| 443 | 527.1 | 1.63 |
| 444 | 560.1 | 1.86 |
| 445 | 542.0 | 1.88 |
| 446 | 555.1 | 1.81 |
| 447 | 555.1 | 1.83 |
| 448 | 490.1 | 1.75 |
| 449 | 530.0 | 1.72 |
| 450 | 542.0 | 1.81 |
| 451 | 542.0 | 1.87 |
| 452 | 560.0 | 1.84 |
| 453 | 576.0 | 1.78 |
| 454 | 564.0 | 1.79 |
| 455 | 551.1 | 1.72 |
| 456 | 565.1 | 1.80 |
| 457 | 552.0 | 1.54 |
| 458 | 556.1 | 1.82 |
| 459 | 580.0 | 1.89 |
| 460 | 533.1 | 1.82 |
| 461 | 597.1 | 1.62 |
| 462 | 555.1 | 1.78 |
| 463 | 609.1 | 1.87 |
| 464 | 591.1 | 1.81 |

TABLE 3-8

| Ex | m/z | tR (min) |
|---|---|---|
| 465 | 555.1 | 1.73 |
| 466 | 604.1 | 1.75 |
| 467 | 604.1 | 1.75 |
| 468 | 541.1 | 1.65 |
| 469 | 541.1 | 1.69 |
| 470 | 542.1 | 1.68 |
| 471 | 541.1 | 1.86 |
| 472 | 542.1 | 1.60 |
| 473 | 542.1 | 1.63 |
| 474 | 566.1 | 1.62 |
| 475 | 578.1 | 1.78 |
| 476 | 597.1 | 1.70 |
| 477 | 586.1 | 1.85 |
| 478 | 584.1 | 1.81 |
| 479 | 547.1 | 1.66 |
| 480 | 569.1 | 1.76 |
| 481 | 583.1 | 1.64 |
| 482 | 545.1 | 1.86 |
| 483 | 519.1 | 1.70 |
| 484 | 506.0 | 1.66 |
| 485 | 543.1 | 1.60 |
| 486 | 550.1 | 1.64 |
| 487 | 505.1 | 1.57 |
| 488 | 542.0 | 1.81 |
| 489 | 543.1 | 1.84 |
| 490 | 586.1 | 1.82 |
| 491 | 567.1 | 1.65 |
| 492 | 566.1 | 1.77 |

TABLE 3-8-continued

| Ex | m/z | tR (min) |
|---|---|---|
| 493 | 555.1 | 1.88 |
| 494 | 579.1 | 1.95 |
| 495 | 563.0 | 1.80 |
| 496 | 547.0 | 1.59 |
| 497 | 558.1 | 1.70 |
| 498 | 595.1 | 1.81 |
| 499 | 536.0 | 1.82 |
| 500 | 599.1 | 1.60 |
| 501 | 581.1 | 1.74 |
| 502 | 595.1 | 1.78 |
| 503 | 599.1 | 1.62 |
| 504 | 599.1 | 1.62 |
| 505 | 611.1 | 1.70 |
| 506 | 527.0 | 1.89 |
| 507 | 567.0 | 1.69 |
| 508 | 569.0 | 1.64 |
| 509 | 609.1 | 1.75 |
| 510 | 583.1 | 1.74 |
| 511 | 543.1 | 1.69 |
| 512 | 543.1 | 1.67 |
| 513 | 559.1 | 1.71 |
| 514 | 569.1 | 1.88 |
| 515 | 605.1 | 1.85 |
| 516 | 542.0 | 1.88 |
| 517 | 555.1 | 1.66 |
| 518 | 558.0 | 1.97 |
| 519 | 561.1 | 1.77 |
| 520 | 542.0 | 1.72 |
| 521 | 543.1 | 1.64 |
| 522 | 539.0 | 1.83 |
| 523 | 596.0 | 1.64 |
| 524 | 610.1 | 1.78 |
| 525 | 583.0 | 1.77 |
| 526 | 570.1 | 1.76 |
| 527 | 583.1 | 1.70 |
| 528 | 599.1 | 1.67 |
| 529 | 583.1 | 1.76 |
| 530 | 587.1 | 1.69 |

TABLE 3-9

| Ex | m/z | tR (min) |
|---|---|---|
| 531 | 602.1 | 1.88 |
| 532 | 566.2 | 1.83 |
| 533 | 584.1 | 1.82 |
| 534 | 534.0 | 1.65 |
| 535 | 631.1 | 1.75 |
| 536 | 543.1 | 1.69 |
| 537 | 542.1 | 1.70 |
| 538 | 542.0 | 1.95 |
| 539 | 541.1 | 1.66 |
| 540 | 543.1 | 1.81 |
| 541 | 541.1 | 1.88 |
| 542 | 553.0 | 1.66 |
| 543 | 567.1 | 1.82 |
| 544 | 573.1 | 1.83 |
| 545 | 573.1 | 1.79 |
| 546 | 627.0 | 1.91 |
| 547 | 566.0 | 1.64 |
| 548 | 587.0 | 1.74 |
| 549 | 601.1 | 1.73 |
| 550 | 611.0 | 1.62 |
| 551 | 583.0 | 1.76 |
| 552 | 523.0 | 1.72 |
| 553 | 554.0 | 1.61 |
| 554 | 597.1 | 1.79 |
| 555 | 603.0 | 1.69 |
| 556 | 583.0 | 1.70 |
| 557 | 606.0 | 1.83 |
| 558 | 610.0 | 1.67 |
| 559 | 583.0 | 1.66 |
| 560 | 597.0 | 1.76 |
| 561 | 609.0 | 1.82 |
| 562 | 587.0 | 1.69 |

TABLE 3-9-continued

| Ex | m/z | tR (min) |
|---|---|---|
| 563 | 573.0 | 1.67 |
| 564 | 573.0 | 1.59 |
| 565 | 574.0 | 1.92 |
| 566 | 596.0 | 1.92 |
| 567 | 591.1 | 1.74 |
| 568 | 542.0 | 1.85 |
| 569 | 577.1 | 1.73 |
| 570 | 578.0 | 1.72 |
| 571 | 571.1 | 1.54 |
| 572 | 585.1 | 1.73 |
| 573 | 505.0 | 1.64 |
| 574 | 505.0 | 1.69 |
| 575 | 566.0 | 1.60 |
| 576 | 566.0 | 1.55 |
| 577 | 583.0 | 1.74 |
| 578 | 566.0 | 1.67 |
| 579 | 555.1 | 1.78 |
| 580 | 558.0 | 1.87 |
| 581 | 541.0 | 1.65 |
| 582 | 551.1 | 1.61 |
| 583 | 567.0 | 1.80 |
| 584 | 637.1 | 1.69 |
| 585 | 595.0 | 1.77 |
| 586 | 530.2 | 1.85 |
| 587 | 546.2 | 1.72 |
| 588 | 600.2 | 1.68 |
| 589 | 642.3 | 1.76 |
| 590 | 520.2 | 1.81 |
| 591 | 531.2 | 1.62 |
| 592 | 494.2 | 1.63 |
| 593 | 549.0 | 1.65 |
| 594 | 603.3 | 1.58 |
| 595 | 556.2 | 1.74 |
| 596 | 548.3 | 1.85 |

TABLE 3-10

| Ex | m/z | tR (min) |
|---|---|---|
| 597 | 603.4 | 1.72 |
| 598 | 615.4 | 1.88 |
| 599 | 628.4 | 1.81 |
| 600 | 558.2 | 1.83 |
| 601 | 558.3 | 1.82 |
| 602 | 529.3 | 1.69 |
| 603 | 546.1 | 1.92 |
| 604 | 566.2 | 1.51 |
| 605 | 608.3 | 1.74 |
| 606 | 618.3 | 1.82 |
| 607 | 616.3 | 1.91 |
| 608 | 562.3 | 1.78 |
| 609 | 562.3 | 1.78 |
| 610 | 550.1 | 1.61 |
| 611 | 541.2 | 1.79 |
| 612 | 564.0 | 1.78 |
| 613 | 560.0 | 2.01 |
| 614 | 569.1 | 1.79 |
| 615 | 615.1 | 1.68 |
| 616 | 578.1 | 1.89 |
| 617 | 594.0 | 1.83 |
| 618 | 563.1 | 1.64 |
| 619 | 556.0 | 1.68 |
| 620 | 537.0 | 1.66 |
| 621 | 585.1 | 1.54 |
| 622 | 542.0 | 1.93 |
| 623 | 542.0 | 2.02 |
| 624 | 523.0 | 1.65 |
| 625 | 523.0 | 1.65 |
| 626 | 559.0 | 1.73 |
| 627 | 554.0 | 1.84 |
| 628 | 587.0 | 1.69 |
| 629 | 599.0 | 1.67 |
| 630 | 545.9 | 1.85 |
| 631 | 576.0 | 1.72 |
| 632 | 564.0 | 1.70 |

TABLE 3-10-continued

| Ex | m/z | tR (min) |
|---|---|---|
| 633 | 542.0 | 1.62 |
| 634 | 579.0 | 1.62 |
| 635 | 542.0 | 1.83 |
| 636 | 542.0 | 1.71 |
| 637 | 542.0 | 1.87 |
| 638 | 590.0 | 1.69 |
| 639 | 559.0 | 1.80 |
| 640 | 614.0 | 1.70 |
| 641 | 613.1 | 1.86 |
| 642 | 587.0 | 1.70 |
| 643 | 601.0 | 1.79 |
| 644 | 584.1 | 1.62 |
| 645 | 546.0 | 1.88 |
| 646 | 504.0 | 1.81 |
| 647 | 519.0 | 1.86 |
| 648 | 555.0 | 1.92 |
| 649 | 519.0 | 1.82 |
| 650 | 555.0 | 1.89 |
| 651 | 555.0 | 1.85 |
| 652 | 556.0 | 1.66 |
| 653 | 542.0 | 1.89 |
| 654 | 556.0 | 1.68 |
| 655 | 556.0 | 1.71 |
| 656 | 556.0 | 1.80 |
| 657 | 592.1 | 1.87 |
| 658 | 570.0 | 1.52 |
| 659 | 555.0 | 2.08 |
| 660 | 541.0 | 1.77 |
| 661 | 541.0 | 1.72 |
| 662 | 541.0 | 1.90 |

TABLE 3-11

| Ex | m/z | tR (min) |
|---|---|---|
| 663 | 573.0 | 1.94 |
| 664 | 603.0 | 1.78 |
| 665 | 559.0 | 1.78 |
| 666 | 595.0 | 1.67 |
| 667 | 541.0 | 1.56 |
| 668 | 523.0 | 1.70 |
| 669 | 613.0 | 1.70 |
| 670 | 599.0 | 1.62 |
| 671 | 599.0 | 1.62 |
| 672 | 559.0 | 1.77 |
| 673 | 565.0 | 1.78 |
| 674 | 579.0 | 1.93 |
| 675 | 576.0 | 1.87 |
| 676 | 563.9 | 1.86 |
| 677 | 560.0 | 1.82 |
| 678 | 555.0 | 1.79 |
| 679 | 556.0 | 1.57 |
| 680 | 556.0 | 1.62 |
| 681 | 591.1 | 1.85 |
| 682 | 592.1 | 1.66 |
| 683 | 542.0 | 1.74 |
| 684 | 578.0 | 1.98 |
| 685 | 579.0 | 1.75 |
| 686 | 597.1 | 1.84 |
| 687 | 579.0 | 1.73 |
| 688 | 579.0 | 1.76 |
| 689 | 543.0 | 1.69 |
| 690 | 574.0 | 1.73 |
| 691 | 596.0 | 1.66 |
| 692 | 559.0 | 1.83 |
| 693 | 576.0 | 1.69 |
| 694 | 530.0 | 1.67 |
| 695 | 542.0 | 1.56 |
| 696 | 541.0 | 1.66 |
| 697 | 577.0 | 1.73 |
| 698 | 542.0 | 1.51 |
| 699 | 592.1 | 1.71 |
| 700 | 591.1 | 1.91 |
| 701 | 592.1 | 1.74 |
| 702 | 592.1 | 1.78 |

TABLE 3-11-continued

| Ex | m/z | tR (min) |
|---|---|---|
| 703 | 578.1 | 1.78 |
| 704 | 577.1 | 1.78 |
| 705 | 577.1 | 1.78 |
| 706 | 595.0 | 1.83 |
| 707 | 610.1 | 1.81 |
| 708 | 580.0 | 1.74 |
| 709 | 581.0 | 1.55 |
| 710 | 560.0 | 1.79 |
| 711 | 570.1 | 1.57 |
| 712 | 590.1 | 1.64 |
| 713 | 589.1 | 1.56 |
| 714 | 590.1 | 1.66 |
| 715 | 571.2 | 1.55 |
| 716 | 590.1 | 1.68 |
| 717 | 596.1 | 1.63 |
| 718 | 564.0 | 1.67 |
| 719 | 560.1 | 1.64 |
| 720 | 560.1 | 1.73 |
| 721 | 546.0 | 1.64 |
| 722 | 560.1 | 1.78 |
| 723 | 560.1 | 1.64 |
| 724 | 560.1 | 1.65 |
| 725 | 560.2 | 1.73 |
| 726 | 560.2 | 1.65 |
| 727 | 569.1 | 1.69 |
| 728 | 533.2 | 1.60 |

TABLE 3-12

| Ex | m/z | tR (min) |
|---|---|---|
| 729 | 587.1 | 1.74 |
| 730 | 566.2 | 1.66 |
| 731 | 609.2 | 1.74 |
| 732 | 595.1 | 1.64 |
| 733 | 578.2 | 1.62 |
| 734 | 595.1 | 1.57 |
| 735 | 610.2 | 1.76 |
| 736 | 614.1 | 1.66 |
| 737 | 592.2 | 1.74 |

TABLE 3-12-continued

| Ex | m/z | tR (min) |
|---|---|---|
| 738 | 566.1 | 1.59 |
| 739 | 578.1 | 1.57 |
| 740 | 541.1 | 1.59 |
| 741 | 577.1 | 1.68 |
| 742 | 541.1 | 1.55 |
| 743 | 577.1 | 1.63 |
| 744 | 593.1 | 1.97 |
| 745 | 557.1 | 1.91 |
| 746 | 593.1 | 1.80 |
| 747 | 557.1 | 1.72 |
| 748 | 579.1 | 1.77 |
| 749 | 543.1 | 1.68 |
| 750 | 564.0 | 1.70 |
| 751 | 564.1 | 1.71 |
| 752 | 564.1 | 1.89 |
| 753 | 594.0 | 1.73 |
| 754 | 594.0 | 1.75 |
| 755 | 594.1 | 1.93 |
| 756 | 578.1 | 1.83 |
| 757 | 578.1 | 1.69 |
| 758 | 578.1 | 1.70 |
| 759 | 578.1 | 1.84 |
| 760 | 582.0 | 1.73 |
| 761 | 582.1 | 1.74 |
| 762 | 582.1 | 1.91 |
| 763 | 578.1 | 1.79 |
| 764 | 578.1 | 1.70 |
| 765 | 578.1 | 1.71 |
| 766 | 578.1 | 1.80 |
| 767 | 595.1 | 1.78 |
| 768 | 530.1 | 1.85 |
| 769 | 577.1 | 1.62 |
| 770 | 589.2 | 1.59 |
| 771 | 559.2 | 1.69 |
| 772 | 560.2 | 1.65 |
| 773 | 596.2 | 1.73 |
| 774 | 610.2 | 1.88 |
| 775 | 559.2 | 1.84 |
| 776 | 595.2 | 1.91 |
| 777 | 610.2 | 1.80 |

TABLE 4-1

| | |
|---|---|
| Ex 3 | $^1$H-NMR (400 MHz, DMSO-$d_6$) delta 8.53 (1H, d, J = 2.3 Hz), 8.39 (1H, d, J = 8.2 Hz), 7.78 (1H, d, J = 2.7 Hz), 7.25-7.19 (2H, m), 7.10-7.01 (2H, m), 3.82 (2H, dd, J = 11.4, 2.7 Hz), 3.77-3.62 (5H, m), 3.22 (2H, t, J = 11.4 Hz), 2.46 (3H, s), 2.10-1.98 (1H, m), 1.94-1.58 (5H, m), 1.51-1.40 (2H, m), 1.35-1.12 (6H, m). |
| Ex 21 | $^1$H-NMR (400 MHz, DMSO-$d_6$) delta 8.53 (1H, d, J = 2.3 Hz), 8.41 (1H, d, J = 8.2 Hz), 7.79 (1H, d, J = 2.3 Hz), 7.55-7.45 (4H, m), 7.33 (1H, d, J = 7.8 Hz), 7.14 (1H, dt, J = 7.8, 1.4 Hz), 7.09-6.98 (2H, m), 5.32 (1H, t, J = 5.5 Hz), 4.58 (2H, d, J = 6.9 Hz), 3.78 (2H, d, J = 6.9 Hz), 3.78-3.65 (1H, m), 2.47 (3H, s), 1.98-1.69 (5H, m), 1.29-1.12 (4H, m). |
| Ex 31 | $^1$H-NMR (400 MHz, DMSO-$d_6$) delta 8.64 (1H, d, J = 2.3 Hz), 8.53 (1H, d, J = 2.7 Hz), 8.39 (1H, d, J = 8.2 Hz), 7.90 (1H, dd, J = 8.2, 2.3 Hz), 7.79 (1H, d, J = 2.7 Hz), 7.47 (1H, d, J = 8.2 Hz), 7.35 (1H, d, J = 7.8 Hz), 7.16 (1H, td, J = 7.8, 1.8 Hz), 7.11-7.01 (2H, m), 3.78 (2H, d, J = 6.9 Hz), 3.78-3.63 (1H, m), 2.56 (3H, s), 2.47 (3H, s), 1.98-1.70 (5H, m), 1.31-1.14 (4H, m). |
| Ex 50 | $^1$H-NMR (400 MHz, DMSO-$d_6$) delta 8.48 (1H, d, J = 2.7 Hz), 8.30 (1H, d, J = 2.7 Hz), 7.78 (1H, dd, J = 8.7, 2.7 Hz), 7.61 (1H, d, J = 2.7 Hz), 7.17 (1H, td, J = 7.7, 1.4 Hz), 7.12-7.05 (2H, m), 7.02 (1H, d, J = 7.3 Hz), 6.96 (1H, d. J = 8.7 Hz), 5.66 (1H, d, J = 8.2 Hz), 4.53-4.50 (2H, m), 4.20-3.90 (3H, m), 3.81 (2H, d, J = 6.9 Hz), 3.16 (1H, t, J = 5.5 Hz), 2.61 (3H, s), 2.15 (2H, br d, J = 9.6 Hz), 2.00-1.84 (3H, m), 1.40-1.15 (4H, m). |
| Ex 59 | $^1$H-NMR (400 MHz, DMSO-$d_6$) delta 8.53 (1H, d, J = 2.3 Hz), 8.39 (1H, d, J = 7.8 Hz), 8.27 (1H, dd, J = 2.7, 0.9 Hz), 7.83 (1H, dd, J = 8.7, 2.7 Hz), 7.79 (1H, d, J = 2.3 Hz), 7.17 (1H, d, J = 7.8 Hz), 7.02 (1H, t, J = 7.8 Hz), 6.95 (1H, d, J = 8.7 Hz), 6.81 (1H, J = 7.8 Hz), 4.49-4.31 (2H, m), 3.73 (2H, d, J = 7.3 Hz), 3.78-3.64 (1H, m), 3.73 (2H, d, J = 5.9 Hz), 2.47 (3H, s), 2.22 (6H, s), 1.83 (3H, s), 1.97-1.68 (5H, m), 1.29-1.12 (4H, m). |
| Ex 63 | $^1$H-NMR (400 MHz, CDCl$_3$) delta 8.84 (1H, d, J = 2.3 Hz), 8.49 (1H, d, J = 2.3 Hz), 8.37 (1H, d, J = 8.2 Hz), 8.10 (1H, dd, J = 8.2, 2.3 Hz), 8.05-7.95 (1H, m), 7.61 (1H, d, J = 2.3 Hz), 7.25-7.05 (4H, m), 5.65-5.55 (1H, m), 4.02-3.90 (1H, m), 3.83 (2H, d, J = 6.9 Hz), 3.08 (3H, d, J = 5.0 Hz), 2.62 (3H, s), 2.20-2.13 (2H, m), 2.01-1.87 (3H, m), 1.42-1.15 (4H, m). |

TABLE 4-1-continued

| | |
|---|---|
| Ex 70 | $^1$H-NMR (400 MHz, CDCl$_3$) delta 8.81 (1H, d, J = 2.4 Hz), 8.49 (1H, d, J = 2.4 Hz), 7.90 (1H, dd, J = 8.6, 2.4 Hz), 7.61 (1H, d, J = 2.4 Hz), 7.52 (1H, d, J = 7.9 Hz), 7.23-7.07 (4H, m), 6.89 (1H, dd, J = 17.1, 11.0 Hz), 6.26 (1H, d, J = 17.1 Hz), 5.57 (1H, br), 5.56 (1H, d, J = 11.0 Hz), 4.06-3.91 (1H, m), 3.82 (2H, d, J = 6.7 Hz), 2.61 (3H, s), 2.16 (2H, brd, J = 11.6 Hz), 2.00-1.90 (3H, m), 1.39-1.17 (4H, m). |
| Ex 81 | $^1$H-NMR (400 MHz, DMSO-d$_6$) delta 8.53 (1H, d, J = 2.7 Hz), 8.41 (1H, d, J = 7.8 Hz), 8.16 (1H, d, J = 2.7 Hz), 7.79 (1H, d, J = 2.3 Hz), 7.61 (1H, dd, J = 8.7, 2.7 Hz), 7.30 (1H, d, J = 7.8 Hz), 7.11 (1H, dd, J = 7.8, 6.9 Hz), 7.03 (1H, dd, J = 7.8, 6.9 Hz), 6.88 (1H, d, J = 6.9 Hz), 6.58 (1H, d, J = 8.7 Hz), 5.00 (1H, d, J = 3.7 Hz), 4.42 (1H, br s), 3.76 (2H, d, J = 6.9 Hz), 3.80-3.64 (1H, m), 3.60-3.47 (4H, m), 2.47 (3H, s), 2.10-1.99(1H, m), 1.99-1.70 (6H, m), 1.29-1.15 (4H, m). |
| Ex 170 | $^1$H-NMR (400 MHz, DMSO-d$_6$) delta 8.53 (1H, d, J = 2.3 Hz), 8.40 (1H, d, J = 7.8 Hz), 7.86 (1H, d, J = 1.8 Hz), 7.79 (1H, d, J = 2.3 Hz), 7.62 (1H, d, J = 8.7 Hz), 7.41 (1H, dd, J = 8.7, 1.8 Hz), 7.33 (1H, d, J = 7.8 Hz), 7.13 (1H, t, J = 7.8 Hz), 7.04 (1H, t, J = 7.8 Hz), 6.94 (1H, d, J = 7.8 Hz), 3.88-3.66 (3H, m), 2.53-2.48 (3H, m), 2.47 (3H, s), 2.00-1.70 (5H, m), 1.32-1.12 (4H, m). A signal due to NH is not observed. |

TABLE 4-2

| | |
|---|---|
| Ex 171 | 1H-NMR (CDCl$_3$) delta 8.49 (1H, d, J = 2.7 Hz), 7.80-7.75 (2H, m), 7.61 (1H, d, J = 2.7 Hz), 7.57 (1H, dd, J = 8.5, 1.6 Hz), 7.23-7.17 (2H, m), 7.15-7.07 (2H, m), 5.58 (1H, d, J = 8.2 Hz), 4.03-3.90 (1H, m), 3.84 (2H, d, J = 6.9 Hz), 2.64 (3H, s), 2.61 (3H, s), 2.23-2.09 (2H, m), 2.04-1.87 (3H, m), 1.43-1.29 (2H, m), 1.29-1.15 (2H, m). |
| Ex 172 | $^1$H-NMR (400 MHz, DMSO-d$_6$) delta 8.62 (1H, d, J = 2.3 Hz), 8.53 (1H, d, J = 2.3 Hz), 8.41 (1H, d, J = 7.8 Hz), 8.16 (1H, d, J = 2.3 Hz), 7.80 (1H, d, J = 2.3 Hz), 7.38 (1H, d, J = 7.8 Hz), 7.21-7.15 (1H, m), 7.13-7.04 (2H. m), 3.81 (2H, d, J = 6.9 Hz), 3.78-3.66 (1H, m), 2.59 (3H, s), 2.47 (3H, s), 2.01-1.70 (5H, m), 1.32-1.15 (4H, m). A signal due to NH is not observed. |
| Ex 199 | 1H-NMR (400 MHz, CDCl$_3$) delta 8.50 (1H, d, J = 2.3 Hz), 8.49 (1H, s), 8.26 (1H, s), 8.00 (1H, br d, J = 5.0 Hz), 7.61 (1H, d, J = 2.3 Hz), 7.23-7.18 (1H, m), 7.11-7.06 (2H, m), 6.72 (1H, d, J = 7.8 Hz), 5.57 (1H, br d, J = 8.2 Hz), 4.01-3.91 (1H, m), 3.84 (2H, d, J = 6.9 Hz), 3.07 (3H, d, J = 5.0 Hz), 2.61 (3H, s), 2.31 (3H, s), 2.24-2.15 (2H, m), 2.03-1.88 (3H, m), 1.41-1.18 (4H, m). |
| Ex 288 | $^1$H-NMR (400 MHz, CDCl$_3$) delta 8.68 (1H, d, J = 2.3 Hz), 8.04 (1H, dd, J = 5.2, 1.4 Hz), 7.90 (1H, d, J = 2.3 Hz), 7.65-7.58 (1H, m), 7.55-7.42 (3H, m), 7.30-7.24 (1H, m), 7.08 (1H, dd, J = 7.8, 5.2 Hz), 5.60 (1H, d, J = 8.2 Hz), 4.05-3.91 (1H, m), 3.91-3.72 (2H, m), 2.28-2.09 (2H, m), 2.09-1.83 (3H, m), 1.43-1.13 (4H, m). |
| Ex 296 | $^1$H-NMR (400 MHz, CDCl$_3$) delta 8.49 (1H, d, J = 2.7 Hz), 8.18 (1H, s), 8.06 (1H, dt, J = 7.5, 1.0 Hz), 7.64 (1H, t, J = 1.0 Hz), 7.61 (1H, d, J = 2.7 Hz), 7.51 (1H, s), 7.22-7.16 (2H, m), 7.16-7.10 (1H, m), 7.08 (1H, d, J = 7.8 Hz), 6.85 (1H, dd, J = 7.5, 2.1 Hz), 5.60 (1H, d, J = 7.8 Hz), 4.02-3.90 (1H, m), 3.82 (2H, d, J = 6.9 Hz), 2.61 (3H, s), 2.21-2.11 (2H, m), 2.02-1.85 (3H, m), 1.42-1.13 (4H, m). |
| Ex 301 | $^1$H-NMR (400 MHz, DMSO-d$_6$) delta 8.67 (1H. d, J = 2.3 Hz), 8.31 (1H, d, J = 2.7 Hz), 7.88 (1H, d, J = 2.7 Hz), 7.79 (1H, dd, J = 8.7, 2.7 Hz), 7.20-7.14 (1H, m), 7.12-7.00 (3H, m), 6.97 (1H, d, J = 8.7 Hz), 5.70-5.63 (1H. m), 4.55-4.51 (2H, m), 4.03-3.90 (3H, m), 3.80 (2H, d, J = 6.9 Hz), 3.11 (1H, t, J = 5.9 Hz), 2.20-2.11 (2H. m), 2.00-1.87 (3H, m), 1.40-1.15 (4H, m). |
| Ex 325 | $^1$H-NMR (400 MHz, DMSO-d$_6$) delta 8.90 (1H, d, J = 2.3 Hz), 8.87 (1H, br q, J = 5.0 Hz), 8.83 (1H, d, J = 2.3 Hz), 8.66 (1H, d, J = 7.8 Hz), 8.27-8.20 (2H, m), 8.15 (1H, d, J = 2.3 Hz), 7.39 (1H, d, J = 7.8 Hz), 7.21 (2H, t, J = 7.8 Hz), 7.15 (1H, t, J = 54.0 Hz), 7.11 (1H, t, J = 7.8 Hz), 3.80 (2H, d, J = 6.9 Hz), 3.78-3.65 (1H, m ), 2.86 (3H, d, J = 5.0 Hz), 2.00-1.71 (5H, m), 1.32-1.15 (4H, m). |
| Ex 365 | $^1$H-NMR (400 MHz, DMSO-d$_6$) delta 8.64 (1H, d, J = 2.3 Hz), 8.31 (1H, d, J = 2.7 Hz), 7.92 (1H, d, J = 2.3 Hz), 7.79 (1H, dd, J = 8.7, 2.7 Hz), 7.17 (1H, t, J = 7.8 Hz), 7.13-7.00 (3H, m), 6.97 (1H, d, J = 9.1 Hz), 6.86 (1H, t, J = 54.9 Hz), 5.92 (1H, d, J = 7.8 Hz), 4.57-4.50 (2H, m), 4.05-3.92 (3H, m), 3.81 (2H, d, J = 6.9 Hz), 3.12 (1H, t, J = 5.9 Hz), 2.20-2.10 (2H, m), 2.01-1.87 (3H, m), 1.40-1.17 (4H, m). |

Pharmacological Assays

The in vitro and in vivo inhibitory activities of the compounds of this invention against CRHR2 or CRHR1 are determined by the following procedures.

cAMP functional assay for human CRHR1 and CRHR2

The ability of the compounds of this invention to inhibit either CRHR2 or CRHR1 is assessed by 3',5'-cyclic adenosine monophosphate (cAMP) production in cells using the LANCE Ultra cAMP assay kit (ParkinElmer), which are designed based on the homogeneous time-resolved fluorescence resonance energy transfer (TR-FRET) immunoassay.

CHO-K1 (Chinese hamster ovary) cells stably expressing either human CRHR2-alpha (DiscoveRX, Cat. 95-0048C2) or human CRHR1-beta (DiscoveRX, Cat. 95-0047C2) are grown in HAM's F12 media supplemented with 10% fetal bovine serum (FBS), 100 units/mL penicillin, 100 microg/mL hygromycin and 0.5 microg/mL geneticin at 37° C. in 5% $CO_2$ humidified incubator to 80% confluence. After 7 hours starvation treatment in culture media containing 0.1% FBS, the cells are washed with Hanks balanced salt solution (HBSS) and cryopreserved.

For cAMP assay, frozen cells are thawed and washed with HBSS, followed by resuspended in assay buffer (HBSS containing 0.1% bovine serum albumin, 0.5 mM isobutyl-methylxanthine and 5 mM Hepes, pH 7.4) at the appropriate concentration for the assay. The cell suspensions are plated on 384-well microplates (Greiner Bio-One) at a density of 4,000 cells per well. After preincubating the cells with various concentrations of the compounds for 30 min at 25° C., an assay buffer containing $EC_{80}$ concentration of each agonist is added and the cells are incubated for 30 min at 25° C. Human urocortin2 (Peptide Institute) and CRF (Peptide Institute) are used as agonists for CRHR2 and CRHR1, respectively. For the termination of assay, europium-labeled cAMP tracer and ULight (registered trademark) dye labeled cAMP antibodies, both prepared with Lance-Ultra cAMP detection reagent (Perkin Elmer) are added in the plate and incubate for 60 min at 25° C. After incubation, TR-FRET signal is detected by EnVision plate reader (PerkinElmer). The $IC_{50}$ values for compounds are calculated from dose-response curves by fitting the percent inhibition using XLfit (ID Business Solutions).

All tested compounds show less than about 1 microM of $IC_{50}$ against CRHR2 in the above assays. Preferable compounds show less than about 0.3 microM of $IC_{50}$ against CRHR2 in the above assays.

Compounds with $IC_{50}$ against CRHR2<0.3 microM are:
Example 2, 5, 9, 10, 12, 13, 15, 18, 25, 27, 30, 32, 33, 34, 35, 36, 37, 38, 39, 41, 42, 44, 45, 46, 50, 52, 53, 54, 55, 57, 58, 62, 63, 64, 66, 67, 70, 72, 82, 84, 86, 89, 90, 91, 92, 94, 95, 96, 97, 101, 105, 107, 108, 109, 110, 111, 112, 113, 115, 116, 118, 119, 120, 121, 122, 123, 124, 125, 126, 127, 128, 130, 133, 134, 140, 141, 144, 145, 146, 147, 148, 149, 150, 151, 152, 153, 154, 155, 156, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 194, 195, 196, 197, 198, 199, 200, 201, 202, 203, 204, 205, 206, 208, 209, 210, 211, 212, 213, 214, 215, 216, 218, 219, 220, 221, 222, 223, 224, 225, 226, 227, 228, 229, 230, 231, 232, 233, 234, 235, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 379, 380, 381, 382, 383, 384, 385, 386, 387, 389, 390, 391, 392, 393, 394, 395, 396, 397, 398, 399, 400, 401, 402, 403, 404, 405, 406, 407, 408, 409, 410, 411, 412, 413, 415, 416, 417, 418, 419, 420, 421, 422, 423, 424, 425, 427, 428, 429, 430, 431, 432, 435, 436, 437, 438, 439, 440, 441, 442, 443, 444, 445, 446, 447, 448, 449, 450, 451, 452, 453, 454, 455, 456, 458, 459, 460, 461, 462, 463, 464, 465, 466, 467, 468, 469, 470, 471, 472, 474, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 527, 528, 529, 530, 531, 532, 533, 534, 537, 539, 541, 542, 543, 544, 545, 547, 548, 549, 551, 552, 553, 554, 555, 556, 557, 558, 559, 560, 561, 562, 563, 566, 567, 568, 569, 570, 571, 572, 573, 574, 576, 578, 579, 580, 581, 582, 583, 584, 585, 593, 624, 625, 626, 627, 628, 630, 631, 633, 635, 636, 637, 638, 639, 640, 641, 643, 645, 646, 647, 648, 649, 650, 651, 652, 654, 655, 656, 657, 658, 659, 660, 661, 662, 663, 664, 665, 666, 667, 668, 669, 671, 672, 673, 674, 675, 676, 678, 679, 680, 681, 682, 683, 684, 685, 686, 687, 688, 690, 691, 692, 693, 695, 696, 697, 699, 700, 701, 702, 703, 704, 705, 706, 707, 708, 709, 710, 712, 713, 715, 717, 718, 720, 721, 722, 724, 725, 726, 730, 731, 732, 733, 735, 736, 737, 743, 748, 767, 772, 773, 774, 776, and 777.

The compounds of this invention show preferable activity, which show the above-mentioned practical use.

All tested compounds show less than about 3 microM of $IC_{50}$ against CRHR1 in the above assays. Preferable compounds show less than about 1 microM of $IC_{50}$ against CRHR1 in the above assays.

Compounds with $IC_{50}$ against CRHR1<1 microM are:
Example 3, 15, 18, 21, 25, 27, 30, 31, 32, 34, 43, 45, 50, 59, 61, 62, 63, 64, 65, 67, 68, 69, 73, 74, 80, 81, 91, 92, 94, and 136.

Echocardiogram analysis of mice loaded CRHR2 agonist

Male C57BL/6 mice at 8 weeks old are purchased from Charles River Japan, and housed in groups of 6 per cage under a 12-h light/dark cycle with access to food and water ad libitum. Under conscious condition, transthoracic echocardiography is performed using Vivo1100 imaging system (FUJIFILM VisualSonics). Left ventricular end-systolic diameter (LVDs) and left ventricular end-diastolic diameters (LVDd) are measured to calculate percent fractional shortening (% FS) in M-mode. The % FS is calculated by the following equation: % FS=(LVDd−LVDs)/LVDd×100. After measuring % FS, the animals are anesthetized with an anesthetic mixture (medetomidine, midazolam, butorphanol), and an Alzet (registered trademark) osmotic pump (DURECT) that release mouse urocortin 2 (Peptide Institute) at an infusion rate of 0.11 microL/h (100 ng/g/day) is implanted subcutaneously in the back. Two days after the implantation, examining urocortin 2-induced increase of the % FS, the animals are selected for evaluation and randomized to be nearly equal across all groups. The compounds of the invention or their vehicles are administered systemically. The post-value of % FS is measured at an appropriate time point after compound administration. Statistical analysis is performed by parametric methods.

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centrifuged at 48,000×g at 4° C. for 20 min. The pellets are then resuspended, homogenized, and centrifuged once more in the same manner. The final pellets are resuspended in an appropriate volume of 50 mM Tris-HCl, 10 mM KCl, 1 mM $MgCl_2$ (pH 7.4 at 4° C.), homogenized, ali-quoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at room temperature. Nonspecific binding is determined by 10 microM E4031 at the final concentration.

All tested compounds of the invention show higher $IC_{50}$ values in human dofetilide binding than $IC_{50}$ values in CRHR1 and/or CRHR2 Assay. The high $IC_{50}$ values in human dofetilide binding activities lead to reducing the risk of cardiovascular adverse events.

Metabolic Stability Assay:

Half-Life in Human Liver Microsomes (HLM)

Test compounds (1 microM) are incubated with 3.3 mM $MgCl_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations: Half-life=ln 2/k The compounds of this invention show preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam (ULTRAFINE UC-429) 2 microM) at 3 microM of the each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM $MgCl_2$ and probes as substrate for 5 min. Reaction is started by adding a 20 microL of 10 mM NADPH (20 microL of NADPH generating system, which consist of 10 mM $NADP^+$, 50 mM DL-lsocitric acid and 10 U/mL Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug-drug interaction is interpreted based on generation % of metabolites in the presence or absence of test compound.

The compounds of this invention show preferable results, which show the above-mentioned practical use.

Plasma Protein Binding Assay

Plasma protein binding of the test compound (1 microM) is measured by the method of equilibrium dialysis using 96-well plate type equipment. HTD96a (registered trademark), regenerated cellulose membranes (molecular weight cut-off 12,000-14,000, 22 mm×120 mm) are soaked for over night in distilled water, then for 15 minutes in 30% ethanol, and finally for 20 minutes in dialysis buffer (Dulbecco's phosphate buffered saline, pH 7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile containing internal standard compounds for analysis. The concentration of the compound is determined with LC/MS/MS analysis. The fraction of the compound unbound is calculated by the following equation (A) or (B):

$$(A) fu = 1 - \{([plasma]_{eq} - [buffer]_{eq})/([plasma]_{eq})\} \quad [\text{Math. 1}]$$

wherein $[plasma]_{eq}$ and $[buffer]_{eq}$ are the concentrations of the compound in plasma and buffer, respectively.

[Math. 2]

$$fu(\%) = \frac{Cb/Cis,b \times 4}{Cp/Cis,p \times 4/3} \times 100 \quad (B)$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively.

The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate iso-pore membrane. The concentration of samples is determined by a general gradient HPLC method (J. Pharm. Sci. 2006, 95, 2115-2122).

The compounds of this invention show preferable aqueous solubility, which show the above-mentioned practical use.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

INDUSTRIAL APPLICABILITY

The fused cyclic urea derivatives of the present invention are useful in the treatment of a wide range of disorders in which CRHR1 and/or CRHR2 is involved.

The invention claimed is:
1. A compound of the following formula (I):

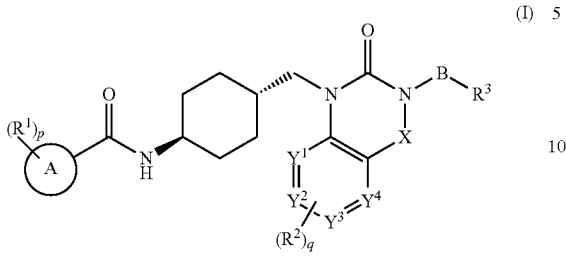

wherein:
A is aryl or heteroaryl;
$R^1$ is independently selected from the group consisting of:
(1) hydrogen, (2) halogen, (3) $C_{1-6}$ alkyl, (4) $C_{3-7}$ cycloalkyl, (5) —O—$C_{1-6}$ alkyl, (6) $C_{1-6}$ alkoxy$C_{1-6}$ alkyl, (7) —NH$C_{1-6}$ alkyl, (8) —N($C_{1-6}$ alkyl)$_2$, and (9) —NH$C_{3-7}$ cycloalkyl, wherein the $C_{1-6}$ alkyl, the $C_{3-7}$ cycloalkyl, the —O—$C_{1-6}$ alkyl, the $C_{1-6}$ alkoxy$C_{1-6}$ alkyl, the —NH$C_{1-6}$ alkyl, the —N($C_{1-6}$ alkyl)$_2$, or the —NH$C_{3-7}$ cycloalkyl is unsubstituted or substituted with one or more substituents independently selected from the group consisting of: halogen and hydroxyl; or two $R^1$ may form a 5 to 7 membered cycloalkyl ring;
p is 1, 2, or 3;
$R^2$ is independently selected from the group consisting of:
(1) hydrogen, (2) halogen, (3) hydroxyl, (4) $C_{1-6}$ alkyl, (5) —O—$C_{1-6}$ alkyl, and (6) —CN;
q is 1, 2, or 3;
$Y^1$, $Y^2$, $Y^3$, and $Y^4$ are independently selected from the group consisting of CH, $CR^2$, and N, number of nitrogen atom is two at most at the same time;
X is a chemical bond or $CH_2$;
B is a chemical bond, —$C_{1-3}$ alkylene-, —$C_{1-3}$ alkylene-O—, or —$CH_2$—(C=O)—;
$R^3$ is selected from the group consisting of:
(1) phenyl, (2) 5 to 6-membered heteroaryl with 1-3 heteroatoms independently selected from O, N, and S, (3) 8 to 10-membered unsaturated or partially saturated bi-cyclic heteroaryl with 1-4 heteroatoms independently selected from O, N, and S, (4) 5 to 6-membered heterocyclyl with 1-2 heteroatoms independently selected from O, N, and S, and (5) indanyl; wherein the phenyl, the 5 to 6-membered heteroaryl, the 8 to 10-membered unsaturated or partially saturated bi-cyclic heteroaryl, the 5 to 6-membered heterocyclyl, or the indanyl is unsubstituted or substituted with one or more substituents independently selected from $R^4$;
$R^4$ is independently selected from the group consisting of:
(1) hydrogen, (2) halogen, (3) hydroxyl, (4) $C_{1-6}$ alkyl, (5) —O—$C_{1-6}$ alkyl, (6) $C_{2-6}$ alkenyl, (7) $C_{3-7}$ cycloalkyl, (8) —O—$C_{3-7}$ cycloalkyl, (9) $C_{3-7}$ cycloalkyl$C_{1-6}$ alkoxyl, (10) —(C=O)—$R^5$, (11) —(C=O)—$NR^5R^6$, (12) —$NR^5$(C=O)$R^6$, (13) —$NR^5R^6$, (14) aryl, (15) heterocyclyl which is 4 to 7 membered partially unsaturated or saturated heterocyclic ring with 1-2 heteroatoms independently selected from O, N, and S, (16) —O-heterocyclyl, (17) heterocyclyl$C_{1-6}$ alkyl, (18) heterocyclyl$C_{1-6}$ alkoxyl, (19) —$NR^5$—S(O)$_2R^6$, (20) —S(O)$_2$—$R^5$, (21) —CN, (22) nitro, (23) heteroaryl, (24) —O-heteroaryl, (25) —S—$C_{1-6}$ alkyl, (26) —O—$C_{1-6}$ alkyl-(C=O)—$NR^5R^6$, and (27) —(C=O)—$NR^5OC_{1-6}$ alkyl, wherein the $C_{1-6}$ alkyl, the —O—$C_{1-6}$ alkyl, the $C_{3-7}$ cycloalkyl, the —O—$C_{3-7}$ cycloalkyl, or the —S—$C_{1-6}$ alkyl is unsubstituted or substituted with one or more substituents independently selected from halogen, hydroxyl, —$NR^5R^6$, —O—$C_{1-6}$ alkyl, and $C_{3-7}$ cycloalkyl, wherein the aryl, the heterocyclyl, the —O-heterocyclyl, the heterocyclyl$C_{1-6}$ alkyl, the heterocyclyl$C_{1-6}$ alkoxyl, the heteroaryl, or the —O-heteroaryl, is unsubstituted or substituted with one or more substituents independently selected from the group consisting of: halogen, hydroxyl, $C_{1-6}$ alkyl, hydroxyl$C_{1-6}$ alkyl, $C_{1-6}$ alkoxyl, and —(C=O)—$R^5$;
$R^5$ is independently selected from the group consisting of:
(1) hydrogen and (2) $C_{1-6}$ alkyl;
$R^6$ is independently selected from the group consisting of:
(1) hydrogen, (2) $C_{1-6}$ alkyl, (3) $C_{3-7}$ cycloalkyl, (4) heterocyclyl, (5) $C_{3-7}$ cycloalkyl$C_{1-6}$ alkyl, (6) heterocyclyl$C_{1-6}$ alkyl, (7) aryl, (8) aryl$C_{1-6}$ alkyl, (9) heteroaryl, and (10) heteroaryl$C_{1-6}$ alkyl, wherein the $C_{1-6}$ alkyl, the $C_{3-7}$ cycloalkyl, the heterocyclyl, the $C_{3-7}$ cycloalkyl$C_{1-6}$ alkyl, the heterocyclyl$C_{1-6}$ alkyl, the aryl, the aryl$C_{1-6}$ alkyl, the heteroaryl, or the heteroaryl$C_{1-6}$ alkyl is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, hydroxy$C_{1-6}$ alkoxyl, $C_{1-6}$ haloalkyl, $C_{1-6}$ haloalkoxyl, —$NR^7R^8$, and —(C=O)—$NR^7R^8$; or $R^5$ may form a 4 to 7 membered ring with $R^6$ which may contain a nitrogen atom, an oxygen atom, or a carbonyl; or
$R^5$ may form a 7 to 11 membered spiro-ring with $R^6$ which may contain a nitrogen atom, an oxygen atom, or carbonyl; wherein the 4 to 7 membered ring or the 7 to 11 membered spiro-ring is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, $C_{1-6}$ haloalkyl, and $C_{1-6}$ haloalkoxyl;
$R^7$ and $R^8$ are independently selected from the group consisting of:
(1) hydrogen and (2) $C_{1-6}$ alkyl; or $R^7$ may form a 4 to 7 membered ring with $R^8$ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, and $C_{1-6}$ haloalkyl;
or a pharmaceutically acceptable salt thereof or a prodrug thereof.
2. The compound of the following formula (II) according to claim 1:

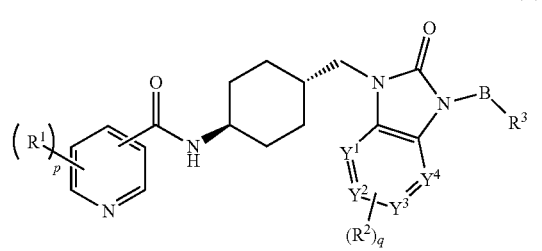

wherein:
R¹ is independently selected from the group consisting of:
(1) hydrogen, (2) halogen, (3) $C_{1-6}$ alkyl, (4) $C_{3-7}$ cycloalkyl, (5) —O—$C_{1-6}$ alkyl, (6) $C_{1-6}$ alkoxyl$C_{1-6}$ alkyl, (7) —NH$C_{1-6}$ alkyl, (8) —N($C_{1-6}$ alkyl)$_2$, and (9) —NH$C_{3-7}$ cycloalkyl, wherein the $C_{1-6}$ alkyl, the $C_{3-7}$ cycloalkyl, the —O—$C_{1-6}$ alkyl, the $C_{1-6}$ alkoxyl$C_{1-6}$ alkyl, the —NH$C_{1-6}$ alkyl, the —N($C_{1-6}$ alkyl)$_2$, or the —NH$C_{3-7}$ cycloalkyl is unsubstituted or substituted with one or more substituents independently selected from the group consisting of: halogen and hydroxyl; or two R¹ may form a 5 to 7 membered cycloalkyl ring;
p is 1, 2, or 3;
R² is independently selected from the group consisting of:
(1) hydrogen, (2) halogen, (4) $C_{1-6}$ alkyl, and (6) —CN;
q is 1, 2, or 3;
$Y^1$, $Y^2$, $Y^3$, and $Y^4$ are independently selected from the group consisting of: CH, CR², and N, number of nitrogen atom is two at most at the same time;
B is a chemical bond, —CH$_2$—, —CH$_2$CH$_2$—, or —CH$_2$—(C=O)—;
R³ is selected from the group consisting of:
(1) phenyl, (2) 5 to 6-membered heteroaryl with 1-3 heteroatoms independently selected from O, N, and S, (3) 8 to 10-membered unsaturated or partially saturated bi-cyclic heteroaryl with 1-4 heteroatoms independently selected from O, N, and S, and (4) 5 to 6-membered heterocyclyl with 1-2 heteroatoms independently selected from O, N, and S; wherein the phenyl, the 5 to 6-membered heteroaryl, the 8 to 10-membered unsaturated or partially saturated bi-cyclic heteroaryl, or the 5 to 6-membered heterocyclyl is unsubstituted or substituted with one or more substituents independently selected from R⁴;
R⁴ is independently selected from the group consisting of:
(1) hydrogen, (2) halogen, (3) hydroxyl, (4) $C_{1-6}$ alkyl, (5) —O—$C_{1-6}$ alkyl, (6) $C_{2-6}$ alkenyl, (7) $C_{3-7}$ cycloalkyl, (8) —O—$C_{3-7}$ cycloalkyl, (9) $C_{3-7}$ cycloalkyl$C_{1-6}$ alkoxyl, (10) —(C=O)—R⁵, (11) —(C=O)—NR⁵R⁶, (12) —NR⁵(C=O)R⁶, (13) —NR⁵R⁶, (14) aryl, (15) heterocyclyl which is 4 to 7 membered partially unsaturated or saturated heterocyclic ring with 1-2 heteroatoms independently selected from O, N, and S, (16) —O-heterocyclyl, (17) heterocyclyl$C_{1-6}$ alkyl, (18) heterocyclyl$C_{1-6}$ alkoxyl, (19) —NR⁵—S(O)$_2$R⁶, (20) —S(O)$_2$—R⁵, (21) —CN, (22) nitro, (23) heteroaryl, (24) —O-heteroaryl, (25) —S—$C_{1-6}$ alkyl, (26) —O—$C_{1-6}$ alkyl-(C=O)—NR⁵R⁶, and (27) —(C=O)—NR⁵O$C_{1-6}$ alkyl, wherein the $C_{1-6}$ alkyl, the —O—$C_{1-6}$ alkyl, the $C_{3-7}$ cycloalkyl, the —O—$C_{3-7}$ cycloalkyl, or the —S—$C_{1-6}$ alkyl is unsubstituted or substituted with one or more substituents independently selected from halogen, hydroxyl, —NR⁵R⁶, —O—$C_{1-6}$ alkyl, and $C_{3-7}$ cycloalkyl, wherein the aryl, the heterocyclyl, the —O-heterocyclyl, the heterocyclyl$C_{1-6}$ alkyl, the heterocyclyl$C_{1-6}$ alkoxyl, the heteroaryl, or the —O-heteroaryl, is unsubstituted or substituted with one or more substituents independently selected from halogen, hydroxyl, $C_{1-6}$ alkyl, hydroxyl$C_{1-6}$ alkyl, and —(C=O)—R⁵;
R⁵ is independently selected from the group consisting of:
(1) hydrogen and (2) $C_{1-6}$ alkyl;
R⁶ is independently selected from the group consisting of:
(1) hydrogen, (2) $C_{1-6}$ alkyl, (3) $C_{3-7}$ cycloalkyl, (4) heterocyclyl, (5) $C_{3-7}$ cycloalkyl$C_{1-6}$ alkyl, (6) heterocyclyl$C_{1-6}$ alkyl, (7) aryl, (8) aryl$C_{1-6}$ alkyl, (9) heteroaryl, and (10) heteroaryl$C_{1-6}$ alkyl, wherein the $C_{1-6}$ alkyl, the $C_{3-7}$ cycloalkyl, the heterocyclyl, the $C_{3-7}$ cycloalkyl$C_{1-6}$ alkyl, the heterocyclyl$C_{1-6}$ alkyl, the aryl, the aryl$C_{1-6}$ alkyl, the heteroaryl, or the heteroaryl$C_{1-6}$ alkyl is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, hydroxy$C_{1-6}$ alkoxyl, $C_{1-6}$ haloalkyl, $C_{1-6}$ haloalkoxyl, —NR⁷R⁸, and —(C=O)—NR⁷R⁸; or R⁵ may form a 4 to 7 membered ring with R⁶ which may contain a nitrogen atom, an oxygen atom, or carbonyl;
wherein the 4 to 7 membered ring is unsubstituted or substituted with one or more substituents independently selected from the group consisting of: halogen, hydroxyl, $C_{1-6}$ alkyl, $C_{1-6}$ alkoxyl, hydroxy$C_{1-6}$ alkyl, $C_{1-6}$ haloalkyl, and $C_{1-6}$ haloalkoxyl;
R⁷ and R⁸ are independently selected from the group consisting of:
(1) hydrogen and (2) $C_{1-6}$ alkyl; or R⁷ may form a 4 to 7 membered ring with R⁸ which may contain a nitrogen atom, an oxygen atom, or carbonyl; wherein the 4 to 7 membered ring is unsubstituted or substituted with one or more substituents independently selected from the group consisting of: halogen, hydroxyl, $C_{1-6}$ alkyl, and $C_{1-6}$ haloalkyl;
or a pharmaceutically acceptable salt thereof or a prodrug thereof.

3. The compound according to claim 1:
wherein:
R¹ is independently selected from the group consisting of:
(1) hydrogen, (2) halogen, and (3) $C_{1-6}$ alkyl; wherein the $C_{1-6}$ alkyl is unsubstituted or substituted with one or more substituents independently selected from the group consisting of: halogen and hydroxyl;
or a pharmaceutically acceptable salt thereof or a prodrug thereof.

4. The compound according to claim 1:
wherein:

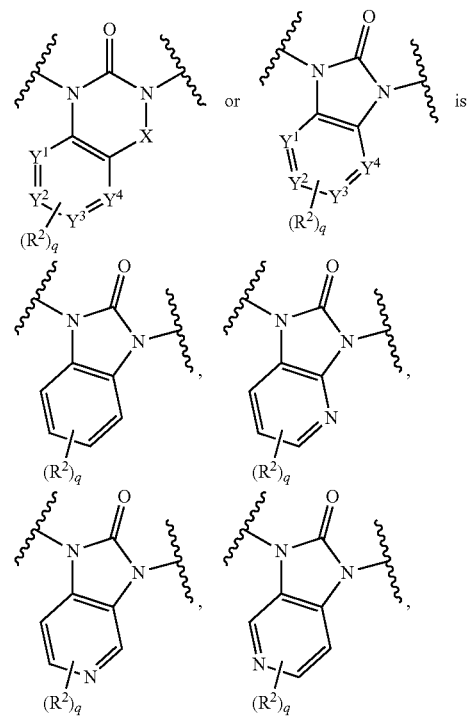

-continued

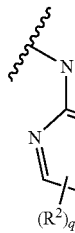 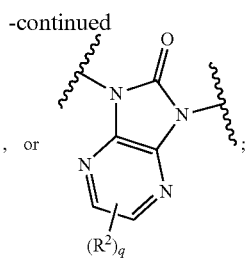

or a pharmaceutically acceptable salt thereof or a prodrug thereof.

5. The compound according to claim 1:
wherein:
B is a chemical bond or —CH$_2$—;
R$^3$ is selected from the group consisting of:
(1) phenyl, (2) 5 to 6-membered heteroaryl selected from pyrazole, pyridine, pyrazine, pyridazine, and pyrimidine, and (3) 8 to 10-membered unsaturated or partially saturated bi-cyclic heteroaryl with 1-4 heteroatoms independently selected from O, N, and S selected from indole, pyrrolo[2,3-b]pyridine, pyrrolo[2,3-c]pyridine, indazole, pyrazolo[3,4-b]pyridine, pyrazolo[4,3-b]pyridine, benzoxazole, and 2,3-dihydro-pyrrolo[2,3-b]pyridine, wherein the phenyl, the 5 to 6-membered heteroaryl or the 8 to 10-membered unsaturated or partially saturated bi-cyclic heteroaryl is unsubstituted or substituted with one or more substituents independently selected from R$^4$;
R$^4$ is independently selected from the group consisting of:
(1) hydrogen, (2) halogen, (3) hydroxyl, (4) C$_{1-6}$ alkyl, (5) —O—C$_{1-6}$ alkyl, (7) C$_{3-7}$ cycloalkyl, (8) —O—C$_{3-7}$ cycloalkyl, (10) —(C=O)—R$^5$, (11) —(C=O)—NR$^5$R$^6$, (13) —NR$^5$R$^6$, (14) aryl, and (23) heteroaryl wherein the C$_{1-6}$ alkyl, the —O—C$_{1-6}$ alkyl, the C$_{3-7}$ cycloalkyl, or the —O—C$_{3-7}$ cycloalkyl is unsubstituted or substituted with one or more substituents independently selected from halogen and hydroxyl; wherein the aryl or the heteroaryl is unsubstituted or substituted with one or more substituents independently selected from halogen, hydroxyl, C$_{1-6}$ alkyl, hydroxylC$_{1-6}$ alkyl, and —(C=O)—R$^5$;
R$^6$ is independently selected from the group consisting of:
(1) hydrogen, (2) C$_{1-6}$ alkyl, (3) C$_{3-7}$ cycloalkyl, (4) heterocyclyl, (5) C$_{3-7}$ cycloalkylC$_{1-6}$ alkyl, (6) heterocyclylC$_{1-6}$ alkyl, (7) aryl, (8) arylC$_{1-6}$ alkyl, (9) heteroaryl, and (10) heteroarylC$_{1-6}$ alkyl, wherein the C$_{1-6}$ alkyl, the C$_{3-7}$ cycloalkyl, the heterocyclyl, the C$_{3-7}$ cycloalkylC$_{1-6}$ alkyl, the heterocyclylC$_{1-6}$ alkyl, the aryl, the arylC$_{1-6}$ alkyl, the heteroaryl, or the heteroarylC$_{1-6}$ alkyl is unsubstituted or substituted with one or more substituents independently selected from the group consisting of: halogen, hydroxyl, C$_{1-6}$ alkyl, C$_{1-6}$ alkoxyl, hydroxyC$_{1-6}$ alkyl, hydroxyC$_{1-6}$ alkoxyl, C$_{1-6}$ haloalkyl, C$_{1-6}$ haloalkoxyl, —NR$^7$R$^8$, and —(C=O)—NR$^7$R$^8$; or R$^5$ may form a 4 to 7 membered ring with R$^6$ which may contain a nitrogen atom, an oxygen atom, or carbonyl;
wherein the 4 to 7 membered ring is unsubstituted or substituted with one or more substituents independently selected from the group consisting of: halogen, hydroxyl, C$_{1-6}$ alkyl, C$_{1-6}$ alkoxyl, hydroxyC$_{1-6}$ alkyl, C$_{1-6}$ haloalkyl, and C$_{1-6}$ haloalkoxyl;
R$^7$ and R$^8$ are independently selected from the group consisting of:
(1) hydrogen and (2) C$_{1-6}$ alkyl; or R$^7$ may form a 4 to 7 membered ring with R$^8$ which may contain a nitrogen atom, an oxygen atom, or carbonyl; wherein the 4 to 7 membered ring is unsubstituted or substituted with one or more substituents independently selected from the group consisting of: halogen, hydroxyl, C$_{1-6}$ alkyl, and C$_{1-6}$ haloalkyl;
or a pharmaceutically acceptable salt thereof or a prodrug thereof.

6. The compound according to claim 1, which is selected from the group consisting of:
5-chloro-2-methyl-N-((1r,4r)-4-((2-oxo-3-phenyl-2,3-dihydro-1H-benzo[d]imidazol-1-yl)methyl)cyclohexyl)nicotinamide;
N-((1r,4r)-4-((3-benzyl-2-oxo-2,3-dihydro-1H-benzo[d]imidazol-1-yl)methyl)cyclohexyl)-5-chloro-2-methylnicotinamide;
5-chloro-2-methyl-N-((1r,4r)-4-((2-oxo-3-((tetrahydro-2H-pyran-4-yl)methyl)-2,3-dihydro-1H-benzo[d]imidazol-1-yl)methyl)cyclohexyl)nicotinamide;
5-chloro-2-methyl-N-((1r,4r)-4-((3-(3-(methylcarbamoyl)benzyl)-2-oxo-2,3-dihydro-1H-benzo[d]imidazol-1-yl)methyl)cyclohexyl)nicotinamide;
5-chloro-2-methyl-N-((1r,4r)-4-((2-oxo-3-(2-oxo-2-phenylethyl)-2,3-dihydro-1H-benzo[d]imidazol-1-yl)methyl)cyclohexyl)nicotinamide;
5-chloro-2-methyl-N-((1r,4r)-4-((2-oxo-3-(pyridin-2-ylmethyl)-2,3-dihydro-1H-benzo[d]imidazol-1-yl)methyl)cyclohexyl)nicotinamide;
5-chloro-2-methyl-N-((1r,4r)-4-((2-oxo-3-(pyridin-3-ylmethyl)-2,3-dihydro-1H-benzo[d]imidazol-1-yl)methyl)cyclohexyl)nicotinamide;
5-chloro-2-methyl-N-((1r,4r)-4-((2-oxo-3-(pyridin-4-ylmethyl)-2,3-dihydro-1H-benzo[d]imidazol-1-yl)methyl)cyclohexyl)nicotinamide;
5-chloro-N-((1r,4r)-4-((3-(2-(4-methoxyphenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(2-(2-methoxyphenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(2-(hydroxymethyl)benzyl)-2-oxo-2,3-dihydro-1H-benzo[d]imidazol-1-yl)methyl)cyclohexyl)-2-methylnicotinamide;
5-chloro-N-((1r,4r)-4-((3-(2-(2,4-difluorophenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(2-(4-cyanophenyl)-2-oxoethyl)-2-oxo-2,3-dihydro-1H-benzo[d]imidazol-1-yl)methyl)cyclohexyl)-2-methylnicotinamide;
5-chloro-2-methyl-N-((1r,4r)-4-((2-oxo-3-(pyridin-4-yl)-2,3-dihydro-1H-benzo[d]imidazol-1-yl)methyl)cyclohexyl)nicotinamide;
5-chloro-N-((1r,4r)-4-((3-(4-fluorophenyl)-2-oxo-2,3-dihydro-1H-benzo[d]imidazol-1-yl)methyl)cyclohexyl)-2-methylnicotinamide;
5-chloro-N-((1r,4r)-4-((3-(3-fluorophenyl)-2-oxo-2,3-dihydro-1H-benzo[d]imidazol-1-yl)methyl)cyclohexyl)-2-methylnicotinamide;
N-((1r,4r)-4-((3-(3-acetylphenyl)-2-oxo-2,3-dihydro-1H-benzo[d]imidazol-1-yl)methyl)cyclohexyl)-5-chloro-2-methylnicotinamide;
N-((1r,4r)-4-((3-(4-acetylphenyl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(4-(1-hydroxyethyl)phenyl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)phenyl)-2-oxo-2,3-dihydro-1H-benzo[d]imidazol-1-yl)methyl)cyclohexyl)-2-methylnicotinamide;

5-chloro-N-((1r,4r)-4-((3-(4-(hydroxymethyl)phenyl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)benzyl)-2-oxo-2,3-dihydro-1H-benzo[d]imidazol-1-yl)methyl)cyclohexyl)-2-methylnicotinamide;

5-chloro-N-((1r,4r)-4-((3-(4-(hydroxymethyl)benzyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-phenethyl-2,3-dihydro-1H-benzo[d]imidazol-1-yl)methyl)cyclohexyl)nicotinamide;

5-chloro-2-methyl-N-((1r,4r)-4-((2-oxo-3-(p-tolyl)-2,3-dihydro-1H-benzo[d]imidazol-1-yl)methyl)cyclohexyl)nicotinamide;

5-chloro-N-((1r,4r)-4-((3-(4-chlorophenyl)-2-oxo-2,3-dihydro-1H-benzo[d]imidazol-1-yl)methyl)cyclohexyl)-2-methylnicotinamide;

5-chloro-N-((1r,4r)-4-((3-(4-methoxyphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(4-(trifluoromethyl)phenyl)-2,3-dihydro-1H-benzo[d]imidazol-1-yl)methyl)cyclohexyl)nicotinamide;

5-chloro-2-methyl-N-((1r,4r)-4-((2-oxo-3-(6-(trifluoromethyl)pyridin-3-yl)-2,3-dihydro-1H-benzo[d]imidazol-1-yl)methyl)cyclohexyl)nicotinamide;

5-chloro-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2-fluorophenyl)-2-oxo-2,3-dihydro-1H-benzo[d]imidazol-1-yl)methyl)cyclohexyl)-2-methylnicotinamide;

5-chloro-N-((1r,4r)-4-((3-(2-methoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(6-(2,2-difluoroethoxy)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-ethoxypyridin-3-yl)-2-oxo-2,3-dihydro-1H-benzo[d]imidazol-1-yl)methyl)cyclohexyl)-2-methylnicotinamide;

2-ethyl-N-((1r,4r)-4-((3-(4-methoxyphenyl)-2-oxo-2,3-dihydro-1H-benzo[d]imidazol-1-yl)methyl)cyclohexyl)-2H-indazole-3-carboxamide;

2-ethyl-N-((1r,4r)-4-((3-(6-methylpyridin-3-yl)-2-oxo-2,3-dihydro-1H-benzo[d]imidazol-1-yl)methyl)cyclohexyl)-2H-indazole-3-carboxamide;

2-ethyl-N-((1r,4r)-4-((3-(6-methoxypyridin-3-yl)-2-oxo-2,3-dihydro-1H-benzo[d]imidazol-1-yl)methyl)cyclohexyl)-2H-indazole-3-carboxamide;

2-(2-hydroxyethyl)-N-((1r,4r)-4-((2-oxo-3-(p-tolyl)-2,3-dihydro-1H-benzo[d]imidazol-1-yl)methyl)cyclohexyl)-2H-indazole-3-carboxamide;

N-((1r,4r)-4-((3-(4-acetylphenyl)-2-oxo-2,3-dihydro-1H-benzo[d]imidazol-1-yl)methyl)cyclohexyl)-2-ethyl-2H-indazole-3-carboxamide;

2-ethyl-N-((1r,4r)-4-((3-(4-(1-hydroxyethyl)phenyl)-2-oxo-2,3-dihydro-1H-benzo[d]imidazol-1-yl)methyl)cyclohexyl)-2H-indazole-3-carboxamide;

5-chloro-N-((1r,4r)-4-((3-(2-methoxypyrimidin-5-yl)-2-oxo-2,3-dihydro-1H-benzo[d]imidazol-1-yl)methyl)cyclohexyl)-2-methylnicotinamide;

5-chloro-N-((1r,4r)-4-((3-(3,4-dimethoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(2-methoxypyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(2,4-difluorophenyl)-2-oxo-2,3-dihydro-1H-benzo[d]imidazol-1-yl)methyl)cyclohexyl)-2-methylnicotinamide;

5-chloro-N-((1r,4r)-4-((3-(4-fluoro-2-methylphenyl)-2-oxo-2,3-dihydro-1H-benzo[d]imidazol-1-yl)methyl)cyclohexyl)-2-methylnicotinamide;

5-chloro-N-((1r,4r)-4-((3-(4-fluoro-3-methoxyphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(2-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(3-methylpyridin-4-yl)-2-oxo-2,3-dihydro-1H-benzo[d]imidazol-1-yl)methyl)cyclohexyl)nicotinamide;

5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((2-methoxyethyl)(methyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-morpholinopyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(4-methylpiperazin-1-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-methylpyridin-4-yl)-2-oxo-2,3-dihydro-1H-benzo[d]imidazol-1-yl)methyl)cyclohexyl)nicotinamide;

5-chloro-2-methyl-N-((1r,4r)-4-((4-methyl-3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(6-methoxypyridin-3-yl)-4-methyl-2-oxo-2,3-dihydro-1H-benzo[d]imidazol-1-yl)methyl)cyclohexyl)-2-methylnicotinamide;

5-chloro-N-((1r,4r)-4-((3-(6-(2-(dimethylamino)ethoxy)pyridin-3-yl)-4-methyl-2-oxo-2,3-dihydro-1H-benzo[d]imidazol-1-yl)methyl)cyclohexyl)-2-methylnicotinamide;

5-chloro-N-((1r,4r)-4-((3-(6-methoxypyridin-3-yl)-7-methyl-2-oxo-2,3-dihydro-1H-benzo[d]imidazol-1-yl)methyl)cyclohexyl)-2-methylnicotinamide;

5-chloro-N-((1S,4r)-4-((3-(6-((S)-3-(dimethylamino)pyrrolidin-1-yl)pyridin-3-yl)-2-oxo-2,3-dihydro-1H-benzo[d]imidazol-1-yl)methyl)cyclohexyl)-2-methylnicotinamide;

5-(3-(((1r,4r)-4-(5-chloro-2-methylnicotinamido)cyclohexyl)methyl)-2-oxo-2,3-dihydro-1H-benzo[d]imidazol-1-yl)picolinamide;

5-(3-(((1r,4r)-4-(5-chloro-2-methylnicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-(2-hydroxyethyl)piperazin-1-yl)pyridin-3-yl)-2-oxo-2,3-dihydro-1H-benzo[d]imidazol-1-yl)methyl)cyclohexyl)-2-methylnicotinamide;

N-((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-(dimethylamino)pyridazin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(4-methylpiperazin-1-yl)pyridazin-3-yl)-2-oxo-2,3-dihydro-1H-benzo[d]imidazol-1-yl)methyl)cyclohexyl)nicotinamide;

5-chloro-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide;

N-((1r,4r)-4-((3-(2-bromopyridin-4-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-ethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(4-(2-(dimethylamino)ethoxy)phenyl)-2-oxo-2,3-dihydro-1H-benzo[d]imidazol-1-yl)methyl)cyclohexyl)-2-methylnicotinamide;

5-chloro-2-methyl-N-((1R,4r)-4-((3-(6-((R)-morpholin-2-ylmethoxy)pyridin-3-yl)-2-oxo-2,3-dihydro-1H-benzo[d]imidazol-1-yl)methyl)cyclohexyl)nicotinamide;

5-chloro-2-methyl-N-((1S,4r)-4-((3-(6-(((S)-4-methylmorpholin-2-yl)methoxy)pyridin-3-yl)-2-oxo-2,3-dihydro-1H-benzo[d]imidazol-1-yl)methyl)cyclohexyl)nicotinamide;

5-chloro-2-methyl-N-((1R,4r)-4-((3-(6-(((R)-4-methylmorpholin-2-yl)methoxy)pyridin-3-yl)-2-oxo-2,3-dihydro-1H-benzo[d]imidazol-1-yl)methyl)cyclohexyl)nicotinamide;

N-((1R,4r)-4-((3-(6-(((R)-4-acetylmorpholin-2-yl)methoxy)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-((1-acetylazetidin-3-yl)oxy)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-((1-acetylazetidin-3-yl)methoxy)pyridin-3-yl)-2-oxo-2,3-dihydro-1H-benzo[d]imidazol-1-yl)methyl)cyclohexyl)-5-chloro-2-methylnicotinamide;

5-chloro-N-((1S,4r)-4-((3-(6-((S)-3-hydroxypyrrolidin-1-yl)pyridin-3-yl)-2-oxo-2,3-dihydro-1H-benzo[d]imidazol-1-yl)methyl)cyclohexyl)-2-methylnicotinamide;

5-chloro-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(2-vinylpyridin-4-yl)-2,3-dihydro-1H-benzo[d]imidazol-1-yl)methyl)cyclohexyl)nicotinamide;

5-chloro-N-((1r,4r)-4-((3-(2-ethylpyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3,6-dihydro-2H-pyran-4-yl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(1',2',3',6'-tetrahydro-[2,4'-bipyridin]-5-yl)-2,3-dihydro-1H-benzo[d]imidazol-1-yl)methyl)cyclohexyl)nicotinamide;

5-chloro-N-((1r,4r)-4-((3-(6-cyclopropylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-(tetrahydro-2H-pyran-4-yl)pyridin-3-yl)-2,3-dihydro-1H-benzo[d]imidazol-1-yl)methyl)cyclohexyl)nicotinamide;

5-chloro-2-methyl-N-((1r,4r)-4-((3-(1-methyl-1H-pyrazol-4-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-phenylpyridin-3-yl)-2,3-dihydro-1H-benzo[d]imidazol-1-yl)methyl)cyclohexyl)nicotinamide;

5-chloro-N-((1r,4r)-4-((3-(6-(2-(hydroxymethyl)phenyl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(ethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((3-hydroxypropyl)(methyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide;

N-((1r,4r)-4-((3-(6-acetamidopyridin-3-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-(2-(hydroxymethyl)morpholino)pyridin-3-yl)-2-oxo-2,3-dihydro-1H-benzo[d]imidazol-1-yl)methyl)cyclohexyl)-2-methylnicotinamide;

5-chloro-N-(4-((3-(6-(difluoromethyl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-methylnicotinamide;

5-chloro-2-methyl-N-((1R,4r)-4-((3-(6-(((R)-4-methylmorpholin-3-yl)methoxy)pyridin-3-yl)-2-oxo-2,3-dihydro-1H-benzo[d]imidazol-1-yl)methyl)cyclohexyl)nicotinamide;

5-chloro-2-methyl-N-((1S,4r)-4-((3-(6-(((S)-4-methyl-morpholin-3-yl)methoxy)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(methylamino)pyridazin-3-yl)-2-oxo-2,3-dihydro-1H-benzo[d]imidazol-1-yl)methyl)cyclohexyl)nicotinamide;

5-chloro-N-((1r,4r)-4-((3-(6-((cyclopropylmethyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)nicotinamide;

5-chloro-2-methyl-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide;

5-chloro-N-((1r,4r)-4-((3-(6-((3,3-difluorocyclobutyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1S,4r)-4-((2-oxo-3-(6-((((S)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1R,4r)-4-((2-oxo-3-(6-((((R)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide;

5-chloro-N-(4-((3-(6-(cyclopropylmethoxy)pyridin-3-yl)-2-oxo-2,3-dihydro-1H-benzo[d]imidazol-1-yl)methyl)cyclohexyl)-2-methylnicotinamide;

5-chloro-N-(4-((3-(6-cyclopropoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2,3-dihydro-[1,4]dioxino[2,3-b]pyridin-7-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(methylamino)pyrazin-2-yl)-2-oxo-2,3-dihydro-1H-benzo[d]imidazol-1-yl)methyl)cyclohexyl)nicotinamide;

5-chloro-N-((1r,4r)-4-((3-(5-(dimethylamino)pyrazin-2-yl)-2-oxo-2,3-dihydro-1H-benzo[d]imidazol-1-yl)methyl)cyclohexyl)-2-methylnicotinamide;

5-chloro-N-((1S,4r)-4-((3-(5-((S)-3-hydroxypyrrolidin-1-yl)pyrazin-2-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxy-5-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((4-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((5-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((6-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((7-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclobutylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-methoxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)-4-methylphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide;

5-chloro-N-((1r,4r)-4-((3-(2-(hydroxymethyl)-4-methylphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-(oxetan-3-ylcarbamoyl)phenyl)-2-oxo-2,3-dihydro-1H-benzo[d]imidazol-1-yl)methyl)cyclohexyl)nicotinamide;

5-chloro-N-((1r,4r)-4-((5-cyano-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxy-4-methylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(3-hydroxypropoxy)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-phenyl-3,4-dihydroquinazolin-1(2H)-yl)methyl)cyclohexyl)nicotinamide;

5-chloro-2-methyl-N-((1r,4r)-4-((2-oxo-3-(p-tolyl)-2,3-dihydro-1H-imidazo[4,5-b]pyrazin-1-yl)methyl)cyclohexyl)nicotinamide;

5-chloro-N-((1r,4r)-4-((3-(6-(dimethylamino)pyridin-3-yl)-2-oxo-2,3-dihydro-1H-imidazo[4,5-b]pyridin-1-yl)methyl)cyclohexyl)-2-methylnicotinamide;

5-chloro-N-((1r,4r)-4-((1-(6-(dimethylamino)pyridin-3-yl)-2-oxo-1H-imidazo[4,5-c]pyridin-3(2H)-yl)methyl)cyclohexyl)-2-methylnicotinamide;

5-chloro-2-methyl-N-((1r,4r)-4-((3-(6-(oxetan-3-yloxy)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(1-methyl-1H-indazol-5-yl)-2-oxo-2,3-dihydro-1H-benzo[d]imidazol-1-yl)methyl)cyclohexyl)nicotinamide;

N-((1r,4r)-4-((3-(1H-indol-6-yl)-2-oxo-2,3-dihydro-1H-benzo[d]imidazol-1-yl)methyl)cyclohexyl)-5-chloro-2-methylnicotinamide;

N-((1r,4r)-4-((3-(6-aminopyridin-3-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-(3-methoxyazetidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3-fluoroazetidin-1-yl)pyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(6-(3,3-difluoroazetidin-1-yl)pyridin-3-yl)-2-oxo-2,3-dihydro-1H-benzo[d]imidazol-1-yl)methyl)cyclohexyl)-2-methylnicotinamide;
5-chloro-2-methyl-N-((1r,4r)-4-((3-(6-(oxetan-3-ylamino)pyridin-3-yl)-2-oxo-2,3-dihydro-1H-benzo[d]imidazol-1-yl)methyl)cyclohexyl)nicotinamide;
5-chloro-2-methyl-N-((1r,4r)-4-((3-(1-methyl-1H-pyrrolo[2,3-b]pyridin-5-yl)-2-oxo-2,3-dihydro-1H-benzo[d]imidazol-1-yl)methyl)cyclohexyl)nicotinamide;
5-chloro-N-((1r,4r)-4-((3-(6-methoxy-2-methylpyridin-3-yl)-2-oxo-2,3-dihydro-1H-benzo[d]imidazol-1-yl)methyl)cyclohexyl)-2-methylnicotinamide;
5-chloro-2-methyl-N-((1r,4r)-4-((3-(2-methyl-6-(methylamino)pyridin-3-yl)-2-oxo-2,3-dihydro-1H-benzo[d]imidazol-1-yl)methyl)cyclohexyl)nicotinamide;
5-(3-(((1r,4r)-4-(5-chloro-2-methylnicotinamido)cyclohexyl)methyl)-2-oxo-2,3-dihydro-1H-benzo[d]imidazol-1-yl)-N-cyclopropylpicolinamide;
5-chloro-N-((1r,4r)-4-((3-(2,3-dihydro-1H-pyrrolo[2,3-b]pyridin-5-yl)-2-oxo-2,3-dihydro-1H-benzo[d]imidazol-1-yl)methyl)cyclohexyl)-2-methylnicotinamide;
N-((1r,4r)-4-((3-(benzo[d]oxazol-6-yl)-2-oxo-2,3-dihydro-1H-benzo[d]imidazol-1-yl)methyl)cyclohexyl)-5-chloro-2-methylnicotinamide;
5-chloro-2-methyl-N-((1r,4r)-4-((3-(1-methyl-2,3-dihydro-1H-pyrrolo[2,3-b]pyridin-5-yl)-2-oxo-2,3-dihydro-1H-benzo[d]imidazol-1-yl)methyl)cyclohexyl)nicotinamide;
N-((1r,4r)-4-((3-(1-acetyl-2,3-dihydro-1H-pyrrolo[2,3-b]pyridin-5-yl)-2-oxo-2,3-dihydro-1H-benzo[d]imidazol-1-yl)methyl)cyclohexyl)-5-chloro-2-methylnicotinamide; and
5-chloro-2-methyl-N-((1r,4r)-4-((2-oxo-3-(pyridin-3-yl)-2,3-dihydro-1H-benzo[d]imidazol-1-yl)methyl)cyclohexyl)nicotinamide;
or a pharmaceutically acceptable salt thereof or a prodrug thereof.

7. The compound according to claim 1, which is selected from the group consisting of:
N-((1r,4r)-4-((3-benzyl-2-oxo-2,3-dihydro-1H-benzo[d]imidazol-1-yl)methyl)cyclohexyl)-5-chloro-2-methylnicotinamide;
5-chloro-2-methyl-N-((1r,4r)-4-((2-oxo-3-(2-oxo-2-phenylethyl)-2,3-dihydro-1H-benzo[d]imidazol-1-yl)methyl)cyclohexyl)nicotinamide;
5-chloro-N-((1r,4r)-4-((3-(2-(4-methoxyphenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(2-(2-methoxyphenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(2-(2,4-difluorophenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(2-(4-cyanophenyl)-2-oxoethyl)-2-oxo-2,3-dihydro-1H-benzo[d]imidazol-1-yl)methyl)cyclohexyl)-2-methylnicotinamide;
5-chloro-N-((1r,4r)-4-((3-(4-fluorophenyl)-2-oxo-2,3-dihydro-1H-benzo[d]imidazol-1-yl)methyl)cyclohexyl)-2-methylnicotinamide;
N-((1r,4r)-4-((3-(4-acetylphenyl)-2-oxo-2,3-dihydro-1H-benzo[d]imidazol-1-yl)methyl)cyclohexyl)-5-chloro-2-methylnicotinamide;
5-chloro-2-methyl-N-((1r,4r)-4-((2-oxo-3-(p-tolyl)-2,3-dihydro-1H-benzo[d]imidazol-1-yl)methyl)cyclohexyl)nicotinamide;
5-chloro-N-((1r,4r)-4-((3-(4-methoxyphenyl)-2-oxo-2,3-dihydro-1H-benzo[d]imidazol-1-yl)methyl)cyclohexyl)-2-methylnicotinamide;
5-chloro-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(2-fluorophenyl)-2-oxo-2,3-dihydro-1H-benzo[d]imidazol-1-yl)methyl)cyclohexyl)-2-methylnicotinamide;
5-chloro-N-((1r,4r)-4-((3-(2-methoxyphenyl)-2-oxo-2,3-dihydro-1H-benzo[d]imidazol-1-yl)methyl)cyclohexyl)-2-methylnicotinamide;
5-chloro-N-((1r,4r)-4-((3-(6-(2,2-difluoroethoxy)pyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(6-ethoxypyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(3,4-dimethoxyphenyl)-2-oxo-2,3-dihydro-1H-benzo[d]imidazol-1-yl)methyl)cyclohexyl)-2-methylnicotinamide;
5-chloro-N-((1r,4r)-4-((3-(2-methoxypyridin-4-yl)-2-oxo-2,3-dihydro-1H-benzo[d]imidazol-1-yl)methyl)cyclohexyl)-2-methylnicotinamide;
5-chloro-N-((1r,4r)-4-((3-(2,4-difluorophenyl)-2-oxo-2,3-dihydro-1H-benzo[d]imidazol-1-yl)methyl)cyclohexyl)-2-methylnicotinamide;
5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-methylnicotinamide;
5-chloro-N-((1r,4r)-4-((3-(6-((2-methoxyethyl)(methyl)amino)pyridin-3-yl)-2-oxo-2,3-dihydro-1H-benzo[d]imidazol-1-yl)methyl)cyclohexyl)-2-methylnicotinamide;
5-chloro-2-methyl-N-((1r,4r)-4-((3-(6-morpholinopyridin-3-yl)-2-oxo-2,3-dihydro-1H-benzo[d]imidazol-1-yl)methyl)cyclohexyl)nicotinamide;
5-chloro-2-methyl-N-((1r,4r)-4-((3-(6-(4-methylpiperazin-1-yl)pyridin-3-yl)-2-oxo-2,3-dihydro-1H-benzo[d]imidazol-1-yl)methyl)cyclohexyl)nicotinamide;
5-chloro-2-methyl-N-((1r,4r)-4-((4-methyl-3-(6-methylpyridin-3-yl)-2-oxo-2,3-dihydro-1H-benzo[d]imidazol-1-yl)methyl)cyclohexyl)nicotinamide;
5-chloro-N-((1r,4r)-4-((3-(6-methoxypyridin-3-yl)-4-methyl-2-oxo-2,3-dihydro-1H-benzo[d]imidazol-1-yl)methyl)cyclohexyl)-2-methylnicotinamide;
5-(3-(((1r,4r)-4-(5-chloro-2-methylnicotinamido)cyclohexyl)methyl)-2-oxo-2,3-dihydro-1H-benzo[d]imidazol-1-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-methylpicolinamide;
5-chloro-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)-2-methylnicotinamide;

N-((1r,4r)-4-((3-(6-bromopyridin-3-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-(dimethylamino)pyridazin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-vinylpyridin-3-yl)-2,3-dihydro-1H-benzo[d]imidazol-1-yl)methyl)cyclohexyl)nicotinamide;

5-chloro-N-((1r,4r)-4-((3-(6-ethylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(2-vinylpyridin-4-yl)-2,3-dihydro-1H-benzo[d]imidazol-1-yl)methyl)cyclohexyl)nicotinamide;

5-chloro-N-((1r,4r)-4-((3-(6-(3,6-dihydro-2H-pyran-4-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-cyclopropylpyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(6-phenylpyridin-3-yl)-2,3-dihydro-1H-benzo[d]imidazol-1-yl)methyl)cyclohexyl)nicotinamide;

5-chloro-N-((1r,4r)-4-((3-(6-(2-(hydroxymethyl)phenyl)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(ethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((3-hydroxypropyl)(methyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(3-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-hydroxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(difluoromethoxy)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-((cyclopropylmethyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1R,4R)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide;

5-chloro-N-((1r,4r)-4-((3-(6-((3,3-difluorocyclobutyl)amino)pyridin-3-yl)-2-oxo-2,3-dihydro-1H-benzo[d]imidazol-1-yl)methyl)cyclohexyl)-2-methylnicotinamide;

5-chloro-2-methyl-N-((1S,4r)-4-((2-oxo-3-(6-(((S)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1R,4r)-4-((2-oxo-3-(6-((((R)-tetrahydrofuran-2-yl)methyl)amino)pyridin-3-yl)-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide;

5-chloro-N-(4-((3-(6-(cyclopropylmethoxy)pyridin-3-yl)-2-oxo-2,3-dihydro-1H-benzo[d]imidazol-1-yl)methyl)cyclohexyl)-2-methylnicotinamide;

5-chloro-N-(4-((3-(6-cyclopropoxypyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(methylamino)pyrazin-2-yl)-2-oxo-2,3-dihydro-1H-benzo[d]imidazol-1-yl)methyl)cyclohexyl)nicotinamide;

5-chloro-N-((1r,4r)-4-((3-(5-(dimethylamino)pyrazin-2-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxy-5-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((4-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((5-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((6-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((7-fluoro-3-(6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(cyclobutylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-(4-methoxypiperidin-1-yl)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(3-(hydroxymethyl)-4-methylphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(1H-pyrazolo[3,4-b]pyridin-5-yl)-2,3-dihydro-1H-benzo[d]imidazol-1-yl)methyl)cyclohexyl)nicotinamide;

5-chloro-2-methyl-N-((1r,4r)-4-((3-(4-(oxetan-3-ylcarbamoyl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(6-(3-hydroxypropoxy)pyridin-3-yl)-2-oxo-2,3-dihydro-1H-benzo[d]imidazol-1-yl)methyl)cyclohexyl)-2-methylnicotinamide;

trans-5-chloro-2-methyl-N-(4-((3-(6-(oxetan-3-yloxy)pyridin-3-yl)-2-oxo-2,3-dihydro-1H-benzo[d]imidazol-1-yl)methyl)cyclohexyl)nicotinamide;

trans-5-chloro-2-methyl-N-(4-((3-(1-methyl-1H-indazol-5-yl)-2-oxo-2,3-dihydro-1H-benzo[d]imidazol-1-yl)methyl)cyclohexyl)nicotinamide;

trans-5-chloro-N-(4-((3-(6-(3-methoxyazetidin-1-yl)pyridin-3-yl)-2-oxo-2,3-dihydro-1H-benzo[d]imidazol-1-yl)methyl)cyclohexyl)-2-methylnicotinamide;
trans-5-chloro-N-(4-((3-(6-(3-fluoroazetidin-1-yl)pyridin-3-yl)-2-oxo-2,3-dihydro-1H-benzo[d]imidazol-1-yl)methyl)cyclohexyl)-2-methylnicotinamide;
trans-5-chloro-N-(4-((3-(6-(3,3-difluoroazetidin-1-yl)pyridin-3-yl)-2-oxo-2,3-dihydro-1H-benzo[d]imidazol-1-yl)methyl)cyclohexyl)-2-methylnicotinamide;
trans-5-chloro-2-methyl-N-(4-((3-(6-(oxetan-3-ylamino)pyridin-3-yl)-2-oxo-2,3-dihydro-1H-benzo[d]imidazol-1-yl)methyl)cyclohexyl)nicotinamide;
trans-5-chloro-N-(4-((3-(1-methyl-1H-pyrrolo[2,3-b]pyridin-5-yl)-2-oxo-2,3-dihydro-1H-benzo[d]imidazol-1-yl)methyl)cyclohexyl)nicotinamide;
trans-5-chloro-N-(4-((3-(6-methoxy-2-methylpyridin-3-yl)-2-oxo-2,3-dihydro-1H-benzo[d]imidazol-1-yl)methyl)cyclohexyl)-2-methylnicotinamide;
trans-5-chloro-2-methyl-N-(4-((3-(2-methyl-6-(methylamino)pyridin-3-yl)-2-oxo-2,3-dihydro-1H-benzo[d]imidazol-1-yl)methyl)cyclohexyl)nicotinamide;
trans-5-(3-((4-(5-chloro-2-methylnicotinamido)cyclohexyl)methyl)-2-oxo-2,3-dihydro-1H-benzo[d]imidazol-1-yl)-N-cyclopropylpicolinamide;
trans-5-chloro-N-(4-((3-(2,3-dihydro-1H-pyrrolo[2,3-b]pyridin-5-yl)-2-oxo-2,3-dihydro-1H-benzo[d]imidazol-1-yl)methyl)cyclohexyl)-2-methylnicotinamide;
trans-N-(4-((3-(benzo[d]oxazol-6-yl)-2-oxo-2,3-dihydro-1H-benzo[d]imidazol-1-yl)methyl)cyclohexyl)-5-chloro-2-methylnicotinamide;
trans-5-chloro-2-methyl-N-(4-((3-(1-methyl-2,3-dihydro-1H-pyrrolo[2,3-b]pyridin-5-yl)-2-oxo-2,3-dihydro-1H-benzo[d]imidazol-1-yl)methyl)cyclohexyl)nicotinamide;
trans-N-(4-((3-(1-acetyl-2,3-dihydro-1H-pyrrolo[2,3-b]pyridin-5-yl)-2-oxo-2,3-dihydro-1H-benzo[d]imidazol-1-yl)methyl)cyclohexyl)-5-chloro-2-methylnicotinamide;
5-chloro-2-methyl-N-((1r,4r)-4-((2-oxo-3-(pyridin-3-yl)-2,3-dihydro-1H-benzo[d]imidazol-1-yl)methyl)cyclohexyl)nicotinamide;
5-chloro-2-methyl-N-((1r,4r)-4-((3-(1-methyl-1H-pyrrolo[3,2-b]pyridin-6-yl)-2-oxo-2,3-dihydro-1H-benzo[d]imidazol-1-yl)methyl)cyclohexyl)nicotinamide;
5-chloro-2-methyl-N-((1r,4r)-4-((2-oxo-3-(1H-pyrrolo[3,2-b]pyridin-6-yl)-2,3-dihydro-1H-benzo[d]imidazol-1-yl)methyl)cyclohexyl)nicotinamide;
5-chloro-N-((1r,4r)-4-((3-(3,4-dihydro-2H-pyrido[3,2-b][1,4]oxazin-7-yl)-2-oxo-2,3-dihydro-1H-benzo[d]imidazol-1-yl)methyl)cyclohexyl)-2-methylnicotinamide;
5-chloro-2-methyl-N-((1r,4r)-4-((3-(4-methyl-3,4-dihydro-2H-pyrido[3,2-b][1,4]oxazin-7-yl)-2-oxo-2,3-dihydro-1H-benzo[d]imidazol-1-yl)methyl)cyclohexyl)nicotinamide;
5-chloro-N-((1r,4r)-4-((3-(6-(3-(dimethylamino)azetidin-1-yl)pyridin-3-yl)-2-oxo-2,3-dihydro-1H-benzo[d]imidazol-1-yl)methyl)cyclohexyl)-2-methylnicotinamide;
N-((1r,4r)-4-((3-(6-(azetidin-1-yl)pyridin-3-yl)-2-oxo-2,3-dihydro-1H-benzo[d]imidazol-1-yl)methyl)cyclohexyl)-5-chloro-2-methylnicotinamide;
5-chloro-2-methyl-N-((1r,4r)-4-((3-(1-methyl-1H-pyrazolo[3,4-b]pyridin-5-yl)-2-oxo-2,3-dihydro-1H-benzo[d]imidazol-1-yl)methyl)cyclohexyl)nicotinamide;
5-chloro-2-methyl-N-((1r,4r)-4-((3-(3-methyl-2-oxo-2,3-dihydrobenzo[d]oxazol-6-yl)-2-oxo-2,3-dihydro-1H-benzo[d]imidazol-1-yl)methyl)cyclohexyl)nicotinamide;
5-chloro-2-methyl-N-((1r,4r)-4-((2-oxo-3-(quinoxalin-6-yl)-2,3-dihydro-1H-benzo[d]imidazol-1-yl)methyl)cyclohexyl)nicotinamide;
2-ethyl-N-((1r,4r)-4-((3-(6-(methylcarbamoyl)pyridin-3-yl)-2-oxo-2,3-dihydro-1H-benzo[d]imidazol-1-yl)methyl)cyclohexyl)-2H-indazole-3-carboxamide;
5-chloro-N-((1r,4r)-4-((3-(chroman-3-yl)-2-oxo-2,3-dihydro-1H-benzo[d]imidazol-1-yl)methyl)cyclohexyl)-2-methylnicotinamide;
5-chloro-N-((1r,4r)-4-((1',2'-dimethyl-2-oxo-1'H-[1,5'-bibenzo[d]imidazol]-3(2H)-yl)methyl)cyclohexyl)-2-methylnicotinamide;
5-chloro-N-((1r,4r)-4-((1',3'-dimethyl-2,2'-dioxo-2',3'-dihydro-1'H-[1,5'-bibenzo[d]imidazol]-3(2H)-yl)methyl)cyclohexyl)-2-methylnicotinamide;
5-chloro-2-methyl-N-((1r,4r)-4-((3-(3-methyl-1H-indazol-5-yl)-2-oxo-2,3-dihydro-1H-benzo[d]imidazol-1-yl)methyl)cyclohexyl)nicotinamide;
5-chloro-2-methyl-N-((1r,4r)-4-((3-(3-methylbenzo[d]isoxazol-6-yl)-2-oxo-2,3-dihydro-1H-benzo[d]imidazol-1-yl)methyl)cyclohexyl)nicotinamide;
5-chloro-2-methyl-N-((1r,4r)-4-((3-(3-methyl-1H-pyrazolo[4,3-b]pyridin-6-yl)-2-oxo-2,3-dihydro-1H-benzo[d]imidazol-1-yl)methyl)cyclohexyl)nicotinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(1-methyl-1H-pyrazol-3-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-2-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(pyridazin-3-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(isoxazol-3-ylmethyl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-3-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(pyrimidin-5-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(oxazol-4-ylmethyl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-((4-methylthiazol-2-yl)methyl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(pyridin-4-yl)picolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-ethylpicolinamide;
5-(3-(((1r,4r)-4-(5-chloro-2-methylnicotinamido)cyclohexyl)methyl)-2-oxo-2,3-dihydro-1H-benzo[d]imidazol-1-yl)-N-(1H-pyrazol-3-yl)picolinamide;
5-chloro-N-((1r,4r)-4-((3-(2,3-dihydro-1H-inden-2-yl)-2-oxo-2,3-dihydro-1H-benzo[d]imidazol-1-yl)methyl)cyclohexyl)-2-methylnicotinamide;
5-chloro-N-((1r,4r)-4-((3-(2,3-dimethyl-2H-indazol-5-yl)-2-oxo-2,3-dihydro-1H-benzo[d]imidazol-1-yl)methyl)cyclohexyl)-2-methylnicotinamide;
5-chloro-N-((1r,4r)-4-((3-(imidazo[1,2-a]pyridin-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(quinazolin-5-yl)-2,3-dihydro-1H-benzo[d]imidazol-1-yl)methyl)cyclohexyl)nicotinamide;

N-((1r,4r)-4-((3-(2-acetylisoindolin-5-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2,3-dihydro-1H-inden-5-yl)-2-oxo-2,3-dihydro-1H-imidazo[4,5-b]pyridin-1-yl)methyl)cyclohexyl)-2-methylnicotinamide;

5-chloro-N-((1r,4r)-4-((3-(4-methoxyphenyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(1,3-dimethyl-1H-indazol-6-yl)-2-oxo-2,3-dihydro-1H-benzo[d]imidazol-1-yl)methyl)cyclohexyl)-2-methylnicotinamide;

5-(3-(((1r,4r)-4-(5-chloro-2-methylnicotinamido)cyclohexyl)methyl)-7-methyl-2-oxo-2,3-dihydro-1H-benzo[d]imidazol-1-yl)-N-methylpicolinamide;

5-(3-(((1r,4r)-4-(5-chloro-2-methylnicotinamido)cyclohexyl)methyl)-6-fluoro-2-oxo-2,3-dihydro-1H-benzo[d]imidazol-1-yl)-N-methylpicolinamide;

5-(3-(((1r,4r)-4-(5-chloro-2-methylnicotinamido)cyclohexyl)methyl)-5-methoxy-2-oxo-2,3-dihydro-1H-benzo[d]imidazol-1-yl)-N-methylpicolinamide;

5-chloro-N-((1r,4r)-4-((3-(3-(cyclopropylmethyl)-2-oxo-2,3-dihydrobenzo[d]oxazol-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-methyl-3-oxo-3,4-dihydro-2H-pyrido[3,2-b][1,4]oxazin-7-yl)-2-oxo-2,3-dihydro-1H-benzo[d]imidazol-1-yl)methyl)cyclohexyl)nicotinamide;

N-((1r,4r)-4-((3-(3-amino-1H-indazol-6-yl)-2-oxo-2,3-dihydro-1H-benzo[d]imidazol-1-yl)methyl)cyclohexyl)-5-chloro-2-methylnicotinamide;

N-((1r,4r)-4-((3-(3-aminobenzo[d]isoxazol-6-yl)-2-oxo-2,3-dihydro-1H-benzo[d]imidazol-1-yl)methyl)cyclohexyl)-5-chloro-2-methylnicotinamide;

5-(3-(((1r,4r)-4-(5-chloro-2-methylnicotinamido)cyclohexyl)methyl)-2-oxo-2,3-dihydro-1H-benzo[d]imidazol-1-yl)-N,4-dimethylpicolinamide;

N-((1r,4r)-4-((3-(benzo[d]thiazol-6-yl)-2-oxo-2,3-dihydro-1H-imidazo[4,5-b]pyridin-1-yl)methyl)cyclohexyl)-5-chloro-2-methylnicotinamide;

N-((1r,4r)-4-((3-([2,3'-bipyridin]-5-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(6-(oxazol-5-yl)pyridin-3-yl)-2-oxo-2,3-dihydro-1H-benzo[d]imidazol-1-yl)methyl)cyclohexyl)nicotinamide;

N-((1r,4r)-4-((3-(6-(1H-pyrazol-4-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(4-bromo-2-cyanophenyl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(3-methyl-1H-indazol-6-yl)-2-oxo-2,3-dihydro-1H-benzo[d]imidazol-1-yl)methyl)cyclohexyl)nicotinamide;

5-chloro-2-methyl-N-((1r,4r)-4-((1'-methyl-2-oxo-1'H-[1,5'-bibenzo[d]imidazol]-3(2H)-yl)methyl)cyclohexyl)nicotinamide;

5-chloro-2-methyl-N-((1r,4r)-4-((3'-methyl-2-oxo-3'H-[1,5'-bibenzo[d]imidazol]-3(2H)-yl)methyl)cyclohexyl)nicotinamide;

5-chloro-N-((1r,4r)-4-((3-(3-chloro-1-methyl-1H-indazol-6-yl)-2-oxo-2,3-dihydro-1H-benzo[d]imidazol-1-yl)methyl)cyclohexyl)-2-methylnicotinamide;

5-chloro-N-((1r,4r)-4-((2',3'-dimethyl-2-oxo-3'H-[1,5'-bibenzo[d]imidazol]-3(2H)-yl)methyl)cyclohexyl)-2-methylnicotinamide;

5-chloro-N-((1r,4r)-4-((3-(3-chloro-1H-indazol-6-yl)-2-oxo-2,3-dihydro-1H-benzo[d]imidazol-1-yl)methyl)cyclohexyl)-2-methylnicotinamide;

N-((1r,4r)-4-((1-(5-bromo-2,3-dihydro-1H-inden-2-yl)-2-oxo-1H-imidazo[4,5-c]pyridin-3(2H)-yl)methyl)cyclohexyl)-5-chloro-2-methylnicotinamide;

5-chloro-2-methyl-N-((1r,4r)-4-((3-(3-methyl-1H-indazol-5-yl)-2-oxo-2,3-dihydro-1H-imidazo[4,5-b]pyridin-1-yl)methyl)cyclohexyl)nicotinamide;

5-chloro-N-((1r,4r)-4-((3-(1,3-dimethyl-1H-indazol-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-(1-methyl-1H-pyrazol-4-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methyl-2-oxo-2,3-dihydrooxazolo[4,5-b]pyridin-6-yl)-2-oxo-2,3-dihydro-1H-benzo[d]imidazol-1-yl)methyl)cyclohexyl)nicotinamide;

N-((1r,4r)-4-((3-(6'-amino-[2,3'-bipyridin]-5-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(4-(pyridin-4-yloxy)phenyl)-2,3-dihydro-1H-benzo[d]imidazol-1-yl)methyl)cyclohexyl)nicotinamide;

N-((1r,4r)-4-((3-(2-acetyl-1,2,3,4-tetrahydroisoquinolin-6-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2-cyanophenyl)-2-oxo-2,3-dihydro-1H-benzo[d]imidazol-1-yl)methyl)cyclohexyl)-2-methylnicotinamide;

N-((1r,4r)-4-((3-(6-methoxypyridin-3-yl)-2-oxo-2,3-dihydro-1H-benzo[d]imidazol-1-yl)methyl)cyclohexyl)-2-methyl-2H-indazole-3-carboxamide;

N-((1r,4r)-4-((3-(6-methoxypyridin-3-yl)-2-oxo-2,3-dihydro-1H-benzo[d]imidazol-1-yl)methyl)cyclohexyl)-2-methyl-4,5,6,7-tetrahydro-2H-indazole-3-carboxamide;

5-chloro-N-((1r,4r)-4-((3-(3-chloro-1H-indazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxypyridin-3-yl)-2-oxo-2,3-dihydro-1H-benzo[d]imidazol-1-yl)methyl)cyclohexyl)-2-methylbenzamide;

5-chloro-2-methyl-N-((1r,4r)-4-((2-oxo-3-(3-oxo-3,4-dihydro-2H-pyrido[3,2-b][1,4]oxazin-7-yl)-2,3-dihydro-1H-benzo[d]imidazol-1-yl)methyl)cyclohexyl)nicotinamide;

5-(3-(((1r,4r)-4-(5-chloro-2-methylnicotinamido)cyclohexyl)methyl)-5-methyl-2-oxo-2,3-dihydro-1H-benzo[d]imidazol-1-yl)-N-methylpicolinamide;

5-(3-(((1r,4r)-4-(5-chloro-2-methylnicotinamido)cyclohexyl)methyl)-5-fluoro-2-oxo-2,3-dihydro-1H-benzo[d]imidazol-1-yl)-N-methylpicolinamide;

5-bromo-N-((1r,4r)-4-((3-(6-methoxypyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(6-methoxypyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(1-(2-(methoxymethoxy)ethyl)-3-methyl-1H-indazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(1-(2-hydroxyethyl)-3-methyl-1H-indazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-4-methoxyphenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(1-methyl-1H-benzo[d][1,2,3]triazol-6-yl)-2-oxo-2,3-dihydro-1H-benzo[d]imidazol-1-yl)methyl)cyclohexyl)nicotinamide;

5-chloro-2-methyl-N-((1r,4r)-4-((3-(2-nitrophenyl)-2-oxo-2,3-dihydro-1H-benzo[d]imidazol-1-yl)methyl)cyclohexyl)nicotinamide;

5-chloro-N-((1r,4r)-4-((3-(2-chlorophenyl)-2-oxo-2,3-dihydro-1H-imidazo[4,5-b]pyridin-1-yl)methyl)cyclohexyl)-2-methylnicotinamide;

5-(3-(((1r,4r)-4-(5-chloro-2-methylnicotinamido)cyclohexyl)methyl)-7-fluoro-2-oxo-2,3-dihydro-1H-benzo[d]imidazol-1-yl)-N-methylpicolinamide;

5-chloro-2-methyl-N-((1r,4r)-4-((3-(2-(1-methyl-1H-pyrazol-4-yl)ethyl)-2-oxo-2,3-dihydro-1H-benzo[d]imidazol-1-yl)methyl)cyclohexyl)nicotinamide;

2,5-dichloro-N-((1r,4r)-4-((3-(6-methoxypyridin-3-yl)-2-oxo-2,3-dihydro-1H-benzo[d]imidazol-1-yl)methyl)cyclohexyl)nicotinamide;

5-chloro-N-((1r,4r)-4-((1-(2,3-dihydro-1H-inden-4-yl)-2-oxo-1H-imidazo[4,5-c]pyridin-3(2H)-yl)methyl)cyclohexyl)-2-methylnicotinamide;

5-chloro-N-((1r,4r)-4-((3-(2-cyanopyridin-3-yl)-2-oxo-2,3-dihydro-1H-benzo[d]imidazol-1-yl)methyl)cyclohexyl)-2-methylnicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(2-cyanobenzyl)-2-oxo-2,3-dihydro-1H-benzo[d]imidazol-1-yl)methyl)cyclohexyl)-2-methylnicotinamide;

5-chloro-N-((1r,4r)-4-((3-(3-cyanobenzyl)-2-oxo-2,3-dihydro-1H-benzo[d]imidazol-1-yl)methyl)cyclohexyl)-2-methylnicotinamide;

6-(3-(((1r,4r)-4-(5-chloro-2-methylnicotinamido)cyclohexyl)methyl)-2-oxo-2,3-dihydro-1H-benzo[d]imidazol-1-yl)benzo[d]isoxazole-3-carboxamide;

6-(3-(((1r,4r)-4-(5-chloro-2-methylnicotinamido)cyclohexyl)methyl)-2-oxo-2,3-dihydro-1H-benzo[d]imidazol-1-yl)-N-methylbenzo[d]isoxazole-3-carboxamide;

6-(3-(((1r,4r)-4-(5-chloro-2-methylnicotinamido)cyclohexyl)methyl)-2-oxo-2,3-dihydro-1H-benzo[d]imidazol-1-yl)-N,N-dimethylbenzo[d]isoxazole-3-carboxamide;

5-chloro-N-((1r,4r)-4-((3-(2-cyano-3-methoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-4-methylphenyl)-2-oxo-2,3-dihydro-1H-benzo[d]imidazol-1-yl)methyl)cyclohexyl)-2-methylnicotinamide;

5-chloro-N-((1r,4r)-4-((3-(4-cyanopyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(3-cyanopyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(1-ethyl-1H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(2,4-dimethoxybenzyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(1-(cyclopropylmethyl)-1H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(1-(2-hydroxyethyl)-1H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(2-ethyl-2H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(1-methyl-1H-benzo[d][1,2,3]triazol-5-yl)-2-oxo-2,3-dihydro-1H-benzo[d]imidazol-1-yl)methyl)cyclohexyl)nicotinamide;

5-chloro-N-((1r,4r)-4-((1-(2-chlorophenyl)-2-oxo-1H-imidazo[4,5-b]pyridin-3(2H)-yl)methyl)cyclohexyl)-2-methylnicotinamide;

5-chloro-2-methyl-N-((1r,4r)-4-((2-oxo-1-(2-(trifluoromethyl)phenyl)-1H-imidazo[4,5-b]pyridin-3(2H)-yl)methyl)cyclohexyl)nicotinamide;

5-(3-(((1r,4r)-4-(5-chloro-2-methylnicotinamido)cyclohexyl)methyl)-6-methoxy-2-oxo-2,3-dihydro-1H-benzo[d]imidazol-1-yl)-N-methylpicolinamide;

5-chloro-N-((1r,4r)-4-((3-(2-cyano-5-methoxyphenyl)-2-oxo-2,3-dihydro-1H-benzo[d]imidazol-1-yl)methyl)cyclohexyl)-2-methylnicotinamide;

5-chloro-N-((1r,4r)-4-((3-(3-methyl-1H-indazol-5-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(3-(hydroxymethyl)benzo[d]isoxazol-6-yl)-2-oxo-2,3-dihydro-1H-benzo[d]imidazol-1-yl)methyl)cyclohexyl)-2-methylnicotinamide;

5-chloro-N-((1r,4r)-4-((3-(3-chloropyridin-4-yl)-2-oxo-2,3-dihydro-1H-benzo[d]imidazol-1-yl)methyl)cyclohexyl)-2-methylnicotinamide;

N-((1r,4r)-4-((3-(2-aminobenzo[d]oxazol-5-yl)-2-oxo-2,3-dihydro-1H-benzo[d]imidazol-1-yl)methyl)cyclohexyl)-5-chloro-2-methylnicotinamide;

N-((1r,4r)-4-((3-(benzo[d]oxazol-5-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)nicotinamide;

5-chloro-2-cyclopropyl-N-((1r,4r)-4-((3-(6-methylpyridin-3-yl)-2-oxo-2,3-dihydro-1H-benzo[d]imidazol-1-yl)methyl)cyclohexyl)benzamide;

5-chloro-2-methyl-N-((1r,4r)-4-((3-(6-methylpyridin-3-yl)-2-oxo-2,3-dihydro-1H-benzo[d]imidazol-1-yl)methyl)cyclohexyl)benzamide;

5-methyl-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)benzamide;

2,5-dichloro-N-((1r,4r)-4-((3-(6-methylpyridin-3-yl)-2-oxo-2,3-dihydro-1H-benzo[d]imidazol-1-yl)methyl)cyclohexyl)benzamide;

5-chloro-N-((1r,4r)-4-((3-(6-methylpyridin-3-yl)-2-oxo-2,3-dihydro-1H-benzo[d]imidazol-1-yl)methyl)cyclohexyl)-2-(trifluoromethyl)benzamide;

5-chloro-2-methyl-N-((1r,4r)-4-((3-(3-methyl-1H-pyrazolo[3,4-b]pyridin-5-yl)-2-oxo-2,3-dihydro-1H-benzo[d]imidazol-1-yl)methyl)cyclohexyl)nicotinamide;

5-chloro-N-((1r,4r)-4-((3-(imidazo[1,2-a]pyridin-7-yl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-5-(dimethylamino)phenyl)-2-oxo-2,3-dihydro-1H-benzo[d]imidazol-1-yl)methyl)cyclohexyl)-2-methylnicotinamide;

5-chloro-N-((1r,4r)-4-((3-(imidazo[1,5-a]pyridin-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(3-methyl-3H-[1,2,3]triazolo[4,5-b]pyridin-6-yl)-2-oxo-2,3-dihydro-1H-benzo[d]imidazol-1-yl)methyl)cyclohexyl)nicotinamide;

5-chloro-N-((1r,4r)-4-((3-(1-(2-hydroxyethyl)-1H-benzo[d][1,2,3]triazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(3-ethyl-2-oxo-2,3-dihydrooxazolo[4,5-b]pyridin-6-yl)-2-oxo-2,3-dihydro-1H-benzo[d]imidazol-1-yl)methyl)cyclohexyl)-2-methylnicotinamide;

N-((1r,4r)-4-((3-([1,2,4]triazolo[1,5-a]pyridin-6-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(6-cyclobutylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((2-oxo-3-(pyridin-4-ylmethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(pyridin-4-ylmethyl)-2,3-dihydro-1H-benzo[d]imidazol-1-yl)methyl)cyclohexyl)-2-(trifluoromethyl)benzamide;

5-chloro-N-((1r,4r)-4-((2-oxo-3-(pyridin-2-ylmethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(pyridin-2-ylmethyl)-2,3-dihydro-1H-benzo[d]imidazol-1-yl)methyl)cyclohexyl)-2-(trifluoromethyl)benzamide;

5-chloro-N-((1r,4r)-4-((2-oxo-3-(pyridin-3-ylmethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(2-oxo-2-phenylethyl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(2-oxo-2-phenylethyl)-2,3-dihydro-1H-benzo[d]imidazol-1-yl)methyl)cyclohexyl)-2-(trifluoromethyl)benzamide;

2,5-dichloro-N-((1r,4r)-4-((2-oxo-3-(2-oxo-2-phenylethyl)-2,3-dihydro-1H-benzo[d]imidazol-1-yl)methyl)cyclohexyl)benzamide;

5-chloro-N-((1r,4r)-4-((3-(2-chlorophenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(3-methylpyridin-4-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(trifluoromethyl)nicotinamido)cyclohexyl)methyl)-5-fluoro-2-oxo-2,3-dihydro-1H-benzo[d]imidazol-1-yl)-N-methylpicolinamide;

5-chloro-N-((1r,4r)-4-((3-(2-cyanophenyl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-cyano-5-methoxyphenyl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-cyanopyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(1-(2-methoxyethyl)-1H-benzo[d][1,2,3]triazol-5-yl)-2-oxo-2,3-dihydro-1H-benzo[d]imidazol-1-yl)methyl)cyclohexyl)-2-methylnicotinamide;

5-chloro-N-((1r,4r)-4-((3-(2-ethyl-3-methyl-2H-pyrazolo[3,4-b]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((3-(imidazo[1,5-a]pyridin-7-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(pyrido[2,3-b]pyrazin-7-yl)-2,3-dihydro-1H-benzo[d]imidazol-1-yl)methyl)cyclohexyl)nicotinamide;

5-chloro-N-((1r,4r)-4-((3-(5-(methylamino)pyrazin-2-yl)-2-oxo-2,3-dihydro-1H-benzo[d]imidazol-1-yl)methyl)cyclohexyl)-2-(trifluoromethyl)nicotinamide;

5-chloro-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)-2-(trifluoromethyl)nicotinamide;

5-chloro-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)-2-(trifluoromethyl)nicotinamide;

5-chloro-N-((1r,4r)-4-((3-(6-(2-hydroxyethoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((4-methyl-3-(6-methylpyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-(1-methyl-1H-pyrazol-4-yl)ethyl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(1-ethyl-1H-benzo[d][1,2,3]triazol-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(4-oxo-3,4-dihydroquinazolin-7-yl)-2,3-dihydro-1H-benzo[d]imidazol-1-yl)methyl)cyclohexyl)nicotinamide;

5-chloro-N-((1r,4r)-4-((3-(2-cyano-4-formylphenyl)-2-oxo-2,3-dihydro-1H-benzo[d]imidazol-1-yl)methyl)cyclohexyl)-2-methylnicotinamide;

N-((1r,4r)-4-((3-(5-bromo-2-cyanophenyl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(4-cyano-6-methylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2-cyano-3-(dimethylamino)phenyl)-2-oxo-2,3-dihydro-1H-benzo[d]imidazol-1-yl)methyl)cyclohexyl)-2-methylnicotinamide;

5-chloro-N-((1r,4r)-4-((3-(4-cyano-6-((2-methoxyethyl)amino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(4-cyanopyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(3-cyanopyridin-2-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N,4-dimethylpicolinamide;

5-chloro-N-((1r,4r)-4-((2-oxo-3-(thiazol-4-ylmethyl)-2,3-dihydro-1H-benzo[d]imidazol-1-yl)methyl)cyclohexyl)-2-(trifluoromethyl)nicotinamide;

5-chloro-N-((1r,4r)-4-((3-(2,6-dimethylpyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-methylpyridin-4-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-cyclopropylnicotinamido)cyclohexyl)methyl)-2-oxo-2,3-dihydro-1H-benzo[d]imidazol-1-yl)-N-methylpicolinamide;

5-chloro-2-methyl-N-((1r,4r)-4-((2-oxo-3-(2-(trifluoromethyl)pyridin-3-yl)-2,3-dihydro-1H-benzo[d]imidazol-1-yl)methyl)cyclohexyl)nicotinamide;

N-((1r,4r)-4-((3-(4-aminopyrido[3,2-d]pyrimidin-7-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(3-(trifluoromethyl)pyridin-4-yl)-2,3-dihydro-1H-benzo[d]imidazol-1-yl)methyl)cyclohexyl)nicotinamide;

5-(3-(((1r,4r)-4-(5-chloro-2-(2-methoxyethyl)nicotinamido)cyclohexyl)methyl)-2-oxo-2,3-dihydro-1H-benzo[d]imidazol-1-yl)-N-methylpicolinamide;

5-(3-(((1r,4r)-4-(5-chloro-2-cyclobutylnicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(6-methoxypyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-methylpyridin-3-yl)-2-oxo-2,3-dihydro-1H-benzo[d]imidazol-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((1'-methyl-2-oxo-1'H-[1,5'-bibenzo[d]imidazol]-3(2H)-yl)methyl)cyclohexyl)-2-(trifluoromethyl)nicotinamide;

5-chloro-N-((1r,4r)-4-((3-(imidazo[1,5-a]pyridin-6-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(dimethylamino)nicotinamido)cyclohexyl)methyl)-2-oxo-2,3-dihydro-1H-benzo[d]imidazol-1-yl)-N-methylpicolinamide;

5-chloro-2-(methoxymethyl)-N-((1r,4r)-4-((3-(6-methylpyridin-3-yl)-2-oxo-2,3-dihydro-1H-benzo[d]imidazol-1-yl)methyl)cyclohexyl)nicotinamide;

5-chloro-N-((1r,4r)-4-((3-(4,6-dimethylpyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(2,3-dimethylpyridin-4-yl)-2-oxo-2,3-dihydro-1H-benzo[d]imidazol-1-yl)methyl)cyclohexyl)-2-methylnicotinamide;

5-chloro-N-((1r,4r)-4-((3-(6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(6-(dimethylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(3-chloropyridin-4-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(methoxymethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(2,5-dimethylpyridin-4-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(quinolin-8-yl)-2,3-dihydro-1H-benzo[d]imidazol-1-yl)methyl)cyclohexyl)nicotinamide;

5-chloro-N-((1r,4r)-4-((3-(isoquinolin-4-yl)-2-oxo-2,3-dihydro-1H-benzo[d]imidazol-1-yl)methyl)cyclohexyl)-2-methylnicotinamide;

5-(3-(((1r,4r)-4-(5-chloro-2-methylnicotinamido)cyclohexyl)methyl)-7-methyl-2-oxo-2,3-dihydro-1H-benzo[d]imidazol-1-yl)-N,4-dimethylpicolinamide;

5-chloro-2-methyl-N-((1r,4r)-4-((3-(2-(oxetan-3-yl)-2H-benzo[d][1,2,3]triazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(1-(oxetan-3-yl)-1H-benzo[d][1,2,3]triazol-5-yl)-2-oxo-2,3-dihydro-1H-benzo[d]imidazol-1-yl)methyl)cyclohexyl)nicotinamide;

5-chloro-N-((1r,4r)-4-((3-(imidazo[1,5-a]pyridin-7-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(isoquinolin-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((2-oxo-3-(quinolin-6-yl)-2,3-dihydro-1H-benzo[d]imidazol-1-yl)methyl)cyclohexyl)nicotinamide;

5-chloro-2-methyl-N-((1r,4r)-4-((2-oxo-3-(quinolin-5-yl)-2,3-dihydro-1H-benzo[d]imidazol-1-yl)methyl)cyclohexyl)nicotinamide;

5-chloro-2-methyl-N-((1r,4r)-4-((2-oxo-3-(quinolin-3-yl)-2,3-dihydro-1H-benzo[d]imidazol-1-yl)methyl)cyclohexyl)nicotinamide;

5-chloro-2-methyl-N-((1r,4r)-4-((3-(1-methyl-1H-indazol-4-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(3-phenyl-1H-indazol-5-yl)-2,3-dihydro-1H-benzo[d]imidazol-1-yl)methyl)cyclohexyl)nicotinamide;

5-(3-(((1r,4r)-4-(5-chloro-2-(2,2-difluoroethyl)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(imidazo[1,2-a]pyridin-5-yl)-2-oxo-2,3-dihydro-1H-benzo[d]imidazol-1-yl)methyl)cyclohexyl)-2-methylnicotinamide;

5-chloro-N-((1r,4r)-4-((2-oxo-3-(quinolin-6-yl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(quinolin-3-yl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(quinolin-8-yl)-2,3-dihydro-1H-benzo[d]imidazol-1-yl)methyl)cyclohexyl)-2-(trifluoromethyl)nicotinamide;

5-chloro-N-((1r,4r)-4-((3-(isoquinolin-4-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-ethyloxazolo[4,5-b]pyridin-6-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(2-methyloxazolo[4,5-b]pyridin-6-yl)-2-oxo-2,3-dihydro-1H-benzo[d]imidazol-1-yl)methyl)cyclohexyl)nicotinamide;

5-chloro-N-((1r,4r)-4-((3-(6-(2-hydroxyethoxy)-4-methylpyridin-3-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((2-oxo-1-(quinolin-6-yl)-1H-imidazo[4,5-b]pyridin-3(2H)-yl)methyl)cyclohexyl)nicotinamide;

5-chloro-2-methyl-N-((1r,4r)-4-((2-oxo-1-(quinolin-3-yl)-1H-imidazo[4,5-b]pyridin-3(2H)-yl)methyl)cyclohexyl)nicotinamide;

5-chloro-N-((1r,4r)-4-((2-oxo-1-(quinolin-6-yl)-1H-imidazo[4,5-b]pyridin-3(2H)-yl)methyl)cyclohexyl)-2-(trifluoromethyl)nicotinamide;

5-chloro-2-(difluoromethyl)-N-((1r,4r)-4-((2-oxo-1-(quinolin-6-yl)-1H-imidazo[4,5-b]pyridin-3(2H)-yl)methyl)cyclohexyl)nicotinamide;

5-chloro-2-(difluoromethyl)-N-((1r,4r)-4-((2-oxo-3-(quinolin-6-yl)-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N,4-dimethylpicolinamide;

5-chloro-2-(difluoromethyl)-N-((1r,4r)-4-((3-(2,3-dimethylpyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-hydroxyethoxy)pyridin-3-yl)-2-oxo-2,3-dihydro-1H-benzo[d]imidazol-1-yl)methyl)cyclohexyl)nicotinamide;

5-chloro-N-((1r,4r)-4-((3-(2-chlorophenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((1-(2-chlorophenyl)-2-oxo-1H-imidazo[4,5-c]pyridin-3(2H)-yl)methyl)cyclohexyl)-2-(difluoromethyl)nicotinamide;

5-chloro-N-((1r,4r)-4-((3-(2-cyanopyridin-3-yl)-2-oxo-2,3-dihydro-1H-benzo[d]imidazol-1-yl)methyl)cyclohexyl)-2-(difluoromethyl)nicotinamide;

5-chloro-N-((1r,4r)-4-((3-(3-cyanopyrazin-2-yl)-2-oxo-2,3-dihydro-1H-benzo[d]imidazol-1-yl)methyl)cyclohexyl)-2-(difluoromethyl)nicotinamide;

5-chloro-2-methyl-N-((1r,4r)-4-((2-oxo-3-(quinolin-4-yl)-2,3-dihydro-1H-benzo[d]imidazol-1-yl)methyl)cyclohexyl)nicotinamide;

5-chloro-N-((1r,4r)-4-((3-(isoquinolin-6-yl)-2-oxo-2,3-dihydro-1H-benzo[d]imidazol-1-yl)methyl)cyclohexyl)-2-methylnicotinamide;

5-chloro-2-(difluoromethyl)-N-((1S,4r)-4-((2-oxo-3-(6-(((S)-tetrahydrofuran-3-yl)amino)pyridin-3-yl)-2,3-dihydro-1H-benzo[d]imidazol-1-yl)methyl)cyclohexyl)nicotinamide;

5-chloro-N-((1r,4r)-4-((3-(4-cyanopyridin-3-yl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(1-methyl-1H-indazol-4-yl)-2-oxo-2,3-dihydro-1H-benzo[d]imidazol-1-yl)methyl)cyclohexyl)nicotinamide;

5-chloro-N-((1r,4r)-4-((3-(3-cyanopyridin-2-yl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(2,6-dimethylpyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methylpyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((1-(2,3-dihydro-1H-inden-4-yl)-2-oxo-1H-imidazo[4,5-c]pyridin-3(2H)-yl)methyl)cyclohexyl)nicotinamide;

5-chloro-2-(difluoromethyl)-N-((1R,4r)-4-((2-oxo-3-(6-(((R)-tetrahydrofuran-3-yl)amino)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(methylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(dimethylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-((2-hydroxyethyl)(methyl)amino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-morpholinopyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(4-(hydroxymethyl)phenyl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(1-(2-hydroxyethyl)-1H-benzo[d][1,2,3]triazol-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((1'-methyl-2-oxo-1'H-[1,5'-bibenzo[d]imidazol]-3(2H)-yl)methyl)cyclohexyl)nicotinamide;

N-((1r,4r)-4-((3-(benzo[d]thiazol-6-yl)-2-oxo-2,3-dihydro-1H-imidazo[4,5-b]pyridin-1-yl)methyl)cyclohexyl)-5-chloro-2-(difluoromethyl)nicotinamide;

5-chloro-2-(difluoromethyl)-N-((1r,4r)-4-((3-(4-methoxyphenyl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((2-oxo-3-(p-tolyl)-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-6-methoxy-2-oxo-2,3-dihydro-1H-benzo[d]imidazol-1-yl)-N-methylpicolinamide;

5-chloro-2-(difluoromethyl)-N-((1r,4r)-4-((3-(5-(methylamino)pyrazin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinolin-6-yl)-2,3-dihydro-1H-benzo[d]imidazol-1-yl)methyl)cyclohexyl)nicotinamide;

N-((1r,4r)-4-((3-(1,8-naphthyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((2-oxo-3-(quinazolin-6-yl)-2,3-dihydro-1H-benzo[d]imidazol-1-yl)methyl)cyclohexyl)nicotinamide;

5-chloro-2-methyl-N-((1r,4r)-4-((2-oxo-3-(quinolin-7-yl)-2,3-dihydro-1H-benzo[d]imidazol-1-yl)methyl)cyclohexyl)nicotinamide;

5-chloro-N-((1r,4r)-4-((3-(isoquinolin-7-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(isoquinolin-6-yl)-2-oxo-2,3-dihydro-1H-benzo[d]imidazol-1-yl)methyl)cyclohexyl)nicotinamide;

5-chloro-N-((1r,4r)-4-((3-(isoquinolin-6-yl)-2-oxo-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((3-(4-fluoro-3-methoxyphenyl)-2-oxo-2,3-dihydro-1H-imidazo[4,5-b]pyridin-1-yl)methyl)cyclohexyl)nicotinamide;

N-((1r,4r)-4-((3-(4-acetylphenyl)-2-oxo-2,3-dihydro-1H-imidazo[4,5-b]pyridin-1-yl)methyl)cyclohexyl)-5-chloro-2-(difluoromethyl)nicotinamide;

5-chloro-N-((1r,4r)-4-((3-(3-(cyclopentyloxy)-4-methoxyphenyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(4-ethoxyphenyl)-2-oxo-2,3-dihydro-1H-imidazo[4,5-b]pyridin-1-yl)methyl)cyclohexyl)-2-methylnicotinamide;

5-(3-(((1r,4r)-4-(5-chloro-2-methylnicotinamido)cyclohexyl)methyl)-2-oxo-2,3-dihydro-1H-benzo[d]imidazol-1-yl)-1-methyl-1H-indole-2-carboxamide;

5-(3-(((1r,4r)-4-(5-chloro-2-methylnicotinamido)cyclohexyl)methyl)-2-oxo-2,3-dihydro-1H-benzo[d]imidazol-1-yl)-N,1-dimethyl-1H-indole-2-carboxamide;

5-(3-(((1r,4r)-4-(5-chloro-2-methylnicotinamido)cyclohexyl)methyl)-2-oxo-2,3-dihydro-1H-benzo[d]imidazol-1-yl)-N,N,1-trimethyl-1H-indole-2-carboxamide;

5-chloro-2-(difluoromethyl)-N-((1r,4r)-4-((3'-methyl-2-oxo-3'H-[1,5'-bibenzo[d]imidazol]-3(2H)-yl)methyl)cyclohexyl)nicotinamide;

5-chloro-N-((1r,4r)-4-((2-oxo-3-(quinoxalin-6-yl)-2,3-dihydro-1H-benzo[d]imidazol-1-yl)methyl)cyclohexyl)-2-(trifluoromethyl)nicotinamide;

5-chloro-2-methyl-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide;

5-chloro-N-((1r,4r)-4-((3-(1,3-dimethyl-1H-pyrrolo[2,3-b]pyridin-5-yl)-2-oxo-2,3-dihydro-1H-benzo[d]imidazol-1-yl)methyl)cyclohexyl)-2-methylnicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-(2-fluoroethyl)picolinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-(2,2-difluoroethyl)picolinamide;

5-chloro-N-((1r,4r)-4-((3-(6-((2-hydroxyethyl)thio)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-morpholinopyridin-3-yl)-2-oxo-2,3-dihydro-1H-benzo[d]imidazol-1-yl)methyl)cyclohexyl)nicotinamide;

5-chloro-N-((1r,4r)-4-((3-(2,4-dichlorophenyl)-2-oxo-2,3-dihydro-1H-imidazo[4,5-b]pyridin-1-yl)methyl)cyclohexyl)-2-methylnicotinamide;

5-chloro-2-(difluoromethyl)-N-((1r,4r)-4-((3-(imidazo[1,5-a]pyridin-7-yl)-2-oxo-2,3-dihydro-1H-benzo[d]imidazol-1-yl)methyl)cyclohexyl)nicotinamide;

5-chloro-N-((1r,4r)-4-((3-(6-(2-methoxyethoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(6-(2-methoxyethoxy)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(isoquinolin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinolin-8-yl)-2,3-dihydro-1H-benzo[d]imidazol-1-yl)methyl)cyclohexyl)nicotinamide;

5-chloro-2-(difluoromethyl)-N-((1r,4r)-4-((3-(imidazo[1,2-a]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methyl-2H-indazol-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinolin-7-yl)-2,3-dihydro-1H-benzo[d]imidazol-1-yl)methyl)cyclohexyl)nicotinamide;

5-chloro-2-(difluoromethyl)-N-((1r,4r)-4-((3-(isoquinolin-7-yl)-2-oxo-2,3-dihydro-1H-benzo[d]imidazol-1-yl)methyl)cyclohexyl)nicotinamide;

5-chloro-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)-2-(trifluoromethyl)nicotinamide;

5-chloro-N-((1r,4r)-4-((3-(3-methyl-1H-pyrrolo[2,3-b]pyridin-5-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

5-chloro-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)-2-(trifluoromethyl)nicotinamide;

5-chloro-2-(difluoromethyl)-N-((1R,4r)-4-((2-oxo-3-(6-(((R)-tetrahydrofuran-3-yl)oxy)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(2-hydroxy-2-methylpropoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1S,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)nicotinamide;

5-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-methoxypicolinamide;

5-chloro-2-(difluoromethyl)-N-((1r,4r)-4-((3-(6-(2-fluoroethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-morpholinoethoxy)pyridin-3-yl)-2-oxo-2,3-dihydro-1H-benzo[d]imidazol-1-yl)methyl)cyclohexyl)nicotinamide;

N-((1r,4r)-4-((3-(6-(2-amino-2-oxoethoxy)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-methyl-N-((1r,4r)-4-((3-(4-methyl-6-(methylamino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)nicotinamide;

5-chloro-N-((1r,4r)-4-((3-(6-((2,2-difluoroethyl)amino)pyridin-3-yl)-2-oxo-2,3-dihydro-1H-benzo[d]imidazol-1-yl)methyl)cyclohexyl)-2-methylnicotinamide;

5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(((1-methyl-1H-pyrazol-4-yl)methyl)amino)pyridin-3-yl)-2-oxo-2,3-dihydro-1H-benzo[d]imidazol-1-yl)methyl)cyclohexyl)nicotinamide;

N-((1r,4r)-4-((3-(1,5-naphthyridin-3-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(quinazolin-7-yl)-2,3-dihydro-1H-benzo[d]imidazol-1-yl)methyl)cyclohexyl)nicotinamide;

5-chloro-2-methyl-N-((1r,4r)-4-((3-(3-morpholinophenyl)-2-oxo-2,3-dihydro-1H-benzo[d]imidazol-1-yl)methyl)cyclohexyl)nicotinamide;

5-chloro-N-((1r,4r)-4-((3-(4-(isoxazol-3-yl)phenyl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(4-(1-methyl-1H-pyrazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(4-(1-methyl-1H-pyrazol-3-yl)phenyl)-2-oxo-2,3-dihydro-1H-benzo[d]imidazol-1-yl)methyl)cyclohexyl)nicotinamide;

N-((1r,4r)-4-((3-benzyl-2-oxo-2,3-dihydro-1H-imidazo[4,5-b]pyridin-1-yl)methyl)cyclohexyl)-5-chloro-2-methylnicotinamide;

5-chloro-2-(difluoromethyl)-N-((1r,4r)-4-((3-(2-fluorophenyl)-2-oxo-2,3-dihydro-1H-imidazo[4,5-b]pyridin-1-yl)methyl)cyclohexyl)nicotinamide;

5-chloro-2-methyl-N-((1r,4r)-4-((3-(4-(oxazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(4-(oxazol-2-yl)phenyl)-2-oxo-2,3-dihydro-1H-benzo[d]imidazol-1-yl)methyl)cyclohexyl)nicotinamide;

5-chloro-N-((1r,4r)-4-((3-(2-chloro-4-methylphenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(2-chloro-5-methoxyphenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(2-chloro-5-fluorophenyl)-2-oxo-2,3-dihydro-1H-imidazo[4,5-b]pyridin-1-yl)methyl)cyclohexyl)-2-(difluoromethyl)nicotinamide;

5-chloro-2-(difluoromethyl)-N-((1r,4r)-4-((2-oxo-3-(1H-pyrrolo[2,3-b]pyridin-5-yl)-2,3-dihydro-1H-benzo[d]imidazol-1-yl)methyl)cyclohexyl)nicotinamide;

5-chloro-2-(difluoromethyl)-N-((1r,4r)-4-((3-(3-methyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(1H-pyrrolo[2,3-b]pyridin-5-yl)-2,3-dihydro-1H-imidazo[4,5-b]pyridin-1-yl)methyl)cyclohexyl)nicotinamide;

5-chloro-2-(difluoromethyl)-N-((1r,4r)-4-((2-oxo-3-(2-phenoxyethyl)-2,3-dihydro-1H-imidazo[4,5-b]pyridin-1-yl)methyl)cyclohexyl)nicotinamide;

5-chloro-N-((1r,4r)-4-((3-(2,4-dichlorophenyl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(6-(isopropylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-methyl-6-(methylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)nicotinamide;

5-chloro-N-((1r,4r)-4-((3-(6-((2,2-difluoroethyl)amino)pyridin-3-yl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(4-methyl-6-(methylamino)pyridin-3-yl)-2-oxo-2,3-dihydro-1H-benzo[d]imidazol-1-yl)methyl)cyclohexyl)nicotinamide;

5-chloro-N-((1R,4r)-4-((3-(6-((R)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide;

5-chloro-N-((1S,4r)-4-((3-(6-((S)-2-hydroxypropoxy)pyridin-3-yl)-2-oxo-2,3-dihydro-1H-benzo[d]imidazol-1-yl)methyl)cyclohexyl)-2-(trifluoromethyl)nicotinamide;

N-((1r,4r)-4-((3-(4-(1H-imidazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-pyrazol-5-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-1,2,3-triazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-pyrazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(6-(1H-imidazol-1-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(2-(1H-imidazol-1-yl)pyridin-4-yl)-2-oxo-2,3-dihydro-1H-benzo[d]imidazol-1-yl)methyl)cyclohexyl)-5-chloro-2-methylnicotinamide;

5-chloro-2-(difluoromethyl)-N-((1r,4r)-4-((3-(3-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

N-((1r,4r)-4-((3-(4-(1H-imidazol-1-yl)pyridin-2-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(5-morpholinopyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-methoxyethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(oxetan-3-yloxy)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-propionamidopyridin-3-yl)-2,3-dihydro-1H-benzo[d]imidazol-1-yl)methyl)cyclohexyl)nicotinamide;

5-chloro-N-((1r,4r)-4-((3-(6-((3,3-difluoropropyl)amino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(oxetan-3-ylamino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(5-(pyrrolidin-1-yl)pyridin-3-yl)-2,3-dihydro-1H-benzo[d]imidazol-1-yl)methyl)cyclohexyl)nicotinamide;

5-chloro-N-((1r,4r)-4-((3-(5-(dimethylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5-methoxypyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(oxazol-5-yl)pyridin-3-yl)-2-oxo-2,3-dihydro-1H-benzo[d]imidazol-1-yl)methyl)cyclohexyl)nicotinamide;

5-chloro-N-((1r,4r)-4-((3-(5-(2-methoxyethoxy)pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(5-(methylamino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(3-(oxazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(5-(oxazol-5-yl)pyridin-2-yl)-2-oxo-2,3-dihydro-1H-benzo[d]imidazol-1-yl)methyl)cyclohexyl)nicotinamide;

5-(3-(((1r,4r)-4-(2-chloro-5-(trifluoromethyl)benzamido)cyclohexyl)methyl)-2-oxo-2,3-dihydro-1H-benzo[d]imidazol-1-yl)-N-methylpicolinamide;

N-methyl-5-(3-(((1r,4r)-4-(2-methyl-5-(trifluoromethyl)nicotinamido)cyclohexyl)methyl)-2-oxo-2,3-dihydro-1H-benzo[d]imidazol-1-yl)picolinamide;

N-methyl-5-(3-(((1r,4r)-4-(5-methyl-2-(trifluoromethyl)benzamido)cyclohexyl)methyl)-2-oxo-2,3-dihydro-1H-benzo[d]imidazol-1-yl)picolinamide;

5-chloro-2-(difluoromethyl)-N-((1r,4r)-4-((3-(6-(ethylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(1,3-dimethyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(quinoxalin-6-yl)-2,3-dihydro-1H-benzo[d]imidazol-1-yl)methyl)cyclohexyl)nicotinamide;

5-chloro-N-((1r,4r)-4-((3-(3-chloropyridin-4-yl)-2-oxo-2,3-dihydro-1H-imidazo[4,5-b]pyridin-1-yl)methyl)cyclohexyl)-2-(difluoromethyl)nicotinamide;

5-chloro-N-((1r,4r)-4-((3-(2-(hydroxymethyl)-1-methyl-1H-indol-5-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)nicotinamide;

5-chloro-N-((1r,4r)-4-((3-(2-cyanophenyl)-2-oxo-2,3-dihydro-1H-benzo[d]imidazol-1-yl)methyl)cyclohexyl)-2-(difluoromethyl)nicotinamide;

5-chloro-2-(difluoromethyl)-N-((1r,4r)-4-((3-(6-(2-(methylamino)-2-oxoethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-(2-oxoazetidin-1-yl)pyridin-3-yl)-2,3-dihydro-1H-benzo[d]imidazol-1-yl)methyl)cyclohexyl)nicotinamide;

5-chloro-N-((1r,4r)-4-((3-(6-(cyclopropanecarboxamido)pyridin-3-yl)-2-oxo-2,3-dihydro-1H-benzo[d]imidazol-1-yl)methyl)cyclohexyl)-2-(difluoromethyl)nicotinamide;

N-((1S,4r)-4-((3-(6-(((S)-1-amino-1-oxopropan-2-yl)oxy)pyridin-3-yl)-2-oxo-2,3-dihydro-1H-benzo[d]imidazol-1-yl)methyl)cyclohexyl)-5-chloro-2-(difluoromethyl)nicotinamide;

N-((1R,4r)-4-((3-(6-(((R)-1-amino-1-oxopropan-2-yl)oxy)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((2-oxo-3-(6-(3-oxomorpholino)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(p-tolyl)-2,3-dihydro-1H-imidazo[4,5-b]pyrazin-1-yl)methyl)cyclohexyl)nicotinamide;

5-chloro-N-((1r,4r)-4-((3-(2-cyano-5-methoxyphenyl)-2-oxo-2,3-dihydro-1H-imidazo[4,5-b]pyridin-1-yl)methyl)cyclohexyl)-2-(difluoromethyl)nicotinamide;

N-((1r,4r)-4-((3-(6-acetamidopyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((2-oxo-3-(6-(2-oxopiperidin-1-yl)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-propionamidopyridin-3-yl)-2,3-dihydro-1H-benzo[d]imidazol-1-yl)methyl)cyclohexyl)nicotinamide;

N-((1r,4r)-4-((3-(6-(1H-1,2,3-triazol-1-yl)pyridin-3-yl)-2-oxo-2,3-dihydro-1H-benzo[d]imidazol-1-yl)methyl)cyclohexyl)-5-chloro-2-methylnicotinamide;

N-((1r,4r)-4-((3-(6-(2H-1,2,3-triazol-2-yl)pyridin-3-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((2-oxo-3-(1-(pyridin-3-yl)piperidin-4-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(isopropylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-((2,2-difluoropropyl)amino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(3-(oxazol-2-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(1-methyl-1H-imidazol-5-yl)phenyl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(4-(thiazol-2-yl)phenyl)-2,3-dihydro-1H-benzo[d]imidazol-1-yl)methyl)cyclohexyl)nicotinamide;

5-chloro-2-methyl-N-((1r,4r)-4-((3-(2-morpholinopyridin-4-yl)-2-oxo-2,3-dihydro-1H-benzo[d]imidazol-1-yl)methyl)cyclohexyl)nicotinamide;

N-((1r,4r)-4-((3-(6-(1H-imidazol-1-yl)pyridin-2-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(2-(oxazol-5-yl)pyridin-4-yl)-2-oxo-2,3-dihydro-1H-benzo[d]imidazol-1-yl)methyl)cyclohexyl)nicotinamide;

5-chloro-N-((1r,4r)-4-((3-(5-chloro-6-(methylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((2-oxo-3-(6-(2-oxoimidazolidin-1-yl)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(3-methyl-2-oxoimidazolidin-1-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methylbenzo[d]thiazol-5-yl)-2-oxo-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpyrazine-2-carboxamide;

5-(3-(((1r,4r)-4-(5-chloro-2-(difluoromethyl)nicotinamido)cyclohexyl)methyl)-7-methyl-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-5-methoxy-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-5-methyl-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-5-fluoro-2-oxo-2,3-dihydro-1H-benzo[d]imidazol-1-yl)-N-methylpicolinamide;

5-(3-(((1r,4r)-4-(5-chloro-2-(trifluoromethoxy)benzamido)cyclohexyl)methyl)-2-oxo-2,3-dihydro-1H-benzo[d]imidazol-1-yl)-N-methylpicolinamide;

N-methyl-5-(3-(((1r,4r)-4-(2-methyl-5-(trifluoromethyl)benzamido)cyclohexyl)methyl)-2-oxo-2,3-dihydro-1H-benzo[d]imidazol-1-yl)picolinamide;

5-(3-(((1r,4r)-4-(5-chloro-2-(difluoromethoxy)benzamido)cyclohexyl)methyl)-2-oxo-2,3-dihydro-1H-benzo[d]imidazol-1-yl)-N-methylpicolinamide;

5-(3-(((1r,4r)-4-(2-amino-5-chloronicotinamido)cyclohexyl)methyl)-2-oxo-2,3-dihydro-1H-benzo[d]imidazol-1-yl)-N-methylpicolinamide;

5-(3-(((1r,4r)-4-(5-bromo-2-(trifluoromethyl)nicotinamido)cyclohexyl)methyl)-2-oxo-2,3-dihydro-1H-benzo[d]imidazol-1-yl)-N-methylpicolinamide;

N-((1r,4r)-4-((3-(2-(2H-1,2,3-triazol-2-yl)pyridin-4-yl)-2-oxo-2,3-dihydro-1H-benzo[d]imidazol-1-yl)methyl)cyclohexyl)-5-chloro-2-methylnicotinamide;

N-((1r,4r)-4-((3-(3-(1H-1,2,3-triazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(3-(2H-1,2,3-triazol-2-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(3-(1H-imidazol-1-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(6-(1H-1,2,3-triazol-1-yl)pyridin-2-yl)-2-oxo-2,3-dihydro-1H-benzo[d]imidazol-1-yl)methyl)cyclohexyl)-5-chloro-2-methylnicotinamide;

N-((1r,4r)-4-((3-(3-(1H-pyrazol-1-yl)phenyl)-2-oxo-2,3-dihydro-1H-benzo[d]imidazol-1-yl)methyl)cyclohexyl)-5-chloro-2-methylnicotinamide;

5-(3-(((1r,4r)-4-(2,5-dichloronicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-(cyclopropylamino)pyridin-3-yl)-2-oxo-2,3-dihydro-1H-benzo[d]imidazol-1-yl)methyl)cyclohexyl)-2-(difluoromethyl)nicotinamide;

5-chloro-N-((1r,4r)-4-((3-(5-methyl-6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(4-methyl-6-(methylamino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(6-((2,2,2-trifluoroethyl)amino)pyridin-3-yl)-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((3-(1-methyl-1H-indazol-5-yl)-2-oxo-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-4-fluoro-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-(2-fluoroethyl)picolinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-(oxetan-3-yl)picolinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-ethylpicolinamide;

5-chloro-N-((1r,4r)-4-((3-(5-fluoro-6-(methylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(3-methoxyazetidin-1-yl)pyridin-3-yl)-2-oxo-2,3-dihydro-1H-benzo[d]imidazol-1-yl)methyl)cyclohexyl)nicotinamide;

3-chloro-5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N,6-dimethylpicolinamide;

N-((1r,4r)-4-((3-(6-(methylcarbamoyl)pyridin-3-yl)-2-oxo-2,3-dihydro-1H-benzo[d]imidazol-1-yl)methyl)cyclohexyl)-2-(2,2,2-trifluoroethyl)-2H-indazole-3-carboxamide;

5-chloro-2-(difluoromethyl)-N-((1r,4r)-4-((3-(4-methyl-6-(2-oxoimidazolidin-1-yl)pyridin-3-yl)-2-oxo-2,3-dihydro-1H-benzo[d]imidazol-1-yl)methyl)cyclohexyl)nicotinamide;

N-((1r,4r)-4-((3-(6-acetamido-4-methylpyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(4-methyl-6-propionamidopyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(4-methyl-6-(2-oxopyrrolidin-1-yl)pyridin-3-yl)-2-oxo-2,3-dihydro-1H-benzo[d]imidazol-1-yl)methyl)cyclohexyl)nicotinamide;

5-(3-(((1r,4r)-4-(5-chloro-2-(difluoromethyl)nicotinamido)cyclohexyl)methyl)-6-fluoro-2-oxo-2,3-dihydro-1H-benzo[d]imidazol-1-yl)-N-methylpicolinamide;

5-chloro-2-(difluoromethyl)-N-((1r,4r)-4-((3-(5-(2-hydroxyethoxy)pyrazin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(2-hydroxyethoxy)pyridazin-3-yl)-2-oxo-2,3-dihydro-1H-benzo[d]imidazol-1-yl)methyl)cyclohexyl)nicotinamide;

5-(3-(((1r,4r)-4-(5-chloro-2-(cyclopropylamino)nicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(3-morpholinophenyl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(4-(1-methyl-1H-imidazol-2-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(oxazol-4-yl)phenyl)-2-oxo-2,3-dihydro-1H-benzo[d]imidazol-1-yl)methyl)cyclohexyl)nicotinamide;

N-((1r,4r)-4-((3-(4-(1H-imidazol-1-yl)phenyl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(2-(1H-imidazol-1-yl)pyridin-4-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-(methylamino)pyridin-4-yl)-2-oxo-2,3-dihydro-1H-benzo[d]imidazol-1-yl)methyl)cyclohexyl)nicotinamide;

5-chloro-2-methyl-N-((1r,4r)-4-((3-(5-(methylamino)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(3-methyl-1H-indazol-6-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(3-methyl-1H-indazol-5-yl)-2-oxo-2,3-dihydro-1H-imidazo[4,5-b]pyridin-1-yl)methyl)cyclohexyl)nicotinamide;

5-(3-(((1r,4r)-4-(5-chloro-2-(difluoromethyl)nicotinamido)cyclohexyl)methyl)-4-methyl-2-oxo-2,3-dihydro-1H-benzo[d]imidazol-1-yl)-N-methylpicolinamide;

5-chloro-2-(difluoromethyl)-N-((1r,4r)-4-((1-(3-methyl-1H-pyrrolo[2,3-b]pyridin-5-yl)-2-oxo-1H-imidazo[4,5-b]pyridin-3(2H)-yl)methyl)cyclohexyl)nicotinamide;

5-chloro-2-methyl-N-((1r,4r)-4-((3-(4-(1-methyl-1H-pyrazol-4-yl)phenyl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(4-(thiazol-5-yl)phenyl)-2,3-dihydro-1H-benzo[d]imidazol-1-yl)methyl)cyclohexyl)nicotinamide;

N-((1r,4r)-4-((3-(4-(1H-pyrazol-4-yl)phenyl)-2-oxo-2,3-dihydro-1H-benzo[d]imidazol-1-yl)methyl)cyclohexyl)-5-chloro-2-methylnicotinamide;

5-(3-(((1r,4r)-4-(5-chloro-2-(fluoromethyl)nicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(3-methylbenzo[d]isoxazol-6-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((2-oxo-3-(6-(7-oxo-6-oxa-6-azaspiro[3.4]octan-6-yl)pyridin-3-yl)-2,3-dihydro-1H-benzo[d]imidazol-1-yl)methyl)cyclohexyl)nicotinamide;

5-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-cyclopropylpicolinamide;

5-chloro-2-methyl-N-((1r,4r)-4-((3-(3-methylbenzo[d]isoxazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(3-methyl-2-oxo-2,3-dihydrobenzo[d]oxazol-5-yl)-2-oxo-2,3-dihydro-1H-benzo[d]imidazol-1-yl)methyl)cyclohexyl)nicotinamide;

5-chloro-N-((1r,4r)-4-((3-(1-(2-(dimethylamino)ethyl)-3-methyl-1H-indazol-5-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(3-methyl-1-(2-morpholinoethyl)-1H-indazol-5-yl)-2-oxo-2,3-dihydro-1H-benzo[d]imidazol-1-yl)methyl)cyclohexyl)nicotinamide;

5-chloro-N-((1r,4r)-4-((3-(6-methoxypyridin-3-yl)-2-oxo-3,4-dihydroquinazolin-1(2H)-yl)methyl)cyclohexyl)-2-methylnicotinamide;

N-((1r,4r)-4-((3-(3-aminobenzo[d]isoxazol-5-yl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2-fluorophenyl)-2-oxo-2,3-dihydro-1H-imidazo[4,5-b]pyridin-1-yl)methyl)cyclohexyl)-2-methylnicotinamide;

5-chloro-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)-2-methylnicotinamide;

6-(3-(((1r,4r)-4-(5-chloro-2-methylnicotinamido)cyclohexyl)methyl)-2-oxo-2,3-dihydro-1H-benzo[d]imidazol-1-yl)-N-(2-hydroxyethyl)benzo[d]isoxazole-3-carboxamide;

5-chloro-N-((1r,4r)-4-((3-(4-cyanopyridazin-3-yl)-2-oxo-2,3-dihydro-1H-benzo[d]imidazol-1-yl)methyl)cyclohexyl)-2-(trifluoromethyl)nicotinamide;

5-(3-(((1r,4r)-4-(5-chloro-2-(methylamino)nicotinamido)cyclohexyl)methyl)-2-oxo-2,3-dihydro-1H-benzo[d]imidazol-1-yl)-N-methylpicolinamide;

5-chloro-N-((1r,4r)-4-((3-(6-((2-hydroxyethyl)(methyl) amino)pyridin-3-yl)-2-oxo-2,3-dihydro-1H-benzo[d] imidazol-1-yl)methyl)cyclohexyl)-2-(trifluoromethyl) nicotinamide;

5-chloro-N-((1r,4r)-4-((3-(6-morpholinopyridin-3-yl)-2-oxo-2,3-dihydro-1H-benzo[d]imidazol-1-yl)methyl) cyclohexyl)-2-(trifluoromethyl)nicotinamide;

5-chloro-N-((1r,4r)-4-((3-(6-(4-methylpiperazin-1-yl) pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(4,6-dimethylpyridin-3-yl)-2-oxo-2,3-dihydro-1H-benzo[d]imidazol-1-yl)methyl) cyclohexyl)-2-(trifluoromethyl)nicotinamide;

5-chloro-N-((1r,4r)-4-((3-(2,3-dimethylpyridin-4-yl)-2-oxo-2,3-dihydro-1H-benzo[d]imidazol-1-yl)methyl) cyclohexyl)-2-(trifluoromethyl)nicotinamide;

5-chloro-2-methyl-N-((1r,4r)-4-((3-(2-methyl-2H-indazol-4-yl)-2-oxo-2,3-dihydro-1H-benzo[d]imidazol-1-yl)methyl)cyclohexyl)nicotinamide;

5-chloro-N-((1r,4r)-4-((3-(4-chlorophenyl)-2-oxo-2,3-dihydro-1H-imidazo[4,5-b]pyridin-1-yl)methyl)cyclohexyl)-2-(difluoromethyl)nicotinamide;

5-chloro-2-(difluoromethyl)-N-((1r,4r)-4-((2-oxo-3-(1,2,3,4-tetrahydroisoquinolin-7-yl)-2,3-dihydro-1H-benzo [d]imidazol-1-yl)methyl)cyclohexyl)nicotinamide;

N-((1r,4r)-4-((3-(2-acetyl-1,2,3,4-tetrahydroisoquinolin-7-yl)-2-oxo-2,3-dihydro-1H-benzo[d]imidazol-1-yl) methyl)cyclohexyl)-5-chloro-2-(difluoromethyl)nicotinamide;

5-chloro-N-((1r,4r)-4-((3-(6-(2-hydroxy-2-methylpropoxy)pyridin-3-yl)-2-oxo-2,3-dihydro-1H-benzo[d] imidazol-1-yl)methyl)cyclohexyl)-2-(trifluoromethyl) nicotinamide;

5-chloro-N-((1S,4r)-4-((2-oxo-3-(6-(((S)-tetrahydrofuran-3-yl)oxy)pyridin-3-yl)-2,3-dihydro-1H-benzo[d] imidazol-1-yl)methyl)cyclohexyl)-2-(trifluoromethyl) nicotinamide;

5-chloro-2-methyl-N-((1R,4r)-4-((2-oxo-3-(6-(((R)-tetrahydrofuran-3-yl)oxy)pyridin-3-yl)-2,3-dihydro-1H-benzo[d]imidazol-1-yl)methyl)cyclohexyl)nicotinamide;

5-chloro-2-methyl-N-((1S,4r)-4-((2-oxo-3-(6-(((S)-tetrahydrofuran-3-yl)oxy)pyridin-3-yl)-2,3-dihydro-1H-benzo[d]imidazol-1-yl)methyl)cyclohexyl)nicotinamide;

5-chloro-N-((1S,4r)-4-((3-(6-((S)-2-hydroxypropoxy) pyridin-3-yl)-2-oxo-2,3-dihydro-1H-benzo[d]imidazol-1-yl)methyl)cyclohexyl)-2-methylnicotinamide;

5-chloro-2-methyl-N-((1r,4r)-4-((3-(6-methylquinolin-3-yl)-2-oxo-2,3-dihydro-1H-imidazo[4,5-b]pyridin-1-yl) methyl)cyclohexyl)nicotinamide;

5-chloro-N-((1r,4r)-4-((3-(2-chloro-4-fluorophenyl)-2-oxo-2,3-dihydro-1H-imidazo[4,5-b]pyridin-1-yl) methyl)cyclohexyl)-2-(difluoromethyl)nicotinamide;

5-chloro-N-((1r,4r)-4-((3-(3-chloro-4-methylphenyl)-2-oxo-2,3-dihydro-1H-imidazo[4,5-b]pyridin-1-yl) methyl)cyclohexyl)-2-(difluoromethyl)nicotinamide;

5-chloro-N-((1r,4r)-4-((3-(6-((2,2-difluoropropyl)amino) pyridin-3-yl)-2-oxo-2,3-dihydro-1H-benzo[d]imidazol-1-yl)methyl)cyclohexyl)-2-methylnicotinamide;

5-chloro-N-((1R,4r)-4-((3-(6-((R)-3-hydroxypyrrolidin-1-yl)pyridin-3-yl)-2-oxo-2,3-dihydro-1H-benzo[d]imidazol-1-yl)methyl)cyclohexyl)-2-(trifluoromethyl) nicotinamide;

5-chloro-N-((1r,4r)-4-((3-(2-chloro-4-methylphenyl)-2-oxo-2,3-dihydro-1H-imidazo[4,5-b]pyridin-1-yl) methyl)cyclohexyl)-2-(trifluoromethyl)nicotinamide;

5-chloro-N-((1r,4r)-4-((3-(2-chloro-5-methoxyphenyl)-2-oxo-2,3-dihydro-1H-imidazo[4,5-b]pyridin-1-yl) methyl)cyclohexyl)-2-(trifluoromethyl)nicotinamide;

5-chloro-N-((1r,4r)-4-((3-(6-(2-methoxyacetamido)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(dimethylamino)pyridin-3-yl)-2-oxo-2,3-dihydro-1H-imidazo [4,5-b]pyridin-1-yl)methyl)cyclohexyl)nicotinamide;

5-chloro-N-((1r,4r)-4-((3-(2-cyanophenyl)-2-oxo-2,3-dihydro-1H-imidazo[4,5-b]pyridin-1-yl)methyl)cyclohexyl)-2-(difluoromethyl)nicotinamide;

5-chloro-2-(difluoromethyl)-N-((1r,4r)-4-((3-(6-(2-hydroxyacetamido)pyridin-3-yl)-2-oxo-2,3-dihydro-1H-benzo[d]imidazol-1-yl)methyl)cyclohexyl)nicotinamide;

N-((1r,4r)-4-((3-(2-(1H-pyrazol-1-yl)pyridin-4-yl)-2-oxo-2,3-dihydro-1H-benzo[d]imidazol-1-yl)methyl) cyclohexyl)-5-chloro-2-methylnicotinamide;

N-((1r,4r)-4-((3-(6-(1H-pyrazol-1-yl)pyridin-2-yl)-2-oxo-2,3-dihydro-1H-benzo[d]imidazol-1-yl)methyl) cyclohexyl)-5-chloro-2-methylnicotinamide;

5-chloro-N-((1r,4r)-4-((6-fluoro-3-(6-(methylamino)pyridin-3-yl)-2-oxo-2,3-dihydro-1H-benzo[d]imidazol-1-yl)methyl)cyclohexyl)-2-methylnicotinamide;

5-chloro-N-((1r,4r)-4-((5-fluoro-3-(6-(methylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((5-fluoro-3-(6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((3-(2-cyano-4-fluorophenyl)-2-oxo-2,3-dihydro-1H-benzo[d]imidazol-1-yl)methyl) cyclohexyl)-2-(difluoromethyl)nicotinamide;

5-(3-(((1r,4r)-4-(5-chloro-2-(difluoromethyl)nicotinamido)cyclohexyl)methyl)-7-fluoro-2-oxo-2,3-dihydro-1H-benzo[d]imidazol-1-yl)-N-methylpicolinamide;

5-(3-(((1r,4r)-4-(5-chloro-2-(difluoromethyl)nicotinamido)cyclohexyl)methyl)-7-methoxy-2-oxo-2,3-dihydro-1H-benzo[d]imidazol-1-yl)-N-methylpicolinamide;

5-chloro-N-((1r,4r)-4-((1-(2-chlorophenyl)-2-oxo-1H-imidazo[4,5-b]pyridin-3(2H)-yl)methyl)cyclohexyl)-2-(difluoromethyl)nicotinamide;

5-chloro-N-((1r,4r)-4-((1-(2-chloro-5-methoxyphenyl)-2-oxo-1H-imidazo[4,5-c]pyridin-3(2H)-yl)methyl)cyclohexyl)-2-(difluoromethyl)nicotinamide;

5-chloro-N-((1r,4r)-4-((1-(2-chloro-5-fluorophenyl)-2-oxo-1H-imidazo[4,5-c]pyridin-3(2H)-yl)methyl)cyclohexyl)-2-(difluoromethyl)nicotinamide;

N-((1r,4r)-4-((3-(4-(1H-1,2,3-triazol-4-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-1,2,3-triazol-1-yl)phenyl)-2-oxo-2,3-dihydro-1H-imidazo[4,5-b]pyridin-1-yl)methyl) cyclohexyl)-5-chloro-2-(difluoromethyl)nicotinamide;

5-chloro-2-methyl-N-((1r,4r)-4-((3-(4-(oxazol-4-yl)phenyl)-2-oxo-2,3-dihydro-1H-benzo[d]imidazol-1-yl) methyl)cyclohexyl)nicotinamide;

N-((1r,4r)-4-((3-(5-(1H-pyrazol-1-yl)pyridin-3-yl)-2-oxo-2,3-dihydro-1H-benzo[d]imidazol-1-yl)methyl) cyclohexyl)-5-chloro-2-methylnicotinamide;

N-((1r,4r)-4-((3-(6-(1H-pyrazol-1-yl)pyridin-3-yl)-2-oxo-2,3-dihydro-1H-benzo[d]imidazol-1-yl)methyl)cyclohexyl)-5-chloro-2-methylnicotinamide;

5-chloro-2-(difluoromethyl)-N-((1r,4r)-4-((3-(5-fluoro-6-(2-hydroxyethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-fluoro-6-(methylamino)pyridin-3-yl)-2-oxo-2,3-dihydro-1H-benzo[d]imidazol-1-yl)methyl)cyclohexyl)nicotinamide;

5-chloro-N-((1r,4r)-4-((2-oxo-3-(6-(2-oxoimidazolidin-1-yl)pyridin-3-yl)-2,3-dihydro-1H-benzo[d]imidazol-1-yl)methyl)cyclohexyl)-2-(trifluoromethyl)nicotinamide;

5-chloro-N-((1r,4r)-4-((2-oxo-3-(6-(2-oxopyrrolidin-1-yl)pyridin-3-yl)-2,3-dihydro-1H-benzo[d]imidazol-1-yl)methyl)cyclohexyl)-2-(trifluoromethyl)nicotinamide;

N-((1r,4r)-4-((3-(6-acetamidopyridin-3-yl)-2-oxo-2,3-dihydro-1H-benzo[d]imidazol-1-yl)methyl)cyclohexyl)-5-chloro-2-(trifluoromethyl)nicotinamide;

5-chloro-N-((1r,4r)-4-((2-oxo-3-(6-propionamidopyridin-3-yl)-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((3-(6-(3-methylureido)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-methylbenzo[d]thiazol-5-yl)-2-oxo-2,3-dihydro-1H-benzo[d]imidazol-1-yl)methyl)cyclohexyl)nicotinamide;

5-chloro-2-methyl-N-((1r,4r)-4-((3-(4-(methylamino)phenyl)-2-oxo-2,3-dihydro-1H-benzo[d]imidazol-1-yl)methyl)cyclohexyl)nicotinamide;

5-chloro-N-((1r,4r)-4-((3-(5-(dimethylamino)pyridin-2-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(5-(dimethylamino)pyridin-2-yl)-2-oxo-2,3-dihydro-1H-benzo[d]imidazol-1-yl)methyl)cyclohexyl)nicotinamide;

5-chloro-N-((1r,4r)-4-((3-(2-(dimethylamino)pyridin-4-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(2-(dimethylamino)pyridin-4-yl)-2-oxo-2,3-dihydro-1H-benzo[d]imidazol-1-yl)methyl)cyclohexyl)nicotinamide;

5-chloro-2-methyl-N-((1r,4r)-4-((3-(3-(1-methyl-1H-pyrazol-3-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(5-(1-methyl-1H-pyrazol-3-yl)pyridin-3-yl)-2-oxo-2,3-dihydro-1H-benzo[d]imidazol-1-yl)methyl)cyclohexyl)nicotinamide;

N-((1r,4r)-4-((3-(5-(1H-pyrazol-1-yl)pyridin-2-yl)-2-oxo-2,3-dihydro-1H-benzo[d]imidazol-1-yl)methyl)cyclohexyl)-5-chloro-2-methylnicotinamide;

5-chloro-2-methyl-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)nicotinamide;

5-chloro-2-methyl-N-((1r,4r)-4-((3-(2-(1-methyl-1H-pyrazol-3-yl)pyridin-4-yl)-2-oxo-2,3-dihydro-1H-benzo[d]imidazol-1-yl)methyl)cyclohexyl)nicotinamide;

5-chloro-2-methyl-N-((1r,4r)-4-((3-(6-(1-methyl-1H-pyrazol-4-yl)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(1-methyl-1H-pyrazol-4-yl)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-ureidopyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(dimethylamino)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-(methylamino)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-(methylamino)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(6-(methylamino)pyridin-2-yl)-2-oxo-2,3-dihydro-1H-benzo[d]imidazol-1-yl)methyl)cyclohexyl)nicotinamide;

5-chloro-N-((1r,4r)-4-((3-(2-(dimethylamino)pyridin-4-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(6-((2-methoxyethyl)amino)pyridin-3-yl)-2-oxo-2,3-dihydro-1H-benzo[d]imidazol-1-yl)methyl)cyclohexyl)-2-(trifluoromethyl)nicotinamide;

5-chloro-N-((1r,4r)-4-((3-(2-(methylamino)pyridin-4-yl)-2-oxo-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((3-(1-(2-hydroxyethyl)-1H-pyrrolo[2,3-b]pyridin-5-yl)-2-oxo-2,3-dihydro-1H-benzo[d]imidazol-1-yl)methyl)cyclohexyl)nicotinamide;

N-((1r,4r)-4-((3-(4-(1H-imidazol-4-yl)phenyl)-2-oxo-2,3-dihydro-1H-benzo[d]imidazol-1-yl)methyl)cyclohexyl)-5-chloro-2-methylnicotinamide;

5-chloro-N-((1r,4r)-4-((7-fluoro-3-(6-(methylamino)pyridin-3-yl)-2-oxo-2,3-dihydro-1H-benzo[d]imidazol-1-yl)methyl)cyclohexyl)-2-methylnicotinamide;

5-chloro-2-(difluoromethyl)-N-((1r,4r)-4-((3-(6-(2-hydroxy-2-methylpropanamido)pyridin-3-yl)-2-oxo-2,3-dihydro-1H-benzo[d]imidazol-1-yl)methyl)cyclohexyl)nicotinamide;

5-chloro-2-(difluoromethyl)-N-((1R,4r)-4-((3-(6-((R)-2-hydroxypropanamido)pyridin-3-yl)-2-oxo-2,3-dihydro-1H-benzo[d]imidazol-1-yl)methyl)cyclohexyl)nicotinamide;

5-chloro-2-(difluoromethyl)-N-((1S,4r)-4-((3-(6-((S)-2-hydroxypropanamido)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((7-fluoro-3-(6-(methylamino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(1,2-dimethyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-N-((1r,4r)-4-((1-(2-chloro-5-methoxyphenyl)-2-oxo-1H-imidazo[4,5-b]pyridin-3(2H)-yl)methyl)cyclohexyl)-2-(difluoromethyl)nicotinamide;
5-chloro-N-((1r,4r)-4-((1-(2-chloro-5-fluorophenyl)-2-oxo-1H-imidazo[4,5-b]pyridin-3(2H)-yl)methyl)cyclohexyl)-2-(difluoromethyl)nicotinamide;
5-chloro-2-(difluoromethyl)-N-((1r,4r)-4-((1-(4-fluoro-3-methoxyphenyl)-2-oxo-1H-imidazo[4,5-b]pyridin-3(2H)-yl)methyl)cyclohexyl)nicotinamide;
5-chloro-2-methyl-N-((1r,4r)-4-((3-(3-(1-methyl-1H-pyrazol-4-yl)phenyl)-2-oxo-2,3-dihydro-1H-benzo[d]imidazol-1-yl)methyl)cyclohexyl)nicotinamide;
5-chloro-2-methyl-N-((1r,4r)-4-((3-(5-(1-methyl-1H-pyrazol-4-yl)pyridin-3-yl)-2-oxo-2,3-dihydro-1H-benzo[d]imidazol-1-yl)methyl)cyclohexyl)nicotinamide;
5-chloro-2-methyl-N-((1r,4r)-4-((3-(2-(1-methyl-1H-pyrazol-4-yl)pyridin-4-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(3-(1-methyl-1H-pyrazol-4-yl)phenyl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(5-(1-methyl-1H-pyrazol-4-yl)pyridin-3-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(5-methoxypyridin-3-yl)-2-oxo-2,3-dihydro-1H-benzo[d]imidazol-1-yl)methyl)cyclohexyl)nicotinamide;
N-((1r,4r)-4-((3-(4-(2H-1,2,3-triazol-2-yl)phenyl)-2-oxo-2,3-dihydro-1H-benzo[d]imidazol-1-yl)methyl)cyclohexyl)-5-chloro-2-(difluoromethyl)nicotinamide;
N-((1r,4r)-4-((3-(6-(2H-1,2,3-triazol-2-yl)pyridin-3-yl)-2-oxo-2,3-dihydro-1H-benzo[d]imidazol-1-yl)methyl)cyclohexyl)-5-chloro-2-(difluoromethyl)nicotinamide;
5-chloro-2-(difluoromethyl)-N-((1r,4r)-4-((3-(2-morpholinopyridin-4-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(2-(oxazol-5-yl)pyridin-4-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(5-(oxazol-2-yl)pyridin-3-yl)-2-oxo-2,3-dihydro-1H-benzo[d]imidazol-1-yl)methyl)cyclohexyl)nicotinamide;
5-chloro-2-methyl-N-((1r,4r)-4-((3-(5-(oxazol-2-yl)pyridin-3-yl)-2-oxo-2,3-dihydro-1H-benzo[d]imidazol-1-yl)methyl)cyclohexyl)nicotinamide;
5-chloro-2-methyl-N-((1r,4r)-4-((3-(2-(3-methyl-2-oxoimidazolidin-1-yl)pyridin-4-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((2-oxo-3-(2-(2-oxoimidazolidin-1-yl)pyridin-4-yl)-2,3-dihydro-1H-benzo[d]imidazol-1-yl)methyl)cyclohexyl)nicotinamide;
5-chloro-N-((1r,4r)-4-((3-(5-(methylamino)pyridin-2-yl)-2-oxo-2,3-dihydro-1H-benzo[d]imidazol-1-yl)methyl)cyclohexyl)-2-(trifluoromethyl)nicotinamide;
5-chloro-N-((1r,4r)-4-((3-(2-chloro-5-methoxyphenyl)-2-oxo-2,3-dihydro-1H-imidazo[4,5-c]pyridin-1-yl)methyl)cyclohexyl)-2-(difluoromethyl)nicotinamide;
5-chloro-2-(difluoromethyl)-N-((1r,4r)-4-((3-(3-fluorophenyl)-2-oxo-2,3-dihydro-1H-imidazo[4,5-c]pyridin-1-yl)methyl)cyclohexyl)nicotinamide;
N-((1r,4r)-4-((3-(6-(1H-imidazol-2-yl)pyridin-3-yl)-2-oxo-2,3-dihydro-1H-benzo[d]imidazol-1-yl)methyl)cyclohexyl)-5-chloro-2-methylnicotinamide;
N-((1r,4r)-4-((3-(3-(1H-pyrazol-4-yl)phenyl)-2-oxo-2,3-dihydro-1H-benzo[d]imidazol-1-yl)methyl)cyclohexyl)-5-chloro-2-methylnicotinamide;
N-((1r,4r)-4-((3-(3-(1H-pyrazol-4-yl)phenyl)-2-oxo-2,3-dihydro-1H-benzo[d]imidazol-1-yl)methyl)cyclohexyl)-5-chloro-2-(difluoromethyl)nicotinamide;
N-((1r,4r)-4-((3-(2-(1H-pyrazol-4-yl)pyridin-4-yl)-2-oxo-2,3-dihydro-1H-benzo[d]imidazol-1-yl)methyl)cyclohexyl)-5-chloro-2-methylnicotinamide;
5-chloro-2-(difluoromethyl)-N-((1r,4r)-4-((3-(2-(1-methyl-1H-pyrazol-4-yl)pyridin-4-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(3-(1-methyl-1H-pyrazol-3-yl)phenyl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(5-(1-methyl-1H-pyrazol-3-yl)pyridin-3-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(2-(1-methyl-1H-pyrazol-3-yl)pyridin-4-yl)-2-oxo-2,3-dihydro-1H-benzo[d]imidazol-1-yl)methyl)cyclohexyl)nicotinamide;
N-((1r,4r)-4-((3-(5-(1H-pyrazol-1-yl)pyridin-3-yl)-2-oxo-2,3-dihydro-1H-benzo[d]imidazol-1-yl)methyl)cyclohexyl)-5-chloro-2-(difluoromethyl)nicotinamide;
5-chloro-N-((1r,4r)-4-((6-fluoro-3-(6-(methylamino)pyridin-3-yl)-2-oxo-2,3-dihydro-1H-benzo[d]imidazol-1-yl)methyl)cyclohexyl)-2-(trifluoromethyl)nicotinamide;
5-chloro-N-((1r,4r)-4-((5-fluoro-3-(6-(methylamino)pyridin-3-yl)-2-oxo-2,3-dihydro-1H-benzo[d]imidazol-1-yl)methyl)cyclohexyl)-2-(trifluoromethyl)nicotinamide;
5-chloro-2-(difluoromethyl)-N-((1r,4r)-4-((2-oxo-3-(2-(2-oxopyrrolidin-1-yl)pyridin-4-yl)-2,3-dihydro-1H-benzo[d]imidazol-1-yl)methyl)cyclohexyl)nicotinamide;
5-chloro-2-(difluoromethyl)-N-((1r,4r)-4-((3-(2-(3-methyl-2-oxoimidazolidin-1-yl)pyridin-4-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(1,2-dimethyl-1H-pyrrolo[2,3-b]pyridin-5-yl)-2-oxo-2,3-dihydro-1H-imidazo[4,5-b]pyridin-1-yl)methyl)cyclohexyl)nicotinamide;
5-chloro-2-(difluoromethyl)-N-((1r,4r)-4-((3-(2-(hydroxymethyl)-1H-pyrrolo[2,3-b]pyridin-5-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((3-(3-fluoro-4-methoxyphenyl)-2-oxo-2,3-dihydro-1H-imidazo[4,5-b]pyridin-1-yl)methyl)cyclohexyl)nicotinamide;
5-chloro-2-(difluoromethyl)-N-((1r,4r)-4-((3-(6-(3-hydroxypropyl)pyridin-3-yl)-2-oxo-2,3-dihydro-1H-benzo[d]imidazol-1-yl)methyl)cyclohexyl)nicotinamide;
5-chloro-2-(difluoromethyl)-N-((1r,4r)-4-((6-fluoro-3-(6-(2-hydroxyethoxy)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(6-((2-hydroxyethyl)amino)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(2-(2-hydroxyethoxy)pyridin-4-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(5-((2-hydroxyethyl)amino)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-3-(5-(2-hydroxyethoxy)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((2-oxo-3-(5-(2-oxoimidazolidin-1-yl)pyridin-2-yl)-2,3-dihydro-1H-benzo[d]imidazol-1-yl)methyl)cyclohexyl)nicotinamide;

5-chloro-N-((1r,4r)-4-((3-(2-chloro-5-fluorophenyl)-2-oxo-2,3-dihydro-1H-imidazo[4,5-c]pyridin-1-yl)methyl)cyclohexyl)-2-(difluoromethyl)nicotinamide;

5-chloro-2-(difluoromethyl)-N-((1r,4r)-4-((3-(3-fluoro-4-methoxyphenyl)-2-oxo-2,3-dihydro-1H-imidazo[4,5-c]pyridin-1-yl)methyl)cyclohexyl)nicotinamide;

5-chloro-2-(difluoromethyl)-N-((1r,4r)-4-((1-(2-fluoro-5-methoxyphenyl)-2-oxo-1H-imidazo[4,5-b]pyridin-3(2H)-yl)methyl)cyclohexyl)nicotinamide;

5-chloro-N-((1r,4r)-4-((3-(2-chlorophenyl)-2-oxo-2,3-dihydro-1H-imidazo[4,5-c]pyridin-1-yl)methyl)cyclohexyl)-2-(difluoromethyl)nicotinamide;

5-chloro-2-(difluoromethyl)-N-((1r,4r)-4-((1-(3-fluoro-4-methoxyphenyl)-2-oxo-1H-imidazo[4,5-b]pyridin-3(2H)-yl)methyl)cyclohexyl)nicotinamide;

5-chloro-2-(difluoromethyl)-N-((1r,4r)-4-((3-(2-fluoro-5-methoxyphenyl)-2-oxo-2,3-dihydro-1H-imidazo[4,5-c]pyridin-1-yl)methyl)cyclohexyl)nicotinamide;

5-chloro-2-(difluoromethyl)-N-((1r,4r)-4-((1-(3-fluoro-4-methoxyphenyl)-2-oxo-1H-imidazo[4,5-c]pyridin-3(2H)-yl)methyl)cyclohexyl)nicotinamide;

5-chloro-2-(difluoromethyl)-N-((1r,4r)-4-((3-(2-fluoro-5-methoxyphenyl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((1-(2-fluoro-5-methoxyphenyl)-2-oxo-1H-imidazo[4,5-c]pyridin-3(2H)-yl)methyl)cyclohexyl)nicotinamide;

4-(3-(((1r,4r)-4-(5-chloro-2-(difluoromethyl)nicotinamido)cyclohexyl)methyl)-2-oxo-2,3-dihydro-1H-benzo[d]imidazol-1-yl)-N-methylpicolinamide;

4-(3-(((1r,4r)-4-(5-chloro-2-methylnicotinamido)cyclohexyl)methyl)-2-oxo-2,3-dihydro-1H-benzo[d]imidazol-1-yl)-N-methylpicolinamide;

4-(3-(((1r,4r)-4-(5-chloro-2-(trifluoromethyl)nicotinamido)cyclohexyl)methyl)-2-oxo-2,3-dihydro-1H-benzo[d]imidazol-1-yl)-N-methylpicolinamide;

5-chloro-2-(difluoromethyl)-N-((1r,4r)-4-((3-(1-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(1-(2-hydroxyethyl)-3-methyl-1H-pyrrolo[2,3-b]pyridin-5-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-(hydroxymethyl)-1-methyl-1H-pyrrolo[2,3-b]pyridin-5-yl)-2-oxo-2,3-dihydro-1H-benzo[d]imidazol-1-yl)methyl)cyclohexyl)nicotinamide;

N-((1r,4r)-4-((3-(6-(1H-imidazol-2-yl)pyridin-3-yl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(2-(hydroxymethyl)-1-methyl-1H-indol-5-yl)-2-oxo-2,3-dihydro-1H-imidazo[4,5-b]pyridin-1-yl)methyl)cyclohexyl)nicotinamide;

5-chloro-2-(difluoromethyl)-N-((1r,4r)-4-((3-(5-(3-methyl-2-oxoimidazolidin-1-yl)pyridin-2-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((6-fluoro-2-oxo-3-(6-(2-oxoimidazolidin-1-yl)pyridin-3-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(2-methyl-1H-pyrrolo[2,3-b]pyridin-5-yl)-2-oxo-2,3-dihydro-1H-imidazo[4,5-b]pyridin-1-yl)methyl)cyclohexyl)nicotinamide;

N-((1r,4r)-4-((3-(2-(1H-pyrazol-4-yl)pyridin-4-yl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(3-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-methylnicotinamide;

N-((1r,4r)-4-((3-(4-(1H-imidazol-2-yl)phenyl)-2-oxo-2,3-dihydro-1H-benzo[d]imidazol-1-yl)methyl)cyclohexyl)-5-chloro-2-(difluoromethyl)nicotinamide;

5-chloro-2-(difluoromethyl)-N-((1r,4r)-4-((3-(3-(5-methyl-1,2,4-oxadiazol-3-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(5-methyl-1,2,4-oxadiazol-3-yl)phenyl)-2-oxo-2,3-dihydro-1H-benzo[d]imidazol-1-yl)methyl)cyclohexyl)nicotinamide;

5-chloro-2-(difluoromethyl)-N-((1r,4r)-4-((3-(3-(5-methyl-1,3,4-oxadiazol-2-yl)phenyl)-2-oxo-2,3-dihydro-1H-benzo[d]imidazol-1-yl)methyl)cyclohexyl)nicotinamide;

5-chloro-2-methyl-N-((1r,4r)-4-((3-(3-(5-methyl-1,3,4-oxadiazol-2-yl)phenyl)-2-oxo-2,3-dihydro-1H-benzo[d]imidazol-1-yl)methyl)cyclohexyl)nicotinamide;

N-((1r,4r)-4-((3-(3-(1,3,4-oxadiazol-2-yl)phenyl)-2-oxo-2,3-dihydro-1H-benzo[d]imidazol-1-yl)methyl)cyclohexyl)-5-chloro-2-(difluoromethyl)nicotinamide;

N-((1r,4r)-4-((3-(3-(1,3,4-oxadiazol-2-yl)phenyl)-2-oxo-2,3-dihydro-1H-benzo[d]imidazol-1-yl)methyl)cyclohexyl)-5-chloro-2-methylnicotinamide;

5-chloro-N-((1r,4r)-4-((3-(2-chlorophenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-chlorophenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-chlorophenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(2-chloro-5-methoxyphenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-chloro-5-methoxyphenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-chloro-5-methoxyphenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(3-fluoro-4-methoxyphenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(3-fluoro-4-methoxyphenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(3-fluoro-4-methoxyphenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(3-fluoro-4-methoxyphenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(2-chloro-5-fluorophenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-chloro-5-fluorophenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-chloro-5-fluorophenyl)-2-oxo-1H-imidazo[4,5-b]pyridin-3(2H)-yl)methyl)cyclohexyl)-2-(trifluoromethyl)nicotinamide;

5-chloro-N-((1r,4r)-4-((3-(2-fluoro-5-methoxyphenyl)-2-oxo-2,3-dihydro-1H-imidazo[4,5-b]pyridin-1-yl)methyl)cyclohexyl)-2-(trifluoromethyl)nicotinamide;

5-chloro-N-((1r,4r)-4-((3-(2-fluoro-5-methoxyphenyl)-2-oxo-2,3-dihydro-1H-imidazo[4,5-c]pyridin-1-yl)methyl)cyclohexyl)-2-(trifluoromethyl)nicotinamide;

5-chloro-N-((1r,4r)-4-((1-(2-fluoro-5-methoxyphenyl)-2-oxo-1H-imidazo[4,5-c]pyridin-3(2H)-yl)methyl)cyclohexyl)-2-(trifluoromethyl)nicotinamide;

5-chloro-N-((1r,4r)-4-((1-(2-fluoro-5-methoxyphenyl)-2-oxo-1H-imidazo[4,5-b]pyridin-3(2H)-yl)methyl)cyclohexyl)-2-(trifluoromethyl)nicotinamide;

5-chloro-2-(difluoromethyl)-N-((1r,4r)-4-((2-oxo-3-(5-(2-oxopyrrolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((1-(3-fluorophenyl)-2-oxo-1H-imidazo[4,5-b]pyridin-3(2H)-yl)methyl)cyclohexyl)nicotinamide;

N-((1r,4r)-4-((3-(4-(1H-imidazol-5-yl)phenyl)-2-oxo-2,3-dihydro-1H-benzo[d]imidazol-1-yl)methyl)cyclohexyl)-5-chloro-2-(difluoromethyl)nicotinamide;

5-chloro-N-((1r,4r)-4-((3-(6-((2-hydroxyethyl)amino)pyridin-3-yl)-2-oxo-2,3-dihydro-1H-benzo[d]imidazol-1-yl)methyl)cyclohexyl)-2-(trifluoromethyl)nicotinamide;

5-chloro-2-methyl-N-((1r,4r)-4-((2-oxo-3-(5-(2-oxopyrrolidin-1-yl)pyridin-2-yl)-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxoimidazolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-(2-oxoimidazolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((3-(6-(3-methyl-2-oxoimidazolidin-1-yl)pyridin-2-yl)-2-oxo-2,3-dihydro-1H-benzo[d]imidazol-1-yl)methyl)cyclohexyl)nicotinamide;

5-chloro-2-methyl-N-((1r,4r)-4-((2-oxo-3-(6-(2-oxopyrrolidin-1-yl)pyridin-2-yl)-2,3-dihydro-1H-benzo[d]imidazol-1-yl)methyl)cyclohexyl)nicotinamide;

5-chloro-2-(difluoromethyl)-N-((1r,4r)-4-((2-oxo-3-(6-(2-oxopyrrolidin-1-yl)pyridin-2-yl)-2,3-dihydro-1H-benzo[d]imidazol-1-yl)methyl)cyclohexyl)nicotinamide;

5-chloro-N-((1r,4r)-4-((3-(6-(1-methyl-1H-pyrazol-3-yl)pyridin-3-yl)-2-oxo-2,3-dihydro-1H-benzo[d]imidazol-1-yl)methyl)cyclohexyl)-2-(trifluoromethyl)nicotinamide;

5-chloro-2-(difluoromethyl)-N-((1r,4r)-4-((6-fluoro-3-(5-(2-hydroxyethoxy)pyrazin-2-yl)-2-oxo-2,3-dihydro-1H-benzo[d]imidazol-1-yl)methyl)cyclohexyl)nicotinamide; and 5-chloro-2-(difluoromethyl)-N-((1r,4r)-4-((3-(2-(hydroxymethyl)-1H-indol-5-yl)-2-oxo-2,3-dihydro-1H-imidazo[4,5-b]pyridin-1-yl)methyl)cyclohexyl)nicotinamide;

or a pharmaceutically acceptable salt thereof or a prodrug thereof.

8. A method for the treatment of a condition or disorder in which CRHR1 and/or CRHR2 are involved, in an animal, including a human, which comprises administering to the animal in need of such treatment a therapeutically effective amount of a compound or a prodrug thereof or a pharmaceutically acceptable salt thereof, according to claim 1.

9. The method as described in claim 8, wherein said condition or disorder is selected from the group consisting of: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart disease, and combinations thereof.

10. The method according to claim 9, wherein the heart disease is selected from the group consisting of: acute and chronic heart failure, cardiovascular disease, hyper tension, myocardial infarction, coronary artery disease, and abdominal aortic aneurysm.

11. A pharmaceutical composition comprising a compound or a pharmaceutically acceptable salt thereof or a prodrug thereof, according to claim 1, and a pharmaceutically acceptable carrier.

12. The pharmaceutical composition according to claim 11, further comprising another pharmacologically active agent.

13. A process for preparing a pharmaceutical composition, wherein the process comprises mixing a compound according to claim 1 or a pharmaceutically acceptable salt thereof or a prodrug thereof and a pharmaceutically acceptable carrier or excipient.

14. An assay process for identifying a compound which has CRHR1 and/or CRHR2 antagonistic activity, comprising administering of a compound according to claim 1 to mice loaded exogenous CRHR2 agonist within 1 week and investigating cardiovascular functions.

15. An assay process for identifying a compound which has CRHR1 and/or CRHR2 antagonistic activity, comprising administering of a compound according to claim 1 to mice infused urocortin 2 within 2 days and measuring cardiac function by echocardiography.

\* \* \* \* \*